(12) United States Patent
Sherman

(10) Patent No.: US 11,986,532 B2
(45) Date of Patent: May 21, 2024

(54) MODULATORS OF BCL6 PROTEOLYSIS AND ASSOCIATED METHODS OF USE

(71) Applicant: Arvinas Operations, Inc., New Haven, CT (US)

(72) Inventor: Dan Sherman, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 17/721,916

(22) Filed: Apr. 15, 2022

(65) Prior Publication Data

US 2022/0395576 A1 Dec. 15, 2022

Related U.S. Application Data

(60) Provisional application No. 63/175,678, filed on Apr. 16, 2021.

(51) Int. Cl.
*A61K 47/55* (2017.01)
*A61K 45/06* (2006.01)
*A61K 47/54* (2017.01)
*A61P 35/00* (2006.01)

(52) U.S. Cl.
CPC .............. *A61K 47/55* (2017.08); *A61K 45/06* (2013.01); *A61K 47/545* (2017.08); *A61P 35/00* (2018.01)

(58) Field of Classification Search
CPC ....... A61K 47/55; A61K 47/545; A61K 45/06
See application file for complete search history.

(56) References Cited

U.S. PATENT DOCUMENTS

| 4,522,811 | A | 6/1985 | Eppstein et al. |
| 6,306,663 | B1 | 10/2001 | Kenten et al. |
| 6,670,348 | B1 | 12/2003 | Rosen et al. |
| 7,041,298 | B2 | 5/2006 | Deshaies et al. |

(Continued)

FOREIGN PATENT DOCUMENTS

| CN | 1844118 A | 10/2006 |
| CN | 103688176 A | 3/2014 |

(Continued)

OTHER PUBLICATIONS

Ahn, D., et al., "HIF-1α Peptide Derivatives with modifications at the hydroxyproline residue as activators of HIF-1α", Bioorganic & Medicinal Chemistry Letters (2009); 19(15): 4403-4405.

(Continued)

*Primary Examiner* — Rayna Rodriguez
(74) *Attorney, Agent, or Firm* — COOLEY LLP

(57) ABSTRACT

Bifunctional compounds, which find utility as modulators of B-cell lymphoma 6 protein (BCL6; target protein), are described herein. In particular, the bifunctional compounds of the present disclosure contain on one end a cereblon ligand that binds to the respective E3 ubiquitin ligase and on the other end a moiety which binds the target protein, such that the target protein is placed in proximity to the ubiquitin ligase to effect degradation (and inhibition) of target protein. The bifunctional compounds of the present disclosure exhibit a broad range of pharmacological activities associated with degradation/inhibition of target protein. Diseases or disorders that result from aggregation or accumulation of the target protein are treated or prevented with compounds and compositions of the present disclosure.

4 Claims, 1 Drawing Sheet

(56) References Cited

U.S. PATENT DOCUMENTS

| | | | |
|---|---|---|---|
| 7,208,157 B2 | 4/2007 | Dashaies et al. |
| 8,338,464 B2 | 12/2012 | Melnick et al. |
| 9,447,070 B2 | 9/2016 | Muller et al. |
| 9,500,653 B2 | 11/2016 | Crews et al. |
| 9,632,089 B2 | 4/2017 | Crews et al. |
| 10,647,698 B2 | 5/2020 | Crew et al. |
| 11,439,635 B2 | 9/2022 | Barish et al. |
| 11,505,539 B2 | 11/2022 | Isaac et al. |
| 11,512,095 B2 | 11/2022 | Bellenie et al. |
| 11,518,764 B2 | 12/2022 | Al-Awar et al. |
| 2003/0096841 A1 | 5/2003 | Robarge et al. |
| 2008/0051432 A1 | 2/2008 | Zhang |
| 2008/0214501 A1 | 9/2008 | Pan et al. |
| 2012/0014979 A1 | 1/2012 | Dent |
| 2012/0270800 A1 | 10/2012 | Verdine et al. |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0291562 A1 | 10/2015 | Crew et al. |
| 2015/0344473 A1 | 12/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |
| 2022/0323457 A1 | 10/2022 | Berlin et al. |

FOREIGN PATENT DOCUMENTS

| | | |
|---|---|---|
| EP | 2985285 A1 | 2/2016 |
| JP | 2010502627 A | 1/2010 |
| RU | 2008112221 A | 10/2009 |
| RU | 2448101 C2 | 4/2012 |
| RU | 2011121567 A | 12/2012 |
| RU | 2012138709 A | 3/2014 |
| WO | WO-9803502 A1 | 1/1998 |
| WO | WO-0066119 A1 | 11/2000 |
| WO | WO-02066512 A1 | 8/2002 |
| WO | WO-2005016326 A2 | 2/2005 |
| WO | WO-2006113942 A2 | 10/2006 |
| WO | WO-2007106670 A2 | 9/2007 |
| WO | WO-2008011392 A2 | 1/2008 |
| WO | WO-2009015254 A1 | 1/2009 |
| WO | WO-2010053732 A1 | 5/2010 |
| WO | WO-2010141805 A1 | 12/2010 |
| WO | WO-2012003281 A2 | 1/2012 |
| WO | WO-2012040527 A2 | 3/2012 |
| WO | WO-2012078559 A2 | 6/2012 |
| WO | WO-2012090104 A1 | 7/2012 |
| WO | WO-2012142498 A2 | 10/2012 |
| WO | WO-2013106646 A2 | 7/2013 |
| WO | WO-2013170147 A1 | 11/2013 |
| WO | WO-2014108452 A1 | 7/2014 |
| WO | WO-2014123418 A1 | 8/2014 |
| WO | WO-2015000868 A1 | 1/2015 |
| WO | WO-2015160845 A2 | 10/2015 |
| WO | WO-2016105518 A1 | 6/2016 |
| WO | WO-2016146985 A1 | 9/2016 |
| WO | WO-2016149668 A1 | 9/2016 |
| WO | WO-2016169989 A1 | 10/2016 |
| WO | WO-2016172134 A2 | 10/2016 |
| WO | WO-2016187723 A1 | 12/2016 |
| WO | WO-2016197114 A1 | 12/2016 |
| WO | WO-2017007612 A1 | 1/2017 |
| WO | WO-2017011590 A1 | 1/2017 |
| WO | WO-2017024317 A2 | 2/2017 |
| WO | WO-2017024318 A1 | 2/2017 |
| WO | WO-2017024319 A1 | 2/2017 |
| WO | WO-2017030814 A1 | 2/2017 |
| WO | WO-2017046036 A1 | 3/2017 |
| WO | WO-2017079267 A1 | 5/2017 |
| WO | WO-2017117473 A1 | 7/2017 |
| WO | WO-2017117474 A1 | 7/2017 |
| WO | WO-2017161119 A1 | 9/2017 |
| WO | WO-2017176957 A1 | 10/2017 |
| WO | WO-2017176958 A1 | 10/2017 |
| WO | WO-2017185023 A1 | 10/2017 |
| WO | WO-2017185031 A1 | 10/2017 |
| WO | WO-2017185034 A1 | 10/2017 |
| WO | WO-2017185036 A1 | 10/2017 |
| WO | WO-2017197051 A1 | 11/2017 |
| WO | WO-2017197055 A1 | 11/2017 |
| WO | WO-2017197056 A1 | 11/2017 |
| WO | WO-2017223415 A1 | 12/2017 |
| WO | WO-2017223452 A1 | 12/2017 |
| WO | WO-2018052945 A1 | 3/2018 |
| WO | WO-2018052949 A1 | 3/2018 |
| WO | WO-2018064589 A1 | 4/2018 |
| WO | WO-2018089736 A1 | 5/2018 |
| WO | WO-2018098275 A1 | 5/2018 |
| WO | WO-2018098280 A1 | 5/2018 |
| WO | WO-2018098288 A1 | 5/2018 |
| WO | WO-2018102725 A1 | 6/2018 |
| WO | WO-2018106870 A1 | 6/2018 |
| WO | WO-2018108704 A1 | 6/2018 |
| WO | WO-2018148440 A1 | 8/2018 |
| WO | WO-2018215798 A1 | 11/2018 |
| WO | WO-2018215801 A1 | 11/2018 |
| WO | WO-2018237026 A1 | 12/2018 |
| WO | WO-2019060693 A1 | 3/2019 |
| WO | WO-2019060742 A1 | 3/2019 |
| WO | WO-2019084026 A1 | 5/2019 |
| WO | WO-2019084030 A1 | 5/2019 |
| WO | WO-2019099926 A1 | 5/2019 |
| WO | WO-2019099868 A3 | 6/2019 |
| WO | WO-2019119138 A1 | 6/2019 |
| WO | WO-2019195201 A1 | 10/2019 |
| WO | WO-2021074620 A1 | 4/2021 |
| WO | WO-2021077010 A1 | 4/2021 |
| WO | WO-2022169780 A1 | 8/2022 |
| WO | WO-2023015164 A1 | 2/2023 |
| WO | WO-2023114460 A1 | 6/2023 |

OTHER PUBLICATIONS

[Author Unknown] "Cancer" Medline Plus Trusted Health Information for You [online] www.nlm.nih.gov/medlineplus/cancer.html (Jul. 6, 2007); 10 pages.

Bellenie, B. R., et al., "Achieving In Vivo Target Depletion through the Discovery and Optimization of Benzimidazolone BCL6 Degraders", Journal of Medicinal Chemistry (2020);63(8): 4047-4068.

Beveridge, R., et al., "Native Mass Spectrometry Can Effectively Predict PROTAC Efficacy", ACS Central Science (Jul. 6, 2020); 6: 1223-1230.

Bondeson, D. P., et al., "Catalytic in vivo protein knockdown by small-molecule PROTACS", Nature Chemical Biology (2015); 11(8): 611-617.

Bondeson, D. P., et al., "Lessons in PROTAC design from selective degradation with a promiscuous warhead", Cell Chemical Biology (2018); 25(1): 78-87.

(56) References Cited

OTHER PUBLICATIONS

Bondeson, D. P., et al., "Targeted Protein Degradation by Small Molecules", Annual Review of Pharmacology and Toxicology (2017); 57 :107-123.
Bouzide, A., et al., "Silver(I) oxide-mediated facile and practical sulfonylation of alcohols", Tetrahedron Letters (Oct. 9, 2001); 42(50): 8781-8783.
Buckley, D. L., et al., "HaloPROTACS: use of small molecule PROTACS to induce degradation of HaloTag fusion proteins", ACS Chemical Biology (2015); 10(8): 1831-1837.
Buckley, D. L., et al., "Small-molecule inhibitors of the interaction between the E3 ligase VHL and HIF1α", Angewandte Chemie (International Ed. in English) (2012); 51(46): 11463-11467.
Buckley, D. L., et al., "Targeting the von Hippel-Lindau E3 ubiquitin ligase using small molecules to disrupt the VHL/HIF-1α interaction", Journal of the American Chemical Society (2012); 134(10): 4465-4468.
Burslem, G. M., et al., "Small-Molecule Modulation of Protein Homeostasis", Chemical Reviews (2017); 117(17): 11269-11301.
Burslem, G. M., et al., "The Advantages of Targeted Protein Degradation Over Inhibition: An RTK Case Study", Cell Chemical Biology (2018); 25(1): 67-77.
Capitosti, S. M., et al., "Thalidomide analogues demonstrate dual inhibition of both angiogenesis and prostate cancer", Bioorganic & Medicinal Chemistry (2004); 12(2): 327-336.
Cardenas, M. G., et al., "Rationally designed BCL6 inhibitors target activated B cell diffuse large B cell lymphoma", Journal of Clinical Investigation (Sep. 1, 2016);126(9): 3351-3362.
Carmony, K. C., et al., "PROTAC-induced proteolytic targeting", Methods in Molecular Biology (2012); 832: 627-638.
Database STN, CAS Registry No. 1542127-97-8, "4,7,10,13-Tetraoxa-16-azaheneicosanamide, N-[4-[3-(4-amino-1,3-dihydro-1,3-dioxo-2H-isoindol-2-yl)-2,6-dioxo-3-piperidinyl]butyl]-21-[(3aS,4S,6aR)-hexahydro-2-oxo-1H-thieno[3,4-d]imidazol-4-yl]-17-oxo-", Chemical Abstracts Service, American Chemical Society; entered Feb. 11, 2014, 4 Pages.
Cerchietti, L. C., et al., "A Small-Molecule Inhibitor of BCL6 Kills DLBCL Cells In Vitro and In Vivo", Cancer Cell (2010); 17(4): 400-411.
Chan, K., et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (IBET726) BET Inhibitor Scaffolds", Journal of Medicinal Chemistry (Jun. 8, 2018) ; 61(2): 504-513.
Chen, J., et al., "A review on the latest progress of Chan-Lam coupling reaction", Advanced Synthesis and Catalysis (Jul. 14, 2020); 62(16): 3311-3331.
Churcher, I., "Protac-Induced Protein Degradation in Drug Discovery: Breaking the Rules or Just Making New Ones?", Journal of Medicinal Chemistry (2018); 61(2): 444-452.
Contino-Pepin, C., et al., "Preliminary biological evaluations of new thalidomide analogues for multiple sclerosis application", Bioorganic & Medicinal Chemistry Letters (2009); 19(3): 878-881.
Corson, T. W., et al., "Design and applications of bifunctional small molecules: why two heads are better than one", ACS Chemical Biology (2008); 3(11): 677-692.
Crew, A. P., et al., "Identification and Characterization of Von Hippel-Lindau-Recruiting Proteolysis Targeting Chimeras (PROTACs) of TANK-Binding Kinase 1", Journal of Medicinal Chemistry (2018); 61(2): 583-598.
Crews, C. M., "Targeting the undruggable proteome: the small molecules of my dreams", Chemistry & Biology (2010); 17(6): 551-555.
Cromm, P. M., et al., "Targeted protein degradation: from chemical biology to drug discovery", Cell chemical Biology (2017); 24(9): 1181-1190.
Cyrus, K., et al., "Impact of linker length on the activity of PROTACs", Molecular BioSystems (2011); 7(2): 359-364.
Cyrus, K. et al., "Jostling for position: Optimizing linker location in the design of estrogen receptor-targeting PROTACs", ChemMedChem (2010); 5(7): 979-985.
Cyrus, K., et al., "Two-Headed PROTAC: An Effective New Tool for Targeted Protein Degradation", Chembiochem (2010); 11(11): 1531-1534.
Database STN, CAS Registry No. 1004933-70-3, "2-Pyrrolidinecarboxamide, N-(4-bromo-2-fluorophenyl)-4-hydroxy-1-(2-naphthalenylsulfonyl)-, (2S,4R)-", Chemical Abstracts Service, American Chemical Society; entered Feb. 21, 2008; 1 page.
Database STN, CAS Registry No. 871986-52-6, "2-Pyrrolidinecarboxamide, N-[(1S)-3 [(3aR,6aS)-5-(2,6-dimethylbenzoyl)hexahydropyrrolo[3,4-c]pyrrol-2(1H)-yl]-1-phenylpropyl]-1-(2-furanylcarbonyl)-4-hydroxy-", Chemical Abstracts Service, American Chemical Society; entered Jan. 16, 2006; 1 page.
Duplantier, A. J., et al., "Discovery, SAR, and Pharmacokinetics of a Novel 3-Hydroxyquinolin-2(1H)-one Series of Potent d-Amino Acid Oxidase (DAAO) Inhibitors", Journal of Medicinal Chemistry (May 13, 2009); 52(11): 3576-3585.
Fischer, E. S., et al., "Structure of the DDB1-CRBN E3 Ubiquitin ligase in complex with thalidomide", Nature (2014); 512(7512): 49-53.
Gadd, M. S., et al., "Structural basis of PROTAC cooperative recognition for selective protein degradation", Nature Chemical Biology (2017); 13(5): 514-521.
Galdeano, C., et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities", Journal of Medicinal Chemistry (2014); 57(20): 8657-8663.
Golub, T. R., et al., "Molecular classification of cancer: class discovery and class prediction by gene expression monitoring", Science (1991); 286: 531-537.
Gosink, M., et al., "Redirecting the specificity of ubiquitination by modifying ubiquitin-conjugating enzymes", Proceedings of the National Academy of Sciences (1995); 92(20): 9117-9121.
Guo, W., et al., "Synthesis and Biological Evaluation of B-Cell Lymphoma 6 Inhibitors of N-Phenyl-4-pyrimidinamine Derivatives Bearing Potent Activities against Tumor Growth", Journal of Medicinal Chemistry (Jan. 23, 2020); 63(2): 676-695.
Han, X., et al., "Discovery of ARD-69 as a highly potent proteolysis targeting chimera (PROTAC) degrader of androgen receptor (AR) for the treatment of prostate cancer", Journal of Medicinal Chemistry (2019); 62(2): 941-964.
Hines, J., et al., "Posttranslational protein knockdown coupled to receptor tyrosine kinase activation with phosphoPROTACs", Proceedings of the National Academy of Sciences (2013); 110(22): 8942-8947.
Hon, W., et al., "Structural basis for the recognition of hydroxyproline in HIF-1α by pVHL", Nature (2002); 417(6892): 975-978.
Hu, J., et al., "Discovery of ERD-308 as a Highly Potent Proteolysis Targeting Chimera (PROTAC) Degrader of Estrogen Receptor (ER)", Journal of Medicinal Chemistry (2019); 62: 1420-1442.
Huang, H. T., et al., "A Chemoproteomic Approach to Query the Degradable Kinome Using a Multi-kinase Degrader", Cell Chemical Biology (2018); 25(1): 88-99.
Huang, X. et al., "Drugging the undruggables: exploring the ubiquitin system for drug development", Cell Research (2016); 26(4): 484-498.
Hughes, S. J., et al., "Molecular recognition of ternary complexes: a new dimension in the structure-guided design of chemical degraders", Essays in Biochemistry (2017); 61(5): 505-516.
Hurtz, C., et al., "Rationale for targeting BCL6 in MLL-rearranged acute lymphoblastic leukemia" Genes & Development (2019); 33(17-18): 1265-1279.
International Search Report and Written Opinion for International Application No. PCT/US2020/056145, dated Dec. 1, 2020, 10 Pages.
Itoh, Y., et al., "Development of target protein selective degradation inducer for protein knockdown," Bioorganic & Medicinal Chemistry (2011); 19(10): 3229-3241.
Itoh, Y., et al., "Protein knockdown using methyl bestatin-ligand hybrid molecules: design and synthesis of inducers of ubiquitination-

(56) References Cited

OTHER PUBLICATIONS mediated degradation of cellular retinoic acid-binding proteins", Journal of the American Chemical Society (2010); 132(16): 5820-5826.

Ivan, M., et al., "HIFα targeted for VHL-mediated destruction by proline hydroxylation: implications for $O_2$ sensing", Science (2001); 292(5516): 464-468.

Jang, E. R., et al., "Targeted Degradation of Proteins by PROTACs", Current Protocols in Chemical Biology (2010); 2(2): 71-87.

Kamada, Y., et al., "Discovery of a B-Cell Lymphoma 6 Protein-Protein Interaction Inhibitor by a Biophysics-Driven Fragment-Based Approach", Journal of Medicinal Chemistry (May 25, 2017); 60(10): 4358-4368.

Kerres, N., et al., "Chemically Induced Degradation of the Oncogenic Transcription Factor BCL6", Cell Reports (Sep. 19, 2017); 20(12): 2860-2875.

Knott, E. B., "Compounds containing sulphur chromophores. Part I. The action of bases on heterocyclic sulphide quarternary salts", Journal of the Chemical Society (Resumed) (1955); 916-927.

Krönke, J., et al., "Lenalidomide causes selective degradation of IKZF1 and IKZF3 in multiple myeloma cells", Science (2014); 343(6168): 301-305.

Lai, A. C., et al., "Induced protein degradation: an emerging drug discovery paradigm", Nature Reviews Drug Discovery (2017); 16(2): 101-114.

Lai, A. C., et al., "Modular PROTAC design for the degradation of oncogenic BCR-ABL", Angewandte Chemie International Edition (2016); 55(2): 807-810.

Lala, P. K., et al., "Role of nitric oxide in tumor progression: lessons from experimental tumors", Cancer and Metastasis Reviews (1998); 17: 91-106.

Lebraud, H., et al., "Protein degradation by in-cell self-assembly of proteolysis targeting chimeras", ACS Central Science (2016); 2(12): 927-934.

Lee, H., et al., "Targeted degradation of the aryl hydrocarbon receptor by the PROTAC approach: a useful chemical genetic tool", Chembiochem (2007); 8(17): 2058-2062.

Levine, P. M., et al., "Targeting the androgen receptor with steroid conjugates: miniperspective", Journal of Medicinal Chemistry (2014); 57(20): 8224-8237.

Li, Y., et al., "Single polymer-drug conjugate carrying two drugs for fixed-dose co-delivery", Medicinal Chemistry (2014); 4(10): 676-683.

Liu, K, et al., "Design and biological characterization of hybrid compounds of curcumin and thalidomide for multiple myeloma", Organic & Biomolecular Chemistry (2013); 11(29): 4757-4763.

Lopez-Girona, A. E. A., et al., "Cereblon is a direct protein target for immunomodulatory and antiproliferative activities of lenalidomide and pomalidomide", Leukemia (2012); 26(11): 2326-2335.

Lu, G., et al., "The myeloma drug lenalidomide promotes the cereblon-dependent destruction of Ikaros proteins", Science (2014); 343(6168): 305-309.

Lu, J., et al., "Hijacking the E3 ubiquitin ligase cereblon to efficiently target BRD4", Chemistry & Biology (2015); 22(6): 755-763.

Maniaci, C., et al., "Homo-PROTACs: bivalent small-molecule dimerizers of the VHL E3 ubiquitin ligase to induce self-degradation", Nature Communications (2017); 8(1): 1-14.

McCoull, W., et al., "Development of a Novel B-Cell Lymphoma 6 (BCL6) PROTAC To Provide Insight into Small Molecule Targeting of BCL6", ACS Chemical Biology (Nov. 16, 2018); 13(11): 3131-3141.

McCoull, W., et al., "Discovery of Pyrazolo[1,5-a]pyrimidine B-Cell Lymphoma 6 (BCL6) Binders and Optimization to High Affinity Macrocyclic Inhibitors", Journal of Medicinal Chemistry (May 25, 2017); 60(10): 4386-4402.

Min, J., et al., "Structure of an HIF-1α-pVHL complex: hydroxyproline recognition in signaling", Science (2002); 296(5574): 1886-1889.

Mullard, A., "First targeted protein degrader hits the clinic", Nature Reviews, Drug Discovery (Apr. 2019); 18: 237-239.

Muller, G. W., et al., "Amino-substituted thalidomide analogs: potent inhibitors of TNF-α production", Bioorganic & Medicinal Chemistry Letters (1999); 9(11): 1625-1630.

Neklesa, T.K. et al., "Greasy tags for protein removal", Nature (2012); 487(7407): 308-309.

Neklesa, T.K. et al., "Targeted protein degradation by PROTACs", Pharmacology & Therapeutics (2017); 174: 138-144.

Noguchi-Yachide, T., et al., "BET Bromodomain as a Target of Epigenetic Therapy", Chemical and Pharmaceutical Bulletin (Jun. 1, 2016); 64(6): 540-547.

Ohoka, N., et al., "SNIPER (TACC3) induces cytoplasmic vacuolization and sensitizes cancer cells to Bortezomib", Cancer Science (2017); 108(5): 1032-1041.

Osher, E. L., et al., "A genetically selected cyclic peptide inhibitor of BCL6 homodimerization", Bioorganic & Medicinal Chemistry (Jul. 15, 2018); 26(11): 3034-3038.

Ottis, P., et al., "Assessing different E3 ligases for small molecule induced protein ubiquitination and degradation", ACS Chemical Biology (2017); 12(10): 2570-2578.

Ottis, P., et al., "Proteolysis-targeting chimeras: induced protein degradation as a therapeutic strategy", ACS Chemical Biology (2017); 12(4): 892-898.

Pfaff, P., et al., "Reversible Spatiotemporal Control of Induced Protein Degradation, by Bistable Photo PROTACS", ACS Chemical Biology (2019); 5: 1682-1690.

Powell, C. E., et al., "Chemically Induced Degradation of Anaplastic Lymphoma Kinase (ALK)", Journal of Medicinal Chemistry (2018); 61: 4249-4255.

Puppala, D., et al., "Development of an aryl hydrocarbon receptor antagonist using the proteolysis-targeting chimeric molecules approach: a potential tool for chemoprevention", Molecular Pharmacology (2008); 73(4): 1064-1071.

Raina, K., et al., "Chemical Inducers of Targeted Protein Degradation", Journal of Biological Chemistry (2010); 285(15): 11057-11060.

Raina, K., et al., "PROTAC-induced BET protein degradation as a therapy for castration-resistant prostate cancer", Proceedings of the National Academy of Sciences (2016); 113(26): 7124-7129.

Raina, K., et al., "Targeted protein knockdown using small molecule degraders", Current Opinion in Chemical Biology (2017); 39: 46-53.

Remillard, D., et al., "Degradation of the BAF complex factor BRD9 by heterobifunctional ligands", Angewandte Chemie International Edition (2017); 56(21): 5738-5743.

Rodriguez-Gonzalez, A., et al., "Targeting steroid hormone receptors for ubiquitination and degradation in breast and prostate cancer", Oncogene (2008); 27(57): 7201-7211.

Rosania, G. R., et al., "Targeting hyperproliferative disorders with cyclin dependent kinase inhibitors", Expert Opinion on Therapeutic Patents (2000); 10(2): 215-230.

Rotili, D., et al., "Photoactivable peptides for identifying enzyme-substrate and protein-protein interactions", Chemical Communications (2011); 47(5): 1488-1490.

Ruchelman, A., et al., "Isosteric analogs of lenalidomide and pomalidomide: Synthesis and biological activity", Bioorganic & Medicinal Chemistry Letters (2013); 23(1): 360-365.

Sakamoto, K. M., et al., "Development of Protacs to target cancer-promoting proteins for ubiquitination and degradation", Molecular & Cellular Proteomics (2003); 2(12): 1350-1358.

Sakamoto, K. M., et al., "Protacs: Chimeric molecules that target proteins to the Skp1-Cullin-F box complex for ubiquitination and degradation", Proceedings of the National Academy of Sciences (2001); 98(15): 8554-8559.

Salami, J., et al., "Waste disposal—An attractive strategy for cancer therapy", Science (2017); 355(6330): 1163-1167.

Sameshima, T., et al., "Discovery of an Irreversible and Cell-Active BCL6 Inhibitor Selectively Targeting Cys53 Located at the Protein-Protein Interaction Interface", Biochemistry (Feb. 27, 2018); 57(8): 1369-1379.

Schiedel, M., et al., "Chemically induced degradation of sirtuin 2 (Sirt2) by a proteolysis targeting chimera (PROTAC) based on sirtuin rearranging ligands (SirReals)", Journal of Medicinal Chemistry (2018); 61(2): 482-491.

(56) References Cited

OTHER PUBLICATIONS

Schlager, S., et al., "Inducible knock-out of BCL6 in lymphoma cells results in tumor stasis", Oncotarget (Mar. 3, 2020); 11(9): 875-890.
Schneekloth, A. R., et al., "Targeted intracellular protein degradation induced by a small molecule: En route to chemical proteomics", Bioorganic & Medicinal Chemistry Letters (2008); 18(22): 5904-5908.
Schneekloth Jr, J. S., et al., "Chemical genetic control of protein levels: selective in vivo targeted degradation", Journal of the American Chemical Society (2004); 126(12): 3748-3754.
Scudellari, M., "The protein slayers", Nature (Mar. 21, 2019); 567: 298-300.
Stanton, B. Z., et al., "Chemically induced proximity in biology and medicine", Science (Mar. 9, 2018); 359(1117): 1-9.
Stewart, S. G., et al., "Efforts toward elucidating Thalidomide's molecular target: an expedient synthesis of the first Thalidomide biotin analogue", Organic & Biomolecular Chemistry (2010); 8(18): 4059-4062.
Stoppler, M. C., "Endometriosis definition and facts", MedicineNet. com [online] http://www.medicinenet.com/endometriosis/article.htm (Retrieved on Apr. 5, 2017); 7 pages.
Stoppler, M. C., "What about surgery for Endometriosis?", MedicineNet.com [online] http://www.medicinenet.com/endometriosis/article.htm (Retrieved on Apr. 5, 2017); 7 pages.
Sun, B., et al., "BET protein proteolysis targeting chimera (PROTAC) exerts potent lethal activity against mantle cell lymphoma cells", Leukemia (2018); 32: 343-352.
Teng, M., et al., "Rationally Designed Covalent BCL6 Inhibitor That Targets a Tyrosine Residue in the Homodimer Interface", ACS Medicinal Chemistry Letters (Apr. 30, 202); 11(6): 1269-1273.
Toure, M., et al., "Small-molecule PROTACS: new approaches to protein degradation", Angewandte Chemie International Edition (2016); 55(6): 1966-1973.
Turk, B. E., et al., "Binding of thalidomide to alpha1-acid glycoprotein may be involved in its inhibition of tumor necrosis factor alpha production", Proceedings of the National Academy of Sciences (1996); 93(15): 7552-7556.
Van Molle, I., et al., "Dissecting fragment-based lead discovery at the von Hippel-Lindau protein: hypoxia inducible factor 1α protein-protein interface", Chemistry & Biology (2012); 19(10): 1300-1312.
Watson, I. D., et al., "Abstract 7: Discovery of OICR-10268: A potent and selective BCL6 inhibitor", Proceedings: AACR Annual Meeting 2019; Mar. 29-Apr. 3, 2019; Atlanta, GA; 1 page.
Winter, G. E., et al., "Phthalimide conjugation as a strategy for in vivo target protein degradation", Science (2015); 348(6241): 1376-1381.
Yasui, T., et al., "Discovery of a novel B-cell lymphoma 6 (BCL6)-corepressor interaction inhibitor by utilizing structure based drug design", Bioorganic & Medicinal Chemistry (Sep. 1, 2017); 25(17): 4876-4886.
Yu, J., et al., "BCL6 induces EMT by promoting the ZEB1-mediated transcription repression of E-cadherin in breast cancer cells", Cancer Letters (2015); 365(2): 190-200.
Zengerle, M., et al., "Selective small molecule induced degradation of the BET bromodomain protein BRD4", ACS Chemical Biology (2015); 10(8): 1770-1777.
Zhang, D. et al., "Targeted Degradation of Proteins by Small Molecules: A Novel Tool for Functional Proteomics", Combinatorial Chemistry & High Throughput Screening (2004); 7(7): 689-697.
Zhou, B., et al., "Discovery of a Small-Molecule Degrader of Bromodomain and Extra-Terminal (BET) Proteins with Picomolar Cellular Potencies and Capable of Achieving Tumor Regression", Journal of Medicinal Chemistry (2018); 61(2): 462-481.
Khadra, A., et al., "Pd-PEPPSI-IPentCI: A Useful Catalyst for the Coupling of 2-Aminopyridine Derivatives," Chemistry-A European Journal (2017); 23(13): 3206-3212.
Thirumurugan, P., et al., "Click chemistry for drug development and diverse chemical-biology applications." Chemical Reviews (2013); 113(7): 4905-4979.
Xie, H., et al., "The clinical advances of proteolysis targeting chimeras in oncology", Exploration of Targeted Anti-tumor Therapy (2021); 2(6): 511-521.
Co-pending U.S. Appl. No. 18/407,150, inventors Sherman; Dan et al., filed Jan. 8, 2024.
Co-pending U.S. Appl. No. 18/490,704, inventor Sherman; Dan, filed Oct. 19, 2023.

MODULATORS OF BCL6 PROTEOLYSIS AND ASSOCIATED METHODS OF USE

CROSS-REFERENCE TO RELATED APPLICATION

The present disclosure claims priority to and the benefit of U.S. Provisional Application No. 63/175,678, filed 16 Apr. 2021, titled MODULATORS OF BCL6 PROTEOLYSIS AND ASSOCIATED METHODS OF USE, which is incorporated herein in its entirety for all purposes.

INCORPORATION BY REFERENCE

U.S. patent application Ser. No. 17/073,135, filed on 16 Oct. 2020; and U.S. patent application Ser. No. 15/730,728, filed on Oct. 11, 2017, published as U.S. Patent Application Publication No. 2018/0099940; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872, are incorporated herein by reference in their entirety. Furthermore, all references cited herein are incorporated by reference herein in their entirety.

FIELD OF THE INVENTION

The description provides bifunctional compounds comprising a target protein binding moiety and a E3 ubiquitin ligase binding moiety, and associated methods of use. The bifunctional compounds are useful as modulators of targeted ubiquitination, such as B-cell lymphoma 6 protein (BCL6), which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Bifunctional compounds such as those that are described in U.S. Patent Application Publications 2015-0291562 and 2014-0356322 (incorporated herein by reference), function to recruit endogenous proteins to an E3 ubiquitin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

An ongoing need exists in the art for effective treatments for disease associated with (i) aberrant BCL 6 expression and/or activity and/or (ii) overexpression or aggregation of B-cell lymphoma 6 protein (BCL6). However, non-specific effects, and the inability to target and modulate BCL6, remain as obstacles to the development of effective treatments. As such, small-molecule therapeutic agents that target BCL6 and that leverage or potentiate E3 ubiquitin ligase (e.g., cereblon's) substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., lymphoma, B-cell non-Hodgkin lymphomas, large B-cell lymphoma, Burkitt's lymphoma, follicular lymphoma, intravascular large B-cell lymphoma, B-cell leukemia, B-cell acute lymphoblastic leukemia, chronic myeloid leukemia, non-small cell lung cancer.

As such, in one aspect the disclosure provides bifunctional compounds, which comprise an E3 ubiquitin ligase binding moiety (i.e., a ligand for an E3 ubiquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be a cereblon E3 ubiquitin ligase binding moiety (CLM). For example, the structure of the bifunctional compound can be depicted as:

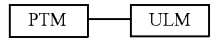

The respective positions of the PTM and ULM moieties (e.g., CLM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

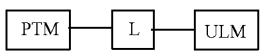

where PTM is a protein/polypeptide targeting moiety, L is a linker, e.g., a bond or a chemical group coupling PTM to ULM, and ULM is a cereblon E3 ubiquitin ligase binding moiety (CLM).

For example, the structure of the bifunctional compound can be depicted as:

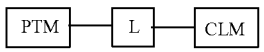

wherein: PTM is a protein/polypeptide targeting moiety; "L" is a linker (e.g. a bond or a chemical linker group) coupling the PTM and aCLM; and CLM is cereblon E3 ubiquitin ligase binding moiety that binds to cereblon.

In certain embodiments, the compounds as described herein comprise multiple independently selected ULMs, multiple PTMs, multiple chemical linkers or a combination thereof.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising a PTM and a CLM, preferably linked through a linker moiety, as otherwise described herein, wherein the CLM is coupled to the PTM through a linker to target protein that binds to PTM for degradation. Similarly, the PTM can be coupled to CLM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
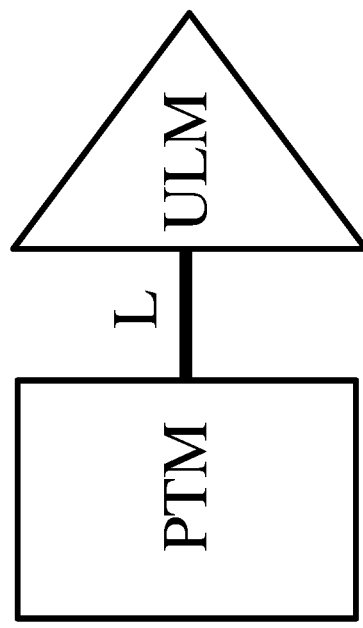
FIGS. 1A and 1B. Illustration of general principle for the heterobifunctional degradative compounds of the present disclosure. (A) Exemplary heterobifunctional degradative compounds comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the heterobifunctional degradative compounds as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 1B:
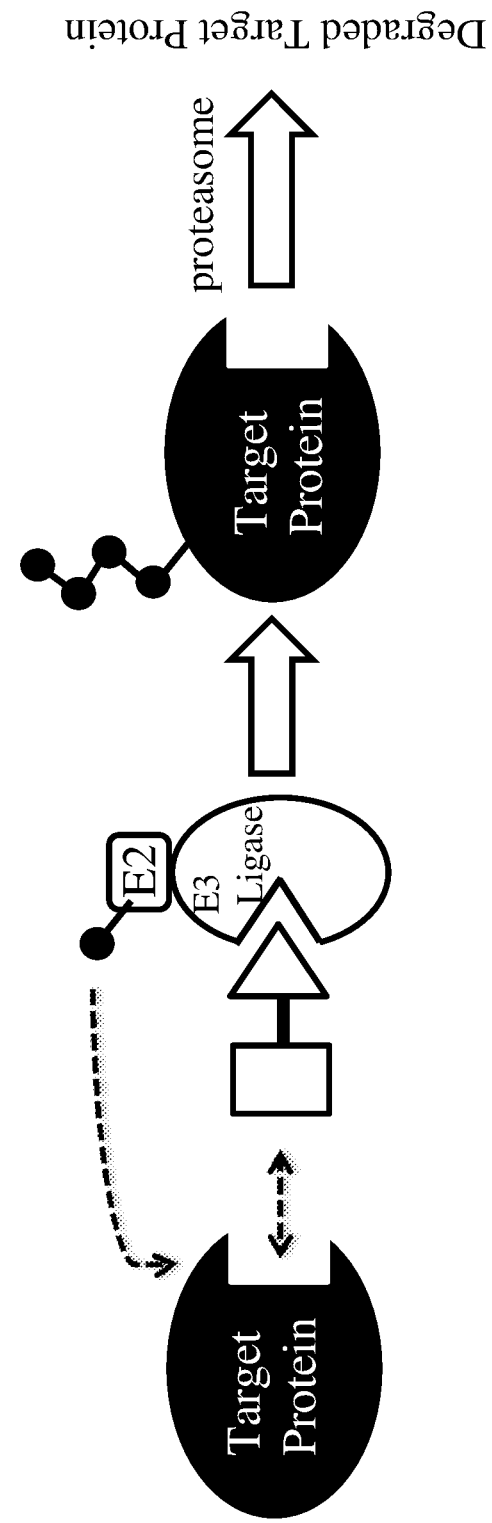

Presently described are compositions and methods that relate to the surprising and unexpected discovery that an E3 ubiquitin ligase protein (e.g., a cereblon E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquitin ligase binding moiety ("ULM") coupled to a protein target binding moiety ("PTM"), which result in the ubiquitination of a chosen target protein, which leads to degradation of the target protein by the proteasome (see FIGS. 1A and 1B). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or bifunctional degradation molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, cereblon an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is a cereblon E3 ubiquitin ligase binding moiety (a "CLM"). In an exemplary embodiment, the ULM is coupled to a target protein binding moiety (PTM) via a chemical linker (L) according to the structure:

$$\text{PTM-L-ULM} \tag{A}$$

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM and CLM are used in their inclusive sense unless the context indicates otherwise. For example, the term ULM is inclusive of all ULMs, including those that bind cereblon (i.e., CLM). Further, the term CLM is inclusive of all cereblon binding moieties.

In another aspect, the present disclosure provides bifunctional or multifunctional compounds useful for regulating protein activity by inducing the degradation of a target protein. In certain embodiments, the compound comprises a CLM coupled, e.g., linked covalently, directly or indirectly, to a moiety that binds a target protein (i.e., a protein targeting moiety or a "PTM"). In certain embodiments, the CLM and PTM are joined or coupled via a chemical linker (L). The CLM binds the cereblon E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-CLM  (B)

In certain embodiments, the bifunctional compound further comprises a chemical linker ("L"). For example, the bifunctional compound can be depicted as:

PTM-L-CLM  (C)

wherein the PTM is a protein/polypeptide targeting moiety, the L is a chemical linker, and the CLM is a cereblon E3 ubiquitin ligase binding moiety.

In certain embodiments, the ULM (e.g., a CLM) shows activity or binds to the E3 ubiquitin ligase (e.g., cereblon E3 ubiquitin ligase) with an $IC_{50}$ of less than about 200 PM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., cereblon) or a combination thereof. In any of the aspects or embodiments described herein, the PTMs and ULMs (e.g., CLM) can be coupled directly or via one or more chemical linkers or a combination thereof. In additional embodiments, where a compound has multiple ULMs, the ULMs can be for the same E3 ubiquitin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as a CLM and/or a CLM'.

In additional embodiments, the description provides the compounds as described herein including their enantiomers, diastereomers, solvates and polymorphs, including pharmaceutically acceptable salt forms thereof, e.g., acid and base salt forms.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$ or —$(CH_2CH_2O)_m$ group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —$N(R_1)$—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$ (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (monocyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

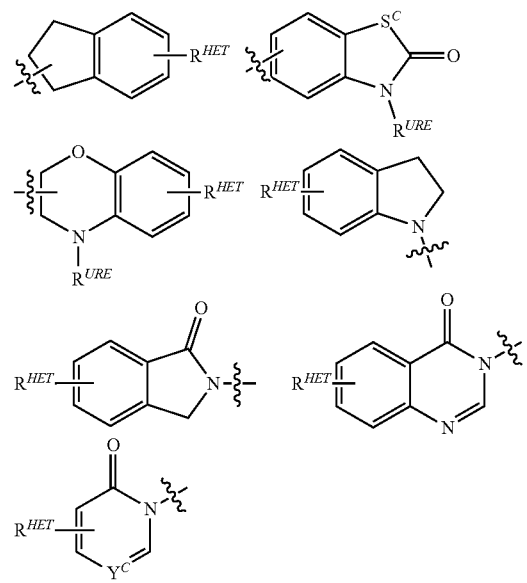

wherein:
$S^c$ is $CHR^{SS}$, $NR^{URE}$, or O;
$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

$R^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (═O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

Exemplary CLMs

Neo-Imide Compounds

In one aspect the description provides compounds useful for binding and/or inhibiting cereblon. In certain embodiments, the compound is selected from the group consisting of chemical structures:

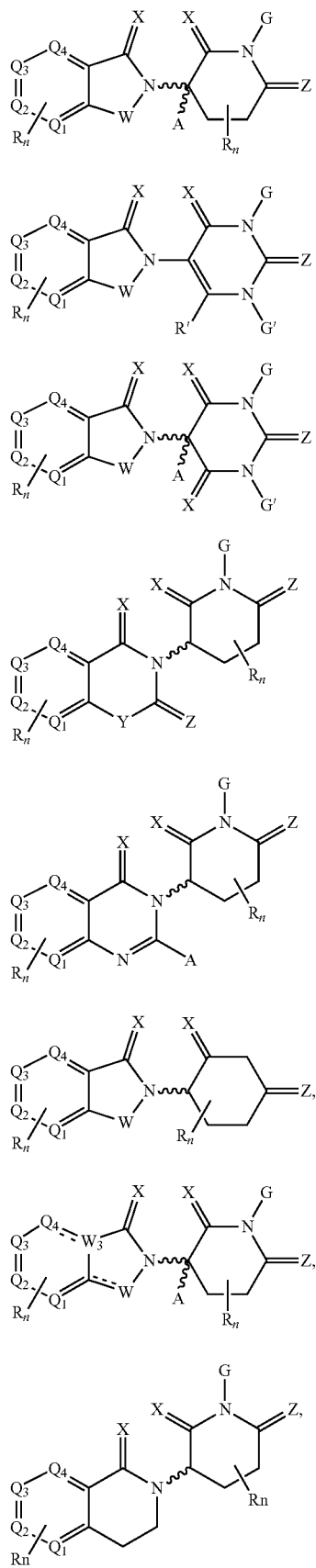

wherein:
W of Formulas (a) through (f) is selected from the group $CH_2$, O, CHR, C=O, $SO_2$, NH, N, optionally substituted cyclopropyl group, optionally substituted cyclobutyl group, and N-alkyl;

$W_3$ is C or N;

X of Formulas (a) through (f) is independently selected from the group absent, O, S and $CH_2$;

Y of Formulas (a) through (f) is independently selected from the group $CH_2$, —C=CR', NH, N-alkyl, N-aryl, N-heteroaryl, N-cycloalkyl, N-heterocyclyl, O, and S;

Z of Formulas (a) through (f) is independently selected from the group absent, O, S, and $CH_2$ except that both X and Z cannot be $CH_2$ or absent;

G and G' of Formulas (a) through (f) are independently selected from the group H, optionally substituted linear or branched alkyl, OH, R'OCOOR, R'OCONRR", $CH_2$-heterocyclyl optionally substituted with R', and benzyl optionally substituted with R';

each of Q1-Q4 of Formulas (a) through (f) independently represent a carbon C or N substituted with a group independently selected from H, R, N or N-oxide; or each of Q1-Q4 of Formulas (a) through (f) independently represent a N, CH, or CR;

A of Formulas (a) through (f) is selected from the group H, optionally substituted linear or branched alkyl, cycloalkyl, Cl and F;

n of Formulas (a) through (f) represent an integer from 1 to 10 (e.g., 1-4, 1, 2, 3, 4, 5, 6, 7, 8, 9, or 10);

R of Formulas (a) through (f) comprises, but is not limited to: H, —C(=O)R' (e.g., a carboxy group), —CONR'R" (e.g., an amide group), —OR' (e.g., OH or $OCH_3$), —NR'R" (e.g., an amine group), —SR', —$SO_2$R', —$SO_2$NR'R", —CR'R"—, —CR'NR'R"—, (—CR'O)$_n$'R", optionally substituted heterocyclyl, optionally substituted aryl, (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted heteroaryl, optionally substituted alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

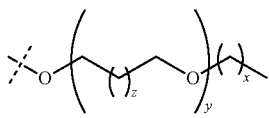

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

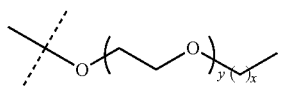

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ and —OCF$_3$;

each of x, y, and z are independently 0, 1, 2, 3, 4, 5, or 6;

R' and R" of Formulas (a) through (f) are each independently selected from H, optionally substituted linear or branched alkyl (e.g., methyl or ethyl), optionally substituted cycloalkyl, optionally substituted aryl, optionally substituted heteroaryl, optionally substituted heterocyclic, —C(=O)A, optionally substituted heterocyclyl;

n' of Formulas (a) through (f) is an integer from 1-10 (e.g. 1-4, 1, 2, 3, 4, 5, 6, 7, 8, 9, or 10);

⁓ represents a single bond or a double bond; and

∼ of Formulas (a) through (f) represents a bond that may be stereospecific ((R) or (S)) or non-stereospecific.

Exemplary CLMs

In any of the compounds described herein, the CLM comprises a chemical structure selected from the group:

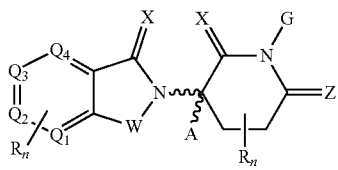
(a1)

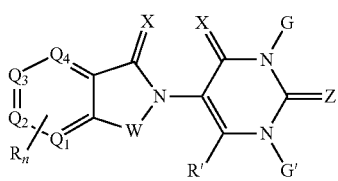
(b)

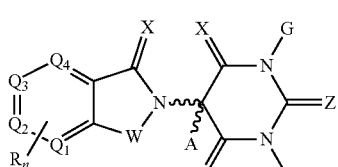
(c)

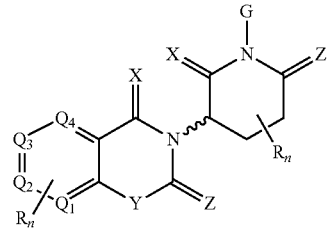
(d2)

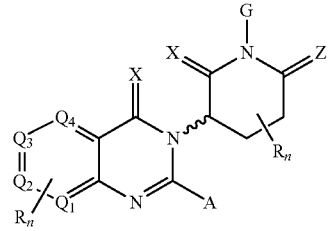
(e)

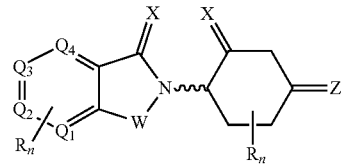
(f)

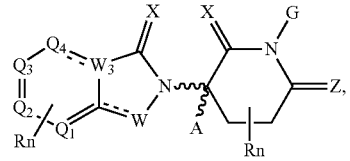
(a2)

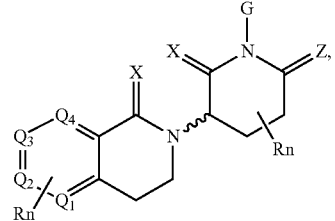
(d2)

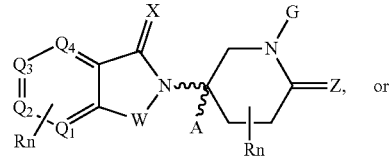
(a3)

or

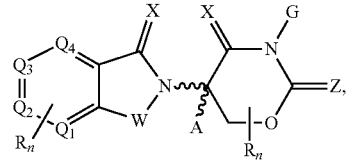
(a4)

wherein:

W of Formulas (a) through (f) is selected from the group CH$_2$, O, CHR, C=O, SO$_2$, NH, N, optionally substituted cyclopropyl group, optionally substituted cyclobutyl group, and N-alkyl;

W$_3$ is C or N;

X of Formulas (a) through (f) is independently selected from the group absent, O, S, and CH$_2$;

Y of Formulas (a) through (f) is independently selected from the group $CH_2$, —C=CR', NH, N-alkyl, N-aryl, N-hetaryl, N-cycloalkyl, N-heterocyclyl, O, and S;

Z of Formulas (a) through (f) is independently selected from the group absent, O, S, and $CH_2$ except that both X and Z cannot be $CH_2$ or absent;

G and G' of Formulas (a) through (f) are independently selected from the group H, optionally substituted linear or branched alkyl, OH, R'OCOOR, R'OCONRR", $CH_2$-heterocyclyl optionally substituted with R', and benzyl optionally substituted with R';

each of Q1-Q4 of Formulas (a) through (f) independently represent a carbon C or N substituted with a group independently selected from H, R, N or N-oxide; or each of Q1-Q4 of Formulas (a) through (f) independently represent a N, CH, or CR;

A of Formulas (a) through (f) is selected from the group H, optionally substituted linear or branched alkyl, cycloalkyl, Cl and F;

n of Formulas (a) through (f) represent an integer from 1 to 10 (e.g., 1-4, 1, 2, 3, 4, 5, 6, 7, 8, 9, or 10);

R of Formulas (a) through (f) comprises, but is not limited to: H, —C(=O)R' (e.g., a carboxy group), —CONR'R" (e.g., an amide group), —OR' (e.g., OH), —NR'R" (e.g. an amine group), —SR', —SO$_2$R', —SO$_2$NR'R", —CR'R"—, —CR'NR'R"—, (—CR'O)$_n$'R", optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted hetaryl, -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

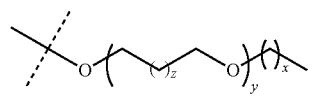

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

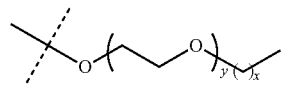

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF5 and —OCF3;

each of x, y, and z are independently 0, 1, 2, 3, 4, 5, or 6;

R' and R" of Formulas (a) through (f) are each independently selected from a bond, H, optionally substituted linear or branched alkyl, optionally substituted cycloalkyl, optionally substituted aryl, optionally substituted heteroaryl, optionally substituted heterocyclic, —C(=O)A, optionally substituted heterocyclyl;

n' of Formulas (a) through (f) is an integer from 1-10 (e.g., 1-4, 1, 2, 3, 4, 5, 6, 7, 8, 9, or 10); and ⌇⌇⌇ of Formulas (a) through (f) represents a bond that may be stereospecific ((R) or (S)) or non-stereospecific.

In any aspect or embodiment described herein, the CLM or ULM comprises a chemical structure selected from the group

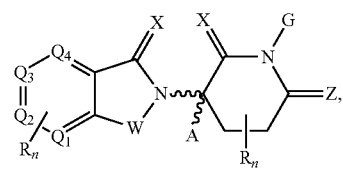

wherein:

W is selected from the group consisting of $CH_2$, O, CHR, C=O, NH, and N;

each X is independently selected from the group consisting of absent, O, S, and $CH_2$;

Z is selected from the group consisting of absent, O, S, and $CH_2$;

G is selected from the group consisting of H, methyl, OH;

each of $Q_1$, $Q_2$, $Q_3$, and $Q_4$ independently represent a N or a C substituted with a group independently selected from H, R, N or N-oxide; or each of $Q_1$, $Q_2$, $Q_3$, and $Q_4$ independently represent a N, CH, or CR;

A is independently selected from the group H, unsubstituted or substituted linear or branched alkyl, cycloalkyl, Cl and F;

n is an integer from 1 to 4 (e.g., 1 or 2, 1-3, 1, 2, 3, or 4);

R comprises bond, H, —OR', —NR'R", —CR'R"—, -unsubstituted or substituted linear or branched $C_1$-$C_6$ linear or branched alkyl (e.g. $C_1$-$C_3$ alkyl and/or optionally substituted with one or more halogen), unsubstituted or substituted alkoxyl group (e.g., a methoxy, ethoxy, butoxy, propoxy, pentoxy, or hexoxy; wherein the alkoxyl optionally substituted with one or more halogen, $C_1$-$C_3$ alkyl, haloalky, or $C_1$-$C_3$ fluoroalkyl), optionally substituted 4-6 membered cycloalkyl, optionally substituted 4-6 membered heterocycloalkyl, —Cl, —F, —Br, —I, —CF$_3$, —CN, and —NO$_2$, wherein one R is covalently joined to the L;

R' and R" are independently selected from the group consisting of bond H, and substituted or unsubstituted C1-C4 alkyl (e.g., methyl or ethyl);

⌇⌇⌇ represents a bond that may be stereospecific ((R) or (S)) or non-stereospecific.

In any aspect or embodiment described herein, the CLM or ULM comprises a chemical structure selected from the group:

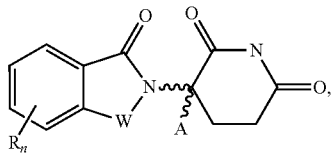

Formula (g)

wherein:
W of Formula (g) is selected from the group CH$_2$, O, C=O, NH, and N-alkyl;
A of Formula (g) is a H, methyl, or optionally substituted linear or branched alkyl;
n is an integer from 1 to 4;
R of Formula (g) is independently selected from a H, O, OH, N, NH, NH$_2$, methyl, optionally substituted linear or branched alkyl (e.g., optionally substituted linear or branched C1-C6 alkyl), C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy), wherein one R or W is optionally modified to be covalently joined to a PTM, a chemical linker group (L), a ULM, CLM (or CLM'), or combination thereof; and
〜 of Formula (g) represents a bond that may be stereospecific ((R) or (S)) or non-stereospecific.

In any aspect or embodiment described herein, the CLM or ULM has the structure:

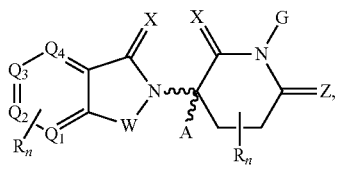

wherein:
W is CH$_2$, O, CHR (e.g., CH(CH$_3$)), C=O, NH, or N;
each X is independently selected from absent, O, S, and CH$_2$;
Z is O, S, or CH$_2$;
G is H, methyl, or OH;
each of Q$_1$, Q$_2$, Q$_3$, and Q$_4$ independently represent a N or a C substituted with an H or an R;
A is H, unsubstituted or substituted linear or branched alkyl, Cl, or F;
n is an integer from 1 to 4 (e.g., 1 or 2, 1-3, 1, 2, 3, or 4);
each R is independently bond, H, —OR', —NR'R", —CR'R"—, -unsubstituted or substituted linear or branched C1-C6 linear or branched alkyl (e.g. C1-C3 alkyl and/or optionally substituted with one or more halogen), unsubstituted or substituted alkoxyl group (e.g., a methoxy, ethoxy, butoxy, propoxy, pentoxy, or hexoxy; wherein the alkoxyl optionally substituted with one or more halogen, C1-C3 alkyl, haloalky, or C1-C3 fluoroalkyl), optionally substituted 4-6 membered cycloalkyl, optionally substituted 4-6 membered heterocycloalkyl, —Cl, —F, —Br, —I, —CF$_3$, —CN, or —NO$_2$, wherein one R is covalently joined to the L;
R' and R" are each independently selected from bond H, and substituted or unsubstituted C1-C4 alkyl (e.g., methyl or ethyl); and
〜 represents a bond that may be stereospecific ((R) or (S)) or non-stereospecific.

In any aspect or embodiment described herein, the CLM or ULM has the structure:

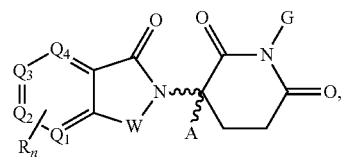

wherein:
W is CH$_2$, O, CH(C$_{1-3}$ alkyl) (e.g., CH(CH$_3$)), C=O;
G is H, methyl, or OH;
each of Q$_1$, Q$_2$, Q$_3$, and Q$_4$ independently represent N, CH, or CR;
A is H, unsubstituted or substituted linear or branched alkyl, Cl, or F;
n is an integer from 1 to 4;
R is bond, H, —OR', —NR'R", —CR'R"—, -unsubstituted or substituted linear or branched C1-C6 linear or branched alkyl (e.g. C1-C3 alkyl and/or optionally substituted with one or more halogen), unsubstituted or substituted alkoxyl group (e.g., a methoxy, ethoxy, butoxy, propoxy, pentoxy, or hexoxy; wherein the alkoxyl optionally substituted with one or more halogen, C1-C3 alkyl, haloalky, or C1-C3 fluoroalkyl), optionally substituted 4-6 membered cycloalkyl, optionally substituted 4-6 membered heterocycloalkyl, —Cl, —F, —Br, —I, —CF$_3$, —CN, or —NO$_2$, wherein one R is covalently joined to the L;
R' and R" are each independently selected from bond H, and substituted or unsubstituted C1-C4 alkyl (e.g., methyl or ethyl); and
〜 represents a bond that may be stereospecific ((R) or (S)) or non-stereospecific.

In any aspect or embodiment described herein, R is selected from: O, OH, N, NH, NH$_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy).

In any aspect or embodiment described herein, at least one R (e.g. an R group selected from the following O, OH, N, NH, NH$_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) or W is modified to be covalently joined to a PTM, a chemical linker group (L), a ULM, a CLM' (e.g., CLM' is an additional CLM that has the same or different structure as a first CLM), or a combination thereof In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

In any of the aspects or embodiments described herein, R$_n$ comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, on the aryl or heteroaryl of the CLM, and optionally, one of which is modified to be covalently joined to a PTM, a chemical linker group (L), a ULM, CLM (or CLM') or combination thereof.

More specifically, non-limiting examples of CLMs include those shown below as well as those "hybrid" molecules that arise from the combination of 1 or more of the different features shown in the molecules below.
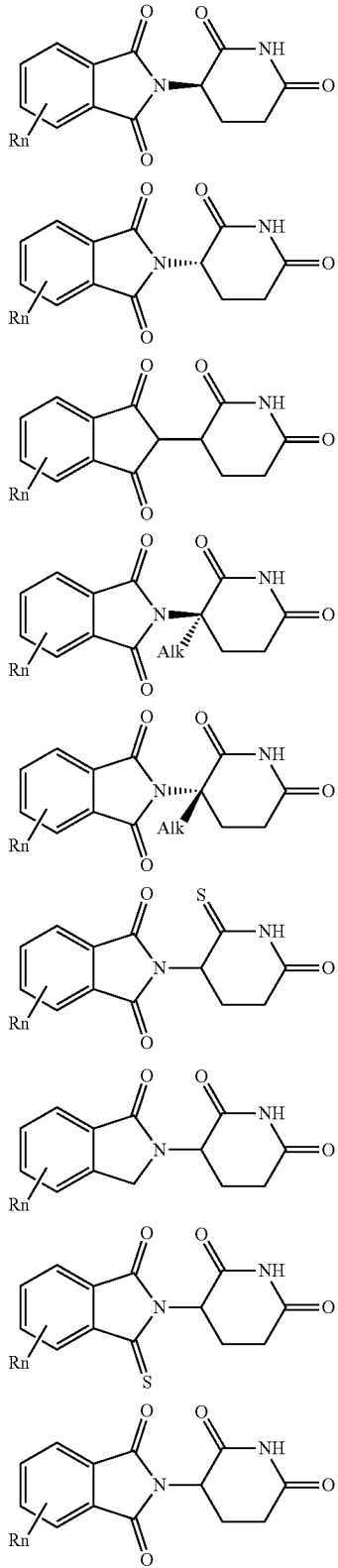
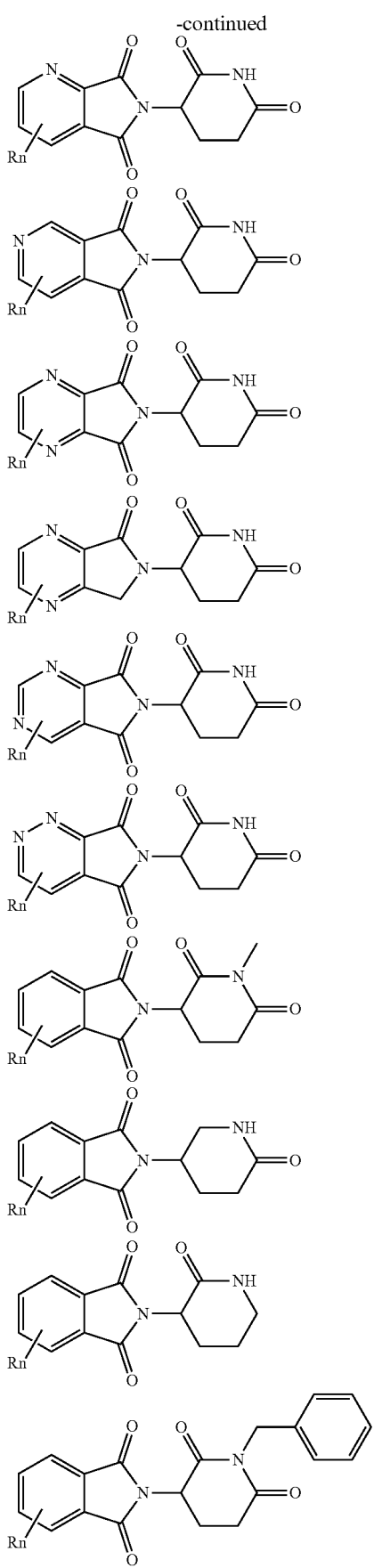

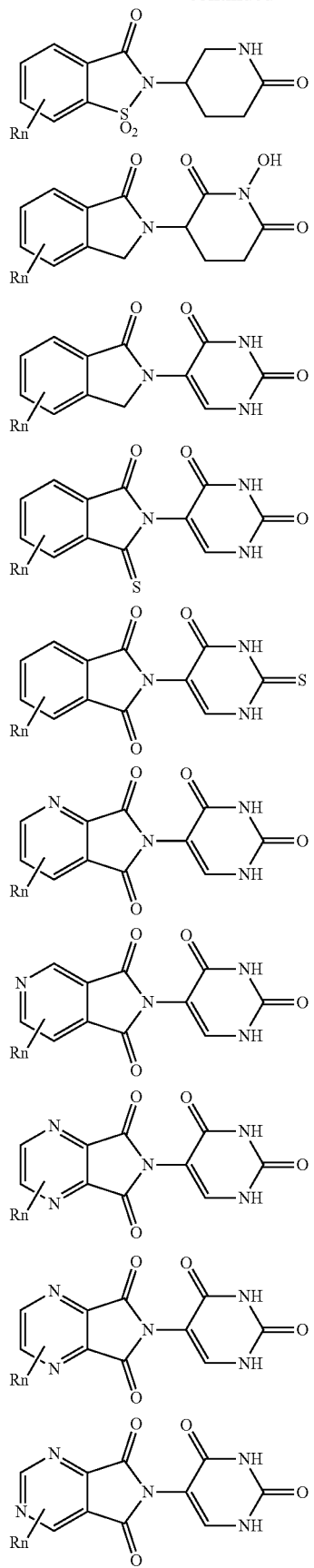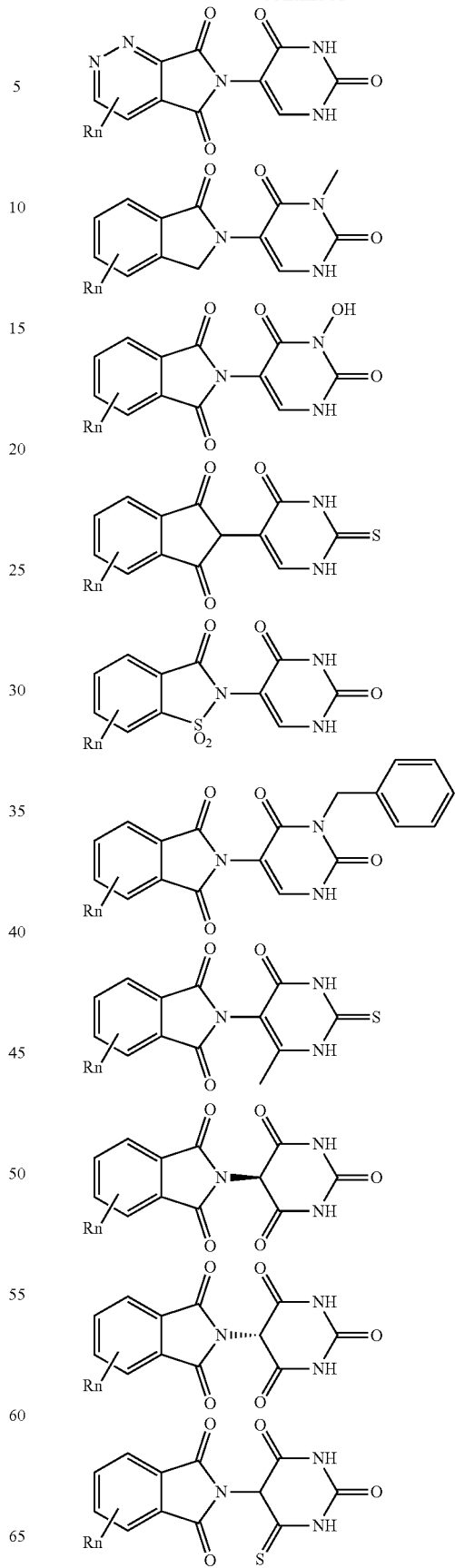

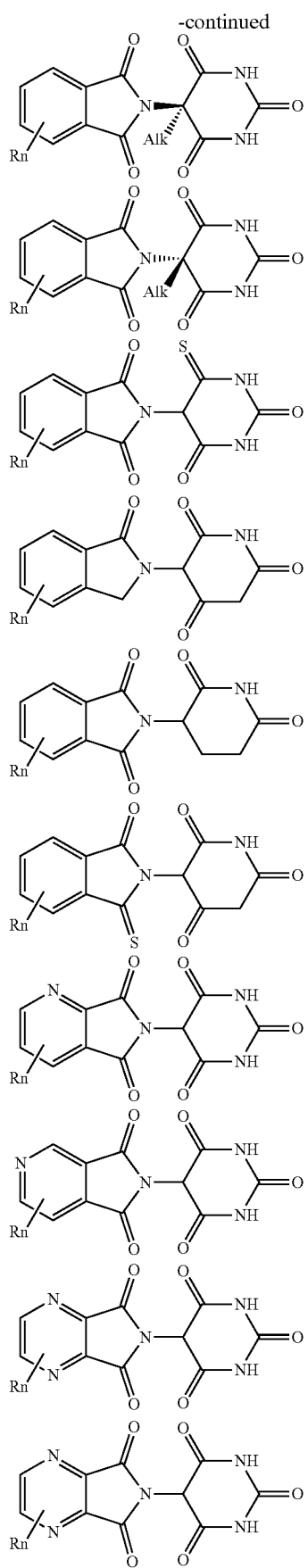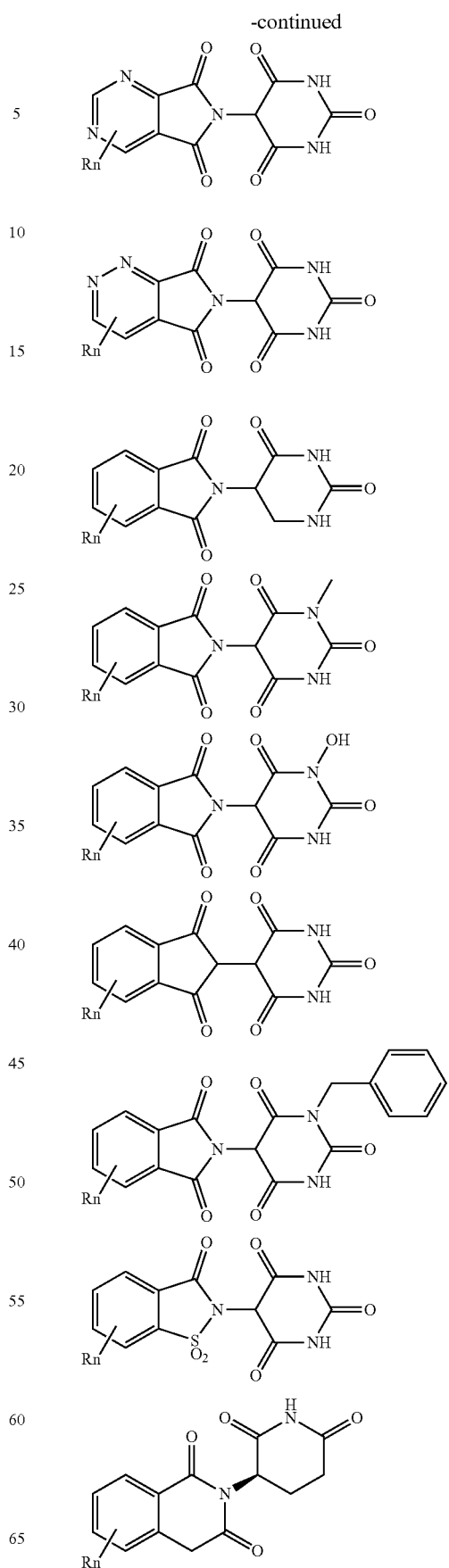

31
-continued
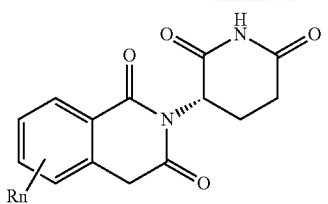
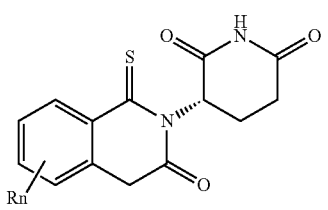
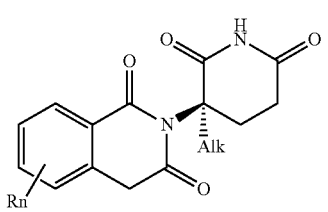
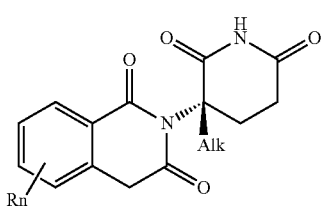
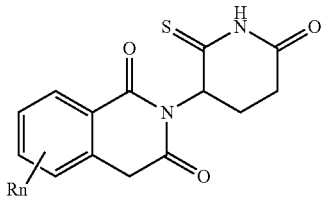
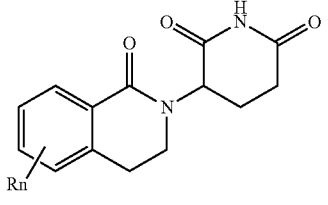
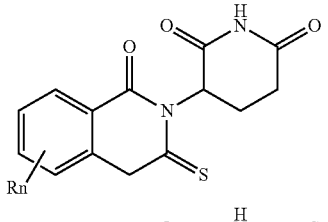
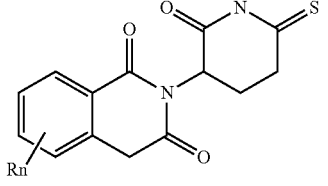
32
-continued
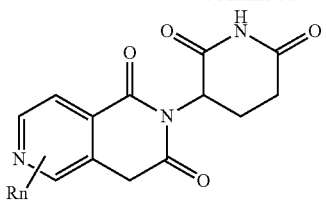
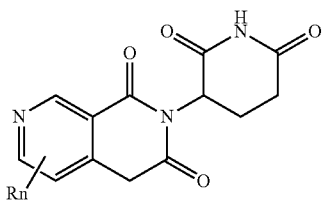
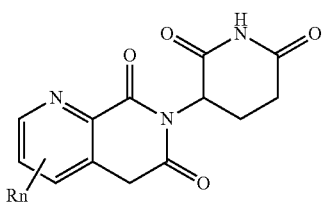
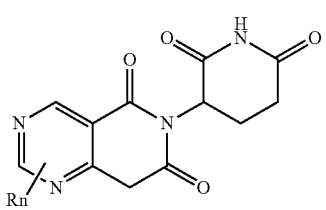
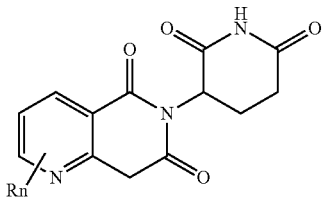
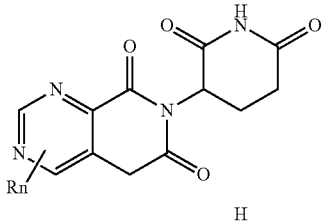
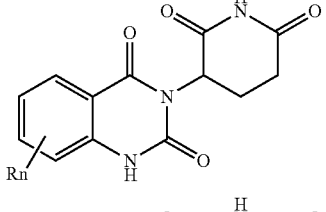
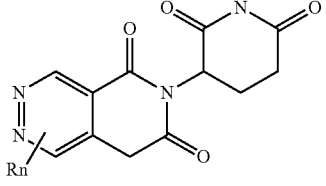

-continued
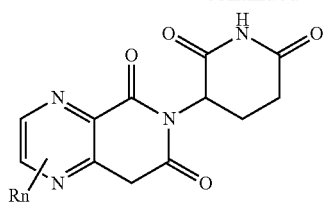
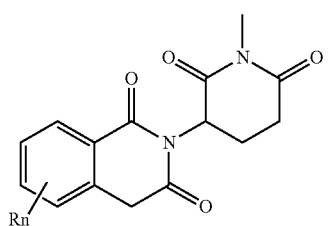
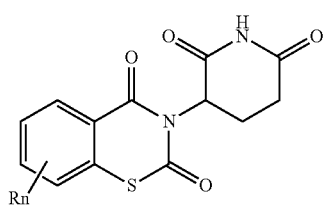
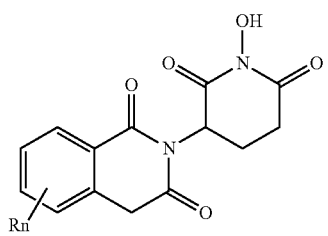
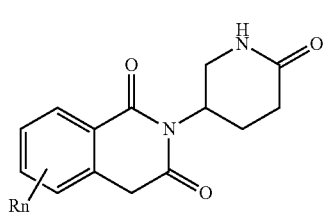
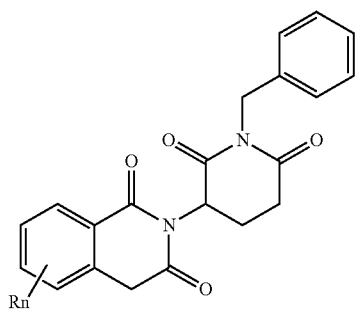
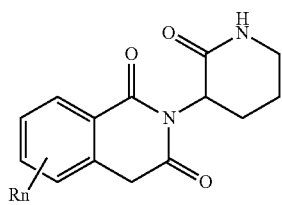
-continued
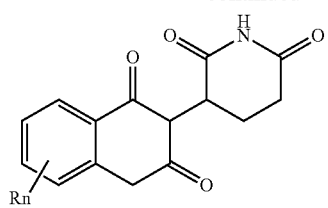
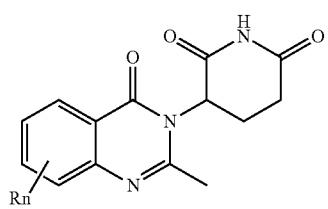
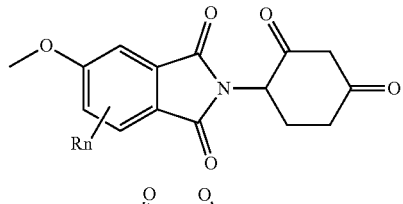
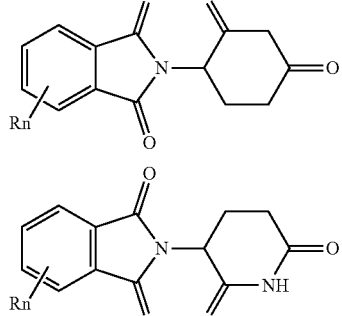
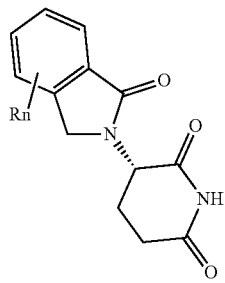
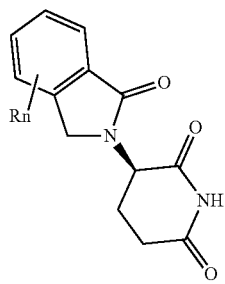
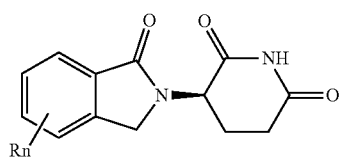

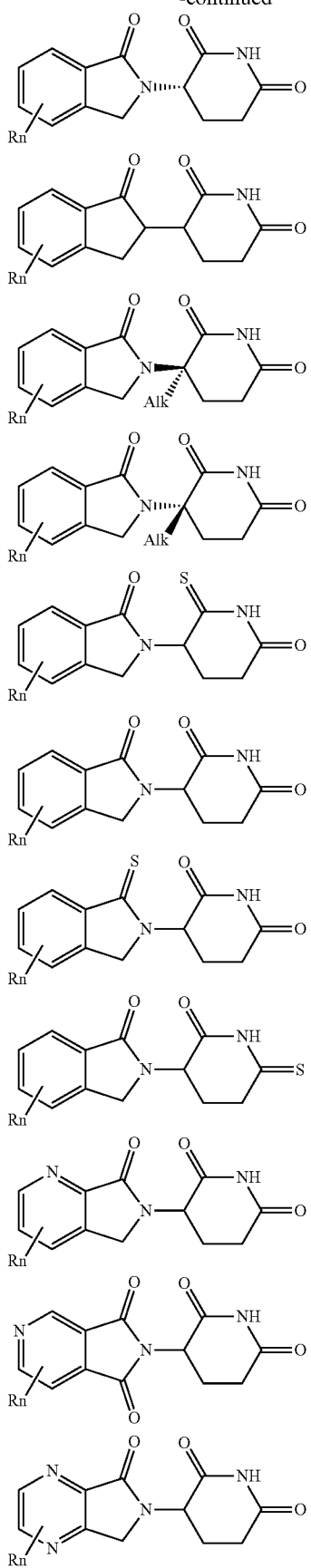
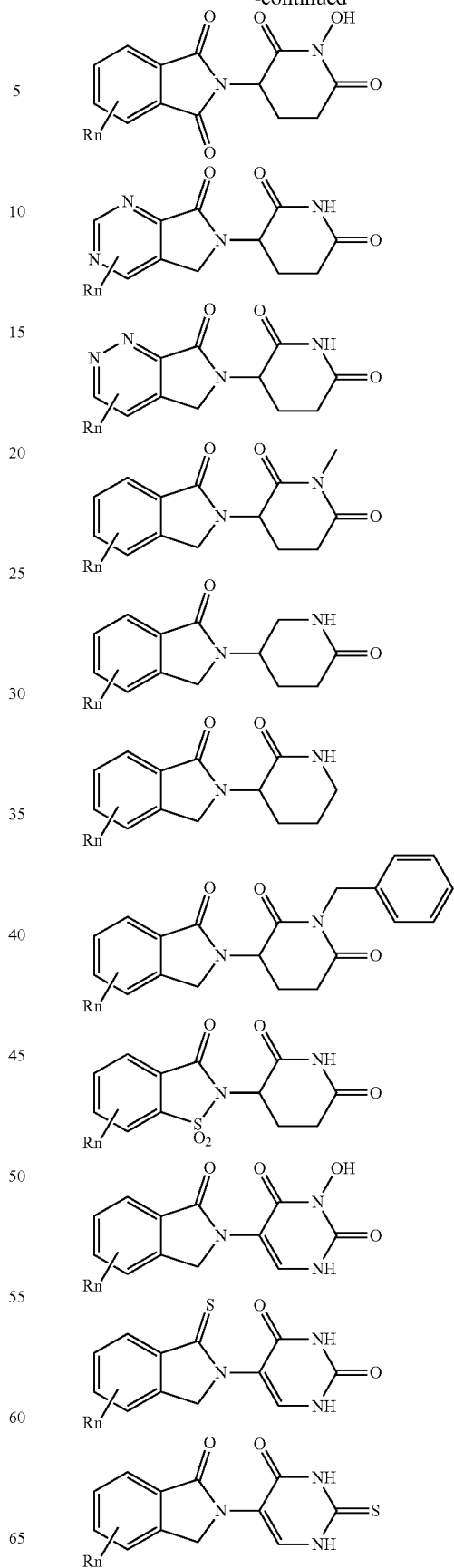

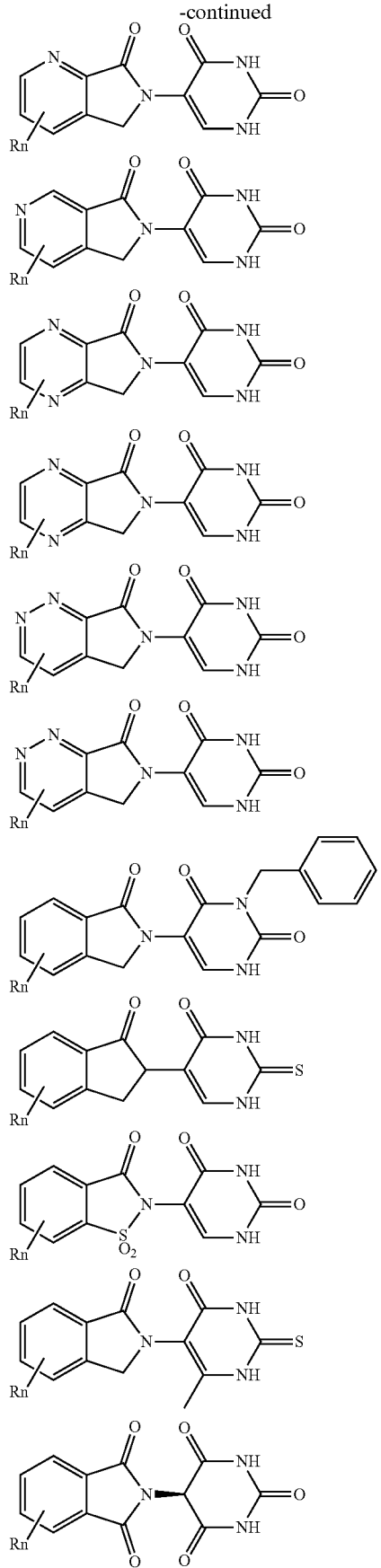
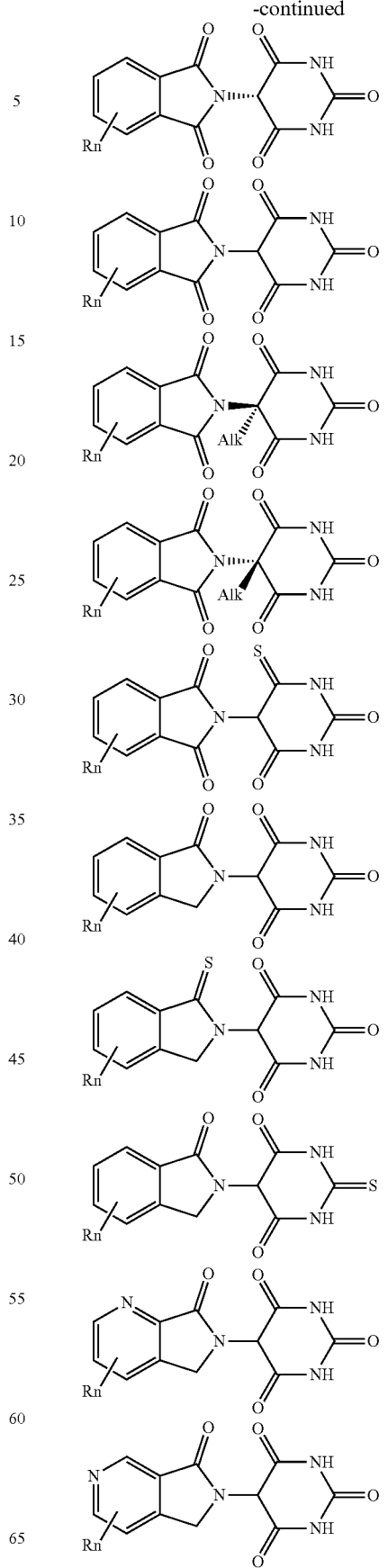

-continued
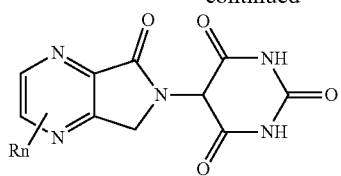
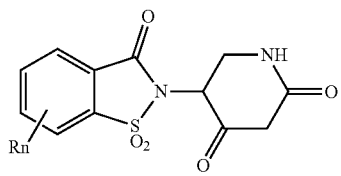
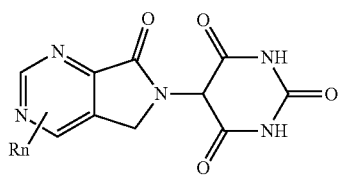
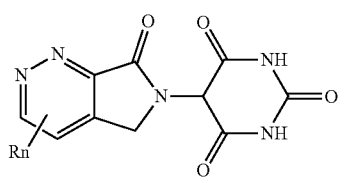
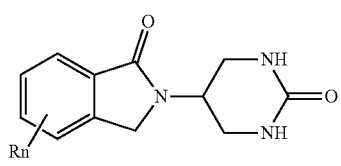
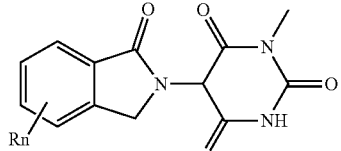
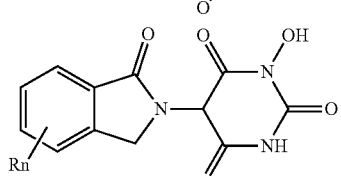
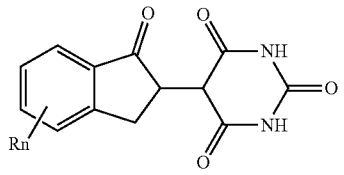
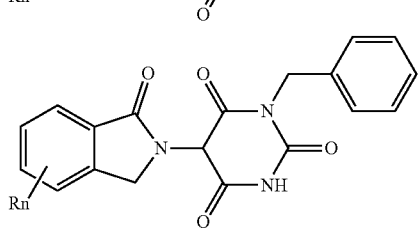
-continued
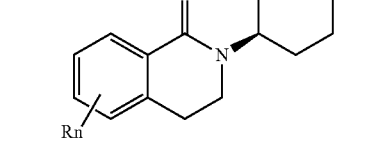
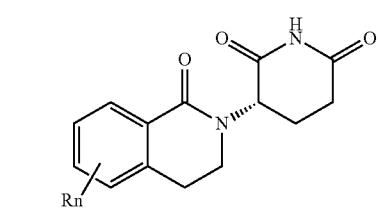
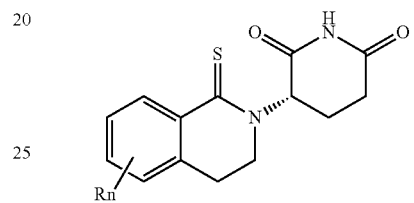
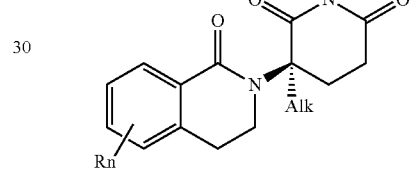
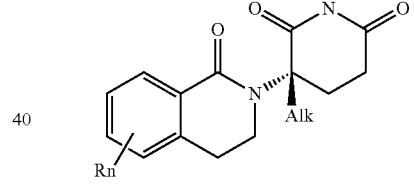
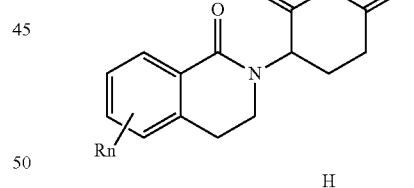
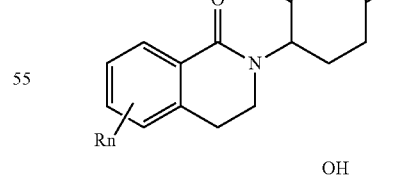
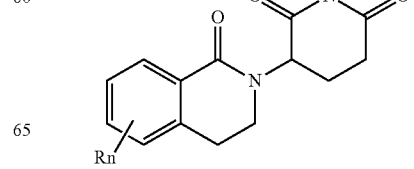

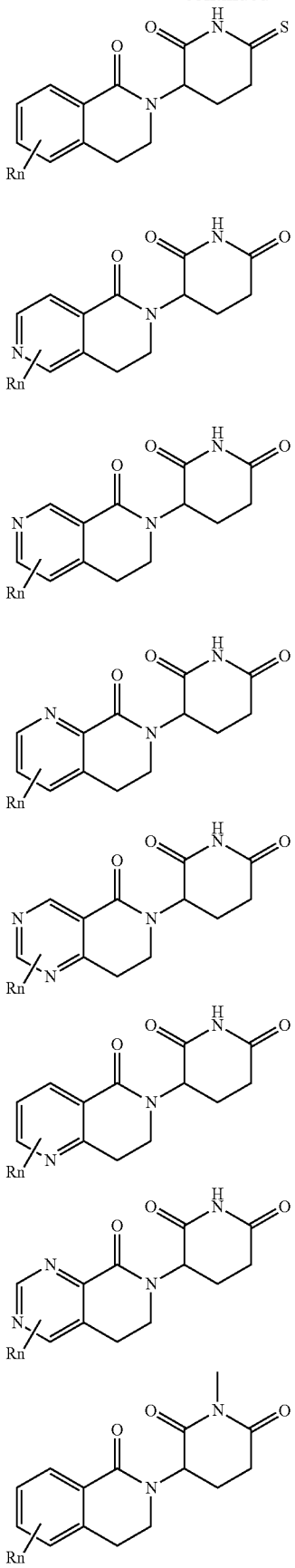
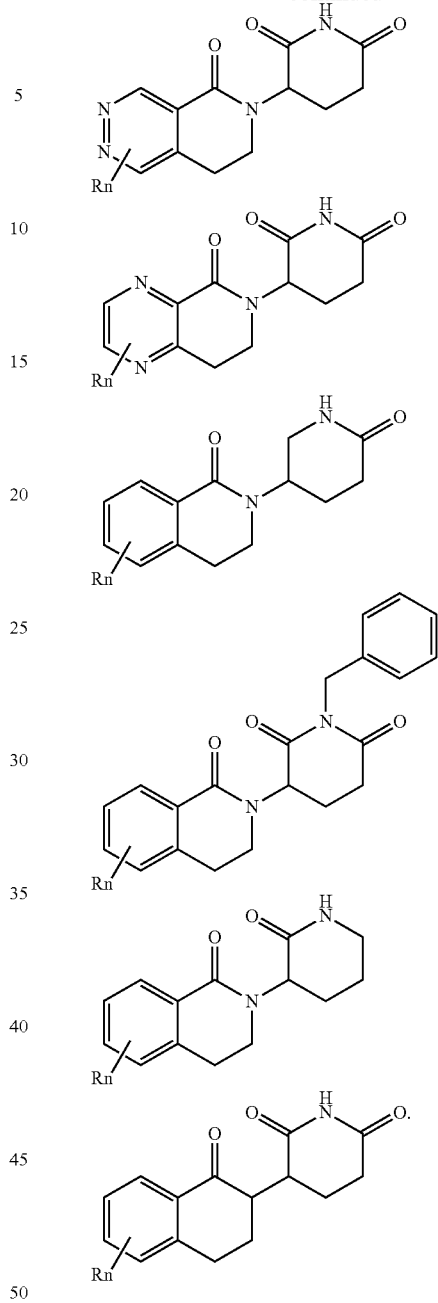

In any of the embodiments described herein, the W, $R^1$, $R^2$, $Q_1$, $Q_2$, $Q_3$, $Q_4$, and Rn can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn can independently be covalently coupled to a linker and/or a linker to which is attached one or more PTM, ULM, ULM', CLM or CLM' groups.

In any aspect or embodiment described herein, $R_n$ is modified to be covalently joined to the linker group (L), a PTM, a ULM, a second CLM having the same chemical structure as the CLM, a CLM', a second linker, or any multiple or combination thereof.

In certain cases, "CLM" can be imides that bind to cereblon E3 ligase. These imides and linker attachment point can be but not limited to the following structures:
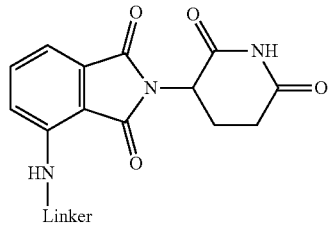
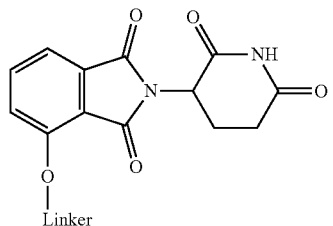
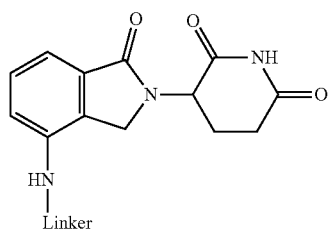
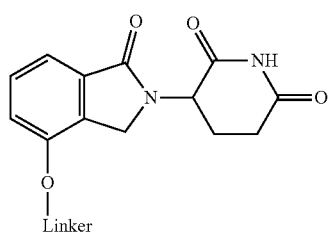
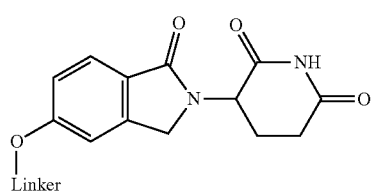
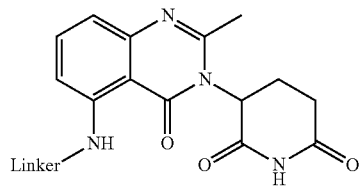
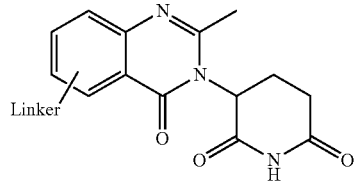
-continued
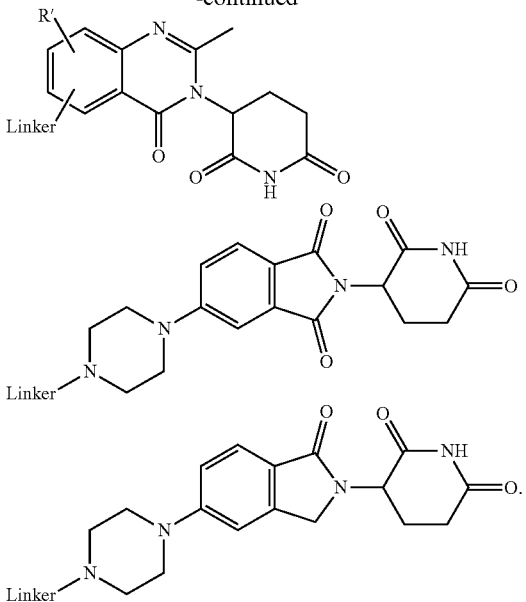
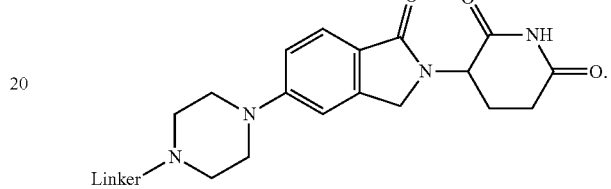
In any aspect or embodiment described herein, the CLM is selected from:
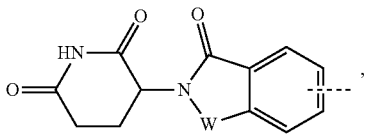
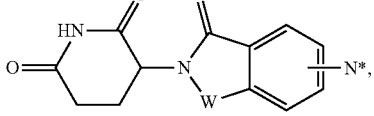
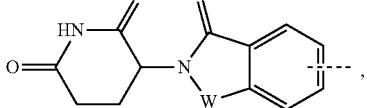
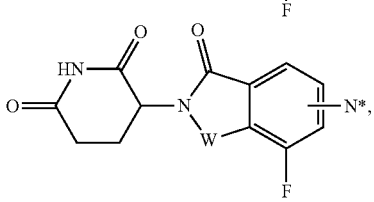
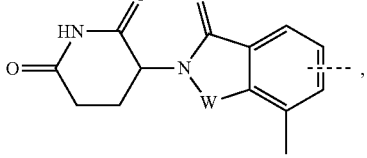
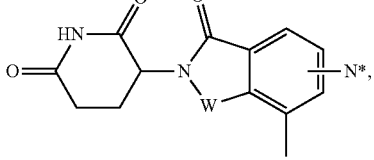

-continued
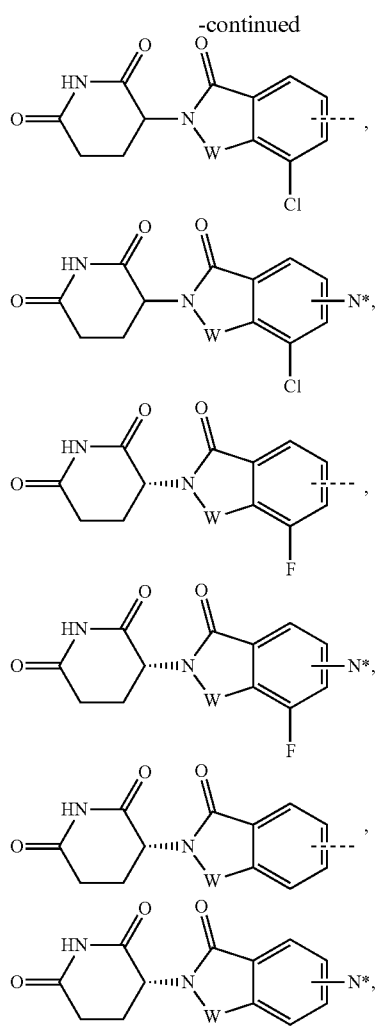
wherein:
- ⸺ of the CLM indicates the point of attachment with the L; and
- N* is a nitrogen atom that is shared with the chemical linker group.
In any aspect or embodiment described herein, the CLM is selected from:
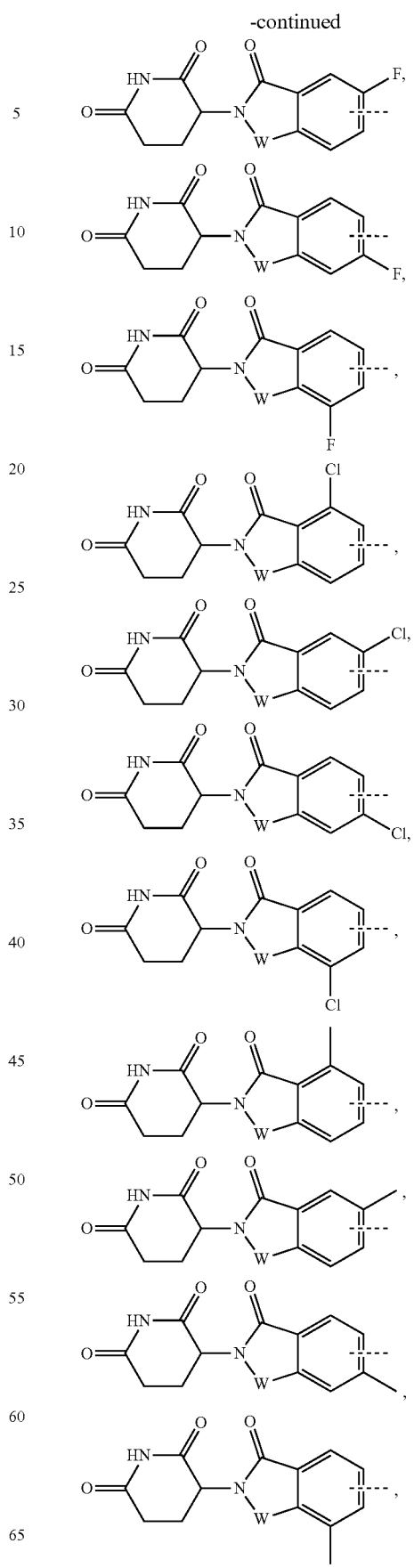

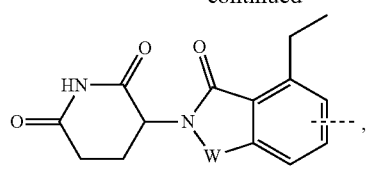,
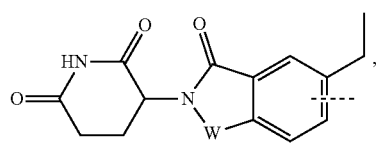,
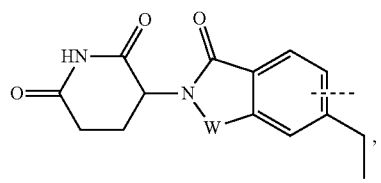,
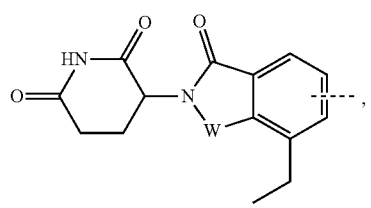,
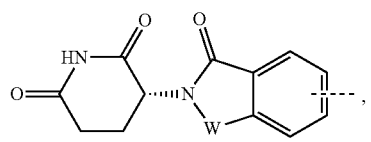,
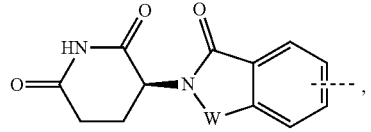,
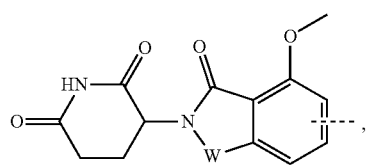,
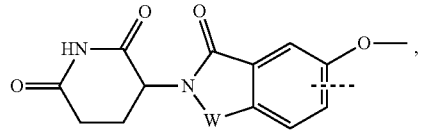,
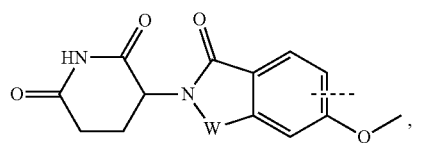,
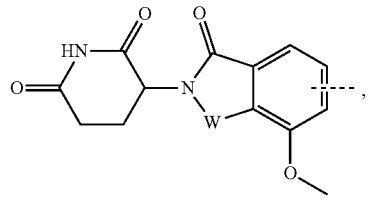,
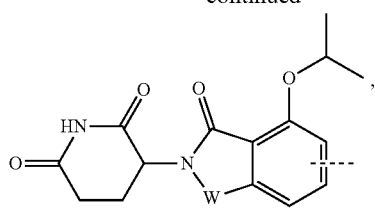,
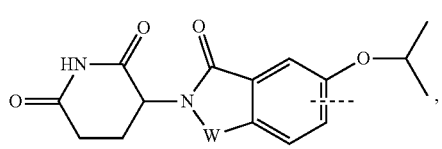,
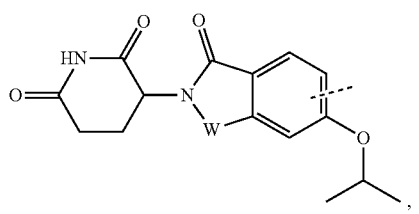,
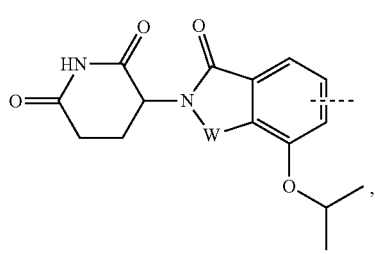,
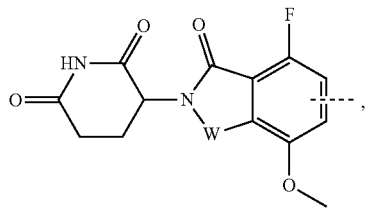,
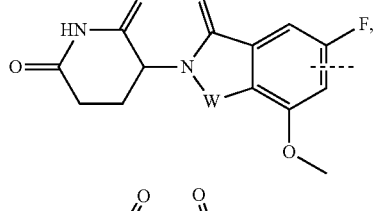,
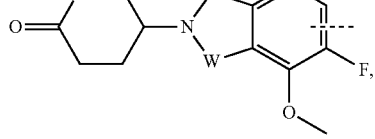,
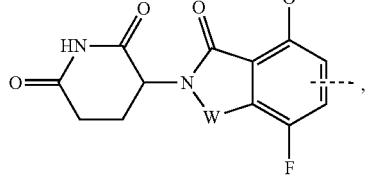,

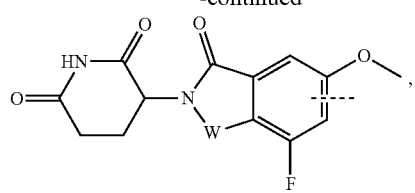
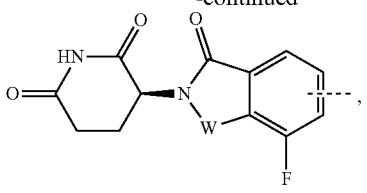

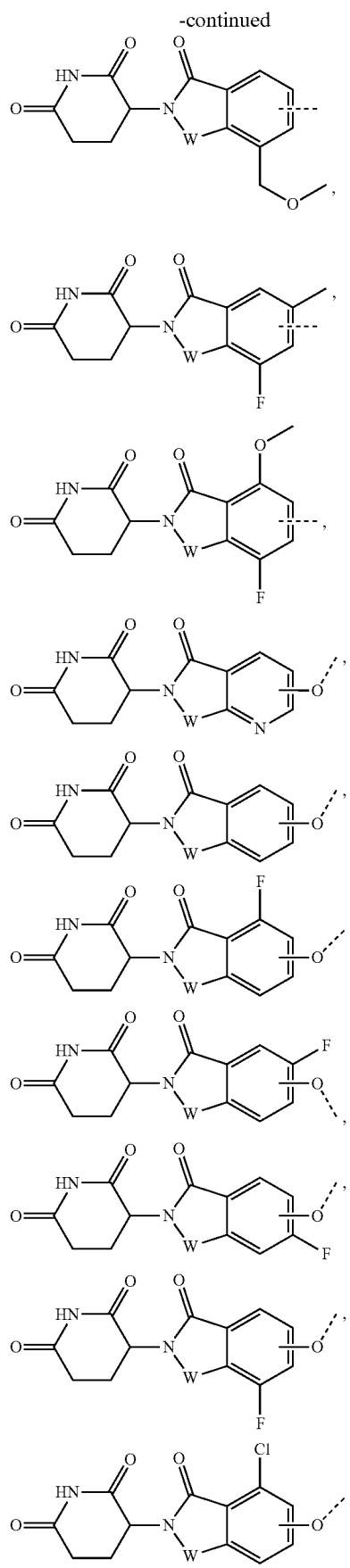
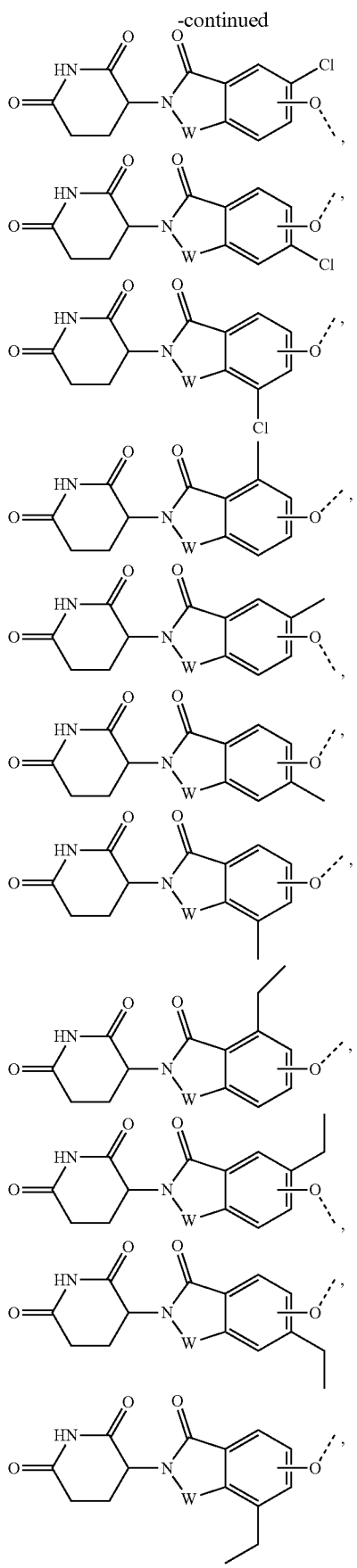

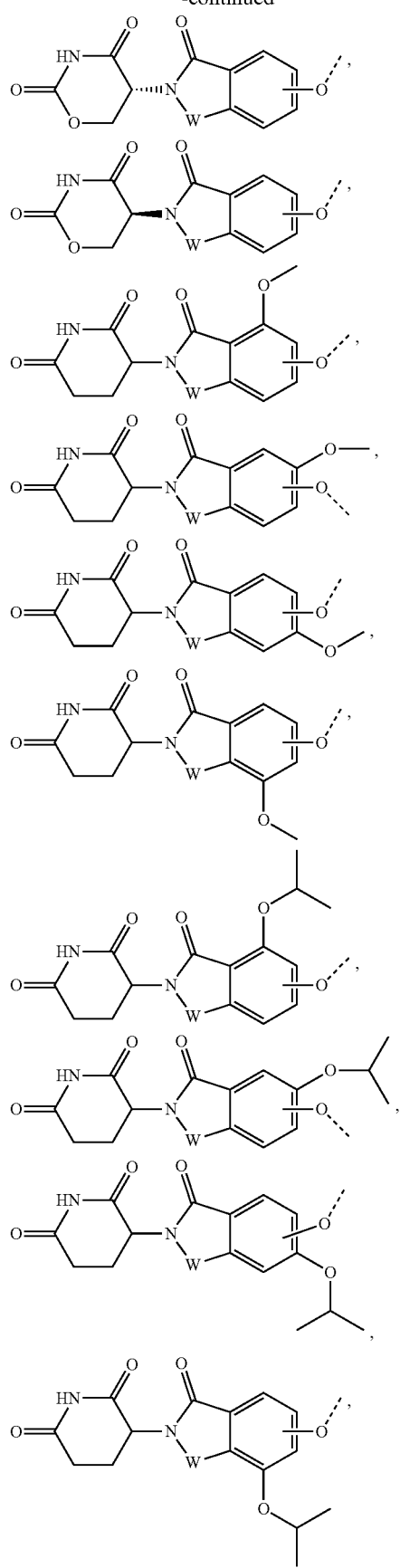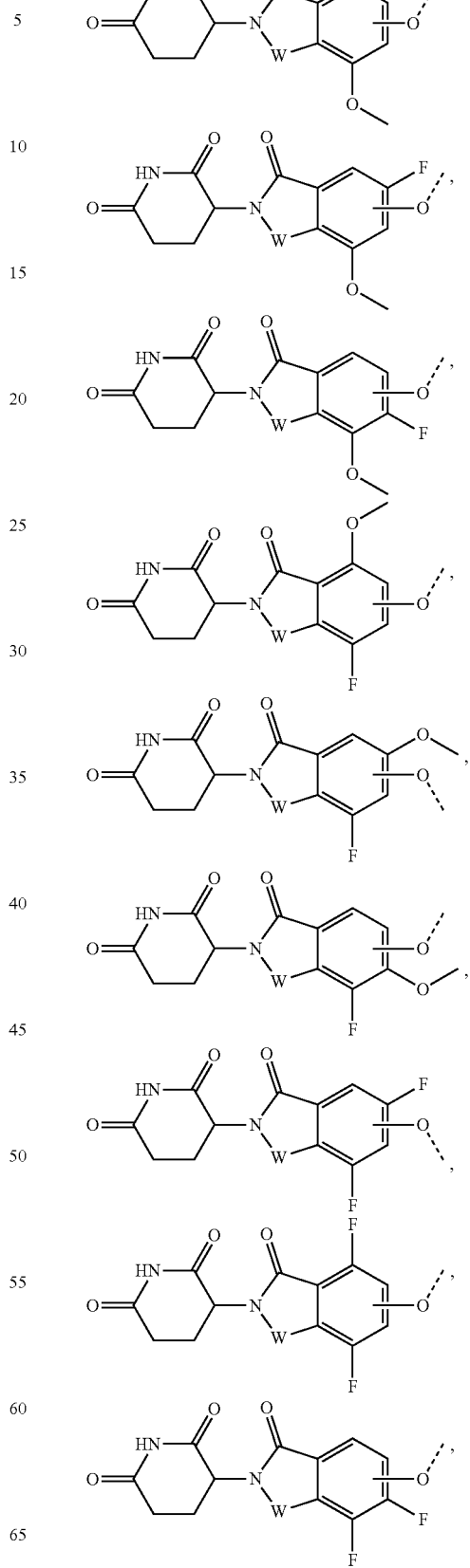

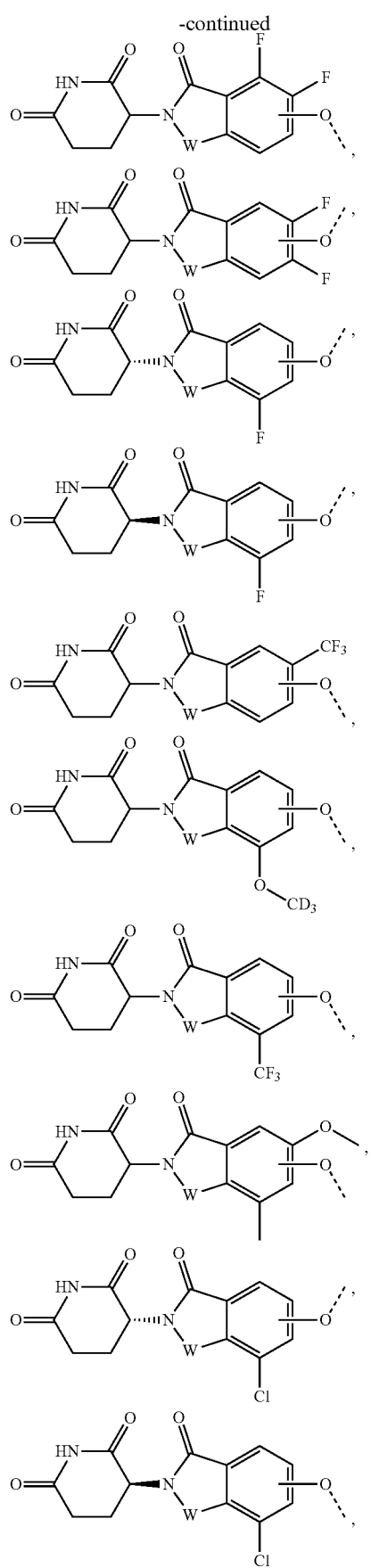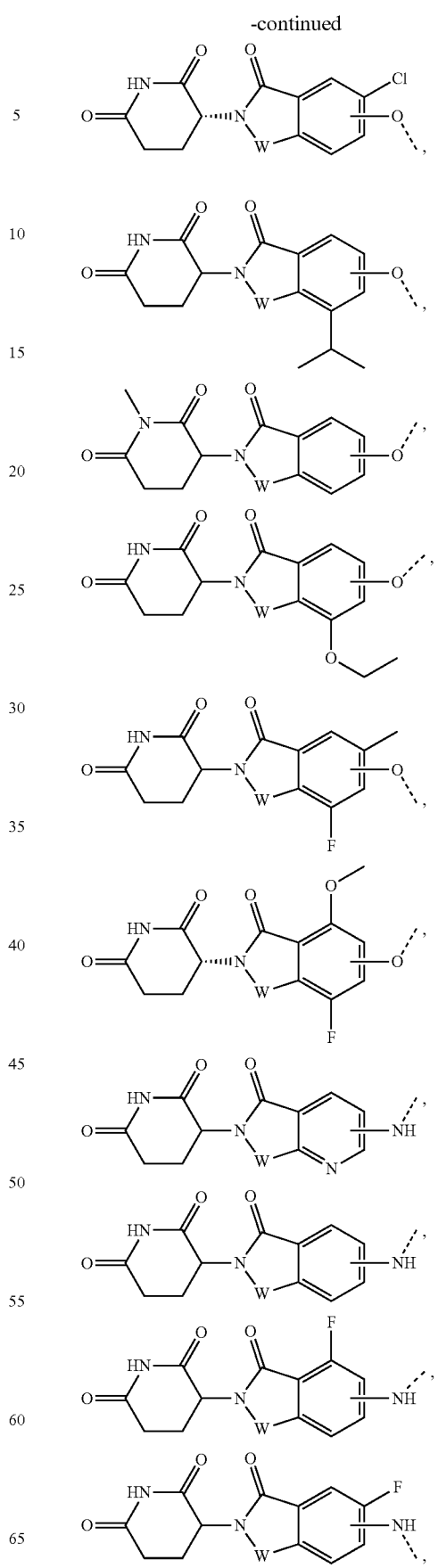

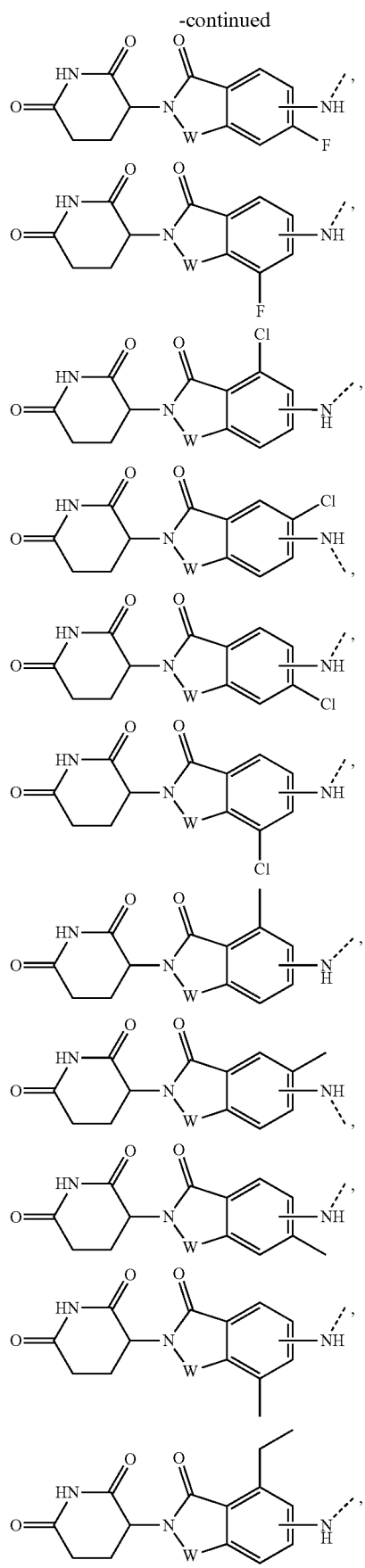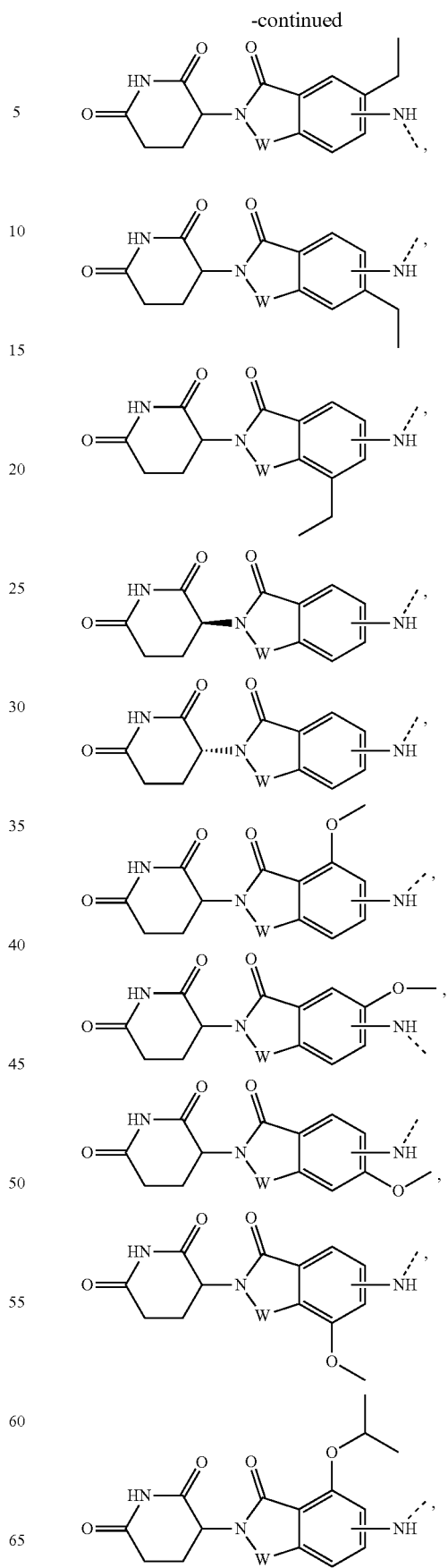

59
-continued
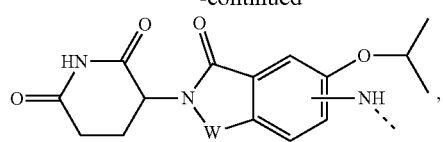
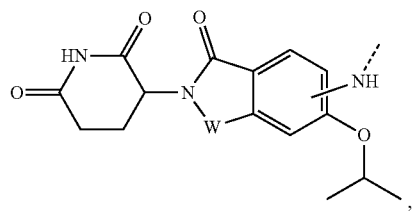
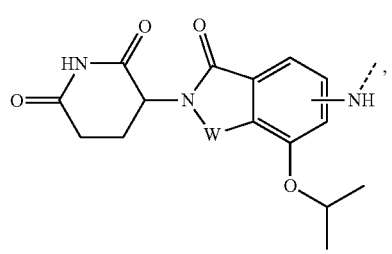
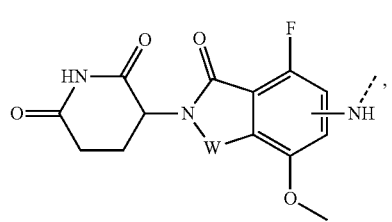
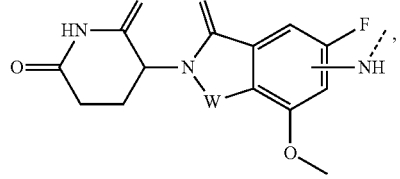
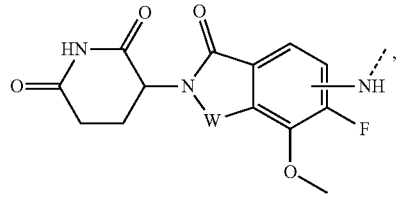
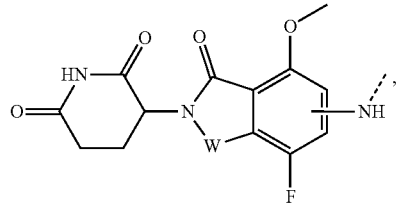
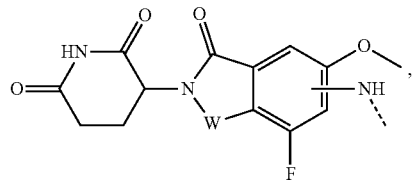
60
-continued
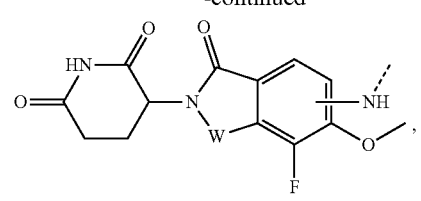
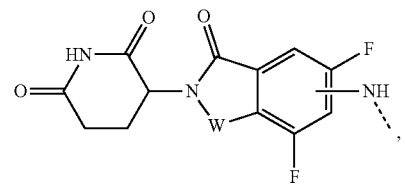
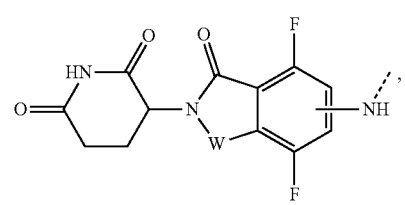
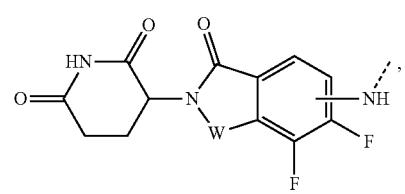
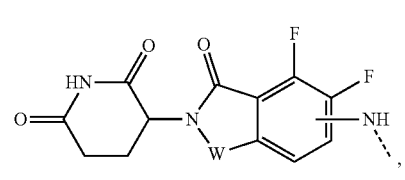
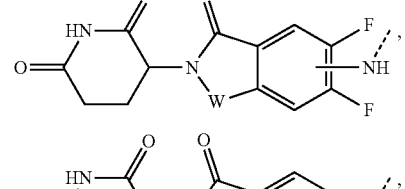
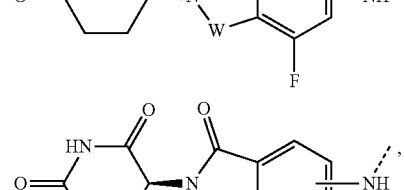
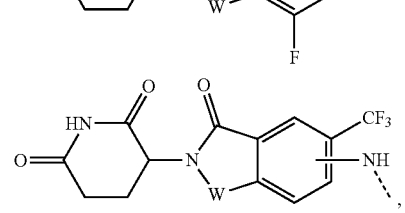

-continued
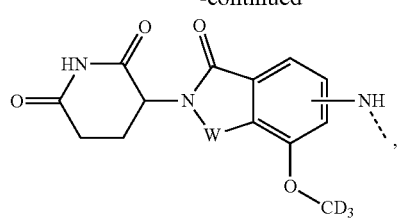
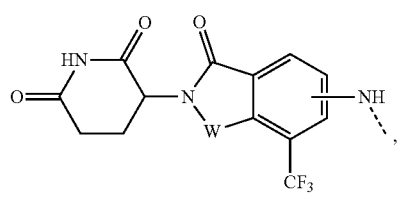
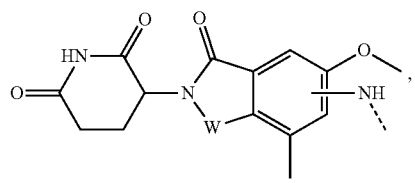
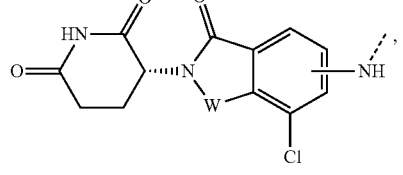
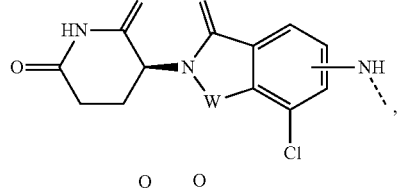
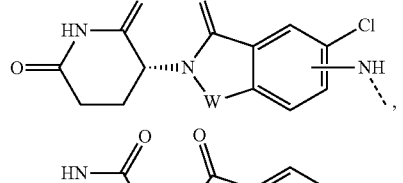
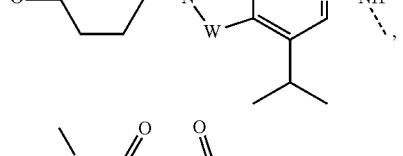
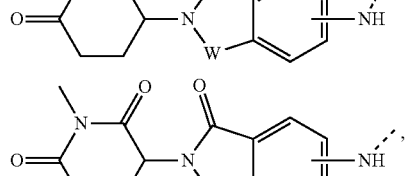
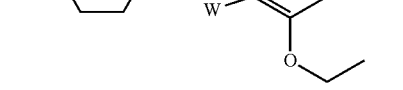
-continued
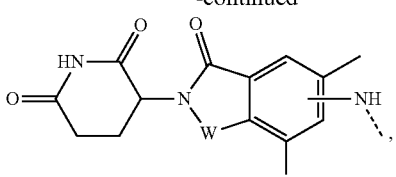
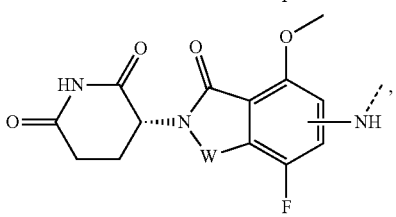
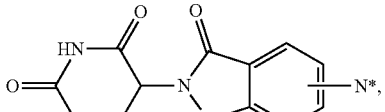
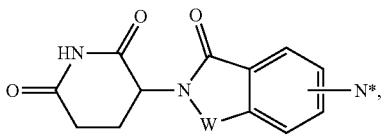
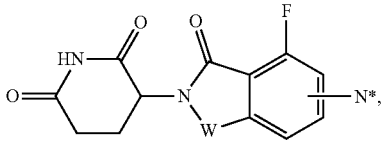
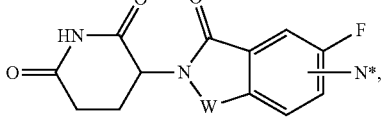
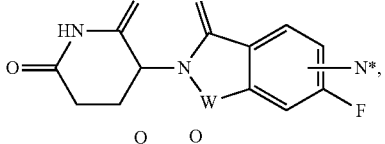
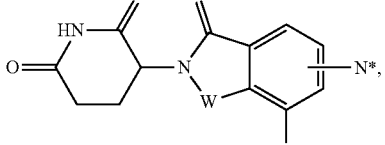
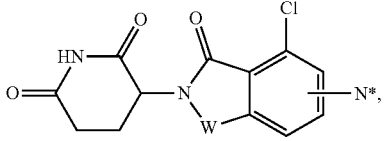
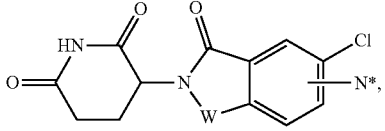
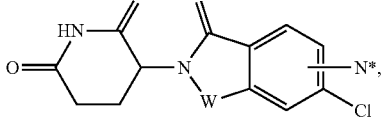

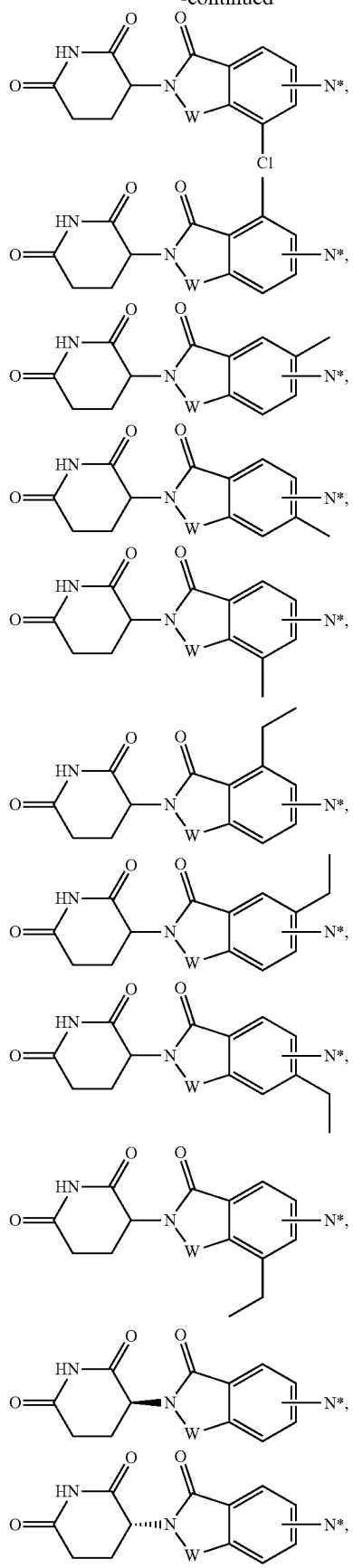
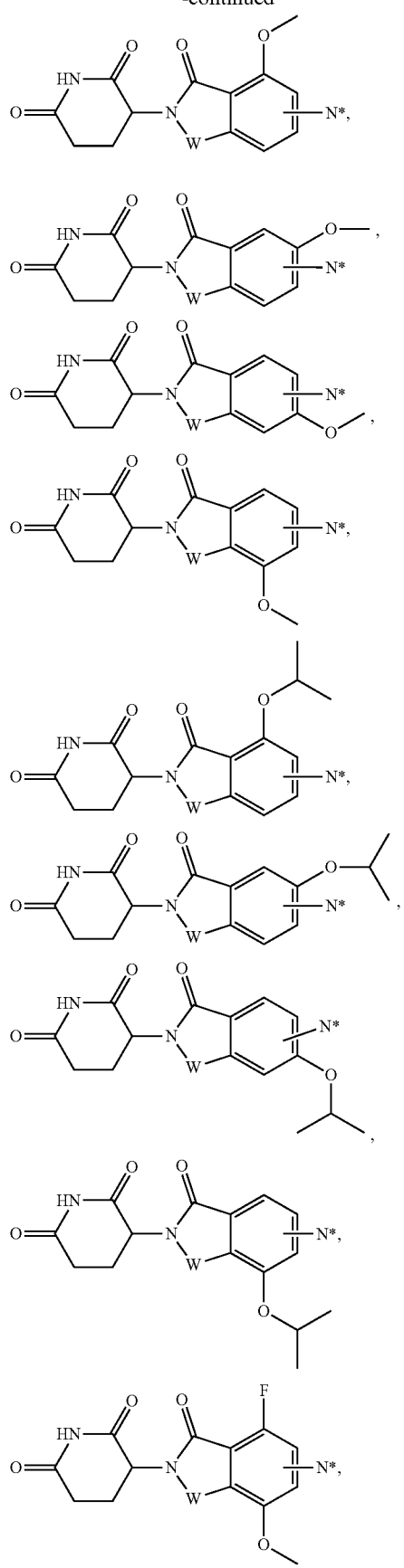

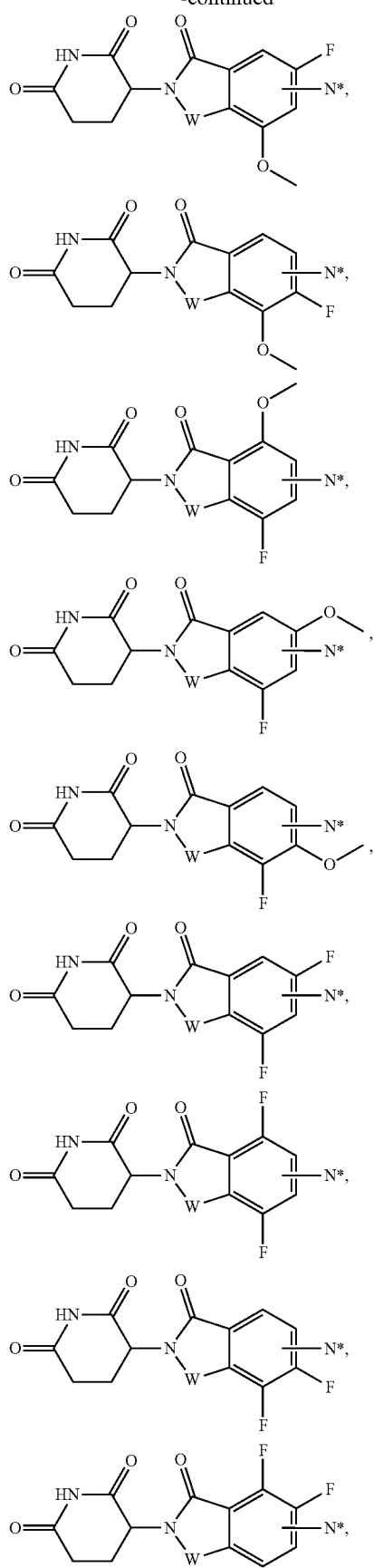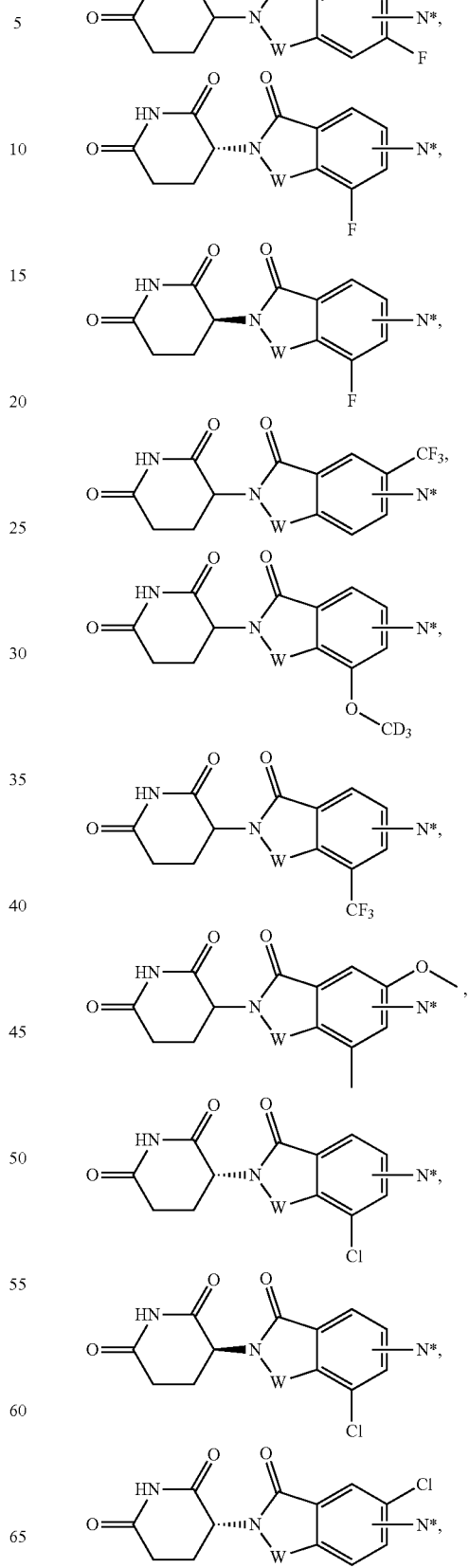

wherein:
- ⋯ of the CLM indicates the point of attachment with the L; and
- N* is a nitrogen atom that is shared with the chemical linker group.
In any aspect or embodiment described herein, the CLM is selected from:
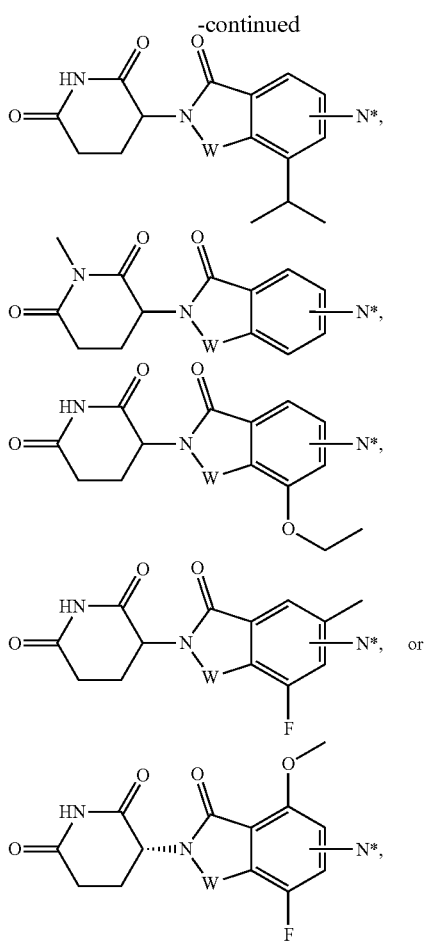

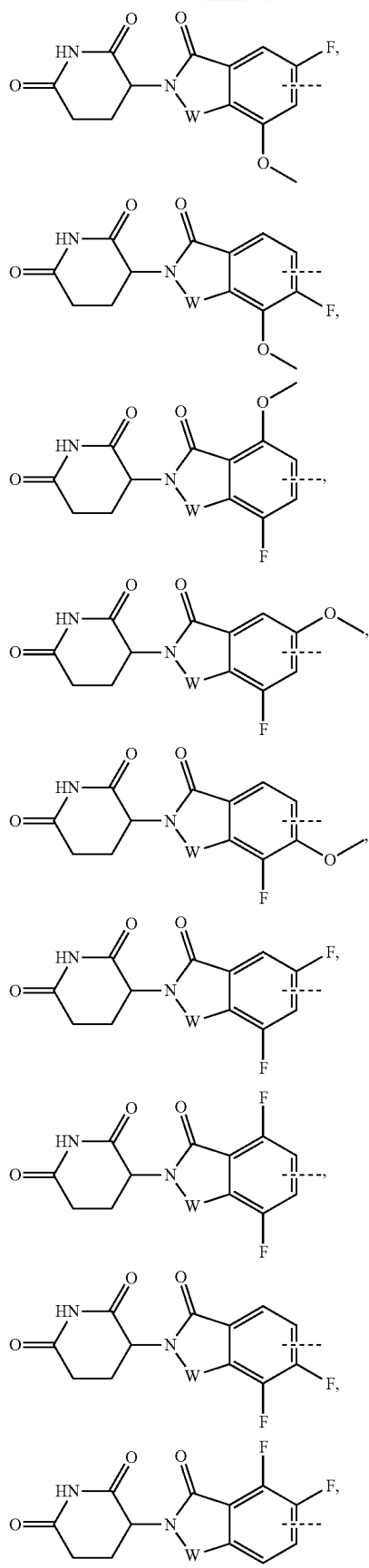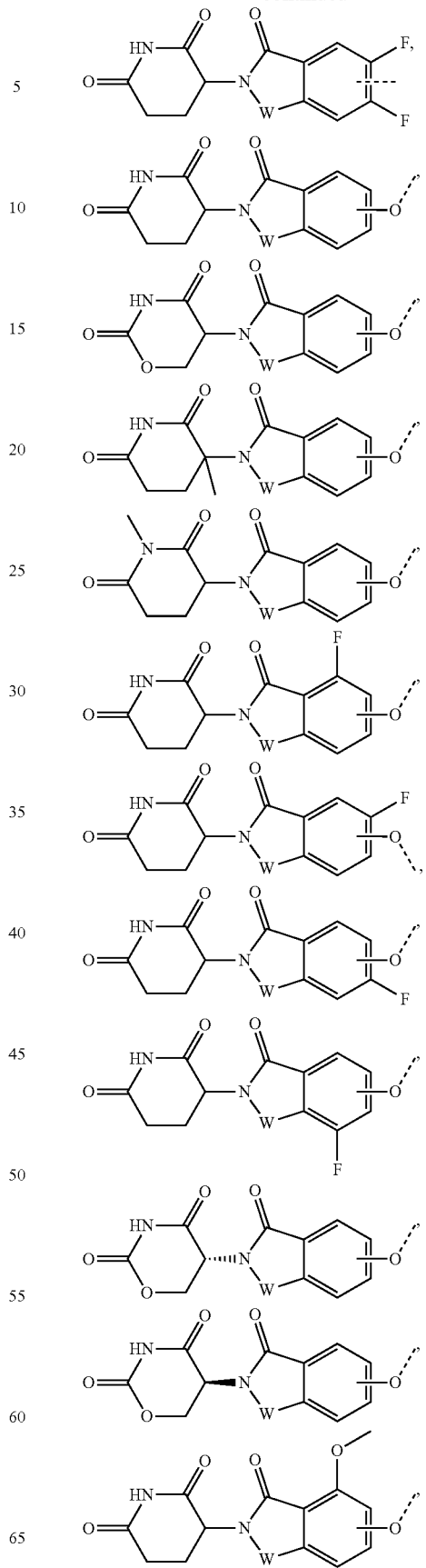

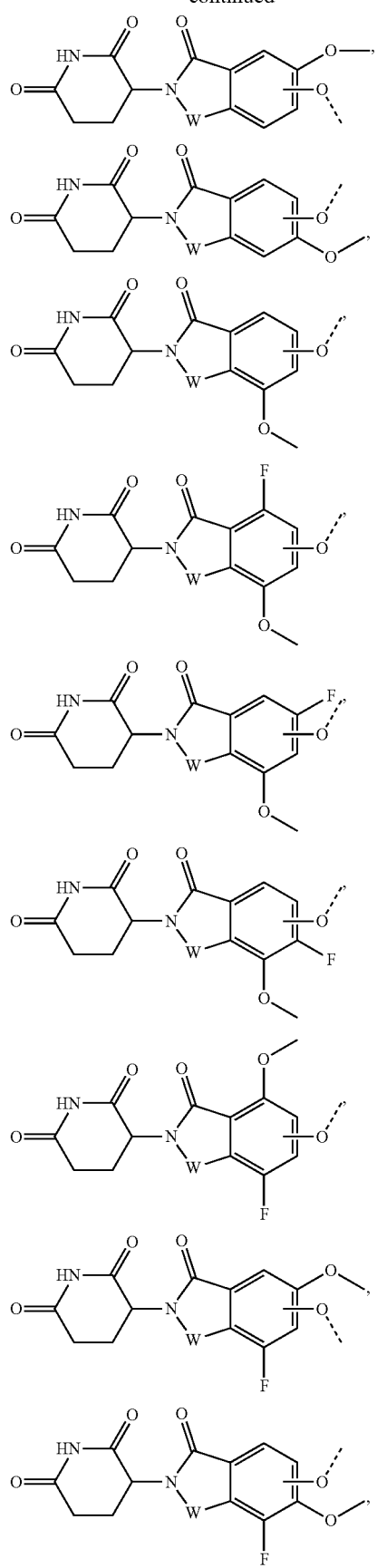
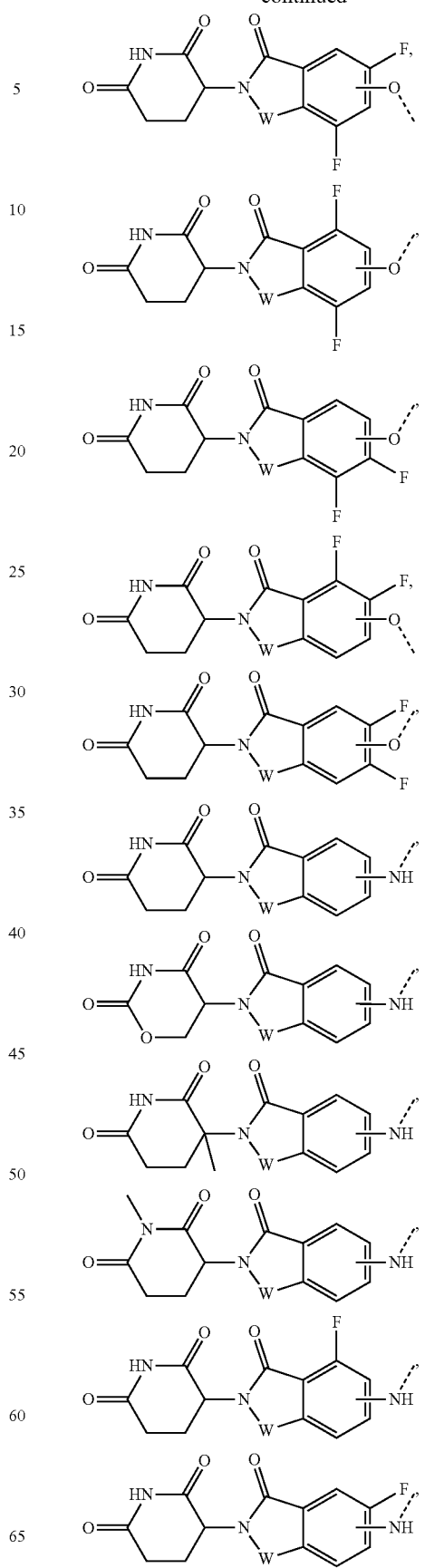

-continued
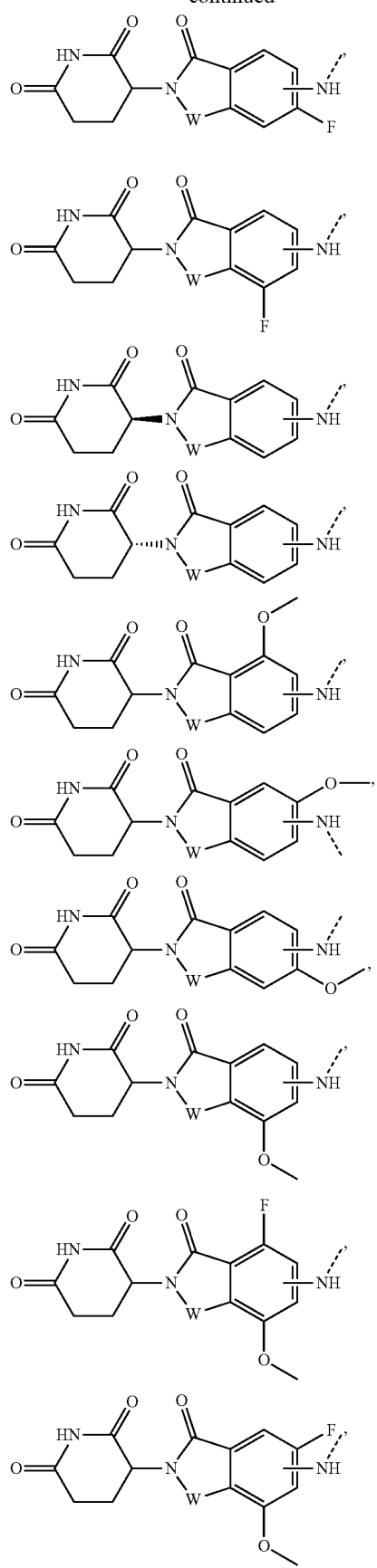
-continued
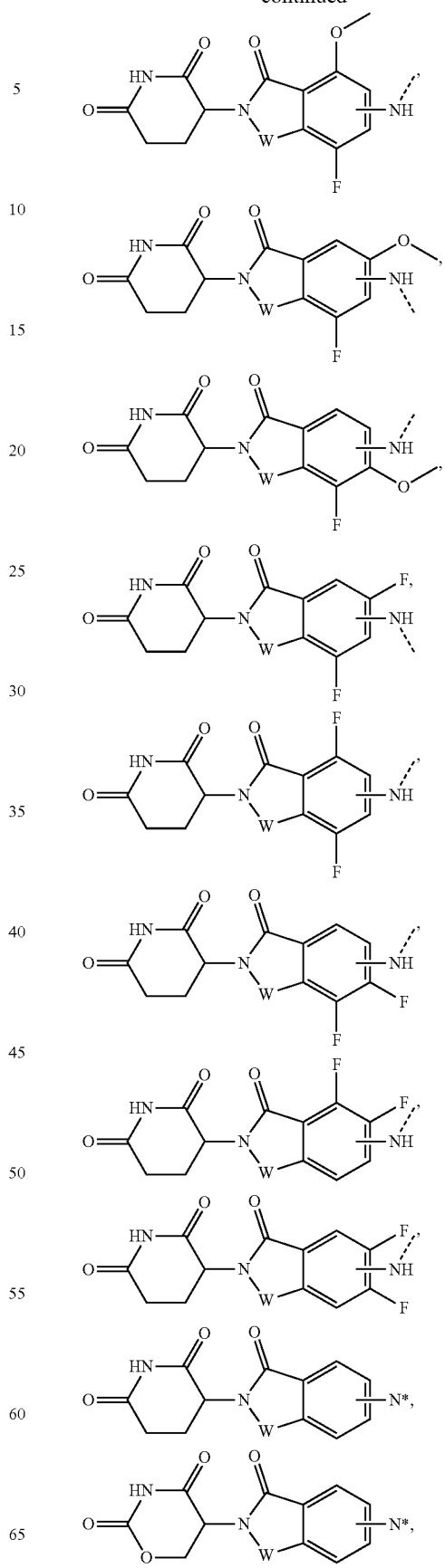

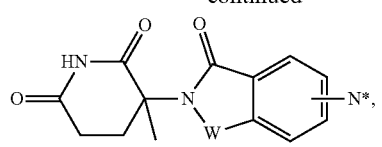
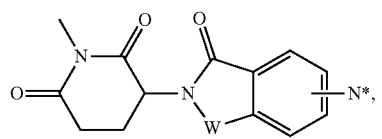
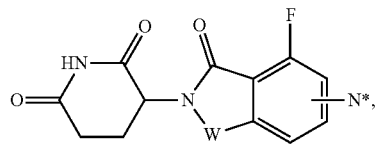
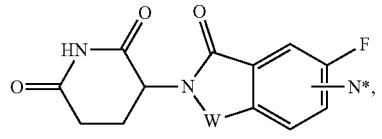
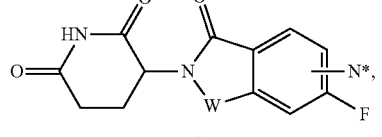
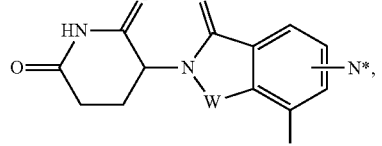
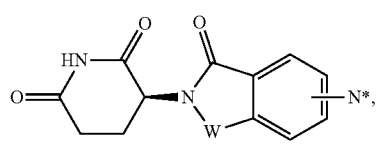
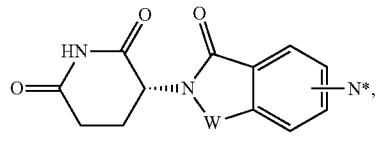
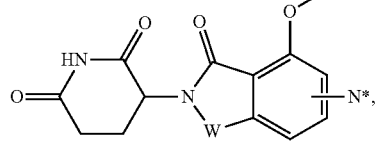
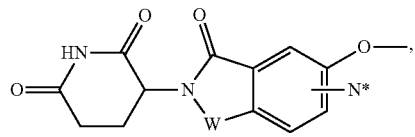
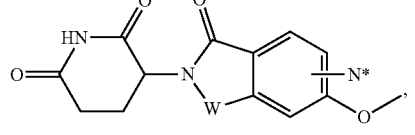
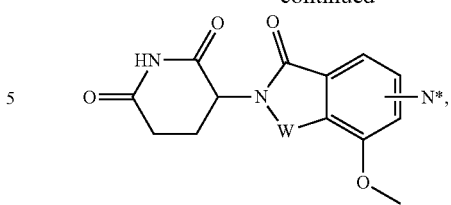
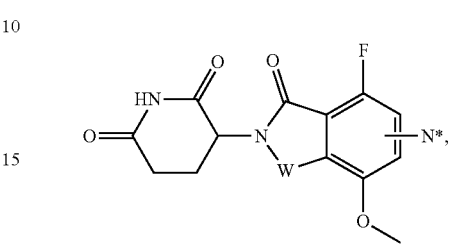
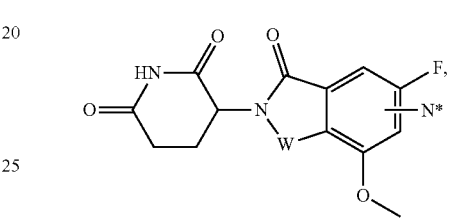
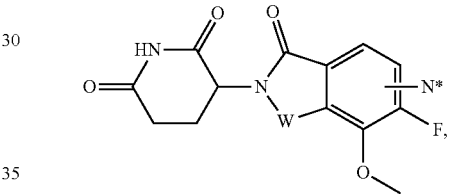
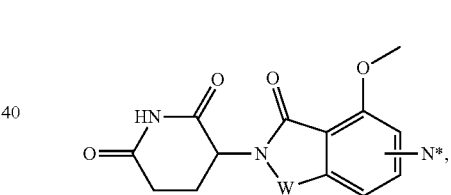
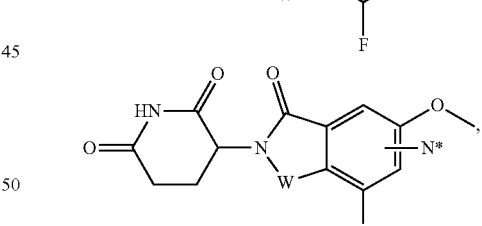
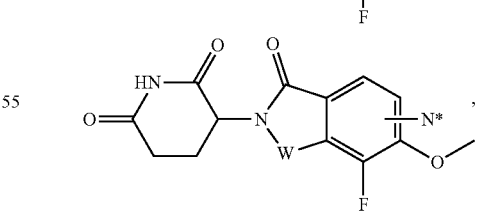
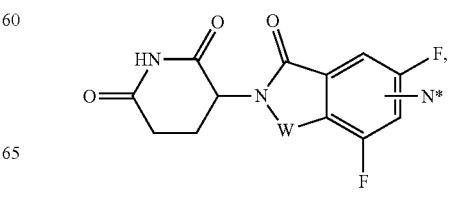

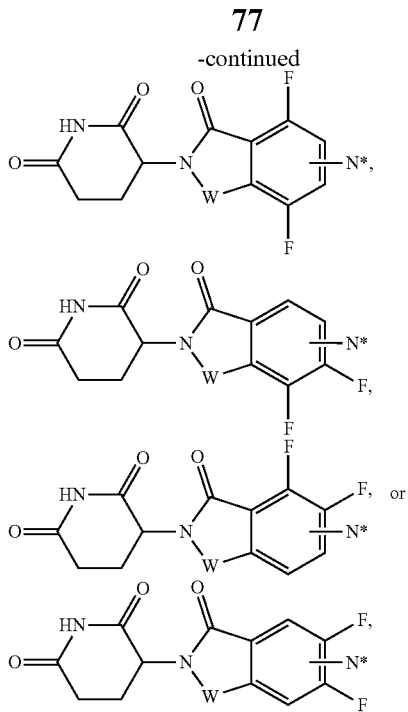
wherein:
- ⋯ of the ULM indicates the point of attachment with the linker group or the PTM; and
- N* is a nitrogen atom that is shared with the chemical linker group or the PTM.
In any aspect or embodiment described herein, the ULM is selected from the group consisting of:
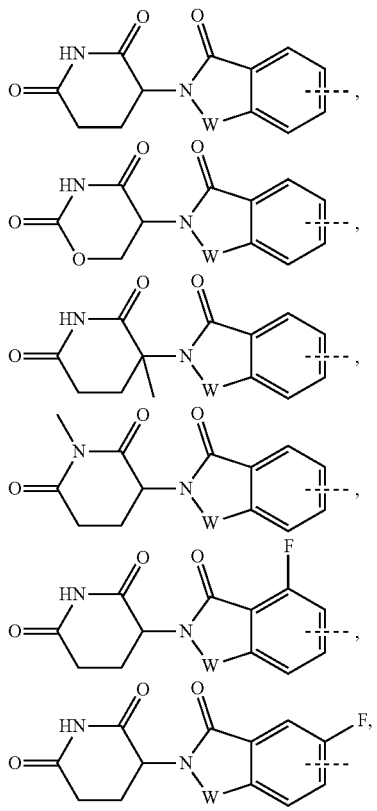
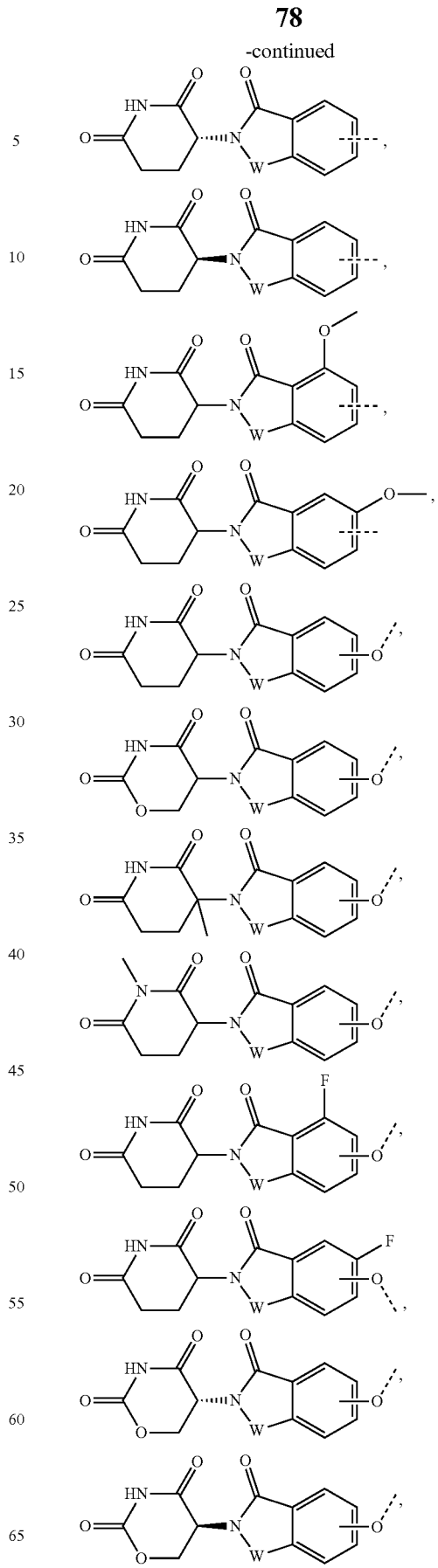

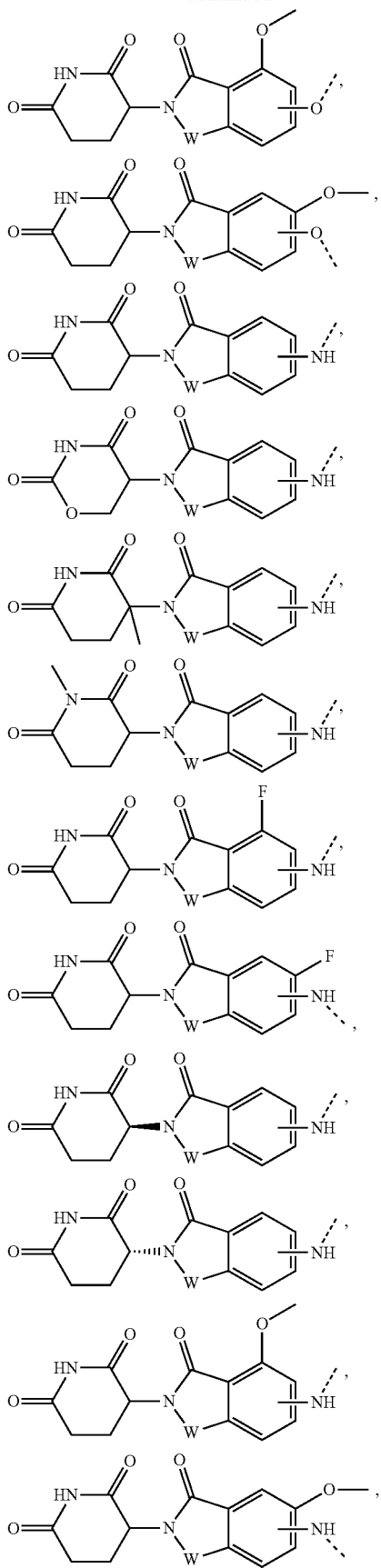
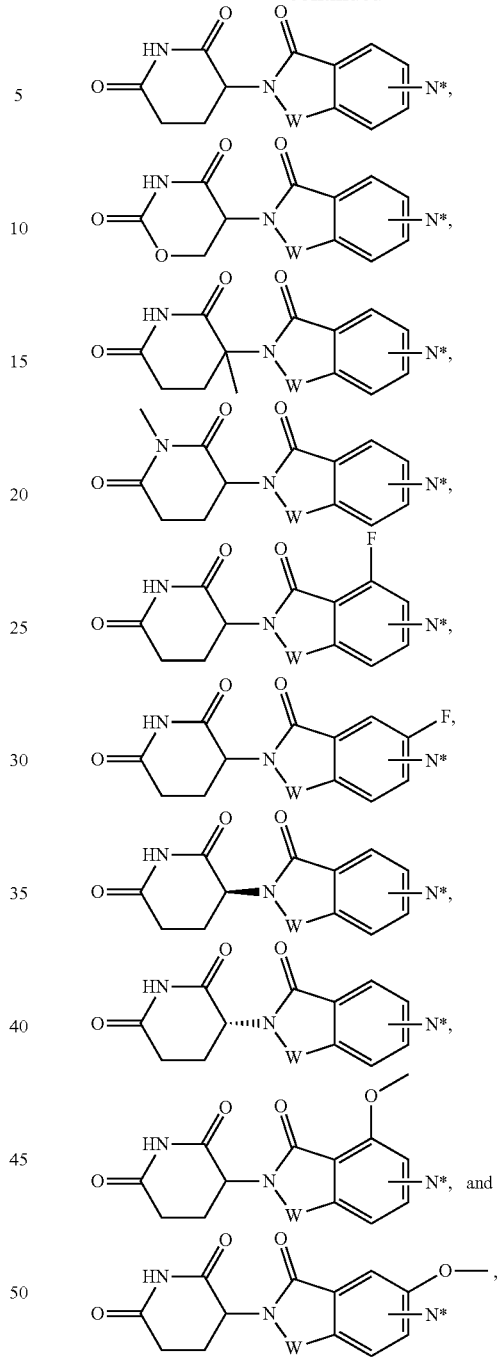

wherein:
- ⁓ of the ULM indicates the point of attachment with a chemical linker group or a PTM; and
- N* is a nitrogen atom that is shared with a chemical linker group or PTM.

Exemplary Linkers

In certain embodiments, the compounds as described herein include one or more PTMs chemically linked or coupled to one or more ULMs (e.g., at least one CLM) via a chemical linker (L). In certain embodiments, the linker group L is a group comprising one or more covalently connected structural units (e.g., -$A^L_1$ ... $(A^L)_q$- or -$(A^L)_q$-), wherein $A^L_1$ is a group coupled to PTM, and $(A^L)_q$ is a group coupled to ULM.

In any aspect or embodiment described herein, the linker (L) to ULM (e.g., CLM) connection or coupling is a stable L-ULM connection. For example, in any aspect or embodiment described herein, when a linker (L) and a ULM is connected via a heteroatom, any subsequent heteroatom, if present, is separated by at least one single carbon atom (e.g., —CH$_2$—), such as with an acetal or aminal group. By way of further example, in any aspect or embodiment described herein, when a linker (L) and a ULM is connected via a heteroatom, the heteroatom is not part of an ester.

In any aspect or embodiment described herein, the linker group L is a bond or a chemical linker group represented by the formula -(A$^L$)$_q$-, wherein A is a chemical moiety and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80), and wherein L is covalently bound to the PTM and the ULM, and provides for sufficient binding of the PTM to the protein target and the ULM to an E3 ubiquitin ligase to result in target protein ubiquitination.

In any aspect or embodiment described herein, the linker group L is -(A$^L$)$_q$-, wherein:

(A$^L$)$_q$ is a group which is connected to at least one of a ULM (such as a CLM), PTM moiety, or a combination thereof;

q of the linker is an integer greater than or equal to 1;

each A$^L$ is independently selected from, a bond, CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, monocyclic or bicyclic C$_{3-11}$cycloalkyl optionally substituted with 0-6 R$^{L1}$ and/or R$^{L2}$ groups, C$_{5-13}$ spirocycloalkyl optionally substituted with 1-9 R$^{L1}$ and/or R$^{L2}$ groups, monocyclic or bicyclic C$_{3-11}$heterocyclyl optionally substituted with 0-6 R$^{L1}$ and/or R$^{L2}$ groups, C$_{5-13}$ spiroheterocyclyl optionally substituted with 1-8 R$^{L1}$ and/or R$^{L2}$ groups, aryl optionally substituted with 1-6 R$^{L1}$ and/or R$^{L2}$ groups, and heteroaryl optionally substituted with 1-6 R$^{L1}$ and/or R$^{L2}$ groups, wherein R$^{L1}$ or R$^{L2}$, each independently are optionally linked to other groups to form cycloalkyl and/or heterocyclyl moiety, optionally substituted with 1-4 R$^{L5}$ groups; and R$^{L1}$, R$^{L2}$, R$^{L3}$, R$^{L4}$ and R$^{L5}$ are, each independently, H, halogen, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, monocyclic or bicyclic aryl, monocyclic or bicyclic heteroaryl, C$_{3-11}$heterocyclyl, OC$_{3-5}$cycloalkyl, SC$_{3-5}$cycloalkyl, NHC$_{3-5}$cycloalkyl, N(C$_{3-5}$cycloalkyl)$_2$, N(C$_{3-5}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$ alkyl, CCH, CH=CH(C$_{1-8}$alkyl), C(C$_{1-8}$alkyl)=CH (C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$ alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, or NH SO$_2$NH$_2$.

In any aspect or embodiment described herein, preferably each A is independently selected from CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, C$_{3-11}$ monocyclic or bicyclic cycloalkyl optionally substituted with 1-6 R$^{L1}$ and/or R$^{L2}$ groups, C$_{5-13}$ spirocycloalkyl optionally substituted with 1-9 R$^{L1}$ and/or R$^{L2}$ groups, C$_{3-11}$ monocyclic or bicyclic heterocyclyl optionally substituted with 1-6 R$^{L1}$ and/or R$^{L2}$ groups, C$_{5-13}$ spiroheterocyclyl optionally substituted with 1-8 R$^{L1}$ and/or R$^{L2}$ groups, aryl optionally substituted with 1-6 R$^{L1}$ and/or R$^{L2}$ groups, and heteroaryl optionally substituted with 1-6 R$^{L1}$ and/or R$^{L2}$ groups.

In any aspect or embodiment described herein, each R$^{L1}$, R$^{L2}$, R$^{L3}$, R$^{L4}$ and R$^{L5}$ is independently H, halogen, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, 5- or 6-membered aryl, 5- or 6-membered heteroaryl, C$_{3-11}$heterocyclyl, OC$_{3-8}$cycloalkyl, SC$_{3-8}$cycloalkyl, NHC$_{3-8}$cycloalkyl, N(C$_{3-5}$cycloalkyl)$_2$, N(C$_{3-5}$cycloalkyl)(C$_{1-8}$alkyl), OH, NH$_2$, SH, SO$_2$C$_{1-8}$alkyl, CC—C$_{1-8}$ alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, COC$_{1-8}$alkyl, CO$_2$H, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH (C$_{1-8}$ alkyl), N(C$_{1-8}$alkyl)CON(C$_{1-8}$alkyl)$_2$, NHCONH(C$_{1-8}$ alkyl), NHCON(C$_{1-8}$alkyl)$_2$, NHCONH$_2$, N(C$_{1-8}$alkyl) SO$_2$NH(C$_{1-8}$alkyl), N(C$_{1-8}$alkyl) SO$_2$N(C$_{1-8}$alkyl)$_2$, NHSO$_2$NH(C$_{1-8}$alkyl), NH SO$_2$N(C$_{1-8}$alkyl)$_2$, or NH SO$_2$NH$_2$.

In any aspect or embodiment described herein, q of the linker is an integer greater than or equal to 0. In certain embodiments, q is an integer greater than or equal to 1.

In any aspect or embodiment described herein, e.g., where q of the linker is greater than 2, (A$^L$)$_q$ is a group which is A$^{L1}$ and (A$^L$)$_q$ wherein the units A$^L$ are couple a PTM to a ULM.

In any aspect or embodiment described herein, e.g., where q of the linker is 2, (A$^L$)$_q$ is a group which is connected to A$^{L1}$ and to a ULM.

In any aspect or embodiment described herein, e.g., where q of the linker is 1, the structure of the linker group L is -A$^{L1}$-, and A$^{L1}$ is a group which is connected to a ULM moiety and a PTM moiety.

In any aspect or embodiment described herein, the unit A$^L$ of linker (L) comprises a group represented by a general structure selected from the group consisting of:

—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cycloalkyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-Aryl-O—CH$_2$—, —NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$—, —NR(CH$_2$CH$_2$O)$_n$-(cyclo alkyl)-O-Aryl-O—CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)1-, —NR(CH$_2$CH$_2$)$_n$-(cycloalkyl)-O-(heterocyclyl)-CH$_2$, —NR(CH$_2$CH$_2$)$_n$-(heterocyclyl)-(heterocyclyl)-CH$_2$, —N(R$_1$R$_2$)-(heterocyclyl)-CH$_2$; where n of the linker can be 0 to 10;

R of the linker can be H, lower alkyl;

R1 and R2 of the linker can form a ring with the connecting N.

In any aspect or embodiment described herein, the linker (L) includes an optionally substituted C$_1$-C$_{50}$ alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, C$_{31}$, C$_{32}$, C$_{33}$, C$_{34}$, C$_{35}$, C$_{36}$, C$_{37}$, C$_{38}$, C$_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein each carbon is optionally substituted with (1) a heteroatom selected from N, S, P, or Si atoms that has an appropriate number of hydrogens, substitutions, or both to complete valency, (2) an optionally substituted cycloalkyl or bicyclic cycloalkyl, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linker or adjacently located).

In any aspect or embodiment describe herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, Cis, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally replaced with $CR^{L1}R^{L2}$, O, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, monocyclic or bicyclic $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, monocyclic or bicyclic $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, monocyclic or bicyclic aryl optionally substituted with 1-6 $R^{L1}$ and/or $R^{L2}$ groups, or monocyclic or bicyclic heteroaryl optionally substituted with 1-6 $R^{L1}$ and/or $R^{L2}$ groups, wherein $R^{L1}$ or $R^{L2}$, each independently are optionally linked to other groups to form cycloalkyl and/or heterocyclyl moiety, optionally substituted with 1-4 $R^{L5}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-5}$cycloalkyl, $SC_{1-5}$cycloalkyl, $NHC_{1-8}$cycloalkyl, $N(C_{1-5}$cycloalkyl$)_2$, $N(C_{1-8}$cycloalkyl$)(C_{1-8}$alkyl$)$, OH, $NH_2$, SH, $SO_2C_{1-8}$alkyl, $P(O)(OC_{1-8}$alkyl$)(C_{1-8}$alkyl$)$, $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl$)CONH(C_{1-8}$alkyl$)$, $N(C_{1-8}$alkyl$)CON(C_{1-8}$alkyl$)_2$, $NHCONH(C_{1-8}$alkyl$)$, $NHCON(C_{1-8}$alkyl$)_2$, $NHCONH_2$, $N(C_{1-8}$alkyl$)SO_2NH(C_{1-8}$alkyl$)$, $N(C_{1-8}$alkyl$) SO_2N(C_{1-8}$alkyl$)_2$, NH $SO_2NH(C_{1-8}$alkyl$)$, NH $SO_2N(C_{1-8}$alkyl$)_2$, or NH $SO_2NH_2$. In any aspect or embodiment described herein, the linker (L) does not have heteroatom-heteroatom bonding (e.g., no heteroatoms are covalently linker or adjacently located).

In any aspect or embodiment described herein, each carbon the optionally substituted $C_1$-$C_{50}$ alkyl (and subgroups described herein) of the linker is optionally replaced with $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $C_{3-11}$ monocyclic or bicyclic cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, monocyclic or bicyclic $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups.

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency. For example, in any aspect or embodiment described herein, the linker (L) has a chemical structure selected from:

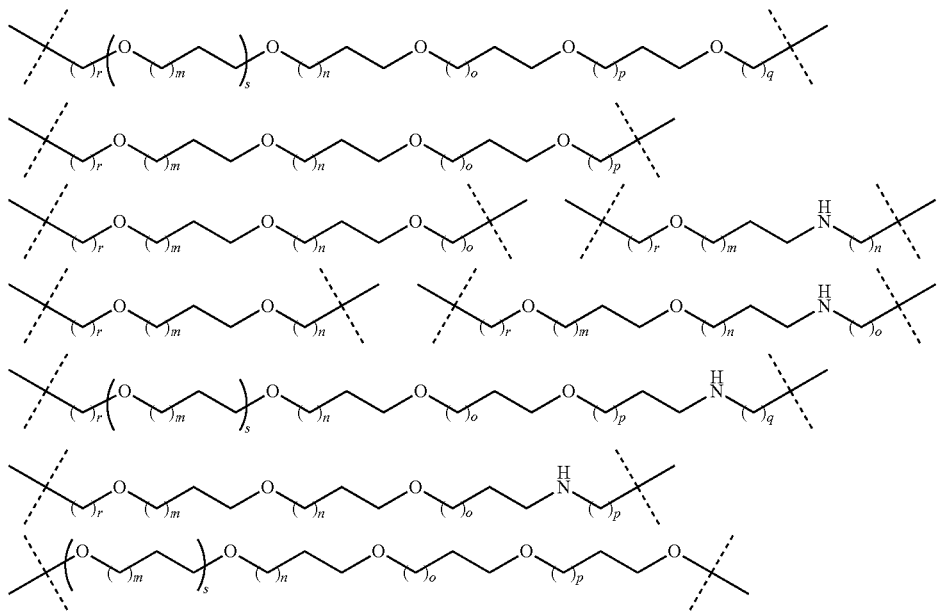

-continued

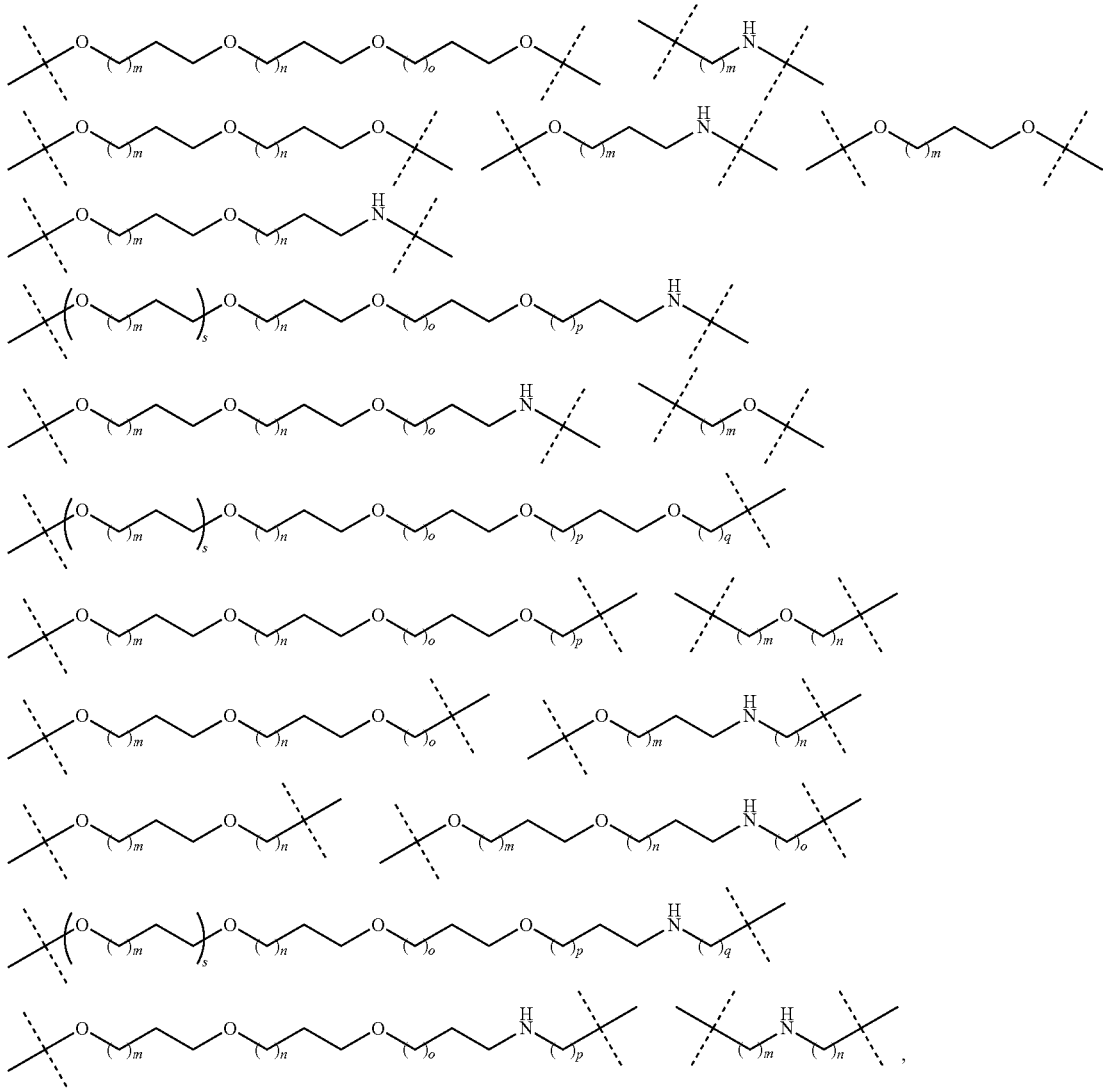

wherein carbon or oxygen may be substituted with a heteroatom selected from N, S, P, or Si atoms with an appropriate number of hydrogens to complete valency, and m, n, o, p, q, r, and s are independently selected from 0, 1, 2, 3, 4, 5, 6, 7, 8, 9, 10, 11, 12, 13, 14, 15, 16, 17, 18, 19, and 20.

In any aspect or embodiment described herein, the unit $A^L$ of the linker (L) comprises a group represented by a general structure selected from the group consisting of:

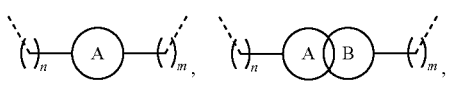

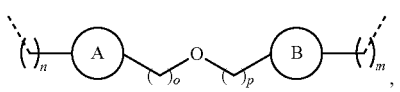

-continued

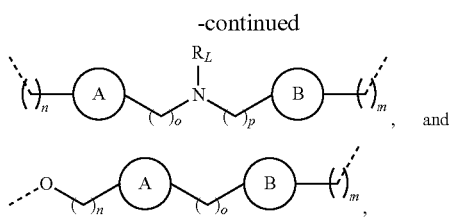

wherein:

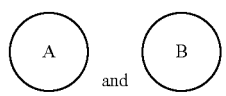

are each independently a 3-7 membered cycloalkyl or a 3-7 membered heterocycloalkyl (e.g., 4-6 membered cycloalkyl or 4-6 membered heterocycloalkyl), wherein overlapping circles indicates spirocyclic rings;

each m, n, o, and p is independently 0, 1, 2, 3, 4, 5, or 6;

$R_L$ is selected from H and $C_{1-3}$ alkyl;

the linker is optionally substituted with at least one of: (i) =O and (ii) 1-4 (e.g., 1, 2, 3, or 4) substitutions independently selected from a $C_{1-3}$ alkyl (e.g., methyl) and a halogen (e.g., F, Cl, or Br); and ⟋ indicates the attachment point to the PTM or the ULM.

In any aspect or embodiment described herein, the linker (L) has a chemical structure selected from:

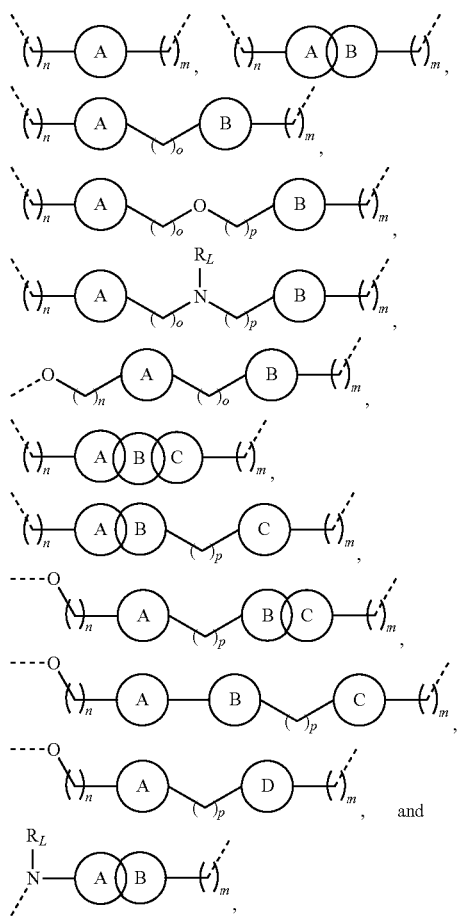

wherein:

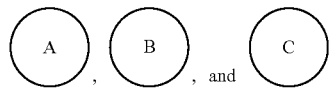

and are each independently a 3-7 membered cycloalkyl or a 3-7 membered heterocycloalkyl (e.g., 4-6 membered cycloalkyl or 4-6 membered heterocycloalkyl), wherein overlapping circles indicates spirocyclic rings;

is a 8-10 membered bridged cycloalkyl, a 8-10 membered bridge heterocycloalkyl, a 3-7 membered heterocyclyl having one or two double bonds (e.g., 3-7 membered heterocyclyl having one or two double bonds), or a 7-10 membered fused bicyclic heterocycloalkyl (e.g., a 7-9 membered fused bicyclic heterocycloalkyl);

each m, n, o, and p is independently 0, 1, 2, 3, 4, 5, or 6;

$R_L$ is selected from H and $C_{1-3}$ alkyl;

the linker is optionally substituted with at least one of: (i) =O and (ii) 1-4 (e.g., 1, 2, 3, or 4) substitutions independently selected from a $C_{1-3}$ alkyl (e.g., methyl), OH, and a halogen (e.g., F, Cl, or Br); and ⟋ indicates the attachment point to the PTM or the CLM.

In any aspect or embodiment described herein, the chemical linker group is selected from

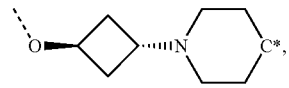

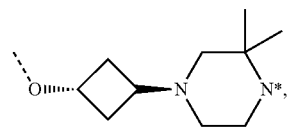

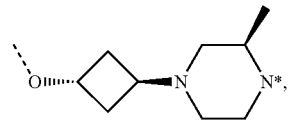

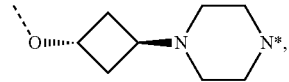

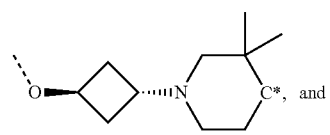

wherein * indicates an atom (e.g., a carbon or nitrogen) that is covalently linked to the CLM or PTM, or that is shared with the CLM or PTM, and each of ⟋ indicates the point of attachment with the CLM or the PTM.

In any aspect or embodiment described herein, the chemical linker group is selected from

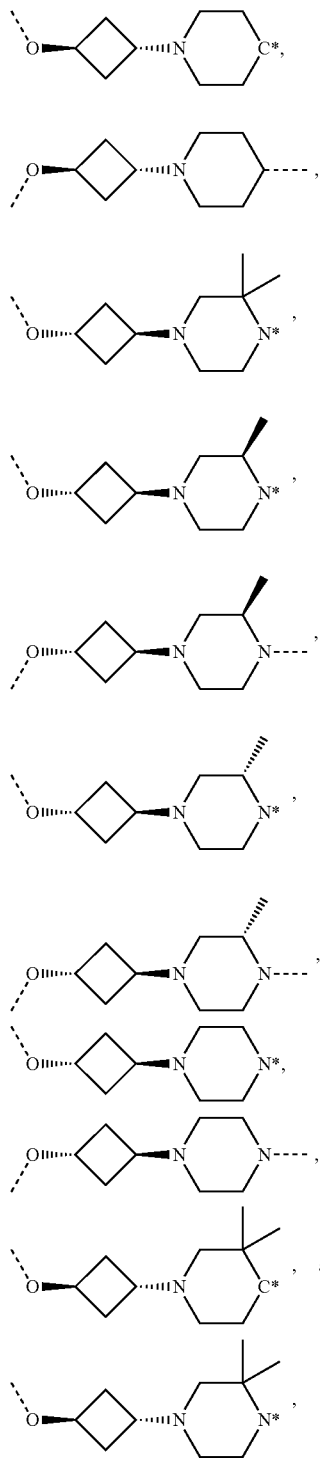

wherein * indicates an atom (e.g., a carbon or nitrogen) that is covalently linked to the CLM or PTM, or that is shared with the CLM or PTM, and each of ⁓ indicates the point of attachment with the CLM or the PTM.

In any aspect or embodiment described herein, the chemical linker group is:

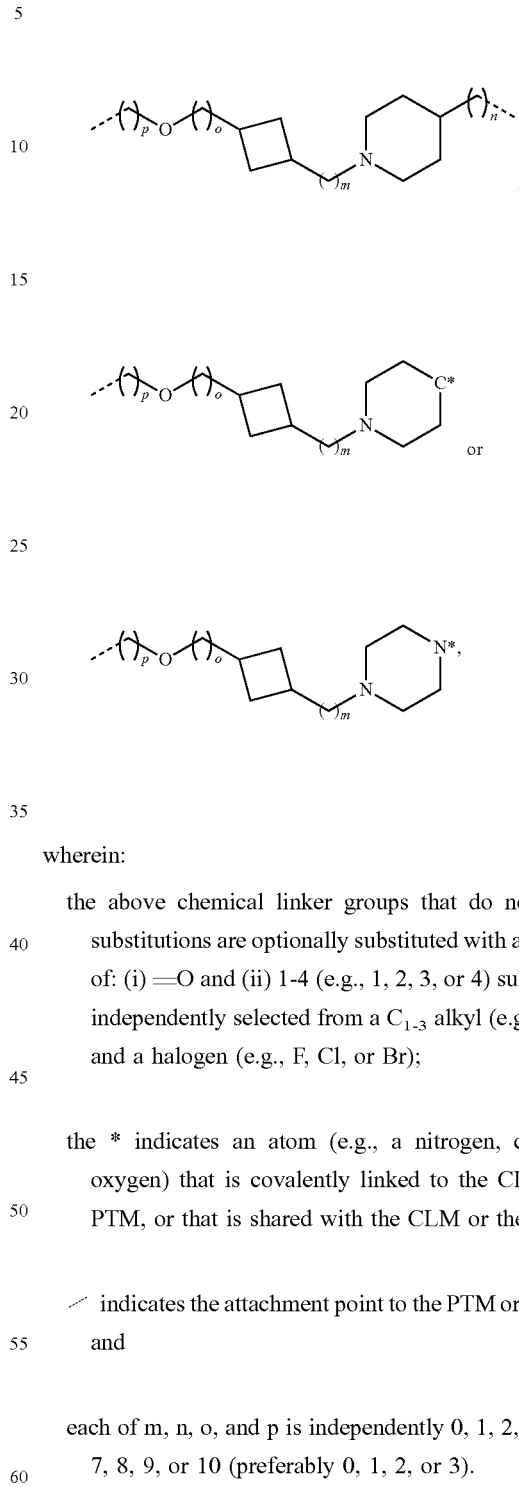

wherein:

the above chemical linker groups that do not include substitutions are optionally substituted with at least one of: (i) =O and (ii) 1-4 (e.g., 1, 2, 3, or 4) substitutions independently selected from a $C_{1-3}$ alkyl (e.g., methyl) and a halogen (e.g., F, Cl, or Br);

the * indicates an atom (e.g., a nitrogen, carbon, or oxygen) that is covalently linked to the CLM or the PTM, or that is shared with the CLM or the PTM;

⁓ indicates the attachment point to the PTM or the CLM; and each of m, n, o, and p is independently 0, 1, 2, 3, 4, 5, 6, 7, 8, 9, or 10 (preferably 0, 1, 2, or 3).

In any aspect or embodiment described herein: the chemical linker group is optionally substituted with 1 or 2 substitutions independently selected from a $C_{1-3}$ alkyl (preferably, methyl); p and o are each 0; and m is 1.

In any aspect or embodiment described herein, the chemical linker group is:
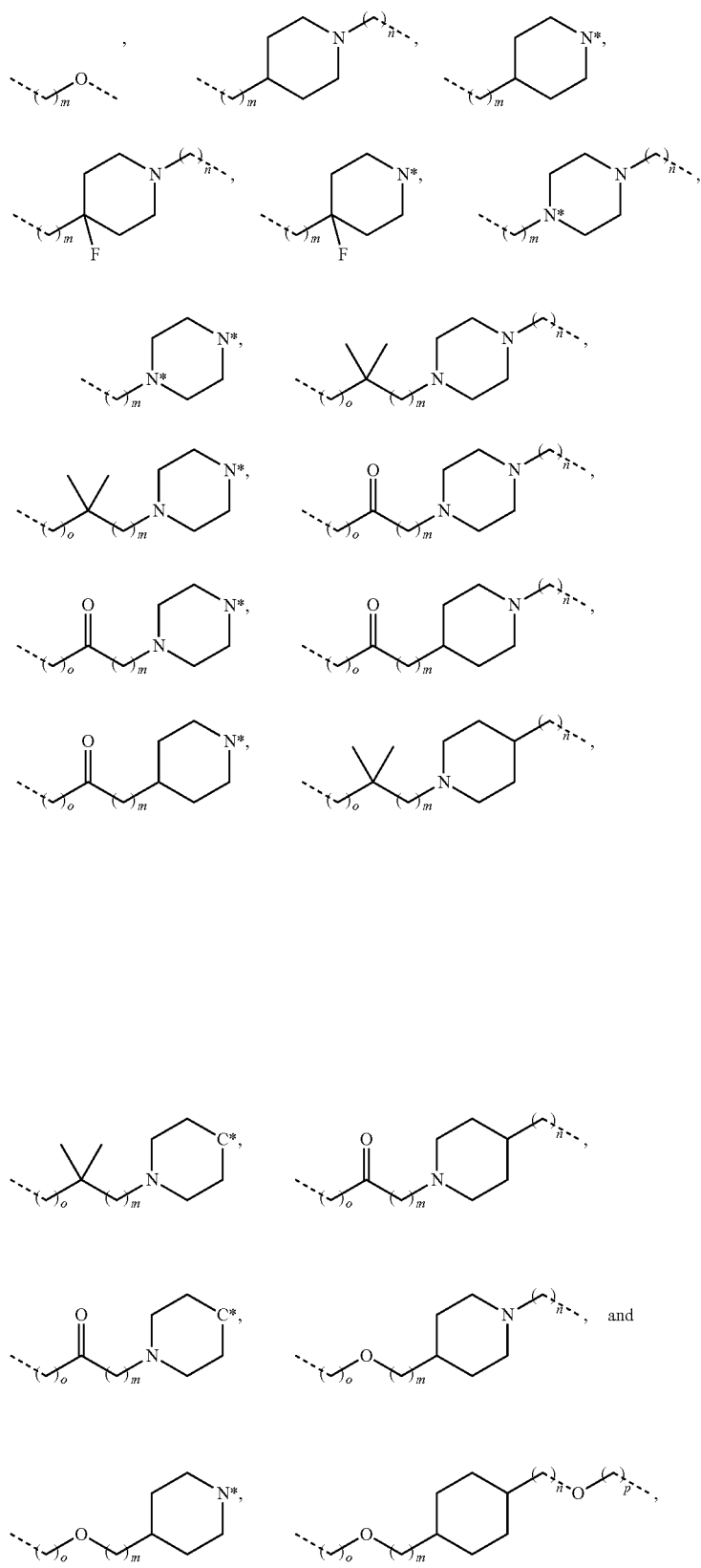

wherein:
  the above chemical linker groups that do not include substitutions are optionally substituted with at least one of: (i) =O and (ii) 1-4 (e.g., 1, 2, 3, or 4) substitutions independently selected from a $C_{1-3}$ alkyl (e.g., methyl) and a halogen (e.g., F, Cl, or Br); the * indicates an atom (e.g., a nitrogen or carbon) that is covalently linked to the CLM or the PTM, or that is shared with the CLM or the PTM;

indicates the attachment point to the PTM or the CLM; and each m, n, o, and p is independently 0, 1, 2, 3, 4, 5, 6, 7, 8, 9, or 10 (preferably 0, 1, 2, or 3).

In any aspect or embodiment described herein, the chemical linker group is:

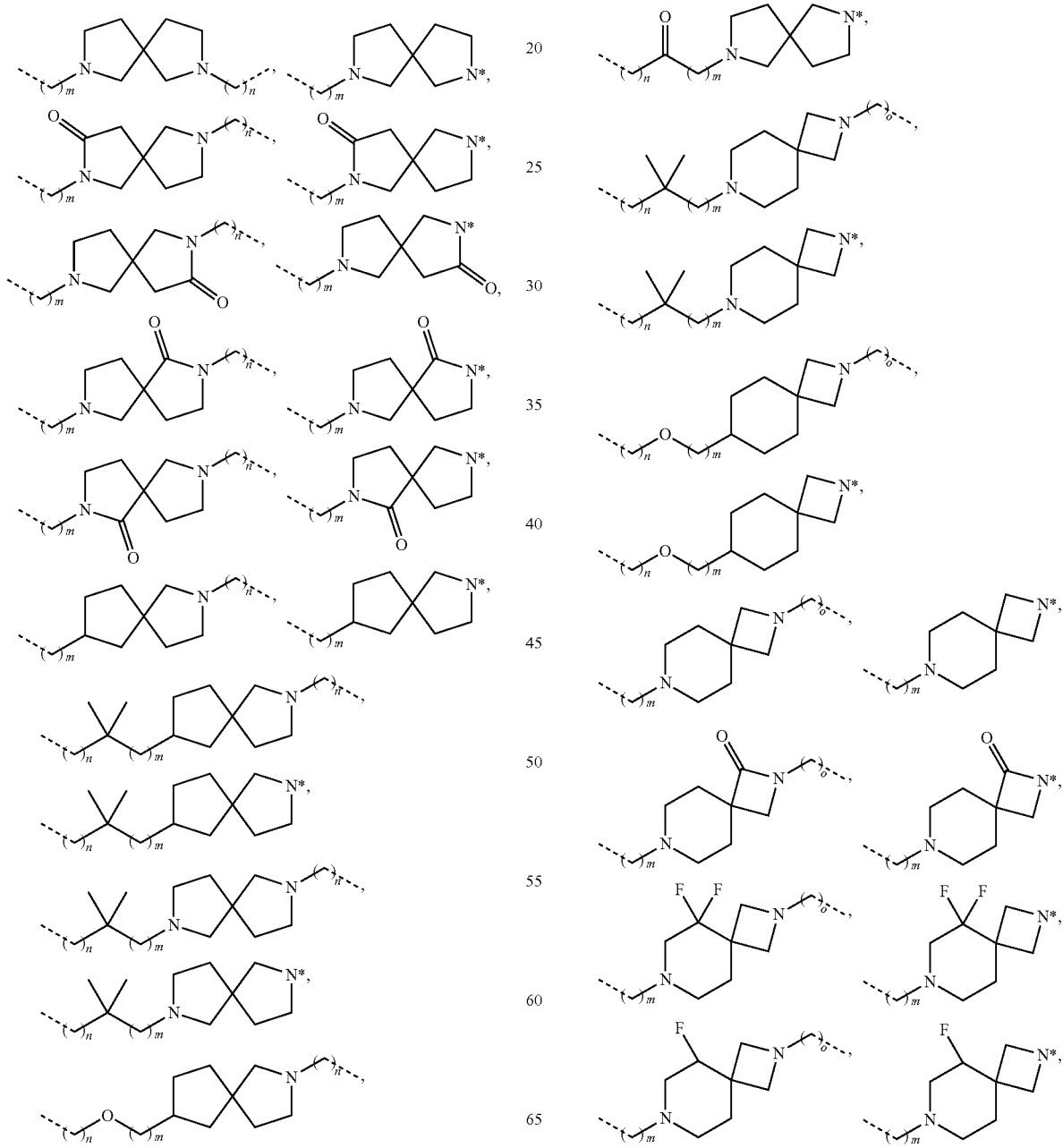

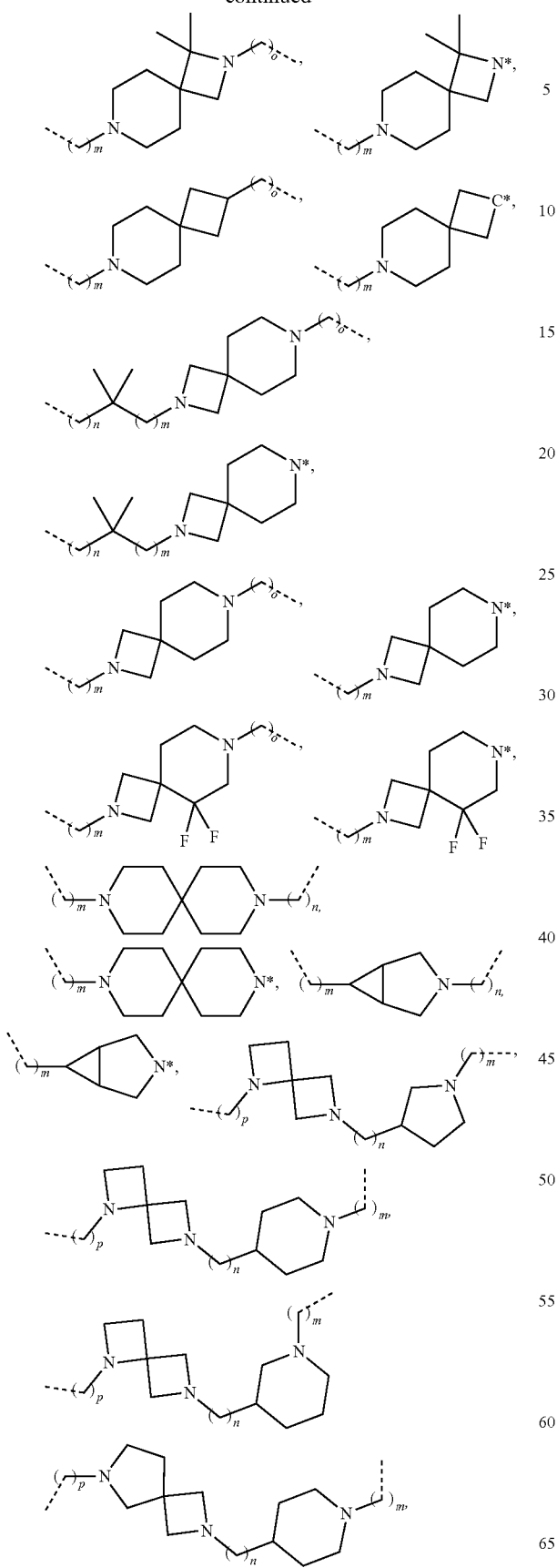
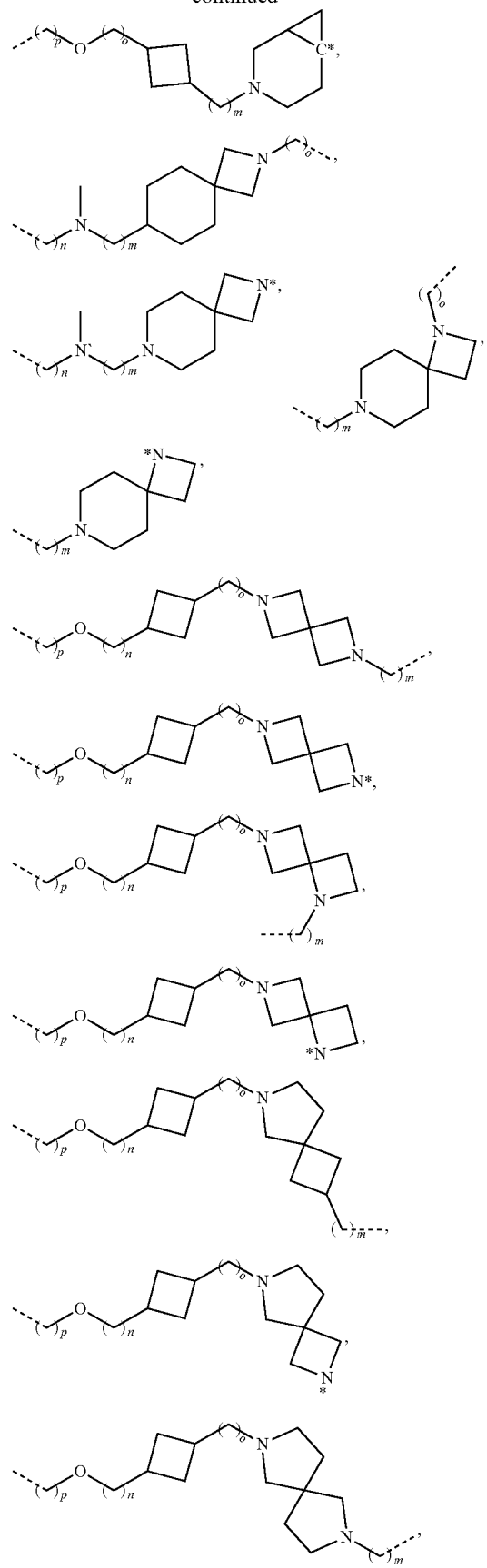

-continued

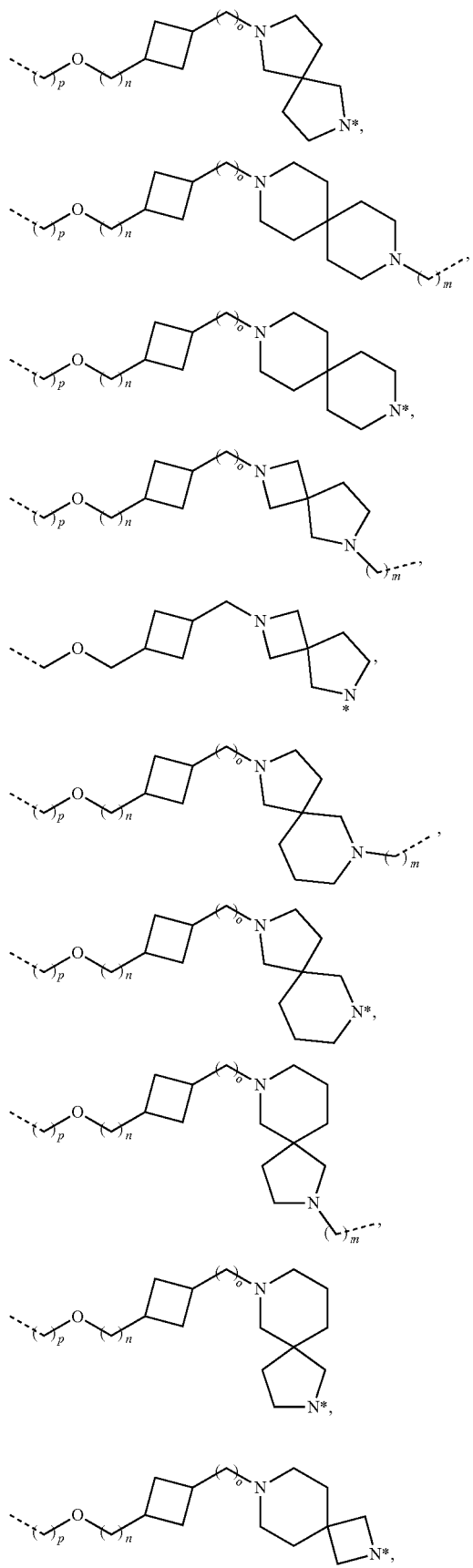

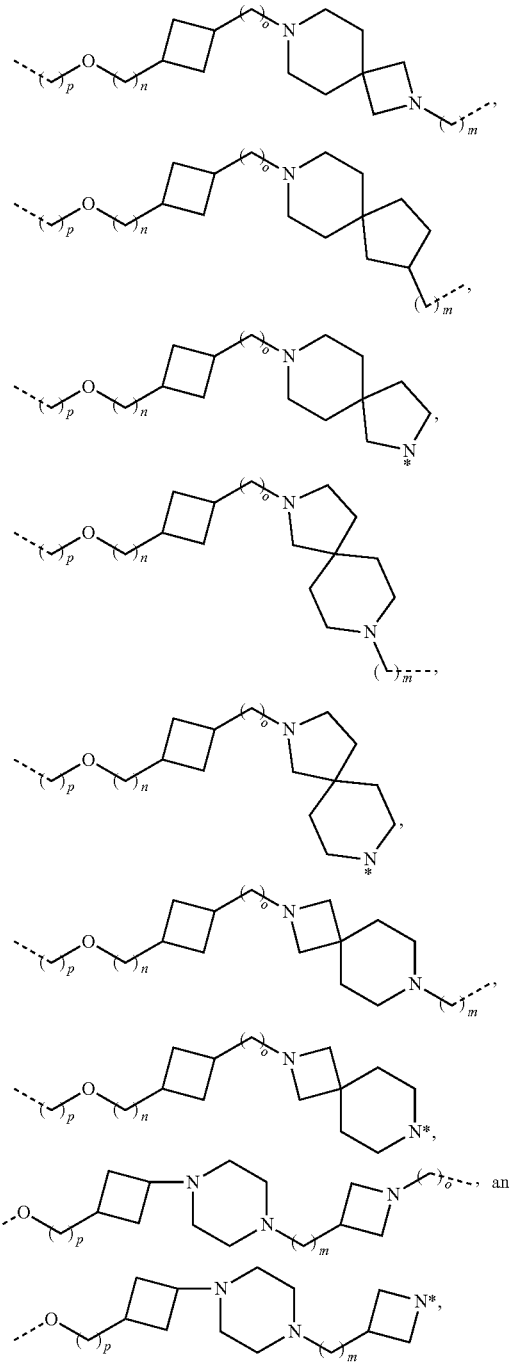

wherein:
the above chemical linker groups that do not include substitutions are optionally substituted with at least one of: (i) =O and (ii) 1-4 (e.g., 1, 2, 3, or 4) substitutions independently selected from a $C_{1-3}$ alkyl (e.g., methyl) and a halogen (e.g., F, Cl, or Br);
the * indicates an atom (e.g., a nitrogen or carbon) that is covalently linked to the CLM or the PTM, or that is shared with the CLM or the PTM;
⌒ indicates the attachment point to the PTM or the CLM; and
each m, n, and o is independently 0, 1, 2, 3, 4, 5, 6, 7, 8, 9, or 10 (preferably 0, 1, 2, or 3).

In any aspect or embodiment described herein, the chemical linker group is:
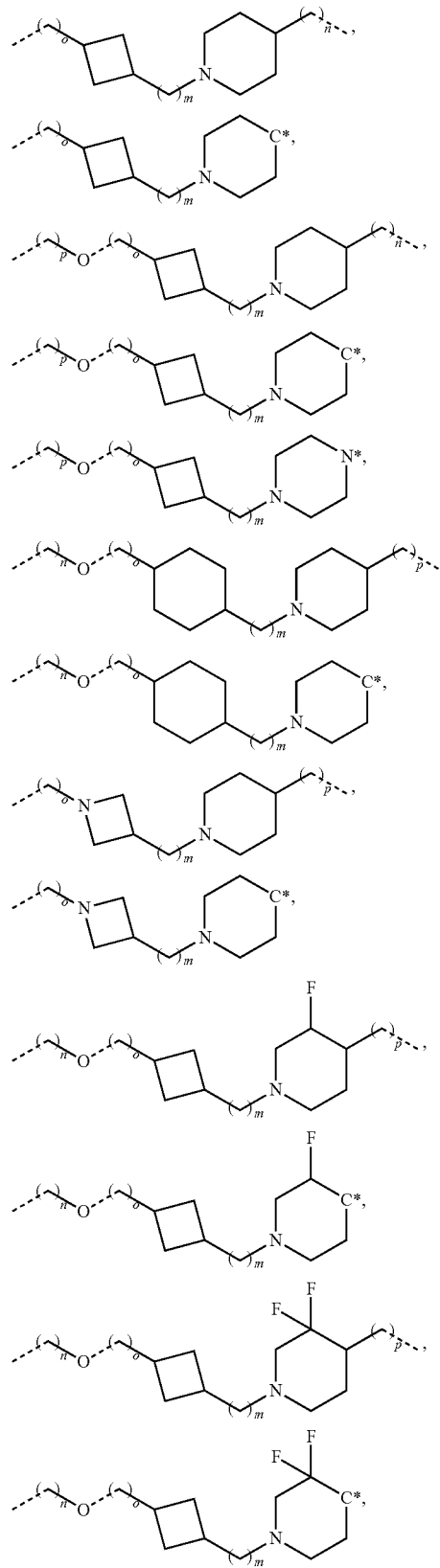
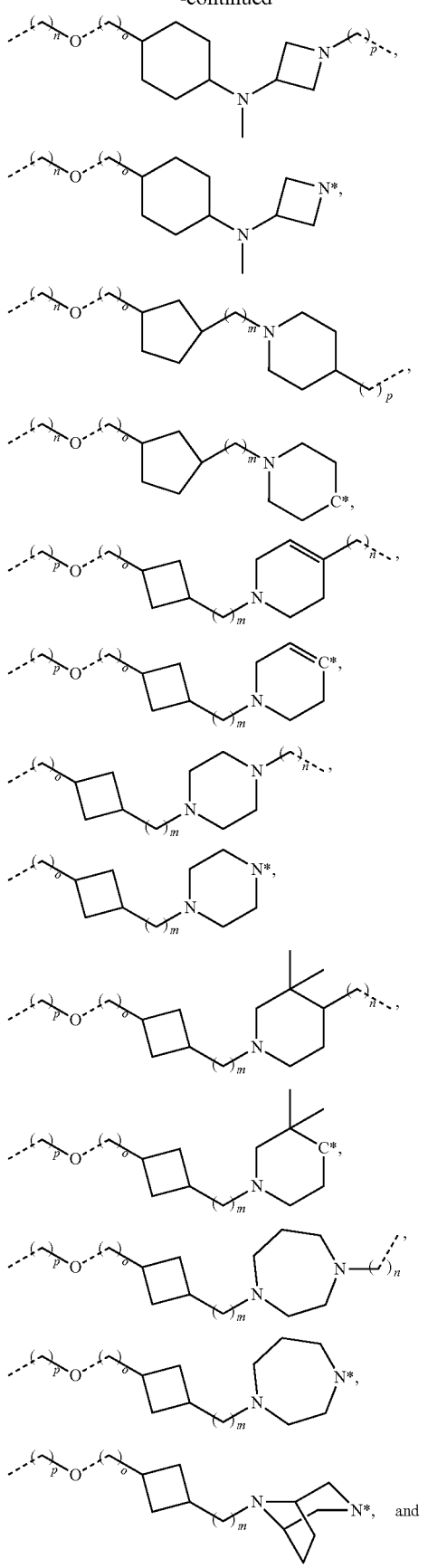

-continued

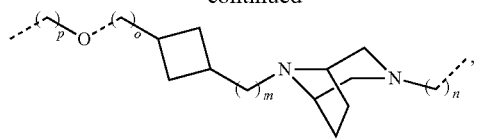

wherein:
  the above chemical linker groups that do not include substitutions are optionally substituted with at least one of: (i) =O and (ii) 1-4 (e.g., 1, 2, 3, or 4) substitutions independently selected from a $C_{1-3}$ alkyl (e.g., methyl) and a halogen (e.g., F, Cl, or Br);
  the * indicates an atom (e.g., a nitrogen or carbon) that is covalently linked to the CLM or the PTM, or that is shared with the CLM or the PTM;
  ⌁ indicates the attachment point to the PTM or the CLM; and
  each m, n, o, and p is independently 0, 1, 2, 3, 4, 5, 6, 7, 8, 9, or 10 (preferably 0, 1, 2, or 3).

In any aspect or embodiment described herein, the unit $A^L$ of the linker (L) comprises a group represented by a general structure selected from:

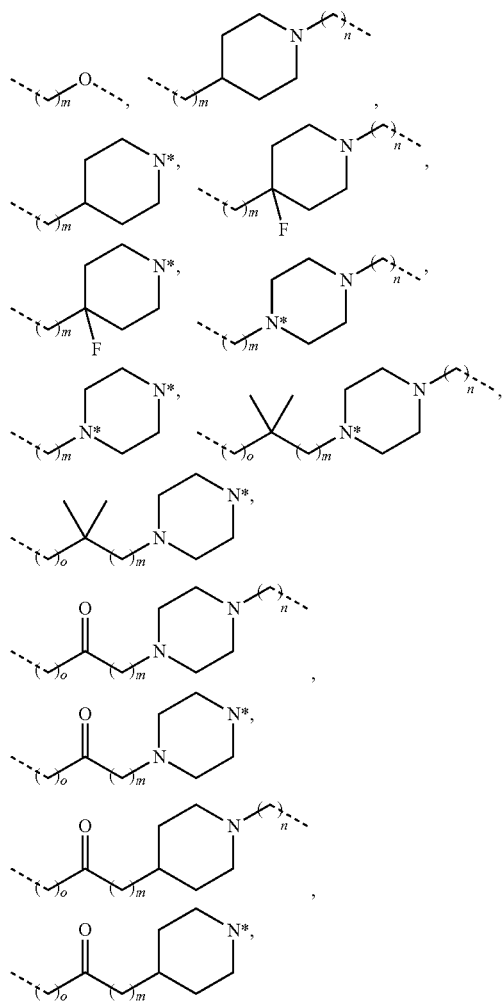

-continued

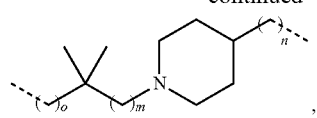
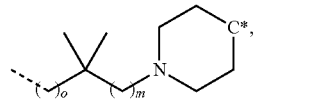
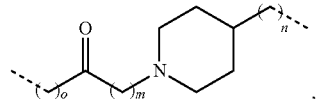
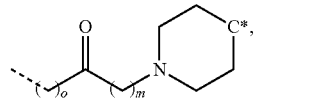
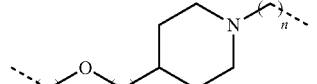
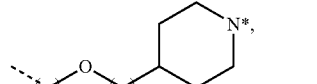
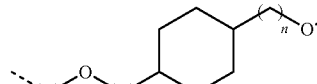
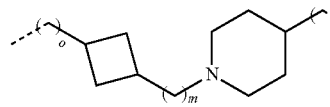
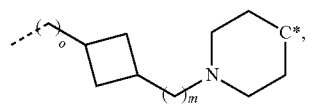
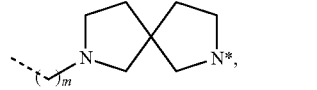
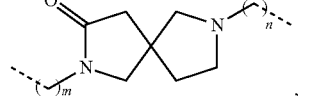

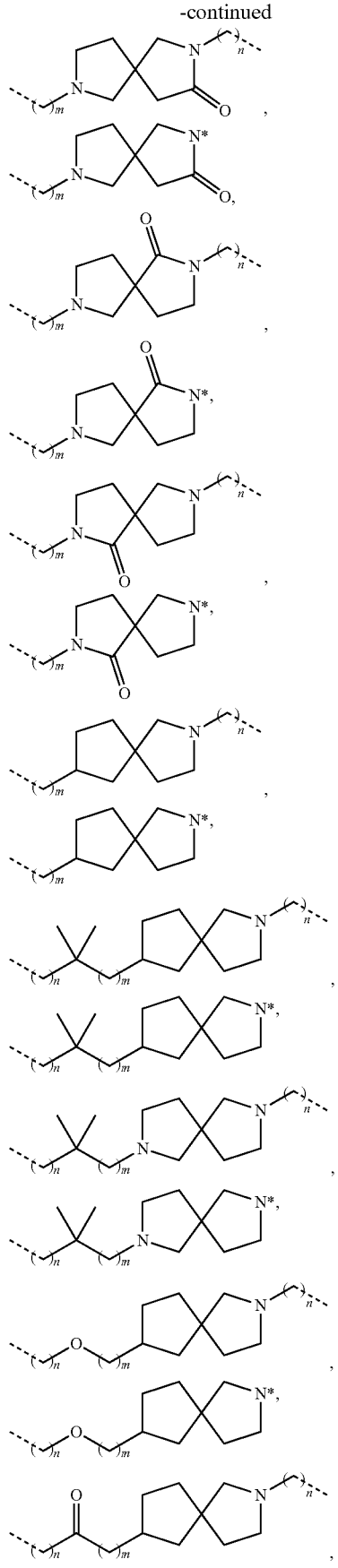
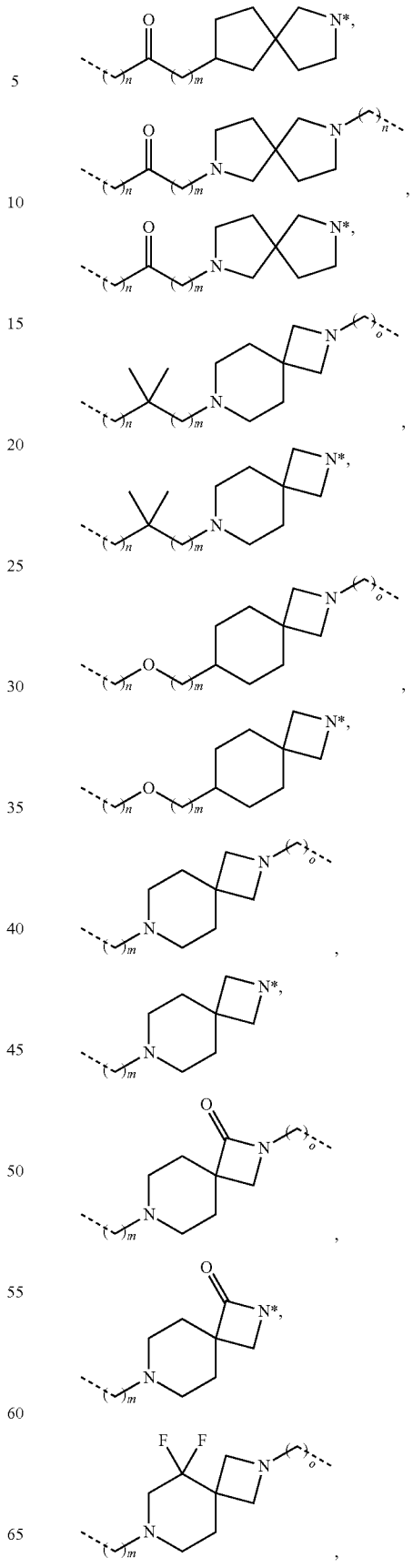

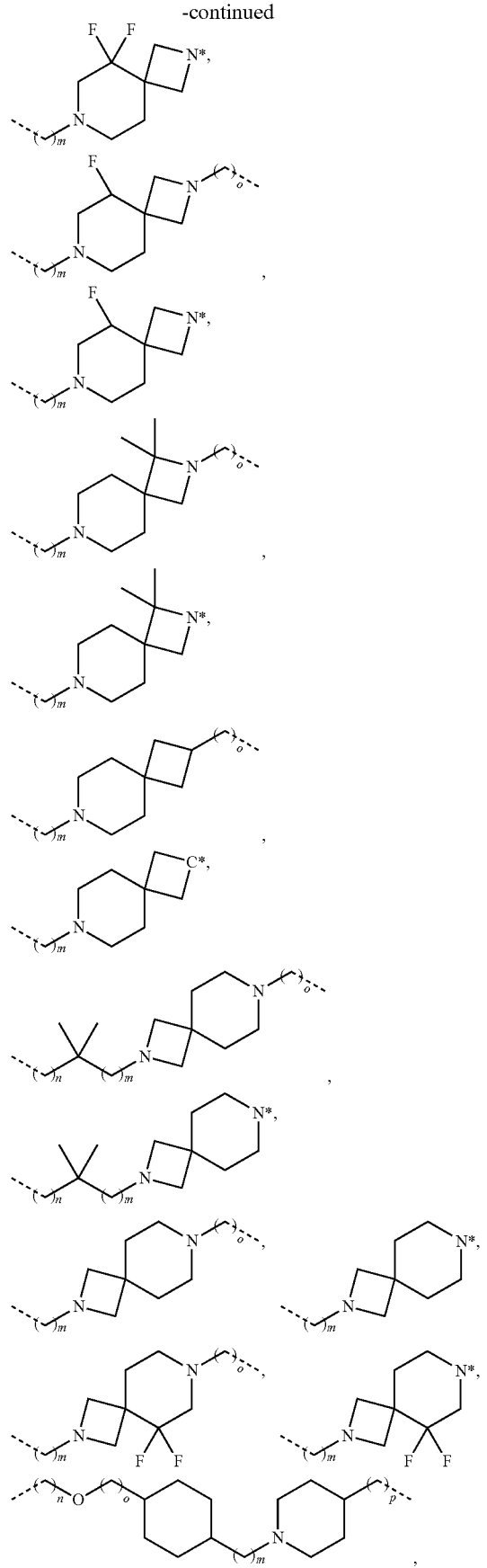
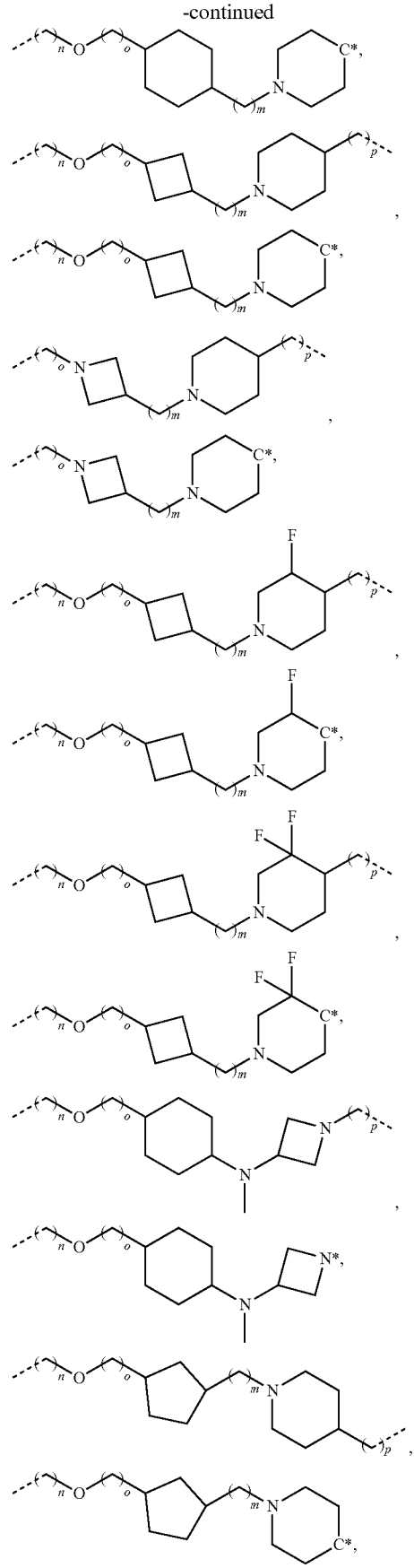

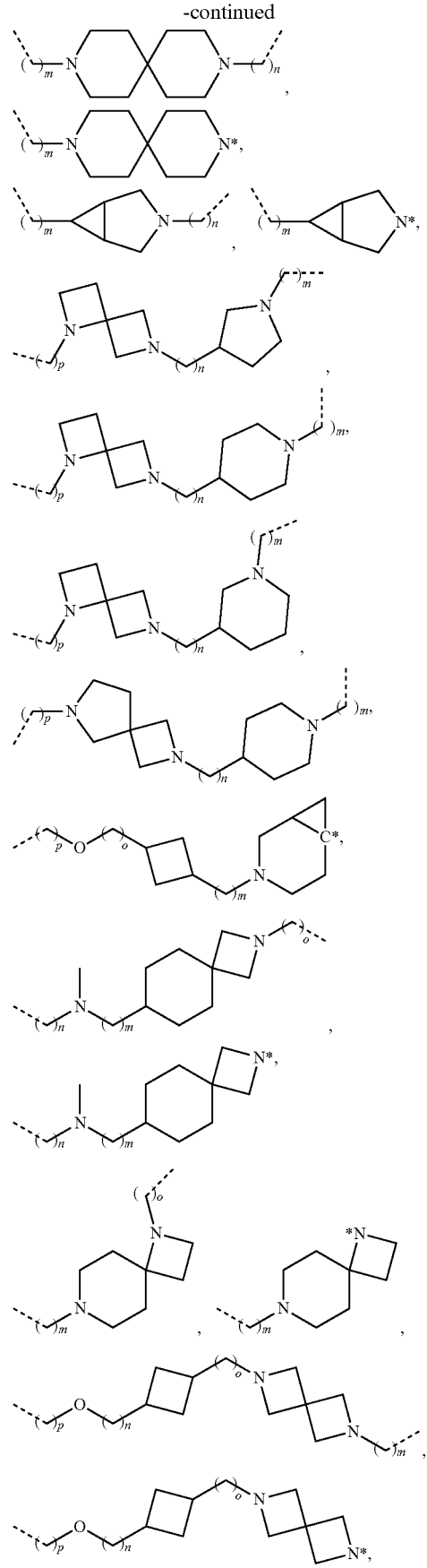
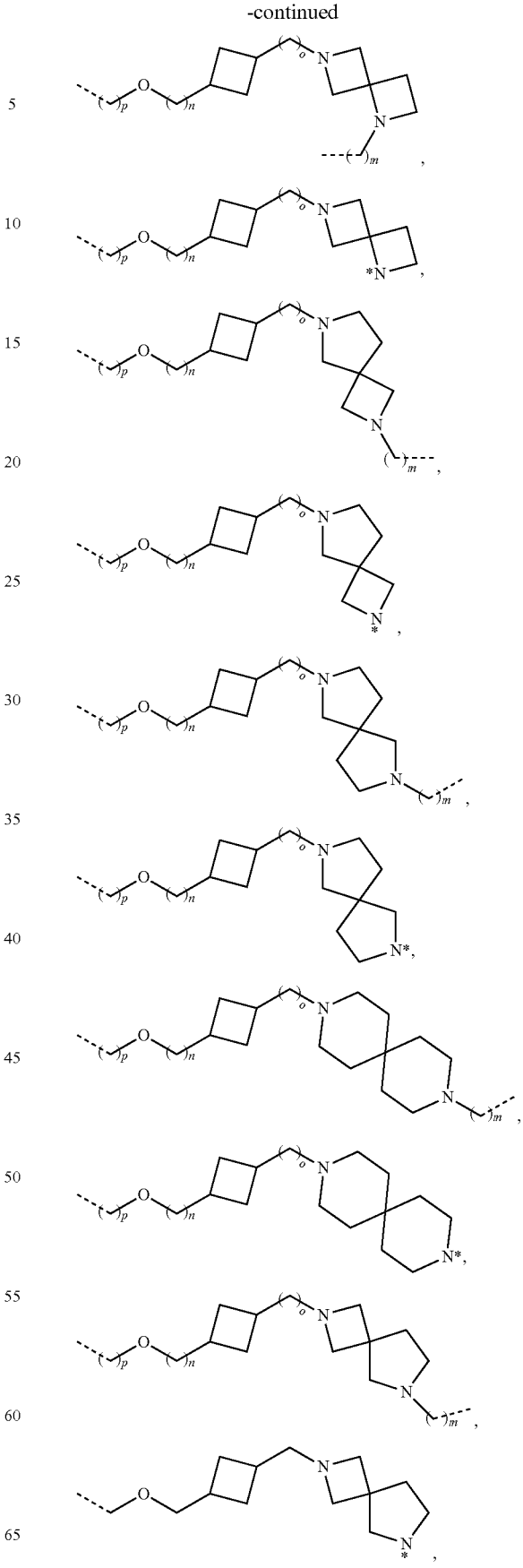

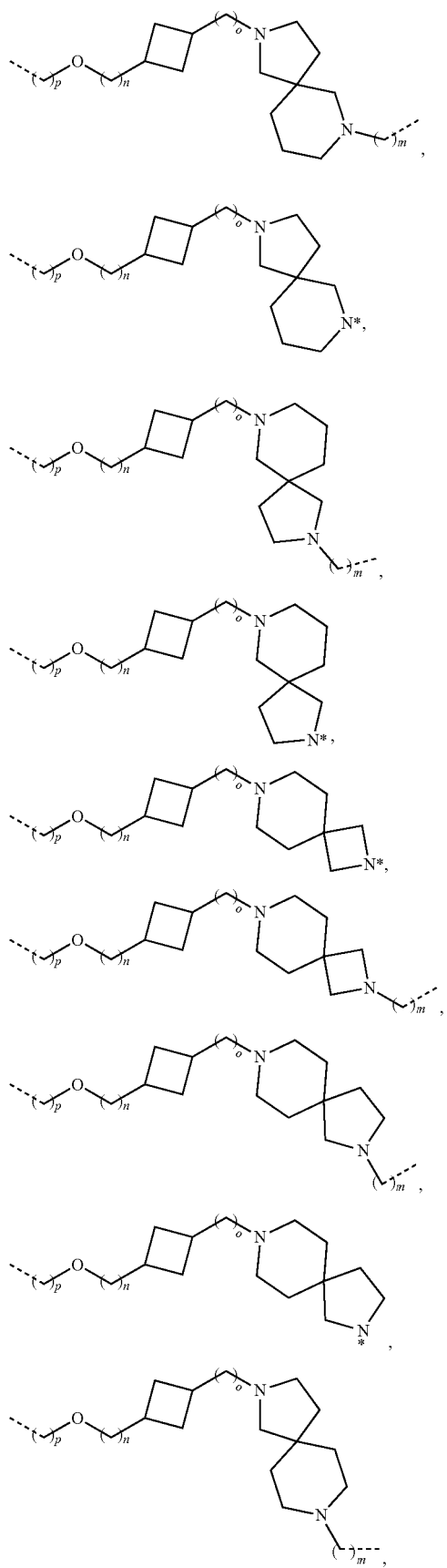

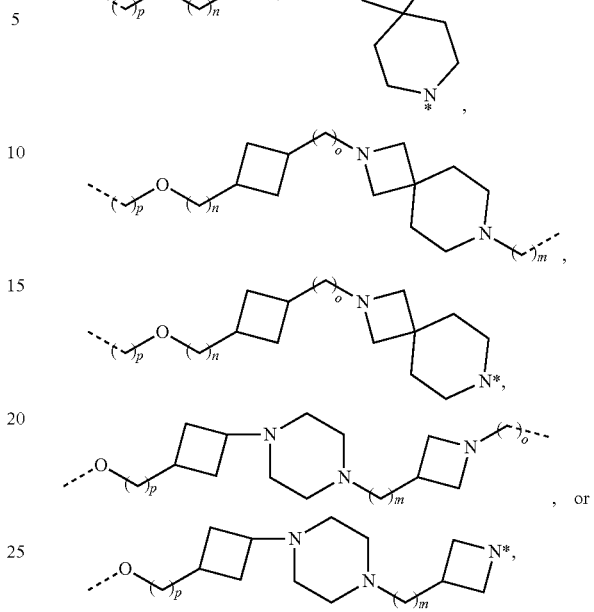

wherein:
the above linkers (L) that do not include substitutions are optionally substituted with at least one of: (i) =O and (ii) 1-4 (e.g., 1, 2, 3, or 4) substitutions independently selected from a $C_{1-3}$ alkyl (e.g., methyl) and a halogen (e.g., F, Cl, or Br);
the * indicates an atom (e.g., a nitrogen, carbon, or oxygen) that is covalently linked to the ULM or the PTM, or that is shared with the ULM or the PTM;
⌐ indicates the attachment point to the PTM or the ULM; and
each m, n, o, and is independently 0, 1, 2, 3, 4, 5, 6, 7, 8, 9, or 10 (preferably 0, 1, 2, or 3).

In any aspect or embodiment described herein, the linker has the chemical structure:

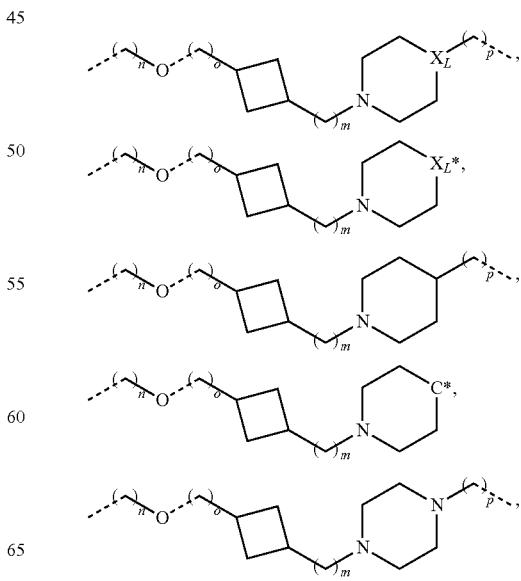

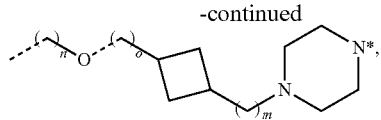

wherein:
X_L is a N or CH group;
each m, n, o, and p is independently 0, 1, 2, 3, 4, 5, 6, 7, 8, 9, or 10 (preferably 0, 1, 2, or 3);
the * indicates an atom (e.g., a nitrogen or carbon) that is covalently linked to the CLM or the PTM, or that is shared with the CLM or the PTM;
⁓ indicates the attachment point to the PTM or the CLM; and
the chemical linker includes 0-4 substitutions (preferably 0, 1, or 2 substitutions), each substitution independently a $C_{1-3}$ alkyl (preferably, methyl).

In any aspect or embodiment described herein, the linker has the chemical structure:

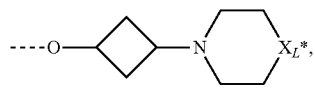

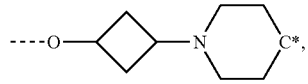

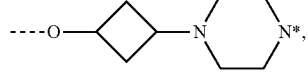

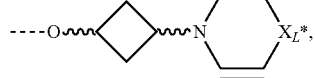

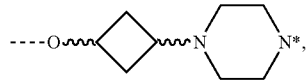

wherein:
X_L is N or CH group;
⁓ represents a stereospecific bond, wherein one has an (R) configuration and the other has an (S) configuration;
the * indicates an atom (e.g., a nitrogen or carbon) that is covalently linked to the CLM or the PTM, or that is shared with the CLM or the PTM;
⁓ indicates the attachment point to the PTM or the CLM; and the chemical linker includes 0-4 substitutions (preferably 0, 1, or 2 substitutions), each substitution independently a $C_{1-3}$ alkyl (preferably, methyl).

In any aspect or embodiment described herein, the unit $A^L$ of the linker (L) comprises a group represented by a structure selected from the group consisting of:

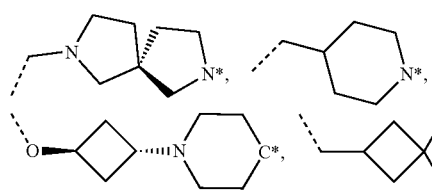

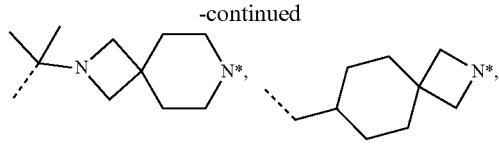

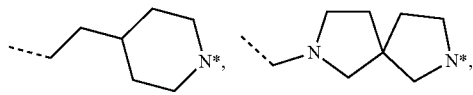

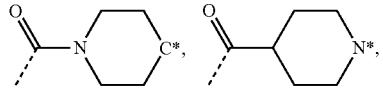

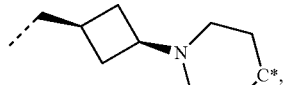

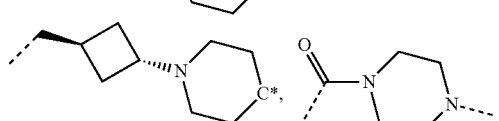

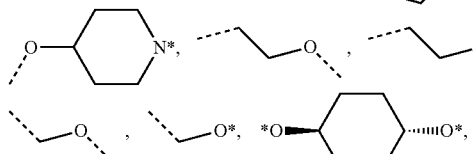

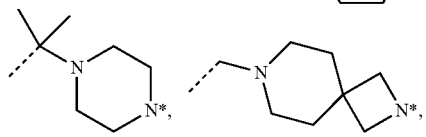

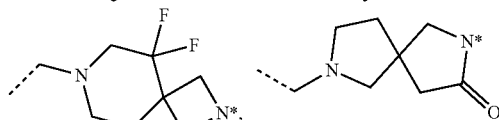

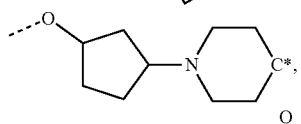

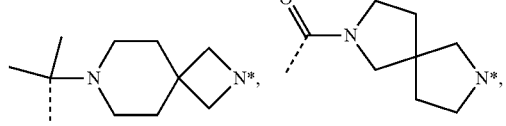

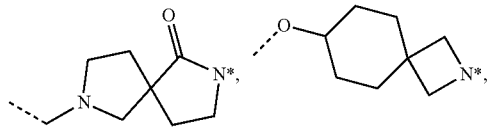

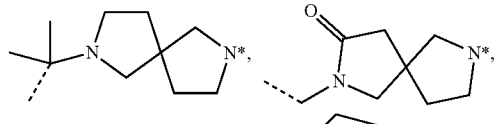

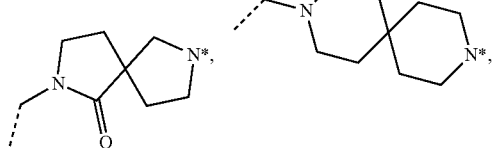

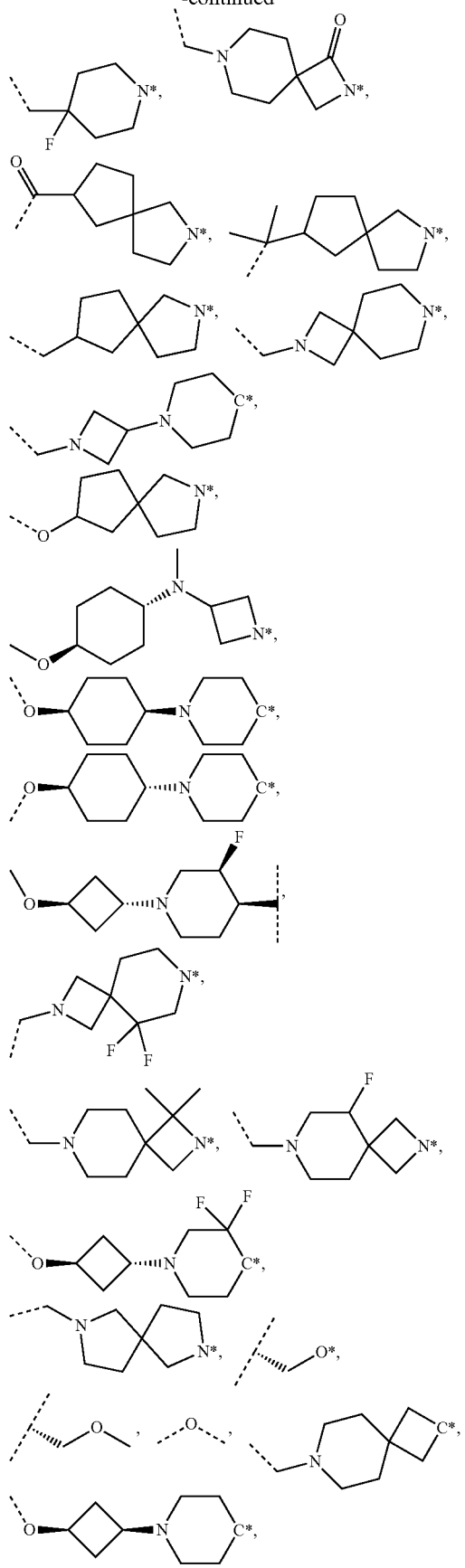
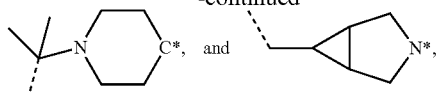

wherein * indicates an atom (e.g., a carbon, nitrogen, or oxygen) that is covalently linked to the ULM or PTM, or that is shared with the ULM or PTM, and each of ⋯, ⊦, ⊦, and ⊦ indicates the point of attachment with the ULM or the PTM.

In any aspect or embodiment described herein, the unit $A^L$ of the linker (L) comprises a group represented by a structure selected from the group consisting of:

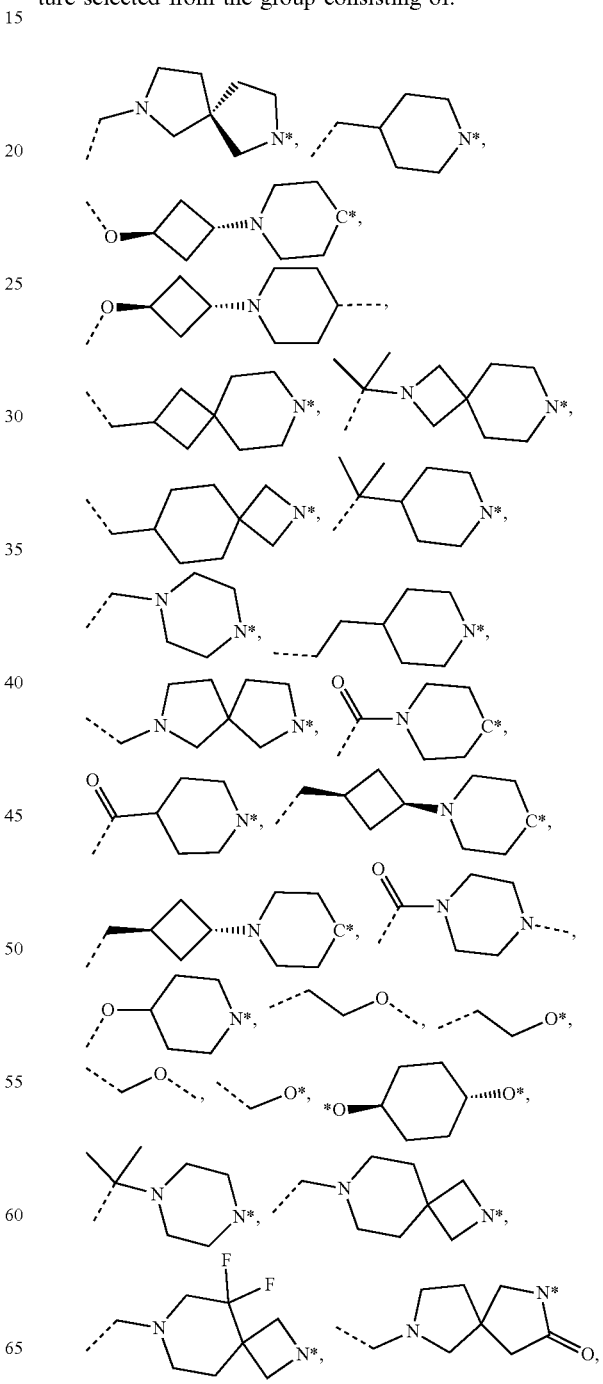

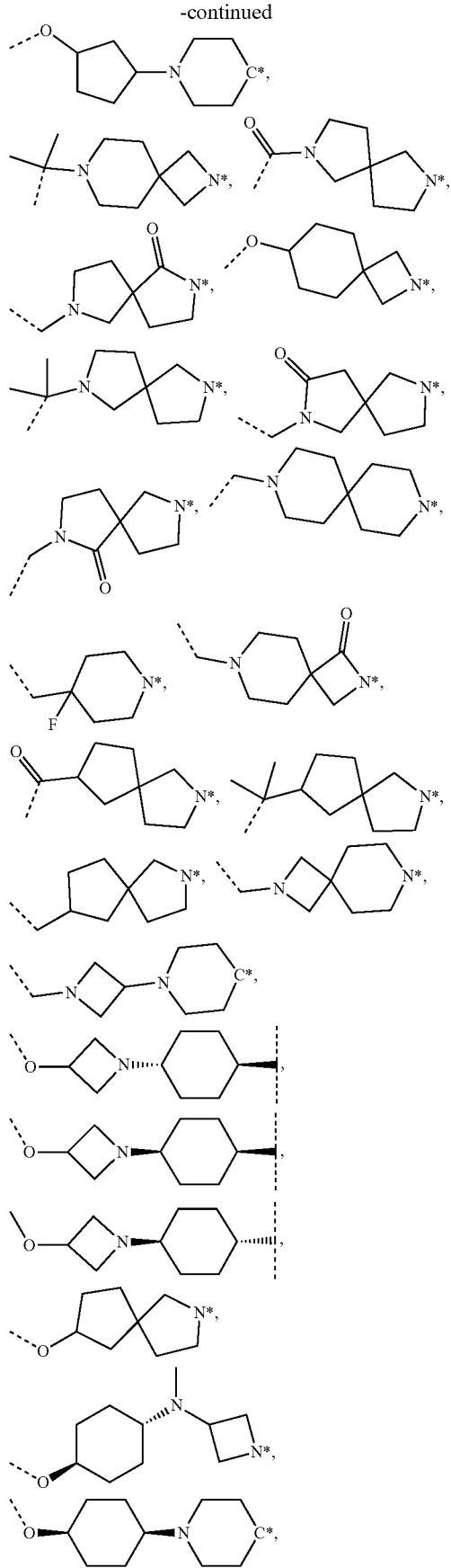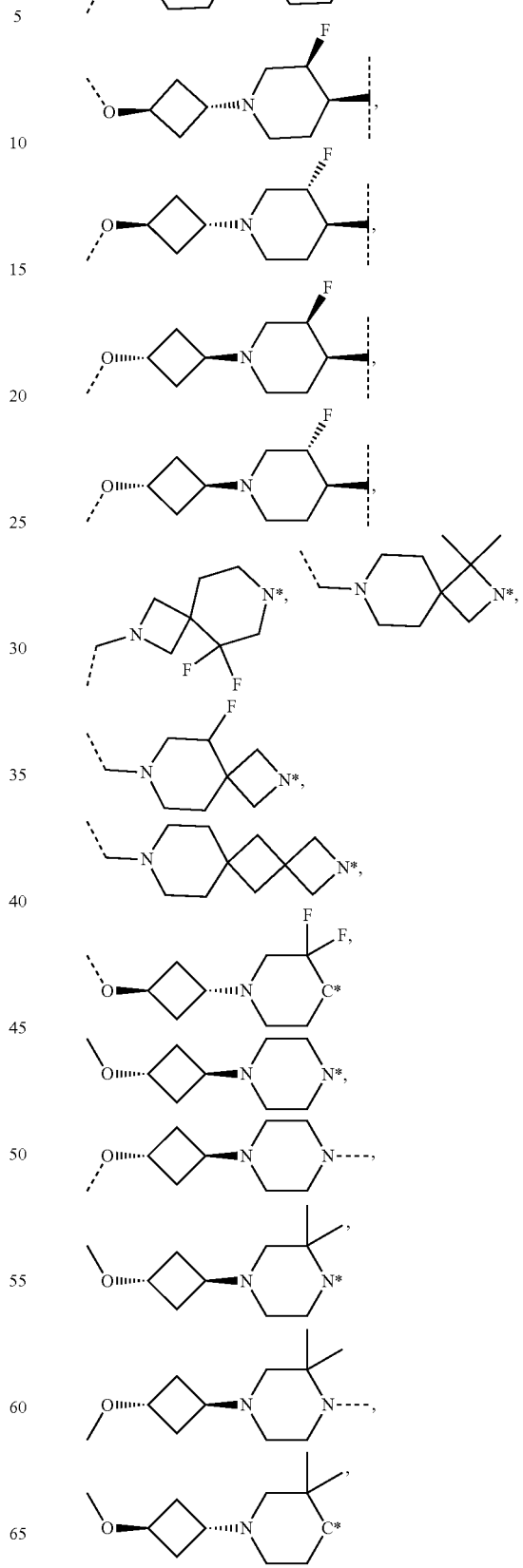

-continued
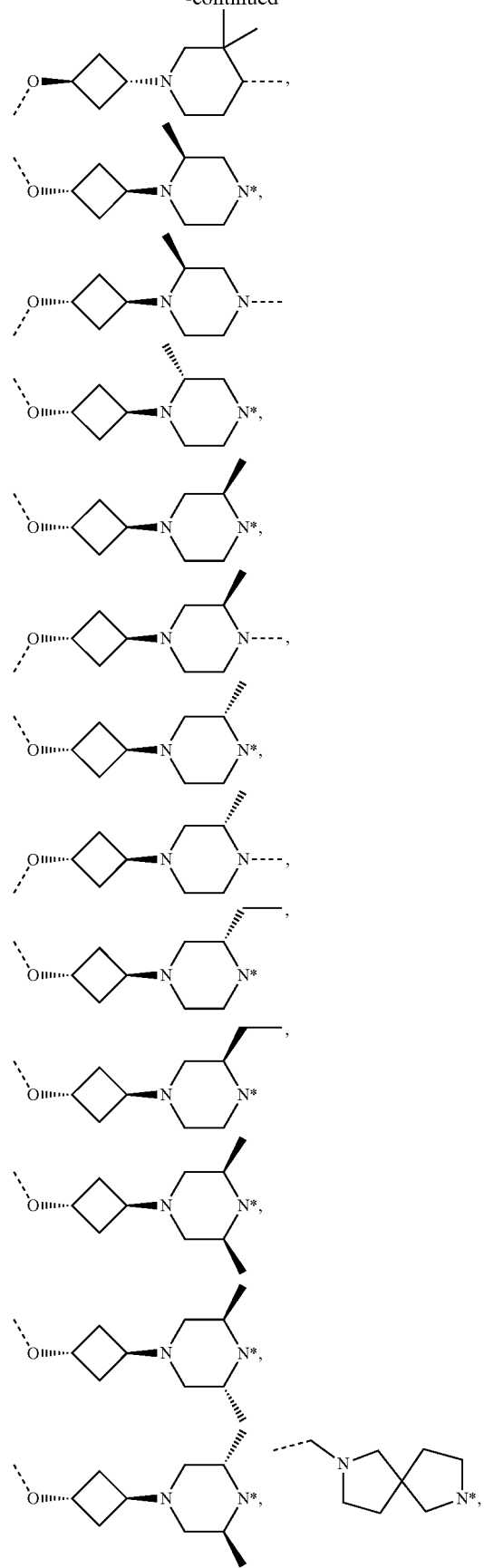
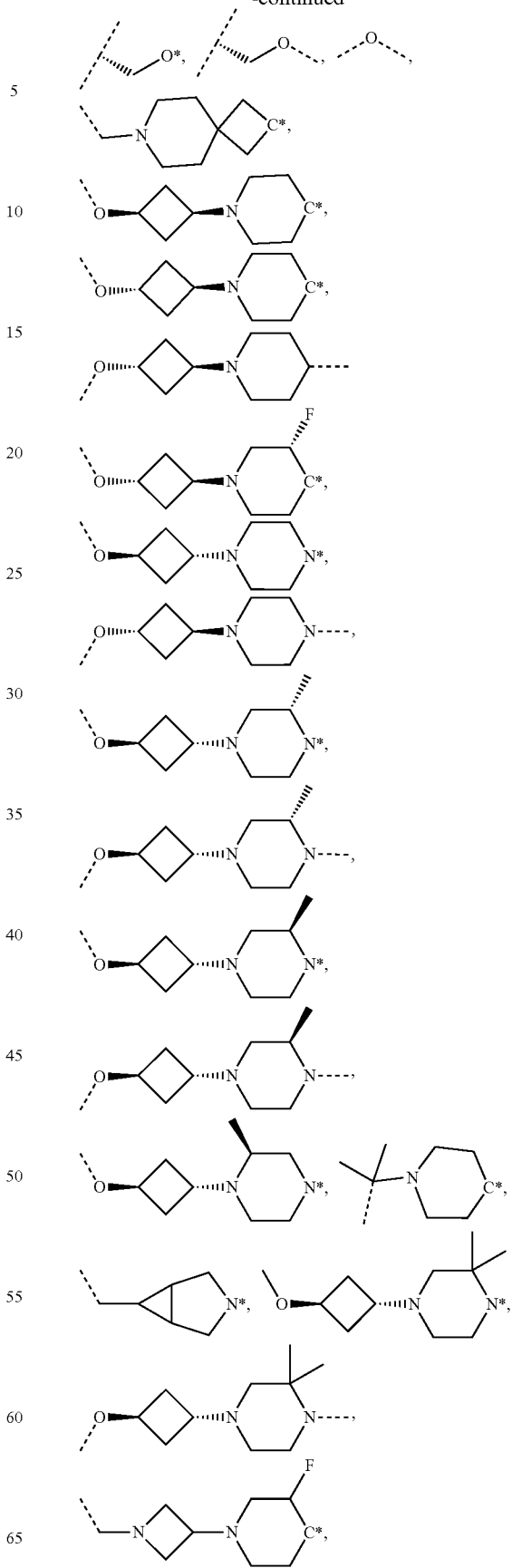

-continued
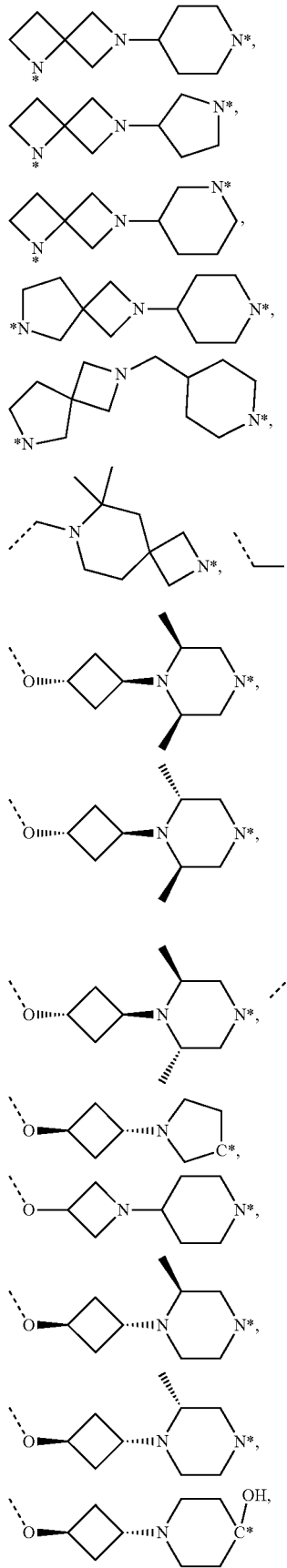
-continued
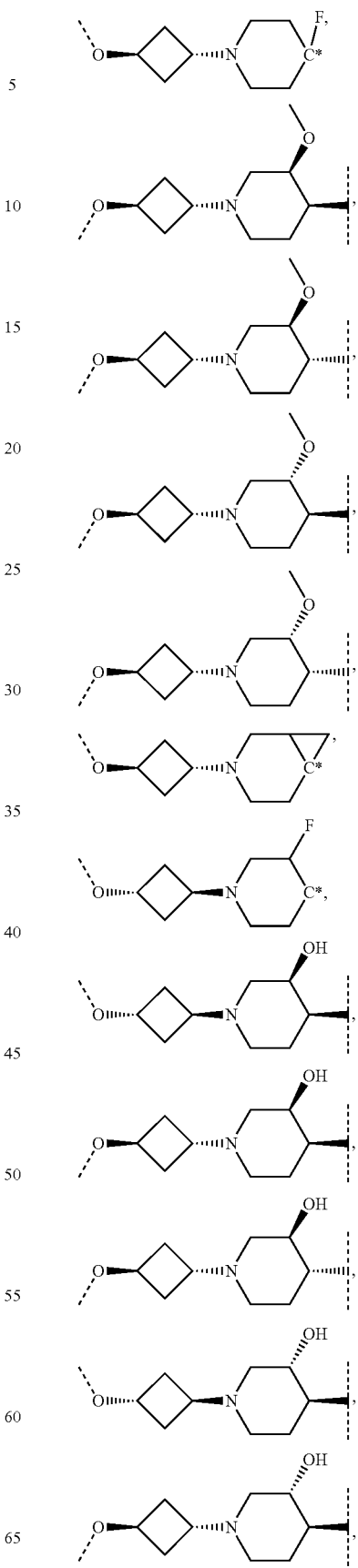

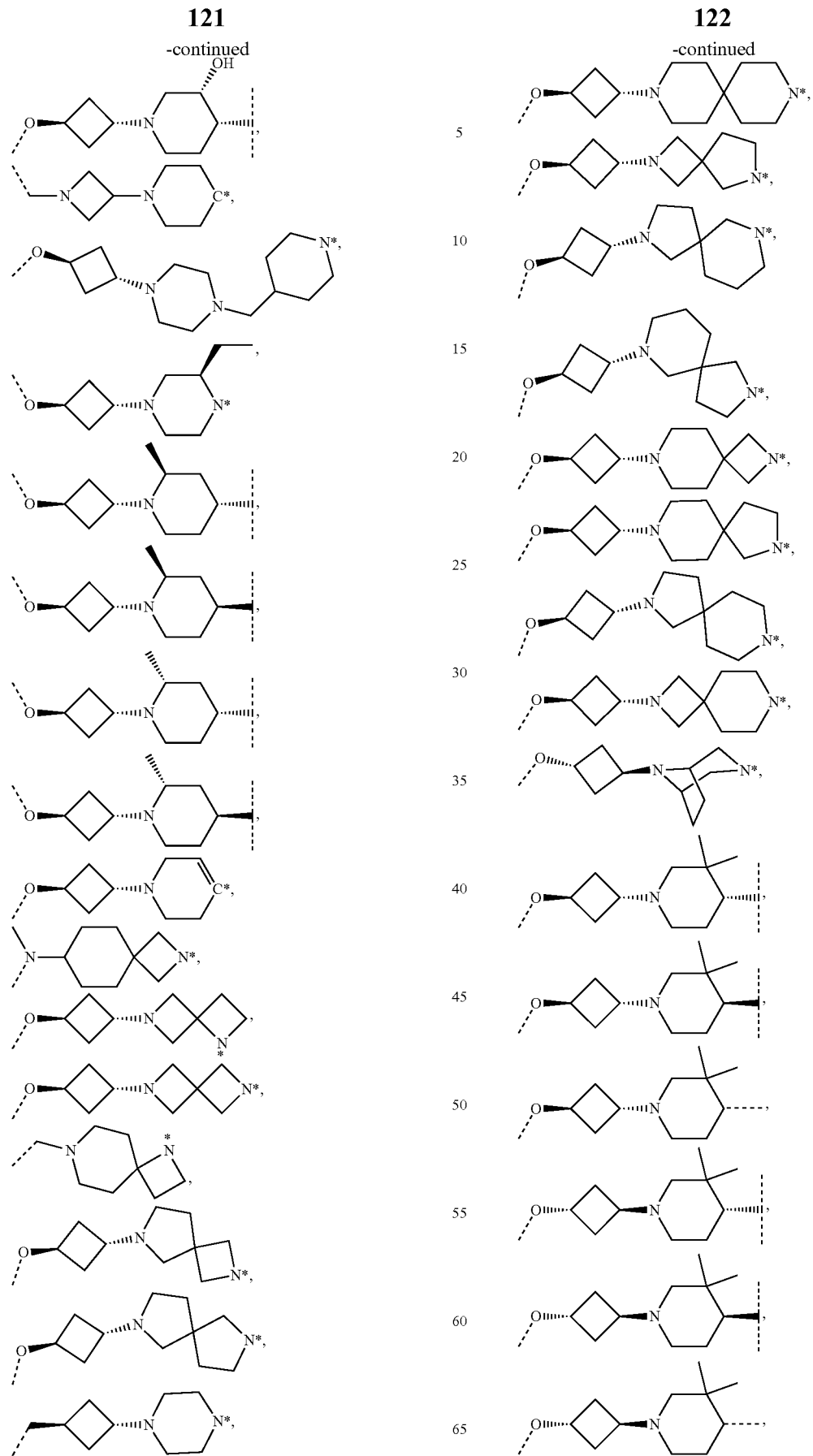

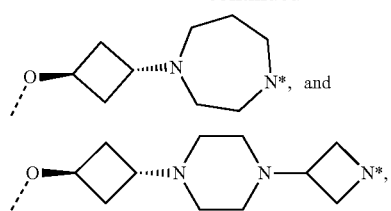

wherein * indicates an atom (e.g., a carbon, nitrogen, or oxygen) that is covalently linked to the CLM or PTM, or that is shared with the CLM or PTM, and each of ⋯, ⋎, ⋏, ⋰, ⋱, and ⋮ indicates the point of attachment with the CLM or the PTM.

In any aspect or embodiment described herein, the unit $A^L$ of the linker (L) comprises a group represented by a general structure selected from the group consisting of:

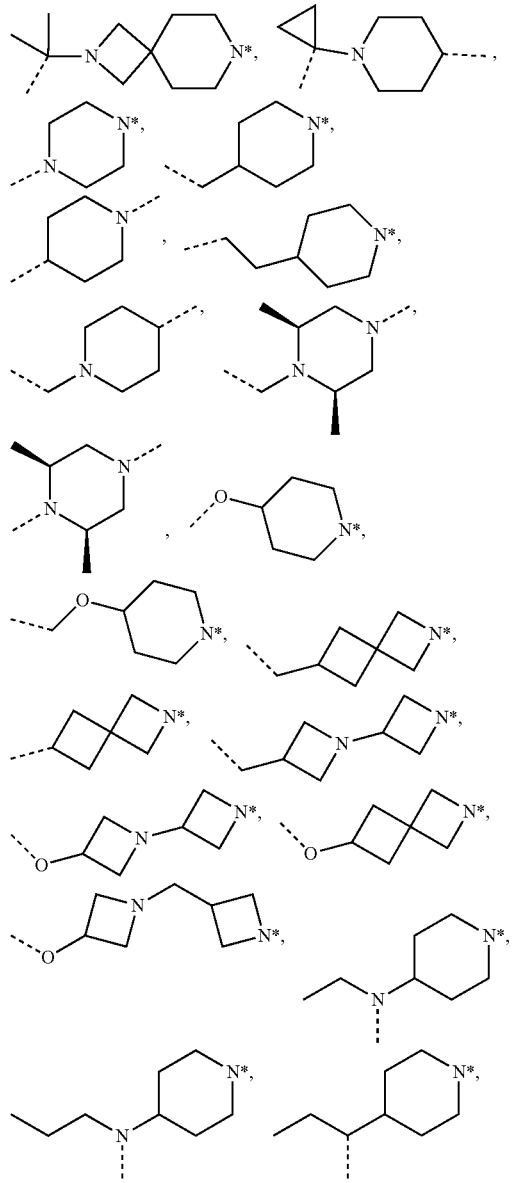
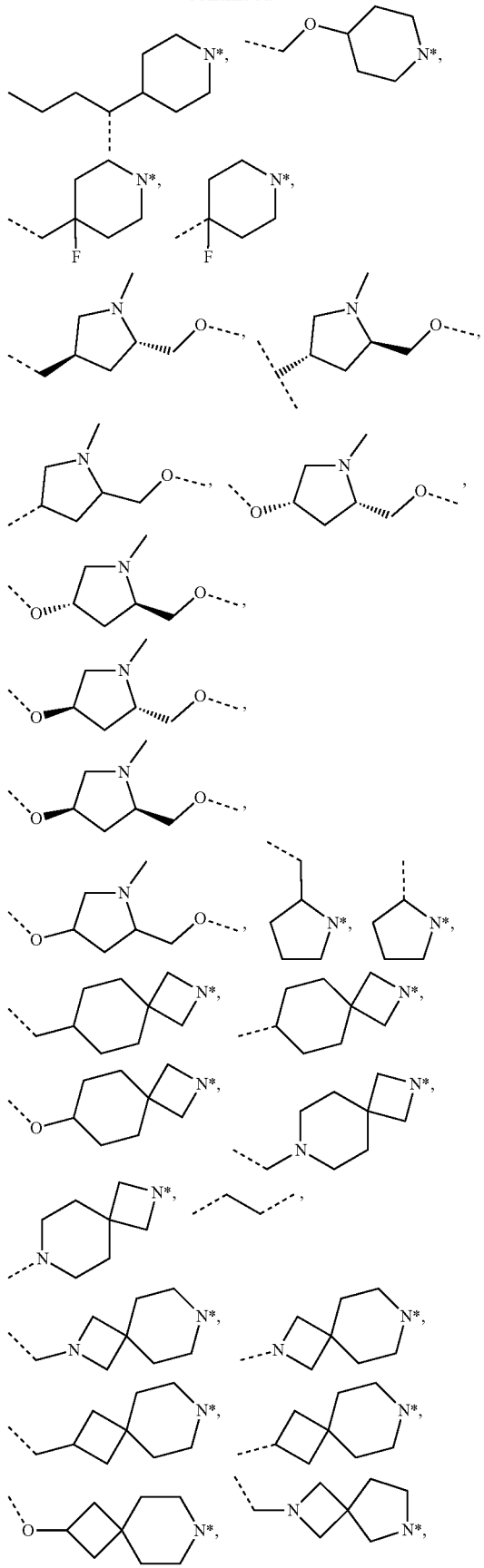

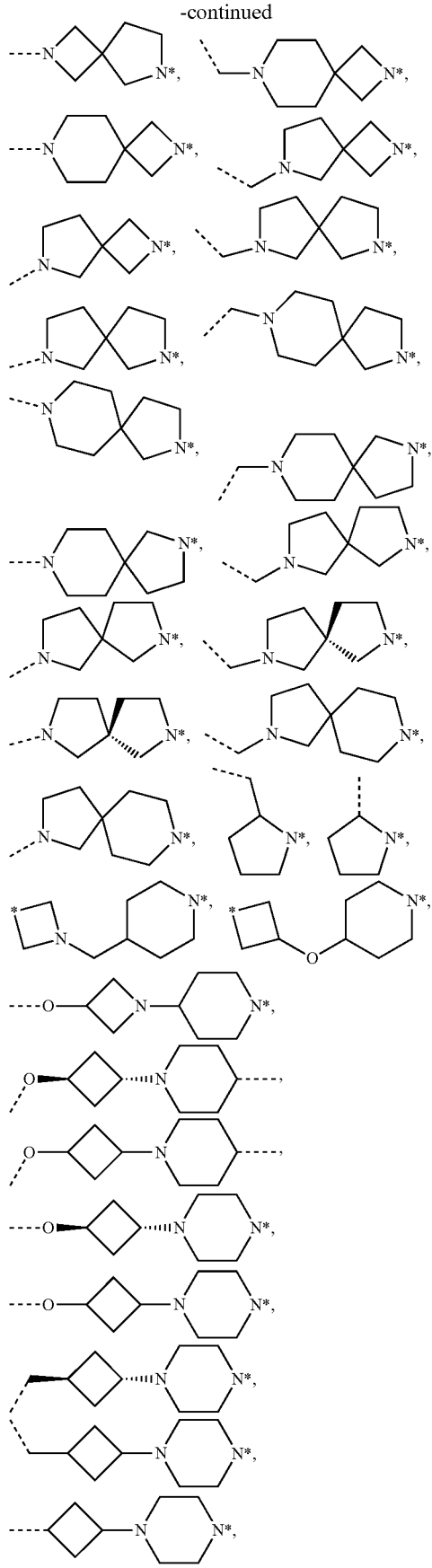

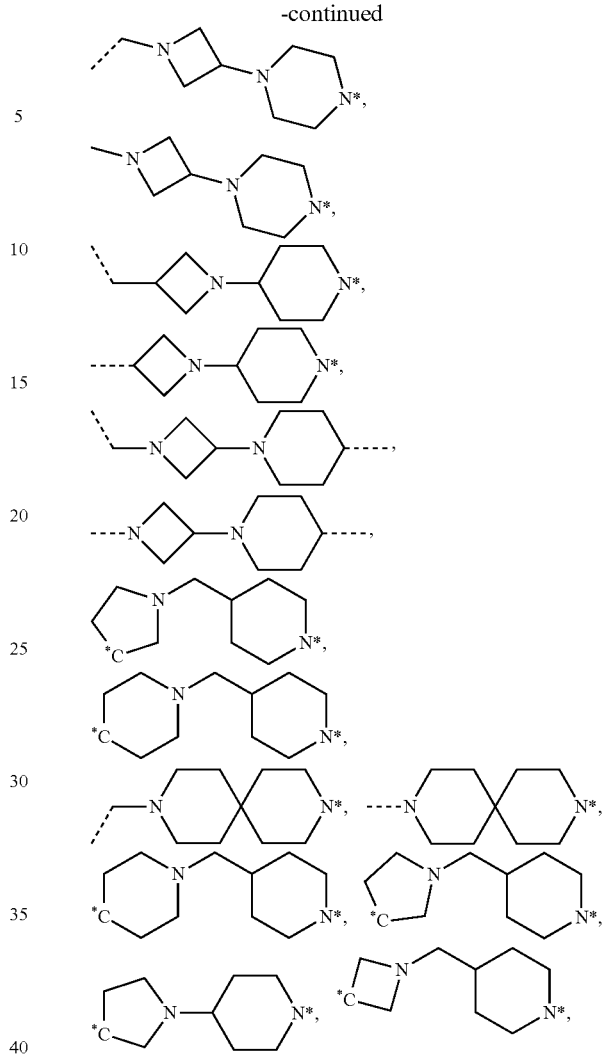

wherein * is a nitrogen or a carbon atom that is covalently linked to the ULM or PTM, or that is shared with the ULM or PTM, and ⋰ indicates the point of attachment with the ULM or the PTM.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: Hsp90 inhibitors, kinase inhibitors, BCL6 inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

The present disclosure may be used to treat a number of disease states and/or conditions, including any disease state and/or condition in which proteins are dysregulated and where a patient would benefit from the degradation and/or inhibition of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is lymphoma, B-cell non-Hodgkin lymphomas, large B-cell lymphoma, Burkitt's lymphoma, follicular lymphoma, intravascular large B-cell lymphoma, B-cell leukemia, B-cell acute lymphoblastic leukemia, chronic myeloid leukemia, non-small cell lung cancer.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. CLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFR1m, TNFR2, NADPH oxidase, BcllBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, BCL6, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvyl-shikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. The compositions described below exemplify some of the members of the small molecule target proteins. Exemplary protein target moieties according to the present disclosure include, haloalkane halogenase inhibitors, Hsp90 inhibitors, kinase inhibitors, BCL6 inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any aspect or embodiment described herein, the PTM is a small molecule that binds BCL6. For example, in any aspect or embodiment described herein, the PTM is represented by the chemical structure PTMI, PTMII, PTMIII, or PTMIV:

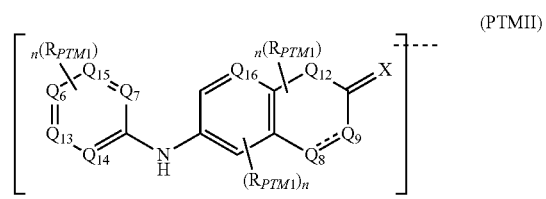

(PTMII)

wherein:
each $R_{PTM1}$ is independently: H; halogen (e.g., Cl or F); —CN; —OH; —NO$_2$; —NH$_2$; optionally substituted linear or branched alkyl (e.g., optionally substituted linear or branched C1-C6 alkyl or optionally substituted linear or branched C1-C4 alkyl or C1-C8 alkyl optionally substituted with OH or an isopropyl group); O-optionally substituted linear or branched C1-C4 alkyl; an optionally substituted C1-C4 alkynyl; an optionally substituted C1-C4 alkyne; optionally substituted linear or branched hydroxyalkyl (e.g., optionally substituted linear or branched C1-C7 hydroxyalkyl); optionally substituted alkylcycloalkyl (e.g., includes optionally substituted C1-C6 alkyl, optionally substituted C3-C10 cycloalkyl; or both); optionally substituted alkyl-aryl (e.g., includes an optionally substituted linear or branched C1-C6 alkyl, an optionally substituted 5-10 member heteroaryl, or both); optionally substituted alkyl-heteroaryl (e.g., includes an optionally substituted linear or branched C1-C6 alkyl, an optionally substituted 5-10 member heteroaryl, or both); optionally substituted alkyl-heteroaryl (e.g., includes a C1-C6 alkyl, an optionally substituted 5 or 6 member heteroaryl, optionally substituted with a C1-C4 alkyl; the heteroaryl is selected from oxazol-4-yl, 1,3,4-triazol-2-yl, and imidazole-1-yl; or combination thereof); optionally substituted —NH-alkyl-heteroaryl (e.g., an optionally substituted linear or branched C1-C5 alkyl, an optionally substituted 5-8 member heteroaryl, optionally substituted with a C1-C4 alkyl, N—CH$_2$-pyrazol-4-yl, or a combination thereof); optionally substituted alkoxy (e.g., an optionally substituted linear or branched C1-C6 alkyl or —OCH$_3$); optionally substituted O-heterocyclyl (e.g., includes an optionally substituted 3-12 or 4-7 member heterocyclyl; an optionally substituted heterocycloalkyl; an optionally substituted $C_{3-12}$ monocyclic or bicyclic heterocycloalkyl; optionally substituted with at least one OH, C1-C5 alkyl (such as a methyl), =O, NH$_2$, or a combination thereof; or a combination thereof); optionally substituted S-heterocyclyl (e.g., includes an optionally substituted 4-7 member heterocyclyl; an optionally substituted heterocycloalkyl;

optionally substituted with at least one C1-C4 alkyl (such as a methyl), =O, or a combination thereof; or a combination thereof); optionally substituted

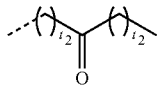

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5); optionally substituted

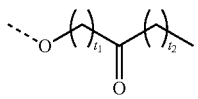

(e.g., optionally substituted with a linear or branched C1-C4 alkyl; —O(CH$_2$)$_u$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$CO-CH$_3$, or —OCH$_2$(CH$_3$)COCH$_3$, wherein each u, v, w, and x is independently selected from 1, 2, 3, 4 or 5); optionally substituted

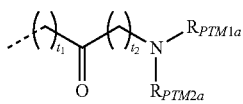

(e.g., optionally substituted with a linear or branched C1-C4 alkyl; —(CH$_2$)$_u$CO(CH$_2$)$_v$NR$_{PTM1a}$R$_{PTM2a}$, —CONR$_{PTM1a}$R$_{PTM2a}$, —CH$_2$CONR$_{PTM1a}$R$_{PTM2a}$, —CH$_2$CH$_2$CO-NR$_{PTM1a}$R$_{PTM2a}$, —CONHCH$_3$, or —CH$_2$CONHCH$_3$, wherein each u and v is independently selected from 1, 2, 3, 4 or 5); optionally substituted

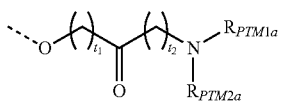

(e.g., optionally substituted with a linear or branched C1-C4 alkyl; —O(CH$_2$)$_u$CO(CH$_2$)$_v$NR$_{PTM1a}$R$_{PTM2a}$, —O(CH$_2$)$_n$CH((CH$_2$)$_x$CH$_3$)(CH$_2$)$_w$CO(CH$_2$)$_v$NR$_{PTM1a}$R$_{PTM2a}$, —O—CH(CH$_3$)CONR$_{PTM1a}$R$_{PTM2a}$, —O—CH$_2$CONR$_{PTM1a}$R$_{PTM2a}$, or —OCH$_2$C(O)NHOCH$_3$, wherein each u, v, w, and x is independently selected from 1, 2, 3, 4 or 5); optionally substituted

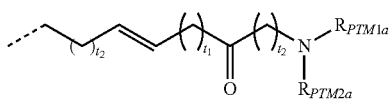

(e.g., optionally substituted with a linear or branched C1-C4 alkyl; —(CH$_2$)$_n$CHCH(CH$_2$)$_w$CO(CH$_2$)$_v$ NR$_{PTM1a}$R$_{PTM2a}$ or —CHCHCONR$_{PTM1a}$R$_{PTM2a}$, wherein each u, v, and w is independently selected from 1, 2, 3, 4 or 5); optionally substituted

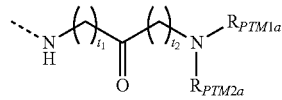

(e.g., optionally substituted with a linear or branched C1-C4 alkyl; —NH—(CH$_2$)$_u$CO(CH$_2$)$_v$NR$_{PTM1a}$R$_{PTM2a}$ or —NH—CH$_2$CONR$_{PTM1a}$R$_{PTM2a}$, wherein each u and v is independently selected from 1, 2, 3, 4 or 5); fluoroalkoxy (e.g., a mono-, bi- and/or tri-fluoroalkoxy); optionally substituted monocyclic or bicyclic cycloalkyl (e.g., an optionally substituted 3-12 member cycloalkyl; optionally substituted with at least one of OH, =O, linear or branched C1-C6 alkyl (such as a methyl, ethyl, or butyl), or NH$_2$; or a combination thereof); optionally substituted hydroxycycloalkyl; optionally substituted aryl (e.g., an optionally substitute C5-C10 aryl, an optionally substituted 5-7 member aryl; optionally substituted with at least one halogen or C1-C3 alkyl (e.g., methyl or ethyl); or a combination thereof), optionally substituted heteroaryl (e.g., an optionally substituted 5-10 or member heteroaryl, an optionally substituted 5-7 member heteroaryl; an optionally substituted 5-member heteroaryl; optionally substituted with at least one halogen or C1-C3 alkyl (e.g., methyl or ethyl); or a combination thereof) optionally linked to Q$_6$, Q$_7$, Q$_8$, Q$_9$, Q$_{10}$, Q$_{11}$, Q$_{12}$, Q$_{13}$, Q$_{14}$, or Q$_{15}$ via a C or N-atom of the heteroaryl (e.g., at least one of optionally linked to Q$_{16}$, optionally linked via an optionally substituted —(CH$_2$)$_u$O(CH$_2$)$_v$O(CH$_2$)$_x$—, or a combination thereof); optionally substituted monocyclic or bicyclic heterocyclyl (e.g., an optionally substituted 3-12 member heterocyclyl; an C3-C12 monocyclic or bicyclic heterocycloalkyl, azetidine1-yl, pyrrolidin-1-yl, piperidin-1yl, piperazin-1-yl, or morpholin-4-yl, or homopiperazin-1-yl, each optionally substituted with OH, a linear or branched C1-C5 alkyl (a methyl, ethyl, or butyl group) or NH$_2$) optionally linked to Q$_6$, Q$_7$, Q$_8$, Q$_9$, Q$_{10}$, Q$_{11}$, Q$_{12}$, Q$_{13}$, Q$_{14}$, or Q$_{15}$ via a C or N atom of the heterocyclyl (e.g., at least one of optionally linked to Q$_{16}$, optionally linked via an optionally substituted —(CH$_2$)$_u$O(CH$_2$)$_v$O(CH$_2$)$_x$—, or both);

each t$_1$ is independently 1, 2, 3, 4, or 5;
each t$_2$ is independently 0, 1, 2, 3, 4, or 5;
each R$_{PTM1a}$ and R$_{PTM2a}$ is independently H, optionally substituted C1-C4 alkyl (e.g., a CH$_3$ or CH$_2$CH$_3$), optionally substituted C1-C4 alkoxy (e.g., —OCH$_2$ or —CH$_2$CH$_3$), CH$_2$OCH$_3$ or R$_{PTM1a}$ and R$_{PTM2a}$ are joined together form a 3-10 member ring;
Q$_6$, Q$_7$, Q$_8$, Q$_9$, Q$_{12}$, Q$_{13}$, Q$_{14}$, and Q$_{15}$ are each independently N, O, or C, each optionally substituted with one or more independently selected R$_{PTM1}$ (e.g., 1, 2, or 3 independently selected R$_{PTM1}$, depending upon valency);
Q$_{16}$ is C substituted with H, halogen (e.g., Cl or F), —CN, —OH, —NO$_2$, —NH$_2$, optionally substituted linear or branched alkyl (e.g., optionally substituted linear or branched C1-C6 alkyl or optionally substituted linear or branched C1-C4 alkyl or C1-C8 alkyl optionally substituted with OH or an isopropyl group), O-optionally substituted linear or branched C1-C4 alkyl, an optionally substituted C1-C4 alkynyl, an optionally substituted C1-C4 alkyne, or optionally substituted linear or branched hydroxyalkyl (e.g., optionally substituted linear or branched C1-C7 hydroxyalkyl), preferably H, halogen, —CN, —OH, —NO$_2$, —NH$_2$, or optionally substituted linear or branched alkyl;

X is O, S, or CH₂;
⚞ is a single bond or a double bond;
n is an integer from 0 to 10; and
⚞ of the PTM indicates the point of attachment with a chemical linker group or a ULM.

In any aspect or embodiment described herein, the PTM is selected from:

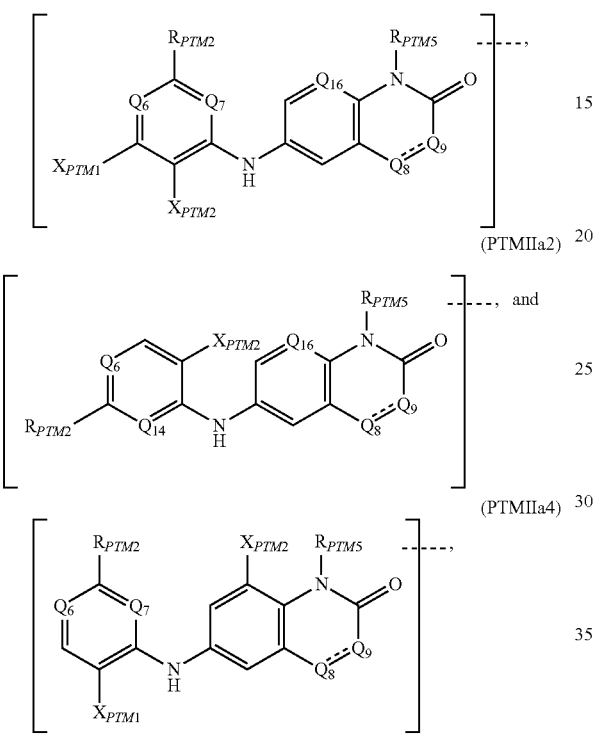

wherein:
$R_{PTM5}$ is H, optionally substituted linear or branched C1-C6 alkyl (e.g. methy, ethyl, or isopropyl group), C1-C4 alkyl-O(C1-C3 alkyl), C1-C4 alkyl-O—, C1-C4 alkyl-NH(C1-C3 alkyl), C1-C4 alkyl-N(C1-C3 alkyl)₂, optionally substituted C5-C10 aryl, optionally substituted C5-C10 heteroaryl, optionally substituted C3-C10 cycloalkyl, or optionally substituted C3-C10 heterocyclyl;
$Q_6$ and $Q_{16}$ are each independently N or CH;
$Q_7$ and $Q_{14}$ are each independently N or CH;
$X_{PTM1}$ is H, Cl, or F;
$X_{PTM2}$ is H, Cl, F, or CN;
⚞ of $Q_8$ and $Q_9$ is a single bond or a double bond, wherein
when $Q_8$ and $Q_9$ are connected by a single bond:
$Q_8$ is CH₂; and
$Q_9$ is CH($R_{PTM3}$) or N($R_{PTM3}$);
when $Q_8$ and $Q_9$ are connected by a double bond:
$Q_8$ is CH; and
$Q_9$ is C($R_{PTM3}$);
$R_{PTM3}$ is: —OH; —Cl; —F; —CN; optionally substituted linear or branched C1-C6 alkyl, optionally substituted C1-C6 alkoxy (e.g., —OCH₃, or —OCH₂CH₃); optionally substituted

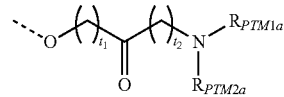

(e.g., optionally substituted with a linear or branched C1-C4 alkyl, C1-C4 alkoxy, —Cl; —F, —CN, or —OH); or optionally substituted

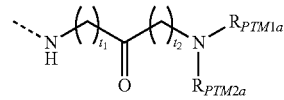

(e.g., optionally substituted with a linear or branched C1-C4 alkyl, C1-C4 alkoxy, —Cl, —F, —CN, or —OH);
each $R_{PTM1a}$ and $R_{PTM2a}$ is independently H, optionally substituted C1-C4 alkyl (e.g., a CH₃ or CH₂CH₃), optionally substituted C1-C4 alkoxy (e.g., —OCH₃ or —OCH₂CH₃), or CH₂OCH₃;
each $t_1$ is independently 1, 2, 3, 4, or 5; and
each $t_2$ is independently 0, 1, 2, 3, 4, or 5;
$R_{PMT2}$ is H, OH, CN, —F, —Cl, optionally substituted linear or branched C1-C4 alkyl, optionally substituted —NH₂ (e.g., —N(C1-C3 alkyl)₂ or —NH(C1-C3 alkyl)), optionally substituted linear or branched —O—C1-C4 alkyl, an optionally substituted monocyclic or bicyclic C3-C12 heterocycloalkyl (e.g., azetidine1-yl, azetidine1-yl-3-ol, pyrrolidin-1-yl, piperidin-1yl, piperazin-1-yl, or morpholin-4-yl, homopiperazin-1-yl,

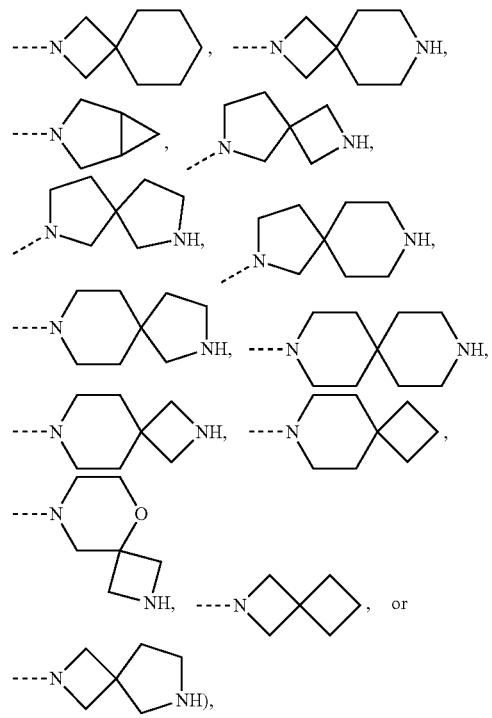

each optionally substituted with one or more of OH, a linear or branched C1-C6 alkyl, C1-C6 alkoxy —CN, —F, —Cl, or NH₂), an optionally substituted —O—C₃₋₁₂ monocyclic or bicyclic heterocycloalkyl (e.g. optionally substituted with one or more OH, a linear or branched C1-C6 alkyl, C1-C6 alkoxy, —CN, —F, —Cl, or NH$_2$), or an optionally substituted C3-C12 cycloalkyl (e.g., optionally substituted with one or more of OH, linear or branched C1-C6 alkyl, C1-C6 alkoxy, —CN, —F, —Cl, or NH$_2$), an optionally substituted C5-C6 heteroaryl (e.g. optionally substituted with one or more linear or branched C1-C6 alkyl, C1-C6 alkoxy, —CN, —F, —Cl, or NH$_2$), or an optionally substituted C5-C6 aryl (e.g. optionally substituted with one or more linear or branched C1-C6 alkyl, C1-C6 alkoxy, —CN, —F, —Cl, or NH$_2$); and the ⋰ of the PTM indicates the point of attachment with the L.

In any aspect or embodiment described herein, ⋰ of $Q_8$ and $Q_9$ is a double bond, $Q_8$ is CH, and $Q_9$ is C($R_{PTM3}$)

In any aspect or embodiment described herein, at least one $R_{PMT1}$ of PTMII, or the associated location of other PTM structures described herein is modified to be covalently linked to a linker group (L) or a ULM. In any aspect or embodiment described herein, at least one of $Q_6$-$Q_{15}$ of PTMII, or the associated location of other PTM structures described herein is modified to be covalently linked to a chemical linker group (L) or a ULM.

In any aspect or embodiment described herein, the X of the PTM (e.g., PTMII, or the associated location of other PTM structures described herein) is O.

In any aspect or embodiment described herein, the PTM is selected from:

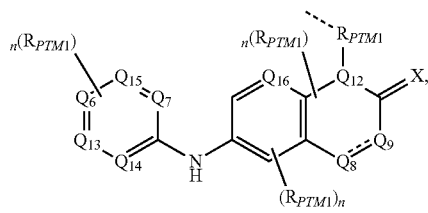

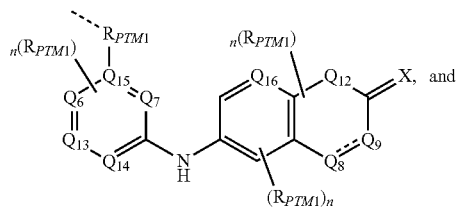

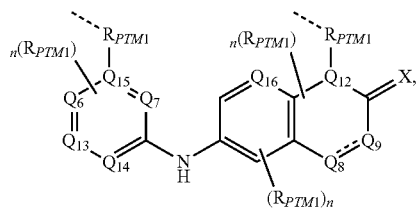

wherein the ⋰ of the PTM indicates the point of attachment with a chemical linker group (L) or a ULM.

In any aspect or embodiment described herein, the PTM is selected from:

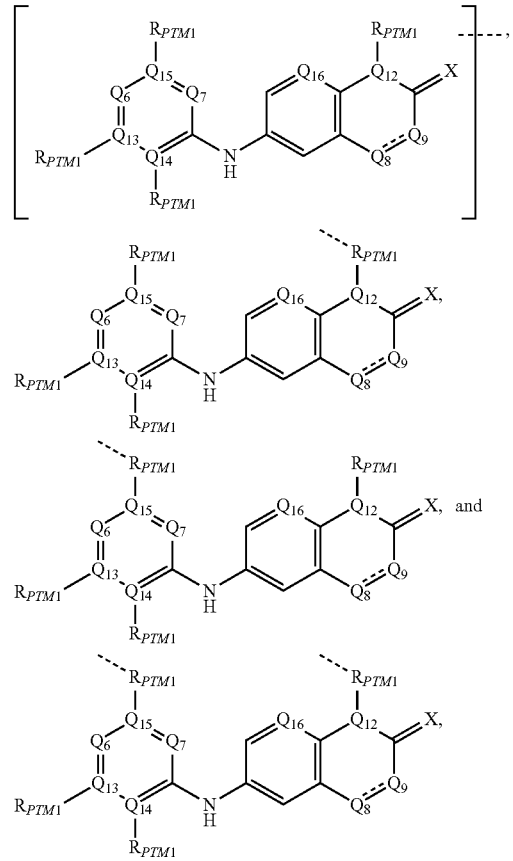

wherein the ⋰ of the PTM indicates the point of attachment with a chemical linker group (L) or a ULM.

In any aspect or embodiment described herein, at least one $R_{PTM1}$ is selected from

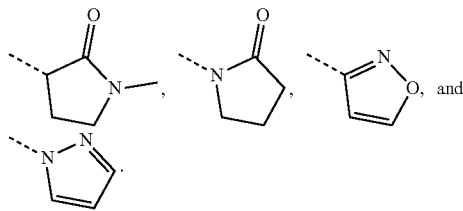

In any aspect or embodiment described herein, the PTM has the chemical structure:

(PTMIIa1)

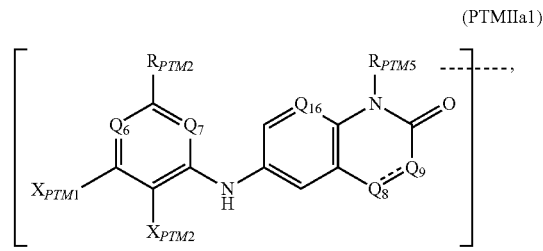

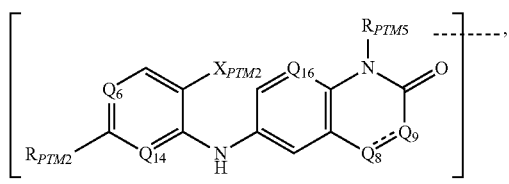
(PTMIIa2)
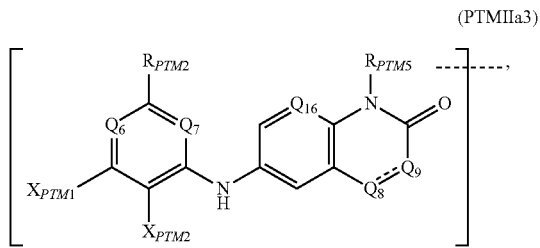
(PTMIIa3)
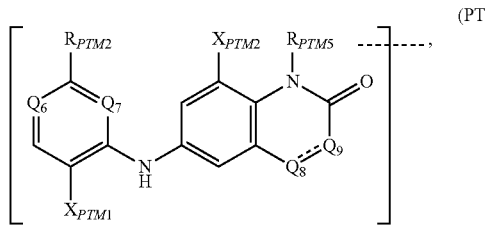
(PTMIIa4)
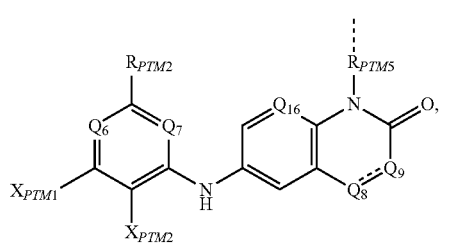
(PTMIIb1)
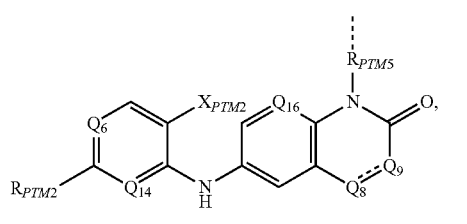
(PTMIIb2)
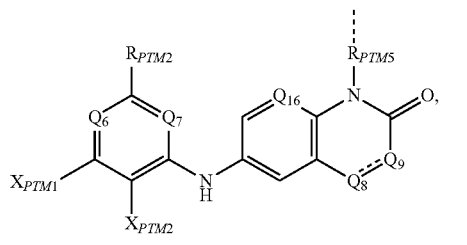
(PTMIIb3)
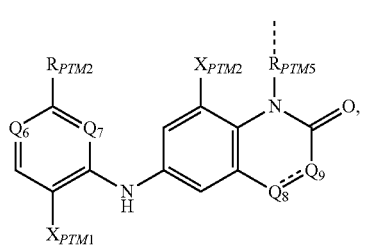
(PTMIIb4)
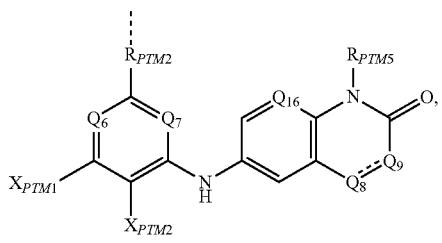
(PTMIIc1)
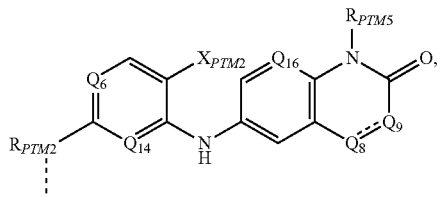
(PTMIIc2)
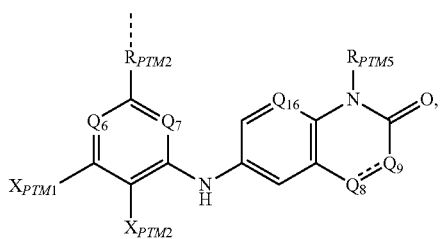
(PTMIIc3)
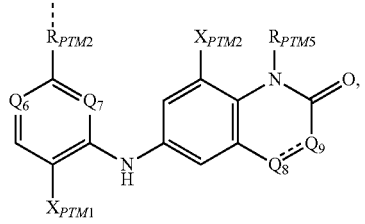
(PTMIIc4)
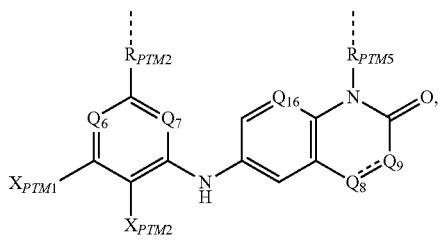
(PTMIId1)

-continued

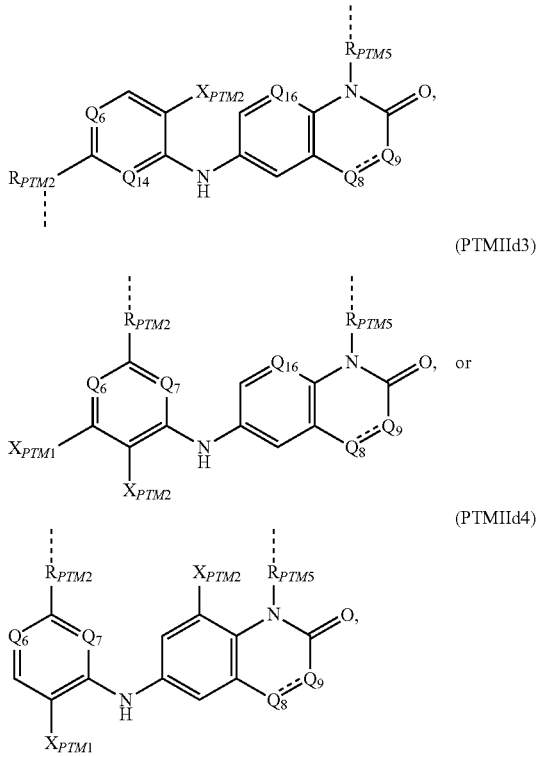

(PTMIId2)

(PTMIId3)

(PTMIId4)

wherein:
R$_{PTM5}$ is H, optionally substituted linear or branched alkyl (e.g., optionally substituted linear or branched C1-C6 alkyl, methyl, ethyl, or isopropyl group, C1-C4 alkyl-O(C1-C3 alkyl), C1-C4 alkyl-O—, C1-C4 alkyl-NH(C1-C3 alkyl) or C1-C4 alkyl-N(C1-C3 alkyl)$_2$, optionally substituted -alkyl-aryl (e.g., optionally substituted C1-C6 alkyl, optionally substituted C5-C10 aryl, or both), optionally substituted -alkyl-heteroaryl (e.g., optionally substituted C1-C6 alkyl, optionally substituted C5-C10 heteroaryl, or both), optionally substituted aryl (e.g., optionally substituted C5-C10 aryl), optionally substituted heteroaryl (e.g., optionally substituted C5-C10 heteroaryl), optionally substituted cycloalkyl (e.g., optionally substituted C3-C10 cycloalkyl), optionally substituted -alkyl-cycloalkyl (e.g., optionally substituted C1-C6 alkyl, optionally substituted C3-C10 cycloalkyl, or both), optionally substitute heterocyclyl (e.g., optionally substituted C3-C10 heterocyclyl);

Q$_6$ is N, CH, C(NO$_2$), or C(CN);
Q$_7$ and Q$_{14}$ are each independently N or CH;
X$_{PTM1}$ is H, Cl, or F;
X$_{PTM2}$ is H, Cl, F, or CN;
⌇ of Q$_8$ and Q$_9$ is a single bond, a double bond, or absent when Q$_8$ is absent;
when Q$_8$ is absent, ⌇ is absent and Q$_{10}$ is absent;
when Q$_8$ and Q$_9$ are connected by a single bond:
Q$_8$ is CH$_2$, O, CH(R$_{PTM3}$), NH, N(R$_{PTM3}$), or N(CH$_3$); and
Q$_9$ is CH$_2$, O, CH(R$_{PTM3}$), NH, N(R$_{PTM3}$), N(CH$_3$), N(CH$_2$CH$_2$CONHCH$_3$), or N(CH$_2$CH$_2$COCH$_3$);

when Q$_8$ and Q$_9$ are connected by a double bond:
Q$_8$ is CH, C(R$_{PTM3}$), N(R$_{PTM3}$), N, or optionally substituted C(NH-alkyl-heteroaryl) (such as a optionally substituted C1-C5 alky, an optionally substituted 5-7 member heteroaryl, or both);
Q$_9$ is CH, C(R$_{PTM3}$), N, or N(R$_{PTM3}$); and
R$_{PTM3}$ is: —OH; —Cl; —F; —CN; optionally substituted linear or branched C1-C6 alkyl, optionally substituted C1-C6 alkoxy (e.g., optionally substituted with a linear or branched C1-C4 alkyl, —OCH$_3$ or —OCH$_2$CH$_3$); optionally substituted

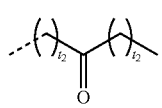

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5); optionally substituted

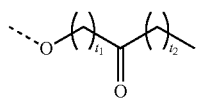

(e.g., optionally substituted with a linear or branched C1-C4 alkyl; —O(CH$_2$)$_n$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$COCH$_3$, or —OCH$_2$(CH$_3$)COCH$_3$, wherein each u, v, w, and x is independently selected from 1, 2, 3, 4 or 5); optionally substituted

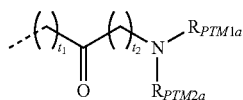

(e.g., optionally substituted with a linear or branched C1-C4 alkyl; —(CH$_2$)$_u$CO(CH$_2$)$_v$NR$_{PTM1a}$R$_{PTM2a}$, —CONR$_{PTM1a}$R$_{PTM2a}$, —CH$_2$CONR$_{PTM1a}$R$_{PTM2a}$, —CH$_2$CH$_2$CONR$_{PTM1a}$R$_{PTM2a}$, —CONHCH$_3$, or —CH$_2$CONHCH$_3$, wherein each u and v is independently selected from 1, 2, 3, 4 or 5); optionally substituted

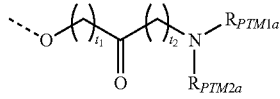

(e.g., optionally substituted with a linear or branched C1-C4 alkyl; C1-C4 alkoxy; —Cl; —F; —CN; —OH; —O(CH$_2$)$_u$CO(CH$_2$)$_v$NR$_{PTM1a}$R$_{PTM2a}$, —O(CH$_2$)$_n$CH((CH$_2$)$_x$CH$_3$)(CH$_2$)$_w$CO(CH$_2$)$_v$NR$_{PTM1a}$R$_{PTM2a}$, —O—CH(CH$_3$)CONR$_{PTM1a}$R$_{PTM2a}$, —O—CH$_2$CONR$_{PTM1a}$R$_{PTM2a}$, or —OCH$_2$C(O)NHOCH$_3$, wherein each u, v, w, and x is independently selected from 1, 2, 3, 4 or 5); optionally substituted

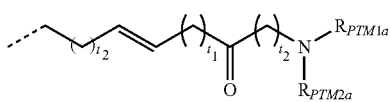

(e.g., optionally substituted with a linear or branched C1-C4 alkyl; —(CH$_2$)$_u$CHCH(CH$_2$)$_w$CO(CH$_2$)$_v$NR$_{PTM1a}$R$_{PTM2a}$ or —CHCHCONR$_{PTM1a}$R$_{PTM2a}$, wherein each u, v, and w is independently selected from 1, 2, 3, 4 or 5); optionally substituted

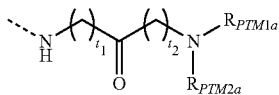

(e.g., optionally substituted with a linear or branched C1-C4 alkyl; C1-C4 alkoxy; —Cl; —F; —CN; —OH; —NH—(CH$_2$)$_u$CO(CH$_2$)$_v$NR$_{PTM1a}$R$_{PTM2a}$ or —NH—CH$_2$CONR$_{PTM1a}$R$_{PTM2a}$, wherein each u and v is independently selected from 1, 2, 3, 4 or 5); optionally substituted -alkyl-heteroaryl (e.g., optionally substituted with a C1-C4 alkyl; —(CH$_2$)$_{t2}$-optionally substituted 5 or 6 member heteroaryl; the heteroaryl is selected from oxazol-4-yl, 1,3,4-triazol-2-yl, and imidazole-1-yl; and combination thereof); optionally substituted —NH-alkyl-heteroaryl (e.g., optionally substituted with a C1-C4 alkyl, or combination thereof, —NH—(CH$_2$)$_{t2}$— optionally substituted 5 or 6 member heteroaryl, N—CH$_2$-pyrazol-4-yl); optionally substituted alkyl-cycloalkyl or alkyl-heterocycloalkyl (e.g., optionally substituted with a C1-C4 alkyl, —(CH$_2$)$_{t2}$— an optionally substituted 3-6 member cycloalkyl or heterocycloalkyl); optionally substituted —NH-alkyl-cycloalkyl or —NH-alkyl-heterocycloalkyl (e.g., optionally substituted with C1-C4 alkyl, —NH—(CH$_2$)$_{t2}$-optionally substituted 3-6 member cycloalkyl or heterocycloalkyl); optionally substituted —O—cycloalkyl or —O-heterocycloalkyl (e.g., optionally substituted 3-5 member cycloalkyl or heterocycloalkyl; —O—(oxetan-3-yl)); optionally substituted —O-alkyl-cycloalkyl or —O— alkyl-heterocycloalkyl (e.g., O—(CH$_2$)$_{t2}$— optionally substituted 3-5 member cycloalkyl or heterocycloalkyl; optionally substituted with at least one of =O, OH, and C1-C4 alkyl); optionally substituted S-heterocyclyl (e.g., includes an optionally substituted 4-7 member heterocyclyl; an optionally substituted heterocycloalkyl; optionally substituted with at least one C1-C4 alkyl (such as a methyl), =O, or a combination thereof; or a combination thereof);

each R$_{PTM1a}$ and R$_{PTM2a}$ are independently H, optionally substituted C1-C4 alkyl (e.g., a CH$_3$ or CH$_2$CH$_3$), optionally substituted C1-C4 alkoxy (e.g., —OCH$_3$ or —CH$_2$CH$_3$ or —OCH$_2$CH$_3$), CH$_2$OCH$_3$ or R$_{PTM1a}$ and R$_{PTM2a}$ are joined together form a 3-10 member ring; each t$_1$ is independently selected from 1, 2, 3, 4, or 5; and each t$_2$ is independently is independently selected from 0, 1, 2, 3, 4, or 5;

R$_{PMT2}$ is H, OH, CN, optionally substituted linear or branched C1-C4 alkyl, optionally substituted —NH$_2$ (e.g., —N(C1-C3 alkyl) or —NH(C1-C3 alkyl)), optionally substituted linear or branched —O—C1-C4 alkyl, O-optionally substituted linear or branched C1-C4 alkyl, an optionally substituted C1-C4 alkynyl, an optionally substituted C1-C4 alkyne, an optionally substituted monocyclic or bicyclic C3-C12 heterocycloalkyl (e.g., an optionally substituted C3-C12 monocyclic or bicyclic heterocycloalkyl, such as an C3-C12 monocyclic or bicyclic heterocycloalkyl, azetidine1-yl, azetidine1-yl-3-ol, pyrrolidin-1-yl, piperidin-1yl, piperazin-1-yl, or morpholin-4-yl, homopiperazin-1-yl,

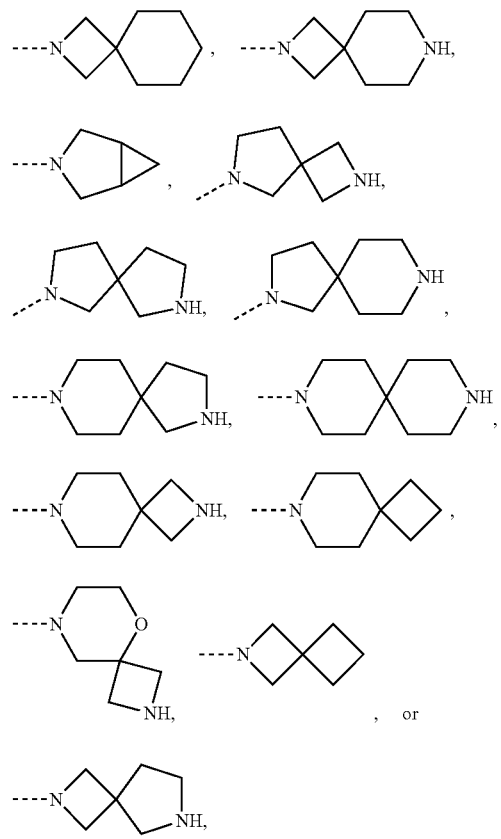

each optionally substituted with one or more of OH, a linear or branched C1-C5 alkyl, a linear or branched C1-C6 alkyl, C1-C6 alkoxy —CN, —F, —Cl, or NH$_2$), or an optionally substituted —O—C$_{3-12}$ monocyclic or bicyclic heterocyclyl (e.g., an optionally substituted —O—C3-12 monocyclic or bicyclic heterocycloalkyl, such as —O—C$_{3-12}$ monocyclic or bicyclic heterocycloalkyl optionally substituted with one or more OH, a linear or branched C1-C5 alkyl, a linear or branched C1-C6 alkyl, C1-C6 alkoxy, —CN, —F, —Cl, a linear or branched C1-C6 alkyl, C1-C6 alkoxy, —CN, —F, —Cl, or NH$_2$), an optionally substituted C5-C6 heteroaryl (e.g. optionally substituted with one or more linear or branched C1-C6 alkyl, C1-C6 alkoxy, —CN, —F, —Cl, or NH$_2$), or an optionally substituted C5-C6 aryl (e.g. optionally substituted with one or more linear or branched C1-C6 alkyl, C1-C6 alkoxy, —CN, —F, —Cl, or NH$_2$), or an optionally substituted C3-C12 member ring (e.g., an optionally substituted C3-C12 non-aryl membered ring optionally substituted with one or more of OH, linear or branched C1-C5 alkyl, or NH$_2$), wherein when R$_{PTM2}$ is a ring structure it is optionally covalently linked to Q$_{16}$ via a C or N of the R$_{PTM2}$ ring; and the ⟋ of the PTM indicates the point of attachment with a chemical linker group (L) or a ULM.

In any aspect or embodiment described herein, the PTM has the chemical structure:

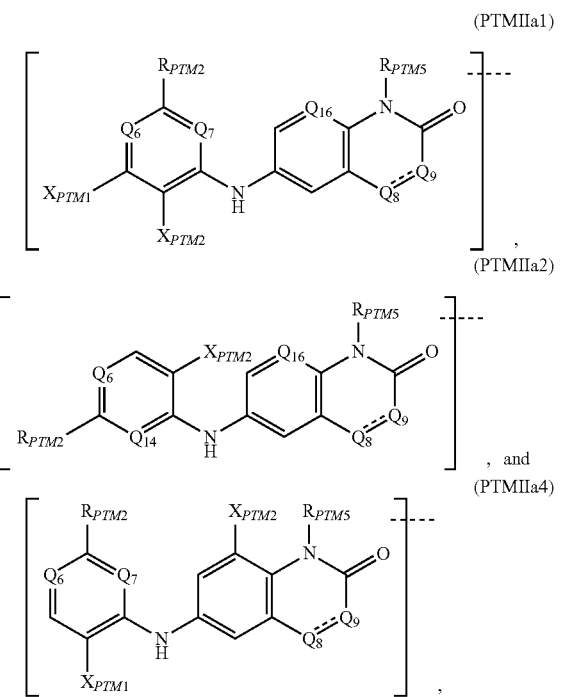

(PTMIIa1)

(PTMIIa2)

, and (PTMIIa4)

,

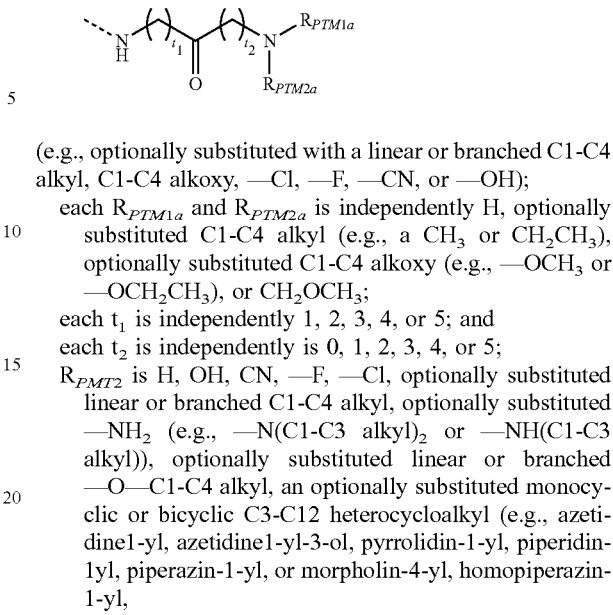

(e.g., optionally substituted with a linear or branched C1-C4 alkyl, C1-C4 alkoxy, —Cl, —F, —CN, or —OH);

each $R_{PTM1a}$ and $R_{PTM2a}$ is independently H, optionally substituted C1-C4 alkyl (e.g., a $CH_3$ or $CH_2CH_3$), optionally substituted C1-C4 alkoxy (e.g., —$OCH_3$ or —$OCH_2CH_3$), or $CH_2OCH_3$;

each $t_1$ is independently 1, 2, 3, 4, or 5; and each $t_2$ is independently is 0, 1, 2, 3, 4, or 5;

$R_{PMT2}$ is H, OH, CN, —F, —Cl, optionally substituted linear or branched C1-C4 alkyl, optionally substituted —$NH_2$ (e.g., —$N(C1-C3\ alkyl)_2$ or —$NH(C1-C3\ alkyl)$), optionally substituted linear or branched —O—C1-C4 alkyl, an optionally substituted monocyclic or bicyclic C3-C12 heterocycloalkyl (e.g., azetidine1-yl, azetidine1-yl-3-ol, pyrrolidin-1-yl, piperidin-1yl, piperazin-1-yl, or morpholin-4-yl, homopiperazin-1-yl, wherein:

$R_{PTM5}$ is H, optionally substituted linear or branched C1-C6 alkyl (e.g. methy, ethyl, or isopropyl group), C1-C4 alkyl-O(C1-C3 alkyl), C1-C4 alkyl-O—, C1-C4 alkyl-NH(C1-C3 alkyl), C1-C4 alkyl-N(C1-C3 alkyl)$_2$, optionally substituted C5-C10 aryl, optionally substituted C5-C10 heteroaryl, optionally substituted C3-C10 cycloalkyl, or optionally substituted C3-C10 heterocyclyl;

$Q_6$ is N or CH;

$Q_7$ and $Q_{14}$ are each independently N or CH;

$X_{PTM1}$ is H, Cl, or F;

$X_{PTM2}$ is H, Cl, F, or CN;

⌒ of $Q_8$ and $Q_9$ is a single bond or a double bond, wherein when $Q_8$ and $Q_9$ are connected by a single bond:

$Q_8$ is $CH_2$, CH($R_{PTM3}$), NH, or N($R_{PTM3}$); and $Q_9$ is $CH_2$, O, CH($R_{PTM3}$), NH, or N($R_{PTM3}$);

when $Q_8$ and $Q_9$ are connected by a double bond:

$Q_8$ is CH, C($R_{PTM3}$), N($R_{PTM3}$), or N;

$Q_9$ is CH, C($R_{PTM3}$), N, or N($R_{PTM3}$); and $R_{PTM3}$ is: —OH; —Cl; —F; —CN; optionally substituted linear or branched C1-C6 alkyl, optionally substituted C1-C6 alkoxy (e.g., —$OCH_3$, or —$OCH_2CH_3$); optionally substituted

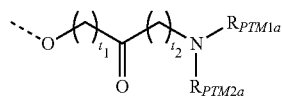

(e.g., optionally substituted with a linear or branched C1-C4 alkyl, C1-C4 alkoxy, —Cl; —F, —CN, or —OH); or optionally substituted

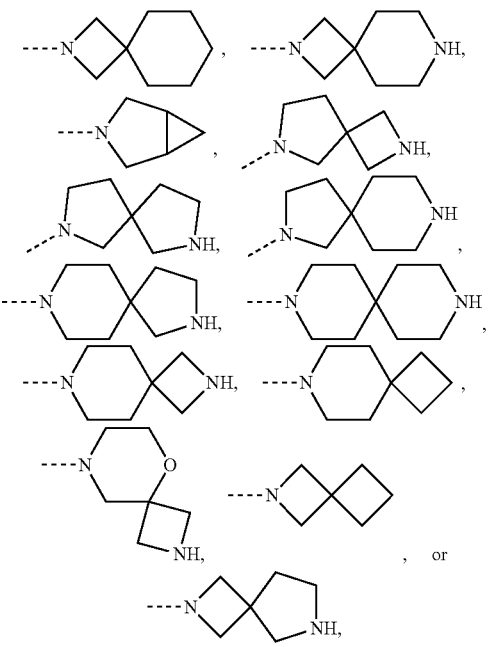

each optionally substituted with one or more of OH, a linear or branched C1-C6 alkyl, C1-C6 alkoxy —CN, —F, —Cl, or $NH_2$), an optionally substituted —O—$C_{3-12}$ monocyclic or bicyclic heterocycloalkyl (e.g. optionally substituted with one or more OH, a linear or branched C1-C6 alkyl, C1-C6 alkoxy, —CN, —F, —Cl, or $NH_2$), or an optionally substituted C3-C12 cycloalkyl (e.g., optionally substituted with one or more of OH, linear or branched C1-C6 alkyl, C1-C6 alkoxy, —CN, —F, —Cl, or $NH_2$), an optionally substituted C5-C6 heteroaryl (e.g. optionally substituted with one or more linear or branched C1-C6 alkyl, C1-C6 alkoxy, —CN, —F, —Cl, or $NH_2$), or an optionally substituted C5-C6 aryl (e.g. optionally substituted with one or more linear or branched C1-C6 alkyl, C1-C6 alkoxy, —CN, —F, —Cl, or $NH_2$); and the ⌇ of the PTM indicates the point of attachment with the L or ULM.

In any aspect or embodiment described herein, at least one (e.g., 1, 2, or 3) of $R_{PTM1}$, $R_{PTM2}$, $Q_6$, $Q_7$, $Q_8$, $Q_9$, $X_{PTM1}$, $X_{PTM2}$ of PTMII, or the associated location of other PTM structures described herein is directly or indirectly covalently linked to a ULM or a chemical linker group (L).

In any aspect or embodiment described herein, the $R_{PTM2}$ or the corresponding location of a PTM described herein (e.g. PTMII, and derivatives thereof) may be substituted with one or more groups selected from: OH, linear or branched C1-C5 alkyl, or $NH_2$.

In any aspect or embodiment described herein, the $R_{PTM5}$ or the corresponding location of any PTM described herein (e.g. PTMII, and derivatives thereof) is: H, optionally substituted linear or branched alkyl (e.g., optionally substituted linear or branched C1-C6 alkyl or C1-C4 alkyl-NH(C1-C3 alkyl) or C1-C4 alkyl-N(C1-C3 alkyl)$_2$), optionally substituted -alkyl-aryl (e.g., optionally substituted C1-C6 alkyl, optionally substituted C5-C10 aryl, or both), optionally substituted -alkyl-heteroaryl (e.g., optionally substituted C1-C6 alkyl, optionally substituted C5-C10 heteroaryl, or both), optionally substituted aryl (e.g., optionally substituted C5-C10 aryl), optionally substituted heteroaryl (e.g., optionally substituted C5-C10 heteroaryl), optionally substituted cycloalkyl (e.g., optionally substituted C3-C10 cycloalkyl), optionally substituted -alkyl-cycloalkyl (e.g., optionally substituted C1-C6 alkyl, optionally substituted C3-C10 cycloalkyl, or both), optionally substitute heterocyclyl (e.g., optionally substituted C3-C10 heterocyclyl).

In any aspect or embodiment described herein, the $R_{PTM5}$ or the corresponding location of a PTM described herein (e.g. PTMII, and derivatives thereof) is selected from H, methyl, $CFH_2$, $CF_2H$, ethyl, propyl, isopropyl, cyclopropyl, butyl, pentyl, hexyl, $-CH_2CH_2OCH_3$, $-CH_2CH(CH_3)_2$, $-CH_2CHN(CH_3)_2$, $-CH_2$-cyclopropyl, $-CH_2-CH_2$-cyclopropyl,

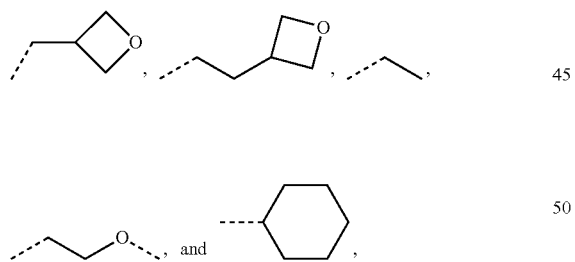

wherein ⌇ indicates the point of attachment of $R_{PTM5}$ to the nitrogen of the biheteroaryl or biheterocycle of the PTM.

In any aspect or embodiment described herein, the $X_{PTM1}$ or the corresponding location of any PTM described herein (e.g. PTMII, and derivatives thereof) is H or F.

In any aspect or embodiment described herein, the $X_{PTM2}$ or the corresponding location of any PTM described herein (e.g. PTMII, and derivatives thereof is H, Cl, F, or CN.

In any aspect or embodiment described herein, the $R_{PTM2}$ or the corresponding location of a PTM described herein (e.g. PTMII, and derivatives thereof) is selected from: H, OH, ethyl, $NH_2$, $-N(CH_3)_2$, methyl, ethyl,

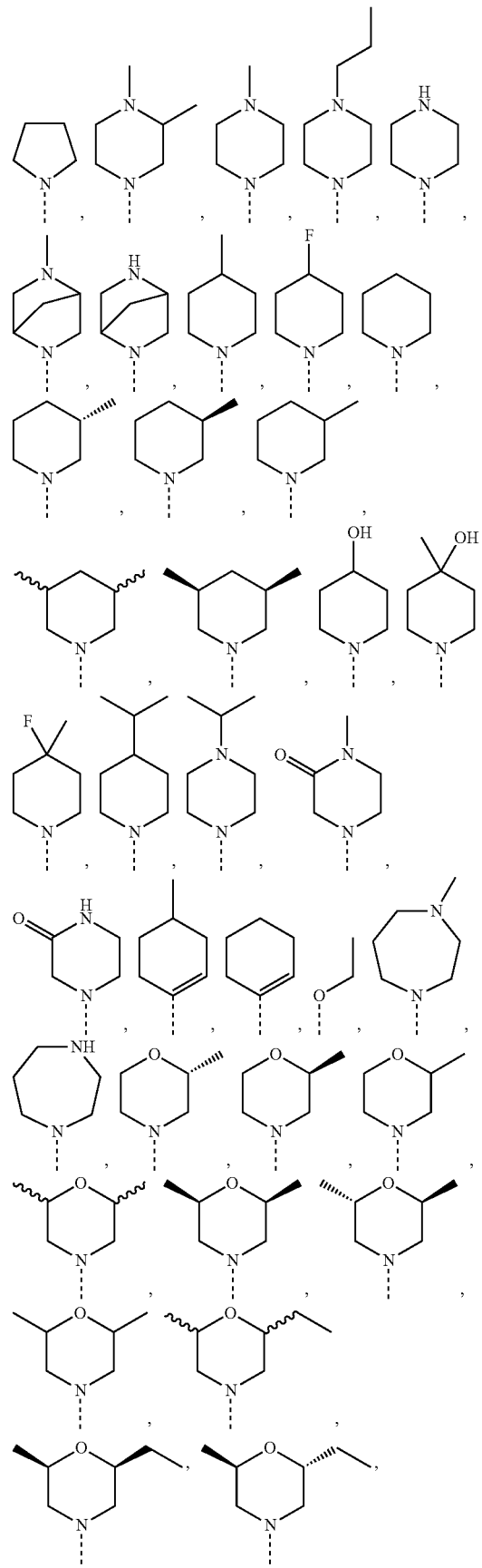

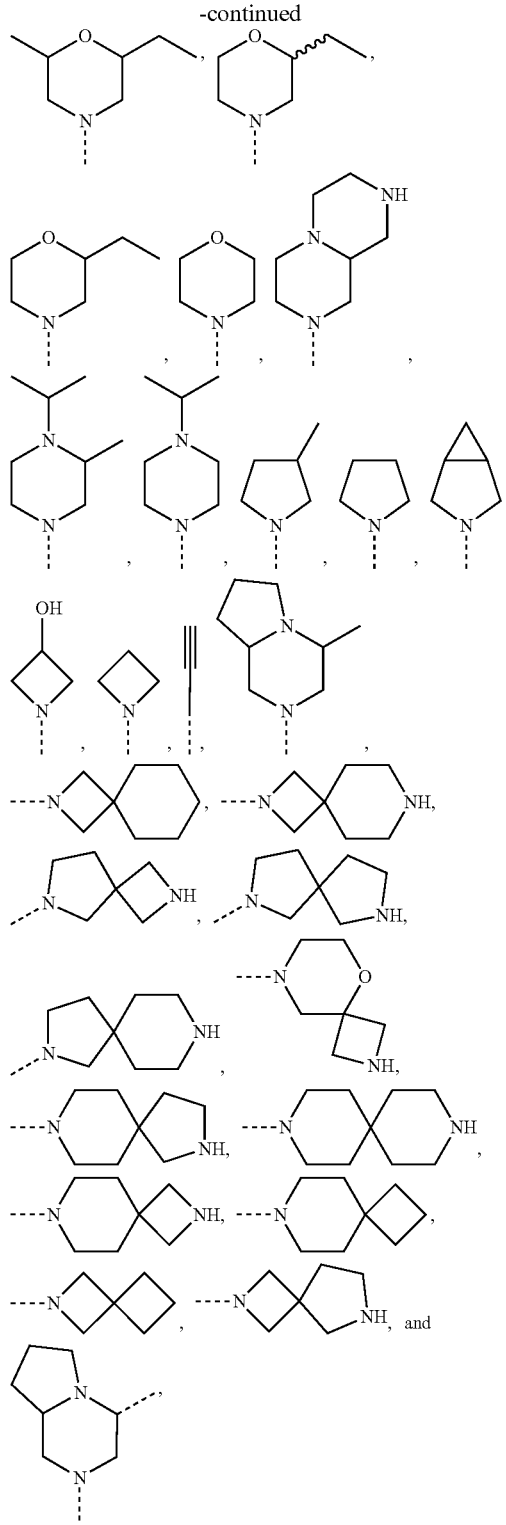

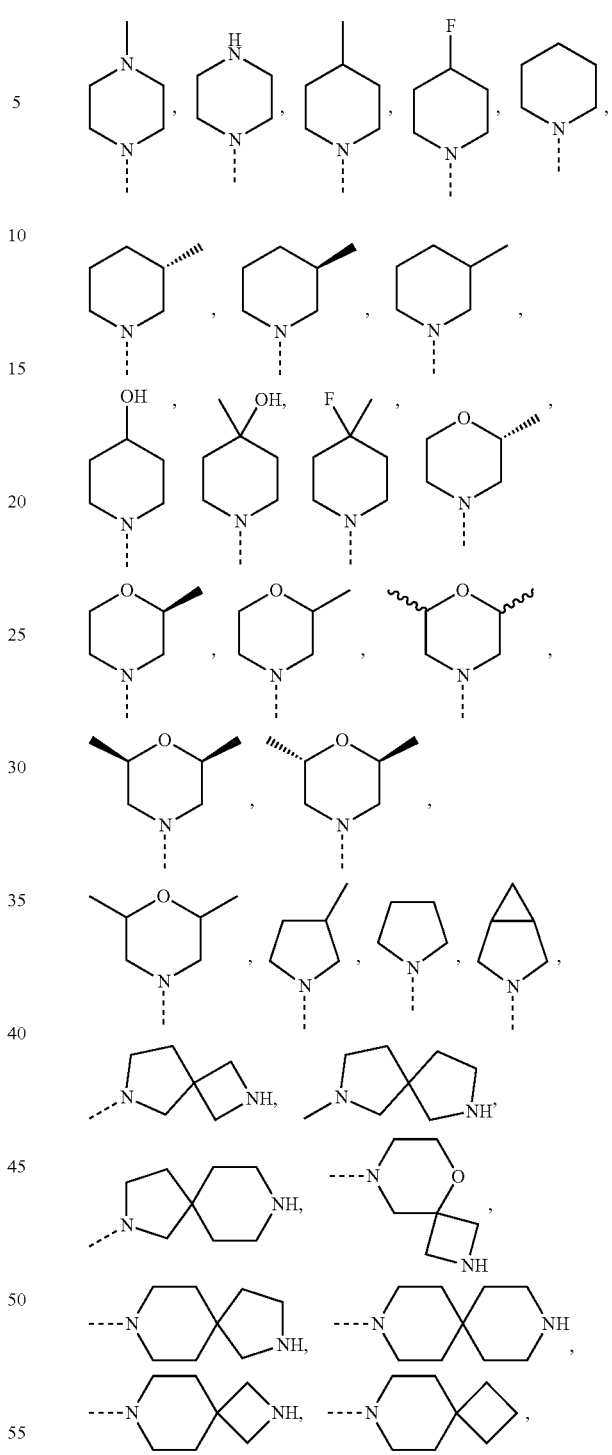

wherein ⋯ represents a bond that may be stereospecific ((R) or (S)) or non-stereospecific and ⋰ indicates the point of attachment of R_{PTM2} to the aryl or heteroaryl of the PTM.

In any aspect or embodiment described herein, the R_{PTM2} or the corresponding location of a PTM described herein (e.g. PTMII, and derivatives thereof) is selected from: H, OH, NH$_2$, —N(CH$_3$)$_2$, methyl, ethyl, wherein ⋯ represents a bond that may be stereospecific ((R) or (S)) or non-stereospecific and ⋰ indicates the point of attachment of R_{PTM2} to the aryl or heteroaryl of the PTM.

In any aspect or embodiment described herein, the R_{PTM3} or the corresponding location of any PTM described herein (e.g. PTMI, PTMIII, and derivatives thereof) is: OH; optionally substitute linear or branched alkyl, optionally substituted alkoxy (e.g., optionally substituted with a linear or branched C1-C4 alkyl or —OCH$_3$); optionally substituted

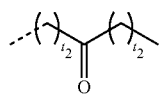

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5); optionally substituted

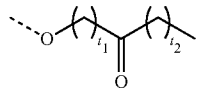

(e.g., optionally substituted with a linear or branched C1-C4 alkyl; —O(CH$_2$)$_n$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$COCH$_3$, or —OCH$_2$(CH$_3$)COCH$_3$, wherein each u, v, w, and x is independently selected from 1, 2, 3, 4 or 5); optionally substituted

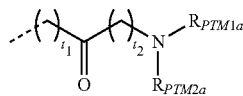

(e.g., optionally substituted with a linear or branched C1-C4 alkyl; —(CH$_2$)UCO(CH$_2$)$_v$NR$_{PTM1a}$R$_{PTM2a}$, —CO-NR$_{PTM1a}$R$_{PTM2a}$, —CH$_2$CONR$_{PTM1a}$R$_{PTM2a}$, —CH$_2$CH$_2$CONR$_{PTM1a}$R$_{PTM2a}$, —CONHCH$_3$, or —CH$_2$CONHCH$_3$, wherein each u and v is independently selected from 1, 2, 3, 4 or 5); optionally substituted

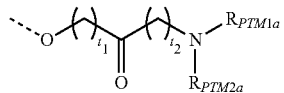

(e.g., optionally substituted with a linear or branched C1-C4 alkyl; —O(CH$_2$)$_u$CO(CH$_2$)$_v$NR$_{PTM1a}$R$_{PTM2a}$, —O(CH$_2$)$_n$CH((CH$_2$)$_x$CH$_3$)(CH$_2$)$_w$CO(CH$_2$)$_v$NR$_{PTM1a}$R$_{PTM2a}$, —O—CH(CH$_3$)CONR$_{PTM1a}$R$_{PTM2a}$, —O—CH$_2$CONR$_{PTM1a}$R$_{PTM2a}$, or —OCH$_2$C(O)NHOCH$_3$, wherein each u, v, w, and x is independently selected from 1, 2, 3, 4 or 5); optionally substituted

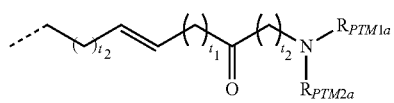

(e.g., optionally substituted with a linear or branched C1-C4 alkyl; —(CH$_2$)$_n$CHCH(CH$_2$)$_w$CO(CH$_2$)$_v$ NR$_{PTM1a}$R$_{PTM2a}$ or —CHCHCONR$_{PTM1a}$R$_{PTM2a}$, wherein each u, v, and w is independently selected from 1, 2, 3, 4 or 5); optionally substituted

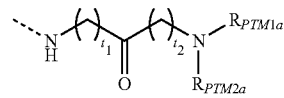

(e.g., optionally substituted with a linear or branched C1-C4 alkyl; —NH—(CH$_2$)$_u$CO(CH$_2$)$_v$NR$_{PTM1a}$R$_{PTM2a}$ or —NH—CH$_2$CONR$_{PTM1a}$R$_{PTM2a}$, wherein each u and v is independently selected from 1, 2, 3, 4 or 5); optionally substituted -alkyl-heteroaryl (e.g., optionally substituted with a C1-C4 alkyl; —(CH$_2$)$_{t2}$-optionally substituted 5 or 6 member heteroaryl; the heteroaryl is selected from oxazol-4-yl, 1,3,4-triazol-2-yl, and imidazole-1-yl; and combination thereof); optionally substituted —NH-alkyl-heteroaryl (e.g., optionally substituted with a C1-C4 alkyl, or combination thereof, —NH—(CH$_2$)$_{t2}$-optionally substituted 5 or 6 member heteroaryl, N—CH$_2$-pyrazol-4-yl); optionally substituted alkyl-cycloalkyl or alkyl-heterocycloalkyl (e.g., optionally substituted with a C1-C4 alkyl, —(CH$_2$)$_{t2}$— an optionally substituted 3-6 member cycloalkyl or heterocycloalkyl); optionally substituted —NH-alkyl-cycloalkyl or —NH-alkyl-heterocycloalkyl (e.g., optionally substituted with C1-C4 alkyl, —NH—(CH$_2$)$_{t2}$-optionally substituted 3-6 member cycloalkyl or heterocycloalkyl); optionally substituted —O-cycloalkyl or —O-heterocycloalkyl (e.g., optionally substituted 3-5 member cycloalkyl or heterocycloalkyl; —O-(oxetan-3-yl)); optionally substituted —O-alkyl-cycloalkyl or —O-alkyl-heterocycloalkyl (e.g., O—(CH$_2$)$_{t2}$— optionally substituted 3-5 member cycloalkyl or heterocycloalkyl; optionally substituted with at least one of =O, OH, and C1-C4 alkyl,); optionally substituted S-heterocyclyl (e.g., includes an optionally substituted 4-7 member heterocyclyl; an optionally substituted heterocycloalkyl; optionally substituted with at least one C1-C4 alkyl (such as a methyl), =O, or a combination thereof; or a combination thereof.

In any aspect or embodiment described herein, the R$_{PTM3}$ or the corresponding location of any PTM described herein (e.g. PTMII, and derivatives thereof) is selected from:

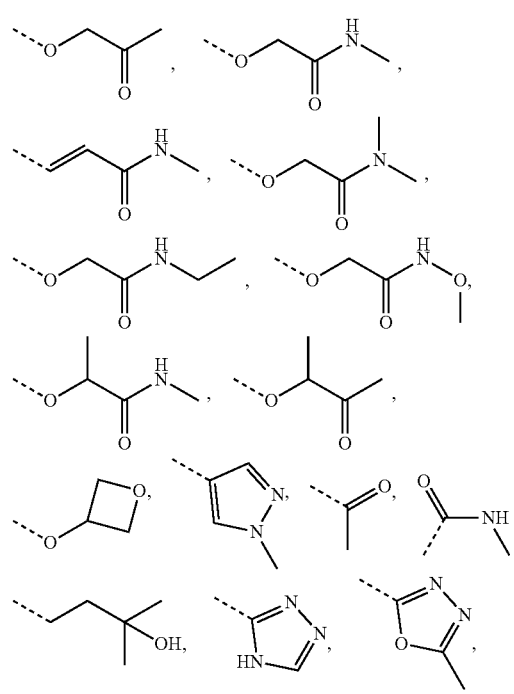

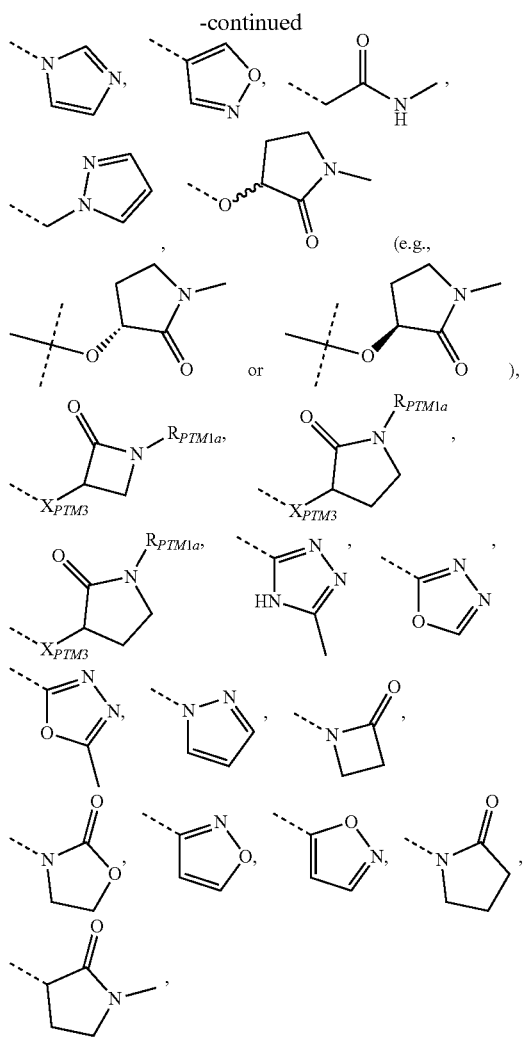

wherein: ⌇ represents a bond that may be stereospecific ((R) or (S)) or non-stereospecific, wherein ⌇ indicates the point of attachment of $R_{PTM3}$ to the biheteroaryl or biheterocycle of the PTM, and $X_{PTM3}$ is selected from $CH_2$, O, and S.

In any aspect or embodiment described herein, the $R_{PTM5}$ or the corresponding location of any PTM described herein is selected from: H, methyl, $CFH_2$, $CF_2H$, ethyl, propyl, isopropyl, cyclopropyl, butyl, pentyl, hexyl,

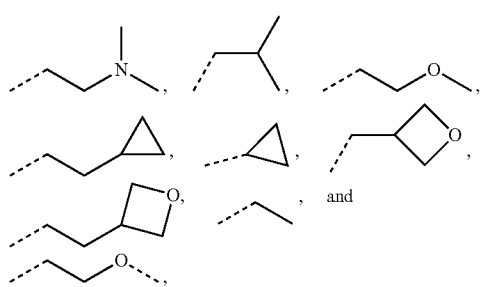

where ⌇ indicates the point of attachment of $R_{PTM5}$ to the nitrogen of the biheteroaryl or biheterocycle of the PTM.

In any aspect or embodiment described herein, the $R_{PTM4}$ or the corresponding location of any PTM described herein (e.g. PTMII, and derivatives thereof) is a linear or branched C1-C8 alkyl optionally substituted with OH.

In any aspect or embodiment described herein, the $R_{PMT2}$ or the corresponding location of any PTM described herein (e.g. PTMII, and derivatives thereof) is H, OH, CN, optionally substituted linear or branched C1-C4 alkyl, optionally substituted —$NH_2$ (e.g., —N(C1-C3 alkyl) or —NH(C1-C3 alkyl) or —$N(CH_3)_2$), O-optionally substituted linear or branched C1-C4 alkyl, an optionally substituted C1-C4 alkynyl, an optionally substituted C1-C4 alkyne, an optionally substituted monocyclic or bicyclic C3-C12 heterocyclyl (e.g., an optionally substituted C3-C12 monocyclic or bicyclic heterocycloalkyl, such as an C3-C12 monocyclic or bicyclic heterocycloalkyl, azetidine1-yl, pyrrolidin-1-yl, piperidin-1yl, piperazin-1-yl, or morpholin-4-yl, or homopiperazin-1-yl, each optionally substituted with one or more of OH, a linear or branched C1-C5 alkyl or $NH_2$), or an optionally substituted —O—$C_{3-12}$ monocyclic or bicyclic heterocyclyl (e.g., an optionally substituted —O—$C_{3-12}$ monocyclic or bicyclic heterocycloalkyl, such as —O—$C_{3-12}$ monocyclic or bicyclic heterocycloalkyl optionally substituted with at least one OH, a linear or branched C1-C5 alkyl or $NH_2$), or an optionally substituted C3-C12 member ring (e.g., an optionally substituted C3-C12 non-aryl membered ring optionally substituted with one or more of OH, linear or branched C1-C5 alkyl, or $NH_2$), wherein when $R_{PTM2}$ is a ring structure it is optionally covalently linked to $Q_{16}$ via a C or N of the $R_{PTM2}$ ring.

In any aspect or embodiment described herein, the PTM is represented by a chemical structure selected from:

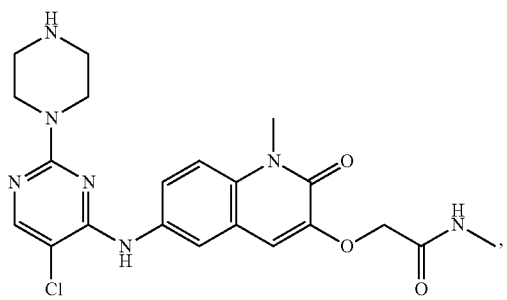

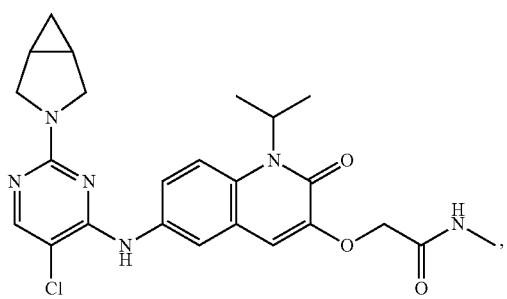

153
-continued
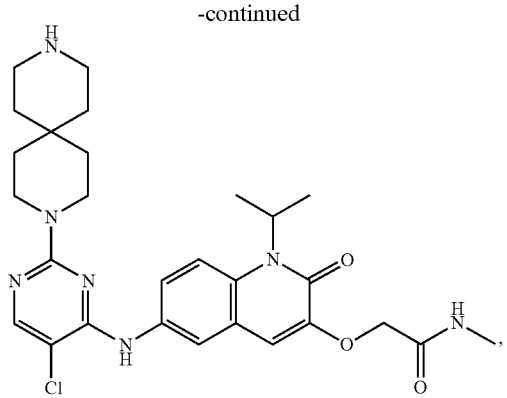
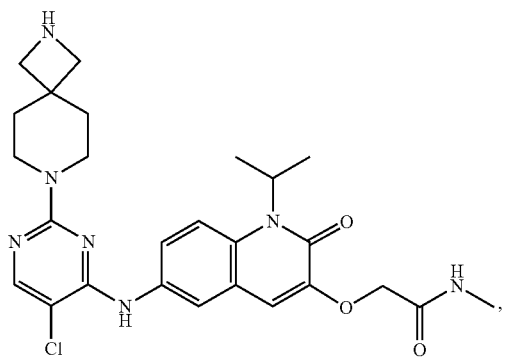
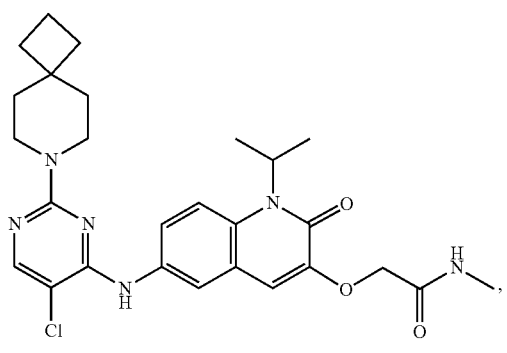
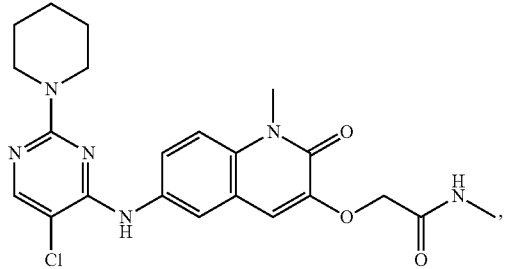
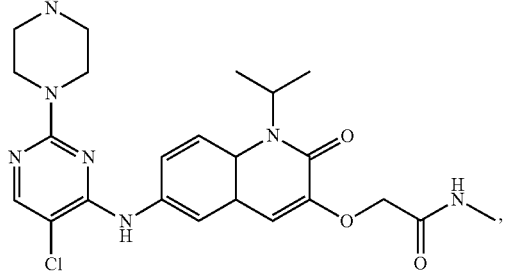
154
-continued
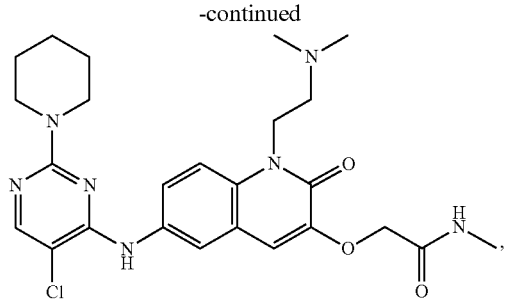
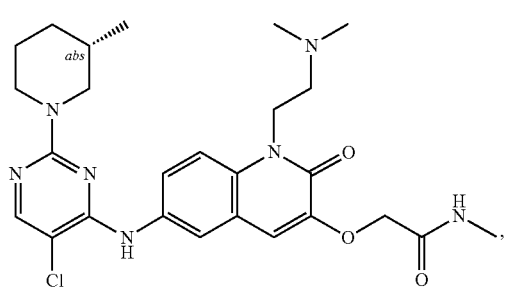
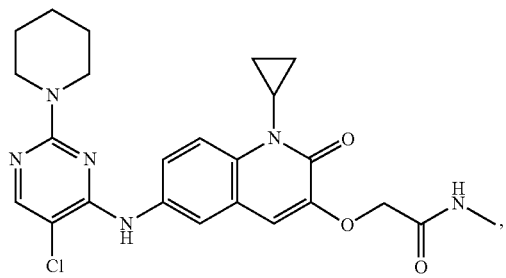
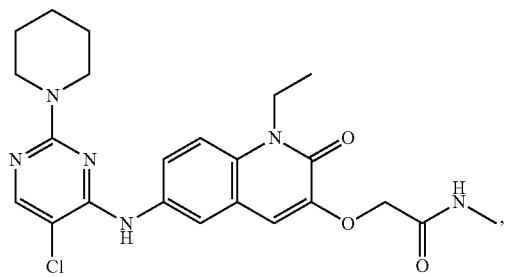
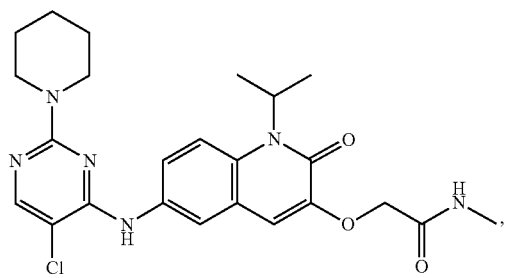
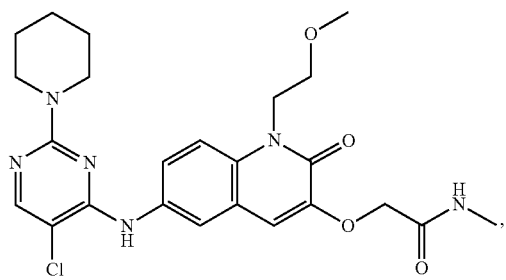

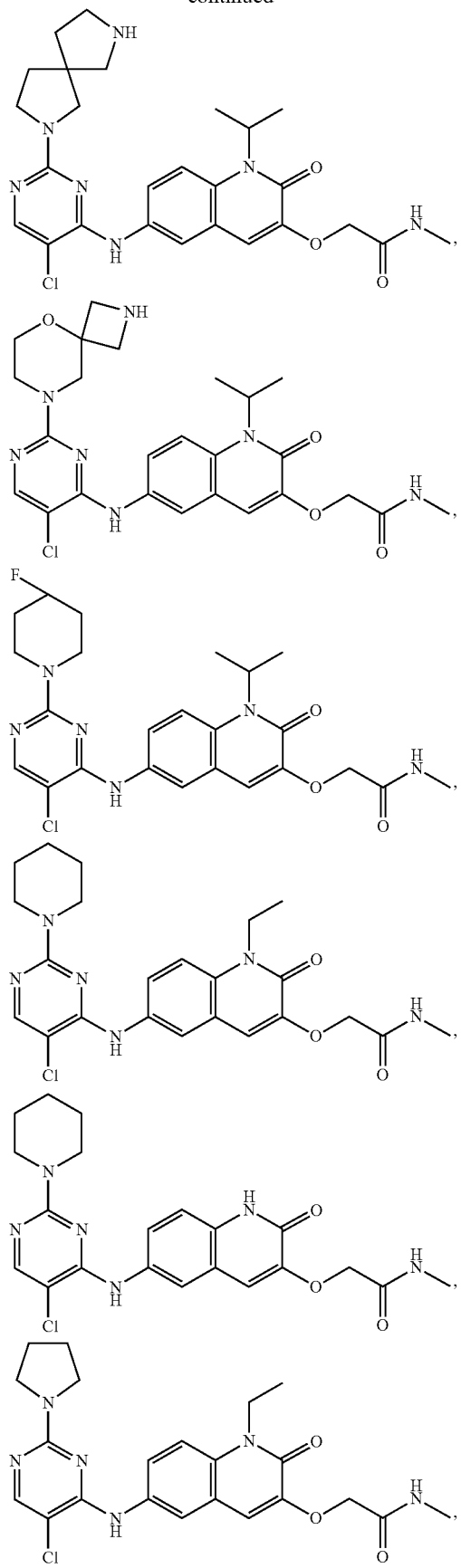
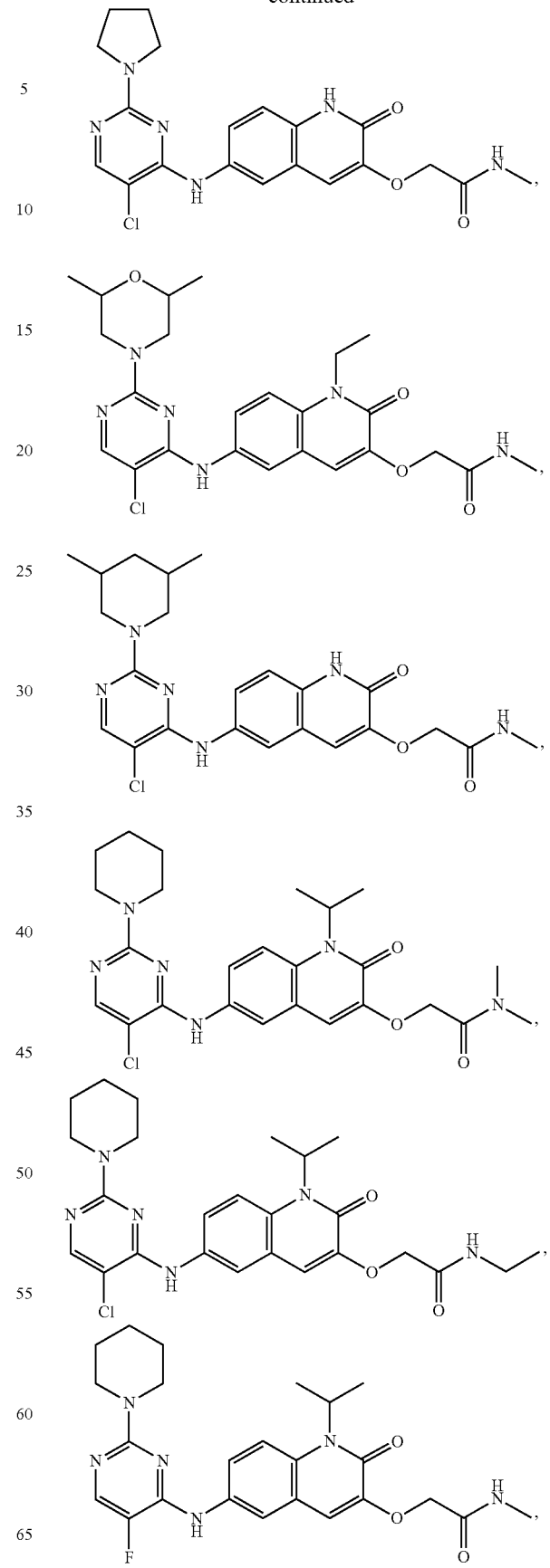

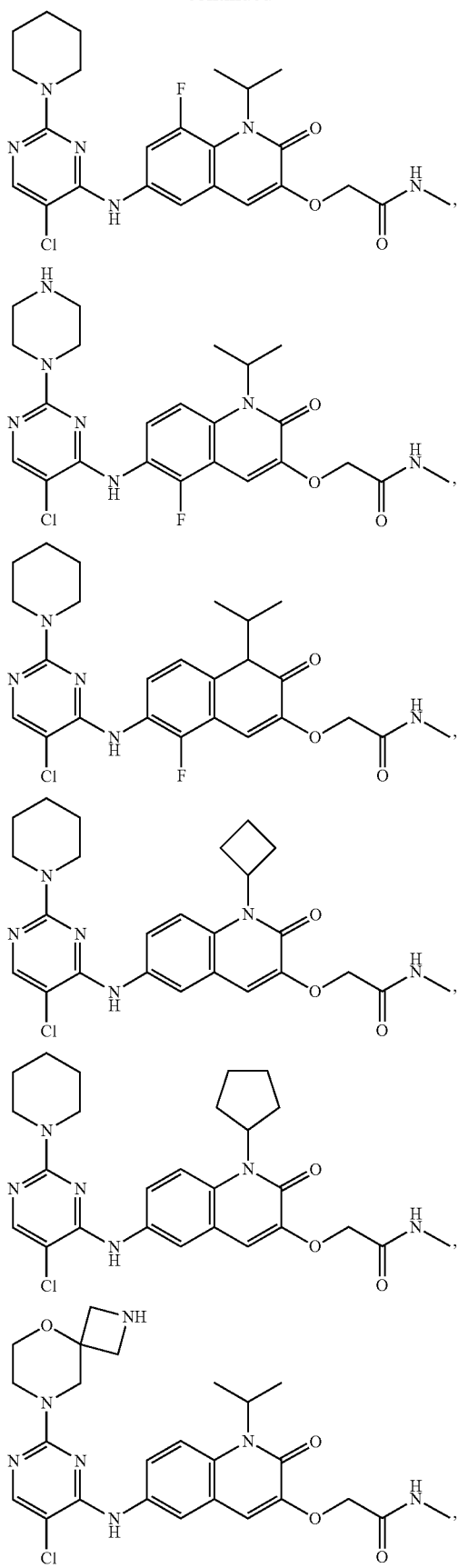
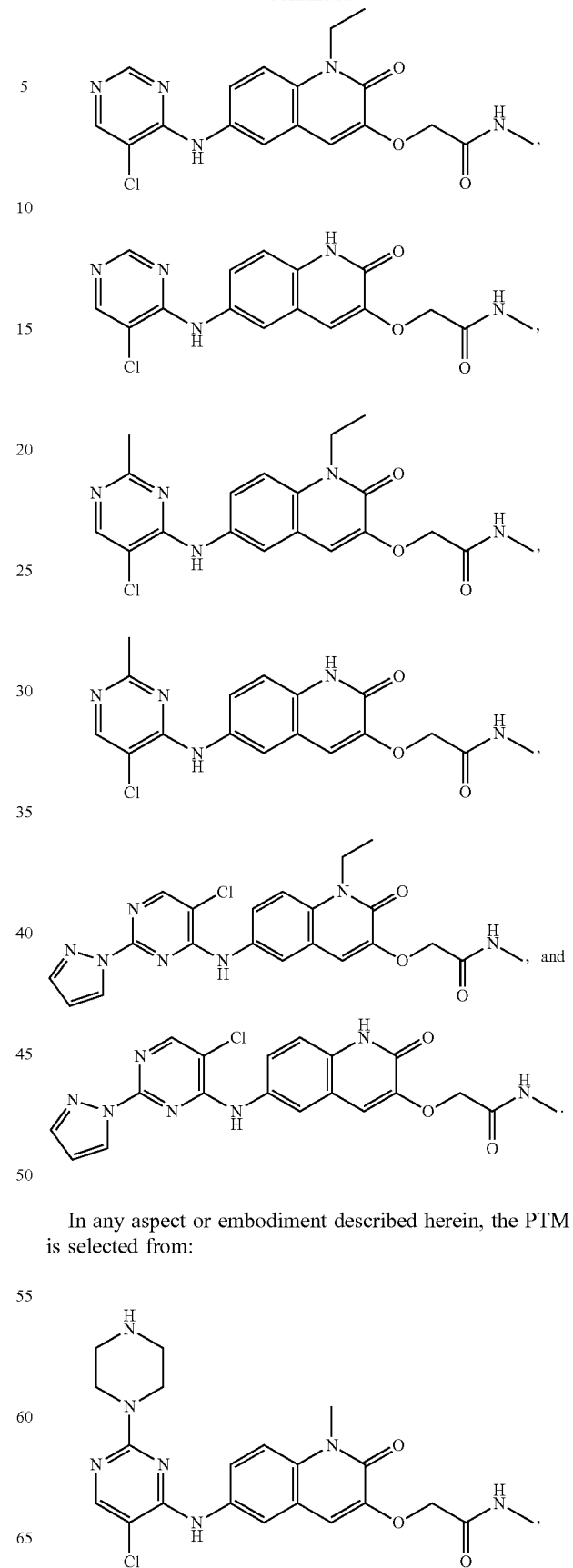
In any aspect or embodiment described herein, the PTM is selected from:

159
-continued
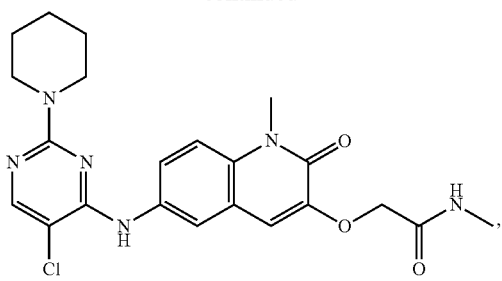
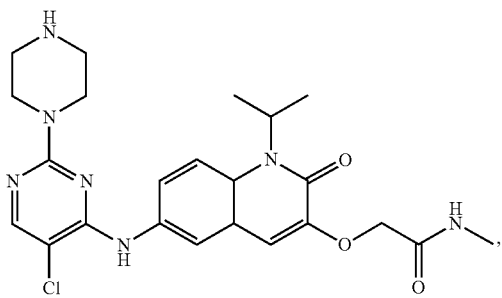
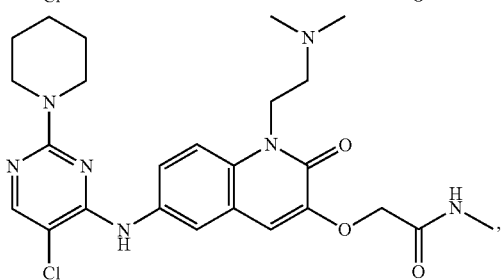
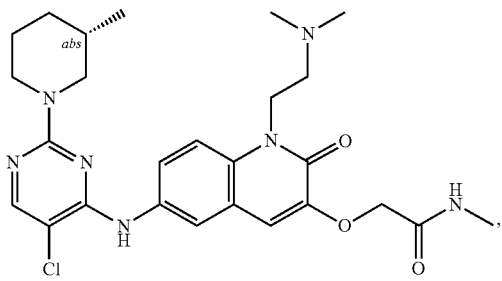
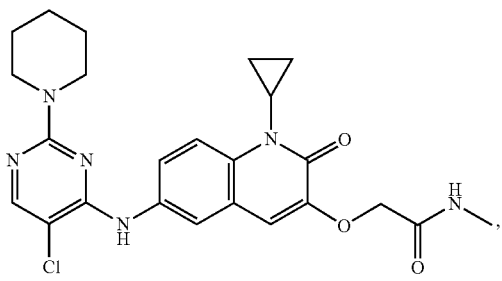
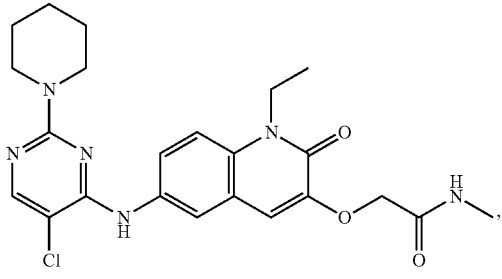
160
-continued
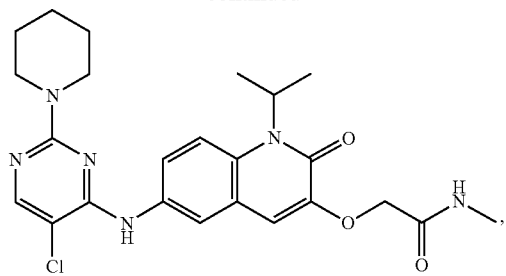
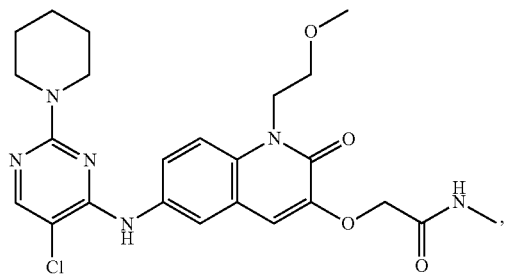
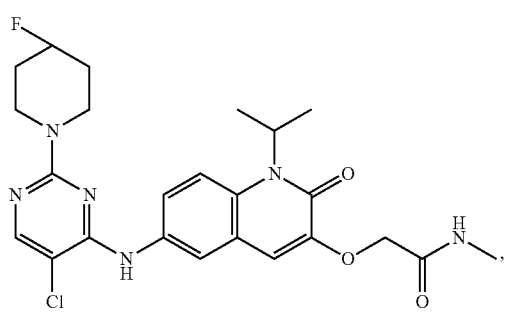
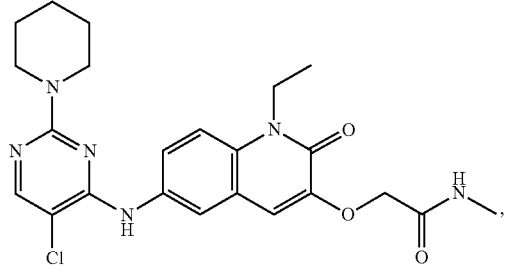
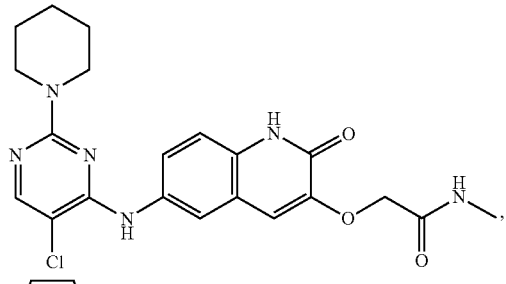
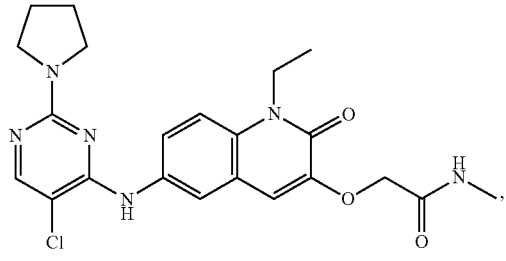

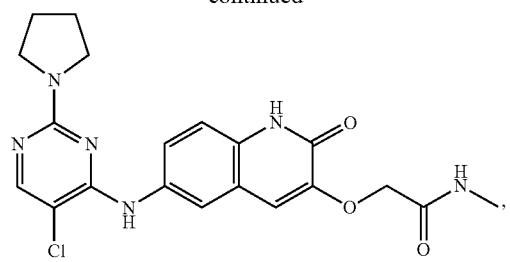
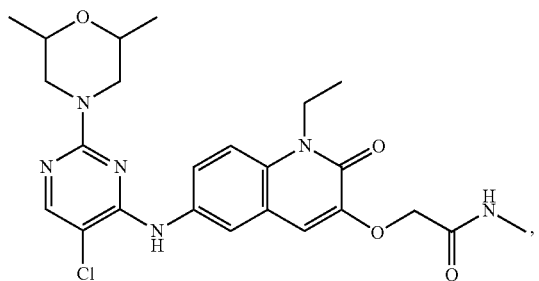
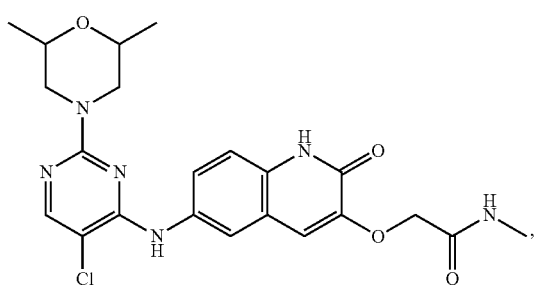
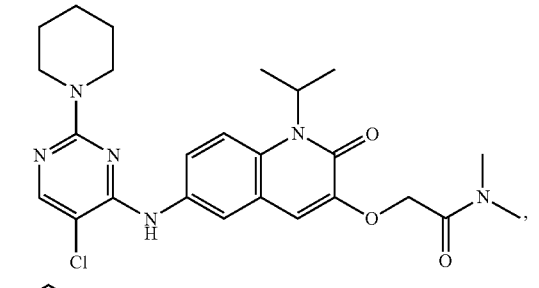
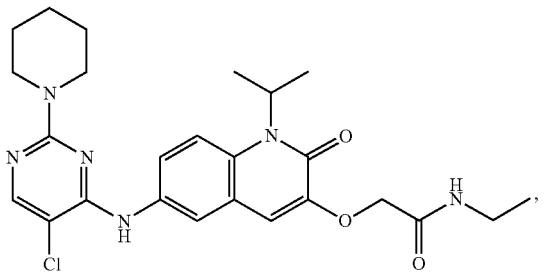
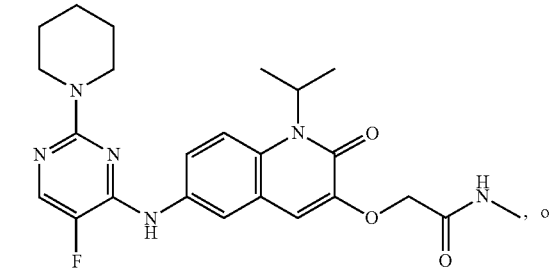
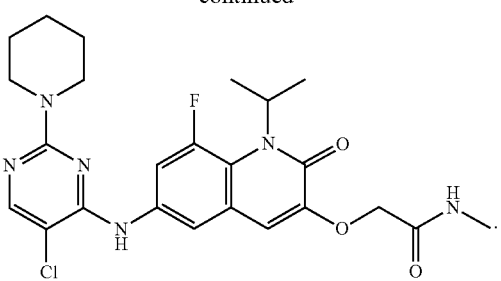
In any aspect or embodiment described herein, the PTM is selected from:
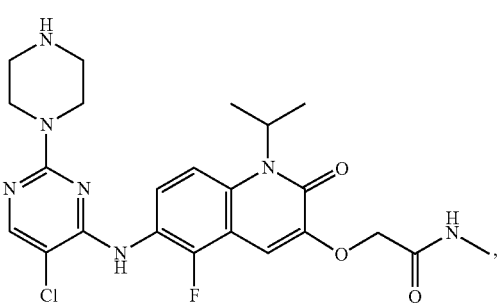
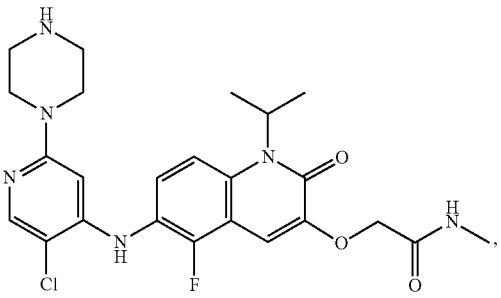
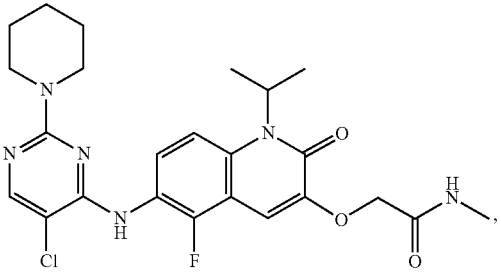
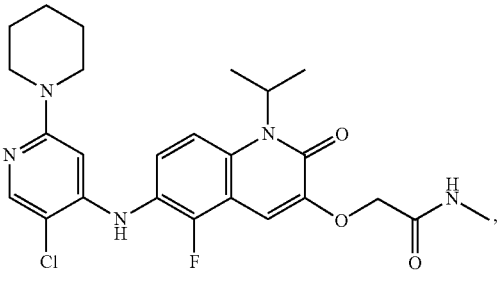

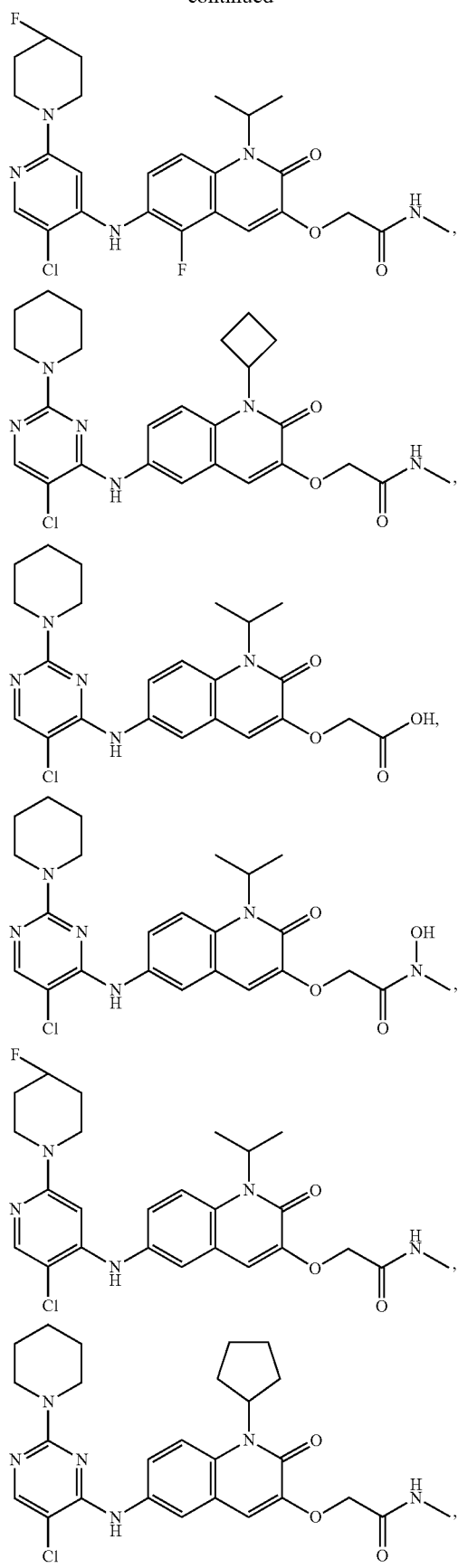
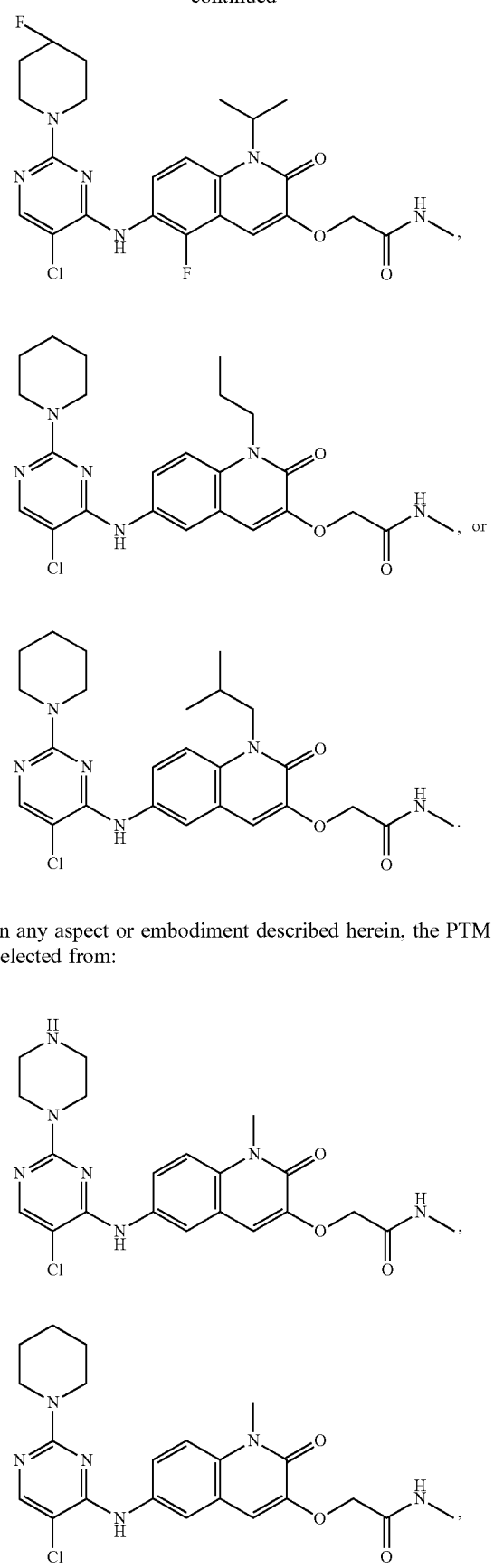
In any aspect or embodiment described herein, the PTM is selected from:

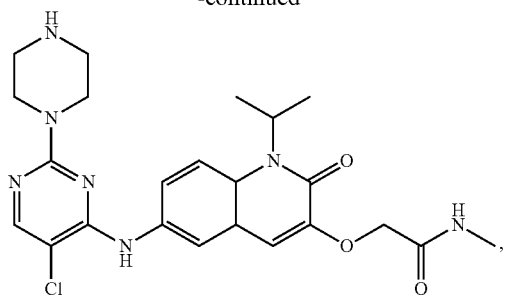
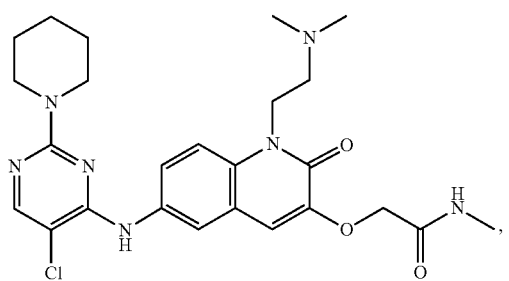
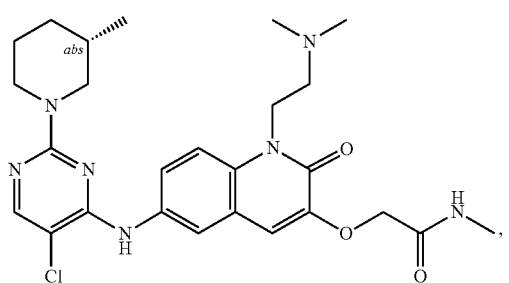
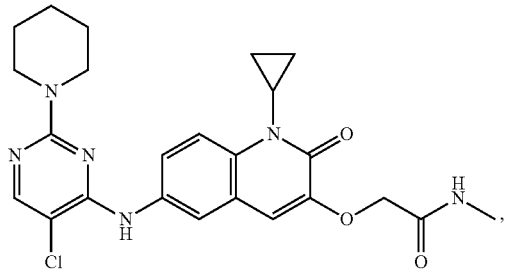
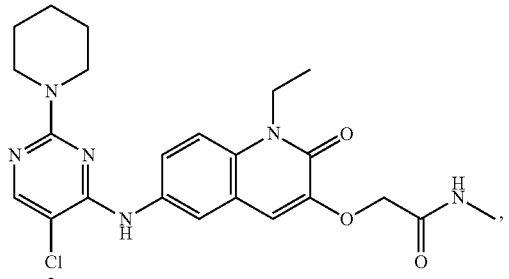
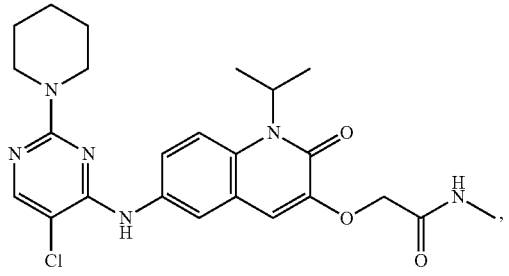
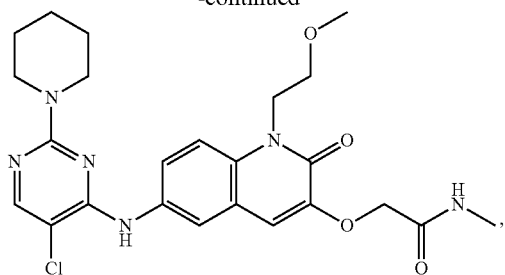
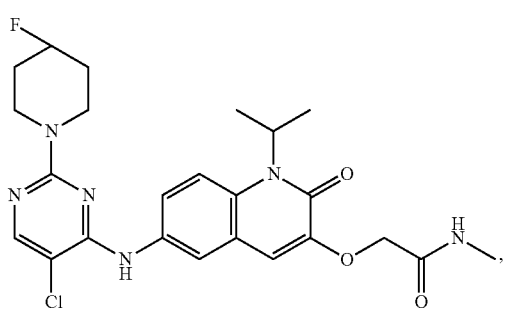
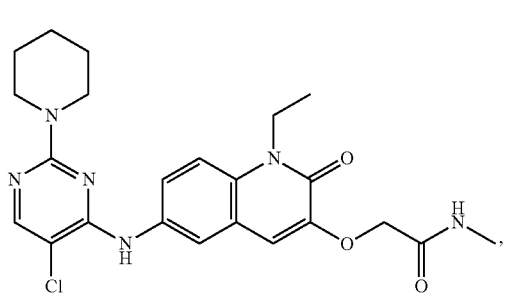
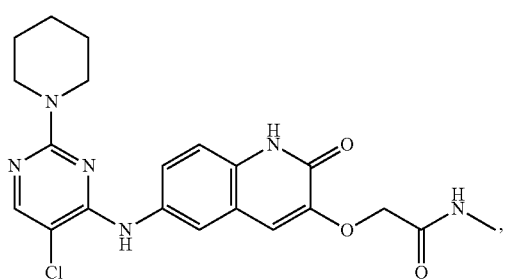
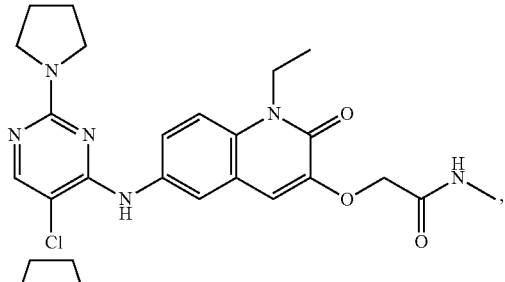
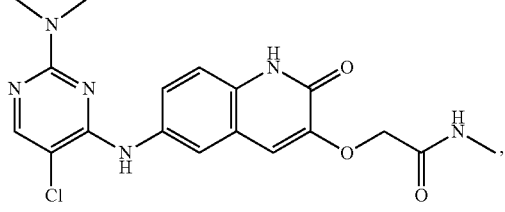

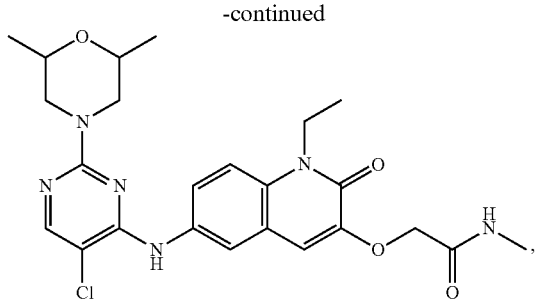
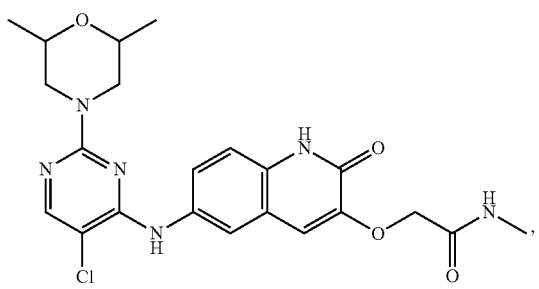
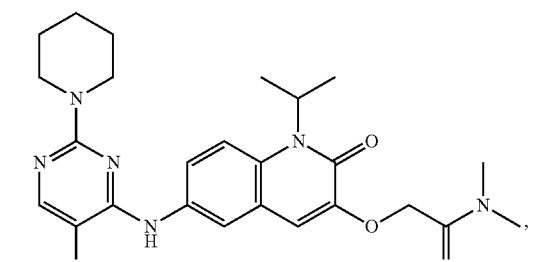
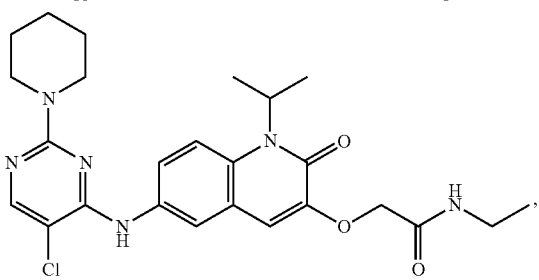
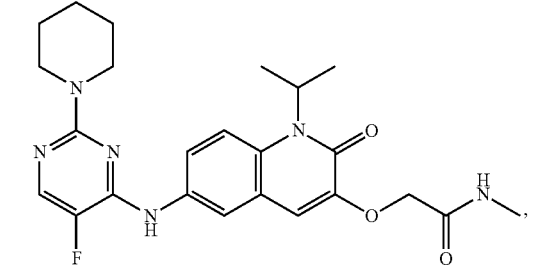
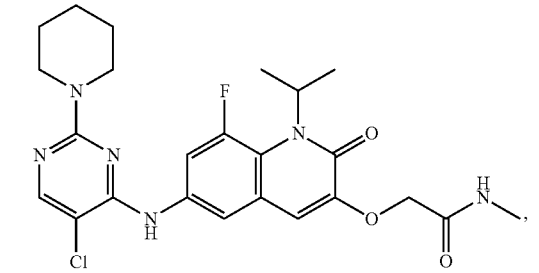
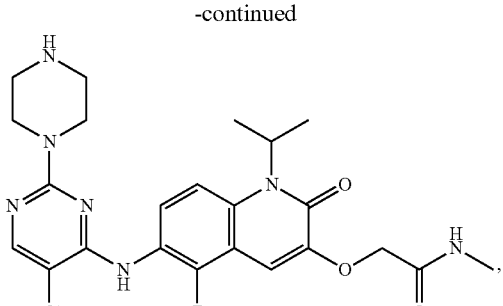
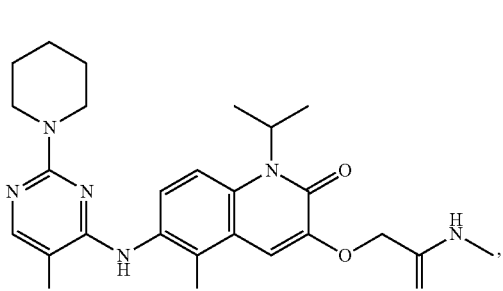
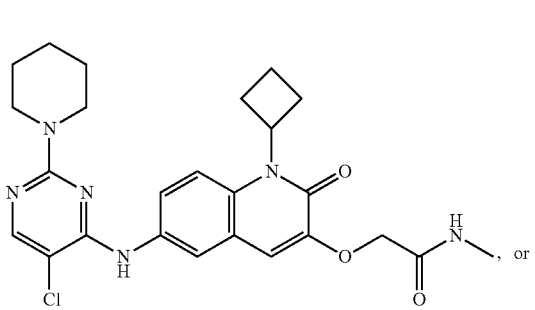
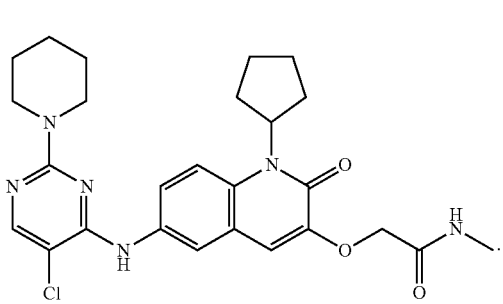
In any aspect or embodiment described herein, the PTM is selected from:
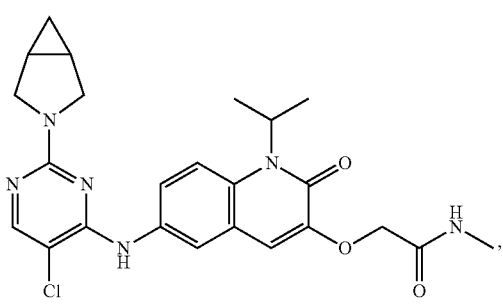

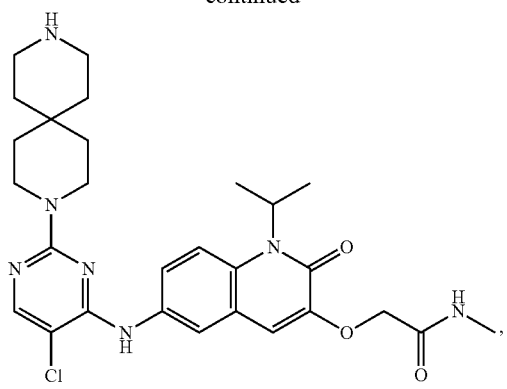
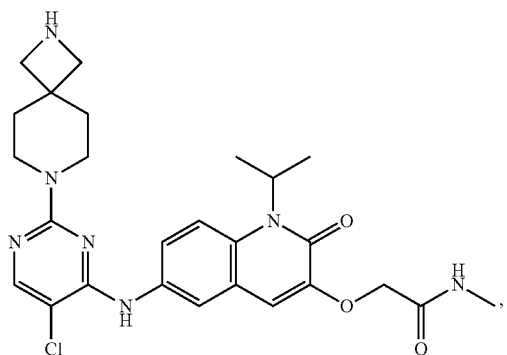
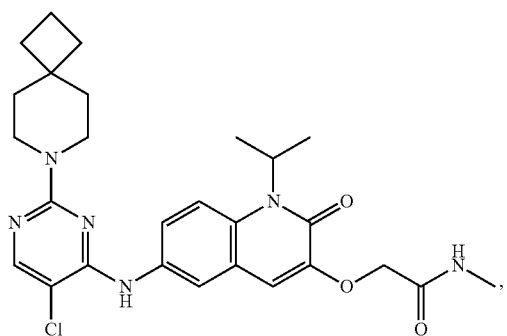
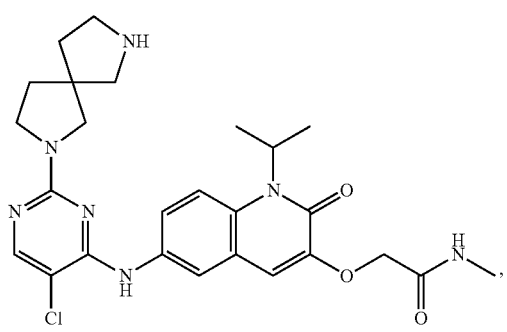
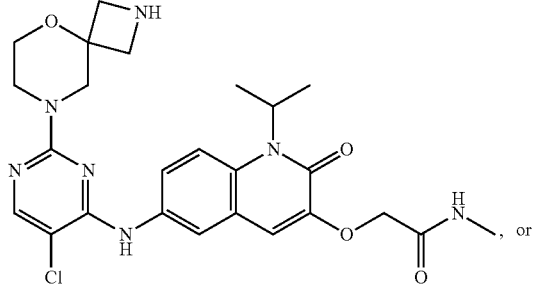
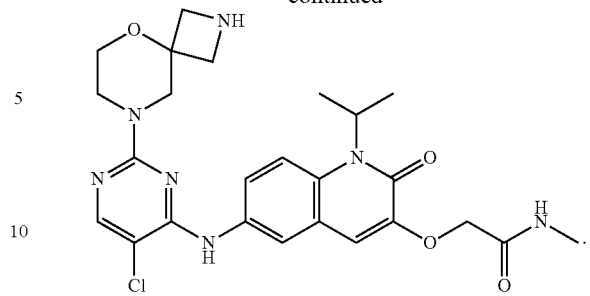
In any aspect or embodiment described herein, the PTM is selected from:
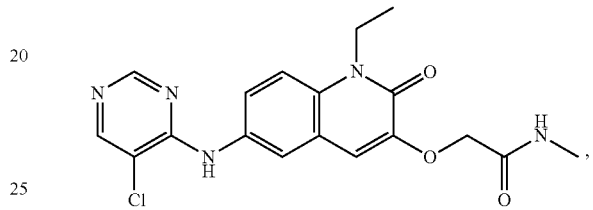
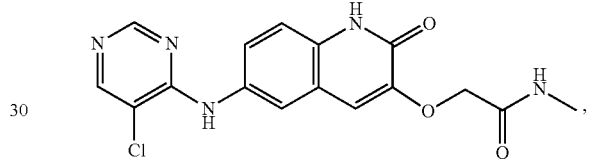
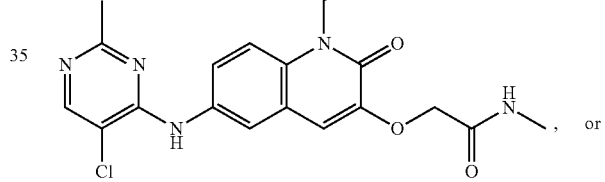
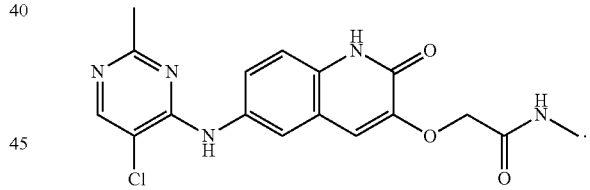
In any aspect or embodiment described herein, the PTM is represented by
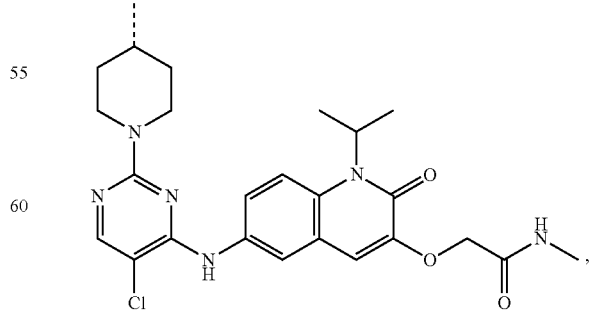
wherein ⋰ of the PTM indicates the point of attachment with the L.

In any aspect or embodiment described herein, the PTM is selected from:
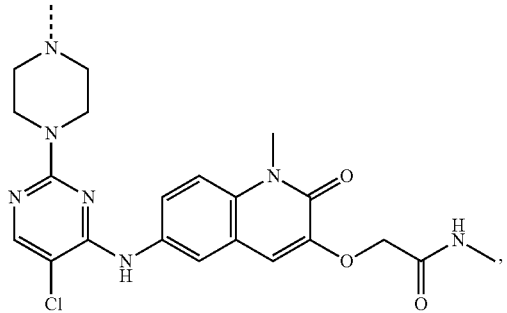
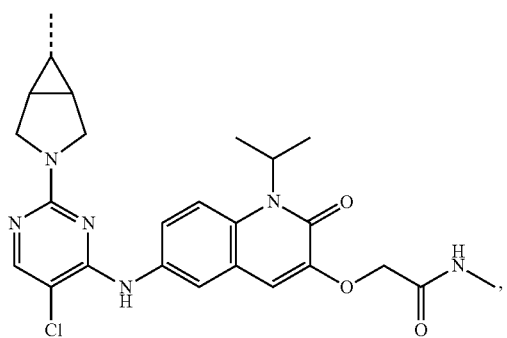
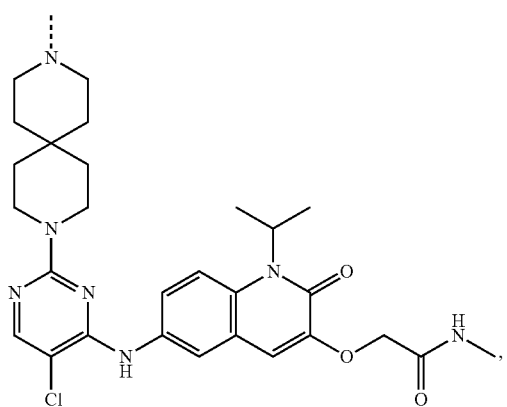
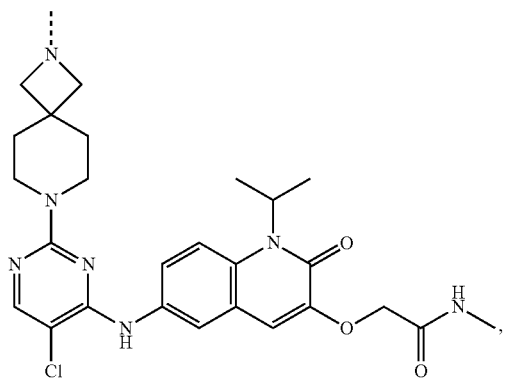
-continued
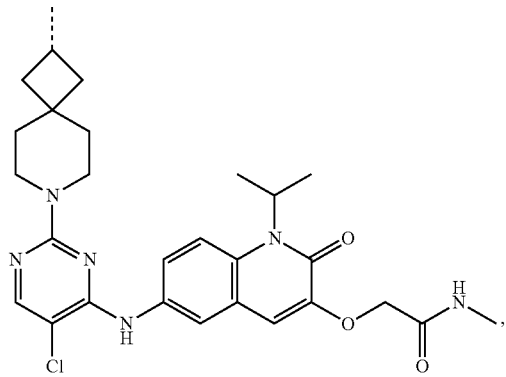
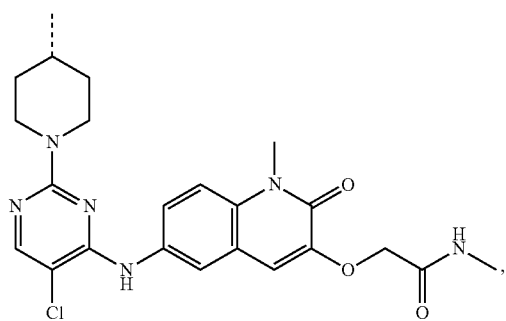
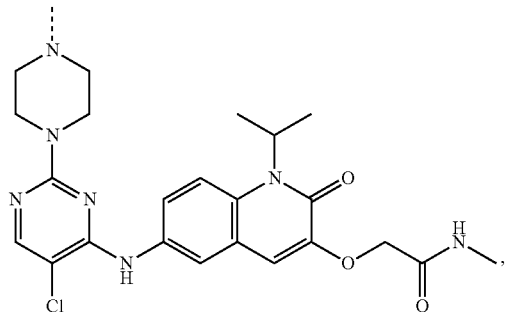
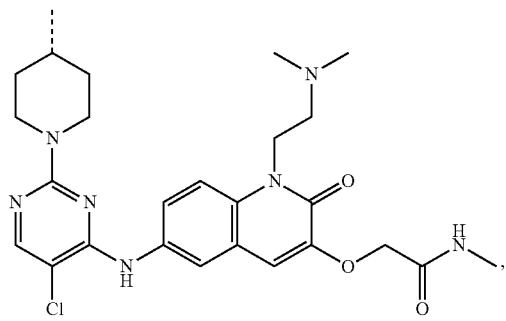
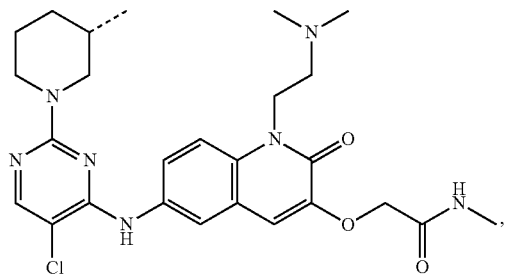

173
-continued
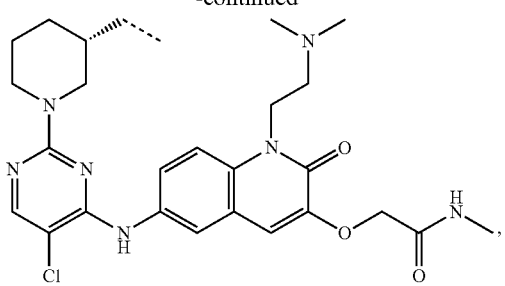
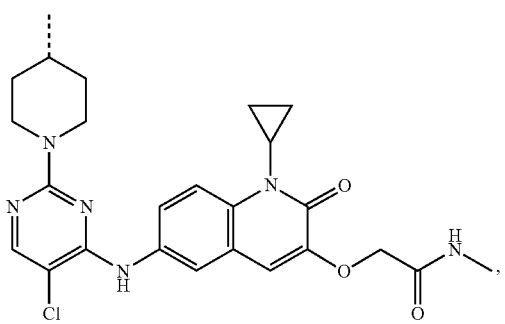
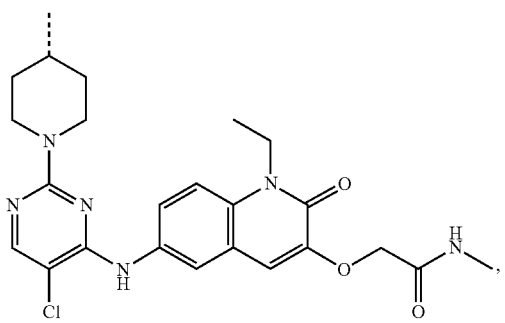
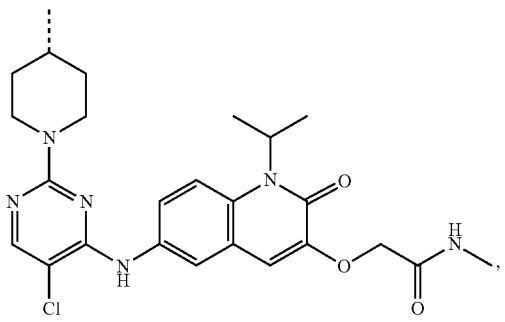
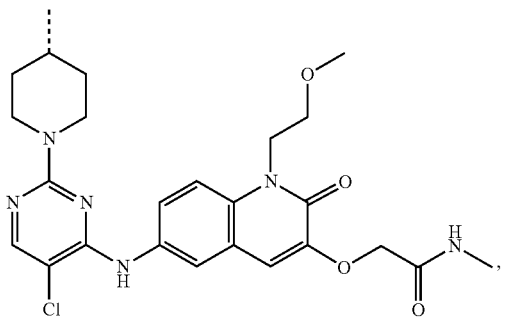
174
-continued
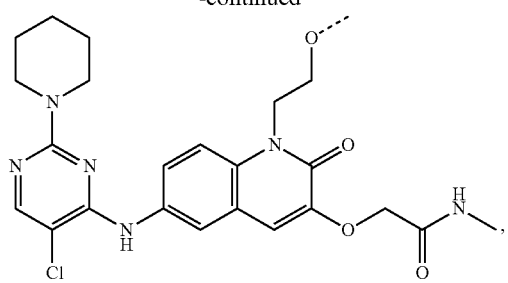
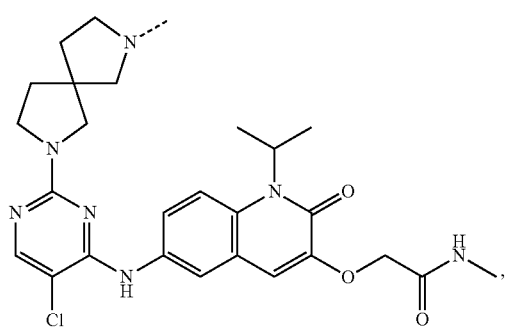
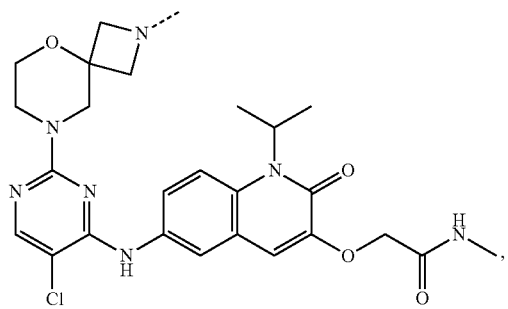
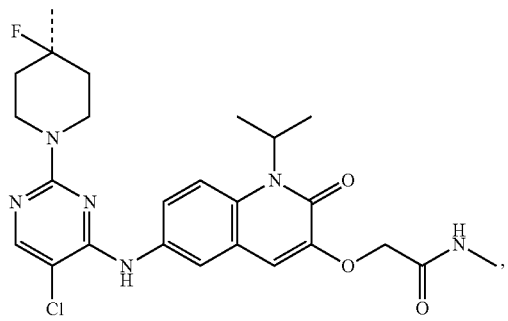
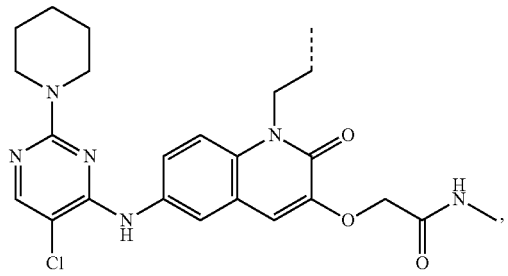

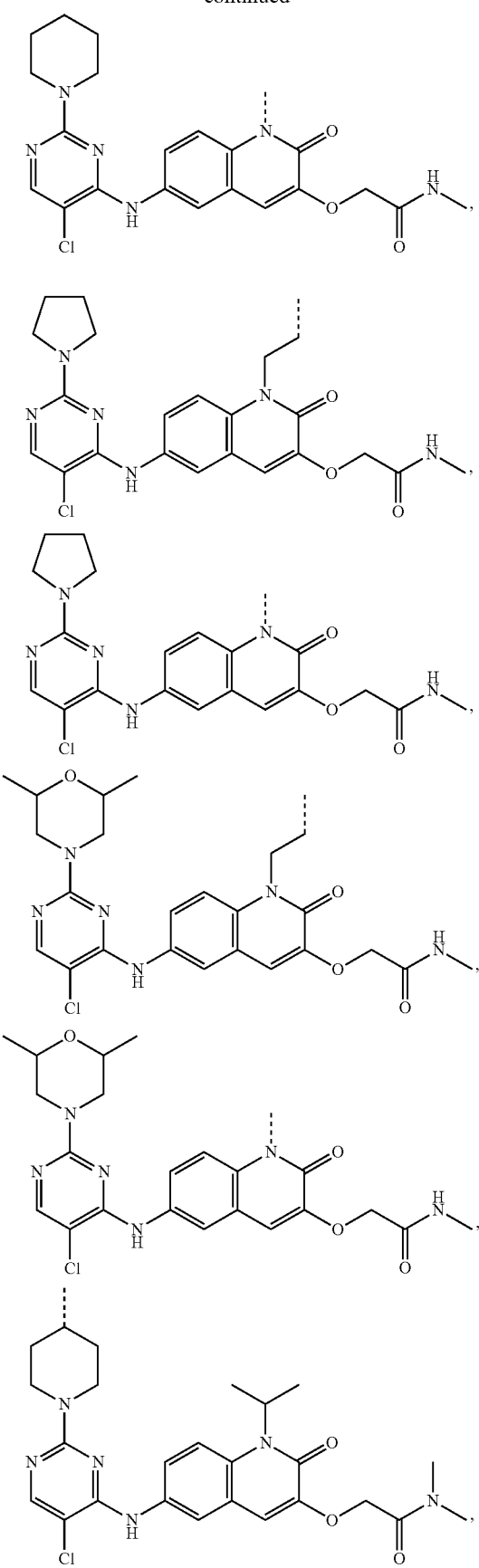
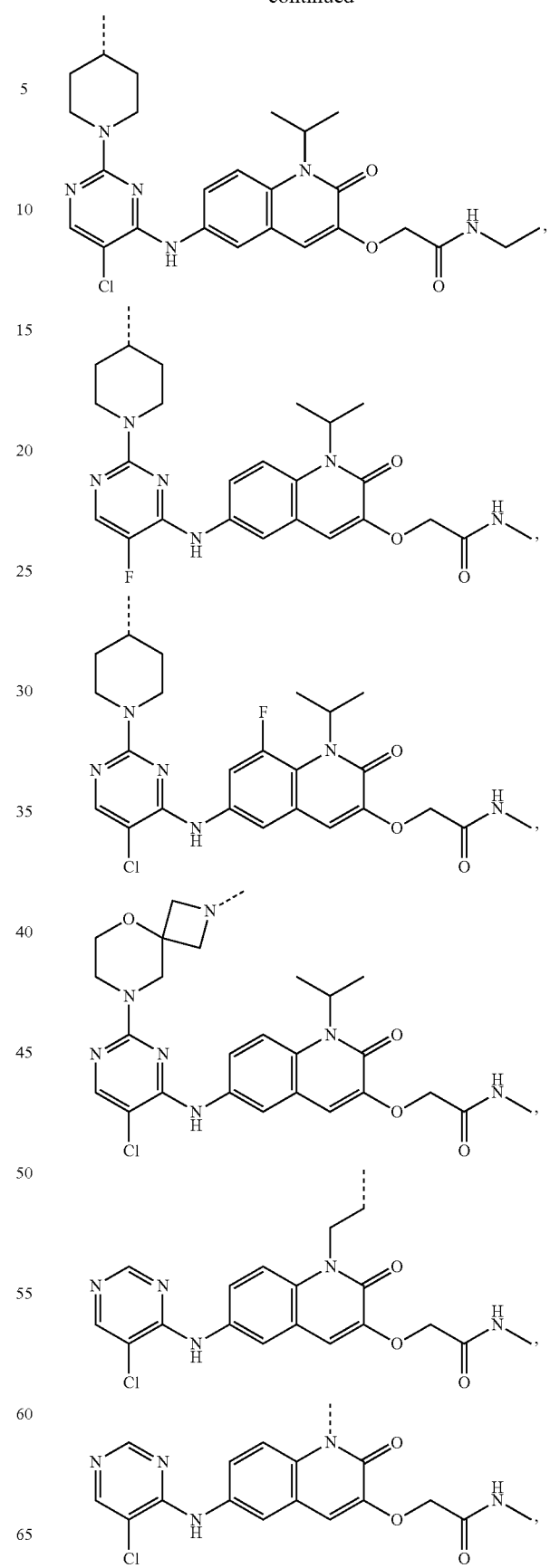

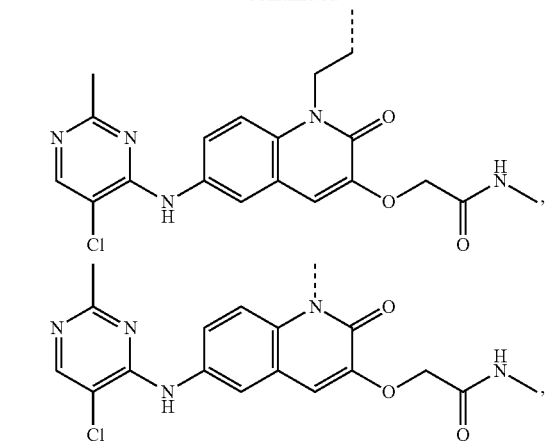
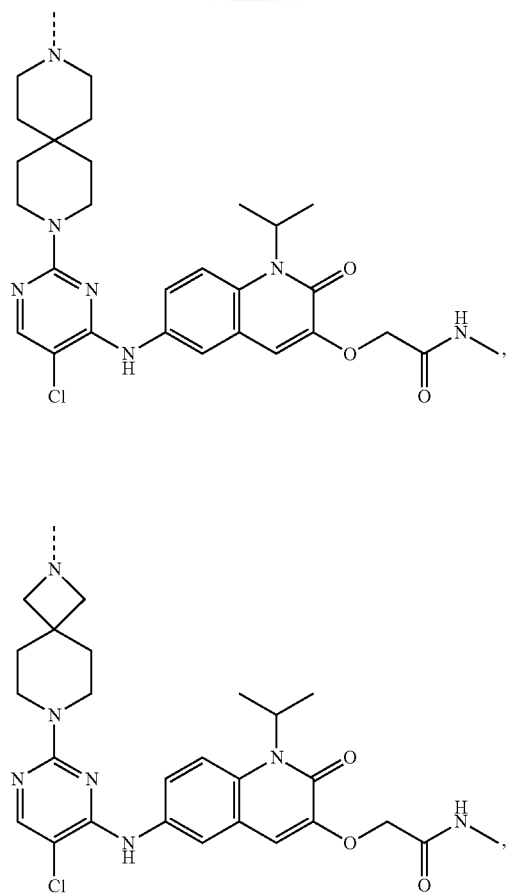
wherein --- of the PTM indicates the point of attachment with the L.
In any aspect or embodiment described herein, the PTM is selected from:
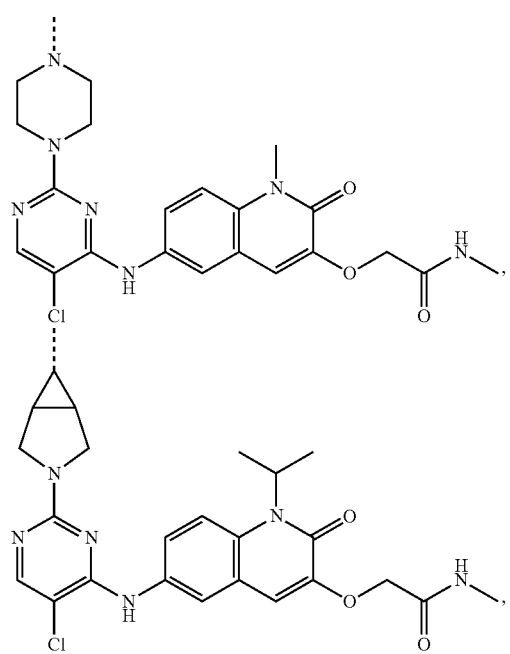
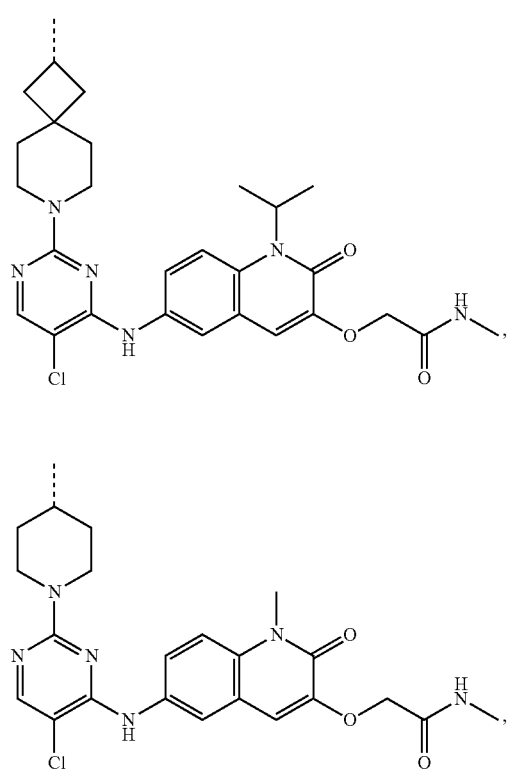

179
-continued
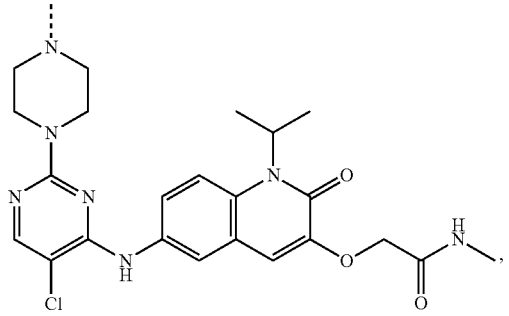
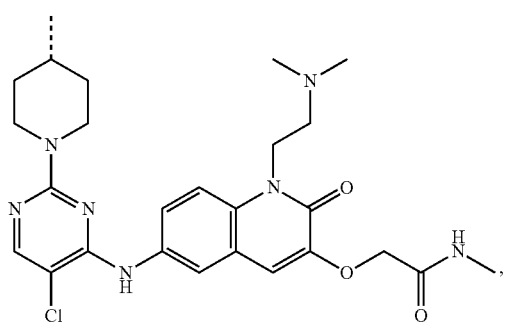
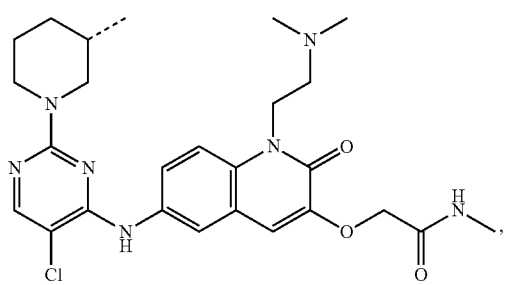
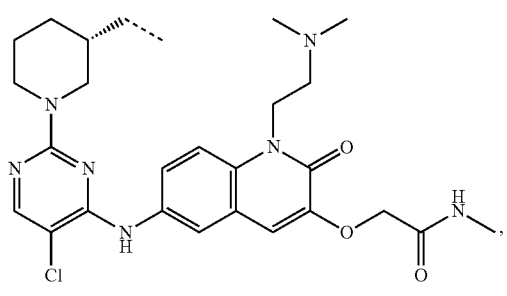
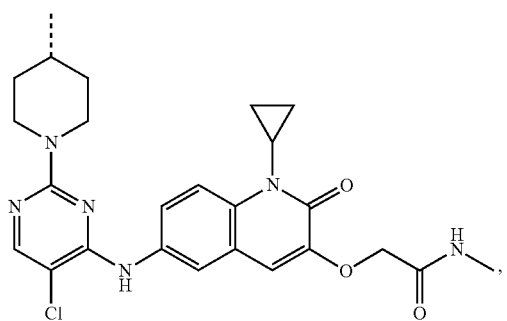
180
-continued
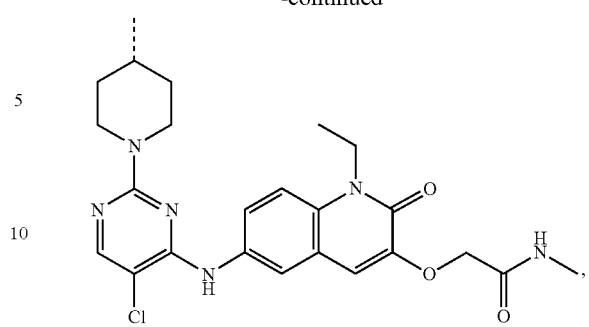
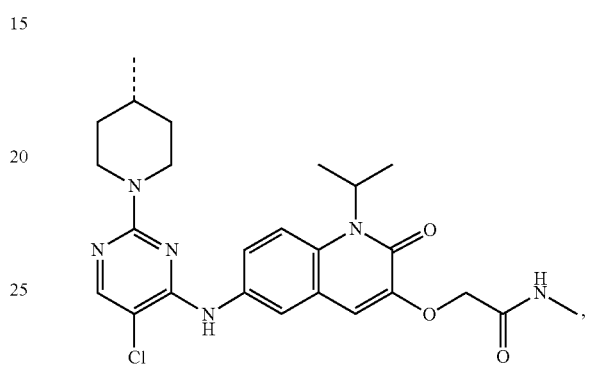
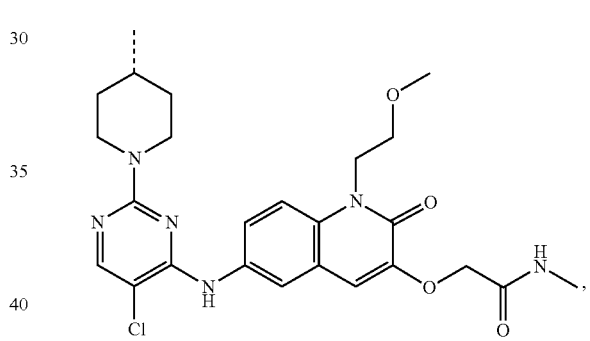
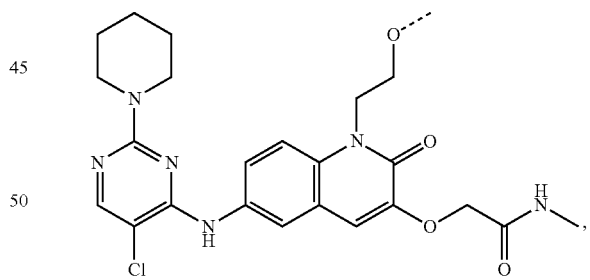
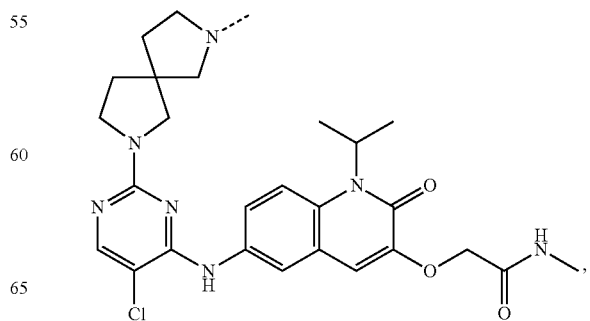

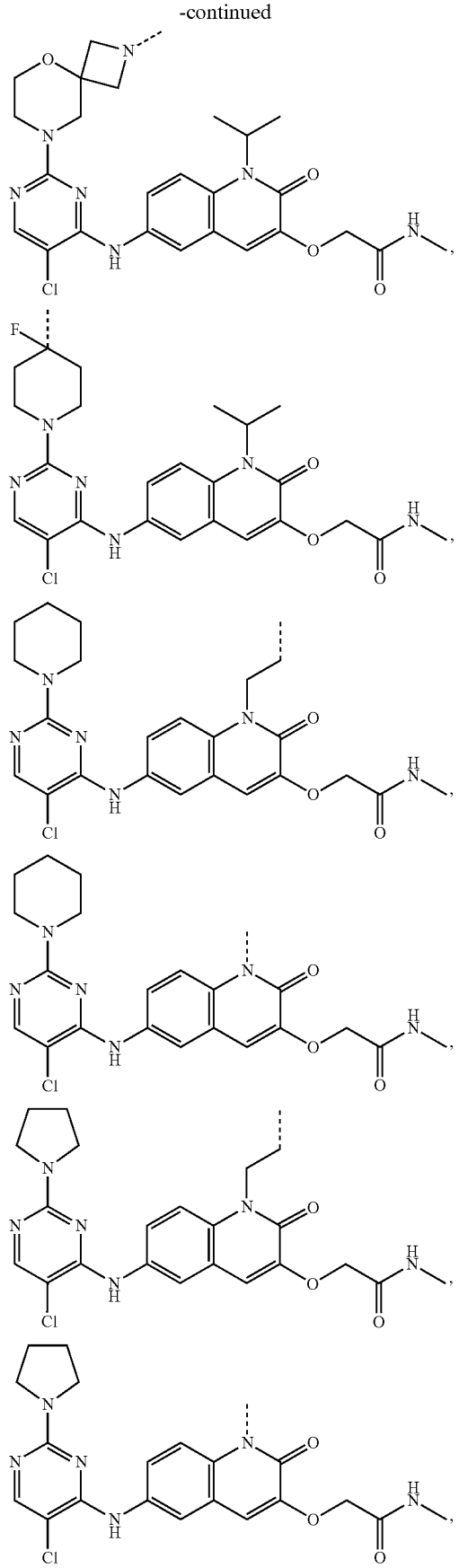
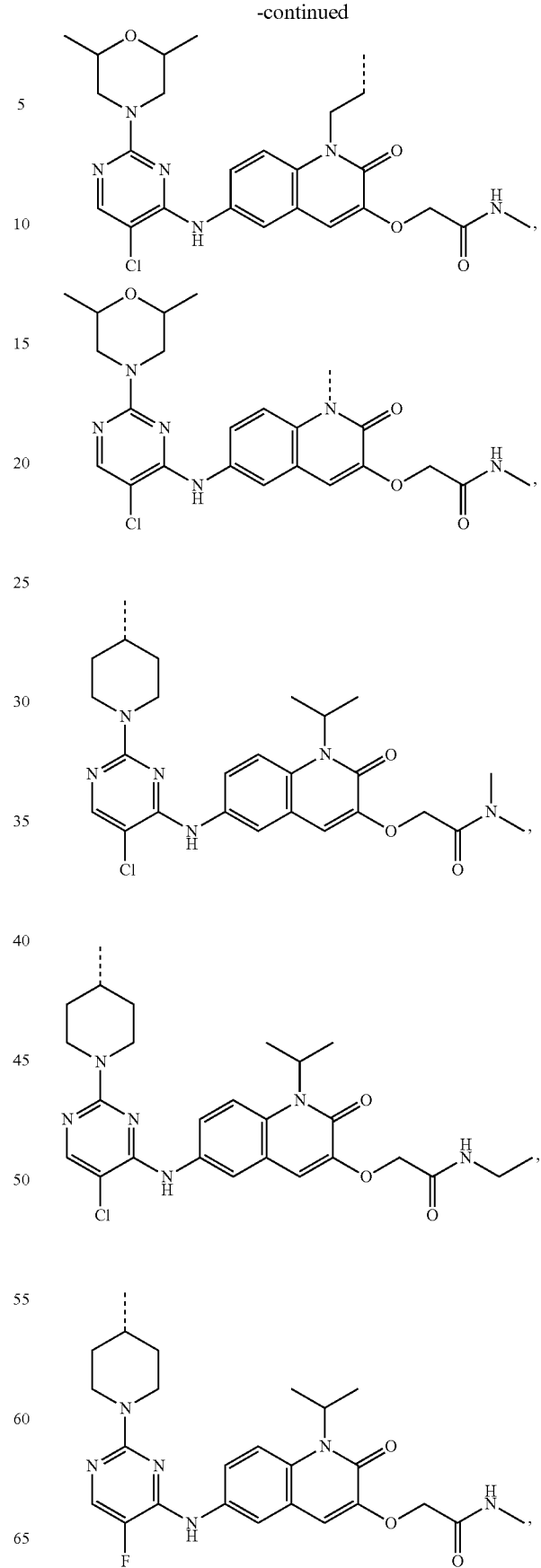

183
-continued
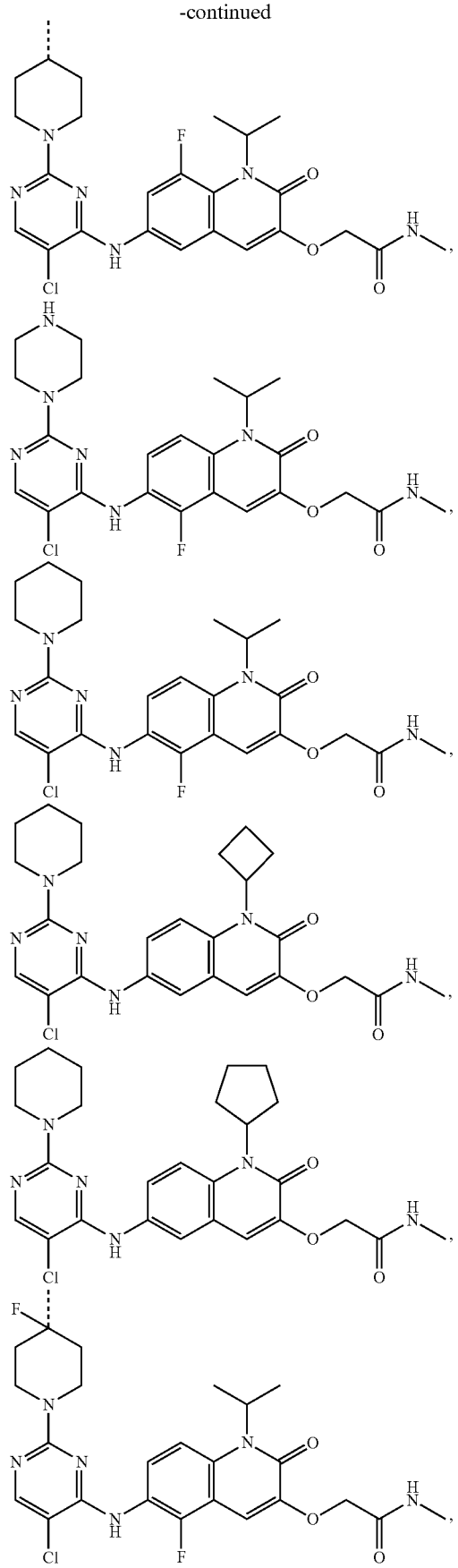
184
-continued
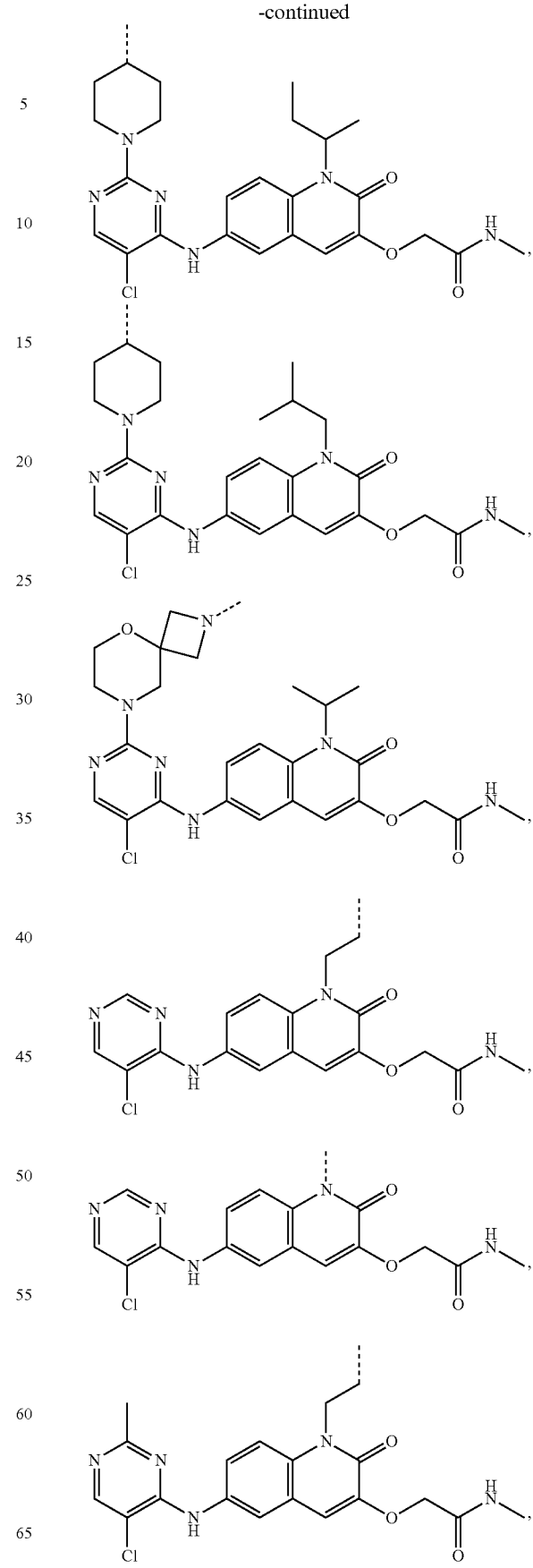

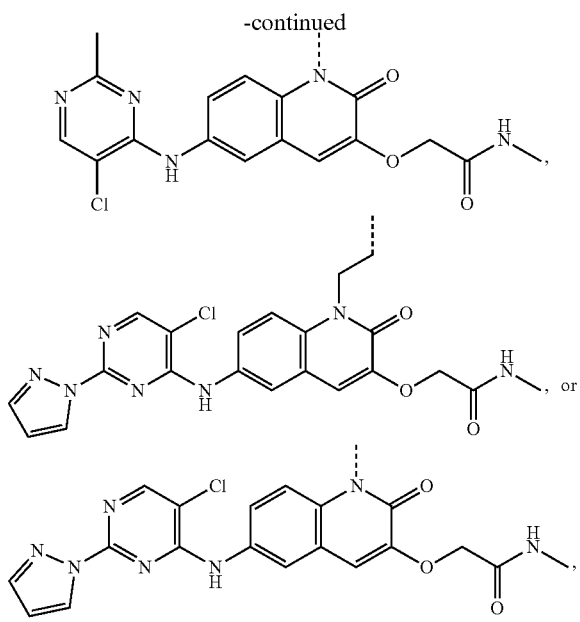

wherein ⋯ of the PTM indicates the point of attachment with the linker group (L) or the ULM.

The bifunctional compound represented by:

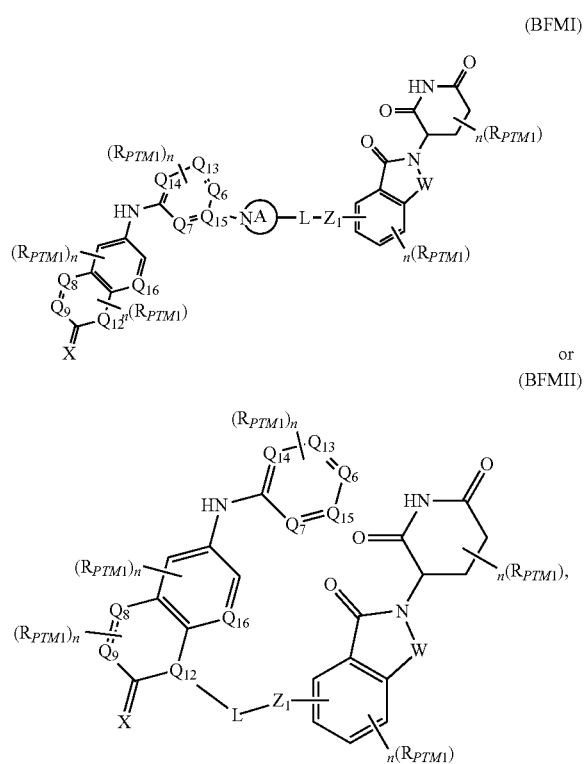

wherein:
each of $R_{PTM1}$, $Q_6$, $Q_7$, $Q_8$, $Q_9$, $Q_{12}$, $Q_{13}$, $Q_{14}$, $Q_{15}$, $Q_{16}$, n, W and L are as described in any aspect or embodiment described herein;

A is an optionally substituted N-heterocyclyl (e.g., includes an optionally substituted 3-12 or 4-7 member heterocyclyl; an optionally substituted heterocycloalkyl; an optionally substituted $C_{3-12}$ monocyclic or bicyclic heterocycloalkyl; optionally substituted with at least one OH, halo (such as F, Cl, Br), C1-C5 alkyl (such as a methyl), =O, $NH_2$, or a combination thereof; or a combination thereof); and $Z_1$ is an R group of a CLM as described in any aspect or embodiment described herein that is modified to be covalently linked to L, such a group selected from —C(=O)—, —CONR'—, —O—, —NR'—, a carbon shared with a cyclic group of L, or a nitrogen shared with a cyclic group of L.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, as described herein among others. In certain preferred aspects of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In any aspect or embodiment described herein, the disease or disorder is associated with abberant BCL6 expression and or activity.

In any aspect or embodiment described herein, the disease or disorder is a cancer associated with abberant BCL6 expression and or activity.

In any aspect or embodiment described herein, the disease or disorder is associated with BCL6 accumulation and aggregation.

In any aspect or embodiment described herein, the disease or disorder is a cancer associated with BCL6 accumulation and aggregation.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, renal cell carcinomas, bladder cancer, bowel cancer, breast cancer, cervical cancer, colon cancer, esophageal cancer, cancer of the head, kidney cancer, liver cancer, lung cancer, neck cancer, ovarian cancer, pancreatic cancer, prostate cancer, stomach cancer; leukemia; benign lymphoma, malignant lymphoma, Burkitt's lymphoma, Non-Hodgkin's lymphoma, benign melanoma, malignant melanomas, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas, prostate cancer, uterine cancer, testicular cancer, thyroid cancer, astrocytoma, stomach cancer, melanoma, carcinosarcoma, Hodgkin's disease, Wilms' tumor, teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, follicular lymphoma, intravascular large B-cell lymphoma, B-cell leukemia, chronic myeloid leukemia, non-small cell lung cancer.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIG 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5′-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucleoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4''-dimethoxy-5',5''-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs//CLMs.

With PTMs and ULMs (e.g. CLMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus, a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Scheme 1

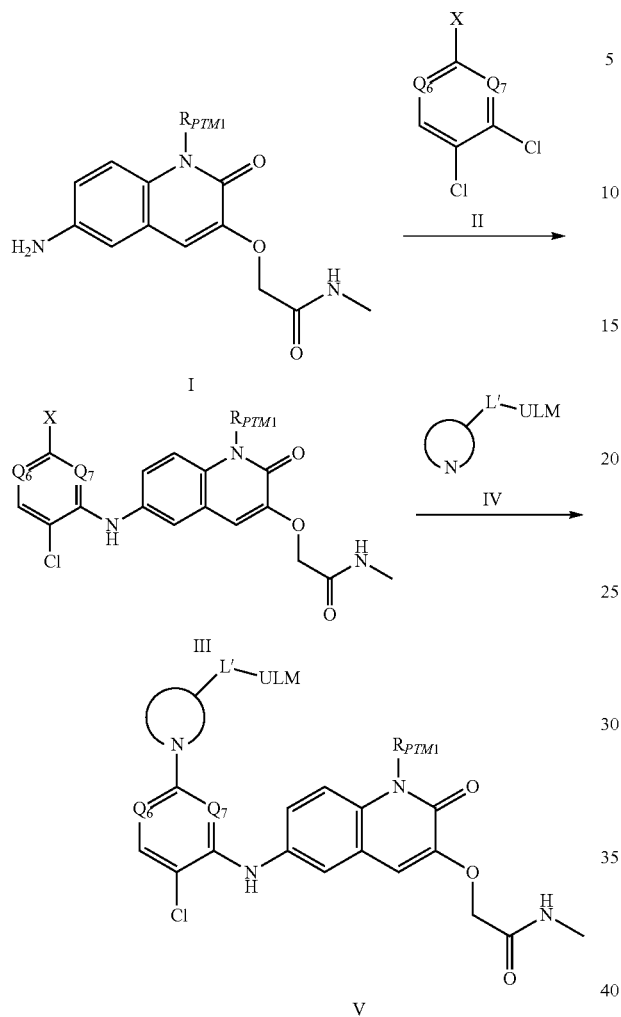

A compound of formula I (commercially available or readily prepared using standard reaction techniques known to one skilled in the art) may be reacted with a compound of formula II (also commercially available or readily prepared by the skilled artisan) in a solvent such as DMSO or DMF, with a base such as triethylamine or DIEA and with heating to produce a compound of formula III. In this case the X on compound II can be a leaving group such as a halogen and $Q_6$ and $Q_7$ are such that the selective displacement shown here is favored. Non-limiting examples are where X=Cl and $Q_6$ and $Q_7$ are both N. Compounds of formula III can generate a PROTAC™ of formula V by reaction with a compound of formula IV by heating in a solvent such as DMSO, in the presence of a base such as DIEA. Compounds of formula IV are advanced building blocks where the ULM, linker and part of the PTM form a complete subunit. Wherein

represents a 4-8 member cyclic amine or spirocyclic amine (any 2-ring combination from 4,4; 4,5; 4,6; 5,4; 5,5; 5,6; 6,4; 6,5; and 6,6) optionally including a second N if >2 carbons are between them. L' can be a bond, linker, or part of linker.

Scheme 2

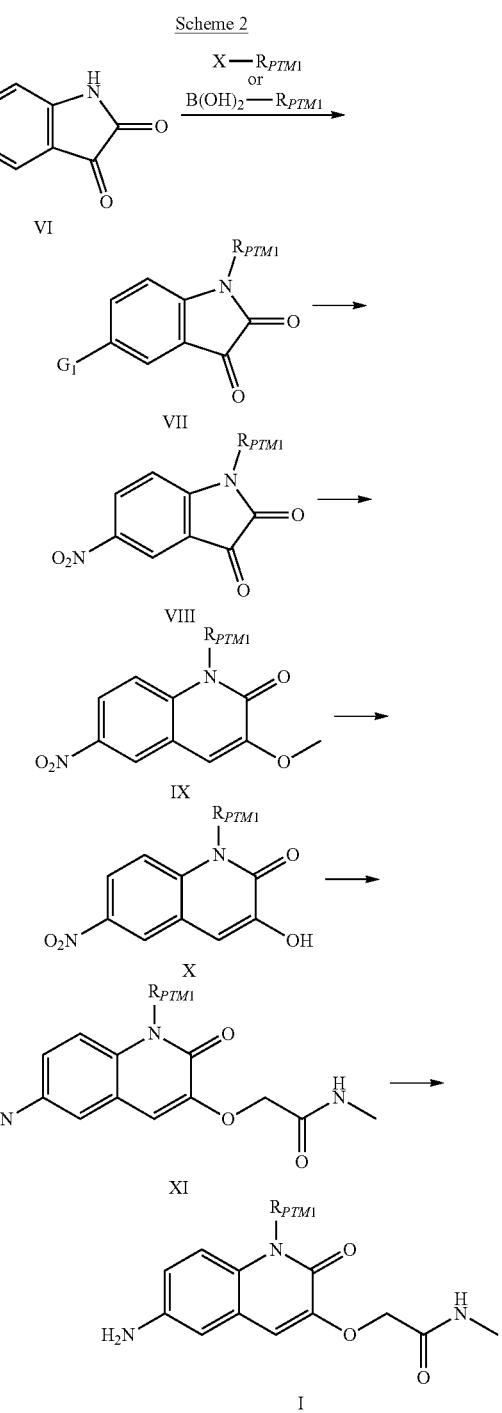

Compounds of formula I in Scheme I can be prepared using procedures found and/or adapted from Kerres et al., 2017, *Cell Reports* 20, 2860-2875 and are shown in Scheme 2. When $G_1$ is $NO_2$, a compound of formula VI can be dissolved in a solvent such as DMF, treated with a base such as, but not limited to, $K_2CO_3$ and alkylated with an $R_{PTM1}$-X. In this case X can be a leaving group such as, but not limited to, iodo or bromo. Generally, $R_{PTM1}$-X are commercially available or readily prepared by someone skilled in the art. Alternatively, the boronic acid analogue of $R_{PTM1}$ can be attached to a compound of formula VI using the Chan-Lam coupling reaction (for a review see Chen et al., 2020, Advanced Synthesis and Catalysis 62 (16), 3311-3331) wherein the boronic acid and compound of formula VI are combined with a copper salt such as $Cu(OAc)_2$, a base such as $Na_2CO_3$ in a solvent such as DCE and heated. In this case it may be preferable to have $G_1$=H and conduct a nitration as shown in the third step of scheme 2 using $KNO_3$ under acidic conditions. The skilled artisan will realize that the nitration step is skipped when alkylating a 5-nitroisatin (VI with $G_1$=$NO_2$) with $R_{PTM1}$-X as compounds of formula VIII are generated directly. Compounds of formula VIII can be reacted with TMS-diazomethane under basic conditions (See Duplantier et al., 2009, J. Med. Chem. 52, 3576-3585 and references cited therein) to give the ring expanded compounds of formula IX. The hydroxy group of compounds of formula X can be unmasked by treating compounds of formula IX with $BBR_3$. Compounds of formula I can me obtained in 2 additional steps by alkylation of the hydroxy group of X with a 2-haloacetamide followed by reduction of the nitro group. Numerous methods are available to the skilled artisan to effect the nitro reduction.

Compounds of formula I from Scheme can also be obtained using the approach shown in Scheme 3. Compounds of formula XII (commercially available or readily prepared by methods known to one skilled in the art) can be treated with nitric acid in sulfuric acid to form compounds of formula XIII. Heating a compound of formula XIII in a mixture of sodium bromate/HBr can afford a compound of formula XIV. Similarly, as in Scheme 2, a compound of formula XIV can be alkylated with $R_{PTM1}$-X under basic conditions to afford a compound of formula XV. Heating this compound with BrettPhos Palladacycle Gen4 in a mixture of dioxane, water and KOH can furnish a compound of formula X. The final two steps are as shown in Scheme 2.

Synthetic Procedures

Example 1: 2-{[6-({5-chloro-2-[4-(2-{1-[2-(2,6-dioxopiperidin-3-yl)-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide (Compound 13)

Step 1: Synthesis of 1-isopropyl-5-nitro-indoline-2,3-dione

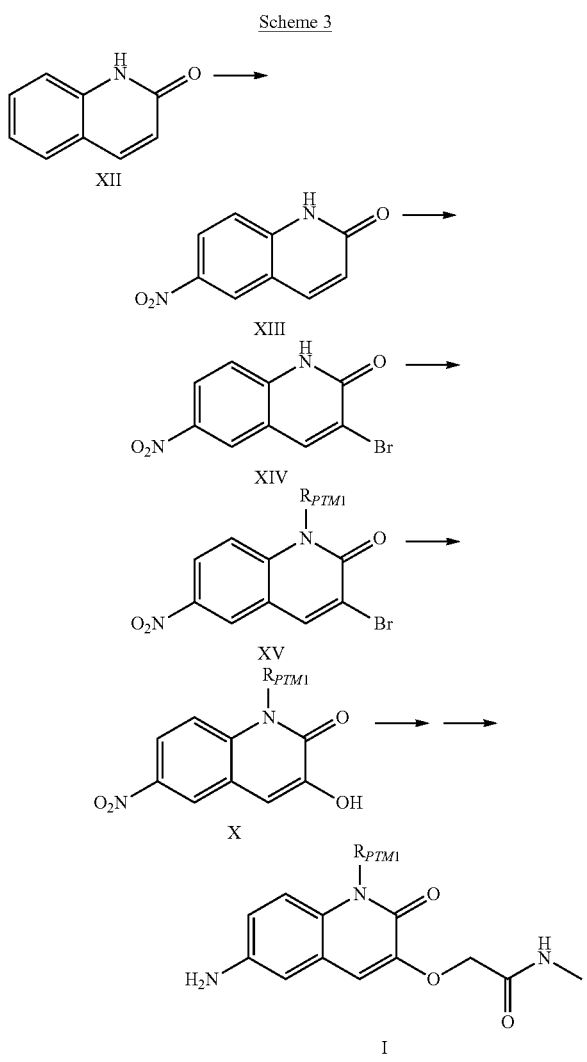

To a mixture of 5-nitroindoline-2,3-dione (5.00 g, 26.02 mmol, 1.00 eq) in N,N-dimethylformamide (50 mL) was added potassium carbonate (7.19 g, 52.05 mmol, 2.00 eq) and 2-iodopropane (6.64 g, 39.04 mmol, 3.90 mL, 1.50 eq). The mixture was stirred at 25° C. for 48 h. The mixture was poured into water (300 mL) and extracted with ethyl acetate (50 mL×3). The organic layer was washed with brine (100 mL), dried over anhydrous sodium sulfate, filtered and concentrated under reduced pressure to give 1-isopropyl-5-nitro-indoline-2,3-dione (4.00 g, 17.08 mmol, 66% yield) as yellow solid, which was used in next step directly. H NMR (400 MHz, DMSO-d6) δ=8.46 (dd, J=8.8, 2.4 Hz, 1H), 8.21 (d, J=2.4 Hz, 1H), 7.52 (d, J=8.8 Hz, 1H), 4.60-4.45 (m, 1H), 1.46 (d, J=6.8 Hz, 6H).

Step 2: Synthesis of 1-isopropyl-3-methoxy-6-nitro-quinolin-2-one

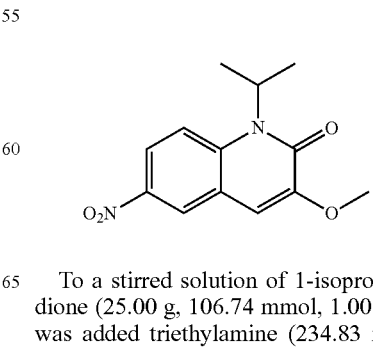

To a stirred solution of 1-isopropyl-5-nitro-indoline-2,3-dione (25.00 g, 106.74 mmol, 1.00 eq) in ethanol (400 mL) was added triethylamine (234.83 mmol, 33 mL, 2.20 eq)

followed by TMS-diazomethane in hexane (2 M, 117 mL, 2.20 eq) at 25° C. After stirring for 12 hours at 25° C. the reaction mixture was poured into water (1500 mL) and extracted with dichloromethane (500 mL×3). The organic layers were combined and concentrated under reduced pressure. The residue was stirred in a mixture of ethyl acetate (50 mL) and petroleum ether (500 mL) at 25° C. for 2 h then filtered. The filter cake was dried under reduced pressure to give 1-isopropyl-3-methoxy-6-nitro-quinolin-2-one as a yellow solid (45.00 g, crude). LCMS (ESI) m/z: 263.1 [M+1]$^+$. $^1$H NMR (400 MHz, DMSO-d6) δ=8.59 (d, J=2.8 Hz, 1H), 8.17 (dd, J=9.6, 2.8 Hz, 1H), 7.52 (d, J=9.6 Hz, 1H), 7.49 (s, 1H), 5.45-5.28 (m, 1H), 3.84 (s, 3H), 1.55 (d, J=6.8 Hz, 6H).

Step 3: Synthesis of 3-hydroxy-1-isopropyl-6-nitro-quinolin-2-one

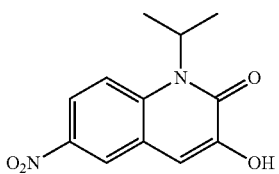 [SMILES: CC(C)n1c(=O)c(O)cc2cc([N+](=O)[O-])ccc21]

A solution of boron tribromide (46.14 mmol, 4.5 mL, 1.10 eq) in dichloromethane (40 mL) was added, dropwise, to a mixture of 1-isopropyl-3-methoxy-6-nitro-quinolin-2-one (11.00 g, 41.94 mmol, 1.00 eq) in 400 mL dichloromethane at 0° C. After stirring at 0° C. for 2 h, the mixture was poured into saturated sodium bicarbonate (1000 mL) and extracted with dichloromethane (500 mL×3). The organic layers were combined, washed with brine (100 mL), dried over anhydrous sodium sulfate and concentrated under reduced pressure. The residue was stirred with a mixture of ethyl acetate (50 mL), petroleum ether (500 mL) and acetonitrile (50 mL) at 25° C. for 12 h then filtered. The filtrate was concentrated under reduced pressure to give 3-hydroxy-1-isopropyl-6-nitro-quinolin-2-one (28.00 g, 112.80 mmol, 90% yield) as brown solid. LCMS (ESI) m/z: 280.2 [M+23]+. $^1$H NMR (400 MHz, DMSO-d6) δ=9.95 (s, 1H), 8.54 (d, J=2.8 Hz, 1H), 8.14 (dd, J=9.2, 2.4 Hz, 1H), 7.92 (d, J=9.2 Hz, 1H), 7.33 (s, 1H), 5.58-5.14 (m, 1H), 1.59 (d, J=6.8 Hz, 6H).

Step 4: Synthesis of 2-[(1-isopropyl-6-nitro-2-oxo-3-quinolyl)oxy]-N-methyl-acetamide

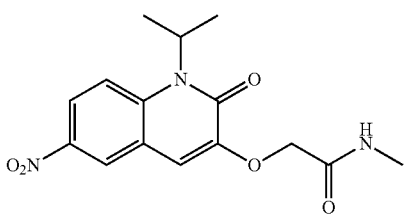 [SMILES: CNC(=O)COc1cc2cc([N+](=O)[O-])ccc2n(C(C)C)c1=O]

This compound was prepared analogously to 2-[(6-amino-1-ethyl-2-oxo-3-quinolyl)oxy]-N-methyl-acetamide. LCMS (ESI) m/z: 320.1 [M+1]$^+$. $^1$H NMR (400 MHz, DMSO-d6) δ=8.60 (d, J=2.8 Hz, 1H), 8.21 (dd, J=9.6, 2.8 Hz, 1H), 8.01-7.88 (m, 2H), 7.48 (s, 1H), 5.70-5.15 (m, 1H), 4.57 (s, 2H), 2.68 (d, J=4.8 Hz, 3H), 1.58 (d, J=7.2 Hz, 6H).

Step 5: Synthesis of 2-[(6-amino-1-isopropyl-2-oxoquinolin-3-yl)oxy]-N-methylacetamide

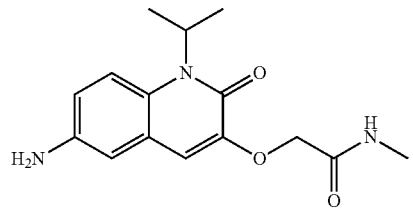

2-[(1-isopropyl-6-nitro-2-oxoquinolin-3-yl)oxy]-N-methylacetamide (300.00 mg, 0.94 mmol, 1.00 equiv) was added to a 50-mL round-bottom flask under nitrogen and taken up in DMF (15 mL) and MeOH (15 mL). After adding Pd/C (30.00 mg, 0.28 mmol, 0.30 equiv) the flask was evacuated and flushed with hydrogen. The mixture was allowed to stir for 4 hours at rt then filtered through a Celite pad and concentrated under reduced pressure to afford 253 mg of 2-[(6-amino-1-isopropyl-2-oxoquinolin-3-yl)oxy]-N-methylacetamide as a light yellow solid (92%). LC-MS (ES$^+$): m/z 290.00 [M+H$^+$], $t_R$=0.59 min (1.20 minute run).

Step 6: Synthesis of 2-([6-[(2,5-dichloropyrimidin-4-yl)amino]-1-isopropyl-2-oxoquinolin-3-yl]oxy)-N-methylacetamide

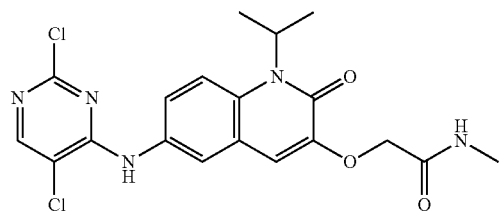 [SMILES: CNC(=O)COc1cc2cc(Nc3nc(Cl)ncc3Cl)ccc2n(C(C)C)c1=O]

Into a 50-mL round-bottom flask, DIEA (268.01 mg, 2.07 mmol, 3 equiv), 2,4,5-trichloropyrimidine (152.14 mg, 0.83 mmol, 1.2 equiv) was added to a mixture of 2-[(6-amino-1-isopropyl-2-oxoquinolin-3-yl)oxy]-N-methylacetamide (200.00 mg, 0.69 mmol, 1.00 equiv), DMSO (5 mL). The resulting solution was stirred for 2 hr at 100° C. The crude product was purified by Flash-Prep-HPLC with the following conditions: Column, C18 silica gel; mobile phase, H2O:ACN=100:0 increasing to H2O:ACN=60:40 within 30 min; Detector: 254 nm. To afford 183 mg (60%) of 2-([6-[(2,5-dichloropyrimidin-4-yl)amino]-1-isopropyl-2-oxoquinolin-3-yl]oxy)-N-methylacetamide as a light yellow solid. LC-MS (ES+): m/z 436.00 [M+H+], tR=0.81 min (1.20 minute run).

Step 7: Preparation of tert-butyl 4-(1-benzyloxycarbonylpiperidine-4-carbonyl)piperazine-1-carboxylate

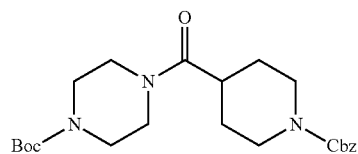 [SMILES: CC(C)(C)OC(=O)N1CCN(C(=O)C2CCN(C(=O)OCc3ccccc3)CC2)CC1]

A solution of 1-benzyloxycarbonylpiperidine-4-carboxylic acid (70.68 g, 268.45 mmol, 1 eq) and O-(7-Azabenzotriazol-1-yl)-N,N,N',N'-tetramethyluronium Hexafluorophosphate (153.11 g, 402.68 mmol, 1.5 eq) in N,N-dimethylformamide (500 mL) was added tert-butyl piperazine-1-carboxylate (50 g, 268.45 mmol, 1 eq) and N,N-diisopropylethylamine (104.09 g, 805.36 mmol, 140.3 mL, 3 eq) at 25° C., then the mixture was stirred for 2 h at 25° C. LCMS showed desired m/z and the reaction completed. The mixture was poured into water (500 mL) and extracted with ethyl acetate (500 mL×3). The organic layer was washed with brine (500 mL), dried over anhydrous sodium sulfate and filtered. The filtrate was concentrated under reduced pressure. The residue was purified by prep-HPLC (column: Phenomenex luna c18 250 mm*100 mm*10 um; mobile phase: [water (0.1% TFA)-ACN]; B %: 40%-60%, 18 min). tert-butyl 4-(1-benzyloxycarbonylpiperidine-4-carbonyl) piperazine-1-carboxylate (100 g, 231.74 mmol, 86.32% yield) was obtained as a white solid. MS (ESI) m/z: 432.2 [M+1]$^+$. $^1$H NMR: (400 MHz, DMSO-d6) δ: 7.37-7.15 (m, 5H), 5.07 (s, 2H), 4.02-3.95 (m, 2H), 3.66-3.55 (m, 1H), 3.52-3.47 (m, 2H), 3.35-3.25 (m, 5H), 2.95-2.80 (m, 3H), 1.70-1.57 (m, 2H), 1.40 (s, 9H), 1.28-1.22 (m, 2H).

Step 8: Preparation of tert-butyl 4-[1-(1-benzyloxycarbonyl-4-piperidyl)-1-methyl-ethyl]piperazine-1-carboxylate

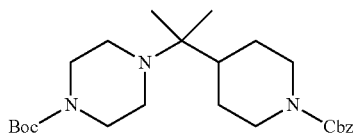 [SMILES: CC(C)(C)OC(=O)N1CCN(C(C)(C)C2CCN(C(=O)OCc3ccccc3)CC2)CC1]

To a mixture of Zirconium tetrachloride (18.15 g, 77.86 mmol, 6.5 mL, 1.6 eq) in tetrahydrofuran (200 mL) was added a solution of tert-butyl 4-(1-benzyloxycarbonyl piperidine-4-carbonyl)piperazine-1-carboxylate (21 g, 48.66 mmol, 1 eq) in tetrahydrofuran (600 mL) drop wise at −60° C. over a period of 30 min under nitrogen. Then the mixture was added methylmagnesium bromide (3 M, 64.9 mL, 4 eq) at −60° C. and stirred for 30 min. The resulting mixture was warmed to 25° C. and stirred for 6 h. The mixture was quenched with saturated ammonium chloride solution (2 L) and extracted with Ethyl acetate (2 L×3), the combined organic phase washed with brine (2 L), dried over anhydrous sodium sulfate, filtered and concentrated under reduced pressure. The residue was purified by prep-HPLC (column: Phenomenex luna C18 (250*70 mm, 10 um); mobile phase: [water (0.1% TFA)-ACN]; B %: 25%-55%, 20 min). tert-butyl 4-[1-(1-benzyloxycarbonyl-4-piperidyl)-1-methyl-ethyl]piperazine-1-carboxylate (10 g, 22.44 mmol, 46% yield) was obtained as a yellow oil. MS (ESI) m/z: 446.1 [M+1]+.

Step 9: Preparation of tert-butyl 4-[1-methyl-1-(4-piperidyl)ethyl] piperazine-1-carboxylate

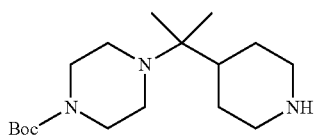 [SMILES: CC(C)(C)OC(=O)N1CCN(C(C)(C)C2CCNCC2)CC1]

A solution of tert-butyl 4-[1-(1-benzyloxycarbonyl-4-piperidyl)-1-methyl-ethyl]piperazine-1-carboxylate (40 g, 89.77 mmol, 1 eq) in trifluoroethanol (100 mL) and tetrahydrofuran (300 mL) was added palladium on activated carbon catalyst (5 g, 10% purity) and palladium hydroxide on activated carbon catalyst (10 g, 20% purity) at 30° C., then the mixture was stirred at 30° C. for 12 h under hydrogen (Psi=50 Psi). TLC (Dichloromethane/Methanol=10/1) showed the reaction completed. The mixture was filtered by celite and the filtrate was concentrated under vacuum to get the crude product. tert-butyl 4-[1-methyl-1-(4-piperidyl) ethyl]piperazine-1-carboxylate (25 g, 80.27 mmol, 89% yield) was obtained as a white solid. MS (ESI) m/z: 312.3 [M+1]+.

Step 10: Preparation of tert-butyl 4-[1-[1-[2-(2,6-dioxo-3-piperidyl)-1-oxo-isoindolin-5-yl]-4-piperidyl]-1-methyl-ethyl]piperazine-1-carboxylate

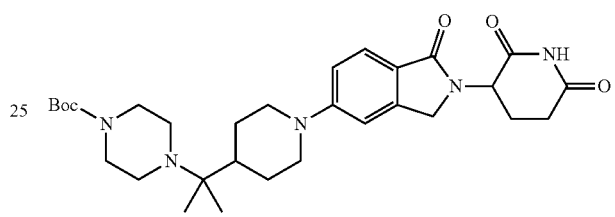

A mixture of 3-(5-bromo-1-oxo-isoindolin-2-yl)piperidine-2,6-dione (6 g, 18.57 mmol, 1 eq), tert-butyl 4-[1-methyl-1-(4-piperidyl)ethyl]piperazine-1-carboxylate (6.94 g, 22.28 mmol, 1.2 eq), cesium carbonate (12.10 g, 37.14 mmol, 2 eq) and Pd-PEPPSI-IPentCl-O-picoline (903 mg, 0.93 mmol, 0.05 eq) in N,N-dimethyl formamide (60 mL) was stirred at 100° C. for 8 hr under nitrogen. LCMS showed desired m/z and the reaction completed. The mixture was poured into water (50 mL) and extracted with ethyl acetate (50 mL×3). The organic layer was washed with brine (50 mL), dried over anhydrous sodium sulfate and filtered. The filtrate was concentrated under reduced pressure. The residue was purified by prep-HPLC (column: Phenomenex luna C18 (250*70 mm, 10 um); mobile phase: [water (0.225% FA)-ACN]; B %: 5%-40%, 25 min). tert-butyl 4-[1-[1-[2-(2,6-dioxo-3-piperidyl)-1-oxo-isoindolin-5-yl]-4-piperidyl]-1-methyl-ethyl]piperazine-1-carboxylate (3.5 g, 6.32 mmol, 34% yield) was obtained as a yellow solid. (ESI) m/z: 554.2 [M+1]+.

Step 11: Preparation of 3-[5-[4-(1-methyl-1-piperazin-1-yl-ethyl)-1-piperidyl]-1-oxo-isoindolin-2-yl]piperidine-2,6-dione

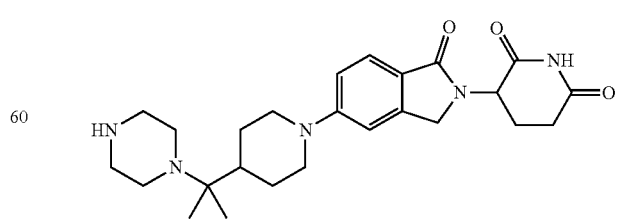

To a mixture of tert-butyl 4-[1-[1-[2-(2,6-dioxo-3-piperidyl)-1-oxo-isoindolin-5-yl]-4-piperidyl]-1-methyl-ethyl]

piperazine-1-carboxylate (4.00 g, 7.22 mmol, 1 eq) in dichloromethane (50 mL) was added trifluoroacetic acid (30.80 g, 270.12 mmol, 20.00 mL, 37.39 eq) and stirred at 25° C. for 1 h. LCMS showed desired m/z. The mixture was concentrated in vacuo. The residue was triturated with methyl tert-butyl ether (50 mL). 3-[5-[4-(1-methyl-1-piperazin-1-yl-ethyl)-1-piperidyl]-1-oxo-isoindolin-2-yl]piperidine-2,6-dione (4.10 g, 7.22 mmol, 100% yield, trifluoroacetate) was obtained as a yellow solid. MS (ESI) m/z: 454.5 [M+1]$^+$.

Step 12: Preparation of 2-[[6-[[5-chloro-2-[4-[1-[1-[2-(2,6-dioxo-3-piperidyl)-1-oxo-isoindolin-5-yl]-4-piperidyl]-1-methyl-ethyl]piperazin-1-yl]pyrimidin-4-yl]amino]-1-isopropyl-2-oxo-3-quinolyl]oxy]-N-methyl-acetamide

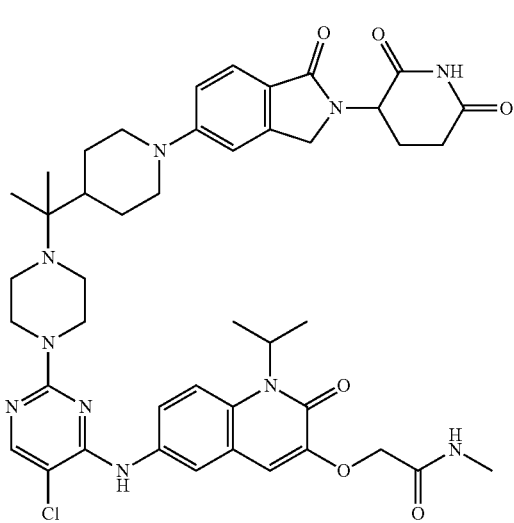 [SMILES: CNC(=O)COc1cc2cc(Nc3nc(N4CCN(C(C)(C)C5CCN(c6ccc7c(c6)CN(C6CCC(=O)NC6=O)C7=O)CC5)CC4)ncc3Cl)ccc2n(C(C)C)c1=O]

To a solution of 3-[5-[4-[1-methyl-1-(4-piperidyl)ethyl]piperazin-1-yl]-1-oxo-isoindolin-2-yl] piperidine-2,6-dione (4.10 g, 7.22 mmol, 1 eq, trifluoroacetate) in dimethyl sulfoxide (80 mL) was added N,N-diisopropylethylamine (5.60 g, 43.34 mmol, 7.6 mL, 6 eq) and 2-[[6-[(2,5-dichloropyrimidin-4-yl)amino]-1-isopropyl-2-oxo-3-quinolyl]oxy]-N-methyl-acetamide (2.84 g, 6.50 mmol, 0.9 eq). The mixture was stirred at 120° C. for 3 h. LCMS showed desired m/z and the reaction was completed. The mixture was diluted with ethyl acetate (200 mL). The combined organic phase was washed with brine (50 mL×3), dried with anhydrous sodium sulfate, filtered and concentrated in vacuum. The residue was firstly purified by silica gel chromatography (dichloromethane/methanol=100/1 to 20/1); then further purified by prep-HPLC (column: Phenomenex luna C18 (250*70 mm, 10 um); mobile phase: [water (0.1% TFA)-ACN]; B %: 15%-45%, 20 min). 2-[[6-[[5-chloro-2-[4-[1-[1-[2-(2,6-dioxo-3-piperidyl)-1-oxo-isoindolin-5-yl]-4-piperidyl]-1-methyl-ethyl]piperazin-1-yl]pyrimidin-4-yl]amino]-1-isopropyl-2-oxo-3-quinolyl]oxy]-N-methyl-acetamide (4.3 g, 4.99 mmol, 71% yield, 99% purity) was obtained as an off-white solid. MS (ESI) m/z: 853.3 [M]$^+$. $^1$H NMR: (400 MHz, DMSO-d6) δ: 10.94 (s, 1H), 8.82 (s, 1H), 8.05 (s, 1H), 8.02-7.95 (m, 2H), 7.75-7.65 (m, 2H), 7.52-7.45 (m, 1H), 7.10-7.00 (m, 3H), 5.50-5.11 (m, 1H), 5.04 (dd, J=13.2, 5.2 Hz, 1H), 4.55 (s, 2H), 4.36-4.28 (m, 1H), 4.25-4.15 (m, 1H), 3.95 (d, J=11.6 Hz, 2H), 3.65-3.60 (m, 3H), 2.97-2.85 (m, 1H), 2.82-2.72 (m, 2H), 2.66 (d, J=4.8 Hz, 3H), 2.63-2.52 (m, 6H), 2.45-2.27 (m, 1H), 2.00-1.90 (m, 1H), 1.85-1.75 (m, 3H), 1.57 (d, J=6.8 Hz, 6H), 1.38-1.20 (m, 2H), 0.89 (s, 6H).

Example 2: 2-{[6-({5-chloro-2-[4-({1-[2-(2,6-dioxopiperidin-3-yl)-6-fluoro-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide (Compound 15)

Step 1: Preparation of methyl 4-bromo-2-(bromomethyl)-5-fluorobenzoate

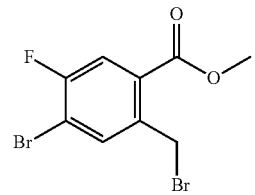

To a mixture of methyl 4-bromo-5-fluoro-2-methylbenzoate (1.4 g, 5.7 mmol, 1.0 equiv) and AIBN (0.1 g, 0.9 mmol, 0.2 equiv) in CCl$_4$ was added NBS (1.2 g, 6.8 mmol, 1.2 equiv). The resulting mixture was stirred for overnight at 70° C. under nitrogen atmosphere. The reaction was quenched with sat. NH$_4$Cl (aq.). The resulting mixture was extracted with CH$_2$Cl$_2$. The combined organic layers was washed with brine, dried over anhydrous Na$_2$SO$_4$. After filtration, the filtrate was concentrated under reduced pressure. The crude product was purified by Flash-Prep-HPLC with the following conditions: Column, C18 silica gel; mobile phase, acetonitrile/water (10 mmol/L NH$_4$HCO$_3$)=0:100 increasing to acetonitrile/water (10 mmol/L NH$_4$HCO$_3$)= 80:20 within 30 min; Detector, 254 nm. To afford methyl 4-bromo-2-(bromomethyl)-5-fluorobenzoate (1.3 g, 68%) as a black solid.

Step 2: Preparation of 3-(5-bromo-6-fluoro-1-oxo-3H-isoindol-2-yl)piperidine-2,6-dione

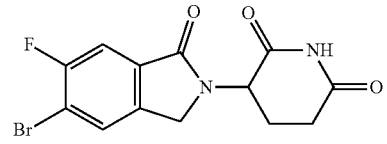 [SMILES: O=C1CCC(N2Cc3cc(Br)c(F)cc3C2=O)C(=O)N1]

To a stirred mixture of methyl 4-bromo-2-(bromomethyl)-5-fluorobenzoate (1.3 g, 3.9 mmol, 1.0 equiv) and 3-aminopiperidine-2,6-dione (0.6 g) in acetonitrile was added TEA (0.7 g). The resulting mixture was stirred for overnight at 60□ under nitrogen atmosphere. The resulting mixture was concentrated under reduced pressure. To the above mixture was added HOAC (5 mL). The resulting mixture was stirred for additional 4 h at 120 □. The resulting mixture was concentrated under reduced pressure. To the above mixture was added cold water. The precipitated solids were collected by filtration and washed with cold water. This resulted in 635.0 mg (48%) of 3-(5-bromo-6-fluoro-1-oxo-3H-isoindol-2-yl)piperidine-2,6-dione as black solid. MS (ES⁺): m/z 341.05 [MH⁺].

Step 3: Synthesis of tert-butyl 4-({1-[2-(2,6-dioxopiperidin-3-yl)-6-fluoro-1-oxo-3H-isoindol-5-yl]piperidin-4-yl}methyl)piperazine-1-carboxylate

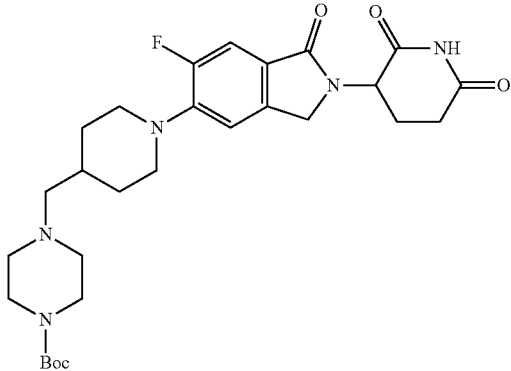 [SMILES: CC(C)(C)OC(=O)N1CCN(CC2CCN(c3cc4c(cc3F)C(=O)N(C3CCC(=O)NC3=O)C4)CC2)CC1]

To a mixture of 3-(5-bromo-6-fluoro-1-oxo-3H-isoindol-2-yl)piperidine-2,6-dione (350.0 mg, 1.0 mmol, 1.0 equiv) and tert-butyl 4-(piperidin-4-ylmethyl) piperazine-1-carboxylate (348.9 mg, 1.2 mmol, 1.2 equiv) in DMF were added Pd-PEPPSI-pent C1-O-picoline (86.2 mg, 0.1 mmol, 0.1 equiv) and Cs₂CO₃ (1002.9 mg, 3.0 mmol, 3.0 equiv). The resulting mixture was stirred for 4 h at 80□ under nitrogen atmosphere. The resulting mixture was diluted with CH₂Cl₂. To the above mixture was added HOAc. The resulting mixture was extracted with CH₂Cl₂. The combined organic layers were dried over anhydrous Na₂SO₄. After filtration, the filtrate was concentrated under reduced pressure. The crude product was purified by Flash-Prep-HPLC with the following conditions: Column, C18 silica gel; mobile phase, acetonitrile/water (10 mmol/L NH₄HCO₃)=0:100 increasing to acetonitrile/water (10 mmol/L NH₄HCO₃)= 80:20 within 30 min; Detector, 254 nm. To afford tert-butyl 4-({1-[2-(2,6-dioxopiperidin-3-yl)-6-fluoro-1-oxo-3H-isoindol-5-yl]piperidin-4-yl}methyl)piperazine-1-carboxylate (145.0 mg, 26%) as a yellow solid. MS (ES⁺): m/z 544.25 [MH⁺]

Step 4: Synthesis of 3-{6-fluoro-1-oxo-5-[4-(piperazin-1-ylmethyl)piperidin-1-yl]-3H-isoindol-2-yl}piperidine-2,6-dione

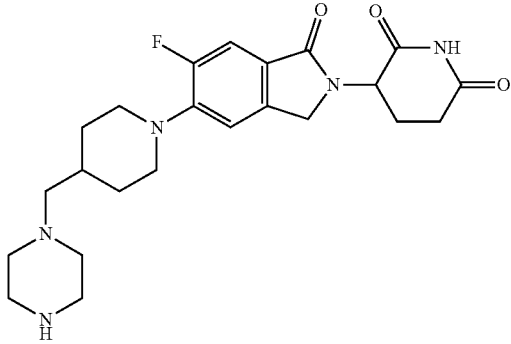 [SMILES: O=C1CCC(N2Cc3cc(N4CCC(CN5CCNCC5)CC4)c(F)cc3C2=O)C(=O)N1]

A mixture of tert-butyl 4-({1-[2-(2,6-dioxopiperidin-3-yl)-6-fluoro-1-oxo-3H-isoindol-5-yl]piperidin-4-yl}methyl)piperazine-1-carboxylate (145.0 mg, 0.3 mmol, 1.0 equiv) and hydrogen chloride (2 mL) in dioxane was stirred for overnight at room temperature under air atmosphere. The resulting mixture was concentrated under reduced pressure. To afford 3-{6-fluoro-1-oxo-5-[4-(piperazin-1-ylmethyl)piperidin-1-yl]-3H-isoindol-2-yl}piperidine-2,6-dione (118.3 mg, 100%) as solid. MS (ES⁺): m/z 444.25 [MH⁺]

Step 5: Synthesis of 2-{[6-({5-chloro-2-[4-({1-[2-(2,6-dioxopiperidin-3-yl)-6-fluoro-1-oxo-3H-isoindol-5-yl]piperidin-4-yl}methyl)piperazin-1-yl]pyrimidin-4-yl}amino)-1-isopropyl-2-oxoquinolin-3-yl]oxy}-N-methylacetamide

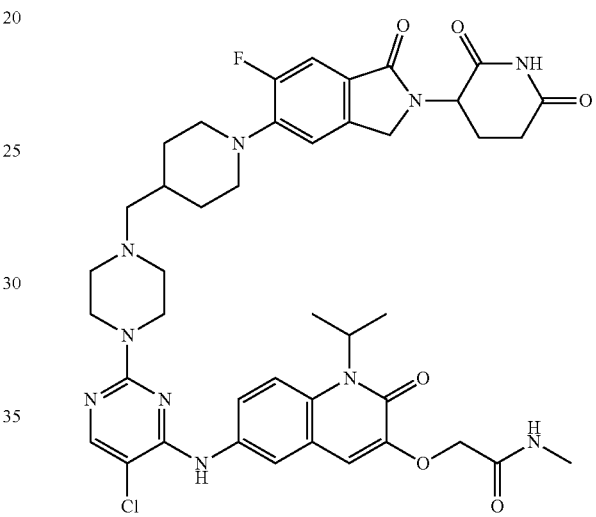

Into a 10-mL sealed tube, was placed 3-{6-fluoro-1-oxo-5-[4-(piperazin-1-ylmethyl)piperidin-1-yl]-3H-isoindol-2-yl}piperidine-2,6-dione (117.6 mg, 0.3 mmol, 1.3 equiv), 2-({6-[(2,5-dichloropyrimidin-4-yl)amino]-1-isopropyl-2-oxoquinolin-3-yl}oxy)-N-methylacetamide (89.0 mg, 0.2 mmol, 1.0 equiv), DMSO, DIEA (2 mL). The resulting solution was stirred for 6 h at 100□. The crude product was purified by Flash-Prep-HPLC with the following conditions: Column, C18 silica gel; mobile phase, acetonitrile/water (10 mmol/L NH₄HCO₃)=0:100 increasing to acetonitrile/water (10 mmol/L NH₄HCO₃)=80:20 within 30 min; Detector, 254 nm. This resulted in 54.7 mg (31.8%) of 2-{[6-({5-chloro-2-[4-({1-[2-(2,6-dioxopiperidin-3-yl)-6-fluoro-1-oxo-3H-isoindol-5-yl]piperidin-4-yl}methyl)piperazin-1-yl]pyrimidin-4-yl}amino)-1-isopropyl-2-oxoquinolin-3-yl]oxy}-N-methylacetamide as off-white solid. ¹HNMR (400 MHz, DMSO-d₆, ppm): δ 10.98 (s, 1H), 8.86 (s, 1H), 8.06 (s, 1H), 7.96 (s, 2H), 7.70 (s, 2H), 7.42-7.39 (m, 1H), 7.24-7.22 (m, 1H), 7.03 (s, 1H), 5.09-5.05 (m, 1H), 4.55 (s, 2H), 4.33 (s, 1H), 4.25 (s, 1H), 3.65 (s, 4H), 3.47 (s, 2H), 2.87-2.90 (m, 1H), 2.77-2.74 (m, 2H), 2.67-2.66 (m, 3H), 2.51-2.49 (m, 1H), 2.40 (s, 6H), 2.22-2.08 (m, 2H), 1.99-1.96 (m, 1H), 1.85-1.82 (m, 3H), 1.60-1.50 (m, 6H), 1.35-1.20 (m, 2H) MS (ES⁺): m/z 843.15 [MH⁺].

Example 3: 2-{[6-({5-chloro-2-[4-({1-[2-(2,6-di-oxopiperidin-3-yl)-1-oxo-3H-isoindol-5-yl]-4-fluoropiperidin-4-yl}methyl)piperazin-1-yl]pyrimidin-4-yl}amino)-1-isopropyl-2-oxoquinolin-3-yl]oxy}-N-methylacetamide (Compound 113)

Step 1: Preparation of benzyl 4-{[1-(tert-butoxycarbonyl)-4-hydroxypiperidin-4-yl]methyl}piperazine-1-carboxylate

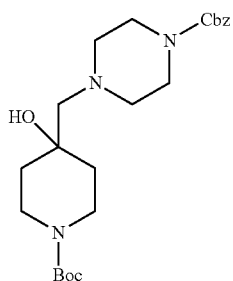 [SMILES: CC(C)(C)OC(=O)N1CCC(O)(CN2CCN(C(=O)OCc3ccccc3)CC2)CC1]

To a stirred solution of tert-butyl 1-oxa-6-azaspiro[2.5]octane-6-carboxylate (3.9 g, 18 mmol, 1.5 equiv) and benzyl piperazine-1-carboxylate (2.7 g, 12 mmol, 1 equiv) in ethanol was added DIEA (4 mL). The resulting mixture was stirred for 2 h at 80 D. The resulting mixture was concentrated under reduced pressure. The aqueous layer was extracted with EtOAc. The residue was purified by reverse flash chromatography with the following conditions: column, C18 silica gel; mobile phase, acetonitrile/water (10 mmol/L NH$_4$HCO$_3$), 10% to 50% gradient in 30 min; detector, UV 254 nm. This resulted in benzyl 4-{[1-(tert-butoxycarbonyl)-4-hydroxypiperidin-4-yl]methyl}piperazine-1-carboxylate (3.6 g, 67%) as a brown oil. MS (ES+): m/z 434.10, [MH$^+$]

Step 2: Preparation of benzyl 4-{[1-(tert-butoxycarbonyl)-4-fluoropiperidin-4-yl]methyl}piperazine-1-carboxylate

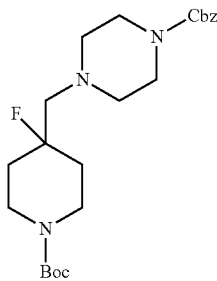 [SMILES: CC(C)(C)OC(=O)N1CCC(F)(CN2CCN(C(=O)OCc3ccccc3)CC2)CC1]

To a stirred solution of benzyl 4-{[1-(tert-butoxycarbonyl)-4-hydroxypiperidin-4-yl]methyl}piperazine-1-carboxylate (3.6 g, 8 mmol, 1 equiv) in CH$_2$Cl$_2$ was added DAST (2 g, 12 mmol, 1.5 equiv) dropwise at −78 □ under nitrogen atmosphere. The resulting mixture was stirred for 2 h at room temperature under nitrogen atmosphere. The aqueous layer was extracted with CH$_2$Cl$_2$. The residue was purified by reverse flash chromatography with the following conditions: column, silica gel; mobile phase, acetonitrile/water (10 mmol/L NH$_4$HCO$_3$), 10% to 50% gradient in 30 min; detector, UV 254 nm. This resulted in benzyl 4-{[1-(tert-butoxycarbonyl)-4-fluoropiperidin-4-yl]methyl}piperazine-1-carboxylate (1.2 g, 33%) as an off-white solid. MS (ES+): m/z 436.20, [MH$^+$].

Step 3: Preparation of benzyl 4-[(4-fluoropiperidin-4-yl)methyl]piperazine-1-carboxylate

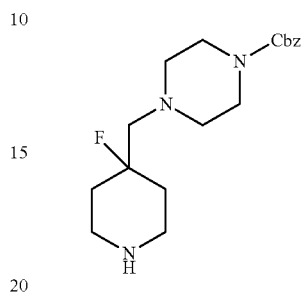

To a stirred solution benzyl 4-{[1-(tert-butoxycarbonyl)-4-fluoropiperidin-4-yl]methyl}piperazine-1-carboxylate (900 mg, 2 mmol, 1 equiv) in DCM was added TFA (2 mL) dropwise room temperature. The resulting mixture was stirred for additional 2 h at room temperature. The resulting mixture was concentrated under reduced pressure. The residue was neutralized to pH 7 with saturated Na$_2$CO$_3$ (aq.). The aqueous layer was extracted with CH$_2$Cl$_2$. This resulted in benzyl 4-[(4-fluoropiperidin-4-yl)methyl]piperazine-1-carboxylate (660 mg, 95%) as an off-white solid. MS (ES+): m/z 336.20, [MH$^+$].

Step 4: Preparation of benzyl 4-({1-[2-(2,6-dioxopiperidin-3-yl)-1-oxo-3H-isoindol-5-yl]-4-fluoropiperidin-4-yl}methyl)piperazine-1-carboxylate

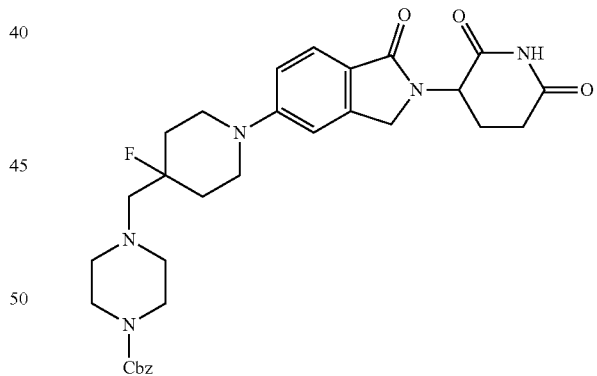

To a solution of benzyl 4-[(4-fluoropiperidin-4-yl)methyl]piperazine-1-carboxylate (300 mg, 0.89 mmol, 1 equiv) and 3-(5-bromo-1-oxo-3H-isoindol-2-yl)piperidine-2,6-dione (289 mg, 0.89 mmol, 1 equiv) in DMF (10 mL) were added Cs$_2$CO$_3$ (582 mg, 1.78 mmol, 2 equiv) and Pd-PEPPSI-IPentCl 2-methylpyridine (o-picoline (75 mg, 0.089 mmol, 0.1 equiv). After stirring for 4 h at 80 □ under a nitrogen atmosphere, the resulting mixture was concentrated under reduced pressure. The aqueous layer was extracted with CH$_2$Cl$_2$ and acid water (10 mL H$_2$O+0.5 mL HOAc). The residue was purified by reverse flash chromatography with the following conditions: column, silica gel; mobile phase, acetonitrile/water (10 mmol/L NH$_4$HCO$_3$), 10% to 50% gradient in 30 min; detector, UV 254 nm. This resulted in benzyl 4-({1-[2-(2,6-dioxopiperidin-3-yl)-1-oxo-3H-isoindol-5-yl]-4-fluoropiperidin-4-yl}methyl)piperazine-1-carboxylate (280 mg, 54%) as an off-white solid. MS (ES+): m/z 578.25, [MH+].

Step 5: Preparation of 3-{5-[4-fluoro-4-(piperazin-1-ylmethyl)piperidin-1-yl]-1-oxo-3H-isoindol-2-yl}piperidine-2,6-dione

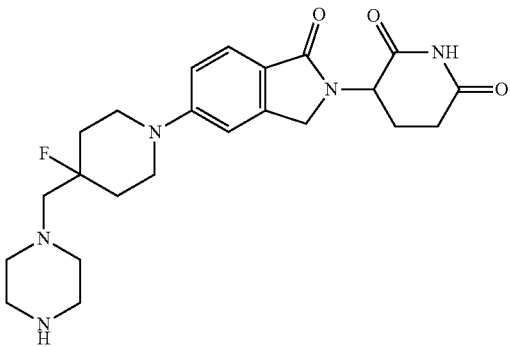 [SMILES: O=C1CCC(N2Cc3cc(N4CCC(F)(CN5CCNCC5)CC4)ccc3C2=O)C(=O)N1]

To a solution of benzyl 4-({1-[2-(2,6-dioxopiperidin-3-yl)-1-oxo-3H-isoindol-5-yl]-4-fluoropiperidin-4-yl}methyl)piperazine-1-carboxylate (280 mg, 0.48 mmol, 1 equiv) in 10 mL i-PrOH and THF (5 mL) was added Pd(OH)$_2$/C (100 mg) (10%) under nitrogen atmosphere in a 50 mL round-bottom flask. The mixture was hydrogenated at room temperature for 4 h under hydrogen atmosphere using a hydrogen balloon, filtered through a Celite pad and concentrated under Step 7. Preparation of 2-{[6-({5-chloro-2-[4-({1-[2-(2,6-dioxopiperidin-3-yl)-1-oxo-3H-isoindol-5-yl]-4-fluoropiperidin-4-yl}methyl)piperazin-1-yl]pyrimidin-4-yl}amino)-1-isopropyl-2-oxoquinolin-3-yl]oxy}-N-methylacetamide

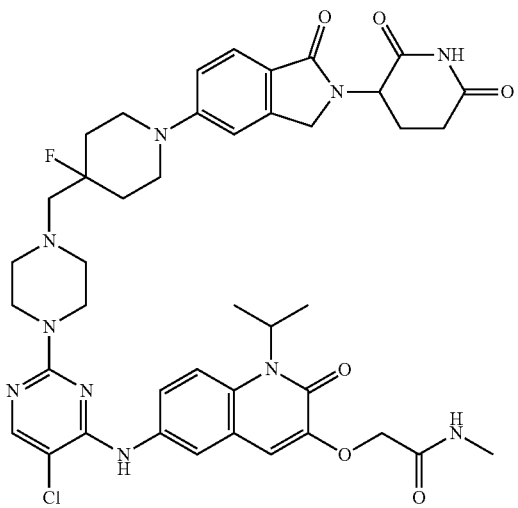 [SMILES: CNC(=O)COc1cc2cc(Nc3nc(N4CCN(CC5(F)CCN(c6ccc7c(c6)CN(C6CCC(=O)NC6=O)C7=O)CC5)CC4)ncc3Cl)ccc2n(C(C)C)c1=O]

To a stirred solution of 3-{5-[4-fluoro-4-(piperazin-1-ylmethyl)piperidin-1-yl]-1-oxo-3H-isoindol-2-yl}pipe-ridine-2,6-dione (182 mg, 0.4 mmol, 1.5 equiv) and 2-({6-[(2,5-dichloropyrimidin-4-yl)amino]-1-isopropyl-2-oxoquinolin-3-yl}oxy)-N-methylacetamide (120 mg, 0.2 mmol, 1 equiv) in DMSO was added DIEA (0.5 mL) dropwise at room temperature. The resulting mixture was stirred for additional 2 h at 100° C. The residue was purified by reverse flash chromatography with the following conditions: column, silica gel; mobile phase, acetonitrile/water (10 mmol/L NH$_4$HCO$_3$), 10% to 50% gradient in 30 min; detector, UV 254 nm. This resulted in 2-{[6-({5-chloro-2-[4-({1-[2-(2,6-dioxopiperidin-3-yl)-1-oxo-3H-isoindol-5-yl]-4-fluoropiperidin-4-yl}methyl)piperazin-1-yl]pyrimidin-4-yl}amino)-1-isopropyl-2-oxoquinolin-3-yl]oxy}-N-methylacetamide (55.3 mg, 23%) as a off-white solid. $^1$H NMR (400 MHz, DMSO-d6, ppm) 10.93 (s, 1H), 8.84 (s, 1H), 8.05 (s, 1H), 7.94-7.89 (m, 2H), 7.70-7.67 (m, 2H), 7.53-7.51 (m, 1H), 7.08-7.05 (m, 3H), 5.06-5.02 (m, 1H), 4.53 (s, 2H), 4.34-4.30 (m, 1H), 4.22-4.18 (m, 1H), 3.64-3.33 (m, 5H), 3.18-3.13 (m, 2H), 2.90-2.89 (m, 1H), 2.66-2.60 (m, 3H), 2.53-2.50 (m, 2H), 2.50-2.34 (m, 7H), 2.33-2.32 (m, 1H), 1.97-1.94 (m, 3H), 1.81-1.73 (m, 2H), 1.57-1.55 (m, 6H). MS (ES+): m/z=843.40 [M+]

Example 4: 2-{[6-({5-chloro-2-[4-({1-[2-(2,6-dioxopiperidin-3-yl)-1-oxo-2,3-dihydro-1H-isoindol-4-yl]-4-fluoropiperidin-4-yl}methyl)piperazin-1-yl]pyrimidin-4-yl}amino)-2-oxo-1-(propan-2-yl)-1,2-dihydroquinolin-3-yl]oxy}-N-methylacetamide (Compound 114)

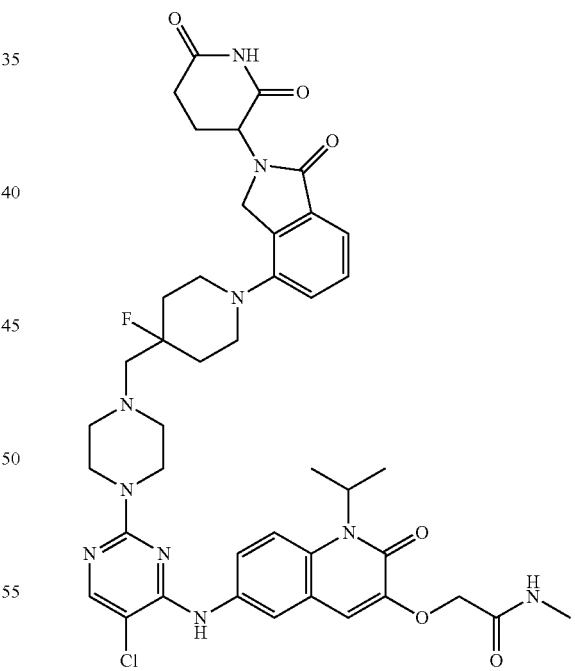

Example 4 was prepared analogously to Example 3 replacing 3-(5-bromo-1-oxo-3H-isoindol-2-yl)piperidine-2,6-dione with 3-(4-bromo-1-oxoisoindolin-2-yl)piperidine-2,6-dione. $^1$H NMR (400 MHz, DMSO-d6, ppm) 10.97 (s, 1H), 8.84 (s, 1H), 8.05 (s, 1H), 7.94-7.89 (m, 2H), 7.72-7.70 (m, 2H), 7.43-7.42 (m, 1H), 7.32-7.31 (m, 1H), 7.22-7.20 (m, 1H), 7.05 (s, 1H), 5.11-5.10 (m, 1H), 4.53 (s, 2H), 4.47-4.43 (m, 1H), 4.32-4.28 (m, 1H), 3.64-3.63 (m, 4H), 3.31-3.30 (m, 2H), 2.97-2.89 (m, 3H), 2.67-2.62 (m, 5H), 2.55-2.50 (m, 7H), 2.03-1.98 (m, 3H), 1.97-1.94 (m, 2H), 1.57-1.55 (m, 6H). MS (ES+): m/z 843.45 [M+]

Example 5: 2-{[6-({5-chloro-2-[4-({1-[2-(2,6-di-oxopiperidin-3-yl)-7-fluoro-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide (Compound 18)

Step 1: Preparation of methyl 4-bromo-2-(bromomethyl)-6-fluorobenzoate

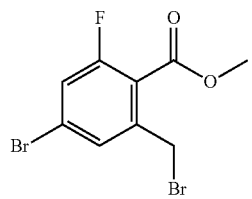

To a mixture of methyl 4-bromo-2-fluoro-6-methylbenzoate (1.5 g, 6.0 mmol, 1.0 equiv) and AIBN (0.2 g, 1.2 mmol, 0.2 equiv) in CCl₄ was added NBS (1.3 g, 7.3 mmol, 1.2 equiv). The resulting mixture was stirred for overnight at 65° C. under nitrogen atmosphere. The reaction was quenched with sat. NH₄Cl (aq.). The resulting mixture was extracted with CH₂Cl₂. The combined organic layers were washed with brine, dried over anhydrous Na₂SO₄. After filtration, the filtrate was concentrated under reduced pressure. The crude product was purified by Flash-Prep-HPLC with the following conditions: Column, C18 silica gel; mobile phase, acetonitrile/water (10 mmol/L NH₄HCO₃)=0:100 increasing to acetonitrile/water (10 mmol/L NH₄HCO₃)= 80:20 within 30 min; Detector, 254. To afford methyl 4-bromo-2-(bromomethyl)-6-fluorobenzoate (1.4 g, 68%) as a yellow oil. MS (ES⁺): m/z 324.05 [MH⁺].

Step 2: Preparation of 3-(5-bromo-7-fluoro-1-oxo-3H-isoindol-2-yl)piperidine-2,6-dione

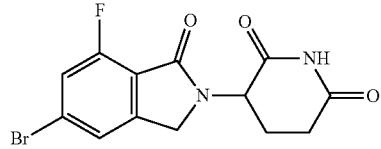 [SMILES: O=C1CCC(N2Cc3cc(Br)cc(F)c3C2=O)C(=O)N1]

To a mixture of methyl 4-bromo-2-(bromomethyl)-6-fluorobenzoate (1.4 g, 4.1 mmol, 1.0 equiv) and 3-amino-2,6-dioxopiperidin hydrochloride (0.5 g, 4.1 mmol, 1. equiv) in acetonitrile was added TEA (0.8 g, 8.3 mmol, 2.0 equiv). The resulting mixture was stirred for overnight at 60° C. under nitrogen atmosphere. The resulting mixture was concentrated under reduced pressure. To the above mixture was added HOAc (5 mL). The resulting mixture was stirred for additional 3 h at 120° C. The resulting mixture was concentrated under reduced pressure. To the above mixture was added cold water. The precipitated solids were collected by filtration and washed with cold water. This resulted in 718.0 mg (51%) of 3-(5-bromo-7-fluoro-1-oxo-3H-isoindol-2-yl)piperidine-2,6-dione as black solid. MS (ES⁺): m/z 341.05 [MH⁺]

Steps 3-5: Preparation of 2-{[6-({5-chloro-2-[4-({1-[2-(2,6-dioxopiperidin-3-yl)-7-fluoro-1-oxo-3H-isoindol-5-yl]piperidin-4-yl}methyl)piperazin-1-yl]pyrimidin-4-yl}amino)-1-isopropyl-2-oxoquinolin-3-yl]oxy}-N-methylacetamide

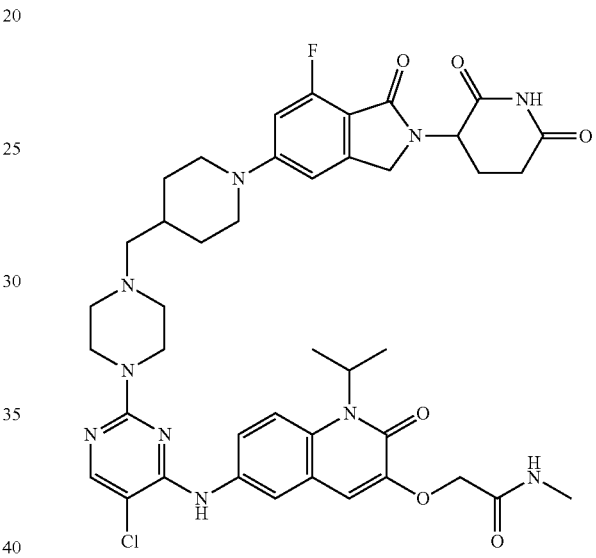

Example 5 was prepared analogously to Example 2 replacing 3-(5-bromo-6-fluoro-1-oxo-3H-isoindol-2-yl)piperidine-2,6-dione in Step 3 with 3-(5-bromo-7-fluoro-1-oxo-3H-isoindol-2-yl)piperidine-2,6-dione. The crude product was purified by Flash-Prep-HPLC with the following conditions: Column, C18 silica gel; mobile phase, acetonitrile/water (10 mmol/L NH₄HCO₃)=0:100 increasing to acetonitrile/water (10 mmol/L NH₄HCO₃)=80:20 within 30 min; Detector, 254 nm. To afford 2-{[6-({5-chloro-2-[4-({1-[2-(2,6-dioxopiperidin-3-yl)-7-fluoro-1-oxo-3H-isoindol-5-yl]piperidin-4-yl}methyl)piperazin-1-yl]pyrimidin-4-yl}amino)-1-isopropyl-2-oxoquinolin-3-yl]oxy}-N-methylacetamide (57.4 mg, 30%) as a tan solid. ¹H NMR (400 MHz, DMSO-d₆, ppm): δ 10.93 (s, 1H), 8.83 (s, 1H), 8.04-7.95 (m, 3H), 7.69 (s, 2H), 7.03 (s, 1H), 6.85 (m, 2H), 5.10-4.90 (m, 1H), 4.54 (s, 2H), 4.40-4.21 (m, 2H), 4.00-3.80 (m, 2H), 3.64 (s, 4H), 2.95-2.86 (m, 3H), 2.65 (s, 4H), 2.38 (s, 5H), 2.17 (s, 2H), 2.00-1.80 (m, 4H), 1.70-1.55 (m, 7H), 1.35-1.20 (m, 2H). MS (ES⁺): m/z 843.35 [MH⁺].

Example 6: 2-{[6-({5-chloro-2-[4-({1-[2-(2,6-di-oxopiperidin-3-yl)-4-methoxy-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide (Compound 26)

Step 1: Synthesis of 4-bromo-2-methoxy-6-methylbenzamide

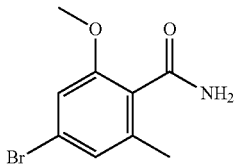

Into a 250-mL round-bottom flask, was placed 4-bromo-2-methoxy-6-methylbenzonitrile (2.00 g, 8.847 mmol, 1.00 equiv), MeOH (50 mL), H2O (50 mL), NaOH (1.06 g, 26.540 mmol, 3.00 equiv). The resulting solution was stirred for 20 h at 100 □ in an oil bath. The resulting solution was extracted with ethyl acetate (3×50 mL), and dried over anhydrous sodium sulfate and concentrated under vacuum. This resulted in 1.56 g (72%) of 4-bromo-2-methoxy-6-methylbenzamide as a yellow solid.

2. Synthesis of 4-bromo-2-methoxy-6-methylbenzoic acid

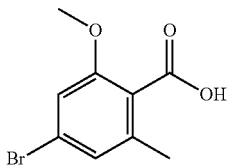

Into a 100-mL round-bottom flask, was placed 4-bromo-2-methoxy-6-methylbenzamide (1.50 g, 6.145 mmol, 1.00 equiv), dichloromethane (30 mL), H2O (10 mL), nitrosyl sulfuric acid (10 mL). The resulting solution was stirred for 2 h at room temperature. The reaction was then quenched by the addition of water (10 mL). The resulting solution was extracted with dichloromethane (2×40 mL), and dried over anhydrous sodium sulfate and concentrated under vacuum. This resulted in 1.2 g (80%) of 4-bromo-2-methoxy-6-methylbenzoic acid as a yellow solid.

Step 3: Synthesis of methyl 4-bromo-2-methoxy-6-methylbenzoate

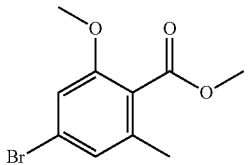

Into a 100-mL round-bottom flask, was placed 4-bromo-2-methoxy-6-methylbenzoic acid (1.20 g, 4.897 mmol, 1.00 equiv), DMF (15 mL), K2CO3 (2.03 g, 14.690 mmol, 3.00 equiv), CH3I (1.04 g, 7.345 mmol, 1.50 equiv). The resulting solution was stirred for 3 h at room temperature. The reaction was then quenched by the addition of water (20 mL). The resulting solution was extracted with ethyl acetate (2×40 mL). The resulting mixture was washed with brine (1×30 mL). The mixture was dried over anhydrous sodium sulfate. The residue was applied onto a silica gel column with ethyl acetate/petroleum ether (1/2). The collected fractions were combined and concentrated under vacuum. This resulted in 1.1 g (87%) of methyl 4-bromo-2-methoxy-6-methylbenzoate as a yellow solid.

Step 4: Synthesis of methyl 4-bromo-2-(bromomethyl)-6-methoxybenzoate

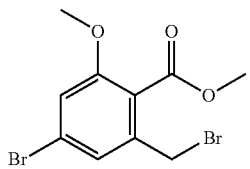

Into a 100-mL round-bottom flask, was placed methyl 4-bromo-2-methoxy-6-methylbenzoate (1.10 g, 4.245 mmol, 1.00 equiv), carbon tetrachloride (15 mL), NBS (831.19 mg, 4.670 mmol, 1.10 equiv), 2,2-azobisisobutyronitrile (69.71 mg, 0.425 mmol, 0.10 equiv). The resulting solution was stirred for overnight at 70° C. in an oil bath. The reaction was then quenched by the addition of water (20 mL). The resulting solution was extracted with dichloromethane (2×30 mL). The resulting mixture was washed with brine (2×20 mL). The mixture was dried over anhydrous sodium sulfate. The residue was applied onto a silica gel column with ethyl acetate/petroleum ether (1/2). The collected fractions were combined and concentrated under vacuum. This resulted in 1.3 g (91%) of methyl 4-bromo-2-(bromomethyl)-6-methoxybenzoate as yellow oil. MS (ES+): m/z 338.95 [MH+]

Step 5. Synthesis of 3-(5-bromo-7-methoxy-1-oxo-3H-isoindol-2-yl)piperidine-2,6-dione

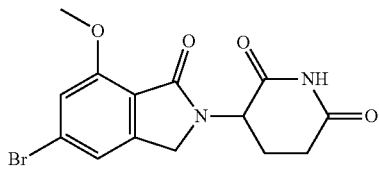 [SMILES: COc1cc(Br)cc2c1C(=O)N(C1CCC(=O)NC1=O)C2]

Into a 100-mL round-bottom flask, was placed 3-aminopiperidine-2,6-dione hydrochloride (949.57 mg, 5.769 mmol, 1.50 equiv), acetonitrile (15 mL), Diisopropylethylamine (1.49 g, 11.539 mmol, 3.00 equiv), methyl 4-bromo-2-(bromomethyl)-6-methoxybenzoate (1.30 g, 3.846 mmol, 1.00 equiv). The resulting solution was stirred for 1 h at 60° C. in an oil bath. Then the mixture was added HOAC (15 mL), the resulting solution was allowed to react, with stirring, for an additional 1 h while the temperature was maintained at 120° C. in an oil bath. The reaction was then quenched by the addition of water (50 mL). The solids were collected by filtration. This resulted in 1.1 g (81%) of 3-(5-bromo-7-methoxy-1-oxo-3H-isoindol-2-yl)piperidine-2,6-dione as a dark blue solid. MS (ES+): m/z 353.05 [MH+]

Steps 6-8: Preparation of 2-{[6-({5-chloro-2-[4-({1-[2-(2,6-dioxopiperidin-3-yl)-7-methoxy-1-oxo-3H-isoindol-5-yl]piperidin-4-yl}methyl)piperazin-1-yl]pyrimidin-4-yl}amino)-1-isopropyl-2-oxoquinolin-3-yl]oxy}-N-methylacetamide

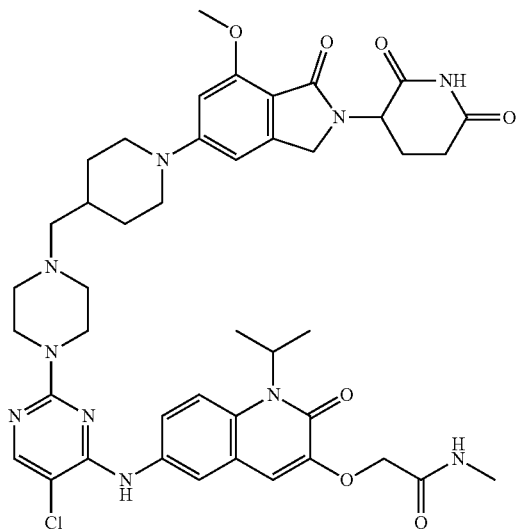 [SMILES: CNC(=O)COc1cc2cc(Nc3nc(N4CCN(CC5CCN(c6cc7c(c(OC)c6)C(=O)N(C6CCC(=O)NC6=O)C7)CC5)CC4)ncc3Cl)ccc2n(C(C)C)c1=O]

Example 6 was prepared analogously to Example 2 replacing 3-(5-bromo-6-fluoro-1-oxo-3H-isoindol-2-yl)piperidine-2,6-dione in Step 3 with 3-(5-bromo-7-methoxy-1-oxo-3H-isoindol-2-yl)piperidine-2,6-dione. The crude product was purified by reverse phase flash chromatography with the following conditions: column, C18 silica gel; mobile phase, acetonitrile/water (10 mmol/L NH$_4$HCO$_3$), 0% to 60% gradient in 30 min; detector, UV 254 nm. To afford as a 2-{[6-({5-chloro-2-[4-({1-[2-(2,6-dioxopiperidin-3-yl)-7-methoxy-1-oxo-3H-isoindol-5-yl]piperidin-4-yl}methyl)piperazin-1-yl]pyrimidin-4-yl}amino)-1-isopropyl-2-oxoquinolin-3-yl]oxy}-N-methylacetamide (58.0 mg) light yellow solid. $^1$H NMR (400 MHz, DMSO-d$_6$, ppm): δ 10.91 (s, 1H), 8.86 (s, 1H), 8.06 (s, 1H), 7.97 (s, 2H), 7.69 (d, J=1.6 Hz, 2H), 7.03 (s, 1H), 6.59 (s, 1H), 6.45 (s, 1H), 4.99 (d, J=13.2, 5.2 Hz, 1H), 4.55 (s, 2H), 4.22 (s, 1H), 4.09 (s, 1H), 3.89 (s, 2H), 3.82 (s, 3H), 3.64 (s, 4H), 3.29 (s, 1H), 2.99-2.86 (m, 3H), 2.66 (s, 3H), 2.56 (d, J=16.6 Hz, 1H), 2.40 (s, 4H), 2.35-2.24 (m, 1H), 2.18 (s, 2H), 1.91 (s, 1H), 1.80 (d, J=12.4 Hz, 3H), 1.56 (d, J=6.8 Hz, 6H), 1.25-1.14 (m, 2H). MS (ES$^+$): m/z 855.25[MH$^+$].

The following compounds were prepared using procedures analogous to those in Examples 1-6

| Compound | Structure |
|---|---|
| 67 | 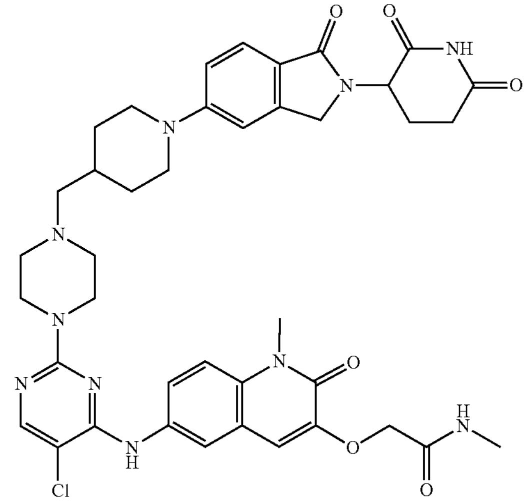 [SMILES: CNC(=O)COc1cc2cc(Nc3nc(N4CCN(CC5CCN(c6ccc7c(c6)CN(C6CCC(=O)NC6=O)C7=O)CC5)CC4)ncc3Cl)ccc2n(C)c1=O] |
| 25 | 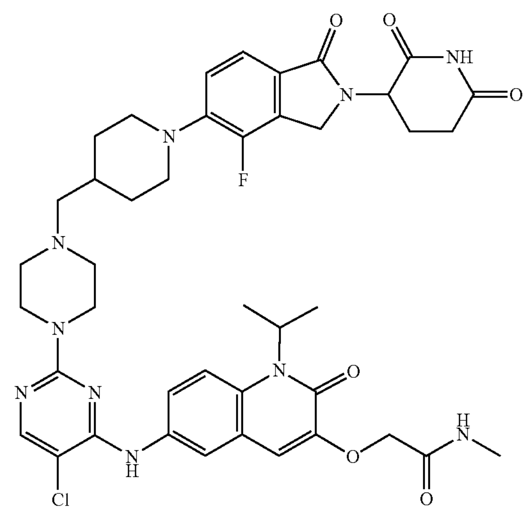 [SMILES: CNC(=O)COc1cc2cc(Nc3nc(N4CCN(CC5CCN(c6ccc7c(c6F)CN(C6CCC(=O)NC6=O)C7=O)CC5)CC4)ncc3Cl)ccc2n(C(C)C)c1=O] |
| 78 | 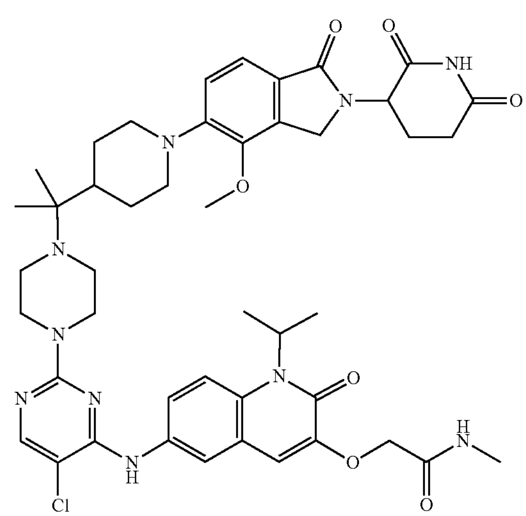 [SMILES: CNC(=O)COc1cc2cc(Nc3nc(N4CCN(C(C)(C)C5CCN(c6ccc7c(c6OC)CN(C6CCC(=O)NC6=O)C7=O)CC5)CC4)ncc3Cl)ccc2n(C(C)C)c1=O] |

| Compound | Structure |
|---|---|
| 62 | 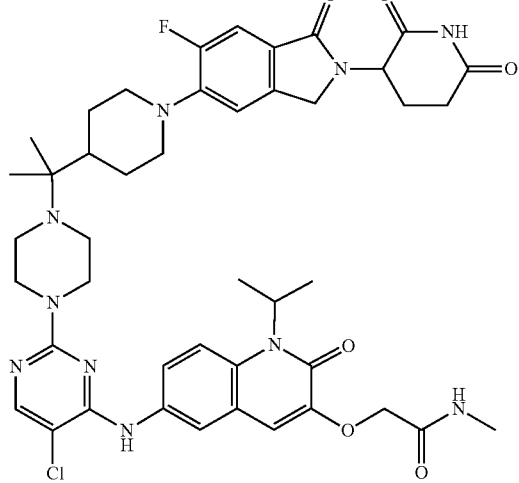 |
| 76 | 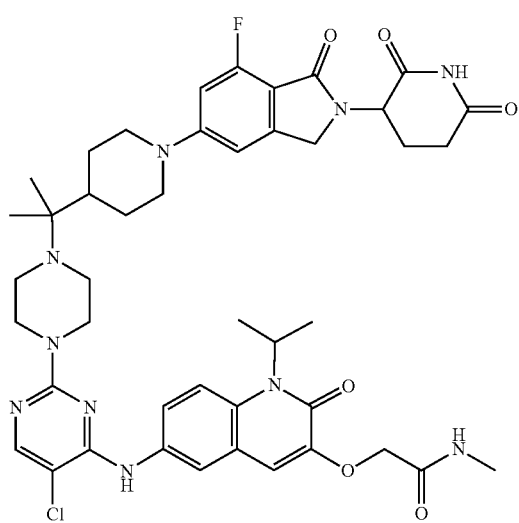 [SMILES: CNC(=O)COc1cc2cc(Nc3nc(N4CCN(C(C)(C)C5CCN(c6cc(F)c7c(c6)CN(C6CCC(=O)NC6=O)C7=O)CC5)CC4)ncc3Cl)ccc2n(C(C)C)c1=O] |
| 89 | 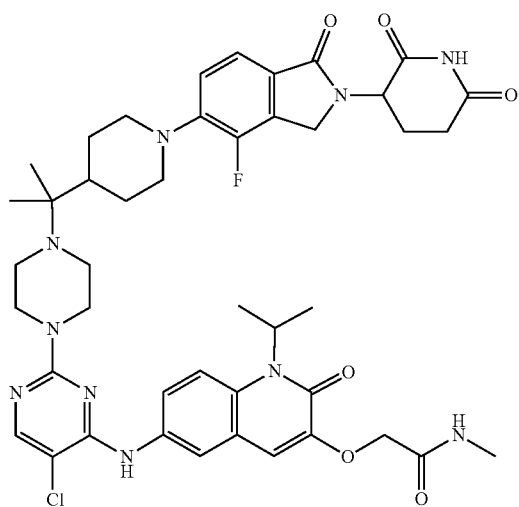 [SMILES: CNC(=O)COc1cc2cc(Nc3nc(N4CCN(C(C)(C)C5CCN(c6ccc7c(c6F)CN(C6CCC(=O)NC6=O)C7=O)CC5)CC4)ncc3Cl)ccc2n(C(C)C)c1=O] |
| Compound | Structure |
|---|---|
| 77 | 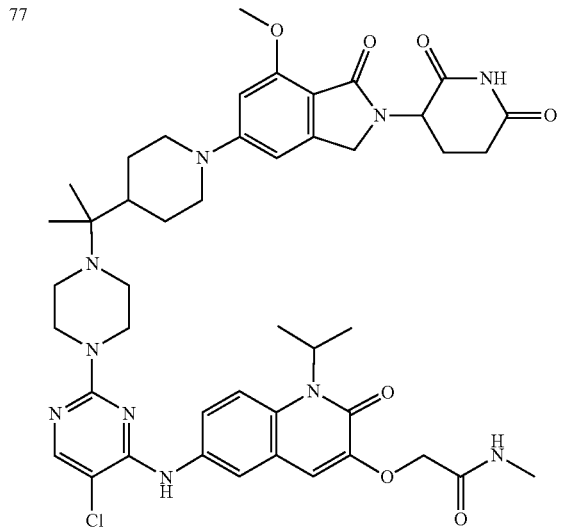 |
| 21 | 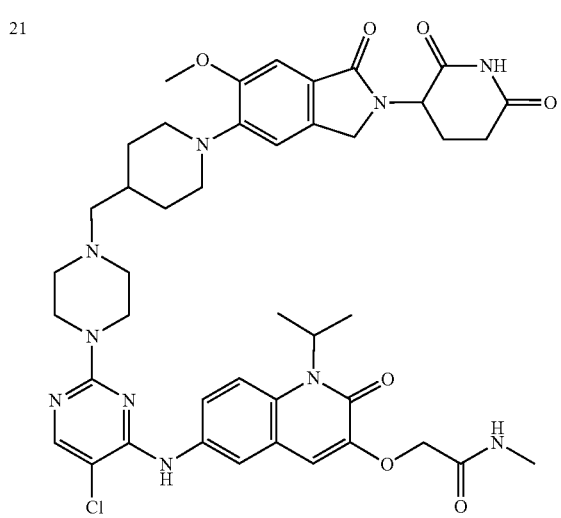 |
| 112 | 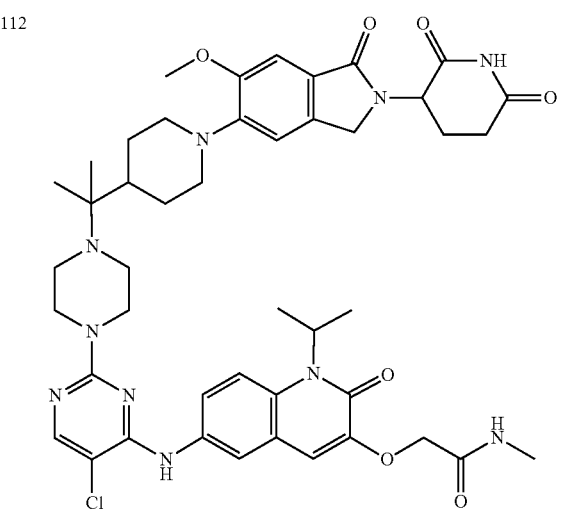 |

| Compound | Structure |
|---|---|
| 104 | (structure) |
| 105 | (structure) |
| 119 | (structure) |
| 120 | (structure) |
| 121 | (structure) |

Example 21: 2-{[6-({5-chloro-2-[4-({1-[2-(2,6-di-oxopiperidin-3-yl)-5-fluoro-1,3-dioxo-2,3-dihydro-1H-isoindol-4-yl]piperidin-4-yl}methyl)piperazin-1-yl]pyrimidin-4-yl}amino)-1-methyl-2-oxo-1,2-dihydroquinolin-3-yl]oxy}-N-methylacetamide (Compound 35)

Step 1: Preparation of 3-bromo-4-fluoro-2-methylbenzoic acid

A mixture of 2,2,6,6-tetramethylpiperidine (14.2 g, 100.5 mmol, 2.2 equiv) and butyllithium (100.5 mL, 100.5 mmol, 2.2 equiv) in THF was stirred for 30 min at −20° C. under nitrogen atmosphere. To the above mixture was added 3-bromo-4-fluorobenzoic acid (10.0 g, 45.7 mmol, 1.0 equiv) at −50° C. The resulting mixture was stirred for additional 1 h at −50° C. To the above mixture was added methyl iodide (25.9 g, 182.6 mmol, 4.0 equiv). The resulting mixture was stirred for additional overnight at room temperature. The reaction was then quenched by the addition of water. The pH value of the solution was adjusted to 3-4 with HCl (1 mol/L). The resulting solution was extracted with 100 mL of ethyl acetate and the organic layers combined. The resulting mixture was washed with 30 mL of brine. The mixture was dried over anhydrous sodium sulfate and concentrated. The crude product was purified by Prep-HPLC with the following conditions (Column, C18 silica gel; mobile phase, acetonitrile/water (10 mmol/L TFA)=0:100 increasing to MeCN:H$_2$O (10 mmol/L TFA)=80:20 within 30 min; Detector, 254 nm) to afford 3-bromo-4-fluoro-2-methylbenzoic acid (14.0 g) as a brown solid. MS (ES$^+$): m/z 233.65 [MH$^+$].

Step 2: Synthesis of 3-bromo-4-fluorobenzene-1,2-dicarboxylic acid

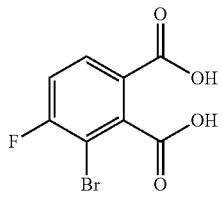 [SMILES: O=C(O)c1ccc(F)c(Br)c1C(=O)O]

To a mixture of KMnO$_4$ (5.4 g, 34.4 mmol, 8.0 equiv) and NaOH (0.5 g, 12.9 mmol, 3.0 equiv) in water was added 3-bromo-4-fluoro-2-methylbenzoic acid (1.0 g, 4.3 mmol, 1.0 equiv). The resulting mixture was stirred for 2 h at 100° C. The resulting mixture was filtered. The filtrate was neutralized with HCl (3M), concentrated under reduced pressure. To afford 3-bromo-4-fluorobenzene-1,2-dicarboxylic acid (3.0 g) as a white solid. MS (ES$^+$): m/z 263.15 [MH$^+$].

Step 3: Preparation of 4-bromo-2-(2,6-dioxopiperidin-3-yl)-5-fluoroisoindole-1,3-dione

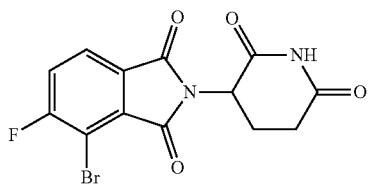

To a stirred mixture of 3-aminopiperidine-2,6-dione hydrochloride (1.4 g, 8.6 mmol, 1.5 equiv) and 3-bromo-4-fluorobenzene-1,2-dicarboxylic acid (3.0 g, 5.7 mmol, 1.0 equiv) in AcOH was added NaOAc (2.3 g, 17.1 mmol, 3.0 equiv). The resulting mixture was stirred for 5 h at 120° C. under nitrogen atmosphere. The resulting mixture was concentrated under reduced pressure. To the above mixture was added cold water. The precipitated solids were collected by filtration. The resulting solid was dried. This resulted in 4-bromo-2-(2,6-dioxopiperidin-3-yl)-5-fluoroisoindole-1,3-dione (600.0 mg, 30%) as a black solid. MS (ES$^+$): m/z 355.00 [MH$^+$].

Steps 4-6: Preparation of 2-{[6-({5-chloro-2-[4-({1-[2-(2,6-dioxopiperidin-3-yl)-5-fluoro-1,3-dioxo-2,3-dihydro-1H-isoindol-4-yl]piperidin-4-yl}methyl)piperazin-1-yl]pyrimidin-4-yl}amino)-1-methyl-2-oxo-1,2-dihydroquinolin-3-yl]oxy}-N-methylacetamide Example 21 was prepared analogously to steps 3-5 in Example 2 replacing 3-(5-bromo-6-fluoro-1-oxo-3H-isoindol-2-yl)piperidine-2,6-dione with 4-bromo-2-(2,6-dioxopiperidin-3-yl)-5-fluoroisoindole-1,3-dione and, in the final step, replacing 2-({6-[(2,5-dichloropyrimidin-4-yl)amino]-1-isopropyl-2-oxoquinolin-3-yl}oxy)-N-methylacetamide with 2-({6-[(2,5-dichloropyrimidin-4-yl)amino]-1-methyl-2-oxoquinolin-3-yl}oxy)-N-methylacetamide. 2-({6-[(2,5-dichloropyrimidin-4-yl)amino]-1-methyl-2-oxoquinolin-3-yl}oxy)-N-methylacetamide. The crude product was purified by Prep-HPLC with the following conditions): Column, C18 silica gel; mobile phase, acetonitrile/water (10 mmol/L NH$_4$HCO$_3$)=0:100 increasing to acetonitrile/water (10 mmol/L NH$_4$HCO$_3$)=80:20 within 30 min; Detector, 254 nm, to afford 2-{[6-({5-chloro-2-[4-({1-[2-(2,6-dioxopiperidin-3-yl)-5-fluoro-1,3-dioxoisoindol-4-yl]piperidin-4-yl}methyl)piperazin-1-yl]pyrimidin-4-yl}amino)-1-methyl-2-oxoquinolin-3-yl]oxy}-N-methylacetamide (17.5 mg, 39%) as a yellow solid. $^1$H NMR (400 MHz, DMSO-d6, ppm): δ 11.10 (s, 1H), 8.87 (s, 1H), 8.06 (s, 1H), 7.99 (s, 1H), 7.94 (m, 1H), 7.75 (m, 1H), 7.54-7.48 (m, 2H), 7.38 (m, 1H), 7.13 (s, 1H), 5.08 (m, 1H), 4.59 (s, 2H), 3.68 (s, 3H), 3.64 (s, 4H), 3.48 (m, 1H), 3.45 (s, 1H), 3.20 (s, 2H), 2.93-2.80 (m, 1H), 2.66 (m, 4H), 2.61 (s, 1H), 2.40 (s, 4H), 2.21 (s, 2H), 2.02 (m, 1H), 1.78 (m, 3H), 1.32 (m, 2H). MS (ES$^+$): m/z 829.35 [MH$^+$].

Example 22: 2-[[6-[[5-chloro-2-[4-[3-[4-[2-(2,6-dioxo-3-piperidyl)-1,3-dioxo-isoindolin-5-yl]-1-piperidyl]cyclobutoxy]-1-piperidyl]pyrimidin-4-yl]amino]-1-ethyl-2-oxo-3-quinolyl]oxy]-N-methyl-acetamide (Compound 5)

Step 1: Synthesis of 6-nitro-1H-quinolin-2-oneSynthesis of 3-bromo-1-ethyl-6-nitroquinolin-2-one

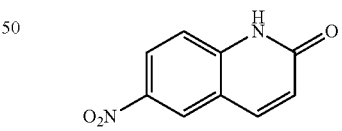

To a mixture of 1H-quinolin-2-one (3.50 g, 24.11 mmol, 1.00 eq) in concentrated sulfuric acid (15 mL) was added dropwise concentrated nitric acid (11.11 mmol, 0.5 mL, 0.46 eq) at 0° C. The mixture was stirred at 0° C. for 3 h. Then to the mixture was added nitric acid (22.22 mmol, 1 mL, 0.92 eq). The reaction mixture was stirred at 0° C. for 1 h. LCMS showed the reaction was completed. Then the reaction mixture was poured into ice water (100 mL). The precipitate that formed was filtered and washed with water (100 mL). The solid was concentrated under reduced pressure to give 6-nitro-1H-quinolin-2-one (2.50 g, 13.15 mmol, 55% yield) as a yellow solid, which was used in next step directly. LC/MS (ESI) m/z: 191.2 [M+1]⁺. ¹H NMR: (400 MHz, DMSO-d₆) δ=8.67 (s, 1H), 8.31 (dd, J=9.2, 2.4 Hz, 1H), 8.11 (d, J=9.6 Hz, 1H), 7.44 (d, J=9.2 Hz, 1H), 6.66 (d, J=9.6 Hz, 1H).

Step 2: Synthesis of
3-bromo-6-nitro-1H-quinolin-2-one

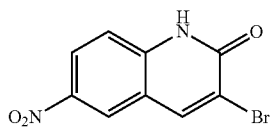

To a suspension of 6-nitro-1H-quinolin-2-one (12.00 g, 63.11 mmol, 1.00 eq), sodium bromate (12.38 g, 82.04 mmol, 1.30 eq) and water (100 mL) was added hydrogen bromide (2120 mmol, 240 mL, 48% purity, 33.62 eq) and the reaction mixture was heated at 100° C. for 4 h. LCMS showed the reaction was completed. Then the reaction mixture was poured into ice water (300 mL). The mixture was filtered. The filter cake was concentrated under reduced pressure to give 3-bromo-6-nitro-1H-quinolin-2-one (15.00 g, 55.75 mmol, 88% yield) as a yellow solid, which was used in next step directly. LC/MS (ESI) m/z: 269.0 [M+1]⁺. ¹H NMR: (400 MHz, DMSO-d6) δ=12.77 (brs, 1H), 8.76 (s, 1H), 8.68 (d, J=2.8 Hz, 1H), 8.34 (dd, J=9.6, 2.8 Hz, 1H), 7.47 (d, J=9.2 Hz, 1H).

Step 3: Synthesis of
3-bromo-1-ethyl-6-nitro-quinolin-2-one

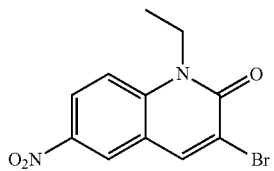 [SMILES: CCn1c(=O)c(Br)cc2cc([N+](=O)[O-])ccc21]

To a solution of 3-bromo-6-nitro-1H-quinolin-2-one (6.00 g, 22.30 mmol, 1.00 eq) in N,N'-dimethylformamide (50 mL) was added potassium carbonate (10.90 g, 78.86 mmol, 3.54 eq) and iodoethane (44.60 mmol, 3.57 mL, 2.00 eq). The reaction was stirred at 25° C. for 0.5 h. LCMS showed the reaction was complete. Then the reaction mixture was poured into ice water (100 mL) and filtered. The filter cake was treated with a solution of petroleum ether (300 mL) and ethyl acetate (30 mL). The mixture was stirred at 25° C. for 0.5 h and filtered. The filter cake was collected and dried under reduced pressure to give 3-bromo-1-ethyl-6-nitro-quinolin-2-one (4.00 g, 13.46 mmol, 30% yield) as a yellow solid, which was used in next step directly. LCMS (ESI) m/z: 299.0 [M+1]⁺. ¹H NMR: (400 MHz, DMSO-d6) δ=8.79-8.74 (m, 2H), 8.42 (dd, J=9.6, 2.8 Hz, 1H), 7.83 (d, J=9.6 Hz, 1H), 4.39 (q, J=7.2 Hz, 2H), 1.26 (t, J=7.2 Hz, 3H).

Step 4: Synthesis of
1-ethyl-3-hydroxy-6-nitro-quinolin-2-one

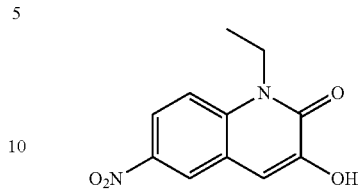

To a solution of 3-bromo-1-ethyl-6-nitro-quinolin-2-one (3.00 g, 10.10 mmol, 1.00 eq) in dioxane (50 mL) and water (100 mL) was added potassium hydroxide (1.70 g, 30.29 mmol, 3.00 eq) and methanesulfonato(2-dicyclohexylphosphino-3,6-dimethoxy-2',4',6'-tri-1-propyl-1,1'-biphenyl)(2'-amino-1,1'-biphenyl-2-yl)palladium (II) (0.92 g, 1.01 mmol, 0.10 eq). The mixture was heated under nitrogen atmosphere at 100° C. for 12 h. The reaction mixture was concentrated under reduced pressure. The residue was adjusted pH=6 with hydrochloric acid (1 M) and the mixture was filtered. The filter cake was concentrated under reduced pressure to give 1-ethyl-3-hydroxy-6-nitro-quinolin-2-one (2.20 g, 9.39 mmol, 93% yield) as a yellow solid. LCMS: (ESI) m/z: 235.1 [M+1]⁺. ¹H NMR (400 MHz, DMSO-d6) δ=10.10 (s, 1H), 8.59 (s, 1H), 8.21 (dd, J=9.6, 2.8 Hz, 1H), 7.75 (d, J=9.2 Hz, 1H), 7.38 (s, 1H), 4.40 (q, J=7.2 Hz, 2H), 1.26 (t, J=7.2 Hz, 3H).

Step 5: Synthesis of 2-[(1-ethyl-6-nitro-2-oxo-3-quinolyl)oxy]-N-methyl-acetamide

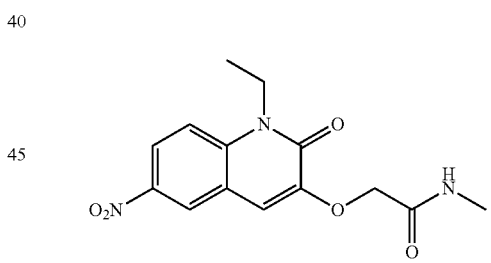

To a solution of 1-ethyl-3-hydroxy-6-nitro-quinolin-2-one (1.00 g, 4.27 mmol, 1.00 eq) in acetonitrile (5 mL) was added potassium carbonate (1.77 g, 12.81 mmol, 3.00 eq) and 2-bromo-N-methyl-acetamide (0.65 g, 4.27 mmol, 1.00 eq). The reaction was stirred at 80° C. for 0.5 h. To the mixture was added water (50 mL). The mixture was filtered. The filter cake was concentrated under reduced pressure to give 2-[(1-ethyl-6-nitro-2-oxo-3-quinolyl)oxy]-N-methyl-acetamide (1.20 g, 3.93 mmol, 92% yield) as a yellow solid. LCMS (ESI) m/z: 328.2 [M+23]⁺. HNMR (400 MHz, DMSO-d6) δ=8.64 (d, J=2.8 Hz, 1H), 8.27 (dd, J=9.2, 2.8 Hz, 1H), 7.96 (d, J=3.6 Hz, 1H), 7.77 (d, J=9.6 Hz, 1H), 7.53 (s, 1H), 4.60 (s, 2H), 4.38 (q, J=7.2 Hz, 2H), 2.68 (d, J=4.8 Hz, 3H), 1.26 (t, J=7.2 Hz, 3H).

Step 6: 2-[(6-amino-1-ethyl-2-oxo-3-quinolyl)oxy]-N-methyl-acetamide

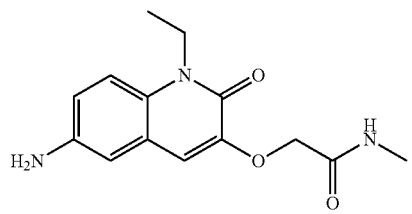 [SMILES: CCn1c(=O)c(OCC(=O)NC)cc2cc([N+](=O)[O-])ccc21]

To a mixture of 2-[(1-ethyl-6-nitro-2-oxo-3-quinolyl)oxy]-N-methyl-acetamide (1.00 g, 3.28 mmol, 1.00 eq) in tetrahydrofuran (25 mL) and methanol (30 mL) was added palladium on carbon (0.15 g, 10% purity). The mixture was stirred under 1 atmosphere of hydrogen atmosphere at 25° C. for 12 h. Then the reaction mixture was filtered. The filtrate was concentrated under reduced pressure to give 2-[(6-amino-1-ethyl-2-oxo-3-quinolyl)oxy]-N-methyl-acetamide (1.00 g, crude) as a yellow solid, which was used in next step directly without further purification. LCMS (ESI) m/z: 276.1 [M+1]$^+$. $^1$H NMR (400 MHz, DMSO-d6) δ=7.99 (d, J=4.0 Hz, 1H), 7.25 (d, J=8.8 Hz, 1H), 7.04 (s, 1H), 6.81 (dd, J=9.2, 2.8 Hz, 1H), 6.71 (d, J=2.8 Hz, 1H), 5.06 (s, 2H), 4.51 (s, 2H), 4.24 (q, J=7.2 Hz, 2H), 2.67 (d, J=4.8 Hz, 3H), 1.20 (t, J=7.2 Hz, 3H).

Step 7: Synthesis of 2-[[6-[(2,5-dichloropyrimidin-4-yl)amino]-1-ethyl-2-oxo-3-quinolyl]oxy]-N-methyl-acetamide

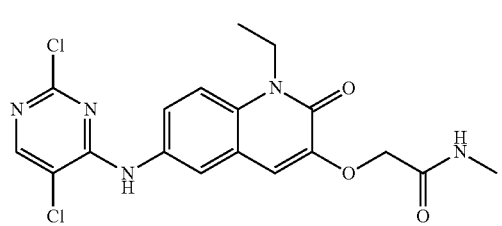 [SMILES: CCn1c(=O)c(OCC(=O)NC)cc2cc(Nc3nc(Cl)ncc3Cl)ccc21]

To a mixture of 2-[(6-amino-1-ethyl-2-oxo-3-quinolyl)oxy]-N-methyl-acetamide (1.00 g, 3.63 mmol, 1.00 eq) and diisopropylethylamine (10.90 mmol, 1.90 mL, 3.00 eq) in dimethylsulfoxide (30 mL) was added 2,4,5-trichloropyrimidine (1.33 g, 7.26 mmol, 2.00 eq). The mixture was stirred at 100° C. for 1 h, poured into ice water (50 mL) and filtered. The filter cake was treated with a solution of petroleum ether (50 mL) and ethyl acetate (10 mL) and filtered to give 2-[[6-[(2,5-dichloropyrimidin-4-yl)amino]-1-ethyl-2-oxo-3-quinolyl]oxy]-N-methyl-acetamide (1.20 g, 2.84 mmol, 78% yield) as a white solid, which was used in next step directly. LCMS (ESI) m/z: 422.3 [M+1]$^+$. $^1$H NMR (400 MHz, DMSO-d6) δ=9.66 (s, 1H), 8.39 (s, 1H), 7.97 (d, J=4.0 Hz, 1H), 7.77 (d, J=2.4 Hz, 1H), 7.68 (dd, J=9.6, 2.4 Hz, 1H), 7.59 (d, J=9.2 Hz, 1H), 7.23 (s, 1H), 4.59 (s, 2H), 4.35 (q, J=7.2 Hz, 2H), 2.68 (d, J=4.8 Hz, 3H), 1.25 (t, J=7.2 Hz, 3H).

Step 8: Synthesis of 1. Synthesis of tert-butyl 4-[(1R,3R)-3-[4-[2-(2,6-dioxopiperidin-3-yl)-1,3-dioxoisoindol-5-yl]piperidin-1-yl]cyclobutoxy]piperidine-1-carboxylate

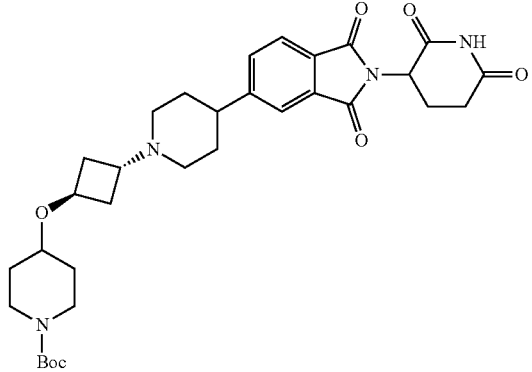 [SMILES: CC(C)(C)OC(=O)N1CCC(O[C@H]2C[C@H](N3CCC(c4ccc5c(c4)C(=O)N(C4CCC(=O)NC4=O)C5=O)CC3)C2)CC1]

Into a 20-mL sealed tube purged and maintained with an inert atmosphere of nitrogen, was placed 2-(2,6-dioxopiperidin-3-yl)-5-(piperidin-4-yl)isoindole-1,3-dione (200 mg, 0.6 mmol, 1.0 equiv), DMF (20 ml), DIEA (227 mg, 1.8 mmol, 3.0 equiv), tert-butyl 4-[(1S,3S)-3-[(4-nitrobenzenesulfonyl)oxy]cyclobutoxy]piperidine-1-carboxylate (WO2018102725, 267.5 mg, 0.6 mmol, 1.0 equiv). The resulting solution was stirred for 36 h at 65° C. in an oil bath. The crude product was purified by Flash-Prep-HPLC with the following conditions: Column, C18 silica gel; mobile phase, acetonitrile/water=10 increasing to acetonitrile/water=70 within 25 min; Detector, 254 nm. This resulted in 60 mg (17%) of tert-butyl 4-[(1R,3R)-3-[4-[2-(2,6-dioxopiperidin-3-yl)-1,3-dioxoisoindol-5-yl]piperidin-1-yl]cyclobutoxy]piperidine-1-carboxylate as yellow oil. MS (ES$^+$): m/z 595.30 [MH$^+$].

Step 9: Synthesis of 2-(2,6-dioxopiperidin-3-yl)-5-[1-[(1r,3r)-3-(piperidin-4-yloxy)cyclobutyl]piperidin-4-yl]isoindole-1,3-dione

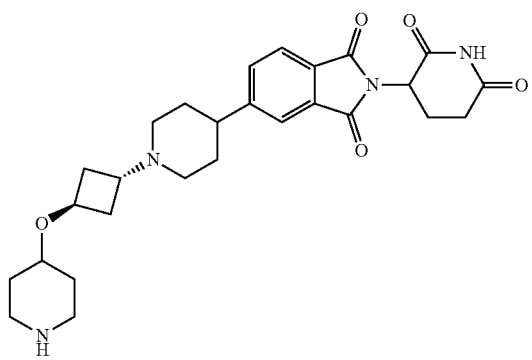 [SMILES: O=C1CCC(N2C(=O)c3ccc(C4CCN([C@H]5C[C@H](OC6CCNCC6)C5)CC4)cc3C2=O)C(=O)N1]

Into a 25-mL round-bottom flask, was placed tert-butyl 4-[(1r,3r)-3-[4-[2-(2,6-dioxopiperidin-3-yl)-1,3-dioxoisoindol-5-yl]piperidin-1-yl]cyclobutoxy]piperidine-1-carboxylate (60 mg, 0.1 mmol, 1.0 equiv), DCM (10 mL), TFA (3 mL). The resulting solution was stirred for 2 h at room temperature. The resulting mixture was concentrated. This resulted in 55 mg (99%) of 2-(2,6-dioxopiperidin-3-yl)-5-

[1-[(1r,3r)-3-(piperidin-4-yloxy)cyclobutyl]piperidin-4-yl]isoindole-1,3-dione as yellow oil. LC-MS (ES+): m/z 495.30 [MH+].

Step 10: 2-[[6-[[5-chloro-2-[4-[3-[4-[2-(2,6-dioxo-3-piperidyl)-1,3-dioxo-isoindolin-5-yl]-1-piperidyl]cyclobutoxy]-1-piperidyl]pyrimidin-4-yl]amino]-1-ethyl-2-oxo-3-quinolyl]oxy]-N-methyl-acetamide

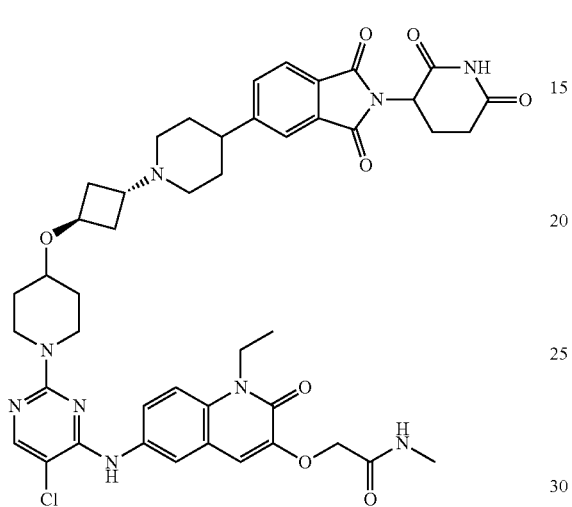

To a solution of 2-[[6-[(2,5-dichloropyrimidin-4-yl)amino]-1-ethyl-2-oxo-3-quinolyl]oxy]-N-methyl-acetamide (120 mg, 0.28 mmol, 1 eq) and N,N-diisopropylethylamine (110 mg, 0.85 mmol, 0.1 mL, 3 eq) in dimethyl sulfoxide (6 mL) was added 2-(2,6-dioxo-3-piperidyl)-5-[1-[3-(4-piperidyloxy)cyclobutyl]-4-piperidyl]isoindoline-1,3-dione (190 mg, 0.31 mmol, 1.1 eq, trifluoroacetate) at 25° C., then the mixture was stirred for 12 h at 120° C. LCMS showed desired m/z and the reaction was completed. Water (10 mL) was added to the mixture and extracted with Ethyl acetate (10 mL×3), the combined organic phase washed with brine (10 mL), dried over anhydrous sodium sulfate, filtered and concentrated under reduced pressure. The residue was firstly purified by prep-HPLC (column: Welch Ultimate XB-SiOH 250*50*10 um; mobile phase: [Hexane-EtOH]; B %: 20%-60%, 15 min). Then further purified by prep-HPLC (column: Phenomenex Gemini-NX C18 75*30 mm*3 um; mobile phase: [water (0.225% FA)-ACN]; B %: 12%-42%, 7 min). 2-[[6-[[5-chloro-2-[4-[3-[4-[2-(2,6-dioxo-3-piperidyl)-1,3-dioxo-isoindolin-5-yl]-1-piperidyl]cyclobutoxy]-1-piperidyl]pyrimidin-4-yl]amino]-1-ethyl-2-oxo-3-quinolyl]oxy]-N-methyl-acetamide (35.08 mg, 0.04 mmol, 13% yield, 96.5% purity) was obtained as an off-white solid. $^1$H NMR (400 MHz, DMSO-d$_6$) δ: 11.13 (s, 1H), 8.85 (s, 1H), 8.04 (s, 1H), 8.03-7.99 (m, 1H), 7.95 (d, J=2.4 Hz, 1H), 7.87-7.82 (m, 1H), 7.79-7.76 (m, 2H), 7.74-7.69 (m, 1H), 7.55-7.49 (m, 1H), 7.08 (s, 1H), 5.13 (dd, J=12.8, 5.2 Hz, 1H), 4.57 (s, 2H), 4.37-4.27 (m, 2H), 4.20-4.05 (m, 3H), 3.25-3.22 (m, 2H), 3.02-2.95 (m, 2H), 2.92-2.80 (m, 2H), 2.77-2.70 (m, 1H), 2.67 (d, J=4.8 Hz, 3H), 2.63-2.53 (m, 3H), 2.20-2.10 (m, 2H), 2.08-1.95 (m, 3H), 1.85-1.75 (m, 6H), 1.72-1.60 (m, 2H), 1.43-1.30 (m, 2H), 1.23 (t, J=7.2 Hz, 3H). MS (ESI) m/z: 880.3 [M+1]+.

Example 23: 2-[[6-[[5-chloro-2-[4-[3-[4-[2-(2,6-dioxo-3-piperidyl)-4-methoxy-1-oxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide (Compound 72)

Step 1: Preparation of methyl 4-bromo-3-hydroxy-2-methyl-benzoate

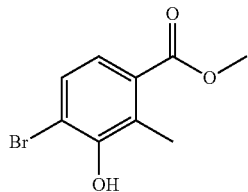

To a solution of 2-methylpropan-2-amine (440 mg, 6.02 mmol, 0.6 mL, 1 eq) in dichloromethane (40 mL) at −70° C. was added a solution of bromine (961 mg, 6.02 mmol, 0.3 mL, 1 eq) in dichloromethane (2 mL) drop wise and the mixture was stirred at −70° C. for 1 hour. A solution of methyl 3-hydroxy-2-methyl-benzoate (1 g, 6.02 mmol, 1 eq) in dichloromethane (2 mL) was then added drop wise and the resulting mixture allowed to warm to 25° C. and stirred for 11 h. The reaction mixture was diluted with water (200 mL) and extracted with dichloromethane (200 mL×2). The combined organic phase was dried with anhydrous sodium sulfate, filtered and concentrated in vacuum. The residue was purified by silica gel chromatography (Petroleum ether/Ethyl acetate=1/0 to 150/1). Compound methyl 4-bromo-3-hydroxy-2-methyl-benzoate (780 mg, 3.18 mmol, 52% yield) was obtained as a white solid. $^1$H NMR (400 MHz, DMSO-d$_6$) δ: 9.38 (s, 1H), 7.46 (d, J=8.4 Hz, 1H), 7.18 (d, J=8.4 Hz, 1H), 3.81 (s, 3H), 2.38 (s, 3H). MS (ESI) m/z: 246.9 [M+1]+

Step 2: Preparation of methyl 4-bromo-3-methoxy-2-methyl-benzoate

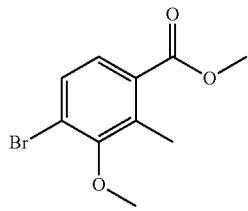

To a solution of methyl 4-bromo-3-hydroxy-2-methyl-benzoate (780 mg, 3.18 mmol, 1 eq) in acetonitrile (6 mL) was added potassium carbonate (527 mg, 3.82 mmol, 1.2 eq) and iodomethane (1.36 g, 9.55 mmol, 0.5 mL, 3 eq). The mixture was stirred at 50° C. for 5 hr. Several new peaks were shown on LCMS and the desired compound was detected. The reaction mixture was filtered and diluted with water (100 mL) and extracted with ethyl acetate (100 mL×2). The combined organic phase was washed with saturated brine (200 mL), dried with anhydrous sodium sulfate, filtered and concentrated in vacuum. The residue was purified by silica gel chromatography (Petroleum ether/Ethyl acetate=1/0 to 50/1). Compound methyl 4-bromo-3- methoxy-2-methyl-benzoate (740 mg, 2.86 mmol, 89% yield) was obtained as a white solid. ¹H NMR (400 MHz, CDCl₃) δ: 7.58-7.50 (m, 1H), 7.50-7.43 (m, 1H), 3.91 (s, 3H), 3.82 (s, 3H), 2.58 (s, 3H). MS (ESI) m/z: 259.0 [M+1]⁺

Step 3: Preparation of WX-ARV-DS-021F-3, methyl 4-bromo-2-(bromomethyl)-3-methoxy-benzoate

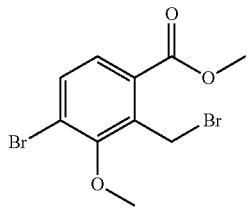

To a solution of methyl 4-bromo-3-methoxy-2-methyl-benzoate (145 mg, 0.55 mmol, 1 eq) in carbon tetrachloride (1 mL) was added n-bromosuccinimide (119 mg, 0.67 mmol, 1.2 eq) and AIBN (2 mg, 0.02 mmol, 0.03 eq). The mixture was stirred at 70° C. for 3 hr under nitrogen atmosphere. The reaction mixture was diluted with water (50 mL) and extracted with ethyl acetate (50 mL×2). The combined organic phase was washed with saturated brine (100 mL), dried with anhydrous sodium sulfate, filtered and concentrated in vacuum. The residue was purified by silica gel chromatography (Petroleum ether/Ethyl acetate=1/0 to 10/1). The title compound was obtained as a white solid (170 mg, 0.50 mmol, 89% yield). ¹H NMR (400 MHz, CDCl₃) δ: 7.62 (dd, J=8.4, 13.6 Hz, 2H), 5.11 (s, 2H), 4.04 (s, 3H), 3.06 (s, 3H)

Step 4: Preparation of tert-butyl 5-amino-4-(5-bromo-4-methoxy-1-oxo-isoindolin-2-yl)-5-oxo-pentanoate

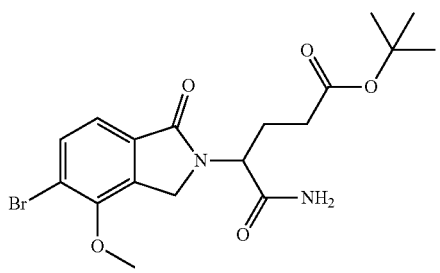 [SMILES: COc1c(Br)ccc2c1CN(C(CCC(=O)OC(C)(C)C)C(N)=O)C2=O]

To a solution of methyl 4-bromo-2-(bromomethyl)-3-methoxy-benzoate (750 mg, 2.22 mmol, 1 eq) and tert-butyl 4,5-diamino-5-oxo-pentanoate (673 mg, 3.33 mmol, 1.5 eq) in N,N-dimethylformamide (7 mL) was added N,N-diisopropylethylamine (860 mg, 6.66 mmol, 1.16 mL, 3 eq). The mixture was stirred at 110° C. for 1 h. The reaction mixture was diluted with water (100 mL) and extracted with ethyl acetate (100 mL×2). The combined organic phase was washed with saturated brine (200 mL), dried with anhydrous sodium sulfate, filtered and concentrated in vacuum. The residue was purified by silica gel chromatography (Petroleum ether/Ethyl acetate=1/0 to 1/2). Compound tert-butyl 5-amino-4-(5-bromo-4-methoxy-1-oxo-isoindolin-2-yl)-5-oxo-pentanoate (880 mg, 2.06 mmol, 92% yield) was obtained as a white solid. MS (ESI) m/z: 427.1 [M+1]⁺.

Step 5: Preparation of benzyl 4-[2-(4-tert-butoxy-1-carbamoyl-4-oxo-butyl)-4-methoxy-1-oxo-isoindolin-5-yl]-3,6-dihydro-2H-pyridine-1-carboxylate

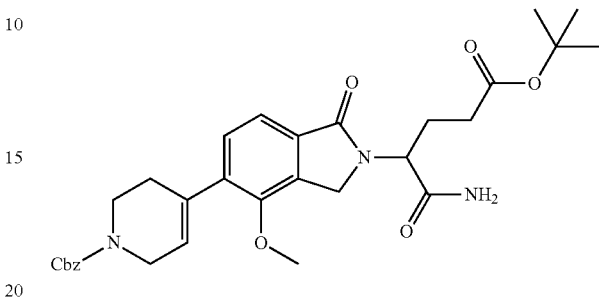

A mixture of tert-butyl 5-amino-4-(5-bromo-4-methoxy-1-oxo-isoindolin-2-yl)-5-oxo-pentanoate (780 mg, 1.83 mmol, 1 eq), benzyl 4-(4,4,5,5-tetramethyl-1,3,2-dioxaborolan-2-yl)-3,6-dihydro-2H-pyridine-1-carboxylate (751 mg, 2.19 mmol, 1.2 eq), ditert-butyl (cyclopentyl)phosphane; dichloropalladium; iron (118 mg, 0.18 mmol, 0.1 eq) and cesium fluoride (831 mg, 5.48 mmol, 0.2 mL, 3 eq) in dioxane (10 mL) and water (1 mL) was degassed and purged with nitrogen for 3 times, and then the mixture was stirred at 90° C. for 6 h under nitrogen atmosphere. The reaction mixture was diluted with water (200 mL). The organic layer was extracted with ethyl acetate (100 mL×2). The combined organic layer was washed with brine (200 mL). The organic layer was dried over anhydrous sodium sulfate, filtered and concentrated under vacuum to get the residue. The residue was purified by prep-HPLC (column: Phenomenex luna C18 (250*70 mm, 10 um); mobile phase: [water (0.225% FA)-ACN]; B %: 50%-75%, 17 min). Compound benzyl 4-[2-(4-tert-butoxy-1-carbamoyl-4-oxo-butyl)-4-methoxy-1-oxo-isoindolin-5-yl]-3,6-dihydro-2H-pyridine-1-carboxylate (900 mg, 1.60 mmol, 87% yield) was obtained as a white solid.). ¹H NMR (400 MHz, CDCl₃) δ: 7.56-7.49 (m, 1H), 7.46-7.32 (m, 5H), 7.30-7.23 (m, 1H), 6.54 (s, 1H), 5.96-5.78 (m, 1H), 5.69 (br s, 1H), 5.21 (m, 2H), 4.93 (dd, J=6.4, 8.4 Hz, 1H), 4.58 (d, J=17.2 Hz, 2H), 4.23-4.14 (m, 2H), 3.84 (s, 3H), 3.72 (t, J=5.2 Hz, 2H), 2.53 (br s, 2H), 2.42-2.14 (m, 4H), 1.42 (s, 9H). MS (ESI) m/z: 564.4 [M+1]⁺.

Step 6: Preparation of tert-butyl 5-amino-4-[4-methoxy-1-oxo-5-(4-piperidyl)isoindolin-2-yl]-5-oxo-pentanoate

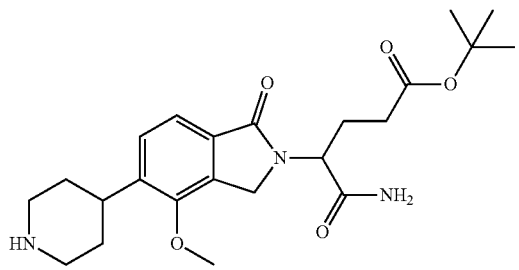 [SMILES: COc1c(C2CCNCC2)ccc2c1CN(C(CCC(=O)OC(C)(C)C)C(N)=O)C2=O]

233

To a solution of benzyl 4-[2-(4-tert-butoxy-1-carbamoyl-4-oxo-butyl)-4-methoxy-1-oxo-isoindolin-5-yl]-3,6-dihydro-2H-pyridine-1-carboxylate (900 mg, 1.60 mmol, 1 eq) in 2,2,2-trifluoroethanol (10 mL) and tetrahydrofuran (10 mL) was added palladium on activated carbon catalyst (200 mg, 10% purity) and palladium hydroxide on activated carbon catalyst (200 mg, 20% purity) under nitrogen atmosphere. The suspension was degassed and purged with hydrogen for three times. The mixture was stirred under hydrogen (50 Psi) at 30° C. for 12 h. The reaction mixture was filtered and concentrated under reduced pressure to give a residue. The crude product was used into the next step without further purification. Compound tert-butyl 5-amino-4-[4-methoxy-1-oxo-5-(4-piperidyl)isoindolin-2-yl]-5-oxopentanoate (680 mg, 1.58 mmol, 98% yield) was obtained as a white solid.). $^1$H NMR (400 MHz, CDCl$_3$) δ: 7.47 (br d, J=7.6 Hz, 1H), 7.28 (d, J=7.6 Hz, 1H), 4.82 (br t, J=7.2 Hz, 1H), 4.62-4.41 (m, 2H), 3.96-3.96 (m, 2H), 3.85 (s, 3H), 3.65 (q, J=7.2 Hz, 2H), 2.81-2.63 (m, 2H), 2.36-2.08 (m, 4H), 1.75-1.65 (m, 2H), 1.62-1.56 (m, 1H), 1.34 (s, 9H).

Step 7: Preparation of benzyl 4-((1s,3s)-3-(benzyloxy)cyclobutoxy)piperidine-1-carboxylate

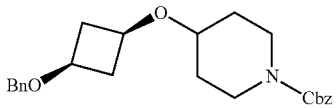 [SMILES: O=C(OCc1ccccc1)N1CCC(O[C@H]2C[C@@H](OCc3ccccc3)C2)CC1]

A mixture of cis-3-benzyloxycyclobutanol (100 g, 561.08 mmol, 1 eq) and benzyl 4-oxopiperidine-1-carboxylate (143.97 g, 617.19 mmol, 123.1 mL, 1.1 eq) in acetonitrile (2000 mL) was degassed and purged with nitrogen for 3 times, and then was added chloro(dimethyl)silane (53.09 g, 561.08 mmol, 1 eq) at 0° C. The mixture was stirred at 25° C. for 12 h under nitrogen atmosphere. LCMS showed the desired mass was detected. The reaction mixture was diluted with water (2 L). The organic layer was extracted with ethyl acetate (1 L×2). The combined organic layer was washed with brine (500 mL). The organic layer was dried over anhydrous sodium sulfate, filtered and concentrated under vacuum to get the residue. The residue was purified by silica gel chromatography (Petroleum ether/Ethyl acetate=30/1, 20/1) to get the product. The title compound was obtained as a colorless oil (89 g, 225.04 mmol, 40% yield). MS (ESI) m/z: 396.3 [M+1]$^+$.

Step 8: Preparation of benzyl 4-((1s,3s)-3-hydroxycyclobutoxy)piperidine-1-carboxylate

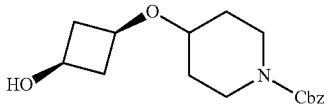 [SMILES: O=C(OCc1ccccc1)N1CCC(O[C@H]2C[C@@H](O)C2)CC1]

To a solution of benzyl 4-((1s,3s)-3-(benzyloxy)cyclobutoxy)piperidine-1-carboxylate (65 g, 164.35 mmol, 1 eq) in ethanol (300 mL) and tetrahydrofuran (300 mL) was added palladium on activated carbon catalyst (6 g, 1.44 mmol, 10% purity), palladium hydroxide on activated carbon catalyst (6 g, 8.54 mmol, 20% purity) and di-tert-butyl dicarbonate (53.80 g, 246.53 mmol, 56.6 mL, 1.5 eq) under nitrogen

234 atmosphere. The suspension was degassed and purged with hydrogen for three times. The mixture was stirred under hydrogen (50 Psi) at 40° C. for 16 h. Thin-Layer Chromatography (Petroleum ether:Ethyl acetate=1:1) indicated the starting material was consumed completely and two new spot formed. The reaction mixture was filtered and concentrated under reduced pressure to give a residue. The crude product was purified by silica gel chromatography (Petroleum ether/Ethyl acetate=50/1, 0/1). The title product was obtained as a white (30.8 g, 113.51 mmol, 69% yield). $^1$H NMR (400 MHz, CDCl$_3$) δ: 3.94-3.85 (m, 1H), 3.82-3.71 (m, 2H), 3.68-3.57 (m, 1H), 3.49-3.35 (m, 1H), 3.08-2.92 (m, 2H), 2.76-2.64 (m, 2H), 1.96-1.88 (m, 2H), 1.84-1.72 (m, 2H), 1.54-1.37 (m, 11H)

Step 9: Preparation of benzyl 4-((1s,3s)-3-((tert-butylsulfonyl)oxy)cyclobutoxy)piperidine-1-carboxylate

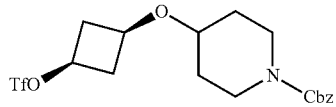 [SMILES: O=C(OCc1ccccc1)N1CCC(O[C@H]2C[C@@H](OS(=O)(=O)C(F)(F)F)C2)CC1]

To a solution of benzyl 4-((1s,3s)-3-hydroxycyclobutoxy)piperidine-1-carboxylate (4 g, 14.74 mmol, 1 eq) and triethylamine (4.47 g, 44.22 mmol, 6.16 mL, 3 eq) in dichloromethane (120 mL) was added trifluoromethanesulfonyl anhydride (4.57 g, 16.22 mmol, 2.68 mL, 1.1 eq) at 0° C. The mixture was stirred at 25° C. for 0.5 h. TLC showed the reaction was completed. The reaction was quenched with water (20 mL). The solution was extracted with dichloromethane (20 mL×2). The organic layers were combined, dried over anhydrous sodium sulfate, filtered and concentrated under reduced pressure to give a residue. The residue was purified by silica gel chromatography (2-5% ethyl acetate in petroleum ether). The title compound was obtained as a yellow solid (2.5 g, 6.20 mmol, 42% yield). $^1$H NMR (400 MHz, CDCl$_3$) δ: 4.83 (quin, J=7.2 Hz, 1H), 3.76-3.61 (m, 3H), 3.43-3.34 (m, 1H), 2.99 (ddd, J=3.6, 9.6, 13.2 Hz, 2H), 2.88-2.74 (m, 2H), 2.48-2.21 (m, 2H), 1.74-1.65 (m, 2H), 1.45-1.36 (m, 11H).

Step 10: Preparation of tert-butyl 4-((1r,3r)-3-(4-(2-(1-amino-5-(tert-butoxy)-1,5-dioxopentan-2-yl)-4-methoxy-1-oxoisoindolin-5-yl)piperidin-1-yl)cyclobutoxy)piperidine-1-carboxylate

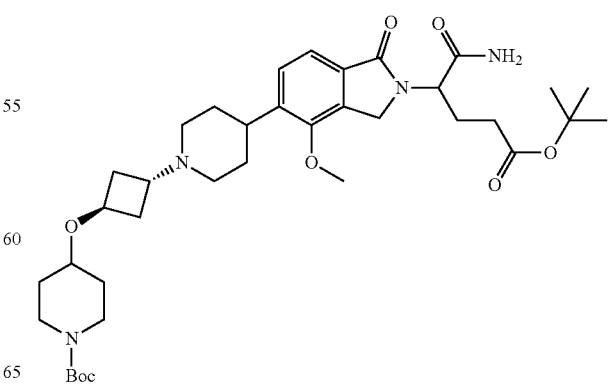

To a solution of tert-butyl 5-amino-4-[4-methoxy-1-oxo-5-(4-piperidyl)isoindolin-2-yl]-5-oxo-pentanoate (330 mg, 0.76 mmol, 1 eq) and benzyl 4-((1s,3s)-3-((tert-butylsulfonyl)oxy)cyclobutoxy)piperidine-1-carboxylate (339 mg, 0.84 mmol, 1.1 eq) in acetonitrile (10 mL) was added N,N-diisopropylethylamine (296 mg, 2.29 mmol, 0.3 mL, 3 eq). The mixture was stirred at 25° C. for 12 h. The reaction mixture was diluted with water (100 mL). The organic layer was extracted with ethyl acetate (100 mL×2). The combined organic layer was washed with brine (100 mL). The organic layer was dried over anhydrous sodium sulfate, filtered and concentrated under vacuum to get the residue. The residue was purified by prep-HPLC (column: Phenomenex luna C18 (250*70 mm, 10 um); mobile phase: [water (0.225% FA)-ACN]; B %: 10%-40%, 20 min) to obtain the title compound as a yellow oil (290 mg, 0.42 mmol, 55% yield). MS (ESI) m/z: 685.3 [M+1]+.

Step 11: Preparation of 3-(4-methoxy-1-oxo-5-(1-((1r,3r)-3-(piperidin-4-yloxy)cyclobutyl)piperidin-4-yl)isoindolin-2-yl)piperidine-2,6-dione

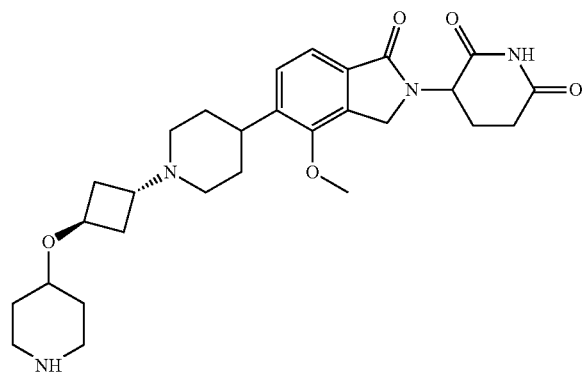 [SMILES: COc1c(C2CCN([C@H]3C[C@H](OC4CCNCC4)C3)CC2)ccc2c1CN(C1CCC(=O)NC1=O)C2=O]

A mixture of tert-butyl 4-((1r,3r)-3-(4-(2-(1-amino-5-(tert-butoxy)-1,5-dioxopentan-2-yl)-4-methoxy-1-oxoisoindolin-5-yl)piperidin-1-yl)cyclobutoxy)piperidine-1-carboxylate (290 mg, 0.42 mmol, 1 eq) and [(1R,4S)-7,7-dimethyl-2-oxo-norbornan-1-yl]methanesulfonic acid (245 mg, 1.06 mmol, 2.5 eq) in acetonitrile (10 mL) was stirred at 80° C. for 12 h. The reaction mixture was basified by N,N-diisopropylethylamine and then concentrated under reduced pressure to give a residue. The crude product was used into the next step without further purification. The title compound was obtained as a colorless gum (260 mg, 0.41 mmol, 98% yield, trifluoroacetate). MS (ESI) m/z: 529.3 [M+18]+.

Step 12: Preparation of 2-({6-[(5-chloro-2-{4-[(1r,3r)-3-{4-[2-(2,6-dioxopiperidin-3-yl)-1,3-dioxo-2,3-dihydro-1H-isoindol-5-yl]piperidin-1-yl}cyclobutoxy]piperidin-1-yl}pyrimidin-4-yl)amino]-1-ethyl-2-oxo-1,2-dihydroquinolin-3-yl}oxy)-N-methylacetamide

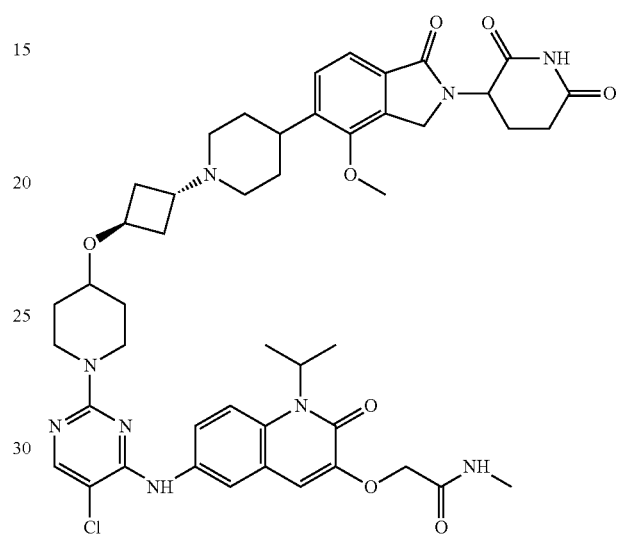

To a solution of 3-(4-methoxy-1-oxo-5-(1-((1r,3r)-3-(piperidin-4-yloxy)cyclobutyl)piperidin-4-yl)isoindolin-2-yl)piperidine-2,6-dione (260 mg, 0.41 mmol, 1 eq, trifluoroacetate) and 2-[[6-[(2,5-dichloropyrimidin-4-yl)amino]-1-isopropyl-2-oxo-3-quinolyl]oxy]-N-methyl-acetamide (181 mg, 0.41 mmol, 1 eq) in dimethyl sulfoxide (3 mL) was added N,N-diisopropylethylamine (161 mg, 1.25 mmol, 0.2 mL, 3 eq). The mixture was stirred at 120° C. for 1 h. The reaction mixture was filtered and concentrated under reduced pressure to give a residue. The residue was purified by prep-HPLC (column: Phenomenex Synergi C18 150*25 mm*10 um; mobile phase: [water (0.1% TFA)-ACN]; B %: 18%-48%, 10 min). The title compound was obtained as a white solid (47.8 mg, 0.05 mmol, 12% yield, 98% purity). $^1$H NMR (400 MHz, DMSO-$d_6$) δ: 10.9 (s, 1H), 8.83 (s, 1H), 8.05 (s, 1H), 8.01-7.92 (m, 2H), 7.69 (s, 2H), 7.40 (s, 2H), 7.03 (s, 1H), 5.59-5.19 (m, 1H), 5.10 (dd, J=5.2, 13.2 Hz, 1H), 4.70-4.60 (m, 1H), 4.55 (s, 2H), 4.50-4.42 (m, 1H), 4.24-4.11 (m, 2H), 3.91 (s, 3H), 3.54 (br s, 1H), 3.30 (s, 3H), 3.27-3.19 (m, 2H), 3.05-2.86 (m, 4H), 2.68 (d, J=4.4 Hz, 3H), 2.65-2.59 (m, 2H), 2.16 (br s, 2H), 2.04-19.6 (m, 3H), 1.88-1.76 (m, 4H), 1.72-1.66 (m, 3H), 1.58 (d, J=7.2 Hz, 6H), 1.43-1.33 (m, 2H). MS (ESI) m/z: 910.2 [M+1]+.

Example 24: 2-({6-[(5-chloro-2-{4-[(1r,3r)-3-{4-[2-(2,6-dioxopiperidin-3-yl)-6-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 79)

Step 1: Preparation of methyl 4-bromo-5-fluoro-2-methyl-benzoate

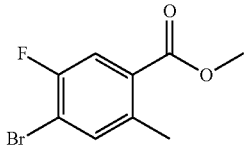

To a solution of 4-bromo-5-fluoro-2-methyl-benzoic acid (10.50 g, 45.06 mmol, 1.00 eq) in dimethyl formamide (110 mL) were added potassium carbonate (15.57 g, 112.64 mmol, 2.50 eq) and iodomethane (19.19 g, 135.17 mmol, 8.4 mL, 3.00 eq) at 20° C. and the mixture was stirred at 20° C. for 2 h. Thin layer chromatography (dichloromethane:methanol=10:1) showed the reaction was completed. The mixture was filtered and the filtrate was diluted with water (600 mL) and extracted with ethyl acetate (50 mL). The organic layer was washed with water (600 mL×2), brine (600 mL×2), dried over sodium sulfate and then concentrated under reduced pressure to give methyl 4-bromo-5-fluoro-2-methyl-benzoate (11.00 g, 44.52 mmol, 99% yield) as a yellow oil. $^1$H NMR (400 MHz, CDCl$_3$) δ: 7.68 (d, J=9.2 Hz, 1H), 7.46 (d, J=6.4 Hz, 1H), 3.91 (s, 3H), 2.56 (s, 3H).

Step 2: Preparation of methyl 4-bromo-2-(bromomethyl)-5-fluoro-benzoate

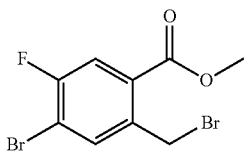

To a solution of methyl 4-bromo-5-fluoro-2-methyl-benzoate (11 g, 44.52 mmol, 1.00 eq) in dichloroethane (150 mL) were added N-Bromosuccinimide (8.72 g, 48.98 mmol, 1.10 eq) and 2,2-azobisisobutyronitrile (731 mg, 4.45 mmol, 0.10 eq) at 20° C. and the mixture was warmed to 80° C. The mixture was stirred at 80° C. for 6 h. Thin layer chromatography (petroleum ether:ethyl acetate=3:1) showed the reaction was completed. The mixture was filtered and the filtrate was diluted with saturated sodium thiosulfate (500 mL) and extracted with dichloromethane (300 mL). The organic layer was washed with water (500 mL×2), brine (500 mL×2), dried over sodium sulfate and then concentrated under reduced pressure to give a residue. The residue was purified by column chromatography on silica gel (petroleum ether:ethyl acetate=30:1 to 20:1) to give methyl 4-bromo-2-(bromomethyl)-5-fluoro-benzoate (13.00 g, 39.88 mmol, 90% yield) as a colorless oil. $^1$H NMR (400 MHz, CDCl$_3$) δ: 7.75-7.67 (m, 2H), 4.89 (s, 2H), 3.95 (s, 3H).

Step 3: Preparation of tert-butyl 5-amino-4-(5-bromo-6-fluoro-1-oxo-isoindolin-2-yl)-5-oxo-pentanoate

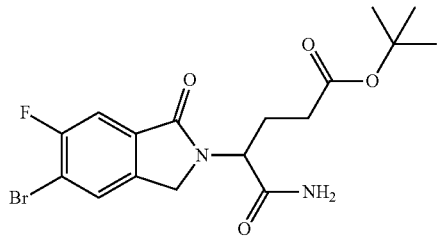 [SMILES: CC(C)(C)OC(=O)CCC(C(N)=O)N1Cc2cc(Br)c(F)cc2C1=O]

To a solution of methyl 4-bromo-2-(bromomethyl)-5-fluoro-benzoate (2.00 g, 6.14 mmol, 1.00 eq) in dimethyl formamide (20 mL) were added diisopropylethylamine (3.17 g, 24.54 mmol, 4.3 mL, 4.00 eq) and tert-butyl 4,5-diamino-5-oxo-pentanoate (1.24 g, 6.14 mmol, 1.00 eq) at 80° C. and the mixture was stirred at 80° C. for 12 h. Thin layer chromatography (dichloromethane:methanol=20:1) showed the reaction was completed. The mixture was diluted with water (100 mL) and extracted with ethyl acetate (100 mL). The organic layer was washed with water (100 mL×2 mL), brine (100 mL), dried over sodium sulfate and then concentrated under reduced pressure to give a light-yellow solid. The solid was triturated with petroleum ether:ethyl acetate (80 mL, 3:1) to give tert-butyl 5-amino-4-(5-bromo-6-fluoro-1-oxo-isoindolin-2-yl)-5-oxo-pentanoate (4.50 g, 10.84 mmol, 88% yield) as a white solid. δ: 8.02 (d, J=6.0 Hz, 1H), 7.72-7.54 (m, 2H), 7.24 (s, 1H), 4.79-4.67 (m, 1H), 4.65-4.55 (m, 1H), 4.52-4.35 (m, 1H), 2.23-2.09 (m, 3H), 2.05-1.90 (m, 1H), 1.33 (s, 9H).

Step 4: Preparation of benzyl 4-[2-(4-tert-butoxy-1-carbamoyl-4-oxo-butyl)-6-fluoro-1-oxo-isoindolin-5-yl]-3,6-dihydro-2H-pyridine-1-carboxylate

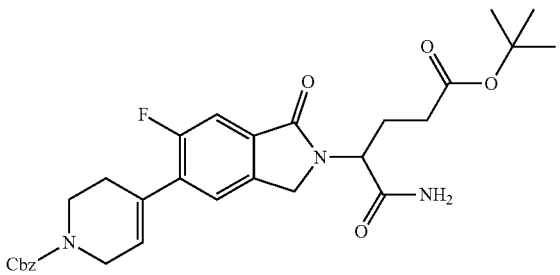 [SMILES: CC(C)(C)OC(=O)CCC(C(N)=O)N1Cc2cc(C3=CCN(C(=O)OCc4ccccc4)CC3)c(F)cc2C1=O]

The title compound was prepared analogously to Example 23, Step 5. The crude product was purified by column chromatography on silica gel (petroleum ether:ethyl acetate=5:1 to 0:1) to give benzyl 4-[2-(4-tert-butoxy-1-carbamoyl-4-oxo-butyl)-6-fluoro-1-oxo-isoindolin-5-yl]-3,6-dihydro-2H-pyridine-1-carboxylate (2.20 g, 3.91 mmol, 81% yield, 98% purity) as a light brown solid. $^1$H NMR (400 MHz, CDCl$_3$) δ: 7.47 (d, J=9.6 Hz, 1H), 7.44-7.28 (m, 6H), 6.40 (s, 1H), 5.97 (d, J=9.6 Hz, 1H), 5.54 (s, 1H), 5.19 (s, 2H), 4.90 (dd, J=6.4, 8.4 Hz, 1H), 4.58-4.48 (m, 1H), 4.45-4.36 (m, 1H), 4.18 (d, J=2.4 Hz, 2H), 3.72 (t, J=5.2 Hz, 2H), 2.53 (br s, 2H), 2.43-2.09 (m, 4H), 1.42 (s, 9H). MS (ESI) m/z: 552.2 [M+1]$^+$.

Step 5: Preparation of tert-butyl 5-amino-4-[6-fluoro-1-oxo-5-(4-piperidyl)isoindolin-2-yl]-5-oxopentanoate

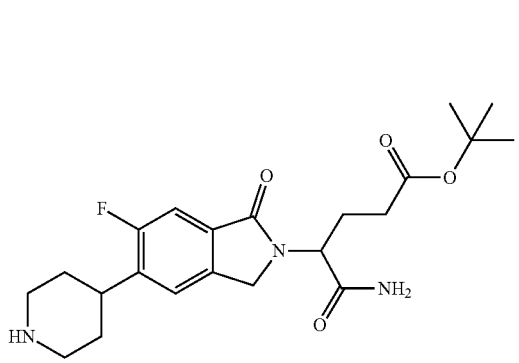 [SMILES: CC(C)(C)OC(=O)CCC(C(N)=O)N1Cc2cc(C3CCNCC3)c(F)cc2C1=O]

The title compound was prepared analogously to Example 23, Step 6. The crude product (720 mg, 1.72 mmol, 95% yield) was used in the next step without further purification. $^1$H NMR (400 MHz, DMSO-$d_6$) δ: 7.66-7.51 (m, 2H), 7.42 (d, J=9.2 Hz, 1H), 7.20 (s, 1H), 4.76-4.67 (m, 1H), 4.62-4.51 (m, 1H), 4.47-4.36 (m, 1H), 3.12-2.93 (m, 3H), 2.66 (t, J=11.2 Hz, 2H), 2.16 (s, 3H), 2.00-1.94 (m, 1H), 1.78-1.55 (m, 4H), 1.32 (s, 9H). MS (ESI) m/z: 420.2 [M+1]$^+$.

Step 6: Preparation of tert-butyl 4-((1r,3r)-3-(4-(2-(1-amino-5-(tert-butoxy)-1,5-dioxopentan-2-yl)-6-fluoro-1-oxoisoindolin-5-yl)piperidin-1-yl)cyclobutoxy)piperidine-1-carboxylate

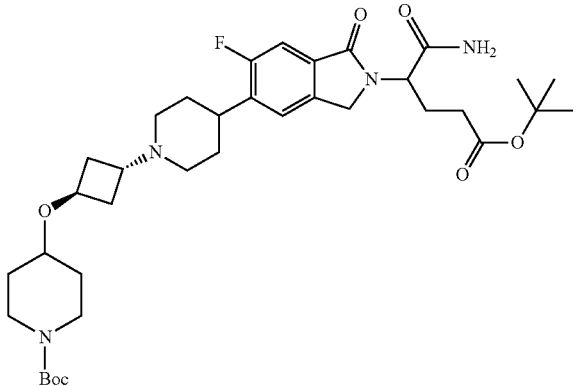 [SMILES: CC(C)(C)OC(=O)CCC(C(N)=O)N1Cc2cc(C3CCN([C@H]4C[C@H](OC5CCN(C(=O)OC(C)(C)C)CC5)C4)CC3)c(F)cc2C1=O]

The title compound was prepared analogously to Example 23, step 10. The crude product was purified by column chromatography on silica gel (petroleum ether:ethyl acetate=1:1 to dichloromethane:methanol=20:1) to afford the title product as a light yellow oil (600 mg, 0.89 mmol, 53% yield). MS (ESI) m/z: 673.3 [M+1]$^+$.

Step 7: Preparation of 3-(6-fluoro-1-oxo-5-(1-((1r,3r)-3-(piperidin-4-yloxy)cyclobutyl)piperidin-4-yl)isoindolin-2-yl)piperidine-2,6-dione

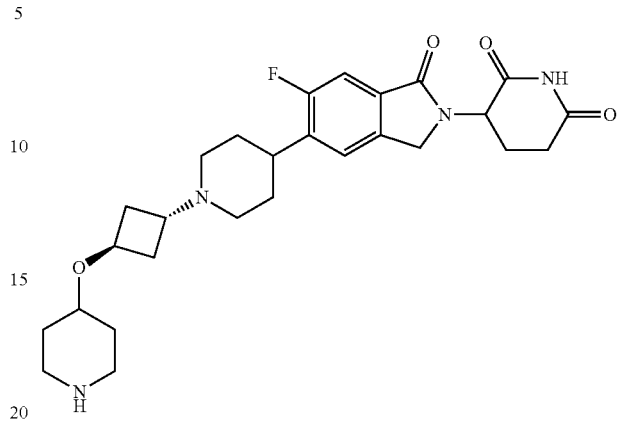

The title compound was prepared analogously to Example 23, Step 11. The crude product was purified by preparative high performance liquid chromatography (column: 3-Phenomenex Luna C18 75*30 mm*3 um; mobile phase: [water (0.1% TFA)-ACN]; B %: 2%-32%, 7 min) to give the title product as a white solid (200 mg, 0.33 mmol, 56% yield, trifluoroacetate). MS (ESI) m/z: 613.2 [M+1]$^+$.

Step 8: Preparation of 2-({6-[(5-chloro-2-{4-[(1r,3r)-3-{4-[2-(2,6-dioxopiperidin-3-yl)-6-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide

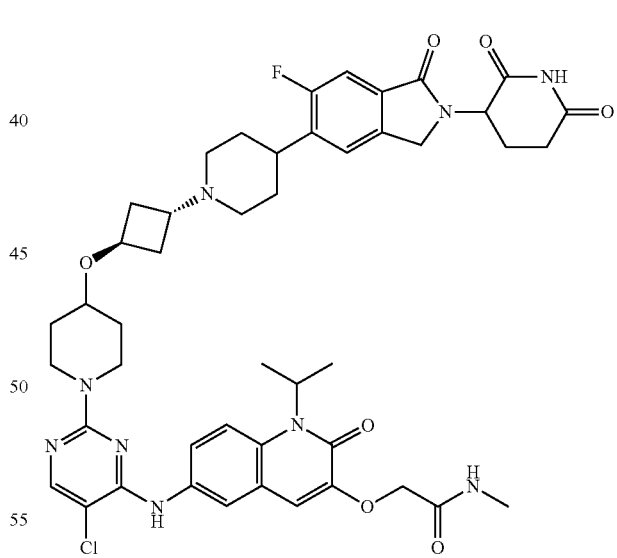

The title compound was prepared analogously to Example 23, Step 12. The crude product was purified by preparative high performance liquid chromatography (column: Phenomenex Synergi C18 150*25 mm*10 um; mobile phase: [water (0.225% FA)-ACN]; B %: 11%-41%, 10 min) to give the title product as a white solid (77.4 mg, 25% yield). $^1$H NMR (400 MHz, DMSO-$d_6$) δ: 11.00 (s, 1H), 8.83 (s, 1H), 8.16 (s, 1H), 8.05 (s, 1H), 7.99-7.90 (m, 2H), 7.69 (s, 2H), 7.62 (d, J=6.0 Hz, 1H), 7.50-7.43 (m, 1H), 7.03 (s, 1H), 5.64-5.18 (m, 1H), 5.16-5.05 (m, 1H), 4.61-4.50 (m, 2H), 4.47-4.39 (m, 1H), 4.33-4.26 (m, 1H), 4.22-4.16 (m, 1H), 4.15-4.07

(m, 2H), 3.57-3.50 (m, 1H), 3.24 (t, J=10.4 Hz, 2H), 3.02 (d, J=10.4 Hz, 2H), 2.94-2.86 (m, 2H), 2.68 (d, J=4.8 Hz, 3H), 2.64-2.58 (m, 2H), 2.42-2.36 (m, 2H), 2.21-2.14 (m, 2H), 2.03-1.98 (m, 2H), 1.86-1.79 (m, 4H), 1.77-1.69 (m, 4H), 1.57 (d, J=6.8 Hz, 6H), 1.43-1.34 (m, 2H).

Example 25: 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 81)

Step 1: Preparation of 4-bromo-3-fluoro-2-methyl-benzoic acid

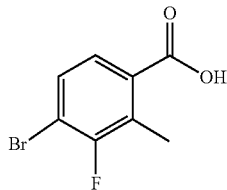

To a solution of 4-bromo-3-fluoro-benzoic acid (20.00 g, 91.32 mmol, 1.00 eq) in tetrahydrofuran (200 mL) was added lithium diisopropylamide (2 M, 96.0 mL, 2.10 eq) at −70° C. and the mixture was stirred at −70° C. for 1 h. Then iodomethane (38.89 g, 273.96 mmol, 17.1 mL, 3.00 eq) was added at −70° C. Then the mixture was warmed to 20° C. and the mixture was stirred at 20° C. for 12 h. The mixture was quenched with saturated ammonium chloride solution (400 mL) and extracted with ethyl acetate (400 mL). The organic layer was dried over sodium sulfate and then concentrated under reduced pressure to give 4-bromo-3-fluoro-2-methyl-benzoic acid as a yellow solid (16.00 g, 68.66 mmol, 75% yield). $^1$H NMR (400 MHz, DMSO-$d_6$) δ: 7.55-7.47 (m, 1H), 7.46-7.36 (m, 1H), 2.42 (d, J=2.0 Hz, 3H).

Step 2: Preparation of methyl 4-bromo-3-fluoro-2-methyl-benzoate

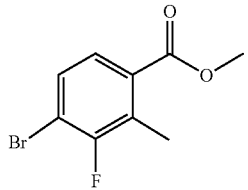

To a solution of 4-bromo-3-fluoro-2-methyl-benzoic acid (14.00 g, 60.08 mmol, 1.00 eq) in methanol (100 mL) was added thionyl chloride (42.88 g, 360.46 mmol, 26.1 mL, 6.00 eq) at 20° C. and the mixture was stirred at 20° C. for 1 h. The mixture was concentrated under reduced pressure to give a residue. The residue was quenched with saturated sodium bicarbonate solution (1000 mL) and extracted with ethyl acetate (500 mL). The organic layer was dried over sodium sulfate and then concentrated under reduced pressure to give a residue. The residue was purified by column chromatography on silica gel (petroleum ether:ethyl acetate=10:1) to give methyl 4-bromo-3-fluoro-2-methyl-benzoate (6.00 g, 24.09 mmol, 40% yield) as a colorless oil. $^1$H NMR (400 MHz, CDCl$_3$) δ: 7.58-7.52 (m, 1H), 7.45-7.39 (m, 1H), 3.90 (s, 3H), 2.53 (d, J=2.6 Hz, 3H).

Step 3: Preparation of methyl 4-bromo-2-(bromomethyl)-3-fluoro-benzoate

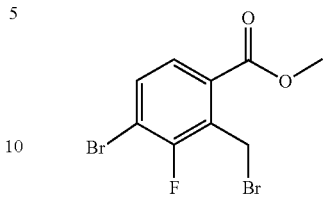

To a solution of methyl 4-bromo-3-fluoro-2-methyl-benzoate (6.20 g, 25.10 mmol, 1.00 eq) in dichloroethane (70 mL) were added N-Bromosuccinimide (4.91 g, 27.60 mmol, 1.10 eq) and 2,2-azobisisobutyronitrile (412.09 mg, 2.51 mmol, 0.10 eq) at 20° C. and the mixture was warmed to 80° C. The mixture was stirred at 80° C. for 6 h. The mixture was filtered and the filtrate was diluted with saturated sodium thiosulfate solution (100 mL) and extracted with dichloromethane (50 mL). The organic layer was washed with water (100 mL×2), brine (100 mL), dried over sodium sulfate and then concentrated under reduced pressure to give a residue. The residue was purified by column chromatography on silica gel (petroleum ether:ethyl acetate=30:1 to 20:1) to give methyl 4-bromo-2-(bromomethyl)-3-fluoro-benzoate (7.00 g, 21.48 mmol, 86% yield) as a colorless oil. $^1$H NMR (400 MHz, CDCl$_3$) δ: 7.71-7.62 (m, 1H), 7.62-7.51 (m, 1H), 5.00 (s, 2H), 3.96 (s, 3H).

Steps 4-9: Preparation of 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide

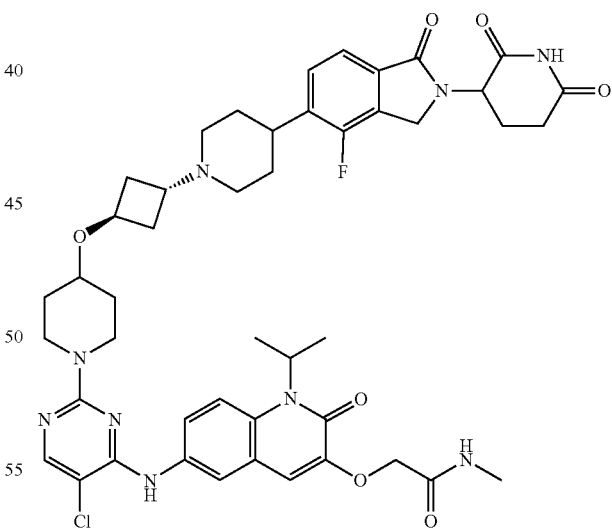

Example 25 was prepared analogously to Example 24 following Steps 3-8 with the material made in step 3 of this Example. The crude product was purified by preparative high performance liquid chromatography (column: Phenomenex Synergi C18 150*25 mm*10 um; mobile phase: [water (0.225% FA)-ACN]; B %: 11%-41%, 10 min) to afford the title product as a white solid (83.5 mg, 22% yield, formate). $^1$H NMR (400 MHz, DMSO-$d_6$) δ: 11.00 (s, 1H), 8.83 (s, 1H), 8.18 (s, 1H), 8.04 (s, 1H), 7.99-7.91 (m, 2H), 7.69 (s, 2H), 7.61-7.47 (m, 2H), 7.03 (s, 1H), 5.58-5.15 (m, 1H), 5.11 (dd, J=5.2, 13.2 Hz, 1H), 4.59-4.50 (m, 3H), 4.37 (d, J=17.4 Hz, 1H), 4.24-4.06 (m, 3H), 3.56-3.51 (m, 1H), 3.24 (t, J=10.4 Hz, 2H), 3.01 (d, J=10.0 Hz, 2H), 2.97-2.82 (m, 3H), 2.68 (d, J=4.8 Hz, 3H), 2.60 (d, J=16.0 Hz, 1H), 2.46-2.39 (m, 1H), 2.21-2.13 (m, 2H), 2.05-1.96 (m, 3H), 1.87-1.79 (m, 4H), 1.78-1.69 (m, 4H), 1.57 (d, J=6.8 Hz, 6H), 1.43-1.34 (m, 2H). MS (ESI) m/z: 748.2 [M+1]$^+$.

Example 26: 2-({6-[(5-chloro-2-{4-[(1r,3r)-3-{4-[2-(2,6-dioxopiperidin-3-yl)-7-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 103)

Step 1: Preparation of tert-butyl 4-(3-cyano-5-methoxy-4-methoxycarbonyl-phenyl)-3,6-dihydro-2H-pyridine-1-carboxylate

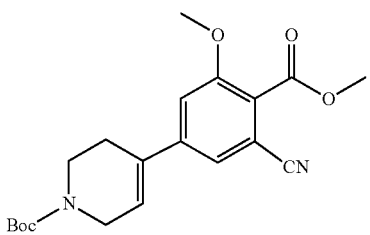 [SMILES: COC(=O)c1c(C#N)cc(C2=CCN(C(=O)OC(C)(C)C)CC2)cc1OC]

To a solution of methyl 2-cyano-6-methoxy-4-(1,1,2,2,3,3,4,4,4-nonafluorobutylsulfonyl) benzoate (4 g, 8.45 mmol, 1 eq), tert-butyl 4-(4,4,5,5-tetramethyl-1,3,2-dioxaborolan-2-yl)-3,6-dihydro-2H-pyridine-1-carboxylate (2.87 g, 9.30 mmol, 1.1 eq) in dioxane (40 mL) and water (8 mL) was added cesium fluoride (3.21 g, 21.13 mmol, 2.5 eq) and [1,1'-bis(diphenylphosphino)ferrocene]dichloropalladium (II) (618 mg, 0.84 mmol, 0.1 eq) under nitrogen. The reaction mixture was stirred at 80° C. for 6 h. Water (100 mL) was added to the mixture, the aqueous phase was extracted with ethyl acetate (100 mL×3). The combined organic phase was washed with brine (100 mL), dried over sodium sulfate, filtered and concentrated in vacuo. The residue was purified by silica gel chromatography (Petroleum ether: Ethyl acetate=100:1 to 1:1) to afford the title product as a yellow solid (2.9 g, 7.79 mmol, 92% yield) was obtained. $^1$HNMR (400 MHz, CDCl$_3$) δ: 7.21 (s, 1H), 7.06 (s, 1H), 6.09 (br s, 1H), 4.09-4.02 (m, 2H), 3.91 (s, 3H), 3.85 (s, 3H), 3.58 (br t, J=5.6 Hz, 2H), 2.43 (br s, 2H), 1.42 (s, 9H). MS (ESI) m/z: 373.1 [M+1]$^+$.

Step 2: Preparation of tert-butyl 4-(3-cyano-5-methoxy-4-methoxy carbonyl-phenyl)piperidine-1-carboxylate

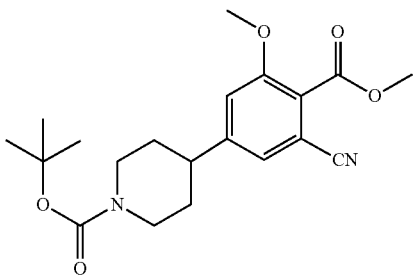 [SMILES: COC(=O)c1c(C#N)cc(C2CCN(C(=O)OC(C)(C)C)CC2)cc1OC]

To a solution of tert-butyl 4-(3-cyano-5-methoxy-4-methoxycarbonyl-phenyl)-3,6-dihydro-2H-pyridine-1-carboxylate (2.9 g, 7.79 mmol, 1 eq) in tetrahydrofuran (20 mL) and ethanol (60 mL) was added palladium on activated carbon catalyst (300 mg, 10% purity) under nitrogen. The reaction mixture was stirred at 30° C. under Hydrogen (50 Psi) for 12 h. The mixture was filtered and the filtrate was concentrated in vacuo. The desired product was obtained as a yellow oil (2.8 g, 7.48 mmol, 96% yield). MS (ESI) m/z: 375.1 [M+1]$^+$.

Step 3: Preparation of methyl 2-cyano-6-methoxy-4-(piperidin-4-yl)benzoate

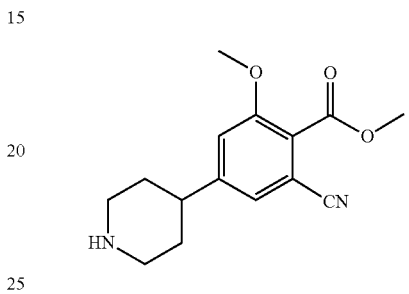

To a solution of tert-butyl 4-(3-cyano-5-methoxy-4-methoxycarbonyl-phenyl)piperidine-1-carboxylate (2.3 g, 6.14 mmol, 1 eq) in dichloromethane (20 mL) was added trifluoroacetic acid (7.70 g, 67.53 mmol, 5 mL, 10.99 eq). The reaction mixture was stirred at 20° C. for 1 h. The mixture was concentrated in vacuum. Methyl 2-cyano-6-methoxy-4-(piperidin-4-yl)benzoate (2.3 g, 5.92 mmol, 96% yield, trifluoroacetate) was obtained as a yellow oil. MS (ESI) m/z: 275.4 [M+1]$^+$.

Step 4: Preparation of 2-trimethylsilylethyl 4-(3-cyano-5-methoxy-4-methoxycarbonyl-phenyl)piperidine-1-carboxylate

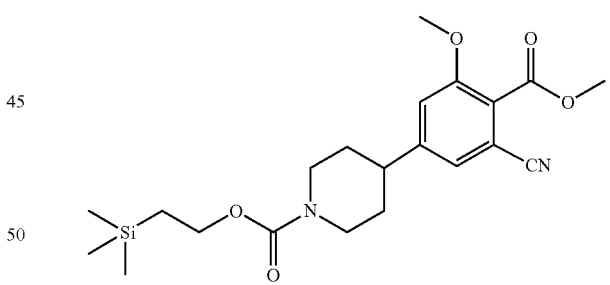

To a solution of methyl 2-cyano-6-methoxy-4-(4-piperidyl)benzoate (2.3 g, 5.92 mmol, 1 eq, trifluoroacetate) in tetrahydrofuran (20 mL) and water (20 mL) was added sodium bicarbonate (2.49 g, 29.61 mmol, 5 eq) and (2,5-dioxopyrrolidin-1-yl) 2-trimethylsilylethylcarbonate (1.84 g, 7.11 mmol, 1.2 eq). The reaction mixture was stirred at 20° C. for 12 h. Water (20 mL) was added to the mixture, the aqueous phase was extracted with ethyl acetate (20 mL×3). The combined organic phase was washed with brine (20 mL), dried over sodium sulfate, filtered and concentrated in vacuum. The residue was purified by silica gel chromatography (Petroleum ether:Ethyl acetate=100:1 to 5:1). The desired product was obtained as a light yellow oil (1.3 g, 3.11 mmol, 52% yield). δ: 7.14 (s, 1H), 7.00 (s, 1H), 4.34 (br d, J=12.0 Hz, 2H), 4.25-4.18 (m, 2H), 3.98 (s, 3H), 3.90 (s, 3H), 2.86 (br t, J=12.4 Hz, 2H), 2.73 (tt, J=3.6, 12.0 Hz, 1H), 1.85 (br d, J=12.8 Hz, 2H), 1.64-1.56 (m, 2H), 1.12-0.99 (m, 2H), 0.06 (s, 9H)

Step 5: Preparation of 2-trimethylsilylethyl 4-(3-formyl-5-methoxy-4-methoxycarbonyl-phenyl)piperidine-1-carboxylate

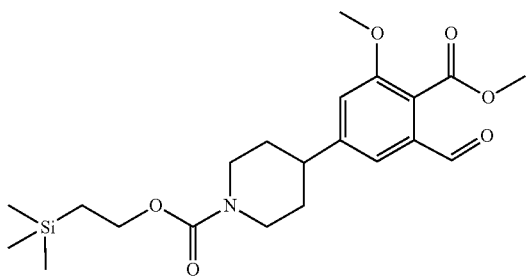

To a solution of 2-trimethylsilylethyl 4-(3-cyano-5-methoxy-4-methoxycarbonyl-phenyl) piperidine-1-carboxylate (1.3 g, 3.11 mmol, 1 eq) in pyridine (10 mL), ethyl acid (5 mL) and water (4 mL) was added sodium; dihydrogen phosphate; hydrate (2.14 g, 15.53 mmol, 5 eq) and Raney-Ni (266 mg, 3.11 mmol, 1 eq). The reaction mixture was stirred at 50° C. for 2 h under nitrogen. The mixture was filtered and the filtrate was diluted with water (50 mL). The aqueous phase was extracted with ethyl acetate (50 mL×3). The combined organic phase was washed with brine (50 mL×2), dried over anhydrous sodium sulfate, filtered and concentrated in vacuum. 2-Trimethylsilylethyl 4-(3-formyl-5-methoxy-4-methoxycarbonyl-phenyl)piperidine-1-carboxylate (1.3 g, crude) was obtained as a yellow oil. MS (ESI) m/z: 444.1 [M+23]$^+$.

Step 6: Preparation of 2-trimethylsilylethyl 4-[2-(4-tert-butoxy-1-carbamoyl-4-oxo-butyl)-7-methoxy-1-oxo-isoindolin-5-yl]piperidine-1-carboxylate

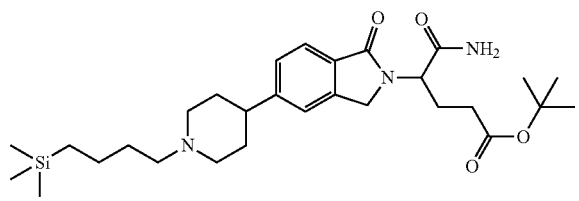 [SMILES: CC(C)(C)OC(=O)CCC(C(N)=O)N1Cc2cc(C3CCN(CCCC[Si](C)(C)C)CC3)ccc2C1=O]

To a solution of 2-trimethylsilylethyl 4-(3-formyl-5-methoxy-4-methoxycarbonyl-phenyl) piperidine-1-carboxylate (1.3 g, 3.08 mmol, 1 eq), tert-butyl 4,5-diamino-5-oxo-pentanoate (624 mg, 3.08 mmol, 1 eq) in methanol (10 mL) and 1,2-dichloroethane (10 mL) was added acetic acid (185 mg, 3.08 mmol, 1 eq), the mixture was stirred at 40° C. for 0.5 h. Then sodium cyanoborohydride (387 mg, 6.17 mmol, 2 eq) was added to the mixture, the reaction mixture was stirred at 40° C. for 11.5 h. Water (50 mL) was added to the mixture, the aqueous phase was extracted with ethyl acetate (50 mL×3). The combined organic phase was washed with brine (50 mL×2), dried over anhydrous sodium sulfate, filtered and concentrated in vacuum. The residue was purified by silica gel chromatography (Petroleum ether: Ethyl acetate=10:1 to 0:1) to afford the desired product as a light-yellow solid (660 mg, 1.09 mmol, 35% yield, 95% purity). $^1$HNMR (400 MHz, CDCl$_3$) δ: 6.91 (s, 1H), 6.78-6.63 (m, 2H), 5.71 (br s, 1H), 4.81 (br t, J=7.2 Hz, 1H), 4.54-4.45 (m, 1H), 4.42-4.27 (m, 3H), 4.25-4.18 (m, 2H), 3.96 (s, 3H), 2.95-2.70 (m, 3H), 2.38-2.05 (m, 5H), 1.85 (br d, J=11.6 Hz, 2H), 1.64 (br d, J=11.2 Hz, 2H), 1.39 (s, 9H), 1.07-0.99 (m, 2H), 0.05 (s, 9H). MS (ESI) m/z: 576.4 [M+1]$^+$.

Step 7: Preparation of tert-butyl 5-amino-4-[7-methoxy-1-oxo-5-(4-piperidyl)isoindolin-2-yl]-5-oxo-pentanoate

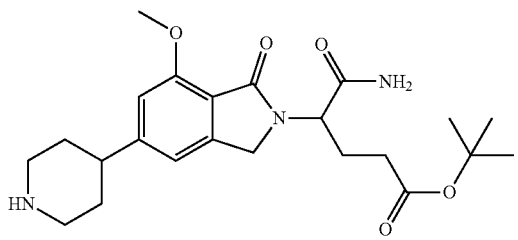 [SMILES: COc1cc(C2CCNCC2)cc2c1C(=O)N(C(CCC(=O)OC(C)(C)C)C(N)=O)C2]

To a solution of 2-trimethylsilylethyl 4-[2-(4-tert-butoxy-1-carbamoyl-4-oxo-butyl)-7-methoxy-1-oxo-isoindolin-5-yl]piperidine-1-carboxylate (660 mg, 1.15 mmol, 1 eq) in tetrabutylammonium fluoride (1 M, 3 mL, 2.62 eq). The reaction mixture was stirred at 30° C. for 12 h. Water (20 mL) was added to the mixture, the aqueous phase was extracted with ethyl acetate (20 mL×3). The combined organic phase was washed with brine (20 mL×2), dried over anhydrous sodium sulfate, filtered and concentrated in vacuum. The residue was purified by silica gel chromatography (Dichloromethane:Methanol=100:1 to 8:1) to afford the title product as a yellow oil (400 mg, 0.92 mmol, 80% yield). MS (ESI) m/z: 432.2 [M+1]$^+$ Steps 7-9: Preparation of 2-({6-[(5-chloro-2-{4-[(1r,3r)-3-{4-[2-(2,6-dioxopiperidin-3-yl)-7-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide

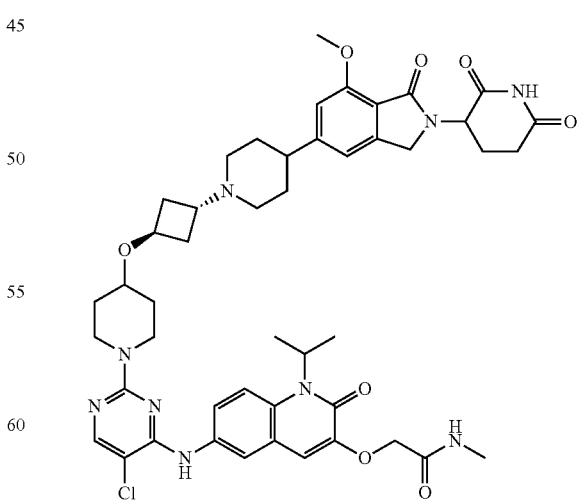

Using tert-butyl 5-amino-4-[7-methoxy-1-oxo-5-(4-piperidyl)isoindolin-2-yl]-5-oxo-pentanoate, Example 26 was prepared analogously to Example 24 via Example 24 Steps 6-8. The crude product was purified by prep-HPLC (column:

Unisil 3-100 C18 Ultra 150*50 mm*3 um; mobile phase: [water (0.225% FA)-ACN]; B %: 15%-45%, 10 min) to afford Example 26 as yellow solid (36.5 mg, 4% yield, Formate). $^1$H NMR (400 MHz, DMSO-d$_6$) δ: 10.95 (s, 1H), 8.85 (s, 1H), 8.05 (s, 1H), 7.96 (s, 2H), 7.70 (s, 2H), 7.02 (d, J=9.6 Hz, 2H), 6.92 (s, 1H), 5.56-5.52 (m, 1H), 5.02 (dd, J=5.2, 13.2 Hz, 1H), 4.55 (s, 2H), 4.37-4.29 (m, 1H), 4.25-4.08 (m, 4H), 3.90-3.84 (m, 3H), 3.59-3.40 (m, 1H), 3.29-3.16 (m, 2H), 3.07 (br d, J=8.8 Hz, 2H), 3.01-2.84 (m, 2H), 2.71-2.53 (m, 4H), 2.48-2.35 (m, 1H), 2.33-2.32 (m, 1H), 2.23-2.10 (m, 2H), 2.04 (br s, 2H), 2.00-1.89 (m, 2H), 1.89-1.68 (m, 7H), 1.58 (d, J=6.8 Hz, 6H), 1.45-1.37 (m, 2H). MS (ESI) m/z: 910.3 [M+1]$^+$.

Example 27: 2-({6-[(5-chloro-2-{4-[(1r,3r)-3-{4-[2-(2,6-dioxopiperidin-3-yl)-7-fluoro-4-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 128)

Step 1: Preparation of 2-fluoro-N-(2-hydroxy-1,1-dimethyl-ethyl)-5-methoxybenzamide

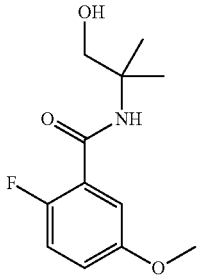 [SMILES: COc1ccc(F)c(C(=O)NC(C)(C)CO)c1]

A mixture of 2-fluoro-5-methoxy-benzoic acid (1 g, 5.88 mmol, 1 eq) and thionyl chloride (5 mL) was stirred at 85° C. for 1 h. Then the mixture was concentrated under reduced pressure to give a residue. The residue was dissolved in dichloromethane (15 mL), then added 2-amino-2-methyl-propan-1-ol (1.05 g, 11.76 mmol, 1.1 mL, 2 eq) in dichloromethane (12 mL) at 0° C. The mixture was stirred at 25° C. for 1 h. The reaction mixture was concentrated under reduced pressure to give a residue. The residue was taken up in ethyl acetate and filtered, the filtrate was washed with 10% hydrogen chloride, water and brine and dried over anhydrous sodium sulfate, filtered and concentrated under reduced pressure to give a residue. The residue was purified by silica gel chromatography (Petroleum ether/Ethyl acetate=10/1 to 1:1) to afford the desired product as a yellow oil (1.35 g, 5.60 mmol, 95% yield).

Step 2: 2-(2-fluoro-5-methoxy-phenyl)-4,4-dimethyl-5H-oxazole

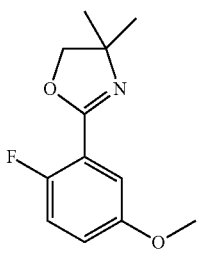 [SMILES: COc1ccc(F)c(C2=NC(C)(C)CO2)c1]

To a solution of 2-fluoro-N-(2-hydroxy-1,1-dimethyl-ethyl)-5-methoxybenzamide (1.2 g, 4.97 mmol, 1 eq) in dichloromethane (5 mL) was added thionyl chloride (2.38 g, 1.5 mL) at 0° C. The mixture was stirred at 25° C. for 20 min. TLC showed the reaction was completed. The reaction mixture was quenched by addition saturated sodium bicarbonate solution 50 mL, and extracted with ethyl acetate (50 mL×2). The combined organic layers were washed with brine (50 mL), dried over anhydrous sodium sulfate, filtered and concentrated under reduced pressure to give a residue. The residue was used into the next step without further purification. Compound 2-(2-fluoro-5-methoxy-phenyl)-4,4-dimethyl-5H-oxazole (1.1 g, 4.93 mmol, 99% yield) was obtained as a white solid.

Step 3: 2-(6-fluoro-3-methoxy-2-methyl-phenyl)-4,4-dimethyl-5H-oxazole

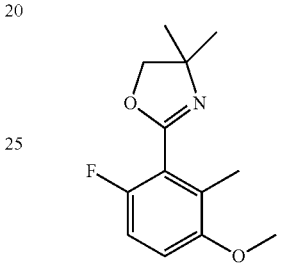

To a solution of 2-(2-fluoro-5-methoxy-phenyl)-4,4-dimethyl-5H-oxazole (1 g, 4.48 mmol, 1 eq) in tetrahydrofuran (30 mL) was added n-butyllithium (2.5 M, 2.3 mL, 1.3 eq) at −78° C. The mixture was stirred at −78° C. for 0.5 h. Then methyl iodide (3.18 g, 22.40 mmol, 1.4 mL, 5 eq) was added at −78° C., and the mixture was stirred at −78° C. for 20 min. The reaction mixture was quenched by addition hydrogen chloride (4 N) 100 mL, and then extracted with ethyl acetate (100 mL×2). The combined organic layers were dried over anhydrous sodium sulfate, filtered and concentrated under reduced pressure to give a residue. The residue was purified prep-HPLC (column: Phenomenex luna C18 (250*70 mm, 10 um); mobile phase: [water (0.225% FA)-ACN]; B %: 10%-45%, 20 min). Compound 2-(6-fluoro-3-methoxy-2-methyl-phenyl)-4,4-dimethyl-5H-oxazole (530 mg, 2.23 mmol, 50% yield) was obtained as a yellow oil. $^1$HNMR (400 MHz, DMSO-d$_6$) δ: 7.28-7.08 (m, 2H), 4.07 (s, 2H), 3.79 (s, 3H), 2.13 (s, 3H), 1.30 (s, 6H). MS (ESI) m/z: 237.9 [M+1]$^+$ Step 4: Preparation of WX-ARV-DS-021L-4,6-fluoro-3-methoxy-2-methyl-benzoic acid

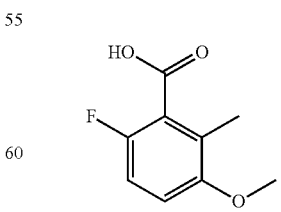

To a solution of 2-(6-fluoro-3-methoxy-2-methyl-phenyl)-4,4-dimethyl-5H-oxazole (10 g, 42.15 mmol, 1 eq) in acetone (50 mL) was added potassium carbonate (17.47 g, 126.44 mmol, 3 eq) and methyl iodide (59.82 g, 421.46 mmol, 26.2 mL, 10 eq). The mixture was stirred at 25° C. for 15 h. Then the mixture was filtered and concentrated under reduced pressure to give a residue. The residue was dissolved in methanol (50 mL) and sodium hydroxide solution 1N in water (200 mL). The mixture was stirred at 75° C. for 3 h. The reaction mixture was quenched by addition hydrogen chloride (6 N) 100 mL, and then extracted with ethyl acetate (100 mL×2). The combined organic layers were dried over anhydrous sodium sulfate, filtered and concentrated under reduced pressure to give a residue. The residue was used into the next step without further purification. Compound 6-fluoro-3-methoxy-2-methyl-benzoic acid (5.1 g, 27.69 mmol, 66% yield) was obtained as a white solid. ¹HNMR (400 MHz, CDCl3) δ: 7.08-6.81 (m, 2H), 3.91 (s, 1H), 3.86 (s, 2H), 2.36 (s, 3H). (ESI) m/z: 185.1 [M+1]⁺.

Step 5: Preparation of methyl 6-fluoro-3-methoxy-2-methyl-benzoate

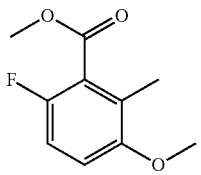

To a solution of 6-fluoro-3-methoxy-2-methyl-benzoic acid (8.5 g, 46.15 mmol, 1 eq) in N,N-dimethylformamide (2 mL) was added potassium carbonate (19.14 g, 138.46 mmol, 3 eq) and methyl iodide (19.65 g, 138.46 mmol, 8.6 mL, 3 eq). The mixture was stirred at 25° C. for 0.5 h. The reaction mixture was diluted with saturated ammonium chloride solution 500 mL and extracted with ethyl acetate (500 mL×3). The combined organic layers were washed with brine 50 mL, dried over anhydrous sodium sulfate, filtered and concentrated under reduced pressure to give a residue. The residue was purified by silica gel chromatography (Petroleum ether/Ethyl acetate=50/1 to 20:1) to afford the desired product as a colorless oil (7.6 g, 38.35 mmol, 83% yield). ¹HNMR (400 MHz, CDCl₃) δ: 7.02-6.78 (m, 2H), 3.96 (s, 3H), 3.83 (s, 3H), 2.23 (s, 3H).

Step 6: Preparation of methyl 4-bromo-6-fluoro-3-methoxy-2-methyl-benzoate

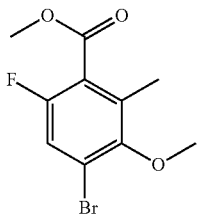

To a solution of methyl 6-fluoro-3-methoxy-2-methyl-benzoate (1.9 g, 9.59 mmol, 1 eq) in N,N-dimethylformamide (20 mL) was added n-bromosuccinimide (1.71 g, 9.59 mmol, 1 eq) at 0° C. The mixture was stirred at 70° C. for 12 h. The reaction mixture was diluted with saturated sodium hydrogen carbonate 100 mL and extracted with ethyl acetate (50 mL×3). The combined organic layers were washed with brine 50 mL, dried over anhydrous sodium sulfate, filtered and concentrated under reduced pressure to give a residue. The residue was purified by silica gel chromatography (Petroleum ether/Ethyl acetate=50/1 to 20:1) to afford the desired product as a yellow oil (0.9 g, 3.25 mmol, 17% yield). MS (ESI) m/z: 279.0 [M+1]⁺.

Step 7: Preparation of methyl 4-bromo-2-(bromomethyl)-6-fluoro-3-methoxy-benzoate

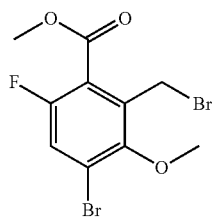

To a solution of methyl 4-bromo-6-fluoro-3-methoxy-2-methyl-benzoate (200 mg, 0.72 mmol, 1 eq) in perbromomethane (3 mL) was added n-bromosuccinimide (167 mg, 0.94 mmol, 1.3 eq) and azobisisobutyronitrile (50 mg, 0.29 mmol, 0.4 eq). The mixture was stirred at 80° C. for 1 h. The reaction mixture was diluted with saturated sodium hydrogen carbonate 100 mL and extracted with ethyl acetate (50 mL×3). The combined organic layers were washed with brine 50 mL, dried over anhydrous sodium sulfate, filtered, and concentrated under reduced pressure to give a residue which was purified by prep-TLC (20% ethyl acetate in petroleum ether) to afford the desired product as a yellow oil (150 mg, 0.42 mmol, 58% yield). ¹HNMR (400 MHz, CDCl₃) δ: 7.28 (d, J=8.4 Hz, 1H), 4.69 (s, 2H), 3.90 (d, J=7.6 Hz, 6H).

Steps 8-13: Preparation of 2-({6-[(5-chloro-2-{4-[(1r,3r)-3-{4-[2-(2,6-dioxopiperidin-3-yl)-7-fluoro-4-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide

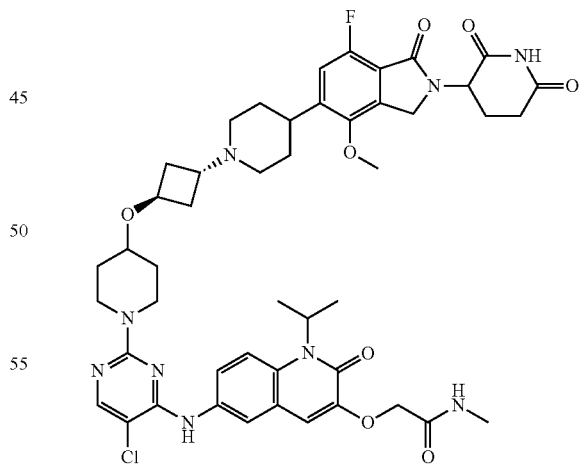

Example 27 was prepared analogously to Example 24 following Steps 3-8 with the material made in step 7 of this Example. The crude product was purified by prep-HPLC (column: Unisil 3-100 C18 Ultra 150*50 mm*3 um; mobile phase: [water (0.225% FA)-ACN]; B %: 15%-45%, 10 min) to afford the desired product as an off-white solid (50.1 mg, 0.05 mmol, 30% yield, formate). ¹HNMR (400 MHz, DMSO-d$_6$) δ: 11.01 (s, 1H), 8.84 (s, 1H), 8.25 (s, 1H), 8.05 (s, 1H), 8.00-7.89 (m, 2H), 7.70 (s, 2H), 7.21 (br d, J=10.4 Hz, 1H), 7.03 (s, 1H), 5.33 (br s, 1H), 5.07 (br dd, J=4.8, 13.2 Hz, 1H), 4.64-4.51 (m, 3H), 4.42 (br d, J=17.6 Hz, 1H), 4.23-4.06 (m, 3H), 3.84 (s, 3H), 3.54 (br s, 1H), 3.29-3.24 (m, 1H), 3.04-2.80 (m, 6H), 2.69 (d, J=4.8 Hz, 3H), 2.62 (br s, 2H), 2.40 (br s, 1H), 2.21-2.10 (m, 2H), 2.01 (br d, J=7.2 Hz, 3H), 1.89-1.77 (m, 3H), 1.73-1.65 (m, 4H), 1.58 (d, J=6.8 Hz, 6H), 1.46-1.36 (m, 2H). MS (ESI) m/z: 928.4 [M+1]$^+$.
The following examples were prepared using methods analogous to those found in Examples 22-27:
| Compound | Structure |
|---|---|
| 92 | 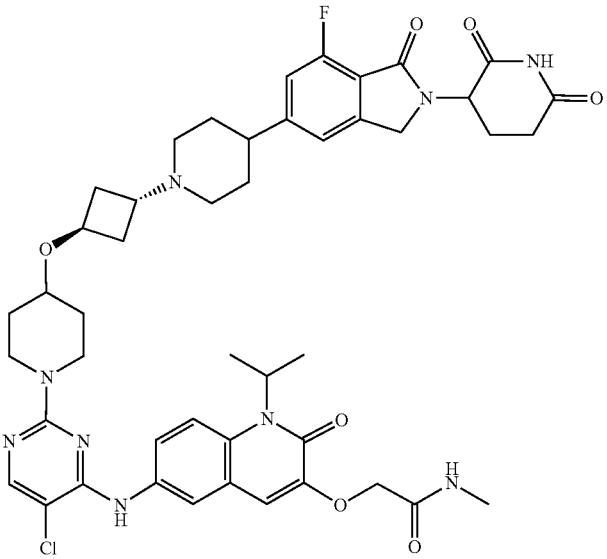 [SMILES: CNC(=O)COc1cc2cc(Nc3nc(N4CCC(O[C@H]5C[C@H](N6CCC(c7cc(F)c8c(c7)CN(C7CCC(=O)NC7=O)C8=O)CC6)C5)CC4)ncc3Cl)ccc2n(C(C)C)c1=O] |
| 116 | 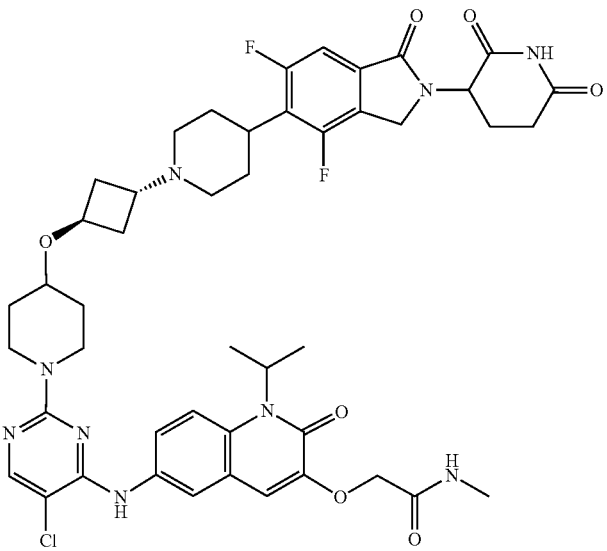 [SMILES: CNC(=O)COc1cc2cc(Nc3nc(N4CCC(O[C@H]5C[C@H](N6CCC(c7c(F)cc8c(c7F)CN(C7CCC(=O)NC7=O)C8=O)CC6)C5)CC4)ncc3Cl)ccc2n(C(C)C)c1=O] |

Example 30: 2-((6-((5-chloro-2-(4-((1S,3r)-3-((3S,4R)-4-(2-(2,6-dioxopiperidin-3-yl)-1,3-dioxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide and 2-((6-((5-chloro-2-(4-((1R,3r)-3-((3R,4S)-4-(2-(2,6-dioxopiperidin-3-yl)-1,3-dioxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide (Compound 118)

Step 1: Preparation dimethyl 4-(1-tert-butoxycarbonyl-3,6-dihydro-2H-pyridin-4-yl)benzene-1,2-dicarboxylate

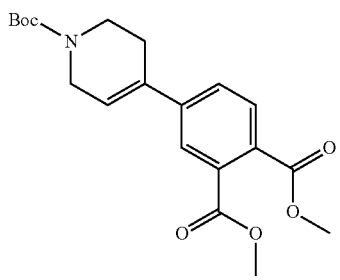 [SMILES: COC(=O)c1ccc(C2=CCN(C(=O)OC(C)(C)C)CC2)cc1C(=O)OC]

A mixture of dimethyl 4-bromobenzene-1,2-dicarboxylate (5 g, 18.31 mmol, 1 eq), tert-butyl 4-(4,4,5,5-tetramethyl-1,3,2-dioxaborolan-2-yl)-3,6-dihydro-2H-pyridine-1-carboxylate (6.79 g, 21.97 mmol, 1.2 eq), ditert-butyl (cyclopentyl)phosphane; dichloropalladium; iron (1 g, 1.53 mmol, 8.38e-2 eq) and cesium fluoride (8.34 g, 54.93 mmol, 3 eq) in dioxane (50 mL) and water (5 mL) was degassed and purged with nitrogen for 3 times, and then the mixture was stirred at 100° C. for 3 h under nitrogen atmosphere. The reaction mixture was filtered and diluted with water 400 mL and extracted with ethyl acetate (200 mL×2). The combined organic phase was washed with saturated brine (200 mL), dried with anhydrous sodium sulfate, filtered and concentrated in vacuum. The residue was purified by silica gel chromatography (Petroleum ether/Ethyl acetate=1/0 to 20/1) to afford the desired product as a yellow (6 g, 15.98 mmol, 87% yield). MS (ESI) m/z: 376.4 [M+1]⁺.

Step 2: Preparation of dimethyl 4-((3R,4R)-1-(tert-butoxycarbonyl)-3-hydroxypiperidin-4-yl)phthalate and dimethyl 4-((3S,4S)-1-(tert-butoxycarbonyl)-3-hydroxypiperidin-4-yl)phthalate

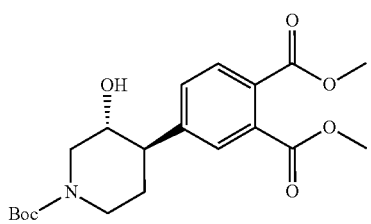

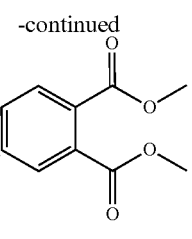

A solution of dimethyl 4-(1-tert-butoxycarbonyl-3,6-dihydro-2H-pyridin-4-yl)benzene-1,2-dicarboxylate (3.3 g, 8.79 mmol, 1 eq) in tetrahydrofuran (30 mL) was added dropwise boron; methylsulfanylmethane (10 M, 1.9 mL, 2.2 eq) at 0° C., then the mixture was stirred for 2 h at 25° C. After that a solution of sodium; 3-oxidodioxaborirane; tetrahydrate (4.06 g, 26.37 mmol, 5.1 mL, 3 eq) in water (20 mL) was added at 0° C., then the mixture was stirred for 2 h at 25° C. The reaction mixture was quenched with saturated sodium sulfite solution (50 mL) and the mixture was extracted with ethyl acetate (50 mL×3). The combined organic phase was washed with brine (50 mL), dried with anhydrous sodium sulfate, filtered and concentrated in vacuo. The residue was purified by silica gel column chromatography (Petroleum ether/Ethyl acetate=20/1 to 1/1). The desired product was isolated as a yellow oil containing a mixture of trans isomers (2.8 g, 7.12 mmol, 81% yield). ¹NMR (400 MHz, CDCl₃) δ: 7.74 (d, J=8.0 Hz, 1H), 7.61 (s, 1H), 7.44 (d, J=8.0 Hz, 1H), 4.50-4.35 (m, 1H), 4.27-4.17 (m, 1H), 3.91 (d, J=3.2 Hz, 6H), 3.80-3.67 (m, 1H), 2.85-2.71 (m, 1H), 2.70-2.60 (m, 2H), 1.88-1.77 (m, 1H), 1.65-1.60 (m, 1H), 1.49 (s, 9H).

Step 3: Preparation of dimethyl 4-((3S,4R)-1-(tert-butoxycarbonyl)-3-fluoropiperidin-4-yl)phthalate and dimethyl 4-((3R,4S)-1-(tert-butoxycarbonyl)-3-fluoropiperidin-4-yl)phthalate

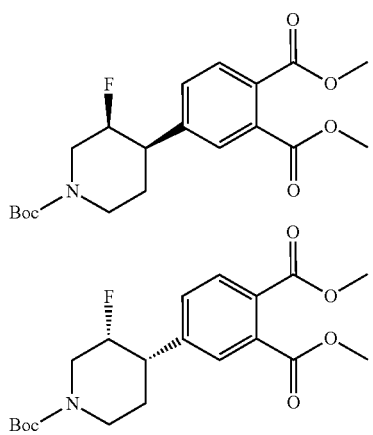

A solution of dimethyl 4-((3R,4R)-1-(tert-butoxycarbonyl)-3-hydroxypiperidin-4-yl)phthalate and dimethyl 4-((3S,4S)-1-(tert-butoxycarbonyl)-3-hydroxypiperidin-4-yl)phthalate (2.3 g, 5.85 mmol, 1 eq) in dichloromethane (40 mL) was added drop wise 2-methoxy-N-(2-methoxyethyl)-N-(trifluoro-κ⁴-sulfanyl)ethanamine (1.94 g, 8.77 mmol, 1.9 mL, 1.5 eq) at −78° C., then the mixture was stirred for 2 h at 25° C. The reaction mixture was quenched with saturated sodium bicarbonate solution (50 mL) and the mixture was extracted with ethyl acetate (50 mL×3). The combined organic phase was washed with brine (50 mL), dried with anhydrous sodium sulfate, filtered and concentrated in vacuo. The residue was purified by column chromatography on silica gel (Petroleum ether/Ethyl acetate=20/1 to 1/1) to afford the desired product as a yellow oil containing a mixture of cis isomers (1.8 g, 4.55 mmol, 78% yield). $^1$HNMR (400 MHz, DMSO-$d_6$) δ: 7.73 (d, J=8.0 Hz, 1H), 7.61 (s, 1H), 7.47-7.40 (m, 1H), 4.70-4.40 (m, 2H), 4.30-4.15 (m, 1H), 3.92 (d, J=3.6 Hz, 6H), 3.00-2.70 (m, 3H), 1.95-1.85 (m, 1H), 1.84-1.70 (m, 1H), 1.49 (s, 9H). MS (ESI) m/z: 418.2 [M+23]$^+$.

Step 4: Preparation of dimethyl 4-((3S,4R)-3-fluoropiperidin-4-yl)phthalate and dimethyl 4-((3R,4S)-3-fluoropiperidin-4-yl)phthalate

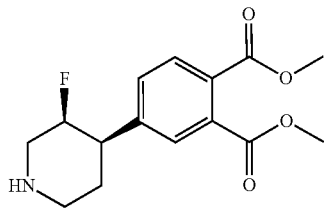

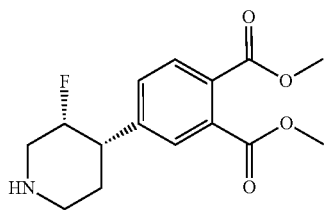

A solution of dimethyl 4-((3S,4R)-1-(tert-butoxycarbonyl)-3-fluoropiperidin-4-yl)phthalate and dimethyl 4-((3R,4S)-1-(tert-butoxycarbonyl)-3-fluoropiperidin-4-yl)phthalate (4.00 g, 10.12 mmol, 1 eq) in dichloromethane (20 mL) was added trifluoroacetic acid (30.80 g, 270.13 mmol, 20 mL, 26.70 eq), then the mixture was stirred for 0.5 h at 25° C. The reaction mixture was concentrated in vacuo, the residue was quenched with saturated sodium bicarbonate solution (20 mL) and the mixture was extracted with ethyl acetate (20 mL×3). The combined organic phase was washed with brine (50 mL), dried with anhydrous sodium sulfate, filtered and concentrated in vacuo. The desired product mixture was obtained as a yellow oil (2.5 g, 8.47 mmol, 84% yield). MS (ESI) m/z: 296.2 [M+1]$^+$.

Step 5: Preparation of dimethyl 4-((3S,4R)-1-((1r,3S)-3-((1-(tert-butoxycarbonyl)piperidin-4-yl)oxy)cyclobutyl)-3-fluoropiperidin-4-yl)phthalate and dimethyl 4-((3R,4S)-1-((1r,3R)-3-((1-(tert-butoxycarbonyl)piperidin-4-yl)oxy)cyclobutyl)-3-fluoropiperidin-4-yl)phthalate

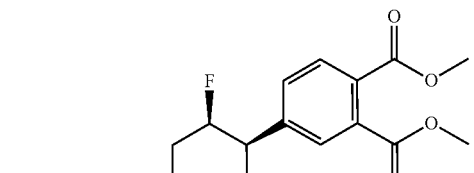

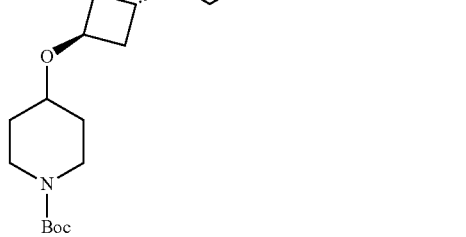

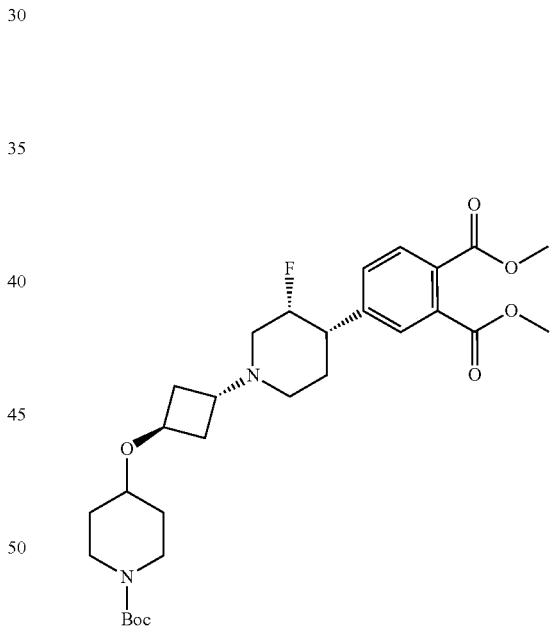

A solution of tert-butyl 4-[3-(trifluoromethylsulfonyloxy)cyclobutoxy]piperidine-1-carboxylate (2.66 g, 6.60 mmol, 1.3 eq), dimethyl 4-((3S,4R)-3-fluoropiperidin-4-yl)phthalate and dimethyl 4-((3R,4S)-3-fluoropiperidin-4-yl)phthalate (1.50 g, 5.08 mmol, 1 eq) and N,N-diisopropylethylamine (1.97 g, 15.24 mmol, 2.7 mL, 3 eq) in acetonitrile (20 mL) was stirred at 35° C. for 12 h. The mixture was concentrated under reduced pressure to give the residue which was purified by silica gel column chromatography (Petroleum ether/Ethyl acetate=20/1 to 1/1) to afford the desired products as a yellow oil (1.6 g, 2.92 mmol, 57% yield). MS (ESI) m/z: 571.2 [M+23]$^+$.

Step 6: Preparation of tert-butyl 4-((1S,3r)-3-((3S,4R)-4-(2-(2,6-dioxopiperidin-3-yl)-1,3-dioxoisoindolin-5-yl)-3-fluoropiperidin-1-yl)cyclobutoxy)piperidine-1-carboxylate and tert-butyl 4-((1R,3r)-3-((3R,4S)-4-(2-(2,6-dioxopiperidin-3-yl)-1,3-dioxoisoindolin-5-yl)-3-fluoropiperidin-1-yl)cyclobutoxy)piperidine-1-carboxylate Step 7 & 8: Preparation of 2-((6-((5-chloro-2-(4-((1S,3r)-3-((3S,4R)-4-(2-(2,6-dioxopiperidin-3-yl)-1,3-dioxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide and 2-((6-((5-chloro-2-(4-((1R,3r)-3-((3R,4S)-4-(2-(2,6-dioxopiperidin-3-yl)-1,3-dioxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide

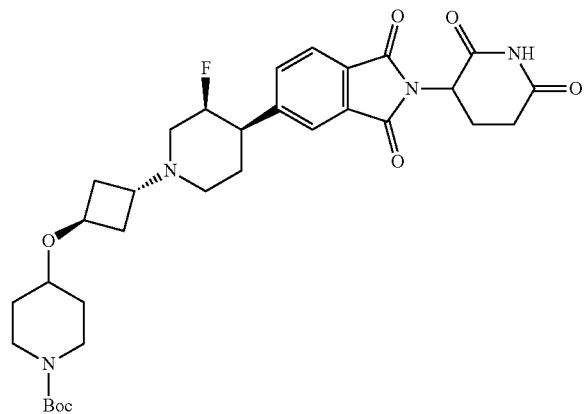

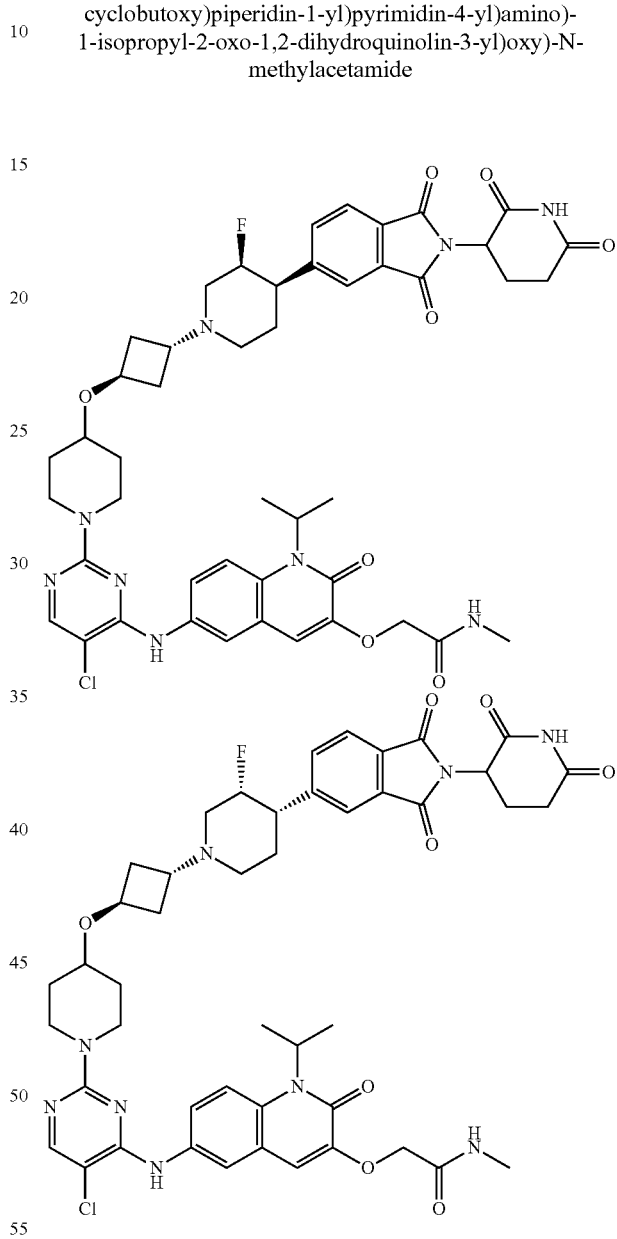

A solution of dimethyl 4-((3S,4R)-1-((1r,3S)-3-((1-(tert-butoxycarbonyl)piperidin-4-yl)oxy)cyclobutyl)-3-fluoropiperidin-4-yl)phthalate and dimethyl 4-((3R,4S)-1-((1r,3R)-3-((1-(tert-butoxycarbonyl)piperidin-4-yl)oxy)cyclobutyl)-3-fluoropiperidin-4-yl)phthalate (700 mg, 1.28 mmol, 1 eq), 3-aminopiperidine-2,6-dione hydrochloride (420 mg, 2.55 mmol, 2 eq) in pyridine (10 mL) was added lithium iodide (1.37 g, 10.21 mmol, 8 eq) at 25° C., then the mixture was stirred at 130° C. for 12 h. The reaction mixture was concentrated in vacuo and purified by silica gel column chromatography (Petroleum ether/Ethyl acetate=20/1 to 0/1) to afford the desired products as a yellow oil (500 mg, 0.82 mmol, 64% yield). MS (ESI) m/z: 613.3 [M+1]⁺.

Example 30 was prepared analogously to Example 24 following Steps 7-8 with the material made in Step 6 of this Example. The crude product was purified by prep-HPLC (column: Phenomenex Synergi C18 150*25 mm*10 um; mobile phase: [water (0.225% FA)-ACN]; B %: 13%-43%, 10 min) to afford the desired products as as an off-white solid (40.9 mg, 0.04 mmol, 31% yield, 95% purity). ¹HNMR (400 MHz, DMSO-$d_6$) δ: 11.29 (s, 1H), 8.84 (s, 1H), 8.06 (s, 1H), 7.98-7.92 (m, 2H), 7.91-7.88 (m, 1H), 7.87-7.83 (m, 2H), 7.72-7.62 (m, 2H), 7.02 (s, 1H), 5.60-5.10 (m, 2H), 5.00-4.70 (m, 1H) 4.54 (s, 2H), 4.22-4.05 (m, 3H), 3.60-3.45 (m, 1H), 3.25-3.20 (m, 1H), 3.05-2.80 (m, 4H), 2.67 (d, J=4.8 Hz, 3H), 2.64-2.56 (m, 2H), 2.25-2.13 (m, 2H), 2.10-1.96 (m, 4H), 1.92-1.69 (m, 7H), 1.57 (d, J=6.8 Hz, 6H), 1.42-1.31 (m, 2H). MS (ESI) m/z: 912.5 [M]+.

Example 31: 2-({6-[(5-chloro-2-{4-[(1r,3r)-3-{4-[2-(2,6-dioxopiperidin-3-yl)-1,3-dioxo-2,3-dihydro-1H-isoindol-5-yl]-3,3-difluoropiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 137)

Step 1: Preparation of dimethyl 4-(1-tert-butoxycarbonyl-3-oxo-4-piperidyl)benzene-1,2-dicarboxylate

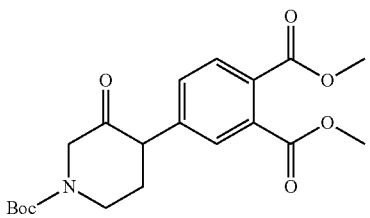 [SMILES: COC(=O)c1ccc(C2CCN(C(=O)OC(C)(C)C)CC2=O)cc1C(=O)OC]

A solution of dimethyl 4-(1-tert-butoxycarbonyl-3-hydroxy-4-piperidyl)benzene-1,2-dicarboxylate (2 g, 5.08 mmol, 1 eq) in dichloromethane (40 mL) was added Dess-Martin reagent (3.23 g, 7.63 mmol, 1.5 eq) at 0° C., then the mixture was stirred for 2 h at 25° C. The reaction mixture was quenched with saturated sodium bicarbonate solution (50 mL) and the mixture was extracted with ethyl acetate (50 Ml×3). The combined organic phase was washed with brine (50 mL), dried with anhydrous sodium sulfate, filtered and concentrated in vacuo. The residue was purified by silica gel column chromatography (Petroleum ether/Ethyl acetate=20/1 to 1/1) to afford dimethyl 4-(1-tert-butoxycarbonyl-3-oxo-4-piperidyl)benzene-1,2-dicarboxylate (1.4 g, 3.58 mmol, 70% yield) as a yellow oil. ¹HNMR (400 MHz, CDCl₃) δ: 7.74 (d, J=8.0 Hz, 1H), 7.52-7.48 (m, 1H), 7.35-7.30 (m, 1H), 4.32-4.22 (m, 1H), 4.10-3.98 (m, 2H), 3.91 (d, J=1.6 Hz, 6H), 3.77-3.68 (m, 1H), 3.59-3.50 (m, 1H), 2.38-2.17 (m, 2H), 1.49 (s, 9H). MS (ESI) m/z: 336.1 [M-55]+.

Step 2: Preparation of dimethyl 4-(1-tert-butoxycarbonyl-3,3-difluoro-4-piperidyl)benzene-1,2-dicarboxylate

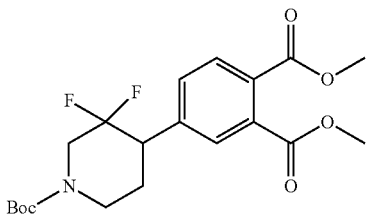 [SMILES: COC(=O)c1ccc(C2CCN(C(=O)OC(C)(C)C)CC2(F)F)cc1C(=O)OC]

A solution of dimethyl 4-(1-tert-butoxycarbonyl-3-oxo-4-piperidyl)benzene-1,2-dicarboxylate (1.40 g, 3.58 mmol, 1 eq) in dichloromethane (40 mL) was added drop wise 2-methoxy-N-(2-methoxyethyl)-N-(trifluoro-λ⁴-sulfanyl) ethanamine (1.98 g, 8.94 mmol, 2.0 mL, 2.5 eq) at −78° C., then the mixture was stirred for 2 h at 25° C. The reaction mixture was quenched with saturated sodium bicarbonate solution (50 mL) and the mixture was extracted with ethyl acetate (50 mL×3). The combined organic phase was washed with brine (50 mL), dried with anhydrous sodium sulfate, filtered and concentrated in vacuo. The residue was purified by prep-HPLC (column: Welch Ultimate XB-SiOH 250*50*10 um; mobile phase: [Hexane-EtOH (0.1% FA)]; B %: 1%-30%, 15 min) to afford the desired product a yellow oil (650 mg, 1.57 mmol, 44% yield). ¹HNMR (400 MHz, CDCl₃) δ: 7.73 (d, J=8.0 Hz, 1H), 7.67 (s, 1H), 7.50 (d, J=7.6 Hz, 1H), 4.38-4.25 (m, 2H), 3.92 (s, 6H), 3.20-3.10 (m, 1H), 3.05-2.70 (m, 2H), 2.30-2.10 (m, 1H), 1.95-1.80 (m, 1H), 1.49 (s, 9H). MS (ESI) m/z: 436.3 [M+23]+.

Steps 4-8: 2-({6-[(5-chloro-2-{4-[(1r,3r)-3-{4-[2-(2,6-dioxopiperidin-3-yl)-1,3-dioxo-2,3-dihydro-1H-isoindol-5-yl]-3,3-difluoropiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide

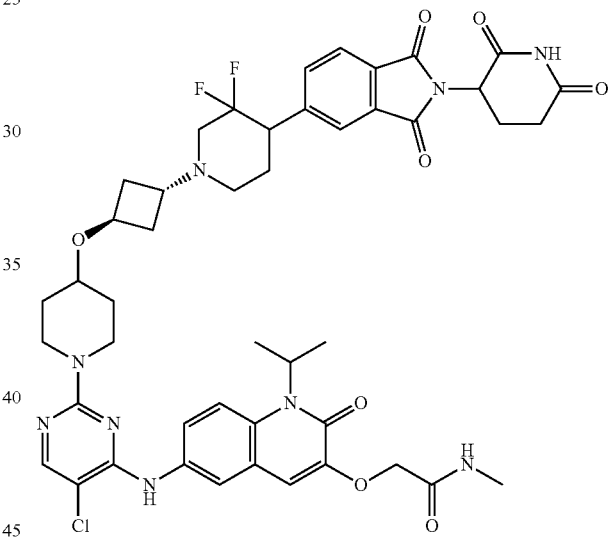

Example 31 was prepared analogously to Example 30 by substituting dimethyl 4-(1-tert-butoxycarbonyl-3,3-difluoro-4-piperidyl)benzene-1,2-dicarboxylate (prepared in Step 2 of this example) for dimethyl 4-((3S,4R)-1-(tert-butoxycarbonyl)-3-fluoropiperidin-4-yl)phthalate and dimethyl 4-((3R,4S)-1-(tert-butoxycarbonyl)-3-fluoropiperidin-4-yl)phthalate in Step 4 of Example 30. The crude product was purified by prep-HPLC (column: Unisil 3-100 C18 Ultra 150*50 mm*3 um; mobile phase: [water (0.225% FA)-ACN]; B %: 25%-55%, 10 min) to afford the desired product as a white solid (19.3 mg, 0.02 mmol, 14% yield, 100% purity). ¹HNMR (400 MHz, DMSO-d₆) δ: 11.12 (s, 1H), 8.84 (s, 1H), 8.04 (s, 1H), 7.98-7.92 (m, 3H), 7.86-7.80 (m, 2H), 7.69 (s, 2H), 7.02 (s, 1H), 5.70-5.23 (m, 1H), 5.20-5.10 (m, 1H), 4.54 (s, 2H), 4.25-4.05 (m, 3H), 3.60-3.40 (m, 2H), 3.25-3.14 (m, 3H), 3.07-2.97 (m, 2H), 2.95-2.82 (m, 1H), 2.67 (d, J=4.8 Hz, 3H), 2.64-2.56 (m, 1H), 2.28-2.09 (m, 5H), 2.08-1.96 (m, 4H), 1.91-1.77 (m, 3H), 1.57 (d, J=6.8 Hz, 6H), 1.45-1.31 (m, 2H). MS (ESI) m/z: 930.6 [M]+.

Example 32: 2-((6-((5-chloro-2-(4-((1S,3r)-3-((3S, 4R)-4-(2-(2,6-dioxopiperidin-3-yl)-1-oxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide and 2-((6-((5-chloro-2-(4-((1R,3r)-3-((3R,4S)-4-(2-(2,6-dioxopiperidin-3-yl)-1-oxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide (Compound 131)

Step 1: Preparation of tert-butyl 3-(5-(3-fluoro-1-((1r,3r)-3-(piperidin-4-yloxy)cyclobutyl)piperidin-4-yl)-3-hydroxy-1-oxoisoindolin-2-yl)piperidine-2,6-dione and 3-(5-(3-fluoro-1-((1r,3r)-3-(piperidin-4-yloxy)cyclobutyl)piperidin-4-yl)-1-hydroxy-3-oxoisoindolin-2-yl)piperidine-2,6-dione

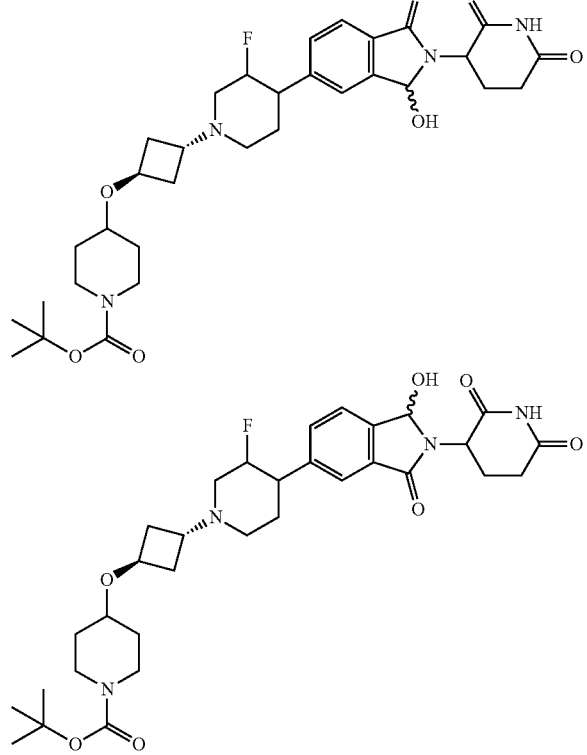

To a solution of tert-butyl 4-((1S,3r)-3-((3S,4R)-4-(2-(2,6-dioxopiperidin-3-yl)-1,3-dioxoisoindolin-5-yl)-3-fluoropiperidin-1-yl)cyclobutoxy)piperidine-1-carboxylate and tert-butyl 4-((1R,3r)-3-((3R,4S)-4-(2-(2,6-dioxopiperidin-3-yl)-1,3-dioxoisoindolin-5-yl)-3-fluoropiperidin-1-yl)cyclobutoxy)piperidine-1-carboxylate (Example 30, Step 6; 450 mg, 0.73 mmol, 1 eq) in acetic acid (10 mL) was added zinc powder (816 mg, 12.49 mmol, 17 eq). The mixture was stirred at 90° C. for 2 h. The reaction mixture was quenched with saturated sodium bicarbonate solution (500 mL) and the mixture was extracted with ethyl acetate (100 mL×3). The combined organic phase was washed with brine (500 mL), dried with anhydrous sodium sulfate, filtered and concentrated in vacuo. A mixture of the desired products was obtained as a yellow oil (400 mg, 0.6 mmol, 88% yield). MS (ESI) m/z: 615.2 [M+1]$^+$.

Step 2: Preparation of 3-(5-((cis)-3-fluoro-1-((1r,3s)-3-(piperidin-4-yloxy)cyclobutyl)piperidin-4-yl)-1-oxoisoindolin-2-yl)piperidine-2,6-dione and 3-(5-((cis)-3-fluoro-1-((1r,3r)-3-(piperidin-4-yloxy)cyclobutyl)piperidin-4-yl)-1-oxoisoindolin-2-yl)piperidine-2,6-dione

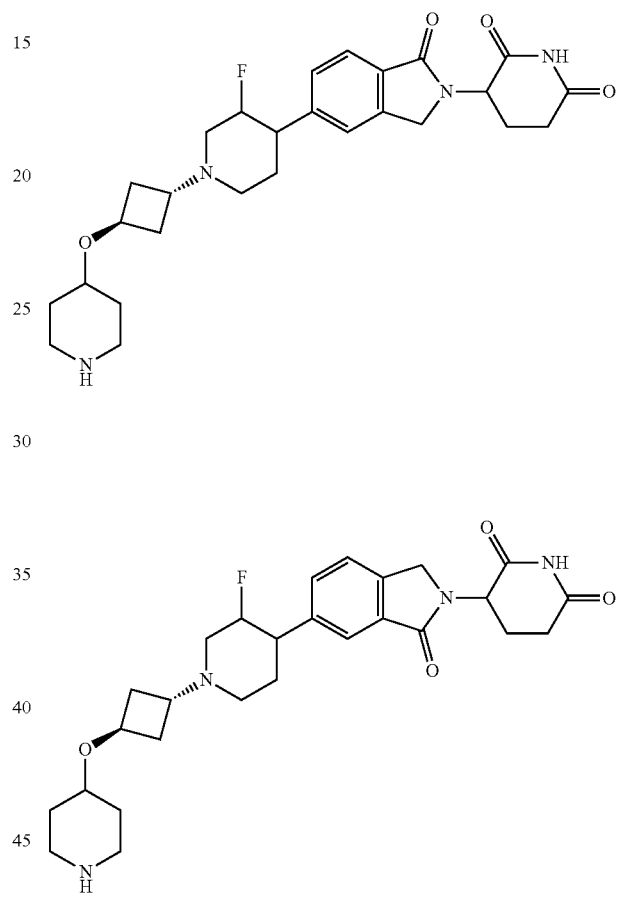

To a solution of the products from Example 32, Step 1 (400 mg, 0.64 mmol, 1 eq) in dichloromethane (5 mL) was added triethylsilane (378 mg, 3.25 mmol, 5 eq) and trifluoroacetic acid (1.48 g, 13.01 mmol, 1.0 mL, 20 eq) at 0° C., then the mixture was stirred at 25° C. for 1 h. The reaction mixture was concentrated in vacuo. The residue was purified by prep-HPLC (column: Phenomenex Synergi C18 150*25 mm*10 um; mobile phase: [water (0.1% TFA)-ACN]; B %: 8%-38%, 10 min) to isolate 2 impure fractions. Fraction 1: 3-[5-[3-fluoro-1-[3-(4-piperidyloxy)cyclobutyl]-4-piperidyl]-1-oxo-isoindolin-2-yl]piperidine-2,6-dione (150 mg, 0.30 mmol, 46% yield, Rt=0.233 min, which also contains the 2$^{nd}$ peak) was obtained as a yellow oil. Fraction 2: 3-[6-[3-fluoro-1-[3-(4-piperidyloxy)cyclobutyl]-4-piperidyl]-1-oxo-isoindolin-2-yl]piperidine-2,6-dione (150 mg, 0.30 mmol, 46% yield, Rt=0.317 min, which also contains peak 1) was obtained as a yellow oil. MS (ESI) m/z: 499.3 [M+1]$^+$.

Step 3: Preparation of tert-butyl 4-((1S,3r)-3-((3S,4R)-4-(2-(2,6-dioxopiperidin-3-yl)-1-oxoisoindolin-5-yl)-3-fluoropiperidin-1-yl)cyclobutoxy)piperidine-1-carboxylate and tert-butyl 4-((1R,3r)-3-((3R,4S)-4-(2-(2,6-dioxopiperidin-3-yl)-1-oxoisoindolin-5-yl)-3-fluoropiperidin-1-yl)cyclobutoxy)piperidine-1-carboxylate

Step 4: Preparation of 3-(5-((3S,4R)-3-fluoro-1-((1r,3S)-3-(piperidin-4-yloxy)cyclobutyl)piperidin-4-yl)-1-oxoisoindolin-2-yl)piperidine-2,6-dione and 3-(5-((3R,4S)-3-fluoro-1-((1r,3R)-3-(piperidin-4-yloxy)cyclobutyl)piperidin-4-yl)-1-oxoisoindolin-2-yl)piperidine-2,6-dione

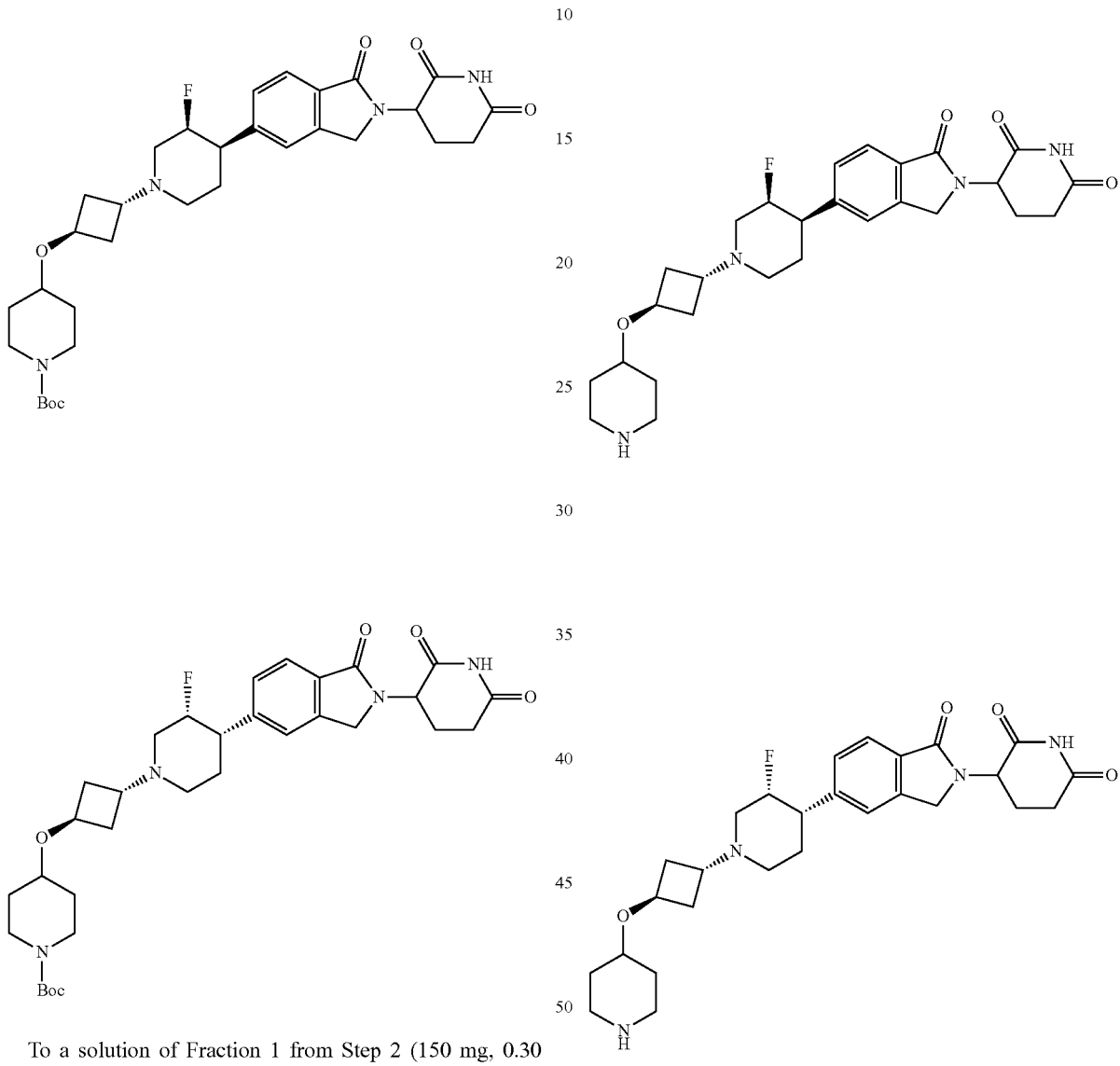

To a solution of Fraction 1 from Step 2 (150 mg, 0.30 mmol, 1 eq) and triethylamine (91 mg, 0.90 mmol, 0.1 mL, 3 eq) in dichloromethane (5 mL) was added tert-butyl (2-methylpropan-2-yl) oxycarbonyl carbonate (131 mg, 0.60 mmol, 0.1 mL, 2 eq) at 25° C., then the mixture was stirred for 2 h at 25° C. The reaction mixture was concentrated in vacuo. The residue was purified by preparative TLC (Dichloromethane/Methanol=15/1) to afford the desired products as a white solid. $^1$HNMR (400 MHz, CDCl$_3$) δ: 8.00 (s, 1H), 7.90-7.80 (m, 1H), 7.45-7.35 (m, 2H), 5.27-5.17 (m, 1H), 4.85-4.60 (m, 1H), 4.55-4.45 (m, 1H), 4.40-4.30 (m, 1H), 4.25-4.15 (m, 1H), 3.90-3.75 (m, 2H), 3.50-3.40 (m, 1H) 3.39-3.30 (m, 1H), 3.10-2.95 (m, 4H), 2.90-2.70 (m, 3H), 2.45-2.30 (m, 1H), 2.25-2.10 (m, 5H), 1.97-1.80 (m, 5H), 1.67-1.55 (m, 2H), 1.54-1.47 (m, 2H), 1.45 (s, 9H). MS (ESI) m/z: 599.3 [M+1]$^+$.

To a solution of tert-butyl 4-[3-[4-[2-(2,6-dioxo-3-piperidyl)-1-oxo-isoindolin-5-yl]-3-fluoro-1-piperidyl]cyclobutoxy]piperidine-1-carboxylate (100 mg, 0.17 umol, 1.0 eq) in dichloromethane (3 mL) was added trifluoroacetic acid (3.85 g, 33.74 mmol, 2.5 mL, 202.02 eq), then the mixture was stirred for 0.5 h at 25° C. The mixture was concentrated under reduced pressure to afford the crude desired products as a yellow oil (80 mg, 0.16 mmol, 96% yield). MS (ESI) m/z: 499.3 [M+1]$^+$.

Step 5: Preparation of 2-((6-((5-chloro-2-(4-((1S, 3r)-3-((3S,4R)-4-(2-(2,6-dioxopiperidin-3-yl)-1-oxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide and 2-((6-((5-chloro-2-(4-((1R,3r)-3-((3R,4S)-4-(2-(2,6-dioxopiperidin-3-yl)-1-oxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide

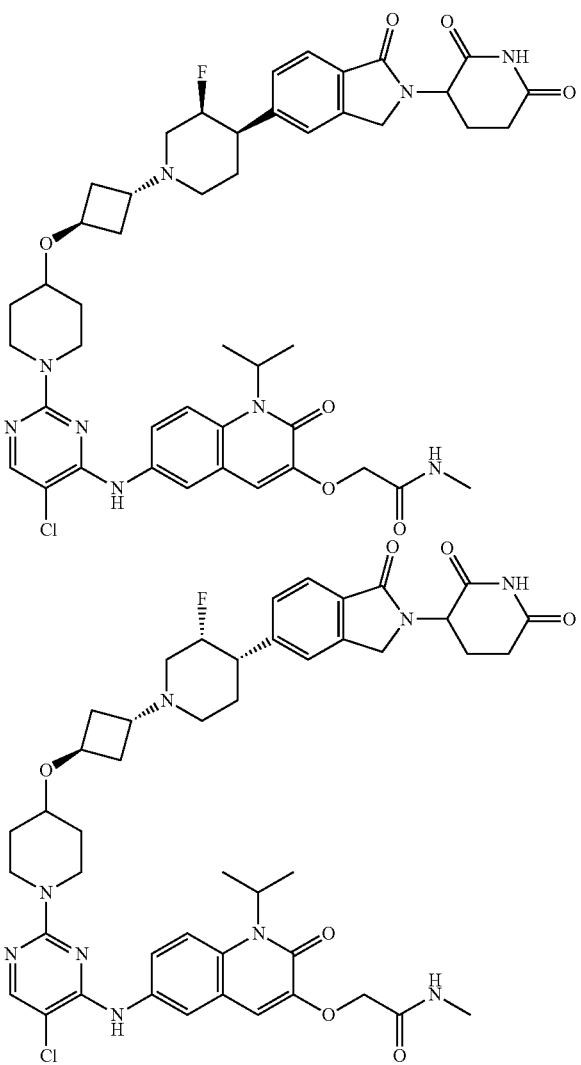

Example 32 was prepared analogously to Example 23 Step 12. The crude product was purified by prep-HPLC (column: Unisil 3-100 C18 Ultra 150*50 mm*3 um; mobile phase: [water (0.225% FA)-ACN]; B %: 17%-47%, 10 min) to afford the desired products as an off-white solid (56.6 mg, 0.06 mmol, 38% yield, 98% purity). $^1$HNMR (400 MHz, DMSO-$d_6$) δ. 10.98 (s, 1H), 8.04 (s, 1H), 7.98-7.92 (m, 2H), 7.71-7.62 (m, 3H), 7.60-7.54 (m, 1H), 7.50-7.42 (m, 1H), 7.02 (s, 1H), 5.57-5.25 (m, 1H), 5.15-5.05 (m, 1H), 4.88-4.65 (m, 1H), 4.54 (s, 2H), 4.48-4.40 (m, 1H), 4.35-4.25 (m, 1H), 4.22-4.07 (m, 3H), 3.58-3.50 (m, 1H), 3.26-3.18 (m, 1H), 3.00-2.80 (s, 4H), 2.67 (d, J=4.8 Hz, 3H), 2.63-2.53 (m, 1H), 2.45-2.30 (m, 3H), 2.25-2.15 (m, 2H), 2.05-1.95 (m, 3H), 1.90-1.80 (m, 5H), 1.77-1.67 (m, 1H), 1.57 (d, J=6.8 Hz, 6H), 1.45-1.31 (m, 2H). MS (ESI) m/z: 898.4 [M]$^+$.

Example 33: 2-((6-((5-chloro-2-(4-((1S,3r)-3-((3S, 4R)-4-(2-(2,6-dioxopiperidin-3-yl)-3-oxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide and 2-((6-((5-chloro-2-(4-((1R,3r)-3-((3R,4S)-4-(2-(2,6-dioxopiperidin-3-yl)-3-oxoisoindolin-5-yl)-3-fluoropiperidin-1-yl)cyclobutoxy)piperidin-1-yl)pyrimidin-4-yl)amino)-1-isopropyl-2-oxo-1,2-dihydroquinolin-3-yl)oxy)-N-methylacetamide (Compound 132)

Step 1: Preparation of tert-butyl 4-((1S,3r)-3-((3S, 4R)-4-(2-(2,6-dioxopiperidin-3-yl)-3-oxoisoindolin-5-yl)-3-fluoropiperidin-1-yl)cyclobutoxy)piperidine-1-carboxylate and tert-butyl 4-((1R,3r)-3-((3R,4S)-4-(2-(2,6-dioxopiperidin-3-yl)-3-oxoisoindolin-5-yl)-3-fluoropiperidin-1-yl)cyclobutoxy)piperidine-1-carboxylate

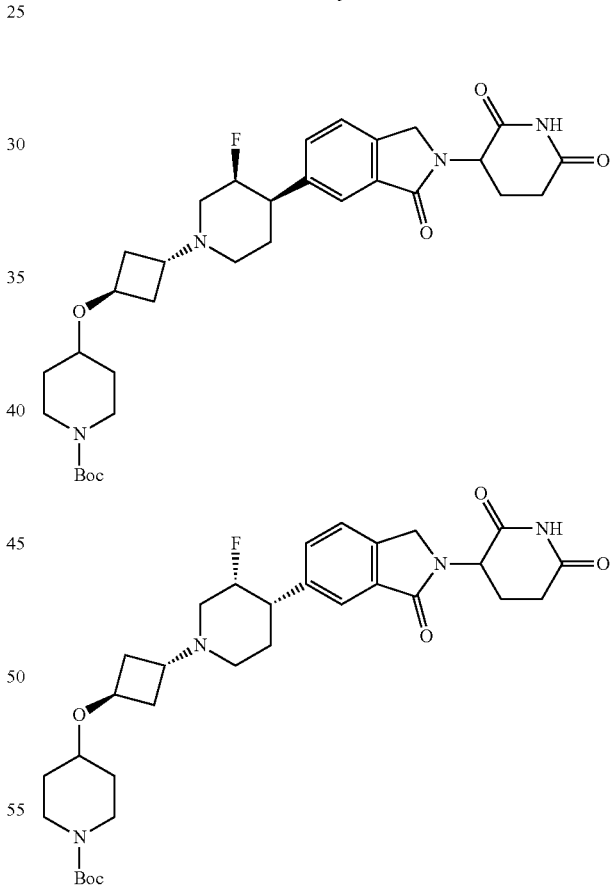

To a solution of Fraction 2 from Example 32, Step 2 (150 mg, 0.30 mmol, 1 eq) and triethylamine (91 mg, 0.90 mmol, 3 eq) in dichloromethane (5 mL) was added tert-butyl (2-methylpropan-2-yl)oxycarbonyl carbonate (131 mg, 0.60 mmol, 2 eq) at 25° C., then the mixture was stirred for 2 h at 25° C. The reaction mixture was concentrated in vacuo. The residue was purified by preparative TLC (Dichloromethane:Methanol=15:1, Rf=0.43) to afford the desired products as a white (110 mg, 0.18 mmol, 61% yield). ¹HNMR (400 MHz, CDCl₃) δ: 8.00 (s, 1H), 7.90-7.80 (m, 1H), 7.55-7.35 (m, 2H), 5.25-5.20 (m, 1H), 4.82-4.57 (m, 1H), 4.55-4.45 (m, 1H), 4.40-4.30 (m, 1H), 4.25-4.15 (m, 1H), 3.90-3.75 (m, 2H), 3.50-3.40 (m, 1H) 3.39-3.30 (m, 1H), 3.10-2.95 (m, 4H), 2.90-2.70 (m, 3H), 2.45-2.30 (m, 1H), 2.25-2.10 (m, 5H), 1.97-1.80 (m, 5H), 1.67-1.55 (m, 2H), 1.54-1.47 (m, 2H), 1.45 (s, 9H). MS (ESI) m/z: 599.3 [M+1]⁺.

Steps 2-3: Preparation of 3-(6-((3S,4R)-3-fluoro-1-((1r,3S)-3-(piperidin-4-yloxy)cyclobutyl)piperidin-4-yl)-1-oxoisoindolin-2-yl)piperidine-2,6-dione and 3-(6-((3R,4S)-3-fluoro-1-((1r,3R)-3-(piperidin-4-yloxy)cyclobutyl)piperidin-4-yl)-1-oxoisoindolin-2-yl)piperidine-2,6-dione

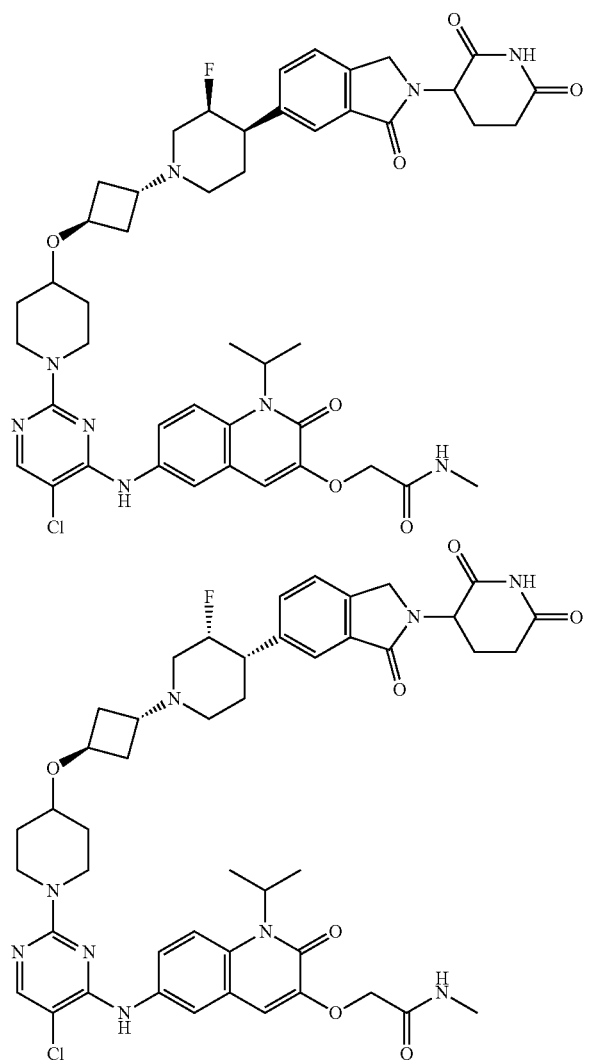

Example 33 was prepared analogously to Example 32, Steps 4 and 5. The crude material was purified by prep-HPLC {column: Unisil 3-100 C18 Ultra 150*50 mm*3 um; mobile phase: [water (0.225% FA)-ACN]; B %: 15%-45%, 10 min} to afford the desired products as an off-white solid (52.2 mg, 54.17 umol, 38.58% yield, 98% purity, Formate salt). ¹HNMR (400 MHz, DMSO-d₆) δ: 11.05 (s, 1H), 8.81 (s, 1H), 8.23 (s, 1H), 8.04 (s, 1H), 7.98-7.92 (m, 2H), 7.71-7.66 (m, 2H), 7.65-7.45 (m, 3H), 7.03 (s, 1H), 5.57-5.25 (m, 1H), 5.15-5.05 (m, 1H), 4.88-4.65 (m, 1H), 4.54 (s, 2H), 4.48-4.40 (m, 1H), 4.35-4.25 (m, 1H), 4.22-4.07 (m, 3H), 3.58-3.50 (m, 1H), 3.26-3.18 (m, 1H), 3.00-2.80 (s, 4H), 2.67 (d, J=4.8 Hz, 3H), 2.63-2.53 (m, 1H), 2.45-2.30 (m, 3H), 2.25-2.15 (m, 2H), 2.05-1.95 (m, 3H), 1.90-1.80 (m, 5H), 1.77-1.67 (m, 1H), 1.57 (d, J=6.8 Hz, 6H), 1.45-1.31 (m, 2H). MS (ESI) m/z: 898.4 [M]⁺.

Example 34: Synthesis of 2-[[6-[[5-chloro-2-[4-[3-[4-[2-(2,6-dioxo-3-piperidyl)-6-isopropoxy-1,3-dioxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide (Compound 159)

Step 1: preparation of dimethyl 4-isopropoxy-5-nitro-benzene-1,2-dicarboxylate

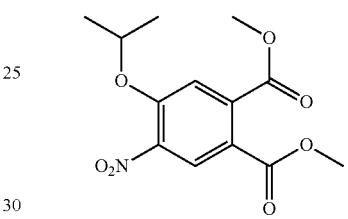

To a mixture of dimethyl 4-hydroxy-5-nitro-benzene-1,2-dicarboxylate (3.00 g, 11.8 mmol, 1 eq) and 2-iodopropane (3.00 g, 17.6 mmol, 1.5 eq) in N,N-dimethylformamide (30 mL) was added potassium carbonate (4.87 g, 35.3 mmol, 3 eq) in one portion at 25° C. under nitrogen. The mixture was stirred at 80° C. for 2 hours, then cooled to 25° C. and poured into ice-water (w/w=1/1) (50 mL) and stirred for 5 minutes. The aqueous phase was extracted with ethyl acetate (2×100 mL). The combined organic phase was washed with brine (3×100 mL), dried over anhydrous sodium sulphate, filtered, and concentrated in vacuum. The residue was purified by silica gel chromatography (petroleum ether/ethyl acetate=10/1, 5/1) to afford dimethyl 4-isopropoxy-5-nitro-benzene-1,2-dicarboxylate (2.9 g, 82%) as a yellow oil.

Step 2: preparation of dimethyl 4-amino-5-isopropoxy-benzene-1,2-dicarboxylate

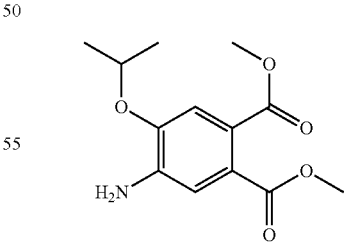

To a mixture of dimethyl 4-isopropoxy-5-nitro-benzene-1,2-dicarboxylate (2.9 g, 9.8 mmol, 1 eq) and ammonium chloride (5.22 g, 97.6 mmol, 10 eq) in ethanol (50 mL) and water (5 mL) was added iron (2.18 g, 39.0 mmol, 4 eq) in one portion at 25° C. under nitrogen. Then the mixture was stirred at 50° C. for 2 hours, cooled to 25° C. and concentrated in reduced pressure at 45° C. The residue was poured into ice-water (w/w=1/1) (50 mL) and stirred for 15 minutes.

The aqueous phase was extracted with ethyl acetate (3×50 mL). The combined organic phase was washed with brine (2×50 mL), dried over anhydrous sodium sulphate, filtered, and concentrated in vacuum to obtain dimethyl 4-amino-5-isopropoxy-benzene-1,2-dicarboxylate (2.6 g, 99%) as a yellow oil. This material was used for the next step without any further purification. MS (ESI) m/z: 268.1 [M+H]+.

Step 3: preparation of dimethyl 4-bromo-5-isopropoxy-benzene-1,2-dicarboxylate

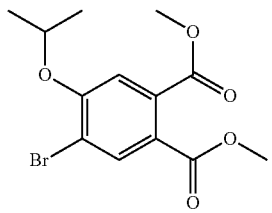 [SMILES: COC(=O)c1cc(Br)c(OC(C)C)cc1C(=O)OC]

To a mixture of dimethyl 4-amino-5-isopropoxy-benzene-1,2-dicarboxylate (2.6 g, 9.7 mmol, 1 eq) and copper bromide (1.81 g, 12.6 mmol, 1.3 eq) in acetonitrile (60 mL) was added tert-butyl nitrite (3.0 g, 29.1 mmol, 2.99 eq) at 0° C. under nitrogen. Then the reaction was warmed to 25° C. and stirred for 6 hours. The mixture was poured into ice-water (w/w=1/1) (100 mL) and stirred for 5 minutes. The aqueous phase was extracted with ethyl acetate (3×100 mL). The combined organic phase was washed with brine (3×100 mL), dried over anhydrous sodium sulphate, filtered, and concentrated in vacuum. The residue was purified by silica gel chromatography (petroleum ether/ethyl acetate=20/1 to 10/1) to afford dimethyl 4-bromo-5-isopropoxy-benzene-1,2-dicarboxylate (1.71 g, 53%) as yellow oil. MS (ESI) m/z: 352.7 [M+H]+; 1H NMR (400 MHz, CDCl3) δ 8.03 (s, 1H), 7.07 (s, 1H), 4.69-4.66 (m, 1H), 3.91 (s, 3H). 3.88 (s, 3H), 1.42 (d, J=6.0 Hz, 6H).

Step 4: preparation of dimethyl 4-(1-benzyloxycarbonyl-3,6-dihydro-2H-pyridin-4-yl)-5-isopropoxy-benzene-1,2-dicarboxylate

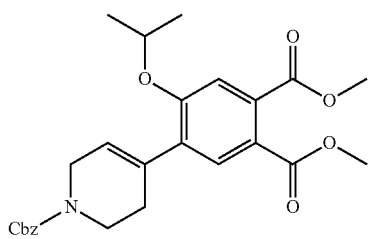 [SMILES: COC(=O)c1cc(OC(C)C)c(C2=CCN(C(=O)OCc3ccccc3)CC2)cc1C(=O)OC]

A mixture of dimethyl 4-bromo-5-isopropoxy-benzene-1,2-dicarboxylate (1.70 g, 5.1 mmol, 1 eq), benzyl 4-(4,4,5,5-tetramethyl-1,3,2-dioxaborolan-2-yl)-3,6-dihydro-2H-pyridine-1-carboxylate (2.64 g, 7.7 mmol, 1.5 eq), ditert-butyl(cyclopentyl)phosphane; dichloropalladium; iron (167 mg, 0.2 mmol, 0.05 eq) and cesium fluoride (1.56 g, 10.3 mmol, 2 eq) in 1,4-dioxane (30 mL) and water (5 mL) was degassed and purged with nitrogen for 3 times, and then the mixture was stirred at 90° C. for 2 hours under nitrogen atmosphere. The mixture was cooled to 25° C. and concentrated in reduced pressure at 45° C. The residue was poured into ice-water (w/w=1/1) (100 mL) and stirred for 5 minutes. The aqueous phase was extracted with ethyl acetate (3×50 mL). The combined organic phase was washed with brine (2×50 mL), dried over anhydrous sodium sulphate, filtered, and concentrated in vacuum. The residue was purified by silica gel chromatography (petroleum ether/ethyl acetate=10/1 to 5/1) to afford dimethyl 4-(1-benzyloxycarbonyl-3,6-dihydro-2H-pyridin-4-yl)-5-isopropoxy-benzene-1,2-dicarboxylate (2.2 g, 91%) as yellow oil. MS (ESI) m/z: 468.2 [M+H]+; 1H NMR (400 MHz, CDCl3)(7.53 (s, 1H), 7.32-7.26 (s, 5H), 6.97 (s, 1H), 5.76-5.75 (m, 1H), 5.15 (s, 2H), 4.59-4.56 (m, 1H), 4.07-4.01 (m, 2H), 3.83 (s, 3H), 3.81 (s, 3H), 3.59-3.57 (m, 2H), 2.41 (br s, 2H), 1.20 (s, 3H), 1.19 (s, 3H), 1.18 (s, 9H).

Step 5: preparation of dimethyl 4-(1-benzyloxycarbonyl-3,6-dihydro-2H-pyridin-4-yl)-5-isopropoxy-benzene-1,2-dicarboxylate

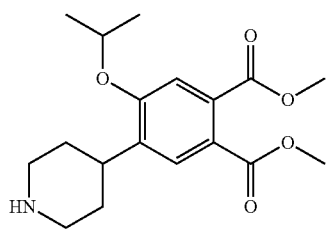 [SMILES: COC(=O)c1cc(OC(C)C)c(C2CCNCC2)cc1C(=O)OC]

To a solution of dimethyl 4-(1-benzyloxycarbonyl-3,6-dihydro-2H-pyridin-4-yl)-5-isopropoxy-benzene-1,2-dicarboxylate (2.2 g, 4.7 mmol, 1 eq) in tetrahydrofuran (20 mL) and trifluoroethanol (20 mL) was added 10% palladium on carbon (0.5 g) and 10% palladium hydroxide on carbon (0.5 g) under nitrogen. The suspension was degassed under vacuum and purged with hydrogen several times. The mixture was stirred under hydrogen (50 psi) at 35° C. for 6 hours, upon which the reaction mixture was filtered and the filtrate solution was concentrated to get dimethyl 4-isopropoxy-5-(4-piperidyl)benzene-1,2-dicarboxylate (1.5 g, 95%) as a yellow oil. The crude product was used for the next step without any further purification. MS (ESI) m/z: 336.1 [M+H]+; 1H NMR (400 MHz, CDCl3)(7.64 (s, 1H), 7.04 (s, 1H), 4.69-4.64 (m, 1H), 3.97-3.93 (m, 2H), 3.90 (s, 3H), 3.87 (s, 3H), 3.24-3.21 (m, 2H), 2.96-2.82 (m, 1H), 2.76-2.75 (m, 2H), 1.83-1.80 (m, 2H), 1.65-1.64 (m, 2H), 1.39 (d, J=6.0 Hz, 6H), 1.36 (s, 9H).

Step 6: preparation of dimethyl 4-[1-[3-[(1-tert-butoxycarbonyl-4-piperidyl)oxy]cyclobutyl]-4-piperidyl]-5-isopropoxy-benzene-1,2-dicarboxylate

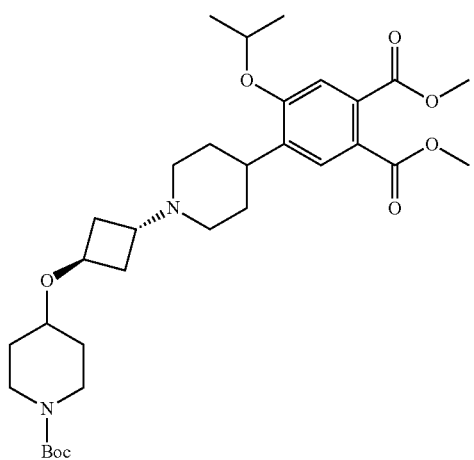 [SMILES: COC(=O)c1cc(OC(C)C)c(C2CCN([C@H]3C[C@H](OC4CCN(C(=O)OC(C)(C)C)CC4)C3)CC2)cc1C(=O)OC]

To a mixture of dimethyl 4-isopropoxy-5-(4-piperidyl) benzene-1,2-dicarboxylate (1.5 g, 4.5 mmol, 1 eq) and tert-butyl 4-[3-(trifluoromethylsulfonyloxy)cyclobutoxy]piperidine-1-carboxylate (1.89 g, 4.7 mmol, 1.05 eq) in acetonitrile (30 mL) was added N,N-diisopropylethylamine (1.73 g, 13.4 mmol, 3 eq) and stirred at 25° C. for 1 hour under nitrogen. To this mixture was added water (50 mL), stirred at 25° C. for 5 minutes. Then aqueous phase was extracted with ethyl acetate (3×50 mL). The combined organic phase was washed with brine (2×50 mL), dried over anhydrous sodium sulphate, filtered and concentrated in vacuum. The residue was purified by prep-HPLC (mobile phase: [water (0.1% TFA)-ACN]; B %: 25%-55%, 20 min) to afford dimethyl 4-[1-[3-[(1-tert-butoxycarbonyl-4-piperidyl)oxy]cyclobutyl]-4-piperidyl]-5-isopropoxy-benzene-1,2-dicarboxylate (2.1 g, 79%) as a yellow oil. MS (ESI) m/z: 589.3 $[M+H]^+$.

Step 7: preparation of 4-[1-[3-[(1-tert-butoxycarbonyl-4-piperidyl) oxy]cyclobutyl]-4-piperidyl]-5-isopropoxy-phthalic acid

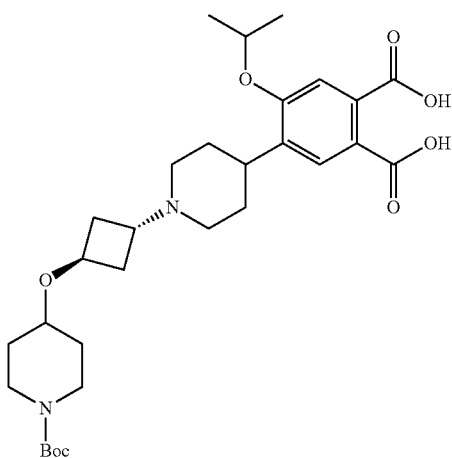 [SMILES: CC(C)Oc1cc(C(=O)O)c(C(=O)O)cc1C1CCN([C@H]2C[C@H](OC3CCN(C(=O)OC(C)(C)C)CC3)C2)CC1]

To a mixture of dimethyl 4-[1-[3-[(1-tert-butoxycarbonyl-4-piperidyl)oxy]cyclobutyl]-4-piperidyl]-5-isopropoxy-benzene-1,2-dicarboxylate (2.0 g, 3.4 mmol, 1 eq) in tetrahydrofuran (10 mL), methanol (10 mL) and water (10 mL) was added potassium hydroxide (953 mg, 17.0 mmol, 5 eq) and heated to 50° C. for 6 hours. The reaction was then cooled to 0° C. and adjusted pH to 5-6 by trifluoroacetic acid. The aqueous phase was concentrated in vacuum. The residue was purified by prep-HPLC (mobile phase: [water (0.225% FA)-ACN]; B %: 30%-60%, 20 min) to afford 4-[1-[3-[(1-tert-butoxycarbonyl-4-piperidyl)oxy]cyclobutyl]-4-piperidyl]-5-isopropoxy-phthalic acid (1.4 g, 73%) as a white solid. MS (ESI) m/z: 561.3 $[M+H]^+$.

Step 8: preparation of tert-butyl 4-[3-[4-[2-(2,6-dioxo-3-piperidyl)-6-isopropoxy-1,3-dioxo-isoindolin-5-yl]-1-piperidyl]cyclobutoxy]piperidine-1-carboxylate

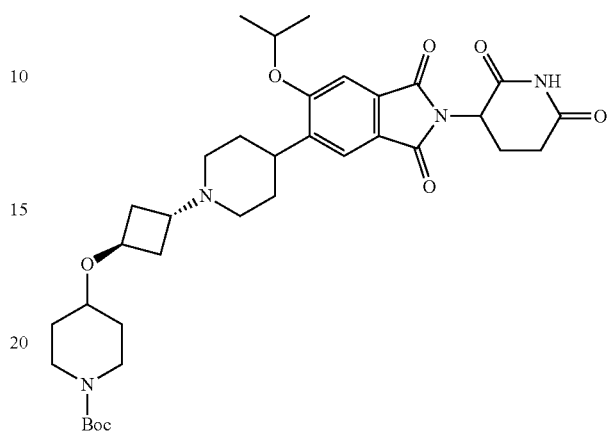

A mixture of 4-[1-[3-[(1-tert-butoxycarbonyl-4-piperidyl)oxy]cyclobutyl]-4-piperidyl]-5-isopropoxy-phthalic acid (0.7 g, 1.2 mmol, 1 eq) and 3-aminopiperidine-2,6-dione hydrochloride (410 mg, 2.5 mmol, 2 eq) in pyridine (10 mL) was heated to 110° C. and stirred for 6 hours under nitrogen. Then the reaction was cooled to 25° C. and concentrated in reduced pressure at 45° C. The residue was purified by silica gel chromatography (ethyl acetate/methanol=50/1 to 10/1) to afford tert-butyl 4-[3-[4-[2-(2,6-dioxo-3-piperidyl)-6-isopropoxy-1,3-dioxo-isoindolin-5-yl]-1-piperidyl]cyclobutoxy]piperidine-1-carboxylate (0.7 g, 85%) as a blue solid. MS (ESI) m/z: 653.4 $[M+H]^+$.

Step 9: preparation of 2-(2,6-dioxo-3-piperidyl)-5-isopropoxy-6-[1-[3-(4-piperidyloxy)cyclobutyl]-4-piperidyl]isoindoline-1,3-dione

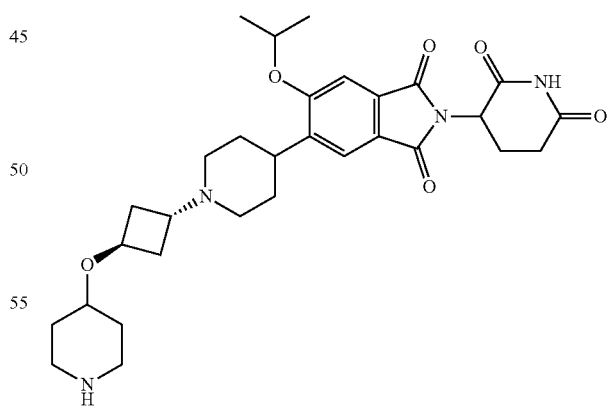

To a mixture of tert-butyl 4-[3-[4-[2-(2,6-dioxo-3-piperidyl)-6-isopropoxy-1,3-dioxo-isoindolin-5-yl]-1-piperidyl]cyclobutoxy]piperidine-1-carboxylate (1.0 g, 1.5 mmol, 1 eq) in tetrahydrofuran (20 mL) was added hydrogen chloride/dioxane (4 M, 20 mL, 52.22 eq) and stirred at 25° C. for 1 hours. Then the mixture was cooled to 25° C. and concentrated in reduced pressure at 45° C. to afford 2-(2,6-

Step 10: preparation of 2-[[6-[[5-chloro-2-[4-[3-[4-[2-(2,6-dioxo-3-piperidyl)-6-isopropoxy-1,3-dioxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide

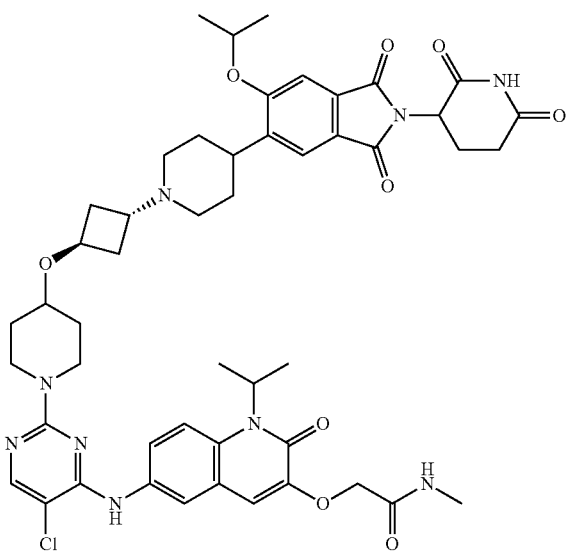 [SMILES: CNC(=O)COc1cc2cc(Nc3nc(N4CCC(O[C@H]5C[C@H](N6CCC(c7cc8c(cc7OC(C)C)C(=O)N(C7CCC(=O)NC7=O)C8=O)CC6)C5)CC4)ncc3Cl)ccc2n(C(C)C)c1=O]

To a mixture of 2-(2,6-dioxo-3-piperidyl)-5-isopropoxy-6-[1-[3-(4-piperidyloxy)cyclobutyl]-4-piperidyl]isoindoline-1,3-dione dihydrochloride (680 mg, 1.1 mmol, 1 eq) and 2-[[6-[(2,5-dichloropyrimidin-4-yl)amino]-1-isopropyl-2-oxo-3-quinolyl]oxy]-N-methyl-acetamide (379.39 mg, 869.6 umol, 0.8 eq) in (methylsulfinyl)methane (10 mL) was added N,N-diisopropylethylamine (1 mL, 5.4 mmol, 5 eq) and stirred at 100° C. for 6 hours under nitrogen. The mixture was cooled to 25° C. and poured into ice-water (w/w=1/1) (100 mL) and stirred for 5 minutes. The aqueous phase was extracted with ethyl acetate (3×100 mL). The combined organic phase was washed with brine (3×100 mL), dried over anhydrous sodium sulfate, filtered, and concentrated under vacuum. The residue was purified by prep-HPLC (mobile phase: [water (0.225% FA)-ACN]; B %: 15%-45%, 10 min) to afford 2-[[6-[[5-chloro-2-[4-[3-[4-[2-(2,6-dioxo-3-piperidyl)-6-isopropoxy-1,3-dioxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide formate (135 mg, 13%) as a pink solid. MS (ESI) m/z: 952.4 [M+H]+; 1H NMR (400 MHz, DMSO-d6) δ 11.10 (s, 1H), 8.83 (s, 1H), 8.25 (s, 1H), 8.07 (s, 1H), 8.04-7.95 (m, 2H), 7.69 (s, 2H), 7.64 (s, 1H), 7.47 (s, 1H), 7.03 (s, 1H), 5.59-5.19 (m, 1H), 5.14 (dd, J=5.2, 13.2 Hz, 1H), 5.00-4.92 (m, 1H), 4.55 (s, 2H), 4.18-4.13 (m, 3H), 3.55-3.43 (m, 1H), 3.26-3.23 (m, 2H), 3.02 (d, J=10.4 Hz, 2H), 2.94-2.84 (m, 3H), 2.69 (d, J=8.4 Hz, 3H), 2.62-3.57 (m, 2H), 2.22-2.13 (m, 2H), 2.08-1.99 (m, 3H), 1.93-1.76 (m, 6H), 1.72-1.60 (m, 2H), 1.58 (d, J=6.8 Hz, 6H), 1.42-1.37 (m, 2H), 1.58 (d, J=6.0 Hz, 6H).

Compound 160 may be prepared by a procedure analogous to compound 159.

Example 35: Synthesis of 2-{[6-({5-chloro-2-[4-({2-[2-(2,6-dioxopiperidin-3-yl)-1-oxo-2,3-dihydro-1H-isoindol-5-yl]-2,7-diazaspiro[3.5]nonan-7-yl}methyl)piperidin-1-yl]pyrimidin-4-yl}amino)-5-fluoro-2-oxo-1-(propan-2-yl)-1,2-dihydroquinolin-3-yl]oxy}-N-methylacetamide (Compound 161)

Step 1: preparation of 4-fluoro-1-isopropylindole-2,3-dione

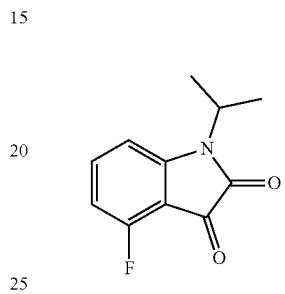

To a stirred solution of DMF (40 mL) was added 4-fluoroindoline-2,3-dione (5 g, 30 mmol, 1 equiv) and NaH (0.87 g, 36 mmol, 1.2 equiv) at 0° C. under nitrogen atmosphere. The resulting mixture was stirred for 1 hour at room temperature under nitrogen atmosphere. To the above mixture was added 2-iodopropane (7.7 g, 45 mmol, 1.5 equiv) dropwise over 5 minutes at 0° C. The resulting mixture was stirred overnight at 40° C. The reaction was cooled to room temperature, adjusted the pH to 5 with HCl. The aqueous layer was extracted with EtOAc (100 mL), the organic layer was concentrated in vacuo. The residue was purified by reverse flash chromatography (mobile phase: MeCN in water (10 mmol/L NH4HCO3), 10% to 50% gradient in 30 min; detector: UV 254 nm) to afford 4-fluoro-1-isopropylindole-2,3-dione (3 g, 47%) as a brown solid. MS (ESI): m/z 208.10.

Step 2: preparation of 5-bromo-4-fluoro-1-isopropylindole-2,3-dione

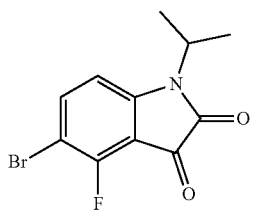 [SMILES: CC(C)N1C(=O)C(=O)c2c1ccc(Br)c2F]

To a stirred solution of 4-fluoro-1-isopropylindole-2,3-dione (2 g, 9.6 mmol, 1 equiv) in MeCN (10 mL) and water (10 mL) was added NBS (2.2 g, 12 mmol, 1.3 equiv) in portions at room temperature. The resulting mixture was stirred overnight at room temperature. The precipitated solids were collected by filtration and washed with water to afford 5-bromo-4-fluoro-1-isopropylindole-2,3-dione (2.1 g, 76%) as a brown solid. MS (ESI): m/z 285.90.

Step 3: preparation of 6-bromo-5-fluoro-3-hydroxy-1-isopropylquinolin-2-one

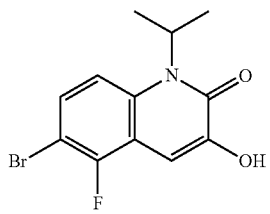

To a stirred solution 5-bromo-4-fluoro-1-isopropylindole-2,3-dione (2.1 g, 7.3 mmol, 1 equiv) and TEA (1.5 g, 14.6 mmol, 2 equiv) in ethanol was added TMSCHN$_2$ (0.84 g, 7.3 mmol, 1 equiv) dropwise at 0° C. under nitrogen atmosphere. The resulting mixture was stirred overnight at room temperature under nitrogen atmosphere, then concentrated under reduced pressure. The residue was purified by silica gel column chromatography (CH$_2$Cl$_2$/PE=8:1) to afford 6-bromo-5-fluoro-3-hydroxy-1-isopropylquinolin-2-one (1.2 g, 54%) as a yellow solid. MS (ESI): m/z 300.25.

Step 4: preparation of 2-({6-[(diphenylmethylidene)amino]-5-fluoro-1-isopropyl-2-oxoquinolin-3-yl}oxy)-N-methylacetamide)

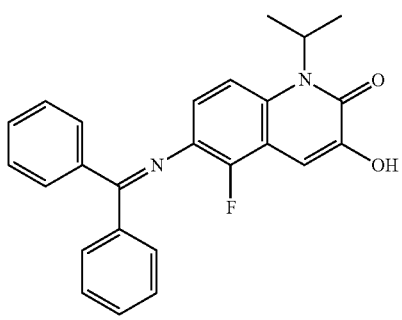 [SMILES: CC(C)n1c(=O)c(O)cc2c(F)c(N=C(c3ccccc3)c3ccccc3)ccc21]

To a solution of 6-bromo-5-fluoro-3-hydroxy-1-isopropylquinolin-2-one (700 mg, 2.3 mmol, 1 equiv) and diphenylmethanimine (422 mg, 2.3 mmol, 1 equiv) in THF (15 mL) were added sodium 2-methylpropan-2-olate (448 mg, 4.6 mmol, 2 equiv), BINAP (290 mg, 0.46 mmol, 0.2 equiv) and Pd$_2$(dba)$_3$ (213. mg, 0.2 mmol, 0.1 equiv). After stirring for overnight at 90° C. under a nitrogen atmosphere, the mixture was concentrated under reduced pressure. The residue was purified by flash column chromatography (PE/EA=10:1) to afford 6-[(diphenylmethylidene)amino]-5-fluoro-3-hydroxy-1-isopropylquinolin-2-one (470 mg, 50%) as a brown solid. MS (ESI): m/z 401.20.

Step 5: preparation of 2-({6-[(diphenylmethylidene)amino]-5-fluoro-1-isopropyl-2-oxoquinolin-3-yl}oxy)-N-methylacetamide

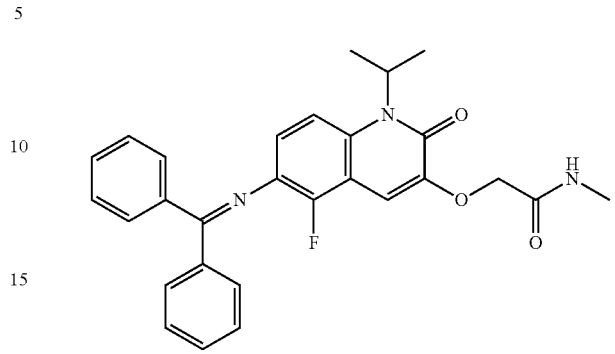

To a stirred solution of 6-[(diphenylmethylidene)amino]-5-fluoro-3-hydroxy-1-isopropylquinolin-2-one (420 mg, 1.0 mmol, 1 equiv) and 2-bromo-N-methylacetamide (159 mg, 1 mmol, 1 equiv) in DMF (2 mL) was added K$_2$CO$_3$ (289 mg, 2 mmol, 2 equiv) in portions at room temperature. The resulting mixture was stirred for 2 hours at room temperature, Then suspended in ice-cold water, the solids were collected by filtration to afford 2-({6-[(diphenylmethylidene)amino]-5-fluoro-1-isopropyl-2-oxoquinolin-3-yl}oxy)-N-methylacetamide (350 mg, 70%) as a brown solid. MS (ESI): m/z 472.15.

Step 6: preparation of 2-[(6-amino-5-fluoro-1-isopropyl-2-oxoquinolin-3-yl)oxy]-N-methylacetamide

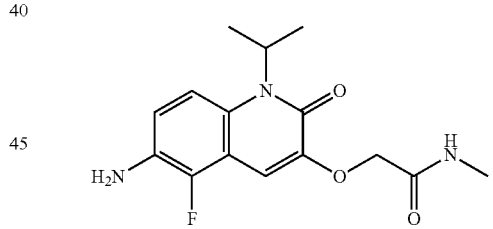

To a stirred solution of 2-({6-[(diphenylmethylidene)amino]-5-fluoro-1-isopropyl-2-oxoquinolin-3-yl}oxy)-N-methylacetamide (350 mg, 0.7 mmol, 1 equiv) and NaOAc (61 mg, 0.7 mmol, 1 equiv) in MeOH (5 mL) was dropwise added hydroxylamine hydrochloride (154 mg, 2.2 mmol, 3 equiv). The resulting mixture was stirred for 2 hours at room temperature. The aqueous layer was extracted with EtOAc. The organic layer was concentrated under reduced pressure. The residue was purified by silica gel column chromatography (CH$_2$Cl$_2$:MeOH=96%) to afford 2-[(6-amino-5-fluoro-1-isopropyl-2-oxoquinolin-3-yl)oxy]-N-methylacetamide (150 mg, 65%) as a brown solid. MS (ESI): m/z 308.20.

Step 7: preparation of 2-({6-[(2,5-dichloropyrimidin-4-yl)amino]-5-fluoro-1-isopropyl-2-oxoquinolin-3-yl}oxy)-N-methylacetamide

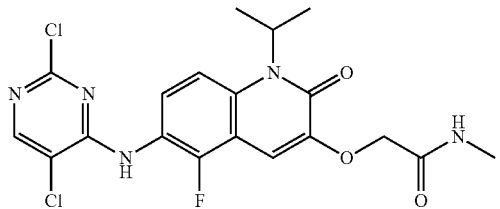 [SMILES: CNC(=O)COc1cc2c(F)c(Nc3nc(Cl)ncc3Cl)ccc2n(C(C)C)c1=O]

Into a 10 mL sealed tube were added 2-[(6-amino-5-fluoro-1-isopropyl-2-oxoquinolin-3-yl)oxy]-N-methylacetamide (320 mg, 1 mmol, 1 equiv) and 2,4,5-trichloropyrimidine (381 mg, 2 mmol, 2 equiv), BuOH (5 mL) and DIEA (0.5 mL). The resulting mixture was stirred overnight at 120° C., then cooled to room temperature and concentrated under reduced pressure. The resulting residue was suspended in PE, filtered and the filter cake was washed with PE to afford 2-({6-[(2,5-dichloropyrimidin-4-yl)amino]-5-fluoro-1-isopropyl-2-oxoquinolin-3-yl}oxy)-N-methylacetamide (420 mg, 88%) as a brown solid. MS (ESI): m/z 454.25.

Step 8: preparation of tert-butyl 7-([1-[(benzyloxy)carbonyl]piperidin-4-yl]methyl)-2,7-diazaspiro[3.5]nonane-2-carboxylate

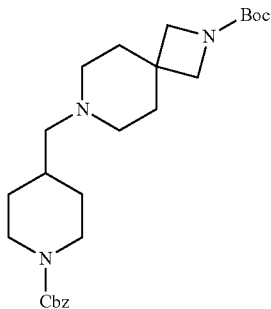 [SMILES: CC(C)(C)OC(=O)N1CC2(CCN(CC3CCN(C(=O)OCc4ccccc4)CC3)CC2)C1]

To a stirred solution of tert-butyl 2,7-diazaspiro[3.5]nonane-2-carboxylate (10.0 g, 44.2 mmol, 1.00 equiv) in DCM (100 mL) was added benzyl 4-formylpiperidine-1-carboxylate (10.93 g, 44.2 mmol, 1.00 equiv) at room temperature under nitrogen atmosphere. The mixture was stirred overnight at 25° C. under nitrogen atmosphere. To the above mixture was added NaBH(OAc)$_3$ (28.1 g, 132.5 mmol, 3.00 equiv). The reaction was stirred for additional 2 hours at room temperature. The resulting mixture was extracted with CH$_2$Cl$_2$ (2×200 mL). The combined organic layers were washed with water (2×200 mL), dried over anhydrous Na$_2$SO$_4$. After filtration, the filtrate solution was concentrated under reduced pressure. The residue was purified by reverse flash chromatography (mobile phase, MeOH in water, 10% to 60% gradient in 20 min; detector, UV 254 nm) to afford tert-butyl 7-([1-[(benzyloxy)carbonyl]piperidin-4-yl]methyl)-2,7-diazaspiro[3.5]nonane-2-carboxylate (20 g, 98%) as a brown oil. MS (ESI): m/z 458.29 [MH$^+$].

Step 9: preparation of benzyl 4-{2,7-diazaspiro[3.5]nonan-7-ylmethyl}piperidine-1-carboxylate

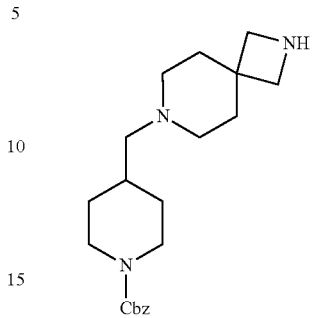

To a stirred solution of tert-butyl 7-({1-[(benzyloxy)carbonyl]piperidin-4-yl}methyl)-2,7-diazaspiro[3.5]nonane-2-carboxylate (5.5 g, 1 equiv) in DCM (60 mL) was added TFA (15 mL) at room temperature. The reaction was stirred overnight at room temperature, then concentrated under reduced pressure. The PH of the residue was adjusted to 8 by the addition of aq. Na$_2$CO$_3$ (10 mL), extracted with DCM (3×100 mL). The combined organic layers were washed with brine (20 mL), filtered, and concentrated under reduced pressure to afford benzyl 4-{2,7-diazaspiro[3.5]nonan-7-ylmethyl}piperidine-1-carboxylate as a yellow solid (3.46 g, 80%). MS (ESI): m/z 357.5 [M+H]$^+$.

Step 10: preparation of benzyl 4-([2-[3-cyano-4-(methoxycarbonyl)phenyl]-2,7-diazaspiro[3.5]nonan-7-yl]methyl)piperidine-1-carboxylate

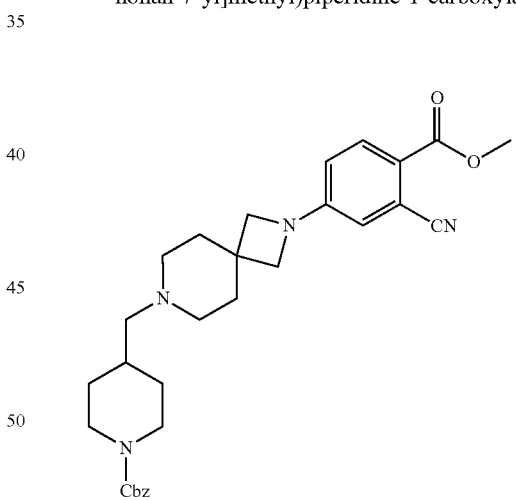

To a stirred mixture of benzyl 4-[2,7-diazaspiro[3.5]nonan-7-ylmethyl]piperidine-1-carboxylate (1.0 g, 2.8 mmol, 1.0 equiv) and methyl 2-cyano-4-fluorobenzoate (0.75 g, 0.004 mmol, 1.5 equiv) in DMSO (10 mL) was added DIEA (1.0 mL). The resulting mixture was stirred for 4 hours at 100° C. under nitrogen atmosphere. Then cooled to room temperature, diluted with water (100 mL), extracted with CH$_2$Cl$_2$ (2×200 mL). The combined organic layers were washed with water (2×100 mL), dried over anhydrous Na$_2$SO$_4$. After filtration, the filtrate solution was concentrated under reduced pressure. The residue was purified by reverse flash chromatography (mobile phase, acetonitrile/NH$_4$HCO$_3$ in water, 10% to 65% gradient in 25 minutes;

detector, UV 254 nm) to afford benzyl 4-([2-[3-cyano-4-(methoxycarbonyl)phenyl]-2,7-diazaspiro[3.5]nonan-7-yl]methyl)piperidine-1-carboxylate (800 mg, 55%) as a yellow solid. MS (ESI): m/z 517.20 [M+H]+.

Step 11: preparation of benzyl 4-([2-[3-formyl-4-(methoxycarbonyl)phenyl]-2,7-diazaspiro[3.5]nonan-7-yl]methyl)piperidine-1-carboxylate

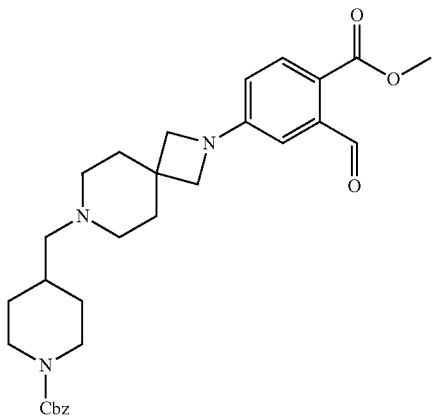 [SMILES: COC(=O)c1ccc(N2CC3(CCN(CC4CCN(C(=O)OCc5ccccc5)CC4)CC3)C2)cc1C=O]

To a stirred solution of benzyl 4-([2-[3-cyano-4-(methoxycarbonyl)phenyl]-2,7-diazaspiro[3.5]nonan-7-yl]methyl)piperidine-1-carboxylate (800.0 mg, 1.5 mmol, 1.0 equiv) in pyridine (40 mL) AcOH (20 mL) and water (20 mL) were added Raney Nickel (454.4 mg, 7.7 mmol, 5.0 equiv) and sodium hypophosphite 1362.3 mg, 15.5 mmol, 10.0 equiv). The resulting mixture was stirred overnight at 70° C., then cooled to room temperature and filtered. The filter cake was washed with CH$_2$Cl$_2$ (2×100 mL), the filtrate solution was concentrated under reduced pressure. The residue was purified by reverse flash chromatography (mobile phase, acetonitrile/NH$_4$HCO$_3$ in water, 10% to 60% gradient in 25 minutes; detector, UV 254 nm) to afford benzyl 4-([2-[3-formyl-4-(methoxycarbonyl)phenyl]-2,7-diazaspiro[3.5]nonan-7-yl]methyl)piperidine-1-carboxylate (400 mg, 50%) as a yellow solid.

Step 12: Preparation of benzyl 4-([2-[2-(2,6-dioxopiperidin-3-yl)-1-oxo-3H-isoindol-5-yl]-2,7-diazaspiro[3.5]nonan-7-yl]methyl)piperidine-1-carboxylate

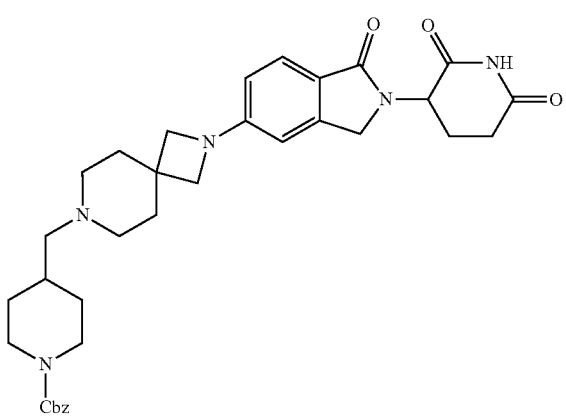 [SMILES: O=C1CCC(N2Cc3cc(N4CC5(CCN(CC6CCN(C(=O)OCc7ccccc7)CC6)CC5)C4)ccc3C2=O)C(=O)N1]

To a stirred solution of benzyl 4-([2-[3-formyl-4-(methoxycarbonyl)phenyl]-2,7-diazaspiro[3.5]nonan-7-yl]methyl)piperidine-1-carboxylate (400.0 mg, 0.8 mmol, 1.0 equiv) in DCE (20 mL)/MeOH (4 mL), HOAc (two drop) was added 3-aminopiperidine-2,6-dione hydrochloride (190.0 mg, 1.2 mmol, 1.5 equiv). The resulting mixture was stirred overnight at 35° C. To the above mixture was added NaBH$_3$CN (145.1 mg, 2.3 mmol, 3 equiv). The reaction was stirred for an additional 2 hours at room temperature, then diluted with water (50 mL), extracted with CH$_2$Cl$_2$ (2×100 mL). The combined organic layers were washed with water (2×100 mL), dried over anhydrous Na$_2$SO$_4$. After filtration, the filtrate solution was concentrated under reduced pressure. The residue was purified by reverse flash chromatography (mobile phase, acetonitrile/water (10 mmol/L) NH$_4$HCO$_3$, 10% to 65% gradient in 25 minutes; detector, UV 254 nm) to afford benzyl 4-([2-[2-(2,6-dioxopiperidin-3-yl)-1-oxo-3H-isoindol-5-yl]-2,7-diazaspiro[3.5]nonan-7-yl]methyl)piperidine-1-carboxylate (270 mg, 58%) as a brown solid. MS (ESI): m/z 600.30 [M+H]+.

Step 13: Preparation of 3-[1-oxo-5-[7-(piperidin-4-ylmethyl)-2,7-diazaspiro[3.5]nonan-2-yl]-3H-isoindol-2-yl]piperidine-2,6-dione

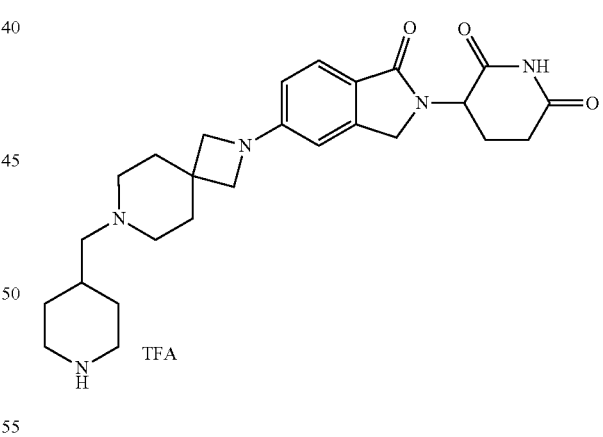

A solution of benzyl 4-([2-[2-(2,6-dioxopiperidin-3-yl)-1-oxo-3H-isoindol-5-yl]-2,7-diazaspiro[3.5]nonan-7-yl]methyl)piperidine-1-carboxylate (270.0 mg, 0.4 mmol, 1.0 equiv) in TFA (5 mL) was stirred for 3 hours at 60° C., then concentrated under reduced pressure to afford 3-[1-oxo-5-[7-(piperidin-4-ylmethyl)-2,7-diazaspiro[3.5]nonan-2-yl]-3H-isoindol-2-yl]piperidine-2,6-dione, trifluoroacetic acid (200 mg, 95%) as a brown oil. MS (ESI): m/z 466.4 [M+H]+.

Step 14: Preparation of 2-{[6-({5-chloro-2-[4-({2-[2-(2,6-dioxopiperidin-3-yl)-1,3-dioxoisoindol-5-yl]-2,7-diazaspiro[3.5]nonan-7-yl}methyl)piperidin-1-yl]pyrimidin-4-yl}amino)-5-fluoro-1-isopropyl-2-oxoquinolin-3-yl]oxy}-N-methylacetamide

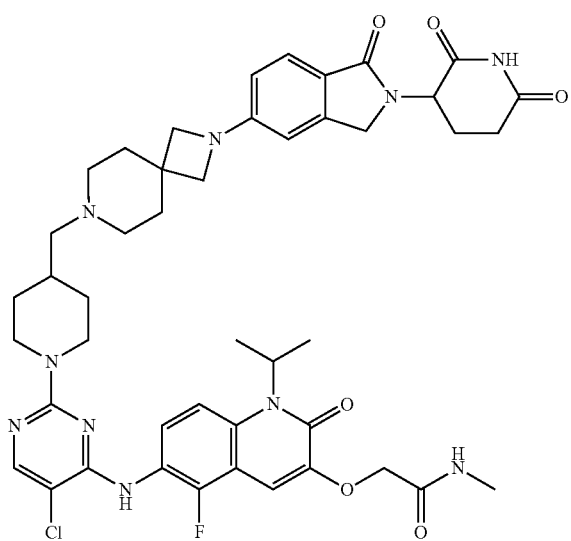 [SMILES: CNC(=O)COc1cc2c(F)c(Nc3nc(N4CCC(CN5CCC6(CC5)CN(c5ccc7c(c5)CN(C5CCC(=O)NC5=O)C7=O)C6)CC4)ncc3Cl)ccc2n(C(C)C)c1=O]

Into a 10 mL sealed tube were added 3-{1-oxo-5-[7-(piperidin-4-ylmethyl)-2,7-diazaspiro[3.5]nonan-2-yl]-3H-isoindol-2-yl}piperidine-2,6-dione (200 mg, 0.4 mmol, 1 equiv) and 2-({6-[(2,5-dichloropyrimidin-4-yl)amino]-5-fluoro-1-isopropyl-2-oxoquinolin-3-yl}oxy)-N-methylacetamide (195 mg, 0.4 mmol, 1 equiv). To the above mixture was added DIEA (0.5 mL) and DMSO (5 mL). The resulting mixture was stirred for additional 5 hours at 100° C. The crude material was purified by reverse flash chromatography (mobile phase, MeCN in water (10 mmol/L NH$_4$HCO$_3$), 10% to 50% gradient in 30 minutes; detector, UV 254 nm) to afford 2-{[6-({5-chloro-2-[4-({2-[2-(2,6-dioxopiperidin-3-yl)-1-oxo-3H-isoindol-5-yl]-2,7-diazaspiro[3.5]nonan-7-yl}methyl)piperidin-1-yl]pyrimidin-4-yl}amino)-5-fluoro-1-isopropyl-2-oxoquinolin-3-yl]oxy}-N-methylacetamide (75.2 mg, 19%) as an off-white solid. $^1$H NMR (400 MHz, DMSO-d6, ppm) 10.09 (s, 1H), 8.69 (s, 1H), 8.01-7.99 (m, 2H), 7.56-7.55 (m, 2H), 7.48-7.45 (m, 1H), 7.12 (s, 1H), 6.50-6.48 (m, 2H), 5.06-5.04 (m, 1H), 5.02-5.01 (m, 1H), 4.60 (s, 2H), 4.33-4.19 (m, 4H), 3.61 (s, 4H), 2.70-2.68 (m, 1H), 2.66-2.60 (m, 5H), 2.50-2.49 (m, 1H), 2.37-2.27 (m, 5H), 2.07-2.00 (m, 2H), 1.95-1.90 (m, 1H), 1.73-1.70 (m, 5H), 1.67-1.60 (m, 2H), 1.57-1.48 (m, 6H), 0.98-0.88 (m, 2H); MS (ESI): m/z 881.45 [M+H]$^+$.

Compound 169 and 171 may be prepared by a procedure analogous to compound 161.
Compounds 172 and 173 may be prepared by procedures analogous to compounds 159 and 161.

Example 36: Synthesis of 2-{[6-({5-chloro-2-[4-({2-[2-(2,6-dioxopiperidin-3-yl)-4-fluoro-1-oxo-2,3-dihydro-1H-isoindol-5-yl]-1,1-dimethyl-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide (Compound 162)

Step 1: preparation of 3-(5-bromo-4-fluoro-1-oxo-3H-isoindol-2-yl)piperidine-2,6-dione

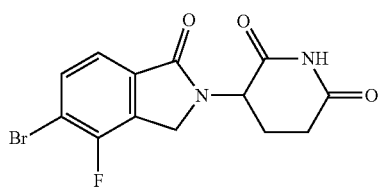 [SMILES: O=C1CCC(N2Cc3c(ccc(Br)c3F)C2=O)C(=O)N1]

To a stirred solution of methyl 4-bromo-2-(bromomethyl)-3-fluorobenzoate (1.15 g, 3.5 mmol, 1 equiv) and 3-aminopiperidine-2,6-dione (0.45 g, 3.5 mmol, 1 equiv) in acetonitrile was added TEA (1 mL) at room temperature under nitrogen atmosphere. The resulting mixture was stirred for overnight at 60° C. under nitrogen atmosphere. Then the resulting mixture was concentrated under vacuum. The resulting residue was stirred for 2 hours at 120° C. under nitrogen atmosphere in acetic acid, then concentrated under vacuum. Ice-water was added to the above mixture. The suspension was filtered, and the filter cake was dried to yield 3-(5-bromo-4-fluoro-1-oxo-3H-isoindol-2-yl)piperidine-2,6-dione (650 mg, 54%) as a brown solid. MS (ESI): m/z 340.95 [M+H]$^+$.

Step 2: preparation of 2-(benzylamino)acetonitrile

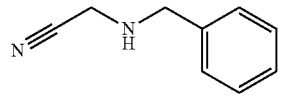 [SMILES: N#CCNCc1ccccc1]

A solution of benzylamine (30 g, 279.9 mmol, 1.00 equiv) and chloroacetonitrile (21 g, 279.9 mmol, 1.0 equiv) in 500 mL acetonitrile was added K$_2$CO$_3$ (46.5 g, 335.8 mmol, 1.2 equiv). The reaction was stirred for 4 hours at 60° C. under air atmosphere. The reaction mixture was concentrated in reduced pressure, the residue was purified by silica gel column chromatography (PE/EA=1:1) to afford 2-(benzylamino)acetonitrile (36.0 g, 88%) as oil. MS (ESI): m/z 147.35 [M+H]$^+$.

Step 3: preparation of tert-butyl 2-benzyl-1-oxo-2,7-diazaspiro[3.5]nonane-7-carboxylate

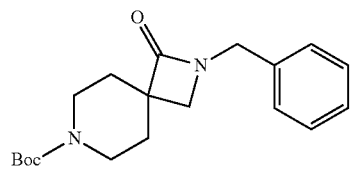 [SMILES: CC(C)(C)OC(=O)N1CCC2(CC1)CN(Cc1ccccc1)C2=O]

In a 1 L round bottom flask, to a solution of 1-tert-butyl 4-ethyl piperidine-1,4-dicarboxylate (68.02 g, 264.3 mmol, 1.0 equiv) in THF (300 mL) was added lithium diisopropylamide (2 M in THF, 247 mL, 2 equiv) dropwise at −78° C. under N₂ atmosphere. The resulting mixture was stirred at −78° C. for 60 minutes, and then dropwise added a solution of 2-{[(3Z)-2-methylidenepent-3-en-1-yl]amino}acetonitrile (36 g, 264.3 mmol, 1.00 equiv) in 100 mL THF. The reaction mixture was stirred for 60 min at −78° C., slowly warmed up to room temperature over 60 minutes period and kept stirring for another 6 hours. The reaction was quenched with NH₄Cl (200 mL), The resulting mixture was extracted with EtOAc (3×200 mL). The combined organic layers were washed with brine (3×100 mL), dried over anhydrous Na₂SO₄. After filtration, the filtrate solution was concentrated under reduced pressure. The residue was purified by silica gel column chromatography, eluted with PE/EA (2:1) to afford tert-butyl 2-benzyl-1-oxo-2,7-diazaspiro[3.5]nonane-7-carboxylate (26.2 g, 32%) as oil. MS (ESI): m/z 331.35 [M+H]⁺.

Step 4: preparation of tert-butyl 2-benzyl-1,1-dimethyl-2,7-diazaspiro[3.5]nonane-7-carboxylate

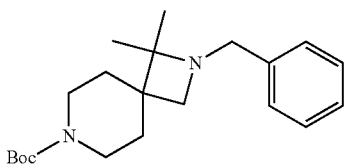 [SMILES: CC(C)(C)OC(=O)N1CCC2(CC1)CN(Cc1ccccc1)C2(C)C]

In a 1-L round bottom flask, to a solution of tert-butyl 2-benzyl-1-oxo-2,7-diazaspiro[3.5]nonane-7-carboxylate (26.2 g, 78.7 mmol, 1.00 equiv) and 2,6-di-tert-butyl-4-methylpyridine (19.54 g, 95.1 mmol, 1.2 equiv) in DCM (500 mL) at room temperature was dropwise added trifluoromethanesulfonic anhydride (26.84 g, 95.1 mmol, 1.2 equiv) at −78° C. under N₂ atmosphere. The resulting mixture was stirred at −78° C. for 45 min, and then dropwise added a solution of MeMgBr (in 3M Et₂O, 28.15 g, 236.0 mmol, 3.0 equiv) in 50 mL DCM. The reaction mixture was stirred for 30 minutes at −78° C., (slowly warmed up to room temperature over 30 min period and kept stirring for another overnight). The reaction was quenched with sat. NH₄Cl (aq.) (100 mL) at room temperature. The resulting mixture was extracted with CH₂Cl₂ (3×200 mL). The combined organic layers were washed with brine (3×100 mL), dried over anhydrous Na₂SO₄. After filtration, the filtrate solution was concentrated under reduced pressure. The residue was purified by reverse flash chromatography (mobile phase, CH₃CN/water (10 mmol/L NH₄HCO₃), 5% to 65% gradient in 30 min; detector, UV 254 nm) to afford tert-butyl 1,1-dimethyl-2,7-diazaspiro[3.5]nonane-7-carboxylate (2.7 g, 10%) as a white solid. MS (ESI): m/z 345.30 [M+H]⁺.

Step 5: preparation of tert-butyl 1,1-dimethyl-2,7-diazaspiro[3.5]nonane-7-carboxylate

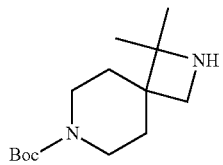 [SMILES: CC(C)(C)OC(=O)N1CCC2(CC1)CNC2(C)C]

To a solution of tert-butyl 2-benzyl-1,1-dimethyl-2,7-diazaspiro[3.5]nonane-7-carboxylate (1.8 g, 5.2 mmol, 1.0 equiv) in 15 mL MeOH was added Pd(OH)₂/C (0.37 g, 2.6 mmol, 0.5 equiv) in a pressure tank. The resulting mixture was stirred at 40° C. under 20 psi of hydrogen pressure for 20 hours, then filtered through a Celite pad and the filtrate solution was concentrated under reduced pressure to get tert-butyl 1,1-dimethyl-2,7-diazaspiro[3.5]nonane-7-carboxylate (1.3 g, 98%) as off-white solid. MS (ESI): m/z 255.35 [M+H]⁺.

Step 6: Preparation of 2-{[6-({5-chloro-2-[4-(dimethoxymethyl)piperidin-1-yl]pyrimidin-4-yl}amino)-1-isopropyl-2-oxoquinolin-3-yl]oxy}-N-methylacetamide

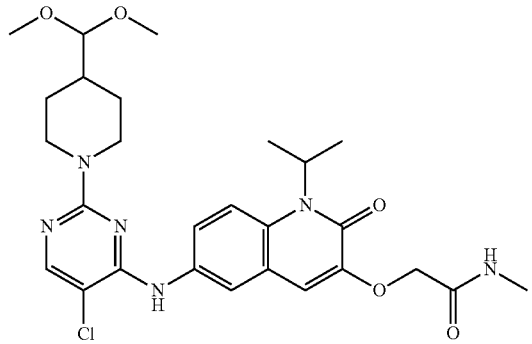

To a stirred mixture of 2-({6-[(2,5-dichloropyrimidin-4-yl)amino]-1-isopropyl-2-oxoquinolin-3-yl}oxy)-N-methylacetamide (2 g, 4.6 mmol, 1.00 equiv) and 4-(dimethoxymethyl)piperidine (1.09 g, 6.9 mmol, 1.5 equiv) in 10 mL DMSO was added DIEA (2.40 mL, 13.8 mmol, 3 equiv). The resulting mixture was stirred for 4 hours at 100° C. under air atmosphere. After that, the reaction was cooled to room temperature, added cold water. The suspension was filtered, the filter cake was washed with water to afford 2-{[6-({5-chloro-2-[4-(dimethoxymethyl)piperidin-1-yl]pyrimidin-4-yl}amino)-1-isopropyl-2-oxoquinolin-3-yl]oxy}-N-methylacetamide (2.45 g, 96%) as a white solid.

Step 7: Preparation of 2-((6-((5-chloro-2-(4-formylpiperidin-1-yl)pyrimidin-4-yl)amino)-1-isopropyl-2-oxo-1,2-dihydroquinolin-3-yl)oxy)-N-methylacetamide

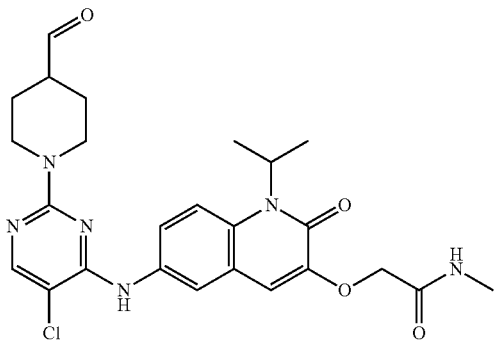

Into a 50-mL round-bottom flask, combined 2-[[6-([5-chloro-2-[4-(dimethoxymethyl)piperidin-1-yl]pyrimidin-4-yl]amino)-1-isopropyl-2-oxoquinolin-3-yl]oxy]-N-methylacetamide (220 mg), water (1.0 mL), TFA (2.0 mL) and DCM (4.0 mL). The resulting mixture was stirred overnight at 40° C. under air atmosphere. Then, the reaction mixture was concentrated under reduced pressure to get 2-[(6-[[5-chloro-2-(4-formylpiperidin-1-yl)pyrimidin-4-yl]amino]-1-isopropyl-2-oxoquinolin-3-yl)oxy]-N-methylacetamide (202 mg) as a yellow oil, which was used in the next step without further purification.

Step 8: Preparation of tert-butyl 2-[2-(2,6-dioxopiperidin-3-yl)-4-fluoro-1-oxo-3H-isoindol-5-yl]-1,1-dimethyl-2,7-diazaspiro[3.5]nonane-7-carboxylate

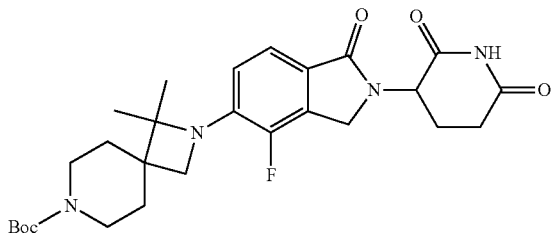 [SMILES: CC(C)(C)OC(=O)N1CCC2(CC1)CN(c1ccc3c(c1F)CN(C1CCC(=O)NC1=O)C3=O)C2(C)C]

To a stirred solution of tert-butyl 1,1-dimethyl-2,7-diazaspiro[3.5]nonane-7-carboxylate (450.0 mg, 1.8 mmol, 1.0 equiv) and 3-(5-bromo-4-fluoro-1-oxo-3H-isoindol-2-yl)piperidine-2,6-dione (603.5 mg, 1.8 mmol, 1.0 equiv) in DMF (5 mL) was added Pd-PEPPSI-IPent$^{Cl}$-o-picoline (148.8 mg, 0.2 mmol, 0.1 equiv) and Cs$_2$CO$_3$ (1729.2 mg, 5.3 mmol, 3.0 equiv). The resulting mixture was stirred for 3 hours at 80° C. under nitrogen atmosphere. The crude material was purified by reverse flash chromatography (column, C18 silica gel; mobile phase, acetonitrile/water (10 mmol/L NH$_4$HCO$_3$), 0% to 65% gradient in 30 minutes; detector, UV 254 nm) to afford tert-butyl 2-[2-(2,6-dioxopiperidin-3-yl)-4-fluoro-1-oxo-3H-isoindol-5-yl]-1,1-dimethyl-2,7-diazaspiro[3.5]nonane-7-carboxylate (420 mg, 45%) as a solid. MS (ESI): m/z 513.25 [M+H]$^+$.

Step 9: Preparation of 3-(5-{1,1-dimethyl-2,7-diazaspiro[3.5]nonan-2-yl}-4-fluoro-1-oxo-3H-isoindol-2-yl)piperidine-2,6-dione

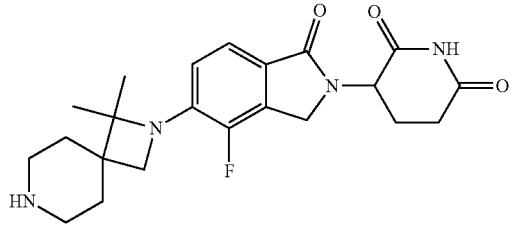 [SMILES: CC1(C)N(c2ccc3c(c2F)CN(C2CCC(=O)NC2=O)C3=O)CC12CCNCC2]

t-Butyl 2-[2-(2,6-dioxopiperidin-3-yl)-4-fluoro-1-oxo-3H-isoindol-5-yl]-1,1-dimethyl-2,7-diazaspiro[3.5]nonane-7-carboxylate (420.0 mg, 0.8 mmol, 1.0 equiv) and TMSOTf (544.2 mg, 2.5 mmol, 3.0 equiv) were taken up in DCM (12 mL) at room temperature. The resulting mixture was stirred for 2 hours, then concentrated under reduced pressure to afford 3-(5-{1,1-dimethyl-2,7-diazaspiro[3.5]nonan-2-yl}-4-fluoro-1-oxo-3H-isoindol-2-yl)piperidine-2,6-dione (362 mg, crude) as a solid. MS (ESI): m/z 415.25 [M+H]$^+$.

Step 10: Preparation of 2-{[6-({5-chloro-2-[4-({2-[2-(2,6-dioxopiperidin-3-yl)-4-fluoro-1-oxo-3H-isoindol-5-yl]-1,1-dimethyl-2,7-diazaspiro[3.5]nonan-7-yl}methyl)piperidin-1-yl]pyrimidin-4-yl}amino)-1-isopropyl-2-oxoquinolin-3-yl]oxy}-N-methylacetamide

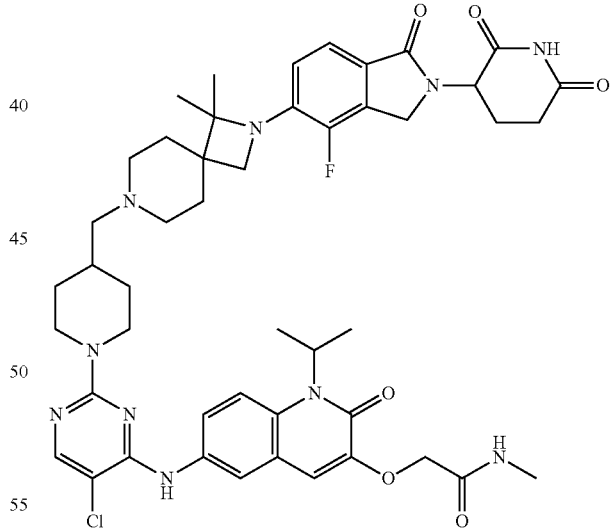

3-(5-{1,1-dimethyl-2,7-diazaspiro[3.5]nonan-2-yl}-4-fluoro-1-oxo-3H-isoindol-2-yl)piperidine-2,6-dione (169.0 mg, 0.4 mmol, 1.0 equiv) and 2-[(6-{[5-chloro-2-(4-formylpiperidin-1-yl)pyrimidin-4-yl]amino}-1-isopropyl-2-oxoquinolin-3-yl)oxy]-N-methylacetamide (209.2 mg, 0.4 mmol, 1.0 equiv) were combined in DCE (15 mL). The resulting mixture was stirred overnight at room temperature under nitrogen atmosphere. Then added NaBH(OAc)$_3$ (259.3 mg, 1.2 mmol, 3.0 equiv) and stirred for another 2 hours at room temperature under nitrogen atmosphere. The reaction was quenched by water (30 mL), the mixture was extracted with CH₂Cl₂/MeOH (10:1, 3×50 mL). The combined organic layers were washed with brine (3×30 mL), dried over anhydrous sodium sulfate, and concentrated under reduced pressure. The residue was purified by reverse flash chromatography (mobile phase, acetonitrile/water (10 mmol/L NH₄HCO₃), 0% to 60% gradient in 30 minutes; detector, UV 254 nm) to afford 2-{[6-({5-chloro-2-[4-({2-[2-(2,6-dioxopiperidin-3-yl)-4-fluoro-1-oxo-3H-isoindol-5-yl]-1,1-dimethyl-2,7-diazaspiro[3.5]nonan-7-yl}methyl)piperidin-1-yl]pyrimidin-4-yl}amino)-1-isopropyl-2-oxoquinolin-3-yl]oxy}-N-methylacetamide (77.6 mg, 21%) as a white solid. ¹H NMR (400 MHz, DMSO-d₆): δ 10.95 (s, 1H), 8.79 (s, 1H), 8.03 (s, 1H), 7.97-7.92 (m, 2H), 7.76-7.65 (m, 2H), 7.35 (d, J=8.2 Hz, 1H), 7.03 (s, 1H), 6.73 (d, J=7.8 Hz, 1H), 5.42-5.10 (m, 1H), 5.04 (d, J=13.2 Hz, 1H), 4.51 (s, 2H), 4.43 (d, J=16.8 Hz, 3H), 4.26 (d, J=16.6 Hz, 1H), 3.66 (s, 2H), 2.83-2.70 (s, 5H), 2.68 (d, J=4.6 Hz, 3H), 2.58 (d, J=17.3 Hz, 1H), 2.35 (s, 1H), 2.10 (s, 2H), 1.88-1.71 (m, 7H), 1.57 (d, J=7.0 Hz, 8H), 1.32 (s, 6H), 1.23 (s, 1H), 1.02 (d, J=12.4 Hz, 2H); MS (ESI) m/z 911.40 [M+H]⁺.

Example 37: Synthesis of 2-({6-[(5-chloro-2-{4-[(1r,3r)-3-{4-[4-chloro-2-(2,6-dioxopiperidin-3-yl)-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 163)

Step 1: preparation of tert-butyl N-[3-(4-pyridyloxy)cyclobutyl] carbamate

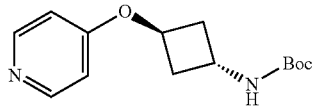 [SMILES: CC(C)(C)OC(=O)N[C@H]1C[C@H](Oc2ccncc2)C1]

To a solution of tert-butyl N-(3-hydroxycyclobutyl)carbamate (28.5 g, 152.2 mmol, 1 eq), pyridin-4-ol (21.71 g, 228.3 mmol, 1.5 eq) and triphenylphosphine (99.81 g, 380.5 mmol, 2.5 eq) in toluene (200 mL) was added di-isopropyl azodicarboxylate (67.71 g, 334.9 mmol, 65.1 mL, 2.2 eq) at 0° C. The reaction solution was stirred at 110° C. for 2 hours, then cooled to 25° C. and concentrated under vacuum. The residue was purified by silica gel column chromatography (petroleum ether/ethyl acetate=10/1 to 0:1) to get the crude product, which was further suspended in petroleum ether/ethyl acetate (3/1, 300 mL), filtered and the filtrate solution was concentrated under vacuum. The residue was purified by prep-HPLC (mobile phase: [water (0.225% FA)-ACN]; B %: 5%-35%, 25 min) to afford tert-butyl N-[3-(4-pyridyloxy)cyclobutyl]carbamate (32.1 g, 79%) as a white solid. MS (ESI) m/z: 265.2 [M+H]⁺; ¹H NMR (400 MHz, DMSO-d₆) δ 8.43-8.29 (m, 2H), 7.31 (br d, J=7.2 Hz, 1H), 6.86-6.74 (m, 2H), 4.93-4.82 (m, 1H), 4.20-3.99 (m, 1H), 2.46-2.25 (m, 4H), 1.38 (s, 9H).

Step 2: preparation of tert-butyl N-[3-(1-benzylpyridin-1-ium-4-yl) oxocyclobutyl]carbamate

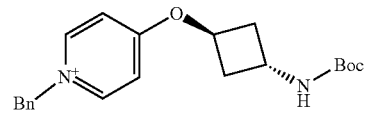 [SMILES: CC(C)(C)OC(=O)N[C@H]1C[C@H](Oc2cc[n+](Cc3ccccc3)cc2)C1]

To a solution of tert-butyl N-[3-(4-pyridyloxy)cyclobutyl] carbamate (32.1 g, 121.4 mmol, 1 eq) in toluene (320 mL) was added benzyl bromide (22.85 g, 133.6 mmol, 15.9 mL, 1.1 eq). The reaction solution was stirred at 80° C. for 12 hours, then cooled to 25° C. and concentrated under vacuum. The residue was triturated with methyl tertiary butyl ether (500 mL) and filtered under vacuum. The filter cake was dissolved with methanol and concentrated under vacuum to afford tert-butyl N-[3-(1-benzylpyridin-1-ium-4-yl)oxycyclobutyl]carbamate (45 g, crude) as a white solid.

Step 3: preparation of tert-butyl N-[3-[(1-benzyl-3,6-dihydro-2H-pyridin-4-yl)oxy]cyclobutyl]carbamate

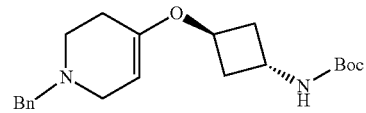 [SMILES: CC(C)(C)OC(=O)N[C@H]1C[C@H](OC2=CCN(Cc3ccccc3)CC2)C1]

To a solution of tert-butyl N-[3-(1-benzylpyridin-1-ium-4-yl)oxycyclobutyl]carbamate (45 g, 126.6 mmol, 1 eq) in ethanol (700 mL) was added sodium borohydride (7.18 g, 189.9 mmol, 1.5 eq) at 0° C. under nitrogen The reaction solution was stirred at 25° C. for 1 hour, then quenched with saturated ammonium chloride solution (200 mL), stirred at 25° C. for 10 minutes and diluted with water (300 mL). The mixture was concentrated under vacuum to remove ethanol, the residue was extracted with ethyl acetate (2×300 mL). The organic layer was washed with brine (2×100 mL). The organic layer was dried over anhydrous sodium sulfate, filtered, and concentrated under vacuum. The residue was purified by silica gel column chromatography (petroleum ether/ethyl acetate=10/1 to 1:2) to afford tert-butyl N-[3-[(1-benzyl-3,6-dihydro-2H-pyridin-4-yl)oxy]cyclobutyl]carbamate (30.5 g, 67%) as a white solid. ¹H NMR (400 MHz, DMSO-d₆) δ 7.32-7.28 (m, 4H), 7.23 (dt, J=2.8, 5.6 Hz, 2H), 4.42 (br t, J=5.6 Hz, 1H), 4.33 (br s, 1H), 4.00-3.93 (m, 1H), 3.50 (s, 2H), 2.85 (br s, 2H), 2.60-2.50 (m, 2H), 2.20 (t, J=6.0 Hz, 4H), 2.05 (br s, 2H), 1.36 (s, 9H).

Step 4: preparation of tert-butyl N-[3-(4-piperidyloxy)cyclobutyl] carbamate

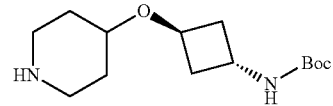 [SMILES: CC(C)(C)OC(=O)N[C@H]1C[C@H](OC2CCNCC2)C1]

To a solution of tert-butyl N-[3-[(1-benzyl-3,6-dihydro-2H-pyridin-4-yl)oxy]cyclobutyl] carbamate (30.5 g, 85.1 mmol, 1 eq) in tetrahydrofuran (400 mL) and ethanol (600 mL) was added 5% palladium on carbon (10 g) and 5% palladium hydroxide on carbon (10 g) under nitrogen. The reaction was stirred at 30° C. under hydrogen (50 Psi) for 24 hours. The mixture was filtered through a pad of celite, the filtrate solution was concentrated under vacuum to afford tert-butyl N-[3-(4-piperidyloxy)cyclobutyl]carbamate (20.41 g, crude) as a light green gum, which was used in the next step without further purification. $^1$H NMR (400 MHz, CDCl$_3$) δ 4.73 (br d, J=1.2 Hz, 1H), 4.31-4.20 (m, 1H), 4.11 (br s, 1H), 3.39-3.24 (m, 1H), 3.07 (td, J=4.0, 12.8 Hz, 2H), 2.65-2.50 (m, 2H), 2.42-2.28 (m, 2H), 2.15 (br dd, J=6.0, 10.8 Hz, 2H), 1.86 (br s, 2H), 1.45-1.37 (m, 11H).

Step 5: preparation of benzyl
4-[3-(tert-butoxycarbonylamino)
cyclobutoxy]piperidine-1-carboxylate

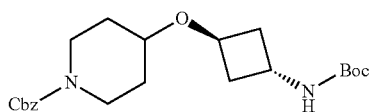 [SMILES: CC(C)(C)OC(=O)N[C@H]1C[C@H](OC2CCN(C(=O)OCc3ccccc3)CC2)C1]

To a solution of tert-butyl N-[3-(4-piperidyloxy)cyclobutyl]carbamate (20.41 g, 75.5 mmol, 1 eq) and benzyl chloroformate (15.45 g, 90.6 mmol, 12.9 mL, 1.2 eq) in tetrahydrofuran (230 mL) was added sodium bicarbonate (1 M, 226.5 mL, 3 eq) at 0° C. The reaction solution was stirred at 25° C. for 12 hours, then diluted with water (15 mL) and extracted with ethyl acetate (20 mL). The organic layer was dried over anhydrous sodium sulfate, filtered, and concentrated under vacuum. The residue was purified by silica gel column chromatography (petroleum ether/ethyl acetate=10/1 to 1:2) to afford benzyl 4-[3-(tert-butoxycarbonylamino)cyclobutoxy]piperidine-1-carboxylate (25.8 g, 84%) as a white solid. $^1$H NMR (400 MHz, 400 MHz, CDCl$_3$) δ 7.38-7.29 (m, 5H), 5.12 (s, 2H), 4.94-4.70 (m, 1H), 4.32-4.17 (m, 1H), 3.97-3.79 (m, 2H), 3.43 (tt, J=4.0, 8.0 Hz, 1H), 3.16 (ddd, J=3.2, 9.6, 13.2 Hz, 2H), 2.47-2.25 (m, 2H), 2.20-2.04 (m, 2H), 1.77 (br dd, J=2.8, 7.6 Hz, 2H), 1.65-1.48 (m, 2H), 1.44 (s, 9H).

Step 6: preparation of benzyl
4-(3-aminocyclobutoxy)piperidine-1-carboxylate

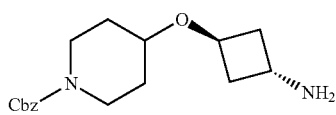 [SMILES: N[C@H]1C[C@H](OC2CCN(C(=O)OCc3ccccc3)CC2)C1]

A solution of benzyl 4-[3-(tert-butoxycarbonylamino)cyclobutoxy]piperidine-1-carboxylate (25.8 g, 63.8 mmol, 1 eq) in hydrogen chloride/methanol (4 M, 230 mL, 14 eq) was stirred at 25° C. for 2 hours. The solution was concentrated under vacuum to afford benzyl 4-(3-aminocyclobutoxy)piperidine-1-carboxylate hydrochloride (21.8 g, crude) as a white solid, which was used in the next step without further purification.

Step 7: preparation of 2-[[6-[[5-chloro-2-[2-[[4-[2-(2,6-dioxo-3-piperidyl)-1,3-dioxo-isoindolin-5-yl]piperazin-1-yl]methyl]-7-azaspiro[3.5]nonan-7-yl]pyrimidin-4-yl]amino]-1-isopropyl-2-oxo-3-quinolyl]oxy]-N-methyl-acetamide

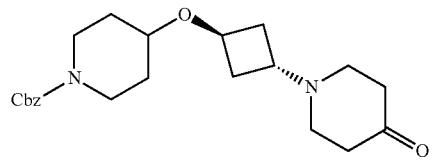 [SMILES: O=C1CCN([C@H]2C[C@H](OC3CCN(C(=O)OCc4ccccc4)CC3)C2)CC1]

To a solution of benzyl 4-(3-aminocyclobutoxy)piperidine-1-carboxylate hydrochloride (21.8 g, 64.0 mmol, 1 eq) and 1,1-dimethyl-4-oxopiperidin-1-ium iodide (27.41 g, 107.4 mmol, 1.7 eq) in ethanol (200 mL) and water (200 mL) was added potassium carbonate (10.96 g, 79.3 mmol, 1.2 eq). The reaction mixture was stirred at 80° C. for 2 hours, then cooled to 25° C. and concentrated under vacuum. The mixture was diluted with water (100 mL) and extracted with ethyl acetate (2×300 mL). The organic layer was washed with brine (2×100 mL), the organic layer was dried over anhydrous sodium sulfate, filtered, and concentrated. The residue was purified by silica gel column chromatography (petroleum ether/ethyl acetate=10/1 to 0:1) to afford benzyl 4-[3-(4-oxo-1-piperidyl)cyclobutoxy]piperidine-1-carboxylate (8.89 g, 36%) as a light yellow gum. MS (ESI) m/z: 405.3 [M+H$_2$O+H]$^+$; $^1$H NMR (400 MHz, CDCl$_3$) δ 7.44-7.29 (m, 5H), 5.13 (s, 2H), 4.22 (br t, J=4.0 Hz, 1H), 3.87 (br d, J=13.2 Hz, 2H), 3.47 (tt, J=4.0, 8.4 Hz, 1H), 3.15 (ddd, J=3.6, 9.6, 13.2 Hz, 2H), 3.08-2.99 (m, 1H), 2.72-2.59 (m, 4H), 2.51-2.42 (m, 4H), 2.40-2.06 (m, 4H), 1.80 (br d, J=2.0 Hz, 2H), 1.58-1.45 (m, 2H).

Step 8: preparation of benzyl 4-[3-(4-hydroxy-1-piperidyl)cyclobutoxy]piperidine-1-carboxylate

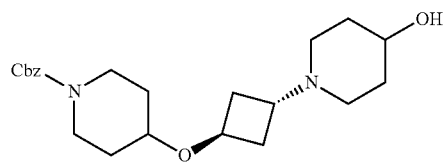 [SMILES: O=C(OCc1ccccc1)N1CCC(O[C@H]2C[C@H](N3CCC(O)CC3)C2)CC1]

To a solution of benzyl 4-[3-(4-oxo-1-piperidyl)cyclobutoxy]piperidine-1-carboxylate (18.9 g, 48.9 mmol, 1 eq) in ethanol (250 mL) was added sodium borohydride (2 g, 52.9 mmol, 1.08 eq) at 0° C. and stirred for 1 hour. The reaction mixture was quenched by the addition of saturated aqueous ammonium chloride (30 mL) at 0° C., then diluted with water 30 mL and extracted with ethyl acetate (3×100 mL). The combined organic layers were washed with brine 50 mL, dried over anhydrous sodium sulfate, filtered, and concentrated under reduced pressure. The residue was purified by preparative reverse phase HPLC (water (0.225% FA)-ACN) to afford benzyl 4-[3-(4-hydroxy-1-piperidyl)cyclobutoxy]piperidine-1-carboxylate formate (18.3 g, 86%) as a colorless oil. $^1$H NMR (400 MHz, CDCl$_3$) δ 7.42-7.29 (m, 5H), 5.13 (s, 2H), 4.19 (br s, 1H), 3.87 (br d, J=11.6 Hz, 2H), 3.81-3.68 (m, 1H), 3.51-3.42 (m, 1H), 3.14

(ddd, J=3.2, 9.6, 13.2 Hz, 2H), 2.99-2.87 (m, 1H), 2.79-2.65 (m, 2H), 2.35-2.02 (m, 5H), 2.04-1.71 (m, 6H), 1.57-1.34 (m, 4H).

Step 9: preparation of benzyl 4-[3-(4-iodo-1-piperidyl)cyclobutoxy] piperidine-1-carboxylate

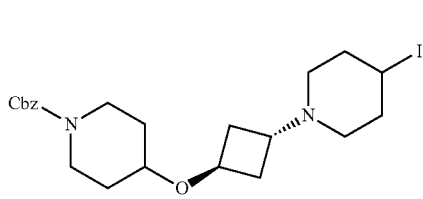 [SMILES: O=C(OCc1ccccc1)N1CCC(O[C@H]2C[C@H](N3CCC(I)CC3)C2)CC1]

A mixture of benzyl 4-[3-(4-hydroxy-1-piperidyl)cyclobutoxy]piperidine-1-carboxylate (1 g, 2.6 mmol, 1 eq), imidazole (526 mg, 7.7 mmol, 3 eq), triphenylphosphine (1.35 g, 5.2 mmol, 2 eq) and iodine (980 mg, 3.9 mmol, 1.5 eq) in toluene (25 mL) was stirred at 120° C. for 2 hours. The reaction mixture was filtered and concentrated under reduced pressure. The residue was purified by preparative reverse phase HPLC (water (0.225% FA)-ACN) to afford benzyl 4-[3-(4-iodo-1-piperidyl) cyclobutoxy]piperidine-1-carboxylate (0.76 g, 59%) as a yellow oil. $^1$H NMR (400 MHz, CDCl$_3$) δ 7.41-7.29 (m, 5H), 5.13 (s, 2H), 4.54-4.01 (m, 2H), 3.91-3.77 (m, 2H), 3.51-3.40 (m, 1H), 3.20-3.10 (m, 2H), 3.02-2.86 (m, 1H), 2.75-2.35 (m, 3H), 2.26-2.07 (m, 7H), 1.79 (br d, J=2.0 Hz, 2H), 1.60-1.48 (m, 4H).

Step 10: preparation of 2-chloro-4-iodo-3-methyl-aniline

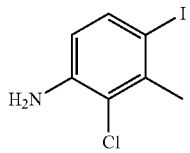

To a solution of 2-chloro-3-methyl-aniline (10 g, 70.6 mmol, 1 eq) in dichloromethane (200 mL) was added 1-iodopyrrolidine-2,5-dione (15.89 g, 70.6 mmol, 1 eq) at 0° C. under nitrogen. The mixture was warmed to 30° C. and stirred for 5 hours. The reaction mixture was poured into ice-water (50 mL) and stirred for 5 minutes. The aqueous phase was extracted with dichloromethane (3×30 mL). The combined organic phase was washed with brine (2×15 mL), dried over anhydrous sodium sulfate, filtered, and concentrated in vacuum. The residue was purified by silica gel chromatography (petroleum ether/ethyl acetate=10/1, 5/1) to afford 2-chloro-4-iodo-3-methyl-aniline (4.8 g, 25%) as a yellow solid. MS (ESI) m/z: 267.7 [M+H]$^+$.

Step 11: Preparation of ethyl 4-amino-3-chloro-2-methyl-benzoate

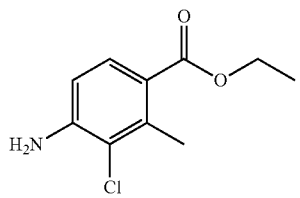

To a solution of 2-chloro-4-iodo-3-methyl-aniline (4.8 g, 17.9 mmol, 1 eq) and triethylamine (3.63 g, 35.9 mmol, 5.0 mL, 2 eq) in ethanol (80 mL) was added bis(triphenylphosphine)palladium(II) dichloride (1.26 g, 1.8 mmol, 0.1 eq) under nitrogen. The suspension was degassed under vacuum and purged with CO several times. Then the mixture was stirred under CO (50 psi) at 80° C. for 16 hours. The reaction mixture was cooled to 20 C and concentrated in reduced pressure at 40° C. The crude product was purified by silica gel chromatography (petroleum ether/ethyl acetate=10:1 to 2/1) to give ethyl 4-amino-3-chloro-2-methyl-benzoate (1.15 g, 30%) as a yellow solid.

Step 12: Preparation of ethyl 4-bromo-3-chloro-2-methyl-benzoate

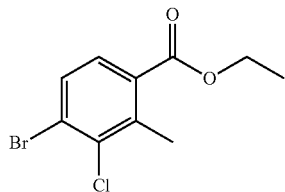

To a mixture of ethyl 4-amino-3-chloro-2-methyl-benzoate (1.2 g, 5.6 mmol, 1 eq) and bromocopper (1.21 g, 8.4 mmol, 1.5 eq) in acetonitrile (50 mL) was added tert-butyl nitrite (1.74 g, 16.8 mmol, 3 eq) in one portion at 0° C. under nitrogen. The mixture was stirred at 25° C. ours for 16 h, then concentrated in reduced pressure. The residue was purified by silica gel chromatography (petroleum ether/ethyl acetate=10/1, 2/1) to afford ethyl 4-bromo-3-chloro-2-methyl-benzoate (1.42 g, crude) as a yellow solid.

Step 13: Preparation of ethyl 4-bromo-2-(bromomethyl)-3-chloro-benzoate

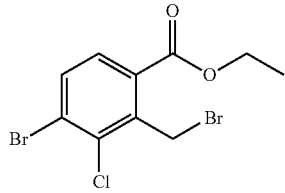

To a mixture of ethyl 4-bromo-3-chloro-2-methyl-benzoate (1.2 g, 4.3 mmol, 1 eq) and NBS (1.15 g, 6.5 mmol, 1.5 eq) in carbon tetrachloride (15 mL) was added AIBN (355 mg, 2.2 mmol, 0.5 eq) in one portion at 80° C. under nitrogen. The mixture was stirred at 80° C. for 16 hours, then cooled to 20° C. and concentrated under reduced pressure. The residue was purified by silica gel chromatography (petroleum ether/ethyl acetate=30/1, 5/1) to afford ethyl 4-bromo-2-(bromomethyl)-3-chloro-benzoate (1.42 g, 92%) as a yellow oil. ¹H NMR (400 MHz, CDCl₃) δ 7.70-7.53 (m, 2H), 5.08 (s, 2H), 4.35 (q, J=7.2 Hz, 2H), 1.35 (t, J=7.2 Hz, 3H)

Step 14: Preparation of tert-butyl 5-amino-4-(5-bromo-4-chloro-1-oxo-isoindolin-2-yl)-5-oxo-pentanoate

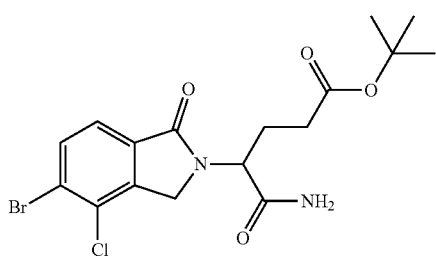 [SMILES: CC(C)(C)OC(=O)CCC(C(N)=O)N1Cc2c(ccc(Br)c2Cl)C1=O]

To a mixture of ethyl 4-bromo-2-(bromomethyl)-3-chloro-benzoate (1.41 g, 4.0 mmol, 1 eq) and tert-butyl 4,5-diamino-5-oxo-pentanoate (960 mg, 4.8 mmol, 1.2 eq) in N,N-dimethylformamide (15 mL) was added N,N-diisopropylethylamine (1.53 g, 11.9 mmol, 3 eq) in one portion at 40° C. The mixture was stirred at 40° C. for 30 minutes, then heated to 100° C. and stirred for 16 hours. The mixture was cooled to 20° C. and concentrated in reduced pressure at 45° C. The residue was purified by silica gel chromatography (petroleum ether/ethyl acetate=10/1 to 0/1) to afford tert-butyl 5-amino-4-(5-bromo-4-chloro-1-oxo-isoindolin-2-yl)-5-oxo-pentanoate (1.51 g, 88%) as a yellow solid. MS (ESI) m/z: 455.3 [M+Na]⁺.

Step 15: Preparation of benzyl 4-[3-[4-[2-(4-tert-butoxy-1-carbamoyl-4-oxo-butyl)-4-chloro-1-oxo-isoindolin-5-yl]-1-piperidyl]cyclobutoxy]piperidine-1-carboxylate

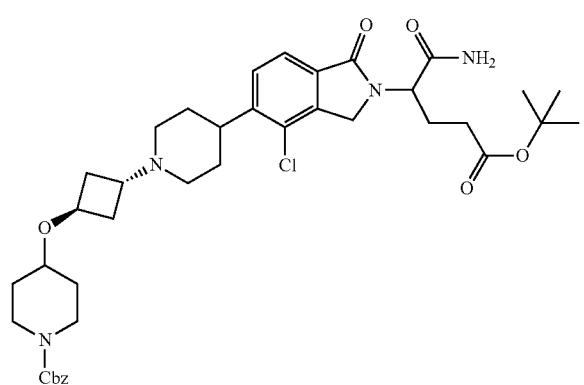 [SMILES: CC(C)(C)OC(=O)CCC(C(N)=O)N1Cc2c(ccc(C3CCN([C@H]4C[C@H](OC5CCN(C(=O)OCc6ccccc6)CC5)C4)CC3)c2Cl)C1=O]

To an 15 mL vial equipped with a stir bar was added tert-butyl 5-amino-4-(5-bromo-4-chloro-1-oxo-isoindolin-2-yl)-5-oxo-pentanoate (285 mg, 0.7 mmol, 1.3 eq), benzyl 4-[3-(4-iodo-1-piperidyl)cyclobutoxy]piperidine-1-car-boxylate (300 mg, 0.6 mmol, 1 eq), Ir[dF(CF₃)ppy]₂(dtbpy)(PF₆) (7 mg, 0.01 mmol, 0.01 eq), nickel(II)(4,4'-di-tert-butyl-2,2'-bipyridine)dichloride (1 mg, 0.003 mmol, 0.005 eq), bis(trimethylsilyl)silyl-trimethylsilane (149 mg, 0.6 mmol, 0.2 mL, 1 eq) and sodium carbonate (127 mg, 1.2 mmol, 2 eq) in 1,2-dimethoxyethane (5 mL) under nitrogen. The vial was sealed and irradiated with a 34 W blue LED lamp (7 cm away), with cooling fan to keep the reaction temperature at 25° C. for 14 hours. The mixture was concentrated under reduced pressure at 45° C. The residue was purified by silica gel chromatography (petroleum ether/ethyl acetate=10/1, 0/1) to afford benzyl 4-[3-[4-[2-(4-tert-butoxy-1-carbamoyl-4-oxo-butyl)-4-chloro-1-oxo-isoindolin-5-yl]-1-piperidyl]cyclobutoxy]piperidine-1-carboxylate (130 mg, 30%) as a yellow solid. MS (ESI) m/z: 723.5 [M+H]⁺.

Step 16: Preparation of benzyl 4-[3-[4-[2-(4-tert-butoxy-1-carbamoyl-4-oxo-butyl)-4-chloro-1-oxo-isoindolin-5-yl]-1-piperidyl]cyclobutoxy]piperidine-1-carboxylate

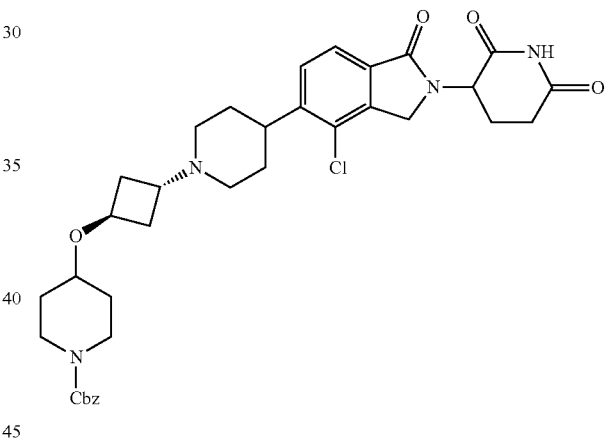

To a mixture of benzyl 4-[3-[4-[2-(4-tert-butoxy-1-carbamoyl-4-oxo-butyl)-4-chloro-1-oxo-isoindolin-5-yl]-1-piperidyl]cyclobutoxy]piperidine-1-carboxylate (250 mg, 0.3 mmol, 1 eq) in acetonitrile (10 mL) was added (1R)-(−)-10-camphor sulfonic acid (401 mg, 1.7 mmol, 5 eq) under nitrogen. Then the reaction was heated to 80° C. for 6 hours. The mixture was cooled to 25° C. and concentrated in reduced pressure at 45° C. The residue was poured into ice-water (50 mL), adjusted pH to 7-8 by solid sodium hydrogen carbonate and stirred for 5 minutes. The aqueous phase was extracted with ethyl acetate (3×50 mL). The combined organic phase was washed with brine (50 mL), dried over anhydrous sodium sulfate, filtered, and concentrated in vacuum. The residue was purified by prep-TLC (dichloromethane:methanol=10:1) to afford benzyl 4-[3-[4-[4-chloro-2-(2,6-dioxo-3-piperidyl)-1-oxo-isoindolin-5-yl]-1-piperidyl]cyclobutoxy]piperidine-1-carboxylate (220 mg, 98%) as a white solid. MS (ESI) m/z: 649.5 [M+H]⁺.

Step 17: Preparation of 3-[4-chloro-1-oxo-5-[1-[3-(4-piperidyloxy) cyclobutyl]-4-piperidyl]isoindolin-2-yl]piperidine-2,6-dione

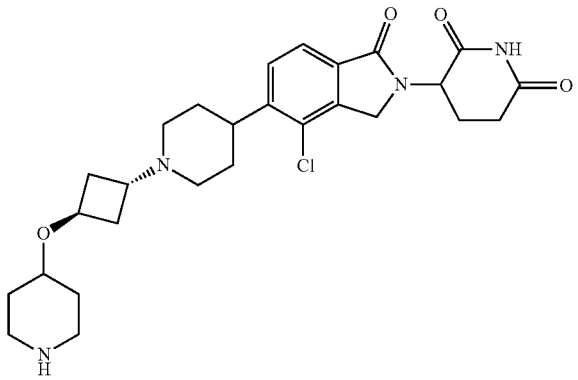 [SMILES: O=C1CCC(N2Cc3c(ccc(C4CCN([C@H]5C[C@H](OC6CCNCC6)C5)CC4)c3Cl)C2=O)C(=O)N1]

To a mixture of benzyl 4-[3-[4-[4-chloro-2-(2,6-dioxo-3-piperidyl)-1-oxo-isoindolin-5-yl]-1-piperidyl]cyclobutoxy]piperidine-1-carboxylate (220 mg, 0.3 mmol, 1.0 eq) in trifluoroacetic acid (2 mL) was added trifluoromethanesulfonic acid (0.1 mL, 1.1 mmol, 3.34 eq) at 0° C. under nitrogen. Then the mixture was warmed to 25° C. and stirred for 30 minutes. The mixture was concentrated under reduced pressure at 45° C. The residue was purified by prep-HPLC (mobile phase: [water (FA)-ACN]; B %: 1%-25%, 10 min) to afford 3-[4-chloro-1-oxo-5-[1-[3-(4-piperidyloxy)cyclobutyl]-4-piperidyl]isoindolin-2-yl]piperidine-2,6-dione formate (120 mg, 63%) as a yellow solid. MS (ESI) m/z: 515.0 [M+H]$^+$.

Step 18: Preparation of 2-[[6-[[5-chloro-2-[4-[3-[4-[4-chloro-2-(2,6-dioxo-3-piperidyl)-1-oxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide

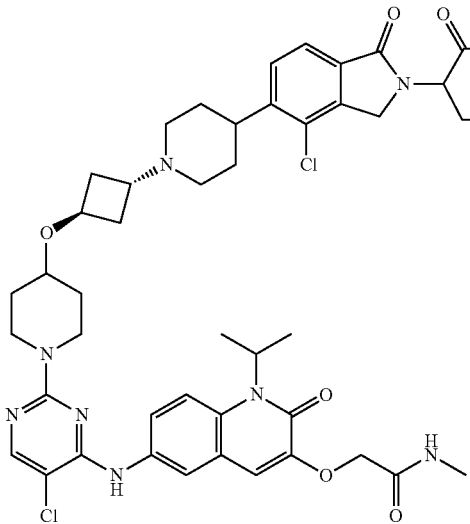

To a mixture of 3-[4-chloro-1-oxo-5-[1-[3-(4-piperidyloxy)cyclobutyl]-4-piperidyl] isoindolin-2-yl]piperidine-2,6-dione formate (120 mg, 0.2 mmol, 1 eq) and 2-[[6-[(2,5-dichloropyrimidin-4-yl)amino]-1-isopropyl-2-oxo-3-quinolyl]oxy]-N-methyl-acetamide (83 mg, 0.2 mmol, 0.9 eq) in (methylsulfinyl)methane (3 mL) was added N,N-diisopropylethylamine (138 mg, 1.1 mmol, 5 eq) at 25° C. under nitrogen. Then the mixture was heated to 100° C. and stirred at 100° C. for 2 hours. The mixture was cooled to 25° C., diluted with dichloromethane (100 mL), washed with brine (3×50 mL), dried over anhydrous sodium sulfate, filtered, and concentrated in vacuum. The residue was purified by prep-HPLC (mobile phase: [water (FA)-ACN]; B %: 10%-40%, 10 min) to afford 2-[[6-[[5-chloro-2-[4-[3-[4-[4-chloro-2-(2,6-dioxo-3-piperidyl)-1-oxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide formate (63.5 mg, 30%) as a white solid. MS (ESI) m/z: 914.4 [M+H]$^+$; $^1$H NMR (400 MHz, DMSO$_6$) δ 11.00 (s, 1H), 8.83 (s, 1H), 8.04 (s, 1H), 7.97-7.95 (m, 2H), 7.70-7.68 (m, 3H), 7.59 (d, J=7.6 Hz, 1H), 7.03 (s, 1H), 5.50-5.24 (m, 1H), 5.15 (dd, J=5.2 Hz, 13.6 Hz, 1H), 4.55 (s, 2H), 4.49 (d, J=17.6 Hz, 1H), 4.32 (d, J=17.6 Hz, 1H), 4.20-4.11 (m, 3H), 3.55-3.45 (m, 1H), 3.27-3.14 (m, 2H), 3.05-3.03 (m, 2H), 2.96-2.87 (m, 2H), 2.69 (d, J=4.8 Hz, 3H), 2.62-2.58 (m, 1H), 2.45-2.42 (m, 1H), 2.20-2.17 (m, 2H), 2.02-2.00 (m, 3H), 1.85-1.66 (m, 8H), 1.58 (d, J=6.8 Hz, 6H), 1.43-1.35 (m, 2H).

Example 38: Synthesis of 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 164)

Step 1: Preparation of benzyl 4-[3-[(1-tert-butoxycarbonyl-4-piperidyl) oxy]cyclobutyl]piperazine-1-carboxylate

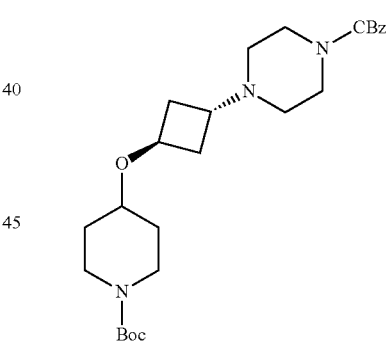

To a solution of benzyl piperazine-1-carboxylate (1 g, 4.5 mmol, 0.9 mL, 1 eq) in dimethyl sulfoxide (2 mL) was added N,N-diisopropylethylamine (1.76 g, 13.6 mmol, 2.37 mL, 3 eq) and tert-butyl 4-[3-(trifluoromethylsulfonyloxy)cyclobutoxy]piperidine-1-carboxylate (1.83 g, 4.5 mmol, 1 eq). The mixture was stirred at 35° C. for 1 hour, then concentrated under reduced pressure. The residue was purified by prep-HPLC (column: Phenomenex luna C18 (250*70 mm, 10 um); mobile phase: [water (0.225% FA)-ACN]; B %: 30%-50%, 15 min) to afford benzyl 4-[3-[(1-tert-butoxycarbonyl-4-piperidyl)oxy]cyclobutyl] piperazine-1-carboxylate (2 g, 93%) as a yellow oil. MS (ESI) m/z: 474.3 [M+1]$^+$; $^1$H NMR (400 MHz, CDCl$_3$) δ 7.42-7.31 (m, 5H), 5.15 (s, 2H), 4.25-4.17 (m, 1H), 3.91-3.76 (m, 2H), 3.59-3.51 (m, 4H), 3.43 (tt, J=4.0, 8.4 Hz, 1H), 3.02 (br s, 2H), 2.92 (br t, J=6.0 Hz, 1H), 2.34 (br s, 4H), 2.21 (td, J=6.0, 12.4 Hz, 2H), 2.11 (dt, J=4.0, 8.4 Hz, 2H), 1.86-1.75 (m, 2H), 1.47 (s, 11H).

Step 2: Preparation of tert-butyl
4-(3-piperazin-1-ylcyclobutoxy)
piperidine-1-carboxylate

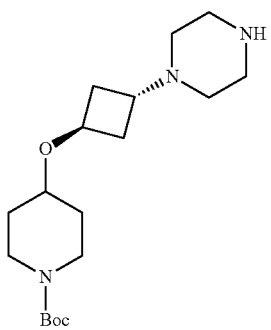

To a solution of benzyl 4-[3-[(1-tert-butoxycarbonyl-4-piperidyl)oxy]cyclobutyl]piperazine-1-carboxylate (2 g, 4.2 mmol, 1 eq) in trifluoroethyl alcohol (10 mL) was added 10% palladium on carbon (100 mg) under nitrogen. The suspension was degassed under vacuum and purged with hydrogen several times. The mixture was stirred under hydrogen (15 psi) at 25° C. for 12 hours, then filtered and concentrated under reduced pressure to afford tert-butyl 4-(3-piperazin-1-ylcyclobutoxy)piperidine-1-carboxylate (1.4 g, 98%) as a yellow oil, which was used in the next step without further purification.

Step 3: Preparation of 5-amino-4-[5-[4-[3-[(1-tert-butoxycarbonyl-4-piperidyl)oxy]cyclobutyl]piperazin-1-yl]-4-fluoro-1-oxo-isoindolin-2-yl]-5-oxo-pentanoic acid

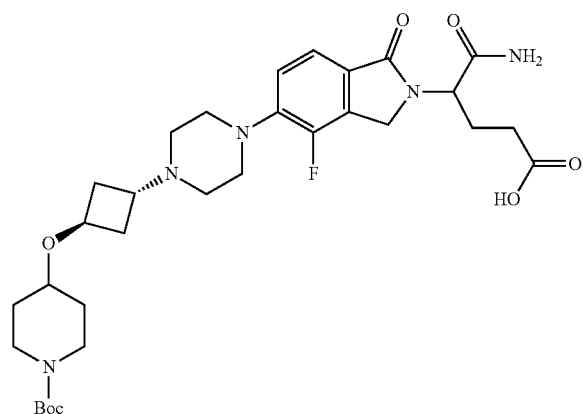 [SMILES: CC(C)(C)OC(=O)N1CCC(O[C@H]2C[C@H](N3CCN(c4ccc5c(c4F)CN(C(CCC(=O)O)C(N)=O)C5=O)CC3)C2)CC1]

To a mixture of 3-(5-bromo-4-fluoro-1-oxo-isoindolin-2-yl)piperidine-2,6-dione (700 mg, 2.1 mmol, 1 eq) and tert-butyl 4-(3-piperazin-1-ylcyclobutoxy)piperidine-1-carboxylate (835 mg, 2.5 mmol, 1.2 eq) in N,N-dimethylformamide (8 mL) was added cesium carbonate (2.01 g, 6.2 mmol, 3 eq) and Pd-PEPPSI-IPent$^{Cl}$-o-picoline (100 mg, 0.1 mmol, 0.05 eq) in one portion at 25° C. under nitrogen. The mixture was stirred at 80° C. for 16 h, then cooled to 20° C. and poured into ice-water (30 mL) and stirred for 5 minutes. The aqueous phase was extracted with ethyl acetate (2×30 mL). The combined organic phase was washed with brine (2×15 mL), dried over anhydrous sodium sulfate, filtered, and concentrated in vacuum. The residue was purified by semi-preparative reverse phase HPLC (TFA condition; mobile phase: [water (0.1% TFA)-ACN]; B %: 20%-50%, 18 min) to afford 5-amino-4-[5-[4-[3-[(1-tert-butoxycarbonyl-4-piperidyl)oxy]cyclobutyl] piperazin-1-yl]-4-fluoro-1-oxo-isoindolin-2-yl]-5-oxo-pentanoic acid (620 mg, 49%) as a yellow solid. MS (ESI) m/z: 618.5 [M+1]$^+$.

Step 4: Preparation of 3-[4-fluoro-1-oxo-5-[4-[3-(4-piperidyloxy) cyclobutyl]piperazin-1-yl]isoindolin-2-yl]piperidine-2,6-dione

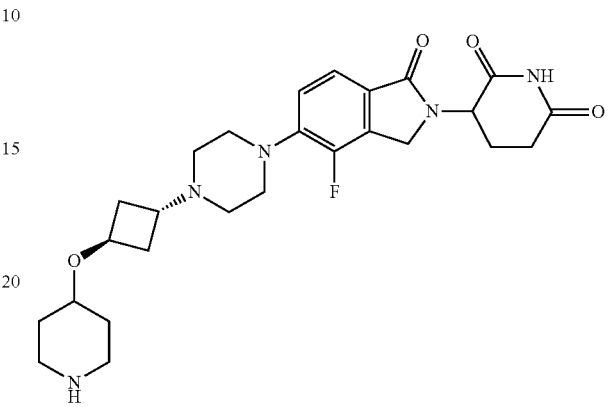

A solution of 5-amino-4-[5-[4-[3-[(1-tert-butoxycarbonyl-4-piperidyl)oxy]cyclobutyl] piperazin-1-yl]-4-fluoro-1-oxo-isoindolin-2-yl]-5-oxo-pentanoic acid (297 mg, 0.5 mmol, 1 eq) and (1R)-(−)-10-camphorsulfonic acid (335 mg, 1.4 mmol, 3 eq) in acetonitrile (13 mL) was stirred at 80° C. for 16 hours. The mixture was concentrated under reduced pressure at 45° C. The residue was purified by semi-preparative reverse phase HPLC (FA condition; mobile phase: [water (0.225% FA)-ACN]; B %: 0%-20%, 7 min) to afford 3-[4-fluoro-1-oxo-5-[4-[3-(4-piperidyloxy)cyclobutyl] piperazin-1-yl]isoindolin-2-yl]piperidine-2,6-dione (160 mg, 67%) as a yellow solid. MS (ESI) m/z: 500.4 [M+1]$^+$.

Step 5: Preparation of 2-[[6-[[5-chloro-2-[4-[3-[7-[2-(2,6-dioxo-3-piperidyl)-1,3-dioxo-isoindolin-5-yl]-2,7-diazaspiro[3.5]nonan-2-yl]cyclobutoxy]-1-piperidyl]pyrimidin-4-yl]amino]-1-isopropyl-2-oxo-3-quinolyl]oxy]-N-methyl-acetamide

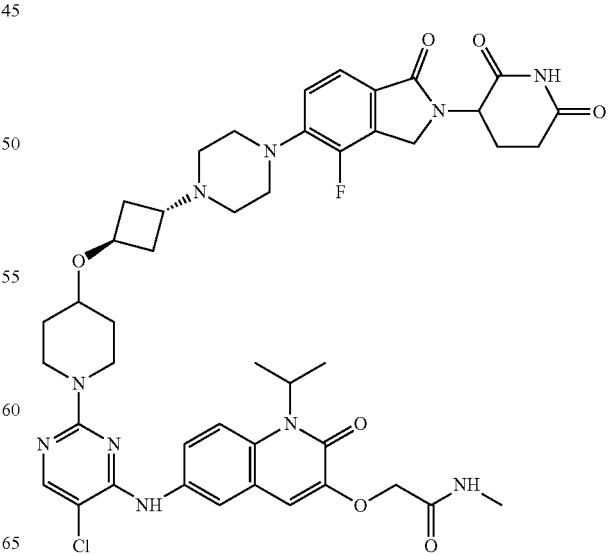

A mixture of 3-[4-fluoro-1-oxo-5-[4-[3-(4-piperidyloxy) cyclobutyl]piperazin-1-yl]isoindolin-2-yl]piperidine-2,6-dione (160 mg, 0.3 mmol, 1 eq), 2-[[6-[(2,5-dichloropyrimidin-4-yl) amino]-1-isopropyl-2-oxo-3-quinolyl]oxy]-N-methyl-acetamide (154 mg, 0.4 mmol, 1.1 eq) and N,N-diisopropylethylamine (0.17 mL, 3 eq) in dimethyl sulfoxide (4 mL) was stirred at 100° C. for 3 hours. The reaction was cooled to room temperature and diluted with water (30 mL), extracted with dichloromethane (3×50 mL). The combined organic layers were washed with brine (30 mL), dried over anhydrous sodium sulfate, filtered, and concentrated under reduced. The residue was purified by semi-preparative reverse phase HPLC (FA condition; mobile phase: [water (0.225% FA)-ACN]; B %: 15%-45%, 7 min) to afford 2-[[6-[[5-chloro-2-[4-[3-[4-[2-(2,6-dioxo-3-piperidyl)-4-fluoro-1-oxo-isoindolin-5-yl]piperazin-1-yl]cyclobutoxy]-1-piperidyl]pyrimidin-4-yl]amino]-1-isopropyl-2-oxo-3-quinolyl]oxy]-N-methyl-acetamide formate (49.5 mg, 16%) as a white solid. MS (ESI) m/z: 899.3 [M+1]$^+$; $^1$H NMR (400 MHz, DMSO-d$_6$) δ 11.00 (s, 1H), 8.85 (s, 1H), 8.17 (s, 1H), 8.04 (s, 2H), 7.95 (s, 1H), 7.69 (s, 2H), 7.49 (d, J=8.0 Hz, 1H), 7.16 (br t, J=8.0 Hz, 1H), 7.04 (s, 1H), 5.08 (dd, J=5.2, 13.2 Hz, 1H), 4.62-4.42 (m, 3H), 4.31 (br d, J=16.8 Hz, 1H), 4.25-4.07 (m, 3H), 3.24 (br d, J=10.8 Hz, 3H), 3.14 (br s, 4H), 2.97-2.80 (m, 3H), 2.68 (d, J=4.8 Hz, 3H), 2.64-2.57 (m, 1H), 2.48-2.32 (m, 5H), 2.25-2.14 (m, 2H), 1.98 (br dd, J=4.8, 7.6 Hz, 3H), 1.89-1.78 (m, 2H), 1.57 (d, J=6.8 Hz, 6H), 1.45-1.30 (m, 2H).

Compounds 175, 176, 178, and 182 may be prepared by a procedure analogous to compound 164.

Example 39: Synthesis of benzyl 4-((1-((1r,4r)-4-(2-(1-amino-5-(tert-butoxy)-1,5-dioxopentan-2-yl)-1-oxoisoindolin-5-yl)cyclohexyl)azetidin-3-yl)oxy) piperidine-1-carboxylate and benzyl 4-((1-((1s,4s)-4-(2-(1-amino-5-(tert-butoxy)-1,5-dioxopentan-2-yl)-1-oxoisoindolin-5-yl)cyclohexyl)azetidin-3-yl) oxy)piperidine-1-carboxylate (Compound 165)

Step 1: Preparation of tert-butyl 3-(pyridin-4-yloxy)azetidine-1-carboxylate

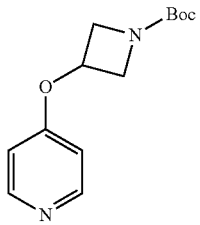 [SMILES: CC(C)(C)OC(=O)N1CC(Oc2ccncc2)C1]

To a solution of pyridin-4-ol (4 g, 42.1 mmol, 1 eq), tert-butyl 3-hydroxyazetidine-1-carboxylate (7.29 g, 42.1 mmol, 1 eq) in tetrahydrofuran (100 mL) was added triphenylphosphine (16.55 g, 63.1 mmol, 1.5 eq) and di-isopropyl azodicarboxylate (12.76 g, 63.1 mmol, 1.5 eq) at 0° C. The mixture was stirred at 80° C. for 12 hours under nitrogen. The reaction was diluted with water (100 mL) and extracted with ethyl acetate (2×150 mL). The combined organic layers were dried over anhydrous sodium sulfate, filtered, and concentrated under reduced pressure. The residue was purified by prep-high performance liquid chromatography (mobile phase: [water (0.225% formic acid)-acetonitrile]; B %: 5%-30%, 25 min) to afford tert-butyl 3-(4-pyridyloxy)azetidine-1-carboxylate (9 g, 79%) as a yellow solid. MS (ESI) m/z: 251.1 [M+H]$^+$; $^1$H NMR (400 MHz, DMSO-d$_6$) δ 8.48-8.32 (m, 2H), 6.94-6.81 (m, 2H), 5.11-5.06 (m, 1H), 4.41-4.27 (m, 2H), 3.88-3.75 (m, 2H), 1.39 (s, 9H).

Step 2: Preparation of tert-butyl 3-(piperidin-4-yloxy)azetidine-1-carboxylate

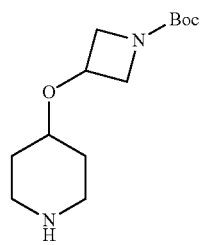 [SMILES: CC(C)(C)OC(=O)N1CC(OC2CCNCC2)C1]

To a solution of tert-butyl 3-(4-pyridyloxy)azetidine-1-carboxylate (8 g, 32.0 mmol, 1 eq) in acetic acid (80 mL) was added platinum dioxide (1.45 g, 6.4 mmol, 0.2 eq) under nitrogen. The suspension was degassed under vacuum and purged with hydrogen several times. The mixture was stirred under hydrogen (50 psi) at 70° C. for 24 hours, then filtered and the filtrate solution was concentrated under reduced pressure to afford tert-butyl 3-(4-piperidyloxy) azetidine-1-carboxylate acetic acid (14 g, crude) as a colorless oil.

Step 3: Preparation of benzyl 4-((1-(tert-butoxycarbonyl)azetidin-3-yl)oxy)piperidine-1-carboxylate

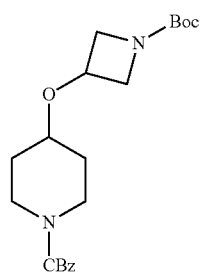

To a solution of tert-butyl 3-(4-piperidyloxy)azetidine-1-carboxylate acetic acid (10 g, 31.6 mmol, 1 eq) in dichloromethane (100 mL) was added triethylamine (15.99 g, 158.0 mmol, 5 eq) at 0° C. and stirred at 0° C. for 15 minutes. Benzyl (2,5-dioxopyrrolidin-1-yl) carbonate (9.45 g, 37.9 mmol, 1.2 eq) in dichloromethane (30 mL) was added at 0° C. and the resulting mixture was stirred at 15° C. for 12 hours. The reaction was diluted with water (60 mL) and extracted with dichloromethane (2×120 mL). The combined organic layers were dried over anhydrous sodium sulfate, filtered, and concentrated under reduced pressure. The residue was purified by flash silica gel chromatography (0-7% ethyl acetate/petroleum ether, 60 mL/min) to afford benzyl 4-(1-tert-butoxycarbonylazetidin-3-yl)oxypiperidine-1-carboxylate (10.3 g, 83%) as a colorless oil. $^1$H NMR (400 MHz, CDCl$_3$) δ 7.44-7.28 (m, 5H), 5.13 (s, 2H), 4.39-4.27 (m, 1H), 4.12-4.10 (m, 2H), 3.84-3.81 (m, 4H), 3.49-3.48 (m, 1H), 3.23-3.16 (m, 2H), 1.78 (s, 2H), 1.57-1.48 (m, 2H), 1.44 (s, 9H).

Step 4: Preparation of benzyl 4-(azetidin-3-yloxy)piperidine-1-carboxylate

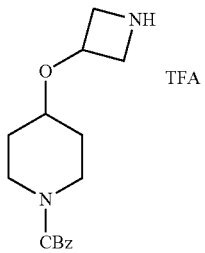

To a solution of benzyl 4-(1-tert-butoxycarbonylazetidin-3-yl)oxypiperidine-1-carboxylate (7.5 g, 19.2 mmol, 1 eq) in dichloromethane (75 mL) was added trifluoroacetic acid (11.55 g, 101.3 mmol, 5.27 eq). The mixture was stirred at 15° C. for 3 hours. The reaction was concentrated under reduced pressure to afford benzyl 4-(azetidin-3-yloxy)piperidine-1-carboxylate trifluoroacetic acid (7.8 g, crude) as a colorless oil, which was used in the next step without further purification. MS (ESI) m/z: 290.8 [M+H]$^+$.

Step 5: Preparation of 4-iodocyclohexanone

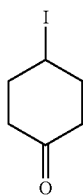

A mixture of 1,4-dioxaspiro[4.5]decan-8-ol (11 g, 69.5 mmol, 1 eq) and imidazole (5.68 g, 83.4 mmol, 1.2 eq), triphenyl phosphine (21.89 g, 83.4 mmol, 1.2 eq) in tetrahydrofuran (150 mL) was cooled to 5° C. under nitrogen. Then to this mixture was added a solution of iodine (21.18 g, 83.4 mmol, 1.2 eq) in tetrahydrofuran (100 mL) while keeping the internal temperature 5-12° C. After the addition was complete, the reaction mixture was warmed to 25° C. and stirred at 25° C. for 6 hours, then diluted with ethyl acetate (200 mL), washed with brine (3×100 mL), dried over anhydrous sodium sulfate, filtered, and concentrated in vacuum. The residue was purified by silica gel chromatography (petroleum ether/ethyl acetate=20/1, 5/1) to afford 4-iodocyclohexanone (1.2 g, 8%) as a yellow oil. $^1$H NMR (400 MHz, CDCl$_3$) δ 4.52 (s, 1H), 2.53-2.50 (m, 2H), 2.32-2.17 (m, 4H), 2.10-2.03 (m, 2H).

Step 6: Preparation of tert-butyl 5-amino-5-oxo-4-[1-oxo-5-(4-oxocyclohexyl)isoindolin-2-yl]pentanoate

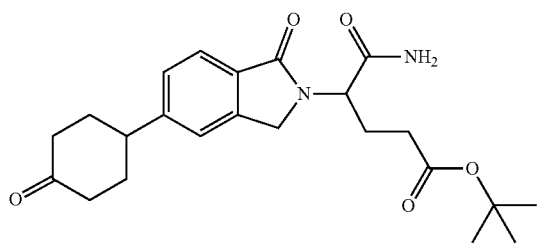 [SMILES: CC(C)(C)OC(=O)CCC(C(N)=O)N1Cc2cc(C3CCC(=O)CC3)ccc2C1=O]

To a 15 mL vial equipped with a stir bar was added tert-butyl 5-amino-4-(5-bromo-1-oxo-isoindolin-2-yl)-5-oxo-pentanoate (2 g, 5.0 mmol, 1 eq), 4-iodocyclohexanone (1.47 g, 6.5 mmol, 1.3 eq), bis[3,5-difluoro-2-[5-(trifluoromethyl)-2-pyridyl]phenyl]iridium (1+); 4-tert-butyl-2-(4-tert-butyl-2-pyridyl)pyridine; hexafluorophosphate (56 mg, 0.05 mmol, 0.01 eq), dichloronickel; 1,2-dimethoxyethane (6 mg, 0.03 mmol, 0.005 eq), bis(trimethylsilyl) silyl-trimethyl-silane (1.25 g, 5.0 mmol, 1.6 mL, 1 eq) and sodium carbonate (1.07 g, 10.1 mmol, 2 eq) in glycol dimethyl ether (20 mL). The vial was sealed under nitrogen. The reaction was stirred and irradiated with a 34 W blue LED lamp (7 cm away), with cooling fan to keep the reaction temperature at 25° C. for 14 hours. Water (20 mL) was added to the mixture and extracted with ethyl acetate (3×20 mL), the combined organic phase washed with brine (20 mL), dried over anhydrous sodium sulfate, filtered, and concentrated under reduced pressure. The residue was purified by column chromatography on silica gel (dichloromethane/methanol=100/1 to 10/1) to afford tert-butyl 5-amino-5-oxo-4-[1-oxo-5-(4-oxocyclohexyl)isoindolin-2-yl]pentanoate (1.4 g, 67%) as a yellow solid. MS (ESI) m/z: 415.9 [M+H]$^+$; $^1$H NMR (400 MHz, CDCl$_3$) δ 7.81 (d, J=7.6 Hz, 1H), 7.40-7.32 (m, 2H), 6.37 (s, 1H), 5.34 (s, 1H), 4.95-4.85 (m, 1H), 4.57-4.50 (m, 1H), 4.47-4.41 (m, 1H), 3.42-3.37 (m, 1H), 3.21-3.10 (m, 1H), 2.59-2.49 (m, 3H), 2.41-2.13 (m, 6H), 2.05-1.89 (m, 2H), 1.42 (s, 9H).

Step 7: Preparation of benzyl 4-((1-((1r,4r)-4-(2-(1-amino-5-(tert-butoxy)-1,5-dioxopentan-2-yl)-1-oxoisoindolin-5-yl)cyclohexyl)azetidin-3-yl)oxy)piperidine-1-carboxylate and benzyl 4-((1-((1s,4s)-4-(2-(1-amino-5-(tert-butoxy)-1,5-dioxopentan-2-yl)-1-oxoisoindolin-5-yl)cyclohexyl)azetidin-3-yl)oxy)piperidine-1-carboxylate

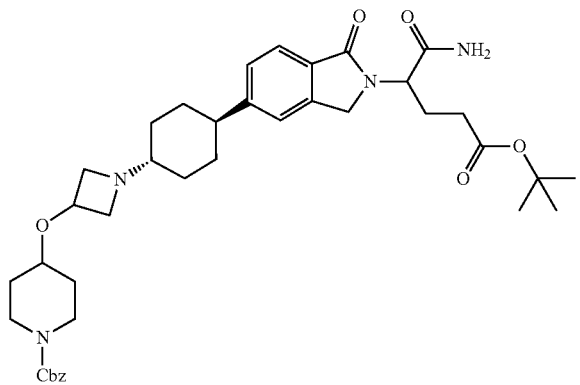

To a solution of benzyl 4-(azetidin-3-yloxy)piperidine-1-carboxylate (975 mg, 3.4 mmol, 1.2 eq) in 1,2-dichloroethane (20 mL) and dimethyl sulfoxide (10 mL) was added 4-methylmorpholine (283 mg, 2.8 mmol, 1 eq) and stirred at 25° C. for 15 minutes. Then tert-butyl 5-amino-5-oxo-4-[1-oxo-5-(4-oxocyclohexyl)isoindolin-2-yl]pentanoate (1.16 g, 2.8 mmol, 1 eq) was added, the mixture was stirred for 0.5 hour at 25° C., after that sodium triacetoxyborohydride (1.78 g, 8.4 mmol, 3 eq) was added and the mixture was stirred at 25° C. for 2 hours. The reaction mixture was quenched with water (20 mL) and extracted with ethyl acetate (3×20 mL). The combined organic phase was washed with brine (20 mL), dried over anhydrous sodium sulfate, filtered, and concentrated in vacuo. The residue was purified by prep-HPLC (mobile phase: [water (0.1% TFA)-ACN]; B %: 25%-55%, 20 min) to afford 2 isomers. The first eluting isomer, tentatively assigned as benzyl 4-((1-((1r,4r)-4-(2-(1-amino-5-(tert-butoxy)-1,5-dioxopentan-2-yl)-1-oxoisoindolin-5-yl)cyclohexyl)azetidin-3-yl)oxy)piperidine-1-carboxylate (550 mg, 29%) was a yellow solid. The second eluting isomer was tentatively assigned as benzyl 4-((1-((1s,4s)-4-(2-(1-amino-5-(tert-butoxy)-1,5-dioxopentan-2-yl)-1-oxoisoindolin-5-yl)cyclohexyl)azetidin-3-yl)oxy)piperidine-1-carboxylate (500 mg, 26%) was also a yellow solid. MS (ESI) m/z: 689.4 [M+H]$^+$; $^1$H NMR (400 MHz, CDCl$_3$) δ 12.16 (s, 1H), 7.79-7.74 (m, 2H), 7.52 (d, J=8.0 Hz, 1H), 7.39-7.31 (m, 5H), 6.31 (s, 1H), 5.29 (s, 1H), 5.13 (s, 2H), 4.88 (dd, J=8.8, 6.4 Hz, 1H), 4.81-4.74 (m, 1H), 4.71-4.64 (m, 2H), 4.47 (d, J=6.4 Hz, 2H), 3.93-3.80 (m, 2H), 3.66-3.53 (m, 3H), 3.41-3.28 (m, 1H), 3.21-3.07 (m, 2H), 2.69-2.56 (m, 1H), 2.44-2.10 (m, 7H), 2.06-1.93 (m, 2H), 1.86-1.72 (m, 6H), 1.43 (s, 9H). $^1$H NMR (400 MHz, CDCl$_3$) δ 7.77 (d, J=8.0 Hz, 1H), 7.45-7.27 (m, 8H), 6.36 (s, 1H), 5.31 (s, 1H), 5.13 (s, 2H), 4.89 (dd, J=8.8, 6.4 Hz, 1H), 4.55-4.46 (m, 1H), 4.45-4.35 (m, 1H), 4.15-4.05 (m, 1H), 3.90-3.80 (m, 2H), 3.57-3.47 (m, 1H), 3.35-3.25 (m, 1H), 3.20-3.10 (m, 2H), 2.72-2.60 (m, 1H), 2.40-2.10 (m, 5H), 2.05-1.90 (m, 5H), 1.85-1.75 (m, 2H), 1.55-1.42 (m, 6H), 1.42 (s, 9H).

Step 8: Preparation of benzyl 4-((1-((1r,4r)-4-(2-(2,6-dioxopiperidin-3-yl)-1-oxoisoindolin-5-yl)cyclohexyl)azetidin-3-yl)oxy)piperidine-1-carboxylate

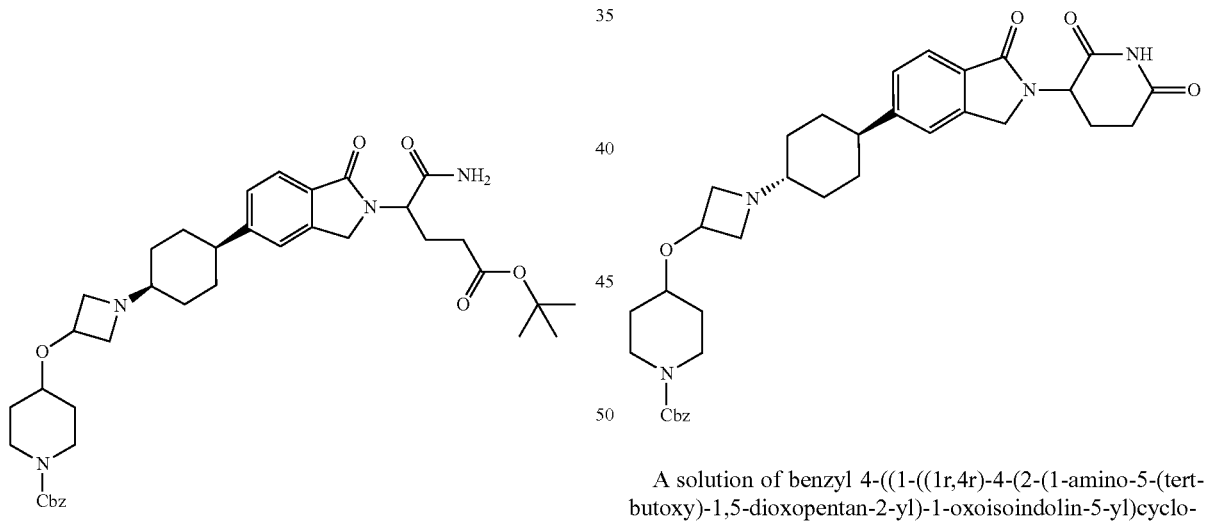

A solution of benzyl 4-((1-((1r,4r)-4-(2-(1-amino-5-(tert-butoxy)-1,5-dioxopentan-2-yl)-1-oxoisoindolin-5-yl)cyclohexyl)azetidin-3-yl)oxy)piperidine-1-carboxylate (550 mg, 0.8 mmol, 1 eq) (1R)-(−)-10-camphorsulfonic acid (927 mg, 4.0 mmol, 5 eq) in acetonitrile (10 mL) was stirred for 12 hours at 80° C. The reaction mixture was quenched with water (20 mL) and extracted with ethyl acetate (3×20 mL). The combined organic phase was washed with brine (20 mL), dried over anhydrous sodium sulfate, filtered, and concentrated in vacuo. The residue was purified by preparative TLC (dichloromethane/methanol=10/1) to afford benzyl 4-((1-((1r,4r)-4-(2-(2,6-dioxopiperidin-3-yl)-1-oxoisoindolin-5-yl)cyclohexyl)azetidin-3-yl)oxy)piperidine-1-carboxylate (300 mg, 61%) as a white solid. MS (ESI) m/z: 615.3 [M+H]$^+$.

Step 9: Preparation of 3-(1-oxo-5-((1r,4r)-4-(3-(piperidin-4-yloxy)azetidin-1-yl)cyclohexyl)isoindolin-2-yl)piperidine-2,6-dione

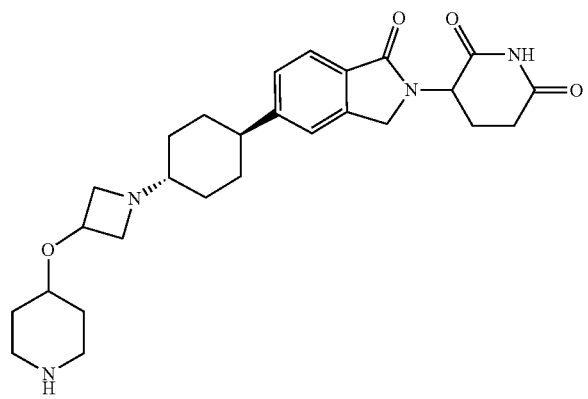 [SMILES: O=C1CCC(N2Cc3cc([C@H]4CC[C@H](N5CC(OC6CCNCC6)C5)CC4)ccc3C2=O)C(=O)N1]

A solution of benzyl 4-((1-((1r,4r)-4-(2-(2,6-dioxopiperidin-3-yl)-1-oxoisoindolin-5-yl)cyclohexyl)azetidin-3-yl)oxy)piperidine-1-carboxylate (120 mg, 0.2 mmol, 1 eq) in trifluoroacetic acid (1 mL) was added trifluoromethanesulfonic acid (85 mg, 0.6 mmol, 2.90 eq) at 0° C. The mixture was stirred for 1 hours at 25° C., then concentrated in vacuo. The residue was purified by prep-HPLC (mobile phase: [water (0.1% TFA)-ACN]; B %: 3%-33%, 7 min) to afford 3-(1-oxo-5-((1r,4r)-4-(3-(piperidin-4-yloxy)azetidin-1-yl)cyclohexyl)isoindolin-2-yl)piperidine-2,6-dione trifluoroacetate (107 mg, 92%) as a white solid. MS (ESI) m/z: 481.3 [M+H]+.

Step 10: Preparation of 2-((6-((5-chloro-2-(4-((1-((1r,4r)-4-(2-(2,6-dioxopiperidin-3-yl)-1-oxoisoindolin-5-yl)cyclohexyl)azetidin-3-yl)oxy)piperidin-1-yl)pyrimidin-4-yl)amino)-1-isopropyl-2-oxo-1,2-dihydroquinolin-3-yl)oxy)-N-methylacetamide

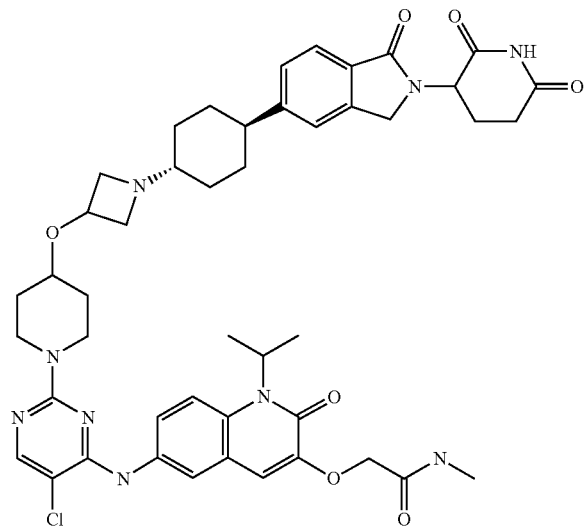

To a solution of 2-[[6-[(2,5-dichloropyrimidin-4-yl)amino]-1-isopropyl-2-oxo-3-quinolyl]oxy]-N-methyl-acetamide (71 mg, 0.2 mmol, 0.9 eq) and 3-(1-oxo-5-((1r,4r)-4-(3-(piperidin-4-yloxy)azetidin-1-yl)cyclohexyl)isoindolin-2-yl)piperidine-2,6-dione trifluoroacetate (107 mg, 0.2 mmol, 1 eq) in dimethyl sulfoxide (3 mL) was added N,N-diisopropylethylamine (70 mg, 0.5 mmol, 3 eq), the mixture was stirred for 2 hours at 120° C., then cooled to room temperature. Water (20 mL) was added to the mixture and extracted with ethyl acetate (3×20 mL), the combined organic phase washed with brine (20 mL), dried over anhydrous sodium sulfate, filtered, and concentrated under reduced pressure. The residue was purified by prep-HPLC (mobile phase: [water (0.225% FA)-ACN]; B %: 15%-35%, 10 min) to afford 2-((6-((5-chloro-2-(4-((1-((1r,4r)-4-(2-(2,6-dioxopiperidin-3-yl)-1-oxoisoindolin-5-yl)cyclohexyl)azetidin-3-yl)oxy)piperidin-1-yl)pyrimidin-4-yl)amino)-1-isopropyl-2-oxo-1,2-dihydroquinolin-3-yl)oxy)-N-methylacetamide (33.8 mg, 21%) as an off-white solid. MS (ESI) m/z: 880.4 [M+H]+; 1H NMR (400 MHz, DMSO-$d_6$) δ 10.98 (s, 1H), 8.83 (s, 1H), 8.04 (s, 1H), 8.00-7.95 (m, 1H), 7.94 (s, 1H), 7.68 (s, 2H), 7.62 (d, J=8.0 Hz, 1H), 7.42 (s, 1H), 7.34 (d, J=8.0 Hz, 1H), 7.02 (s, 1H), 5.50-5.20 (m, 1H), 5.13-5.05 (m, 1H), 4.54 (s, 2H), 4.45-4.37 (m, 1H), 4.32-4.25 (m, 1H), 4.24-4.17 (m, 1H), 4.15-4.07 (m, 2H), 3.63-3.57 (m, 3H), 3.32-3.22 (m, 3H), 2.98-2.85 (m, 1H), 2.75-2.69 (m, 2H), 2.67 (d, J=4.4 Hz, 3H), 2.64-2.56 (m, 2H), 2.44-2.30 (m, 2H), 2.03-1.93 (m, 1H), 1.86-1.73 (m, 4H), 1.72-1.63 (m, 2H), 1.57 (d, J=6.8 Hz, 6H), 1.50-1.44 (m, 3H), 1.42-1.32 (m, 2H).

Example 40: Synthesis of 2-[[6-[[5-chloro-2-[4-[1-[4-[2-(2,6-dioxo-3-piperidyl)-1-oxo-isoindolin-5-yl]cyclohexyl]azetidin-3-yl]oxy-1-piperidyl]pyrimidin-4-yl]amino]-1-isopropyl-2-oxo-3-quinolyl]oxy]-N-methyl-acetamide (Compound 166)

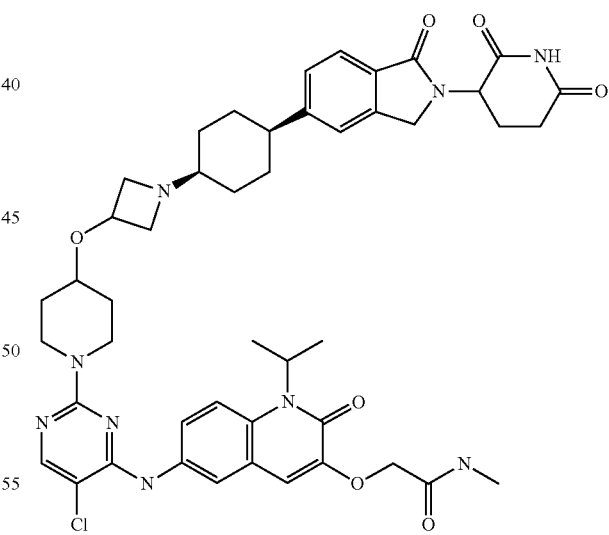

The title compound was prepared analogously to compound 165 by subjecting the second eluting isomer isolated in step 7 to steps 8-10 to afford the title compound as an off-white solid (65.5 mg, 24%). MS (ESI) m/z: 880.4 [M+H]+; 1H NMR (400 MHz, DMSO-$d_6$) δ 10.97 (s, 1H), 8.83 (s, 1H), 8.18 (s, 1H), 8.04 (s, 1H), 7.98-7.90 (m, 2H), 7.74-7.65 (m, 2H), 7.62 (d, J=8.0 Hz, 1H), 7.45 (s, 1H), 7.36 (d, J=8.0 Hz, 1H), 7.02 (s, 1H), 5.53-5.14 (m, 1H), 5.13-5.05 (m, 1H), 4.54 (s, 2H), 4.45-4.37 (m, 1H), 4.31-4.23 (m, 1H), 4.21-4.15 (m, 1H), 4.14-4.06 (m, 2H), 3.62-3.59 (m, 1H), 3.21-3.17 (m, 1H), 2.97-2.85 (m, 2H), 2.84-2.78 (m, 2H), 2.67 (d, J=4.4 Hz, 3H), 2.64-2.56 (m, 3H), 2.45-2.30 (m, 2H), 2.12-2.02 (m, 1H), 2.00-1.95 (m, 1H), 1.87-1.75 (m, 6H), 1.57 (d, J=6.8 Hz, 6H), 1.52-1.42 (m, 2H), 1.40-1.30 (m, 2H), 1.10-0.97 (m, 2H).

Compounds 183, 184, 185, and 186 may be prepared by a procedure analogous to compound 165 and 166.

Example 41: Synthesis of 2-({6-[(5-chloro-2-{4-[(1r,3r)-3-{4-[2-(2,6-dioxopiperidin-3-yl)-4-methyl-1,3-dioxo-2,3-dihydro-1H-isoindol-5-yl]piperidin-1-yl}cyclobutoxy]piperidin-1-yl}pyrimidin-4-yl) amino]-2-oxo-1-(propan-2-yl)-1,2-dihydroquinolin-3-yl}oxy)-N-methylacetamide (Compound 167)

Step 1: preparation of methyl 3-amino-6-iodo-2-methyl-benzoate

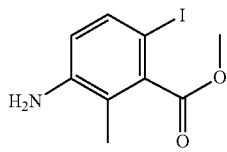

To a solution of methyl 3-amino-2-methyl-benzoate (50 g, 302.7 mmol, 1 eq) in N,N-dimethylformamide (800 mL) was added N-Iodosuccinimide (71.50 g, 317.8 mmol, 1.05 eq) at 0° C., then stirred at 25° C. for 2 hours. The reaction mixture was diluted with 2 L water, then extracted with ethyl acetate (3×1.5 L). The combined organic layers were washed with brine (4×1 L), dried over anhydrous sodium sulfate, filtered, and concentrated. The residue was purified by silica gel column chromatography (petroleum ether/ethyl acetate=10/1 to 3:1) to afford methyl 3-amino-6-iodo-2-methyl-benzoate (82.5 g, 93%) as a brown oil. $^1$H NMR (400 MHz, CDCl$_3$) δ 7.43 (d, J=8.4 Hz, 1H), 6.52 (d, J=8.4 Hz, 1H), 3.95 (s, 3H), 2.12 (s, 3H).

Step 2: preparation of O1-ethyl O2-methyl 4-amino-3-methyl-benzene-1,2-dicarboxylate

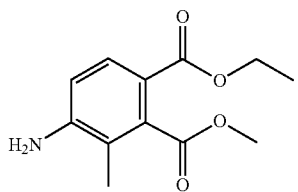 [SMILES: CCOC(=O)c1ccc(N)c(C)c1C(=O)OC]

A mixture of methyl 3-amino-6-iodo-2-methyl-benzoate (41.2 g, 141.5 mmol, 1 eq), triethylamine (42.97 g, 424.6 mmol, 59.1 mL, 3 eq), [1,1'-bis(diphenylphosphino) ferrocene]dichloropalladium(ii) (8.29 g, 11.3 mmol, 0.08 eq) in ethanol (340 mL) and N,N-dimethylformamide (45 mL) was degassed with carbon monoxide several times, the mixture was stirred at 80° C. for 32 hours under carbon monoxide (50 psi) atmosphere. The reaction was cooled to 20° C., filtered through a pad of silica gel (100-200 mesh) and washed with ethyl acetate. The filtrate was diluted with ethyl acetate (2 L). The organic layer was washed with brine (4×1 L), dried over anhydrous sodium sulfate, filtered, and concentrated. The residue was purified by silica gel column chromatography (petroleum ether/ethyl acetate=10/1 to 3:1) to afford O1-ethyl O2-methyl 4-amino-3-methyl-benzene-1,2-dicarboxylate (32.5 g, 96%) as a red oil.

Step 3: preparation of O1-ethyl O2-methyl 4-bromo-3-methyl-benzene-1,2-dicarboxylate

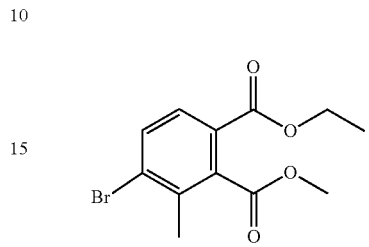

To a solution of O1-ethyl O2-methyl 4-amino-3-methyl-benzene-1,2-dicarboxylate (65 g, 273.9 mmol, 1 eq) and copper(i)bromide (58.95 g, 411.0 mmol, 1.5 eq) in acetonitrile (1300 mL) was added tert-butyl nitrite (84.76 g, 821.9 mmol, 3 eq) at 0° C., then stirred at 25° C. for 12 hours. The reaction mixture was filtered, and the filtered cake was washed with ethyl acetate (3×800 mL). The filtrate solution was washed with saturated ammonium chloride solution (5×1 L). The organic layer was dried over anhydrous sodium sulfate, filtered, and concentrated. The residue was purified by silica gel column chromatography (petroleum ether/ethyl acetate=50/1 to 12:1) to afford O1-ethyl O2-methyl 4-bromo-3-methyl-benzene-1,2-dicarboxylate (53 g, 64%) as a white solid. $^1$H NMR (400 MHz, CDCl$_3$) δ 7.77-7.71 (m, 1H), 7.70-7.64 (m, 1H), 4.35 (q, J=7.2 Hz, 2H), 3.96 (s, 3H), 2.39 (s, 3H), 1.37 (t, J=7.2 Hz, 3H).

Step 4: preparation of O1-ethyl O2-methyl 4-(1-benzyloxycarbonyl-3,6-dihydro-2H-pyridin-4-yl)-3-methyl-benzene-1,2-dicarboxylate

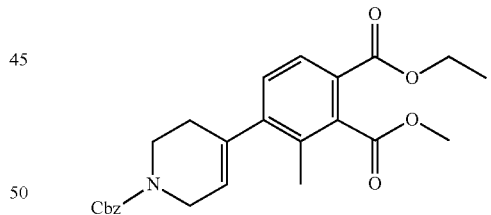

A mixture of benzyl 4-(4,4,5,5-tetramethyl-1,3,2-dioxaborolan-2-yl)-3,6-dihydro-2H-pyridine-1-carboxylate (72.49 g, 211.2 mmol, 1.2 eq), O1-ethyl O2-methyl 4-bromo-3-methyl-benzene-1,2-dicarboxylate (53 g, 176.0 mmol, 1 eq), cesium fluoride (80.20 g, 528.0 mmol, 3 eq), PdCl$_2$(dppf) (8.03 g, 12.3 mmol, 0.07 eq) in dioxane (540 mL) and water (90 mL) was degassed and purged with nitrogen for 3 times, and then the mixture was stirred at 90° C. for 12 hours under nitrogen atmosphere. The reaction mixture was cooled to 25° C., added water (1 L) and extracted with ethyl acetate (3×1 L). The organic layer was washed with brine (3×500 mL), dried over anhydrous sodium sulfate, filtered, and concentrated in vacuum. The residue was purified by silica gel column chromatography (petroleum ether/ethyl acetate=10/1 to 3:1) to afford O1-ethyl O2-methyl 4-(1-benzyloxycarbonyl-3,6-dihydro-2H-pyridin-4-yl)-3-methyl-benzene-1,2-dicarboxylate (78 g, crude) as a brown oil. MS (ESI) m/z: 438.2 [M+H]+; 1H NMR (400 MHz, CDCl3) δ 7.83 (d, J=8.0 Hz, 1H), 7.45-7.30 (m, 5H), 7.17 (d, J=8.0 Hz, 1H), 5.59 (br d, J=11.6 Hz, 1H), 5.20 (s, 2H), 4.35 (q, J=7.2 Hz, 2H), 4.19-4.12 (m, 2H), 3.96 (s, 3H), 3.72 (t, J=5.6 Hz, 2H), 2.33 (br s, 2H), 2.23 (s, 3H), 1.37 (t, J=7.2 Hz, 3H).

Step 5: preparation of O1-ethyl O2-methyl 3-methyl-4-(4-piperidyl) benzene-1,2-dicarboxylate

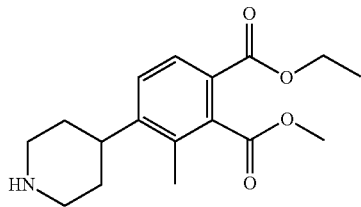 [SMILES: CCOC(=O)c1ccc(C2CCNCC2)c(C)c1C(=O)OC]

To a solution of O1-ethyl O2-methyl 4-(1-benzyloxycarbonyl-3,6-dihydro-2H-pyridin-4-yl)-3-methyl-benzene-1,2-dicarboxylate (39 g, 89.2 mmol, 1 eq) in tetrahydrofuran (400 mL) and 2,2,2-trifluoroethanol (600 mL) was added 10% palladium on carbon (8 g) and 20% palladium hydroxide on carbon (8 g) under nitrogen. The suspension was degassed under vacuum and purged with hydrogen several times. The mixture was stirred under hydrogen (50 psi) at 35° C. for 16 hours, filtered and the filtrate solution was concentrated to afford O1-ethyl O2-methyl 3-methyl-4-(4-piperidyl)benzene-1,2-dicarboxylate (29 g, crude) as a light yellow solid, which was used in the next step without further purification. MS (ESI) m/z: 306.4 [M+H]+; 1H NMR (400 MHz, DMSO-d6) δ 7.78 (d, J=8.0 Hz, 1H), 7.44 (d, J=8.0 Hz, 1H), 4.25 (q, J=7.2 Hz, 2H), 3.91-3.84 (m, 1H), 3.82 (s, 3H), 3.02 (br d, J=12.0 Hz, 2H), 2.91-2.78 (m, 1H), 2.60 (dt, J=2.4, 12.0 Hz, 2H), 2.21 (s, 3H), 1.67-1.57 (m, 2H), 1.55-1.43 (m, 2H), 1.27 (t, J=7.2 Hz, 3H).

Step 6: preparation of O1-ethyl O2-methyl 4-[1-[3-[(1-tert-butoxy carbonyl-4-piperidyl)oxy]cyclobutyl]-4-piperidyl]-3-methyl-benzene-1,2-dicarboxylate

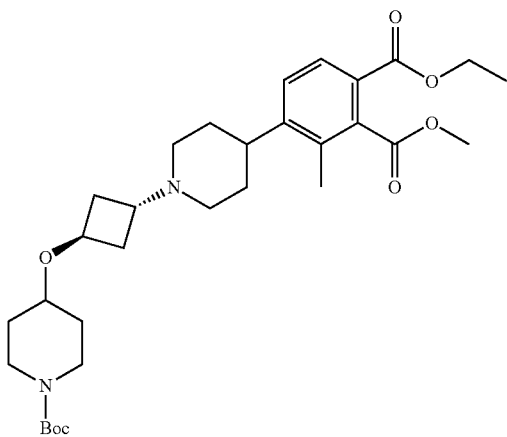 [SMILES: CCOC(=O)c1ccc(C2CCN([C@H]3C[C@H](OC4CCN(C(=O)OC(C)(C)C)CC4)C3)CC2)c(C)c1C(=O)OC]

To a solution of O1-ethyl O2-methyl 3-methyl-4-(4-piperidyl)benzene-1,2-dicarboxylate (19 g, 62.2 mmol, 1 eq) and tert-butyl 4-[3-(trifluoromethylsulfonyloxy)cyclobutoxy]piperidine-1-carboxylate (25.10 g, 62.2 mmol, 1 eq) in acetonitrile (350 mL) was added N,N-diisopropylethylamine (24.12 g, 186.6 mmol, 32.51 mL, 3 eq), then stirred at 25° C. for 30 minutes. The reaction mixture was diluted with 500 mL water, then extracted with ethyl acetate (3×300 mL). The combined organic layers were washed with brine (2×200 mL), dried over anhydrous sodium sulfate, filtered, and concentrated in vacuum. The residue was purified by silica gel column chromatography (petroleum ether/ethyl acetate=10/1 to dichloromethane/methanol=10/1) to afford O1-ethyl O2-methyl 4-[1-[3-[(1-tert-butoxycarbonyl-4-piperidyl)oxy]cyclobutyl]-4-piperidyl]-3-methyl-benzene-1,2-dicarboxylate (29 g, crude) as a brown gum. 1H NMR (400 MHz, CDCl3) δ 7.86 (d, J=8.4 Hz, 1H), 7.40 (d, J=8.4 Hz, 1H), 4.36-4.22 (m, 3H), 3.94 (s, 3H), 3.80 (br d, J=11.6 Hz, 2H), 3.55-3.38 (m, 1H), 3.31 (br d, J=9.6 Hz, 3H), 3.01 (ddd, J=3.2, 10.0, 13.2 Hz, 2H), 2.93-2.81 (m, 1H), 2.48 (br d, J=5.2 Hz, 2H), 2.34-2.16 (m, 7H), 2.01-1.94 (m, 1H), 1.91-1.71 (m, 4H), 1.46-1.41 (m, 12H), 1.35 (t, J=7.2 Hz, 3H).

Step 7: preparation of 4-[1-[3-[(1-tert-butoxycarbonyl-4-piperidyl) oxy]cyclobutyl]-4-piperidyl]-3-methyl-phthalic acid

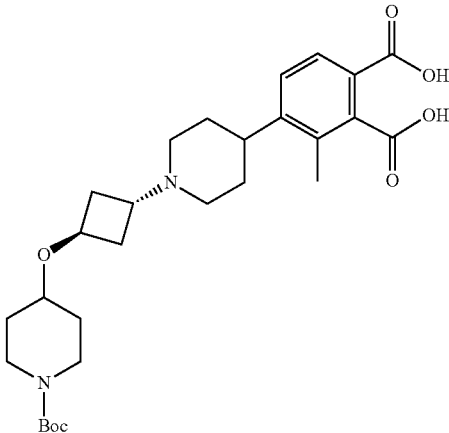 [SMILES: Cc1c(C2CCN([C@H]3C[C@H](OC4CCN(C(=O)OC(C)(C)C)CC4)C3)CC2)ccc(C(=O)O)c1C(=O)O]

To a solution of O1-ethyl O2-methyl 4-[1-[3-[(1-tert-butoxycarbonyl-4-piperidyl)oxy] cyclobutyl]-4-piperidyl]-3-methyl-benzene-1,2-dicarboxylate (36 g, 64.6 mmol, 1 eq) in tetrahydrofuran (120 mL), methanol (120 mL) and water (120 mL) was added potassium hydroxide (36.15 g, 644.4 mmol, 10 eq), then stirred at 60° C. for 16 hours. To the solution was added potassium hydroxide (36.15 g, 644.4 mmol, 10 eq), then stirred at 60° C. for 16 hours. The mixture was cooled to 25° C. and concentrated under reduced pressure at 45° C. to remove most of tetrahydrofuran and methanol. The residue was cooled to −5° C. and adjusted pH to 5-6 by hydrogen chloride (6N) and stirred at −5° C. for 30 minutes. The suspension was filtered, and the filtered cake was dried in vacuum to afford 4-[1-[3-[(1-tert-butoxycarbonyl-4-piperidyl)oxy]cyclobutyl]-4-piperidyl]-3-methyl-phthalic acid (30 g, crude) as a light yellow solid. MS (ESI) m/z: 517.5 [M+H]+.

Step 8: preparation of tert-butyl 4-[3-[4-[2-(2,6-dioxo-3-piperidyl)-4-methyl-1,3-dioxo-isoindolin-5-yl]-1-piperidyl]cyclobutoxy]piperidine-1-carboxylate

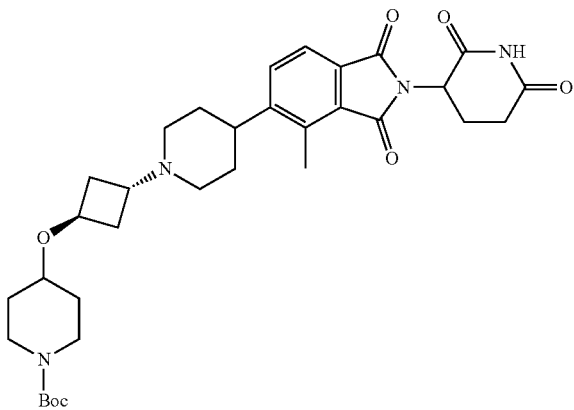 [SMILES: Cc1c(C2CCN([C@H]3C[C@H](OC4CCN(C(=O)OC(C)(C)C)CC4)C3)CC2)ccc2c1C(=O)N(C1CCC(=O)NC1=O)C2=O]

A solution of 3-aminopiperidine-2,6-dione (14.34 g, 87.1 mmol, 1.5 eq, hydrochloride) and 4-[1-[3-[(1-tert-butoxycarbonyl-4-piperidyl)oxy]cyclobutyl]-4-piperidyl]-3-methyl-phthalic acid (30 g, 58.1 mmol, 1 eq) in pyridine (350 mL) was stirred at 125° C. for 12 hours. The reaction mixture was cooled to 25° C. and concentrated under vacuum. The residue was purified by silica gel column chromatography (petroleum ether/ethyl acetate=10/1 to dichloromethane/methanol=10/1) to get the crude product. The crude product was further triturated with t-butyl methyl ether (100 mL), filtered and the filtered cake was dried under vacuum to afford tert-butyl 4-[3-[4-[2-(2,6-dioxo-3-piperidyl)-4-methyl-1,3-dioxo-isoindolin-5-yl]-1-piperidyl]cyclobutoxy]piperidine-1-carboxylate (19.3 g, 54%) as a gray solid. MS (ESI) m/z: 609.6 [M+H]$^+$; $^1$HNMR (400 MHz, DMSO-d$_6$) δ 11.11 (s, 1H), 7.80-7.63 (m, 2H), 5.11 (dd, J=5.2, 12.8 Hz, 1H), 4.19 (br s, 1H), 3.66 (td, J=4.4, 8.8 Hz, 2H), 3.48-3.39 (m, 3H), 3.15 (br d, J=2.4 Hz, 2H), 3.08-2.81 (m, 5H), 2.68 (s, 3H), 2.63-2.54 (m, 2H), 2.44-2.19 (m, 3H), 2.17-1.95 (m, 4H), 1.84-1.65 (m, 6H), 1.39 (s, 9H).

Step 9: preparation of 2-(2,6-dioxo-3-piperidyl)-4-methyl-5-[1-[3-(4-piperidyloxy)cyclobutyl]-4-piperidyl]isoindoline-1,3-dione

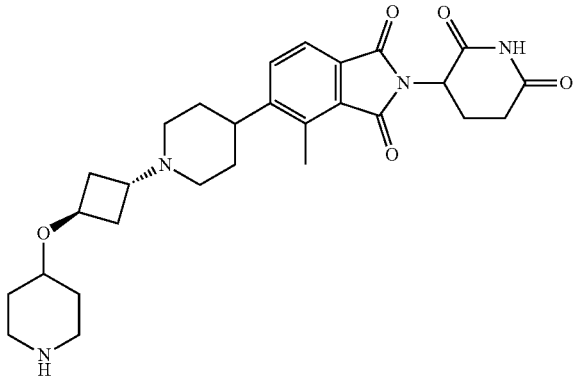 [SMILES: Cc1c(C2CCN([C@H]3C[C@H](OC4CCNCC4)C3)CC2)ccc2c1C(=O)N(C1CCC(=O)NC1=O)C2=O]

To a solution of tert-butyl 4-[3-[4-[2-(2,6-dioxo-3-piperidyl)-4-methyl-1,3-dioxo-isoindolin-5-yl]-1-piperidyl]cyclobutoxy]piperidine-1-carboxylate (10 g, 16.4 mmol, 1 eq) in dichloromethane (150 mL) was added trifluoroacetic acid (46.20 g, 405.2 mmol, 24.66 eq), then stirred at 25° C. for 1 hours. The reaction was concentrated, then the residue was triturated from tert-butyl methyl ether (3×60 mL), filtered and the filtered cake was dried under vacuum to afford 2-(2,6-dioxo-3-piperidyl)-4-methyl-5-[1-[3-(4-piperidyloxy) cyclobutyl]-4-piperidyl]isoindoline-1,3-dione trifluoroacetate (10.2 g, crude) as a gray solid. MS (ESI) m/z: 509.4 [M+H]$^+$.

Step 10: preparation of 2-[[6-[(5-chloro-2-fluoropyrimidin-4-yl)amino]-1-isopropyl-2-oxo-3-quinolyl]oxy]-N-methyl-acetamide

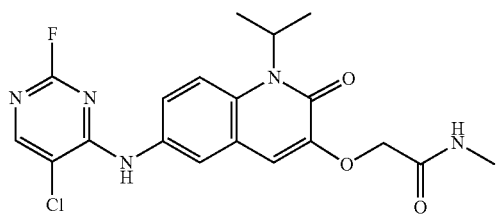 [SMILES: CNC(=O)COc1cc2cc(Nc3nc(F)ncc3Cl)ccc2n(C(C)C)c1=O]

The title compound was prepared analogously to compound 13 following step 6 substituting 2,4,5-trichloropyrimidine with 5-chloro-2,4-difluoro-pyrimidine. MS (ESI) m/z: 420.2 [M+1]$^+$; $^1$H NMR (400 MHz, DMSO-d$_6$) δ 9.70 (s, 1H), 8.38 (s, 1H), 7.95 (br d, J=4.4 Hz, 1H), 7.81-7.69 (m, 2H), 7.61 (dd, J=2.4, 9.2 Hz, 1H), 7.18 (s, 1H), 5.73-5.05 (m, 1H), 4.55 (s, 2H), 2.67 (d, J=4.8 Hz, 3H), 1.57 (d, J=6.8 Hz, 6H.

Step 11: preparation of 2-[[6-[[5-chloro-2-[4-[3-[4-[2-(2,6-dioxo-3-piperidyl)-4-methyl-1,3-dioxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide

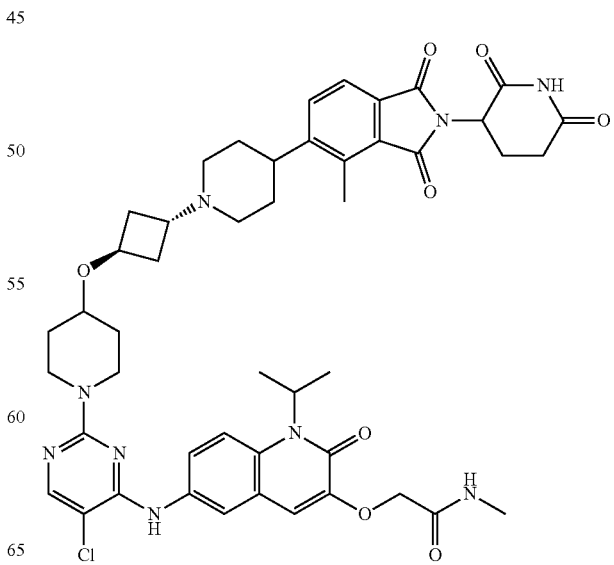

To a solution of 2-(2,6-dioxo-3-piperidyl)-4-methyl-5-[1-[3-(4-piperidyloxy)cyclobutyl]-4-piperidyl]isoindoline-1,3-dione (10.20 g, 16.4 mmol, 1.25 eq, trifluoroacetate) and 2-[[6-[(5-chloro-2-fluoro-pyrimidin-4-yl)amino]-1-isopropyl-2-oxo-3-quinolyl]oxy]-N-methyl-acetamide (5.5 g, 13.1 mmol, 1 eq) in dimethyl sulfoxide (80 mL) was added N,N-diisopropylethylamine (8.47 g, 65.5 mmol, 5 eq). The reaction solution was stirred at 60° C. for 2 hours. To the mixture was added 2-[[6-[(5-chloro-2-fluoro-pyrimidin-4-yl)amino]-1-isopropyl-2-oxo-3-quinolyl]oxy]-N-methyl-acetamide (550 mg, 1.3 mmol, 0.1 eq), the solution was stirred at 60° C. for 4 hours, then cooled to 25° C., diluted with ethyl acetate (1.5 L) and washed with brine (4×500 mL). The organic layer was dried over anhydrous sodium sulfate, filtered, and concentrated under vacuum. The residue was purified by silica gel column chromatography (petroleum ether/ethyl acetate=1/1 to dichloromethane/methanol=10/1) to get the crude product. The crude product was purified by prep-HPLC (mobile phase: [water (TFA)-ACN]; B %: 15%-45%, 19 min). The pH of the resulting solution was adjusted to 8~9 by addition with sodium bicarbonate solid. The water layer was extracted with dichloromethane (3×500 mL). The combined organic layer was washed with aqueous sodium bicarbonate solution (5×400 mL), then water (5×500 mL). The organic layer was dried over anhydrous sodium sulfate, filtered, and concentrated under vacuum. The residue was re-dissolved in acetonitrile (300 mL) and concentrated under vacuum for three times to get rid of residual dichloromethane. The product was dissolved with pure water (300 mL), lyophilized to afford 2-[[6-[[5-chloro-2-[4-[3-[4-[2-(2,6-dioxo-3-piperidyl)-4-methyl-1,3-dioxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide (11.29 g, 84%) as a white solid. MS (ESI) m/z: 908.3 [M+H]$^+$; $^1$H NMR (400 MHz, DMSO-d$_6$) δ 11.11 (s, 1H), 8.83 (s, 1H), 8.04 (s, 1H), 8.00-7.89 (m, 2H), 7.77-7.61 (m, 4H), 7.02 (s, 1H), 5.65-5.21 (m, 1H), 5.11 (dd, J=5.2, 12.8 Hz, 1H), 4.54 (s, 2H), 4.24-4.04 (m, 3H), 3.59-3.45 (m, 1H), 3.22 (br t, J=10.4 Hz, 2H), 2.99 (br d, J=10.4 Hz, 2H), 2.94-2.77 (m, 3H), 2.70-2.63 (m, 6H), 2.61 (br s, 1H), 2.56 (br d, J=9.2 Hz, 1H), 2.20-2.10 (m, 2H), 2.07-1.93 (m, 3H), 1.81 (br t, J=10.0 Hz, 4H), 1.75-1.61 (m, 4H), 1.57 (d, J=6.8 Hz, 6H), 1.43-1.28 (m, 2H).

Example 42: Synthesis of 2-{[6-({5-chloro-2-[4-({2-[2-(2,6-dioxopiperidin-3-yl)-1-oxo-2,3-dihydro-1H-isoindol-5-yl]-2,9-diazadispiro[3.1.5$^6$.1$^4$]dodecan-9-yl}methyl)piperidin-1-yl]pyrimidin-4-yl}amino)-2-oxo-1-(propan-2-yl)-1,2-dihydroquinolin-3-yl]oxy}-N-methylacetamide (Compound 168)

Step 1: Preparation of tert-butyl 2-cyano-7-azaspiro[3.5]nonane-7-carboxylate

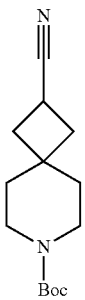

To a stirred mixture of tert-butyl 2-oxo-7-azaspiro[3.5]nonane-7-carboxylate (10 g, 41.8 mmol, 1.00 equiv) and TosMIC (8.97 g, 46.0 mmol, 1.1 equiv) in DME (50 mL) was dropwise added t-BuOK (9.38 g, 83.6 mmol, 2.0 equiv) in Ethanol (50 mL) and DME (50 mL) at 0° C. under N$_2$ atmosphere. The precipitation was collected by filtration and washed with DCM. The filtrate solution was extracted with DCM. The organic layer was washed with brine, dried over anhydrous Na$_2$SO$_4$. After filtration, the filtrate solution was concentrated under reduced pressure. The residue was purified by silica gel column chromatography (PE/EA=3/1) to afford tert-butyl 2-cyano-7-azaspiro[3.5]nonane-7-carboxylate (3.6 g, 34%) as a white solid.

Step 2: Preparation of tert-butyl 2-(chloromethyl)-2-cyano-7-azaspiro[3.5]nonane-7-carboxylate

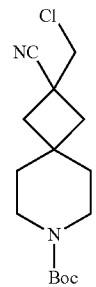 [SMILES: CC(C)(C)OC(=O)N1CCC2(CC1)CC(C#N)(CCl)C2]

To a stirred solution of tert-butyl 2-cyano-7-azaspiro[3.5]nonane-7-carboxylate (3400 mg, 13.6 mmol, 1 equiv) in THF was added LDA (2M THF, 13.6 mL, 127.0 mmol, 9.35 equiv) dropwise at −40° C. under N$_2$ atmosphere, then dropwise added ClCH$_2$I (4.79 g, 27.2 mmol, 2.0 equiv) at −40° C. The resulting mixture was stirred for additional 6 hours at 0° C. The reaction was quenched with NH$_4$Cl (aq.). The aqueous layer was extracted with ethyl acetate. The organic layer was washed with brine, filtered, and concentrated in vacuo. The residue was purified by silica gel column chromatography (PE/EA=1/1) to afford tert-butyl 2-(chloromethyl)-2-cyano-7-azaspiro[3.5]nonane-7-carboxylate (458 mg, 11%) as a light yellow oil.

Step 3: Preparation of tert-butyl 2,9-diazadispiro[3.1.5^{6}.1^{4}]dodecane-9-carboxylate

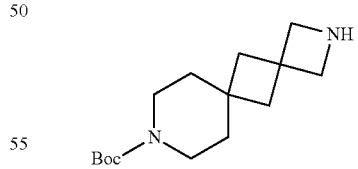

To a stirred solution/mixture of tert-butyl 2-(chloromethyl)-2-cyano-7-azaspiro[3.5]nonane-7-carboxylate (465 mg, 1.6 mmol, 1 equiv) in THF (10 mL) was added LiAlH$_4$ (177.19 mg, 4.7 mmol, 3.00 equiv) in portions at 0° C. under N$_2$ atmosphere. The resulting mixture was stirred for 3 hours at room temperature under N$_2$ atmosphere. The reaction was quenched with water, 15% NaOH, water. The resulting mixture was filtered, the filter cake was washed with DCM. The filtrate solution was concentrated under reduced pressure to afford tert-butyl 2,9-diazadispiro[3.1.5^{6}.1^{4}]

dodecane-9-carboxylate (403 mg, 97%), which was used in the next step without further purification.

Step 4: Preparation of 2-benzyl 9-tert-butyl 2,9-diazadispiro[3.1.5^{6}.1^{4}]dodecane-2,9-dicarboxylate

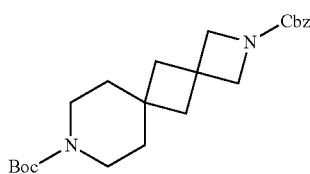 [SMILES: CC(C)(C)OC(=O)N1CCC2(CC1)CC1(CN(C(=O)OCc3ccccc3)C1)C2]

To a stirred solution of tert-butyl 2,9-diazadispiro [3.1.5^{6}.1^{4}]dodecane-9-carboxylate (403 mg, 1.5 mmol, 1 equiv) and triethylamine (459 mg, 4.5 mmol, 3.0 equiv) in DCM (10 mL) was added benzyl chloroformate (387 mg, 2.3 mmol, 1.5 equiv) dropwise at room temperature under $N_2$ atmosphere. The resulting mixture was stirred for 3 hours at room temperature under $N_2$ atmosphere. Then the reaction was extracted with DCM. The organic layer was washed with brine, dried over anhydrous $Na_2SO_4$. After filtration, the filtrate solution was concentrated under reduced pressure. The residue was purified by reverse phase flash chromatography (mobile phase, acetonitrile in water, 10% to 50% gradient in 30 min; detector, UV 254 nm) to afford 2-benzyl 9-tert-butyl 2,9-diazadispiro [3.1.5^{6}.1^{4}]dodecane-2,9-dicarboxylate (160 mg, 26%) as a yellow oil. MS (ESI): m/z 401.15 [M+H]$^+$.

Step 5: Preparation of tert-butyl 2,9-diazadispiro [3.1.5^{6}.1^{4}]dodecane-9-carboxylate

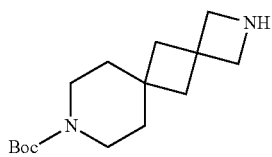 [SMILES: CC(C)(C)OC(=O)N1CCC2(CC1)CC1(CNC1)C2]

To a solution of 2-benzyl 9-tert-butyl 2,9-diazadispiro [3.1.5^{6}.1^{4}]dodecane-2,9-dicarboxylate (160 mg, 0.4 mmol, 1 equiv) in isopropyl alcohol (5 mL, 83.2 mmol, 208 equiv) was added Pd(OH)$_2$/C (80 mg, 0.6 mmol, 1.4 equiv) under nitrogen atmosphere. The mixture was hydrogenated at room temperature for 5 hours under hydrogen atmosphere using a hydrogen balloon. Then the mixture was filtered through a Celite pad and the filtrate solution was concentrated under reduced pressure to afford tert-butyl 2,9-diazadispiro[3.1.5^{6}.1^{4}]dodecane-9-carboxylate (110 mg, crude) as a yellow oil.

Step 6: Preparation of tert-butyl 2-[2-(2,6-dioxopiperidin-3-yl)-1-oxo-3H-isoindol-5-yl]-2,9-diazadispiro[3.1.5^{6}.1^{4}]dodecane-9-carboxylate

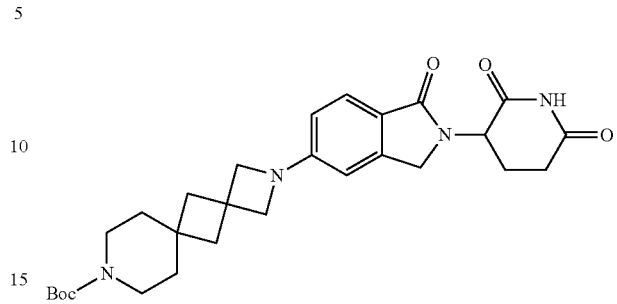

Into a microwave tube were added tert-butyl 2,9-diazadispiro[3.1.5^{6}.1^{4}]dodecane-9-carboxylate (197.0 mg, 0.7 mmol, 1.0 equiv), 3-(5-bromo-1-oxo-3H-isoindol-2-yl)piperidine-2,6-dione (262.8 mg, 0.8 mmol, 1.1 equiv), $Cs_2CO_3$ (602.4 mg, 1.9 mmol, 2.5 equiv) and Pd-PEPPSI-IPentCl 2-methylpyridine (o-picoline (62.2 mg, 0.1 mmol, 0.1 equiv) in DMF (5.0 mL) at room temperature. The resulting mixture was stirred for 6 hours at 80° C. under $N_2$ atmosphere. Then the reaction was suspended in EtOAc. The resulting mixture was filtered, the filter cake was washed with EtOAc. The filtrate solution was concentrated under reduced pressure. Then residue was purified by reverse flash chromatography (mobile phase, acetonitrile in water, 5% to 50% gradient in 10 min; detector, UV 254 nm) to afford tert-butyl 2-[2-(2,6-dioxopiperidin-3-yl)-1-oxo-3H-isoindol-5-yl]-2,9-diazadispiro[3.1.5^{6}.1^{4}]dodecane-9-carboxylate (181.0 mg, 48%) as a light yellow solid. MS (ESI): m/z 509.20 [M+H]$^+$.

Step 7-8: Preparation of 2-{[6-({5-chloro-2-[4-({2-[2-(2,6-dioxopiperidin-3-yl)-1-oxo-3H-isoindol-5-yl]-2,9-diazadispiro[3.1.5^{6}.1^{4}]dodecan-9-yl}methyl)piperidin-1-yl]pyrimidin-4-yl}amino)-1-isopropyl-2-oxoquinolin-3-yl]oxy}-N-methylacetamide

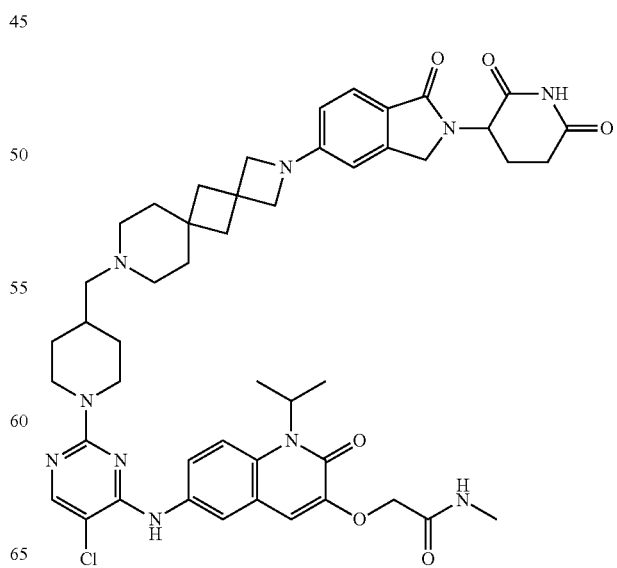

Compound 168 was prepared analogously to compound 162 following step 9-10 with the material made in step 6 of this example. The crude product was purified by reverse phase flash chromatography (mobile phase, CH$_3$CN/water (10 mmol/L NH$_4$HCO$_3$), 5% to 75% gradient in 30 minutes; detector, UV 254 nm) to afford 2-{[6-({5-chloro-2-[4-({2-[2-(2,6-dioxopiperidin-3-yl)-1-oxo-3H-isoindol-5-yl]-2,9-diazadispiro[3.1.5^{6}.1^{4}]dodecan-9-yl}methyl)piperidin-1-yl]pyrimidin-4-yl}amino)-1-isopropyl-2-oxoquinolin-3-yl]oxy}-N-methylacetamide (77.6 mg, 21%) as off-white solid. $^1$H NMR (400 MHz, DMSO-d$_6$, ppm) δ 10.92 (s, 1H), 8.79 (s, 1H), 8.03 (s, 1H), 7.94 (d, J=10.5 Hz, 2H), 7.76-7.65 (m, 2H), 7.47 (d, J=8.2 Hz, 1H), 7.02 (s, 1H), 6.49-6.40 (m, 2H), 5.02 (d, J=13.6 Hz, 1H), 4.53 (s, 2H), 4.48 (d, J=12.8 Hz, 2H), 4.29 (d, J=17.0 Hz, 1H), 4.16 (d, J=17.0 Hz, 1H), 3.89 (s, 4H), 2.85 (d, J=12.4 Hz, 3H), 2.67 (d, J=4.6 Hz, 3H), 2.58 (d, J=16.8 Hz, 1H), 2.40 (s, 1H), 2.23 (s, 3H), 2.07 (s, 2H), 2.01 (s, 4H), 1.94 (s, 1H), 1.72 (d, J=12.9 Hz, 3H), 1.57 (d, J=6.8 Hz, 7H), 1.48 (s, 4H), 1.24 (s, 1H), 1.00 (d, J=8.5 Hz, 2H). MS (ESI): m/z 905.45 [M+H]$^+$.

Example 43: Synthesis of 2-({6-[(5-chloro-2-{4-[(1r,3r)-3-[(3R,5S)-4-[2-(2,6-dioxopiperidin-3-yl)-1-oxo-2,3-dihydro-1H-isoindol-5-yl]-3,5-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide (Compound 174)

Step 1: Preparation of tert-butyl 4-(3-bromo-4-methoxycarbonyl-phenyl)-3,5-dimethyl-piperazine-1-carboxylate

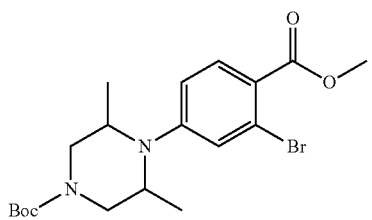 [SMILES: COC(=O)c1ccc(N2C(C)CN(C(=O)OC(C)(C)C)CC2C)cc1Br]

A mixture of tert-butyl N,N-diacetonylcarbamate (7.4 g, 32.3 mmol, 1 eq), methyl 4-amino-2-bromo-benzoate (7.43 g, 32.3 mmol, 1 eq), 2-methylpyridine borane complex (17.26 g, 161.4 mmol, 5 eq) in methanol (50 mL) and acetic acid (5 mL) was degassed and purged with nitrogen for 3 times, and then the mixture was stirred at 50° C. for 4 hours under nitrogen atmosphere. The reaction mixture was diluted with water (200 mL) and extracted with ethyl acetate (2×100 mL). The combined organic phase was washed with saturated brine (200 mL), dried over anhydrous sodium sulfate, filtered, and concentrated in vacuum. The residue was purified by prep-HPLC (mobile phase: [water (FA)-ACN]; B %: 50%-80%, 20 min) to afford tert-butyl 4-(3-bromo-4-methoxycarbonyl-phenyl)-3,5-dimethyl-piperazine-1-carboxylate (4 g, 29%) as a white solid. MS (ESI) m/z: 429.1 [M+H]$^+$.

Step 2: Preparation of tert-butyl (3S,5R)-4-(3-bromo-4-methoxycarbonyl-phenyl)-3,5-dimethyl-piperazine-1-carboxylate

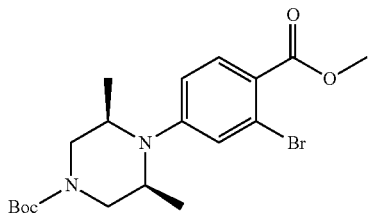 [SMILES: COC(=O)c1ccc(N2[C@H](C)CN(C(=O)OC(C)(C)C)C[C@@H]2C)cc1Br]

The racemic tert-butyl 4-(3-bromo-4-methoxycarbonyl-phenyl)-3,5-dimethyl-piperazine-1-carboxylate (4.5 g, 10.5 mmol, 1 eq) was purified by SFC (mobile phase: ethyl alcohol (0.1% NH$_3$H$_2$O) in CO$_2$ from 20% to 20%; flow rate: 55 mL/min; 220 nm) to afford tert-butyl (3S,5R)-4-(3-bromo-4-methoxycarbonyl-phenyl)-3,5-dimethyl-piperazine-1-carboxylate (2.8 g, 62%) as a pale-yellow solid. $^1$H NMR (400 MHz, DMSO-d$_6$) δ 7.79-7.73 (m, 1H), 7.07-7.02 (m, 1H), 6.88 (dd, J=2.4, 9.2 Hz, 1H), 4.05 (br s, 2H), 3.91-3.78 (m, 2H), 3.76 (s, 3H), 3.23-2.98 (m, 2H), 1.43 (s, 9H), 1.08 (d, J=6.4 Hz, 6H).

Step 3: Preparation of methyl 2-bromo-4-[(2S,6R)-2,6-dimethylpiperazin-1-yl]benzoate

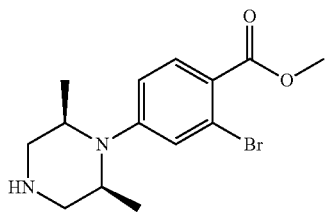 [SMILES: COC(=O)c1ccc(N2[C@H](C)CNC[C@@H]2C)cc1Br]

To a solution of tert-butyl (3S,5R)-4-(3-bromo-4-methoxycarbonyl-phenyl)-3,5-dimethyl-piperazine-1-carboxylate (1 g, 2.3 mmol, 1 eq) in dichloromethane (5 mL) was added trifluoroacetic acid (3.08 g, 27.0 mmol, 12 eq). The mixture was stirred at 25° C. for 30 minutes, then the mixture was filtered and concentrated under reduced pressure. The crude product was triturated with tertiary butyl ether at 25° C. for 10 minutes, the suspension was filtered, and the filter cake was dried in vacuum to afford methyl 2-bromo-4-[(2S,6R)-2,6-dimethylpiperazin-1-yl] benzoate (1 g, 96%) as a pale-yellow solid. MS (ESI) m/z: 329.0 [M+H]$^+$.

Step 4: Preparation of tert-butyl 4-[3-[(3S,5R)-4-(3-bromo-4-methoxycarbonyl-phenyl)-3,5-dimethyl-piperazin-1-yl]cyclobutoxy]piperidine-1-carboxylate

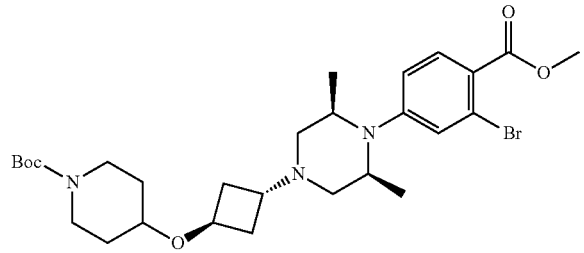 [SMILES: COC(=O)c1ccc(N2[C@H](C)CN([C@H]3C[C@H](OC4CCN(C(=O)OC(C)(C)C)CC4)C3)C[C@@H]2C)cc1Br]

To a solution of methyl 2-bromo-4-[(2S,6R)-2,6-dimethylpiperazin-1-yl]benzoate trifluoroacetate (1 g, 3.1 mmol, 1 eq) and tert-butyl 4-[3-(trifluoromethylsulfonyloxy)cyclobutoxy]piperidine-1-carboxylate (2.47 g, 6.1 mmol, 2 eq) in acetonitrile (10 mL) was added N,N-diisopropylethylamine (1.18 g, 9.2 mmol, 3 eq). The mixture was stirred at 25° C. for 1 hour and then diluted with water (50 mL) and extracted with ethyl acetate (2×50 mL). The combined organic phase was washed with saturated brine (100 mL), dried over anhydrous sodium sulfate, filtered, and concentrated in vacuum. The residue was purified by prep-HPLC (mobile phase: [water (FA)-ACN]; B %: 30%-50%, 20 min) to give tert-butyl 4-[3-[(3S,5R)-4-(3-bromo-4-methoxycarbonyl-phenyl)-3,5-dimethyl-piperazin-1-yl]cyclobutoxy]piperidine-1-carboxylate (1.7 g, 95%) as a yellow solid. MS (ESI) m/z: 582.3 [M+H]$^+$.

Step 5: Preparation of tert-butyl 4-[3-[(3S,5R)-4-(3-formyl-4-methoxycarbonyl-phenyl)-3,5-dimethyl-piperazin-1-yl]cyclobutoxy]piperidine-1-carboxylate

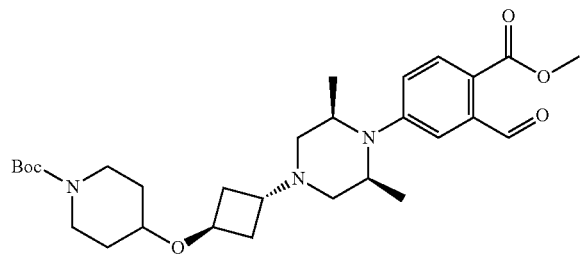 [SMILES: COC(=O)c1ccc(N2[C@H](C)CN([C@H]3C[C@H](OC4CCN(C(=O)OC(C)(C)C)CC4)C3)C[C@@H]2C)cc1C=O]

To a solution of tert-butyl 4-[3-[(3S,5R)-4-(3-bromo-4-methoxycarbonyl-phenyl)-3,5-dimethyl-piperazin-1-yl]cyclobutoxy]piperidine-1-carboxylate (1.7 g, 2.9 mmol, 1 eq) in N,N-dimethylformamide (20 mL) was added diacetoxypalladium (65 mg, 0.3 mmol, 0.1 eq), tricyclohexylphosphane (82 mg, 0.3 mmol, 0.1 eq), disodium; carbonate (310 mg, 2.9 mmol, 1 eq), triethylsilane (1.02 g, 8.8 mmol, 3 eq) and 2-isocyano-2-methyl-propane (486 mg, 5.9 mmol, 2 eq), the mixture was stirred at 65° C. for 12 hours in a teflon reaction vessel The reaction mixture was diluted with water (50 mL) and extracted with ethyl acetate (2×50 mL). The combined organic phase was washed with saturated brine (3×100 mL), dried over anhydrous sodium sulfate, filtered, and concentrated under vacuum. The residue was purified by silica gel chromatography (petroleum ether/ethyl acetate=1/0 to 3/1) to afford tert-butyl 4-[3-[(3S,5R)-4-(3-formyl-4-methoxycarbonyl-phenyl)-3,5-dimethyl-piperazin-1-yl]cyclobutoxy]piperidine-1-carboxylate (800 mg, 51%) as a yellow solid. MS (ESI) m/z: 530.2 [M+H]$^+$; $^1$H NMR (400 MHz, DMSO-d$_6$) δ 10.53 (s, 1H), 7.90-7.77 (m, 1H), 7.12-6.99 (m, 2H), 4.24-4.16 (m, 1H), 4.13-4.03 (m, 2H), 3.82 (s, 3H), 3.71-3.58 (m, 2H), 3.49-3.40 (m, 1H), 3.05-2.90 (m, 2H), 2.84-2.71 (m, 3H), 2.21-2.12 (m, 2H), 2.06-1.95 (m, 4H), 1.78-1.71 (m, 2H), 1.39 (s, 9H), 1.29-1.25 (m, 2H), 1.21-1.18 (m, 6H).

Step 6-8: Preparation of 2-[[6-[[5-chloro-2-[4-[3-[(3S,5R)-4-[2-(2,6-dioxo-3-piperidyl)-1-oxo-isoindolin-5-yl]-3,5-dimethyl-piperazin-1-yl]cyclobutoxy]-1-piperidyl]pyrimidin-4-yl]amino]-1-isopropyl-2-oxo-3-quinolyl]oxy]-N-methyl-acetamide

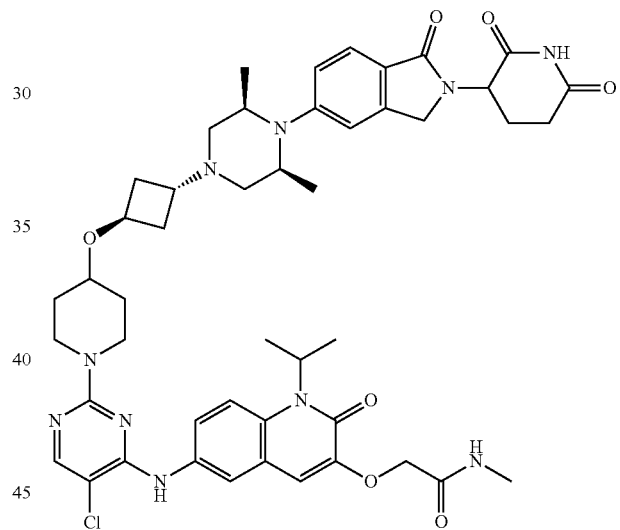

Compound 174 was prepared analogously to compound 161 following step 12-14 with the material made in step 5 of this example. The crude product was purified by prep-HPLC (mobile phase: [water (FA)-ACN]; B %: 13%-43%, 15 min) to afford 2-[[6-[[5-chloro-2-[4-[3-[(3S,5R)-4-[2-(2,6-dioxo-3-piperidyl)-1-oxo-isoindolin-5-yl]-3,5-dimethyl-piperazin-1-yl]cyclobutoxy]-1-piperidyl]pyrimidin-4-yl]amino]-1-isopropyl-2-oxo-3-quinolyl]oxy]-N-methyl-acetamide (85.6 mg, 20%) as a white solid. MS (ESI) m/z: 909.4 [M+H]$^+$; $^1$H NMR (400 MHz, DMSO-d$_6$) δ 10.94 (s, 1H), 8.83 (s, 1H), 8.04 (s, 1H), 8.02-7.97 (m, 1H), 7.94 (s, 1H), 7.68 (s, 2H), 7.54 (d, J=8.4 Hz, 1H), 7.03 (s, 1H), 7.01-6.94 (m, 2H), 5.59-5.13 (m, 1H), 5.04 (dd, J=5.2, 13.6 Hz, 1H), 4.54 (s, 2H), 4.39-4.30 (m, 1H), 4.28-4.17 (m, 2H), 4.17-4.07 (m, 2H), 3.97-3.83 (m, 2H), 2.97-2.88 (m, 1H), 2.86-2.73 (m, 2H), 2.67 (d, J=4.8 Hz, 3H), 2.60 (br s, 2H), 2.36-2.28 (m, 2H), 2.24-2.08 (m, 5H), 2.07-1.92 (m, 4H), 1.89-1.78 (m, 2H), 1.57 (d, J=6.8 Hz, 6H), 1.45-1.34 (m, 2H), 1.11 (d, J=6.4 Hz, 6H).

Compound 179 and 180 may be prepared by a procedure analogous to compound 174.

Example 44: Synthesis of 2-({6-[(5-chloro-2-{4-[(1r,3r)-3-{4-[2-(2,6-dioxopiperidin-3-yl)-4-methyl-1,3-dioxoisoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (Compound 177)

Step 1: Preparation of 2-cyano-4-fluoro-3-methylbenzoic acid

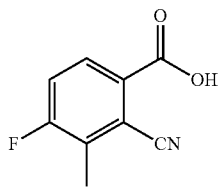

A solution/mixture of 2-bromo-4-fluoro-3-methylbenzoic acid (1.0 g, 4.3 mmol, 1.0 equiv) and cuprous cyanide (0.8 g, 8.6 mmol, 2.0 equiv) in NMP (10 mL) was stirred for 2 hours at 140° C. under air atmosphere. To the above mixture was added water, the resulting mixture was filtered, the filter cake was washed with ethyl acetate to afford 2-cyano-4-fluoro-3-methylbenzoic acid (460.0 mg, 60%) as a yellow solid. MS (ESI): m/z 180.05 [M+H]$^+$.

Step 2: Preparation of 4-fluoro-3-methylbenzene-1,2-dicarboxylic acid

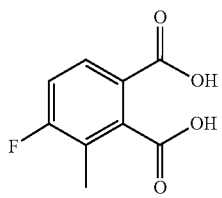

To a stirred solution of 2-cyano-4-fluoro-3-methylbenzoic acid (770.0 mg, 4.3 mmol, 1.0 equiv) and water (5 mL) in dioxane was added caustic soda (859.5 mg, 21.5 mmol, 5.0 equiv). The resulting mixture was stirred overnight at 100° C. under air atmosphere. The reaction was concentrated under vacuum to afford 4-fluoro-3-methylbenzene-1,2-dicarboxylic acid (852.0 mg) as a white solid. MS (ESI): m/z 199.05 [M+H]$^+$.

Step 3: Preparation of 2-(2,6-dioxopiperidin-3-yl)-5-fluoro-4-methylisoindole-1,3-dione

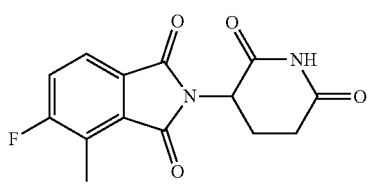 [SMILES: Cc1c(F)ccc2c1C(=O)N(C1CCC(=O)NC1=O)C2=O]

To a stirred solution of 4-fluoro-3-methylbenzene-1,2-dicarboxylic acid (852.0 mg, 4.3 mmol, 1.0 equiv) and 3-aminopiperidine-2,6-dione (881.5 mg, 6.9 mmol, 1.6 equiv) in acetic acid (8 mL) was added NaOAc (1.1 g, 12.9 mmol, 3.0 equiv). The resulting mixture was stirred for 3 hours at 100° C. under air atmosphere, and then poured into ice water. The precipitate was collected by filtration and the filter cake was washed with water to afford 2-(2,6-dioxopiperidin-3-yl)-5-fluoro-4-methylisoindole-1,3-dione (650 mg, 52%) as a black solid. MS (ESI): m/z 291.00 [M+H]$^+$.

Step 4-6: Preparation of 2-({6-[(5-chloro-2-{4-[(1r,3r)-3-{4-[2-(2,6-dioxopiperidin-3-yl)-4-methyl-1,3-dioxoisoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide

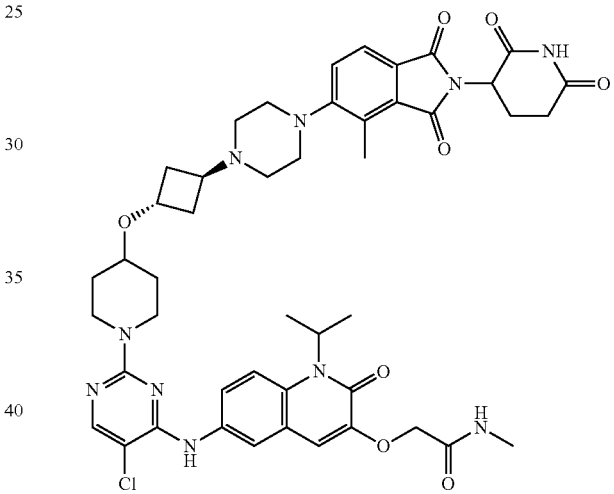

Compound 177 was prepared analogous to compound 164 following step 3-5 with the material made in step 3 of this example. The crude product was purified by reverse phase flash chromatography (mobile phase, MeCN in water (10 mmol/L NH$_4$HCO$_3$), 10% to 80% gradient in 10 min; 254 nm) to afford 2-({6-[(5-chloro-2-{4-[(1r,3r)-3-{4-[2-(2,6-dioxopiperidin-3-yl)-4-methyl-1,3-dioxoisoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (75.7 mg, 60%) as a yellow solid. $^1$H NMR (400 MHz, DMSO-d$_6$) δ 11.11 (s, 1H), 8.84 (s, 1H), 8.04 (s, 1H), 7.96 (m, 2H), 7.69 (m, 3H), 7.36 (m, 1H), 7.02 (s, 1H), 5.09 (m, 1H), 4.54 (s, 2H), 4.20-4.12 (m, 3H), 3.60 (m, 1H), 3.30 (s, 1H), 3.10 (s, 2H), 3.00 (s, 4H), 2.98 (s, 2H), 2.80 (s, 4H), 2.70 (s, 1H), 2.59 (m, 6H), 2.35 (m, 1H), 2.19 (s, 2H), 2.00 (m, 3H), 1.83 (m, 2H), 1.57 (m, 6H), 1.38 (m, 2H). MS (ESI): m/z 907.35 [MH$^+$].

Compounds 194, 195, 199, and 207 may be prepared by a procedure analogous to compound 177.

Example 45: Synthesis of 2-({6-[(5-chloro-2-{4-[(1r,3r)-3-{4-[4-chloro-2-(2,6-dioxopiperidin-3-yl)-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 181)

Step 1: preparation of 3-chloro-4-fluoro-2-methylbenzoic acid

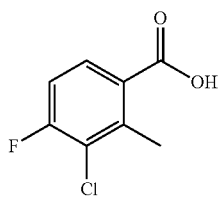

Into a 50 mL 3-necked round-bottom flask were added 2,2,6,6-tetramethylpiperidine (17 mL, 126 mmol, 2.2 equiv) and THF (100 mL). To the above mixture was added butyllithium (8 g, 126 mmol, 2.2 equiv) dropwise at −20° C., and stirred for additional 1 hour at −20° C. To the above mixture was added 3-chloro-4-fluorobenzoic acid (10 g, 57 mmol, 1 equiv) dropwise at −50° C., and stirred for additional 1 hour at −50° C. To the above mixture was added methyl iodide (32 g, 229 mmol, 4 equiv) dropwise at −50° C., and stirred for 1 hour at room temperature under nitrogen atmosphere. The reaction mixture was acidified to pH 3 with 1M HCl solution. The aqueous layer was extracted with EtOAc, the organic layer was dried over sodium sulfate, filtered, and concentrated. The residue was purified by reverse flash chromatography (mobile phase, MeCN in water (0.5% FA), 10% to 50% gradient in 300 min; detector, UV 254 nm) to afford 3-chloro-4-fluoro-2-methylbenzoic acid (10.3 g, 95%) as an off-white solid.

Step 2: preparation of methyl 3-chloro-4-fluoro-2-methylbenzoate

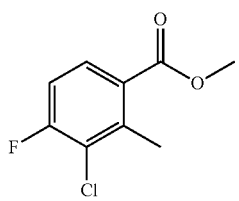

To a stirred solution of 3-chloro-4-fluoro-2-methylbenzoic acid (9 g, 47 mmol, 1 equiv) and $K_2CO_3$ (13 g, 95 mmol, 2 equiv) in DMF was added methyl iodide (3.3 mL, 23 mmol, 0.5 equiv) dropwise at room temperature. The resulting mixture was stirred for 1 hour, then diluted with water. The aqueous layer was extracted with EtOAc. The organic layer was dried over sodium sulfate, filtered, and concentrated to afford methyl 3-chloro-4-fluoro-2-methylbenzoate (9 g, 93%) as a brown oil.

Step 3: preparation of methyl 2-(bromomethyl)-3-chloro-4-fluorobenzoate

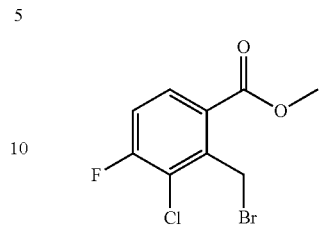

To a stirred solution of methyl 3-chloro-4-fluoro-2-methylbenzoate (9 g, 44 mmol, 1 equiv) and NBS (11 g, 66 mmol, 1.5 equiv) in $CCl_4$ (200 mL) was added AIBN (1 g, 6.6 mmol, 0.15 equiv) in portions at room temperature. The resulting mixture was stirred overnight at 70° C. under nitrogen atmosphere, then cooled to room temperature and diluted with water, the aqueous layer was extracted with $CH_2Cl_2$. The organic layer was dried over sodium sulfate, filtered, and concentrated to afford methyl 2-(bromomethyl)-3-chloro-4-fluorobenzoate (9 g, 75%) as a brown oil.

Step 4: preparation of tert-butyl (4S)-4-carbamoyl-4-(4-chloro-5-fluoro-1-oxo-3H-isoindol-2-yl)butanoate

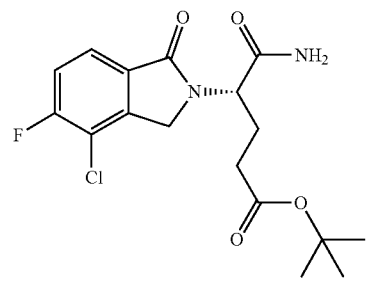 [SMILES: CC(C)(C)OC(=O)CC[C@@H](C(N)=O)N1Cc2c(ccc(F)c2Cl)C1=O]

Into a 100 mL round-bottom flask were added methyl 2-(bromomethyl)-3-chloro-4-fluorobenzoate (9 g, 3 mmol, 1 equiv) and tert-butyl (4S)-4-amino-4-carbamoylbutanoate (6 g, 3 mmol, 1 equiv). To the above mixture was added DIEA (10 mL), MeCN (100 mL). The resulting mixture was stirred overnight at 70° C. The resulting mixture was concentrated under reduced pressure. The residue was purified by reverse flash chromatography (column, silica gel; mobile phase, MeCN in water (10 mmol/L $NH_4HCO_3$), 10% to 50% gradient in 30 min; detector, UV 254 nm) to afford tert-butyl (4S)-4-carbamoyl-4-(4-chloro-5-fluoro-1-oxo-3H-isoindol-2-yl)butanoate (3.9 g, 32%) as an off-white solid. MS (ESI): m/z 371.05 [M+H]$^+$.

Step 5: preparation of tert-butyl 4-{2-[(1S)-4-(tert-butoxy)-1-carbamoyl-4-oxobutyl]-4-chloro-1-oxo-3H-isoindol-5-yl}piperazine-1-carboxylate

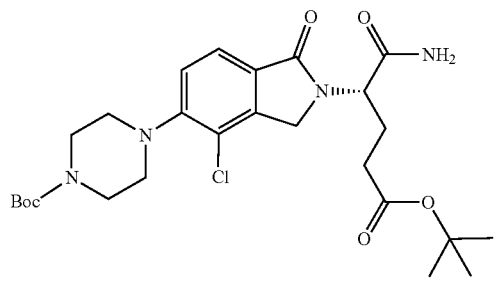 [SMILES: CC(C)(C)OC(=O)CC[C@@H](C(N)=O)N1Cc2c(ccc(N3CCN(C(=O)OC(C)(C)C)CC3)c2Cl)C1=O]

Into a 10 mL sealed tube were added tert-butyl (4S)-4-carbamoyl-4-(4-chloro-5-fluoro-1-oxo-3H-isoindol-2-yl)butanoate (1 g, 2.5 mmol, 1 equiv) and tert-butyl 4-[(1r,3r)-3-(piperazin-1-yl)cyclobutoxy]piperidine-1-carboxylate (0.5 g, 2.5 mmol, 1 equiv). To the above mixture was added DIEA (2 mL) and DMSO (10 mL). The resulting mixture was stirred for additional 7 days at 140° C. The crude reaction was purified by reverse flash chromatography (column, silica gel; mobile phase, MeCN in water (10 mmol/L NH$_4$HCO$_3$), 10% to 80% gradient in 30 min; detector, UV 254 nm) to afford tert-butyl 4-{2-[(1S)-4-(tert-butoxy)-1-carbamoyl-4-oxobutyl]-4-chloro-1-oxo-3H-isoindol-5-yl}piperazine-1-carboxylate (600 mg, 41%) as an off-white solid. MS (ESI): m/z 537.35 [M+H]$^+$.

Step 6: preparation of tert-butyl 4-{2-[(1S)-4-(tert-butoxy)-1-carbamoyl-4-oxobutyl]-4-chloro-1-oxo-3H-isoindol-5-yl}piperazine-1-carboxylate

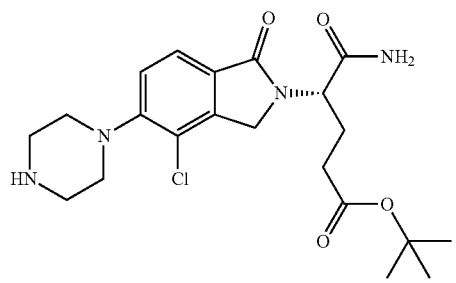 [SMILES: CC(C)(C)OC(=O)CC[C@@H](C(N)=O)N1Cc2c(ccc(N3CCNCC3)c2Cl)C1=O]

To the tert-butyl 4-{2-[(1S)-4-(tert-butoxy)-1-carbamoyl-4-oxobutyl]-4-chloro-1-oxo-3H-isoindol-5-yl}piperazine-1-carboxylate (600 mg, 1.1 mmol, 1 equiv) in dioxane was added HCl (gas) in 1,4-dioxane (10 mL) dropwise at 0° C. The resulting mixture was stirred for 1 hour at 0° C. The pH of the solution was adjusted to 7 by NaHCO$_3$ (aq), concentrated under reduced pressure to afford tert-butyl (4S)-4-carbamoyl-4-[4-chloro-1-oxo-5-(piperazin-1-yl)-3H-isoindol-2-yl]butanoate (252 mg, 50%) as a brown solid. MS (ESI): m/z 437.25 [M+H]$^+$.

Step 7: preparation of tert-butyl 4-[(1r,3r)-3-(4-{2-[(1S)-4-(tert-butoxy)-1-carbamoyl-4-oxobutyl]-4-chloro-1-oxo-3H-isoindol-5-yl}piperazin-1-yl)cyclobutoxy]piperidine-1-carboxylate

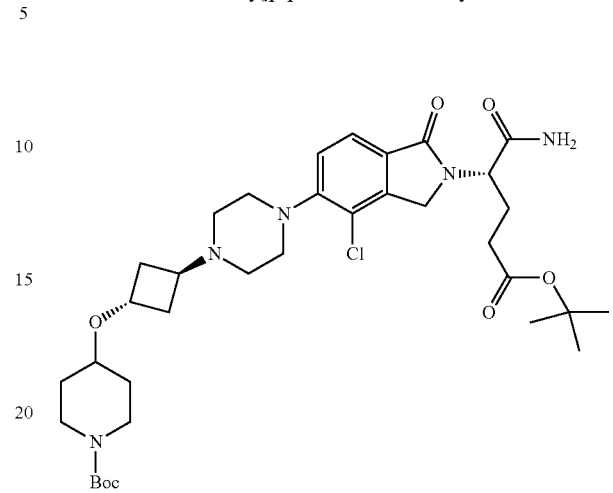

Into a 20 mL sealed tube were added tert-butyl (4S)-4-carbamoyl-4-[4-chloro-1-oxo-5-(piperazin-1-yl)-3H-isoindol-2-yl]butanoate (252 mg, 0.6 mmol, 1 equiv) and tert-butyl 4-[(1s,3s)-3-(trifluoromethanesulfonyloxy)cyclobutoxy]piperidine-1-carboxylate (348 mg, 0.9 mmol, 1.5 equiv) in ACN (10 mL) was added DIEA (2 mL). The resulting mixture was stirred for 2 hours at 30° C. under nitrogen atmosphere, then concentrated. The residue was purified by reverse flash chromatography (column, silica gel; mobile phase, MeCN in water (10 mmol/L NH$_4$HCO$_3$), 10% to 50% gradient in 30 min; detector, UV 254 nm) to afford tert-butyl 4-[(1r,3r)-3-(4-{2-[(1S)-4-(tert-butoxy)-1-carbamoyl-4-oxobutyl]-4-chloro-1-oxo-3H-isoindol-5-yl}piperazin-1-yl)cyclobutoxy]piperidine-1-carboxylate (275 mg, 69%) as a brown solid. MS (ESI): m/z 690.35 [M+H]$^+$.

Step 8: preparation of tert-butyl 4-[(1r,3r)-3-{4-[4-chloro-2-(2,6-dioxopiperidin-3-yl)-1-oxo-3H-isoindol-5-yl]piperazin-1-yl}cyclobutoxy]piperidine-1-carboxylate

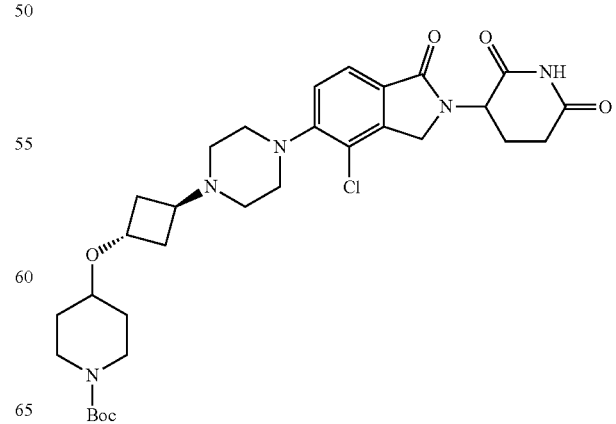

Into a 10 mL sealed tube were added tert-butyl 4-[(1r,3r)-3-(4-{2-[(1S)-4-(tert-butoxy)-1-carbamoyl-4-oxobutyl]-4-chloro-1-oxo-3H-isoindol-5-yl}piperazin-1-yl)cyclobutoxy]piperidine-1-carboxylate (275 mg, 0.2 mmol, 1 equiv) and Cs₂CO₃ (280 mg, 0.5 mmol, 3 equiv) in MeCN (5 mL). The resulting mixture was stirred overnight at 80° C., then cooled to room temperature and diluted with water, extracted with EtOAc. The organic layer was dried over sodium sulfate, filtered, and concentrated to afford tert-butyl 4-[(1r,3r)-3-{4-[4-chloro-2-(2,6-dioxopiperidin-3-yl)-1-oxo-3H-isoindol-5-yl]piperazin-1-yl}cyclobutoxy]piperidine-1-carboxylate (176 mg, 71%) as a brown solid. MS (ESI): m/z 616.35 [M+H]⁺.

Step 9: preparation of 3-(4-chloro-1-oxo-5-{4-[(1r,3r)-3-(piperidin-4-yloxy)cyclobutyl]piperazin-1-yl}-3H-isoindol-2-yl)piperidine-2,6-dione

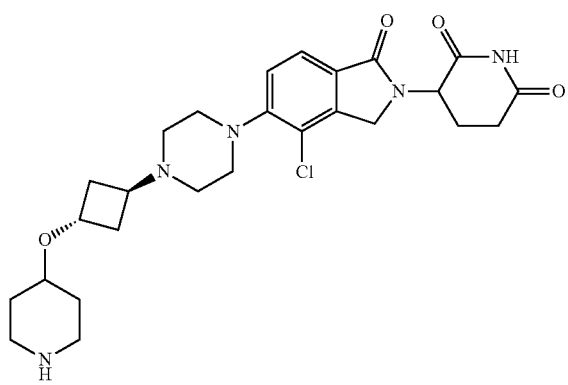 [SMILES: O=C1CCC(N2Cc3c(ccc(N4CCN([C@H]5C[C@H](OC6CCNCC6)C5)CC4)c3Cl)C2=O)C(=O)N1]

A solution of tert-butyl 4-[(1r,3r)-3-{4-[4-chloro-2-(2,6-dioxopiperidin-3-yl)-1-oxo-3H-isoindol-5-yl]piperazin-1-yl}cyclobutoxy]piperidine-1-carboxylate (176 mg, 0.3 mmol, 1 equiv) in 1,4-dioxane (3 mL) was added hydrogen chloride (3 mL) and stirred for 4 hours at room temperature. The reaction was concentrated under reduced pressure to afford 3-(4-chloro-1-oxo-5-{4-[(1r,3r)-3-(piperidin-4-yloxy)cyclobutyl]piperazin-1-yl}-3H-isoindol-2-yl)piperidine-2,6-dione (147 mg, 99%) as a brown solid. MS (ESI): m/z 516.25 [M+H]⁺.

Step 10: preparation of 2-({6-[(5-chloro-2-{4-[(1r,3r)-3-{4-[4-chloro-2-(2,6-dioxopiperidin-3-yl)-1-oxo-3H-isoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide

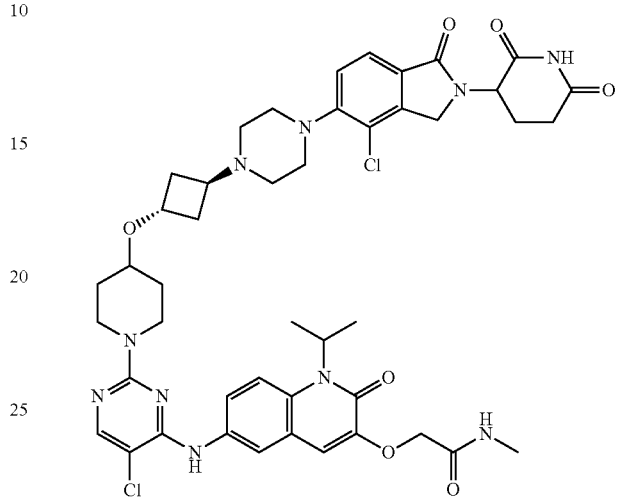

Into a 10 mL sealed tube were added 3-(4-chloro-1-oxo-5-{4-[(1r,3r)-3-(piperidin-4-yloxy)cyclobutyl]piperazin-1-yl}-3H-isoindol-2-yl)piperidine-2,6-dione (147 mg, 0.3 mmol, 1 equiv) and 2-({6-[(2,5-dichloropyrimidin-4-yl)amino]-1-isopropyl-2-oxoquinolin-3-yl}oxy)-N-methylacetamide (124 mg, 0.3 mmol, 1 equiv) in DMSO (3 mL). To the above mixture was added DIEA (2 mL). The resulting mixture was stirred for 5 hours at 100° C., then cooled to room temperature. The crude material was purified by reverse flash chromatography (column, silica gel; mobile phase, MeCN in water (10 mmol/L NH₄HCO₃), 10% to 50% gradient in 30 min; detector, UV 254 nm) to afford 2-({6-[(5-chloro-2-{4-[(1r,3r)-3-{4-[4-chloro-2-(2,6-dioxopiperidin-3-yl)-1-oxo-3H-isoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (67.2 mg, 24%) as an off-white solid. MS (ESI): m/z 937.20 [M+Na]⁺; ¹H NMR (400 MHz, DMSO-d6) δ 8.83 (s, 1H), 8.04-8.01 (m, 2H), 8.00-7.94 (m, 1H), 7.67-7.64 (m, 3H), 7.29-7.26 (m, 1H), 7.03 (s, 1H), 5.45-5.23 (m, 1H), 5.23-5.02 (m, 1H) 4.54-4.50 (m, 3H), 4.48-4.44 (m, 2H), 4.41-4.39 (m, 1H), 4.28-4.10 (m, 4H), 3.90-3.85 (m, 1H), 3.67-3.64 (m, 1H), 3.19-3.08 (m, 3H), 2.94-2.86 (m, 4H), 2.68-2.61 (m, 4H), 2.50-2.42 (m, 3H), 2.19-1.99 (m, 2H), 1.79-1.55 (m, 5H), 1.38-1.36 (m, 5H), 1.23-1.20 (m, 2H), 1.18-1.16 (m, 5H), 1.08-1.00 (s, 1H), 0.85 (s, 1H).

329

Compounds 196, 202, 205, and 206 may be prepared by a procedure analogous to compound 181.

Example 46: Synthesis of 2-({6-[(5-chloro-2-{4-[(1r,3r)-3-{4-[2-(2,6-dioxopiperidin-3-yl)-4-fluoro-1-oxo-3H-isoindol-5-yl]-3,3-dimethylpiperidin-1-yl}cyclobutoxy]piperidin-1-yl}pyrimidin-4-yl)amino]-1-isopropyl-2-oxoquinolin-3-yl}oxy)-N-methylacetamide (Compound 187)

Step 1: preparation of tert-butyl 3,3-dimethyl-4-(trifluoromethanesulfonyloxy)-2,6-dihydropyridine-1-carboxylate

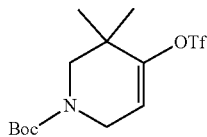

Into a 1 L 3-necked round-bottom flask were added tert-butyl 3,3-dimethyl-4-oxopiperidine-1-carboxylate (10 g, 43 mmol, 1 equiv) in anhydrous THF (100 mL). LiHMDS (10 mL, 61 mmol, 1.4 equiv) was then added dropwise over 5 minutes at −78° C., stirred for 1 hour at −78° C. under nitrogen atmosphere. To the above mixture was added 1,1,1-trifluoro-N-phenyl-N-trifluoromethanesulfonylmethanesulfonamide (17 g, 48 mmol, 1.1 equiv) in anhydrous THF (100 mL) dropwise over 5 minutes at −78° C. The reaction was warmed to room temperature and stirred overnight. The reaction was quenched with sat. NH$_4$Cl (aq.) at 0° C. The aqueous layer was extracted with EtOAc. The organic layer was dried over sodium sulfate, filtered, and concentrated. The residue was purified by silica gel column chromatography (PE/EA=5:1) to afford tert-butyl 3,3-dimethyl-4-(trifluoromethanesulfonyloxy)-2,6-dihydropyridine-1-carboxylate (10 g, 63%) as a colorless oil. MS (ESI): m/z 345.10, [M-15+H]$^+$.

Step 2: preparation of tert-butyl 3,3-dimethyl-4-(4,4,5,5-tetramethyl-1,3,2-dioxaborolan-2-yl)-2,6-dihydropyridine-1-carboxylate

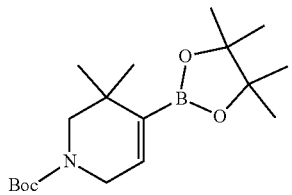 [SMILES: CC(C)(C)OC(=O)N1CC=C(B2OC(C)(C)C(C)(C)O2)C(C)(C)C1]

To a solution of tert-butyl 3,3-dimethyl-4-(trifluoromethanesulfonyloxy)-2,6-dihydropyridine-1-carboxylate (17 g, 47 mmol, 1 equiv) and bis(pinacolato)diboron (18 g, 70 mmol, 1.5 equiv) in dioxane (200 mL) was added KOAc (9 g, 94 mmol, 2 equiv) and Pd(dppf)Cl$_2$ (3.5 g, 4.7 mmol, 0.1 equiv). After stirring for 3 hours at 80° C. under a nitrogen atmosphere, the mixture was concentrated under reduced pressure. The residue was purified by silica gel column chromatography (PE/EA=5:1) to afford tert-butyl 3,3-dimethyl-4-(4,4,5,5-tetramethyl-1,3,2-dioxaborolan-2-yl)-2,6-dihydropyridine-1-carboxylate (7 g, 43%) as a colorless oil. MS (ESI): m/z 323.24, [M-15+H]$^+$.

330

Step 3: preparation of tert-butyl 4-{2-[(1S)-4-(tert-butoxy)-1-carbamoyl-4-oxobutyl]-4-fluoro-1-oxo-3H-isoindol-5-yl}-3,3-dimethyl-2,6-dihydropyridine-1-carboxylate

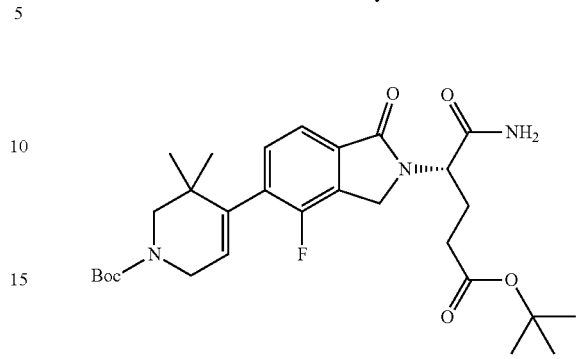

To a solution of tert-butyl (4S)-4-(5-bromo-4-fluoro-1-oxo-3H-isoindol-2-yl)-4-carbamoylbutanoate (2.5 g, 6 mmol, 1 equiv) and tert-butyl 3,3-dimethyl-4-(4,4,5,5-tetramethyl-1,3,2-dioxaborolan-2-yl)-2,6-dihydropyridine-1-carboxylate (2.4 g, mmol, 1.2 equiv) in dioxane (75 mL) and H$_2$O (15 mL) were added CsF (2.7 g, 18 mmol, 3 equiv) and Pd(DtBPF)Cl$_2$ (0.4 g, 0.6 mmol, 0.1 equiv). After stirring for 2 hours at 100° C. under a nitrogen atmosphere, the resulting mixture was concentrated under reduced pressure. The residue was purified by silica gel column chromatography (PE/EA=1:1) to afford tert-butyl 4-{2-[(1S)-4-(tert-butoxy)-1-carbamoyl-4-oxobutyl]-4-fluoro-1-oxo-3H-isoindol-5-yl}-3,3-dimethyl-2,6-dihydropyridine-1-carboxylate (2 g, 60%) as a brown solid. MS (ESI): m/z 546.30 [M+H]$^+$.

Step 4: preparation of tert-butyl 4-{2-[(1S)-4-(tert-butoxy)-1-carbamoyl-4-oxobutyl]-4-fluoro-1-oxo-3H-isoindol-5-yl}-3,3-dimethylpiperidine-1-carboxylate

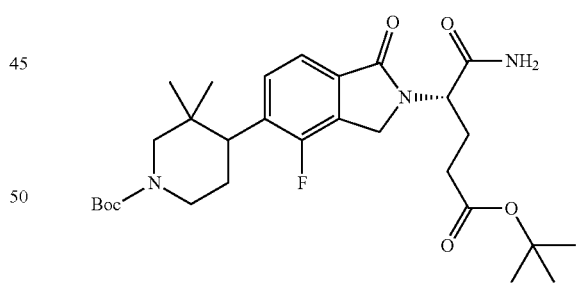

To a solution of tert-butyl 4-{2-[(1S)-4-(tert-butoxy)-1-carbamoyl-4-oxobutyl]-4-fluoro-1-oxo-3H-isoindol-5-yl}-3,3-dimethyl-2,6-dihydropyridine-1-carboxylate (650 mg, 1.2 mmol, 1 equiv) in tetrahydrofuran (2 mL) and propan-2-ol (10 mL) was added Pd(OH)$_2$/C (217 mg). The mixture was hydrogenated at room temperature overnight under hydrogen atmosphere using a hydrogen balloon, filtered through a Celite pad and concentrated under reduced pressure to afford tert-butyl 4-{2-[(1S)-4-(tert-butoxy)-1-carbamoyl-4-oxobutyl]-4-fluoro-1-oxo-3H-isoindol-5-yl}-3,3-dimethylpiperidine-1-carboxylate (550 mg, 84%) as a colorless solid. MS (ESI): m/z 548.35 [M+H]$^+$.

Step 5: preparation of tert-butyl (4S)-4-carbamoyl-4-[5-(3,3-dimethylpiperidin-4-yl)-4-fluoro-1-oxo-3H-isoindol-2-yl]butanoate

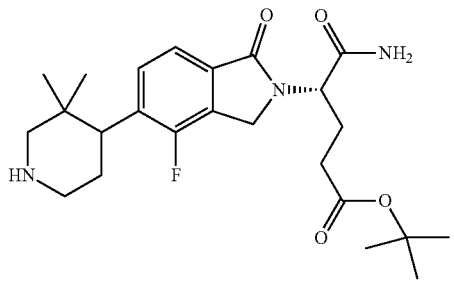 [SMILES: CC(C)(C)OC(=O)CC[C@@H](C(N)=O)N1Cc2c(ccc(C3CCNCC3(C)C)c2F)C1=O]

Into a 10 mL vial were added tert-butyl 4-{2-[(1S)-4-(tert-butoxy)-1-carbamoyl-4-oxobutyl]-4-fluoro-1-oxo-3H-isoindol-5-yl}-3,3-dimethylpiperidine-1-carboxylate (550 mg, 1 mmol, 1 equiv) and chlorotrimethylsilane (1 g, 10 mmol, 10 equiv) in isopropyl alcohol (13 mL). The resulting mixture was stirred overnight at room temperature. The pH of the mixture was adjusted to 8 with saturated NaHCO$_3$ (aq.). The aqueous layer was extracted with CH$_2$Cl$_2$. The organic layer was dried over sodium sulfate, filtered, and concentrated to afford tert-butyl (4S)-4-carbamoyl-4-[5-(3,3-dimethylpiperidin-4-yl)-4-fluoro-1-oxo-3H-isoindol-2-yl]butanoate (420 mg, 93%) as a colorless oil. MS (ESI): m/z 448.25 [M+H]$^+$.

Step 6: preparation of tert-butyl 4-[(1r,3r)-3-(4-{2-[(1S)-4-(tert-butoxy)-1-carbamoyl-4-oxobutyl]-4-fluoro-1-oxo-3H-isoindol-5-yl}-3,3-dimethylpiperidin-1-yl)cyclobutoxy]piperidine-1-carboxylate

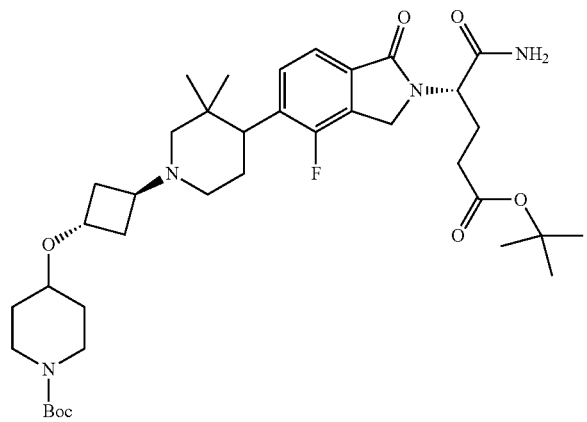 [SMILES: CC(C)(C)OC(=O)CC[C@@H](C(N)=O)N1Cc2c(ccc(C3CCN([C@H]4C[C@H](OC5CCN(C(=O)OC(C)(C)C)CC5)C4)CC3(C)C)c2F)C1=O]

Into a 10 mL sealed tube were added tert-butyl (4S)-4-carbamoyl-4-[5-(3,3-dimethylpiperidin-4-yl)-4-fluoro-1-oxo-3H-isoindol-2-yl]butanoate (300 mg, 0.7 mmol, 1 equiv), tert-butyl 4-[(1s,3s)-3-(trifluoromethanesulfonyloxy)cyclobutoxy]piperidine-1-carboxylate (324 mg, 0.8 mmol, 1.2 equiv) in MeCN (5 mL) and DIEA (1 mL). The resulting mixture was stirred overnight at 30° C. under nitrogen atmosphere, then concentrated. The residue was purified by reverse flash chromatography (column, silica gel; mobile phase, MeCN in water (10 mmol/L NH$_4$HCO$_3$), 10% to 50% gradient in 30 min; detector, UV 254 nm) to afford tert-butyl 4-[(1r,3r)-3-(4-{2-[(1S)-4-(tert-butoxy)-1-carbamoyl-4-oxobutyl]-4-fluoro-1-oxo-3H-isoindol-5-yl}-3,3-dimethylpiperidin-1-yl)cyclobutoxy]piperidine-1-carboxylate (250 mg, 53%) as a colorless solid. MS (ESI): m/z 701.50 [M+H]$^+$.

Step 7: preparation of tert-butyl 4-[(1r,3r)-3-{4-[2-(2,6-dioxopiperidin-3-yl)-4-fluoro-1-oxo-3H-isoindol-5-yl]-3,3-dimethylpiperidin-1-yl}cyclobutoxy]piperidine-1-carboxylate

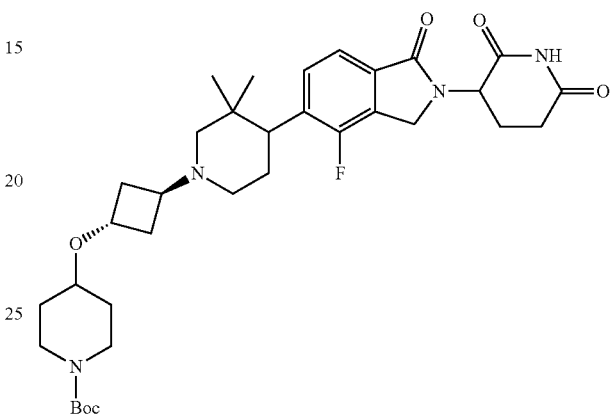

Into a 10 mL sealed tube were added tert-butyl 4-[(1r,3r)-3-(4-{2-[(1S)-4-(tert-butoxy)-1-carbamoyl-4-oxobutyl]-4-fluoro-1-oxo-3H-isoindol-5-yl}-3,3-dimethylpiperidin-1-yl)cyclobutoxy]piperidine-1-carboxylate (270 mg, 0.4 mmol, 1 equiv) and Cs$_2$CO$_3$ (251 mg, 0.8 mmol, 2 equiv) in MeCN (5 mL). The resulting mixture was stirred for 6 hours at 80° C. under nitrogen atmosphere, then diluted with water, extracted with EtOAc. The organic layer was dried over sodium sulfate, filtered, and concentrated under reduced pressure to afford tert-butyl 4-[(1r,3r)-3-{4-[2-(2,6-dioxopiperidin-3-yl)-4-fluoro-1-oxo-3H-isoindol-5-yl]-3,3-dimethylpiperidin-1-yl}cyclobutoxy]piperidine-1-carboxylate (120 mg, 49%) as a colorless solid. MS (ESI): m/z 627.76 [M+H]$^+$.

Step 8: preparation of 3-(5-{3,3-dimethyl-1-[(1r,3r)-3-(piperidin-4-yloxy)cyclobutyl]piperidin-4-yl}-4-fluoro-1-oxo-3H-isoindol-2-yl)piperidine-2,6-dione

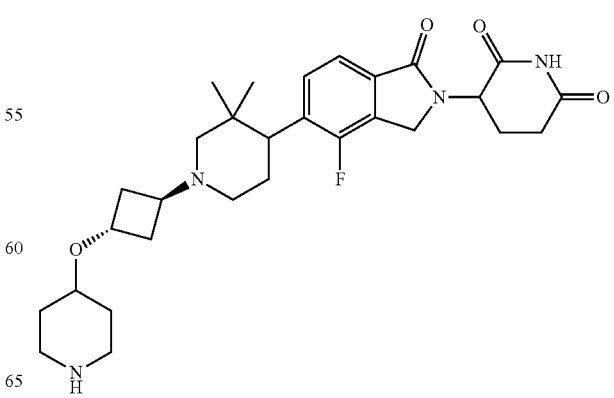

333

To a stirred solution of tert-butyl 4-[(1r,3r)-3-{4-[2-(2,6-dioxopiperidin-3-yl)-4-fluoro-1-oxo-3H-isoindol-5-yl]-3,3-dimethylpiperidin-1-yl}cyclobutoxy]piperidine-1-carboxylate (120 mg, 0.2 mmol, 1 equiv) in 1,4-dioxane (2 mL) was dropwise added hydrogen chloride (2 mL). The resulting mixture was stirred for 2 hours at room temperature, then concentrated under reduced pressure to afford 3-(5-{3,3-dimethyl-1-[(1r,3r)-3-(piperidin-4-yloxy)cyclobutyl]piperidin-4-yl}-4-fluoro-1-oxo-3H-isoindol-2-yl)piperidine-2,6-dione (100 mg, 99%) as an off-white solid. MS (ESI): m/z 527.35 [M+H]$^+$.

Step 9: preparation of 2-({6-[(5-chloro-2-{4-[(1r,3r)-3-{4-[2-(2,6-dioxopiperidin-3-yl)-4-fluoro-1-oxo-3H-isoindol-5-yl]-3,3-dimethylpiperidin-1-yl}cyclobutoxy]piperidin-1-yl}pyrimidin-4-yl)amino]-1-isopropyl-2-oxoquinolin-3-yl}oxy)-N-methylacetamide

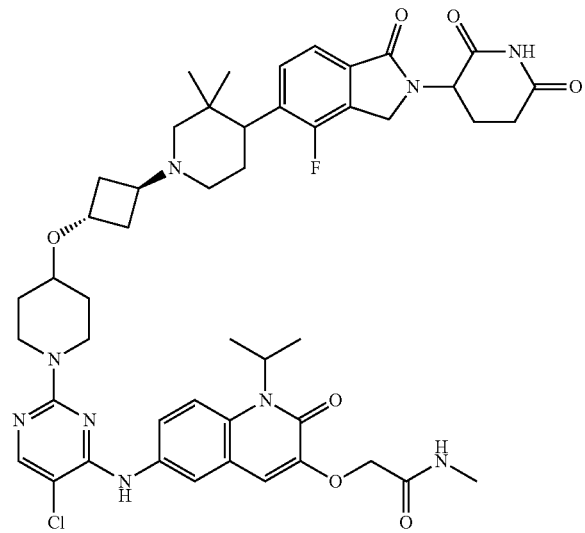

Into a 10 mL sealed tube were added 3-(5-{3,3-dimethyl-1-[(1r,3r)-3-(piperidin-4-yloxy)cyclobutyl]piperidin-4-yl}-4-fluoro-1-oxo-3H-isoindol-2-yl)piperidine-2,6-dione (100 mg, 0.2 mmol, 1 equiv), 2-({6-[(2,5-dichloropyrimidin-4-yl)amino]-1-isopropyl-2-oxoquinolin-3-yl}oxy)-N-methylacetamide (82 mg, 0.2 mmol, 1 equiv) in DMSO (2 mL), and DIEA (0.5 mL). The resulting mixture was stirred overnight at 100° C. The reaction was purified by reverse flash chromatography (column, silica gel; mobile phase, MeCN in water (10 mmol/L NH$_4$HCO$_3$), 10% to 50% gradient in 30 minutes; detector, UV 254 nm) to afford 2-({6-[(5-chloro-2-{4-[(1r,3r)-3-{4-[2-(2,6-dioxopiperidin-3-yl)-4-fluoro-1-oxo-3H-isoindol-5-yl]-3,3-dimethylpiperidin-1-yl}cyclobutoxy]piperidin-1-yl}pyrimidin-4-yl)amino]-1-isopropyl-2-oxoquinolin-3-yl}oxy)-N-methylacetamide (77 mg, 43%) as an off-white solid. MS (ESI): m/z 926.30 [M+H]$^+$; $^1$H NMR (400 MHz, DMSO-d$_6$) δ 11.02 (s, 1H), 8.82 (s, 1H), 8.04 (m, 1H), 7.99-7.95 (m, 2H), 7.69 (m, 2H), 7.55-7.53 (m, 1H), 7.46-7.44 (m, 1H), 7.03 (s, 1H), 5.13-5.11 (m, 1H), 4.54-4.50 (m, 3H), 4.40-4.37 (m, 1H), 4.18-4.10 (m, 3H), 3.26-3.30 (m, 1H), 3.32-3.26 (m, 2H), 3.22-2.68 (m, 4H), 2.67-2.63 (m, 4H), 2.56-2.50 (m, 3H), 2.46-2.44 (m, 2H), 2.21-2.16 (m, 5H), 1.99-1.81 (m, 3H), 1.71-1.61 (m, 3H), 1.58-1.55 (m, 6H), 1.47-1.35 (m, 4H), 0.89-0.88 (m, 3H), 0.72-0.71 (m, 3H).

334

Compounds 209 and 210 may be prepared by a procedure analogous to compound 187.

Example 47: Synthesis of 2-({6-[(5-chloro-2-{4-[(1r,3r)-3-(4-{2-[(3S)-2,6-dioxopiperidin-3-yl]-4,7-difluoro-1-oxo-2,3-dihydro-1H-isoindol-5-yl}piperidin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide (Compound 188)

Step 1: Preparation of 4-bromo-3,6-difluoro-2-methyl-benzoic acid

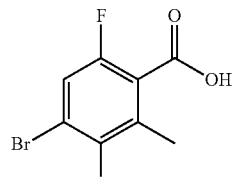

To a mixture of 4-bromo-2,5-difluoro-benzoic acid (25 g, 105.5 mmol, 1 eq) in tetrahydrofuran (280 mL) was dropwise added lithium diisopropylamide (2 M, 132 mL, 2.5 eq) at −70° C. under nitrogen, the mixture was stirred at −70° C. for 30 minutes, then added iodomethane (44.92 g, 316.5 mmol, 3 eq) at −70° C. The reaction mixture was warmed to 25° C. and stirred for another 16 hours. The mixture was quenched with ice water (200 mL). The pH of the aqueous phase was adjusted to 3 with conc. hydrochloric acid, extracted with ethyl acetate (2×300 mL). The combined organic phase was dried with anhydrous sodium sulfate, filtered, and concentrated in vacuum. The residue was purified by silica gel chromatography (petroleum ether/ethyl acetate=30/1 to 5/1) to afford 4-bromo-3,6-difluoro-2-methyl-benzoic acid (27 g, crude) as a yellow solid.

Step 2: Preparation of methyl 4-bromo-3,6-difluoro-2-methyl-benzoate

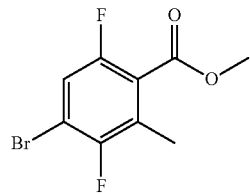

To a mixture of 4-bromo-3,6-difluoro-2-methyl-benzoic acid (26 g, 103.6 mmol, 1 eq) and iodomethane (29.40 g, 207.1 mmol, 2 eq) in N,N-dimethylformamide (150 mL) was added potassium carbonate (28.63 g, 207.2 mmol, 2 eq) in one portion at 25° C. under nitrogen. The mixture was stirred at 25° C. for 16 hours and then poured into ice-water (200 mL) and stirred for 5 minutes. The aqueous phase was extracted with ethyl acetate (2×100 mL). The combined organic phase was washed with brine (2×100 mL), dried over anhydrous sodium sulfate, filtered, and concentrated in vacuum. The residue was purified by silica gel chromatography (petroleum ether/ethyl acetate=50/1 to 10/1) to afford methyl 4-bromo-3,6-difluoro-2-methyl-benzoate (24.8 g, crude) as a yellow solid.

Step 3: Preparation of methyl 4-bromo-2-(bromomethyl)-3,6-difluoro-benzoate

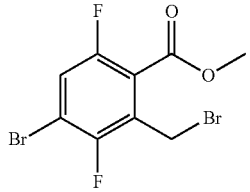

To a mixture of methyl 4-bromo-3,6-difluoro-2-methyl-benzoate (24.8 g, 93.6 mmol, 1 eq) and 1-bromopyrrolidine-2,5-dione (33.31 g, 187.1 mmol, 2 eq) in carbon tetrachloride (300 mL) was added 2,2-azobisisobutyronitrile (12.29 g, 74.9 mmol, 0.8 eq) in one portion at 25° C. under nitrogen. The mixture was stirred at 80° C. for 16 hours, upon which it was cooled to 20° C. and concentrated in reduced pressure at 45° C. The residue was purified by silica gel chromatography (petroleum ether/ethyl acetate=100/1 to 10/1) to afford methyl 4-bromo-2-(bromomethyl)-3,6-difluoro-benzoate (33 g, crude) as a yellow solid.

Step 4: Preparation of tert-butyl 5-amino-4-(5-bromo-4,7-difluoro-1-oxo-isoindolin-2-yl)-5-oxo-pentanoate

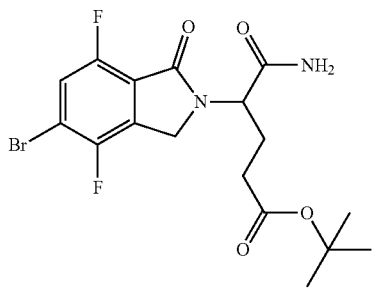 [SMILES: CC(C)(C)OC(=O)CCC(C(N)=O)N1Cc2c(F)c(Br)cc(F)c2C1=O]

To a mixture of tert-butyl 4,5-diamino-5-oxo-pentanoate (13.58 g, 67.2 mmol, 0.7 eq) and methyl 4-bromo-2-(bromomethyl)-3,6-difluoro-benzoate (33 g, 95.9 mmol, 1 eq) in N,N-dimethylformamide (300 mL) was added N,N-diisopropylethylamine (49.60 g, 383.8 mmol, 4 eq) in one portion at 40° C. under nitrogen. The mixture was stirred at 40° C. for 30 minutes, then heated to 100° C. and stirred for 16 hours. The reaction was cooled to 20° C. and concentrated in reduced pressure at 45° C. The residue was purified by silica gel chromatography (petroleum ether/ethyl acetate=10/1 to 0/1) to give the crude product. This material was further purified by semi-preparative reverse phase HPLC (mobile phase: [water (FA)-ACN]; B %: 35%-65%, 21 min) to afford tert-butyl 5-amino-4-(5-bromo-4,7-difluoro-1-oxo-isoindolin-2-yl)-5-oxo-pentanoate (4.6 g, 11%) as a yellow solid. MS (ESI) m/z: 455.1 [M+Na]$^+$.

Step 5-9: Preparation of 2-((6-((5-chloro-2-(4-((1r,3r)-3-(4-(2-(2,6-dioxopiperidin-3-yl)-4,7-difluoro-1-oxoisoindolin-5-yl)piperidin-1-yl)cyclobutoxy)piperidin-1-yl)pyrimidin-4-yl)amino)-1-isopropyl-2-oxo-1,2-dihydroquinolin-3-yl)oxy)-N-methylacetamide

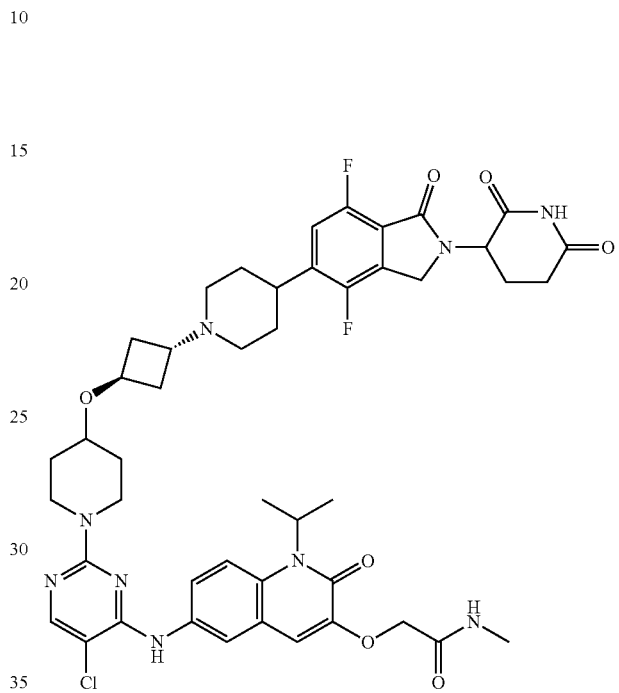

Compound 188 was prepared analogous to compound 72 following step 5-12 with the material made in step 4 of this example. The crude product was purified by silica gel chromatography (dichloromethane:methanol=100/1 to 10/1), then further purified by semi-preparative reverse phase HPLC (mobile phase: [water (FA)-ACN]; B %: 15%-45%, 7 min) to afford 2-[[6-[[5-chloro-2-[4-[3-[4-[2-(2,6-dioxo-3-piperidyl)-4,7-difluoro-1-oxo-isoindolin-5-yl]-1-piperidyl]cyclobutoxy]-1-piperidyl]pyrimidin-4-yl]amino]-1-isopropyl-2-oxo-3-quinolyl]oxy]-N-methyl-acetamide formate (76.4 mg, 30%) as a yellow solid. MS (ESI) m/z: 916.2 [M+H]$^+$; $^1$H NMR (400 MHz, DMSO-d$_6$) δ 11.02 (br s, 1H), 8.83 (s, 1H), 8.25 (s, 1H), 8.04 (s, 1H), 8.02-7.94 (m, 2H), 7.70 (s, 2H), 7.34 (dd, J=10.0, 4.8 Hz, 1H), 7.04 (s, 1H), 5.52-5.18 (m, 1H), 5.16-5.01 (m, 1H), 4.66-4.50 (m, 3H), 4.38 (br d, J=17.6 Hz, 1H), 4.25-4.03 (m, 4H), 3.57-3.50 (m, 2H), 3.30-3.20 (m, 2H), 3.04-2.82 (m, 5H), 2.69 (d, J=4.8 Hz, 3H), 2.60 (br d, J=16.4 Hz, 2H), 2.46-2.34 (m, 1H), 2.20-2.10 (m, 2H), 2.05-1.92 (m, 3H), 1.87-1.70 (m, 8H), 1.58 (d, J=6.8 Hz, 6H), 1.45-1.32 (m, 2H).

Compound 197 may be prepared by a procedure analogous to compound 188.

Example 48: Synthesis of 2-((6-((5-chloro-2-(4-((1r,3r)-3-(4-(6-(2,6-dioxopiperidin-3-yl)-5-oxo-6,7-dihydro-5H-pyrrolo[3,4-b]pyridin-2-yl)piperazin-1-yl)cyclobutoxy)piperidin-1-yl)pyrimidin-4-yl)amino)-1-isopropyl-2-oxo-1,2-dihydroquinolin-3-yl)oxy)-N-methylacetamide (Compound 189)

Step 1: preparation of methyl 6-chloro-2-methylnicotinate

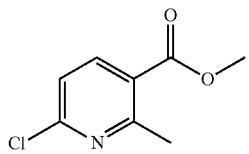

To a solution of 6-chloro-2-methylnicotinic acid (30 g, 174.84 mmol, 1 eq) in N,N-dimethylformamide (300 mL) was added potassium carbonate (60.41 g, 437.1 mmol, 2.5 eq) and iodomethane (99.27 g, 699.4 mmol, 44 mL, 4 eq), then the mixture was stirred at 25° C. for 12 hours. The reaction was diluted with water (50 mL) and extracted with ethyl acetate (2×100 mL). The combined organic layers were washed with brine (2×100 mL), dried over anhydrous sodium sulfate, filtered, and concentrated under reduced pressure to afford methyl 6-chloro-2-methyl-pyridine-3-carboxylate (34.93 g, crude) as a brown oil, which was used in the next step without further purification. MS (ESI) m/z: 186.1 [M+H]$^+$; $^1$H NMR (400 MHz, DMSO-$d_6$) δ 8.17 (br d, J=8.0 Hz, 1H), 7.46 (br d, J=8.0 Hz, 1H), 3.85 (s, 3H), 2.66 (s, 3H).

Step 2: preparation of methyl 2-(bromomethyl)-6-chloronicotinate

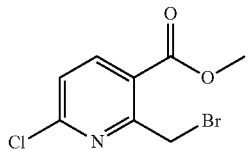

To a solution of methyl 6-chloro-2-methylnicotinate (34.93 g, 188.2 mmol, 1 eq) in carbon tetrachloride (350 mL) was added 2,2'-azobis(2-methylpropionitrile) (927 mg, 5.7 mmol, 0.03 eq) and N-bromosuccinimide (40.19 g, 225.8 mmol, 1.2 eq), then the mixture was stirred at 80° C. for 16 hours. The reaction was diluted with water (150 mL) and extracted with ethyl acetate (2×150 mL). The combined organic layers were washed with sodium sulfite (2×50 mL) and brine (2×50 mL), dried over anhydrous sodium sulfate, filtered, and concentrated under reduced pressure. The residue was purified by prep-HPLC (column: Phenomenex luna C18 (250*70 mm, 10 um); mobile phase: [water (FA)-ACN]; B %: 45%-70%, 21 min) to afford methyl 2-(bromomethyl)-6-chloron-icotinate (10.05 g, 20%) as a white solid. MS (ESI) m/z: 266.0 [M+H]$^+$; $^1$H NMR (400 MHz, DMSO-$d_6$) δ 8.29 (d, J=8.4 Hz, 1H), 7.64 (d, J=8.4 Hz, 1H), 4.92 (s, 2H), 3.93-3.85 (m, 3H).

Step 3: preparation of 3-(2-chloro-5-oxo-5H-pyrrolo[3,4-b]pyridin-6(7H)-yl)piperidine-2,6-dione

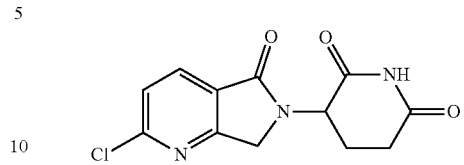

To a solution of methyl 2-(bromomethyl)-6-chloronicotinate (9 g, 34.0 mmol, 1 eq) and 3-aminopiperidine-2,6-dione (5.60 g, 34.0 mmol, 1 eq, hydrochloride) in N,N-dimethyl formamide (90 mL) was added N,N-diisopropylethylamine (13.19 g, 102.1 mmol, 17.8 mL, 3 eq), then the mixture was stirred at 110° C. for 6 hours. The mixture was cooled to 25° C. and poured into ice-water (w/w=1/1) (50 mL) and stirred for 5 minutes. The suspension was filtered and the filter cake was washed with methyl tert-butyl ether (30 mL). The filtrate solution was diluted with water (30 mL) and extracted with ethyl acetate (2×30 mL). The combined organic layers were washed with brine (2×30 mL), dried over anhydrous sodium sulfate, filtered, and concentrated under reduced pressure. The residue was triturated with methyl tert-butyl ether (30 mL) to afford 3-(2-chloro-5-oxo-5H-pyrrolo[3,4-b]pyridin-6(7H)-yl)piperidine-2,6-dione (5.68 g, 59%) as a purple solid. MS (ESI) m/z: 280.1 [M+H]$^+$; $^1$H NMR (400 MHz, DMSO-$d_6$) δ 11.03 (s, 1H), 8.20 (d, J=8.0 Hz, 1H), 7.68 (d, J=8.0 Hz, 1H), 5.17 (dd, J=5.2, 13.2 Hz, 1H), 4.61-4.35 (m, 2H), 2.97-2.90 (m, 1H), 2.65-2.56 (m, 1H), 2.45-2.35 (m, 1H), 2.02 (dtd, J=2.0, 5.2, 12.4 Hz, 1H).

Step 4: preparation of tert-butyl 4-((1r,3r)-3-(4-(6-(2,6-dioxopiperidin-3-yl)-5-oxo-6,7-dihydro-5H-pyrrolo[3,4-b]pyridin-2-yl)piperazin-1-yl)cyclobutoxy)piperidine-1-carboxylate

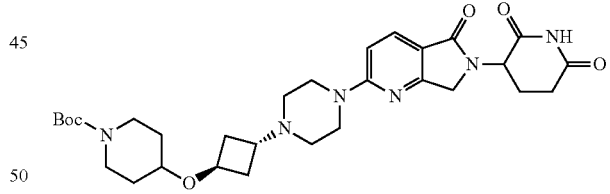

To a solution of 3-(2-chloro-5-oxo-5H-pyrrolo[3,4-b]pyridin-6(7H)-yl)piperidine-2,6-dione (500 mg, 1.8 mmol, 1 eq) and tert-butyl 4-((1r,3r)-3-(piperazin-1-yl)cyclobutoxy)piperidine-1-carboxylate (607 mg, 1.8 mmol, 1 eq) in N,N-dimethyl formamide (5 mL) was added N,N-diisopropylethylamine (693 mg, 5.4 mmol, 0.9 mL, 3 eq), then the mixture was stirred at 120° C. for 12 hours. The reaction mixture was diluted with water (30 mL) and extracted with dichloromethane (2×30 mL). The combined organic layers were washed with brine (2×30 mL), dried over anhydrous sodium sulfate, filtered, and concentrated under reduced pressure. The residue was purified by silica gel chromatography (petroleum ether/ethyl acetate=1/0 to dichloromethane/methanol=10/1) to afford tert-butyl 4-[3-[4-[6-(2,6-dioxo-3-piperidyl)-5-oxo-7H-pyrrolo[3,4-b]pyridine-2-yl]piperazin-1-yl]cyclobutoxy]piperidine-1-carboxylate (535 mg, 51%) as a brown solid. MS (ESI) m/z: 583.3 [M+H]+.

Step 5: preparation of 3-(5-oxo-2-(4-((1r,3r)-3-(piperidin-4-yloxy)cyclo-butyl)piperazin-1-yl)-5H-pyrrolo[3,4-b]pyridin-6(7H)-yl)piperidine-2,6-dione

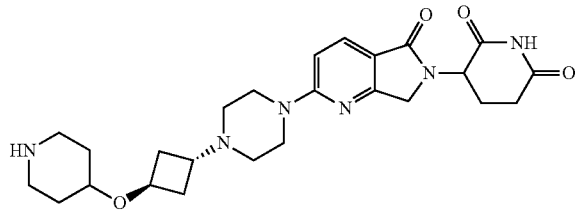 [SMILES: O=C1CCC(N2Cc3nc(N4CCN([C@H]5C[C@H](OC6CCNCC6)C5)CC4)ccc3C2=O)C(=O)N1]

To a solution of tert-butyl 4-((1r,3r)-3-(4-(6-(2,6-dioxopiperidin-3-yl)-5-oxo-6,7-dihydro-5H-pyrrolo[3,4-b]pyridin-2-yl)piperazin-1-yl)cyclobutoxy)piperidine-1-carboxylate (580 mg, 1.0 mmol) in dichloromethane (5 mL) was added trifluoroacetic acid (5 mL) and stirred at 25° C. for 30 minutes. The reaction mixture was concentrated. The residue was purified by prep-HPLC (column: Phenomenex luna C18 150*40 mm*15 um; mobile phase: [water (FA)-ACN]; B %: 1%-17%, 10 min) to afford 3-[5-oxo-2-[4-[3-(4-piperidyloxy)cyclobutyl]piperazin-1-yl]-7H-pyrrolo[3,4-b]pyridin-6-yl]piperidine-2,6-dione formate (304 mg, 57%) as a yellow solid. MS (ESI) m/z: 483.0 [M+H]+; 1H NMR (400 MHz, DMSO-d6) δ 10.96 (s, 1H), 8.73-8.41 (m, 2H), 7.88 (d, J=8.8 Hz, 1H), 7.04 (br d, J=8.8 Hz, 1H), 5.09 (dd, J=5.2, 13.2 Hz, 1H), 4.71-4.37 (m, 2H), 4.36-4.07 (m, 4H), 3.92-3.68 (m, 1H), 3.61-3.51 (m, 2H), 3.17 (br s, 3H), 3.03-2.84 (m, 5H), 2.63-2.53 (m, 3H), 2.46-2.30 (m, 2H), 2.23 (br s, 2H), 2.03-1.86 (m, 3H), 1.67-1.52 (m, 2H).

Step 6: preparation of 2-((6-((5-chloro-2-(4-((1r,3r)-3-(4-(6-(2,6-dioxopiperidin-3-yl)-5-oxo-6,7-dihydro-5H-pyrrolo[3,4-b]pyridin-2-yl)piperazin-1-yl)cyclobutoxy)piperidin-1-yl)pyrimidin-4-yl)amino)-1-isopropyl-2-oxo-1,2-dihydroquinolin-3-yl)oxy)-N-methylacetamide

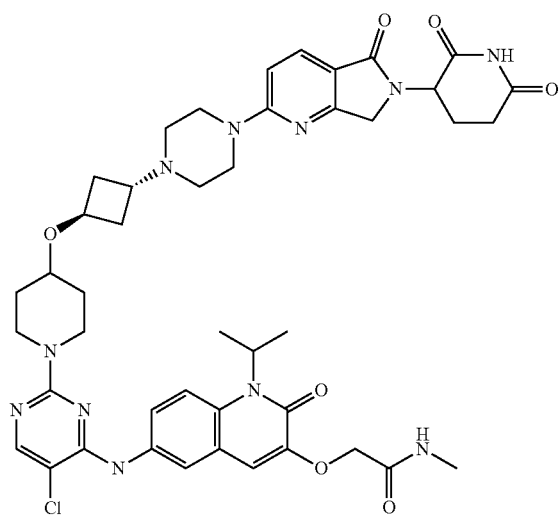

To a solution of 3-(5-oxo-2-(4-((1r,3r)-3-(piperidin-4-yloxy)cyclobutyl)piperazin-1-yl)-5H-pyrrolo[3,4-b]pyridin-6(7H)-yl)piperidine-2,6-dione formate (300 mg, 0.6 mmol, 1 eq) and 2-((6-((5-chloro-2-fluoropyrimidin-4-yl)amino)-1-isopropyl-2-oxo-1,2-dihydroquinolin-3-yl)oxy)-N-methylacetamide (235 mg, 0.6 mmol, 9.86e-1 eq) in dimethyl sulfoxide (3 mL) was added N,N-diisopropylethylamine (401 mg, 3.1 mmol, 0.54 mL, 5.5 eq). The mixture was stirred at 50° C. for 2 hours, then diluted with water (30 mL) and extracted with dichloromethane (2×30 mL). The combined organic layers were washed with brine (2×30 mL), dried over anhydrous sodium sulfate, filtered, and concentrated under reduced pressure. The residue was purified by prep-HPLC (column: Phenomenex luna C18 150*40 mm*15 um; mobile phase: [water (FA)-ACN]; B %: 10%-40%, 10 min) to afford 2-((6-((5-chloro-2-(4-((1r,3r)-3-(4-(6-(2,6-dioxopiperidin-3-yl)-5-oxo-6,7-dihydro-5H-pyrrolo[3,4-b]pyridin-2-yl)piperazin-1-yl)cyclobutoxy)piperidin-1-yl)pyrimidin-4-yl)amino)-1-isopropyl-2-oxo-1,2-dihydroquinolin-3-yl)oxy)-N-methylacetamide formate (150.4 mg, 27%) as an off-white solid. MS (ESI) m/z: 442.1 [M/2+1]+; 1H NMR (400 MHz, DMSO-d6) δ 10.94 (s, 1H), 8.82 (s, 1H), 8.22 (s, 1H), 8.04 (s, 1H), 7.99-7.92 (m, 2H), 7.77 (d, J=8.8 Hz, 1H), 7.68 (s, 2H), 7.02 (s, 1H), 6.90 (d, J=8.8 Hz, 1H), 5.32 (br s, 1H), 5.07 (dd, J=5.2, 13.2 Hz, 1H), 4.54 (s, 2H), 4.19 (br t, J=5.2 Hz, 1H), 4.14-4.03 (m, 3H), 3.64 (br s, 4H), 3.52 (br dd, J=4.0, 7.6 Hz, 2H), 3.22 (br t, J=10.0 Hz, 3H), 2.97-2.83 (m, 1H), 2.82-2.74 (m, 1H), 2.67 (d, J=4.8 Hz, 3H), 2.36 (br d, J=4.4 Hz, 5H), 2.23-2.14 (m, 2H), 2.03-1.91 (m, 3H), 1.86-1.76 (m, 2H), 1.43-1.30 (m, 2H).

Compounds 192 and 198 may be prepared by a procedure analogous to compound 189.

Example 49: Synthesis of 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-1-cyclobutyl-2-oxo-1,2-dihydroquinolin-3-yl}oxy)-N-methylacetamide (Compound 190)

Step 1: Preparation of 2-(2-bromophenyl)-N-cyclobutyl-2-oxoacetamide

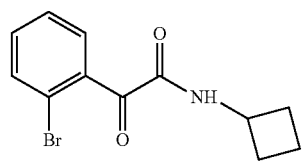 [SMILES: O=C(NC1CCC1)C(=O)c1ccccc1Br]

To a stirred solution of (2-bromophenyl)(oxo)acetic acid (8 g, 34.9 mmol, 1 equiv) and cyclobutylamine (2.48 g, 34.9 mmol, 1 equiv) in DMF (80 mL) were added DIEA (13.54 g, 104.8 mmol, 3 equiv) and T3P (44.46 g, 139.7 mmol, 4 equiv) dropwise at room temperature under nitrogen atmosphere. The resulting mixture was stirred for 3 hours at room temperature under nitrogen atmosphere, and then extracted with EtOAc (3×100 mL). The combined organic layers were washed with brine (2×20 mL), dried over anhydrous Na2SO4. After filtration, the filtrate solution was concentrated under reduced pressure. The residue was purified by silica gel column chromatography (PE/EA=8:1) to afford 2-(2-bromophenyl)-N-cyclobutyl-2-oxoacetamide (6.8 g, 69%) as a yellow solid.

Step 2: Preparation of 1-cyclobutylindole-2,3-dione

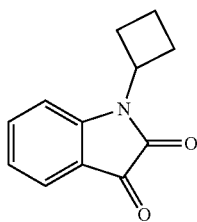 [SMILES: O=C1C(=O)N(C2CCC2)c2ccccc21]

To a stirred solution of 2-(2-bromophenyl)-N-cyclobutyl-2-oxoacetamide (6.8 g, 24.1 mmol, 1 equiv) and TBAB (10.88 g, 33.7 mmol, 1.4 equiv) in toluene (200 mL) were added $K_2CO_3$ (9.99 g, 72.3 mmol, 3 equiv), 1,10-Phenanthroline (0.87 g, 4.8 mmol, 0.2 equiv) and CuI (0.46 g, 2.4 mmol, 0.1 equiv) dropwise at room temperature under nitrogen atmosphere. The resulting mixture was stirred for 3 hours at room temperature under nitrogen atmosphere, upon which it was allowed to cool to room temperature. The resulting mixture was extracted with EtOAc (3×60 mL). The combined organic layers were washed with brine (2×20 mL), dried over anhydrous $Na_2SO_4$. After filtration, the filtrate solution was concentrated under reduced pressure. The residue was purified by silica gel column chromatography (PE/EA=6:1) to afford 1-cyclobutylindole-2,3-dione (2.5 g, 52%) as yellow oil. MS (ESI): m/z 202.20 $[M+H]^+$.

Step 3: Preparation of 1-cyclobutyl-5-nitroindole-2,3-dione

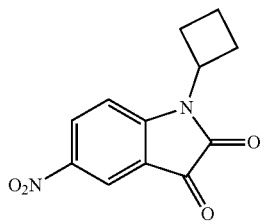 [SMILES: O=C1C(=O)N(C2CCC2)c2ccc([N+](=O)[O-])cc21]

A solution of 1-cyclobutylindole-2,3-dione (2.5 g, 12.4 mmol, 1 equiv) and potassiooxy nitrite (1.88 g, 18.6 mmol, 1.5 equiv) in $H_2SO_4$ (20 mL) was stirred for 2 hours at room temperature under nitrogen atmosphere. The reaction was quenched with water at 0° C. The resulting mixture was extracted with $CH_2Cl_2$ (3×50 mL). The combined organic layers were washed with brine (2×10 mL), dried over anhydrous $Na_2SO_4$. After filtration, the filtrate solution was concentrated under reduced pressure. The residue was purified by flash column chromatography (PE/EA=8:1) to afford 1-cyclobutyl-5-nitroindole-2,3-dione (880 mg, 29%) as a yellow oil. MS (ESI): m/z 247.05 $[M+H]^+$.

Steps 4-8: Preparation of 2-((1-cyclobutyl-6-((2,5-dichloropyrimidin-4-yl)amino)-2-oxo-1,2-dihydroquinolin-3-yl)oxy)-N-methylacetamide

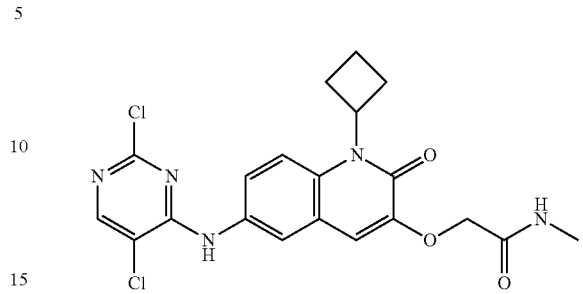

The title compound was prepared analogous to compound 13 following step 2-6 with the material made in step 3 of this example.

Step 9: Preparation of 2-((6-((5-chloro-2-(4-((1r,3r)-3-(4-(2-(2,6-dioxopiperidin-3-yl)-4-fluoro-1-oxoisoindolin-5-yl)piperidin-1-yl)cyclobutoxy)piperidin-1-yl)pyrimidin-4-yl)amino)-1-cyclobutyl-2-oxo-1,2-dihydroquinolin-3-yl)oxy)-N-methylacetamide

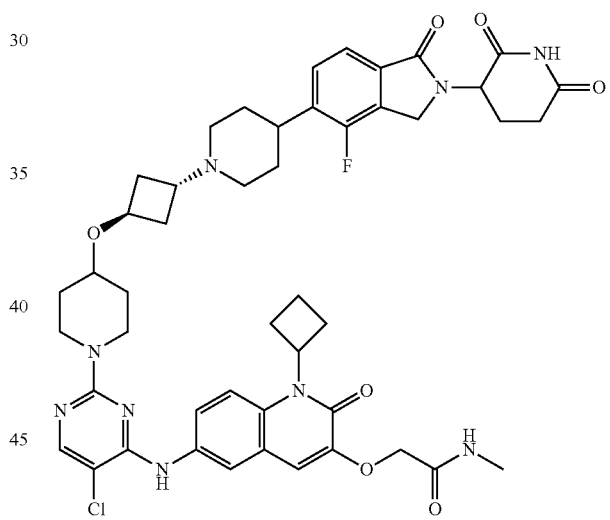

The title compound was prepared analogous to step 9 of compound 187 using 3-(4-fluoro-1-oxo-5-{1-[(1r,3r)-3-(piperidin-4-yloxy)cyclobutyl]piperidin-4-yl}-3H-isoindol-2-yl)piperidine-2,6-dione. The crude product was purified by flash column chromatography ($CH_2Cl_2$/MeOH=15:1) to afford 2-({6-[(5-chloro-2-{4-[(1r,3r)-3-{4-[2-(2,6-dioxopiperidin-3-yl)-4-fluoro-1-oxo-3H-isoindol-5-yl]piperidin-1-yl}cyclobutoxy]piperidin-1-yl}pyrimidin-4-yl)amino]-1-cyclobutyl-2-oxoquinolin-3-yl}oxy)-N-methylacetamide (75 mg, 33%) as an off-white solid. MS (ESI): m/z 910.40 $[M+H]^+$; $^1H$ NMR (400 MHz, DMSO-d6, ppm) δ 11.00 (s, 1H), 8.83 (s, 1H), 8.09-8.00 (m, 2H), 7.90 (d, J=2.5 Hz, 1H), 7.65 (m, 1H), 7.52 (m, 3H), 7.04 (s, 1H), 5.11 (m, 2H), 4.58-4.49 (m, 3H), 4.36 (d, J=17.2 Hz, 1H), 4.18-4.10 (m, 3H), 3.51 (s, 2H), 3.21 (m, 2H), 3.02 (s, 2H), 2.90-2.87 (m, 3H), 2.76-2.65 (m, 5H), 2.65-2.51 (m, 2H), 2.42 (m, 1H), 2.01 (s, 2H), 1.97 (s, 3H), 1.87-1.72 (m, 9H), 1.36 (m, 2H), 1.22 (s, 1H).

Compound 191 may be prepared by a procedure analogous to compound 190.

Example 50: Synthesis of 2-({6-[(5-chloro-2-{4-[(1r,3r)-3-{4-[2-(2,6-dioxopiperidin-3-yl)-4-fluoro-7-methyl-1-oxo-3H-isoindol-5-yl]piperidin-1-yl}cyclobutoxy]piperidin-1-yl}pyrimidin-4-yl)amino]-1-isopropyl-2-oxoquinolin-3-yl}oxy)-N-methylacetamide (Compound 208)

Step 1: Preparation of methyl 4-bromo-5-fluoro-2-methylbenzoate

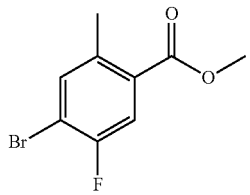

A solution of 4-bromo-5-fluoro-2-methylbenzoic acid (2 g, 8.6 mmol, 1 equiv) and $H_2SO_4$ (2 mL, 37.5 mmol, 4 equiv) in MeOH (25 mL) was stirred overnight at 60° C. under nitrogen atmosphere. The mixture was allowed to cool down to room temperature and concentrated under vacuum to afford methyl 4-bromo-5-fluoro-2-methylbenzoate (2.1 g, 99%) as a yellow oil.

Step 2: Preparation of tert-butyl 4-[2-fluoro-4-(methoxycarbonyl)-5-methylphenyl]-3,6-dihydro-2H-pyridine-1-carboxylate

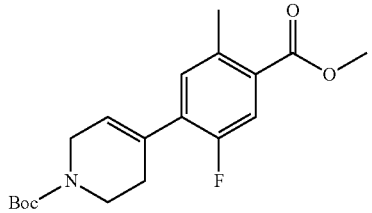 [SMILES: COC(=O)c1cc(F)c(C2=CCN(C(=O)OC(C)(C)C)CC2)cc1C]

To a stirred solution of methyl 4-bromo-5-fluoro-2-methylbenzoate (2.1 g, 8.5 mmol, 1 equiv) and tert-butyl 4-(4,4,5,5-tetramethyl-1,3,2-dioxaborolan-2-yl)-3,6-dihydro-2H-pyridine-1-carboxylate (3.15 g, 10.2 mmol, 1.2 equiv) in 24 mL 1,4-dioxane:$H_2O$ (5:1) were added CsF (3.87 g, 25.5 mmol, 3 equiv) and Pd(dtbpf)$Cl_2$ (553.98 mg, 0.9 mmol, 0.1 equiv). The mixture was stirred at 90° C. under nitrogen atmosphere. Then cool down to room temperature, quenched with water, extracted with EtOAc (3×60 mL). The combined organic layers were washed with brine (2×20 mL), dried over anhydrous sodium sulfate, filtered, and concentrated. The residue was purified by flash column chromatography (PE/EA=3:1) to afford tert-butyl 4-[2-fluoro-4-(methoxycarbonyl)-5-methylphenyl]-3,6-dihydro-2H-pyridine-1-carboxylate (2.2 g, 74%) as a yellow solid.

Step 3: Preparation of tert-butyl 4-[2-fluoro-4-(methoxycarbonyl)-5-methylphenyl]piperidine-1-carboxylate

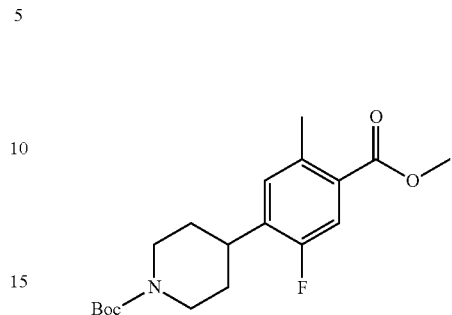

To a solution of tert-butyl 4-[2-fluoro-4-(methoxycarbonyl)-5-methylphenyl]-3,6-dihydro-2H-pyridine-1-carboxylate (2.2 g, 6.3 mmol, 1 equiv) in 20 mL THF was added 10% Pd/C (0.3 g) under nitrogen atmosphere. The mixture was degassed and purged with hydrogen for 3 times. Then the reaction was stirred under hydrogen balloon overnight, then filtered through a pad of Celite and concentrated under reduced pressure to afford tert-butyl 4-[2-fluoro-4-(methoxycarbonyl)-5-methylphenyl]piperidine-1-carboxylate (1.9 g, 86%) as a yellow solid. MS (ESI): m/z 335.10 $[M+H]^+$.

Step 4: Preparation of 4-[1-(tert-butoxycarbonyl)piperidin-4-yl]-5-fluoro-2-methylbenzoic acid

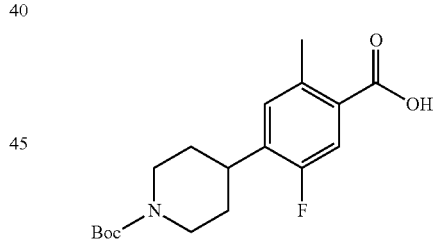

A solution of tert-butyl 4-[2-fluoro-4-(methoxycarbonyl)-5-methylphenyl]piperidine-1-carboxylate (1.9 g, 5.4 mmol, 1 equiv) and caustic soda (0.87 g, 21.6 mmol, 4 equiv) in 20 mL THF:$H_2O$ (1:1) was stirred overnight at 40° C. under nitrogen atmosphere. The pH of the reaction was acidified to 5 with conc. HCl. The resulting mixture was extracted with $CH_2Cl_2$ (3×50 mL). The combined organic layers were washed with brine (2×20 mL), dried over anhydrous $Na_2SO_4$. After filtration, the filtrate solution was concentrated under reduced pressure to afford 4-[1-(tert-butoxycarbonyl)piperidin-4-yl]-5-fluoro-2-methylbenzoic acid (1.6 g, 88%) as a yellow solid.

Step 5: Preparation of tert-butyl 4-(4-fluoro-3-hydroxy-7-methyl-1-oxo-3H-2-benzofuran-5-yl)piperidine-1-carboxylate

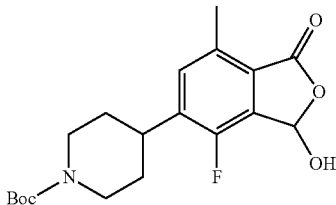 [SMILES: Cc1cc(C2CCN(C(=O)OC(C)(C)C)CC2)c(F)c2c1C(=O)OC2O]

To a solution of 4-[1-(tert-butoxycarbonyl)piperidin-4-yl]-5-fluoro-2-methylbenzoic acid (1.6 g, 4.7 mmol, 1 equiv) in THF (10 mL) was dropwise added n-butyllithium solution (2.5 M in hexane, 4.7 mL, 2.5 mmol) at −78° C. under $N_2$ atmosphere, stirred at −78° C. for 2 hours. Then a solution of dimethylformamide (1.73 g, 23.7 mmol, 5 equiv) in 5 mL THF was dropwise added and the mixture was stirred for another 40 min. The reaction was quenched with sat. $NH_4Cl$ (30 mL), the mixture was extracted with EtOAc (2×50 mL). The combined organic extracts were washed with brine (10 mL), dried over anhydrous $Na_2SO_4$, filtered, and concentrated under vacuum to afford tert-butyl 4-(4-fluoro-3-hydroxy-7-methyl-1-oxo-3H-2-benzofuran-5-yl)piperidine-1-carboxylate (1 g, 58%) as a yellow oil.

Step 6: Preparation of tert-butyl 4-[2-fluoro-3-formyl-4-(methoxycarbonyl)-5-methylphenyl]piperidine-1-carboxylate

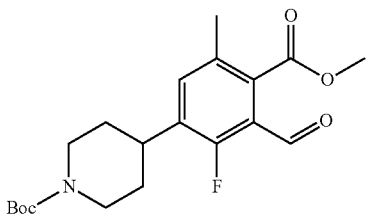 [SMILES: COC(=O)c1c(C)cc(C2CCN(C(=O)OC(C)(C)C)CC2)c(F)c1C=O]

To a stirred solution of tert-butyl 4-(4-fluoro-3-hydroxy-7-methyl-1-oxo-3H-2-benzofuran-5-yl)piperidine-1-carboxylate (1 g, 2.7 mmol, 1 equiv) and $K_2CO_3$ (1.13 g, 8.2 mmol, 3 equiv) in DMF (10 mL) was dropwise added $CH_3I$ (388.45 mg, 2.7 mmol, 1 equiv) at room temperature under nitrogen atmosphere. The reaction was quenched with water at room temperature, extracted with EtOAc (3×50 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EA (1:1) to afford tert-butyl 4-[2-fluoro-3-formyl-4-(methoxycarbonyl)-5-methylphenyl]piperidine-1-carboxylate (680 mg, 65%) as a yellow oil.

Step 7: Preparation of tert-butyl 4-{2-[(1S)-4-(tert-butoxy)-1-carbamoyl-4-oxobutyl]-4-fluoro-7-methyl-1-oxo-3H-isoindol-5-yl}piperidine-1-carboxylate

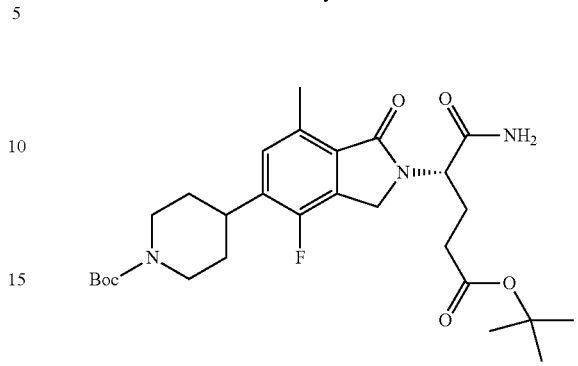

A solution of tert-butyl 4-[2-fluoro-3-formyl-4-(methoxycarbonyl)-5-methylphenyl]piperidine-1-carboxylate (680 mg, 1.8 mmol, 1 equiv) and tert-butyl (4S)-4-amino-4-carbamoylbutanoate (398.72 mg, 2.0 mmol, 1.1 equiv) in 30 mL DCE was stirred overnight at 40° C. under nitrogen atmosphere. Then $NaBH_3CN$ (3 mg, 0.05 mmol, 0.03 equiv) was added and the mixture was stirred for 1 hour at 40° C. under nitrogen atmosphere. The reaction was quenched with water at room temperature, extracted with $CH_2Cl_2$ (3×50 mL). The combined organic layers were washed with brine (2×20 mL), dried over anhydrous $Na_2SO_4$. After filtration, the filtrate was concentrated under reduced pressure. The residue was purified by silica gel column chromatography, eluted with EA/DCM (1:3) to afford tert-butyl 4-{2-[(1S)-4-(tert-butoxy)-1-carbamoyl-4-oxobutyl]-4-fluoro-7-methyl-1-oxo-3H-isoindol-5-yl}piperidine-1-carboxylate (380 mg, 40%) as a yellow solid.

Step 8: Preparation of tert-butyl (4S)-4-carbamoyl-4-[4-fluoro-7-methyl-1-oxo-5-(piperidin-4-yl)-3H-isoindol-2-yl]butanoate

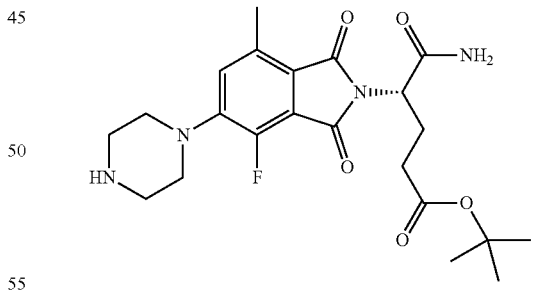

A solution of tert-butyl 4-{2-[(1S)-4-(tert-butoxy)-1-carbamoyl-4-oxobutyl]-4-fluoro-7-methyl-1-oxo-3H-isoindol-5-yl}piperidine-1-carboxylate (380 mg, 0.7 mmol, 1 equiv) and chlorotrimethylsilane (773.61 mg, 7.1 mmol, 10 equiv) in i-PrOH (15 mL) was stirred overnight at room temperature under nitrogen atmosphere. The pH of the reaction was adjusted to 8 with $Na_2CO_3$ (aq.), extracted with DCM. The organic layer was concentrated in vacuo to afford tert-butyl (4S)-4-carbamoyl-4-[4-fluoro-7-methyl-1-oxo-5-(piperidin-4-yl)-3H-isoindol-2-yl]butanoate (260 mg, 84%) as a yellow oil.

Step 9: Preparation of tert-butyl 4-[(1r,3r)-3-(4-{2-[(1S)-4-(tert-butoxy)-1-carbamoyl-4-oxobutyl]-4-fluoro-7-methyl-1-oxo-3H-isoindol-5-yl}piperidin-1-yl)cyclobutoxy]piperidine-1-carboxylate

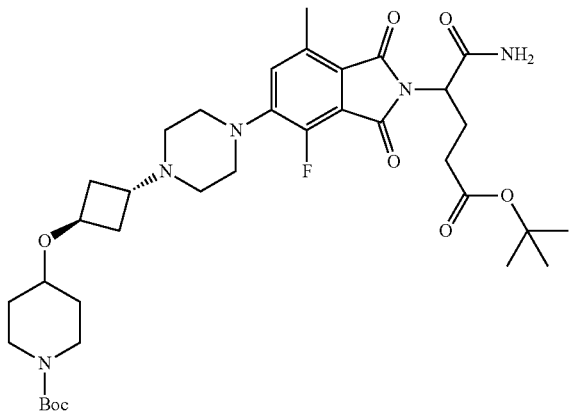 [SMILES: Cc1cc(N2CCN([C@H]3C[C@H](OC4CCN(C(=O)OC(C)(C)C)CC4)C3)CC2)c(F)c2c1C(=O)N(C(CCC(=O)OC(C)(C)C)C(N)=O)C2=O]

To a stirred solution of tert-butyl (4S)-4-carbamoyl-4-[4-fluoro-7-methyl-1-oxo-5-(piperidin-4-yl)-3H-isoindol-2-yl] butanoate (260 mg, 0.6 mmol, 1 equiv) and tert-butyl 4-[(1s,3s)-3-(trifluoromethanesulfonyloxy)cyclobutoxy]piperidine-1-carboxylate (314.52 mg, 0.8 mmol, 1.3 equiv) in MeCN (12 mL) was added DIEA (232.54 mg, 1.8 mmol, 3 equiv) dropwise at 30° C. under nitrogen atmosphere, and stirred for 3 hours. The resulting mixture was concentrated under vacuum. The residue was purified by reverse flash chromatography (mobile phase, MeCN in Water (10 mmol/L NH$_4$HCO$_3$), 40% to 70% gradient in 30 min; 254 nm) to afford tert-butyl 4-[(1r,3r)-3-(4-{2-[(1S)-4-(tert-butoxy)-1-carbamoyl-4-oxobutyl]-4-fluoro-7-methyl-1-oxo-3H-isoindol-5-yl}piperidin-1-yl)cyclobutoxy]piperidine-1-carboxylate (210 mg, 51%) as a yellow solid. MS (ESI): m/z 687.50 [M+H]$^+$.

Step 10: Preparation of tert-butyl 4-[(1r,3r)-3-{4-[2-(2,6-dioxopiperidin-3-yl)-4-fluoro-7-methyl-1-oxo-3H-isoindol-5-yl]piperidin-1-yl}cyclobutoxy]piperidine-1-carboxylate

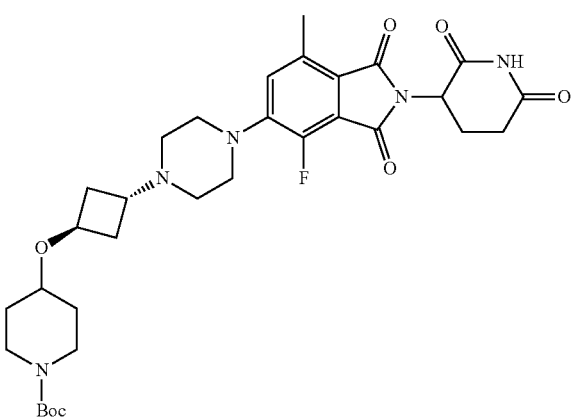 [SMILES: Cc1cc(N2CCN([C@H]3C[C@H](OC4CCN(C(=O)OC(C)(C)C)CC4)C3)CC2)c(F)c2c1C(=O)N(C1CCC(=O)NC1=O)C2=O]

A solution of tert-butyl 4-[(1r,3r)-3-(4-{2-[(1S)-4-(tert-butoxy)-1-carbamoyl-4-oxobutyl]-4-fluoro-7-methyl-1-oxo-3H-isoindol-5-yl}piperidin-1-yl)cyclobutoxy]piperidine-1-carboxylate (210 mg, 0.3 mmol, 1 equiv) and Cs$_2$CO$_3$ (298.84 mg, 0.9 mmol, 3 equiv) in 15 mL acetonitrile was stirred overnight at 80° C. under nitrogen atmosphere. The mixture was allowed to cool down to room temperature, filtered, the filter cake was washed with DCM (3×50 mL). The filtrate solution was concentrated under reduced pressure to afford tert-butyl 4-[(1r,3r)-3-{4-[2-(2,6-dioxopiperidin-3-yl)-4-fluoro-7-methyl-1-oxo-3H-isoindol-5-yl]piperidin-1-yl}cyclobutoxy]piperidine-1-carboxylate (120 mg, 64%) as a yellow oil. MS (ESI): m/z 687.50 [M+H]$^+$.

Step 11: Preparation of 3-(4-fluoro-7-methyl-1-oxo-5-{1-[(1r,3r)-3-(piperidin-4-yloxy)cyclobutyl]piperidin-4-yl}-3H-isoindol-2-yl)piperidine-2,6-dione

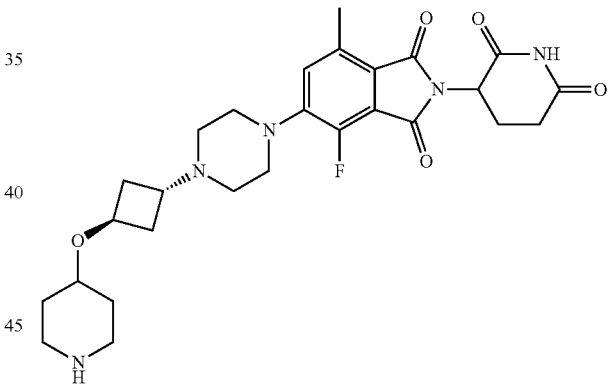

Into a 50 mL round-bottom flask were added tert-butyl 4-[(1r,3r)-3-{4-[2-(2,6-dioxopiperidin-3-yl)-4-fluoro-7-methyl-1-oxo-3H-isoindol-5-yl]piperidin-1-yl}cyclobutoxy]piperidine-1-carboxylate (120 mg, 0.2 mmol, 1 equiv) and HCl (gas) in 1,4-dioxane (2 mL, 65.8 mmol) at room temperature. The resulting mixture was stirred for 2 hours at room temperature under nitrogen atmosphere, then concentrated under vacuum to afford 3-(4-fluoro-7-methyl-1-oxo-5-{1-[(1r,3r)-3-(piperidin-4-yloxy)cyclobutyl]piperidin-4-yl}-3H-isoindol-2-yl)piperidine-2,6-dione (90 mg, 90%) as a yellow solid.

349

Step 12: Preparation of 2-({6-[(5-chloro-2-{4-[(1r, 3r)-3-{4-[2-(2,6-dioxopiperidin-3-yl)-4-fluoro-7-methyl-1-oxo-3H-isoindol-5-yl]piperidin-1-yl}cyclobutoxy]piperidin-1-yl}pyrimidin-4-yl)amino]-1-isopropyl-2-oxoquinolin-3-yl}oxy)-N-methylacetamide

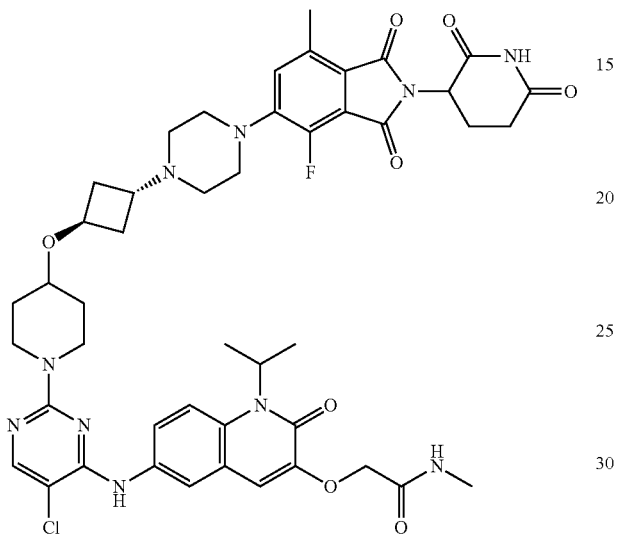

To a stirred solution of 3-(4-fluoro-7-methyl-1-oxo-5-{1-[(1r,3r)-3-(piperidin-4-yloxy)cyclobutyl]piperidin-4-yl}-3H-isoindol-2-yl)piperidine-2,6-dione (126.98 mg, 0.2 mmol, 1.3 equiv) and 2-({6-[(5-chloro-2-fluoropyrimidin-4-yl)amino]-1-isopropyl-2-oxoquinolin-3-yl}oxy)-N-methylacetamide (80 mg, 0.2 mmol, 1.00 equiv) in DMSO (5 mL) was dropwise added DIEA (73.88 mg, 0.6 mmol, 3 equiv) and stirred at 50° C. for 4 hours under nitrogen atmosphere. The mixture was allowed to cool down to room temperature, then purified by reverse flash chromatography (mobile phase, MeCN in water, 45% to 65% gradient in 30 min; 254 nm) to afford 2-({6-[(5-chloro-2-{4-[(1r,3r)-3-{4-[2-(2,6-dioxopiperidin-3-yl)-4-fluoro-7-methyl-1-oxo-3H-isoindol-5-yl]piperidin-1-yl}cyclobutoxy]piperidin-1-yl}pyrimidin-4-yl)amino]-1-isopropyl-2-oxoquinolin-3-yl}oxy)-N-methylacetamide (59.4 mg, 34%) as a white solid. MS (ESI): m/z 912.55 [M+H]$^+$; $^1$H NMR (400 MHz, DMSO-d6) δ 11.00 (s, 1H), 8.84 (s, 1H), 8.04-7.96 (m, 3H), 7.69 (s, 2H), 7.27 (d, J=6.1 Hz, 1H), 7.03 (s, 1H), 5.29 (s, 1H), 5.07 (m, 1H), 4.55-4.45 (m, 3H), 4.28-4.09 (m, 4H), 3.52 (s, 1H), 3.23 (m, 2H), 2.99-2.62 (m, 5H), 2.57 (s, 3H), 2.42 (m, 4H), 2.22 (m, 1H), 2.14 (s, 2H), 2.04-1.94 (m, 3H), 1.86-1.68 (m, 8H), 1.57 (d, J=6.8 Hz, 6H), 1.44-1.34 (m, 2H).

350

Example 51: Synthesis of 2-({6-[(5-chloro-2-{4-[(1r,3r)-3-{4-[2-(2,6-dioxopiperidin-3-yl)-4-fluoro-1,3-dioxoisoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (Compound 193)

Step 1: preparation of benzyl (2R)-2-methyl-4-[(1r,3r)-3-{[1-(tert-butoxycarbonyl)piperidin-4-yl]oxy}cyclobutyl]piperazine-1-carboxylate

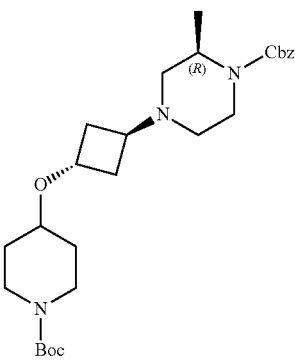

Into a 30 mL sealed tube was added tert-butyl 4-[(1s,3s)-3-(trifluoromethanesulfonyloxy)cyclobutoxy]piperidine-1-carboxylate (700 mg, 1.7 mmol, 1.0 equiv), benzyl (2R)-2-methylpiperazine-1-carboxylate (406 mg, 1.7 mmol, 1.0 equiv), DIEA (1.0 mL) and ACN (20 mL). The resulting mixture was stirred for 6 hours at 30° C. under nitrogen atmosphere. The reaction was quenched by the addition of water (30 mL) at room temperature and the resulting mixture was extracted with CH$_2$Cl$_2$ (3×50 mL). The combined organic layers were washed with brine (3×30 mL), dried over anhydrous sodium sulfate, and concentrated under reduced pressure. The residue was purified by reverse flash chromatography (mobile phase, CH$_3$CN/water (10 mmol/L NH4HCO3), 0% to 55% gradient in 30 min; 254 nm) to afford benzyl (2R)-2-methyl-4-[(1r,3r)-3-{[1-(tert-butoxycarbonyl)piperidin-4-yl]oxy}cyclobutyl]piperazine-1-carboxylate (570 mg, 67%) as a brown oil. MS (ESI): m/z 488.30 [MH$^+$].

Step 2: preparation of tert-butyl 4-[(1r,3r)-3-[(3R)-3-methylpiperazin-1-yl]cyclobutoxy]piperidine-1-carboxylate

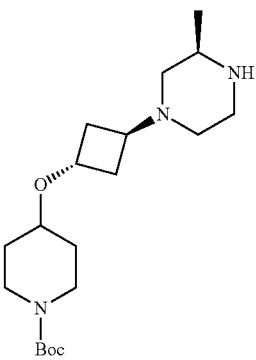 [SMILES: C[C@@H]1CN([C@H]2C[C@H](OC3CCN(C(=O)OC(C)(C)C)CC3)C2)CCN1]

To a solution of benzyl (2R)-2-methyl-4-[(1r,3r)-3-{[1-(tert-butoxycarbonyl)piperidin-4-yl]oxy}cyclobutyl]piperazine-1-carboxylate (620 mg, 1.3 mmol, 1.0 equiv) in 50 mL i-PrOH was added Pd/C (10%, 600 mg). The mixture was degassed under vacuum and purged with hydrogen several times. The reaction was stirred at room temperature for 6 hours under hydrogen atmosphere using a hydrogen balloon, filtered through a celite pad and concentrated under reduced pressure to afford tert-butyl 4-[(1r,3r)-3-[(3R)-3-methylpiperazin-1-yl]cyclobutoxy]piperidine-1-carboxylate (300 mg, 67%) as a brown solid. MS (ESI): m/z 354.40 [MH⁺].

Step 3: preparation of tert-butyl 4-[(1r,3r)-3-[(3R)-4-[4-chloro-2-(2,6-dioxopiperidin-3-yl)-1,3-dioxoisoindol-5-yl]-3-methylpiperazin-1-yl]cyclobutoxy]piperidine-1-carboxylate

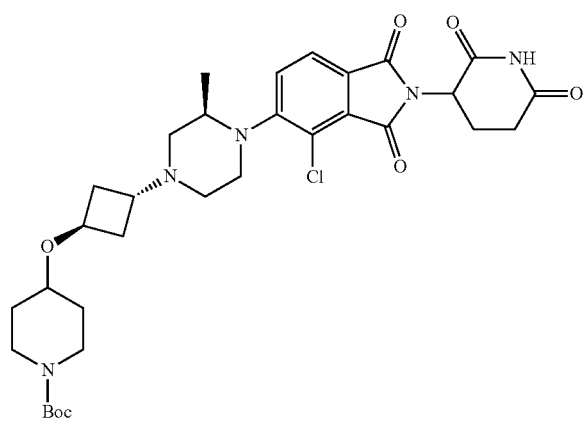 [SMILES: C[C@@H]1CN([C@H]2C[C@H](OC3CCN(C(=O)OC(C)(C)C)CC3)C2)CCN1c1ccc2c(c1Cl)C(=O)N(C1CCC(=O)NC1=O)C2=O]

To a stirred solution/mixture of tert-butyl 4-[(1r,3r)-3-[(3R)-3-methylpiperazin-1-yl]cyclobutoxy]piperidine-1-carboxylate (386 mg, 1.1 mmol, 1.0 equiv) and 4-chloro-2-(2,6-dioxopiperidin-3-yl)-5-fluoroisoindole-1,3-dione (339 mg, 1.1 mmol, 1.0 equiv) in DMSO was added DIEA (0.5 mL). The resulting mixture was stirred for 3 hours at 100° C. under nitrogen atmosphere. The residue was purified by reverse flash chromatography (mobile phase, MeCN in water, 10% to 50% gradient in 30 min; 254 nm) to afford tert-butyl 4-[(1r,3r)-3-[(3R)-4-[4-chloro-2-(2,6-dioxopiperidin-3-yl)-1,3-dioxoisoindol-5-yl]-3-methylpiperazin-1-yl]cyclobutoxy]piperidine-1-carboxylate (300 mg, 43%) as a white solid. MS (ESI): m/z 382.25 [MH⁺].

Step 4: preparation of tert-butyl 4-[(1r,3r)-3-[(3R)-4-[2-(2,6-dioxopiperidin-3-yl)-4-methyl-1,3-dioxoisoindol-5-yl]-3-methylpiperazin-1-yl]cyclobutoxy]piperidine-1-carboxylate

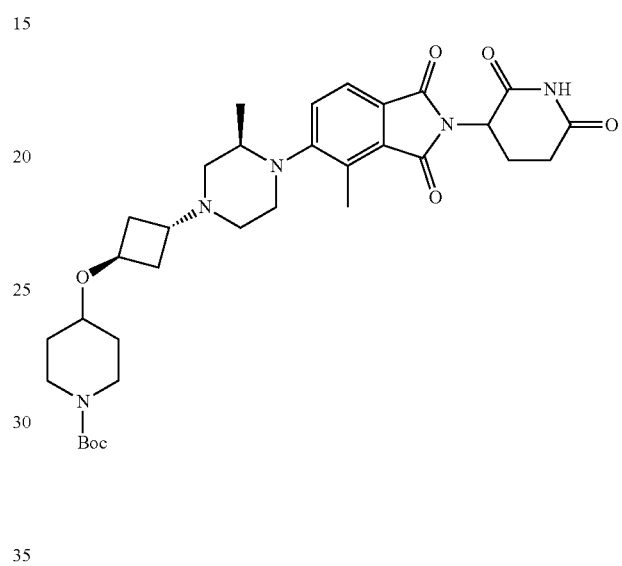

In a 8 mL sealed tube was added tert-butyl 4-[(1r,3r)-3-[(3R)-4-[4-chloro-2-(2,6-dioxopiperidin-3-yl)-1,3-dioxoisoindol-5-yl]-3-methylpiperazin-1-yl]cyclobutoxy]piperidine-1-carboxylate (330 mg, 0.5 mmol, 1.0 equiv), trimethyl-1,3,5,2,4,6-trioxatriborinane (321 mg, 2.6 mmol, 5.0 equiv), [1,3-bis[2,6-bis(propan-2-yl)phenyl]-2,3-dihydro-1H-imidazol-2-yl]dichloro(3-chloropyridin-1-ium-1-yl)palladium (34 mg, 0.05 mmol, 0.1 equiv), K₂CO₃ (212 mg, 1.5 mmol, 3.0 equiv) and dioxane (5 mL), the mixture was stirred at 100° C. for 2 hours. Then the reaction was allowed to cool to room temperature. The resulting mixture was diluted with EtOAc (500 mL) and washed with brine (3×100 mL). The organic phase was dried over anhydrous sodium sulfate, filtered, and concentrated in vacuo. The residue was purified by silica gel column chromatography, eluted with DCM/MeOH (10:1) to afford tert-butyl 4-[(1r,3r)-3-[(3R)-4-[2-(2,6-dioxopiperidin-3-yl)-4-methyl-1,3-dioxoisoindol-5-yl]-3-methylpiperazin-1-yl]cyclobutoxy]piperidine-1-carboxylate (234 mg, 73%) as a brown solid. MS (ESI): m/z 624.30 [M+H]⁺.

Step 5-6: preparation of 2-({6-[(5-chloro-2-{4-[(1r,3r)-3-{4-[2-(2,6-dioxopiperidin-3-yl)-4-fluoro-1,3-dioxoisoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide

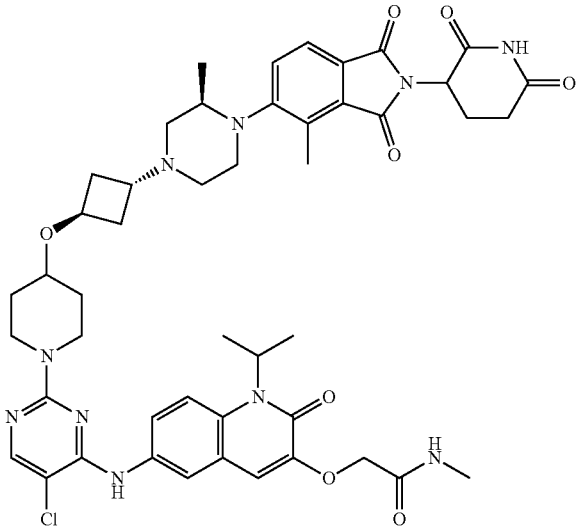 [SMILES: CNC(=O)COc1cc2cc(Nc3nc(N4CCC(O[C@H]5C[C@H](N6CCN(c7ccc8c(c7C)C(=O)N(C7CCC(=O)NC7=O)C8=O)[C@H](C)C6)C5)CC4)ncc3Cl)ccc2n(C(C)C)c1=O]

Compound 193 was prepared analogous to compound 187 following step 8-9 using material made in step 4 of this example. The crude product was purified by reverse flash chromatography (mobile phase, CH$_3$CN/water (10 mmol/L NH$_4$HCO$_3$), 0% to 70% gradient in 30 min; 254 nm) to afford 2-({6-[(5-chloro-2-{4-[(1r,3r)-3-[(3R)-4-[2-(2,6-dioxopiperidin-3-yl)-4-methyl-1,3-dioxoisoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (78.1 mg, 21%) as a yellow solid. MS (ESI): m/z 911.30 [MH$^+$]; $^1$H NMR (400 MHz, DMSO-d$_6$) δ 11.11 (s, 1H), 8.85 (s, 1H), 8.05 (s, 1H), 7.96 (d, J=7.0 Hz, 2H), 7.75-7.67 (m, 3H), 7.03 (s, 1H), 5.31 (s, 1H), 5.10 (dd, J=12.9, 5.4 Hz, 1H), 4.55 (s, 2H), 4.13 (d, J=12.4 Hz, 3H), 3.54 (s, 1H), 3.47 (m, 1H), 3.35 (m, 1H), 3.23 (t, J=11.2 Hz, 2H), 3.07 (s, 1H), 2.92-2.83 (m, 2H), 2.68 (d, J=4.7 Hz, 6H), 2.62 (s, 4H), 2.55 (s, 3H), 2.20-2.01 (d, J=13.0 Hz, 4H), 1.94 (m, 2H), 1.84 (d, J=12.3 Hz, 6H), 1.57 (d, J=6.8 Hz, 2H), 0.84 (d, J=6.0 Hz, 3H).

Example 52: Synthesis of 2-({6-[(5-chloro-2-{4-[(1r,3r)-3-{4-[2-(2,6-dioxopiperidin-3-yl)-4-ethyl-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 200)

Step 1-2: Preparation of 4-chloro-2-(2,6-dioxopiperidin-3-yl)-5-fluoroisoindole-1,3-dione

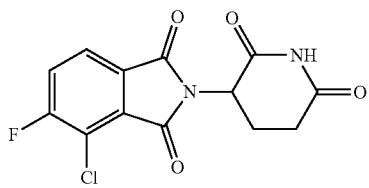

The title compound was prepared analogous to compound 35 following step 2-3 using 3-chloro-4-fluorobenzene-1,2-dicarboxylic acid.

Step 3: Preparation of tert-butyl 4-[(1r,3r)-3-{4-[4-chloro-2-(2,6-dioxopiperidin-3-yl)-1,3-dioxoisoindol-5-yl]piperazin-1-yl}cyclobutoxy]piperidine-1-carboxylate

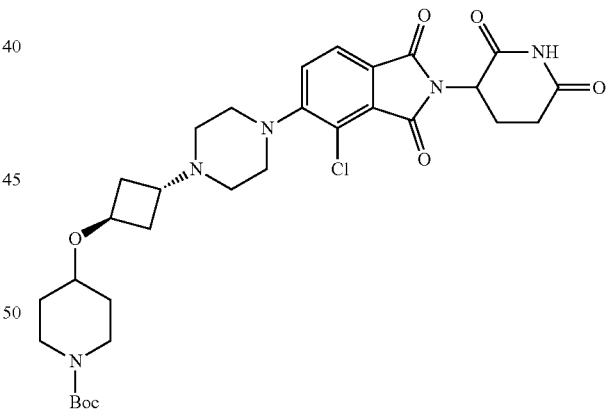

Into a 10 mL tube were added 4-chloro-2-(2,6-dioxopiperidin-3-yl)-5-fluoroisoindole-1,3-dione (440 mg, 1.4 mmol, 1.2 equiv) and tert-butyl 4-[(1r,3r)-3-(piperazin-1-yl)cyclobutoxy]piperidine-1-carboxylate (400 mg, 1.1 mmol, 1 equiv) in DMSO (1.5 mL). To the above mixture was added DIEA (0.5 mL, 2.8 mmol, 2 equiv). The resulting mixture was sealed and stirred overnight at 90° C. The reaction was purified by reverse flash chromatography (mobile phase, MeCN in water (10 mmol/L NH$_4$HCO$_3$), 10% to 50% gradient in 0.30 min; 254 nm) to afford tert-butyl 4-[(1r,3r)-3-{4-[4-chloro-2-(2,6-dioxopiperidin-3-yl)-1,3-dioxoisoindol-5-yl]piperazin-1-yl}cyclobutoxy]piperidine-1-carboxylate (480 mg, 64%) as a yellow solid. MS (ESI): m/z 630.20 [MH$^+$].

Step 4: Preparation of tert-butyl 4-[(1r,3r)-3-{4-[2-(2,6-dioxopiperidin-3-yl)-4-ethenyl-1,3-dioxoisoindol-5-yl]piperazin-1-yl}cyclobutoxy]piperidine-1-carboxylate

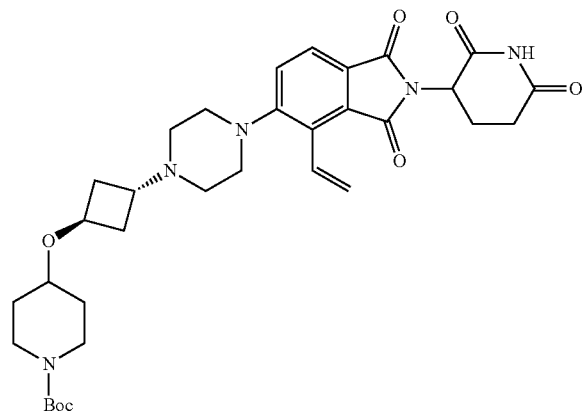 [SMILES: C=Cc1c(N2CCN([C@H]3C[C@H](OC4CCN(C(=O)OC(C)(C)C)CC4)C3)CC2)ccc2c1C(=O)N(C1CCC(=O)NC1=O)C2=O]

Into a 30 mL sealed tube were added tert-butyl 4-[(1r,3r)-3-{4-[4-chloro-2-(2,6-dioxopiperidin-3-yl)-1,3-dioxoisoindol-5-yl]piperazin-1-yl}cyclobutoxy]piperidine-1-carboxylate (300 mg, 0.5 mmol, 1.0 equiv), 2-ethenyl-4,4,5,5-tetramethyl-1,3,2-dioxaborolane (733 mg, 4.8 mmol, 10.0 equiv), Pd-PEPPSI-IPent$^{Cl}$-o-picoline catalyst (38 mg, 0.05 mmol, 0.1 equiv), K$_2$CO$_3$ (197 mg, 1.4 mmol, 3.0 equiv) and dioxane (10 mL). The resulting mixture was stirred overnight at 105° C. under nitrogen atmosphere. The reaction was allowed to cool to room temperature, the resulting mixture was filtered, the filter cake was washed with EtOAc (2×50 mL). The filtrate solution was concentrated under reduced pressure. The residue was purified by silica gel column chromatography, eluted with EA to afford tert-butyl 4-[(1r,3r)-3-{4-[2-(2,6-dioxopiperidin-3-yl)-4-ethenyl-1,3-dioxoisoindol-5-yl]piperazin-1-yl}cyclobutoxy]piperidine-1-carboxylate (180 mg, 61%) as a yellow solid. MS (ESI): m/z 622.35 [M+H]$^+$.

Step 5: Preparation of tert-butyl 4-[(1r,3r)-3-{4-[2-(2,6-dioxopiperidin-3-yl)-4-ethyl-1,3-dioxoisoindol-5-yl]piperazin-1-yl}cyclobutoxy]piperidine-1-carboxylate

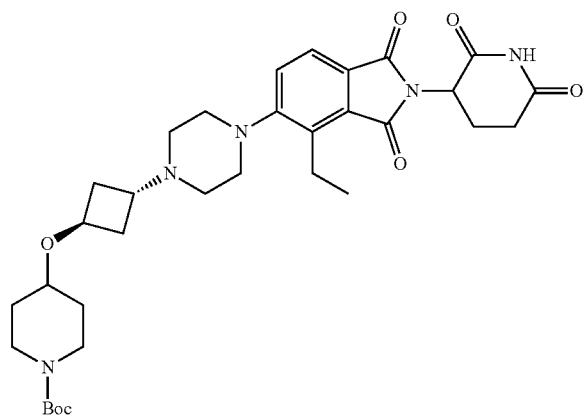 [SMILES: CCc1c(N2CCN([C@H]3C[C@H](OC4CCN(C(=O)OC(C)(C)C)CC4)C3)CC2)ccc2c1C(=O)N(C1CCC(=O)NC1=O)C2=O]

In a 50 mL round-bottom flask were added tert-butyl 4-[(1r,3r)-3-{4-[2-(2,6-dioxopiperidin-3-yl)-4-ethenyl-1,3-dioxoisoindol-5-yl]piperazin-1-yl}cyclobutoxy]piperidine-1-carboxylate (180 mg, 0.3 mmol, 1.0 equiv), THF (5 mL) and 10% Pd/C (90 mg). The resulting mixture was purged with vacuum and then stirred overnight at room temperature under hydrogen atmosphere with a hydrogen balloon. The reaction was filtered, the filter cake was washed with THF (2×100 mL). The filtrate solution was concentrated under reduced pressure to afford tert-butyl 4-[(1r,3r)-3-{4-[2-(2,6-dioxopiperidin-3-yl)-4-ethyl-1,3-dioxoisoindol-5-yl]piperazin-1-yl}cyclobutoxy]piperidine-1-carboxylate (180 mg, 99%) as a yellow solid. MS (ESI): m/z 624.40 [MH$^+$].

Step 6-7: Preparation of 2-({6-[(5-chloro-2-{4-[(1r,3r)-3-{4-[2-(2,6-dioxopiperidin-3-yl)-4-ethyl-1,3-dioxoisoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide

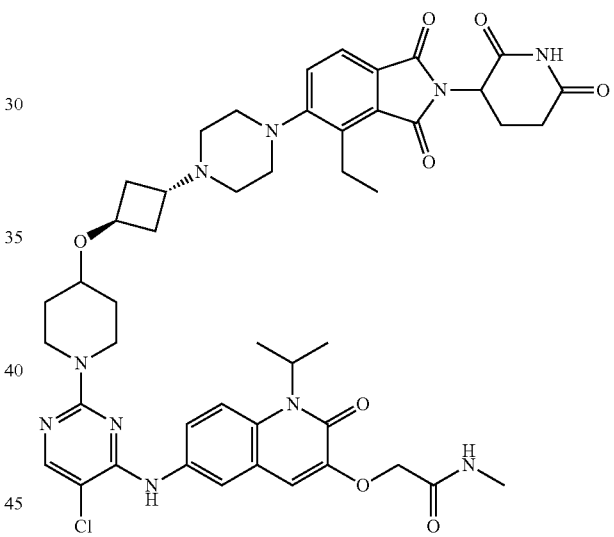

Compound 200 was prepared analogously to compound 208 following step 11-12 using the material made in step 5 of this example. The crude product was purified by reverse flash chromatography (mobile phase, CH$_3$CN: water (c (NH$_4$HCO$_3$)=0.01 M)=0 to 55% gradient over 30 min; 220/254 nm) to afford 2-({6-[(5-chloro-2-{4-[(1r,3r)-3-{4-[2-(2,6-dioxopiperidin-3-yl)-4-ethyl-1,3-dioxoisoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (81.3 mg, 39%) as a yellow solid. MS (ES$^-$): m/z 921.25 [MH$^+$]. $^1$H NMR (400 MHz, DMSO-ds) δ 11.10 (s, 1H), 8.84 (s, 1H), 8.04 (s, 1H), 8.01-7.93 (m, 2H), 7.74-7.67 (m, 3H), 7.47 (d, J=8.1 Hz, 1H), 7.03 (s, 1H), 5.10 (dd, J=12.8, 5.4 Hz, 1H), 4.55 (s, 2H), 4.25-4.05 (m, 3H), 3.53 (s, 1H), 3.23 (t, J=10.9 Hz, 2H), 3.03 (d, J=7.5 Hz, 3H), 2.98-2.91 (m, 3H), 2.90-2.80 (m, 2H), 2.68 (d, J=4.7 Hz, 4H), 2.64-2.52 (m, 2H), 2.26-2.15 (m, 2H), 2.10-1.90 (m, 4H), 1.89-1.73 (m, 2H), 1.62-1.53 (d, J=6.9 Hz, 7H), 1.44-1.35 (m, 2H), 1.25-1.10 (m, 4H).

Example 53: Synthesis of 2-[[6-[[5-chloro-2-[4-[3-[4-[2-(2,6-dioxo-3-piperidyl)-4-fluoro-1-oxo-isoindolin-5-yl]-3-fluoro-1-piperidyl]cyclobutoxy]-1-piperidyl]pyrimidin-4-yl]amino]-1-isopropyl-2-oxo-3-quinolyl]oxy]-N-methyl-acetamide (Compound 201)

Step 1: preparation of benzyl 3-fluoro-4-hydroxy-piperidine-1-carboxylate

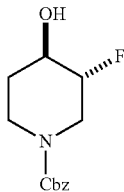

A mixture of benzyl 3-fluoro-4-oxo-piperidine-1-carboxylate (35 g, 139.3 mmol, 1 eq) in ethanol (350 mL) was added sodium borohydride (5.8 g, 153.2 mmol, 1.1 eq) at 0° C., and then the mixture was stirred at 0-25° C. for 2 hours under nitrogen atmosphere. The reaction was slowly added into water (200 mL) at 0° C., then warmed to 25° C. and stirred for 30 minutes. The aqueous mixture was extracted with ethyl acetate (3×200 mL). The combined organic layers were washed with sodium chloride (3×200 mL), dried over sodium sulfate, filtered, and concentrated under reduced pressure. The residue was purified by prep-HPLC (column: Phenomenex luna C18 (250*70 mm, 10 um); mobile phase: [water (TFA)-ACN]; B %: 20%-50%, 20 min) to afford benzyl 3-fluoro-4-hydroxy-piperidine-1-carboxylate (20 g, 56%) as a yellow oil and benzyl 3-fluoro-4-hydroxy-piperidine-1-carboxylate (7 g, 19%) as a yellow oil. $^1$H NMR (400 MHz, DMSO-$d_6$) δ 7.31-7.47 (m, 5H), 5.28-5.17 (m, 2H), 4.47-4.35 (m, 1H), 4.22-3.87 (m, 2H), 3.82-3.73 (m, 2H), 3.44-3.35 (m, 1H), 1.90-1.78 (m, 1H), 1.53-1.42 (m, 1H).

Step 2: preparation of benzyl 3-fluoro-4-iodo-piperidine-1-carboxylate

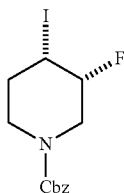

A mixture of benzyl 3-fluoro-4-hydroxy-piperidine-1-carboxylate (5 g, 19.7 mmol, 1 eq), triphenylphosphine (10.36 g, 39.5 mmol, 2 eq), imidazole (4.03 g, 59.2 mmol, 3 eq) and iodine (7.5 g, 29.6 mmol, 1.5 eq) in toluene (70 mL) was degassed and purged with nitrogen for 3 times, then the mixture was stirred at 120° C. for 6 hours under nitrogen atmosphere. The reaction mixture was filtered and concentrated under reduced pressure. The residue was purified by silica gel column chromatography (petroleum ether/ethyl acetate=10/1 to 5/1) to afford benzyl 3-fluoro-4-iodo-piperidine-1-carboxylate (2 g, 27%) as a yellow oil. $^1$H NMR (400 MHz, DMSO-$d_6$) δ 7.44-7.29 (m, 5H), 5.14-5.03 (m, 2H), 4.72-4.60 (m, 1H), 4.13-4.00 (m, 2H), 3.85-3.71 (m, 1H), 3.17-2.92 (m, 1H), 2.19-2.04 (m, 2H).

Step 3: preparation of benzyl 4-[2-(4-tert-butoxy-1-carbamoyl-4-oxo-butyl)-4-fluoro-1-oxo-isoindolin-5-yl]-3-fluoro-piperidine-1-carboxylate

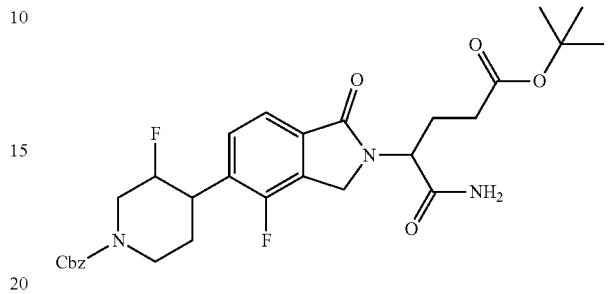

To a 15 mL vial equipped with a stir bar was added benzyl 3-fluoro-4-iodo-piperidine-1-carboxylate (1.8 g, 5.0 mmol, 1 eq), tert-butyl 5-amino-4-(5-bromo-4-fluoro-1-oxo-isoindolin-2-yl)-5-oxo-pentanoate (2.1 g, 5.0 mmol, 1 eq), Ir[dF(CF$_3$)ppy]$_2$(dtbpy)(PF$_6$) (56 mg, 0.05 mmol, 0.01 eq), NiCl$_2$·dtbbpy (9.86 mg, 0.2 mmol, 0.005 eq), TTMSS (1.23 g, 5.0 mmol, 1.53 mL, 1 eq), sodium carbonate (1.1 g, 9.9 mmol, 2 eq) and 1,2-dichloroethane (20 mL), the vial was sealed under nitrogen, the reaction was stirred and irradiated with a 34 W blue LED lamp (7 cm away), with cooling fan to keep the reaction temperature at 25° C. for 14 hours. The reaction mixture was filtered and concentrated under reduced pressure. The residue was purified by prep-HPLC (column: Phenomenex luna C18 (250*70 mm, 10 um); mobile phase: [water (TFA)-ACN]; B %: 40%-70%, 20 min) to afford benzyl 4-[2-(4-tert-butoxy-1-carbamoyl-4-oxo-butyl)-4-fluoro-1-oxo-isoindolin-5-yl]-3-fluoro-piperidine-1-carboxylate (700 mg, 24%) as a yellow oil. MS (ESI) m/z: 572.2 [M+H]$^+$.

Step 4: preparation of tert-butyl 5-amino-4-[4-fluoro-5-(3-fluoro-4-piperidyl)-1-oxo-isoindolin-2-yl]-5-oxo-pentanoate

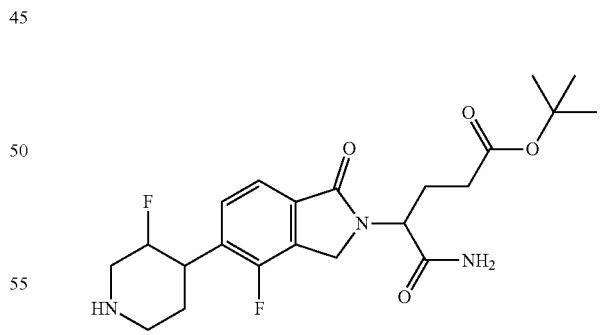

A mixture of benzyl 4-[2-(4-tert-butoxy-1-carbamoyl-4-oxo-butyl)-4-fluoro-1-oxo-isoindolin-5-yl]-3-fluoro-piperidine-1-carboxylate (700 mg, 1.2 mmol, 1 eq) in trifluoroethanol (10 mL), tetrahydrofuran (10 mL) was added 10% palladium on activated carbon (300 mg), 20% palladium hydroxide on activated carbon (200 mg) and then the mixture was stirred at 40° C. for 16 hours under hydrogen (50 psi) atmosphere. The reaction mixture was filtered and concentrated under reduced pressure to afford tert-butyl 5-amino-4-[4-fluoro-5-(3-fluoro-4-piperidyl)-1-oxo-isoindolin-2-yl]-5-oxo-pentanoate (400 mg, 74%) as a yellow oil, which was used in the next step without further purification.

Step 5-7: preparation of 2-[[6-[[5-chloro-2-[4-[3-[4-[2-(2,6-dioxo-3-piperidyl)-4-fluoro-1-oxo-isoindolin-5-yl]-3-fluoro-1-piperidyl]cyclobutoxy]-1-piperidyl]pyrimidin-4-yl]amino]-1-isopropyl-2-oxo-3-quinolyl]oxy]-N-methyl-acetamide

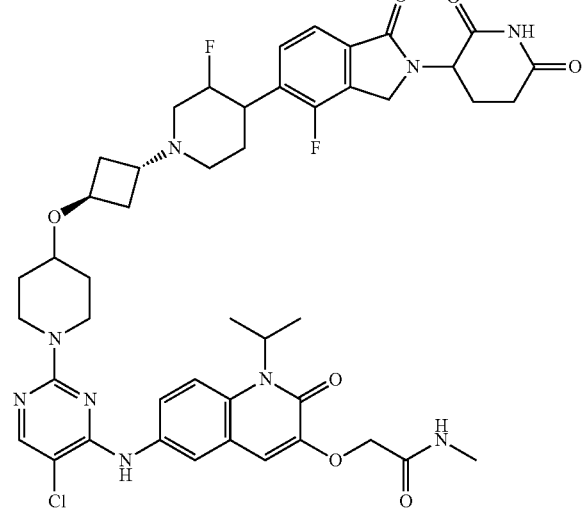

Compound 201 was prepared analogous to compound 188 following step 7-9 using the material made in step 4 of this example. The crude product was purified by prep-HPLC (mobile phase: [water (FA)-ACN]; B %: 12%-42%, 10 min) to afford 2-[[6-[[5-chloro-2-[4-[3-[4-[2-(2,6-dioxo-3-piperidyl)-4-fluoro-1-oxo-isoindolin-5-yl]-3-fluoro-1-piperidyl]cyclobutoxy]-1-piperidyl]pyrimidin-4-yl]amino]-1-isopropyl-2-oxo-3-quinolyl]oxy]-N-methyl-acetamide formate (65.2 mg, 28%) as a white solid. MS (ESI) m/z: 916.2 [M+H]$^+$; $^1$H NMR (400 MHz, DMSO-d$_6$) δ 11.08-10.95 (m, 1H), 8.89-8.80 (m, 1H), 8.29-8.21 (m, 1H), 8.07-8.04 (m, 1H), 8.02-7.94 (m, 2H), 7.72-7.65 (m, 3H), 7.60-7.53 (m, 1H), 7.06-7.01 (m, 1H), 5.57-5.20 (m, 1H), 5.16-5.08 (m, 1H), 4.92-4.72 (m, 1H), 4.62-4.52 (m, 3H), 4.44-4.35 (m, 1H), 4.22-4.09 (m, 3H), 3.54 (br dd, J=8.0, 4.2 Hz, 3H), 2.95-2.84 (m, 3H), 2.71-2.67 (m, 3H), 2.65-2.62 (m, 1H), 2.55 (s, 1H), 2.47-2.33 (m, 2H), 2.27-2.10 (m, 3H), 2.07-1.96 (m, 4H), 1.89-1.79 (m, 4H), 1.58 (d, J=6.8 Hz, 6H), 1.45-1.34 (m, 2H).

Example 54: Synthesis of 2-({6-[(5-chloro-2-{4-[(1r,3r)-3-[(3R)-4-[6-(2,6-dioxopiperidin-3-yl)-7-methyl-5-oxo-5H,6H, 7H-pyrrolo[3,4-b]pyridin-2-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide (Compound 203)

Step 1: Preparation of methyl 2-ethylpyridine-3-carboxylate

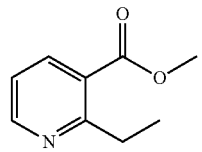

To a mixture of methyl 2-chloropyridine-3-carboxylate (7 g, 40.8 mmol, 5.3 mL, 1 eq) and diethylzinc (1 M, 49.0 mL, 1.2 eq) in dioxane (70 mL) was added [1,1'-bis(diphenylphosphino)ferrocene]dichloropalladium(II) (2.39 g, 3.3 mmol, 0.08 eq) in one portion at 20° C. under nitrogen. The mixture was stirred at 60° C. for 2 hours, then diluted with water (200 mL) and extracted with ethyl acetate (3×300 mL). The combined organic layers were dried over sodium sulfate, concentrated in vacuo. The residue was purified by silica gel chromatography (Petroleum ether/Ethyl acetate=20/1, 5/1) to afford methyl 2-ethylpyridine-3-carboxylate (6.4 g, 95%) as a yellow oil. MS (ESI) m/z: 166.2 [M+H]$^+$.

Step 2: Preparation of methyl 2-ethyl-6-fluoro-pyridine-3-carboxylate

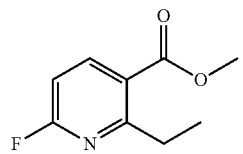

A mixture of methyl 2-ethylpyridine-3-carboxylate (500 mg, 3.0 mmol, 1 eq) and silver(ii) fluoride (1.32 g, 9.1 mmol, 3 eq) in acetonitrile (8 mL) was stirred at 25° C. for 16 hours under nitrogen. The mixture was filtered, and the filtrate solution was concentrated under reduced pressure at 45° C. The residue was purified by silica gel chromatography (petroleum ether/ethyl acetate=30/1 to 7/1) to afford methyl 2-ethyl-6-fluoro-pyridine-3-carboxylate (280 mg, 50%) as a colorless oil.

Step 3: Preparation of methyl 2-(1-bromoethyl)-6-fluoro-pyridine-3-carboxylate

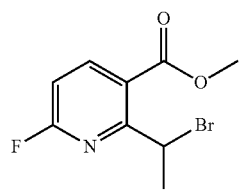

To a mixture of methyl 2-ethyl-6-fluoro-pyridine-3-carboxylate (3.93 g, 21.4 mmol, 1 eq) in carbon tetrachloride (60 mL) was added AIBN (3.52 g, 21.4 mmol, 1 eq) and N-Bromosuccinimide (5.73 g, 32.2 mmol, 1.5 eq) in one portion at 25° C. under nitrogen. The mixture was stirred at 25° C. for 5 minutes, then heated to 80° C. and stirred for 16 hours. The reaction mixture was cooled to 25° C. and filtered. The filtrate solution was concentrated in vacuo at 45° C. The residue was purified by flash silica gel chromatography (0-20% Ethyl acetate/petroleum ether, 120 mL/min) to give methyl 2-(1-bromoethyl)-6-fluoro-pyridine-3-carboxylate (4.87 g, 86%) as a yellow oil.

Step 4: Preparation of 3-(2-fluoro-7-methyl-5-oxo-7H-pyrrolo[3,4-b] pyridin-6-yl)piperidine-2,6-dione

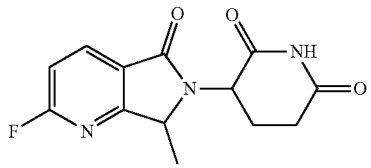 [SMILES: CC1c2nc(F)ccc2C(=O)N1C1CCC(=O)NC1=O]

To a mixture of 3-aminopiperidine-2,6-dione hydrochloride (3.06 g, 18.6 mmol, 1 eq) and methyl 2-(1-bromoethyl)-6-fluoro-pyridine-3-carboxylate (4.87 g, 18.6 mmol, 1 eq) in N,N-dimethylformamide (40 mL) was added N,N-diisopropylethylamine (12.01 g, 92.9 mmol, 5 eq) in one portion at 20° C. under nitrogen. The mixture was stirred at 90° C. for 16 hours, then cooled to 25° C. The mixture was poured into water (200 mL) and stirred for 5 min. The aqueous phase was extracted with ethyl acetate (2×100 mL). The combined organic phase was washed with brine (2×200 mL), dried over anhydrous sodium sulfate, filtered, and concentrated in vacuo. The residue was purified by silica gel chromatography (petroleum ether/ethyl acetate=1/0 to 0/1) to afford 3-(2-fluoro-7-methyl-5-oxo-7H-pyrrolo[3,4-b]pyridin-6-yl)piperidine-2,6-dione (2.14 g, 42%) as a yellow solid. MS (ESI) m/z: 276.1 [M+1]$^+$.

Step 5: Preparation of tert-butyl 4-[3-[(3R)-4-[6-(2,6-dioxo-3-piperidyl)-7-methyl-5-oxo-7H-pyrrolo[3,4-b]pyridin-2-yl]-3-methyl-piperazin-1-yl]cyclobutoxy]piperidine-1-carboxylate

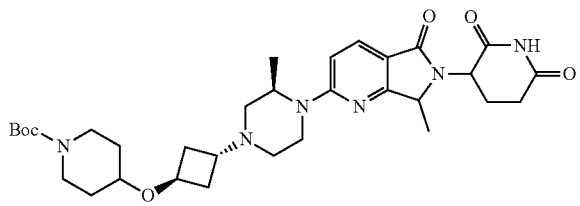 [SMILES: CC1c2nc(N3CCN([C@H]4C[C@H](OC5CCN(C(=O)OC(C)(C)C)CC5)C4)C[C@H]3C)ccc2C(=O)N1C1CCC(=O)NC1=O]

To a solution of 3-(2-fluoro-7-methyl-5-oxo-7H-pyrrolo [3,4-b]pyridin-6-yl)piperidine-2,6-dione (313 mg, 1.1 mmol, 1 eq) and tert-butyl 4-[3-[(3R)-3-methylpiperazin-1-yl] cyclobutoxy]piperidine-1-carboxylate (400 mg, 1.1 mmol, 1 eq) in dimethyl sulfoxide (8 mL) was added N,N-diisopropylethylamine (584 mg, 4.5 mmol, 0.8 mL, 4 eq). The mixture was stirred at 100° C. for 2 hours. The mixture was cooled to 25° C. and concentrated in reduced pressure. The residue was poured into water (20 mL) and stirred for 5 minutes. The aqueous phase was extracted with ethyl acetate (3×10 mL). The combined organic phase was washed with brine (2×20 mL), dried over anhydrous sodium sulfate, filtered, and concentrated in vacuum. The residue was purified by prep-HPLC (mobile phase: [water (FA)-ACN]; B %: 15%-35%, 10 min) to afford tert-butyl 4-[3-[(3R)-4-[6-(2,6-dioxo-3-piperidyl)-7-methyl-5-oxo-7H-pyrrolo[3,4-b]pyridin-2-yl]-3-methyl-piperazin-1-yl] cyclobutoxy]piperidine-1-carboxylate (178 mg, 26%) as a white solid. MS (ESI) m/z: 611.3 [M+1]$^+$.

Step 6-7: Preparation of 2-[[6-[[5-chloro-2-[4-[3-[(3R)-4-[6-(2,6-dioxo-3-piperidyl)-7-methyl-5-oxo-7H-pyrrolo[3,4-b]pyridin-2-yl]-3-methyl-piperazin-1-yl]cyclobutoxy]-1-piperidyl]pyrimidin-4-yl]amino]-1-isopropyl-2-oxo-3-quinolyl]oxy]-N-methyl-acetamide

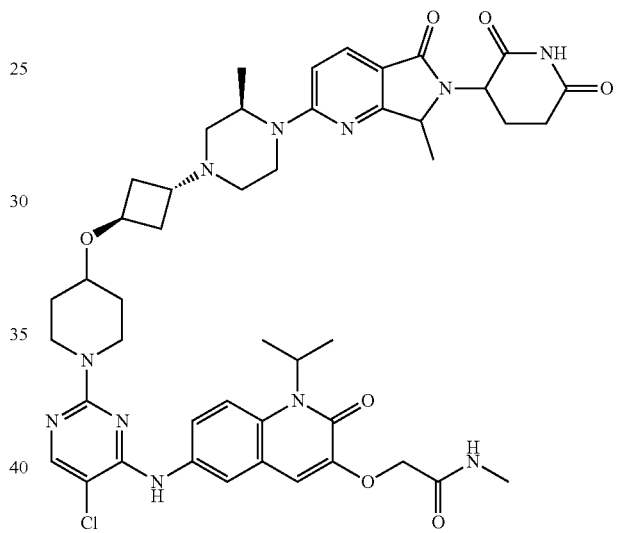

Compound 203 was prepared analogous to compound 189 following step 5-6 using the material made in step 5 of this example. The crude product was purified by prep-HPLC (mobile phase: [water (FA)-ACN]; B %: 10%-40%, 10 min) to afford 2-[[6-[[5-chloro-2-[4-[3-[(3R)-4-[6-(2,6-dioxo-3-piperidyl)-7-methyl-5-oxo-7H-pyrrolo[3,4-b]pyridin-2-yl]-3-methyl-piperazin-1-yl]cyclobutoxy]-1-piperidyl]pyrimidin-4-yl]amino]-1-isopropyl-2-oxo-3-quinolyl]oxy]-N-methyl-acetamide formate (101 mg, 36%) as a white solid. MS (ESI) m/z: 910.3 [M+1]$^+$; $^1$HNMR (400 MHz, DMSO-d$_6$) δ 10.90 (br d, J=12.4 Hz, 1H), 8.84 (s, 1H), 8.22 (s, 1H), 8.05 (s, 1H), 8.01-7.94 (m, 2H), 7.70 (s, 2H), 7.04 (s, 1H), 6.82 (dt, J=3.2, 8.8 Hz, 1H), 5.52-5.17 (m, 1H), 4.71 (br dd, J=5.2 12.4 Hz, 1H), 4.66-4.59 (m, 1H), 4.55 (s, 2H), 4.43 (br d, J=6.8 Hz, 1H), 4.22 (br d, J=4.8 Hz, 2H), 4.15-4.10 (m, 2H), 3.58-3.52 (m, 2H), 3.24 (br t, J=10.4 Hz, 2H), 3.06-2.95 (m, 2H), 2.80-2.74 (m, 2H), 2.69 (d, J=4.5 Hz, 3H), 2.63-2.54 (m, 3H), 2.25-2.13 (m, 2H), 2.03-1.93 (m, 4H), 1.87-1.78 (m, 3H), 1.58 (d, J=6.8 Hz, 6H), 1.39 (br dd, J=6.8, 14.4 Hz, 5H), 1.19 (dd, J=3.2, 6.4 Hz, 3H).

Compound 204 may be prepared by a procedure analogous to compound 203.

Example 55: Synthesis of 2-({6-[(5-chloro-2-{4-[(1r,3r)-3-{4-[2-(2,6-dioxopiperidin-3-yl)-1-oxo-2,3-dihydro-1H-isoindol-5-yl]-3,3-dimethylpiperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide (Compound 211)

Step 1: Preparation of tert-butyl 4-(3-cyano-4-methoxycarbonyl-phenyl)-3,3-dimethyl-piperazine-1-carboxylate

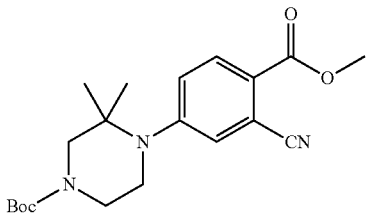 [SMILES: COC(=O)c1ccc(N2CCN(C(=O)OC(C)(C)C)CC2(C)C)cc1C#N]

Combined tert-butyl 3,3-dimethylpiperazine-1-carboxylate (1.5 g, 7.0 mmol, 1 eq), methyl 4-bromo-2-cyanobenzoate (1.68 g, 7.0 mmol, 1 eq), cesium carbonate (6.84 g, 21.0 mmol, 3 eq) and methanesulfonato(2-dicyclohexylphosphino-2',6'-di-1-propoxy-1,1'-biphenyl)(2'-methylamino-1,1'-biphenyl-2-yl)palladium(II) (476 mg, 0.3 mmol, 0.08 eq) in dioxane (30 mL) and degassed with nitrogen for 3 times. The mixture was stirred at 90° C. for 16 hours, then cooled to 20° C., filtered with a pad of celite. The residue was purified by silica gel column chromatography (petroleum ether/ethyl acetate=10/1 to 4:1) to afford tert-butyl 4-(3-cyano-4-methoxycarbonyl-phenyl)-3,3-dimethyl-piperazine-1-carboxylate (1.76 g, 67%) as a yellow gum. MS (ESI) m/z: 374.3 [M+H]$^+$; $^1$H NMR: (400 MHz, CDCl$_3$) δ 8.06 (d, J=8.8 Hz, 1H), 7.50 (br s, 2H), 3.99 (s, 3H), 3.71 (br s, 2H), 3.50 (br s, 2H), 3.33-3.23 (m, 2H), 1.50 (s, 9H), 1.21 (s, 6H).

Step 2: Preparation of tert-butyl 4-[3-formyl-4-(methoxycarbonyl)phenyl]-3,3-dimethylpiperazine-1-carboxylate

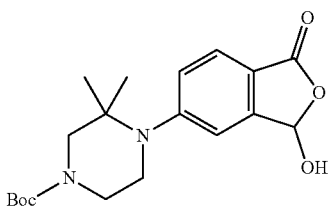

To a stirred solution of methyl 4-({1-[(tert-butoxycarbonyl)amino]-2-methylpropan-2-yl}(methyl)amino)-2-cyanobenzoate (34.6 g, 83.0 mmol, 1.0 equiv) and NaH$_2$PO$_4$ (49.8 g, 415.0 mmol, 5.0 equiv) in pyrazine:AcOH:H$_2$O (4:2:1, 350 ml) was added Raney Ni (21.3 g, 249.0 mmol, 3.0 equiv). The resulting mixture was stirred for 3 days at 70° C. under nitrogen atmosphere. The reaction was filtered, the filter cake was washed with EtOAc (3×200 mL). The filtrate was washed with brine (100 mL), dried over anhydrous sodium sulfate, and concentrated under reduced pressure. The residue was purified by silica gel column chromatography (PE/EA=5:1) to afford tert-butyl 4-[3-formyl-4-(methoxycarbonyl)phenyl]-3,3-dimethylpiperazine-1-carboxylate (24 g, 77%) as an oil. MS (ESI): m/z 361.2 [MH$^+$].

Step 3: Preparation of tert-butyl 4-[3-formyl-4-(methoxycarbonyl)phenyl]-3,3-dimethylpiperazine-1-carboxylate

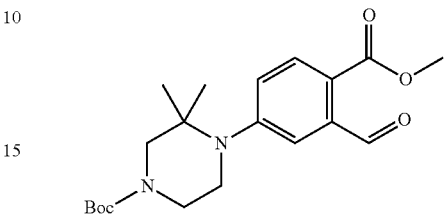

A solution of tert-butyl 4-(3-hydroxy-1-oxo-3H-2-benzofuran-5-yl)-3,3-dimethylpiperazine-1-carboxylate (12.2 g, 33.6 mmol, 1.0 equiv) in 100 mL DMF was treated with K$_2$CO$_3$ (13.9 g, 100.9 mmol, 3.0 equiv) for 3 minutes at room temperature under nitrogen atmosphere, followed by the addition of MeI (7.2 g, 50.5 mmol, 1.5 equiv) dropwise at room temperature. The resulting mixture was stirred for 2 hours at room temperature, then diluted with water, extracted with EtOAc (3×100 mL). The combined organic layers were washed with brine (100 mL), dried over anhydrous Na$_2$SO$_4$, filtered, and concentrated under reduced pressure. The residue was purified by silica gel column chromatography (PE/EA=4:1) to afford tert-butyl 4-[3-formyl-4-(methoxycarbonyl)phenyl]-3,3-dimethylpiperazine-1-carboxylate (9.5 g, 75%) as a solid.

Step 4: Preparation of tert-butyl 4-{2-[(1S)-4-(tert-butoxy)-1-carbamoyl-4-oxobutyl]-1-oxo-3H-isoindol-5-yl}-3,3-dimethylpiperazine-1-carboxylate

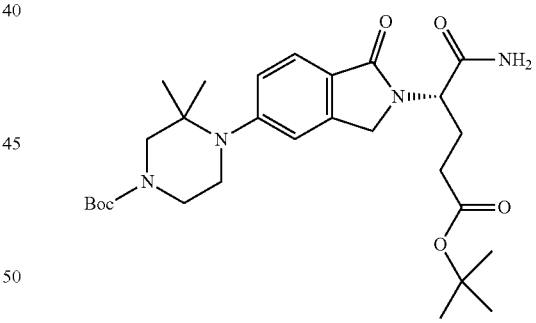

Combined tert-butyl 4-[3-formyl-4-(methoxycarbonyl)phenyl]-3,3-dimethylpiperazine-1-carboxylate (9.5 g, 23.9 mmol, 1.0 equiv) and tert-butyl (4S)-4-amino-4-carbamoylbutanoate hydrochloride (5.7 g, 23.9 mmol, 1.0 equiv) in DCE (100 mL). The resulting mixture was stirred overnight at 40° C. under nitrogen atmosphere. Then added NaBH$_3$CN (4.1 g, 71.7 mmol, 3.0 equiv). The resulting mixture was stirred overnight at 40° C. under nitrogen atmosphere. The reaction was quenched by the addition of water (50 mL) at room temperature and the resulting mixture was extracted with CH$_2$Cl$_2$ (3×100 mL). The combined organic layers were washed with brine (3×50 mL), dried over anhydrous sodium sulfate, and concentrated under reduced pressure. The residue was purified by reverse flash chromatography (mobile phase, CH$_3$CN/water (10 mmol/L NH$_4$HCO$_3$), 5% to 70% gradient in 50 min; 254 nm) to afford tert-butyl 4-{2-[(1S)-4-(tert-butoxy)-1-carbamoyl-4-oxobutyl]-1-oxo-3H-isoindol-5-yl}-3,3-dimethylpiperazine-1-carboxylate (9.6 g, 76%) as a solid. MS (ESI): m/z 531.40 [MH⁺].

Step 5: Preparation of tert-butyl (4S)-4-carbamoyl-4-[5-(2,2-dimethylpiperazin-1-yl)-1-oxo-3H-isoindol-2-yl]butanoate

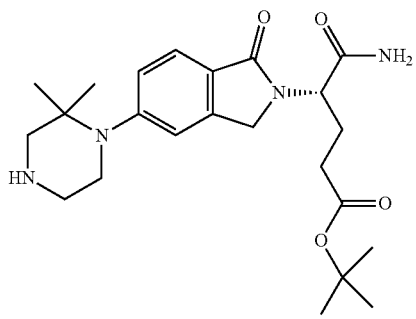 [SMILES: CC(C)(C)OC(=O)CC[C@@H](C(N)=O)N1Cc2cc(N3CCNCC3(C)C)ccc2C1=O]

To a stirred mixture of tert-butyl 4-{2-[(1S)-4-(tert-butoxy)-1-carbamoyl-4-oxobutyl]-1-oxo-3H-isoindol-5-yl}-3,3-dimethylpiperazine-1-carboxylate (9.6 g, 17.9 mmol, 1.0 equiv) in 100 mL i-PrOH was added TMSCl (29.2 g, 268.0 mmol, 15.0 equiv) dropwise at room temperature. The resulting mixture was stirred overnight at room temperature. Then diluted with water (500 mL), neutralized the pH to 7 with saturated Na₂CO₃ (aq.). The resulting mixture was extracted with CH₂Cl₂ (3×200 mL). The combined organic layers were washed with brine (3×100 mL), dried over anhydrous Na₂SO₄, filtered and concentrated under reduced pressure to afford tert-butyl (4S)-4-carbamoyl-4-[5-(2,2-dimethylpiperazin-1-yl)-1-oxo-3H-isoindol-2-yl]butanoate (6.3 g, 82%) as a solid. MS (ESI): m/z 471.30 [MH⁺].

Step 6-8: Preparation of 2-({6-[(5-chloro-2-{4-[(1r,3r)-3-(4-{2-[(3S)-2,6-dioxopiperidin-3-yl]-1-oxo-3H-isoindol-5-yl}-3,3-dimethylpiperazin-1-yl)cyclobutoxy]piperidin-1-yl}pyrimidin-4-yl)amino]-1-isopropyl-2-oxoquinolin-3-yl}oxy)-N-methylacetamide

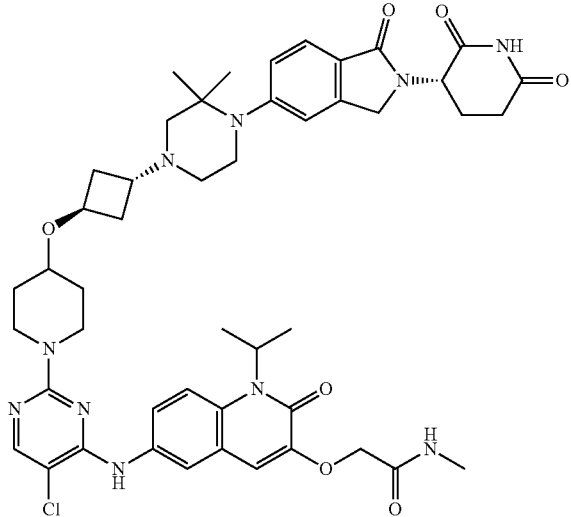 [SMILES: CNC(=O)COc1cc2cc(Nc3nc(N4CCC(O[C@H]5C[C@H](N6CCN(c7ccc8c(c7)CN([C@H]7CCC(=O)NC7=O)C8=O)C(C)(C)C6)C5)CC4)ncc3Cl)ccc2n(C(C)C)c1=O]

Compound 211 was prepared analogous to compound 201 following step 5-7 using the material made in step 5 of this example. The crude product was purified by reverse phase flash chromatography (mobile phase, THF/water (10 mmol/L NH₄HCO₃), 5% to 40% gradient in 45 min; 254 nm) to afford 2-({6-[(5-chloro-2-{4-[(1r,3r)-3-(4-{2-[(3S)-2,6-dioxopiperidin-3-yl]-1-oxo-3H-isoindol-5-yl}-3,3-dimethylpiperazin-1-yl)cyclobutoxy]piperidin-1-yl}pyrimidin-4-yl)amino]-1-isopropyl-2-oxoquinolin-3-yl}oxy)-N-methylacetamide (3.3 g, 54%) as off-white solid. ¹H NMR (300 MHz, DMSO-d₆) δ 10.98 (s, 1H), 8.83 (s, 1H), 8.04 (s, 1H), 7.95 (q, J=4.8, 3.9 Hz, 2H), 7.69 (d, J=1.5 Hz, 2H), 7.58 (d, J=8.2 Hz, 1H), 7.28 (s, 1H), 7.20 (d, J=8.2 Hz, 1H), 7.01 (s, 1H), 5.360-5.10 (m, 1H), 5.07 (d, J=13.2 Hz, 1H), 4.53 (s, 2H), 4.38 (d, J=17.3 Hz, 2H), 4.31-4.11 (m, 3H), 3.52 (s, 1H), 3.22 (d, J=9.9 Hz, 2H), 3.11 (s, 2H), 2.93-2.81 (m, 1H), 2.70 (s, 1H), 2.53 (s, 3H), 2.51 (s, 1H), 2.38 (s, 3H), 2.16 (d, J=13.5 Hz, 4H), 1.97 (s, 3H), 1.82 (d, J=12.3 Hz, 2H), 1.56 (d, J=6.8 Hz, 6H), 1.50 (s, 2H), 1.05 (s, 6H). MS (ESI): m/z 909.30 [MH⁺].

Compound 170 may be prepared by a procedure analogous to compound 211.

Example 56: Synthesis of 2-{[6-({5-chloro-2-[4-({2-[2-(2,6-dioxopiperidin-3-yl)-1,3-dioxoisoindol-5-yl]-2,7-diazaspiro[3.5]nonan-7-yl}methyl)piperidin-1-yl]pyridin-4-yl}amino)-1-isopropyl-2-oxoquinolin-3-yl]oxy}-N-methylacetamide (Compound 215)

Step 1: Preparation of 5-chloro-2-[4-(dimethoxymethyl) piperidin-1-yl]-4-iodopyridine

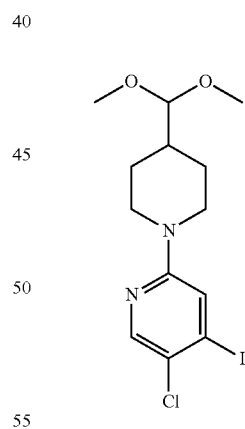

To a stirred solution of 5-chloro-2-fluoro-4-iodopyridine (2.0 g, 7.8 mmol, 1.0 equiv) and 4-(dimethoxymethyl) piperidine (1.2 g, 7.8 mmol, 1.0 equiv) in DMSO (10 mL) was added DIEA (3.0 g, 23.3 mmol, 3.0 equiv) at room temperature. The resulting mixture was stirred for 2 hours at 100 W. The crude reaction was purified by reverse flash chromatography (column, C18 silica gel; mobile phase, acetonitrile/water (10 mmol/L NH₄HCO₃), 0% to 80% gradient in 30 min; detector, UV 254 nm) to afford 5-chloro-2-[4-(dimethoxymethyl) piperidin-1-yl]-4-iodopyridine (2.2 g, 71%) as an oil. MS (ESI): m/z 396.95 [MH⁺].

Step 2: Preparation of 2-{[6-({5-chloro-2-[4-(dimethoxymethyl)piperidin-1-yl]pyridin-4-yl}amino)-1-isopropyl-2-oxoquinolin-3-yl]oxy}-N-methylacetamide)

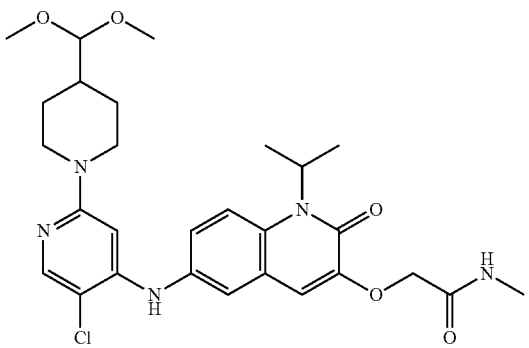

To a stirred solution of 5-chloro-2-[4-(dimethoxymethyl)piperidin-1-yl]-4-iodopyridine (1.2 g, 3.0 mmol, 1.0 equiv) and 2-[(6-amino-1-isopropyl-2-oxoquinolin-3-yl)oxy]-N-methylacetamide (0.9 g, 3.0 mmol, 1.0 equiv) in THF (60 mL) was added chloro(2-dicyclohexylphosphino-2',6'-diisopropoxy-1,1'-biphenyl)[2-(2'-amino-1,1'-biphenyl)]palladium(II) (0.5 g, 0.6 mmol, 0.2 equiv) and Cs$_2$CO$_3$ (2.9 g, 9.1 mmol, 3.0 equiv). The resulting mixture was stirred for 2 hours at 90° C. under nitrogen atmosphere, then cooled to room temperature, diluted with water. The aqueous layer was extracted with CH$_2$Cl$_2$ (3×30 mL), concentrated in vacuo. The residue was purified by silica gel column chromatography (CH$_2$Cl$_2$/MeOH=10:1) to afford 2-{[6-({5-chloro-2-[4-(dimethoxymethyl)piperidin-1-yl]pyridin-4-yl}amino)-1-isopropyl-2-oxoquinolin-3-yl]oxy}-N-methylacetamide) (1.5 g, 90%) as a solid. MS (ESI): m/z 558.40 [MH$^+$].

Step 3: preparation of 2-[(6-{[5-chloro-2-(4-formylpiperidin-1-yl)pyridin-4-yl]amino}-1-isopropyl-2-oxoquinolin-3-yl)oxy]-N-methylacetamide

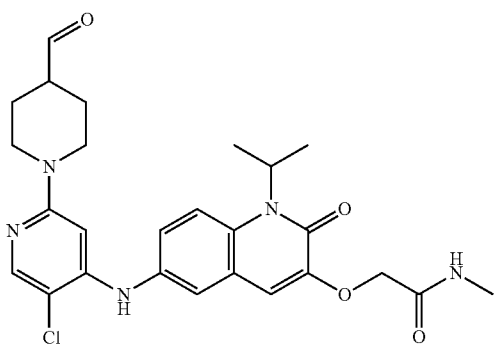 [SMILES: CNC(=O)COc1cc2cc(Nc3cc(N4CCC(C=O)CC4)ncc3Cl)ccc2n(C(C)C)c1=O]

To a stirred solution of 2-{[6-({5-chloro-2-[4-(dimethoxymethyl)piperidin-1-yl]pyridin-4-yl}amino)-1-isopropyl-2-oxoquinolin-3-yl]oxy}-N-methylacetamide (500.0 mg, 0.9 mmol, 1.0 equiv) in 8 mL DCM was added H$_2$O (2 mL) and TFA (4 mL). The resulting mixture was stirred for 2 hours at 40° C., then concentrated under vacuum to afford 2-[(6-{[5-chloro-2-(4-formylpiperidin-1-yl)pyridin-4-yl] amino}-1-isopropyl-2-oxoquinolin-3-yl)oxy]-N-methylacetamide (420 mg) as an oil. MS (ESI): m/z 512.30 [MH$^+$].

Step 4: preparation of tert-butyl 2-[2-(2,6-dioxopiperidin-3-yl)-1,3-dioxoisoindol-5-yl]-2,7-diazaspiro[3.5]nonane-7-carboxylate

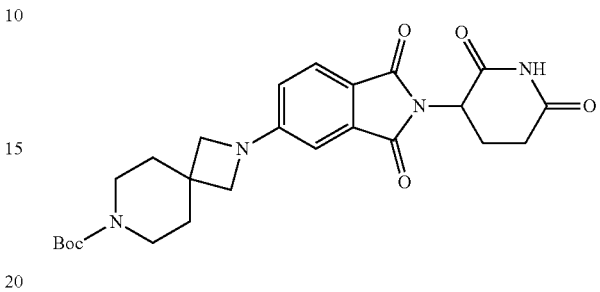

To a stirred solution of tert-butyl 2,7-diazaspiro[3.5]nonane-7-carboxylate (400.0 mg, 1.8 mmol, 1.0 equiv) and 2-(2,6-dioxopiperidin-3-yl)-5-fluoroisoindole-1,3-dione (488.2 mg, 1.8 mmol, 1.0 equiv) in DMSO (4 mL) was added DIEA (685.3 mg, 5.3 mmol, 3.0 equiv) at room temperature. The resulting mixture was stirred overnight at 100° C., then cooled to room temperature, purified by reverse flash chromatography (column, C18 silica gel; mobile phase, acetonitrile/water (10 mmol/L NH$_4$HCO$_3$), 0% to 60% gradient in 30 min; detector, UV 254 nm) to afford tert-butyl 2-[2-(2,6-dioxopiperidin-3-yl)-1,3-dioxoisoindol-5-yl]-2,7-diazaspiro[3.5]nonane-7-carboxylate (280 mg, 32%) as a yellow solid. MS (ESI): m/z 483.30 [MH$^+$].

Step 5: preparation of 5-{2,7-diazaspiro[3.5]nonan-2-yl}-2-(2,6-dioxopiperidin-3-yl)isoindole-1,3-dione

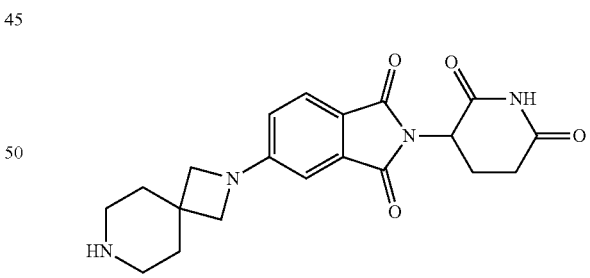

To a stirred solution of tert-butyl 2-[2-(2,6-dioxopiperidin-3-yl)-1,3-dioxoisoindol-5-yl]-2,7-diazaspiro[3.5]nonane-7-carboxylate (280.0 mg, 0.6 mmol, 1.0 equiv) in DCM (5 mL) added TFA (1.5 mL) at room temperature. The reaction was stirred for 2 hours, then concentrated under reduced pressure to afford 5-{2,7-diazaspiro[3.5]nonan-2-yl}-2-(2,6-dioxopiperidin-3-yl)isoindole-1,3-dione (222 mg) as an oil. MS (ESI): m/z 383.15 [MH$^+$].

Step 6: preparation of 2-{[6-({5-chloro-2-[4-({2-[2-(2,6-dioxopiperidin-3-yl)-1,3-dioxoisoindol-5-yl]-2,7-diazaspiro[3.5]nonan-7-yl}methyl)piperidin-1-yl]pyridin-4-yl}amino)-1-isopropyl-2-oxoquinolin-3-yl]oxy}-N-methylacetamide

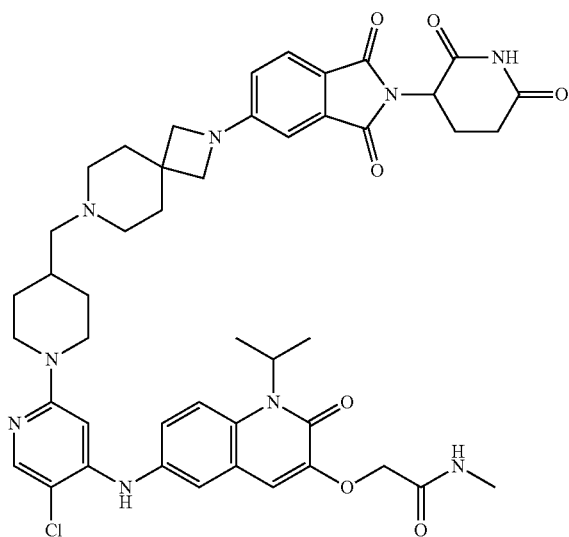 [SMILES: CNC(=O)COc1cc2cc(Nc3cc(N4CCC(CN5CCC6(CC5)CN(c5ccc7c(c5)C(=O)N(C5CCC(=O)NC5=O)C7=O)C6)CC4)ncc3Cl)ccc2n(C(C)C)c1=O]

A mixture of 5-{2,7-diazaspiro[3.5]nonan-2-yl}-2-(2,6-dioxopiperidin-3-yl)isoindole-1,3-dione (222.0 mg, 0.6 mmol, 1.0 equiv) and 2-[(6-{[5-chloro-2-(4-formylpiperidin-1-yl)pyridin-4-yl]amino}-1-isopropyl-2-oxoquinolin-3-yl)oxy]-N-methylacetamide (297.2 mg, 0.6 mmol, 1.0 equiv) in DCE (15 mL) was stirred overnight at room temperature under a nitrogen atmosphere. NaBH(OAc)₃ (369.1 mg, 1.7 mmol, 3.0 equiv) was added and the resulting mixture was stirred 2 hours at room temperature under nitrogen atmosphere. The reaction was quenched by the addition of water (30 mL), the resulting mixture was extracted with CH₂Cl₂/MeOH (10:1) (50 mL×3). The combined organic layers were washed with brine (30 mL×3), dried over anhydrous sodium sulfate, filtered, and concentrated under reduced pressure. The residue was purified by reverse flash chromatography (column, C18 silica gel; mobile phase, acetonitrile/water (10 mmol/L NH₄HCO₃), 0% to 55% gradient in 30 min; detector, UV 254 nm) to afford 2-{[6-({5-chloro-2-[4-({2-[2-(2,6-dioxopiperidin-3-yl)-1,3-dioxoisoindol-5-yl]-2,7-diazaspiro[3.5]nonan-7-yl}methyl)piperidin-1-yl]pyridin-4-yl}amino)-1-isopropyl-2-oxoquinolin-3-yl]oxy}-N-methylacetamide (89.2 mg, 17%) as a yellow solid. ¹H NMR (400 MHz, DMSO-d₆) δ 11.06 (s, 1H), 8.01 (s, 1H), 7.92 (d, J=9.2 Hz, 2H), 7.73 (d, J=9.3 Hz, 1H), 7.62 (d, J=8.3 Hz, 1H), 7.49 (d, J=2.6 Hz, 1H), 7.36 (d, J=9.2, Hz, 1H), 7.19 (s, 1H), 6.76 (d, J=2.1 Hz, 1H), 6.64 (d, J=8.4, Hz, 1H), 6.26 (s, 1H), 5.05 (d, J=12.8, Hz, 1H), 4.52 (s, 2H), 4.00 (d, J=12.4 Hz, 2H), 3.73 (s, 4H), 2.94-2.81 (m, 1H), 2.67 (d, J=4.7 Hz, 4H), 2.61-2.51 (m, 2H), 2.40 (s, 2H), 2.28 (s, 4H), 2.08 (d, J=6.3 Hz, 2H), 2.00 (d, J=11.9 Hz, 1H), 1.73-1.67 (m, 7H), 1.57 (d, J=6.9 Hz, 6H), 1.01 (d, J=12.5 Hz, 2H); MS (ESI): m/z 878.25 [MH⁺].

Using the procedure above and conditions found elsewhere in this application, the skilled artisan can prepare the following compounds: Compound 229, Compound 230, Compound 231, Compound 232, Compound 233, Compound 237, Compound 240, Compound 243, Compound 247, Compound 251, Compound 252, Compound 257, and Compound 258.

Example 57: Synthesis of 2-[[6-[[5-chloro-2-[4-[3-[4-[2-(2,6-dioxo-3-piperidyl)-1-oxo-isoindolin-5-yl]-3,3-difluoro-1-piperidyl]cyclobutoxy]-1-piperidyl]pyrimidin-4-yl]amino]-1-isopropyl-2-oxo-3-quinolyl]oxy]-N-methyl-acetamide (Compound 218)

Step 1: preparation of methyl 2-bromo-4-iodo-benzoate

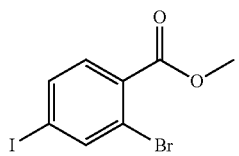

A solution of 2-bromo-4-iodo-benzoic acid (10 g, 30.59 mmol, 1 eq) and potassium carbonate (12.68 g, 91.77 mmol, 3 eq) in N,N-dimethyl formamide (100 mL) was added methyl iodide (8.68 g, 61.18 mmol, 3.8 mL, 2 eq), then the mixture was stirred for 2 hours at 25° C. The reaction mixture was quenched with water (100 mL) and extracted with ethyl acetate (100 mL×3). The combined organic phase was washed with brine (100 mL), dried over anhydrous sodium sulfate, filtered, and concentrated in vacuo. The residue was purified by silica gel column chromatography (petroleum ether/ethyl acetate=50/1 to 5/1) to afford methyl 2-bromo-4-iodo-benzoate (10 g, 96%) as a yellow oil. ¹H NMR (400 MHz, CDCl₃) δ 8.06 (d, J=1.6 Hz, 1H), 7.72 (dd, J=8.0, 1.6 Hz, 1H), 7.53 (d, J=8.0 Hz, 1H), 3.93 (s, 3H).

Step 2: Preparation of tert-butyl 4-(3-bromo-4-methoxycarbonyl-phenyl)-3,6-dihydro-2H-pyridine-1-carboxylate

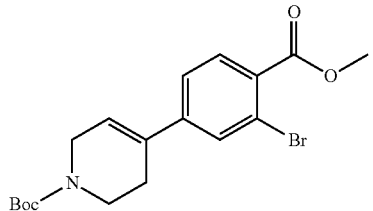 [SMILES: COC(=O)c1ccc(C2=CCN(C(=O)OC(C)(C)C)CC2)cc1Br]

A mixture of methyl 2-bromo-4-iodo-benzoate (6.2 g, 18.19 mmol, 1 eq), tert-butyl 4-(4,4,5,5-tetramethyl-1,3,2-dioxaborolan-2-yl)-3,6-dihydro-2H-pyridine-1-carboxylate (5.62 g, 18.19 mmol, 1 eq), [1,1'-Bis(diphenylphosphino)ferrocene]dichloropalladium(II) dichloromethane (1.33 g, 1.82 mmol, 0.1 eq) and potassium carbonate (5.03 g, 36.37 mmol, 2 eq) in water (10 mL) and dioxane (100 mL) was stirred at 55° C. under nitrogen atmosphere for 12 hours. The reaction mixture was quenched with water (100 mL), extracted with ethyl acetate (100 mL×3). The combined organic phase was washed with brine (100 mL), dried over anhydrous sodium sulfate, filtered, and concentrated in vacuo. The residue was purified by silica gel column chromatography (petroleum ether/ethyl acetate=100/1 to 10/1) to afford tert-butyl 4-(3-bromo-4-methoxycarbonyl-phenyl)-3,6-dihydro-2H-pyridine-1-carboxylate (6.5 g, 90%) as a yellow oil. ¹H NMR (400 MHz, CDCl₃) δ 7.81 (d, J=8.0 Hz, 1H), 7.67 (d, J=1.6 Hz, 1H), 7.35 (dd, J=8.0, 1.6 Hz, 1H), 6.17 (s, 1H), 4.13-4.08 (m, 2H), 3.93 (s, 3H), 3.65 (t, J=5.6 Hz, 2H), 2.55-2.45 (m, 2H), 1.49 (s, 9H).

Step 3: preparation of tert-butyl 4-(3-bromo-4-methoxycarbonyl-phenyl)-3-hydroxy-piperidine-1-carboxylate

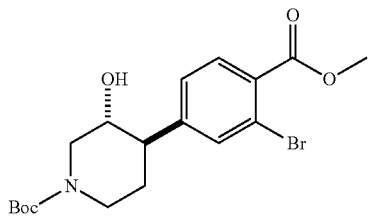

To a solution of tert-butyl 4-(3-bromo-4-methoxycarbonyl-phenyl)-3,6-dihydro-2H-pyridine-1-carboxylate (1 g, 2.52 mmol, 1 eq) in tetrahydrofuran (20 mL) was dropwise added dimethyl sulfide borane (10 M, 0.8 mL, 3 eq) at 0° C., then the mixture was stirred for 12 h at 25° C. After that a solution of sodium perborate tetrahydrate (1.16 g, 7.57 mmol, 1.5 mL, 3 eq) in water (15 mL) was added at 0° C., then the mixture was stirred for 2 hours at 25° C. The reaction mixture was quenched with saturated sodium sulfite solution (50 mL) and extracted with ethyl acetate (50 mL×3). The combined organic phase was washed with brine (50 mL), dried over anhydrous sodium sulfate, filtered, and concentrated in vacuo. The residue was purified by silica gel column chromatography (petroleum ether/ethyl acetate=20/1 to 1/1) to afford tert-butyl 4-(3-bromo-4-methoxycarbonyl-phenyl)-3-hydroxy-piperidine-1-carboxylate (0.8 g, 77%) as a yellow oil. ¹H NMR (400 MHz, CDCl₃) δ 7.80 (d, J=8.0 Hz, 1H), 7.58 (s, 1H), 7.27-7.23 (m, 1H), 4.47-4.35 (m, 1H), 4.27-4.15 (m, 1H), 3.93 (s, 3H), 3.80-3.65 (m, 1H), 2.85-2.55 (m, 3H), 1.90-1.65 (m, 2H), 1.49 (s, 9H).

Step 4: preparation of dimethyl 4-(1-tert-butoxycarbonyl-3-oxo-4-piperidyl)benzene-1,2-dicarboxylate

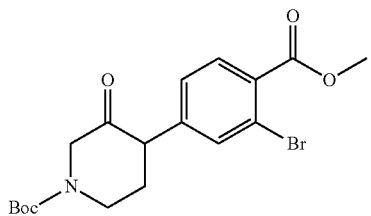 [SMILES: COC(=O)c1ccc(C2CCN(C(=O)OC(C)(C)C)CC2=O)cc1Br]

A solution of dimethyl 4-(1-tert-butoxycarbonyl-3-hydroxy-4-piperidyl)benzene-1,2-dicarboxylate (3.6 g, 9.15 mmol, 1 eq) in dichloromethane (40 mL) was added the Dess-Martin reagent (15.52 g, 36.60 mmol, 4 eq) at 0° C., then the mixture was stirred for 2 hours at 25° C. The reaction mixture was quenched with saturated sodium bicarbonate solution (50 mL) and extracted with dichloromethane (50 mL×3). The combined organic phase was washed with brine (50 mL), dried over anhydrous sodium sulfate, filtered, and concentrated in vacuo. The residue was purified by silica gel column chromatography (petroleum ether/ethyl acetate=20/1 to 1/1) to afford dimethyl 4-(1-tert-butoxycarbonyl-3-oxo-4-piperidyl)benzene-1,2-dicarboxylate (3.2 g, 89%) as a yellow oil. ¹H NMR (400 MHz, CDCl₃) δ: 7.73 (d, J=8.0 Hz, 1H), 7.52-7.48 (m, 1H), 7.35-7.30 (m, 1H), 4.30-4.22 (m, 1H), 4.07-4.00 (m, 1H), 3.95-3.93 (m, 1H), 3.91 (d, J=1.6 Hz, 6H), 3.77-3.68 (m, 1H), 3.59-3.47 (m, 1H), 2.40-2.20 (m, 2H), 1.49 (s, 9H).

Step 5: preparation of dimethyl 4-(1-tert-butoxycarbonyl-3,3-difluoro-4-piperidyl)benzene-1,2-dicarboxylate

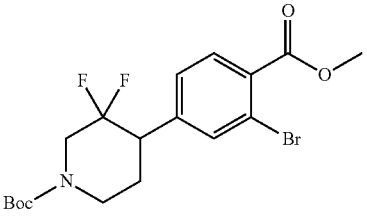 [SMILES: COC(=O)c1ccc(C2CCN(C(=O)OC(C)(C)C)CC2(F)F)cc1Br]

To a solution of dimethyl 4-(1-tert-butoxycarbonyl-3-oxo-4-piperidyl)benzene-1,2-dicarboxylate (3.2 g, 8.18 mmol, 1 eq) in dichloromethane (40 mL) was dropwise added 2-methoxy-N-(2-methoxyethyl)-N-(trifluoro-λ⁴-sulfanyl)ethanamine (4.52 g, 20.44 mmol, 4.5 mL, 2.5 eq) at −78° C., then the mixture was stirred for 2 hours at 25° C. The reaction mixture was quenched with saturated sodium bicarbonate solution (50 mL) and extracted with ethyl acetate (50 mL×3). The combined organic phase was washed with brine (50 mL), dried over anhydrous sodium sulfate, filtered, and concentrated in vacuo. The residue was purified by silica gel column chromatography (petroleum ether/ethyl acetate=0/1 to 1/1) to afford dimethyl 4-(1-tert-butoxycarbonyl-3,3-difluoro-4-piperidyl)benzene-1,2-dicarboxylate (2 g, 59%) as a yellow oil. MS (ESI) m/z: 357.9 [M-55]⁺; ¹H NMR (400 MHz, CDCl₃) δ 7.72 (d, J=8.0 Hz, 1H), 7.67 (s, 1H), 7.50 (d, J=7.6 Hz, 1H), 4.70-4.21 (m, 2H), 3.92 (s, 6H), 3.20-3.07 (m, 1H), 3.05-2.75 (m, 2H), 2.30-2.15 (m, 1H), 1.93-1.80 (m, 1H), 1.49 (s, 9H).

Step 6: preparation of methyl 2-bromo-4-(3,3-difluoro-4-piperidyl) benzoate

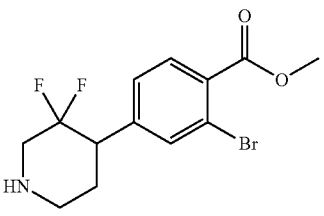 [SMILES: COC(=O)c1ccc(C2CCNCC2(F)F)cc1Br]

A solution of tert-butyl 4-(3-bromo-4-methoxycarbonyl-phenyl)-3,3-difluoro-piperidine-1-carboxylate (1 g, 2.3 mmol, 1 eq) in dichloromethane (10 mL) was dropwise added trifluoroacetic acid (8.14 g, 71.4 mmol, 31.02 eq) at 25° C., then the mixture was stirred for 30 minutes at 25° C. The reaction was concentrated in vacuo, the residue was quenched with saturated sodium bicarbonate solution (50 mL) and the mixture was extracted with ethyl acetate (50 mL×3). The combined organic phase was washed with brine (50 mL), dried over anhydrous sodium sulfate, filtered, and concentrated in vacuo to afford methyl 2-bromo-4-(3,3-difluoro-4-piperidyl)benzoate (760 mg, 99%) as a yellow oil. MS (ESI) m/z: 336.0 [M+H]⁺.

Step 7: preparation of tert-butyl 4-[3-[4-(3-bromo-4-methoxycarbonyl-phenyl)-3,3-difluoro-1-piperidyl]cyclobutoxy]piperidine-1-carboxylate

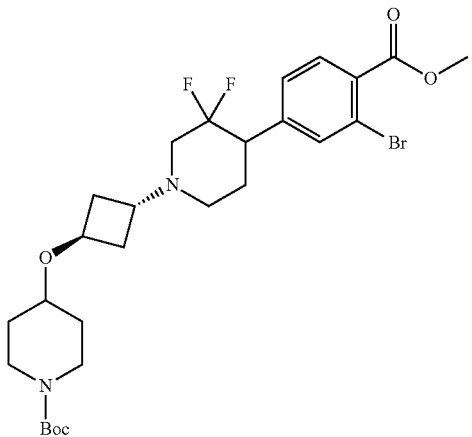 [SMILES: COC(=O)c1ccc(C2CCN([C@H]3C[C@H](OC4CCN(C(=O)OC(C)(C)C)CC4)C3)CC2(F)F)cc1Br]

A solution of tert-butyl 4-[3-(trifluoromethylsulfonyloxy)cyclobutoxy]piperidine-1-carboxylate (956 mg, 2.37 mmol, 1.2 eq), methyl 2-bromo-4-(3,3-difluoro-4-piperidyl) benzoate (660 mg, 1.98 mmol, 1 eq) and N,N-diisopropylethylamine (766 mg, 5.93 mmol, 1 mL, 3 eq) in acetonitrile (30 mL) was stirred at 35° C. for 2 hours. The mixture was concentrated under reduced pressure. The residue was purified by silica gel column chromatography (petroleum ether/ethyl acetate=20/1 to 0/1) to afford tert-butyl 4-[3-[4-(3-bromo-4-methoxy carbonyl-phenyl)-3,3-difluoro-1-piperidyl]cyclobutoxy]piperidine-1-carboxylate (860 mg, 74%) as a yellow oil. MS (ESI) m/z: 589.1 [M+1]$^+$; $^1$H NMR (400 MHz, CDCl$_3$) δ 7.72 (d, J=8.0 Hz, 1H), 7.67 (s, 1H), 7.50 (d, J=7.6 Hz, 1H), 4.28-4.17 (m, 1H), 3.93 (s, 3H), 3.87-3.75 (m, 2H), 3.50-3.40 (m, 1H), 3.30-3.20 (m, 1H), 3.17-2.90 (m, 5H), 2.35-2.10 (m, 6H), 2.00-1.90 (m, 2H), 1.85-1.75 (m, 2H), 1.55-1.50 (m, 2H), 1.46 (s, 9H).

Step 8: preparation of tert-butyl 4-[3-[3,3-difluoro-4-(3-formyl-4-methoxy carbonyl-phenyl)-1-piperidyl]cyclobutoxy]piperidine-1-carboxylate

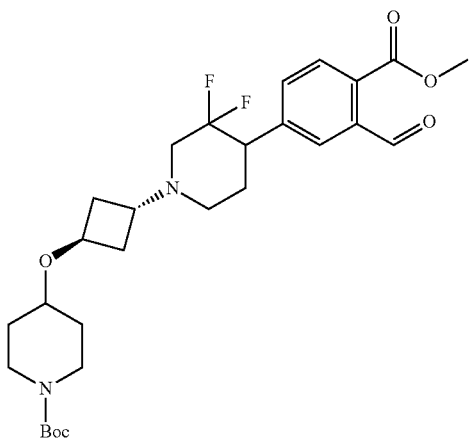 [SMILES: COC(=O)c1ccc(C2CCN([C@H]3C[C@H](OC4CCN(C(=O)OC(C)(C)C)CC4)C3)CC2(F)F)cc1C=O]

To a solution of tert-butyl 4-[3-[4-(3-bromo-4-methoxycarbonyl-phenyl)-3,3-difluoro-1-piperidyl]cyclobutoxy]piperidine-1-carboxylate (860 mg, 1.46 mmol, 1 eq) in N,N-dimethyl formamide (10 mL) was added palladium acetate (33 mg, 1.46 mmol, 0.1 eq), tricyclohexylphosphine (41 mg, 0.15 mmol, 0.1 eq), sodium carbonate (155 mg, 1.46 mmol, 1 eq), triethyl silicane (511 mg, 4.39 mmol, 3 eq) and 2-isocyano-2-methyl-propane (243 mg, 2.93 mmol, 2 eq). The mixture was stirred at 65° C. for 12 hours in a teflon reaction vessel. The reaction was diluted with water (20 mL) and extracted with ethyl acetate (20 mL×2). The combined organic layers were washed with brine (20 mL×2), dried over anhydrous sodium sulfate, filtered, and concentrated in vacuum. The residue was purified by preparative TLC (petroleum ether/ethyl acetate=1/1) to afford tert-butyl 4-[3-[3,3-difluoro-4-(3-formyl-4-methoxycarbonyl-phenyl)-1-piperidyl] cyclobutoxy]piperidine-1-carboxylate (690 mg, 88%) as a yellow oil. MS (ESI) m/z: 537.3 [M+1]$^+$.

Step 9-11: preparation of 2-[[6-[[5-chloro-2-[4-[3-[4-[2-(2,6-dioxo-3-piperidyl)-1-oxo-isoindolin-5-yl]-3,3-difluoro-1-piperidyl]cyclobutoxy]-1-piperidyl]pyrimidin-4-yl]amino]-1-isopropyl-2-oxo-3-quinolyl]oxy]-N-methyl-acetamide

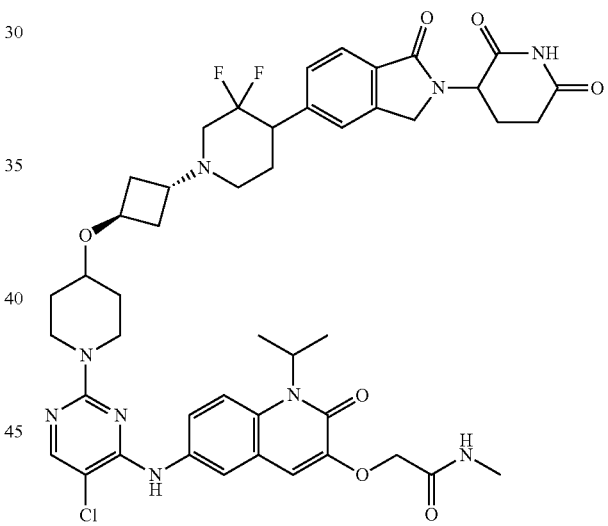

The title compound was prepared in an analogously to compound 161 following steps 12-14 with the material made in step 8 of this Example. The crude product was purified by prep-HPLC (column: Unisil 3-100 C18 Ultra 150*50 mm*3 um; mobile phase: [water (0.225% FA)-ACN]; B %: 16%-46%, 10 min) to afford 2-[[6-[[5-chloro-2-[4-[3-[4-[2-(2,6-dioxo-3-piperidyl)-1-oxo-isoindolin-5-yl]-3,3-difluoro-1-piperidyl]cyclobutoxy]-1-piperidyl]pyrimidin-4-yl]amino]-1-isopropyl-2-oxo-3-quinolyl]oxy]-N-methyl-acetamide formate (48.5 mg, 15%) as an off-white solid. MS (ESI) m/z: 916.3 [M+H]$^+$; $^1$H NMR (400 MHz, DMSO-d$_6$) δ 10.97 (s, 1H), 8.84 (s, 1H), 8.43 (s, 1H), 8.04 (s, 1H), 7.98-7.92 (m, 2H), 7.72-7.65 (m, 3H), 7.60-7.52 (m, 1H), 7.44-7.40 (m, 1H), 7.05-7.00 (m, 1H), 5.70-5.23 (m, 1H), 5.20-5.10 (m, 1H), 4.54 (s, 2H), 4.50-4.43 (m, 1H), 4.37-4.27 (m, 1H), 4.23-4.07 (m, 3H), 3.60-3.50 (m, 1H), 3.22-3.10 (m, 3H), 3.05-2.97 (m, 2H), 2.95-2.85 (m, 1H), 2.70-2.66 (m, 3H), 2.64-2.56 (m, 1H), 2.45-2.31 (m, 2H), 2.28-2.09 (m, 4H), 2.06-1.96 (m, 4H), 1.89-1.79 (m, 3H), 1.60-1.55 (m, 6H), 1.45-1.31 (m, 2H).

Example 58 Synthesis of 2-((6-((5-chloro-2-(4-((2-(2-(2,6-dioxopiperidin-3-yl)-4-(methoxy-d3)-1-oxoisoindolin-5-yl)-2-azaspiro[3.5]nonan-7-yl)oxy)piperidin-1-yl)pyrimidin-4-yl)amino)-1-isopropyl-2-oxo-1,2-dihydroquinolin-3-yl)oxy)-N-methylacetamide (Compound 225)

Step 1: preparation of methyl 4-bromo-3-hydroxy-2-methylbenzoate

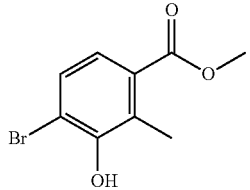

To a solution of tert-butylamine (13.20 g, 180.531 mmol, 1 equiv) in dichloromethane (500 mL) at −78° C. was drop-wise added over 30 minutes a solution of bromine (28.85 g, 180.531 mmol, 1 equiv) in 50 mL of dichloromethane. The solution was stirred at −78° C. for 30 minutes. While maintaining the temperature at −78° C., a solution of methyl 3-hydroxy-2-methylbenzoate (30 g, 180.531 mmol, 1 equiv) in 150 mL of dichloromethane was added to the reaction mixture drop-wise over 30 minutes. The mixture was allowed to warm to room temperature and was stirred for 15 hours. The mixture was washed with 20% aqueous citric acid then brine and dried over anhydrous sodium sulfate, filtered, and concentrated in vacuo. The residue was purified by silica gel column chromatography (10% EA in hexane) to afford methyl 4-bromo-3-hydroxy-2-methylbenzoate (19.0 g, 43%) as white solid.

Step 2: preparation of methyl 4-bromo-3-(methoxy-d3)-2-methylbenzoate

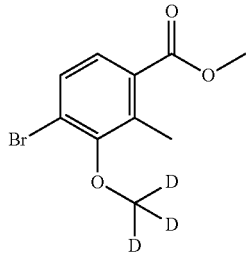 [SMILES: [2H]C([2H])([2H])Oc1c(Br)ccc(C(=O)OC)c1C]

Into a 250 mL round-bottom flask was added methyl 4-bromo-3-hydroxy-2-methylbenzoate (2.43 g, 9.915 mmol, 1.00 equiv), methan-d3-ol (1.80 g, 50 mmol) and triphenylphosphine (5.24 g, 20 mmol) in THF (50 mL). Then a solution of diisopropyl azodicarboxylate (4.04 g, 20 mmol) in THF (50 mL) was added into the reaction system slowly at 0° C. in 15 minutes. After warming to room temperature and stirring for 1 hour, the resulting solution was allowed to stir at 60° C. for 12 hours. The reaction was concentrated under vacuum, the residue was purified by silica gel column chromatography (EtOAc/PE=1/100) to afford methyl 4-bromo-3-(methoxy-d3)-2-methylbenzoate (2.2 g, 85%) as a colorless oil. $^1$H NMR (300 MHz, CDCl3) δ 7.51 (d, J=8.5 Hz, 1H), 7.44 (d, J=8.5 Hz, 1H), 3.89 (s, 3H), 2.56 (s, 3H).

Step 3: preparation of methyl 4-bromo-2-(bromomethyl)-3-(methoxy-d3)benzoate

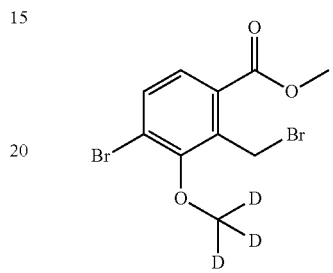

Combined methyl 4-bromo-3-(methoxy-d3)-2-methylbenzoate (1.0 g, 3.815 mmol, 1.00 equiv), N-bromosuccinimide (0.68 g, 3.821 mmol, 1.00 equiv), and azobisisobutyronitrile (0.10 g, 0.609 mmol, 0.16 equiv) in CCl$_4$ (10 mL). The reaction was stirred at 70° C. overnight, concentrated under vacuum to afford methyl 4-bromo-2-(bromomethyl)-3-(methoxy-d3)benzoate (1.3 g) as yellow oil, which was used in the next step without further purification.

Step 4: preparation of 3-(5-bromo-4-(methoxy-d3)-1-oxoisoindolin-2-yl)piperidine-2,6-dione

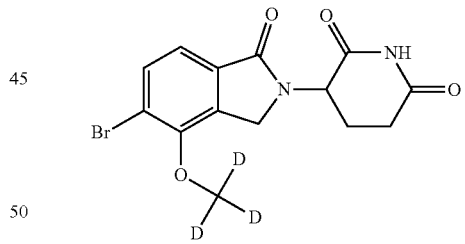

Combined methyl 4-bromo-2-(bromomethyl)-3-(methoxy-d3)benzoate (1.3 g, 3.8 mmol, 1.00 equiv), 2,6-dioxopiperidin-3-aminium chloride (0.63 g, 3.8 mmol, 1.00 equiv), triethylamine (1 mL, 7.2 mmol, 1.89 equiv) in acetonitrile (10 mL). After stirring at 60° C. for 12 hours followed by removing the reaction solvent, acetic acid (2 mL) was added. And the resulting solution was stirred at 120° C. for 2 hours, then concentrated in vacuum. The crude product was washed by H$_2$O (100 mL) and dried under vacuum at 60° C. for more than 2 hours to afford 3-(5-bromo-4-(methoxy-d3)-1-oxoisoindolin-2-yl)piperidine-2,6-dion (0.84 g, 62%) as black solid. MS (ESI): m/z 356.15 [MH$^+$].

Step 5: preparation of tert-butyl 7-(pyridin-4-yloxy)-2-azaspiro[3.5]nonane-2-carboxylate

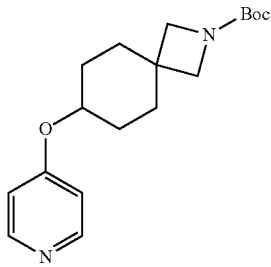 [SMILES: CC(C)(C)OC(=O)N1CC2(CCC(Oc3ccncc3)CC2)C1]

To a stirred solution of 4-chloropyridine (8.8 g, 77 mmol, 1 equiv) and tert-butyl 7-hydroxy-2-azaspiro[3.5]nonane-2-carboxylate (18 g, 77 mmol, 1 equiv) in DMSO (200 mL) was added dropwise potassium tert-butoxide in THF (1M, 395 mg, 3.5 mmol, 4 equiv) at room temperature. The reaction was diluted with water, the aqueous layer was extracted with EtOAc, concentrated in vacuo. The residue was purified by silica gel column chromatography (PE/EA=1:1) to afford tert-butyl 7-(pyridin-4-yloxy)-2-azaspiro[3.5]nonane-2-carboxylate (10 g, 40%) as a white solid. MS (ESI): m/z 379.20 [MH$^+$].

Step 6: preparation of 1-benzyl-4-{[2-(tert-butoxycarbonyl)-2-azaspiro[3.5]nonan-7-yl]oxy}pyridin-1-ium

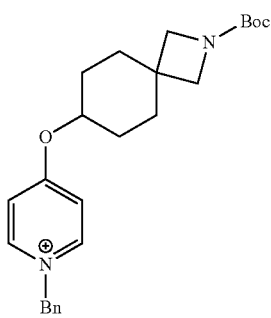 [SMILES: CC(C)(C)OC(=O)N1CC2(CCC(Oc3cc[n+](Cc4ccccc4)cc3)CC2)C1]

To a stirred solution of tert-butyl 7-(pyridin-4-yloxy)-2-azaspiro[3.5]nonane-2-carboxylate (10 g, 31 mmol, 1 equiv) in DCM (100 mL) was dropwise added benzyl bromide (8 g, 47 mmol, 1.5 equiv) at 0° C. The resulting mixture was stirred for 2 hours at room temperature, then concentrated under reduced pressure. The resulting mixture was suspended in PE, filtered, the filter cake was dried to afford 1-benzyl-4-{[2-(tert-butoxycarbonyl)-2-azaspiro[3.5]nonan-7-yl]oxy}pyridin-1-ium (13 g, 100%) as a white solid. MS (ESI): m/z 409.25 [MH$^+$].

Step 7: preparation of tert-butyl 7-[(1-benzyl-3,6-dihydro-2H-pyridin-4-yl)oxy]-2-azaspiro[3.5]nonane-2-carboxylate

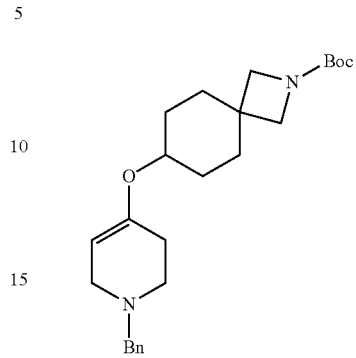

To a stirred solution of 1-benzyl-4-{[2-(tert-butoxycarbonyl)-2-azaspiro[3.5]nonan-7-yl]oxy}pyridin-1-ium (13 g, 31 mmol, 1 equiv) in MeOH (100 mL) was added NaBH$_4$ (4.8 g, 126 mmol, 4 equiv) at 0° C. The resulting mixture was concentrated under reduced pressure, diluted with water, the aqueous layer was extracted with CH$_2$Cl$_2$, concentrated. The residue was purified by silica gel column chromatography (PE/EA=1:1) to afford tert-butyl 7-[(1-benzyl-3,6-dihydro-2H-pyridin-4-yl)oxy]-2-azaspiro[3.5]nonane-2-carboxylate (9 g, 68%) as a white solid. MS (ES+): m/z 413.30 [MH$^+$].

Step 8: preparation of tert-butyl 7-(piperidin-4-yloxy)-2-azaspiro[3.5]nonane-2-carboxylate

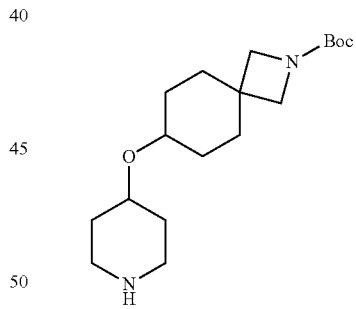

To a solution of tert-butyl 7-[(1-benzyl-3,6-dihydro-2H-pyridin-4-yl)oxy]-2-azaspiro[3.5]nonane-2-carboxylate (9 g, 21 mmol, 1 equiv) in 100 mL MeOH was added Pd(OH)$_2$/C (3 g) under nitrogen atmosphere. The mixture was degassed and purge with hydrogen for a few times, then it was stirred overnight under hydrogen atmosphere using a hydrogen balloon. The reaction was filtered through a Celite pad and concentrated under reduced pressure to afford tert-butyl 7-(piperidin-4-yloxy)-2-azaspiro[3.5]nonane-2-carboxylate (8 g, 100%) as an off-white solid. MS (ESI): m/z 319.15 [MH$^+$].

Step 9: preparation of tert-butyl 7-({1-[(benzyloxy)carbonyl]-3,6-dihydro-2H-pyridin-4-yl}oxy)-2-azaspiro[3.5]nonane-2-carboxylate

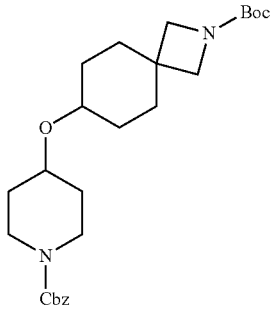

To a stirred solution of tert-butyl 7-(piperidin-4-yloxy)-2-azaspiro[3.5]nonane-2-carboxylate (7 g, 21 mmol, 1 equiv) and Et₃N (6 g, 64 mmol, 3 equiv) in DCM (70 mL) was dropwise added benzyl chloroformate (4 g, 23 mmol, 1.1 equiv) at 0° C. The resulting mixture was stirred for 3 hours at room temperature, then diluted with water. The aqueous layer was extracted with CH₂Cl₂ and concentrated. The residue was purified by reverse flash chromatography (column, silica gel; mobile phase, acetonitrile/water (10 mmol/L NH₄HCO₃), 10% to 50% gradient in 30 min; detector, UV 254 nm) to afford tert-butyl 7-({1-[(benzyloxy)carbonyl]-3,6-dihydro-2H-pyridin-4-yl}oxy)-2-azaspiro[3.5]nonane-2-carboxylate (5 g, 51%) as an off-white solid. MS (ESI): m/z 459.35 [MH⁺].

Step 10: preparation of benzyl 4-{2-azaspiro[3.5]nonan-7-yloxy}piperidine-1-carboxylate

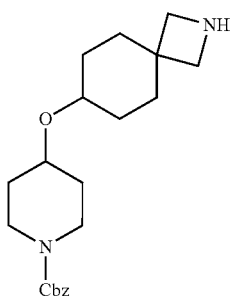 [SMILES: O=C(OCc1ccccc1)N1CCC(OC2CCC3(CC2)CNC3)CC1]

To a stirred solution of tert-butyl 7-({1-[(benzyloxy)carbonyl]piperidin-4-yl}oxy)-2-azaspiro[3.5]nonane-2-carboxylate (5 g, 10 mmol, 1 equiv) in DCM (40 mL) was dropwise added TFA (10 mL) at room temperature. The resulting mixture was stirred for 2 hours at room temperature, then concentrated under reduced pressure. The residue was neutralized to pH 7 with saturated Na₂CO₃ (aq.). The aqueous layer was extracted with CH₂Cl₂, concentrated to afford benzyl 4-{2-azaspiro[3.5]nonan-7-yloxy}piperidine-1-carboxylate (3.7 g, 94%) as a white solid. MS (ESI): m/z 359.20 [MH⁺].

Step 11: preparation of benzyl 4-((2-(2-(2,6-dioxopiperidin-3-yl)-4-(methoxy-d3)-1-oxoisoindolin-5-yl)-2-azaspiro[3.5]nonan-7-yl)oxy)piperidine-1-carboxylate

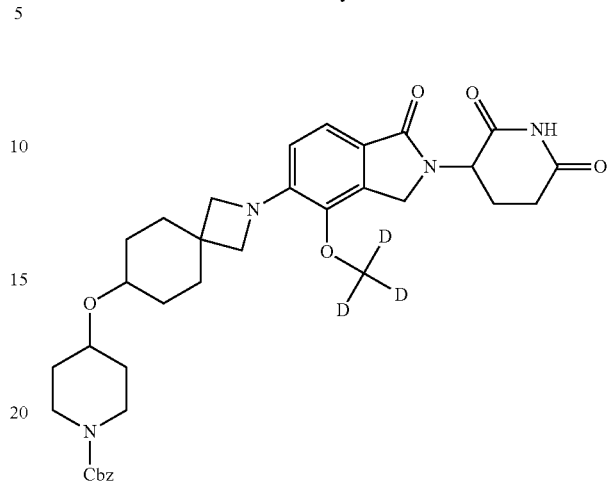

To a solution of benzyl 4-{2-azaspiro[3.5]nonan-7-yloxy}piperidine-1-carboxylate (602 mg, 1.679 mmol, 1.20 equiv) and 3-(5-bromo-4-(methoxy-d3)-1-oxoisoindolin-2-yl)piperidine-2,6-dione (500 mg, 1.404 mmol, 1.00 equiv) in DMF (18 mL) were added Cs₂CO₃ (1.48 g, 4.528 mmol, 2.99 equiv) and [1,3-Bis(2,6-Di-3-pentylphenyl)imidazol-2-ylidene](3-chloropyridyl)dichloropalladium(II) (118 mg, 0.140 mmol, 0.10 equiv). After stirring at 100° C. for 4 hours under nitrogen atmosphere, the reaction was cooled to room temperature, H₂O (100 mL) was added into the mixture and the aqueous layer was extracted with EtOAc. The organic layer was dried over Na₂SO₄, filtered, and concentrated under vacuum. The residue was purified by reverse flash chromatography (column, C18; mobile phase, MeCN in water (10 mmol/L NH₄HCO₃), 10% to 55% gradient in 30 min; detector, UV 254 nm) to afford benzyl 4-({2-[2-(2,6-dioxopiperidin-3-yl)-4-(2H3)methoxy-1-oxo-3H-isoindol-5-yl]-2-azaspiro[3.5]nonan-7-yl}oxy)piperidine-1-carboxylate (367 mg, 41%) as a yellow solid. MS (ESI): m/z 634.25 [MH⁺].

Step 12: preparation of 3-(4-(methoxy-d3)-1-oxo-5-(7-(piperidin-4-yloxy)-2-azaspiro[3.5]nonan-2-yl)isoindolin-2-yl)piperidine-2,6-dione

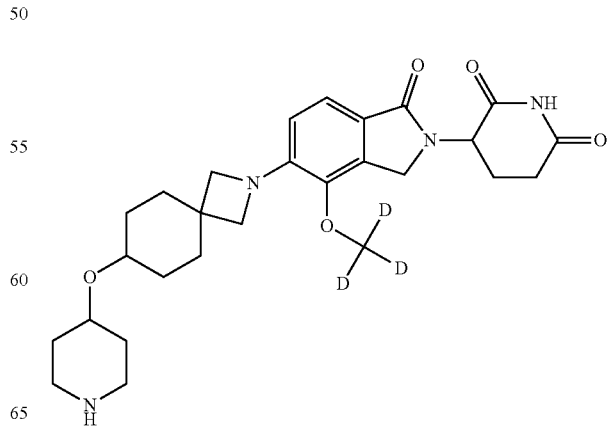

Into a 100 mL round-bottom flask was added benzyl 4-((2-(2-(2,6-dioxopiperidin-3-yl)-4-(methoxy-d3)-1-oxoisoindolin-5-yl)-2-azaspiro[3.5]nonan-7-yl)oxy)piperidine-1-carboxylate (367 mg, 0.6 mmol, 1.00 equiv) in isopropyl alcohol (15 mL) and tetrahydrofuran (3 mL). Then Pd(OH)$_2$/C (220 mg, 1.6 mmol, 2.71 equiv) was added in one portion, the mixture was degassed and purged with H$_2$ gas for several times, and the resulting mixture was stirred at room temperature under H$_2$ atmosphere for 24 hours. The reaction mixture was filtered, and concentrated under reduced pressure to give 3-(4-(methoxy-d3)-1-oxo-5-(7-(piperidin-4-yloxy)-2-azaspiro[3.5]nonan-2-yl)isoindolin-2-yl)piperidine-2,6-dione (280 mg, 97%) as yellow solid, which was used in the next step without further purification. MS (ESI): m/z 500.40 [MH$^+$].

Step 13: preparation of 2-((6-((5-chloro-2-(4-((2-(2-(2,6-dioxopiperidin-3-yl)-4-(methoxy-d3)-1-oxoisoindolin-5-yl)-2-azaspiro[3.5]nonan-7-yl)oxy)piperidin-1-yl)pyrimidin-4-yl)amino)-1-isopropyl-2-oxo-1,2-dihydroquinolin-3-yl)oxy)-N-methylacetamide

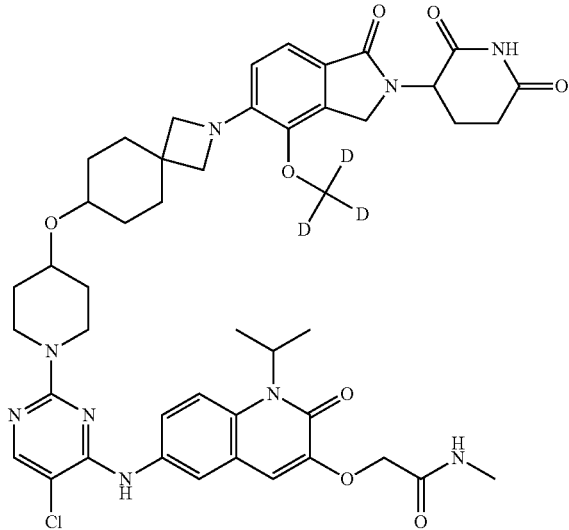 [SMILES: [2H]C([2H])([2H])Oc1c(N2CC3(CCC(OC4CCN(c5ncc(Cl)c(Nc6ccc7c(c6)cc(OCC(=O)NC)c(=O)n7C(C)C)n5)CC4)CC3)C2)ccc2c1CN(C1CCC(=O)NC1=O)C2=O]

In a 10 mL sealed tube, combined 3-(4-(methoxy-d3)-1-oxo-5-(7-(piperidin-4-yloxy)-2-azaspiro[3.5]nonan-2-yl)isoindolin-2-yl)piperidine-2,6-dione (225 mg, 0.5 mmol, 1.50 equiv), DIEA (0.8 mL, 4.6 mmol, 15.32 equiv) and DMSO (5 mL). To the above mixture was added 2-({6-[(2,5-dichloropyrimidin-4-yl)amino]-1-isopropyl-2-oxoquinolin-3-yl}oxy)-N-methylacetamide (130.8 mg, 0.3 mmol, 1.00 equiv). The resulting mixture was stirred for 4 hours at 100□ under nitrogen atmosphere. The crude product was purified by reverse flash chromatography (Column, C18; mobile phase, MeCN/H$_2$O (10 mmol/L NH$_4$HCO$_3$) 10% to 60% gradient in 30 min; Detector 254 nm) to afford 2-((6-((5-chloro-2-(4-((2-(2-(2,6-dioxopiperidin-3-yl)-4-(methoxy-d3)-1-oxoisoindolin-5-yl)-2-azaspiro[3.5]nonan-7-yl)oxy)piperidin-1-yl)pyrimidin-4-yl)amino)-1-isopropyl-2-oxo-1,2-dihydroquinolin-3-yl)oxy)-N-methylacetamide (80 mg, 30%) as off-white solid. MS (ESI): m/z 899.40 [M+1]$^+$; $^1$H NMR (300 MHz, DMSO-d$_6$, ppm) δ 10.94 (s, 1H), 8.82 (s, 1H), 8.04 (s, 1H), 7.95 (s, 2H), 7.69 (s, 2H), 7.28 (d, J=8.1 Hz, 1H), 7.02 (s, 1H), 6.50 (d, J=8.1 Hz, 1H), 5.03 (dd, J=13.1, 5.1 Hz, 1H), 4.55 (s, 2H), 4.50-4.21 (m, 2H), 4.17-4.01 (m, 2H), 3.66-3.69 (m, 5H), 3.54-3.41 (m, 1H), 3.25 (s, 1H), 3.06-2.82 (m, 1H), 2.78-2.57 (m, 4H), 2.46-2.23 (m, 2H), 2.08-1.69 (m, 8H), 1.57 (d, J=6.8 Hz, 8H), 1.44-1.24 (m, 4H).

Using the procedure above and conditions found elsewhere in this application, the skilled artisan can prepare the following compounds: Compound 227.

Example 59: Preparation of 2-[[6-[[5-chloro-2-[4-[3-[(2R,6S)-4-[2-(2,6-dioxo-3-piperidyl)-1,3-dioxoisoindolin-5-yl]-2,6-dimethyl-piperazin-1-yl]cyclobutoxy]-1-piperidyl]pyrimidin-4-yl]amino]-1-isopropyl-2-oxo-3-quinolyl]oxy]-N-methylacetamide (Compound 248)

Step 1: preparation of tert-butyl (3S,5R)-4-[3-[(1-benzyloxycarbonyl-4-piperidyl)oxy]cyclobutyl]-3,5-dimethyl-piperazine-1-carboxylate

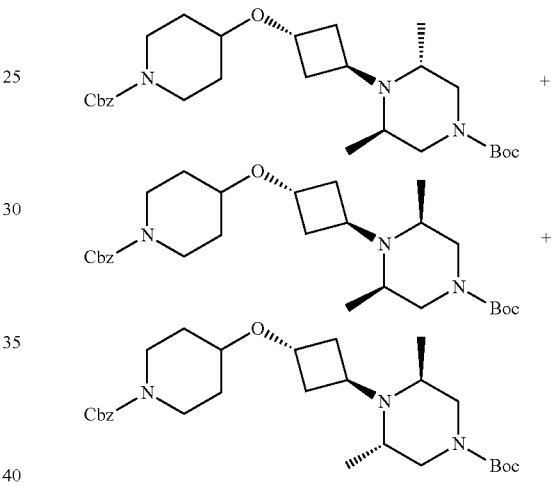

A solution of benzyl 4-(3-aminocyclobutoxy)piperidine-1-carboxylate (5.04 g, 16.6 mmol, 1 eq) and tert-butyl N,N-diacetonylcarbamate (3.8 g, 16.6 mmol, 1 eq) in methanol (50 mL) and acetic acid (5 mL) was added 2-methylpyridine borane (8.86 g, 82.3 mmol, 5 eq) at 25° C., then the mixture was stirred for 12 hours at 50° C. The reaction was concentrated in vacuo, the residue was diluted with sodium bicarbonate (100 mL) and the mixture was extracted with ethyl acetate (100 mL×3). The combined organic phase was washed with brine (100 mL), dried over anhydrous sodium sulfate, filtered, and concentrated in vacuo. The residue was purified by prep-HPLC (column: Phenomenex luna C18 (250*70 mm, 10 um); mobile phase: [water (TFA)-ACN]; B %: 25%-55%, 20 min). The product was separated by chiral SFC (column: DAICEL CHIRALPAK AD 250 mm*50 mm, I.D, 10 um; mobile phase: methanol (0.1% NH3H2O) in CO$_2$ from 35% to 35%; Flow rate: 50 mL/min; Wavelength: 220 nm), then further separated by chiral SFC (column: DAICEL CHIRALPAK AS-H 250 mm*30 mm, I.D, 5 um; mobile phase: methanol (0.1% NH$_3$H$_2$O) in CO$_2$ from 15% to 15%; Flow rate: 50 mL/min; Wavelength: 220 nm). Peak 1, tentatively assigned as tert-butyl (3R,5R)-4-((1r,3R)-3-((1-((benzyloxy)carbonyl)piperidin-4-yl)oxy)cyclobutyl)-3,5-dimethylpiperazine-1-carboxylate (1.6 g, 19%), was obtained as a yellow oil. $^1$H NMR (400 MHz, CDCl$_3$) δ 7.42-7.27 (m, 5H), 5.13 (s, 2H), 4.20-4.10 (m, 1H), 3.95-

3.80 (m, 2H), 3.75-3.60 (m, 1H), 3.55-3.40 (m, 2H), 3.20-3.05 (m, 3H), 3.04-2.90 (m, 1H), 2.30-2.10 (m, 2H), 1.90-1.75 (m, 2H), 1.70-1.57 (m, 4H), 1.55-1.47 (m, 3H), 1.46 (s, 9H), 1.11-1.10 (m, 4H). Peak 2, tentatively assigned as tert-butyl (3S,5R)-4-((1r,3R)-3-((1-((benzyloxy)carbonyl)piperidin-4-yl)oxy)cyclobutyl)-3,5-dimethylpiperazine-1-carboxylate (600 mg, 7%), was obtained as a yellow oil. $^1$H NMR (400 MHz, CDCl$_3$) δ 7.42-7.28 (m, 5H), 5.13 (s, 2H), 4.32-4.10 (m, 1H), 3.97-3.75 (m, 4H), 3.53-3.42 (m, 2H), 3.20-3.06 (m, 3H), 2.26-2.05 (m, 2H), 1.88-1.75 (m, 2H), 1.71-1.57 (m, 5H), 1.55-1.51 (m, 2H), 1.47 (s, 9H), 1.30-0.90 (m, 6H). Peak 3, tentatively assigned as tert-butyl (3S,5S)-4-((1r,3S)-3-((1-((benzyloxy)carbonyl)piperidin-4-yl)oxy)cyclobutyl)-3,5-dimethylpiperazine-1-carboxylate (2.8 g, 33%), was obtained as a yellow oil. $^1$H NMR (400 MHz, CDCl$_3$) δ 7.40-7.28 (m, 5H), 5.13 (s, 2H), 4.15-4.05 (m, 1H), 3.95-3.80 (m, 2H), 3.75-3.50 (m, 3H), 3.47-3.40 (m, 2H), 3.18-3.06 (m, 3H), 3.02-2.80 (m, 1H), 2.65-2.40 (m, 1H), 2.28-2.10 (m, 2H), 1.90-1.75 (m, 2H), 1.70-1.50 (m, 4H), 1.47 (s, 9H), 1.20-0.80 (m, 6H). MS (ESI) m/z: 502.3 [M+1]$^+$.

Step 2: preparation of benzyl 4-[3-[(2S,6R)-2,6-dimethylpiperazin-1-yl]cyclobutoxy]piperidine-1-carboxylate

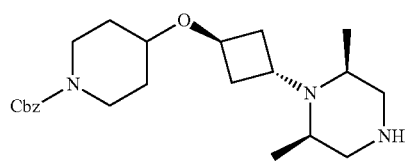 [SMILES: C[C@@H]1CNC[C@H](C)N1[C@H]1C[C@H](OC2CCN(C(=O)OCc3ccccc3)CC2)C1]

A mixture of tert-butyl (3S,5R)-4-[3-[(1-benzyloxycarbonyl-4-piperidyl)oxy]cyclobutyl]-3,5-dimethyl-piperazine-1-carboxylate (500 mg, 1.0 mmol, 1 eq) and hydrochloric acid/dioxane (4 M, 3 mL, 12.04 eq) in dichloromethane (9 mL) was degassed and purged with nitrogen for 3 times, then the mixture was stirred at 25° C. for 1 hour under nitrogen atmosphere. The reaction mixture was filtered and concentrated under reduced pressure to give benzyl 4-[3-[(2S,6R)-2,6-dimethylpiperazin-1-yl] cyclobutoxy]piperidine-1-carboxylate hydrochloride (436 mg, crude) as a yellow solid.

Step 3: preparation of benzyl 4-[3-[(2R,6S)-4-[2-(2,6-dioxo-3-piperidyl)-1,3-dioxo-isoindolin-5-yl]-2,6-dimethyl-piperazin-1-yl]cyclobutoxy]piperidine-1-carboxylate

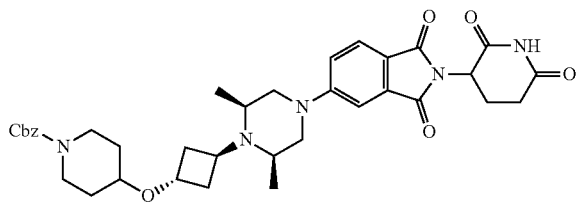 [SMILES: C[C@@H]1CN(c2ccc3c(c2)C(=O)N(C2CCC(=O)NC2=O)C3=O)C[C@H](C)N1[C@H]1C[C@H](OC2CCN(C(=O)OCc3ccccc3)CC2)C1]

A mixture of benzyl 4-[3-[(2S,6R)-2,6-dimethylpiperazin-1-yl]cyclobutoxy]piperidine-1-carboxylate hydrochloride (436 mg, 0.96 mmol, 1 eq), 2-(2,6-dioxo-3-piperidyl)-5-fluoro-isoindoline-1,3-dione (302 mg, 1.09 mmol, 1.1 eq) and diisopropylethylamine (386 mg, 2.99 mmol, 0.5 mL, 3 eq) in dimethyl sulfoxide (5 mL) was degassed and purged with nitrogen for 3 times, and then the mixture was stirred at 120° C. for 6 hours under nitrogen atmosphere. The reaction mixture was diluted with water and extracted with dichloromethane (120 mL), the organic layer was concentrated under reduced pressure. The residue was purified by silica gel column chromatography (petroleum ether/ethyl acetate=1/1 to 1/3) to afford benzyl 4-[3-[(2R,6S)-4-[2-(2,6-dioxo-3-piperidyl)-1,3-dioxo-isoindolin-5-yl]-2,6-dimethyl-piperazin-1-yl]cyclobutoxy]piperidine-1-carboxylate (530 mg, 80%) as a yellow solid. $^1$H NMR (400 MHz, DMSO-d$_6$) δ 11.07 (s, 1H), 7.64 (d, J=8.4 Hz, 1H), 7.40-7.29 (m, 5H), 7.24-7.17 (m, 1H), 7.10 (br d, J=9.2 Hz, 1H), 5.06 (s, 2H), 4.13-4.03 (m, 1H), 3.79-3.59 (m, 4H), 3.52-3.41 (m, 2H), 3.07 (br s, 4H), 2.63-2.54 (m, 1H), 2.63-2.54 (m, 2H), 2.14-1.98 (m, 6H), 1.78 (br d, J=11.2 Hz, 2H), 1.41-1.28 (m, 3H), 1.00 (br d, J=6.4 Hz, 4H), 0.91 (br s, 2H).

Step 4-5: preparation of 2-[[6-[[5-chloro-2-[4-[3-[(2R,6S)-4-[2-(2,6-dioxo-3-piperidyl)-1,3-dioxo-isoindolin-5-yl]-2,6-dimethyl-piperazin-1-yl]cyclobutoxy]-1-piperidyl]pyrimidin-4-yl]amino]-1-isopropyl-2-oxo-3-quinolyl]oxy]-N-methyl-acetamide

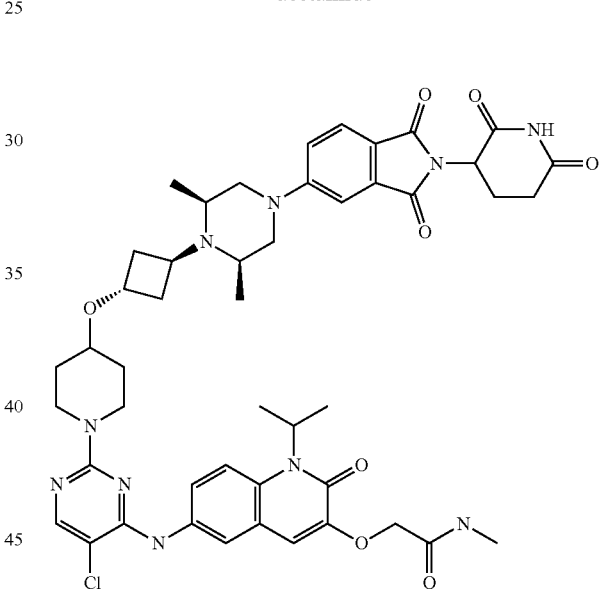

The title compound was prepared analogously to compound 163 following steps 17-18 from the material made in step 3 of this Example. The crude product was purified by prep-HPLC (column: Unisil 3-100 C18 Ultra 150*50 mm*3 um; mobile phase: [water (FA)-ACN]; B %: 11%-41%, 15 min) to afford 2-[[6-[[5-chloro-2-[4-[3-[(2R,6S)-4-[2-(2,6-dioxo-3-piperidyl)-1,3-dioxo-isoindolin-5-yl]-2,6-dimethyl-piperazin-1-yl]cyclobutoxy]-1-piperidyl]pyrimidin-4-yl]amino]-1-isopropyl-2-oxo-3-quinolyl]oxy]-N-methyl-acetamide formate (170.2 mg, 29%) as a yellow solid. $^1$H NMR (400 MHz, DMSO-d$_6$) δ 11.08 (s, 1H), 8.83 (s, 1H), 8.23 (s, 1H), 8.05 (s, 1H), 7.99-7.94 (m, 2H), 7.69 (s, 2H), 7.64 (d, J=8.5 Hz, 1H), 7.23-7.17 (m, 1H), 7.10 (dd, J=2.0, 8.8 Hz, 1H), 7.02 (s, 1H), 5.32 (br s, 1H), 5.06 (dd, J=5.6, 12.8 Hz, 1H), 4.55 (s, 2H), 4.14 (br d, J=14.8 Hz, 3H), 3.70 (br d, J=7.6 Hz, 1H), 3.62 (br dd, J=4.4, 12.8 Hz, 2H), 3.44 (br d, J=10.0 Hz, 1H), 3.37-3.30 (m, 2H), 3.26-3.18 (m, 3H), 3.10-3.04 (m, 2H), 3.02-2.97 (m, 1H), 2.93-2.83 (m, 1H), 2.68 (d, J=4.4 Hz, 3H), 2.58-2.54 (m, 1H), 2.17-1.98 (m, 4H), 1.84 (br d, J=10.0 Hz, 2H), 1.57 (d, J=6.8 Hz, 6H), 1.39 (br d, J=9.6 Hz, 2H), 1.00 (d, J=6.4 Hz, 4H), 0.92 (d, J=6.4 Hz, 2H); MS (ESI) m/z: 924.49 [M+1]⁺.

Using the procedure above and conditions found elsewhere in this application, the skilled artisan can prepare the following compounds: Compound 249, Compound 250, Compound 253, and Compound 254.

Example 60: Preparation of 2-({6-[(5-chloro-2-{4-[(1r,3r)-3-{4-[2-(2,6-dioxopiperidin-3-yl)-1,3-dioxoisoindol-5-yl]-4-hydroxypiperidin-1-yl}cyclobutoxy]piperidin-1-yl}pyrimidin-4-yl)amino]-1-isopropyl-2-oxoquinolin-3-yl}oxy)-N-methylacetamide (Compound 275)

Step 1: preparation of 1,2-dimethyl 4-[1-(tert-butoxycarbonyl)-3,6-dihydro-2H-pyridin-4-yl]phthalate

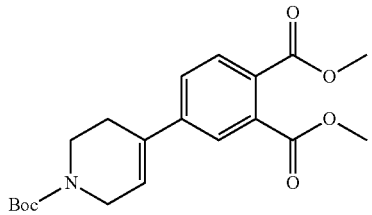 [SMILES: COC(=O)c1ccc(C2=CCN(C(=O)OC(C)(C)C)CC2)cc1C(=O)OC]

Into a 100 mL round-bottom flask was added 1,2-dimethyl 4-bromophthalate (4.5 g, 16.5 mmol, 1 equiv), tert-butyl 4-(4,4,5,5-tetramethyl-1,3,2-dioxaborolan-2-yl)-3,6-dihydro-2H-pyridine-1-carboxylate (6.11 g, 19.8 mmol, 1.2 equiv), 1,1'-bis(di-tert-butylphosphino)ferrocene palladium dichloride (1.07 g, 1.6 mmol, 0.1 equiv), Cs₂CO₃ (16.11 g, 49.4 mmol, 3 equiv), dioxane (50 mL) and H₂O (10 mL) at room temperature. The resulting mixture was stirred for 3 hours at 100° C. under nitrogen atmosphere. The mixture was allowed to cool down to room temperature. The reaction was quenched by the addition of water (50 mL), extracted with EtOAc (2×50 mL). The combined organic layers were washed with brine (2×50 mL), dried over anhydrous Na₂SO₄. After filtration, the filtrate was concentrated under reduced pressure. The residue was purified by reverse flash chromatography (column, silica gel; mobile phase, MeCN in water, 10% to 50% gradient in 60 min; detector, UV 254 nm) to afford 1,2-dimethyl 4-[1-(tert-butoxycarbonyl)-3,6-dihydro-2H-pyridin-4-yl]phthalate (5 g, 81%) as an off-white oil. MS (ES⁺): m/z 294.2 [MH⁺].

Step 2: preparation of 1,2-dimethyl 4-[1-(tert-butoxycarbonyl)-4-hydroxypiperidin-4-yl]phthalate

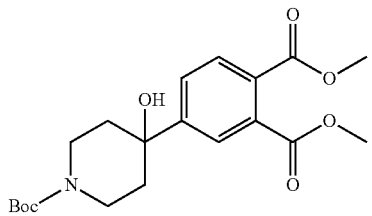 [SMILES: COC(=O)c1ccc(C2(O)CCN(C(=O)OC(C)(C)C)CC2)cc1C(=O)OC]

Into a 100 mL round-bottom flask was added 1,2-dimethyl 4-[1-(tert-butoxycarbonyl)-3,6-dihydro-2H-pyridin-4-yl]phthalate (100 mg, 0.3 mmol, 1.0 equiv), phenylsilane (5 mL) and i-PrOH (7 mL) at 0° C. The resulting mixture was stirred for 15 min at 0° C. under O₂ atmosphere. Then added tris(2,2,6,6-tetramethyl-3,5-heptanedionato)manganese(III) (3 mg, 0.005 mmol, 0.02 equiv) at 0° C. under O₂ atmosphere. The mixture was allowed to warm to room temperature, diluted with water (50 mL) and extracted with CH₂Cl₂ (2×50 mL). The combined organic layers were washed with brine (2×50 mL), dried over anhydrous Na₂SO₄. After filtration, the filtrate was concentrated under reduced pressure. The residue was purified by silica gel column chromatography (PE/EA=3:1) to afford 1,2-dimethyl 4-[1-(tert-butoxycarbonyl)-4-hydroxypiperidin-4-yl]phthalate (63 mg, 60%) as an off-white oil. MS (ESI): m/z 416.5 [MH⁺].

Step 3: preparation of 1,2-dimethyl 4-(4-hydroxypiperidin-4-yl) phthalate

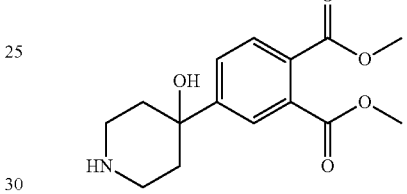

To 1,2-dimethyl 4-[1-(tert-butoxycarbonyl)-4-hydroxypiperidin-4-yl]phthalate (500 mg, 1.271 mmol, 1.0 equiv) in DCM (5 mL) was added TFA (2 mL) at room temperature. The resulting mixture was stirred for 2 hours, then concentrated under reduced pressure to afford 1,2-dimethyl 4-(4-hydroxypiperidin-4-yl) phthalate trifluoroacetic acid (346 mg, 93%) as a yellow oil. MS (ES⁻): m/z 294.3 [MH⁻].

Step 4: preparation of tert-butyl 7-[2-(2,6-dioxopiperidin-3-yl)-3-oxo-1H-isoindol-5-yl]-7-azaspiro[3.5]nonane-2-carboxylate

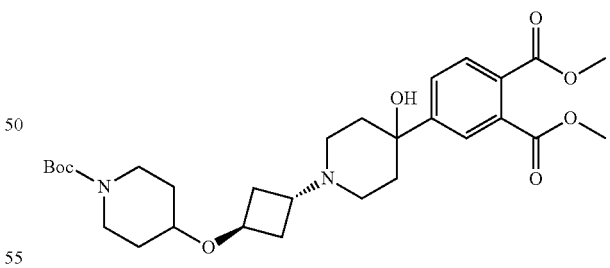

Into a 100 mL round-bottom flask was added 1,2-dimethyl 4-(1,2,3,6-tetrahydropyridin-4-yl)phthalate (456 mg, 1.7 mmol, 1.0 equiv), DIEA (642 mg, 5.0 mmol, 3 equiv) and MeCN (25 mL) at room temperature. The resulting mixture was stirred for 15 min under nitrogen atmosphere. Then added tert-butyl 4-[(1s,3s)-3-(trifluoromethanesulfonyloxy)cyclobutoxy]piperidine-1-carboxylate (668 mg, 1.7 mmol, 1.0 equiv) at 30° C. under nitrogen atmosphere. The reaction was quenched by the addition of sat. NaCl (aq.) (50 mL). The resulting mixture was extracted with CH₂Cl₂ (2×50 mL). The combined organic layers were washed with brine (2×50 mL), dried over anhydrous Na₂SO₄. After filtration, the filtrate was concentrated under reduced pressure. The residue was purified by Prep-TLC (CH₂Cl₂/PE 1:1) to afford 1,2-dimethyl 4-{1-[(1r,3r)-3-{[1-(tert-butoxycarbonyl)piperidin-4-yl]oxy}cyclobutyl]-3,6-dihydro-2H-pyridin-4-yl}phthalate) (348 mg, 38%) as an off-white solid. MS (ESI): m/z 547.1 [MH⁺].

Step 5: preparation of 4-{4-hydroxy-1-[(1r,3r)-3-{[1-(tert-butoxycarbonyl)piperidin-4-yl]oxy}cyclobutyl]piperidin-4-yl}benzene-1,2-dicarboxylic acid

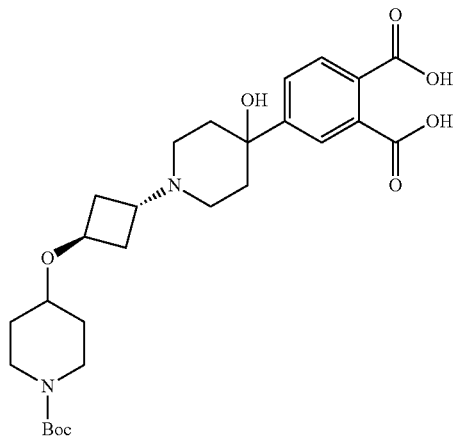 [SMILES: CC(C)(C)OC(=O)N1CCC(O[C@H]2C[C@H](N3CCC(O)(c4ccc(C(=O)O)c(C(=O)O)c4)CC3)C2)CC1]

Into a 100 mL round-bottom flask was added 1,2-dimethyl 4-{4-hydroxy-1-[(1r,3r)-3-{[1-(tert-butoxycarbonyl)piperidin-4-yl]oxy}cyclobutyl]piperidin-4-yl}phthalate (570 mg, 1.0 mmol, 1.0 equiv) and H₂O (38 mL) at room temperature. The resulting mixture was stirred overnight at 50° C. The reaction was acidified to pH 6-7 with HCl. The resulting mixture was concentrated under reduced pressure to afford 4-{4-hydroxy-1-[(1r,3r)-3-{[1-(tert-butoxycarbonyl)piperidin-4-yl]oxy}cyclobutyl]piperidin-4-yl}benzene-1,2-dicarboxylic acid (500 mg, 92%) as an off-white solid. MS (ESI): m/z 519.3 [MH⁺].

Step 6-8: preparation of 2-({6-[(5-chloro-2-{4-[(1r,3r)-3-{4-[2-(2,6-dioxopiperidin-3-yl)-1,3-dioxoisoindol-5-yl]-4-hydroxypiperidin-1-yl}cyclobutoxy]piperidin-1-yl}pyrimidin-4-yl)amino]-1-isopropyl-2-oxoquinolin-3-yl}oxy)-N-methylacetamide

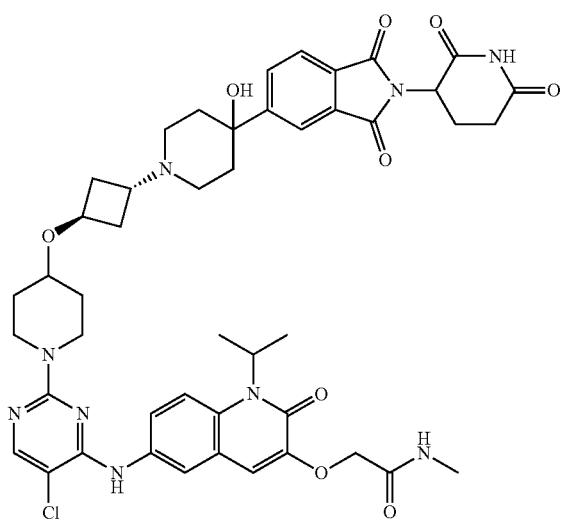

The title compound was prepared analogously to Compound 159 following steps 8-10 using the material made in step 5 of this Example. The residue was purified by reverse flash chromatography (column, silica gel; mobile phase, MeCN in water, 10% to 80% gradient in 40 min; detector, UV 254 nm) to afford 2-({6-[(5-chloro-2-{4-[(1r,3r)-3-{4-[2-(2,6-dioxopiperidin-3-yl)-1,3-dioxoisoindol-5-yl]-4-hydroxypiperidin-1-yl}cyclobutoxy]piperidin-1-yl}pyrimidin-4-yl)amino]-1-isopropyl-2-oxoquinolin-3-yl}oxy)-N-methylacetamide (83.39 mg, 45%) as an off-white solid. MS (ESI): m/z 456.2 [MH⁺]; ¹H NMR (400 MHz, DMSO-d6) δ 11.12 (s, 1H), 8.84 (s, 1H), 8.04 (s, 1H), 8.01-7.93 (m, 4H), 7.88 (m, 1H), 7.69 (m, 2H), 7.02 (s, 1H), 5.33 (s, 1H), 5.15 (m, 1H), 4.55 (s, 2H), 4.21 (m, 1H), 4.12 (m, 2H), 3.54 (m, 1H), 3.23 (m, 2H), 2.90 (m, 2H), 2.78 (s, 2H), 2.68 (s, 3H), 2.65-2.51 (m, 2H), 2.23 (s, 4H), 2.11-2.01 (m, 5H), 1.87-1.78 (m, 2H), 1.70 (m, 2H), 1.65 (m, 7H), 1.38 (m, 2H).

The following compound can be prepared in an analogous manner: Compound 277.

Example 61: Preparation of tert-butyl 4-[(1r,3r)-3-{4-[2-(2,6-dioxopiperidin-3-yl)-1,3-dioxoisoindol-5-yl]-4-hydroxypiperidin-1-yl}cyclobutoxy]piperidine-1-carboxylate (Compound 276)

Step 1: preparation of 1,2-dimethyl 4-[1-(tert-butoxycarbonyl)-4-fluoropiperidin-4-yl]phthalate

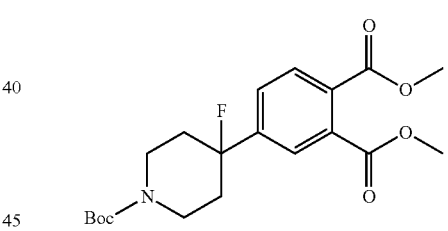

Into a 100 mL 3-necked round-bottom flask was added 1,2-dimethyl 4-[1-(tert-butoxycarbonyl)-4-hydroxypiperidin-4-yl]phthalate (prepared in Step 2 of Example 60, 1.4 g, 3.6 mmol, 1.0 equiv) and DCM (25 mL) at −78° C. The resulting mixture was stirred for 15 minutes at −78° C. under nitrogen atmosphere. Then added DAST (1.72 g, 10.7 mmol, 3.0 equiv) at −78° C. under nitrogen atmosphere. The mixture was allowed to warm to room temperature. The reaction was quenched by the addition of sat. NaCl (aq.) (50 mL). The resulting mixture was extracted with CH₂Cl₂ (2×50 mL). The combined organic layers were washed with brine (2×50 mL), dried over anhydrous Na₂SO₄. After filtration, the filtrate was concentrated under reduced pressure to afford 1,2-dimethyl 4-[1-(tert-butoxycarbonyl)-4-fluoropiperidin-4-yl]phthalate (1.2 g, 85%) as a yellow oil. MS (ESI): m/z 416.1 [MH⁺].

Step 2-7: preparation of tert-butyl 4-[(1r,3r)-3-{4-[2-(2,6-dioxopiperidin-3-yl)-1,3-dioxoisoindol-5-yl]-4-hydroxypiperidin-1-yl}cyclobutoxy]piperidine-1-carboxylate

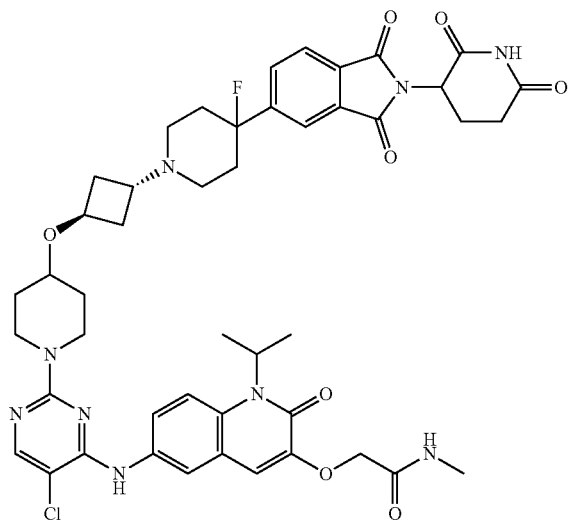 [SMILES: CNC(=O)COc1cc2cc(Nc3nc(N4CCC(O[C@H]5C[C@H](N6CCC(F)(c7ccc8c(c7)C(=O)N(C7CCC(=O)NC7=O)C8=O)CC6)C5)CC4)ncc3Cl)ccc2n(C(C)C)c1=O]

The title compound was prepared analogously to Example 60 following steps 3-8 using the material from step 1 in this Example. The crude material was purified by reverse flash chromatography (column, silica gel; mobile phase, MeCN in water, 10% to 80% gradient in 40 min; detector, UV 254 nm) to afford 2-({6-[(5-chloro-2-{4-[(1r,3r)-3-{4-[2-(2,6-dioxopiperidin-3-yl)-1,3-dioxoisoindol-5-yl]-4-fluoropiperidin-1-yl}cyclobutoxy]piperidin-1-yl}pyrimidin-4-yl)amino]-1-isopropyl-2-oxoquinolin-3-yl}oxy)-N-methylacetamide (54.6 mg, 33%) as a white solid. $^1$H NMR (400 MHz, DMSO-d6) δ 11.13 (s, 1H), 8.83 (s, 1H), 8.04 (s, 7H), 7.69 (m, 1H), 6.31 (s, 1H), 6.16 (m, 1H), 4.54 (s, 2H), 4.12 (m, 3H), 3.52 (m, 1H), 3.23 (m, 2H), 2.87 (m, 3H), 2.81 (m, 2H), 2.71 (m, 4H), 2.25 (m, 5H), 2.05 (s, 6H), 1.83 (m, 2H), 1.57 (m, 9H), 1.39 (s, 3H), 1.23 (s, 1H); MS (ES+): m/z 910.5 [MH$^+$].

The following compound can be prepared in an analogous manner: Compound 278.

Example 62: Preparation of 3-[4-([1-[5-chloro-4-([1-isopropyl-3-[(methylcarbamoyl)methoxy]-2-oxoquinolin-6-yl]amino)pyrimidin-2-yl]piperidin-4-yl]methyl)piperazin-1-yl]-N-(2,6-dioxopiperidin-3-yl)-2-fluoro-5-methoxybenzamide (Compound 280)

Step 1: preparation of tert-butyl 6-(4,4,5,5-tetramethyl-1,3,2-dioxaborolan-2-yl)-3-azabicyclo[4.1.0]heptane-3-carboxylate

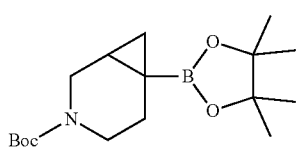 [SMILES: CC(C)(C)OC(=O)N1CCC2(B3OC(C)(C)C(C)(C)O3)CC2C1]

ZnEt$_2$ (15.98 g, 129.4 mmol, 8 equiv) was suspended in DCM (200 mL) at −40° C. under N$_2$ atmosphere. To the above mixture was dropwise added CH$_2$I$_2$ (69.30 g, 258.7 mmol, 16 equiv) at −40° C. The resulting mixture was stirred for 1 hour at −40° C. Then TFA (14.75 g, 129.4 mmol, 8 equiv) in DCM (30 mL) was dropwise added at −40° C., stirred for 1 hour at −15° C. Lastly, tert-butyl 4-(4,4,5,5-tetramethyl-1,3,2-dioxaborolan-2-yl)-3,6-dihydro-2H-pyridine-1-carboxylate (5 g, 16.2 mmol, 1 equiv) was added dropwise at −15° C. The resulting mixture was stirred overnight at room temperature, then concentrated under reduced pressure. To the above residue was added THF (200 mL) and Boc$_2$O (17.65 g, 80.9 mmol, 5 equiv) and DMAP (0.49 g, 4.0 mmol, 0.25 equiv) at room temperature. The resulting mixture was stirred for 1 h at room temperature, then diluted with water, extracted with EtOAc (3×10 mL). The combined organic layers were washed with NaHCO$_3$ (3×10 mL), dried over anhydrous Na$_2$SO$_4$. After filtration, the filtrate was concentrated under reduced pressure. The residue was diluted with THF:H2O=2:1 (100 mL). The resulting mixture was stirred for 30 min at room temperature, then extracted with EtOAc (3×10 mL). The combined organic layers were washed with brine (3×10 mL), dried over anhydrous Na$_2$SO$_4$. After filtration, the filtrate was concentrated under reduced pressure. The residue was purified by silica gel column chromatography (PE/EA=10:1) to afford tert-butyl 6-(4,4,5,5-tetramethyl-1,3,2-dioxaborolan-2-yl)-3-azabicyclo[4.1.0]heptane-3-carboxylate (1.5 g, 29%) as a white solid. MS (ES$^+$): m/z 324.35 [MH$^+$].

Step 2: preparation of tert-butyl 6-(trifluoro-lambda4-boranyl)-3-azabicyclo[4.1.0]heptane-3-carboxylate potassium

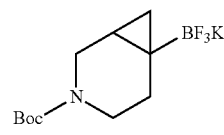

To a stirred solution of tert-butyl 6-(4,4,5,5-tetramethyl-1,3,2-dioxaborolan-2-yl)-3-azabicyclo[4.1.0]heptane-3-carboxylate (2 g, 6.2 mmol, 1 equiv) in MeOH (10 mL) was added potassium hydrogen fluoride (1933.00 mg, 24.7 mmol, 4 equiv) at room temperature. The resulting mixture was stirred for 2 hours, then concentrated under vacuum. The residue was diluted with ACN, stirred for 2 hours at 70° C. The resulting mixture was filtered at 70° C., the filter cake was washed with ACN (3×10 mL). The filtrate was concentrated under reduced pressure to afford tert-butyl 6-(trifluoro-lambda4-boranyl)-3-azabicyclo[4.1.0]heptane-3-carboxylate potassium (830 mg, 44%) as a yellow solid. MS (ES$^+$): m/z 304.35 [MH$^+$].

Step 3: preparation of 1,2-dimethyl 4-[3-(tert-butoxycarbonyl)-3-azabicyclo[4.1.0]heptan-6-yl]phthalate

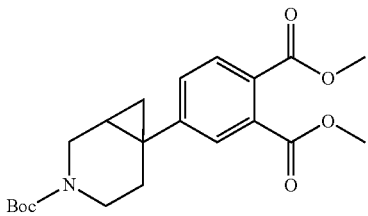 [SMILES: COC(=O)c1ccc(C23CCN(C(=O)OC(C)(C)C)CC2C3)cc1C(=O)OC]

To a stirred mixture of tert-butyl 6-(trifluoro-lambda4-boranyl)-3-azabicyclo[4.1.0]heptane-3-carboxylate potassium (770 mg, 2.5 mmol, 1 equiv) and 1,2-dimethyl 4-bromophthalate (693.58 mg, 2.5 mmol, 1 equiv) in toluene (10 mL) and water (1 mL) was added $Cs_2CO_3$ (2482.57 mg, 7.6 mmol, 3 equiv) and Mesylate[(di(1-adamantyl)-n-butylphosphine)-2-(2'-amino-1,1'-biphenyl)]palladium(II) (92.49 mg, 0.1 mmol, 0.05 equiv). The resulting mixture was stirred for 4 hours at 90° C. under nitrogen atmosphere. The resulting mixture was extracted with $CH_2Cl_2$ (3×10 mL). The combined organic layers were washed with brine (3×10 mL), dried over anhydrous $Na_2SO_4$. After filtration, the filtrate was concentrated under reduced pressure. The residue was purified by reverse flash chromatography (column, silica gel; mobile phase, MeCN in water, 10% to 50% gradient in 10 min; detector, UV 254 nm) to afford 1,2-dimethyl 4-[3-(tert-butoxycarbonyl)-3-azabicyclo[4.1.0]heptan-6-yl]phthalate (450 mg, 45%) as a brown oil. MS (ES$^+$): m/z 390.25 [MH$^+$].

Step 4: preparation of 1,2-dimethyl 4-{3-azabicyclo[4.1.0]heptan-6-yl}phthalate

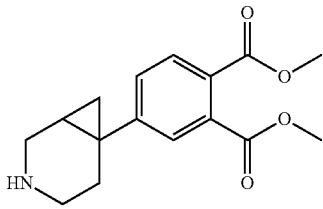 [SMILES: COC(=O)c1ccc(C23CCNCC2C3)cc1C(=O)OC]

A mixture of 1,2-dimethyl 4-[3-(tert-butoxycarbonyl)-3-azabicyclo[4.1.0]heptan-6-yl]phthalate (650 mg, 1.7 mmol, 1 equiv) and trifluoroacetaldehyde (3 mL, 0.005 mmol, 0.10 equiv) in DCM (3 mL) was stirred for 2 hours at room temperature. The solution pH was adjusted to 8 with saturated $NaHCO_3$ (aq.). The resulting mixture was extracted with $CH_2Cl_2$ (3×10 mL). The combined organic layers were washed with brine (3×10 mL), dried over anhydrous Na2SO4, filtered and concentrated under reduced pressure to afford 1,2-dimethyl 4-{3-azabicyclo[4.1.0]heptan-6-yl}phthalate (482 mg, 100%) as a brown oil. MS (ESI): m/z 290.35 [MH$^+$].

Step 5-9: preparation of 3-[4-([1-[5-chloro-4-([1-isopropyl-3-[(methylcarbamoyl)methoxy]-2-oxoquinolin-6-yl]amino)pyrimidin-2-yl]piperidin-4-yl]methyl)piperazin-1-yl]-N-(2,6-dioxopiperidin-3-yl)-2-fluoro-5-methoxybenzamide

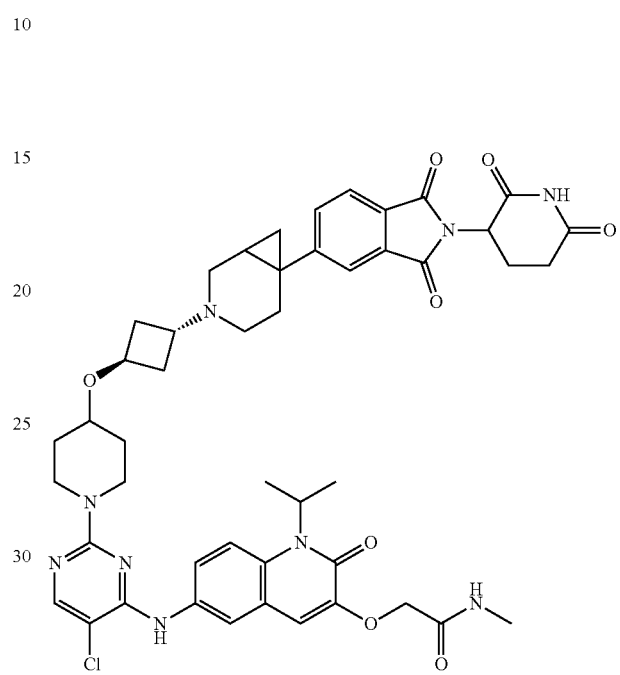

The title compound was prepared analogously to Compound 159 following steps 6-10 with the material made in step 4 of this Example. The crude product was purified by reverse flash chromatography (column, C18 silica gel; mobile phase, $CH_3CN$/water (10 mmol/L $NH_4HCO_3$), 0% to 55% gradient in 30 min; detector, UV 254 nm) To afford 3-[4-([1-[5-chloro-4-([1-isopropyl-3-[(methylcarbamoyl)methoxy]-2-oxoquinolin-6-yl]amino)pyrimidin-2-yl]piperidin-4-yl]methyl)piperazin-1-yl]-N-(2,6-dioxopiperidin-3-yl)-2-fluoro-5-methoxybenzamide (73.3 mg) as off-white solid. $^1$H NMR (400 MHz, DMSO-d6) δ 11.13 (s, 1H), 8.84 (s, 1H), 8.04 (s, 1H), 7.96 (d, J=10.8 Hz, 2H), 7.83 (d, J=7.8 Hz, 1H), 7.76-7.66 (m, 4H), 7.02 (s, 1H), 5.14 (dd, J=12.9, 5.3 Hz, 1H), 4.54 (s, 2H), 4.19-4.08 (m, 3H), 3.51 (s, 3H), 3.22 (t, J=11.5 Hz, 1H), 2.88 (d, J=13.6 Hz, 1H), 2.75 (s, 3H), 2.67 (d, J=4.6 Hz, 2H), 2.63-2.52 (m, 4H), 2.21 (s, 1H), 2.12 (s, 4H), 1.97 (s, 2H), 1.81 (s, 2H), 1.57 (d, J=6.9 Hz, 7H), 1.37 (d, J=11.0 Hz, 2H), 1.05 (s, 1H), 1.06-0.96 (m, 2H). MS (ESI): m/z 906.35 [MH$^+$].

The following compound can be prepared in an analogous manner: Compound 283.

Example 63: Synthesis of 2-({6-[(5-chloro-2-{4-[(1r,3r)-3-[(3R)-4-{4-chloro-2-[(3S)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide (Compound 267) and 2-({6-[(5-chloro-2-{4-[(1r,3r)-3-[(3R)-4-{4-chloro-2-[(3R)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide (Compound 268)

Step 1: preparation of tert-butyl (3R)-4-[3-cyano-4-(methoxycarbonyl)phenyl]-3-methylpiperazine-1-carboxylate

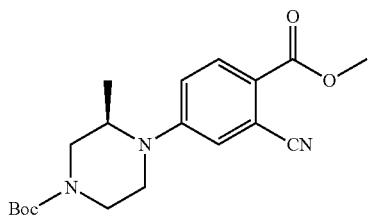 [SMILES: COC(=O)c1ccc(N2CCN(C(=O)OC(C)(C)C)C[C@H]2C)cc1C#N]

To a stirred solution of tert-butyl (3R)-3-methylpiperazine-1-carboxylate (26.5 g, 132.3 mmol, 1 equiv) and methyl 4-bromo-2-cyanobenzoate (28.59 g, 119.1 mmol, 0.9 equiv) in 1,4-dioxane (300 mL) was added Cs$_2$CO$_3$ (129.33 g, 396.9 mmol, 3 equiv) and RuPhos Pd G4 (8.85 g, 10.6 mmol, 0.08 equiv), the reaction mixture was stirred at 90° C. under nitrogen atmosphere overnight. The mixture was allowed to cool down to room temperature, diluted with water. The resulting mixture was extracted with EtOAc (3×200 mL). The combined organic layers were washed with brine (2×50 mL), dried over anhydrous Na$_2$SO$_4$, filtered, and concentrated in vacuo. The residue was purified by silica gel column chromatography (PE/EA=5:1) to afford tert-butyl (3R)-4-[3-cyano-4-(methoxycarbonyl)phenyl]-3-methylpiperazine-1-carboxylate (28.7 g, 60%) as a yellow solid. MS (ESI): m/z 304.15 [MH$^+$].

Step 2: preparation of tert-butyl (3R)-4-[3-formyl-4-(methoxycarbonyl)phenyl]-3-methylpiperazine-1-carboxylate

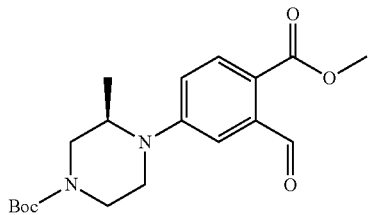 [SMILES: COC(=O)c1ccc(N2CCN(C(=O)OC(C)(C)C)C[C@H]2C)cc1C=O]

To a stirred solution of tert-butyl (3R)-4-[3-cyano-4-(methoxycarbonyl)phenyl]-3-methylpiperazine-1-carboxylate (28.7 g, 79.9 mmol, 1 equiv) and NaH$_2$PO$_4$ (47.90 g, 399.3 mmol, 5 equiv) in 200 mL AcOH/H$_2$O/pyridine (1/1/2) was added Raney Ni (20.52 g, 239.6 mmol, 3 equiv). The resulting mixture was stirred overnight at 50° C. under nitrogen atmosphere, then concentrated under vacuum. The resulting mixture was extracted with EtOAc (3×200 mL). The combined organic layers were washed with brine (2×50 mL), dried over Na$_2$SO$_4$, filtered, and concentrated under reduced pressure. The residue was purified by silica gel column chromatography (PE/EA=1:1) to afford tert-butyl (3R)-4-[3-formyl-4-(methoxycarbonyl)phenyl]-3-methylpiperazine-1-carboxylate (16.8 g, 58%) as a yellow solid. MS (ESI): m/z 363.20 [MH$^+$].

Step 3: preparation of tert-butyl (3R)-4-[2-chloro-3-formyl-4-(methoxycarbonyl)phenyl]-3-methylpiperazine-1-carboxylate

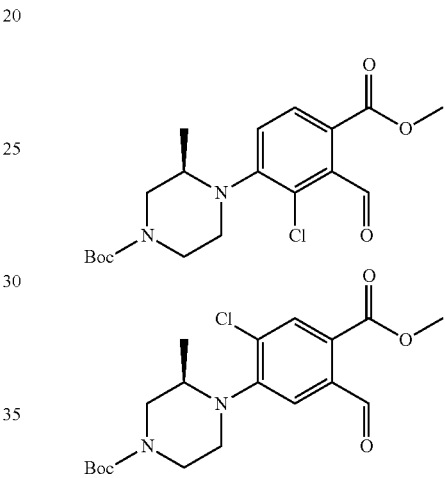

A solution of tert-butyl (3R)-4-[3-formyl-4-(methoxycarbonyl)phenyl]-3-methylpiperazine-1-carboxylate (16.8 g, 46.3 mmol, 1 equiv) and NCS (6.19 g, 46.4 mmol, 1.00 equiv) in acetonitrile (200 mL) was stirred overnight at 40° C. under nitrogen atmosphere. The resulting mixture was extracted with EtOAc (3×150 mL). The combined organic layers were washed with brine (2×40 mL), dried over anhydrous Na$_2$SO$_4$, filtered and concentrated under reduced pressure. The residue was purified by silica gel column chromatography (PE/EA=2:1) to afford two regioisomers. tert-butyl (3R)-4-[2-chloro-3-formyl-4-(methoxycarbonyl)phenyl]-3-methylpiperazine-1-carboxylate (10 g, 54%) was obtained as an off-white solid. MS (ESI): m/z 397.10 [MH$^+$]. $^1$H NMR (300 MHz, DMSO-d$_6$) δ 10.35 (s, 1H), 7.86-7.69 (m, 1H), 7.44 (d, J=8.5 Hz, 1H), 3.99-3.76 (m, 3H), 3.67-3.48 (m, 3H), 3.40 (s, 1H), 3.32 (s, 1H), 2.78-2.67 (m, 1H), 1.43 (s, 9H), 0.88 (d, J=6.1 Hz, 3H). tert-butyl (3R)-4-(2-chloro-5-formyl-4-(methoxycarbonyl)phenyl)-3-methylpiperazine-1-carboxylate (5.3 g, 29%) was obtained as an off-white solid. MS (ESI): m/z 397.05 [MH$^+$]. $^1$H NMR (300 MHz, DMSO-d$_6$) δ 10.40 (s, 1H), 7.93 (s, 1H), 7.50 (s, 1H), 3.88 (s, 3H), 3.79-3.64 (m, 2H), 3.62-3.46 (m, 2H), 3.36-3.19 (m, 1H), 2.80 (m, 1H), 1.43 (s, 9H), 0.88 (d, J=6.4 Hz, 3H).

Step 4: preparation of tert-butyl (3R)-4-{2-[(1S)-4-(tert-butoxy)-1-carbamoyl-4-oxobutyl]-4-chloro-1-oxo-3H-isoindol-5-yl}-3-methylpiperazine-1-carboxylate

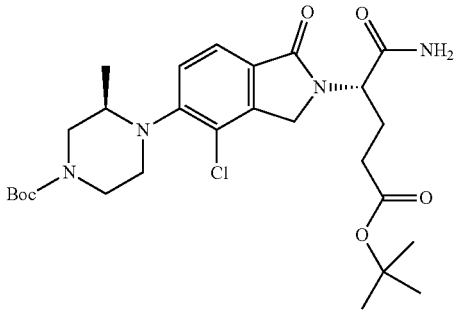 [SMILES: C[C@@H]1CN(C(=O)OC(C)(C)C)CCN1c1ccc2c(c1Cl)CN([C@@H](CCC(=O)OC(C)(C)C)C(N)=O)C2=O]

A solution of tert-butyl (3R)-4-[2-chloro-3-formyl-4-(methoxycarbonyl)phenyl]-3-methylpiperazine-1-carboxylate (9.8 g, 24.7 mmol, 1 equiv) and tert-butyl (4S)-4-amino-4-carbamoylbutanoate (4.99 g, 24.7 mmol, 1 equiv) in DCE (120 mL) was stirred overnight at 50° C. under nitrogen atmosphere at room temperature. Then NaBH₃CN (4.66 g, 74.1 mmol, 3 equiv) was added, the resulting mixture was stirred for 3 hours at 50° C. under nitrogen atmosphere. The reaction mixture was quenched by water (100 mL). The aqueous layer was extracted with dichloromethane (100 mL). The organic phase was washed with brine (30 mL), dried over anhydrous sodium sulfate, and concentrated under reduced pressure. The residue was further purified by silica gel column chromatography (DCM/EA=1:2) to afford tert-butyl (3R)-4-{2-[(1S)-4-(tert-butoxy)-1-carbamoyl-4-oxobutyl]-4-chloro-1-oxo-3H-isoindol-5-yl}-3-methylpiperazine-1-carboxylate (10 g, 74%) as an off-white solid. MS (ESI): m/z 551.40 [MH⁺].

Step 5-8: preparation of 2-({6-[(5-chloro-2-{4-[(1r,3r)-3-[(3R)-4-{4-chloro-2-[(3S)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide and 2-({6-[(5-chloro-2-{4-[(1r,3r)-3-[(3R)-4-{4-chloro-2-[(3R)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide

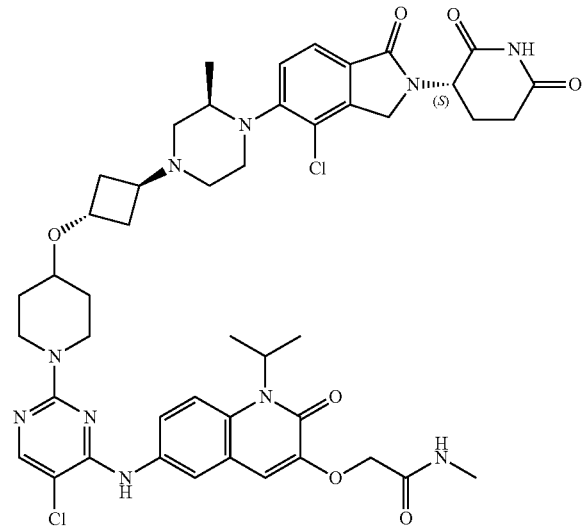

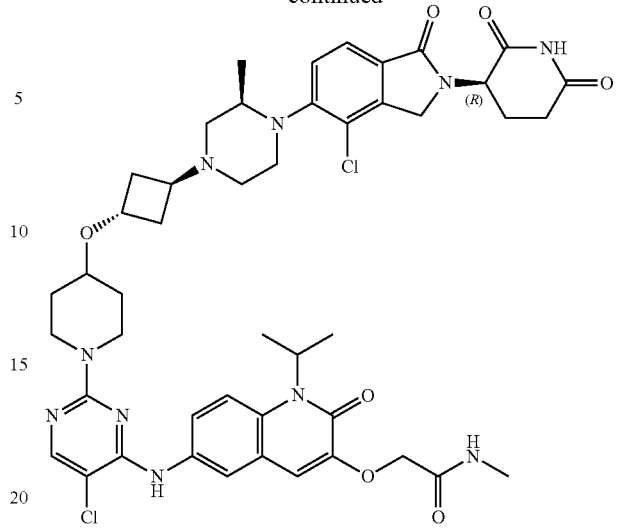

The title compounds were prepared analogously to Compound 211 following steps 5-8 using the material made in step 4 of this Example. The crude product was purified by reverse flash chromatography (column, C18 silica gel; mobile phase, THF in water, 45% to 65% gradient in 50 min; detector, UV 254 nm, then further separated by SFC (column: CHIRALPAK IH-3, 4.6*50 mm, 3 m; mobile phase B: IPA:DCM=1:1 (0.1% DEA); flow rate: 2 mL/min; gradient: isocratic 50% B; UV: 220 nm). 2-({6-[(5-chloro-2-{4-[(1r,3r)-3-[(3R)-4-{4-chloro-2-[(3S)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide (1 g, 21%) was obtained as a white solid. ¹H NMR (400 MHz, DMSO-d₆) δ 11.01 (s, 1H), 8.85 (s, 1H), 8.05 (s, 1H), 8.00-7.92 (m, 2H), 7.71-7.64 (m, 3H), 7.38 (d, J=8.2 Hz, 1H), 7.02 (s, 1H), 5.36-5.11 (m, 2H), 4.55 (s, 2H), 4.44 (d, J=17.6 Hz, 1H), 4.28-4.11 (m, 4H), 3.54 (s, 2H), 3.23 (m, 3H), 2.98-2.84 (m, 2H), 2.81-2.68 (m, 6H), 2.63-2.52 (m, 3H), 2.20-2.15 (m, 2H), 2.03-1.96 (m, 4H), 1.83 (d, J=12.1 Hz, 2H), 1.57 (d, J=6.9 Hz, 6H), 1.37 (d, J=13.8 Hz, 2H), 0.89 (d, J=6.1 Hz, 3H); MS (ESI): m/z 929.40 [MH⁺]. 2-({6-[(5-chloro-2-{4-[(1r,3r)-3-[(3R)-4-{4-chloro-2-[(3R)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide (0.8 g, 16%) was obtained as a white solid. ¹H NMR (400 MHz, DMSO-d₆) δ 11.01 (s, 1H), 8.85 (s, 1H), 8.05 (s, 1H), 8.01-7.92 (m, 2H), 7.74-7.64 (m, 3H), 7.38 (d, J=8.2 Hz, 1H), 7.02 (s, 1H), 5.27 (m, 1H), 5.11 (m, 1H), 4.55 (s, 2H), 4.43 (d, J=17.6 Hz, 1H), 4.27-4.12 (m, 4H), 3.58-3.50 (m, 2H), 3.28-3.18 (m, 3H), 2.91 (m, 2H), 2.82-2.68 (m, 6H), 2.63-2.54 (m, 3H), 2.45-2.16 (m, 2H), 2.03-1.95 (m, 6H), 1.83-1.57 (m, 6H), 1.44-1.37 (m, 2H), 0.89 (d, J=6.2 Hz, 3H). MS (ESI): m/z 929.35 [MH⁺].

Example 64: Synthesis of 2-({6-[(5-chloro-2-{4-[(1r,3r)-3-[(3R)-4-{6-chloro-2-[(3S)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide (Compound 269)

Step 1: preparation of tert-butyl (3R)-4-(2-chloro-5-formyl-4-(methoxycarbonyl)phenyl)-3-methylpiperazine-1-carboxylate

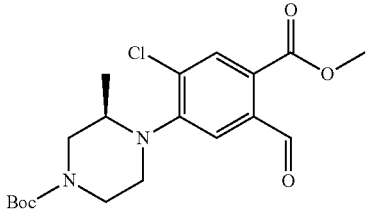 [SMILES: COC(=O)c1cc(Cl)c(N2CCN(C(=O)OC(C)(C)C)C[C@H]2C)cc1C=O]

The title compound was prepared as described in step 2 of Example 63.

Step 2-6: preparation of 2-({6-[(5-chloro-2-{4-[(1r,3r)-3-[(3R)-4-{6-chloro-2-[(3S)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide

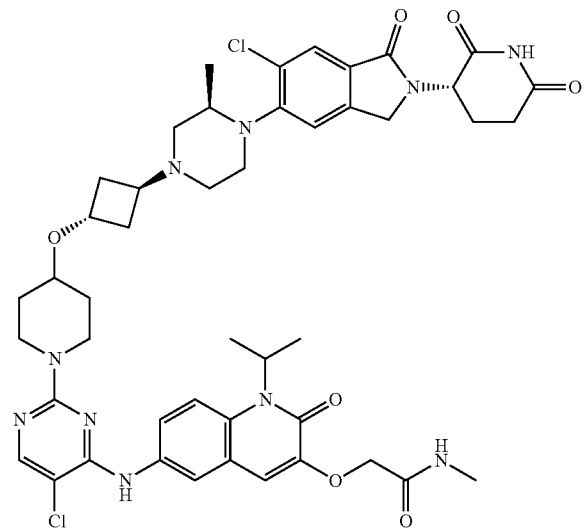 [SMILES: CNC(=O)COc1cc2cc(Nc3nc(N4CCC(O[C@H]5C[C@H](N6CCN(c7cc8c(cc7Cl)C(=O)N([C@H]7CCC(=O)NC7=O)C8)[C@H](C)C6)C5)CC4)ncc3Cl)ccc2n(C(C)C)c1=O]

The title compound was prepared analogously to Compound 211 following steps 4-8 using the material made in step 1 of this Example. The crude product was purified by reverse flash chromatography (column, C18 silica gel; mobile phase, MeCN in Water (10 mmol/L NH4HCO3), 10% to 80% gradient in 30 min; detector, UV 254/220 nm) to afford 2-({6-[(5-chloro-2-{4-[(1r,3r)-3-[(3R)-4-{6-chloro-2-[(3S)-2,6-dioxopiperidin-3-yl]-1-oxo-3H-isoindol-5-yl}-3-methylpiperazin-1-yl]cyclobutoxy]piperidin-1-yl}pyrimidin-4-yl)amino]-1-isopropyl-2-oxoquinolin-3-yl}oxy)-N-methylacetamide (38.1 mg, 21%) as a white solid. MS (ESI): m/z 928.36 [MH+]; $^1$H NMR (300 MHz, DMSO-$d_6$) δ 10.9 (s, 1H), 8.83 (s, 1H), 8.05 (s, 1H), 8.01-7.92 (m, 2H), 7.70 (m, 1H), 7.77-7.66 (m, 2H), 7.48 (m, 1H), 7.03 (s, 1H), 5.15 (s, 1H), 5.01 (m, 1H), 4.55 (s, 2H), 4.24 (m, 2H), 4.23-4.08 (m, 3H), 3.55 (s, 2H), 3.25 (s, 2H), 2.94-2.80 (m, 2H), 2.69 (m, 7H), 2.37 (s, 2H), 2.12 (m, 3H), 2.18-1.94 (m, 4H), 1.88-1.77 (m, 2H), 1.58 (m, 6H), 1.31 (m, 2H), 0.91 (m, 3H).

Example 65: Synthesis of 2-({6-[(5-chloro-2-{4-[(1r,3r)-3-{4-[2-(2,6-dioxopiperidin-3-yl)-4-fluoro-7-methyl-1-oxo-3H-isoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (Compound 296)

Step 1: preparation of tert-butyl 4-[2-fluoro-4-(methoxycarbonyl)-5-methylphenyl]piperazine-1-carboxylate

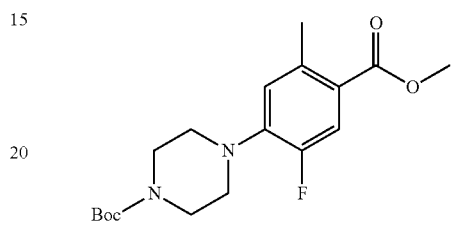

To a stirred solution of methyl 4-bromo-5-fluoro-2-methylbenzoate (3 g, 12.1 mmol, 1 equiv) and tert-butyl piperazine-1-carboxylate (2.26 g, 12.1 mmol, 1 equiv) in 1,4-dioxane (30 mL) were added RuPhos Pd G4 (1.02 g, 1.2 mmol, 0.1 equiv) and Cs$_2$CO$_3$ (11.87 g, 36.4 mmol, 3 equiv), then stirred overnight at 90° C. under nitrogen atmosphere. The mixture was allowed to cool down to room temperature, diluted with water. The resulting mixture was extracted with EtOAc (3×50 mL). The combined organic layers were washed with brine (2×20 mL), dried over anhydrous Na$_2$SO$_4$, filtered, and concentrated under reduced pressure. The residue was purified by silica gel column chromatography (PE/EA=1:1) to afford tert-butyl 4-[2-fluoro-4-(methoxycarbonyl)-5-methylphenyl]piperazine-1-carboxylate (3.5 g, 82%) as a yellow solid. MS (ESI): m/z 353.10 [MH+].

Step 2-10: preparation of 2-({6-[(5-chloro-2-{4-[(1r,3r)-3-{4-[2-(2,6-dioxopiperidin-3-yl)-4-fluoro-7-methyl-1-oxo-3H-isoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide

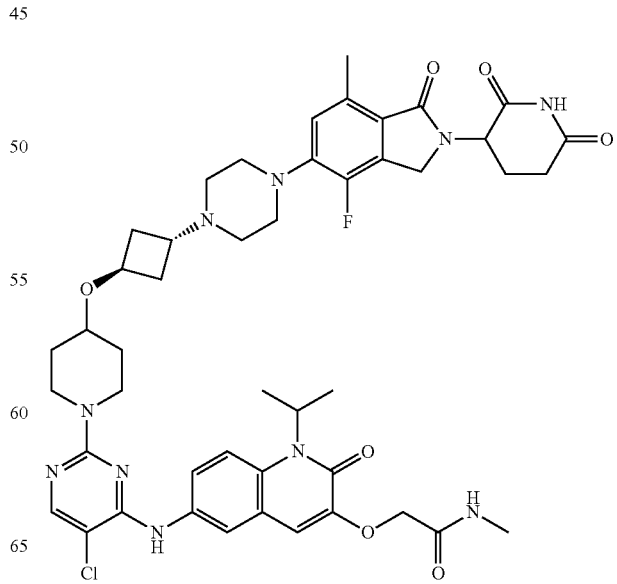

The title compound was prepared analogously to Compound 208 following steps 4-12 using the material made in step 1 of this Example. The crude product was purified by reverse flash chromatography (column, C18 silica gel; mobile phase, MeCN in water, 45% to 65% gradient in 30 min; detector, UV 254 nm) to afford 2-({6-[(5-chloro-2-{4-[(1r,3r)-3-{4-[2-(2,6-dioxopiperidin-3-yl)-4-fluoro-7-methyl-1-oxo-3H-isoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (53 mg, 28%) as an off-white solid. $^1$H NMR (400 MHz, DMSO-d$_6$) δ 10.98 (s, 1H), 8.85 (s, 1H), 8.04-7.97 (m, 3H), 7.71-7.67 (m, 2H), 7.02 (s, 1H), 6.89 (d, J=7.4 Hz, 1H), 5.31-5.03 (m, 2H), 4.55 (s, 2H), 4.40 (d, J=16.9 Hz, 1H), 4.24-4.12 (m, 4H), 3.51 (s, 1H), 3.21 (m, 2H), 3.13 (s, 3H), 2.85 (s, 2H), 2.68 (d, J=4.6 Hz, 3H), 2.60-2.54 (m, 3H), 2.44 (m, 4H), 2.18 (s, 2H), 1.98 (s, 3H), 1.85-1.75 (m, 2H), 1.57 (m, 6H), 1.38 (d, J=8.8 Hz, 2H), 1.23 (s, 1H), 0.91 (m, 1H); MS (ESI): m/z 913.50 [MH$^+$].

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

Specific Embodiments of the Present Disclosure

The present disclosure encompasses embodiments that may include features recited in other embodiments described herein. For example, where applicable, embodiments described herein may also include the features recited in any other embodiment (e.g., an embodiment that precedes or proceeds the embodiment) inclusively or in the alternative (e.g., an eighth embodiment may include the features recited in a first embodiment, as recited, and/or the features of any of the second through seventh embodiments). By way of further example, each of the articulated claims may also include the features recited in any of the other claims or embodiments described herein, except where the language indicates otherwise.

In certain embodiments, the description provides the following exemplary BCL6 bifunctional molecules (compounds of Tables 1-4 or compounds 1-431), including salts, prodrugs, polymorphs, analogs, derivatives, and deuterated forms thereof.

In any aspect or embodiment described herein, a bifunctional compound as described herein has at least one of: the PTM that is a PTM selected from a compound of Tables 1-4 (e.g., selected from exemplary compounds 1-431), the CLM that is a CLM selected from a compound of Tables 1-4 (e.g., selected from exemplary compounds 1-431), the L is a L selected from a compound of Tables 1-4 (e.g., selected from exemplary compounds 1-431), and combinations thereof.

EXAMPLES

Protein Synthesis. BCL6 protein was expressed by transforming Invitrogen One Shot cells with GS63525 pET24a-His-SUMO-TEV-BCLm-Avitag plasmid following manufacturer's instructions. In addition, biotin at a final concentration of 50 PM, and IPTG at a final concentration of 1 mM was added to the culture and incubated at room temperature shaking overnight.

BCL6 TR-FRET Protocol

Assay buffer A: 50 mM HEPES pH 7.5, 125 mM NaCl, 0.01% TritonX.

Assay buffer B (made fresh): buffer A+1 mM Glutathione (or 0.5 mM DTT).

Assay buffer C (made fresh): buffer B+0.03% BSA.

Black Proxy plates, 96 well.

15 µl final reaction volumes (BCoR-Cy5 100 nM, SA-Eu 2 nM, BCL6-avitag 2 nM).

134 µM BCL6-Avitag-Biotin stock: made fresh by adding 2 µl of BCL6-Avitag-Biotin to 31.5 ml Buffer C.

1 mM BCoR-Cy5 peptide (LifeTein) stock in Dimethylformamide (DMF).

300 nM BCoR-Cy5 working stock: made fresh by adding 4.5 µl of the 1 mM BCoR-Cy5 peptide stock to 15 ml Buffer B.

10 µM Eu-Streptavidin (Lance Eu-W1024 Streptavidin, PerkinElmer) stock solution.

6 nM Eu-Streptavidin working stock: made fresh by adding 9 µl Eu-Streptavidin stock solution to 15 ml Buffer A.

Compounds were diluted to 10 mM. Twenty microliters of DMSO was aliquoted to each well of the microtiter plates. From the 10 mM compound stock, 8.7 ul was aliquoted to the 20 ul DMSO and 3-fold serial dilutions (12 pt 3-0.01 uM titaration plate, 96 well, 100% DMSO) performed. Five ul from the titration plate wells was aliquoted to 45 ul Buff C (Intermediate dilution plates, 10% DMSO).

Spot 1.5 µl compound titrations to 384-well plates in duplicate, and spot 3.5 µl [8.5 nM] BCL6-bio protein to each well. The plate was mix briefly, centrifuged, and incubated for 30 minutes at room temperature.

Mix 14 mls of BCoR-Cy5 [300 nM] and 14 mls [6 nM] Eu-Streptavidin. Spot 10 µl BCoR-Cy5/SA-Eu (1:1) mix to each well. The plates were incubated for 2 hours and then read on an Envision plate reader.

Immunofluorescence Protocol for High Content Imaging of BCL6

T47D cells were seeded in 100 µl volume of RPMI1640-10% FBS in a 96-well black/clear bottom plates for adherent lines (Corning #3904).

Day 1. T47D breast cancer epithelial cells were seeded at a density so that confluence is ~70-90% at endpoint. Cells were seeded at 7K/0.1 ml/well the morning prior to the addition of exemplary bifunctional degradation compounds.

Compound Treatment

Day 2. Prepare an 11 point 3-fold serial dilution of exemplary bifunctional compound in DMSO and aliquot an appropriate volume to cell growth media to generate a 2× final concentration of exemplary bifunctional compound. Add an equal volume (0.1 ml) of 2× exemplary bifunctional compound/media mix to previously plated cells, for a final top concentration in aqueous cell growth media of 0.1 or 1 µM. Incubate for 3 days at 37° C., 5% $CO_2$.

Day 5 Immunofluorescence. Discard cell media. Wash wells with 200 µl of room temperature phosphate-buffered saline (PBS). Prepared 4% paraformaldehyde (PFA) from 16% PFA (Electron Microscopy Sciences #15710) using 1×PBS. Fifty µl of 4% PF was added to each well and incubate for 15 minutes at room temperature to fix the cells. The PFA was aspirated and the cells washed twice with PBS (200 µl)).

Prepared 0.1% Triton X-100 in PBS using 10% triton X-100 stock. The cells were permeabilized by adding 100 ul of the 0.1% Triton X-100 in PBS to each well to permeabilize cells and incubating at room temperature for 15 minutes. Cells were washed twice with PBS.

Prepared 3% BSA/PBS (from Thermofisher #37515 Blocker BSA in TBS, 10%), and 100 ul was added to each well. The cells were incubated for at least 1 hour at room temperature.

Prepared 1% BSA/PBS using Blocker BSA/PBS, and the 3% BSA/PBS removed from the wells.

For no primary antibody controls, 50 µl 1% BSA/PBS was added.

Primary antibody (BCL6 Rb Ab, CST-14895, Cell Signaling) was diluted 1:300 in 1% BSA/PBS using Blocker BSA/PBS.

Fifty µl of primary antibody added to all remaining wells (i.e., all wells other than the primary antibody controls) and the cells were incubated overnight at 4° C. with slow orbital movement.

Day 6. Contents of the wells was removed and the cells washed four times with 200 ul PBS. 1% BSA/PBS was prepared using Blocker BSA in PBS.

Diluted secondary antibody goat anti-Rb IgG Alexa-488 1:1000, and cell mask-Alexa-647 1:3000 in 1% BSA/PBS in the same mix. Add 50 µl to each well and incubate at room temperature for 1 hour in the dark.

Cells were washed three times with 200 ul PBS, and then incubated for 10 minutes with 100 ul Hoechst dye at 1 µg/mL (20 mM stock) to stain cell nuclei. Wells were then washed with 200 µl PBS, and 100 ul of PBS was added to each well and the plate covered plate with a plastic opaque cover. Plates were stored at 4° C. and covered in aluminum foil until imaged.

Plates were equilibrated to room temperature prior to reading. The bottom of the plate was wiped with 70% isopropanol immediately prior to imaging.

Imaging:

10×, 4 fields/well, include Top hat smoothing in the analysis protocol.

Supplies/Reagents:

16% paraformaldehyde: Electron Microscopy Sciences #15710

Hoechst: Thermofisher #62249

Blocker BSA in PBS, 10%: Thermofisher #37515

Blocker BSA in TBS, 10%: Thermofisher #37520

Goat anti-rabbit or mouse AlexaFluor-488: Thermofisher #A11008

Cell mask deep red AlexaFluor-647: Thermofisher #C10046

Wash buffer, PBS: 20×PBS, Thermofisher

TABLE 1

Exemplary bifunctional compounds of the present disclosure

| Compound Number | Parent Mol Structure | IUPAC Name |
|---|---|---|
| 1 | 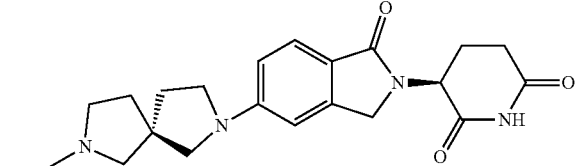 | 2-[(6-{[5-chloro-2-(4-{[(5S)-7-{2-[(3S)-2,6-dioxopiperidin-3-yl]-1-oxo-2,3-dihydro-1H-isoindol-5-yl}-2,7-diazaspiro[4.4]nonan-2-yl]methyl}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 2 | 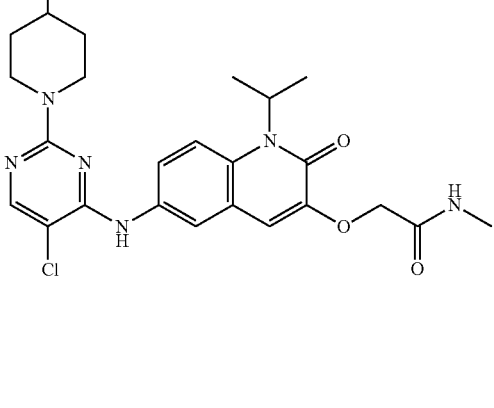 | 2-[(6-{[5-chloro-2-(4-{[(5S)-7-{2-[(3R)-2,6-dioxopiperidin-3-yl]-1-oxo-2,3-dihydro-1H-isoindol-5-yl}-2,7-diazaspiro[4.4]nonan-2-yl]methyl}piperidin-1-yl)pyrimidin-4-yl]amino}-2-oxo-1-(propan-2-yl)-1,2-dihydroquinolin-3-yl)oxy]-N-methylacetamide |
| 3 | 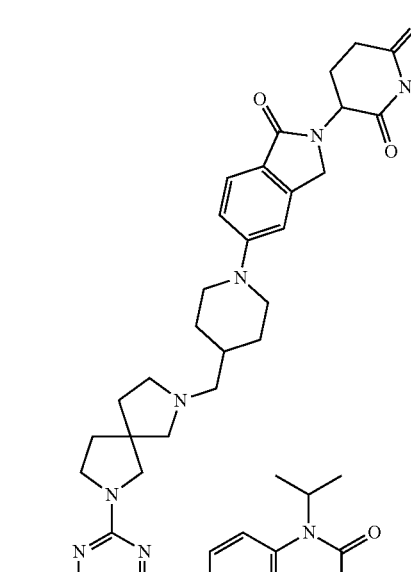 | 2-{[6-({5-chloro-2-[7-({1-[2-(2,6-dioxopiperidin-3-yl)-1-oxo-2,3-dihydro-1H-isoindol-5-yl]piperidin-4-yl}methyl)-2,7-diazaspiro[4.4]nonan-2-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 4 | 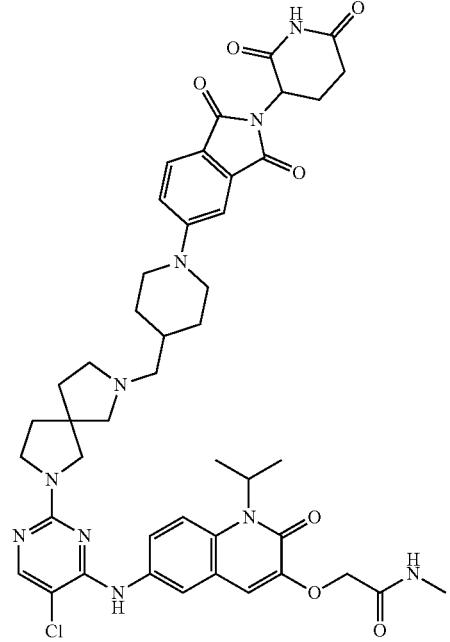 [SMILES: CNC(=O)COc1cc2cc(Nc3nc(N4CCC5(CCN(CC6CCN(c7ccc8c(c7)C(=O)N(C7CCC(=O)NC7=O)C8=O)CC6)C5)C4)ncc3Cl)ccc2n(C(C)C)c1=O] | 2-{[6-({5-chloro-2-[7-({1-[2-(2,6-dioxopiperidin-3-yl)-1,3-dioxo-2,3-dihydro-1H-isoindol-5-yl]piperidin-4-yl}methyl)-2,7-diazaspiro[4.4]nonan-2-yl]pyrimidin-4-yl}amino)-2-oxo-1-(propan-2-yl)-1,2-dihydroquinolin-3-yl]oxy}-N-methylacetamide |
| 5 | 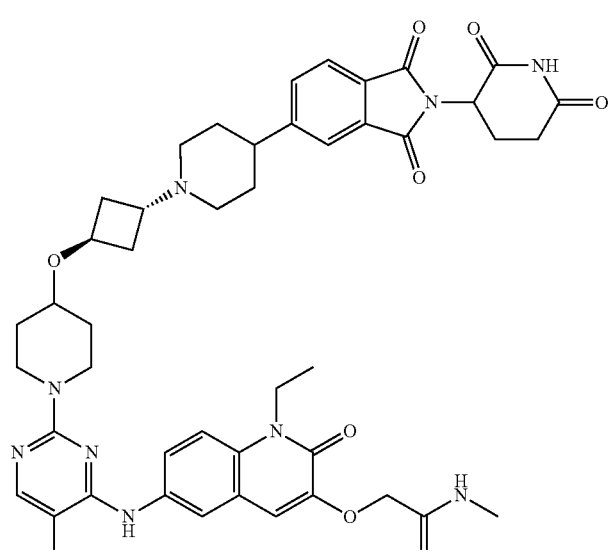 | 2-({6-[(5-chloro-2-{4-[(1r,3r)-3-{4-[2-(2,6-dioxopiperidin-3-yl)-1,3-dioxo-2,3-dihydro-1H-isoindol-5-yl]piperidin-1-yl}cyclobutoxy]piperidin-1-yl}pyrimidin-4-yl)amino]-1-ethyl-2-oxo-1,2-dihydroquinolin-3-yl}oxy)-N-methylacetamide |

TABLE 1-continued

Exemplary bifunctional compounds of the present disclosure

| Compound Number | Parent Mol Structure | IUPAC Name |
|---|---|---|
| 6 | | 2-{[6-({5-chloro-2-[4-({7-[2-(2,6-dioxopiperidin-3-yl)-1-oxo-2,3-dihydro-1H-isoindol-5-yl]-7-azaspiro[3.5]nonan-2-yl}methyl)piperazin-1-yl]pyrimidin-4-yl}amino)-2-oxo-1-(propan-2-yl)-1,2-dihydroquinolin-3-yl]oxy}-N-methylacetamide |
| 7 | | 2-{[6-({5-chloro-2-[4-({7-[2-(2,6-dioxopiperidin-3-yl)-1-oxo-2,3-dihydro-1H-isoindol-4-yl]-7-azaspiro[3.5]nonan-2-yl}methyl)piperazin-1-yl]pyrimidin-4-yl}amino)-2-oxo-1-(propan-2-yl)-1,2-dihydroquinolin-3-yl]oxy}-N-methylacetamide |
| 8 | | 2-{[6-({5-chloro-2-[4-(2-{7-[2-(2,6-dioxopiperidin-3-yl)-1-oxo-2,3-dihydro-1H-isoindol-4-yl]-2,7-diazaspiro[3.5]nonan-2-yl}propan-2-yl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 9 | 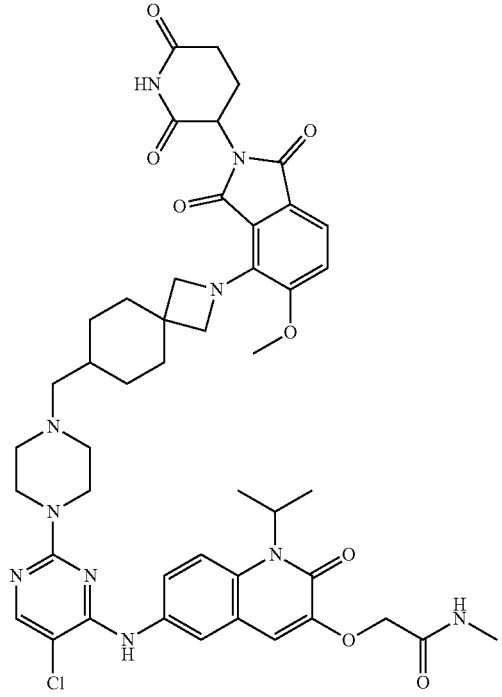 [SMILES: CNC(=O)COc1cc2cc(Nc3nc(N4CCN(CC5CCC6(CC5)CN(c5c(OC)ccc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-5-methoxy-1,3-dioxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |
| 10 | 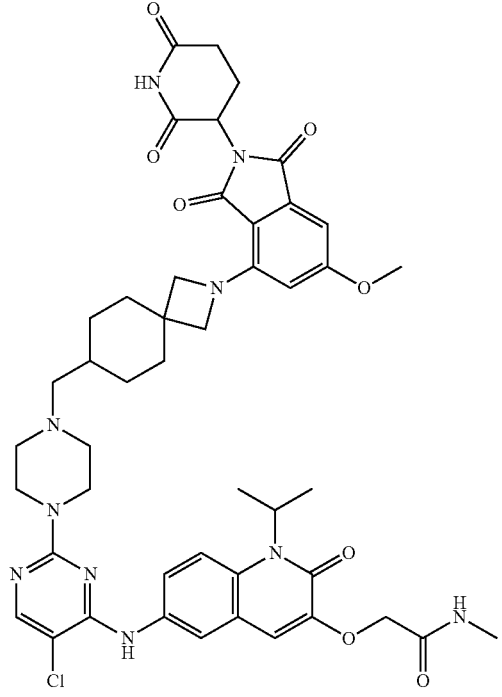 [SMILES: CNC(=O)COc1cc2cc(Nc3nc(N4CCN(CC5CCC6(CC5)CN(c5cc(OC)cc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-6-methoxy-1,3-dioxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 11 | 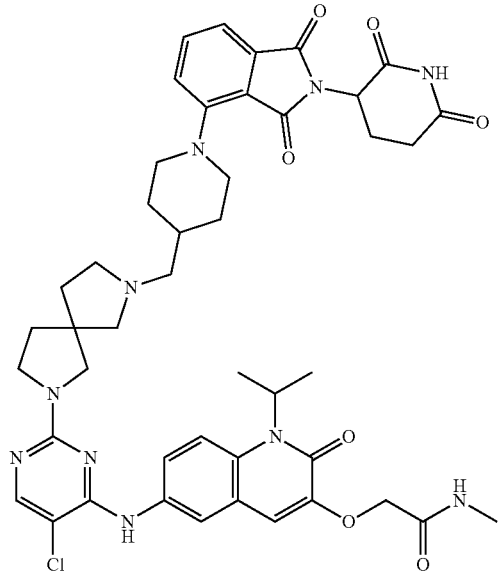 [SMILES: CNC(=O)COc1cc2cc(Nc3nc(N4CCC5(CCN(CC6CCN(c7cccc8c7C(=O)N(C7CCC(=O)NC7=O)C8=O)CC6)C5)C4)ncc3Cl)ccc2n(C(C)C)c1=O] | 2-{[6-({5-chloro-2-[7-({1-[2-(2,6-dioxopiperidin-3-yl)-1-oxo-2,3-dihydro-1H-isoindol-4-yl}methyl)-2,7-diazaspiro[4.4]nonan-2-yl]pyrimidin-4-yl}amino)-2-oxo-1-(propan-2-yl)-1,2-dihydroquinolin-3-yl]oxy}-N-methylacetamide |
| 12 | 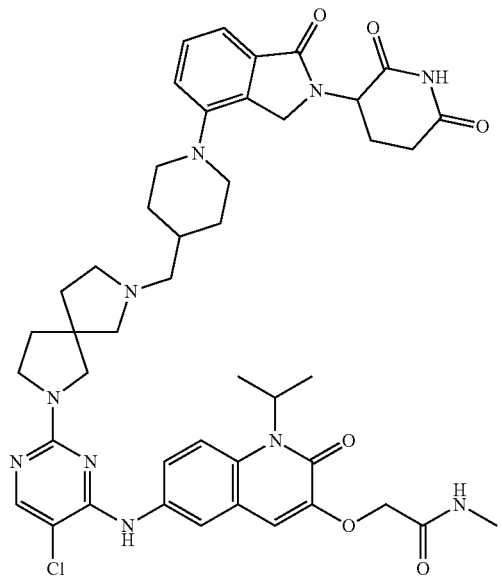 [SMILES: CNC(=O)COc1cc2cc(Nc3nc(N4CCC5(CCN(CC6CCN(c7cccc8c7CN(C7CCC(=O)NC7=O)C8=O)CC6)C5)C4)ncc3Cl)ccc2n(C(C)C)c1=O] | 2-{[6-({5-chloro-2-[7-({1-[2-(2,6-dioxopiperidin-3-yl)-1-oxo-2,3-dihydro-1H-isoindol-4-yl]piperidin-4-yl}methyl)-2,7-diazaspiro[4.4]nonan-2-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 13 | 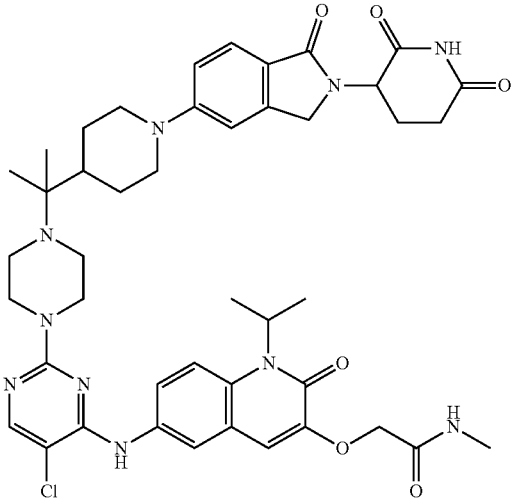 [SMILES: CNC(=O)COc1cc2cc(Nc3nc(N4CCN(C(C)(C)C5CCN(c6ccc7c(c6)CN(C6CCC(=O)NC6=O)C7=O)CC5)CC4)ncc3Cl)ccc2n(C(C)C)c1=O] | 2-{[6-({5-chloro-2-[4-(2-{1-[2-(2,6-dioxopiperidin-3-yl)-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |
| 14 | 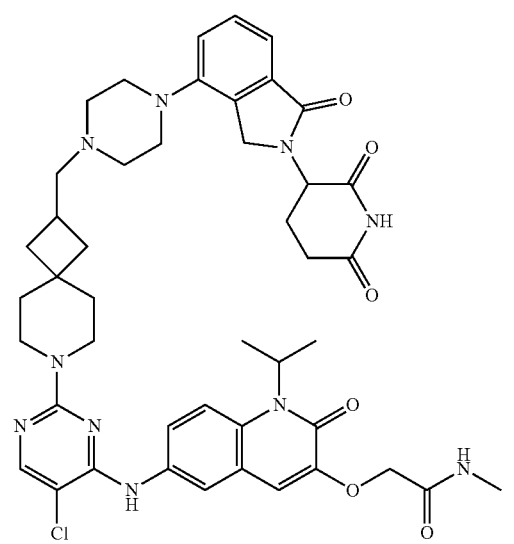 [SMILES: CNC(=O)COc1cc2cc(Nc3nc(N4CCC5(CC4)CC(CN4CCN(c6cccc7c6CN(C6CCC(=O)NC6=O)C7=O)CC4)C5)ncc3Cl)ccc2n(C(C)C)c1=O] | 2-{[6-({5-chloro-2-[2-({4-[2-(2,6-dioxopiperidin-3-yl)-1-oxo-2,3-dihydro-1H-isoindol-4-yl]piperazin-1-yl}methyl)-7-azaspiro[3.5]nonan-7-yl]pyrimidin-4-yl}amino)-2-oxo-1-(propan-2-yl)-1,2-dihydroquinolin-3-yl]oxy}-N-methylacetamide |
| 15 | 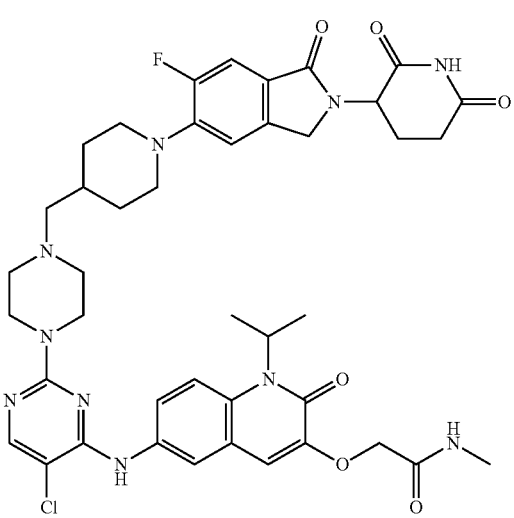 [SMILES: CNC(=O)COc1cc2cc(Nc3nc(N4CCN(CC5CCN(c6cc7c(cc6F)C(=O)N(C6CCC(=O)NC6=O)C7)CC5)CC4)ncc3Cl)ccc2n(C(C)C)c1=O] | 2-{[6-({5-chloro-2-[4-({1-[2-(2,6-dioxopiperidin-3-yl)-6-fluoro-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 16 | | |
| 17 | | 2-{[6-({5-chloro-2-[4-({7-[2-(2,6-dioxopiperidin-3-yl)-1-oxo-2,3-dihydro-1H-isoindol-5-yl]-2,7-diazaspiro[4.4]nonan-2-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |
| 18 | | 2-{[6-({5-chloro-2-[4-({1-[2-(2,6-dioxopiperidin-3-yl)-7-fluoro-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 19 | 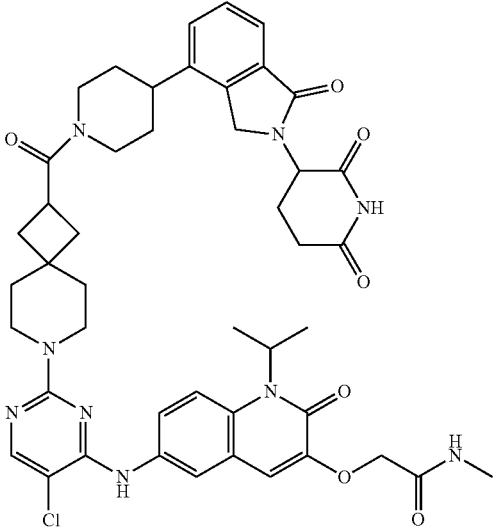 | 2-[(6-{[5-chloro-2-(2-{4-[2-(2,6-dioxopiperidin-3-yl)-1-oxo-2,3-dihydro-1H-isoindol-4-yl]piperidine-1-carbonyl}-7-azaspiro[3.5]nonan-7-yl)pyrimidin-4-yl]amino}-2-oxo-1-(propan-2-yl)-1,2-dihydroquinolin-3-yl)oxy]-N-methylacetamide |
| 20 | 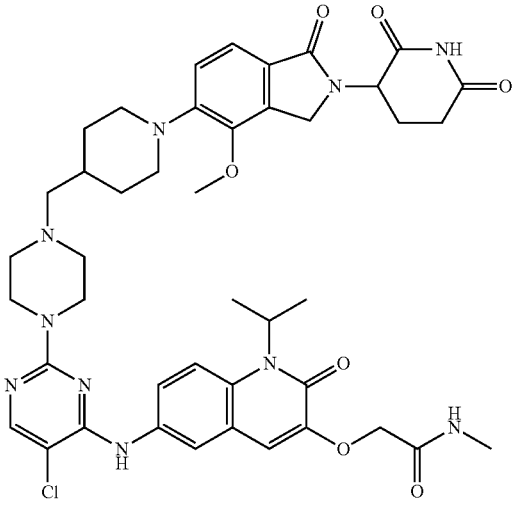 [SMILES: CNC(=O)COc1cc2cc(Nc3nc(N4CCN(CC5CCN(c6ccc7c(c6OC)CN(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-4-methoxy-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 21 | 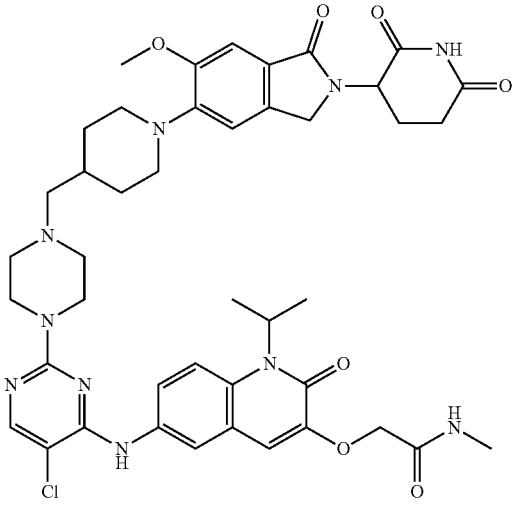 [SMILES: CNC(=O)COc1cc2cc(Nc3nc(N4CCN(CC5CCN(c6cc7c(cc6OC)C(=O)N(C6CCC(=O)NC6=O)C7)CC5)CC4)ncc3Cl)ccc2n(C(C)C)c1=O] | 2-{[6-({5-chloro-2-[4-({1-[2-(2,6-dioxopiperidin-3-yl)-6-methoxy-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 22 | 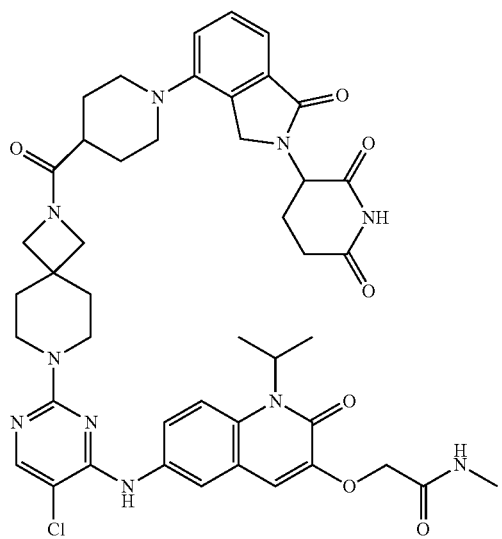 [SMILES: CNC(=O)COc1cc2cc(Nc3nc(N4CCC5(CC4)CN(C(=O)C4CCN(c6cccc7c6CN(C6CCC(=O)NC6=O)C7=O)CC4)C5)ncc3Cl)ccc2n(C(C)C)c1=O] | 2-[(6-{[5-chloro-2-(2-{1-[2-(2,6-dioxopiperidin-3-yl)-1-oxo-2,3-dihydro-1H-isoindol-4-yl]piperidine-4-carbonyl}-2,7-diazaspiro[3.5]nonan-7-yl)pyrimidin-4-yl]amino}-2-oxo-1-(propan-2-yl)-1,2-dihydroquinolin-3-yl)oxy]-N-methylacetamide |
| 23 | 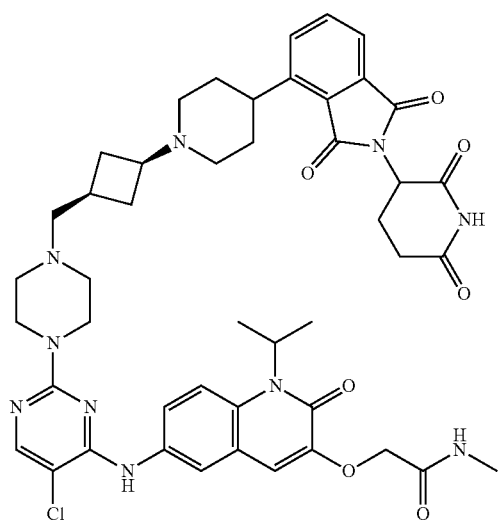 [SMILES: CNC(=O)COc1cc2cc(Nc3nc(N4CCN(C[C@H]5C[C@@H](N6CCC(c7cccc8c7C(=O)N(C7CCC(=O)NC7=O)C8=O)CC6)C5)CC4)ncc3Cl)ccc2n(C(C)C)c1=O] | 2-[(6-{[5-chloro-2-(4-{[(1s,3s)-3-{4-[2-(2,6-dioxopiperidin-3-yl)-1,3-dioxo-2,3-dihydro-1H-isoindol-4-yl]piperidin-1-yl}cyclobutyl]methyl}piperazin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 24 | 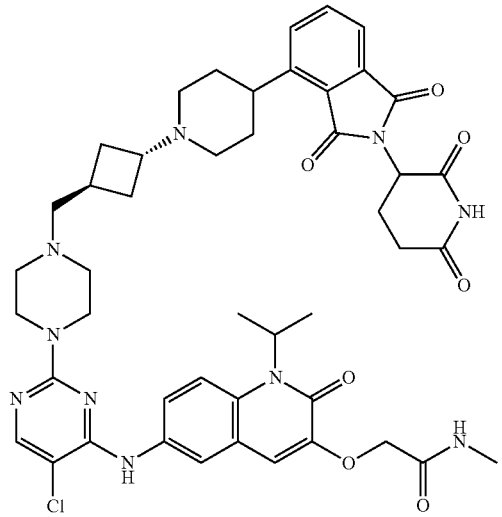 [SMILES: CNC(=O)COc1cc2cc(Nc3nc(N4CCN(C[C@H]5C[C@H](N6CCC(c7cccc8c7C(=O)N(C7CCC(=O)NC7=O)C8=O)CC6)C5)CC4)ncc3Cl)ccc2n(C(C)C)c1=O] | 2-[(6-{[5-chloro-2-(4-{[(1r,3r)-3-{4-[2-(2,6-dioxopiperidin-3-yl)-1,3-dioxo-2,3-dihydro-1H-isoindol-4-yl]piperidin-1-yl}cyclobutyl]methyl}piperazin-1-yl)pyrimidin-4-yl]amino}-2-oxo-1-(propan-2-yl)-1,2-dihydroquinolin-3-yl)oxy]-N-methylacetamide |
| 25 | 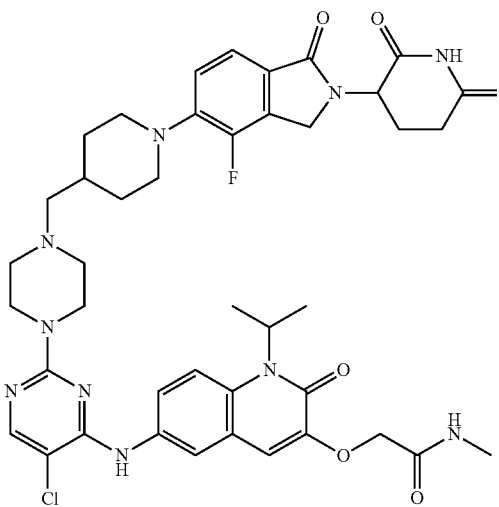 | 2-{[6-({5-chloro-2-[4-({1-[2-(2,6-dioxopiperidin-3-yl)-4-fluoro-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 26 | 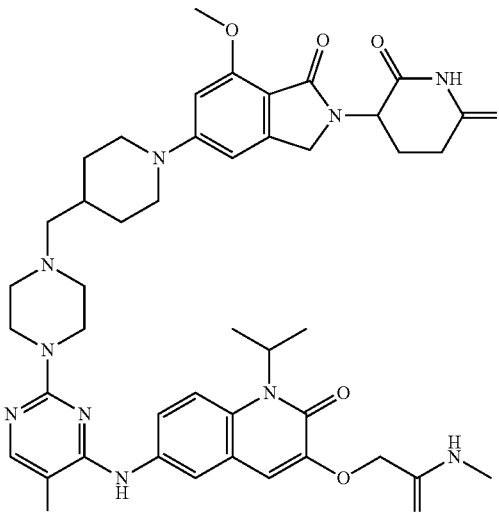 | 2-{[6-({5-chloro-2-[4-({1-[2-(2,6-dioxopiperidin-3-yl)-7-methoxy-1-oxo-2,3-dihydro-1H-isoindol-5-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 27 | 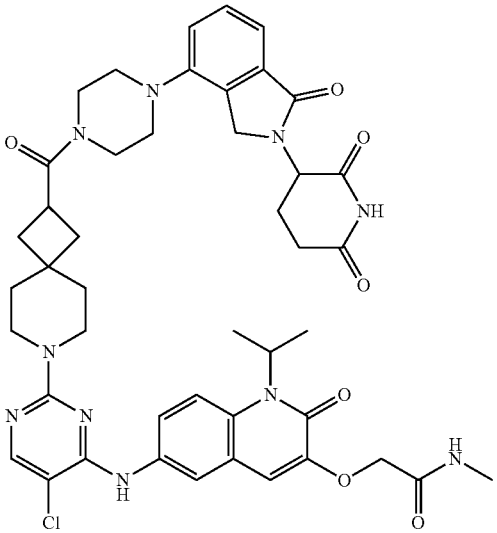 | 2-[(6-{[5-chloro-2-(2-{4-[2-(2,6-dioxopiperidin-3-yl)-1-oxo-2,3-dihydro-1H-isoindol-4-yl]piperazine-1-carbonyl}-7-azaspiro[3.5]nonan-7-yl)pyrimidin-4-yl]amino}-2-oxo-1-(propan-2-yl)-1,2-dihydroquinolin-3-yl)oxy]-N-methylacetamide |
| 28 | 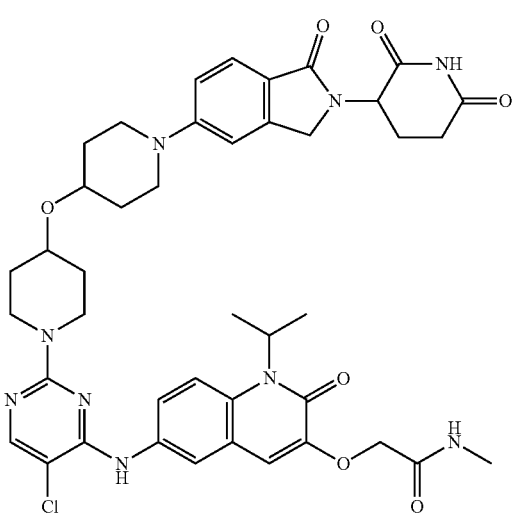 [SMILES: CNC(=O)COc1cc2cc(Nc3nc(N4CCC(OC5CCN(c6ccc7c(c6)CN(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-1-oxo-2,3-dihydro-1H-isoindol-5-yl]piperidin-4-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 29 | 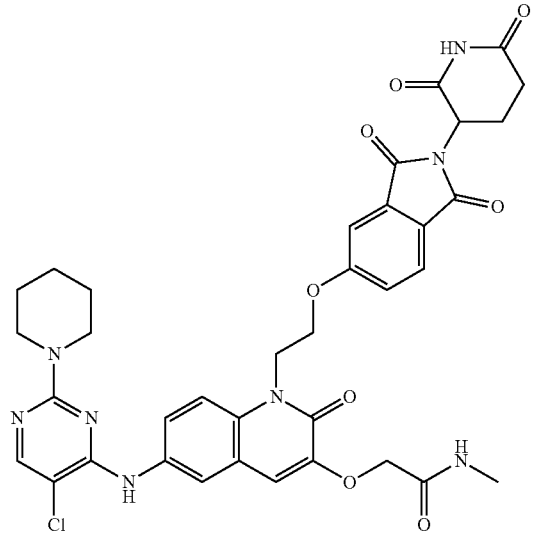 [SMILES: CNC(=O)COc1cc2cc(Nc3nc(N4CCCCC4)ncc3Cl)ccc2n(CCOc2ccc3c(c2)C(=O)N(C2CCC(=O)NC2=O)C3=O)c1=O] | 2-[(6-{[5-chloro-2-(piperidin-1-yl)pyrimidin-4-yl]amino}-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl)oxy]-N-methylacetamide |
| 30 | 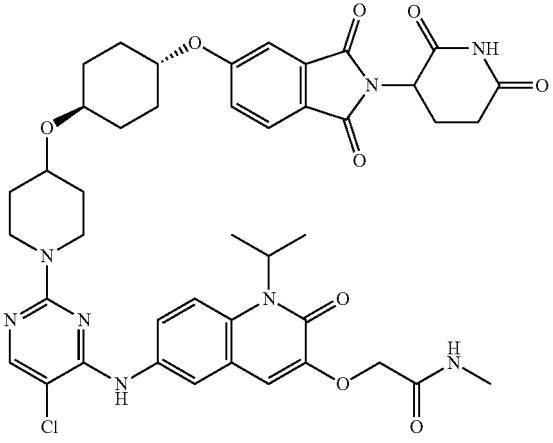 [SMILES: CNC(=O)COc1cc2cc(Nc3nc(N4CCC(O[C@H]5CC[C@H](Oc6ccc7c(c6)C(=O)N(C6CCC(=O)NC6=O)C7=O)CC5)CC4)ncc3Cl)ccc2n(C(C)C)c1=O] | 2-[(6-{[5-chloro-2-(4-{[(1r,4r)-4-{[2-(2,6-dioxopiperidin-3-yl)-1,3-dioxo-2,3-dihydro-1H-isoindol-5-yl]oxy}cyclohexyl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 31 | 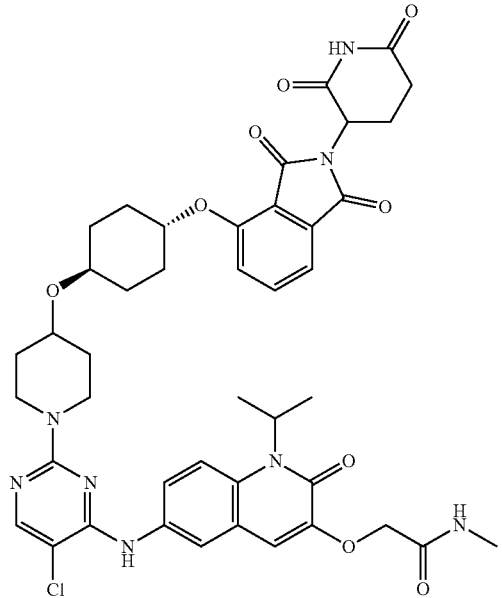 [SMILES: CNC(=O)COc1cc2cc(Nc3nc(N4CCC(O[C@H]5CC[C@H](Oc6cccc7c6C(=O)N(C6CCC(=O)NC6=O)C7=O)CC5)CC4)ncc3Cl)ccc2n(C(C)C)c1=O] | 2-[(6-{[5-chloro-2-(4-{[(1r,4r)-4-{[2-(2,6-dioxopiperidin-3-yl)-1,3-dioxo-2,3-dihydro-1H-isoindol-4-yl]oxy}cyclohexyl]oxy}piperidin-1-yl)pyrimidin-4-yl]amino}-2-oxo-1-(propan-2-yl)-1,2-dihydroquinolin-3-yl)oxy]-N-methylacetamide |
| 32 | 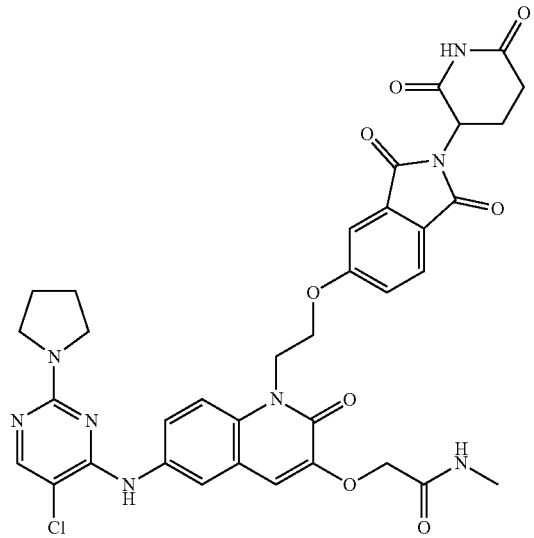 [SMILES: CNC(=O)COc1cc2cc(Nc3nc(N4CCCC4)ncc3Cl)ccc2n(CCOc2ccc3c(c2)C(=O)N(C2CCC(=O)NC2=O)C3=O)c1=O] | 2-[(6-{[5-chloro-2-(pyrrolidin-1-yl)pyrimidin-4-yl]amino}-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 33 | 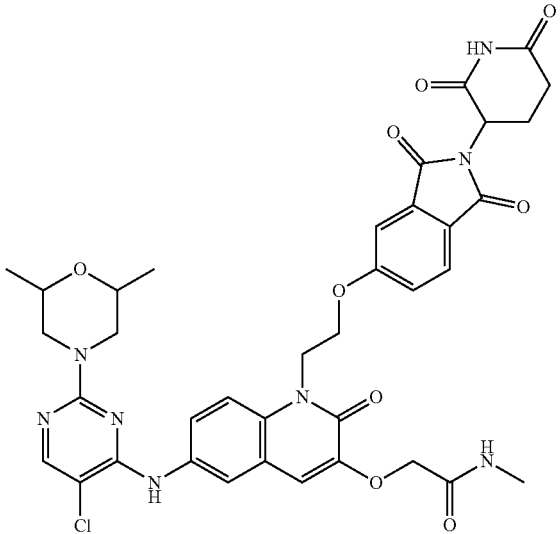 [SMILES: CNC(=O)COc1cc2cc(Nc3nc(N4CC(C)OC(C)C4)ncc3Cl)ccc2n(CCOc2ccc3c(c2)C(=O)N(C2CCC(=O)NC2=O)C3=O)c1=O] | 2-[(6-{[5-chloro-2-(2,6-dimethylmorpholin-4-yl)pyrimidin-4-yl]amino}-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl)oxy]-N-methylacetamide |
| 34 | 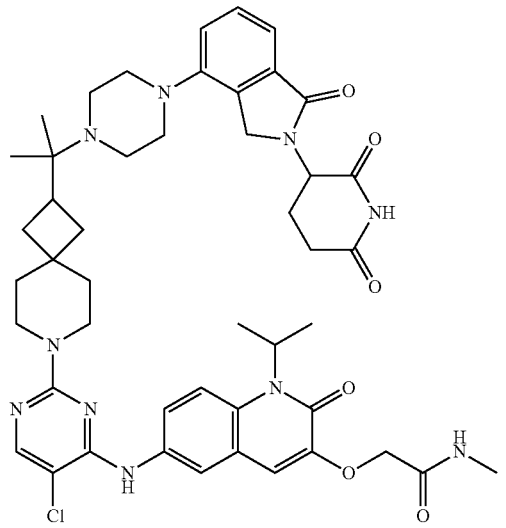 [SMILES: CNC(=O)COc1cc2cc(Nc3nc(N4CCC5(CC4)CC(C(C)(C)N4CCN(c6cccc7c6CN(C6CCC(=O)NC6=O)C7=O)CC4)C5)ncc3Cl)ccc2n(C(C)C)c1=O] | 2-{[6-({5-chloro-2-[2-(2-{4-[2-(2,6-dioxopiperidin-3-yl)-1-oxo-2,3-dihydro-1H-isoindol-4-yl]piperazin-1-yl}propan-2-yl)-7-azaspiro[3.5]nonan-7-yl]pyrimidin-4-yl}amino)-2-oxo-1-(propan-2-yl)-1,2-dihydroquinolin-3-yl]oxy}-N-methylacetamide |
| 35 | 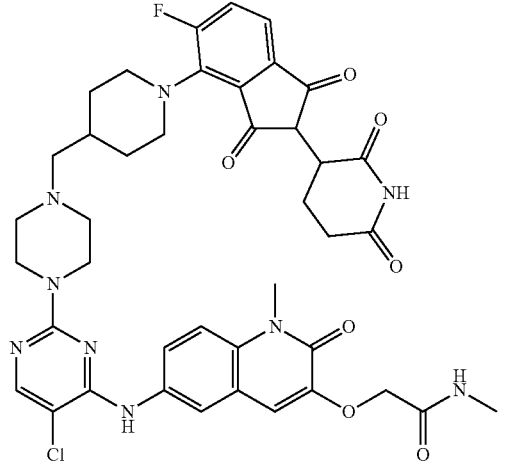 [SMILES: CNC(=O)COc1cc2cc(Nc3nc(N4CCN(CC5CCN(c6c(F)ccc7c6C(=O)C(C6CCC(=O)NC6=O)C7=O)CC5)CC4)ncc3Cl)ccc2n(C)c1=O] | 2-{[6-({5-chloro-2-[4-({1-[2-(2,6-dioxopiperidin-3-yl)-5-fluoro-1,3-dioxo-2,3-dihydro-1H-isoindol-4-yl]piperidin-4-yl}methyl)piperazin-1-yl]pyrimidin-4-yl}amino)-1-methyl-2-oxo-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 36 | 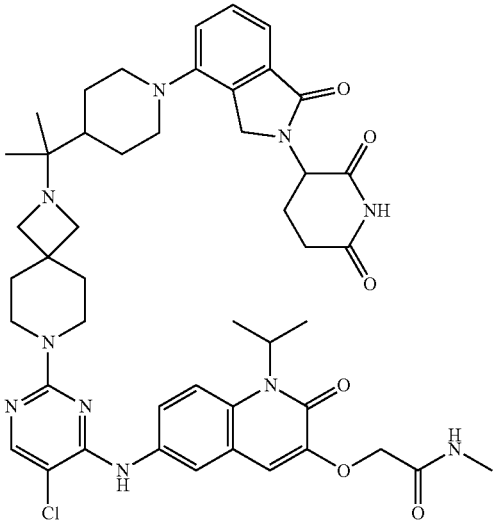 [SMILES: CNC(=O)COc1cc2cc(Nc3nc(N4CCC5(CC4)CN(C(C)(C)C4CCN(c6cccc7c6CN(C6CCC(=O)NC6=O)C7=O)CC4)C5)ncc3Cl)ccc2n(C(C)C)c1=O] | 2-{[6-({5-chloro-2-[2-(2-{1-[2-(2,6-dioxopiperidin-3-yl)-1-oxo-2,3-dihydro-1H-isoindol-4-yl]piperidin-4-yl}propan-2-yl)-2,7-diazaspiro[3.5]nonan-7-yl]pyrimidin-4-yl}amino)-2-oxo-1-(propan-2-yl)-1,2-dihydroquinolin-3-yl]oxy}-N-methylacetamide |
| 37 | 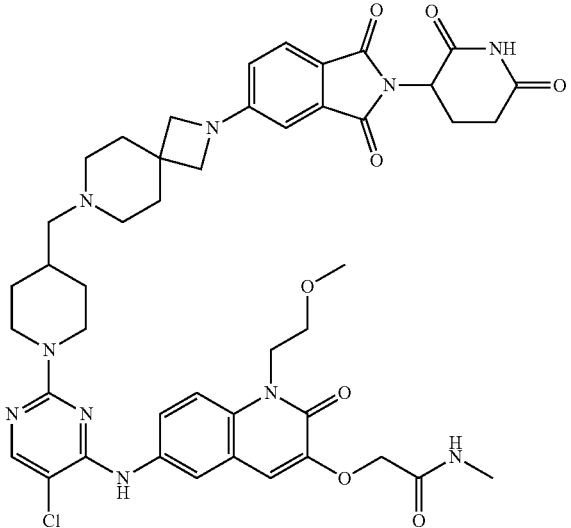 [SMILES: CNC(=O)COc1cc2cc(Nc3nc(N4CCC(CN5CCC6(CC5)CN(c5ccc7c(c5)C(=O)N(C5CCC(=O)NC5=O)C7=O)C6)CC4)ncc3Cl)ccc2n(CCOC)c1=O] | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyrimidin-4-yl}amino)-1-(2-methoxyethyl)-2-oxo-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 38 | 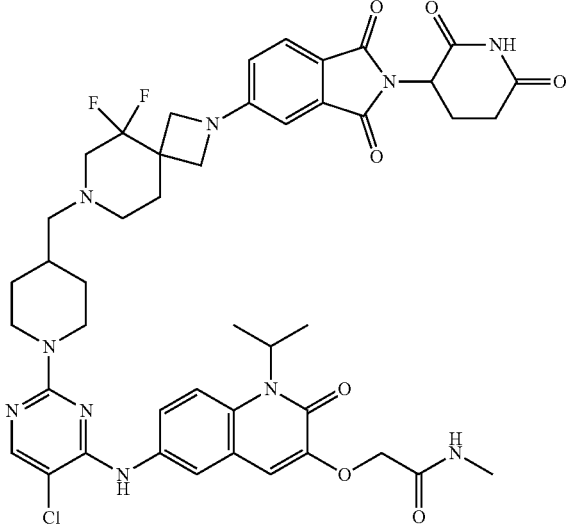 [SMILES: CNC(=O)COc1cc2cc(Nc3nc(N4CCC(CN5CCC6(CN(c7ccc8c(c7)C(=O)N(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-5-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 39 | 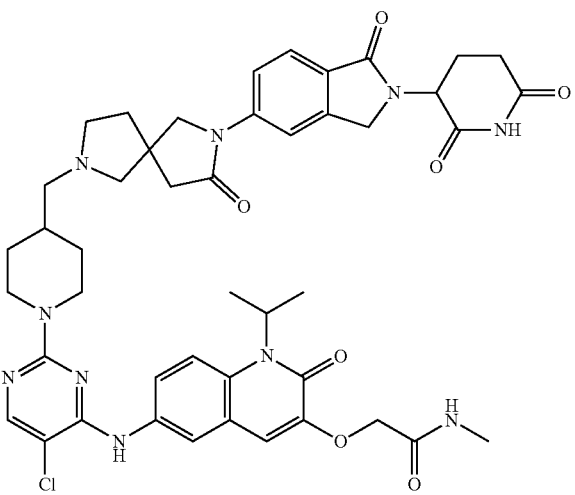 [SMILES: CNC(=O)COc1cc2cc(Nc3nc(N4CCC(CN5CCC6(CC(=O)N(c7ccc8c(c7)CN(C7CCC(=O)NC7=O)C8=O)C6)C5)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-5-yl]-8-oxo-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

…

TABLE 1-continued

Exemplary bifunctional compounds of the present disclosure

| Compound Number | Parent Mol Structure | IUPAC Name |
|---|---|---|
| 40 | 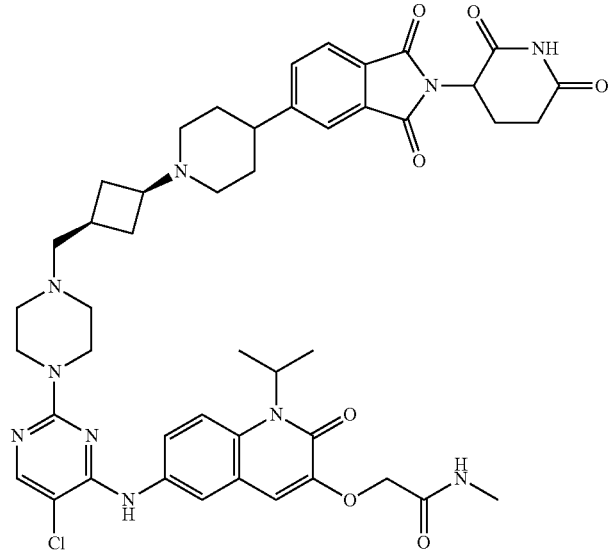 | 2-[(6-{[5-chloro-2-(4-{[(1s,3s)-3-{4-[2-(2,6-dioxopiperidin-3-yl)-1,3-dioxo-2,3-dihydro-1H-isoindol-5-yl]piperidin-1-yl}cyclobutyl]methyl}piperazin-1-yl)pyrimidin-4-yl]amino}-2-oxo-1-(propan-2-yl)-1,2-dihydroquinolin-3-yl)oxy]-N-methylacetamide |
| 41 | 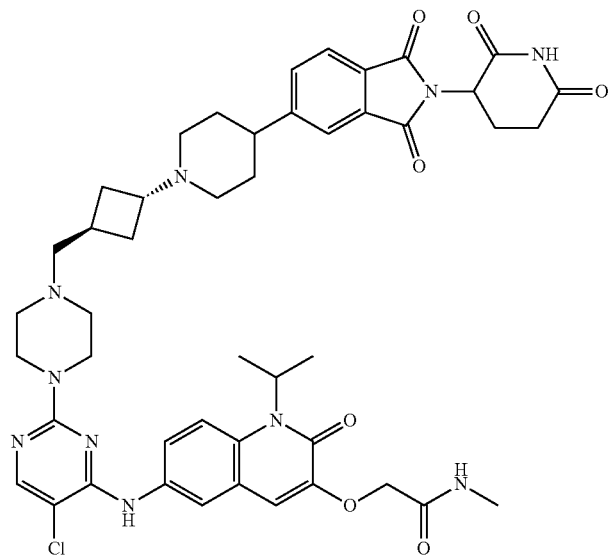 | 2-[(6-{[5-chloro-2-(4-{[(1r,3r)-3-{4-[2-(2,6-dioxopiperidin-3-yl)-1,3-dioxo-2,3-dihydro-1H-isoindol-5-yl]piperidin-1-yl}cyclobutyl]methyl}piperazin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 42 | 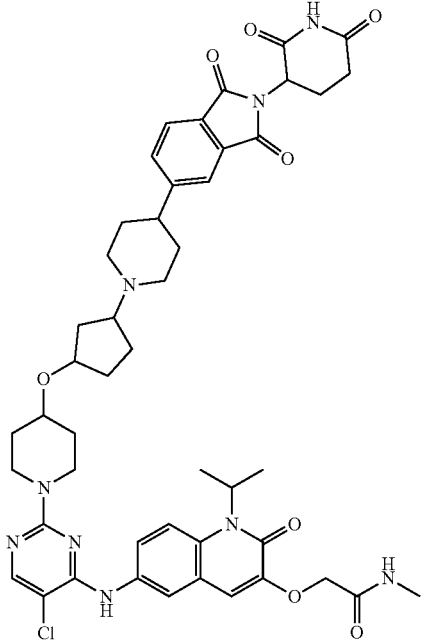 [SMILES: CNC(=O)COc1cc2cc(Nc3nc(N4CCC(OC5CCC(N6CCC(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(3-{4-[2-(2,6-dioxopiperidin-3-yl)-1,3-dioxo-2,3-dihydro-1H-isoindol-5-yl]piperidin-1-yl}cyclopentyl)oxy]piperidin-1-yl}pyrimidin-4-yl)amino]-2-oxo-1-(propan-2-yl)-1,2-dihydroquinolin-3-yl}oxy)-N-methylacetamide |
| 43 | 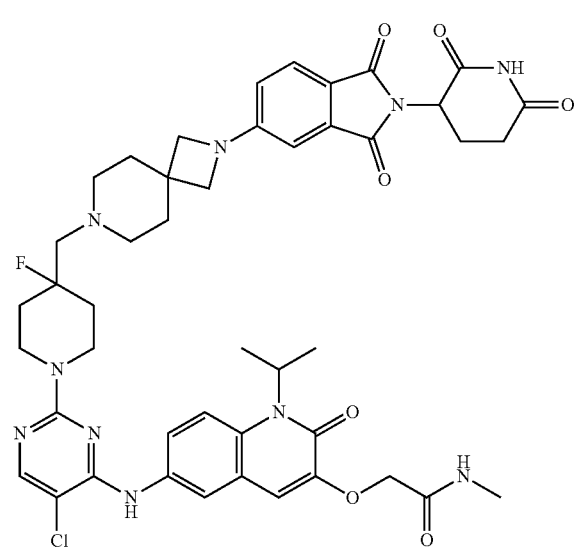 [SMILES: CNC(=O)COc1cc2cc(Nc3nc(N4CCC(F)(CN5CCC6(CC5)CN(c5ccc7c(c5)C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 44 | | 2-{[6-({5-chloro-2-[4-({2-[2-(2,6-dioxopiperidin-3-yl)-1,3-dioxo-2,3-dihydro-1H-isoindol-4-yl]-2,7-diazaspiro[3.5]nonan-7-yl}methyl)-4-fluoropiperidin-1-yl]pyrimidin-4-yl]amino)-2-oxo-1-(propan-2-yl)-1,2-dihydroquinolin-3-yl]oxy}-N-methylacetamide |
| 45 | | 2-{[6-({5-chloro-2-[4-(2-{2-[2-(2,6-dioxopiperidin-3-yl)-1,3-dioxo-2,3-dihydro-1H-isoindol-5-yl]-2,7-diazaspiro[3.5]nonan-7-yl}propan-2-yl)piperidin-1-yl]pyrimidin-4-yl]amino)-2-oxo-1-(propan-2-yl)-1,2-dihydroquinolin-3-yl]oxy}-N-methylacetamide |
| 46 | | 2-{[6-({5-chloro-2-[4-(2-{2-[2-(2,6-dioxopiperidin-3-yl)-1,3-dioxo-2,3-dihydro-1H-isoindol-4-yl]-2,7-diazaspiro[3.5]nonan-7-yl}propan-2-yl)piperidin-1-yl]pyrimidin-4-yl]amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 47 | 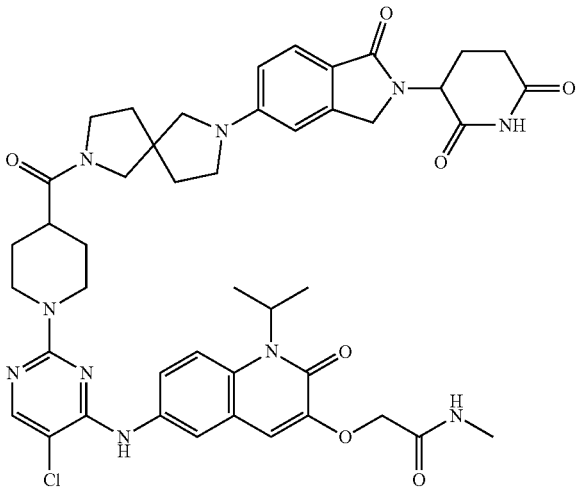 [SMILES: CNC(=O)COc1cc2cc(Nc3nc(N4CCC(C(=O)N5CCC6(CCN(c7ccc8c(c7)CN(C7CCC(=O)NC7=O)C8=O)C6)C5)CC4)ncc3Cl)ccc2n(C(C)C)c1=O] | 2-[(6-{[5-chloro-2-(4-{7-[2-(2,6-dioxopiperidin-3-yl)-1-oxo-2,3-dihydro-1H-isoindol-5-yl]-2,7-diazaspiro[4.4]nonane-2-carbonyl}piperidin-1-yl)pyrimidin-4-yl]amino}-2-oxo-1-(propan-2-yl)-1,2-dihydroquinolin-3-yl)oxy]-N-methylacetamide |
| 48 | 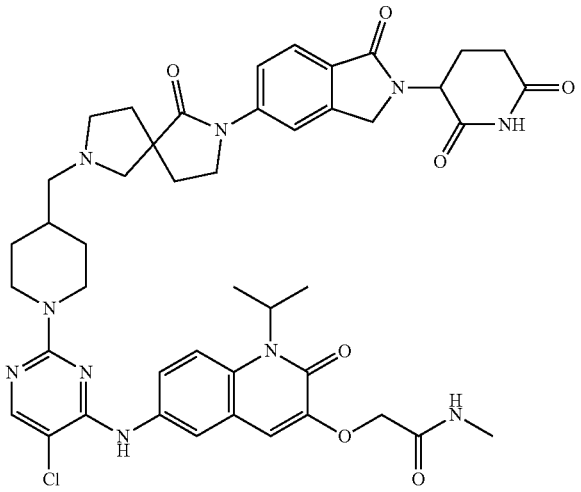 [SMILES: CNC(=O)COc1cc2cc(Nc3nc(N4CCC(CN5CCC6(CCN(c7ccc8c(c7)CN(C7CCC(=O)NC7=O)C8=O)C6=O)C5)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-5-yl]-6-oxo-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 49 | 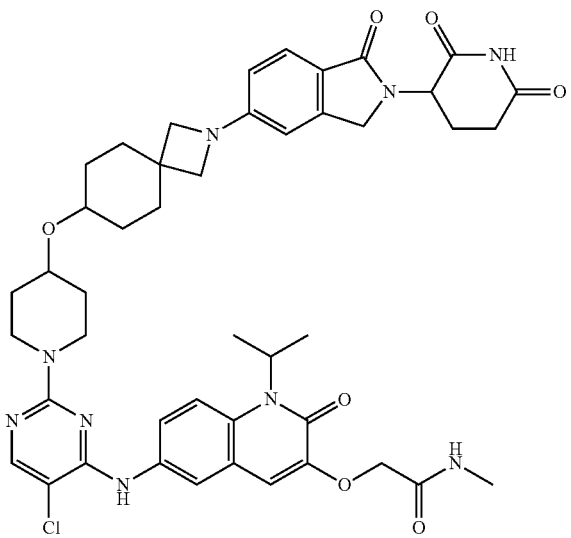 [SMILES: CNC(=O)COc1cc2cc(Nc3nc(N4CCC(OC5CCC6(CC5)CN(c5ccc7c(c5)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 50 | 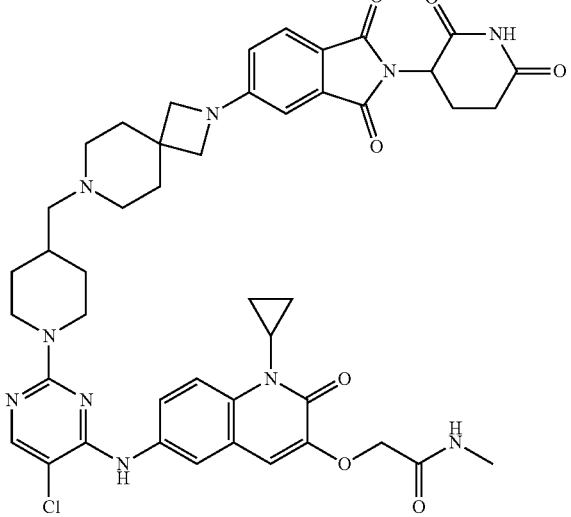 | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyrimidin-4-yl}amino)-1-cyclopropyl-2-oxo-1,2-dihydroquinolin-3-yl]oxy}-N-methylacetamide |
| 51 | 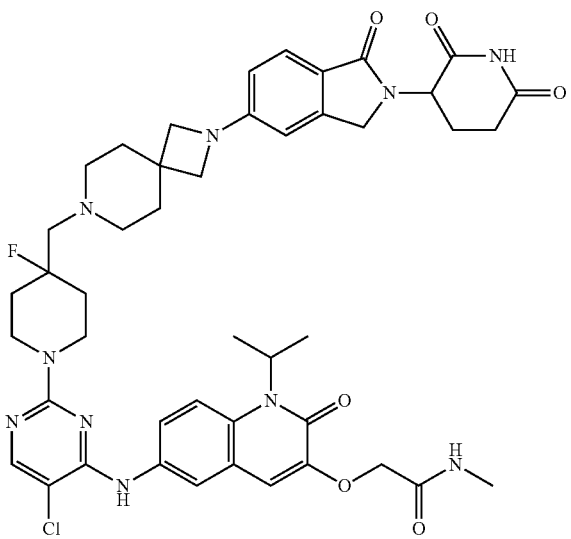 [SMILES: CNC(=O)COc1cc2cc(Nc3nc(N4CCC(F)(CN5CCC6(CC5)CN(c5ccc7c(c5)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-2,7-diazaspiro[3.5]nonan-7-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |
| 52 | 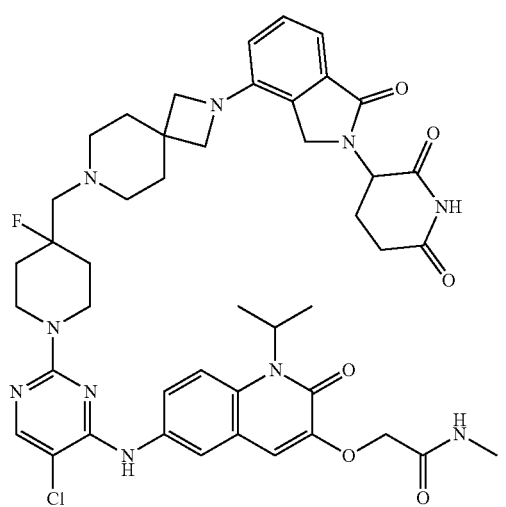 [SMILES: CNC(=O)COc1cc2cc(Nc3nc(N4CCC(F)(CN5CCC6(CC5)CN(c5cccc7c5CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-4-yl]-2,7-diazaspiro[3.5]nonan-7-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 53 | 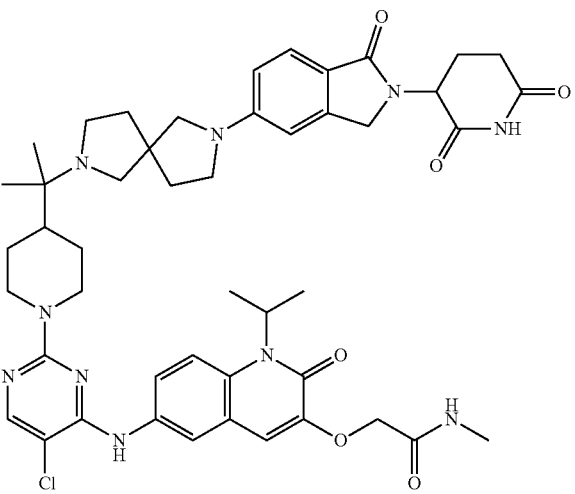 [SMILES: CNC(=O)COc1cc2cc(Nc3nc(N4CCC(C(C)(C)N5CCC6(CCN(c7ccc8c(c7)CN(C7CCC(=O)NC7=O)C8=O)C6)C5)CC4)ncc3Cl)ccc2n(C(C)C)c1=O] | 2-{[6-({5-chloro-2-[4-(2-{7-[2-(2,6-dioxopiperidin-3-yl)-1-oxo-2,3-dihydro-1H-isoindol-5-yl]-2,7-diazaspiro[4.4]nonan-2-yl}propan-2-yl)piperidin-1-yl]pyrimidin-4-yl}amino)-2-oxo-1-(propan-2-yl)-1,2-dihydroquinolin-3-yl]oxy}-N-methylacetamide |
| 54 | 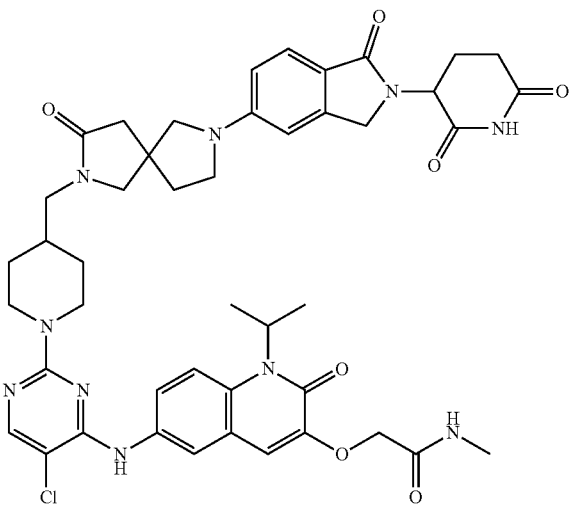 [SMILES: CNC(=O)COc1cc2cc(Nc3nc(N4CCC(CN5CC6(CCN(c7ccc8c(c7)CN(C7CCC(=O)NC7=O)C8=O)C6)CC5=O)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-5-yl]-3-oxo-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 55 | 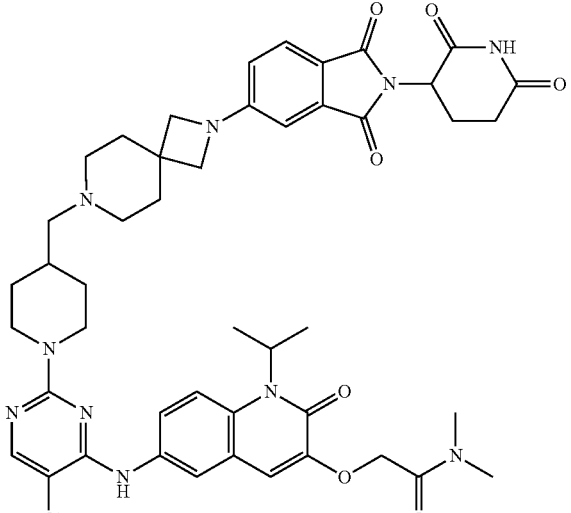 | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N,N-dimethylacetamide |

TABLE 1-continued

Exemplary bifunctional compounds of the present disclosure

| Compound Number | Parent Mol Structure | IUPAC Name |
| --- | --- | --- |
| 56 | 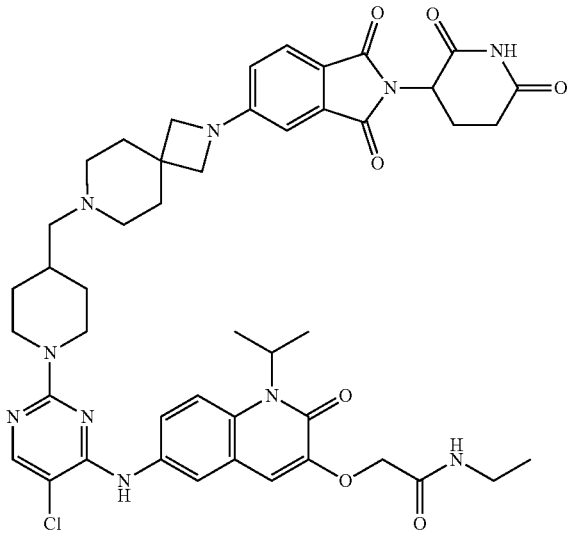 [SMILES: CCNC(=O)COc1cc2cc(Nc3nc(N4CCC(CN5CCC6(CC5)CN(c5ccc7c(c5)C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-ethylacetamide |
| 57 | 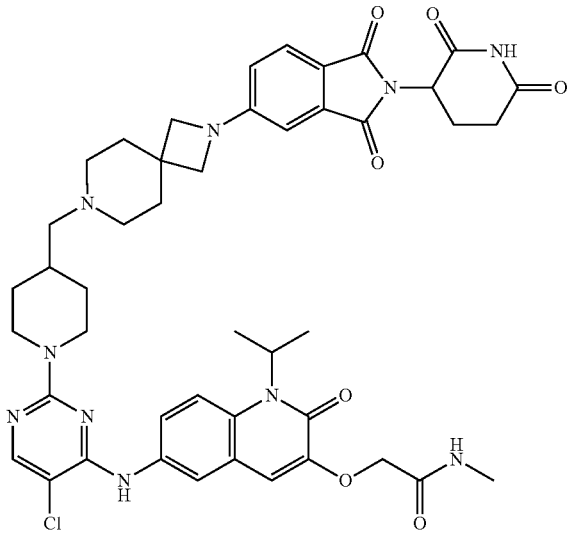 | 2-{[6-({2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]-5-fluoropyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
| --- | --- | --- |
| 58 | 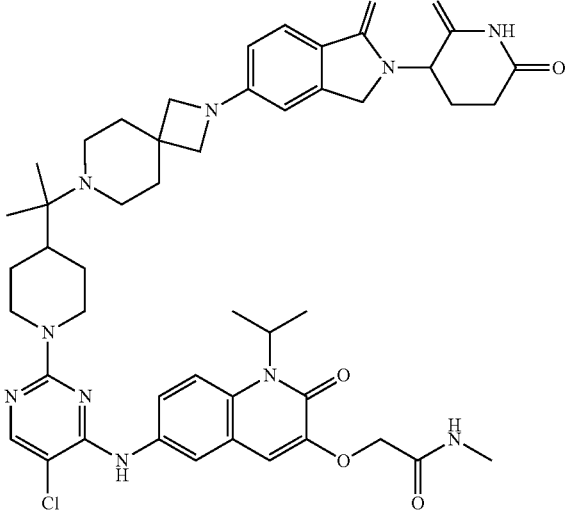 | 2-{[6-({5-chloro-2-[4-(2-{2-[2-(2,6-dioxopiperidin-3-yl)-1-oxo-2,3-dihydro-1H-isoindol-5-yl]-2,7-diazaspiro[3.5]nonan-7-yl}propan-2-yl)piperidin-1-yl]pyrimidin-4-yl}amino)-2-oxo-1-(propan-2-yl)-1,2-dihydroquinolin-3-yl]oxy}-N-methylacetamide |
| 59 | 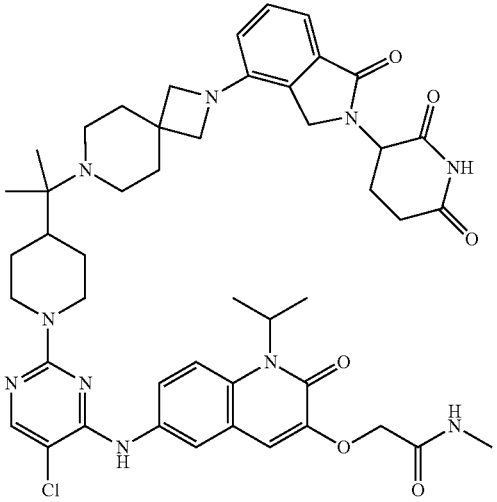 [SMILES: CNC(=O)COc1cc2cc(Nc3nc(N4CCC(C(C)(C)N5CCC6(CC5)CN(c5cccc7c5CN(C5CCC(=O)NC5=O)C7=O)C6)CC4)ncc3Cl)ccc2n(C(C)C)c1=O] | 2-{[6-({5-chloro-2-[4-(2-{2-[2-(2,6-dioxopiperidin-3-yl)-1-oxo-2,3-dihydro-1H-isoindol-4-yl]-2,7-diazaspiro[3.5]nonan-7-yl}propan-2-yl)piperidin-1-yl]pyrimidin-4-yl}amino)-2-oxo-1-(propan-2-yl)-1,2-dihydroquinolin-3-yl]oxy}-N-methylacetamide |
| 60 | 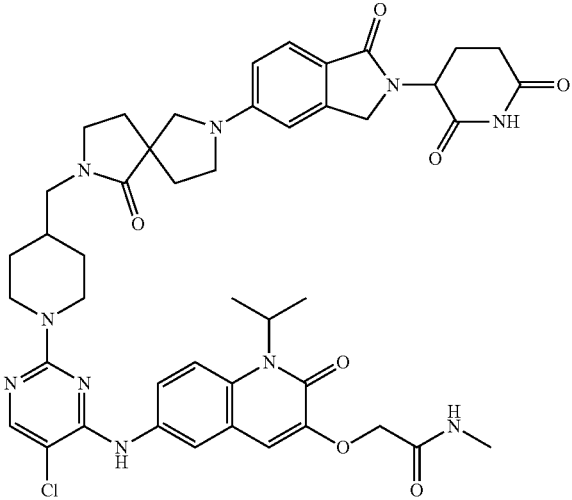 [SMILES: CNC(=O)COc1cc2cc(Nc3nc(N4CCC(CN5CCC6(CCN(c7ccc8c(c7)CN(C7CCC(=O)NC7=O)C8=O)C6)C5=O)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-5-yl]-1-oxo-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 61 | | 2-{[6-({5-chloro-2-[4-({2-[2-(2,6-dioxopiperidin-3-yl)-1-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |
| 62 | | 2-{[6-({5-chloro-2-[4-({9-[2-(2,6-dioxopiperidin-3-yl)-1,3-dioxo-2,3-dihydro-1H-isoindol-4-yl]-3,9-diazaspiro[5.5]undecan-3-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |
| 63 | | 2-{[6-({5-chloro-2-[9-({1-[2-(2,6-dioxopiperidin-3-yl)-1,3-dioxo-2,3-dihydro-1H-isoindol-4-yl]-4-fluoropiperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 64 | | 2-{[6-({5-chloro-2-[4-({2-[2-(2,6-dioxopiperidin-3-yl)-6-fluoro-1-oxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 65 | | 2-{[6-({5-chloro-2-[4-({2-[2-(2,6-dioxopiperidin-3-yl)-1,3-dioxo-2,3-dihydro-1H-isoindol-5-yl]-1-oxo-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
| --- | --- | --- |
| 66 | | 2-[(6-{[5-chloro-2-(4-{2-[2-(2,6-dioxopiperidin-3-yl)-1-oxo-2,3-dihydro-1H-isoindol-5-yl]-2-azaspiro[4.4]nonane-7-carbonyl}piperazin-1-yl)pyrimidin-4-yl]amino}-2-oxo-1-(propan-2-yl)-1,2-dihydroquinolin-3-yl)oxy]-N-methylacetamide |
| 67 | | 2-{[6-({5-chloro-2-[4-({1-[2-(2,6-dioxopiperidin-3-yl)-1-oxo-2,3-dihydro-1H-isoindol-5-yl]piperidin-4-yl}methyl)piperazin-1-yl]pyrimidin-4-yl}amino)-1-methyl-2-oxo-1,2-dihydroquinolin-3-yl]oxy}-N-methylacetamide |
| 68 | | 2-{[6-({5-chloro-2-[4-(2-{1-[2-(2,6-dioxopiperidin-3-yl)-6-fluoro-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 69 | 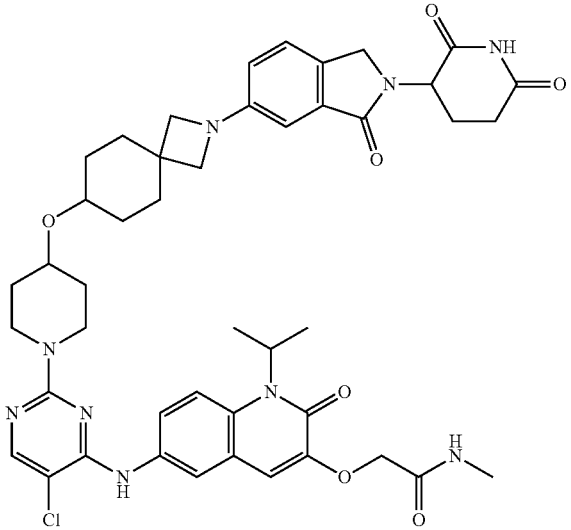 [SMILES: CNC(=O)COc1cc2cc(Nc3nc(N4CCC(OC5CCC6(CC5)CN(c5ccc7c(c5)C(=O)N(C5CCC(=O)NC5=O)C7)C6)CC4)ncc3Cl)ccc2n(C(C)C)c1=O] | 2-{[6-({5-chloro-2-[4-({2-[2-(2,6-dioxopiperidin-3-yl)-3-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |
| 70 | 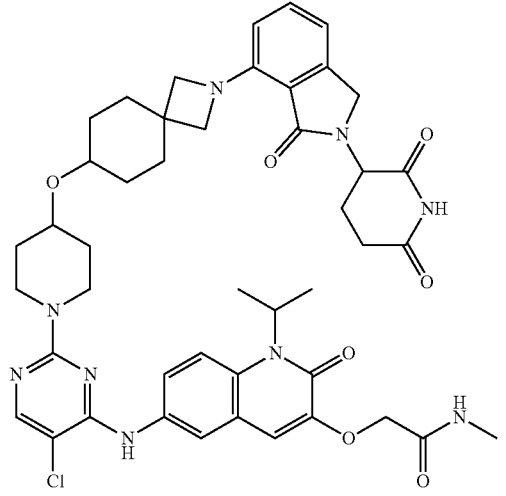 [SMILES: CNC(=O)COc1cc2cc(Nc3nc(N4CCC(OC5CCC6(CC5)CN(c5cccc7c5C(=O)N(C5CCC(=O)NC5=O)C7)C6)CC4)ncc3Cl)ccc2n(C(C)C)c1=O] | 2-{[6-({5-chloro-2-[4-({2-[2-(2,6-dioxopiperidin-3-yl)-3-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |
| 71 | 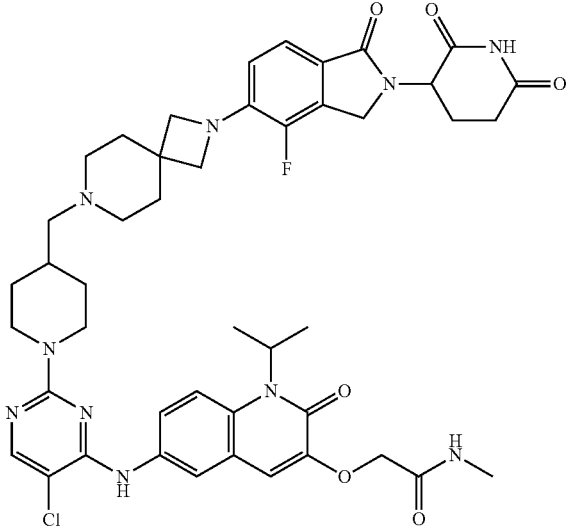 | 2-{[6-({5-chloro-2-[4-({2-[2-(2,6-dioxopiperidin-3-yl)-4-fluoro-1-oxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 72 | 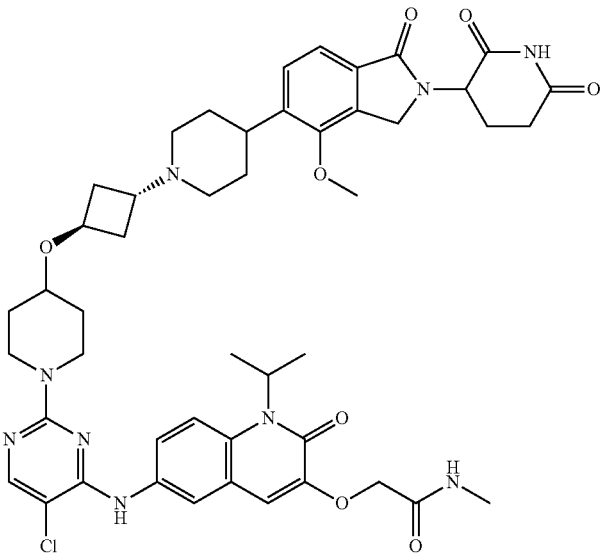 | 2-({6-[(5-chloro-2-{4-[(1r,3r)-3-{4-[2-(2,6-dioxopiperidin-3-yl)-4-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 73 | 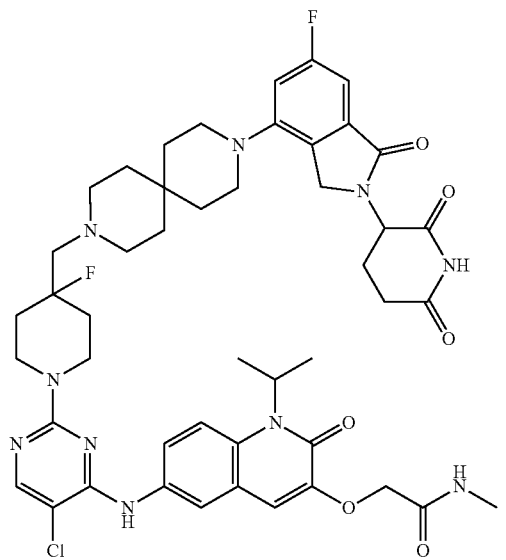 [SMILES: CNC(=O)COc1cc2cc(Nc3nc(N4CCC(F)(CN5CCC6(CC5)CCN(c5cc(F)cc7c5CN(C5CCC(=O)NC5=O)C7=O)CC6)CC4)ncc3Cl)ccc2n(C(C)C)c1=O] | 2-{[6-({5-chloro-2-[4-({9-[2-(2,6-dioxopiperidin-3-yl)-6-fluoro-1-oxo-2,3-dihydro-1H-isoindol-4-yl]-3,9-diazaspiro[5.5]undecan-3-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 74 | 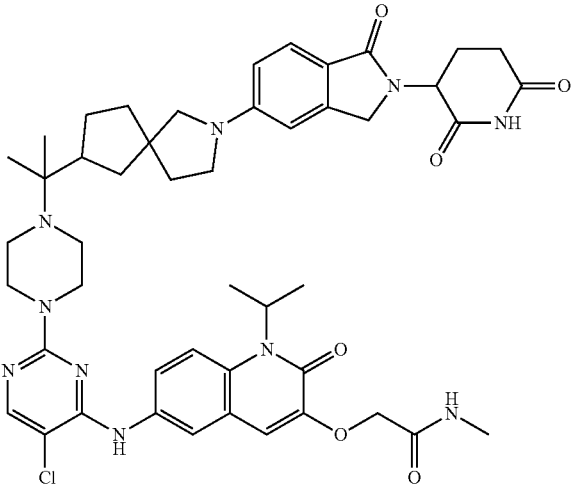 [SMILES: CNC(=O)COc1cc2cc(Nc3nc(N4CCN(C(C)(C)C5CCC6(CCN(c7ccc8c(c7)CN(C7CCC(=O)NC7=O)C8=O)C6)C5)CC4)ncc3Cl)ccc2n(C(C)C)c1=O] | 2-{[6-({5-chloro-2-[4-(2-{2-[2-(2,6-dioxopiperidin-3-yl)-1-oxo-2,3-dihydro-1H-isoindol-5-yl]-2-azaspiro[4.4]nonan-7-yl}propan-2-yl)piperazin-1-yl]pyrimidin-4-yl}amino)-2-oxo-1-(propan-2-yl)-1,2-dihydroquinolin-3-yl]oxy}-N-methylacetamide |
| 75 | 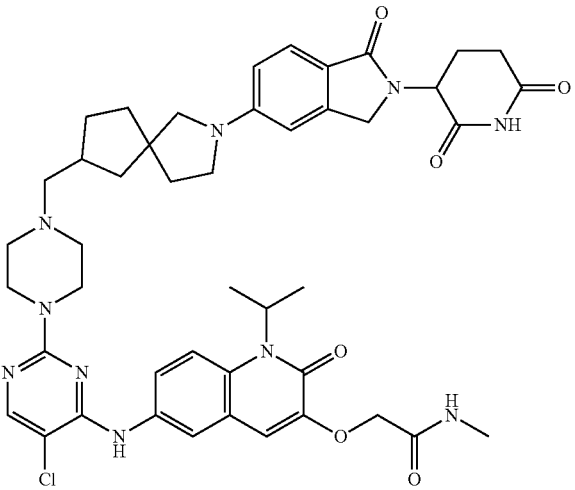 | 2-{[6-({5-chloro-2-[4-({2-[2-(2,6-dioxopiperidin-3-yl)-1-oxo-2,3-dihydro-1H-isoindol-5-yl]-2-azaspiro[4.4]nonan-7-yl}methyl)piperazin-1-yl]pyrimidin-4-yl}amino)-2-oxo-1-(propan-2-yl)-1,2-dihydroquinolin-3-yl]oxy}-N-methylacetamide |
| 76 | 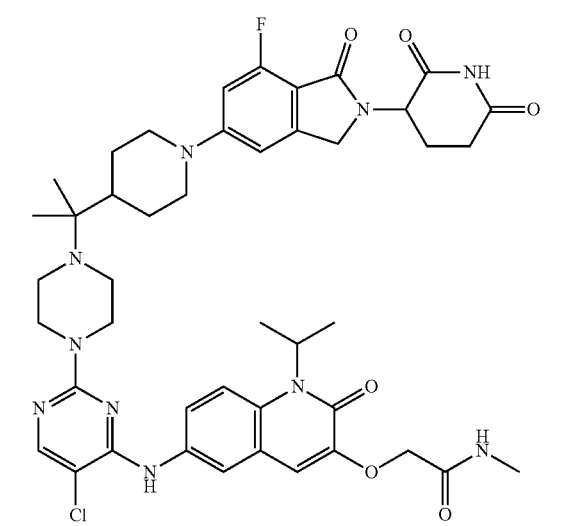 [SMILES: CNC(=O)COc1cc2cc(Nc3nc(N4CCN(C(C)(C)C5CCN(c6cc(F)c7c(c6)CN(C6CCC(=O)NC6=O)C7=O)CC5)CC4)ncc3Cl)ccc2n(C(C)C)c1=O] | 2-{[6-({5-chloro-2-[4-(2-{1-[2-(2,6-dioxopiperidin-3-yl)-7-fluoro-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 77 | 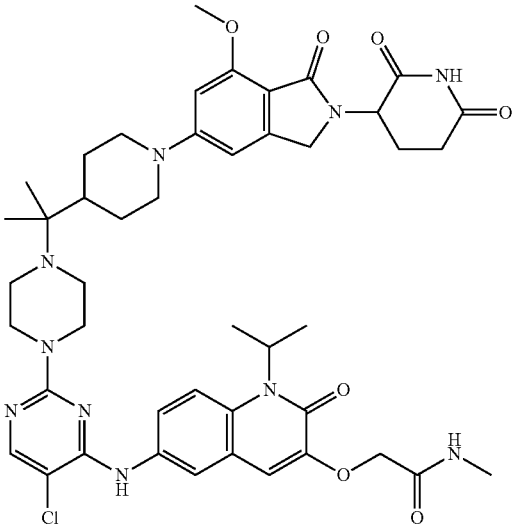 [SMILES: CNC(=O)COc1cc2cc(Nc3nc(N4CCN(C(C)(C)C5CCN(c6cc7c(c(OC)c6)C(=O)N(C6CCC(=O)NC6=O)C7)CC5)CC4)ncc3Cl)ccc2n(C(C)C)c1=O] | 2-{[6-({5-chloro-2-[4-(2-{1-[2-(2,6-dioxopiperidin-3-yl)-7-methoxy-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |
| 78 | 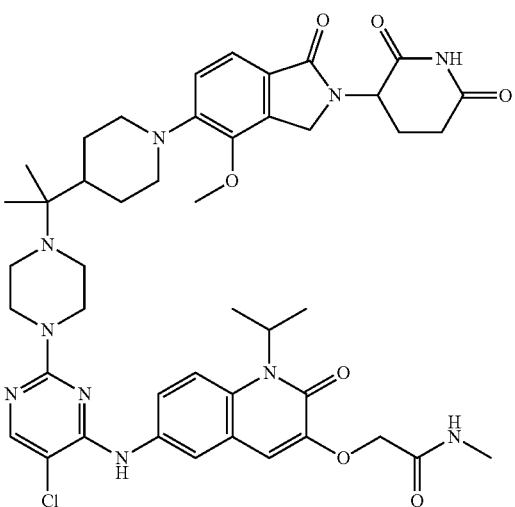 [SMILES: CNC(=O)COc1cc2cc(Nc3nc(N4CCN(C(C)(C)C5CCN(c6ccc7c(c6OC)CN(C6CCC(=O)NC6=O)C7=O)CC5)CC4)ncc3Cl)ccc2n(C(C)C)c1=O] | 2-{[6-({5-chloro-2-[4-(2-{1-[2-(2,6-dioxopiperidin-3-yl)-4-methoxy-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 79 | 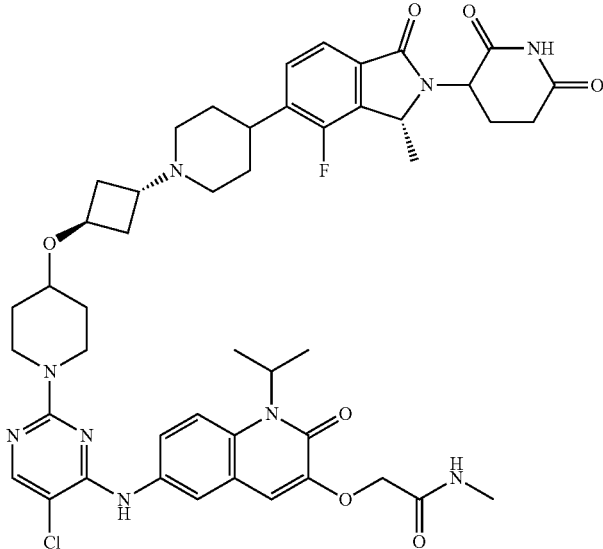 [SMILES: CNC(=O)COc1cc2cc(Nc3nc(N4CCC(O[C@H]5C[C@H](N6CCC(c7ccc8c(c7F)[C@@H](C)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-6-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 80 | 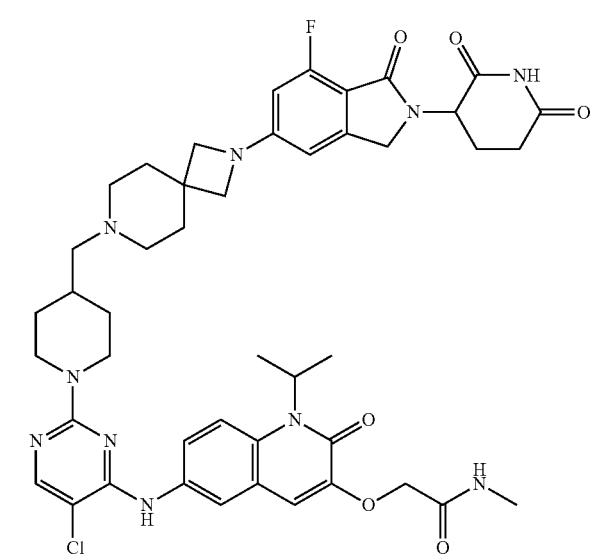 [SMILES: CNC(=O)COc1cc2cc(Nc3nc(N4CCC(CN5CCC6(CC5)CN(c5cc(F)c7c(c5)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-7-fluoro-1-oxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 81 | 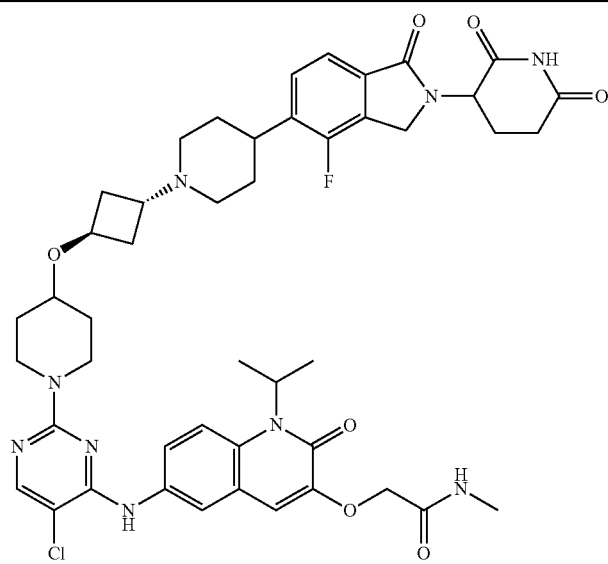 | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 82 | 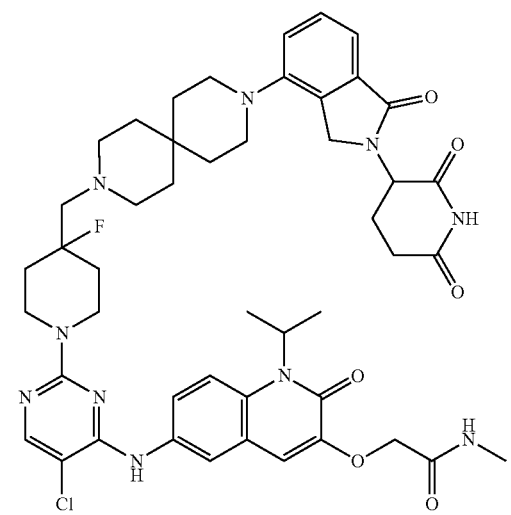 [SMILES: CNC(=O)COc1cc2cc(Nc3nc(N4CCC(F)(CN5CCC6(CC5)CCN(c5cccc7c5CN(C5CCC(=O)NC5=O)C7=O)CC6)CC4)ncc3Cl)ccc2n(C(C)C)c1=O] | 2-{[6-({5-chloro-2-[4-({9-[2-(2,6-dioxopiperidin-3-yl)-1-oxo-2,3-dihydro-1H-isoindol-4-yl]-3,9-diazaspiro[5.5]undecan-3-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 83 | | 2-{[6-({5-chloro-2-[4-({2-[2-(2,6-dioxopiperidin-3-yl)-7-methoxy-1,3-dioxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 84 | | 2-{[6-({5-chloro-2-[4-({7-[2-(2,6-dioxopiperidin-3-yl)-6-fluoro-1-oxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 85 | | 2-{[6-({5-chloro-2-[4-({7-[2-(2,6-dioxopiperidin-3-yl)-6-methoxy-1-oxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 86 | | 2-{[6-({5-chloro-2-[4-({7-[2-(2,6-dioxopiperidin-3-yl)-7-fluoro-1-oxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 87 | | 2-{[6-({5-chloro-2-[4-({7-[2-(2,6-dioxopiperidin-3-yl)-4-fluoro-1-oxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 88 | | 2-{[6-({5-chloro-2-[4-({7-[2-(2,6-dioxopiperidin-3-yl)-4-methoxy-1-oxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 89 | 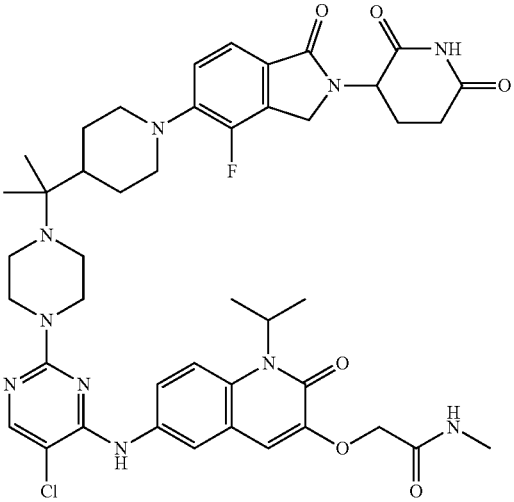 [SMILES: CNC(=O)COc1cc2cc(Nc3nc(N4CCN(C(C)(C)C5CCN(c6ccc7c(c6F)CN(C6CCC(=O)NC6=O)C7=O)CC5)CC4)ncc3Cl)ccc2n(C(C)C)c1=O] | 2-{[6-({5-chloro-2-[4-(2-{1-[2-(2,6-dioxopiperidin-3-yl)-4-fluoro-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |
| 90 | 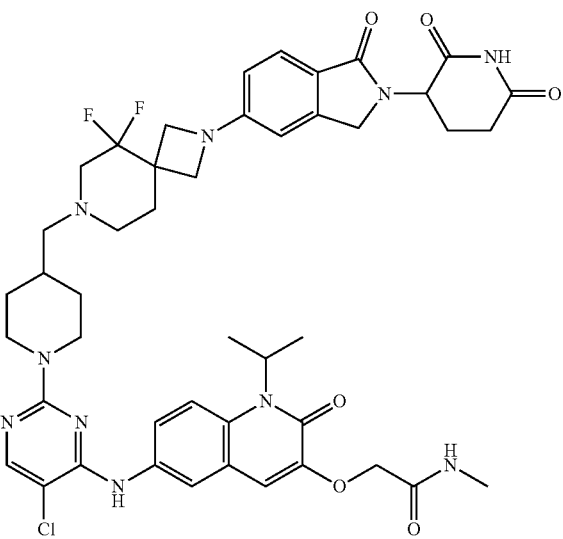 [SMILES: CNC(=O)COc1cc2cc(Nc3nc(N4CCC(CN5CCC6(CN(c7ccc8c(c7)CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 91 | 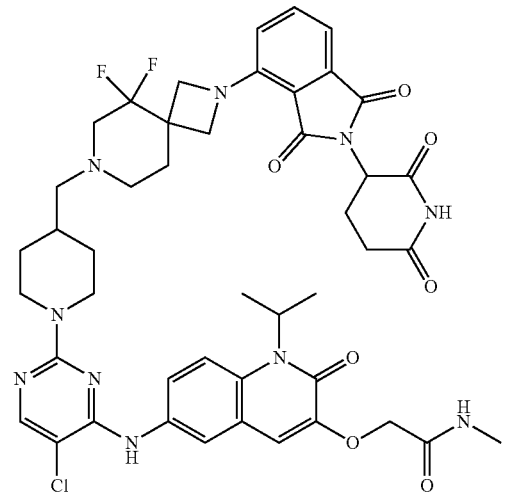 [SMILES: CNC(=O)COc1cc2cc(Nc3nc(N4CCC(CN5CCC6(CN(c7cccc8c7C(=O)N(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-4-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 92 | 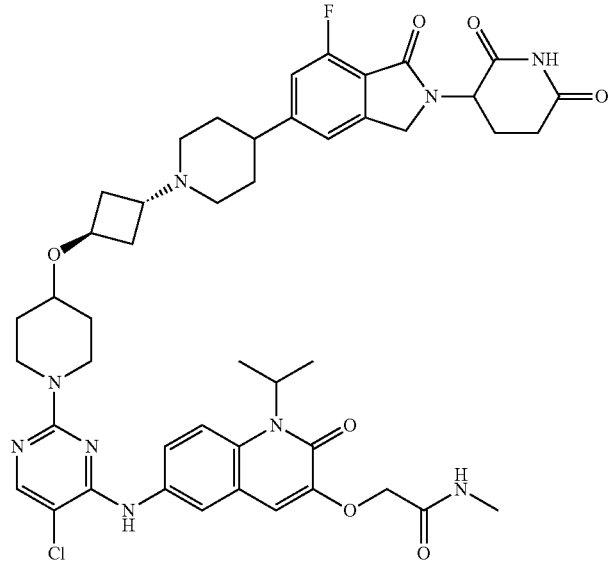 [SMILES: CNC(=O)COc1cc2cc(Nc3nc(N4CCC(O[C@H]5C[C@H](N6CCC(c7cc(F)c8c(c7)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-7-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 93 | 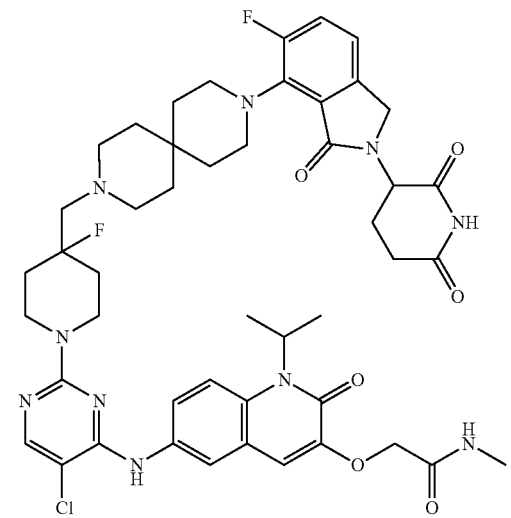 [SMILES: CNC(=O)COc1cc2cc(Nc3nc(N4CCC(F)(CN5CCC6(CC5)CCN(c5c(F)ccc7c5C(=O)N(C5CCC(=O)NC5=O)C7)CC6)CC4)ncc3Cl)ccc2n(C(C)C)c1=O] | 2-{[6-({5-chloro-2-[4-({9-[2-(2,6-dioxopiperidin-3-yl)-5-fluoro-3-oxo-2,3-dihydro-1H-isoindol-4-yl]-3,9-diazaspiro[5.5]undecan-3-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 94 | 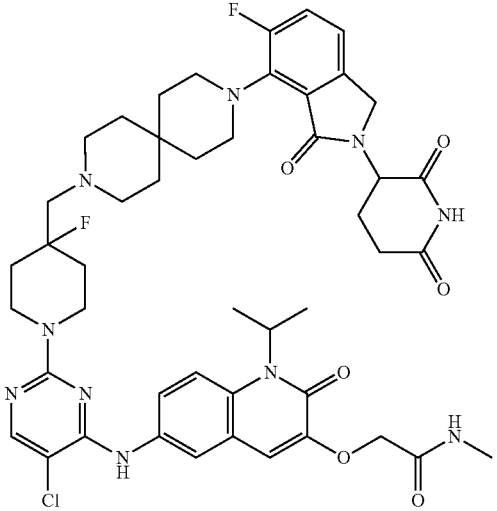 [SMILES: CNC(=O)COc1cc2cc(Nc3nc(N4CCC(F)(CN5CCC6(CC5)CCN(c5c(F)ccc7c5C(=O)N(C5CCC(=O)NC5=O)C7)CC6)CC4)ncc3Cl)ccc2n(C(C)C)c1=O] | 2-{[6-({5-chloro-2-[4-({9-[2-(2,6-dioxopiperidin-3-yl)-7-fluoro-1-oxo-2,3-dihydro-1H-isoindol-4-yl]-3,9-diazaspiro[5.5]undecan-3-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |
| 95 | 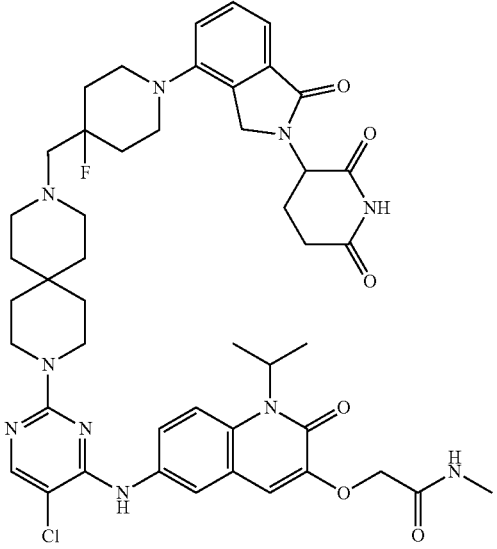 [SMILES: CNC(=O)COc1cc2cc(Nc3nc(N4CCC5(CCN(CC6(F)CCN(c7cccc8c7CN(C7CCC(=O)NC7=O)C8=O)CC6)CC5)CC4)ncc3Cl)ccc2n(C(C)C)c1=O] | 2-{[6-({5-chloro-2-[9-({1-[2-(2,6-dioxopiperidin-3-yl)-1-oxo-2,3-dihydro-1H-isoindol-4-yl]-4-fluoropiperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 96 | 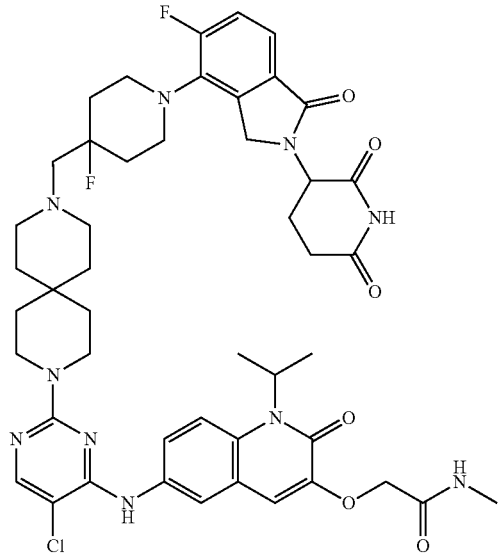 [SMILES: CNC(=O)COc1cc2cc(Nc3nc(N4CCC5(CCN(CC6(F)CCN(c7c(F)ccc8c7CN(C7CCC(=O)NC7=O)C8=O)CC6)CC5)CC4)ncc3Cl)ccc2n(C(C)C)c1=O] | 2-{[6-({5-chloro-2-[9-({1-[2-(2,6-dioxopiperidin-3-yl)-5-fluoro-1-oxo-2,3-dihydro-1H-isoindol-4-yl]-4-fluoropiperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |
| 97 | 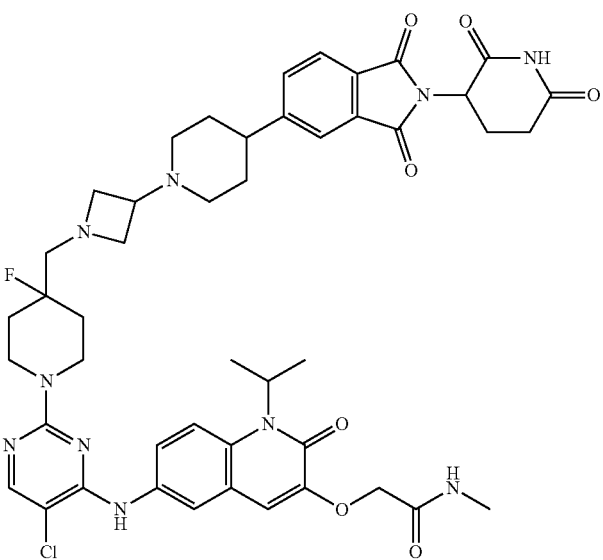 [SMILES: CNC(=O)COc1cc2cc(Nc3nc(N4CCC(F)(CN5CC(N6CCC(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(3-{4-[2-(2,6-dioxopiperidin-3-yl)-1,3-dioxo-2,3-dihydro-1H-isoindol-5-yl]piperidin-1-yl}azetidin-1-yl)methyl]-4-fluoropiperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Compound Number | Parent Mol Structure | IUPAC Name |
|---|---|---|
| 98 | 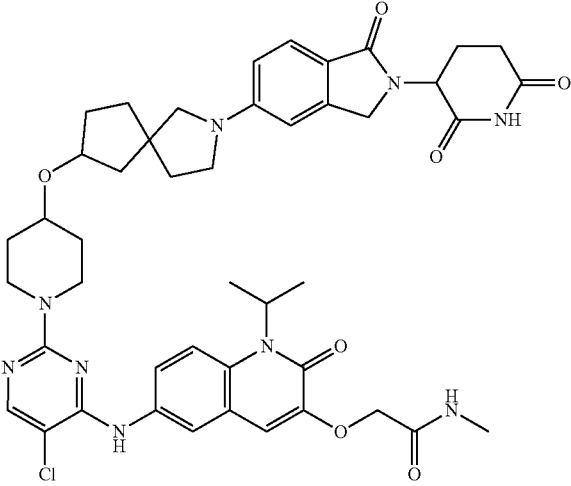 [SMILES: CNC(=O)COc1cc2cc(Nc3nc(N4CCC(OC5CCC6(CCN(c7ccc8c(c7)CN(C7CCC(=O)NC7=O)C8=O)C6)C5)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-2-azaspiro[4.4]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |
| 99 | 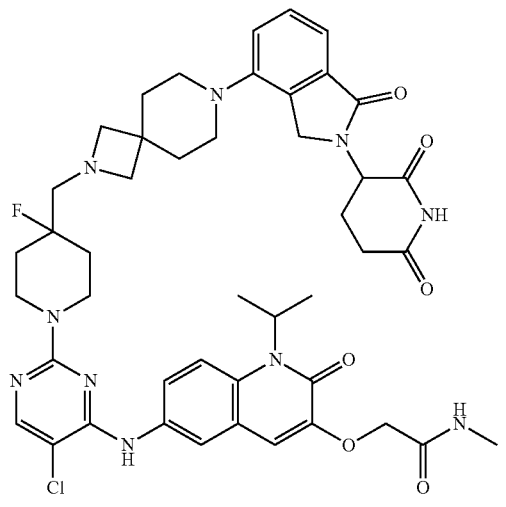 [SMILES: CNC(=O)COc1cc2cc(Nc3nc(N4CCC(F)(CN5CC6(CCN(c7cccc8c7CN(C7CCC(=O)NC7=O)C8=O)CC6)C5)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-4-yl]-2,7-diazaspiro[3.5]nonan-2-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |
| 100 | 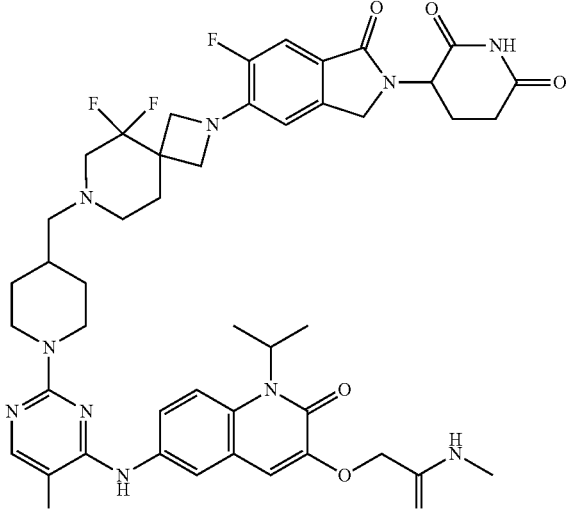 | 2-{[6-({5-chloro-2-[4-({2-[2-(2,6-dioxopiperidin-3-yl)-6-fluoro-1-oxo-2,3-dihydro-1H-isoindol-5-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

487 488

TABLE 1-continued

Exemplary bifunctional compounds of the present disclosure

| Compound Number | Parent Mol Structure | IUPAC Name |
|---|---|---|
| 101 | 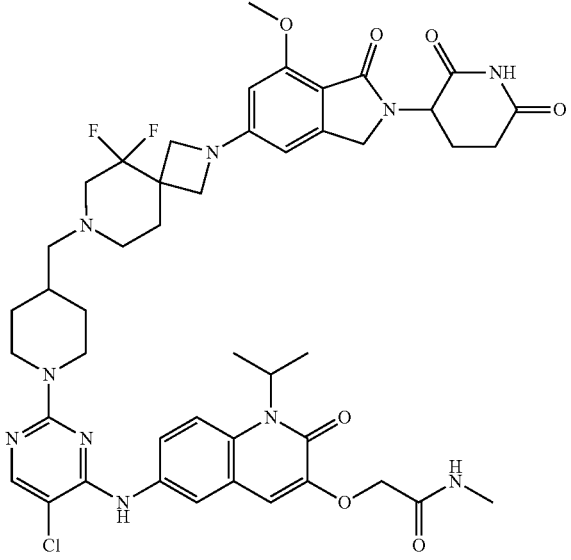 [SMILES: CNC(=O)COc1cc2cc(Nc3nc(N4CCC(CN5CCC6(CN(c7cc8c(c(OC)c7)C(=O)N(C7CCC(=O)NC7=O)C8)C6)C(F)(F)C5)CC4)ncc3Cl)ccc2n(C(C)C)c1=O] | 2-{[6-({5-chloro-2-[4-({2-[2-(2,6-dioxopiperidin-3-yl)-7-methoxy-1-oxo-2,3-dihydro-1H-isoindol-5-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 102 | 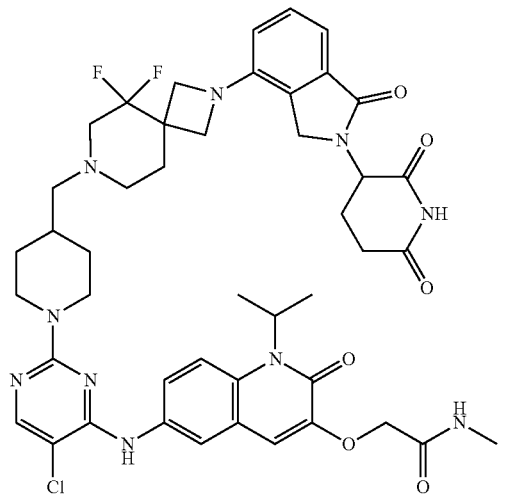 [SMILES: CNC(=O)COc1cc2cc(Nc3nc(N4CCC(CN5CCC6(CN(c7cccc8c7CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-4-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
| --- | --- | --- |
| 103 | | 2-({6-[(5-chloro-2-{4-[(1r,3r)-3-{4-[2-(2,6-dioxopiperidin-3-yl)-7-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 104 | | 2-{[6-({5-chloro-2-[4-(2-{1-[2-(2,6-dioxopiperidin-3-yl)-1-oxo-2,3-dihydro-1H-isoindol-4-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 105 | 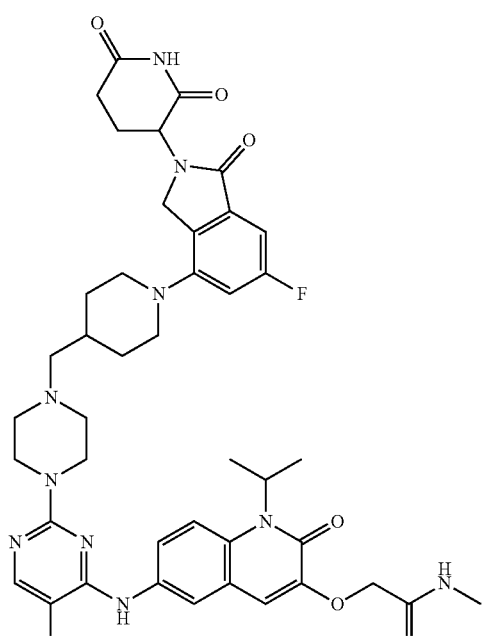 | 2-{[6-({5-chloro-2-[4-({1-[2-(2,6-dioxopiperidin-3-yl)-6-fluoro-1-oxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 106 | 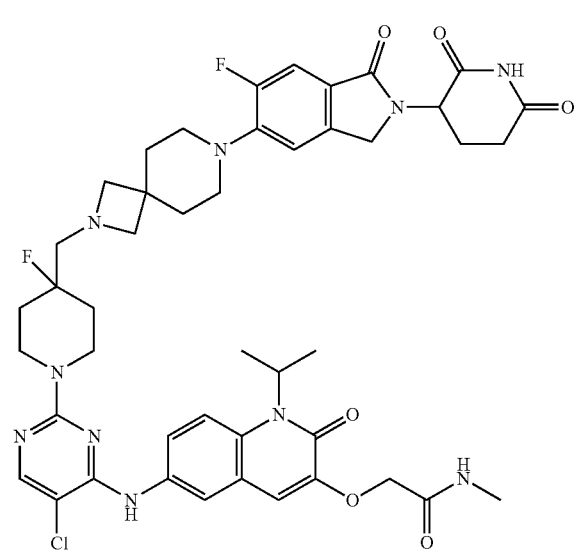 [SMILES: CNC(=O)COc1cc2cc(Nc3nc(N4CCC(F)(CN5CC6(CCN(c7cc8c(cc7F)C(=O)N(C7CCC(=O)NC7=O)C8)CC6)C5)CC4)ncc3Cl)ccc2n(C(C)C)c1=O] | 2-{[6-({5-chloro-2-[4-({7-[2-(2,6-dioxopiperidin-3-yl)-6-fluoro-1-oxo-2,3-dihydro-1H-isoindol-5-yl]-2,7-diazaspiro[3.5]nonan-2-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 107 | | 2-[(6-{[5-chloro-2-(4-{[(1r,4r)-4-({1-[2-(2,6-dioxopiperidin-3-yl)-1,3-dioxo-2,3-dihydro-1H-isoindol-5-yl]azetidin-3-yl}(methyl)amino)cyclohexyl]oxy}piperidin-1-yl)pyrimidin-4-yl]amino}-2-oxo-1-(propan-2-yl)-1,2-dihydroquinolin-3-yl)oxy]-N-methylacetamide |
| 108 | | 2-[(6-{[5-chloro-2-(4-{[(1r,4r)-4-({1-[2-(2,6-dioxopiperidin-3-yl)-1,3-dioxo-2,3-dihydro-1H-isoindol-4-yl]azetidin-3-yl}(methyl)amino)cyclohexyl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 109 | 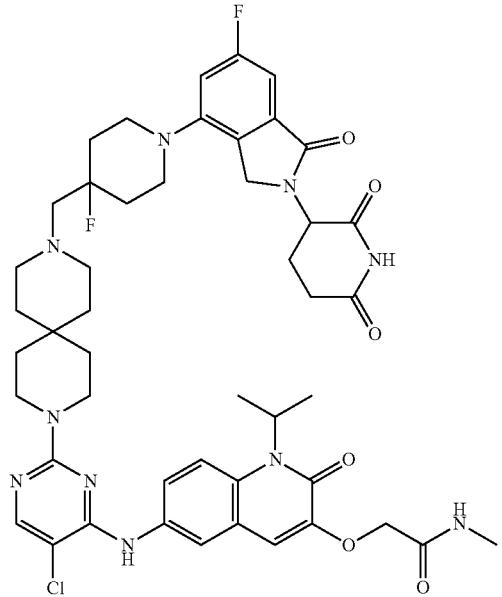 [SMILES: CNC(=O)COc1cc2cc(Nc3nc(N4CCC5(CCN(CC6(F)CCN(c7cc(F)cc8c7CN(C7CCC(=O)NC7=O)C8=O)CC6)CC5)CC4)ncc3Cl)ccc2n(C(C)C)c1=O] | 2-{[6-({5-chloro-2-[9-({1-[2-(2,6-dioxopiperidin-3-yl)-6-fluoro-1-oxo-2,3-dihydro-1H-isoindol-4-yl]-4-fluoropiperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |
| 110 | 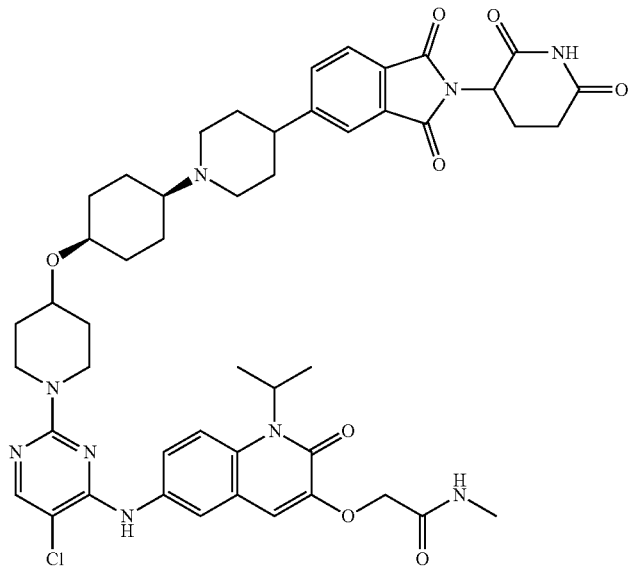 [SMILES: CNC(=O)COc1cc2cc(Nc3nc(N4CCC(O[C@H]5CC[C@@H](N6CCC(c7ccc8c(c7)C(=O)N(C7CCC(=O)NC7=O)C8=O)CC6)CC5)CC4)ncc3Cl)ccc2n(C(C)C)c1=O] | 2-[(6-{[5-chloro-2-(4-{[(1s,4s)-4-{4-[2-(2,6-dioxopiperidin-3-yl)-1,3-dioxo-2,3-dihydro-1H-isoindol-5-yl]piperidin-1-yl}cyclohexyl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 111 | 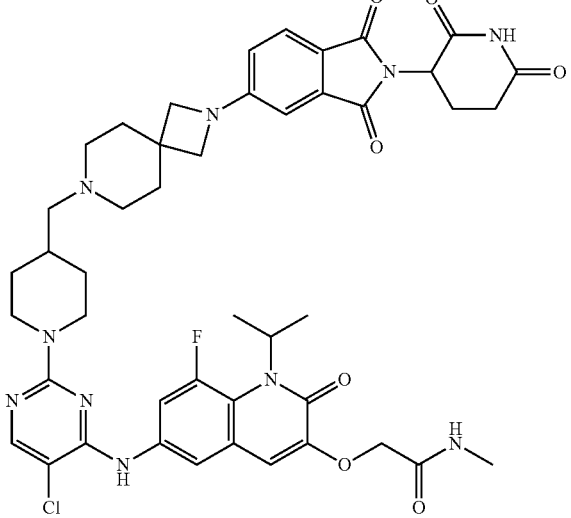 | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyrimidin-4-yl}amino)-8-fluoro-2-oxo-1-(propan-2-yl)-1,2-dihydroquinolin-3-yl]oxy}-N-methylacetamide |
| 112 | 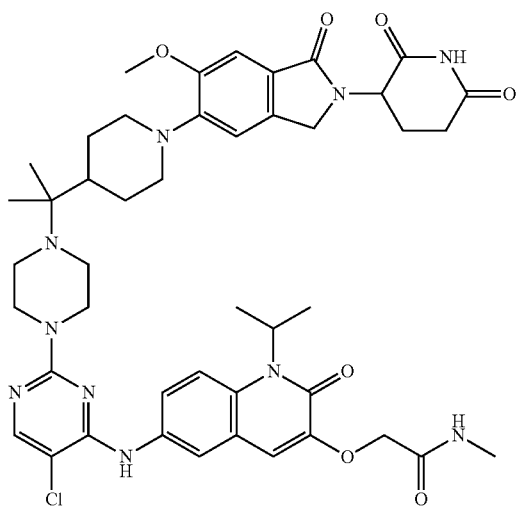 [SMILES: CNC(=O)COc1cc2cc(Nc3nc(N4CCN(C(C)(C)C5CCN(c6cc7c(cc6OC)C(=O)N(C6CCC(=O)NC6=O)C7)CC5)CC4)ncc3Cl)ccc2n(C(C)C)c1=O] | 2-{[6-({5-chloro-2-[4-(2-{1-[2-(2,6-dioxopiperidin-3-yl)-6-methoxy-1-oxo-2,3-dihydro-1H-isoindol-5-yl]piperidin-4-yl}propan-2-yl)piperazin-1-yl]pyrimidin-4-yl}amino)-2-oxo-1-(propan-2-yl)-1,2-dihydroquinolin-3-yl]oxy}-N-methylacetamide |
| 113 | 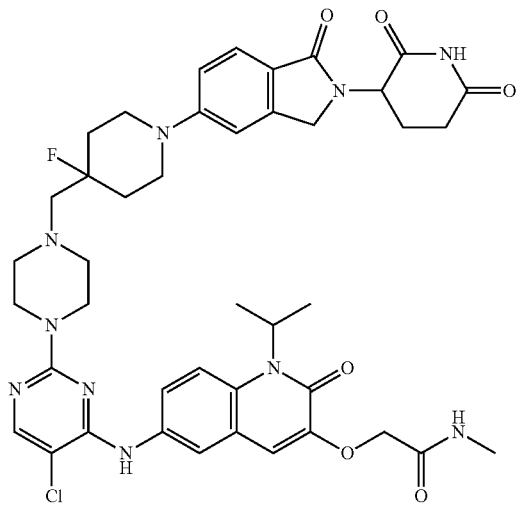 [SMILES: CNC(=O)COc1cc2cc(Nc3nc(N4CCN(CC5(F)CCN(c6ccc7c(c6)CN(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-1-oxo-2,3-dihydro-1H-isoindol-5-yl]-4-fluoropiperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 114 | 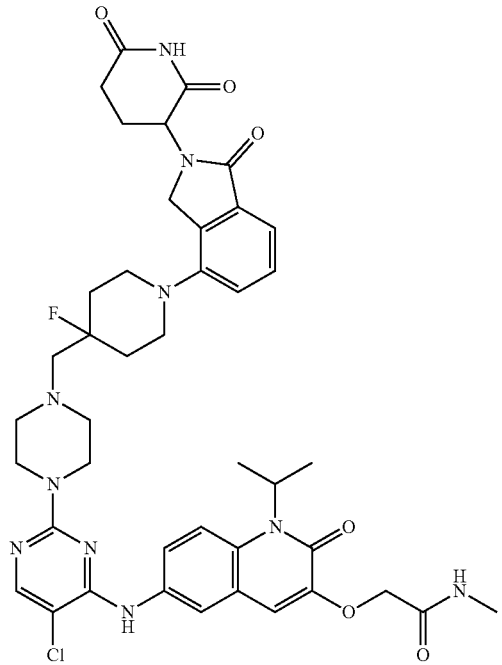 [SMILES: CNC(=O)COc1cc2cc(Nc3nc(N4CCN(CC5(F)CCN(c6cccc7c6CN(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-1-oxo-2,3-dihydro-1H-isoindol-4-yl]-4-fluoropiperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 115 | 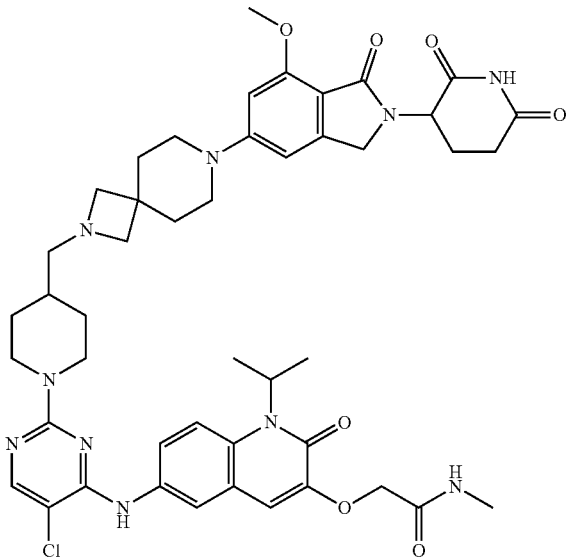 [SMILES: CNC(=O)COc1cc2cc(Nc3nc(N4CCC(CN5CC6(CCN(c7cc8c(c(OC)c7)C(=O)N(C7CCC(=O)NC7=O)C8)CC6)C5)CC4)ncc3Cl)ccc2n(C(C)C)c1=O] | 2-{[6-({5-chloro-2-[4-({7-[2-(2,6-dioxopiperidin-3-yl)-7-methoxy-1-oxo-2,3-dihydro-1H-isoindol-5-yl]-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 116 | 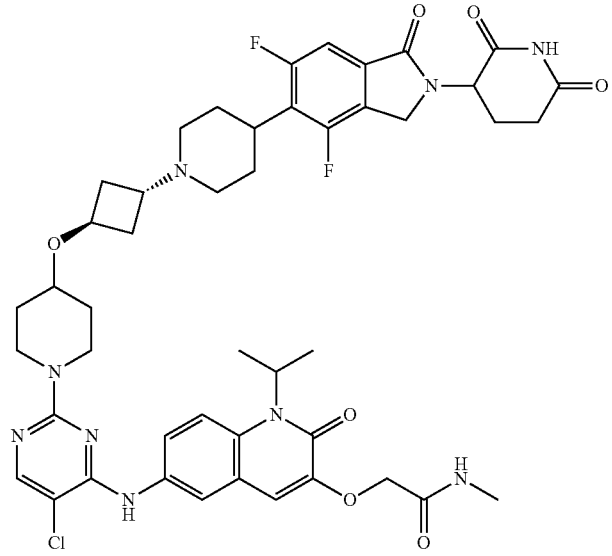 | 2-({6-[(5-chloro-2-{4-[(1r,3r)-3-{4-[2-(2,6-dioxopiperidin-3-yl)-4,6-difluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 117 | 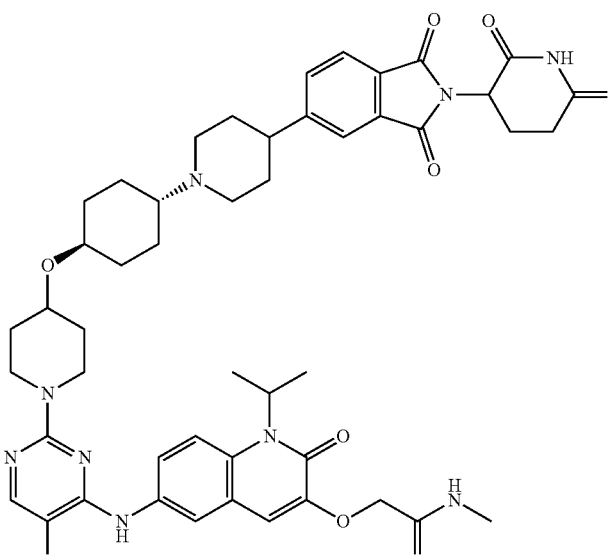 | 2-[(6-{[5-chloro-2-(4-{[(1r,4r)-4-{4-[2-(2,6-dioxopiperidin-3-yl)-1,3-dioxo-2,3-dihydro-1H-isoindol-5-yl]piperidin-1-yl}cyclohexyl]oxy}piperidin-1-yl)pyrimidin-4-yl]amino}-2-oxo-1-(propan-2-yl)-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 118 | 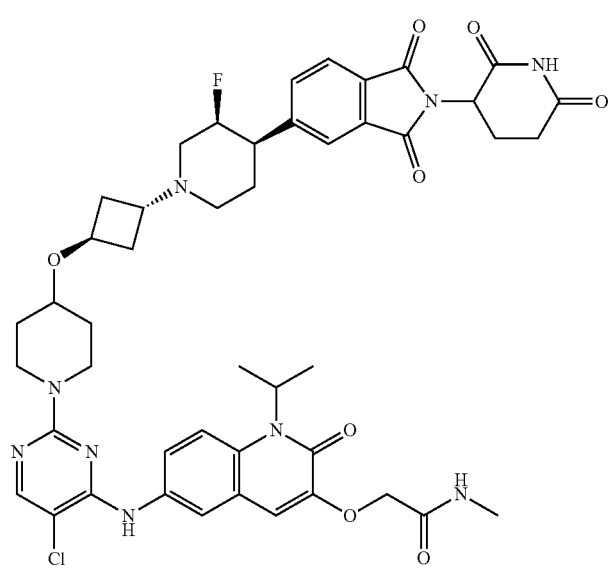 [SMILES: CNC(=O)COc1cc2cc(Nc3nc(N4CCC(O[C@H]5C[C@H](N6CC[C@H](c7ccc8c(c7)C(=O)N(C7CCC(=O)NC7=O)C8=O)[C@H](F)C6)C5)CC4)ncc3Cl)ccc2n(C(C)C)c1=O] | 2-({6-[(5-chloro-2-{4-[(1r,3r)-3-[(3S,4R)-4-[2-(2,6-dioxopiperidin-3-yl)-1,3-dioxo-2,3-dihydro-1H-isoindol-5-yl]-3-fluoropiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 119 | 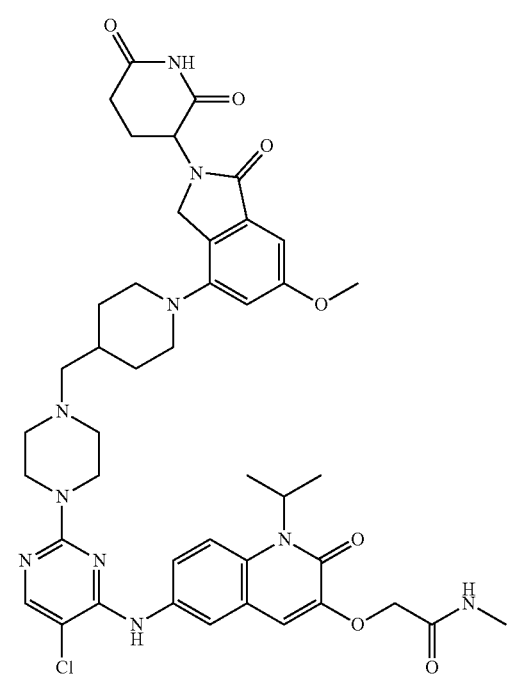 [SMILES: CNC(=O)COc1cc2cc(Nc3nc(N4CCN(CC5CCN(c6cc(OC)cc7c6CN(C6CCC(=O)NC6=O)C7=O)CC5)CC4)ncc3Cl)ccc2n(C(C)C)c1=O] | 2-{[6-({5-chloro-2-[4-({1-[2-(2,6-dioxopiperidin-3-yl)-6-methoxy-1-oxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
| --- | --- | --- |
| 120 | | 2-{[6-({5-chloro-2-[4-({1-[2-(2,6-dioxopiperidin-3-yl)-7-fluoro-1-oxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |
| 121 | | 2-{[6-({5-chloro-2-[4-({1-[2-(2,6-dioxopiperidin-3-yl)-7-methoxy-1-oxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 122 | | 2-{[6-({5-chloro-2-[4-({7-[2-(2,6-dioxopiperidin-3-yl)-1-oxo-2,3-dihydro-1H-isoindol-5-yl]-2,7-diazaspiro[3.5]nonan-2-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |
| 123 | | 2-{[6-({5-chloro-2-[4-({2-[2-(2,6-dioxopiperidin-3-yl)-6-fluoro-1-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |
| 124 | | 2-{[6-({5-chloro-2-[4-({7-[2-(2,6-dioxopiperidin-3-yl)-1,3-dioxo-2,3-dihydro-1H-isoindol-4-yl]-5,5-difluoro-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 125 | 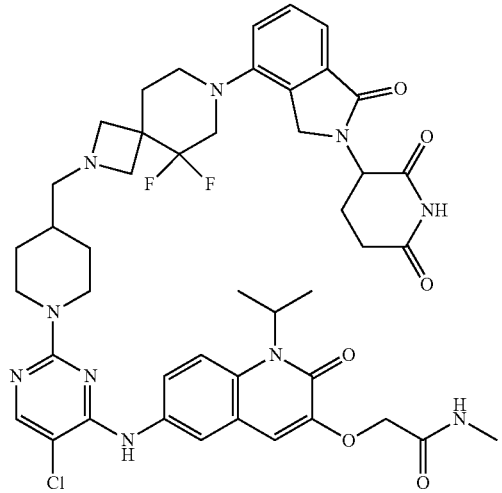 [SMILES: CNC(=O)COc1cc2cc(Nc3nc(N4CCC(CN5CC6(CCN(c7cccc8c7CN(C7CCC(=O)NC7=O)C8=O)CC6(F)F)C5)CC4)ncc3Cl)ccc2n(C(C)C)c1=O] | 2-{[6-({5-chloro-2-[4-({7-[2-(2,6-dioxopiperidin-3-yl)-1-oxo-2,3-dihydro-1H-isoindol-4-yl]-5,5-difluoro-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 126 | 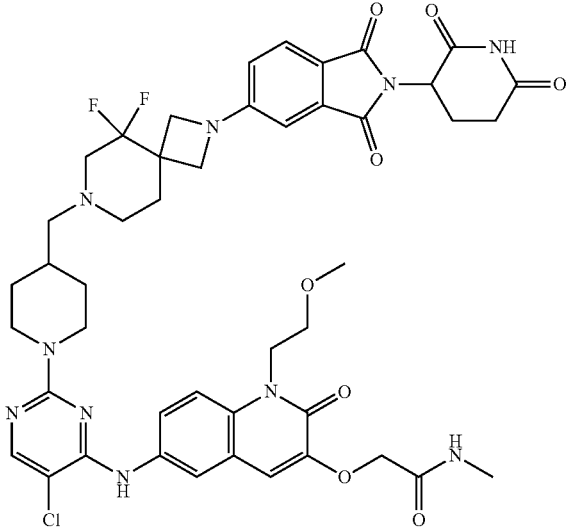 [SMILES: CNC(=O)COc1cc2cc(Nc3nc(N4CCC(CN5CCC6(CN(c7ccc8c(c7)C(=O)N(C7CCC(=O)NC7=O)C8=O)C6)C(F)(F)C5)CC4)ncc3Cl)ccc2n(CCOC)c1=O] | 2-{[6-({5-chloro-2-[4-({2-[2-(2,6-dioxopiperidin-3-yl)-1,3-dioxo-2,3-dihydro-1H-isoindol-5-yl]-5,5-difluoro-2,7-diazaspiro[3.5]nonan-7-yl}methyl)piperidin-1-yl]pyrimidin-4-yl}amino)-1-(2-methoxyethyl)-2-oxo-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 127 | 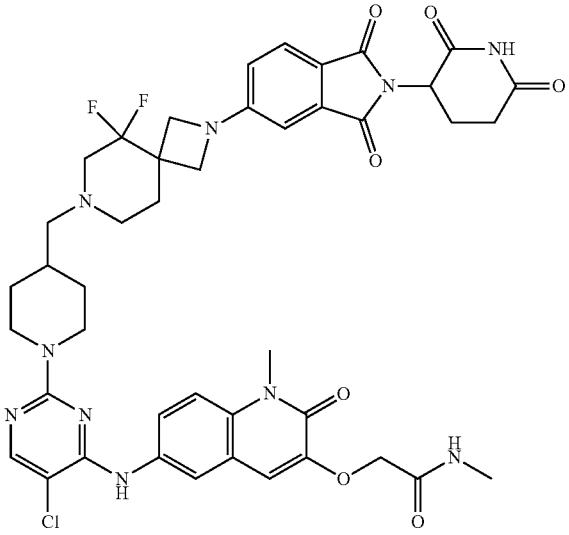 [SMILES: CNC(=O)COc1cc2cc(Nc3nc(N4CCC(CN5CCC6(CN(c7ccc8c(c7)C(=O)N(C7CCC(=O)NC7=O)C8=O)C6)C(F)(F)C5)CC4)ncc3Cl)ccc2n(C)c1=O] | 2-{[6-({5-chloro-2-[4-({2-[2-(2,6-dioxopiperidin-3-yl)-1,3-dioxo-2,3-dihydro-1H-isoindol-5-yl]-5,5-difluoro-2,7-diazaspiro[3.5]nonan-7-yl}methyl)piperidin-1-yl]pyrimidin-4-yl}amino)-1-methyl-2-oxo-1,2-dihydroquinolin-3-yl]oxy}-N-methylacetamide |
| 128 | 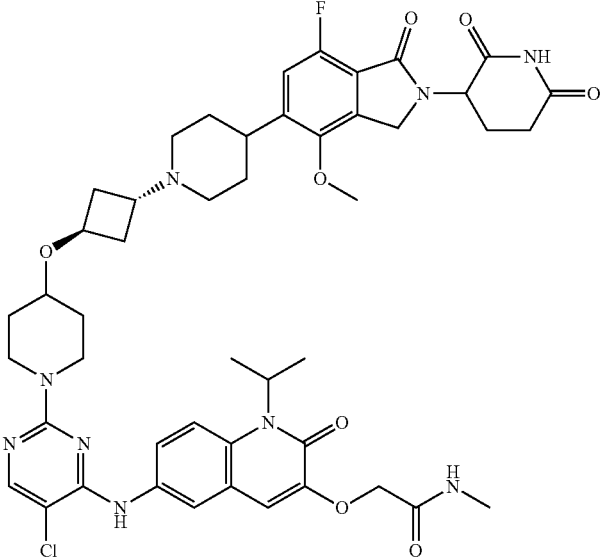 [SMILES: CNC(=O)COc1cc2cc(Nc3nc(N4CCC(O[C@H]5C[C@H](N6CCC(c7cc(F)c8c(c7OC)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-7-fluoro-4-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Compound Number | Parent Mol Structure | IUPAC Name |
|---|---|---|
| 129 | 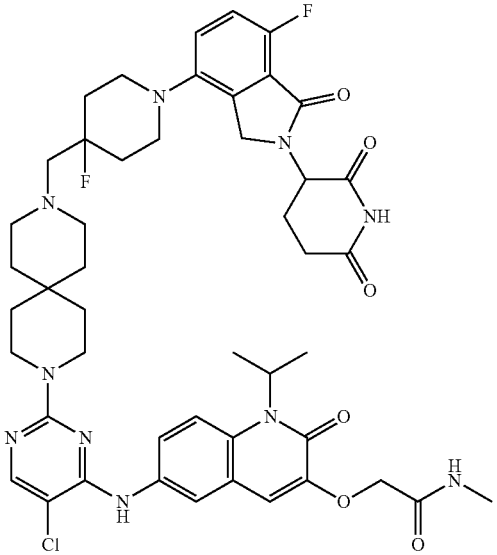 [SMILES: CNC(=O)COc1cc2cc(Nc3nc(N4CCC5(CCN(CC6(F)CCN(c7ccc(F)c8c7CN(C7CCC(=O)NC7=O)C8=O)CC6)CC5)CC4)ncc3Cl)ccc2n(C(C)C)c1=O] | 2-{[6-({5-chloro-2-[9-({1-[2-(2,6-dioxopiperidin-3-yl)-7-fluoro-1-oxo-2,3-dihydro-1H-isoindol-4-yl]-4-fluoropiperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |
| 130 | 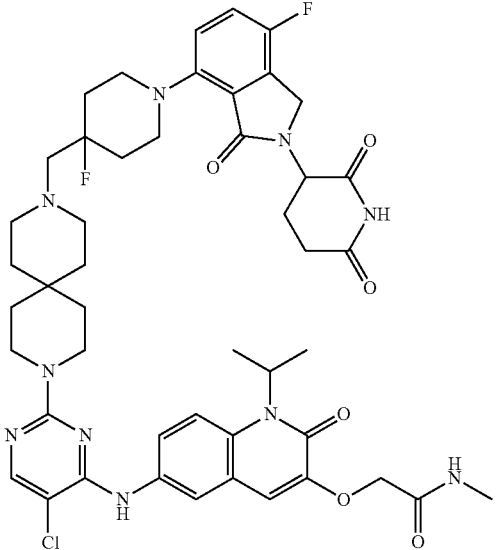 [SMILES: CNC(=O)COc1cc2cc(Nc3nc(N4CCC5(CCN(CC6(F)CCN(c7ccc(F)c8c7C(=O)N(C7CCC(=O)NC7=O)C8)CC6)CC5)CC4)ncc3Cl)ccc2n(C(C)C)c1=O] | 2-{[6-({5-chloro-2-[9-({1-[2-(2,6-dioxopiperidin-3-yl)-7-fluoro-3-oxo-2,3-dihydro-1H-isoindol-4-yl]-4-fluoropiperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 131 | 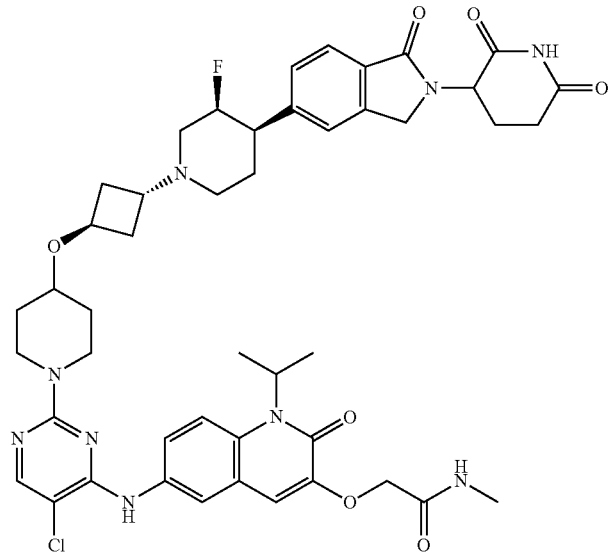 [SMILES: CNC(=O)COc1cc2cc(Nc3nc(N4CCC(O[C@H]5C[C@H](N6CC[C@H](c7ccc8c(c7)CN(C7CCC(=O)NC7=O)C8=O)[C@H](F)C6)C5)CC4)ncc3Cl)ccc2n(C(C)C)c1=O] | 2-({6-[(5-chloro-2-{4-[(1r,3r)-3-[(3S,4R)-4-[2-(2,6-dioxopiperidin-3-yl)-1-oxo-2,3-dihydro-1H-isoindol-5-yl]-3-fluoropiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 132 | 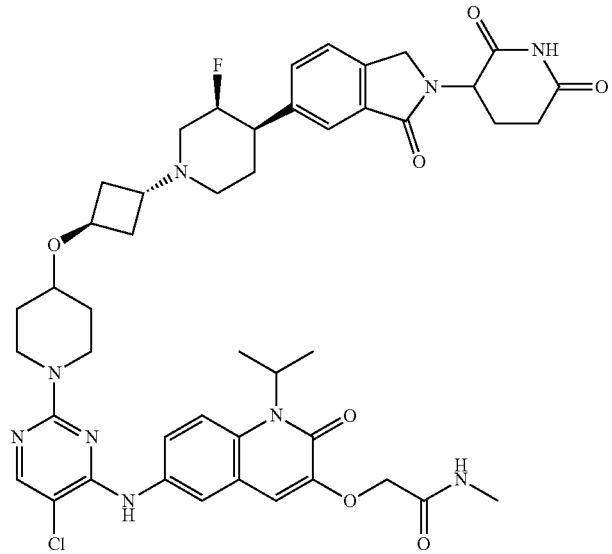 [SMILES: CNC(=O)COc1cc2cc(Nc3nc(N4CCC(O[C@H]5C[C@H](N6CC[C@H](c7ccc8c(c7)C(=O)N(C7CCC(=O)NC7=O)C8)[C@H](F)C6)C5)CC4)ncc3Cl)ccc2n(C(C)C)c1=O] | 2-({6-[(5-chloro-2-{4-[(1r,3r)-3-[(3S,4R)-4-[2-(2,6-dioxopiperidin-3-yl)-3-oxo-2,3-dihydro-1H-isoindol-5-yl]-3-fluoropiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Compound Number | Parent Mol Structure | IUPAC Name |
| --- | --- | --- |
| 133 | | 2-{[6-({5-chloro-2-[4-({2-[2-(2,6-dioxopiperidin-3-yl)-1,3-dioxo-2,3-dihydro-1H-isoindol-5-yl]-1,1-dimethyl-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 134 | | 2-{[6-({5-chloro-2-[4-({2-[2-(2,6-dioxopiperidin-3-yl)-1,3-dioxo-2,3-dihydro-1H-isoindol-5-yl]-5-fluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 135 | | 2-{[6-({5-chloro-2-[4-({7-[2-(2,6-dioxopiperidin-3-yl)-1,3-dioxo-2,3-dihydro-1H-isoindol-5-yl]-5,5-difluoro-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 136 | | 2-{[6-({5-chloro-2-[4-({7-[2-(2,6-dioxopiperidin-3-yl)-1-oxo-2,3-dihydro-1H-isoindol-5-yl]-5,5-difluoro-2,7-diazaspiro[3.5]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

521
522

TABLE 1-continued

Exemplary bifunctional compounds of the present disclosure

| Compound Number | Parent Mol Structure | IUPAC Name |
|---|---|---|
| 137 | 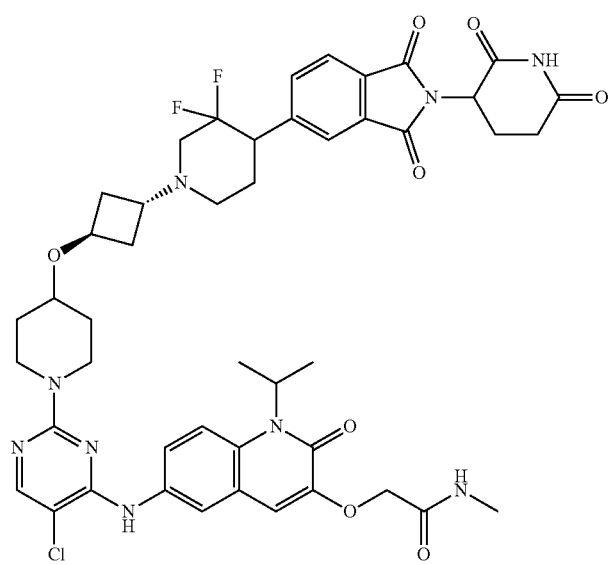 [SMILES: CNC(=O)COc1cc2cc(Nc3nc(N4CCC(O[C@H]5C[C@H](N6CCC(c7ccc8c(c7)C(=O)N(C7CCC(=O)NC7=O)C8=O)C(F)(F)C6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-2,3-dihydro-1H-isoindol-5-yl]-3,3-difluoropiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 138 | 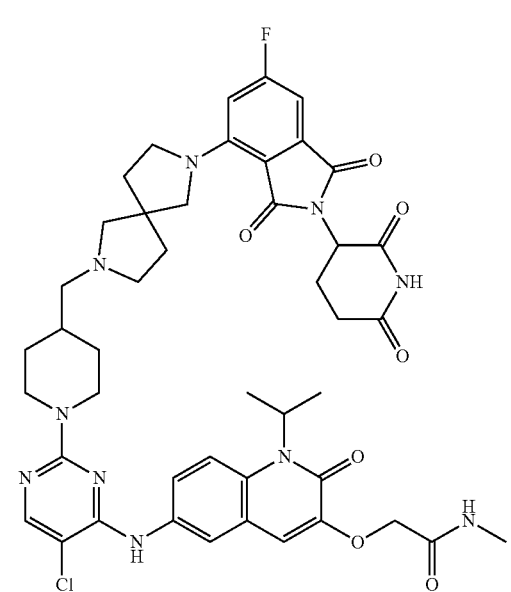 [SMILES: CNC(=O)COc1cc2cc(Nc3nc(N4CCC(CN5CCC6(CCN(c7cc(F)cc8c7C(=O)N(C7CCC(=O)NC7=O)C8=O)C6)C5)CC4)ncc3Cl)ccc2n(C(C)C)c1=O] | 2-{[6-({5-chloro-2-[4-({7-[2-(2,6-dioxopiperidin-3-yl)-6-fluoro-1,3-dioxo-2,3-dihydro-1H-isoindol-4-yl]-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 139 | 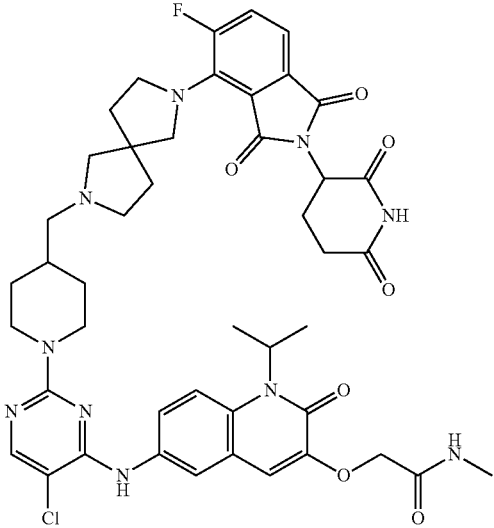 [SMILES: CNC(=O)COc1cc2cc(Nc3nc(N4CCC(CN5CCC6(CCN(c7c(F)ccc8c7C(=O)N(C7CCC(=O)NC7=O)C8=O)C6)C5)CC4)ncc3Cl)ccc2n(C(C)C)c1=O] | 2-{[6-({5-chloro-2-[4-({7-[2-(2,6-dioxopiperidin-3-yl)-5-fluoro-1,3-dioxo-2,3-dihydro-1H-isoindol-4-yl]-2,7-diazaspiro[4.4]nonan-2-yl}methyl)piperidin-1-yl]pyrimidin-4-yl}amino)-2-oxo-1-(propan-2-yl)-1,2-dihydroquinolin-3-yl]oxy}-N-methylacetamide |
| 140 | 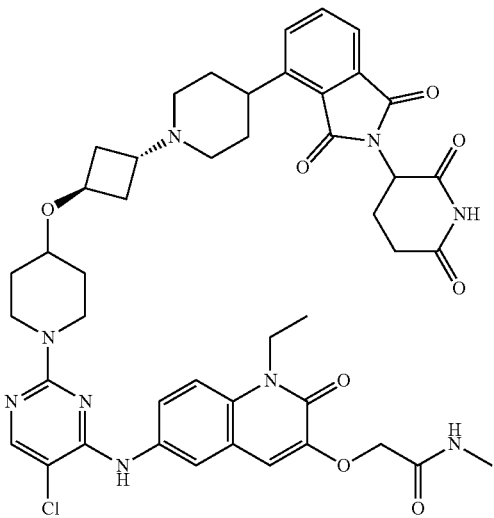 [SMILES: CCn1c(=O)c(OCC(=O)NC)cc2cc(Nc3nc(N4CCC(O[C@H]5C[C@H](N6CCC(c7cccc8c7C(=O)N(C7CCC(=O)NC7=O)C8=O)CC6)C5)CC4)ncc3Cl)ccc21] | 2-({6-[(5-chloro-2-{4-[(1r,3r)-3-{4-[2-(2,6-dioxopiperidin-3-yl)-1,3-dioxo-2,3-dihydro-1H-isoindol-4-yl]piperidin-1-yl}cyclobutoxy]piperidin-1-yl}pyrimidin-4-yl)amino]-1-ethyl-2-oxo-1,2-dihydroquinolin-3-yl}oxy)-N-methylacetamide |

TABLE 1-continued

Exemplary bifunctional compounds of the present disclosure

| Compound Number | Parent Mol Structure | IUPAC Name |
| --- | --- | --- |
| 141 | | 2-{[6-({5-chloro-2-[(3S)-3-({[2-(2,6-dioxopiperidin-3-yl)-1,3-dioxo-2,3-dihydro-1H-isoindol-4-yl]oxy}methyl)piperidin-1-yl]pyrimidin-4-yl}amino)-1-[2-(dimethylamino)ethyl]-2-oxo-1,2-dihydroquinolin-3-yl]oxy}-N-methylacetamide |
| 142 | | 2-{[6-({5-chloro-2-[2-({1-[2-(2,6-dioxopiperidin-3-yl)-1,3-dioxo-2,3-dihydro-1H-isoindol-5-yl]piperidin-4-yl}methyl)-5-oxa-2,8-diazaspiro[3.5]nonan-8-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 143 | 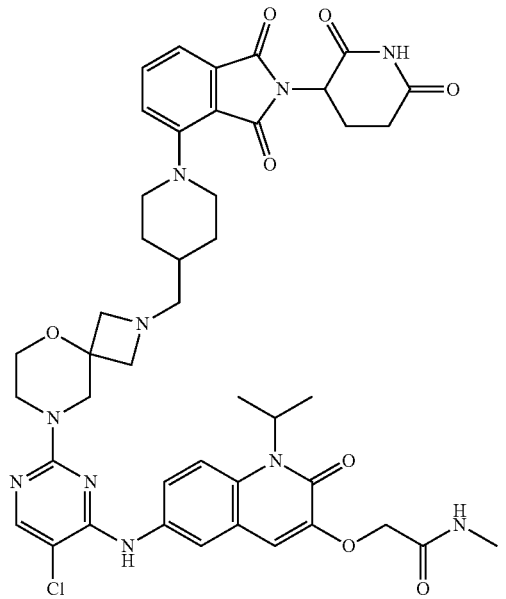 [SMILES: CNC(=O)COc1cc2cc(Nc3nc(N4CCOC5(CN(CC6CCN(c7cccc8c7C(=O)N(C7CCC(=O)NC7=O)C8=O)CC6)C5)C4)ncc3Cl)ccc2n(C(C)C)c1=O] | 2-{[6-({5-chloro-2-[2-({1-[2-(2,6-dioxopiperidin-3-yl)-1,3-dioxo-2,3-dihydro-1H-isoindol-4-yl]piperidin-4-yl}methyl)-5-oxa-2,8-diazaspiro[3.5]nonan-8-yl]pyrimidin-4-yl}amino)-2-oxo-1-(propan-2-yl)-1,2-dihydroquinolin-3-yl]oxy}-N-methylacetamide |
| 144 | 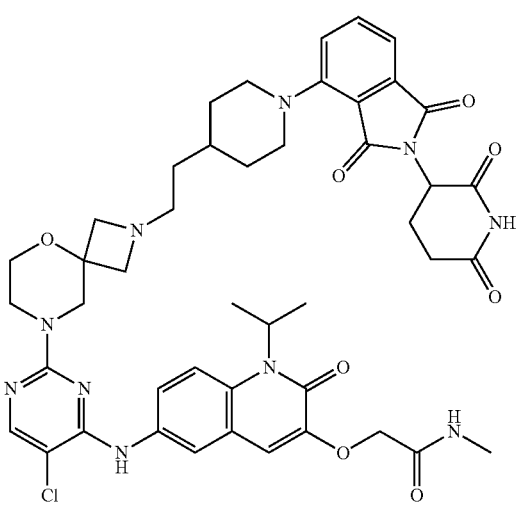 [SMILES: CNC(=O)COc1cc2cc(Nc3nc(N4CCOC5(CN(CCC6CCN(c7cccc8c7C(=O)N(C7CCC(=O)NC7=O)C8=O)CC6)C5)C4)ncc3Cl)ccc2n(C(C)C)c1=O] | 2-{[6-({5-chloro-2-[2-(2-{1-[2-(2,6-dioxopiperidin-3-yl)-1,3-dioxo-2,3-dihydro-1H-isoindol-4-yl]piperidin-4-yl}ethyl)-5-oxa-2,8-diazaspiro[3.5]nonan-8-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 145 | 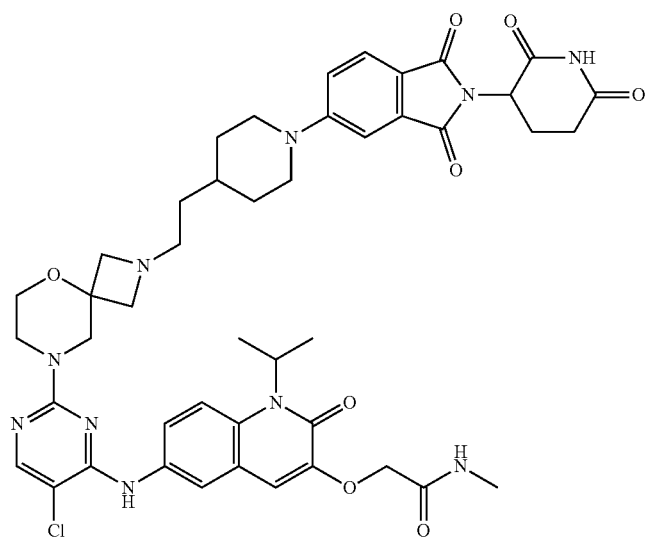 [SMILES: CNC(=O)COc1cc2cc(Nc3nc(N4CCOC5(CN(CCC6CCN(c7ccc8c(c7)C(=O)N(C7CCC(=O)NC7=O)C8=O)CC6)C5)C4)ncc3Cl)ccc2n(C(C)C)c1=O] | 2-{[6-({5-chloro-2-[2-(2-{1-[2-(2,6-dioxopiperidin-3-yl)-1,3-dioxo-2,3-dihydro-1H-isoindol-5-yl]piperidin-4-yl}ethyl)-5-oxa-2,8-diazaspiro[3.5]nonan-8-yl]pyrimidin-4-yl}amino)-2-oxo-1-(propan-2-yl)-1,2-dihydroquinolin-3-yl]oxy}-N-methylacetamide |
| 146 | 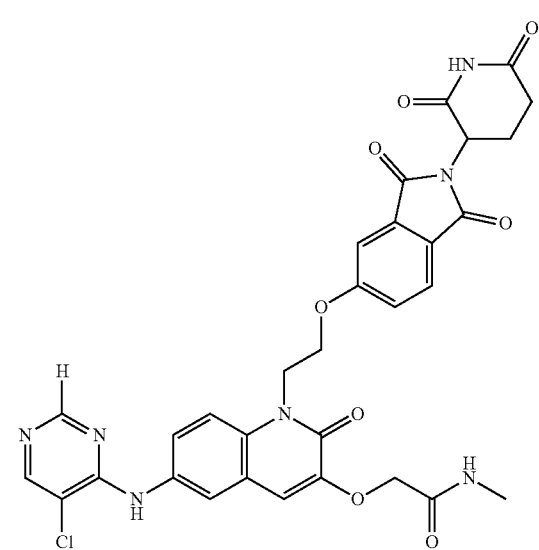 [SMILES: CNC(=O)COc1cc2cc(Nc3ncncc3Cl)ccc2n(CCOc2ccc3c(c2)C(=O)N(C2CCC(=O)NC2=O)C3=O)c1=O] | 2-({6-[(5-chloropyrimidin-4-yl)amino]-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl}oxy)-N-methylacetamide |

TABLE 1-continued

Exemplary bifunctional compounds of the present disclosure

| Compound Number | Parent Mol Structure | IUPAC Name |
| --- | --- | --- |
| 147 | | 2-({6-[(5-chloro-2-methylpyrimidin-4-yl)amino]-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl}oxy)-N-methylacetamide |
| 148 | | 2-({6-[(5-chloro-2-{4-[(3-{4-[2-(2,6-dioxopiperidin-3-yl)-1,3-dioxo-2,3-dihydro-1H-isoindol-4-yl]piperidin-1-yl}cyclopentyl)oxy]piperidin-1-yl}pyrimidin-4-yl)amino]-2-oxo-1-(propan-2-yl)-1,2-dihydroquinolin-3-yl}oxy)-N-methylacetamide |
| 149 | | 2-[(6-{[5-chloro-2-(1H-pyrazol-1-yl)pyrimidin-4-yl]amino}-1-(2-{[2-(2,6-dioxopiperidin-3-yl)-1,3-dioxo-2,3-dihydro-1H-isoindol-5-yl]oxy}ethyl)-2-oxo-1,2-dihydroquinolin-3-yl)oxy]-N-methylacetamide |

TABLE 1-continued

Exemplary bifunctional compounds of the present disclosure

| Compound Number | Parent Mol Structure | IUPAC Name |
|---|---|---|
| 150 | 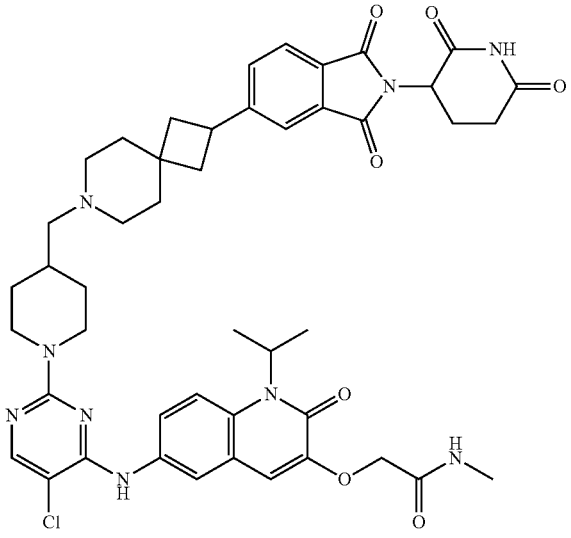 [SMILES: CNC(=O)COc1cc2cc(Nc3nc(N4CCC(CN5CCC6(CC5)CC(c5ccc7c(c5)C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-5-yl]-7-azaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 151 | 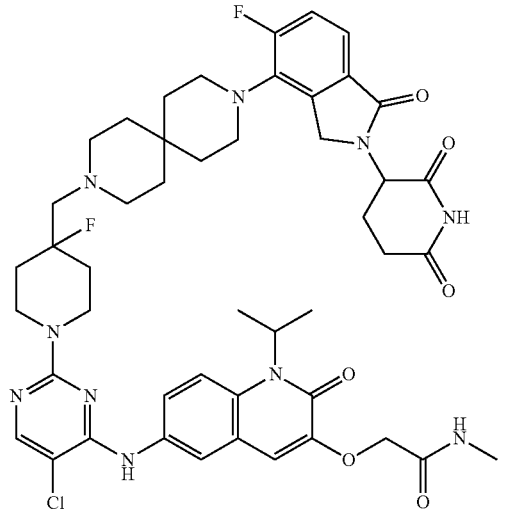 [SMILES: CNC(=O)COc1cc2cc(Nc3nc(N4CCC(F)(CN5CCC6(CC5)CCN(c5c(F)ccc7c5CN(C5CCC(=O)NC5=O)C7=O)CC6)CC4)ncc3Cl)ccc2n(C(C)C)c1=O] | 2-{[6-({5-chloro-2-[4-({9-[2-(2,6-dioxopiperidin-3-yl)-5-fluoro-1-oxo-2,3-dihydro-1H-isoindol-4-yl]-3,9-diazaspiro[5.5]undecan-3-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 152 | 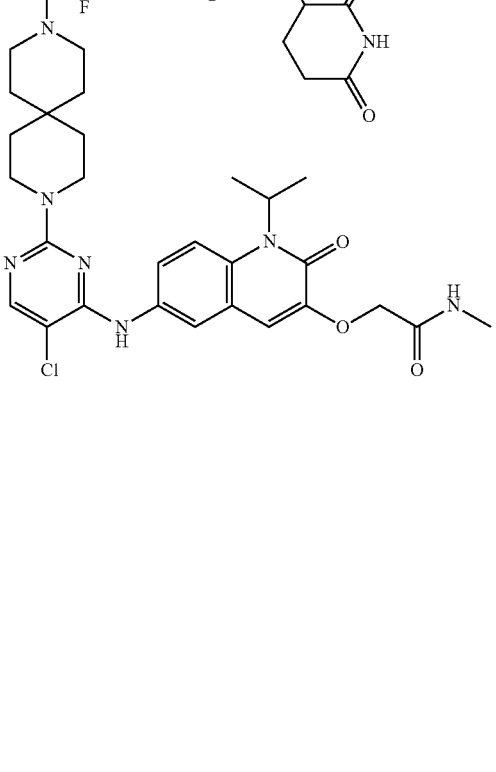 | 2-{[6-({5-chloro-2-[9-({1-[2-(2,6-dioxopiperidin-3-yl)-5-fluoro-3-oxo-2,3-dihydro-1H-isoindol-4-yl]-4-fluoropiperidin-4-yl}methyl)-3,9-diazaspiro[5.5]undecan-3-yl]pyrimidin-4-yl}amino)-2-oxo-1-(propan-2-yl)-1,2-dihydroquinolin-3-yl]oxy}-N-methylacetamide |
| 153 | 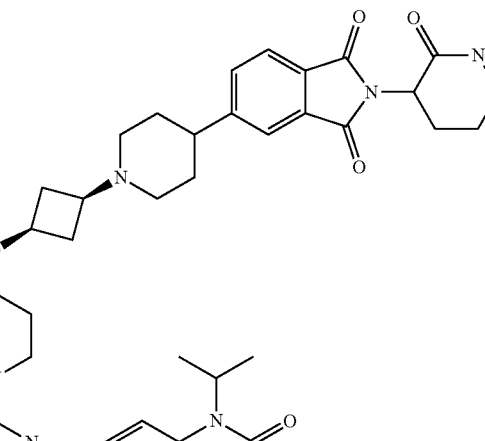 | 2-({6-[(5-chloro-2-{4-[(1s,3s)-3-{4-[2-(2,6-dioxopiperidin-3-yl)-1,3-dioxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 1-continued

Exemplary bifunctional compounds of the present disclosure

| Compound Number | Parent Mol Structure | IUPAC Name |
|---|---|---|
| 154 | | 2-{[6-({5-chloro-2-[2-(2-{4-[2-(2,6-dioxopiperidin-3-yl)-1-oxo-2,3-dihydro-1H-isoindol-4-yl]piperidin-1-yl}propan-2-yl)-7-azaspiro[3.5]nonan-7-yl]pyrimidin-4-yl}amino)-2-oxo-1-(propan-2-yl)-1,2-dihydroquinolin-3-yl]oxy}-N-methylacetamide |
| 155 | | 2-{[6-({5-chloro-2-[4-({3-[2-(2,6-dioxopiperidin-3-yl)-1,3-dioxo-2,3-dihydro-1H-isoindol-5-yl]-3-azabicyclo[3.1.0]hexan-6-yl}methyl)piperazin-1-yl]pyrimidin-4-yl}amino)-2-oxo-1-(propan-2-yl)-1,2-dihydroquinolin-3-yl]oxy}-N-methylacetamide |
| 156 | | 2-{[6-({5-chloro-2-[4-({3-[2-(2,6-dioxopiperidin-3-yl)-1,3-dioxo-2,3-dihydro-1H-isoindol-4-yl]-3-azabicyclo[3.1.0]hexan-6-yl}methyl)piperazin-1-yl]pyrimidin-4-yl}amino)-2-oxo-1-(propan-2-yl)-1,2-dihydroquinolin-3-yl]oxy}-N-methylacetamide |

TABLE 1-continued

Exemplary bifunctional compounds of the present disclosure

| Compound Number | Parent Mol Structure | IUPAC Name |
|---|---|---|
| 157 | 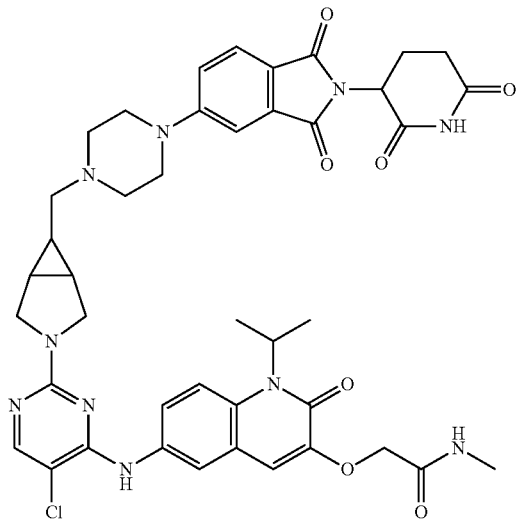 [SMILES: CNC(=O)COc1cc2cc(Nc3nc(N4CC5C(CN6CCN(c7ccc8c(c7)C(=O)N(C7CCC(=O)NC7=O)C8=O)CC6)C5C4)ncc3Cl)ccc2n(C(C)C)c1=O] | 2-{[6-({5-chloro-2-[6-({4-[2-(2,6-dioxopiperidin-3-yl)-1,3-dioxo-2,3-dihydro-1H-isoindol-5-yl]piperazin-1-yl}methyl)-3-azabicyclo[3.1.0]hexan-3-yl]pyrimidin-4-yl}amino)-2-oxo-1-(propan-2-yl)-1,2-dihydroquinolin-3-yl]oxy}-N-methylacetamide |
| 158 | 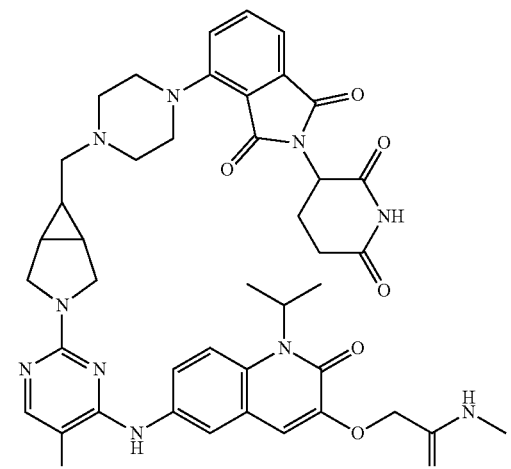 | 2-{[6-({5-chloro-2-[6-({4-[2-(2,6-dioxopiperidin-3-yl)-1,3-dioxo-2,3-dihydro-1H-isoindol-4-yl]piperazin-1-yl}methyl)-3-azabicyclo[3.1.0]hexan-3-yl]pyrimidin-4-yl}amino)-2-oxo-1-(propan-2-yl)-1,2-dihydroquinolin-3-yl]oxy}-N-methylacetamide |

TABLE 2

Additional exemplary bifunctional compounds of the present disclosure

| Compound Number | Parent Mol Structure | IUPAC Name | Analogously Made to Experimental Procedure Ex. Number |
|---|---|---|---|
| 159 | 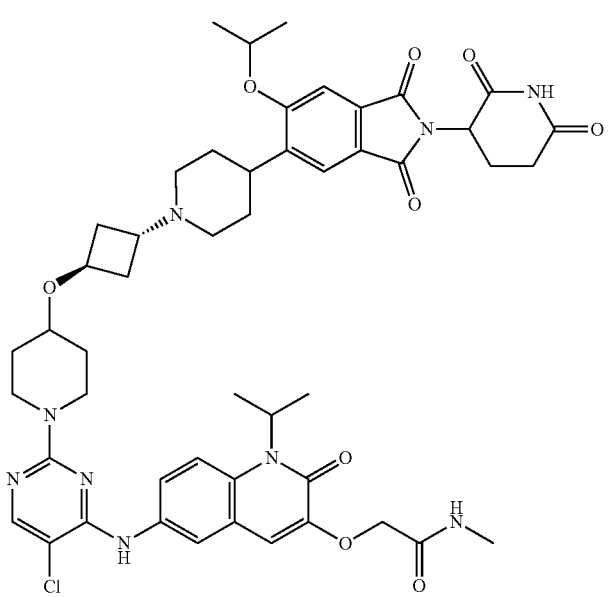 [SMILES: CNC(=O)COc1cc2cc(Nc3nc(N4CCC(O[C@H]5C[C@H](N6CCC(c7cc8c(cc7OC(C)C)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-6-(propan-2-yloxy)-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 34 |
| 160 | 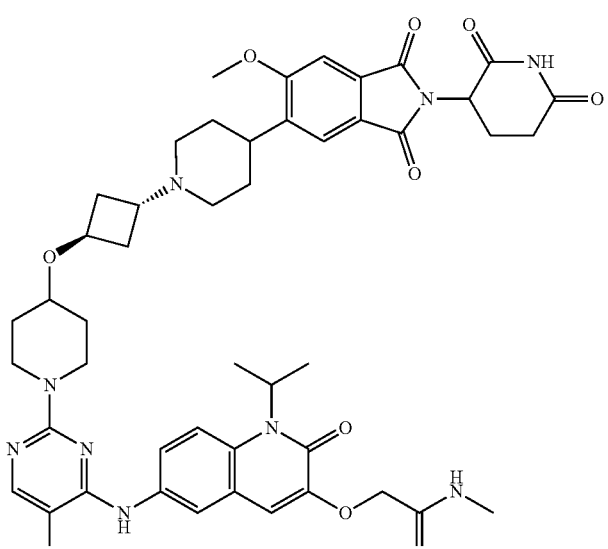 | 2-({6-[(5-chloro-2-{4-[(1r,3r)-3-{4-[2-(2,6-dioxopiperidin-3-yl)-6-methoxy-1,3-dioxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 34 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 161 | | 2-{[6-({5-chloro-2-[4-({2-[2-(2,6-dioxopiperidin-3-yl)-1-oxo-2,3-dihydro-1H-isoindol-5-yl]-2,7-diazaspiro[3.5]nonan-7-yl}methyl)piperidin-1-yl]pyrimidin-4-yl}amino)-5-fluoro-2-oxo-1-(propan-2-yl)-1,2-dihydroquinolin-3-yl]oxy}-N-methylacetamide | 35 |
| 162 | | 2-{[6-({5-chloro-2-[4-({2-[2-(2,6-dioxopiperidin-3-yl)-4-fluoro-1-oxo-2,3-dihydro-1H-isoindol-5-yl]-1,1-dimethyl-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 36 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 163 | 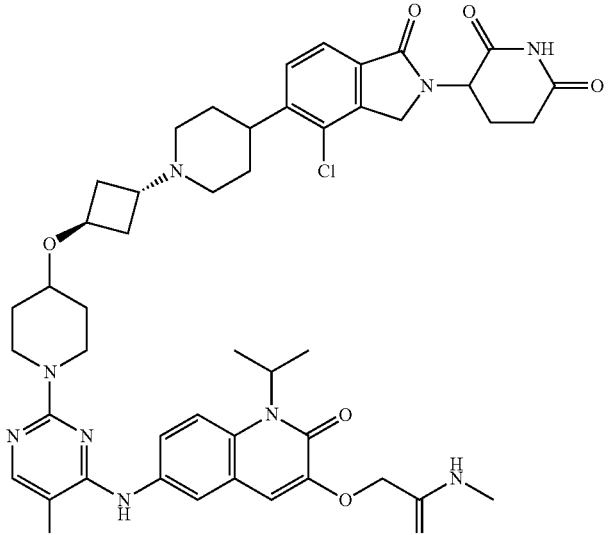 | 2-({6-[(5-chloro-2-{4-[(1r,3r)-3-{4-[4-chloro-2-(2,6-dioxopiperidin-3-yl)-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 37 |
| 164 | 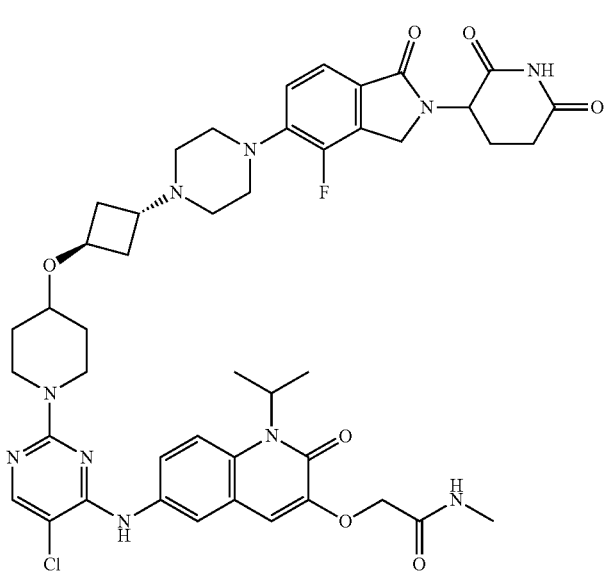 | 2-({6-[(5-chloro-2-{4-[(1r,3r)-3-{4-[2-(2,6-dioxopiperidin-3-y])-4-fluoro-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 38 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 165 | 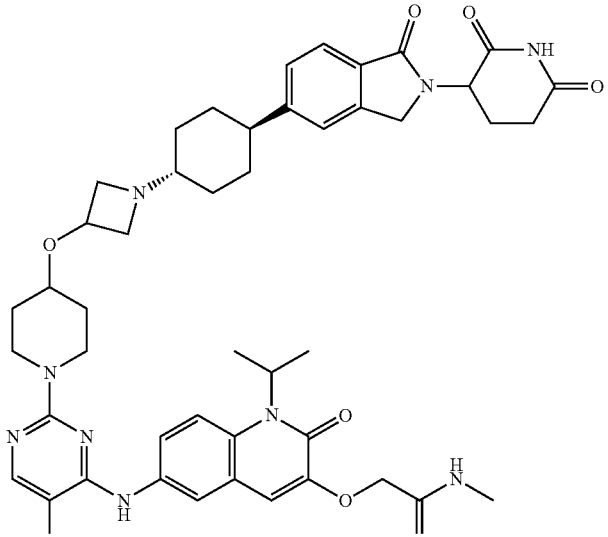 | 2-{[6-({5-chloro-2-[4-({1-[(1r,4r)-4-[2-(2,6-dioxopiperidin-3-yl)-1-oxo-2,3-dihydro-1H-isoindol-5-yl]cyclohexyl]azetidin-3-yl}oxy)piperidin-1-yl]pyrimidin-4-yl}amino)-2-oxo-1-(propan-2-yl)-1,2-dihydroquinolin-3-yl]oxy}-N-methylacetamide | 39 |
| 166 | 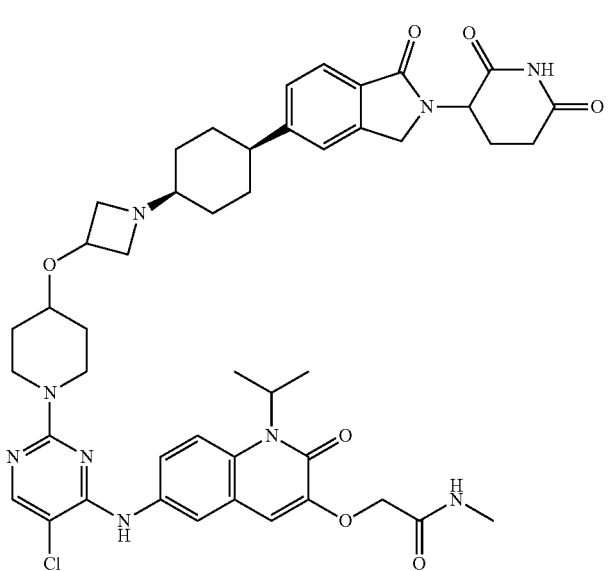 [SMILES: CNC(=O)COc1cc2cc(Nc3nc(N4CCC(OC5CN([C@H]6CC[C@@H](c7ccc8c(c7)CN(C7CCC(=O)NC7=O)C8=O)CC6)C5)CC4)ncc3Cl)ccc2n(C(C)C)c1=O] | 2-{[6-({5-chloro-2-[4-({1-[(1s,4s)-4-[2-(2,6-dioxopiperidin-3-yl)-1-oxo-2,3-dihydro-1H-isoindol-5-yl]cyclohexyl]azetidin-3-yl}oxy)piperidin-1-yl]pyrimidin-4-yl}amino)-2-oxo-1-(propan-2-yl)-1,2-dihydroquinolin-3-yl]oxy}-N-methylacetamide | 40 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 167 | | 2-({6-[(5-chloro-2-{4-[(1r,3r)-3-{4-[2-(2,6-dioxopiperidin-3-yl)-4-methyl-1,3-dioxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 41 |
| 168 | | 2-{[6-({5-chloro-2-[4-({2-[2-(2,6-dioxopiperidin-3-yl)-1-oxo-2,3-dihydro-1H-isoindol-5-yl]-2,9-diazadispiro[3.1.56.14]dodecan-9-yl}methyl)piperidin-1-yl]pyrimidin-4-yl}amino)-2-oxo-1-(propan-2-yl)-1,2-dihydroquinolin-3-yl]oxy}-N-methylacetamide | 42 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 169 | | 2-{[6-({5-chloro-2-[4-({2-[2-(2,6-dioxopiperidin-3-yl)-1,3-dioxo-2,3-dihydro-1H-isoindol-4-yl]-2-azaspiro[3.5]nonan-7-yl}methyl)piperazin-1-yl]pyrimidin-4-yl}amino)-5-fluoro-2-oxo-1-(propan-2-yl)-1,2-dihydroquinolin-3-yl]oxy}-N-methylacetamide | 35 |
| 170 | | 2-({6-[(5-chloro-2-{4-[(1r,3r)-3-{4-[2-(2,6-dioxopiperidin-3-yl)-1-oxo-2,3-dihydro-1H-isoindol-5-yl]-3,3-dimethylpiperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 55 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 171 | | 2-{[6-({5-chloro-2-[4-({2-[2-(2,6-dioxopiperidin-3-yl)-1-oxo-2,3-dihydro-1H-isoindol-5-yl]-5,5-difluoro-2,7-diazaspiro[3.5]nonan-7-yl}methyl)piperidin-1-yl]pyrimidin-4-yl}amino)-5-fluoro-2-oxo-1-(propan-2-yl)-1,2-dihydroquinolin-3-yl]oxy}-N-methylacetamide | 35 |
| 172 | | 2-({6-[(5-chloro-2-{4-[(1r,3r)-3-{4-[2-(2,6-dioxopiperidin-3-yl)-1,3-dioxo-2,3-dihydro-1H-isoindol-5-yl]piperidin-1-yl}cyclobutoxy]piperidin-1-yl}pyrimidin-4-yl)amino]-5-fluoro-2-oxo-1-(propan-2-yl)-1,2-dihydroquinolin-3-yl}oxy)-N-methylacetamide | 34, 35 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 173 | | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-5-fluoro-2-oxo-1-(propan-2-yl])-1,2-dihydroquinolin-3-yl}oxy)-N-methylacetamide | 34, 35 |
| 174 | | 2-({6-[(5-chloro-2-{4-[(1r,3r)-3-[(3R,5S)-4-[2-(2,6-dioxopiperidin-3-yl)-1-oxo-2,3-dihydro-1H-isoindol-5-yl]-3,5-dimethylpiperazin-1-yl]cyclobutoxy]piperidin-1-yl}pyrimidin-4-yl)amino]-2-oxo-1-(propan-2-yl])-1,2-dihydroquinolin-3-yl}oxy)-N-methylacetamide | 43 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 175 | | 2-({6-[(5-chloro-2-{4-[(1r,3r)-3-[(3R)-4-[2-(2,6-dioxopiperidin-3-yl])-4-fluoro-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 38 |
| 176 | | 2-({6-[(5-chloro-2-{4-[(1r,3r)-3-[(3S)-4-[2-(2,6-dioxopiperidin-3-yl])-4-fluoro-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 38 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 177 | 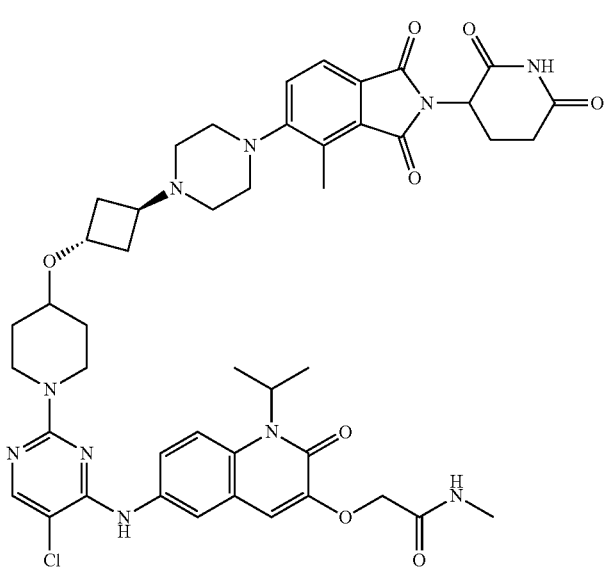 [SMILES: CNC(=O)COc1cc2cc(Nc3nc(N4CCC(O[C@H]5C[C@H](N6CCN(c7ccc8c(c7C)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl])-4-methyl-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 44 |
| 178 | 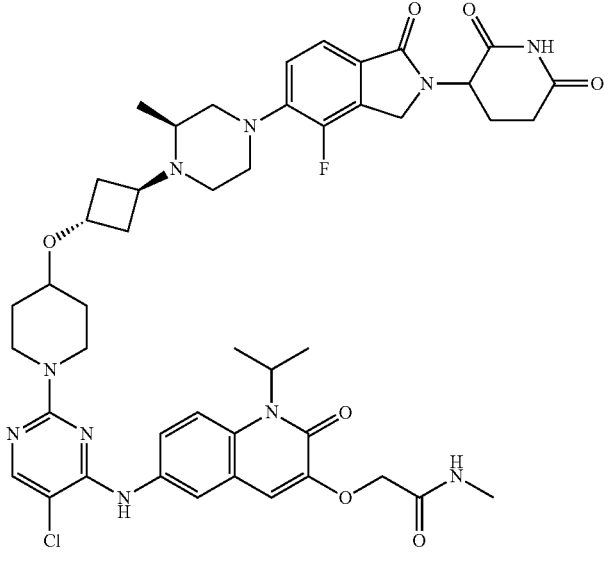 [SMILES: CNC(=O)COc1cc2cc(Nc3nc(N4CCC(O[C@H]5C[C@H](N6CCN(c7ccc8c(c7F)CN(C7CCC(=O)NC7=O)C8=O)C[C@@H]6C)C5)CC4)ncc3Cl)ccc2n(C(C)C)c1=O] | 2-({6-[(5-chloro-2-{4-[(1r,3r)-3-[(2S)-4-[2-(2,6-dioxopiperidin-3-yl])-4-fluoro-1-oxo-2,3-dihydro-1H-isoindol-5-yl]-2-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 38 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 179 | | 2-({6-[(5-chloro-2-{4-[(1r,3r)-3-[(3R*,5R*)-4-[2-(2,6-dioxopiperidin-3-yl)-1-oxo-2,3-dihydro-1H-isoindol-5-yl]-3,5-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 43 |
| 180 | | 2-({6-[(5-chloro-2-{4-[(1r,3r)-3-[(3R*,5R*)-4-[2-(2,6-dioxopiperidin-3-yl)-1-oxo-2,3-dihydro-1H-isoindol-5-yl]-3,5-dimethylpiperazin-1-yl]cyclobutoxy]piperidin-1-yl}pyrimidin-4-yl)amino]-2-ox0-1-(propan-2-yl)-1,2-dihydroquinolin-3-yl}oxy)-N-methylacetamide | 43 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 181 | 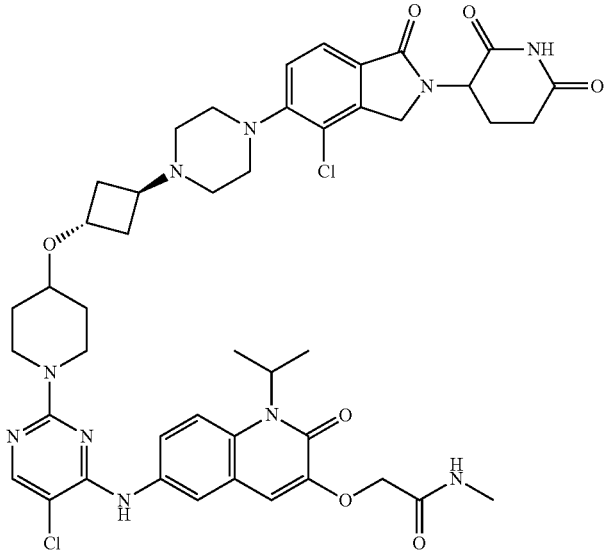 | 2-({6-[(5-chloro-2-{4-[(1r,3r)-3-{4-[4-chloro-2-(2,6-dioxopiperidin-3-yl)-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 45 |
| 182 | 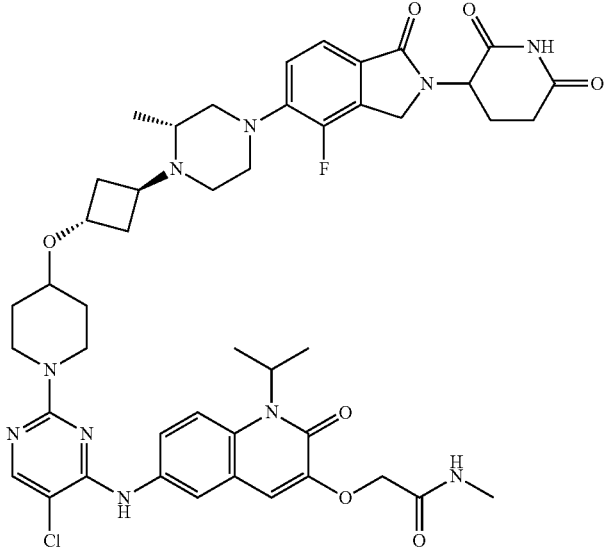 [SMILES: CNC(=O)COc1cc2cc(Nc3nc(N4CCC(O[C@H]5C[C@H](N6CCN(c7ccc8c(c7F)CN(C7CCC(=O)NC7=O)C8=O)C[C@H]6C)C5)CC4)ncc3Cl)ccc2n(C(C)C)c1=O] | 2-({6-[(5-chloro-2-{4-[(1r,3r)-3-[(2R)-4-[2-(2,6-dioxopiperidin-3-y])-4-fluoro-1-oxo-2,3-dihydro-1H-isoindol-5-yl]-2-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 38 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 183 | 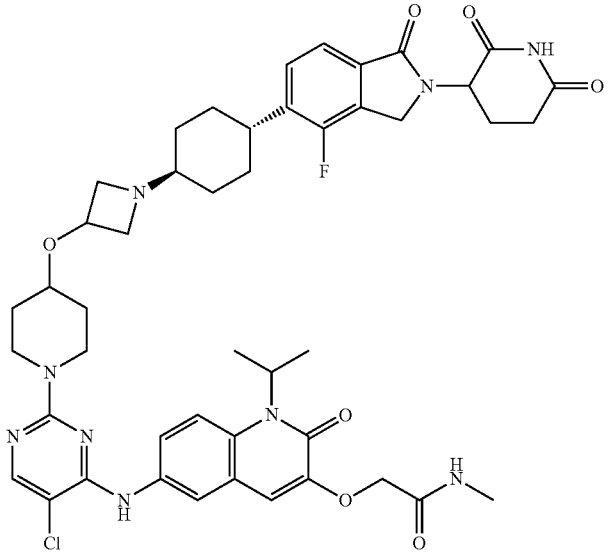 | 2-{[6-({5-chloro-2-[4-({1-[(1r,4r)-4-[2-(2,6-dioxopiperidin-3-yl)-4-fluoro-1-oxo-2,3-dihydro-1H-isoindol-5-yl]cyclohexyl]azetidin-3-yl}oxy)piperidin-1-yl]pyrimidin-4-yl}amino)-2-oxo-1-(propan-2-yl)-1,2-dihydroquinolin-3-yl]oxy}-N-methylacetamide | 39 |
| 184 | 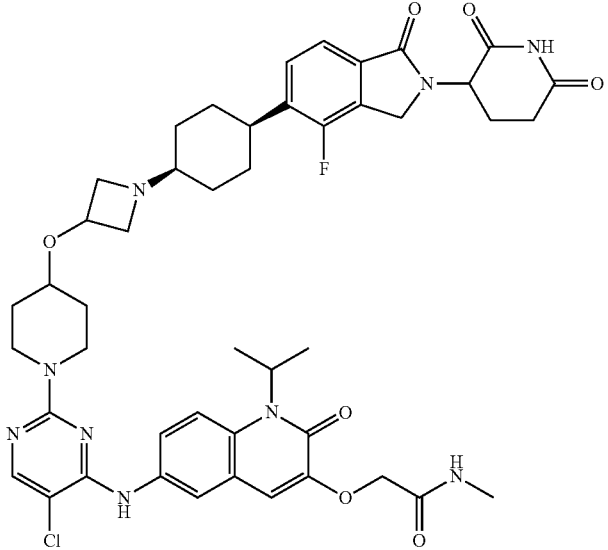 [SMILES: CNC(=O)COc1cc2cc(Nc3nc(N4CCC(OC5CN([C@H]6CC[C@@H](c7ccc8c(c7F)CN(C7CCC(=O)NC7=O)C8=O)CC6)C5)CC4)ncc3Cl)ccc2n(C(C)C)c1=O] | 2-{[6-({5-chloro-2-[4-({1-[(1s,4s)-4-[2-(2,6-dioxopiperidin-3-yl)-4-fluoro-1-oxo-2,3-dihydro-1H-isoindol-5-yl]cyclohexyl]azetidin-3-yl}oxy)piperidin-1-yl]pyrimidin-4-yl}amino)-2-oxo-1-(propan-2-yl)-1,2-dihydroquinolin-3-yl]oxy}-N-methylacetamide | 40 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 185 | 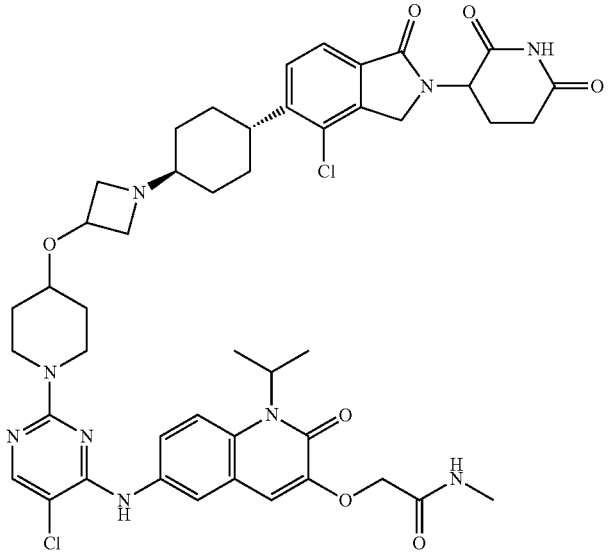 | 2-{[6-({5-chloro-2-[4-({1-[(1r,4r)-4-[4-chloro-2-(2,6-dioxopiperidin-3-yl)-1-oxo-2,3-dihydro-1H-isoindol-5-yl]cyclohexyl]azetidin-3-yl}oxy)piperidin-1-yl]pyrimidin-4-yl}amino)-2-oxo-1-(propan-2-yl)-1,2-dihydroquinolin-3-yl]oxy}-N-methylacetamide | 39, 40 |
| 186 | 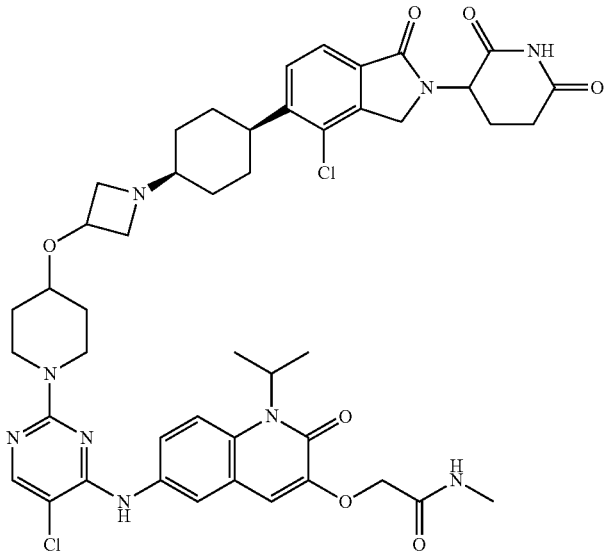 [SMILES: CNC(=O)COc1cc2cc(Nc3nc(N4CCC(OC5CN([C@H]6CC[C@@H](c7ccc8c(c7Cl)CN(C7CCC(=O)NC7=O)C8=O)CC6)C5)CC4)ncc3Cl)ccc2n(C(C)C)c1=O] | 2-{[6-({5-chloro-2-[4-({1-[(1s,4s)-4-[4-chloro-2-(2,6-dioxopiperidin-3-yl)-1-oxo-2,3-dihydro-1H-isoindol-5-yl]cyclohexyl]azetidin-3-yl}oxy)piperidin-1-yl]pyrimidin-4-yl}amino)-2-oxo-1-(propan-2-yl)-1,2-dihydroquinolin-3-yl]oxy}-N-methylacetamide | 40 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 187 | 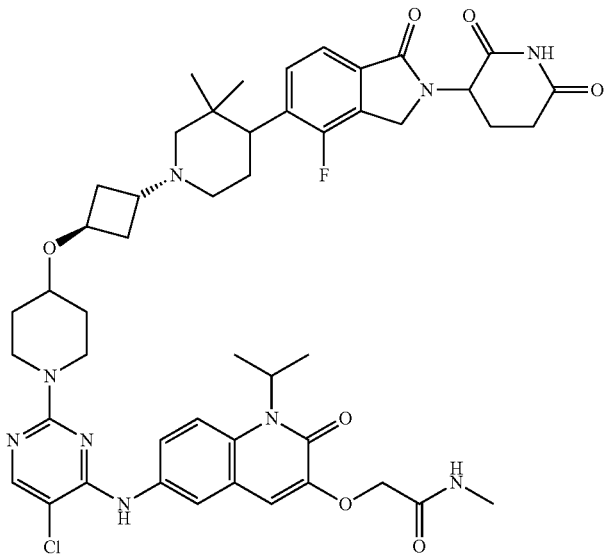 | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]-3,3-dimethylpiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 46 |
| 188 | 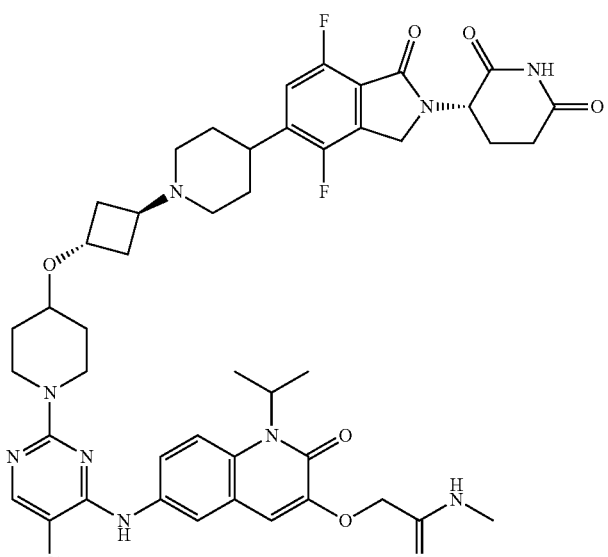 | 2-({6-[(5-chloro-2-{4-[(1r,3r)-3-(4-{2-[(3S)-2,6-dioxopiperidin-3-yl]-4,7-difluoro-1-oxo-2,3-dihydro-1H-isoindol-5-yl}piperidin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 47 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 189 | 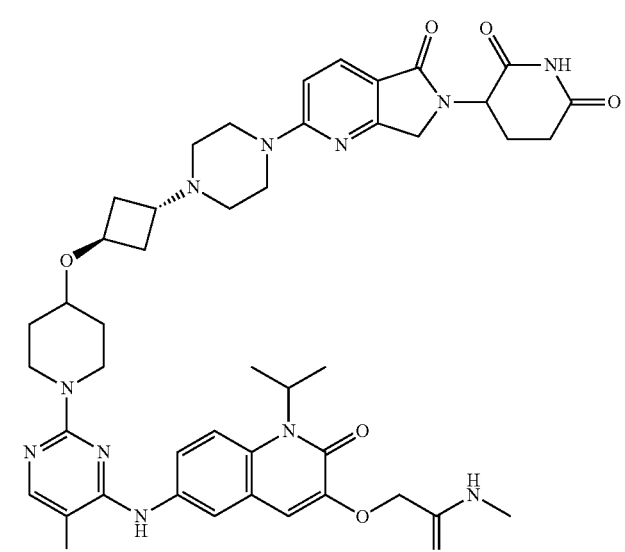 | 2-({6-[(5-chloro-2-{4-[(1r,3r)-3-{4-[6-(2,6-dioxopiperidin-3-yl)-5-oxo-5H,6H,7H-pyrrolo[3,4-b]pyridin-2-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 48 |
| 190 | 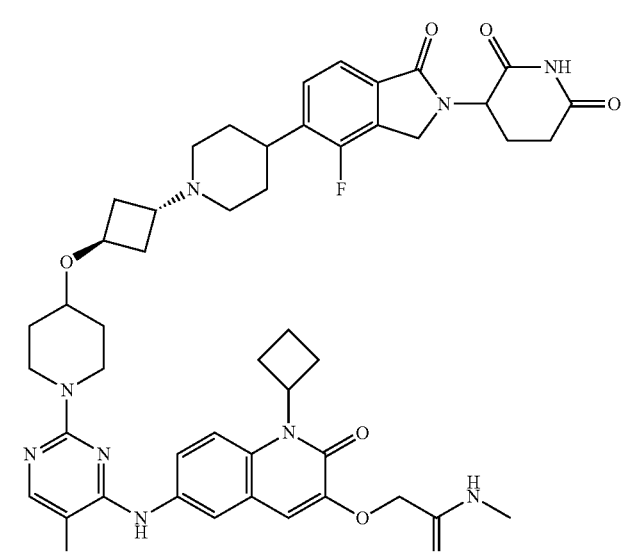 | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-1-cyclobutyl-2-oxo-1,2-dihydroquinolin-3-yl}oxy)-N-methylacetamide | 49 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 191 | | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-1-cyclopentyl-2-oxo-1,2-dihydroquinolin-3-yl}oxy)-N-methylacetamide | 49 |
| 192 | | 2-({6-[(5-chloro-2-{4-[(1r,3r)-3-[(3S)-4-[6-(2,6-dioxopiperidin-3-yl)-5-oxo-5H,6H,7H-pyrrolo[3,4-b]pyridin-2-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 48 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 193 | 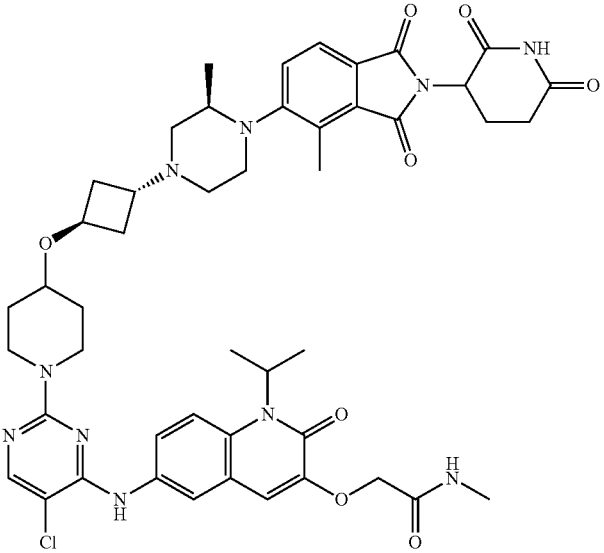 [SMILES: CNC(=O)COc1cc2cc(Nc3nc(N4CCC(O[C@H]5C[C@H](N6CCN(c7ccc8c(c7C)C(=O)N(C7CCC(=O)NC7=O)C8=O)[C@H](C)C6)C5)CC4)ncc3Cl)ccc2n(C(C)C)c1=O] | 2-({6-[(5-chloro-2-{4-[(1r,3r)-3-[(3R)-4-[2-(2,6-dioxopiperidin-3-yl])-4-methyl-1,3-dioxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 51 |
| 194 | 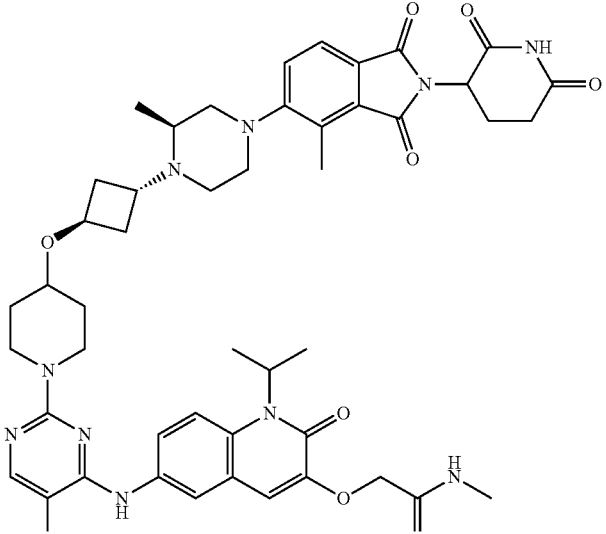 | 2-({6-[(5-chloro-2-{4-[(1r,3r)-3-[(2S)-4-[2-(2,6-dioxopiperidin-3-yl])-4-methyl-1,3-dioxo-2,3-dihydro-1H-isoindol-5-yl]-2-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 44 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 195 | 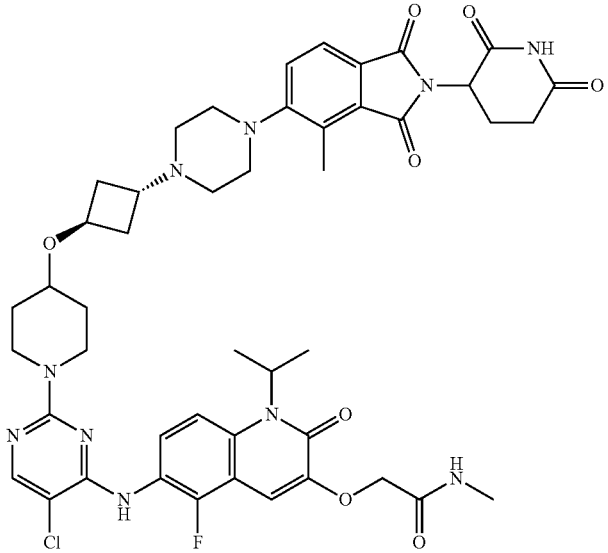 | 2-({6-[(5-chloro-2-{4-[(1r,3r)-3-{4-[2-(2,6-dioxopiperidin-3-yl])-4-methyl-1,3-dioxo-2,3-dihydro-1H-isoindol-5-yl]piperazin-1-yl}cyclobutoxy]piperidin-1-yl}pyrimidin-4-yl)amino]-5-fluoro-2-oxo-1-(propan-2-yl)-1,2-dihydroquinolin-3-yl}oxy)-N-methylacetamide | 44 |
| 196 | 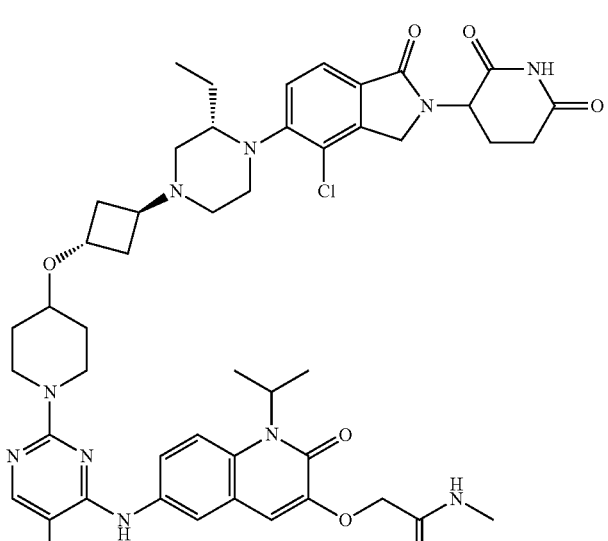 | 2-({6-[(5-chloro-2-{4-[(1r,3r)-3-[(3S)-4-[4-chloro-2-(2,6-dioxopiperidin-3-yl)-1-oxo-2,3-dihydro-1H-isoindol-5-yl]-3-ethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 45 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 197 | 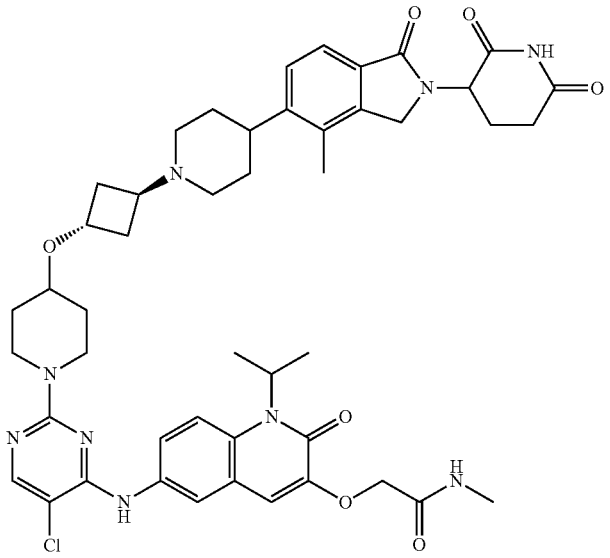 [SMILES: CNC(=O)COc1cc2cc(Nc3nc(N4CCC(O[C@H]5C[C@H](N6CCC(c7ccc8c(c7C)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl])-4-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 47 |
| 198 | 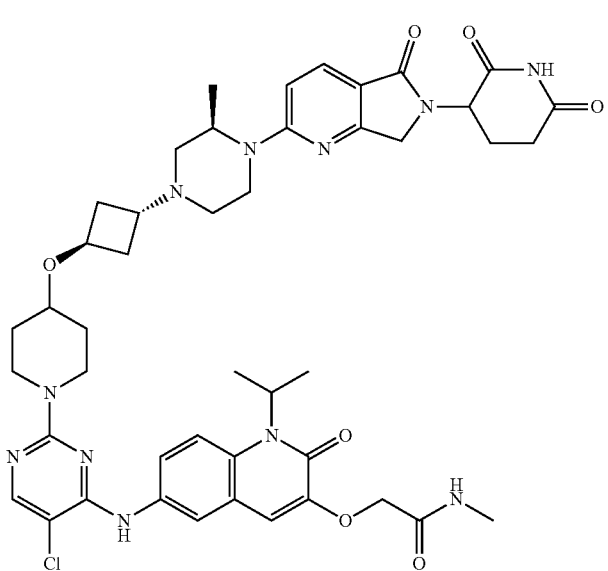 [SMILES: CNC(=O)COc1cc2cc(Nc3nc(N4CCC(O[C@H]5C[C@H](N6CCN(c7ccc8c(n7)CN(C7CCC(=O)NC7=O)C8=O)[C@H](C)C6)C5)CC4)ncc3Cl)ccc2n(C(C)C)c1=O] | 2-({6-[(5-chloro-2-{4-[(1r,3r)-3-[(3R)-4-[6-(2,6-dioxopiperidin-3-yl)-5-oxo-5H,6H,7H-pyrrolo[3,4-b]pyridin-2-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 48 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 199 | | 2-({6-[(5-chloro-2-{4-[(1r,3r)-3-[(3R)-4-[2-(2,6-dioxopiperidin-3-yl)-4-methyl-1,3-dioxo-2,3-dihydro-1H-isoindol-5-yl]-3-methylpiperazin-1-yl]cyclobutoxy]piperidin-1-yl}pyrimidin-4-yl)amino]-5-fluoro-2-oxo-1-(propan-2-yl])-1,2-dihydroquinolin-3-yl}oxy)-N-methylacetamide | 44 |
| 200 | | 2-({6-[(5-chloro-2-{4-[(1r,3r)-3-{4-[2-(2,6-dioxopiperidin-3-yl)-4-ethyl-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 52 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 201 | | 2-({6-[(5-chloro-2-{4-[(1r,3r)-3-[(3R,4S)-4-[2-(2,6-dioxopiperidin-3-yl)-4-fluoro-1-oxo-2,3-dihydro-1H-isoindol-5-yl]-3-fluoropiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 53 |
| 202 | | 2-({6-[(5-chloro-2-{4-[(1r,3r)-3-[(3R)-4-[4-chloro-2-(2,6-dioxopiperidin-3-yl)-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 45 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 203 | | 2-({6-[(5-chloro-2-{4-[(1r,3r)-3-[(3R)-4-[6-(2,6-dioxopiperidin-3-yl])-7-methyl-5-oxo-5H,6H,7H-pyrrolo[3,4-b]pyridin-2-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 54 |
| 204 | | 2-({6-[(5-chloro-2-{4-[(1r,3r)-3-[(3S)-4-[6-(2,6-dioxopiperidin-3-yl])-7-methyl-5-oxo-5H,6H,7H-pyrrolo[3,4-b]pyridin-2-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 54 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 205 | 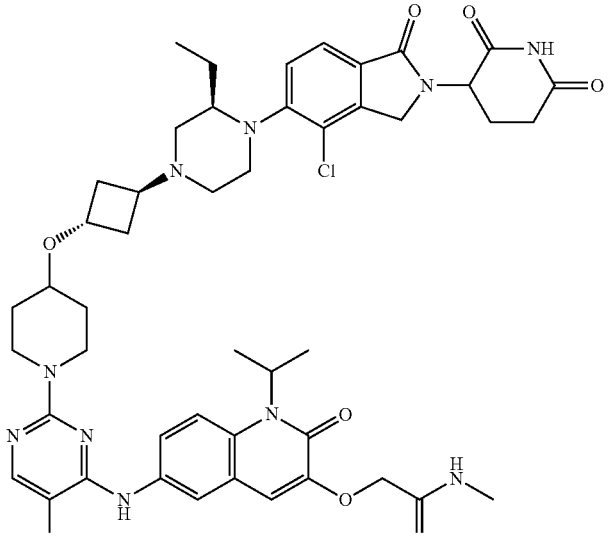 | 2-({6-[(5-chloro-2-{4-[(1r,3r)-3-[(3R)-4-[4-chloro-2-(2,6-dioxopiperidin-3-yl)-1-oxo-2,3-dihydro-1H-isoindol-5-yl]-3-ethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 45 |
| 206 | 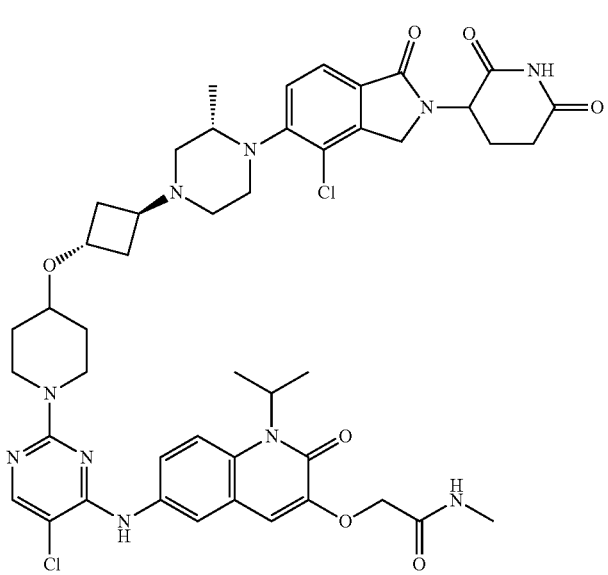 [SMILES: CNC(=O)COc1cc2cc(Nc3nc(N4CCC(O[C@H]5C[C@H](N6CCN(c7ccc8c(c7Cl)CN(C7CCC(=O)NC7=O)C8=O)[C@@H](C)C6)C5)CC4)ncc3Cl)ccc2n(C(C)C)c1=O] | 2-({6-[(5-chloro-2-{4-[(1r,3r)-3-[(3S)-4-[4-chloro-2-(2,6-dioxopiperidin-3-yl)-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 45 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 207 | | 2-({6-[(5-chloro-2-{4-[(1r,3r)-3-[(2S,5R)-4-[2-(2,6-dioxopiperidin-3-yl)-4-methyl-1,3-dioxo-2,3-dihydro-1H-isoindol-5-yl]-2,5-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 44 |
| 208 | | 2-({6-[(5-chloro-2-{4-[(1r,3r)-3-{4-[2-(2,6-dioxopiperidin-3-yl)-4-fluoro-7-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 50 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 209 | 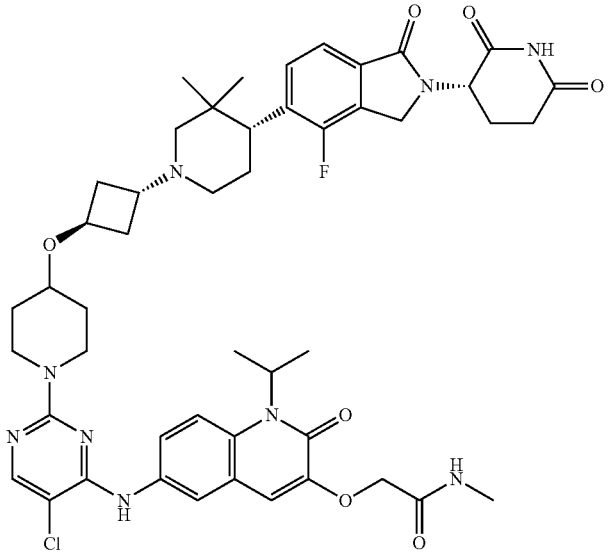 [SMILES: CNC(=O)COc1cc2cc(Nc3nc(N4CCC(O[C@H]5C[C@H](N6CC[C@@H](c7ccc8c(c7F)CN([C@H]7CCC(=O)NC7=O)C8=O)C(C)(C)C6)C5)CC4)ncc3Cl)ccc2n(C(C)C)c1=O] | 2-({6-[(5-chloro-2-{4-[(1r,3r)-3-[(4R)-4-{2-[(3S)-2,6-dioxopiperidin-3-yl]-4-fluoro-1-oxo-2,3-dihydro-1H-isoindol-5-yl}-3,3-dimethylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 46 |
| 210 | 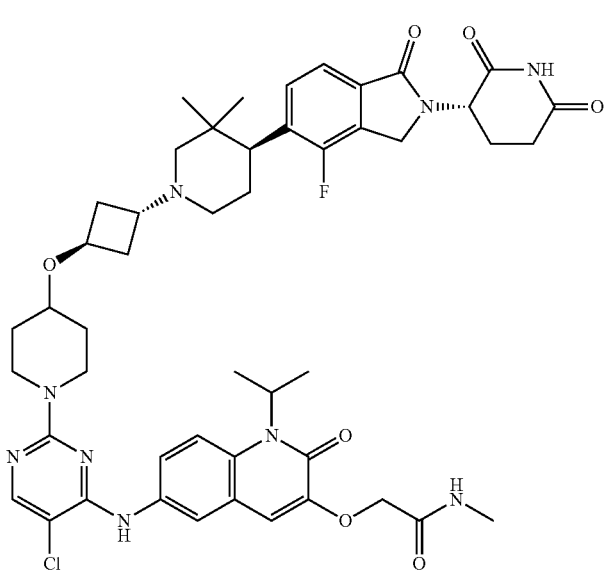 [SMILES: CNC(=O)COc1cc2cc(Nc3nc(N4CCC(O[C@H]5C[C@H](N6CC[C@H](c7ccc8c(c7F)CN([C@H]7CCC(=O)NC7=O)C8=O)C(C)(C)C6)C5)CC4)ncc3Cl)ccc2n(C(C)C)c1=O] | 2-({6-[(5-chloro-2-{4-[(1r,3r)-3-[(4S)-4-{2-[(3S)-2,6-dioxopiperidin-3-yl]-4-fluoro-1-oxo-2,3-dihydro-1H-isoindol-5-yl}-3,3-dimethylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 46 |

TABLE 2-continued

Additional exemplary bifunctional compounds of the present disclosure

| Compound Number | Parent Mol Structure | IUPAC Name | Analogously Made to Experimental Procedure Ex. Number |
|---|---|---|---|
| 211 | | 2-({6-[(5-chloro-2-{4-[(1r,3r)-3-(4-{2-[(3S)-2,6-dioxopiperidin-3-yl]-1-oxo-2,3-dihydro-1H-isoindol-5-yl}-3,3-dimethylpiperazin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 55 |

TABLE 3

Additional exemplary bifufunctional compounds of the present disclosure

| Compound Number | Parent Mol Structure | IUPAC Name |
|---|---|---|
| 212 | | 2-({6-[(5-chloro-2-{4-[(1r,3r)-3-{4-[2-(2,6-dioxopiperidin-3-yl)-1-oxo-6-(trifluoromethyl)-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

US 11,986,532 B2

595    596

TABLE 3-continued

Additional exemplary bifunctional compounds of the present disclosure

| Compound Number | Parent Mol Structure | IUPAC Name |
|---|---|---|
| 213 | 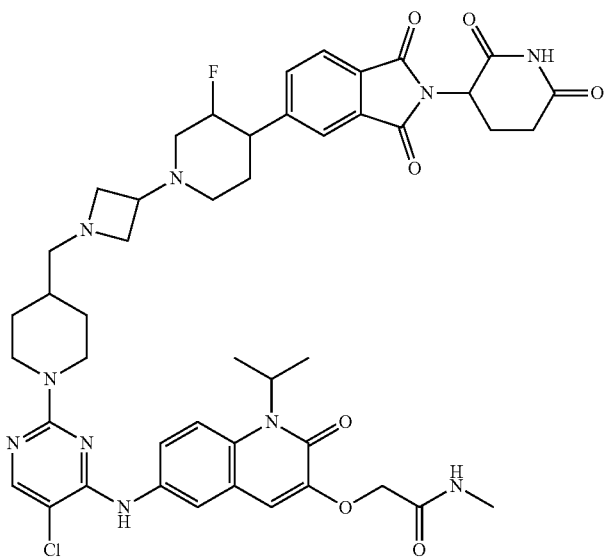 [SMILES: CNC(=O)COc1cc2cc(Nc3nc(N4CCC(CN5CC(N6CCC(c7ccc8c(c7)C(=O)N(C7CCC(=O)NC7=O)C8=O)C(F)C6)C5)CC4)ncc3Cl)ccc2n(C(C)C)c1=O] | 2-({6-[(5-chloro-2-{4-[(3-{4-[2-(2,6-dioxopiperidin-3-yl)-1,3-dioxo-2,3-dihydro-1H-isoindol-5-yl]-3-fluoropiperidin-1-yl}azetidin-1-yl)methyl]piperidin-1-yl}pyrimidin-4-yl)amino]-2-oxo-1-(propan-2-yl)-1,2-dihydroquinolin-3-yl}oxy)-N-methylacetamide |
| 214 | 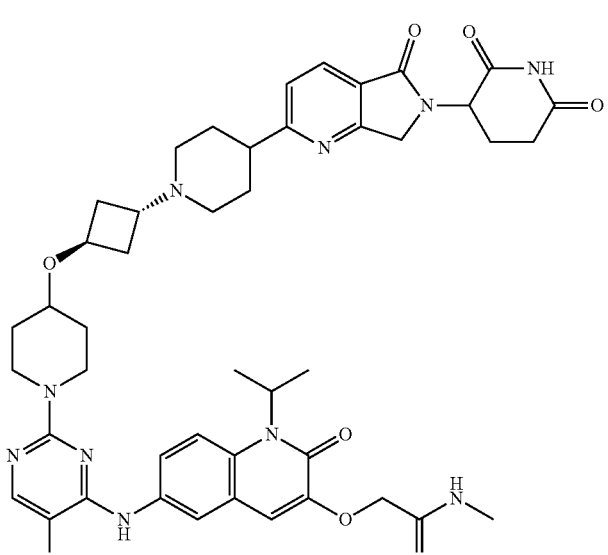 | 2-({6-[(5-chloro-2-{4-[(1r,3r)-3-{4-[6-(2,6-dioxopiperidin-3-yl)-5-oxo-5H,6H,7H-pyrrolo[3,4-b]pyridin-2-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 215 | | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide |
| 216 | | 2-({6-[(5-chloro-2-{4-[(1r,3r)-3-{4-[6-(2,6-dioxopiperidin-3-yl)-7-oxo-5H,6H,7H-pyrrolo[3,4-b]pyridin-3-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 217 | | 2-({6-[(5-chloro-2-{4-[(3-{4-[2-(2,6-dioxopiperidin-3-yl)-1-oxo-2,3-dihydro-1H-isoindol-5-yl]-3-fluoropiperidin-1-yl}azetidin-1-yl)methyl]piperidin-1-yl}pyrimidin-4-yl)amino]-2-oxo-1-(propan-2-yl)-1,2-dihydroquinolin-3-yl}oxy)-N-methylacetamide |
| 218 | | 2-({6-[(5-chloro-2-{4-[(1r,3r)-3-{4-[2-(2,6-dioxopiperidin-3-yl)-1-oxo-2,3-dihydro-1H-isoindol-5-yl]-3,3-difluoropiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

US 11,986,532 B2

TABLE 3-continued

Additional exemplary bifufunctional compounds of the present disclosure

| Compound Number | Parent Mol Structure | IUPAC Name |
|---|---|---|
| 219 | 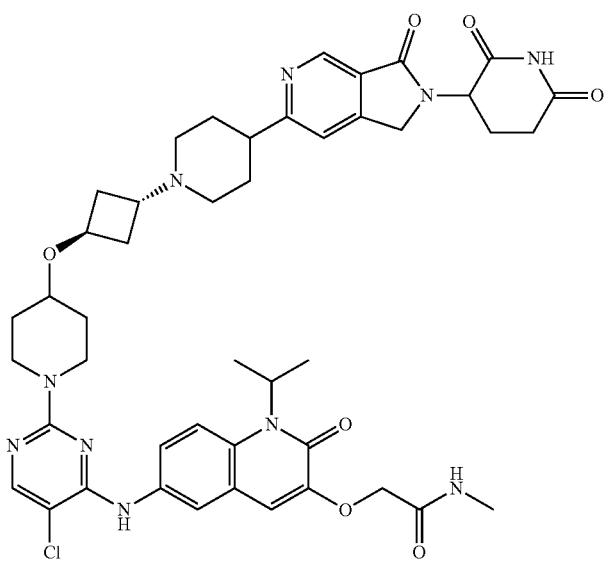 | 2-({6-[(5-chloro-2-{4-[(1r,3r)-3-{4-[2-(2,6-dioxopiperidin-3-yl)-3-oxo-1H,2H,3H-pyrrolo[3,4-c]pyridin-6-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 220 | 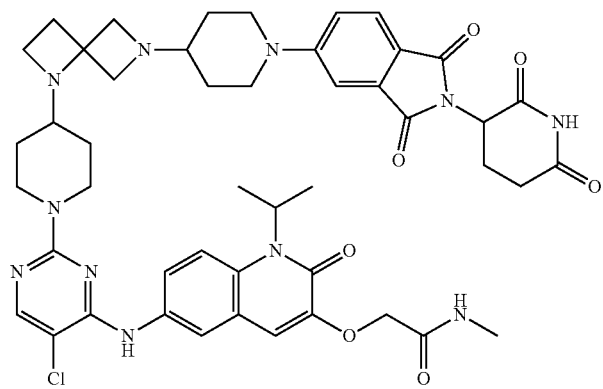 [SMILES: CNC(=O)COc1cc2cc(Nc3nc(N4CCC(N5CCC56CN(C5CCN(c7ccc8c(c7)C(=O)N(C7CCC(=O)NC7=O)C8=O)CC5)C6)CC4)ncc3Cl)ccc2n(C(C)C)c1=O] | 2-{[6-({5-chloro-2-[4-(6-{1-[2-(2,6-dioxopiperidin-3-yl)-1,3-dioxo-2,3-dihydro-1H-isoindol-5-yl]piperidin-4-yl}-1,6-diazaspiro[3.3]heptan-1-yl)piperidin-1-yl]pyrimidin-4-yl}amino)-2-oxo-1-(propan-2-yl)-1,2-dihydroquinolin-3-yl]oxy}-N-methylacetamide |
| 221 | 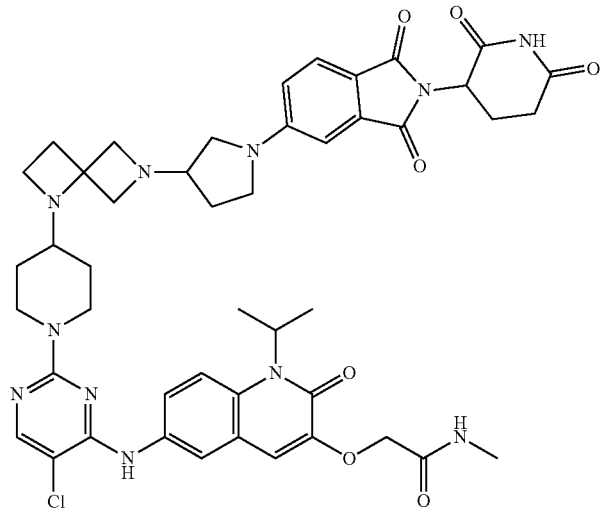 [SMILES: CNC(=O)COc1cc2cc(Nc3nc(N4CCC(N5CCC56CN(C5CCN(c7ccc8c(c7)C(=O)N(C7CCC(=O)NC7=O)C8=O)C5)C6)CC4)ncc3Cl)ccc2n(C(C)C)c1=O] | 2-{[6-({5-chloro-2-[4-(6-{1-[2-(2,6-dioxopiperidin-3-yl)-1,3-dioxo-2,3-dihydro-1H-isoindol-5-yl]pyrrolidin-3-yl}-1,6-diazaspiro[3.3]heptan-1-yl)piperidin-1-yl]pyrimidin-4-yl}amino)-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 222 | | 2-{[6-({5-chloro-2-[4-(6-{1-[2-(2,6-dioxopiperidin-3-yl)-1-oxo-2,3-dihydro-1H-isoindol-5-yl]piperidin-3-yl}-1,6-diazaspiro[3.3]heptan-1-yl)piperidin-1-yl]pyrimidin-4-yl}amino)-2-oxo-1-(propan-2-yl)-1,2-dihydroquinolin-3-yl]oxy}-N-methylacetamide |
| 223 | | 2-{[6-({5-chloro-2-[4-(2-{1-[2-(2,6-dioxopiperidin-3-yl)-1,3-dioxo-2,3-dihydro-1H-isoindol-5-yl]piperidin-3-yl}-1,6-diazaspiro[3.3]heptan-1-yl)piperidin-1-yl]pyrimidin-4-yl}amino)-2-oxo-1-(propan-2-yl)-1,2-dihydroquinolin-3-yl]oxy}-N-methylacetamide |

TABLE 3-continued

Additional exemplary bifunctional compounds of the present disclosure

| Compound Number | Parent Mol Structure | IUPAC Name |
|---|---|---|
| 224 | | 2-{[6-({5-chloro-2-[4-(2-{1-[2-(2,6-dioxopiperidin-3-yl)-1,3-dioxo-2,3-dihydro-1H-isoindol-5-yl]piperidin-4-yl}-2,6-diazaspiro[3.4]octan-6-yl)piperidin-1-yl]pyrimidin-4-yl}amino)-2-oxo-1-(propan-2-yl)-1,2-dihydroquinolin-3-yl]oxy}-N-methylacetamide |
| 225 | | 2-{[6-({5-chloro-2-[4-({2-[2-(2,6-dioxopiperidin-3-yl)-4-($^{2}H_3$)methoxy-1-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide |

TABLE 3-continued

Additional exemplary bifunctional compounds of the present disclosure

| Compound Number | Parent Mol Structure | IUPAC Name |
|---|---|---|
| 226 | 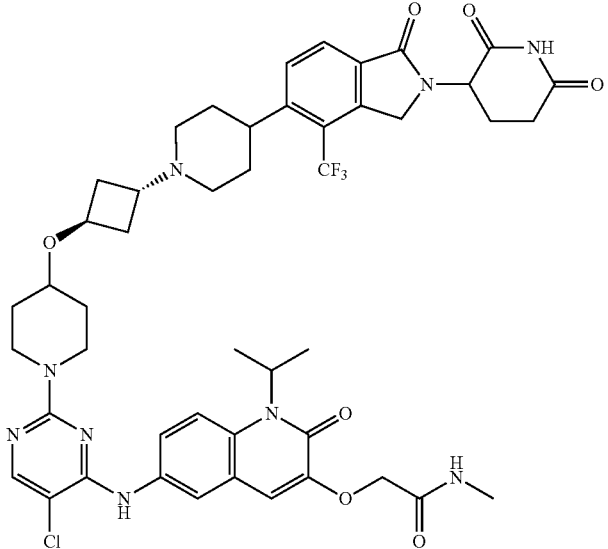 [SMILES: CNC(=O)COc1cc2cc(Nc3nc(N4CCC(O[C@H]5C[C@H](N6CCC(c7ccc8c(c7C(F)(F)F)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1-oxo-4-(trifluoromethyl)-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 227 | 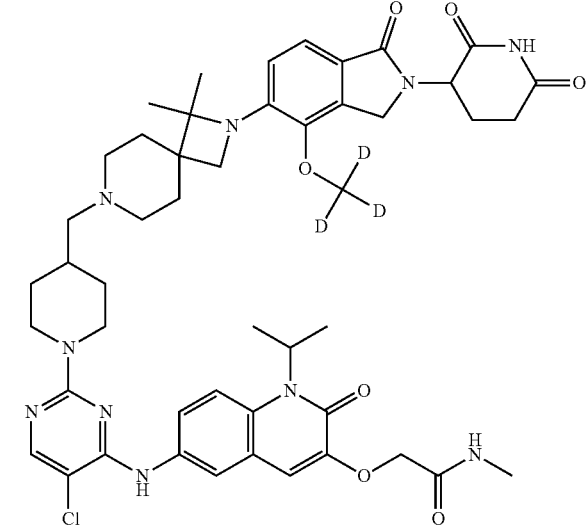 [SMILES: [2H]C([2H])([2H])Oc1c(N2CC3(CCN(CC4CCN(c5ncc(Cl)c(Nc6ccc7c(c6)cc(OCC(=O)NC)c(=O)n7C(C)C)n5)CC4)CC3)C2(C)C)ccc2c1CN(C1CCC(=O)NC1=O)C2=O] | 2-{[6-({5-chloro-2-[4-({2-[2-(2,6-dioxopiperidin-3-yl)-4-($^{2}$H$_3$)methoxy-1-oxo-2,3-dihydro-1H-isoindol-5-yl]-1,1-dimethyl-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 228 | | 2-({6-[(5-chloro-2-{4-[2-({1-[2-(2,6-dioxopiperidin-3-yl)-1,3-dioxo-2,3-dihydro-1H-isoindol-5-yl]piperidin-4-yl}methyl)-2,6-diazaspiro[3.4]octan-6-yl]pyrimidin-1-yl}pyrimidin-4-yl)amino]-2-oxo-1-(propan-2-yl)-1,2-dihydroquinolin-3-yl}oxy)-N-methylacetamide |
| 229 | | 2-{[6-({5-chloro-2-[4-({2-[2-(2,6-dioxopiperidin-3-yl)-4-fluoro-1-oxo-2,3-dihydro-1H-isoindol-5-yl]-1,1-dimethyl-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide |
| 230 | | 2-{[6-({5-chloro-2-[4-({2-[2-(2,6-dioxopiperidin-3-yl)-4-methoxy-1-oxo-2,3-dihydro-1H-isoindol-5-yl]-1,1-dimethyl-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 231 | 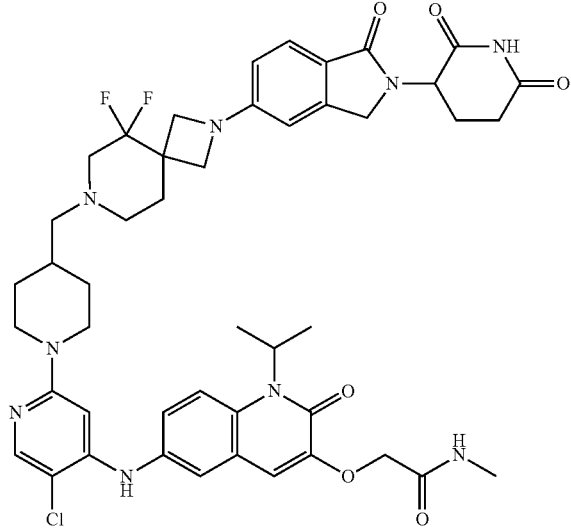 [SMILES: CNC(=O)COc1cc2cc(Nc3cc(N4CCC(CN5CCC6(CN(c7ccc8c(c7)CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-5,5-difluoro-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide |
| 232 | 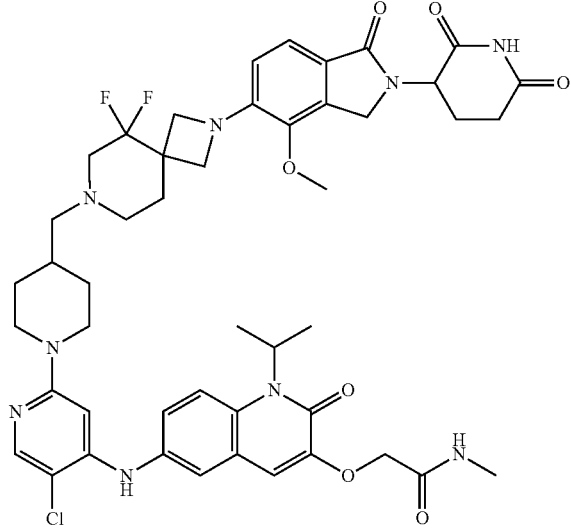 [SMILES: CNC(=O)COc1cc2cc(Nc3cc(N4CCC(CN5CCC6(CN(c7ccc8c(c7OC)CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-4-methoxy-1-oxo-2,3-dihydro-1H-isoindol-5-yl]-5,5-difluoro-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 233 | 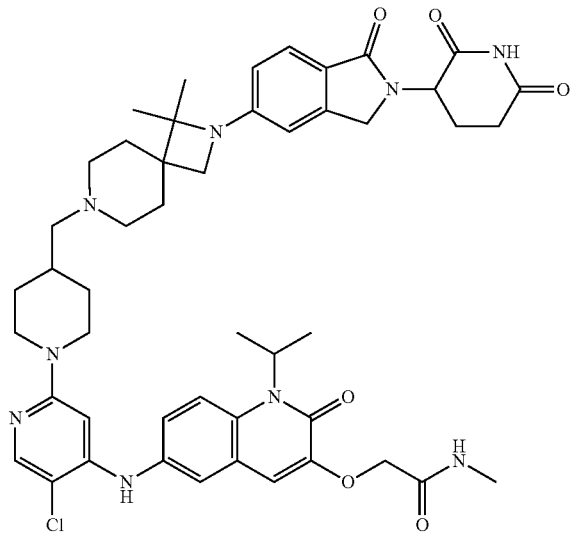 [SMILES: CNC(=O)COc1cc2cc(Nc3cc(N4CCC(CN5CCC6(CC5)CN(c5ccc7c(c5)CN(C5CCC(=O)NC5=O)C7=O)C6(C)C)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-1,1-dimethyl-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide |
| 234 | 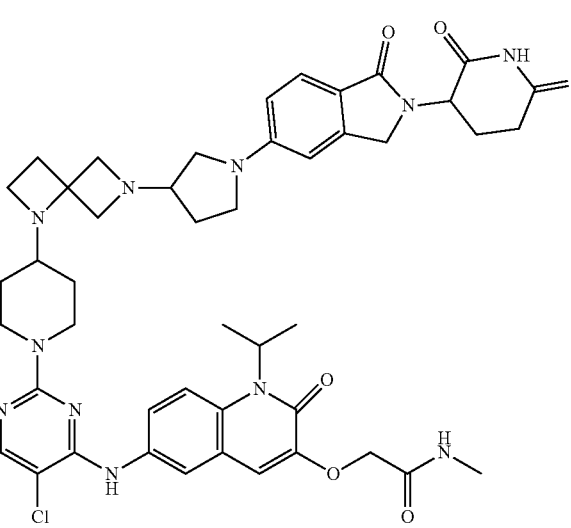 | 2-{[6-({5-chloro-2-[4-(6-{1-[2-(2,6-dioxopiperidin-3-yl)-1-oxo-2,3-dihydro-1H-isoindol-5-yl]pyrrolidin-3-yl}-1,6-diazaspiro[3.3]heptan-1-yl)piperidin-1-yl]pyrimidin-4-yl}amino)-2-oxo-1-(propan-2-yl)-1,2-dihydroquinolin-3-yl]oxy}-N-methylacetamide |

TABLE 3-continued

Additional exemplary bifunctional compounds of the present disclosure

| Compound Number | Parent Mol Structure | IUPAC Name |
| --- | --- | --- |
| 235 | | 2-{[6-({5-chloro-2-[4-(2-{1-[2-(2,6-dioxopiperidin-3-yl)-1-oxo-2,3-dihydro-1H-isoindol-5-yl]piperidin-4-yl}-2,6-diazaspiro[3.4]octan-6-yl)piperidin-1-yl]pyrimidin-4-yl}amino)-2-oxo-1-(propan-2-yl)-1,2-dihydroquinolin-3-yl]oxy}-N-methylacetamide |
| 236 | | 2-({6-[(5-chloro-2-{4-[2-({1-[2-(2,6-dioxopiperidin-3-yl)-1-oxo-2,3-dihydro-1H-isoindol-5-yl]piperidin-4-yl}methyl)-2,6-diazaspiro[3.4]octan-6-yl]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 237 | 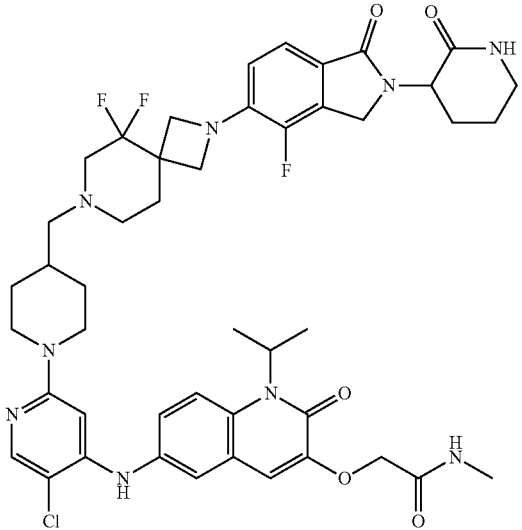 [SMILES: CNC(=O)COc1cc2cc(Nc3cc(N4CCC(CN5CCC6(CN(c7ccc8c(c7F)CN(C7CCCNC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-4-fluoro-1-oxo-2,3-dihydro-1H-isoindol-5-yl]-5,5-difluoro-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide |
| 238 | 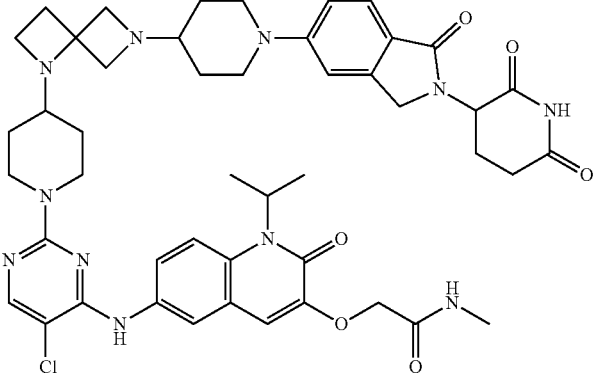 [SMILES: CNC(=O)COc1cc2cc(Nc3nc(N4CCC(N5CCC56CN(C5CCN(c7ccc8c(c7)CN(C7CCC(=O)NC7=O)C8=O)CC5)C6)CC4)ncc3Cl)ccc2n(C(C)C)c1=O] | 2-{[6-({5-chloro-2-[4-(6-{1-[2-(2,6-dioxopiperidin-3-yl)-1-oxo-2,3-dihydro-1H-isoindol-5-yl]piperidin-4-yl}-1,6-diazaspiro[3.3]heptan-1-yl)piperidin-1-yl]pyrimidin-4-yl}amino)-2-oxo-1-(propan-2-yl)-1,2-dihydroquinolin-3-yl]oxy}-N-methylacetamide |
| 239 | 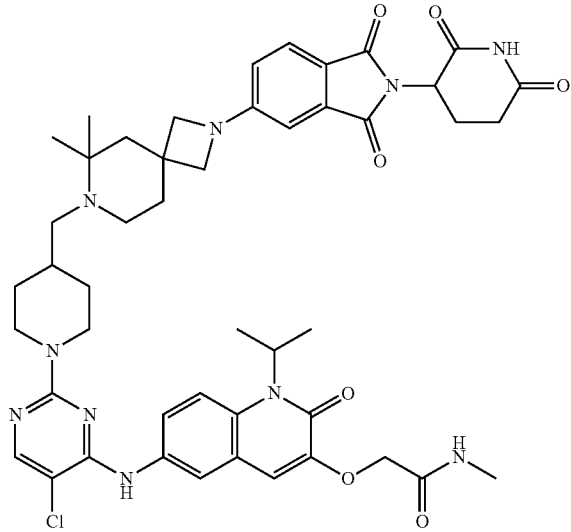 [SMILES: CNC(=O)COc1cc2cc(Nc3nc(N4CCC(CN5CCC6(CN(c7ccc8c(c7)C(=O)N(C7CCC(=O)NC7=O)C8=O)C6)CC5(C)C)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-5-yl]-6,6-dimethyl-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 240 | 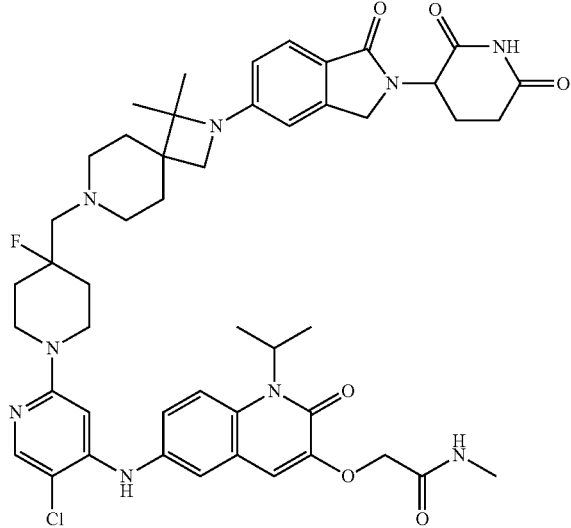 [SMILES: CNC(=O)COc1cc2cc(Nc3cc(N4CCC(F)(CN5CCC6(CC5)CN(c5ccc7c(c5)CN(C5CCC(=O)NC5=O)C7=O)C6(C)C)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-1,1-dimethyl-2,7-diazaspiro[3.5]nonan-7-yl}methyl)-4-fluoropiperidin-1-yl]pyridin-4-yl}amino)-2-oxo-1-(propan-2-yl)-1,2-dihydroquinolin-3-yl]oxy}-N-methylacetamide |
| 241 | 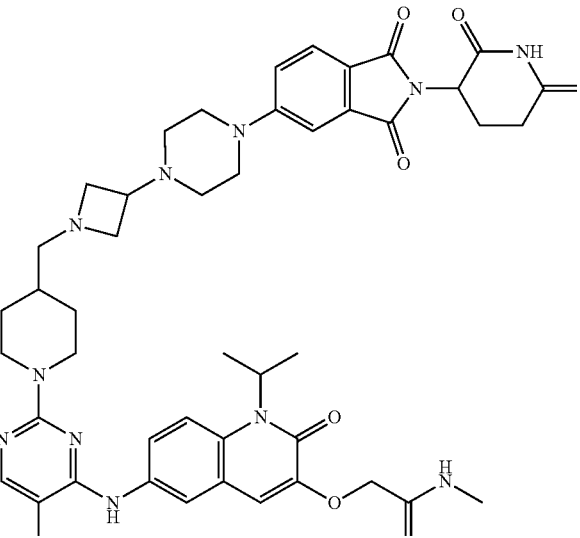 | 2-({6-[(5-chloro-2-{4-[(3-{4-[2-(2,6-dioxopiperidin-3-yl)-1,3-dioxo-2,3-dihydro-1H-isoindol-5-yl]piperazin-1-yl}azetidin-1-yl)methyl]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 242 | 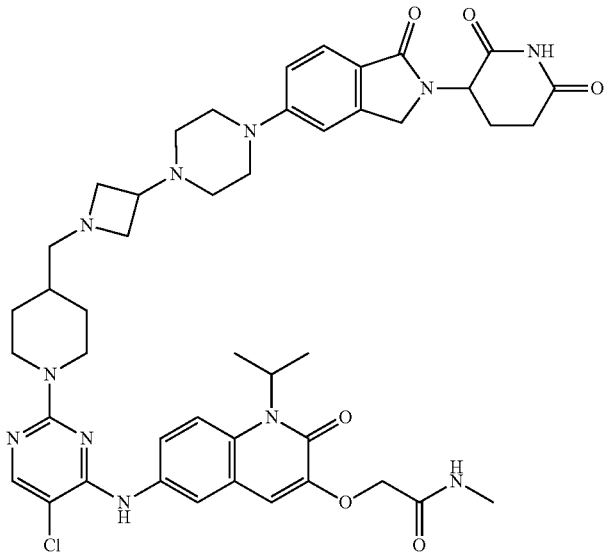 [SMILES: CNC(=O)COc1cc2cc(Nc3nc(N4CCC(CN5CC(N6CCN(c7ccc8c(c7)CN(C7CCC(=O)NC7=O)C8=O)CC6)C5)CC4)ncc3Cl)ccc2n(C(C)C)c1=O] | 2-({6-[(5-chloro-2-{4-[(3-{4-[2-(2,6-dioxopiperidin-3-yl)-1-oxo-2,3-dihydro-1H-isoindol-5-yl]piperazin-1-yl}azetidin-1-yl)methyl]piperidin-1-yl}pyrimidin-4-yl)amino]-2-oxo-1-(propan-2-yl)-1,2-dihydroquinolin-3-yl}oxy)-N-methylacetamide |
| 243 | 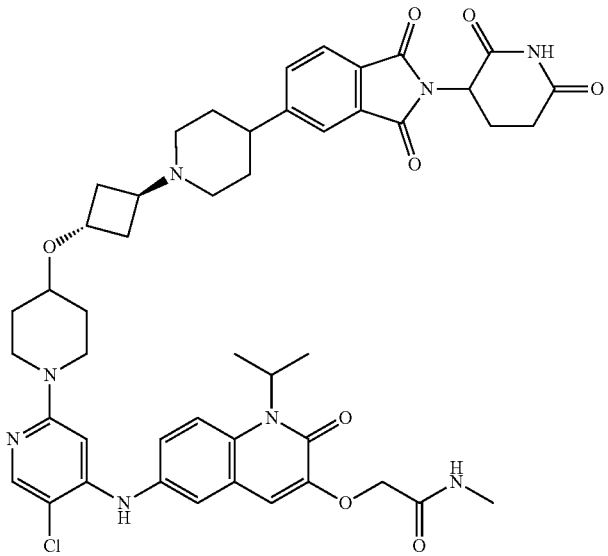 [SMILES: CNC(=O)COc1cc2cc(Nc3cc(N4CCC(O[C@H]5C[C@H](N6CCC(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-2,3-dihydro-1H-isoindol-5-yl]piperidin-1-yl}cyclobutoxy]piperidin-1-yl}pyridin-4-yl)amino]-2-oxo-1-(propan-2-yl)-1,2-dihydroquinolin-3-yl}oxy)-N-methylacetamide |

US 11,986,532 B2

TABLE 3-continued

Additional exemplary bifunctional compounds of the present disclosure

| Compound Number | Parent Mol Structure | IUPAC Name |
|---|---|---|
| 244 | 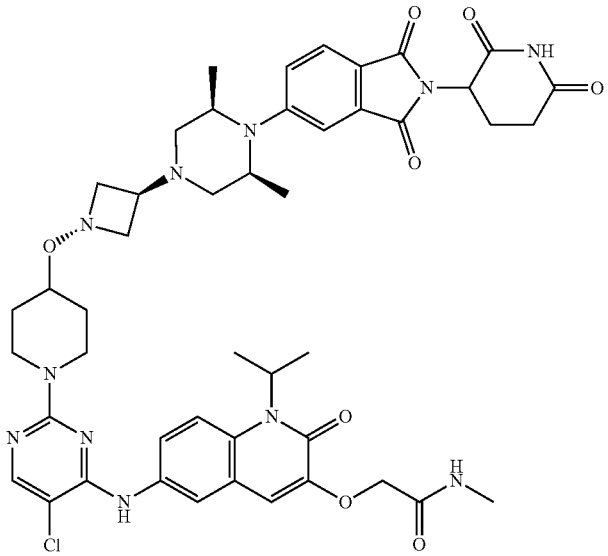 | 2-({6-[(5-chloro-2-{4-[(1r,3r)-3-[(3R,5S)-4-[2-(2,6-dioxopiperidin-3-yl)-1,3-dioxo-2,3-dihydro-1H-isoindol-5-yl]-3,5-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 245 | 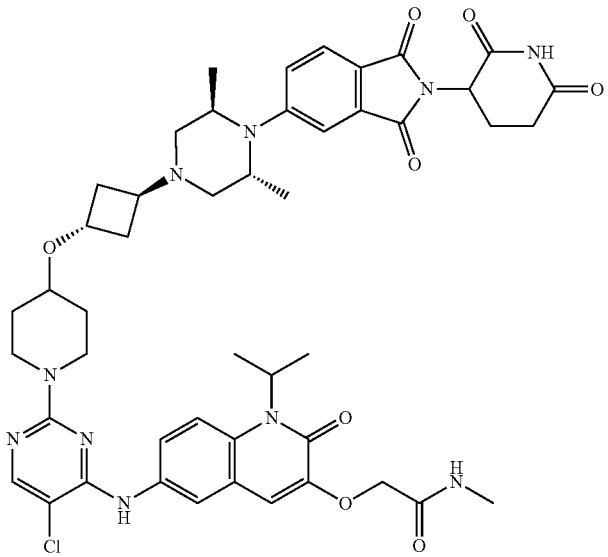 [SMILES: CNC(=O)COc1cc2cc(Nc3nc(N4CCC(O[C@H]5C[C@H](N6C[C@@H](C)N(c7ccc8c(c7)C(=O)N(C7CCC(=O)NC7=O)C8=O)[C@H](C)C6)C5)CC4)ncc3Cl)ccc2n(C(C)C)c1=O] | 2-({6-[(5-chloro-2-{4-[(1r,3r)-3-[(3R,5R)-4-[2-(2,6-dioxopiperidin-3-yl)-1,3-dioxo-2,3-dihydro-1H-isoindol-5-yl]-3,5-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 246 | 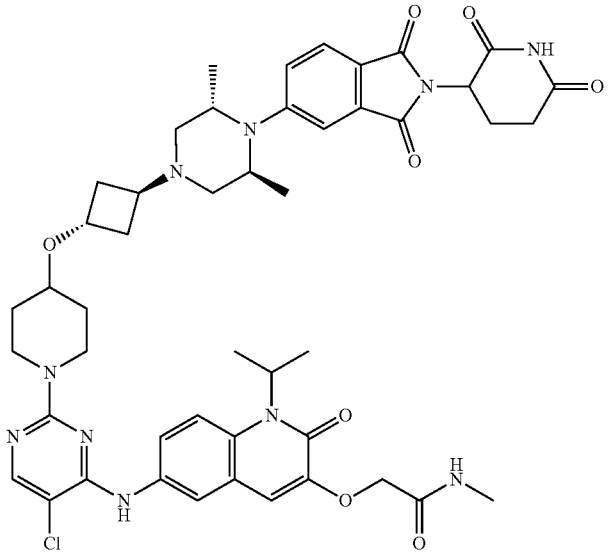 [SMILES: CNC(=O)COc1cc2cc(Nc3nc(N4CCC(O[C@H]5C[C@H](N6C[C@H](C)N(c7ccc8c(c7)C(=O)N(C7CCC(=O)NC7=O)C8=O)[C@@H](C)C6)C5)CC4)ncc3Cl)ccc2n(C(C)C)c1=O] | 2-({6-[(5-chloro-2-{4-[(1r,3r)-3-[(3S,5S)-4-[2-(2,6-dioxopiperidin-3-yl)-1,3-dioxo-2,3-dihydro-1H-isoindol-5-yl]-3,5-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 247 | 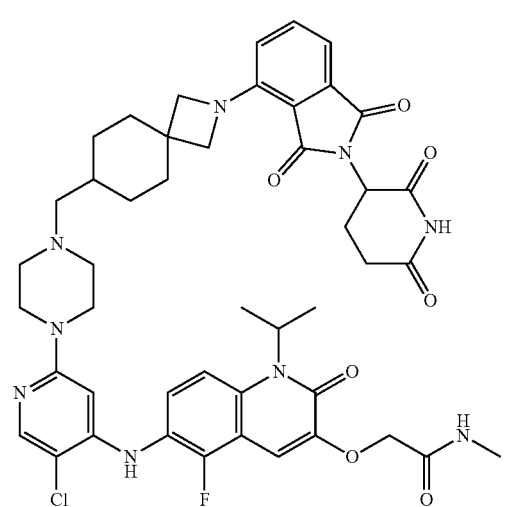 [SMILES: CNC(=O)COc1cc2c(F)c(Nc3cc(N4CCN(CC5CCC6(CC5)CN(c5cccc7c5C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-4-yl]-2-azaspiro[3.5]nonan-7-yl}methyl)piperazin-1-yl]pyridin-4-yl}amino)-5-fluoro-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 248 | 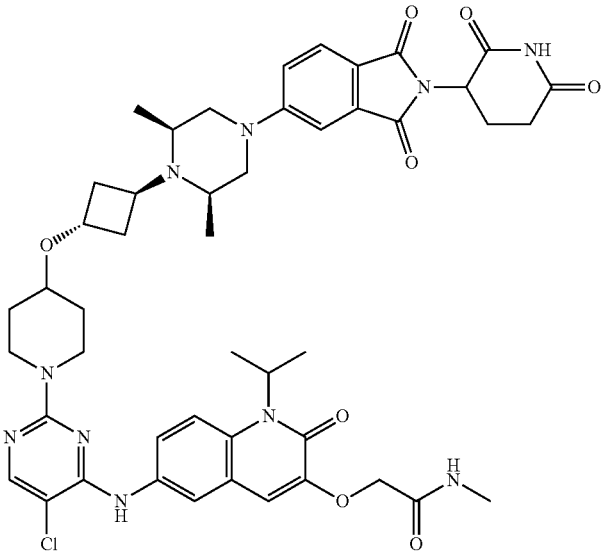 [SMILES: CNC(=O)COc1cc2cc(Nc3nc(N4CCC(O[C@H]5C[C@H](N6[C@H](C)CN(c7ccc8c(c7)C(=O)N(C7CCC(=O)NC7=O)C8=O)C[C@@H]6C)C5)CC4)ncc3Cl)ccc2n(C(C)C)c1=O] | 2-({6-[(5-chloro-2-{4-[(1r,3r)-3-[(2R,6S)-4-[2-(2,6-dioxopiperidin-3-yl)-1,3-dioxo-2,3-dihydro-1H-isoindol-5-yl]-2,6-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 249 | 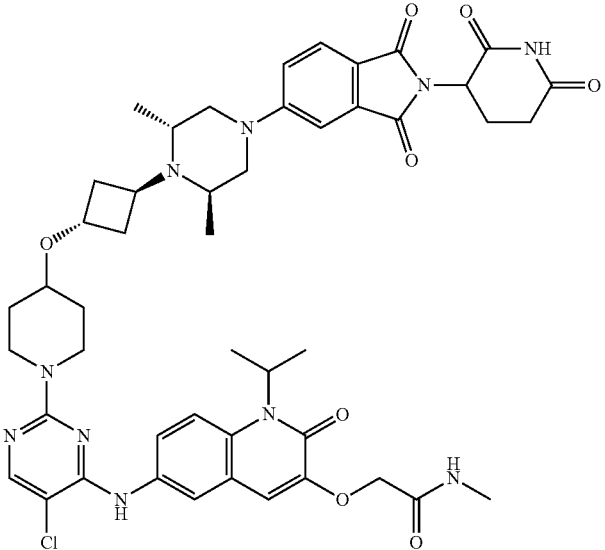 [SMILES: CNC(=O)COc1cc2cc(Nc3nc(N4CCC(O[C@H]5C[C@H](N6[C@H](C)CN(c7ccc8c(c7)C(=O)N(C7CCC(=O)NC7=O)C8=O)C[C@H]6C)C5)CC4)ncc3Cl)ccc2n(C(C)C)c1=O] | 2-({6-[(5-chloro-2-{4-[(1r,3r)-3-[(2R,6R)-4-[2-(2,6-dioxopiperidin-3-yl)-1,3-dioxo-2,3-dihydro-1H-isoindol-5-yl]-2,6-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 250 | 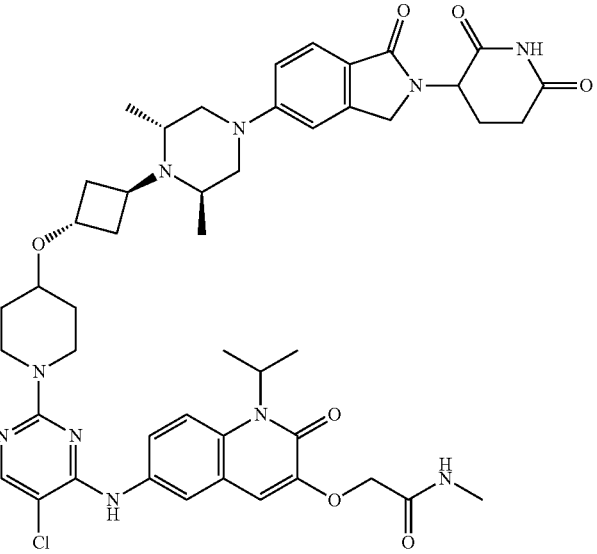 | 2-({6-[(5-chloro-2-{4-[(1r,3r)-3-[(2R,6R)-4-[2-(2,6-dioxopiperidin-3-yl)-1-oxo-2,3-dihydro-1H-isoindol-5-yl]-2,6-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 251 | 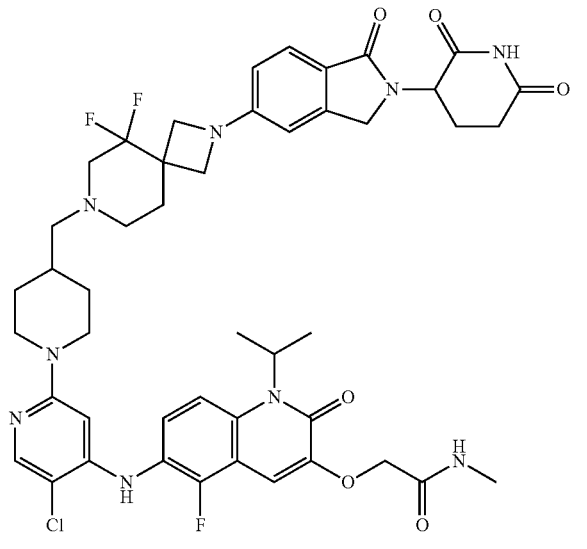 [SMILES: CNC(=O)COc1cc2c(F)c(Nc3cc(N4CCC(CN5CCC6(CN(c7ccc8c(c7)CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-5,5-difluoro-2,7-diazaspiro[3.5]nonan-7-yl}methyl)piperidin-1-yl]pyridin-4-yl}amino)-5-fluoro-2-oxo-1-(propan-2-yl)-1,2-dihydroquinolin-3-yl]oxy}-N-methylacetamide |

TABLE 3-continued

Additional exemplary bifunctional compounds of the present disclosure

| Compound Number | Parent Mol Structure | IUPAC Name |
|---|---|---|
| 252 | 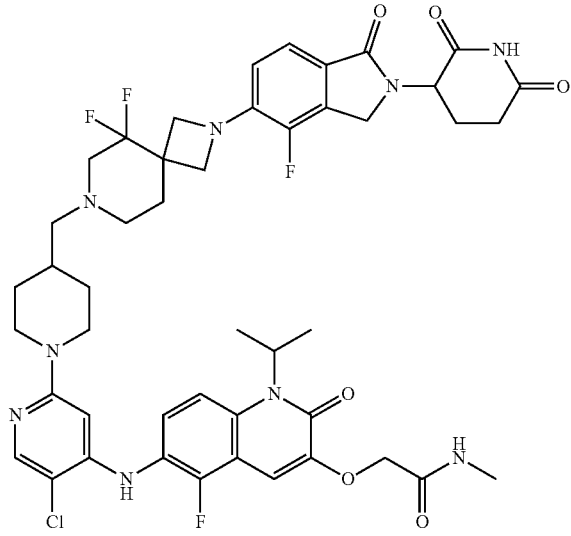 [SMILES: CNC(=O)COc1cc2c(F)c(Nc3cc(N4CCC(CN5CCC6(CN(c7ccc8c(c7F)CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-4-fluoro-1-oxo-2,3-dihydro-1H-isoindol-5-yl]-5,5-difluoro-2,7-diazaspiro[3.5]nonan-7-yl}methyl)piperidin-1-yl]pyridin-4-yl}amino)-5-fluoro-2-oxo-1-(propan-2-yl)-1,2-dihydroquinolin-3-yl]oxy}-N-methylacetamide |
| 253 | 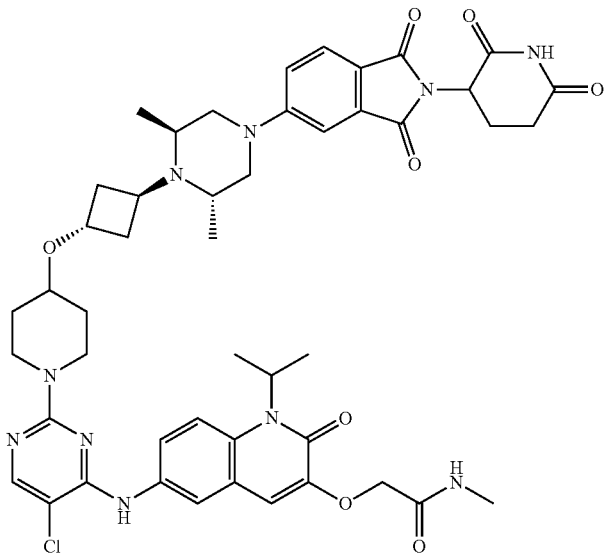 [SMILES: CNC(=O)COc1cc2cc(Nc3nc(N4CCC(O[C@H]5C[C@H](N6[C@@H](C)CN(c7ccc8c(c7)C(=O)N(C7CCC(=O)NC7=O)C8=O)C[C@@H]6C)C5)CC4)ncc3Cl)ccc2n(C(C)C)c1=O] | 2-({6-[(5-chloro-2-{4-[(1r,3r)-3-[(2S,6S)-4-[2-(2,6-dioxopiperidin-3-yl)-1,3-dioxo-2,3-dihydro-1H-isoindol-5-yl]-2,6-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

US 11,986,532 B2

TABLE 3-continued

Additional exemplary bifunctional compounds of the present disclosure

| Compound Number | Parent Mol Structure | IUPAC Name |
|---|---|---|
| 254 | 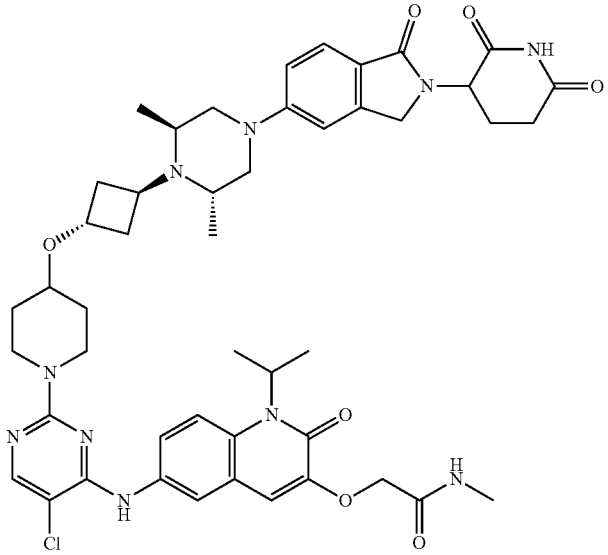 [SMILES: CNC(=O)COc1cc2cc(Nc3nc(N4CCC(O[C@H]5C[C@H](N6[C@@H](C)CN(c7ccc8c(c7)CN(C7CCC(=O)NC7=O)C8=O)C[C@@H]6C)C5)CC4)ncc3Cl)ccc2n(C(C)C)c1=O] | 2-({6-[(5-chloro-2-{4-[(1r,3r)-3-[(2S,6S)-4-[2-(2,6-dioxopiperidin-3-yl)-1-oxo-2,3-dihydro-1H-isoindol-5-yl]-2,6-dimethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 255 | 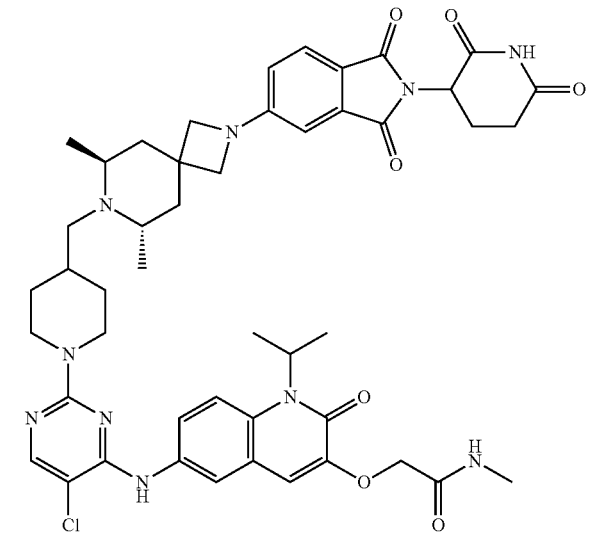 [SMILES: CNC(=O)COc1cc2cc(Nc3nc(N4CCC(CN5[C@@H](C)CC6(C[C@@H]5C)CN(c5ccc7c(c5)C(=O)N(C5CCC(=O)NC5=O)C7=O)C6)CC4)ncc3Cl)ccc2n(C(C)C)c1=O] | 2-[(6-{[5-chloro-2-(4-{[(6S,8S)-2-[2-(2,6-dioxopiperidin-3-yl)-1,3-dioxo-2,3-dihydro-1H-isoindol-5-yl]-6,8-dimethyl-2,7-diazaspiro[3.5]nonan-7-yl]methyl}piperidin-1-yl)pyrimidin-4-yl]amino}-2-oxo-1-(propan-2-yl)-1,2-dihydroquinolin-3-yl)oxy]-N-methylacetamide |

TABLE 3-continued

Additional exemplary bifunctional compounds of the present disclosure

| Compound Number | Parent Mol Structure | IUPAC Name |
|---|---|---|
| 256 | 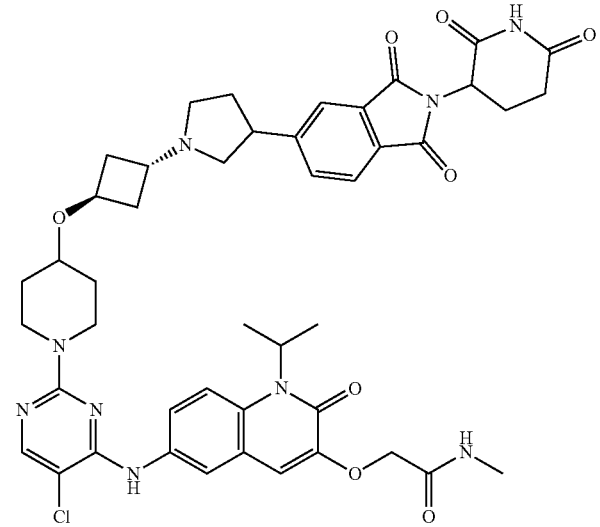 [SMILES: CNC(=O)COc1cc2cc(Nc3nc(N4CCC(O[C@H]5C[C@H](N6CCC(c7ccc8c(c7)C(=O)N(C7CCC(=O)NC7=O)C8=O)C6)C5)CC4)ncc3Cl)ccc2n(C(C)C)c1=O] | 2-({6-[(5-chloro-2-{4-[(1r,3r)-3-{3-[2-(2,6-dioxopiperidin-3-yl)-1,3-dioxo-2,3-dihydro-1H-isoindol-5-yl]pyrrolidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 257 | 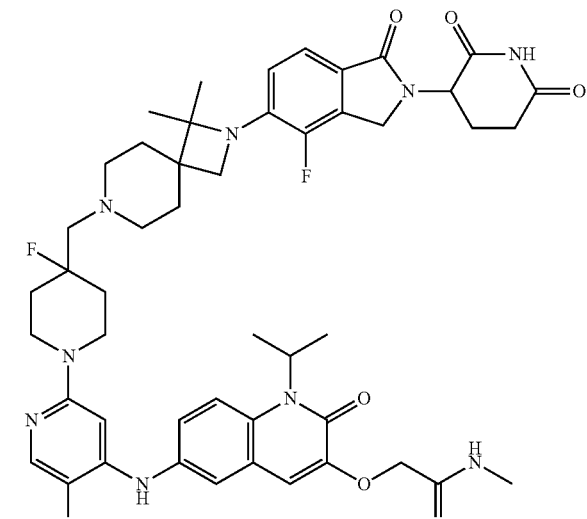 | 2-{[6-({5-chloro-2-[4-({2-[2-(2,6-dioxopiperidin-3-yl)-4-fluoro-1-oxo-2,3-dihydro-1H-isoindol-5-yl]-1,1-dimethyl-2,7-diazaspiro[3.5]nonan-7-yl}methyl)-4-fluoropiperidin-1-yl]pyridin-4-yl}amino)-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 258 | 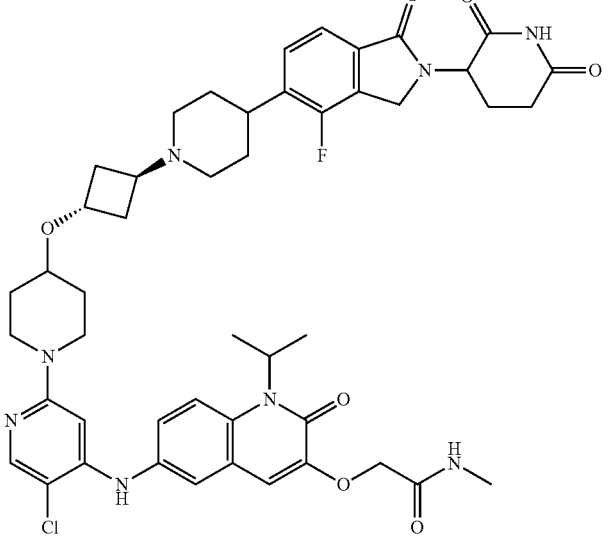 | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyridin-4-yl)amino]-2-oxo-1-(propan-2-yl)-1,2-dihydroquinolin-3-yl}oxy)-N-methylacetamide |
| 259 | 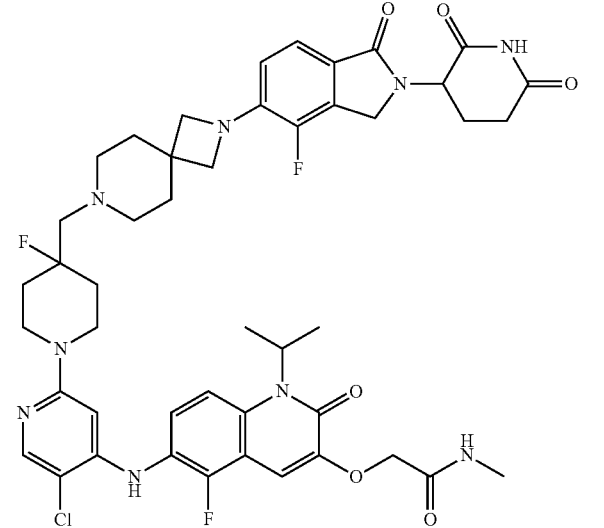 [SMILES: CNC(=O)COc1cc2c(F)c(Nc3cc(N4CCC(F)(CN5CCC6(CC5)CN(c5ccc7c(c5F)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-4-fluoro-1-oxo-2,3-dihydro-1H-isoindol-5-yl]-2,7-diazaspiro[3.5]nonan-7-yl}methyl)-4-fluoropiperidin-1-yl]pyridin-4-yl}amino)-5-fluoro-2-oxo-1-(propan-2-yl)-1,2-dihydroquinolin-3-yl]oxy}-N-methylacetamide |

TABLE 3-continued

Additional exemplary bifufunctional compounds of the present disclosure

| Compound Number | Parent Mol Structure | IUPAC Name |
|---|---|---|
| 260 | 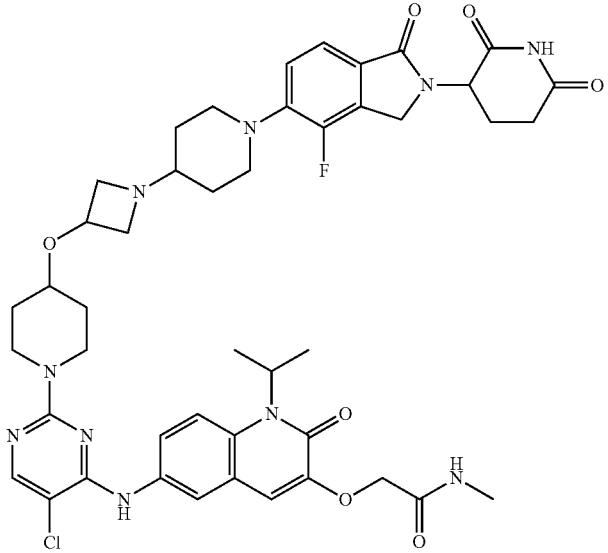 [SMILES: CNC(=O)COc1cc2cc(Nc3nc(N4CCC(OC5CN(C6CCN(c7ccc8c(c7F)CN(C7CCC(=O)NC7=O)C8=O)CC6)C5)CC4)ncc3Cl)ccc2n(C(C)C)c1=O] | 2-({6-[(5-chloro-2-{4-[(1-{1-[2-(2,6-dioxopiperidin-3-yl)-4-fluoro-1-oxo-2,3-dihydro-1H-isoindol-5-yl]piperidin-4-yl}azetidin-3-yl)oxy]piperidin-1-yl}pyrimidin-4-yl)amino]-2-oxo-1-(propan-2-yl)-1,2-dihydroquinolin-3-yl}oxy)-N-methylacetamide |
| 261 | 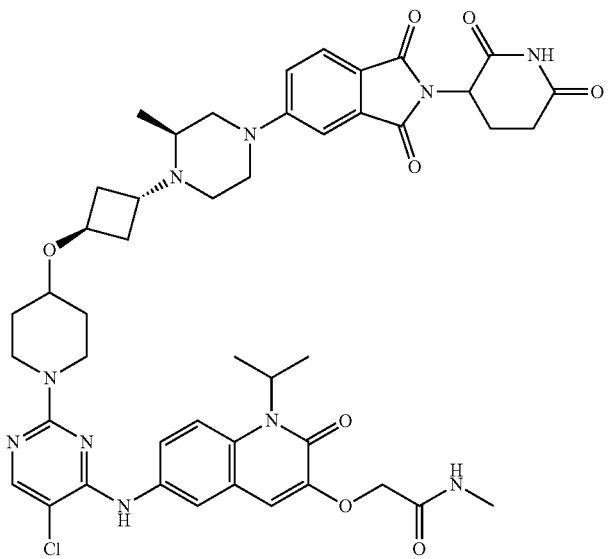 [SMILES: CNC(=O)COc1cc2cc(Nc3nc(N4CCC(O[C@H]5C[C@H](N6CCN(c7ccc8c(c7)C(=O)N(C7CCC(=O)NC7=O)C8=O)C[C@@H]6C)C5)CC4)ncc3Cl)ccc2n(C(C)C)c1=O] | 2-({6-[(5-chloro-2-{4-[(1r,3r)-3-[(2S)-4-[2-(2,6-dioxopiperidin-3-yl)-1,3-dioxo-2,3-dihydro-1H-isoindol-5-yl]-2-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifunctional compounds of the present disclosure

| Compound Number | Parent Mol Structure | IUPAC Name |
|---|---|---|
| 262 | 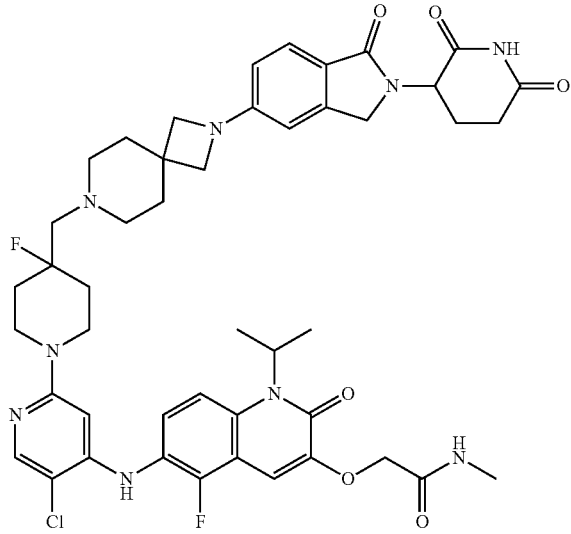 [SMILES: CNC(=O)COc1cc2c(F)c(Nc3cc(N4CCC(F)(CN5CCC6(CC5)CN(c5ccc7c(c5)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-2,3-dihydro-1H-isoindol-5-yl]-2,7-diazaspiro[3.5]nonan-7-yl}methyl)-4-fluoropiperidin-1-yl]pyridin-4-yl}amino)-5-fluoro-2-oxo-1-(propan-2-yl)-1,2-dihydroquinolin-3-yl]oxy}-N-methylacetamide |
| 263 | 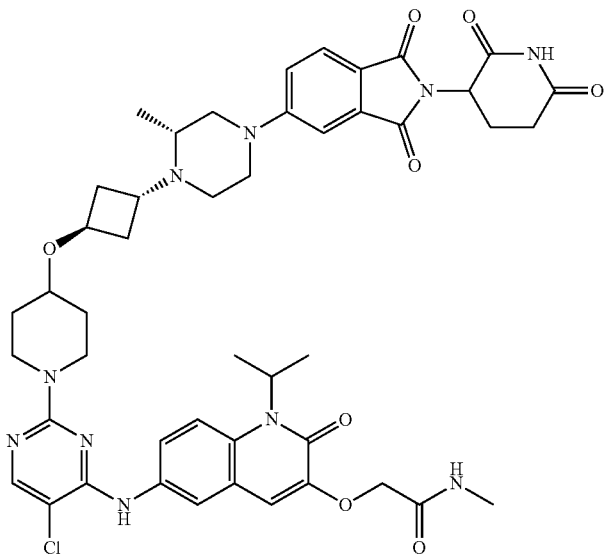 [SMILES: CNC(=O)COc1cc2cc(Nc3nc(N4CCC(O[C@H]5C[C@H](N6CCN(c7ccc8c(c7)C(=O)N(C7CCC(=O)NC7=O)C8=O)C[C@H]6C)C5)CC4)ncc3Cl)ccc2n(C(C)C)c1=O] | 2-({6-[(5-chloro-2-{4-[(1r,3r)-3-[(2R)-4-[2-(2,6-dioxopiperidin-3-yl)-1,3-dioxo-2,3-dihydro-1H-isoindol-5-yl]-2-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifunctional compounds of the present disclosure

| Compound Number | Parent Mol Structure | IUPAC Name |
|---|---|---|
| 264 | 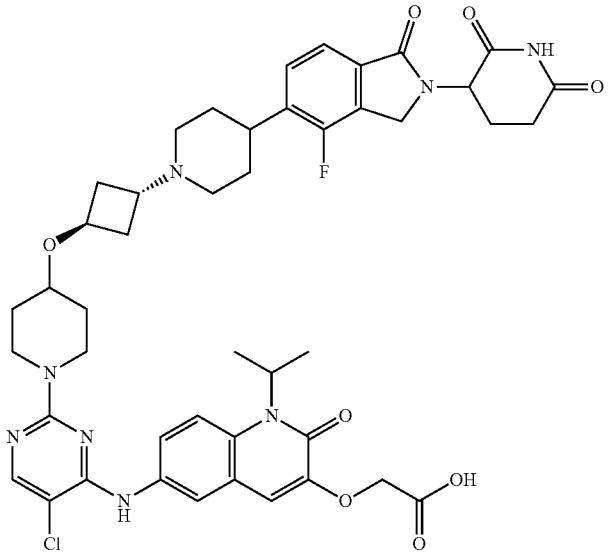 [SMILES: CC(C)n1c(=O)c(OCC(=O)O)cc2cc(Nc3nc(N4CCC(O[C@H]5C[C@H](N6CCC(c7ccc8c(c7F)CN(C7CCC(=O)NC7=O)C8=O)CC6)C5)CC4)ncc3Cl)ccc21] | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)acetic acid |
| 265 | 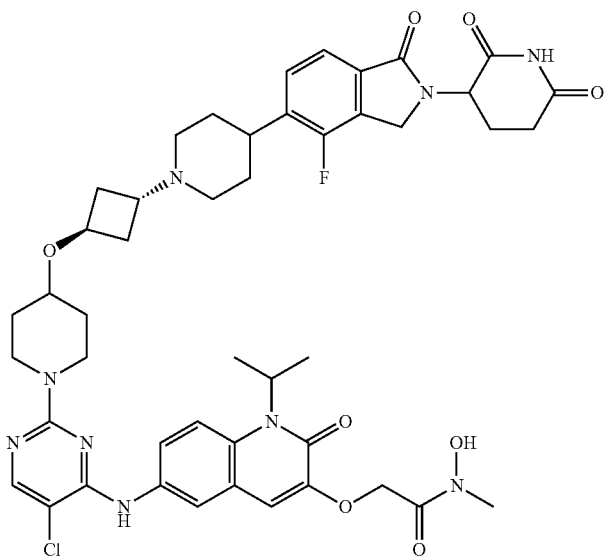 [SMILES: CC(C)n1c(=O)c(OCC(=O)N(C)O)cc2cc(Nc3nc(N4CCC(O[C@H]5C[C@H](N6CCC(c7ccc8c(c7F)CN(C7CCC(=O)NC7=O)C8=O)CC6)C5)CC4)ncc3Cl)ccc21] | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-hydroxy-N-methylacetamide |

TABLE 3-continued

Additional exemplary bifufunctional compounds of the present disclosure

| Compound Number | Parent Mol Structure | IUPAC Name |
| --- | --- | --- |
| 266 | 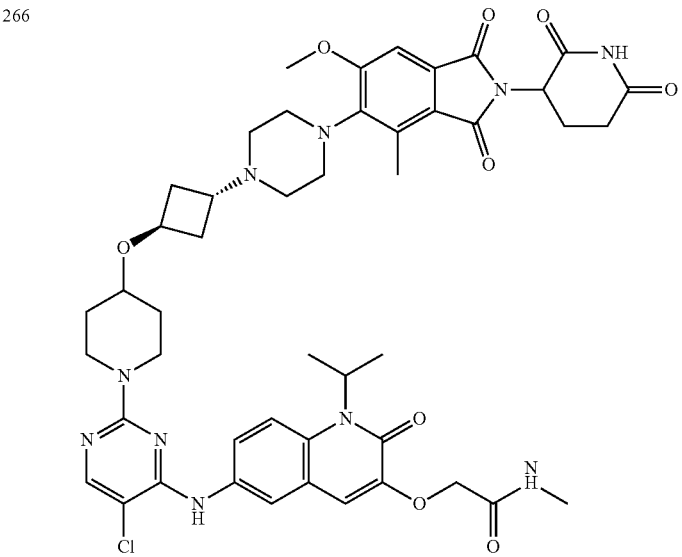 | 2-({6-[(5-chloro-2-{4-[(1r,3r)-3-{4-[2-(2,6-dioxopiperidin-3-yl)-6-methoxy-4-methyl-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 267 | 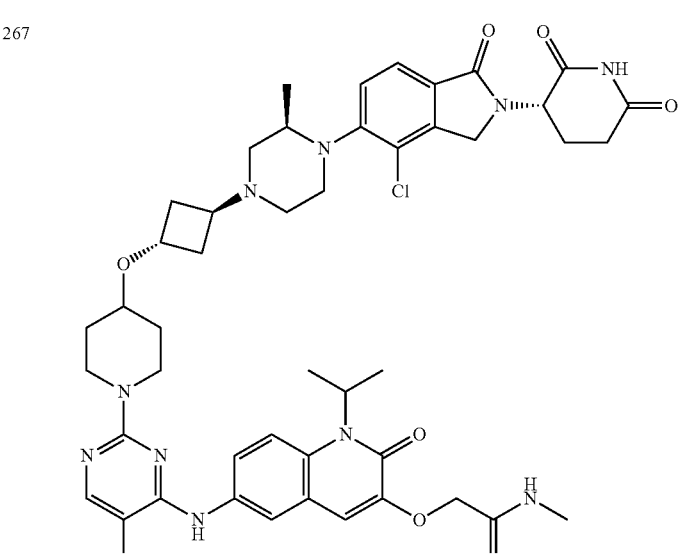 | 2-({6-[(5-chloro-2-{4-[(1r,3r)-3-[(3R)-4-{4-chloro-2-[(3S)-2,6-dioxopiperidin-3-yl]-1-oxo-2,3-dihydro-1H-isoindol-5-yl}-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 268 | | 2-({6-[(5-chloro-2-{4-[(1r,3r)-3-[(3R)-4-{4-chloro-2-[(3R)-2,6-dioxopiperidin-3-yl]-1-oxo-2,3-dihydro-1H-isoindol-5-yl}-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 269 | | 2-({6-[(5-chloro-2-{4-[(1r,3r)-3-[(3R)-4-{6-chloro-2-[(3S)-2,6-dioxopiperidin-3-yl]-1-oxo-2,3-dihydro-1H-isoindol-5-yl}-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

US 11,986,532 B2

TABLE 3-continued

Additional exemplary bifufunctional compounds of the present disclosure

| Compound Number | Parent Mol Structure | IUPAC Name |
|---|---|---|
| 270 | 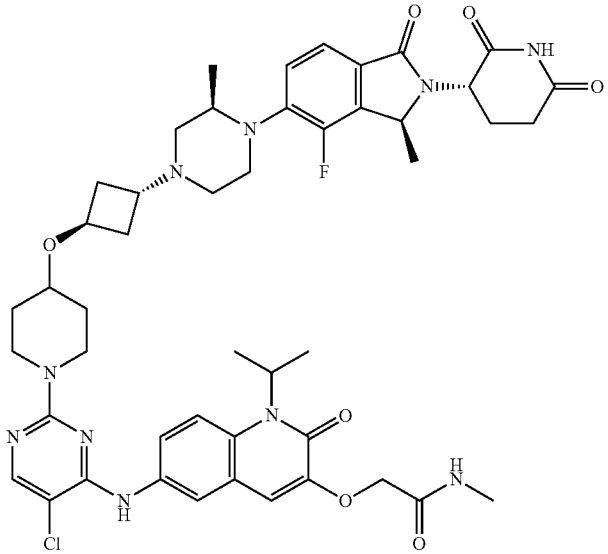 [SMILES: CNC(=O)COc1cc2cc(Nc3nc(N4CCC(O[C@H]5C[C@H](N6CCN(c7ccc8c(c7F)[C@H](C)N([C@H]7CCC(=O)NC7=O)C8=O)[C@H](C)C6)C5)CC4)ncc3Cl)ccc2n(C(C)C)c1=O] | 2-({6-[(5-chloro-2-{4-[(1r,3r)-3-[(3R)-4-[(3S)-2-[(3S)-2,6-dioxopiperidin-3-yl]-4-fluoro-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 271 | 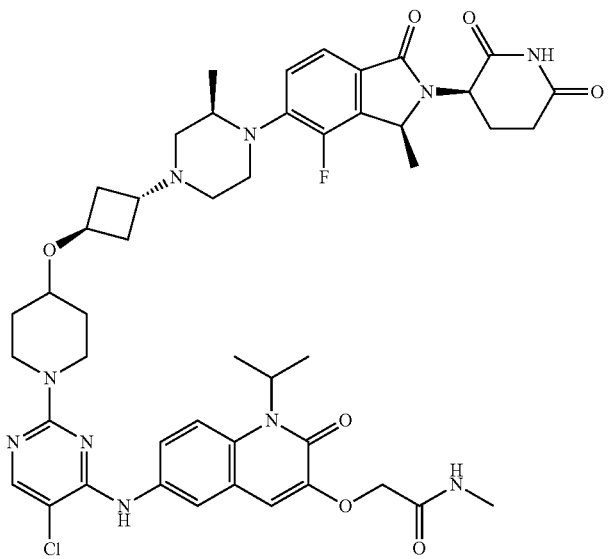 [SMILES: CNC(=O)COc1cc2cc(Nc3nc(N4CCC(O[C@H]5C[C@H](N6CCN(c7ccc8c(c7F)[C@H](C)N([C@@H]7CCC(=O)NC7=O)C8=O)[C@H](C)C6)C5)CC4)ncc3Cl)ccc2n(C(C)C)c1=O] | 2-({6-[(5-chloro-2-{4-[(1r,3r)-3-[(3R)-4-[(3S)-2-[(3R)-2,6-dioxopiperidin-3-yl]-4-fluoro-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

US 11,986,532 B2

TABLE 3-continued

Additional exemplary bifunctional compounds of the present disclosure

| Compound Number | Parent Mol Structure | IUPAC Name |
|---|---|---|
| 272 | 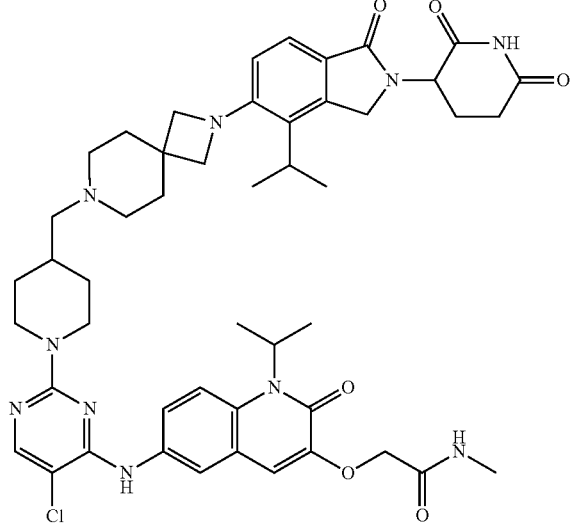 [SMILES: CNC(=O)COc1cc2cc(Nc3nc(N4CCC(CN5CCC6(CC5)CN(c5ccc7c(c5C(C)C)CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1-oxo-4-(propan-2-yl)-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide |
| 273 | 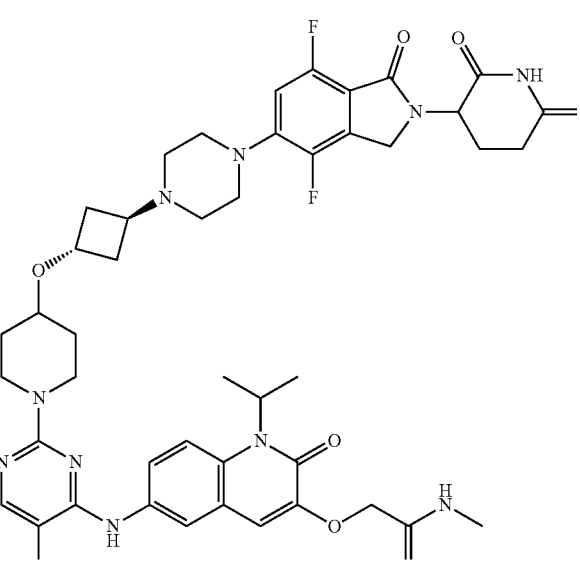 | 2-({6-[(5-chloro-2-{4-[(1r,3r)-3-{4-[2-(2,6-dioxopiperidin-3-yl)-4,7-difluoro-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 274 | 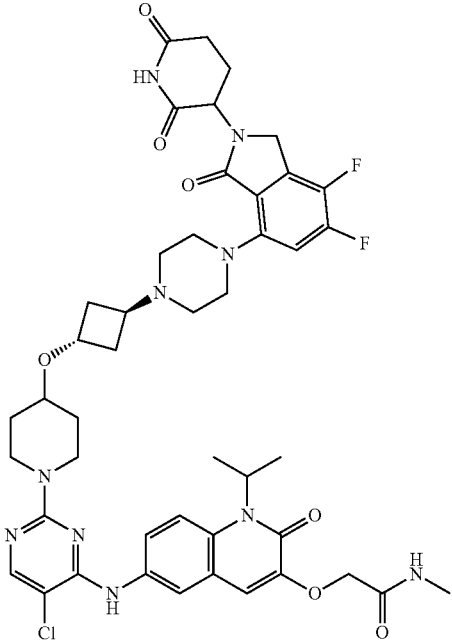 [SMILES: CNC(=O)COc1cc2cc(Nc3nc(N4CCC(O[C@H]5C[C@H](N6CCN(c7cc(F)c(F)c8c7C(=O)N(C7CCC(=O)NC7=O)C8)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-6,7-difluoro-3-oxo-2,3-dihydro-1H-isoindol-4-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 275 | 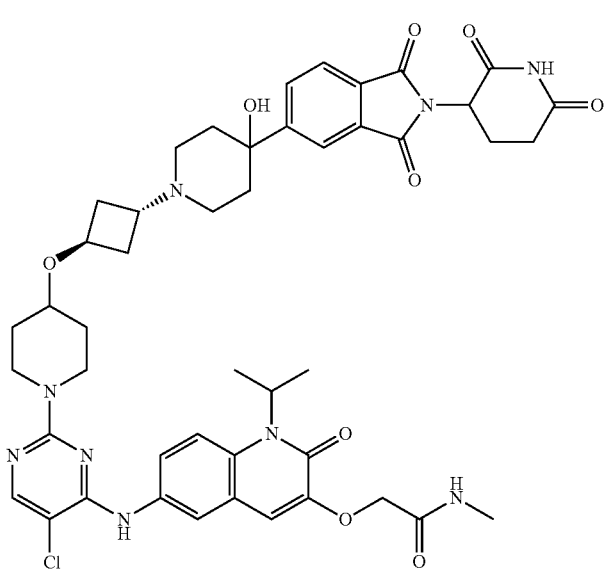 [SMILES: CNC(=O)COc1cc2cc(Nc3nc(N4CCC(O[C@H]5C[C@H](N6CCC(O)(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-2,3-dihydro-1H-isoindol-5-yl]-4-hydroxypiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 276 | 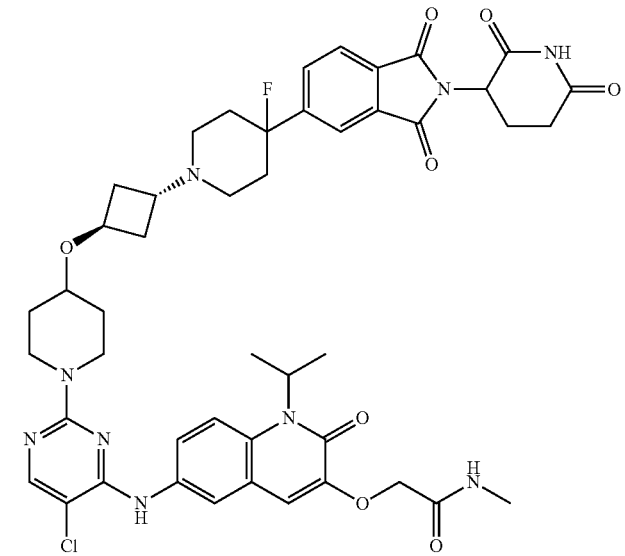 [SMILES: CNC(=O)COc1cc2cc(Nc3nc(N4CCC(O[C@H]5C[C@H](N6CCC(F)(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-2,3-dihydro-1H-isoindol-5-yl]-4-fluoropiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 277 | 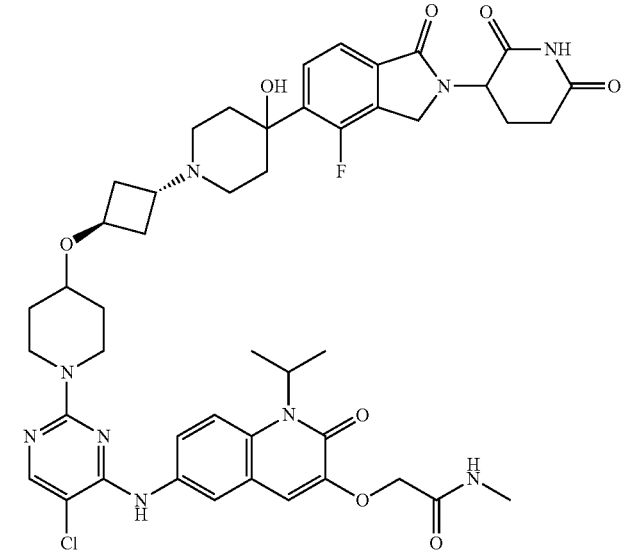 [SMILES: CNC(=O)COc1cc2cc(Nc3nc(N4CCC(O[C@H]5C[C@H](N6CCC(O)(c7ccc8c(c7F)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]-4-hydroxypiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 278 | 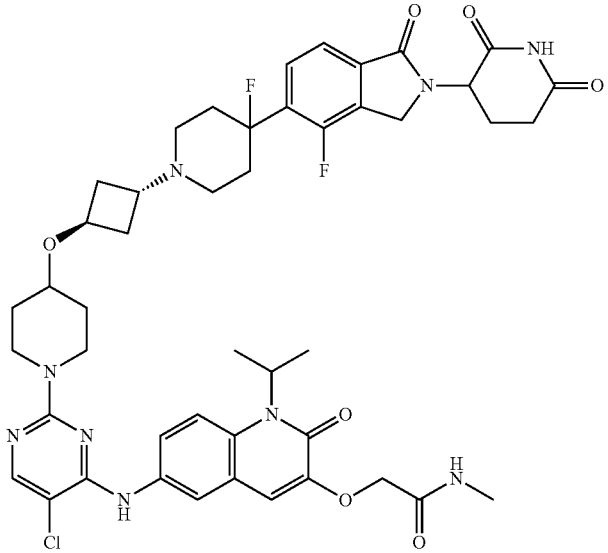 [SMILES: CNC(=O)COc1cc2cc(Nc3nc(N4CCC(O[C@H]5C[C@H](N6CCC(F)(c7ccc8c(c7F)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]-4-fluoropiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 279 | 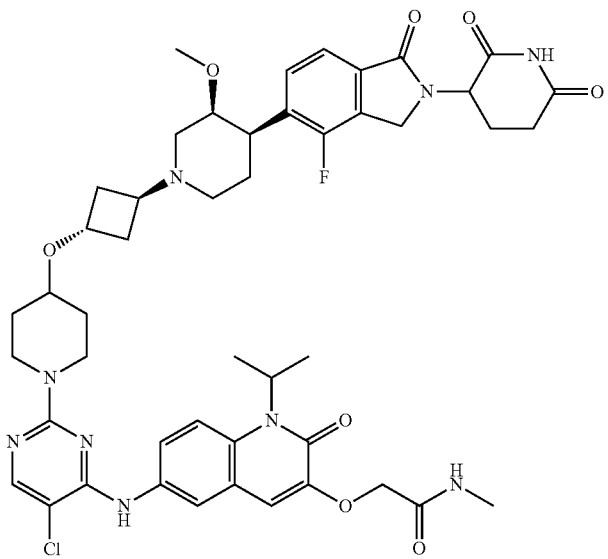 [SMILES: CNC(=O)COc1cc2cc(Nc3nc(N4CCC(O[C@H]5C[C@H](N6CC[C@H](c7ccc8c(c7F)CN(C7CCC(=O)NC7=O)C8=O)[C@H](OC)C6)C5)CC4)ncc3Cl)ccc2n(C(C)C)c1=O] | 2-({6-[(5-chloro-2-{4-[(1r,3r)-3-[(3S,4R)-4-[2-(2,6-dioxopiperidin-3-yl)-4-fluoro-1-oxo-2,3-dihydro-1H-isoindol-5-yl]-3-methoxypiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifunctional compounds of the present disclosure

| Compound Number | Parent Mol Structure | IUPAC Name |
|---|---|---|
| 280 | 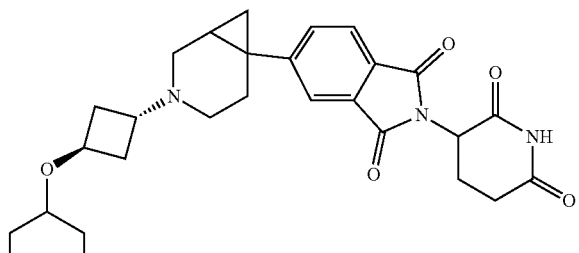 | 2-({6-[(5-chloro-2-{4-[(1r,3r)-3-{6-[2-(2,6-dioxopiperidin-3-yl)-1,3-dioxo-2,3-dihydro-1H-isoindol-5-yl]-3-azabicyclo[4.1.0]heptan-3-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 281 | 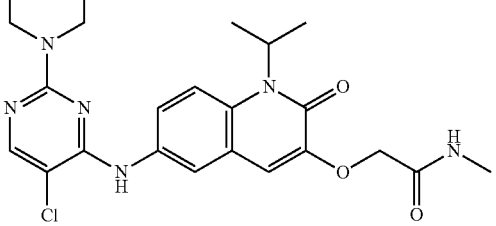 | 2-({6-[(5-chloro-2-{4-[(1r,3r)-3-{4-[2-(2,6-dioxopiperidin-3-yl)-7-fluoro-3-oxo-2,3-dihydro-1H-isoindol-5-yl]-3-fluoropiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 282 | 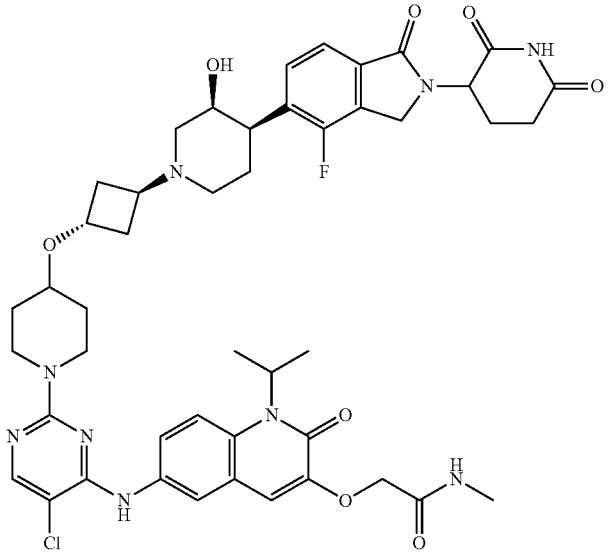 | 2-({6-[(5-chloro-2-{4-[(1r,3r)-3-[(3S,4R)-4-[2-(2,6-dioxopiperidin-3-yl)-4-fluoro-1-oxo-2,3-dihydro-1H-isoindol-5-yl]-3-hydroxypiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 283 | 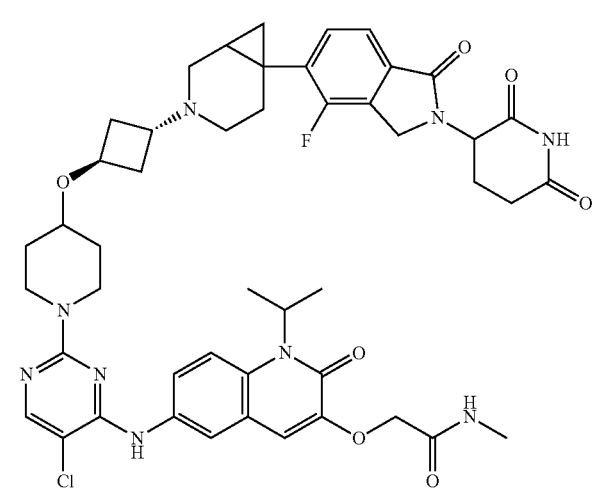 [SMILES: CNC(=O)COc1cc2cc(Nc3nc(N4CCC(O[C@H]5C[C@H](N6CCC7(c8ccc9c(c8F)CN(C8CCC(=O)NC8=O)C9=O)CC7C6)C5)CC4)ncc3Cl)ccc2n(C(C)C)c1=O] | 2-({6-[(5-chloro-2-{4-[(1r,3r)-3-{6-[2-(2,6-dioxopiperidin-3-yl)-4-fluoro-1-oxo-2,3-dihydro-1H-isoindol-5-yl]-3-azabicyclo[4.1.0]heptan-3-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifunctional compounds of the present disclosure

| Compound Number | Parent Mol Structure | IUPAC Name |
|---|---|---|
| 284 | | 2-({6-[(5-chloro-2-{4-[(1r,3r)-3-[(3R,4R)-4-[2-(2,6-dioxopiperidin-3-yl)-4-fluoro-1-oxo-2,3-dihydro-1H-isoindol-5-yl]-3-hydroxypiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 285 | | 2-({6-[(5-chloro-2-{4-[(3-{4-[2-(2,6-dioxopiperidin-3-yl)-4-fluoro-1-oxo-2,3-dihydro-1H-isoindol-5-yl]piperidin-1-yl}azetidin-1-yl)methyl]-4-fluoropiperidin-1-yl}pyrimidin-4-yl)amino]-2-oxo-1-(propan-2-yl)-1,2-dihydroquinolin-3-yl}oxy)-N-methylacetamide |
| 286 | | 2-({6-[(5-chloro-2-{4-[(1r,3r)-3-[4-({1-[2-(2,6-dioxopiperidin-3-yl)-4-fluoro-1-oxo-2,3-dihydro-1H-isoindol-5-yl]piperidin-4-yl}methyl)piperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifunctional compounds of the present disclosure

| Compound Number | Parent Mol Structure | IUPAC Name |
| --- | --- | --- |
| 287 | | 2-({6-[(5-chloro-2-{4-[(1r,3r)-3-[(3R)-4-[2-(2,6-dioxopiperidin-3-yl)-4-methyl-1,3-dioxo-2,3-dihydro-1H-isoindol-5-yl]-3-ethylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 288 | | 2-({6-[(5-chloro-2-{4-[(1r,3r)-3-{4-[(3R)-2-[(3S)-2,6-dioxopiperidin-3-yl]-4-fluoro-3-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 289 | 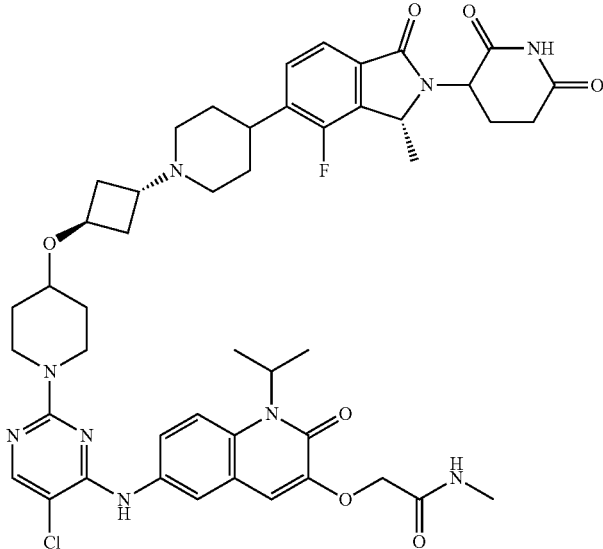 [SMILES: CNC(=O)COc1cc2cc(Nc3nc(N4CCC(O[C@H]5C[C@H](N6CCC(c7ccc8c(c7F)[C@@H](C)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[(3R)-2-(2,6-dioxopiperidin-3-yl)-4-fluoro-3-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 290 | 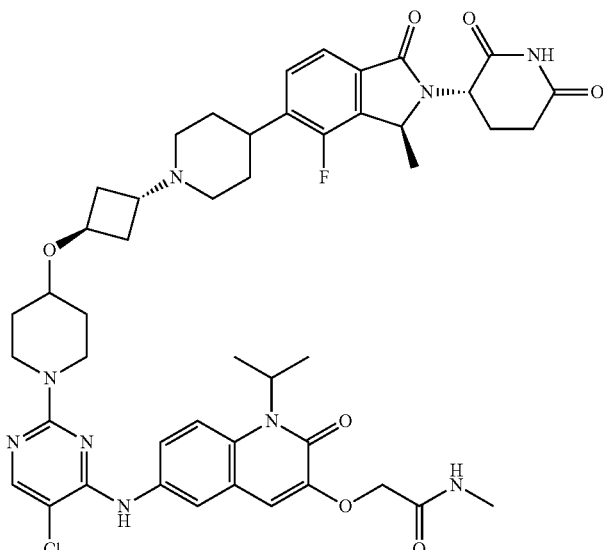 | 2-({6-[(5-chloro-2-{4-[(1r,3r)-3-{4-[(3S)-2-[(3S)-2,6-dioxopiperidin-3-yl]-4-fluoro-3-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifunctional compounds of the present disclosure

| Compound Number | Parent Mol Structure | IUPAC Name |
|---|---|---|
| 291 | 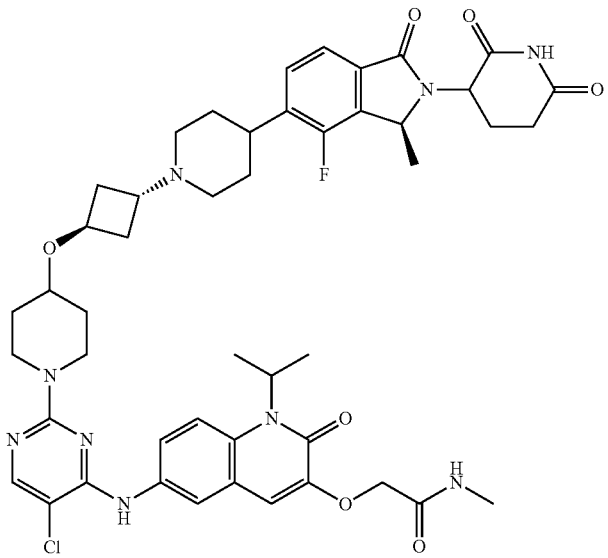 | 2-({6-[(5-chloro-2-{4-[(1r,3r)-3-{4-[(3S)-2-(2,6-dioxopiperidin-3-yl)-4-fluoro-3-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |
| 292 | 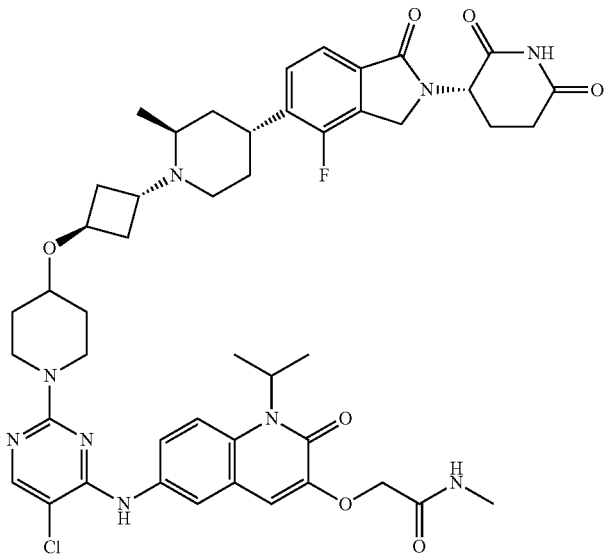 [SMILES: CNC(=O)COc1cc2cc(Nc3nc(N4CCC(O[C@H]5C[C@H](N6CC[C@@H](c7ccc8c(c7F)CN([C@H]7CCC(=O)NC7=O)C8=O)C[C@@H]6C)C5)CC4)ncc3Cl)ccc2n(C(C)C)c1=O] | 2-({6-[(5-chloro-2-{4-[(1r,3r)-3-[(2S,4R)-4-{2-[(3S)-2,6-dioxopiperidin-3-yl]-4-fluoro-1-oxo-2,3-dihydro-1H-isoindol-5-yl}-2-methylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

US 11,986,532 B2

TABLE 3-continued

Additional exemplary bifufunctional compounds of the present disclosure

| Compound Number | Parent Mol Structure | IUPAC Name |
|---|---|---|
| 293 | 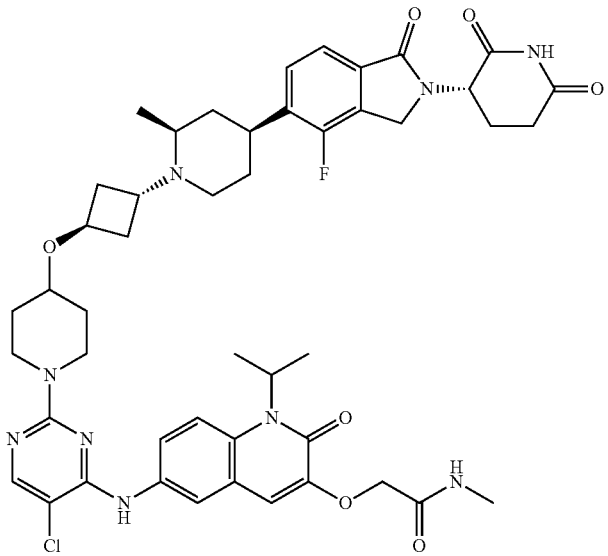 [SMILES: CNC(=O)COc1cc2cc(Nc3nc(N4CCC(O[C@H]5C[C@H](N6CC[C@H](c7ccc8c(c7F)CN([C@H]7CCC(=O)NC7=O)C8=O)C[C@@H]6C)C5)CC4)ncc3Cl)ccc2n(C(C)C)c1=O] | 2-({6-[(5-chloro-2-{4-[(1r,3r)-3-[(2S,4S)-4-{2-[(3S)-2,6-dioxopiperidin-3-yl]-4-fluoro-1-oxo-2,3-dihydro-1H-isoindol-5-yl}-2-methylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 294 | 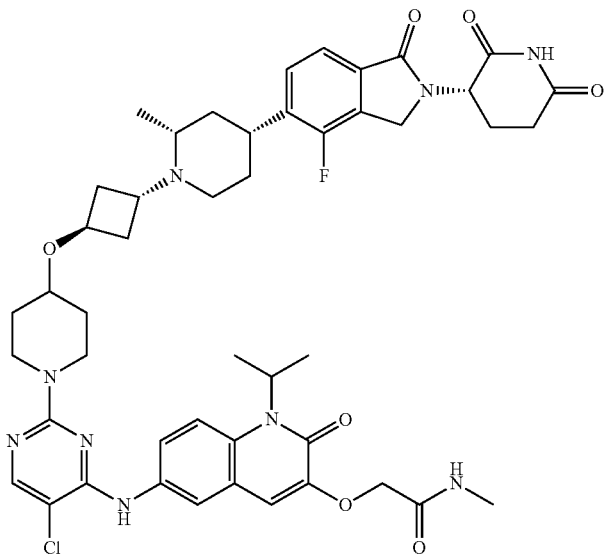 [SMILES: CNC(=O)COc1cc2cc(Nc3nc(N4CCC(O[C@H]5C[C@H](N6CC[C@@H](c7ccc8c(c7F)CN([C@H]7CCC(=O)NC7=O)C8=O)C[C@H]6C)C5)CC4)ncc3Cl)ccc2n(C(C)C)c1=O] | 2-({6-[(5-chloro-2-{4-[(1r,3r)-3-[(2R,4R)-4-{2-[(3S)-2,6-dioxopiperidin-3-yl]-4-fluoro-1-oxo-2,3-dihydro-1H-isoindol-5-yl}-2-methylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 3-continued

Additional exemplary bifufunctional compounds of the present disclosure

| Compound Number | Parent Mol Structure | IUPAC Name |
|---|---|---|
| 295 | 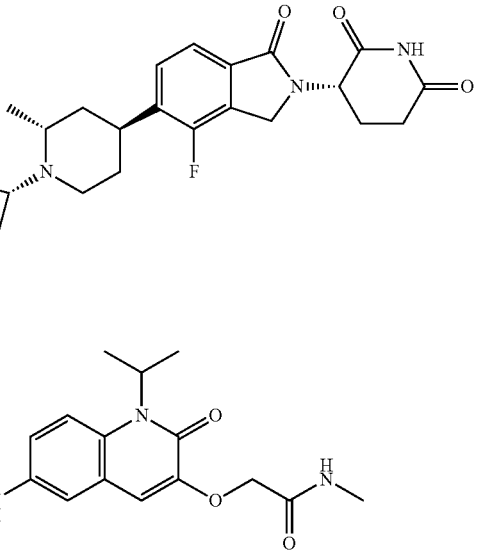 | 2-({6-[(5-chloro-2-{4-[(1r,3r)-3-[(2R,4S)-4-{2-[(3S)-2,6-dioxopiperidin-3-yl]-4-fluoro-1-oxo-2,3-dihydro-1H-isoindol-5-yl}-2-methylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide |
| 296 | 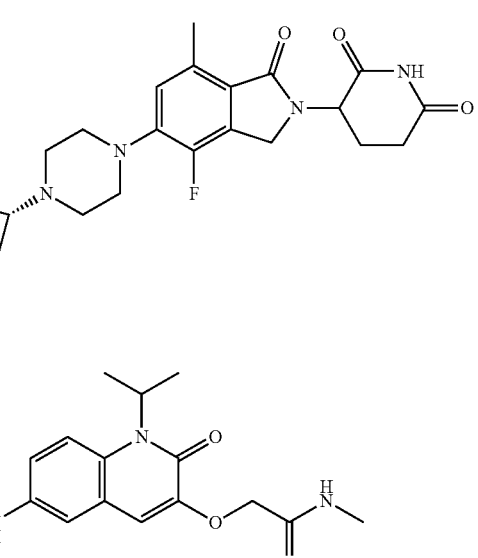 | 2-({6-[(5-chloro-2-{4-[(1r,3r)-3-{4-[2-(2,6-dioxopiperidin-3-yl)-4-fluoro-7-methyl-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide |

TABLE 4

Additional exemplary bifunctional compounds of the present disclosure

| Compound Number | Parent Mol Structure | IUPAC Name | Analogously made to Compound Number |
|---|---|---|---|
| 297 | | 2-{[6-({5-chloro-2-[4-({1-[2-(2,6-dioxopiperidin-3-yl)-5-fluoro-1-oxo-2,3-dihydro-1H-isoindol-4-yl]piperidin-4-yl}methyl)piperazin-1-yl]pyrimidin-4-yl}amino)-2-oxo-1-(propan-2-yl)-1,2-dihydroquinolin-3-yl]oxy}-N-methylacetamide | 105 |
| 298 | | 2-{[6-({5-chloro-2-[4-({2-[2-(2,6-dioxopiperidin-3-yl)-5-fluoro-1-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 61 |

TABLE 4-continued

Additional exemplary bifunctional compounds of the present disclosure

| Compound Number | Parent Mol Structure | IUPAC Name | Analogously made to Compound Number |
|---|---|---|---|
| 299 | 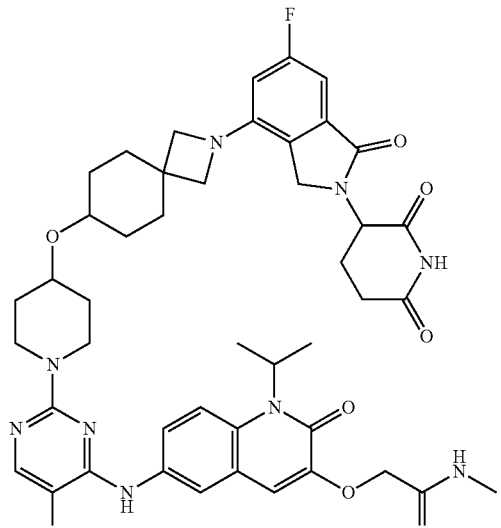 | 2-{[6-({5-chloro-2-[4-({2-[2-(2,6-dioxopiperidin-3-yl)-6-fluoro-1-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 61 |
| 300 | 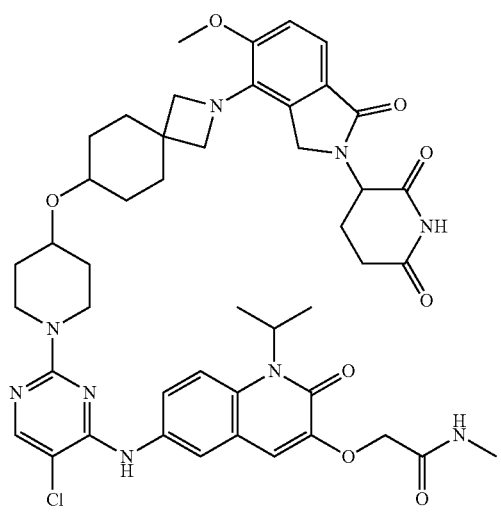 [SMILES: CNC(=O)COc1cc2cc(Nc3nc(N4CCC(OC5CCC6(CC5)CN(c5c(OC)ccc7c5CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-5-methoxy-1-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 61 |

TABLE 4-continued

Additional exemplary bifunctional compounds of the present disclosure

| Compound Number | Parent Mol Structure | IUPAC Name | Analogously made to Compound Number |
|---|---|---|---|
| 301 | | 2-{[6-({5-chloro-2-[4-({2-[2-(2,6-dioxopiperidin-3-yl)-6-methoxy-1-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 61 |
| 302 | | 2-{[6-({5-chloro-2-[4-({2-[2-(2,6-dioxopiperidin-3-yl)-4-methoxy-1-oxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 1 |

TABLE 4-continued

Additional exemplary bifunctional compounds of the present disclosure

| Compound Number | Parent Mol Structure | IUPAC Name | Analogously made to Compound Number |
|---|---|---|---|
| 303 | 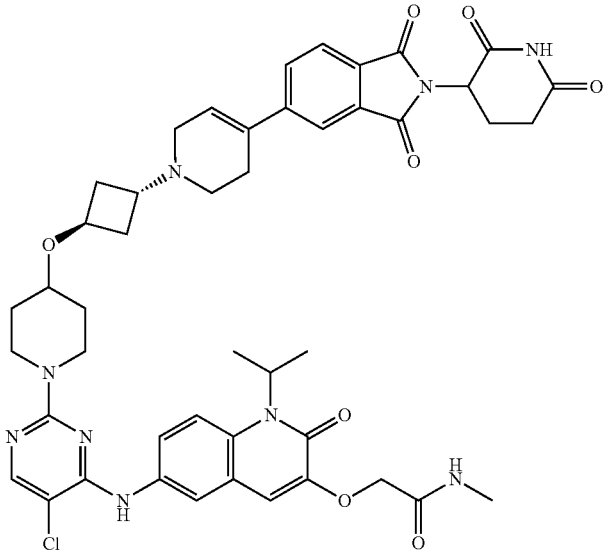 [SMILES: CNC(=O)COc1cc2cc(Nc3nc(N4CCC(O[C@H]5C[C@H](N6CC=C(c7ccc8c(c7)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-2,3-dihydro-1H-isoindol-5-yl]-1,2,3,6-tetrahydropyridin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 167 |
| 304 | 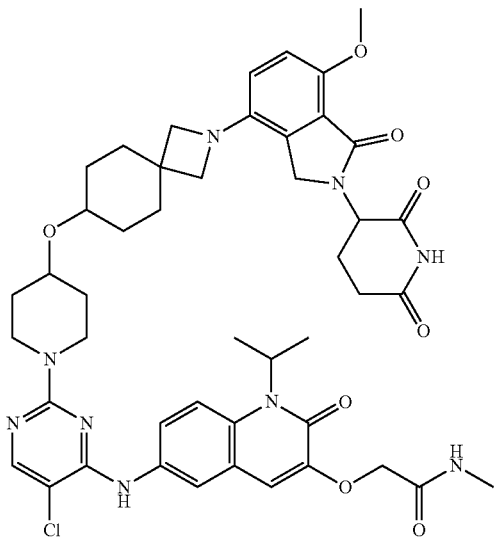 [SMILES: CNC(=O)COc1cc2cc(Nc3nc(N4CCC(OC5CCC6(CC5)CN(c5ccc(OC)c7c5CN(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-7-methoxy-1-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 61 |

TABLE 4-continued

Additional exemplary bifunctional compounds of the present disclosure

| Compound Number | Parent Mol Structure | IUPAC Name | Analogously made to Compound Number |
|---|---|---|---|
| 305 | | 2-{[6-({5-chloro-2-[4-({2-[2-(2,6-dioxopiperidin-3-yl)-1-oxo-2,3-dihydro-1H-isoindol-5-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |
| 306 | | 2-{[6-({5-chloro-2-[4-({2-[2-(2,6-dioxopiperidin-3-yl)-6-fluoro-1-oxo-2,3-dihydro-1H-isoindol-5-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |

TABLE 4-continued

Additional exemplary bifunctional compounds of the present disclosure

| Compound Number | Parent Mol Structure | IUPAC Name | Analogously made to Compound Number |
|---|---|---|---|
| 307 | | 2-{[6-({5-chloro-2-[4-({2-[2-(2,6-dioxopiperidin-3-yl)-4-fluoro-1-oxo-2,3-dihydro-1H-isoindol-5-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |
| 308 | | 2-{[6-({5-chloro-2-[4-({2-[2-(2,6-dioxopiperidin-3-yl)-1,3-dioxo-2,3-dihydro-1H-isoindol-5-yl]-2-azaspiro[3.5]nonan-7-yl}(methyl)amino)piperidin-1-yl]pyrimidin-4-yl}amino)-2-oxo-1-(propan-2-yl)-1,2-dihydroquinolin-3-yl]oxy}-N-methylacetamide | 6 |

TABLE 4-continued

Additional exemplary bifunctional compounds of the present disclosure

| Compound Number | Parent Mol Structure | IUPAC Name | Analogously made to Compound Number |
|---|---|---|---|
| 309 | | 2-({6-[(5-chloro-2-{4-[(1r,3r)-3-{1-[2-(2,6-dioxopiperidin-3-yl)-1-oxo-2,3-dihydro-1H-isoindol-5-yl]-1,6-diazaspiro[3.3]heptan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 310 | | 2-({6-[(5-chloro-2-{4-[(1r,3r)-3-{1-[2-(2,6-dioxopiperidin-3-yl)-3-oxo-2,3-dihydro-1H-isoindol-4-yl]-1,6-diazaspiro[3.3]heptan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 311 | | 2-({6-[(5-chloro-2-{4-[(1r,3r)-3-{6-[2-(2,6-dioxopiperidin-3-yl)-1,3-dioxo-2,3-dihydro-1H-isoindol-5-yl]-2,6-diazaspiro[3.3]heptan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 312 | | 2-{[6-({5-chloro-2-[4-({2-[2-(2,6-dioxopiperidin-3-yl)-7-fluoro-1-oxo-2,3-dihydro-1H-isoindol-4-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 61 |
| 313 | | 2-{[6-({5-chloro-2-[4-({2-[2-(2,6-dioxopiperidin-3-yl)-1-oxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |
| 314 | | 2-{[6-({5-chloro-2-[4-({2-[2-(2,6-dioxopiperidin-3-yl)-5-fluoro-1-oxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |

TABLE 4-continued

Additional exemplary bifunctional compounds of the present disclosure

| Compound Number | Parent Mol Structure | IUPAC Name | Analogously made to Compound Number |
|---|---|---|---|
| 315 | | 2-{[6-({5-chloro-2-[4-({2-[2-(2,6-dioxopiperidin-3-yl)-6-fluoro-1-oxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |
| 316 | | 2-{[6-({5-chloro-2-[4-({2-[2-(2,6-dioxopiperidin-3-yl)-7-fluoro-1-oxo-2,3-dihydro-1H-isoindol-4-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |

… TABLE 4-continued

Additional exemplary bifunctional compounds of the present disclosure

| Compound Number | Parent Mol Structure | IUPAC Name | Analogously made to Compound Number |
|---|---|---|---|
| 317 | 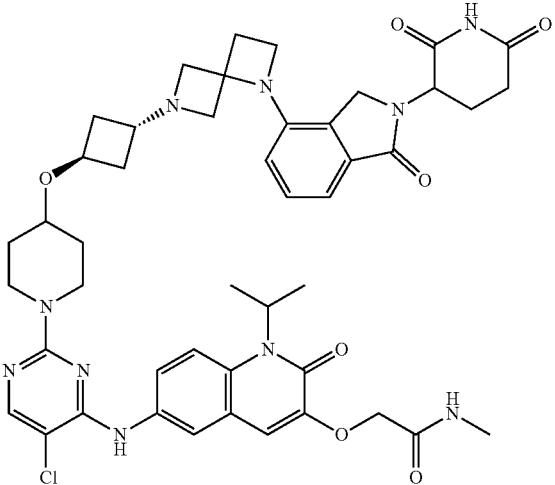 [SMILES: CNC(=O)COc1cc2cc(Nc3nc(N4CCC(O[C@H]5C[C@H](N6CC7(CCN7c7cccc8c7CN(C7CCC(=O)NC7=O)C8=O)C6)C5)CC4)ncc3Cl)ccc2n(C(C)C)c1=O] | 2-({6-[(5-chloro-2-{4-[(1r,3r)-3-{1-[2-(2,6-dioxopiperidin-3-yl)-1-oxo-2,3-dihydro-1H-isoindol-4-yl]-1,6-diazaspiro[3.3]heptan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 318 | 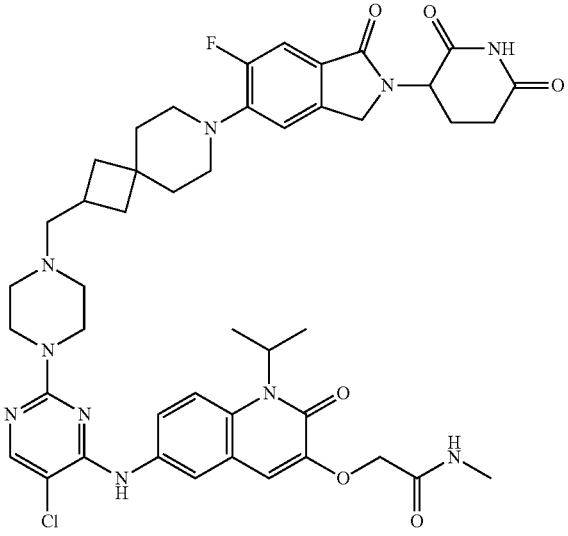 [SMILES: CNC(=O)COc1cc2cc(Nc3nc(N4CCN(CC5CC6(CCN(c7cc8c(cc7F)C(=O)N(C7CCC(=O)NC7=O)C8)CC6)C5)CC4)ncc3Cl)ccc2n(C(C)C)c1=O] | 2-{[6-({5-chloro-2-[4-({7-[2-(2,6-dioxopiperidin-3-yl)-6-fluoro-1-oxo-2,3-dihydro-1H-isoindol-5-yl]-7-azaspiro[3.5]nonan-2-yl}methyl)piperazin-1-yl]pyrimidin-4-yl}amino)-2-oxo-1-(propan-2-yl)-1,2-dihydroquinolin-3-yl]oxy}-N-methylacetamide | 6 |

TABLE 4-continued

Additional exemplary bifunctional compounds of the present disclosure

| Compound Number | Parent Mol Structure | IUPAC Name | Analogously made to Compound Number |
|---|---|---|---|
| 319 | 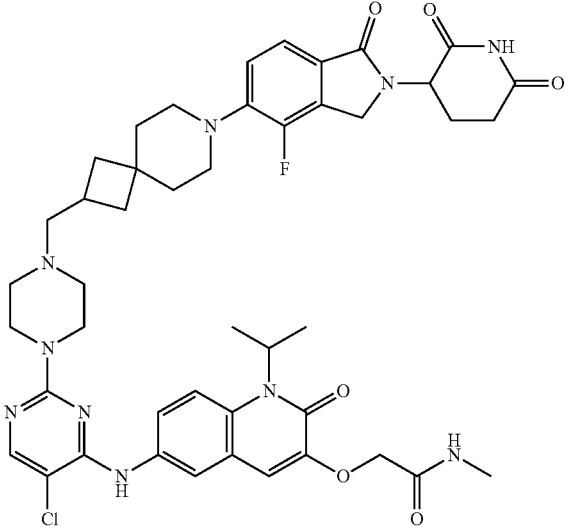 | 2-{[6-({5-chloro-2-[4-({7-[2-(2,6-dioxopiperidin-3-yl)-4-fluoro-1-oxo-2,3-dihydro-1H-isoindol-5-yl]-7-azaspiro[3.5]nonan-2-yl}methyl)piperazin-1-yl]pyrimidin-4-yl}amino)-2-oxo-1-(propan-2-yl)-1,2-dihydroquinolin-3-yl]oxy}-N-methylacetamide | 6 |
| 320 | 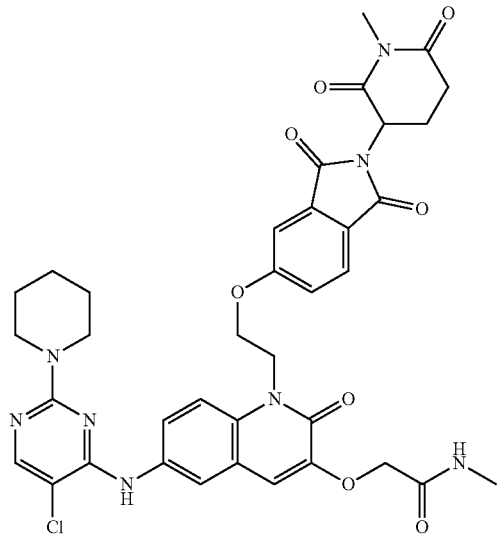 [SMILES: CNC(=O)COc1cc2cc(Nc3nc(N4CCCCC4)ncc3Cl)ccc2n(CCOc2ccc3c(c2)C(=O)N(C2CCC(=O)N(C)C2=O)C3=O)c1=O] | 2-[(6-{[5-chloro-2-(piperidin-1-yl)pyrimidin-4-yl]amino}-1-(2-{[2-(1-methyl-2,6-dioxopiperidin-3-yl)-1,3-dioxo-2,3-dihydro-1H-isoindol-5-yl]oxy}ethyl)-2-oxo-1,2-dihydroquinolin-3-yl)oxy]-N-methylacetamide | 29 |

TABLE 4-continued

Additional exemplary bifunctional compounds of the present disclosure

| Compound Number | Parent Mol Structure | IUPAC Name | Analogously made to Compound Number |
|---|---|---|---|
| 321 | | 2-{[6-({5-chloro-2-[4-({2-[2-(2,6-dioxopiperidin-3-yl)-1-oxo-2,3-dihydro-1H-isoindol-5-yl]-2,7-diazaspiro[3.5]nonan-7-yl}methyl)piperidin-1-yl]pyridin-4-yl}amino)-2-oxo-1-(propan-2-yl)-1,2-dihydroquinolin-3-yl]oxy}-N-methylacetamide | 215 |
| 322 | | 2-{[6-({5-chloro-2-[4-({4-[2-(2,6-dioxopiperidin-3-yl)-4-fluoro-1-oxo-2,3-dihydro-1H-isoindol-5-yl]piperazin-1-yl}methyl)piperidin-1-yl]pyrimidin-4-yl}amino)-2-oxo-1-(propan-2-yl)-1,2-dihydroquinolin-3-yl]oxy}-N-methylacetamide | 1 |

TABLE 4-continued

Additional exemplary bifunctional compounds of the present disclosure

| Compound Number | Parent Mol Structure | IUPAC Name | Analogously made to Compound Number |
|---|---|---|---|
| 323 | | 2-({6-[(5-chloro-2-{4-[(1r,3r)-3-{4-[2-(2,6-dioxopiperidin-3-yl)-1-oxo-2,3-dihydro-1H-isoindol-5-yl]-1,2,3,6-tetrahydropyridin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 81 |
| 324 | | 2-{[6-({5-chloro-2-[4-({2-[2-(2,6-dioxopiperidin-3-yl)-4,6-difluoro-1-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 49 |

TABLE 4-continued

Additional exemplary bifunctional compounds of the present disclosure

| Compound Number | Parent Mol Structure | IUPAC Name | Analogously made to Compound Number |
|---|---|---|---|
| 325 | | 2-{[6-({5-chloro-2-[4-({2-[2-(2,6-dioxopiperidin-3-yl)-1,3-dioxo-2,3-dihydro-1H-isoindol-4-yl]-5-fluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 1 |
| 326 | | 2-{[6-({5-chloro-2-[4-({2-[2-(2,6-dioxopiperidin-3-yl)-1-oxo-2,3-dihydro-1H-isoindol-4-yl]-5-fluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 1 |
| 327 | | 2-{[6-({5-chloro-2-[4-(2-{2-[2-(2,6-dioxopiperidin-3-yl)-5-methoxy-1-oxo-2,3-dihydro-1H-isoindol-4-yl]-2,7-diazaspiro[3.5]nonan-7-yl}propan-2-yl)piperidin-1-yl]pyrimidin-4-yl}amino)-2-oxo-1-(propan-2-yl)-1,2-dihydroquinolin-3-yl]oxy}-N-methylacetamide | 8 |

TABLE 4-continued

Additional exemplary bifunctional compounds of the present disclosure

| Compound Number | Parent Mol Structure | IUPAC Name | Analogously made to Compound Number |
|---|---|---|---|
| 328 | | 2-{[6-({5-chloro-2-[4-(2-{2-[2-(2,6-dioxopiperidin-3-yl)-6-methoxy-1-oxo-2,3-dihydro-1H-isoindol-4-yl]-2,7-diazaspiro[3.5]nonan-7-yl}propan-2-yl)piperidin-1-yl]pyrimidin-4-yl}amino)-2-oxo-1-(propan-2-yl)-1,2-dihydroquinolin-3-yl]oxy}-N-methylacetamide | 8 |
| 329 | | 2-({6-[(5-chloro-2-{4-[(1r,3r)-3-{4-[6-chloro-2-(2,6-dioxopiperidin-3-yl)-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 163 |

TABLE 4-continued

Additional exemplary bifunctional compounds of the present disclosure

| Compound Number | Parent Mol Structure | IUPAC Name | Analogously made to Compound Number |
|---|---|---|---|
| 330 | | 2-({6-[(5-chloro-2-{4-[(1r,3r)-3-{1-[2-(2,6-dioxopiperidin-3-yl)-3-oxo-2,3-dihydro-1H-isoindol-5-yl]-1,6-diazaspiro[3.3]heptan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 331 | | 2-{[6-({5-chloro-2-[4-({2-[2-(2,6-dioxopiperidin-3-yl)-4-methoxy-1-oxo-2,3-dihydro-1H-isoindol-5-yl]-2-azaspiro[3.5]nonan-7-yl}methyl)piperazin-1-yl]pyrimidin-4-yl}amino)-2-oxo-1-(propan-2-yl)-1,2-dihydroquinolin-3-yl]oxy}-N-methylacetamide | 6 |

TABLE 4-continued

Additional exemplary bifunctional compounds of the present disclosure

| Compound Number | Parent Mol Structure | IUPAC Name | Analogously made to Compound Number |
|---|---|---|---|
| 332 | 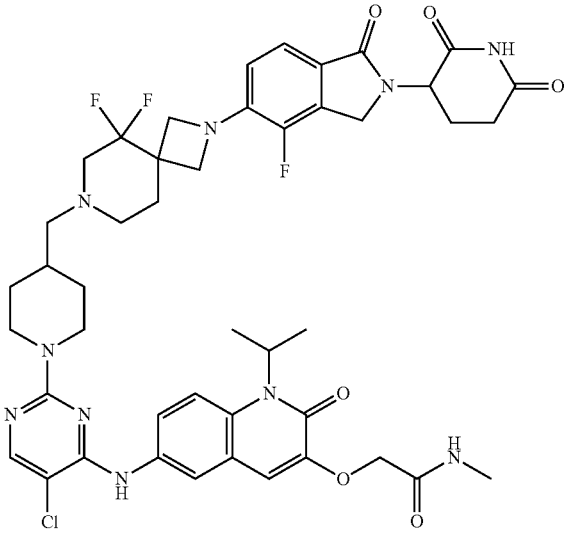 [SMILES: CNC(=O)COc1cc2cc(Nc3nc(N4CCC(CN5CCC6(CN(c7ccc8c(c7F)CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-4-fluoro-1-oxo-2,3-dihydro-1H-isoindol-5-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 90 |
| 333 | 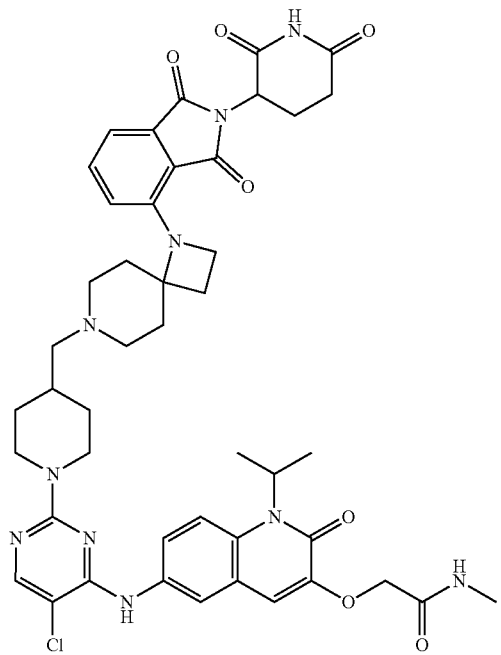 [SMILES: CNC(=O)COc1cc2cc(Nc3nc(N4CCC(CN5CCC6(CC5)CCN6c5cccc6c5C(=O)N(C5CCC(=O)NC5=O)C6=O)CC4)ncc3Cl)ccc2n(C(C)C)c1=O] | 2-{[6-({5-chloro-2-[4-({1-[2-(2,6-dioxopiperidin-3-yl)-1,3-dioxo-2,3-dihydro-1H-isoindol-4-yl]-1,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 38 |

TABLE 4-continued

Additional exemplary bifunctional compounds of the present disclosure

| Compound Number | Parent Mol Structure | IUPAC Name | Analogously made to Compound Number |
|---|---|---|---|
| 334 | | 2-{[6-({5-chloro-2-[4-({1-[2-(2,6-dioxopiperidin-3-yl)-1-oxo-2,3-dihydro-1H-isoindol-4-yl]-1,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 1 |
| 335 | | 2-{[6-({5-chloro-2-[4-({1-[2-(2,6-dioxopiperidin-3-yl)-1,3-dioxo-2,3-dihydro-1H-isoindol-5-yl]-1,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 38 |

TABLE 4-continued

Additional exemplary bifunctional compounds of the present disclosure

| Compound Number | Parent Mol Structure | IUPAC Name | Analogously made to Compound Number |
|---|---|---|---|
| 336 | | 2-{[6-({5-chloro-2-[4-({1-[2-(2,6-dioxopiperidin-3-yl)-1-oxo-2,3-dihydro-1H-isoindol-5-yl]-1,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 1 |
| 337 | | 2-{[6-({5-chloro-2-[4-({2-[2-(2,6-dioxopiperidin-3-yl)-1,3-dioxo-2,3-dihydro-1H-isoindol-4-yl]-1,1-dimethyl-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 162 |

TABLE 4-continued

Additional exemplary bifunctional compounds of the present disclosure

| Compound Number | Parent Mol Structure | IUPAC Name | Analogously made to Compound Number |
|---|---|---|---|
| 338 | 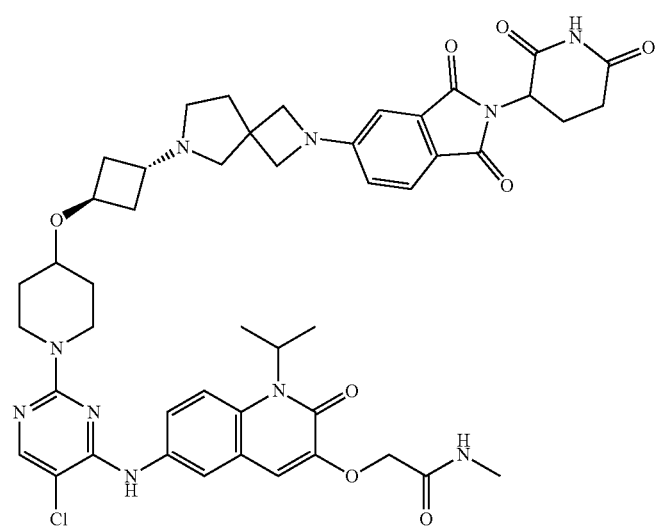 [SMILES: CNC(=O)COc1cc2cc(Nc3nc(N4CCC(O[C@H]5C[C@H](N6CCC7(CN(c8ccc9c(c8)C(=O)N(C8CCC(=O)NC8=O)C9=O)C7)C6)C5)CC4)ncc3Cl)ccc2n(C(C)C)c1=O] | 2-({6-[(5-chloro-2-{4-[(1r,3r)-3-{2-[2-(2,6-dioxopiperidin-3-yl)-1,3-dioxo-2,3-dihydro-1H-isoindol-5-yl]-2,6-diazaspiro[3.4]octan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 339 | 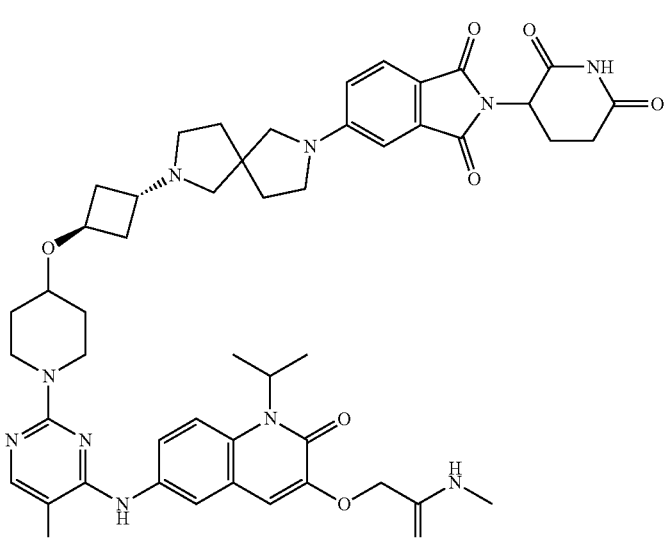 | 2-({6-[(5-chloro-2-{4-[(1r,3r)-3-{7-[2-(2,6-dioxopiperidin-3-yl)-1,3-dioxo-2,3-dihydro-1H-isoindol-5-yl]-2,7-diazaspiro[4.4]nonan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 340 | | 2-{[6-({5-chloro-2-[4-({2-[2-(2,6-dioxopiperidin-3-yl)-4-methoxy-1-oxo-2,3-dihydro-1H-isoindol-5-yl]-1,1-dimethyl-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 162 |
| 341 | | 2-{[6-({5-chloro-2-[4-({1-[(1r,4r)-4-[2-(2,6-dioxopiperidin-3-yl)-1,3-dioxo-2,3-dihydro-1H-isoindol-5-yl]cyclohexyl]azetidin-3-yl}oxy)piperidin-1-yl]pyrimidin-4-yl}amino)-2-oxo-1-(propan-2-yl)-1,2-dihydroquinolin-3-yl]oxy}-N-methylacetamide | 183 |

TABLE 4-continued

Additional exemplary bifunctional compounds of the present disclosure

| Compound Number | Parent Mol Structure | IUPAC Name | Analogously made to Compound Number |
|---|---|---|---|
| 342 | 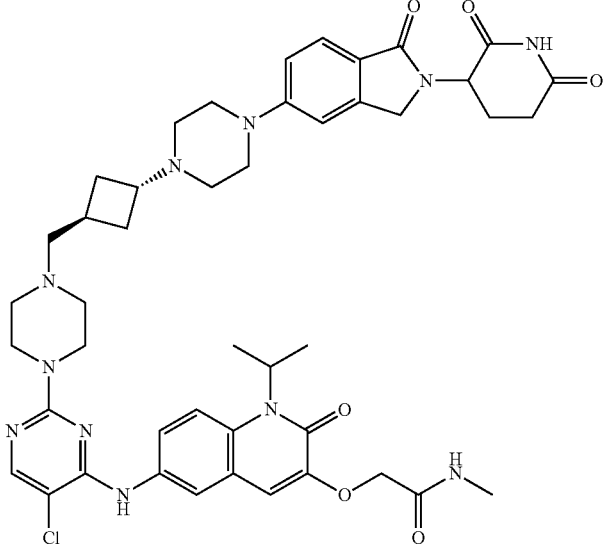 | 2-[(6-{[5-chloro-2-(4-{[(1r,3r)-3-{4-[2-(2,6-dioxopiperidin-3-yl)-1-oxo-2,3-dihydro-1H-isoindol-5-yl]piperazin-1-yl}cyclobutyl]methyl}piperazin-1-yl)pyrimidin-4-yl]amino}-2-oxo-1-(propan-2-yl)-1,2-dihydroquinolin-3-yl)oxy]-N-methylacetamide | 40, 164 |
| 343 | 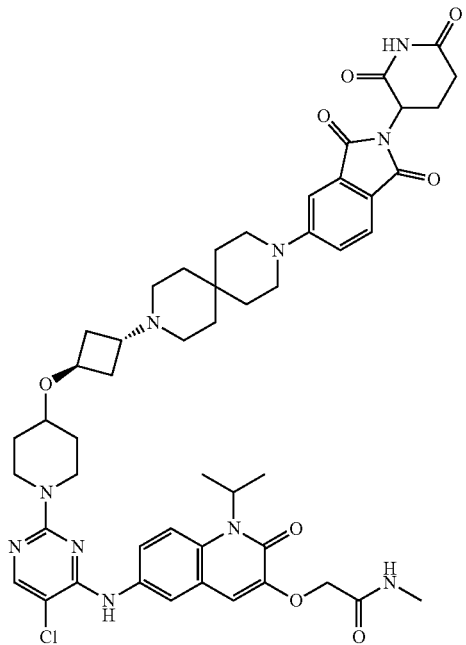 [SMILES: CNC(=O)COc1cc2cc(Nc3nc(N4CCC(O[C@H]5C[C@H](N6CCC7(CCN(c8ccc9c(c8)C(=O)N(C8CCC(=O)NC8=O)C9=O)CC7)CC6)C5)CC4)ncc3Cl)ccc2n(C(C)C)c1=O] | 2-({6-[(5-chloro-2-{4-[(1r,3r)-3-{9-[2-(2,6-dioxopiperidin-3-yl)-1,3-dioxo-2,3-dihydro-1H-isoindol-5-yl]-3,9-diazaspiro[5.5]undecan-3-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 344 | 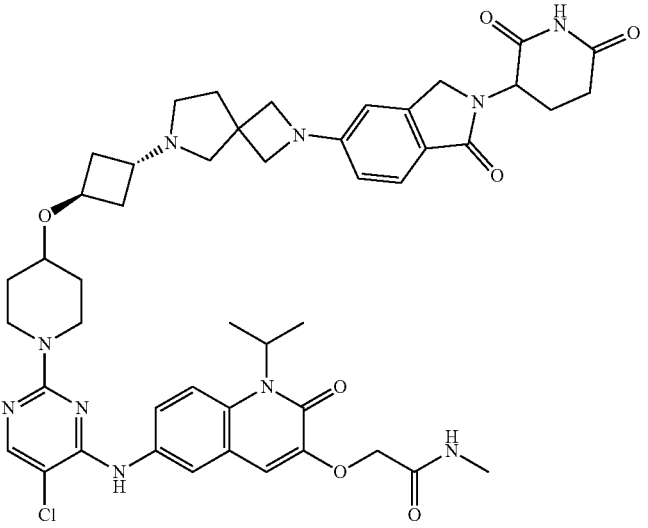 [SMILES: CNC(=O)COc1cc2cc(Nc3nc(N4CCC(O[C@H]5C[C@H](N6CCC7(CN(c8ccc9c(c8)CN(C8CCC(=O)NC8=O)C9=O)C7)C6)C5)CC4)ncc3Cl)ccc2n(C(C)C)c1=O] | 2-({6-[(5-chloro-2-{4-[(1r,3r)-3-{2-[2-(2,6-dioxopiperidin-3-yl)-1-oxo-2,3-dihydro-1H-isoindol-5-yl]-2,6-diazaspiro[3.4]octan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 345 | 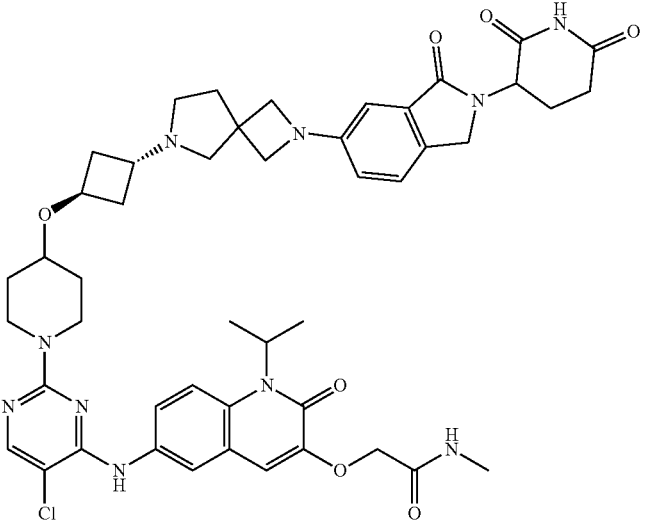 [SMILES: CNC(=O)COc1cc2cc(Nc3nc(N4CCC(O[C@H]5C[C@H](N6CCC7(CN(c8ccc9c(c8)C(=O)N(C8CCC(=O)NC8=O)C9)C7)C6)C5)CC4)ncc3Cl)ccc2n(C(C)C)c1=O] | 2-({6-[(5-chloro-2-{4-[(1r,3r)-3-{2-[2-(2,6-dioxopiperidin-3-yl)-3-oxo-2,3-dihydro-1H-isoindol-5-yl]-2,6-diazaspiro[3.4]octan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

| Compound Number | Parent Mol Structure | IUPAC Name | Analogously made to Compound Number |
|---|---|---|---|
| 346 | 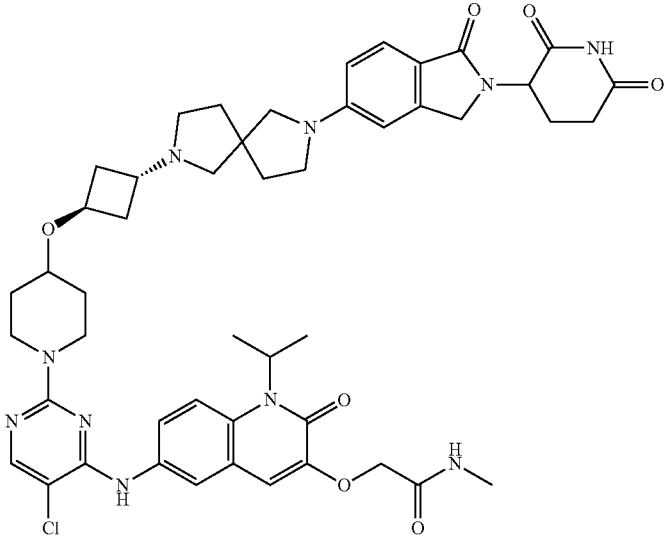 [SMILES: CNC(=O)COc1cc2cc(Nc3nc(N4CCC(O[C@H]5C[C@H](N6CCC7(CCN(c8ccc9c(c8)CN(C8CCC(=O)NC8=O)C9=O)C7)C6)C5)CC4)ncc3Cl)ccc2n(C(C)C)c1=O] | 2-({6-[(5-chloro-2-{4-[(1r,3r)-3-{7-[2-(2,6-dioxopiperidin-3-yl)-1-oxo-2,3-dihydro-1H-isoindol-5-yl]-2,7-diazaspiro[4.4]nonan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 347 | 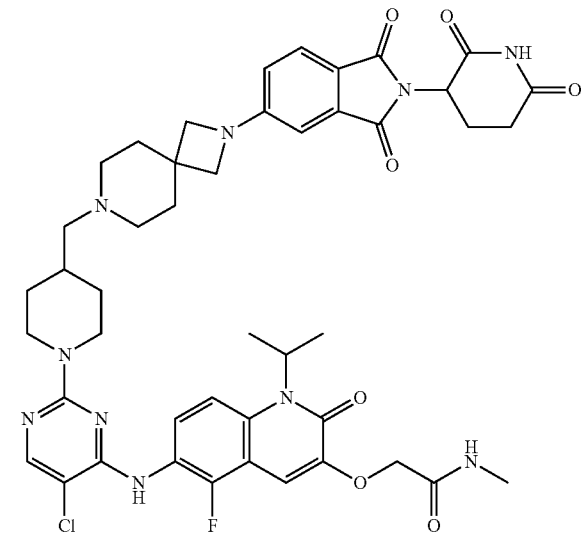 [SMILES: CNC(=O)COc1cc2c(F)c(Nc3nc(N4CCC(CN5CCC6(CC5)CN(c5ccc7c(c5)C(=O)N(C5CCC(=O)NC5=O)C7=O)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-5-yl]-2,7-diazaspiro[3.5]nonan-7-yl}methyl)piperidin-1-yl]pyrimidin-4-yl}amino)-5-fluoro-2-oxo-1-(propan-2-yl)-1,2-dihydroquinolin-3-yl]oxy}-N-methylacetamide | 195 |

TABLE 4-continued

Additional exemplary bifunctional compounds of the present disclosure

| Compound Number | Parent Mol Structure | IUPAC Name | Analogously made to Compound Number |
|---|---|---|---|
| 348 | | 2-({6-[(5-chloro-2-{4-[(1r,3r)-3-{4-[2-(2,6-dioxopiperidin-3-yl)-6-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 103 |
| 349 | | 2-({6-[(5-chloro-2-{4-[(1r,3r)-3-{9-[2-(2,6-dioxopiperidin-3-yl)-1-oxo-2,3-dihydro-1H-isoindol-5-yl]-3,9-diazaspiro[5.5]undecan-3-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 350 | 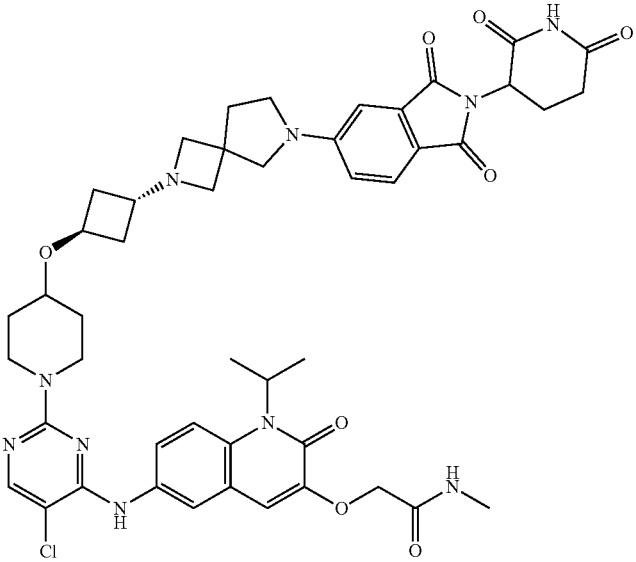 [SMILES: CNC(=O)COc1cc2cc(Nc3nc(N4CCC(O[C@H]5C[C@H](N6CC7(CCN(c8ccc9c(c8)C(=O)N(C8CCC(=O)NC8=O)C9=O)C7)C6)C5)CC4)ncc3Cl)ccc2n(C(C)C)c1=O] | 2-({6-[(5-chloro-2-{4-[(1r,3r)-3-{6-[2-(2,6-dioxopiperidin-3-yl)-1,3-dioxo-2,3-dihydro-1H-isoindol-5-yl]-2,6-diazaspiro[3.4]octan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 351 | 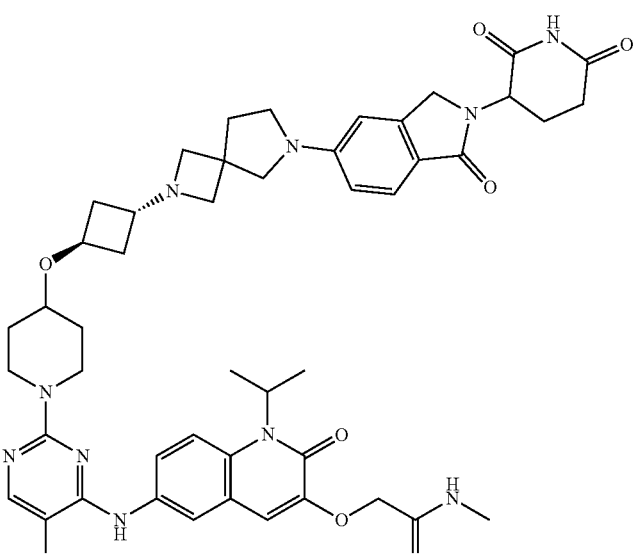 | 2-({6-[(5-chloro-2-{4-[(1r,3r)-3-{6-[2-(2,6-dioxopiperidin-3-yl)-1-oxo-2,3-dihydro-1H-isoindol-5-yl]-2,6-diazaspiro[3.4]octan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 352 | 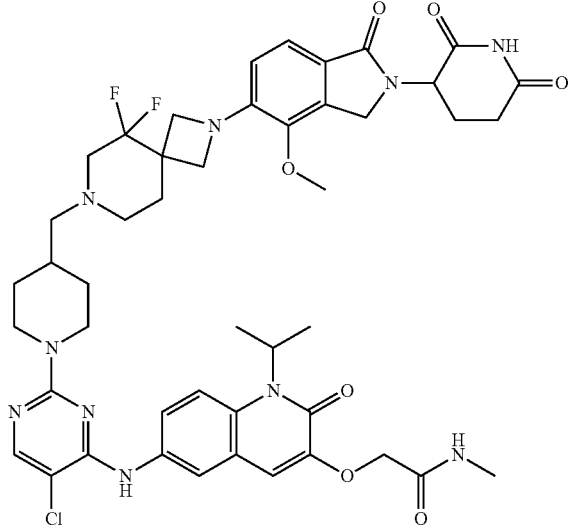 [SMILES: CNC(=O)COc1cc2cc(Nc3nc(N4CCC(CN5CCC6(CN(c7ccc8c(c7OC)CN(C7CCC(=O)NC7=O)C8=O)C6)C(F)(F)C5)CC4)ncc3Cl)ccc2n(C(C)C)c1=O] | 2-{[6-({5-chloro-2-[4-({2-[2-(2,6-dioxopiperidin-3-yl)-4-methoxy-1-oxo-2,3-dihydro-1H-isoindol-5-yl]-5,5-difluoro-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 162 |
| 353 | 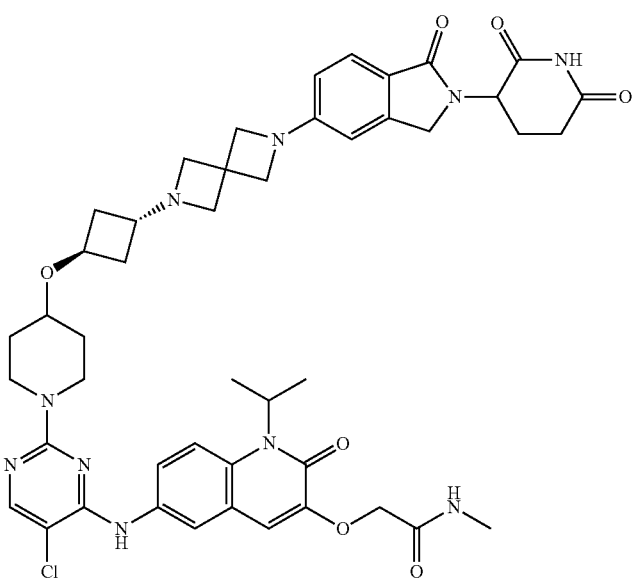 [SMILES: CNC(=O)COc1cc2cc(Nc3nc(N4CCC(O[C@H]5C[C@H](N6CC7(CN(c8ccc9c(c8)CN(C8CCC(=O)NC8=O)C9=O)C7)C6)C5)CC4)ncc3Cl)ccc2n(C(C)C)c1=O] | 2-({6-[(5-chloro-2-{4-[(1r,3r)-3-{6-[2-(2,6-dioxopiperidin-3-yl)-1-oxo-2,3-dihydro-1H-isoindol-5-yl]-2,6-diazaspiro[3.3]heptan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 354 | | 2-({6-[(5-chloro-2-{4-[(1r,3r)-3-{7-[2-(2,6-dioxopiperidin-3-yl)-1-oxo-2,3-dihydro-1H-isoindol-5-yl]-2,7-diazaspiro[4.5]decan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 355 | | 2-({6-[(5-chloro-2-{4-[(1r,3r)-3-{2-[2-(2,6-dioxopiperidin-3-yl)-1,3-dioxo-2,3-dihydro-1H-isoindol-5-yl]-2,7-diazaspiro[4.5]decan-7-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 356 | 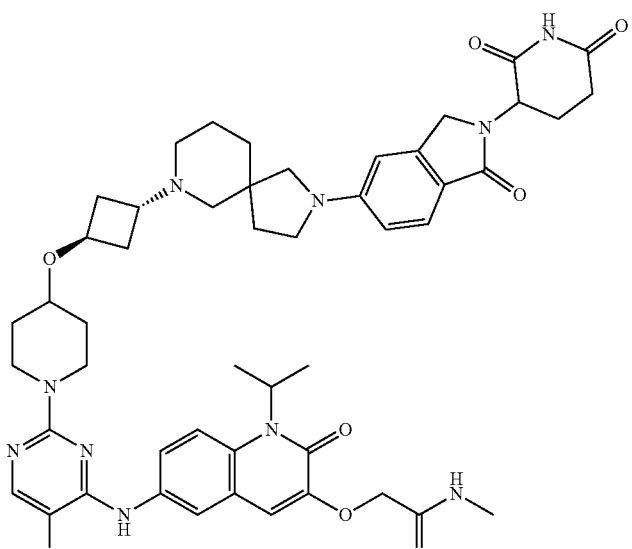 | 2-({6-[(5-chloro-2-{4-[(1r,3r)-3-{2-[2-(2,6-dioxopiperidin-3-yl)-1-oxo-2,3-dihydro-1H-isoindol-5-yl]-2,7-diazaspiro[4.5]decan-7-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 357 | 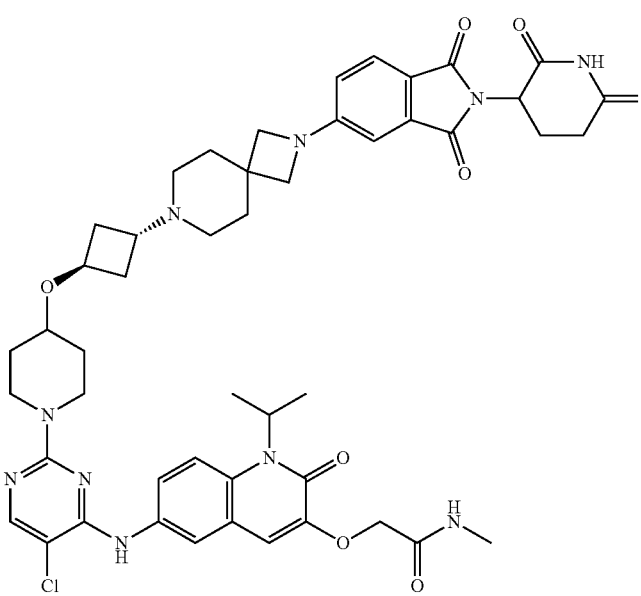 | 2-({6-[(5-chloro-2-{4-[(1r,3r)-3-{2-[2-(2,6-dioxopiperidin-3-yl)-1,3-dioxo-2,3-dihydro-1H-isoindol-5-yl]-2,7-diazaspiro[3.5]nonan-7-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 | ns

TABLE 4-continued

Additional exemplary bifunctional compounds of the present disclosure

| Compound Number | Parent Mol Structure | IUPAC Name | Analogously made to Compound Number |
|---|---|---|---|
| 358 | | 2-{[6-({5-chloro-2-[4-({2-[2-(2,6-dioxopiperidin-3-yl)-4-methyl-1,3-dioxo-2,3-dihydro-1H-isoindol-5-yl]-2,7-diazaspiro[3.5]nonan-7-yl}methyl)piperidin-1-yl]pyrimidin-4-yl}amino)-2-oxo-1-(propan-2-yl)-1,2-dihydroquinolin-3-yl]oxy}-N-methylacetamide | 38 |
| 359 | | 2-({6-[(5-chloro-2-{4-[(1r,3r)-3-{7-[2-(2,6-dioxopiperidin-3-yl)-1,3-dioxo-2,3-dihydro-1H-isoindol-5-yl]-2,7-diazaspiro[4.5]decan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 360 | 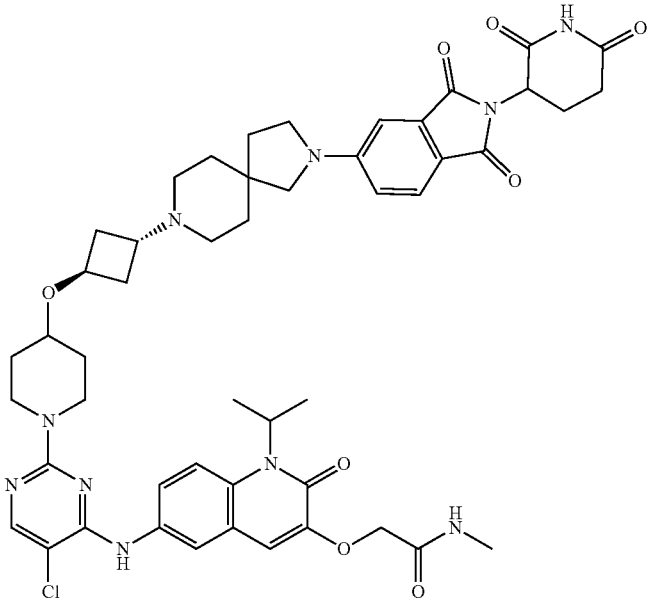 [SMILES: CNC(=O)COc1cc2cc(Nc3nc(N4CCC(O[C@H]5C[C@H](N6CCC7(CCN(c8ccc9c(c8)C(=O)N(C8CCC(=O)NC8=O)C9=O)C7)CC6)C5)CC4)ncc3Cl)ccc2n(C(C)C)c1=O] | 2-({6-[(5-chloro-2-{4-[(1r,3r)-3-{2-[2-(2,6-dioxopiperidin-3-yl)-1,3-dioxo-2,3-dihydro-1H-isoindol-5-yl]-2,8-diazaspiro[4.5]decan-8-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 361 | 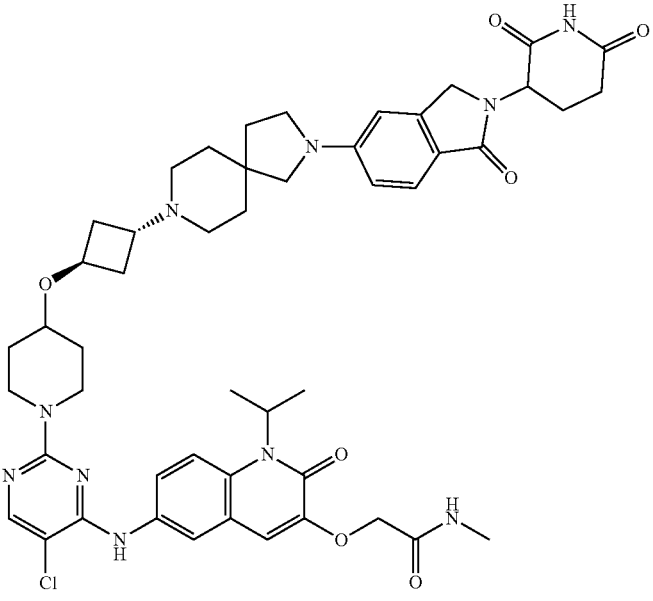 [SMILES: CNC(=O)COc1cc2cc(Nc3nc(N4CCC(O[C@H]5C[C@H](N6CCC7(CCN(c8ccc9c(c8)CN(C8CCC(=O)NC8=O)C9=O)C7)CC6)C5)CC4)ncc3Cl)ccc2n(C(C)C)c1=O] | 2-({6-[(5-chloro-2-{4-[(1r,3r)-3-{2-[2-(2,6-dioxopiperidin-3-yl)-1-oxo-2,3-dihydro-1H-isoindol-5-yl]-2,8-diazaspiro[4.5]decan-8-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 362 | | 2-({6-[(5-chloro-2-{4-[(1r,3r)-3-{8-[2-(2,6-dioxopiperidin-3-yl)-1,3-dioxo-2,3-dihydro-1H-isoindol-5-yl]-2,8-diazaspiro[4.5]decan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 363 | | 2-({6-[(5-chloro-2-{4-[(1r,3r)-3-{8-[2-(2,6-dioxopiperidin-3-yl)-1-oxo-2,3-dihydro-1H-isoindol-5-yl]-2,8-diazaspiro[4.5]decan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 364 | 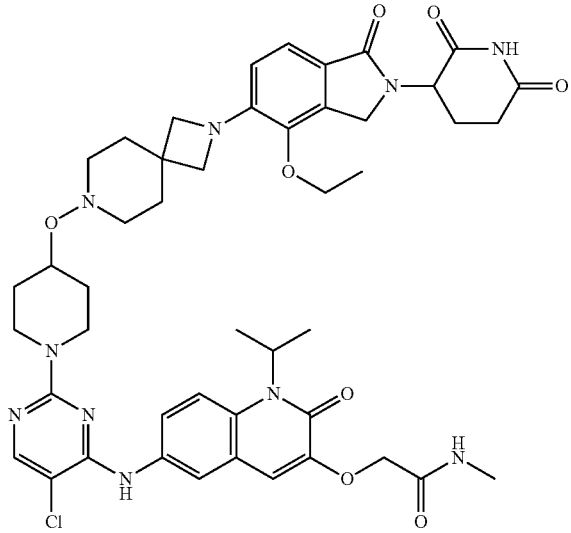 [SMILES: CCOc1c(N2CC3(CCN(OC4CCN(c5ncc(Cl)c(Nc6ccc7c(c6)cc(OCC(=O)NC)c(=O)n7C(C)C)n5)CC4)CC3)C2)ccc2c1CN(C1CCC(=O)NC1=O)C2=O] | 2-{[6-({5-chloro-2-[4-({2-[2-(2,6-dioxopiperidin-3-yl)-4-ethoxy-1-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 49 |
| 365 | 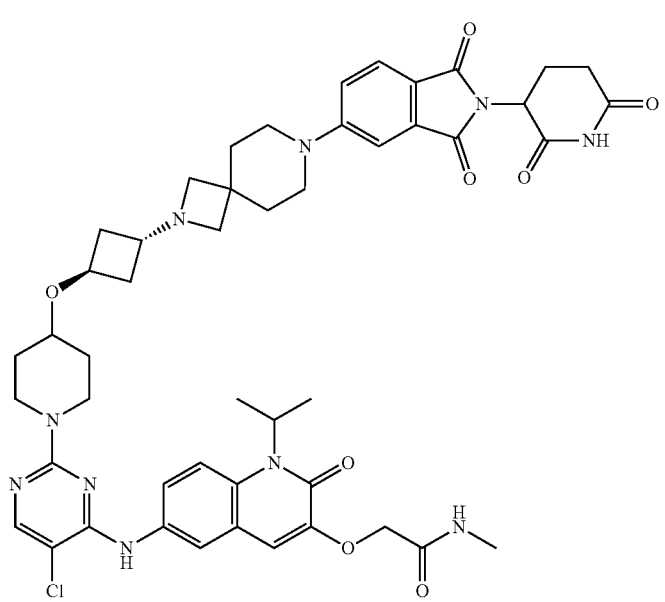 [SMILES: CNC(=O)COc1cc2cc(Nc3nc(N4CCC(O[C@H]5C[C@H](N6CC7(CCN(c8ccc9c(c8)C(=O)N(C8CCC(=O)NC8=O)C9=O)CC7)C6)C5)CC4)ncc3Cl)ccc2n(C(C)C)c1=O] | 2-({6-[(5-chloro-2-{4-[(1r,3r)-3-{7-[2-(2,6-dioxopiperidin-3-yl)-1,3-dioxo-2,3-dihydro-1H-isoindol-5-yl]-2,7-diazaspiro[3.5]nonan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

| Compound Number | Parent Mol Structure | IUPAC Name | Analogously made to Compound Number |
|---|---|---|---|
| 366 | 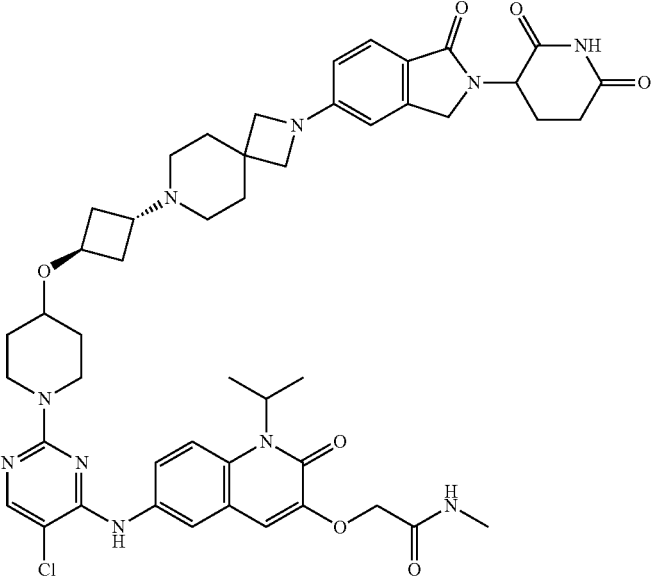 | 2-({6-[(5-chloro-2-{4-[(1r,3r)-3-{2-[2-(2,6-dioxopiperidin-3-yl)-1-oxo-2,3-dihydro-1H-isoindol-5-yl]-2,7-diazaspiro[3.5]nonan-7-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 367 | 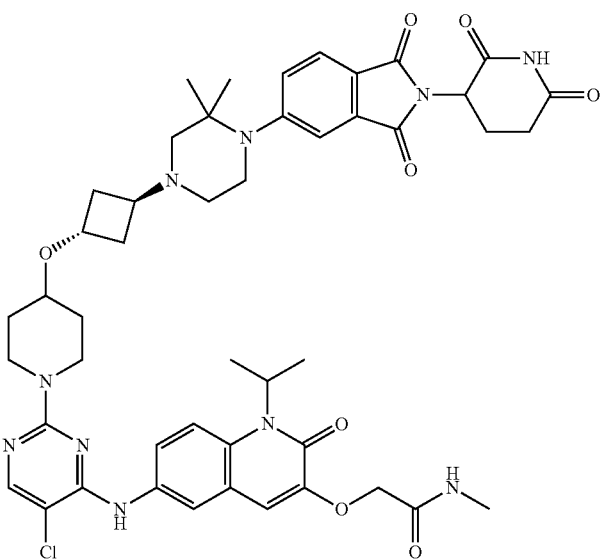 [SMILES: CNC(=O)COc1cc2cc(Nc3nc(N4CCC(O[C@H]5C[C@H](N6CCN(c7ccc8c(c7)C(=O)N(C7CCC(=O)NC7=O)C8=O)C(C)(C)C6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-1,3-dioxo-2,3-dihydro-1H-isoindol-5-yl]-3,3-dimethylpiperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 368 | | 2-({6-[(5-chloro-2-{4-[(1r,3r)-3-{3-[2-(2,6-dioxopiperidin-3-yl)-1-oxo-2,3-dihydro-1H-isoindol-5-yl]-3,8-diazabicyclo[3.2.1]octan-8-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 369 | | 2-({6-[(5-chloro-2-{4-[(1r,3r)-3-{7-[2-(2,6-dioxopiperidin-3-yl)-1-oxo-2,3-dihydro-1H-isoindol-5-yl]-2,7-diazaspiro[3.5]nonan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 370 | 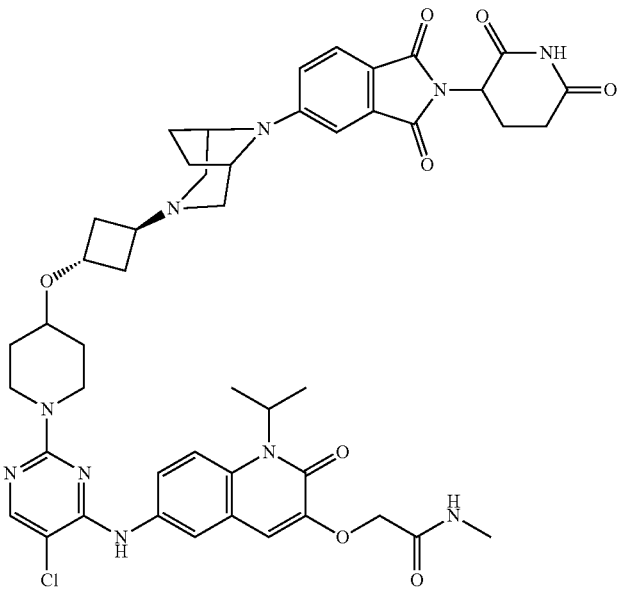 [SMILES: CNC(=O)COc1cc2cc(Nc3nc(N4CCC(O[C@H]5C[C@H](N6CC7CCC(C6)N7c6ccc7c(c6)C(=O)N(C6CCC(=O)NC6=O)C7=O)C5)CC4)ncc3Cl)ccc2n(C(C)C)c1=O] | 2-({6-[(5-chloro-2-{4-[(1r,3r)-3-{8-[2-(2,6-dioxopiperidin-3-yl)-1,3-dioxo-2,3-dihydro-1H-isoindol-5-yl]-3,8-diazabicyclo[3.2.1]octan-3-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 371 | 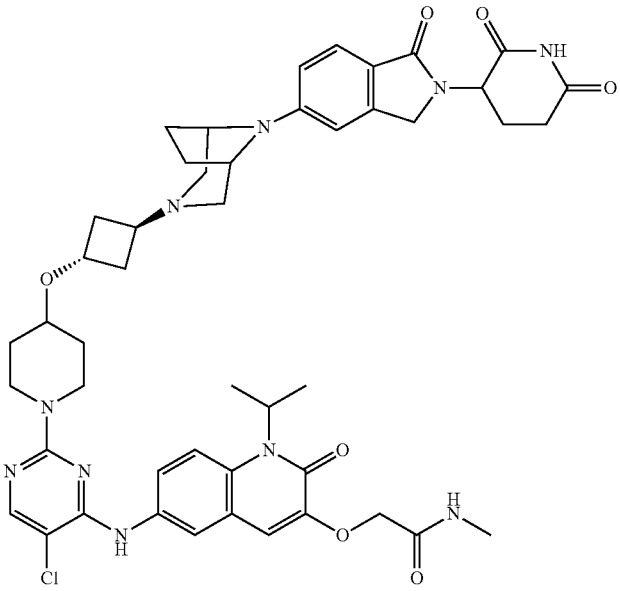 [SMILES: CNC(=O)COc1cc2cc(Nc3nc(N4CCC(O[C@H]5C[C@H](N6CC7CCC(C6)N7c6ccc7c(c6)CN(C6CCC(=O)NC6=O)C7=O)C5)CC4)ncc3Cl)ccc2n(C(C)C)c1=O] | 2-({6-[(5-chloro-2-{4-[(1r,3r)-3-{8-[2-(2,6-dioxopiperidin-3-yl)-1-oxo-2,3-dihydro-1H-isoindol-5-yl]-3,8-diazabicyclo[3.2.1]octan-3-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

| Compound Number | Parent Mol Structure | IUPAC Name | Analogously made to Compound Number |
|---|---|---|---|
| 372 | 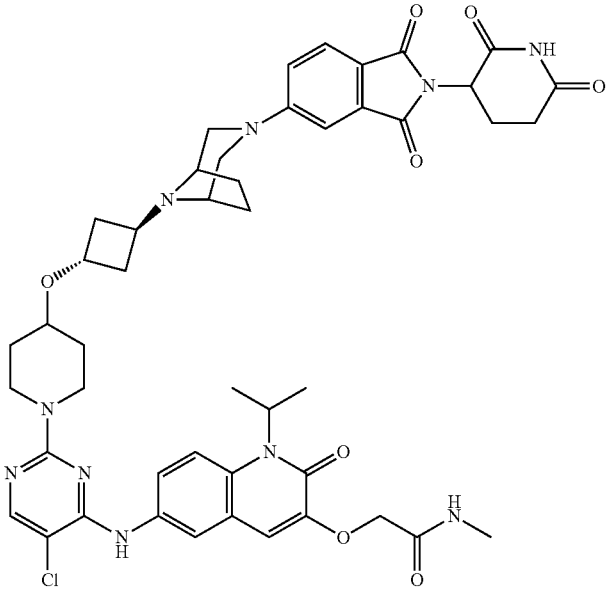 [SMILES: CNC(=O)COc1cc2cc(Nc3nc(N4CCC(O[C@H]5C[C@H](N6C7CCC6CN(c6ccc8c(c6)C(=O)N(C6CCC(=O)NC6=O)C8=O)C7)C5)CC4)ncc3Cl)ccc2n(C(C)C)c1=O] | 2-({6-[(5-chloro-2-{4-[(1r,3r)-3-{3-[2-(2,6-dioxopiperidin-3-yl)-1,3-dioxo-2,3-dihydro-1H-isoindol-5-yl]-3,8-diazabicyclo[3.2.1]octan-8-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 373 | 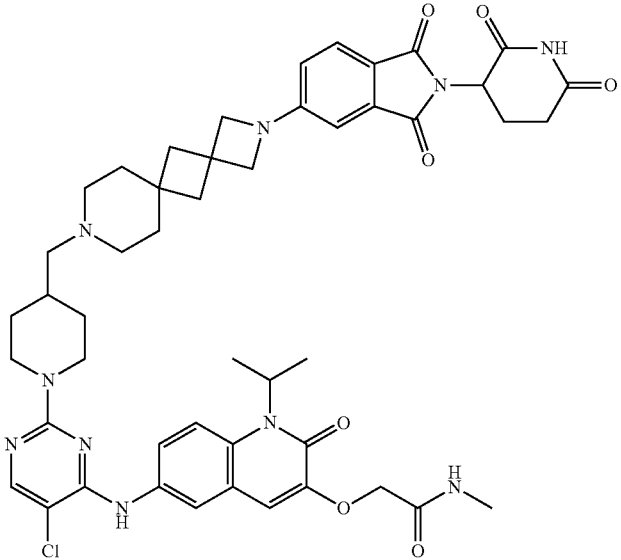 [SMILES: CNC(=O)COc1cc2cc(Nc3nc(N4CCC(CN5CCC6(CC5)CC5(CN(c7ccc8c(c7)C(=O)N(C7CCC(=O)NC7=O)C8=O)C5)C6)CC4)ncc3Cl)ccc2n(C(C)C)c1=O] | 2-{[6-({5-chloro-2-[4-({2-[2-(2,6-dioxopiperidin-3-yl)-1,3-dioxo-2,3-dihydro-1H-isoindol-5-yl]-2,9-diazadispiro[3.1.5$^6$.1$^4$]dodecan-9-yl}methyl)piperidin-1-yl]pyrimidin-4-yl}amino)-2-oxo-1-(propan-2-yl)-1,2-dihydroquinolin-3-yl]oxy}-N-methylacetamide | 38, 168 |

TABLE 4-continued

Additional exemplary bifunctional compounds of the present disclosure

| Compound Number | Parent Mol Structure | IUPAC Name | Analogously made to Compound Number |
|---|---|---|---|
| 374 | 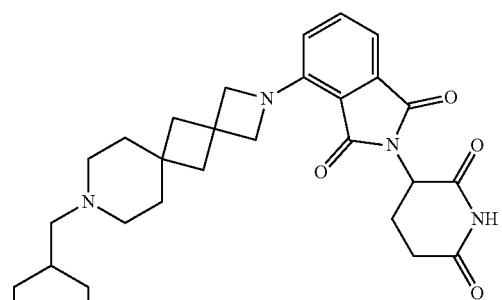 | 2-{[6-({5-chloro-2-[4-({2-[2-(2,6-dioxopiperidin-3-yl)-1,3-dioxo-2,3-dihydro-1H-isoindol-4-yl]-2,9-diazadispiro[3.1.5⁶.1⁴]dodecan-9-yl}methyl)piperidin-1-yl]pyrimidin-4-yl}amino)-2-oxo-1-(propan-2-yl)-1,2-dihydroquinolin-3-yl]oxy}-N-methylacetamide | 38, 168 |
| 375 | 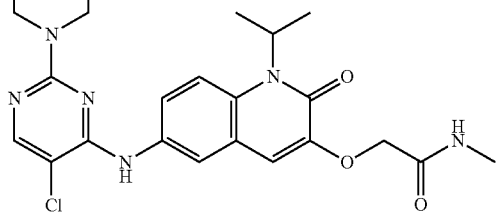 | 2-{[6-({5-chloro-2-[4-({2-[2-(2,6-dioxopiperidin-3-yl)-1,3-dioxo-2,3-dihydro-1H-isoindol-5-yl]-1,1-dimethyl-2,7-diazaspiro[3.5]nonan-7-yl}methyl)piperidin-1-yl]pyrimidin-4-yl}amino)-5-fluoro-2-oxo-1-(propan-2-yl)-1,2-dihydroquinolin-3-yl]oxy}-N-methylacetamide | 161, 162 |

TABLE 4-continued

Additional exemplary bifunctional compounds of the present disclosure

| Compound Number | Parent Mol Structure | IUPAC Name | Analogously made to Compound Number |
|---|---|---|---|
| 376 | 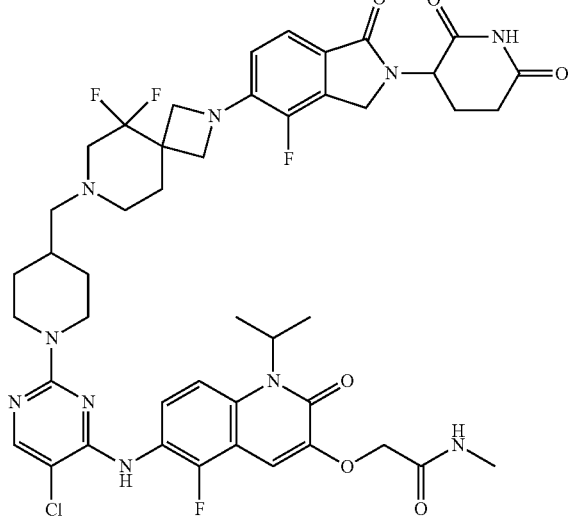 | 2-{[6-({5-chloro-2-[4-({2-[2-(2,6-dioxopiperidin-3-yl)-4-fluoro-1-oxo-2,3-dihydro-1H-isoindol-5-yl]-5,5-difluoro-2,7-diazaspiro[3.5]nonan-7-yl}methyl)piperidin-1-yl]pyrimidin-4-yl}amino)-5-fluoro-2-oxo-1-(propan-2-yl)-1,2-dihydroquinolin-3-yl]oxy}-N-methylacetamide | 171 |
| 377 | 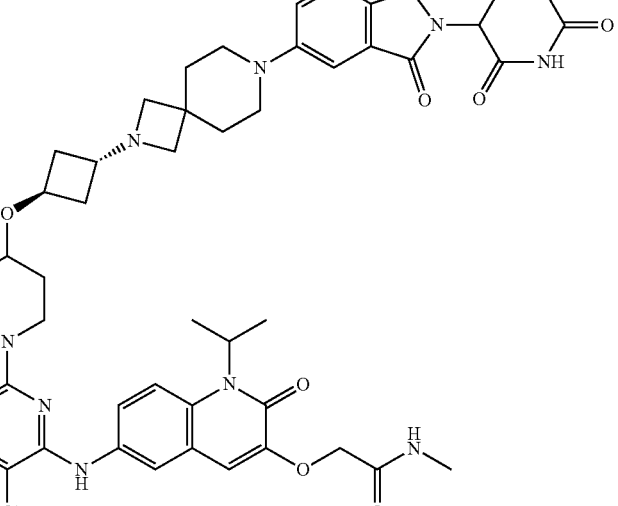 | 2-({6-[(5-chloro-2-{4-[(1r,3r)-3-{7-[2-(2,6-dioxopiperidin-3-yl)-3-oxo-2,3-dihydro-1H-isoindol-5-yl]-2,7-diazaspiro[3.5]nonan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 378 | | 2-({6-[(5-chloro-2-{4-[(1r,3r)-3-{4-[2-(2,6-dioxopiperidin-3-yl)-7-methyl-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 379 | | 2-({6-[(5-chloro-2-{4-[(1r,3r)-3-{4-[2-(2,6-dioxopiperidin-3-yl)-7-methoxy-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 380 | 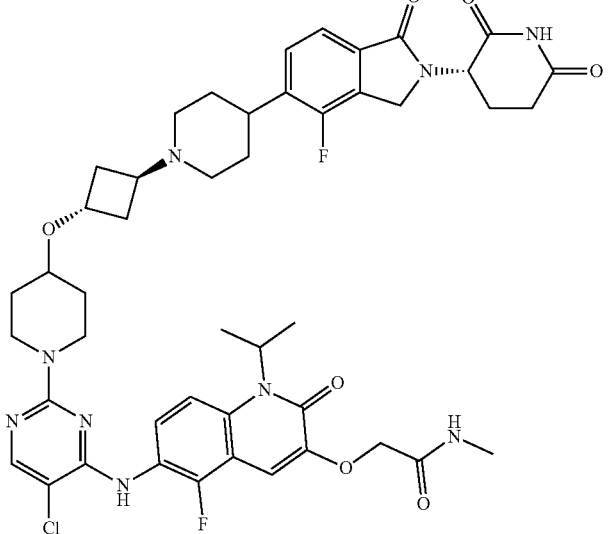 | 2-({6-[(5-chloro-2-{4-[(1r,3r)-3-(4-{2-[(3S)-2,6-dioxopiperidin-3-yl]-4-fluoro-1-oxo-2,3-dihydro-1H-isoindol-5-yl}piperidin-1-yl)cyclobutoxy]piperidin-1-yl}pyrimidin-4-yl)amino]-5-fluoro-2-oxo-1-(propan-2-yl)-1,2-dihydroquinolin-3-yl}oxy)-N-methylacetamide | 173 |
| 381 | 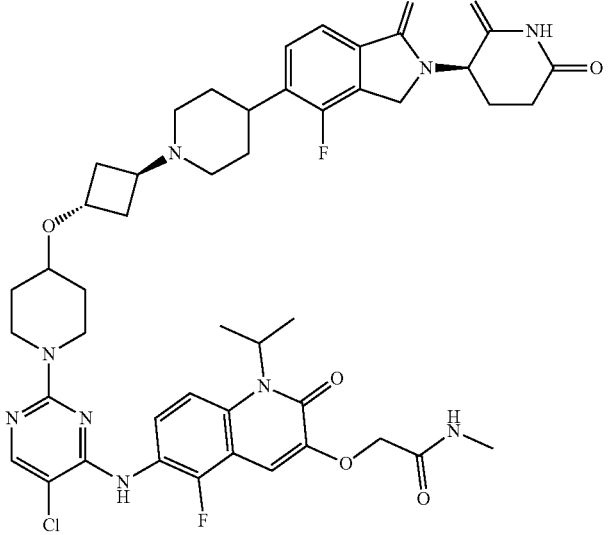 | 2-({6-[(5-chloro-2-{4-[(1r,3r)-3-(4-{2-[(3R)-2,6-dioxopiperidin-3-yl]-4-fluoro-1-oxo-2,3-dihydro-1H-isoindol-5-yl}piperidin-1-yl)cyclobutoxy]piperidin-1-yl}pyrimidin-4-yl)amino]-5-fluoro-2-oxo-1-(propan-2-yl)-1,2-dihydroquinolin-3-yl}oxy)-N-methylacetamide | 173 |

TABLE 4-continued

Additional exemplary bifunctional compounds of the present disclosure

| Compound Number | Parent Mol Structure | IUPAC Name | Analogously made to Compound Number |
|---|---|---|---|
| 382 | | 2-{[6-({5-chloro-2-[4-({2-[2-(2,6-dioxopiperidin-3-yl)-1-oxo-2,3-dihydro-1H-isoindol-5-yl]-1,1-dimethyl-2,7-diazaspiro[3.5]nonan-7-yl}methyl)-4-fluoropiperidin-1-yl]pyrimidin-4-yl}amino)-2-oxo-1-(propan-2-yl)-1,2-dihydroquinolin-3-yl]oxy}-N-methylacetamide | 51, 162 |
| 383 | | 2-{[6-({5-chloro-2-[4-({2-[4-chloro-2-(2,6-dioxopiperidin-3-yl)-1-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 49, 181 |

TABLE 4-continued

Additional exemplary bifunctional compounds of the present disclosure

| Compound Number | Parent Mol Structure | IUPAC Name | Analogously made to Compound Number |
|---|---|---|---|
| 384 | | 2-({6-[(5-chloro-2-{4-[(1r,3r)-3-(4-{2-[(3R)-2,6-dioxopiperidin-3-yl]-4-fluoro-1-oxo-2,3-dihydro-1H-isoindol-5-yl}piperidin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 81 |
| 385 | | 2-({6-[(5-chloro-2-{4-[(1r,3r)-3-(4-{2-[(3S)-2,6-dioxopiperidin-3-yl]-4-fluoro-1-oxo-2,3-dihydro-1H-isoindol-5-yl}piperidin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 81 |

TABLE 4-continued

Additional exemplary bifunctional compounds of the present disclosure

| Compound Number | Parent Mol Structure | IUPAC Name | Analogously made to Compound Number |
|---|---|---|---|
| 386 | | 2-({6-[(5-chloro-2-{4-[(1r,3r)-3-{4-[2-(2,6-dioxopiperidin-3-yl)-4,6-difluoro-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 181 |
| 387 | | 2-({6-[(5-chloro-2-{4-[(1r,3r)-3-[(3R)-4-[2-(2,6-dioxopiperidin-3-yl)-1,3-dioxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 388 | | 2-({6-[(5-chloro-2-{4-[(1r,3r)-3-(4-{2-[(3S)-2,6-dioxopiperidin-3-yl]-4-fluoro-1-oxo-2,3-dihydro-1H-isoindol-5-yl}piperazin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 389 | | 2-{[6-({5-chloro-2-[4-({2-[2-(2,6-dioxopiperidin-3-yl)-1-oxo-2,3-dihydro-1H-isoindol-5-yl]-2,7-diazaspiro[3.5]nonan-7-yl}methyl)-4-fluoropiperidin-1-yl]pyrimidin-4-yl}amino)-5-fluoro-2-oxo-1-(propan-2-yl)-1,2-dihydroquinolin-3-yl]oxy}-N-methylacetamide | 51, 171 |

TABLE 4-continued

Additional exemplary bifunctional compounds of the present disclosure

| Compound Number | Parent Mol Structure | IUPAC Name | Analogously made to Compound Number |
|---|---|---|---|
| 390 | | 2-{[6-({5-chloro-2-[4-({2-[2-(2,6-dioxopiperidin-3-yl)-4-fluoro-1-oxo-2,3-dihydro-1H-isoindol-5-yl]-2,7-diazaspiro[3.5]nonan-7-yl}methyl)-4-fluoropiperidin-1-yl]pyrimidin-4-yl}amino)-5-fluoro-2-oxo-1-(propan-2-yl)-1,2-dihydroquinolin-3-yl]oxy}-N-methylacetamide | 51, 171 |
| 391 | | 2-({6-[(5-chloro-2-{4-[(1r,3r)-3-[(3S)-4-[2-(2,6-dioxopiperidin-3-yl)-1,3-dioxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 392 | 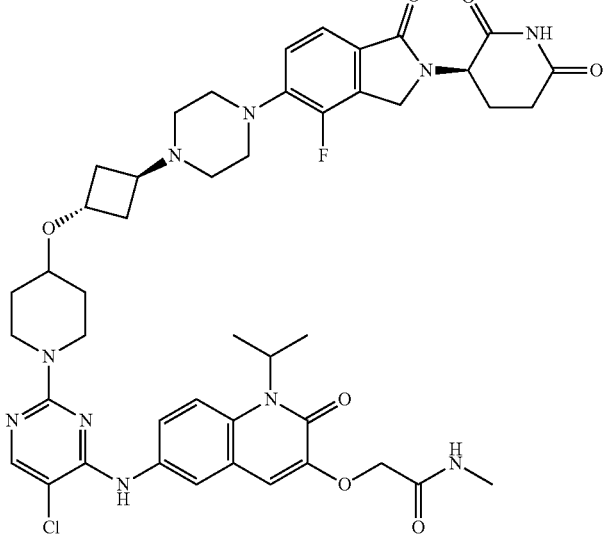 | 2-({6-[(5-chloro-2-{4-[(1r,3r)-3-(4-{2-[(3R)-2,6-dioxopiperidin-3-yl]-4-fluoro-1-oxo-2,3-dihydro-1H-isoindol-5-yl}piperazin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 175 |
| 393 | 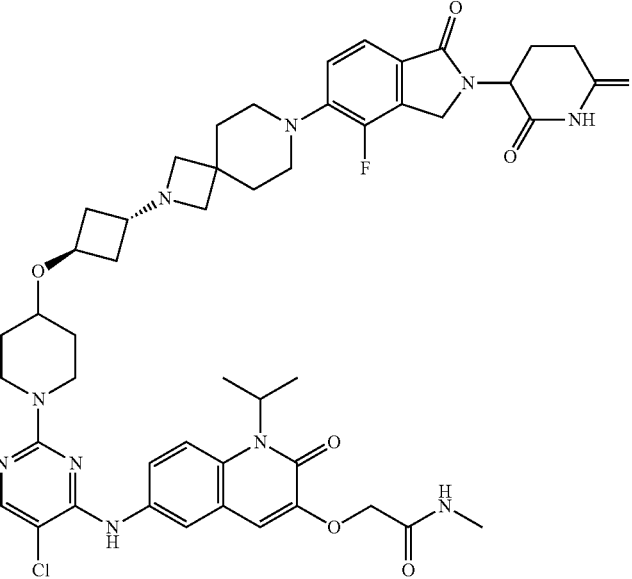 | 2-({6-[(5-chloro-2-{4-[(1r,3r)-3-{7-[2-(2,6-dioxopiperidin-3-yl)-4-fluoro-1-oxo-2,3-dihydro-1H-isoindol-5-yl]-2,7-diazaspiro[3.5]nonan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

TABLE 4-continued

Additional exemplary bifunctional compounds of the present disclosure

| Compound Number | Parent Mol Structure | IUPAC Name | Analogously made to Compound Number |
|---|---|---|---|
| 394 | 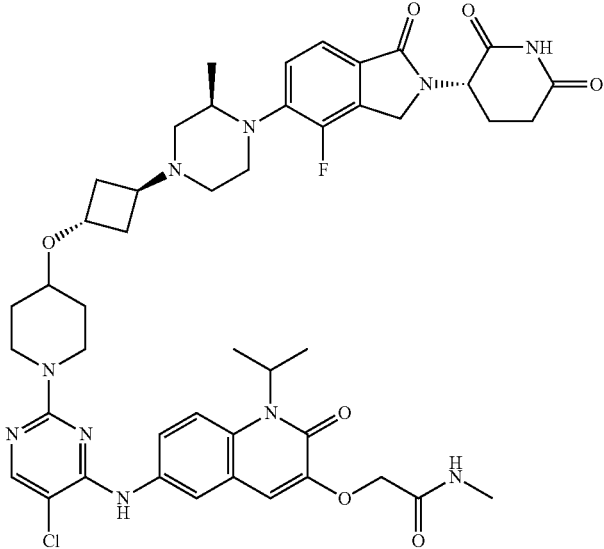 | 2-({6-[(5-chloro-2-{4-[(1r,3r)-3-[(3R)-4-{2-[(3S)-2,6-dioxopiperidin-3-yl]-4-fluoro-1-oxo-2,3-dihydro-1H-isoindol-5-yl}-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 175 |
| 395 | 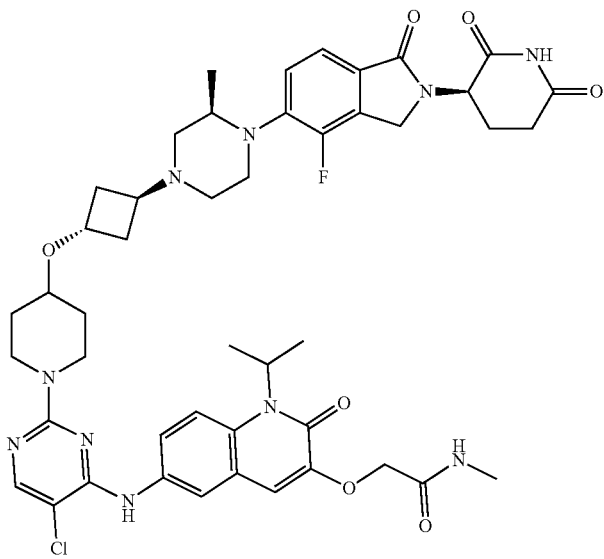 [SMILES: CNC(=O)COc1cc2cc(Nc3nc(N4CCC(O[C@H]5C[C@H](N6CCN(c7ccc8c(c7F)CN([C@@H]7CCC(=O)NC7=O)C8=O)[C@H](C)C6)C5)CC4)ncc3Cl)ccc2n(C(C)C)c1=O] | 2-({6-[(5-chloro-2-{4-[(1r,3r)-3-[(3R)-4-{2-[(3R)-2,6-dioxopiperidin-3-yl]-4-fluoro-1-oxo-2,3-dihydro-1H-isoindol-5-yl}-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 175 |

TABLE 4-continued

Additional exemplary bifunctional compounds of the present disclosure

| Compound Number | Parent Mol Structure | IUPAC Name | Analogously made to Compound Number |
|---|---|---|---|
| 396 | | 2-({6-[(5-chloro-2-{4-[(1r,3r)-3-[(4R)-4-{2-[(3R)-2,6-dioxopiperidin-3-yl]-4-fluoro-1-oxo-2,3-dihydro-1H-isoindol-5-yl}-3,3-dimethylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 209 |
| 397 | | 2-({6-[(5-chloro-2-{4-[(1r,3r)-3-{4-[2-(2,6-dioxopiperidin-3-yl)-4-fluoro-6-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 208 |

TABLE 4-continued

Additional exemplary bifunctional compounds of the present disclosure

| Compound Number | Parent Mol Structure | IUPAC Name | Analogously made to Compound Number |
|---|---|---|---|
| 398 | | 2-({6-[(5-chloro-2-{4-[(1s,3s)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 81 |
| 399 | | 2-({6-[(5-chloro-2-{4-[(1r,3r)-3-{4-[2-(2,6-dioxopiperidin-3-yl)-1,3-dioxo-2,3-dihydro-1H-isoindol-5-yl]-3,3-dimethylpiperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 209 |

TABLE 4-continued

Additional exemplary bifunctional compounds of the present disclosure

| Compound Number | Parent Mol Structure | IUPAC Name | Analogously made to Compound Number |
|---|---|---|---|
| 400 | | 2-({6-[(5-chloro-2-{4-[(1r,3r)-3-{6-[2-(2,6-dioxopiperidin-3-yl)-4-fluoro-1-oxo-2,3-dihydro-1H-isoindol-5-yl]-2,6-diazaspiro[3.4]octan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 401 | | 2-({6-[(5-chloro-2-{4-[(1r,3r)-3-{2-[2-(2,6-dioxopiperidin-3-yl)-4-fluoro-1-oxo-2,3-dihydro-1H-isoindol-5-yl]-2,7-diazaspiro[4.5]decan-7-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 402 | | 2-{[6-({5-chloro-2-[4-({2-[2-(2,6-dioxopiperidin-3-yl)-4-methyl-1-oxo-2,3-dihydro-1H-isoindol-5-yl]-2-azaspiro[3.5]nonan-7-yl}oxy)piperidin-1-yl]pyrimidin-4-yl}amino)-2-oxo-1-(propan-2-yl)-1,2-dihydroquinolin-3-yl]oxy}-N-methylacetamide | 49 |

TABLE 4-continued

Additional exemplary bifunctional compounds of the present disclosure

| Compound Number | Parent Mol Structure | IUPAC Name | Analogously made to Compound Number |
|---|---|---|---|
| 403 | | 2-{[6-({5-chloro-2-[4-({4-[2-(2,6-dioxopiperidin-3-yl)-4-methyl-1,3-dioxo-2,3-dihydro-1H-isoindol-5-yl]piperazin-1-yl}methyl)piperidin-1-yl]pyrimidin-4-yl}amino)-2-oxo-1-(propan-2-yl)-1,2-dihydroquinolin-3-yl]oxy}-N-methylacetamide | 38 |
| 404 | | 2-{[6-({5-chloro-2-[4-({4-[2-(2,6-dioxopiperidin-3-yl)-1,3-dioxo-2,3-dihydro-1H-isoindol-5-yl]piperazin-1-yl}methyl)piperidin-1-yl]pyrimidin-4-yl}amino)-2-oxo-1-(propan-2-yl)-1,2-dihydroquinolin-3-yl]oxy}-N-methylacetamide | 38 |
| 405 | | 2-({6-[(5-chloro-2-{4-[(1r,3r)-3-{2-[2-(2,6-dioxopiperidin-3-yl)-4-fluoro-1-oxo-2,3-dihydro-1H-isoindol-5-yl]-2,6-diazaspiro[3.4]octan-6-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |

US 11,986,532 B2
779　　　　780

TABLE 4-continued

Additional exemplary bifunctional compounds of the present disclosure

| Compound Number | Parent Mol Structure | IUPAC Name | Analogously made to Compound Number |
|---|---|---|---|
| 406 | 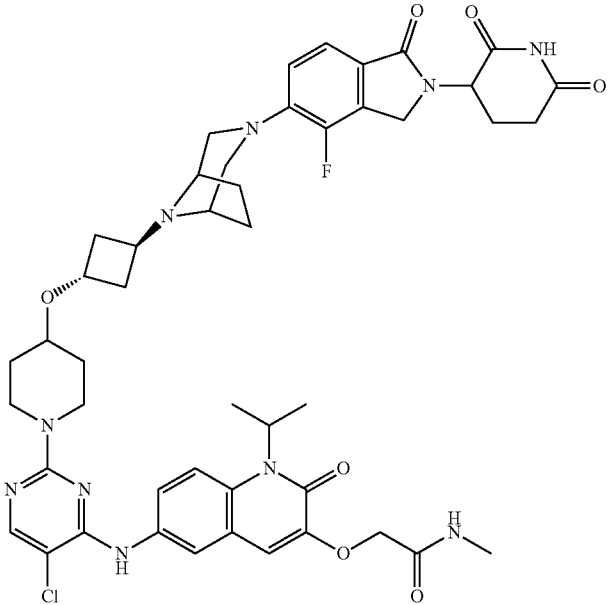 [SMILES: CNC(=O)COc1cc2cc(Nc3nc(N4CCC(O[C@H]5C[C@H](N6C7CCC6CN(c6ccc8c(c6F)CN(C6CCC(=O)NC6=O)C8=O)C7)C5)CC4)ncc3Cl)ccc2n(C(C)C)c1=O] | 2-({6-[(5-chloro-2-{4-[(1r,3r)-3-{3-[2-(2,6-dioxopiperidin-3-yl)-4-fluoro-1-oxo-2,3-dihydro-1H-isoindol-5-yl]-3,8-diazabicyclo[3.2.1]octan-8-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 407 | 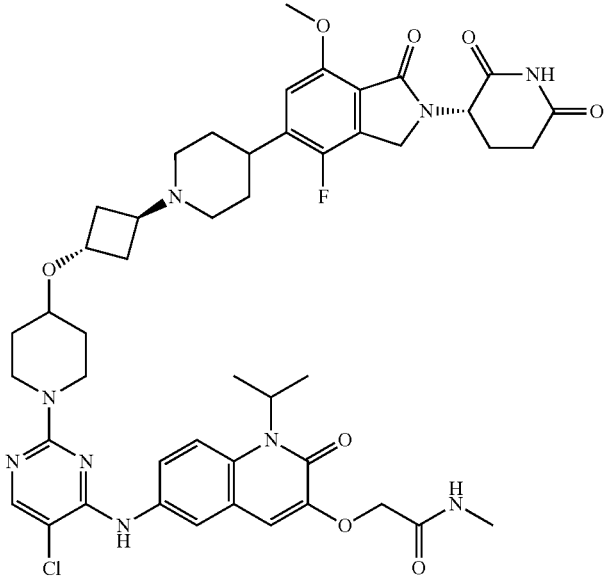 [SMILES: CNC(=O)COc1cc2cc(Nc3nc(N4CCC(O[C@H]5C[C@H](N6CCC(c7cc(OC)c8c(c7F)CN([C@H]7CCC(=O)NC7=O)C8=O)CC6)C5)CC4)ncc3Cl)ccc2n(C(C)C)c1=O] | 2-({6-[(5-chloro-2-{4-[(1r,3r)-3-(4-{2-[(3S)-2,6-dioxopiperidin-3-yl]-4-fluoro-7-methoxy-1-oxo-2,3-dihydro-1H-isoindol-5-yl}piperidin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 81 |

TABLE 4-continued

Additional exemplary bifunctional compounds of the present disclosure

| Compound Number | Parent Mol Structure | IUPAC Name | Analogously made to Compound Number |
|---|---|---|---|
| 408 | 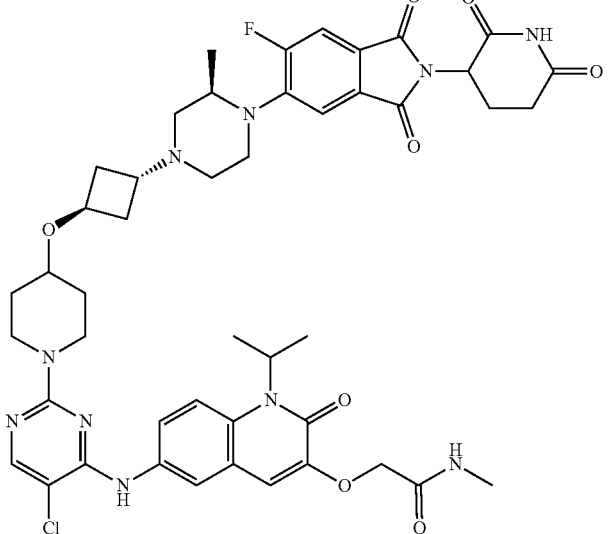 | 2-({6-[(5-chloro-2-{4-[(1r,3r)-3-[(3R)-4-[2-(2,6-dioxopiperidin-3-yl)-6-fluoro-1,3-dioxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 199 |
| 409 | 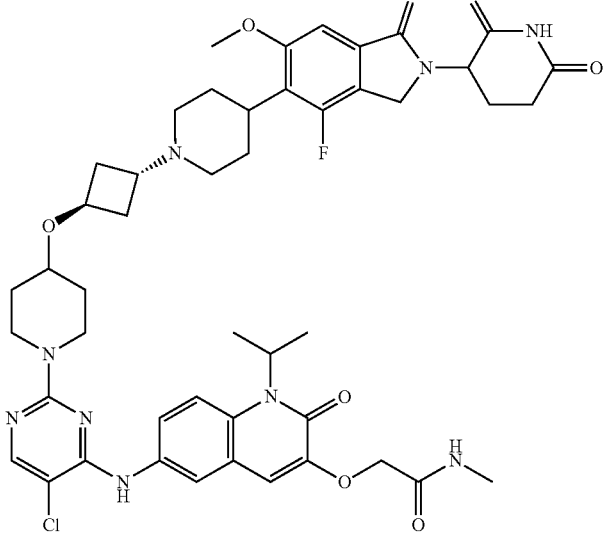 | 2-({6-[(5-chloro-2-{4-[(1r,3r)-3-{4-[2-(2,6-dioxopiperidin-3-yl)-4-fluoro-6-methoxy-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 81 |

TABLE 4-continued

Additional exemplary bifunctional compounds of the present disclosure

| Compound Number | Parent Mol Structure | IUPAC Name | Analogously made to Compound Number |
|---|---|---|---|
| 410 | | 2-({6-[(5-chloro-2-{4-[(1r,3r)-3-{2-[2-(2,6-dioxopiperidin-3-yl)-4-fluoro-1-oxo-2,3-dihydro-1H-isoindol-5-yl]-2,7-diazaspiro[3.5]nonan-7-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 411 | | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-1-cyclohexyl-2-oxo-1,2-dihydroquinolin-3-yl}oxy)-N-methylacetamide | 190 |

TABLE 4-continued

Additional exemplary bifunctional compounds of the present disclosure

| Compound Number | Parent Mol Structure | IUPAC Name | Analogously made to Compound Number |
|---|---|---|---|
| 412 | | 2-({6-[(5-chloro-2-{4-[(1r,3r)-3-{4-[4-chloro-2-(2,6-dioxopiperidin-3-yl)-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 413 | | 2-({6-[(5-chloro-2-{4-[(1r,3r)-3-{4-[2-(2,6-dioxopiperidin-3-yl)-4-fluoro-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 414 | | 2-({6-[(5-chloro-2-{4-[(1r,3r)-3-{2-[2-(2,6-dioxopiperidin-3-yl)-4-methyl-1,3-dioxo-2,3-dihydro-1H-isoindol-5-yl]-2,7-diazaspiro[3.5]nonan-7-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 415 | | 2-({6-[(5-chloro-2-{4-[(1r,3r)-3-[(3R)-4-[6-(2,6-dioxopiperidin-3-yl)-5-oxo-5H,6H,7H-pyrrolo[3,4-b]pyridin-2-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 192 |

US 11,986,532 B2

789                                                                                                 790

TABLE 4-continued

Additional exemplary bifunctional compounds of the present disclosure

| Compound Number | Parent Mol Structure | IUPAC Name | Analogously made to Compound Number |
|---|---|---|---|
| 416 | 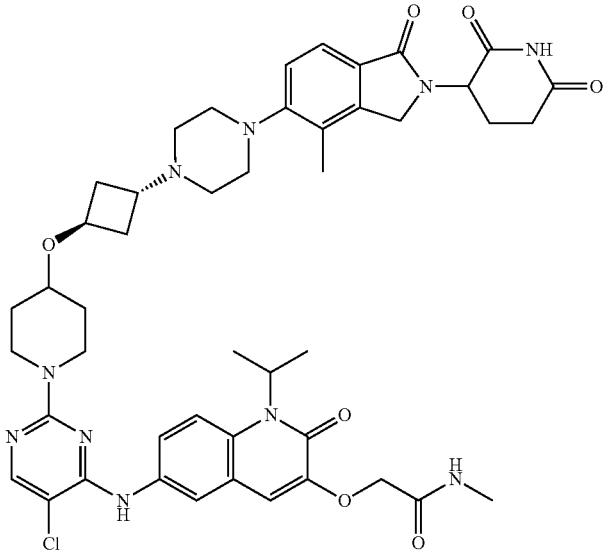 [SMILES: CNC(=O)COc1cc2cc(Nc3nc(N4CCC(O[C@H]5C[C@H](N6CCN(c7ccc8c(c7C)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-4-methyl-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 417 | 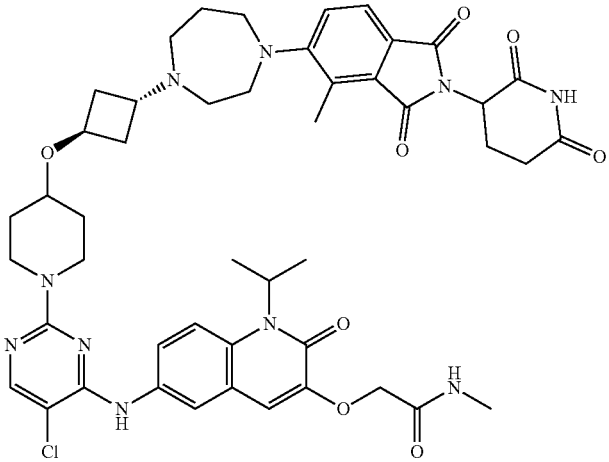 [SMILES: CNC(=O)COc1cc2cc(Nc3nc(N4CCC(O[C@H]5C[C@H](N6CCCN(c7ccc8c(c7C)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-4-methyl-1,3-dioxo-2,3-dihydro-1H-isoindol-5-yl]-1,4-diazepan-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 418 | 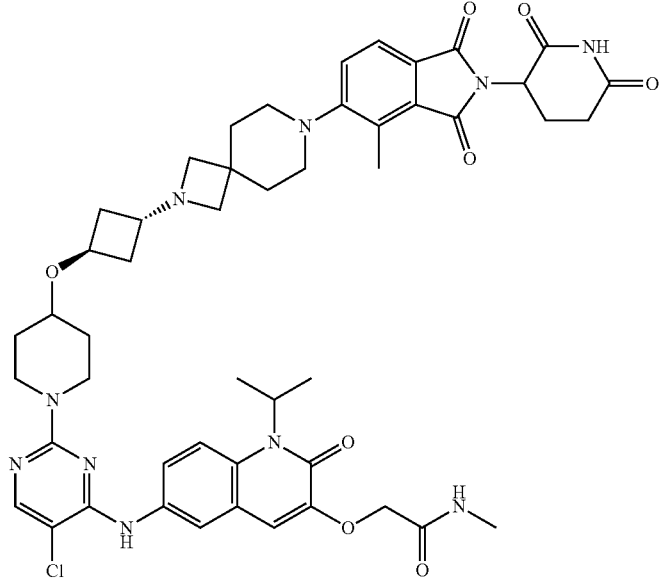 [SMILES: CNC(=O)COc1cc2cc(Nc3nc(N4CCC(O[C@H]5C[C@H](N6CC7(CCN(c8ccc9c(c8C)C(=O)N(C8CCC(=O)NC8=O)C9=O)CC7)C6)C5)CC4)ncc3Cl)ccc2n(C(C)C)c1=O] | 2-({6-[(5-chloro-2-{4-[(1r,3r)-3-{7-[2-(2,6-dioxopiperidin-3-yl)-4-methyl-1,3-dioxo-2,3-dihydro-1H-isoindol-5-yl]-2,7-diazaspiro[3.5]nonan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 419 | 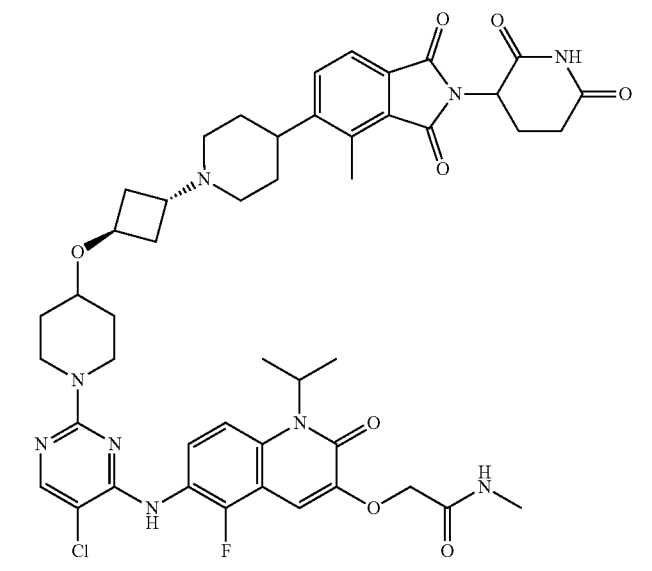 [SMILES: CNC(=O)COc1cc2c(F)c(Nc3nc(N4CCC(O[C@H]5C[C@H](N6CCC(c7ccc8c(c7C)C(=O)N(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[2-(2,6-dioxopiperidin-3-yl)-4-methyl-1,3-dioxo-2,3-dihydro-1H-isoindol-5-yl]piperidin-1-yl}cyclobutoxy]piperidin-1-yl}pyrimidin-4-yl)amino]-5-fluoro-2-oxo-1-(propan-2-yl)-1,2-dihydroquinolin-3-yl}oxy)-N-methylacetamide | 172 |

TABLE 4-continued

Additional exemplary bifunctional compounds of the present disclosure

| Compound Number | Parent Mol Structure | IUPAC Name | Analogously made to Compound Number |
|---|---|---|---|
| 420 | | 2-({6-[(5-chloro-2-{4-[(1r,3r)-3-{6-[2-(2,6-dioxopiperidin-3-yl)-4-methyl-1,3-dioxo-2,3-dihydro-1H-isoindol-5-yl]-2,6-diazaspiro[3.3]heptan-2-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |
| 421 | | 2-{[6-({5-chloro-2-[4-({2-[2-(2,6-dioxopiperidin-3-yl)-1-oxo-2,3-dihydro-1H-isoindol-5-yl]-2,9-diazadispiro[3.1.5⁶.1⁴]dodecan-9-yl}methyl)piperidin-1-yl]pyrimidin-4-yl}amino)-5-fluoro-2-oxo-1-(propan-2-yl)-1,2-dihydroquinolin-3-yl]oxy}-N-methylacetamide | 161, 168 |

TABLE 4-continued

Additional exemplary bifunctional compounds of the present disclosure

| Compound Number | Parent Mol Structure | IUPAC Name | Analogously made to Compound Number |
|---|---|---|---|
| 422 | | 2-({6-[(5-chloro-2-{4-[(1r,3r)-3-(4-{1-[2-(2,6-dioxopiperidin-3-yl)-4-fluoro-1-oxo-2,3-dihydro-1H-isoindol-5-yl]azetidin-3-yl}piperazin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 164 |
| 423 | | 2-({6-[(5-chloro-2-{4-[(1r,3r)-3-{4-[2-(2,6-dioxopiperidin-3-yl)-6-methoxy-1,3-dioxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 177 |

TABLE 4-continued

Additional exemplary bifunctional compounds of the present disclosure

| Compound Number | Parent Mol Structure | IUPAC Name | Analogously made to Compound Number |
|---|---|---|---|
| 424 | 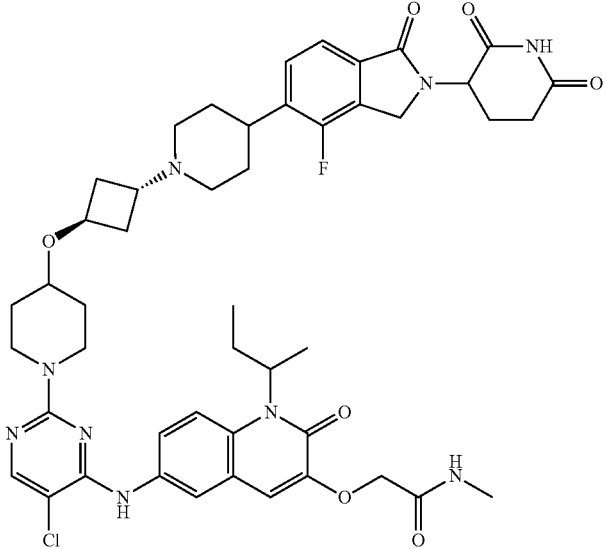 [SMILES: CCC(C)n1c(=O)c(OCC(=O)NC)cc2cc(Nc3nc(N4CCC(O[C@H]5C[C@H](N6CCC(c7ccc8c(c7F)CN(C7CCC(=O)NC7=O)C8=O)CC6)C5)CC4)ncc3Cl)ccc21] | 2-{[1-(butan-2-yl)-6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-2-oxo-1,2-dihydroquinolin-3-yl]oxy}-N-methylacetamide | 81 |
| 425 | 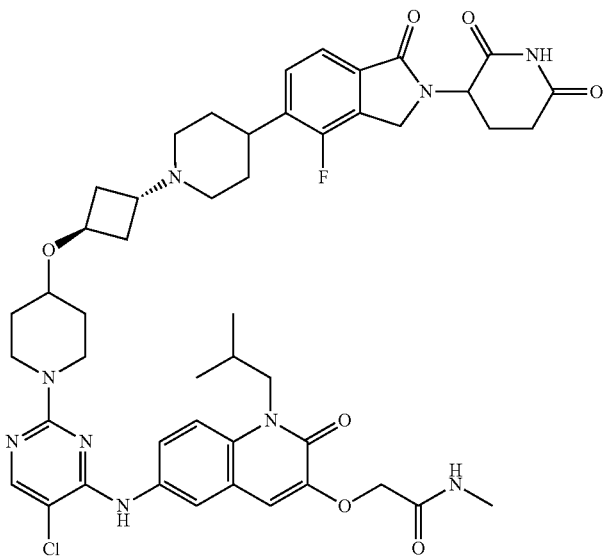 [SMILES: CNC(=O)COc1cc2cc(Nc3nc(N4CCC(O[C@H]5C[C@H](N6CCC(c7ccc8c(c7F)CN(C7CCC(=O)NC7=O)C8=O)CC6)C5)CC4)ncc3Cl)ccc2n(CC(C)C)c1=O] | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]piperidin-1-yl}cyclobutoxy]piperidin-1-yl}pyrimidin-4-yl)amino]-1-(2-methylpropyl)-2-oxo-1,2-dihydroquinolin-3-yl}oxy)-N-methylacetamide | 81 |

TABLE 4-continued

Additional exemplary bifunctional compounds of the present disclosure

| Compound Number | Parent Mol Structure | IUPAC Name | Analogously made to Compound Number |
|---|---|---|---|
| 426 | | 2-({6-[(5-chloro-2-{4-[(1r,3r)-3-{4-[2-(2,6-dioxopiperidin-3-yl)-4-fluoro-1-oxo-2,3-dihydro-1H-isoindol-5-yl]-1,2,3,6-tetrahydropyridin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 81 |
| 427 | | | 168 |

TABLE 4-continued

Additional exemplary bifunctional compounds of the present disclosure

| Compound Number | Parent Mol Structure | IUPAC Name | Analogously made to Compound Number |
|---|---|---|---|
| 428 | 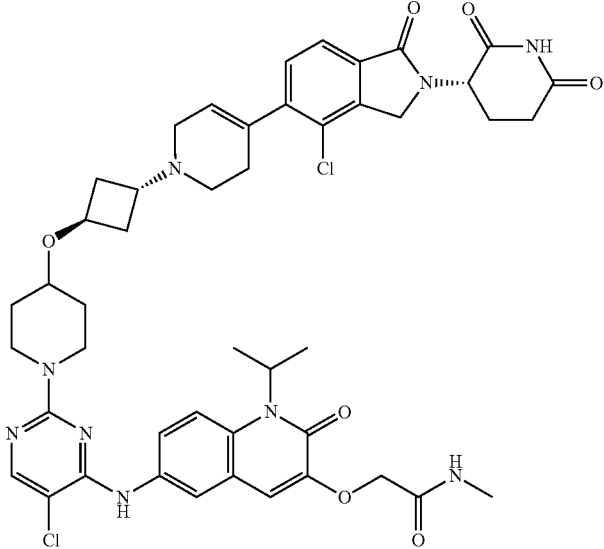 | | 81 |
| 429 | 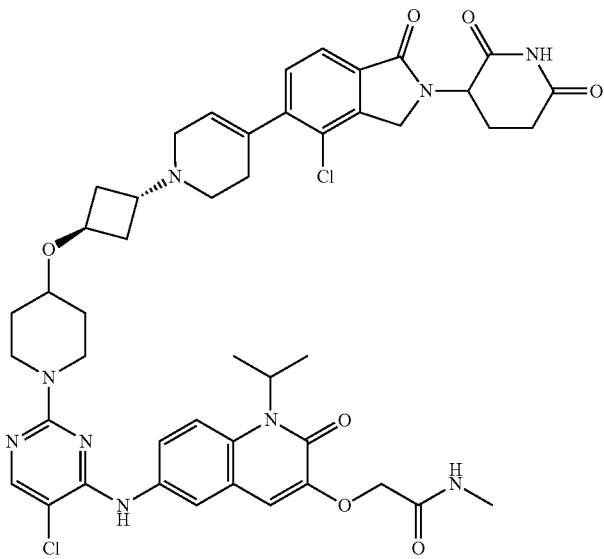 [SMILES: CNC(=O)COc1cc2cc(Nc3nc(N4CCC(O[C@H]5C[C@H](N6CC=C(c7ccc8c(c7F)CN(C7CCC(=O)NC7=O)C8=O)CC6)C5)CC4)ncc3Cl)ccc2n(C(C)C)c1=O] | 2-({6-[(5-chloro-2-{4-[(1r,3r)-3-{4-[4-chloro-2-(2,6-dioxopiperidin-3-yl)-1-oxo-2,3-dihydro-1H-isoindol-5-yl]-1,2,3,6-tetrahydropyridin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 81 |

TABLE 4-continued

Additional exemplary bifunctional compounds of the present disclosure

| Compound Number | Parent Mol Structure | IUPAC Name | Analogously made to Compound Number |
|---|---|---|---|
| 430 | | 2-({6-[(5-chloro-2-{4-[(1r,3r)-3-[(4R)-4-[2-(2,6-dioxopiperidin-3-yl)-4-fluoro-1-oxo-2,3-dihydro-1H-isoindol-5-yl]-3,3-dimethylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 209 |
| 431 | | 2-({6-[(5-chloro-2-{4-[(1r,3r)-3-[(4S)-4-[2-(2,6-dioxopiperidin-3-yl)-4-fluoro-1-oxo-2,3-dihydro-1H-isoindol-5-yl]-3,3-dimethylpiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 210 |

TABLE 5

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 1 | 865.43 | | | A | B |
| 2 | 865.43 | | | A | A |
| 3 | 865.43 | 865.35 | ¹H NMR (400 MHz, DMSO-d₆, ppm) δ 10.94 (s, 1H), 8.75 (s, 1H), 8.21 (s, 1H), 8.03 (s, 1H), 7.96-7.78 (m, 2H), 7.68 (d, J = 9.4 Hz, 1H), 7.48 (d, J = 8.5 Hz, 1H), 7.07-7.02 (m, 3H), 5.04 (s, 1H), 4.53 (s, 2H), 4.31 (s, 1H), 4.19 (s, 1H), 3.84-3.70 (m, 2H), 3.49 (s, 3H), 3.37 (s, 1H), 3.32 (s, 2H), 2.90 (s, 1H), 2.78 (s, 2H), 2.66 (d, J = 4.6 Hz, 4H), 2.50 (s, 2H), 2.43-2.31 (m, 2H), 2.27 (s, 2H), 1.94 (s, 3H), 1.76 (s, 5H), 1.65-1.57 (m, 6H), 1.15 (s, 2H). | A | B |
| 4 | 879.42 | 879.36 | ¹H NMR (400 MHz, DMSO-d₆, ppm) δ 11.07 (s, 1H), 8.75 (s, 1H), 8.19-8.01 (m, 1H), 8.03 (s, 1H), 7.95 (s, 1H), 7.85 (s, 1H), 7.66 (s, 2H), 7.29 (s, 1H), 7.20 (s, 1H), 7.07 (s, 1H), 5.50-5.20 (m, 1H), 5.06 (s, 1H), 4.53 (s, 2H) 3.70-3.48 (m, 5H), 2.92 (d, J = 6.6 Hz, 3H), 2.66 (d, J = 4.6 Hz, 5H), 2.27 (s, 2H), 2.04-1.97 (m, 4H), 1.77 (s, 6H), 1.57 (d, J = 6.8 Hz, 8H), 1.13 (s, 3H). | B | C |
| 5 | 880.40 | 880.3 | ¹H NMR (400 MHz, DMSO-d₆) δ: 11.13 (s, 1H), 8.85 (s, 1H), 8.04 (s, 1H), 8.03-7.99 (m, 1H), 7.95 (d, J = 2.4 Hz, 1H), 7.87-7.82 (m, 1H), 7.79-7.76 (m, 2H), 7.74-7.69 (m, 1H), 7.55-7.49 (m, 1H), 7.08 (s, 1H), 5.13 (dd, J = 12.8, 5.2 Hz, 1H), 4.57 (s, 2H), 4.37-4.27 (m, 2H), 4.20-4.05 (m, 3H), 3.25-3.22 (m, 2H), 3.02-2.95 (m, 2H), 2.92-2.80 (m, 2H), 2.77-2.70 (m, 2H), 2.67 (d, J = 4.8 Hz, 3H), 2.63-2.53 (m, 3H), 2.20-2.10 (m, 2H), 2.08-1.95 (m, 3H), 1.85-1.75 (m, 6H), 1.72-1.60 (m, 2H), 1.43-1.30 (m, 2H), 1.23 (t, J = 7.2 Hz, 3H). | A | A |
| 6 | 865.43 | 865.4 | ¹H NMR (400 MHz, DMSO-d₆) δ: 10.93 (s, 1H), 8.92 (s, 1H), 8.14 (s, 1H), 8.09 (s, 1H), 7.97 (d, J = 4.8 Hz, 1H), 7.93 (s, 1H), 7.69 (s, 2H), 7.49 (d, J = 8.4 Hz, 1H), 7.07-7.00 (m, 3H), 5.54-5.12 (m, 1H), 5.03 (dd, J = 5.2, 13.2 Hz, 1H), 4.55 (s, 2H), 4.35-4.26 (m, 1H), 4.23-4.14 (m, 1H), 3.69 (s, 1H), 3.30-3.26 (m, 4H), 3.21 (s, 3H), 2.94-2.54 (m, 12H), 2.41-2.27 (m, 1H), 2.02-1.92 (m, 3H), 1.67 (s, 2H), 1.59-1.49 (m, 10H). | A | B |
| 7 | 865.43 | 865.4 | ¹H NMR (400 MHz, DMSO-d₆) δ: 10.93 (s, 1H), 8.92 (s, 1H), 8.14 (s, 1H), 8.09 (s, 1H), 7.97 (d, J = 4.8 Hz, 1H), 7.93 (s, 1H), 7.69 (s, 2H), 7.49 (d, J = 8.4 Hz, 1H), 7.07-7.00 (m, 3H), 5.54-5.12 (m, 1H), 5.03 (dd, J = 5.2, 13.2 Hz, 1H), 4.55 (s, 2H), 4.35-4.26 (m, 1H), 4.23-4.14 (m, 1H), 3.69 (s, 1H), 3.30-3.26 (m, 4H), 3.21 (s, 3H), 2.94-2.54 (m, 12H), 2.41-2.27 (m, 1H), 2.02-1.92 (m, 3H), 1.67 (s, 2H), 1.59-1.49 (m, 10H). | A | A |
| 8 | 893.49 | 893.7 | ¹H NMR (400 MHz, DMSO-d₆) δ: 10.98 (s, 1H), 8.78 (s, 1H), 8.19 (s, 1H), 8.02 (s, 1H), 7.99-7.95 (m, 1H), 7.93-7.88 (m, 1H), 7.75-7.65 (m, 2H), 7.30-7.22 (m, 1H), 7.04 (s, 1H), 6.96 (d, J = 7.2 Hz, 1H), 6.65 (d, J = 8.0 Hz, 1H), 5.65-5.00 (m, 2H), 4.75-4.65 (m, 1H), 4.64-4.56 (m, 2H), 4.55-4.47 (m, 3H), 2.97-2.85 (m, 2H), 2.77-2.65 (m, 8H), 2.63-2.52 (m, 4H), 2.47-2.40 (m, 3H), 2.03-1.67 (m, 6H), 1.65-1.60 (m, 1H), 1.57 (d, J = 6.8 Hz, 6H), 1.17-1.05 (m, 2H), 0.90-0.85 (m, 6H). | A | A |
| 9 | 909.44 | 909.3 | ¹H NMR (400 MHz, DMSO-d₆, ppm) δ: 11.03 (br d, J = 0.8 Hz, 1H), 8.84 (s, 1H), 8.04 (s, 1H), 7.99 (br d, J = 4.8 Hz, 1H), 7.94 (s, 1H), 7.69 (s, 2H), | A | C |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
|  |  |  | 7.12-7.08 (m, 1H), 7.06-7.01 (m, 2H), 5.82-5.05 (m, 1H), 4.99 (dd, J = 5.6, 12.8 Hz, 1H), 4.54 (s, 2H), 4.10-3.99 (m, 4H), 3.80 (s, 3H), 3.62 (br s, 4H), 2.91-2.78 (m, 1H), 2.66 (d, J = 4.8 Hz, 3H), 2.61-2.51 (m, 2H), 2.46-2.41 (m, 1H), 2.36-2.32 (m, 3H), 2.13-2.06 (m, 2H), 1.99-1.93 (m, 1H), 1.86 (br d, J = 12.0 Hz, 2H), 1.69 (br d, J = 11.6 Hz, 2H), 1.56 (d, J = 6.8 Hz, 6H), 1.45-1.35 (m, 2H), 1.23 (s, 1H), 0.87 (br d, J = 12.8 Hz, 2H) |  |  |
| 10 | 909.44 | 909.0 | $^1$H NMR (400 MHz, DMSO-d$_6$) δ: 8.85 (s, 1H), 8.34 (s, 1H), 8.05 (s, 1H), 8.02-7.93 (m, 2H), 7.74-7.67 (m, 2H), 7.04 (s, 1H), 6.68 (s, 1H), 6.10 (s, 1H), 5.30 (br s, 1H), 5.01 (dd, J = 5.6, 12.8 Hz, 1H), 4.56 (s, 2H), 3.93-3.80 (m, 7H), 3.64 (s, 3H), 2.94-2.81 (m, 1H), 2.68 (d, J = 4.4 Hz, 3H), 2.63-2.54 (m, 2H), 2.50-2.42 (m, 1H), 2.37 (br s, 4H), 2.21-2.04 (m, 2H), 2.03-1.93 (m, 1H), 1.89 (br d, J = 12.8 Hz, 2H), 1.77-1.67 (m, 2H), 1.62-1.40 (m, 9H), 1.01-0.84 (m, 2H) | B | B |
| 11 | 879.42 | 879.4 | $^1$H NMR (300 MHz, DMSO-d$_6$, ppm) 11.07 (s, 1H), 8.75 (s, 1H), 8.12-8.05 (m, 1H), 8.03 (s, 1H), 7.94-7.85 (m, 2H), 7.68-7.65 (m, 2H), 7.32-7.29 (s, 2H), 7.07 (m, 1H), 5.13-5.12 (m, 2H), 4.53 (s, 2H), 3.79-3.45 (m, 7H), 2.87-2.83 (m, 3H), 2.65-2.61 (m, 6H), 2.51-2.50 (m, 2H), 2.08-1.55 (m, 8H), 1.65-1.55 (m, 7H), 1.11-1.35 (m, 3H). | B | A |
| 12 | 865.43 | 865.45 | $^1$H NMR (300 MHz, DMSO-d$_6$, ppm) 10.97 (s, 1H), 8.75 (s, 1H), 8.12-8.03 (m, 1H), 7.94-7.85 (m, 3H), 7.68-7.65 (m, 1H), 7.43-7.41 (m, 1H), 7.38-7.36 (m, 1H), 7.29-7.27 (m, 1H), 7.14-7.11 (m, 1H), 5.13-5.12 (m, 2H), 4.53-4.30 (m, 4H), 3.49-3.45 (m, 4H), 2.91-2.87 (m, 1H), 2.71-2.61 (m, 7H), 2.50-2.41 (m, 4H), 2.08-1.75 (m, 8H), 1.65-1.55 (m, 9H), 1.11-1.35 (m, 3H). | A | B |
| 13 | 853.42 |  |  | A | A |
| 14 | 865.43 | 865.45 | $^1$H NMR (300 MHz, DMSO-d$_6$, ppm) 10.97 (s, 1H), 8.79 (s, 1H), 8.01-7.94 (m, 3H), 7.68 (s, 2H), 7.45-7.43 (m, 1H), 7.32-7.29 (m, 1H), 7.16-7.13 (m, 1H), 7.00 (s, 1H), 5.13-5.11 (m, 1H), 4.54 (s, 2H), 4.46-4.25 (m, 2H), 3.62-3.53 (m, 4H), 3.43-3.32 (m, 5H), 3.24-3.23 (m, 1H), 3.19-3.15 (m, 6H), 2.97-2.91 (m, 4H), 2.06-2.00 (m, 4H), 1.79-1.37 (m, 13H). | A | A |
| 15 | 843.36 | 843.16 [845.16] | $^1$H NMR (400 MHz, DMSO-d$_6$, ppm): δ 10.98 (s, 1H), 8.86 (s, 1H), 8.06 (s, 1H), 7.96 (s, 2H), 7.70 (s, 2H), 7.42-7.39 (m, 1H), 7.24-7.22 (m, 1H), 7.03 (s, 1H), 5.09-5.05 (m, 1H), 4.55 (s, 2H), 4.33 (s, 1H), 4.25 (s, 1H), 3.65 (s, 4H), 3.47 (s, 2H), 2.87-2.90 (m, 1H), 2.77-2.74 (m, 2H), 2.67-2.66 (m, 3H), 2.51-2.49 (m, 1H), 2.40 (s, 6H), 2.22-2.08 (m, 2H), 1.99-1.96 (m, 1H), 1.85-1.82 (m, 3H), 1.60-1.50 (m, 6H), 1.35-1.20 (m, 2H). | A | B |
| 16 |  |  |  | D | A |
| 17 | 883.42 | 883.35 | $^1$H NMR (400 MHz, DMSO-d$_6$, ppm) 10.94 (s, 1H), 8.85 (s, 1H), 8.06 (s, 1H), 7.96-7.93 (m, 2H), 7.70 (s, 2H), 7.47-7.45 (m, 1H), 7.01 (s, 1H), 6.60-6.58 (m, 2H), 5.05-5.04 (m, 1H), 4.54 (s, 2H), 4.26-4.21 (m, 4H), 3.23-3.21 (m, 4H), 2.93-2.90 (m, 1H), 2.66-2.50 (m, 11H), 1.98-1.94 (m, 6H), 1.94-1.92 (m, 3H), 1.91-1.89 (m, 8H), 1.76-1.75 (m, 1H). | A | C |
| 18 | 843.36 | 843.35 | $^1$H NMR (400 MHz, DMSO-d$_6$, ppm): δ 10.93 (s, 1H), 8.83 (s, 1H), 8.04-7.95 (m, 3H), 7.69 (s, 2H), 7.03 (s, 1H), 6.85 (m, 2H), 5.10-4.90 (m, 1H), 4.54 (s, 2H), 4.40-4.21 (m, 2H), 4.00-3.80 (m, 2H), 3.64 (s, 4H), 2.95-2.86 (m, 3H), 2.65 (s, 4H), 2.38 (s, 5H), 2.17 (s, 2H), 2.00-1.80 (m, 4H), 1.70-1.55 (m, 7H), 1.35-1.20 (m, 2H). | A | B |
| 19 | 878.43 | 878.4 | $^1$H NMR (400 MHz, DMSO-d$_6$, ppm) δ 10.98 (s, 1H), 9.18 (s, 1H), 8.10 (s, 1H), 7.97-7.90 (m, 2H), 7.70 (s, 2H), 7.56-7.47 (m, 3H), 7.02 (s, 1H), 5.17-5.11 (m, 4H), 4.55-4.51 (m, 4H), 3.62-3.55 (m, 4H), 3.43-3.36 (m, 1H), 3.08-2.72 (m, 4H), 2.68-2.50 (m, 6H), 2.00 (s, 5H), 1.78 (s, 3H), 1.65-1.40 (m, 13H). | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 20 | 855.39 | 855.4 | $^1$H NMR (300 MHz, DMSO-d$_6$, ppm) 10.97 (s, 1H), 8.85 (s, 1H), 8.06 (s, 1H), 7.96 (s, 2H), 7.69 (s, 2H), 7.39-7.37 (m, 1H), 7.09-7.07 (m, 1H), 7.02 (s, 1H), 5.13-5.11 (m, 1H), 5.05-5.04 (m, 1H), 4.55 (s, 2H), 4.46-4.24 (m, 2H), 3.86 (s, 3H), 3.65-3.57 (m, 4H), 3.3.56-3.53 (m, 2H), 2.90-2.89 (m, 1H), 2.67-2.66 (m, 4H), 2.62-2.60 (m, 2H), 2.59-2.54 (m, 5H), 2.51-2.50 (m, 2H), 1.98-1.96 (m, 1H), 1.95-1.87 (m, 2H), 1.74-1.73 (m, 1H), 1.57-1.56 (m, 6H), 1.32-1.29 (m, 2H). | D | A |
| 21 | 855.39 | 855.4 | $^1$H NMR (400 MHz, DMSO-d$_6$, ppm) δ 10.96 (s, 1H), 8.85 (s, 1H), 8.05 (s, 1H), 7.96 (s, 2H), 7.70 (m, 2H), 7.16 (s, 1H), 7.05 (m, 2H), 5.07 (m, 1H), 4.55 (s, 2H), 4.17 (m, 2H), 3.85 (s, 3H), 3.65 (s, 4H), 3.47 (s, 2H), 3.34 (s, 1H), 2.93-2.84 (m, 1H), 2.67 (m, 3H), 2.58 (m, 3H), 2.40 (s, 5H), 2.21 (m, 2H), 1.97 (m, 1H), 1.81 (m, 2H), 1.72 (s, 1H), 1.57 (m, 6H), 1.29 (m, 2H). | A | C |
| 22 | 879.42 | 879.25 | $^1$H NMR (400 MHz, DMSO-d$_6$, ppm) δ 11.0 (s, 1H), 8.89 (s, 1H), 8.01 (s, 1H), 8.0 (s, 1H), 7.99 (s, 1H), 7.69 (s, 2H), 7.43 (s, 1H), 7.32 (s, 1H), 7.17 (s, 1H), 7.01 (s, 1H), 5.13-5.09 (m, 1H), 4.55 (s, 2H), 4.41 (s, 1H), 4.31 (s, 1H), 3.96 (s, 2H), 3.75-3.60 (m, 6H), 3.36 (s, 4H), 2.95 (d, J = 6.6 Hz, 1H), 2.88-2.80 (s, 2H), 2.66 (d, J = 4.6 Hz, 3H), 2.60 (s, 1H), 2.50 (m, 1H), 2.04-1.97 (m, 1H), 1.77 (s, 8H), 1.57 (d, J = 6.8 Hz, 6H). | A | B |
| 23 | 893.44 | 893.1 | $^1$H NMR (400 MHz, DMSO-d$_6$) δ: 11.15 (s, 1H), 8.87 (s, 1H), 8.04 (s, 1H), 7.99 (q, J = 4.0 Hz, 1H), 7.93 (s, 1H), 7.85-7.72 (m, 3H), 7.69 (s, 2H), 7.02 (s, 1H), 5.93-4.67 (m, 2H), 4.54 (s, 2H), 3.60 (br s, 5H), 3.41 (s, 1H), 3.05-2.80 (m, 3H), 2.66 (d, J = 4.4 Hz, 3H), 2.63-2.52 (m, 2H), 2.41-2.27 (m, 6H), 2.24-2.11 (m, 3H), 2.09-1.97 (m, 1H), 1.72 (br s, 6H), 1.56 (d, J = 6.8 Hz, 6H), 1.43 (br d, J = 5.6 Hz, 2H) | C | C |
| 24 | 893.44 | 893.5 | $^1$H NMR (400 MHz, DMSO-d$_6$) δ: 11.12 (s, 1H), 8.84 (s, 1H), 8.05 (s, 1H), 8.00-7.91 (m, 2H), 7.87-7.73 (m, 3H), 7.69 (s, 2H), 7.04 (s, 1H), 5.12 (dd, J = 5.6, 12.8 Hz, 1H), 4.55 (s, 2H), 3.73-3.52 (m, 5H), 3.15 (s, 1H), 3.03-2.75 (m, 4H), 2.68 (d, J = 4.4 Hz, 3H), 2.63-2.57 (m, 1H), 2.45-2.36 (m, 6H), 2.10-1.93 (m, 4H), 1.86-1.69 (m, 7H), 1.64-1.51 (m, 6H), 1.24 (s, 2H) | C | C |
| 25 | 843.36 | 843.16 [845.16] | | A | C |
| 26 | 855.39 | 855.25 | $^1$H NMR (400 MHz, DMSO-d$_6$, ppm): δ 10.91 (s, 1H), 8.86 (s, 1H), 8.06 (s, 1H), 7.97 (s, 2H), 7.69 (d, J = 1.6 Hz, 2H), 7.03 (s, 1H), 6.59 (s, 1H), 6.45 (s, 1H), 4.99 (d, J = 13.2, 5.2 Hz, 1H), 4.55 (s, 2H), 4.22 (s, 1H), 4.09 (s, 1H), 3.89 (s, 2H), 3.82 (s, 3H), 3.64 (s, 4H), 3.29 (s, 1H), 2.99-2.86 (m, 3H), 2.66 (s, 3H), 2.56 (d, J = 16.6 Hz, 1H), 2.40 (s, 4H), 2.35-2.24 (m, 1H), 2.18 (s, 2H), 1.91 (s, 1H), 1.80 (d, J = 12.4 Hz, 3H), 1.56 (d, J= 6.8 Hz, 6H), 1.25-1.14 (m, 2H). | A | B |
| 27 | 879.42 | 879.35 | $^1$H NMR (300 MHz, DMSO-d$_6$, ppm) 10.98 (s, 1H), 8.80 (s, 1H), 7.99-7.92 (m, 3H), 7.66 (s, 2H), 7.47-7.44 (m, 1H), 7.35-7.32 (m, 1H), 7.18-7.15 (m, 1H), 7.02 (s, 1H), 5.13-5.11 (m, 1H), 4.54-4.50 (m, 4H), 3.90-3.54 (m, 11H), 3.0.2-2.79 (m, 5H), 2.68-2.62 (m, 4H), 2.06-1.89 (m, 5H), 1.62-1.55 (m, 8H), 1.44-1.43 (m, 2H). | A | B |
| 28 | 826.35 | 826.45 | $^1$H NMR (400 MHz, DMSO-d$_6$, ppm): δ 10.94 (s, 1H), 8.83 (s, 1H), 8.04 (s, 1H), 7.95 (s, 2H), 7.69 (s, 2H), 7.51-7.49 (m, 1H), 7.06-7.01 (m, 3H), 5.29 (s, 1H), 5.04 (m, 1H), 4.54 (s, 2H), 4.31 (s, 1H), 4.19 (m, 1H), 4.08 (m, 2H), 3.78-3.64 (m, 4H), 3.30 (m, 2H), 3.07 (m, 2H), 2.90 (m, 1H), 2.66 (m, 3H), 2.58 (m, 1H), 2.36 (m, 1H), 1.90 (m, 5H), 1.56 (m, 8H), 1.51 (m, 2H). | A | B |
| 29 | 743.17 | 743.3 | $^1$H NMR (400 MHz, DMSO-d$_6$, ppm): δ 11.11 (s, 1H), 8.84 (s, 1H), 8.03 (s, 1H), 8.00-7.90 (m, 2H), 7.86-7.65 (m, 3H), 7.42 (d, J = 2.3 Hz, 1H), 7.28 (dd, J = 8.4, 2.3 Hz, 1H), 7.10 (s, 1H), 5.11 (dd, J = 12.9, 5.4 Hz, 1H), | B | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | 4.83-4.68 (m, 2H), 4.62-4.45 (m, 4H), 3.64 (t, J = 5.3 Hz, 4H), 2.96-2.80 (m, 1H), 2.65 (d, J = 4.6 Hz, 3H), 2.62-2.59 (m, 1H), 2.12-1.97 (m, 2H), 1.68-1.55 (m, 2H), 1.54-1.41 (m, 4H). | | |
| 30 | 855.35 | | ¹H NMR (400 MHz, DMSO-d₆, ppm): δ: 11.10 (s, 1H), 8.83 (s, 1H), 8.04 (s, 1H), 8.00-7.93 (m, 2H), 7.81 (d, J = 8.4 Hz, 1H), 7.69 (s, 2H), 7.45 (d, J = 1.6 Hz, 1H), 7.35 (d, J = 8.4 Hz, 1H), 7.02 (s, 1H), 5.11 (dd, J = 5.2, 12.8 Hz, 1H), 4.69 (s, 1H), 4.54 (s, 2H), 4.09 (d, J = 13.2 Hz, 2H), 3.67 (s, 1H), 3.58 (s, 1H), 3.29-3.22 (m, 2H), 2.96-2.83 (m, 1H), 2.67 (d, J = 4.4 Hz, 3H), 2.59-2.52 (m, 2H), 2.09-1.99 (m, 3H), 1.92 (s, 2H), 1.82 (s, 2H), 1.57 (d, J = 6.8 Hz, 6H), 1.54-1.30 (m, 7H) | B | B |
| 31 | 855.35 | | ¹H NMR (400 MHz, DMSO-d₆, ppm) δ: 11.10 (s, 1H), 8.83 (s, 1H), 8.04 (s, 1H), 7.99 (d, J = 4.8 Hz, 1H), 7.95 (s, 1H), 7.82-7.75 (m, 1H), 7.69 (s, 2H), 7.56 (d, J = 8.8 Hz, 1H), 7.43 (d, J = 7.2 Hz, 1H), 7.02 (s, 1H), 5.07 (dd, J = 5.6, 12.8 Hz, 1H), 4.72 (s, 1H), 4.54 (s, 2H), 4.09 (d, J = 12.8 Hz, 2H), 3.63 (s, 2H), 2.95-2.80 (m, 1H), 2.67 (d, J = 4.4 Hz, 3H), 2.57-2.53 (m, 2H), 2.05-1.98 (m, 3H), 1.95 (d, J = 12.0 Hz, 2H), 1.84 (d, J = 10.0 Hz, 2H), 1.57 (d, J = 7.2 Hz, 8H), 1.50-1.33 (m, 4H), 1.26-1.16 (m, 3H) | A | B |
| 32 | 729.15 | 729.3 | ¹H NMR (400 MHz, DMSO-d₆, ppm): δ: 11.10 (s, 1H), 9.16 (s, 1H), 8.15-8.04 (m, 2H), 8.02-7.93 (m, 1H), 7.89 (dd, J = 9.2, 2.5 Hz, 1H), 7.81 (d, J = 8.3 Hz, 1H), 7.71 (d, J = 9.3 Hz, 1H), 7.41 (d, J = 2.3 Hz, 1H), 7.28 (dd, J = 8.4, 2.3 Hz, 1H), 7.19 (s, 1H), 5.11 (dd, J = 12.8, 5.4 Hz, 1H), 4.82-4.72 (m, 2H), 4.62-4.38 (m, 4H), 3.50-3.42 (m, 5H), 2.96-2.82 (m, 1H), 2.70-2.53 (m, 4H), 2.10-2.00 (m, 1H), 1.92 (s, 4H). | B | B |
| 33 | 773.20 | 773.3 | ¹H NMR (400 MHz, DMSO-d₆, ppm): δ 11.12 (s, 1H), 8.93 (s, 1H), 8.08 (s, 1H), 7.98-7.90 (m, 2H), 7.83 (d, J = 8.3 Hz, 1H), 7.79-7.66 (m, 2H), 7.43 (d, J = 2.2 Hz, 1H), 7.30 (dd, J = 8.4, 2.3 Hz, 1H), 7.23 (s, 1H), 5.12 (dd, J = 12.9, 5.4 Hz, 1H), 4.81-4.72 (m, 2H), 4.63-4.49 (m, 4H), 4.33 (d, J = 12.8 Hz, 2H), 3.67-3.49 (s, 1H), 2.99-2.80 (m, 1H), 2.79-2.61 (m, 5H), 2.46 (s, 1H), 2.28 (s, 1H), 2.04 (d, J = 12.0 Hz, 1H), 1.11 (d, J = 6.1 Hz, 6H). | C | C |
| 34 | 893.49 | 893.3 | ¹H NMR (400 MHz, DMSO-d₆ ppm) 10.98 (s, 1H), 8.80 (s, 1H), 8.02 (s, 1H), 7.97-7.94 (m, 2H), 7.69-7.68 (m, 2H), 7.43-7.41 (m, 1H), 7.40-7.39 (m, 1H), 7.12-7.10 (m, 1H), 7.00 (s, 1H), 5.14-5.10 (m, 2H), 4.55 (s, 2H), 4.55-4.45 (m, 1H), 4.30-4.25 (m, 1H), 3.64-3.54 (m, 4H), 2.99-2.91 (m, 5H), 2.68-2.60 (m, 9H), 2.57-2.54 (m, 1H), 1.99-1.96 (m, 2H), 1.79-1.77 (m, 2H), 1.74-1.61 (m, 10H), 1.57-1.56 (m, 2H), 0.95 (s, 6H). | A | B |
| 35 | 829.29 | 829.35 | ¹H NMR (400 MHz, DMSO-d₆, ppm): δ 11.10 (s, 1H), 8.87 (s, 1H), 8.06 (s, 1H), 7.99 (s, 1H), 7.94 (m, 1H), 7.75 (m, 1H), 7.54-7.48 (m, 2H), 7.38 (m, 1H), 7.13 (s, 1H), 5.08 (m, 1H), 4.59 (s, 2H), 3.68 (s, 3H), 3.64 (s, 4H), 3.48 (m, 1H), 3.45 (s, 1H), 3.20 (s, 2H), 2.93-2.80 (m, 1H), 2.66 (m, 4H), 2.61 (s, 1H), 2.40 (s, 4H), 2.21 (s, 2H), 2.02 (m, 1H), 1.78 (m, 3H), 1.32 (m, 2H). | A | B |
| 36 | 893.49 | | ¹H NMR (400 MHz, DMSO-d₆, ppm): δ 10.98 (s, 1H), 8.82 (s, 1H), 8.03 (s, 1H), 7.98 (s, 1H), 7.90 (d, J = 2.4 Hz, 1H), 7.76-7.66 (m, 2H), 7.41 (d, J = 7.8 Hz, 1H), 7.28 (d, J = 7.4 Hz, 1H), 7.13 (d, J = 7.9 Hz, 1H), 7.03 (s, 1H), 5.11 (d, J = 13.2, 1H), 4.55 (s, 2H), 4.43 (d, J = 17.4 Hz, 1H), 4.28 (d, J = 17.3 Hz, 1H), 3.61 (s, 4H), 3.43-3.30 (m, 3H), 2.93 (s, 5H), 2.71 (s, 3H), 2.61-2.52 (m, 3H), 1.99 (d, J = 12.6 Hz, 1H), 1.79 (d, J = 12.2 Hz, 2H), 1.64 (d, J = 5.4 Hz, | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | 4H), 1.57 (d, J = 6.8 Hz, 6H), 1.32-1.20 (m, 4H), 0.83 (s, 6H). | | |
| 37 | 895.42 | | | A | B |
| 38 | 915.40 | | | A | B |
| 39 | 879.42 | 879.25 | $^1$H NMR (400 MHz, DMSO-d$_6$, ppm): δ 10.89 (s, 1H), 8.78 (s, 1H), 8.03 (s, 1H), 7.97-7.85 (m, 3H), 7.81-7.75 (m, 1H), 7.71 (m, 3H), 7.02 (s, 1H), 5.33 (s, 1H), 5.10 (dd, J = 13.4, 5.1 Hz, 1H), 4.79-4.57 (m, 3H), 4.56-4.23 (m, 3H), 3.85 (s, 2H), 2.89-2.80 (m, 3H), 2.70-2.61 (m, 8H), 2.47-2.31 (m, 2H), 2.31-2.29 (m, 2H), 2.06-1.96 (m, 1H), 1.95-1.82 (m, 2H), 1.80-1.69 (m, 3H), 1.62-1.56 (m, 6H), 1.30-1.12 (m, 1H), 1.04 (d, J = 12.0 Hz, 2H). | A | B |
| 40 | 893.44 | 893.5 | $^1$H NMR (400 MHz, DMSO-d$_6$) δ: 11.13 (s, 1H), 8.85 (s, 1H), 8.19 (s, 1H), 8.04 (s, 1H), 7.94 (s, 2H), 7.86-7.81 (m, 1H), 7.78 (s, 2H), 7.69 (s, 2H), 7.03 (s, 1H), 5.74-5.16 (m, 1H), 5.13 (dd, J = 5.6, 12.8 Hz, 1H), 4.54 (s, 2H), 3.61 (br s, 4H), 2.91 (br d, J = 11.6 Hz, 3H), 2.80-2.69 (m, 1H), 2.67 (d, J = 4.8 Hz, 3H), 2.59 (br d, J = 14.4 Hz, 1H), 2.40-2.28 (m, 7H), 2.18 (br d, J = 4.8 Hz, 4H), 2.08-2.00 (m, 1H), 1.89-1.75 (m, 4H), 1.72-1.61 (m, 2H), 1.56 (d, J = 6.8 Hz, 6H), 1.49-1.38 (m, 2H) | B | B |
| 41 | 893.44 | 893.4 | $^1$H NMR (400 MHz, DMSO-d$_6$) δ: 11.11 (s, 1H), 8.83 (s, 1H), 8.04 (s, 1H), 7.99-7.92 (m, 2H), 7.87-7.82 (m, 1H), 7.80-7.74 (m, 2H), 7.69 (s, 2H), 7.03 (s, 1H), 5.50-5.19 (m, 1H), 5.13 (dd, J = 5.2, 13.2 Hz, 1H), 4.54 (s, 2H), 3.62 (br s, 4H), 2.97-2.84 (m, 3H), 2.67 (d, J = 4.4 Hz, 4H), 2.61 (br d, J = 3.2 Hz, 2H), 2.43 (br s, 6H), 2.09-1.91 (m, 4H), 1.80 (br d, J = 1.6 Hz, 5H), 1.72-1.63 (m, 2H), 1.56 (d, J = 6.8 Hz, 6H), 1.23 (s, 2H) | C | A |
| 42 | 908.45 | | | B | B |
| 43 | 897.41 | | $^1$H NMR (400 MHz, DMSO-d$_6$, ppm): δ 11.07 (s, 1H), 8.85 (s, 1H), 8.06 (s, 1H), 7.95 (m, 2H), 7.70 (m, 2H), 7.55 (m, 1H), 7.09 (m, 1H), 7.02 (s, 1H), 6.77 (m, 1H), 5.04 (m, 1H), 4.54 (s, 2H), 4.24 (m, 2H), 3.89 (s, 4H), 3.21 (m, 2H), 2.93-2.81 (m, 1H), 2.67 (m, 3H), 2.57 (m, 2H), 2.46 (s, 6H), 2.03-1.95 (m, 1H), 1.87 (m, 2H), 1.72 (s, 5H), 1.57 (m, 8H). | B | B |
| 44 | 897.41 | 897.35 | $^1$H NMR (400 MHz, DMSO-d$_6$, ppm): δ 11.07 (s, 1H), 8.85 (s, 1H), 8.06 (s, 1H), 7.95 (m, 2H), 7.70 (m, 2H), 7.55 (m, 1H), 7.09 (m, 1H), 7.02 (s, 1H), 6.77 (m, 1H), 5.04 (m, 1H), 4.54 (s, 2H), 4.24 (m, 2H), 3.89 (s, 4H), 3.21 (m, 2H), 2.93-2.81 (m, 1H), 2.67 (m, 3H), 2.57 (m, 2H), 2.46 (s, 6H), 2.03-1.95 (m, 1H), 1.87 (m, 2H), 1.72 (s, 5H), 1.57 (m, 8H). | A | A |
| 45 | 907.47 | 907.39 | $^1$H NMR (400 MHz, DMSO-d$_6$, ppm): δ 11.08 (s, 1H), 8.78 (s, 1H), 8.02 (s, 1H), 7.99 (q, J = 4.8 Hz, 1H), 7.93 (d, J = 2.3 Hz, 1H), 7.74 (dd, J = 9.3, 2.4 Hz, 1H), 7.69 (d, J = 9.4 Hz, 1H), 7.62 (d, J = 8.2 Hz, 1H), 7.05 (s, 1H), 6.76 (d, J = 2.1 Hz, 1H), 6.63 (dd, J = 8.4, 2.1 Hz, 1H), 5.33 (s, 1H), 5.05 (dd, J = 12.8, 5.5 Hz, 1H), 4.61 (d, J = 12.3 Hz, 2H), 4.53 (s, 2H), 3.71 (s, 4H), 2.95-2.81 (m, 1H), 2.79-2.65 (m, 5H), 2.62-2.51 (m, 2H), 2.43 (s, 4H), 2.00 (d, J = 12.4 Hz, 1H), 1.71 (s, 7H), 1.57 (d, J = 6.8 Hz, 6H), 1.12-1.04 (m, 2H), 0.84 (s, 6H). | A | B |
| 46 | 907.47 | 907.39 | $^1$H NMR (400 MHz, DMSO-d$_6$, ppm): δ 11.07 (s, 1H), 8.78 (s, 1H), 8.02 (s, 1H), 7.95 (dd, J = 15.5, 3.6 Hz, 2H), 7.77-7.66 (m, 2H), 7.54 (dd, J = 8.5, 7.0 Hz, 1H), 7.12-7.02 (m, 2H), 6.76 (d, J = 8.6 Hz, 1H), 5.29 (s, 1H), 5.04 (dd, J = 12.8, 5.4 Hz, 1H), 4.61 (d, J = 12.4 Hz, 2H), 4.53 (s, 2H), 3.87 (s, 4H), 2.94-2.81 (m, 1H), 2.73 (t, J = 12.5 Hz, 5H), 2.67 (d, J = 4.6 Hz, 2H), 2.42 (s, 4H), 1.99 (d, J = 12.3 Hz, 1H), 1.70 (s, 7H), 1.57 (d, J = 6.8 Hz, 6H), 1.09 (s, 2H), 0.84 (s, 6H). | A | A |
| 47 | 879.42 | 879.3 | $^1$H NMR (400 MHz, DMSO-d$_6$, ppm): δ 10.91 (s, 1H), 8.83 (d, J = 3.0 Hz, 1H), 8.05 (d, J = 2.9 Hz, 1H), 7.99-7.90 (m, 2H), 7.69 (s, 2H), 7.54-7.44 (m, 1H), 7.01 (d, J = 2.0 Hz, 1H), 6.64 (m, 2H), 5.36 (s, 1H), 5.03 (dd, J = 13.2, 5.1 Hz, 1H), 4.61-4.41 | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | (m, 4H), 4.39-4.11 (m, 2H), 3.78-3.63 (m, 1H), 3.59 (s, 1H), 3.48-3.40 (m, 3H), 3.01-2.83 (m, 3H), 2.81-2.63 (m, 5H), 2.58-2.56 (m, 1H), 2.36 (d, J = 10.2 Hz, 1H), 2.11-1.81 (m, 6H), 1.79-1.31 (m, 11H). | | |
| 48 | 879.42 | 879.3 | ¹H NMR (400 MHz, DMSO-d₆, ppm): δ 10.98 (s, 1H), 8.80 (s, 1H), 8.05 (s, 1H), 8.01-1.90 (m, 3H), 7.83 (d, J = 8.4 Hz, 1H), 7.78-7.66 (m, 3H), 7.04 (s, 1H), 5.11 (dd, J = 13.3, 5.0 Hz, 1H), 4.59-4.46 (m, 4H), 4.40-4.30 (m, 1H), 3.86 (s, 2H), 2.98-2.71 (m, 5H), 2.70-2.60 (m, 3H), 2.47-2.39 (m, 3H), 2.34-2.27 (m, 3H), 2.25-1.93 (m, 6H), 1.88-1.79 (m, 3H), 1.59 (d, J = 6.8 Hz, 6H), 1.25 (s, 1H), 1.06 (d, J = 12.3 Hz, 2H). | A | B |
| 49 | 866.42 | 866.4 | ¹H NMR (400 MHz, DMSO-d₆) δ: 10.92 (s, 1H), 8.82 (s, 1H), 8.04 (s, 1H), 7.99-7.86 (m, 2H), 7.69 (s, 2H), 7.47 (d, J = 8.4 Hz, 1H), 7.02 (s, 1H), 6.54-6.39 (m, 2H), 5.48-5.11 (m, 1H), 5.02 (dd, J = 4.8, 13.2 Hz, 1H), 4.54 (s, 2H), 4.37-4.25 (m, 1H), 4.21-4.13 (m, 1H), 4.12-4.01 (m, 2H), 3.74-3.65 (m, 1H), 3.61 (d, J = 9.6 Hz, 4H), 3.56-3.46 (m, 1H), 2.98-2.82 (m, 1H), 2.68-2.67 (m, 3H), 2.33-2.32 (m, 2H), 1.98-1.73 (m, 8H), 1.57 (d, J = 6.8 Hz, 9H), 1.44-1.31 (m, 4H) | A | B |
| 50 | 877.40 | | | A | B |
| 51 | 883.42 | | | A | B |
| 52 | 883.42 | | | A | A |
| 53 | 893.49 | 893.35 | ¹H NMR (400 MHz, DMSO-d₆, ppm): δ 10.92 (s, 1H), 8.78 (s, 1H), 8.03 (s, 1H), 7.98-7.91 (m, 2H), 7.78-7.67 (m, 2H), 7.47 (d, J = 8.4 Hz, 1H), 7.05 (s, 1H), 6.65-6.55 (m, 2H), 5.33 (s, 1H), 5.03 (dd, J = 13.3, 5.1 Hz, 1H), 4.70-4.41 (m, 4H), 4.29 (d, J = 16.6 Hz, 1H), 4.18 (dd, J = 16.7, 5.7 Hz, 1H), 3.22 (d, J = 9.7 Hz, 1H), 2.98-2.85 (m, 1H), 2.79-2.64 (m, 8H), 2.60-2.51 (m, 5H), 2.05-1.85 (m, 4H), 1.84-1.76 (m, 4H), 1.68-1.51 (m, 7H), 1.18-1.08 (m, 2H), 0.88 (d, J = 3.2 Hz, 6H). | A | B |
| 54 | 879.42 | 879.35 | ¹H NMR (400 MHz, DMSO-d₆, ppm): δ 10.93 (s, 1H), 8.82 (s, 1H), 8.05 (s, 1H), 8.01-7.93 (m, 2H), 7.70 (d, J = 1.5 Hz, 2H), 7.49 (d, J = 8.4 Hz, 1H), 7.01 (s, 1H), 6.65-6.57 (m, 2H), 5.33 (s, 1H), 4.62-4.41 (m, 4H), 4.31 (d, J = 16.7 Hz, 1H), 4.19 (d, J = 16.8 Hz, 1H), 3.46-3.33 (m, 6H), 3.18-3.03 (m, 2H), 2.98-2.80 (m, 3H), 2.67 (d, J = 4.7 Hz, 3H), 2.42-2.38 (m, 3H), 2.10-1.80 (m, 5H), 1.70-1.50 (m, 9H), 1.15-1.04 (m, 2H). | A | C |
| 55 | 893.44 | | | D | A |
| 56 | 893.44 | | | D | A |
| 57 | 862.96 | 862.39 | ¹H NMR (400 MHz, DMSO-d₆, ppm) 11.06 (s, 1H), 9.34 (s, 1H), 8.02-8.00 (m, 2H), 7.99-7.95 (m, 1H), 7.75-7.74 (m, 1H), 7.70-7.68 (m, 1H), 7.64-7.62 (m, 1H), 6.99 (s, 1H), 6.78-6.77 (m, 1H), 6.66-6.63 (m, 1H), 5.05-5.04 (m, 1H), 4.54-4.51 (m, 2H), 4.50-4.48 (m, 2H), 3.74 (s, 4H), 2.87-2.84 (m, 3H), 2.68-2.67 (m, 3H), 2.54-2.52 (m, 2H), 2.50-2.49 (m, 1H), 2.33-2.32 (m, 4H), 2.12-2.11 (m, 2H), 2.10-2.01 (m, 1H), 1.77-1.76 (m, 7H), 1.57-1.56 (m, 6H), 1.15-1.01 (m, 2H). | B | B |
| 58 | 893.49 | 893.35 | ¹H NMR (400 MHz, DMSO-d₆, ppm) δ: 10.97 (s, 1H), 8.78 (s, 1H), 8.03 (s, 1H), 7.94 (d, J = 5.5 Hz, 2H), 7.76-7.66 (m, 2H), 7.30 (s, 1H), 7.07-6.99 (m, 2H), 6.53 (d, J = 8.0 Hz, 1H), 5.10 (dd, J = 13.2, 5.2 Hz, 1H), 4.61 (s, 2H), 4.53 (s, 2H), 4.46 (d, J = 17.0 Hz, 1H), 4.31 (s, 1H), 3.75-3.65 (m, 4H), 3.23 (s, 1H), 2.97-2.85 (m, 1H), 2.80 (s, 3H), 2.70 (s, 3H), 2.60 (s, 2H), 2.44 (s, 4H), 1.97 (s, 1H), 1.72 (s, 7H), 1.57 (s, 6H), 1.11 (s, 2H), 0.85 (s, 6H). | A | A |
| 59 | 893.49 | 893.4 | ¹H NMR (400 MHz, DMSO-d₆, ppm): δ 10.92 (s, 1H), 8.77 (s, 1H), 8.03 (s, 1H), 7.97-7.91 (m, 2H), 7.70 (s, 2H), 7.47 (d, J = 8.4 Hz, 1H), 7.05 (s, 1H), 6.54-6.44 (m, 2H), 5.03 (d, J = 13.4, 1H), 4.61 (d, J = 12.6 Hz, 2H), 4.53 (s, 2H), 4.29 (d, J = 16.8 Hz, 1H), 4.17 (d, J = 16.8 Hz, 1H), 3.61 (s, 4H), 2.90 (s, 1H), 2.74 (d, J = 12.6 Hz, 2H), 2.67 (d, | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 60 | 879.42 | 879.3 | J = 4.6 Hz, 4H), 2.60 (s, 2H), 2.44 (s, 4H), 1.95 (s, 1H), 1.72 (s, 7H), 1.57 (d, J = 6.8 Hz, 6H), 1.09 (d, J = 13.2 Hz, 2H), 0.85 (s, 6H). ¹H NMR (300 MHz, DMSO-d₆, ppm): δ 10.80 (s, 1H), 8.70 (s, 1H), 7.92 (s, 1H), 7.84 (s, 2H), 7.57 (s, 2H), 7.36 (d, J = 8.4 Hz, 1H), 6.90 (s, 1H), 6.70-6.53 (m, 2H), 5.20 (s, 1H), 4.92 (dd, J = 13.1, 5.0 Hz, 1H), 4.59-4.45 (m, 4H), 4.34-4.13 (m, 2H), 3.51-3.43 (m, 2H) 3.41-3.37 (m, 3H), 3.18-3.09 (m, 2H), 2.97-2.80 (m, 3H), 2.63-2.55 (m, 2H), 2.41-2.28 (m, 2H), 2.15-1.90 (m, 7H), 1.70-1.54 (m, 9H), 1.18-0.98 (m, 2H). | A | B |
| 61 | 866.42 | 866.6 | ¹H NMR (300 MHz, DMSO-d₆, ppm): δ: 10.97 (s, 1H), 8.82 (s, 1H), 8.04 (s, 1H), 7.95 (s, 2H), 7.69 (s, 2H), 7.30 (t, J = 7.6 Hz, 1H), 7.02 (t, J = 3.6 Hz, 2H), 6.52 (d, J = 8.0 Hz, 1H), 5.54-5.17 (m, 1H), 5.10 (dd, J = 5.2, 13.2 Hz, 1H), 4.55 (s, 2H), 4.49-4.41 (m, 1H), 4.29 (d, J = 17.2 Hz, 1H), 4.15-4.01 (m, 2H), 3.75-3.62 (m, 5H), 3.50 (br t, J = 8.0 Hz, 1H), 3.30-3.25 (m, 2H), 2.99-2.87 (m, 1H), 2.67 (d, J = 4.8 Hz, 3H), 2.63-2.55 (m, 1H), 2.47-2.39 (m, 1H), 2.03-1.86 (m, 3H), 1.85-1.70 (m, 4H), 1.57 (d, J = 6.8 Hz, 8H), 1.36 (br dd, J = 9.2, 12.4 Hz, 4H) | A | B |
| 62 | 925.46 | 925.2 | ¹H NMR (400 MHz, DMSO-d₆, ppm): δ: 11.09 (br s, 1H), 8.85 (s, 1H), 8.07 (s, 1H), 8.00-7.90 (m, 2H), 7.79-7.61 (m, 3H), 7.41-7.25 (m, 2H), 7.04 (s, 1H), 5.55-5.18 (m, 1H), 5.09 (dd, J = 5.2, 12.8 Hz, 1H), 4.55 (s, 2H), 4.32-4.17 (m, 2H), 3.31 (br s, 2H), 3.29-3.16 (m, 6H), 2.94-2.81 (m, 1H), 2.68 (d, J = 4.4 Hz, 3H), 2.64-2.54 (m, 6H), 2.09-1.96 (m, 1H), 1.94-1.80 (m, 2H), 1.58 (br d, J = 6.8 Hz, 12H), 1.53-1.44 (m, 4H) | A | A |
| 63 | 925.46 | | ¹H NMR (400 MHz, DMSO-d₆) δ: 10.94 (s, 1H), 8.79 (s, 1H), 8.03 (s, 1H), 7.98-7.90 (m, 2H), 7.75-7.65 (m, 3H), 7.42-7.32 (m, 2H), 7.00 (s, 1H), 5.45-5.05 (m, 2H), 4.54 (s, 2H), 3.73-3.60 (m, 4H), 3.57-3.47 (m, 1H), 3.31-3.29 (m, 2H), 3.17-3.06 (m, 2H), 2.95-2.81 (m, 1H), 2.71-2.64 (m, 4H), 2.63-2.56 (m, 4H), 2.10-1.75 (m, 6H), 1.57 (d, J = 6.8 Hz, 6H), 1.50-1.37 (m, 8H). | B | B |
| 64 | 883.42 | 883.4 | ¹H NMR (400 MHz, DMSO-d₆, ppm) δ: 10.97 (s, 1H), 8.82 (s, 1H), 8.24 (s, 1H), 8.04 (s, 1H), 8.01-7.93 (m, 2H), 7.75-7.66 (m, 2H), 7.31 (d, J = 11.6 Hz, 1H), 7.02 (s, 1H), 6.66 (d, J = 8.0 Hz, 1H), 5.97-5.10 (m, 1H), 5.04 (dd, J = 5.2, 13.2 Hz, 1H), 4.54 (s, 2H), 4.53-4.45 (m, 2H), 4.32-4.26 (m, 1H), 4.21-4.13 (m, 1H), 3.77-3.73 (m, 4H), 2.97-2.79 (m, 3H), 2.68 (d, J = 4.8 Hz, 3H), 2.61-2.54 (m, 1H), 2.40-2.21 (m, 5H), 2.11 (d, J = 6.0 Hz, 2H), 2.00-1.92 (m, 1H), 1.81-1.68 (m, 7H), 1.57 (d, J = 6.8 Hz, 6H), 1.05-0.95 (m, 2H). | A | B |
| 65 | 893.40 | 893.45 | ¹H NMR (400 MHz, DMSO-d₆, ppm) δ 11.12 (s, 1H), 8.79 (s, 1H), 8.03 (s, 1H), 7.96-7.92 (m, 3H), 7.76-7.70 (m, 4H), 7.02 (s, 1H), 5.16-5.14 (m, 1H), 4.54-4.51 (m, 4H), 3.71 (s, 2H), 2.88-2.84 (m, 2H), 2.73-2.70 (m, 6H), 2.68-2.66 (m, 1H), 2.33-2.32 (m, 4H), 2.16-2.15 (m, 2H), 1.88-1.78 (m, 4H), 1.77-1.74 (m, 3H), 1.58-1.56 (m, 7H), 1.04-1.01 (m, 2H). | D | A |
| 66 | 879.42 | 879.25 | ¹H NMR (400 MHz, DMSO-d₆, ppm) δ 10.92 (s, 1H), 8.89 (s, 1H), 8.08 (s, 1H), 7.95 (s, 2H), 7.70 (s, 2H), 7.47 (dd, J = 9.1, 3.8 Hz, 1H), 7.08 (d, J = 3.8 Hz, 1H), 6.59 (s, 2H), 5.03 (ddd, J = 13.2, 4.9, 3.0 Hz, 1H), 4.55 (d, J = 2.6 Hz, 2H), 4.30 (d, J = 16.8 Hz, 1H), 4.22-4.13 (m, 1H), 3.70 (m, 9H), 3.66 (s, 1H), 3.61 (s, 4H), 2.90 (t, J = 15.1 Hz, 1H), 2.67 (dd, J = 6.6, 4.6 Hz, 3H), 2.58 (d, J = 16.0 Hz, 1H), 2.40 (s, 1H), 1.90-2.01 (s, 4H), 1.98-1.81 (m, 3H), 1.72 (s, 2H), 1.70-1.54 (m, 6H). | A | C |
| 67 | 797.31 | 797.35 | ¹H NMR (300 MHz, DMSO-d₆, ppm): δ | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | 10.94 (s, 1H), 8.86 (s, 1H), 8.06 (s, 1H), 7.95 (m, 2H), 7.75 (m, 1H), 7.49 (m, 2H), 7.12 (s, 1H), 7.04 (m, 2H), 5.05 (m, 1H), 4.59 (s, 2H), 4.32-4.20 (m, 2H), 3.88 (m, 2H), 3.68-3.64 (m, 7H), 2.85 (m, 3H), 2.70-2.50 (m, 4H), 2.39-2.38 (m, 5H), 2.18 (m, 2H), 1.96 (m, 1H), 1.81 (m, 3H), 1.19 (m, 2H). | | |
| 68 | 871.41 | 871.35 | $^1$H NMR (300 MHz, DMSO-d$_6$, ppm): δ 10.97 (s, 1H), 8.81 (s, 1H), 8.05 (s, 1H), 8.00-7.91 (m, 2H), 7.79-7.65 (m, 2H), 7.45-7.32 (m, 2H), 7.23 (m, 1H), 7.06 (s, 1H), 5.13-5.01 (m, 2H), 4.55 (s, 2H), 4.37-4.24 (m, 2H), 3.62-3.54 (m, 6H), 2.91 (m, 1H), 2.67 (m, 7H), 2.55 (s, 1H), 1.99 (s, 1H), 1.81 (m, 4H), 1.58 (m, 6H), 1.40 (m, 3H), 0.91 (m, 7H). | A | B |
| 69 | 866.42 | 866.6 | $^1$H NMR (400 MHz, DMSO-d$_6$) δ: 10.95 (br d, J = 3.2 Hz, 1H), 8.81 (s, 1H), 8.04 (s, 1H), 7.99-7.89 (m, 2H), 7.69 (s, 2H), 7.36 (d, J = 8.8 Hz, 1H), 7.01 (s, 1H), 6.75-6.62 (m, 2H), 5.67-5.20 (m, 1H), 5.07 (dd, J = 5.2, 13.2 Hz, 1H), 4.60-4.50 (m, 2H), 4.34-4.26 (m, 1H), 4.22-4.14 (m, 1H), 4.12-4.01 (m, 2H), 3.73-3.63 (m, 1H), 3.55 (d, J = 10.0 Hz, 4H), 3.52-3.46 (m, 1H), 2.98-2.81 (m, 1H), 2.67 (d, J = 4.4 Hz, 4H), 2.62-2.54 (m, 1H), 2.41-2.29 (m, 2H), 2.03-1.93 (m, 1H), 1.91-1.71 (m, 6H), 1.57 (d, J = 7.2 Hz, 8H), 1.44-1.29 (m, 4H) | A | B |
| 70 | 866.42 | 866.3 | $^1$H NMR (400 MHz, DMSO-d$_6$) δ: 10.93 (s, 1H), 8.82 (s, 1H), 8.04 (s, 1H), 8.00-7.92 (m, 2H), 7.69 (s, 2H), 7.34 (t, J = 7.6 Hz, 1H), 7.02 (s, 1H), 6.77 (d, J = 8.0 Hz, 1H), 6.36 (d, J = 8.0 Hz, 1H), 5.62-5.09 (m, 1H), 4.96 (dd, J = 5.2, 13.6 Hz, 1H), 4.54 (s, 2H), 4.36-4.27 (m, 1H), 4.25-4.15 (m, 1H), 4.13-4.02 (m, 2H), 3.85-3.73 (m, 4H), 3.71-3.63 (m, 1H), 3.54-3.44 (m, 1H), 2.95-2.78 (m, 1H), 2.67 (d, J = 4.4 Hz, 4H), 2.58 (br dd, J = 2.8, 16.8 Hz, 1H), 2.40-2.29 (m, 2H), 2.04-1.90 (m, 1H), 1.89-1.70 (m, 6H), 1.60-1.47 (m, 8H), 1.44-1.27 (m, 4H) | B | B |
| 71 | 883.42 | 883.4 | $^1$H NMR (400 MHz, DMSO-d$_6$) δ: 10.96 (s, 1H), 8.69-8.69 (m, 1H), 8.15 (d, J = 1.2 Hz, 1H), 8.04 (s, 1H), 7.98-7.88 (m, 2H), 7.77-7.65 (m, 2H), 7.37 (d, J = 8.0 Hz, 1H), 7.02 (s, 1H), 6.61 (t, J = 8.0 Hz, 1H), 5.54-5.06 (m, 1H), 5.06-4.90 (m, 1H), 4.60-4.46 (m, 4H), 4.43 (d, J = 17.2 Hz, 1H), 4.26 (d, J = 16.8 Hz, 1H), 3.78 (s, 4H), 3.02-2.79 (m, 3H), 2.68 (d, J = 4.8 Hz, 3H), 2.60 (s, 1H), 2.43-2.33 (m, 5H), 2.15 (d, J = 3.6 Hz, 2H), 2.00-1.92 (m, 1H), 1.84-1.69 (m, 7H), 1.58 (d, J = 6.8 Hz, 6H), 1.11-0.97 (m, 2H). | A | B |
| 72 | 910.47 | 910.2 | $^1$H NMR (400 MHz, DMSO-d$_6$) δ: 10.9 (s, 1H), 8.83 (s, 1H), 8.05 (s, 1H), 8.01-7.92 (m, 2H), 7.69 (s, 2H), 7.40 (s, 2H), 7.03 (s, 1H), 5.59-5.19 (m, 1H), 5.10 (dd, J = 5.2, 13.2 Hz, 1H), 4.70-4.60 (m, 1H), 4.55 (s, 2H), 4.50-4.42 (m, 1H), 4.24-4.11 (m, 2H), 3.91 (s, 3H), 3.54 (br s, 1H), 3.30 (s, 3H), 3.27-3.19 (m, 2H), 3.05-2.86 (m, 4H), 2.68 (d, J = 4.4 Hz, 3H), 2.65-2.59 (m, 2H), 2.16 (br s, 2H), 2.04-19.6 (m, 3H), 1.88-1.76 (m, 4H), 1.72-1.66 (m, 3H), 1.58 (d, J = 7.2 Hz, 6H), 1.43-1.33 (m, 2H) | A | B |
| 73 | 929.47 | | | A | B |
| 74 | 893.49 | 893.42 | $^1$H NMR (400 MHz, DMSO-d$_6$) δ 10.91 (s, 1H), 8.79 (s, 1H), 8.03 (d, J = 1.7 Hz, 1H), 7.95 (t, J = 2.9 Hz, 2H), 7.76-7.65 (m, 2H), 7.46 (d, J = 8.8 Hz, 1H), 7.05 (d, J = 3.6 Hz, 1H), 6.58 (d, J = 6.8 Hz, 2H), 5.31 (s, 1H), 4.55 (s, 2H), 4.29 (d, J = 16.6 Hz, 1H), 4.22-4.13 (m, 1H), 3.58 (s, 4H), 3.20 (d, J = 6.5 Hz, 2H), 2.90 (t, J = 14.6 Hz, 1H), 2.66 (t, J = 4.4 Hz, 3H), 2.55 (d, J = 6.3 Hz, 7H), 1.98-1.85 (m, 4H), 1.57 (d, J = 6.9 Hz, 13H), 1.43 (q, J = 12.1, 11.6 Hz, 1H), 0.92 (dd, J = 8.0, 3.1 Hz, 6H). | A | C |
| 75 | 865.43 | 865.25 | $^1$H NMR (300 MHz, DMSO-d$_6$, ppm): δ 10.92 (s, 1H), 8.83 (s, 1H), 8.05 (d, J = 0.8 Hz, 1H), 7.95 (d, J = 6.0 Hz, 2H), 7.70 | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | (s, 2H), 7.47 (d, J = 9.0 Hz, 1H), 7.04 (d, J = 1.3 Hz, 1H), 6.60 (d, J = 6.5 Hz, 2H), 5.32 (s, 1H), 5.03 (dd, J = 13.2, 5.1 Hz, 1H), 4.56 (s, 2H), 4.30 (d, J = 16.7 Hz, 2H), 3.63 (s, 4H), 3.3 (s, 1H), 3.21 (d, J = 8.8 Hz, 2H), 2.94-2.82 (m, 1H), 2.67 (dd, J = 4.7, 2.3 Hz, 3H), 2.62 (s, 1H), 2.41 (s, 9H), 1.86 (ddd, J = 20.9, 12.6, 6.6 Hz, 5H), 1.57 (d, J = 6.8 Hz, 8H), 1.34 (d, J = 8.7 Hz, 3H). | | |
| 76 | 871.41 | 871.35 | $^1$H NMR (400 MHz, DMSO-d$_6$, ppm): δ 10.94 (s, 1H), 8.80 (s, 1H), 8.05 (s, 1H), 7.95 (m, 2H), 7.77-7.65 (m, 2H), 7.05 (s, 1H), 6.86 (m, 1H), 6.80-6.71 (m, 1H), 5.00 (m, 1H), 4.55 (s, 2H), 4.33 (m, 1H), 4.20 (m, 1H), 3.97 (m, 2H), 3.61 (s, 4H), 2.96-2.82 (m, 3H), 2.66 (m, 3H), 2.60-2.54 (m, 6H), 2.35 (m, 1H), 1.95 (m, 1H), 1.81 (m, 3H), 1.57 (m, 6H), 1.25 (m, 2H), 0.88 (s, 6H). | A | B |
| 77 | 883.45 | 883.35 | $^1$H NMR (400 MHz, DMSO-d$_6$, ppm) δ: 10.89 (s, 1H), 8.80 (s, 1H), 8.05 (s, 1H), 7.96 (s, 2H), 7.77-7.65 (m, 2H), 7.05 (s, 1H), 6.58 (s, 1H), 6.45 (s, 1H), 5.05-4.95 (m, 1H), 4.55 (s, 2H), 4.22 (d, J = 17.0 Hz, 1H), 4.09 (d, J = 16.8 Hz, 1H), 3.96 (d, J = 12.1 Hz, 2H), 3.82 (s, 3H), 3.79-3.61 (m, 4H), 2.89 (s, 1H), 2.77 (d, J = 12.2 Hz, 2H), 2.66 (d, J = 4.6 Hz, 3H), 2.55 (d, J = 4.9 Hz, 5H), 2.32-2.24 (m, 2H), 1.92 (s, 1H), 1.80 (s, 3H), 1.57 (s, 6H), 1.40-1.21 (m, 2H), 0.95 (s, 6H). | A | B |
| 78 | 883.45 | 883.5 | $^1$H NMR (400 MHz, DMSO-d$_6$, ppm) 10.97 (s, 1H), 8.80 (s, 1H), 8.05 (s, 1H), 7.96-7.92 (m, 2H), 7.72-7.70 (m, 2H), 7.37-7.35 (m, 1H), 7.08-7.05 (m, 2H), 5.07-5.04 (m, 1H), 4.54-4.51 (m, 2H), 4.49-4.45 (m, 1H), 4.32-4.28 (m, 1H), 3.86 (s, 3H), 3.61-3.55 (m, 4H), 2.95-2.85 (m, 1H), 2.66-2.62 (m, 5H), 2.62-2.59 (m, 2H), 2.52-2.51 (m, 4H), 2.50-2.49 (m, 1H), 1.98-1.98 (m, 1H), 1.87-1.84 (m, 2H), 1.77-1.74 (m, 1H) 1.58-1.56 (m, 6H), 1.54-1.41 (m, 2H), 0.99-0.89 (m, 6H). | A | C |
| 79 | 898.43 | 898.3 | $^1$H NMR (400 MHz, DMSO-d$_6$) δ: 11.00 (s, 1H), 8.83 (s, 1H), 8.16 (s, 1H), 8.05 (s, 1H), 7.99-7.90 (m, 2H), 7.69 (s, 2H), 7.62 (d, J = 6.0 Hz, 1H), 7.50-7.43 (m, 1H), 7.03 (s, 1H), 5.64-5.18 (m, 1H), 5.16-5.05 (m, 1H), 4.61-4.50 (m, 2H), 4.47-4.39 (m, 1H), 4.33-4.26 (m, 1H), 4.22-4.16 (m, 1H), 4.15-4.07 (m, 2H), 3.57-3.50 (m, 1H), 3.24 (t, J = 10.4 Hz, 2H), 3.02 (d, J = 10.4 Hz, 2H), 2.94-2.86 (m, 2H), 2.68 (d, J = 4.8 Hz, 3H), 2.64-2.58 (m, 2H), 2.42-2.36 (m, 2H), 2.21-2.14 (m, 2H), 2.03-1.98 (m, 2H), 1.86-1.79 (m, 4H), 1.77-1.69 (m, 4H), 1.57 (d, J = 6.8 Hz, 6H), 1.43-1.34 (m, 2H). | A | B |
| 80 | 883.42 | 883.4 | $^1$H NMR (400 MHz, DMSO-d$_6$) δ: 10.93 (s, 1H), 8.78 (s, 1H), 8.19 (s, 1H), 8.03 (s, 1H), 7.97-7.90 (m, 2H), 7.75-7.65 (m, 2H), 7.02 (s, 1H), 6.32 (s, 1H), 6.20 (d, J = 11.2 Hz, 1H), 5.60-5.10 (m, 1H), 4.98 (dd, J = 13.2, 5.2 Hz, 1H), 4.54 (s, 2H), 4.51-4.45 (m, 2H), 4.33-4.26 (m, 1H), 4.20-4.12 (m, 1H), 3.63 (s, 3H), 2.95-2.75 (m, 3H), 2.68 (d, J = 4.8 Hz, 3H), 2.62-2.53 (m, 2H), 2.38-2.50 (m, 5H), 2.15-2.05 (m, 2H), 2.00-1.87 (m, 1H), 1.78-1.68 (m, 7H), 1.57 (d, J = 6.8 Hz, 6H), 1.10-0.90 (m, 2H). | A | B |
| 81 | 898.43 | 748.2 | $^1$H NMR (400 MHz, DMSO-d$_6$) δ: 11.00 (s, 1H), 8.83 (s, 1H), 8.18 (s, 1H), 8.04 (s, 1H), 7.99-7.91 (m, 2H), 7.69 (s, 2H), 7.61-7.47 (m, 2H), 7.03 (s, 1H), 5.58-5.15 (m, 1H), 5.11 (dd, J = 5.2, 13.2 Hz, 1H), 4.59-4.50 (m, 3H), 4.37 (d, J = 17.4 Hz, 1H), 4.24-4.06 (m, 3H), 3.56-3.51 (m, 1H), 3.24 (t, J = 10.4 Hz, 2H), 3.01 (d, J = 10.0 Hz, 2H), 2.97-2.82 (m, 3H), 2.68 (d, J = 4.8 Hz, 3H), 2.60 (d, J = 16.0 Hz, 1H), 2.46-2.39 (m, 1H), 2.21-2.13 (m, 2H), 2.05-1.96 (m, 3H), 1.87-1.79 (m, 4H), 1.78-1.69 (m, 4H), 1.57 (d, J = 6.8 Hz, 6H), 1.43-1.34 (m, 2H). | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 82 | 911.48 | 911.5 | $^1$H NMR (400 MHz, DMSO-$d_6$) 10.97 (br s, 1H), 8.84 (s, 1H), 8.06 (s, 1H), 8.01-7.89 (m, 2H), 7.70 (s, 2H), 7.45-7.37 (m, 1H), 7.28 (d, J = 7.6 Hz, 1H), 7.16 (d, J = 8.0 Hz, 1H), 7.03 (s, 1H), 5.59-5.14 (m, 1H), 5.11 (dd, J = 5.2, 13.2 Hz, 1H), 4.54 (s, 2H), 4.45-4.37 (m, 1H), 4.18 (s, 3H), 3.29 (s, 1H), 3.29-3.13 (m, 3H), 3.09-2.81 (m, 5H), 2.67 (d, J = 4.8 Hz, 4H), 2.53 (br s, 3H), 2.04-1.93 (m, 1H), 1.91-1.78 (m, 2H), 1.75-1.52 (m, 12H), 1.48 (br s, 4H), 1.30-1.19 (m, 2H) | A | A |
| 83 | 909.44 | 909.19 [911.19] | | A | B |
| 84 | 883.42 | 883.20 [885.20] | | A | A |
| 85 | 895.46 | 895.22 [897.22] | | A | B |
| 86 | 883.42 | 883.20 [885.20] | | A | B |
| 87 | 883.42 | 883.20 [885.20] | | A | B |
| 88 | 895.46 | 895.22 [897.22] | | A | C |
| 89 | 871.41 | 871.20 [873.20] | $^1$H NMR (400 MHz, DMSO-$d_6$, ppm) 10.97 (s, 1H), 8.80 (s, 1H), 8.05 (s, 1H), 7.96-7.92 (m, 2H), 7.72-7.70 (m, 2H), 7.47-7.45 (m, 1H), 7.17-7.13 (m, 1H), 7.05 (s, 1H), 5.09-5.04 (m, 1H), 4.54-4.51 (m, 2H), 4.49-4.45 (m, 1H), 4.32-4.28 (m, 1H), 3.61-3.55 (m, 6H), 2.90-2.78 (m, 1H), 2.75-2.72 (m, 2H), 2.66-2.61 (m, 4H), 2.54-2.49 (m, 4H), 2.43-2.40 (m, 2H), 1.98-1.88 (m, 1H), 1.87-1.64 (m, 3H), 1.58-1.56 (m, 6H), 1.54-1.41 (m, 2H), 0.99-0.89 (m, 6H). | A | B |
| 90 | 901.41 | 901.19 [903.19] | | A | B |
| 91 | 915.40 | 915.16 [917.16] | | A | B |
| 92 | 898.43 | 898.19 [900.19] | $^1$H NMR (400 MHz, DMSO-$d_6$, ppm) δ: 10.98 (s, 1H), 8.83 (s, 1H), 8.21 (s, 1H), 8.04 (s, 1H), 7.97-7.87 (m, 2H), 7.68 (s, 2H), 7.33 (s, 1H), 7.19 (d, J = 11.2 Hz, 1H), 7.02 (s, 1H), 5.70-5.10 (m, 1H), 5.06 (dd, J = 13.2, 5.2 Hz, 1H), 4.54 (s, 2H) 4.47-4.40 (m, 1H), 4.34-4.25 (m, 1H), 4.20-4.05 (m, 3H), 3.57-3.47 (m, 1H), 3.27-3.17 (m, 2H), 3.01-2.95 (m, 2H), 2.93-2.75 (m, 2H), 2.68 (d, J = 4.8 Hz, 3H), 2.64-2.53 (m, 2H), 2.42-2.30 (m, 1H), 2.20-2.10 (m, 2H), 2.03-1.95 (m, 3H), 1.85-1.72 (m, 6H), 1.70-1.62 (m, 2H), 1.57 (d, J = 6.8 Hz, 6H), 1.43-1.30 (m, 2H). | A | A |
| 93 | 929.47 | 929.21 [931.21] | $^1$H NMR (400 MHz, DMSO-$d_6$) δ: 8.08 (s, 1H), 8.01 (d, J = 2.4 Hz, 1H), 7.83-7.78 (m, 1H), 7.70 (dd, J = 2.4, 9.2 Hz, 1H), 7.31 (dd, J = 8.0, 13.2 Hz, 1H), 7.24 (s, 1H), 7.14 (dd, J = 3.6, 8.0 Hz, 1H), 5.36 (s, 1H), 5.07 (dd, J = 5.2, 13.2 Hz, 1H), 4.64 (s, 2H), 4.50-4.41 (m, 3H), 4.38 (br d, J = 10.0 Hz, 2H), 3.66-3.60 (m, 2H), 3.57-3.48 (m, 4H), 2.89 (s, 3H), 2.84-2.80 (m, 1H), 2.57-2.48 (m, 1H), 2.23-2.07 (m, 6H), 1.97-1.81 (m, 6H), 1.72 (d, J = 6.8 Hz, 8H), 1.33 (br d, J = 17.6 Hz, 3H), 1.20 (t, J = 7.2 Hz, 2H) | D | A |
| 94 | 929.47 | 929.21 [931.21] | $^1$H NMR (400 MHz, DMSO-$d_6$) δ: 10.98 (s, 1H), 8.85 (s, 1H), 8.06 (s, 1H), 7.99-7.91 (m, 2H), 7.70 (s, 2H), 7.26-7.14 (m, 2H), 7.03 (s, 1H), 5.51-5.15 (m, 1H), 5.07 (dd, J = 5.2, 13.2 Hz, 1H), 4.54 (s, 2H), 4.44-4.35 (m, 1H), 4.32-4.15 (m, 3H), 3.32 (s, 5H), 3.21 (br t, J = 11.6 Hz, 2H), 2.98-2.82 (m, 5H), 2.67 (d, J = 4.8 Hz, 3H), 2.60 (br d, J = 2.4 Hz, 1H), 2.56 (br d, J = 0.8 Hz, 1H), 2.47-2.41 (m, 2H), 2.03-1.94 (m, 1H), 1.92-1.82 (m, 2H), 1.74-1.66 (m, 1H), 1.57 (br d, J = 6.8 Hz, 8H), 1.50 (br d, J = 1.6 Hz, 6H). | A | B |
| 95 | 911.48 | 911.23 [913.22] | $^1$H NMR (400 MHz, DMSO-$d_6$) δ: 10.98 (br s, 1H), 8.78 (s, 1H), 8.36 (s, 1H), 8.03 (s, 1H), 7.99-7.92 (m, 2H), 7.77-7.62 (m, 2H), 7.49-7.38 (m, 1H), 7.31 (d, J = 7.6 Hz, 1H), 7.20 (d, J = 8.0 Hz, 1H), 7.00 (s, 1H), 5.60-5.16 (m, 1H), 5.15-5.07 (m, 1H), 4.59-4.51 (m, 2H), 4.49-4.40 (m, 1H), 4.35-4.24 (m, 1H), 3.64 (br s, 5H), 3.45 (br s, 1H), 3.26-3.17 (m, 4H), 3.08-2.82 (m, 4H), 2.67 (d, J = 4.4 Hz, 3H), 2.63-2.55 (m, 2H), 2.05-1.68 (m, 6H), 1.57 (d, J = 6.8 Hz, 6H), 1.51-1.37 (m, 8H) | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 96 | 929.47 | 929.21 [931.21] | $^1$H NMR (400 MHz, DMSO-d$_6$) δ: 10.99 (s, 1H), 8.79 (s, 1H), 8.04 (s, 1H), 8.01-7.92 (m, 2H), 7.77-7.66 (m, 2H), 7.47-7.40 (m, 1H), 7.37-7.28 (m, 1H), 7.01 (s, 1H), 5.59-5.16 (m, 1H), 5.11 (dd, J = 5.2, 13.2 Hz, 1H), 4.62-4.49 (m, 3H), 4.44-4.33 (m, 1H), 3.74-3.56 (m, 4H), 3.31 (s, 6H), 3.27-3.05 (m, 4H), 2.99-2.85 (m, 1H), 2.68 (d, J = 4.8 Hz, 3H), 2.64-2.55 (m, 2H), 2.02-1.69 (m, 5H), 1.58 (d, J = 6.8 Hz, 6H), 1.54-1.46 (m, 4H), 1.45-1.34 (m, 4H) | A | B |
| 97 | 911.43 | 911.19 [913.19] | $^1$H NMR (400 MHz, DMSO-d$_6$) δ: 11.12 (s, 1H), 8.85 (s, 1H), 8.06 (s, 1H), 8.02-7.90 (m, 2H), 7.87-7.82 (m, 1H), 7.81-7.75 (m, 2H), 7.71 (m, 2H), 7.03 (s, 1H), 5.56-5.18 (m, 1H), 5.17-5.10 (m, 1H), 4.55 (s, 2H), 4.29-4.16 (m, 2H), 3.47 (s, 2H), 3.31 (s, 1H), 3.24-3.13 (m, 2H), 2.95-2.84 (m, 4H), 2.80 (br d, J = 10.0 Hz, 2H), 2.73-2.66 (m, 4H), 2.65-2.53 (m, 4H), 2.11-2.01 (m, 1H), 1.92-1.75 (m, 6H), 1.74-1.61 (m, 3H), 1.58 (d, J = 7.2 Hz, 6H) | A | B |
| 98 | 866.42 | 866.18 [868.18] | | A | C |
| 99 | 883.42 | 883.18 [885.18] | | A | B |
| 100 | 919.40 | 919.16 [921.16] | | A | B |
| 101 | 931.44 | 931.17 [933.17] | | A | B |
| 102 | 901.41 | 901.17 [903.17] | | A | B |
| 103 | 910.47 | 910.20 [912.20] | $^1$H NMR (400 MHz, DMSO-d$_6$, ppm) δ: 10.95 (s, 1H), 8.85 (s, 1H), 8.05 (s, 1H), 7.96 (s, 2H), 7.70 (s, 2H), 7.02 (d, J = 9.6 Hz, 2H), 6.92 (s, 1H), 5.56-5.52 (m, 1H), 5.02 (dd, J = 5.2, 13.2 Hz, 1H), 4.55 (s, 2H), 4.37-4.29 (m, 1H), 4.25-4.08 (m, 4H), 3.90-3.84 (m, 3H), 3.59-3.40 (m, 1H), 3.29-3.16 (m, 2H), 3.07 (br d, J = 8.8 Hz, 2H), 3.01-2.84 (m, 2H), 2.71-2.53 (m, 4H), 2.48-2.35 (m, 1H), 2.33-2.32 (m, 1H), 2.23-2.10 (m, 2H), 2.04 (br s, 2H), 2.00-1.89 (m, 2H), 1.89-1.68 (m, 7H), 1.58 (d, J = 6.8 Hz, 6H), 1.45-1.37 (m, 2H). | A | B |
| 104 | 853.42 | 853.21 [855.21] | $^1$H NMR (400 MHz, DMSO-d$_6$, ppm): δ 10.97 (s, 1H), 8.80 (s, 1H), 8.05 (s, 1H), 7.96 (d, J = 8.7 Hz, 2H), 7.77-7.68 (m, 2H), 7.44 (d, J = 7.6 Hz, 1H), 7.29 (d, J = 7.4 Hz, 1H), 7.14 (d, J = 8.0 Hz, 1H), 7.05 (s, 1H), 5.12 (d, J = 13.2 Hz, 1H), 4.55 (s, 2H), 4.44 (d, J = 17.4 Hz, 1H), 4.29 (d, J = 17.4 Hz, 1H), 3.45 (d, J = 12.6 Hz, 4H), 3.31 (s, 2H), 2.94-2.85 (m, 1H), 2.77-2.63 (m, 6H), 2.61 (s, 4H), 2.55 (s, 2H), 1.99 (d, J = 12.4 Hz, 1H), 1.78 (d, J = 11.8 Hz, 2H), 1.62 (s, 1H), 1.57 (d, J = 6.9 Hz, 6H), 1.38 (d, J = 12.9 Hz, 2H), 0.92 (s, 6H). | A | B |
| 105 | 843.36 | 843.17 [845.17] | $^1$H NMR (400 MHz, DMSO-d$_6$, ppm): δ 10.98 (s, 1H), 8.84 (s, 1H), 8.06 (s, 1H), 7.98-7.91 (m, 2H), 7.70 (d, J = 2.2 Hz, 2H), 7.04 (s, 1H), 6.99 (d, J = 7.2 Hz, 1H), 6.94 (d, J = 12.2 Hz, 1H), 5.11 (d, J = 13.2, 1H), 4.55 (s, 2H), 4.43 (d, J = 17.4 Hz, 1H), 4.29 (d, J = 17.2 Hz, 1H), 3.65 (s, 4H), 3.45 (d, J = 11.4 Hz, 2H), 2.91 (s, 1H), 2.77 (d, J = 10.8, 2H), 2.67 (d, J = 4.6 Hz, 3H), 2.59-2.47 (m, 2H), 2.41 (s, 5H), 2.21 (d, J = 6.8 Hz, 2H), 1.99 (d, J = 12.6 Hz, 1H), 1.83-1.77 (m, 3H), 1.57 (d, J = 6.8 Hz, 6H), 1.25 (d, J = 13.2 Hz, 2H). | A | B |
| 106 | 901.41 | 901.19 [903.19] | | A | B |
| 107 | 923.47 | 923.19 [925.19] | $^1$H NMR (400 MHz, DMSO-d$_6$, ppm) δ: 11.06 (s, 1H), 8.82 (s, 1H), 8.5 (s, 1H), 7.96 (s, 2H), 7.73-7.67 (m, 2H), 7.67-7.62 (m, 1H), 7.03 (s, 1H), 6.79 (d, J = 2.0 Hz, 1H), 6.71-6.59 (m, 1H), 5.64-5.17 (m, 1H), 5.06 (dd, J = 5.2, 12.4 Hz, 1H), 4.55 (br s, 2H), 4.15-4.02 (m, 4H), 3.93-3.76 (m, 3H), 3.74-3.59 (m, 1H), 3.30 (s, 3H), 2.95-2.81 (m, 1H), 2.69-2.67 (m, 3H), 2.64-2.58 (m, 2H), 2.16 (br s, 3H), 2.04-1.94 (m, 3H), 1.86-1.78 (m, 2H), 1.68-1.61 (m, 2H), 1.61-1.55 (m, 6H), 1.41-1.14 (m, 7H) | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 108 | 923.47 | 923.20 [925.19] | $^{1}$H NMR (400 MHz, DMSO-$d_6$) ppm δ: 11.06 (s, 1H), 8.81 (s, 1H), 8.03 (s, 1H), 7.94 (br s, 2H), 7.69 (br s, 2H), 7.62-7.44 (m, 1H), 7.11 (d, J = 6.8 Hz, 1H), 7.02 (s, 1H), 6.80 (d, J = 8.8 Hz, 1H), 5.54-5.14 (m, 1H), 5.09-4.99 (m, 1H), 4.54 (br s, 2H), 4.35-4.20 (m, 2H), 4.15-4.02 (m, 2H), 3.98-3.84 (m, 2H), 3.79-3.59 (m, 2H), 3.29 (s, 3H), 2.94-2.76 (m, 1H), 2.68-2.66 (m, 3H), 2.63-2.56 (m, 2H), 2.13 (s, 3H), 2.02-1.93 (m, 3H), 1.86-1.76 (m, 2H), 1.68-1.60 (m, 2H), 1.59-1.54 (m, 6H), 1.40-1.16 (m, 7H) | A | B |
| 109 | 929.47 | 929.20 [931.20] | $^{1}$H NMR (400 MHz, DMSO-$d_6$) δ: 10.98 (s, 1H), 8.78 (s, 1H), 8.03 (s, 1H), 7.98-7.92 (m, 2H), 7.75-7.65 (m, 2H), 7.04-6.97 (m, 3H), 5.67-5.24 (m, 1H), 5.12 (dd, J = 13.2, 5.2 Hz, 1H), 4.54 (s, 2H), 4.47-4.37 (m, 1H), 4.32-4.22 (m, 1H), 3.67-3.60 (m, 4H), 3.30-3.20 (m, 3H), 3.07-2.80 (m, 4H), 2.67 (d, J = 4.8 Hz, 3H), 2.63-2.55 (m, 2H), 2.47-2.40 (m, 2H), 2.05-1.90 (m, 3H), 1.89-1.70 (m, 3H), 1.57 (d, J = 6.8 Hz, 6H), 1.50-1.40 (m, 9H). | A | B |
| 110 | 922.48 | 922.20 [924.20] | $^{1}$H NMR (400 MHz, DMSO-$d_6$) δ: 11.10 (s, 1H), 8.81 (s, 1H), 8.02 (s, 1H), 7.94 (br s, 2H), 7.88-7.80 (m, 1H), 7.78-7.71 (m, 2H), 7.67 (s, 2H), 7.00 (s, 1H), 5.62-5.17 (m, 1H), 5.12 (dd, J = 5.3, 13.1 Hz, 1H), 4.52 (s, 2H), 4.19-3.90 (m, 2H), 3.75-3.49 (m, 2H), 3.12-2.78 (m, 3H), 2.65 (d, J = 4.4 Hz, 4H), 2.62-2.51 (m, 2H), 2.27-2.14 (m, 2H), 2.08-1.98 (m, 2H), 1.95 (br s, 8H), 1.71-1.59 (m, 3H), 1.55 (d, J = 6.8 Hz, 8H), 1.46-1.31 (m, 5H) | D | A |
| 111 | 897.41 | 897.16 [899.16] | $^{1}$H NMR (400 MHz, DMSO-$d_6$, ppm) 11.05 (s, 1H), 8.90 (s, 1H), 8.06 (s, 1H), 7.93-7.92 (m, 1H), 7.76-7.72 (m, 2H), 7.63-7.61 (m, 1H), 6.99-6.98 (m, 1H), 6.78-6.77 (m, 1H), 6.65-6.63 (m, 1H), 5.06-5.02 (m, 2H), 4.55-4.53 (m, 2H), 4.51-4.48 (m, 2H), 3.74 (s, 4H), 2.91-2.84 (m, 3H), 2.67-2.60 (m, 3H), 2.55-2.50 (m, 2H), 2.50-2.34 (m, 4H), 2.33-2.32 (m, 2H), 2.12-2.10 (m, 1H), 1.76-1.57 (m, 7H), 1.57-1.56 (m, 6H), 1.04-1.01 (m, 2H). | A | B |
| 112 | 883.45 | 883.21 [885.21] | $^{1}$H NMR (400 MHz, DMSO-$d_6$, ppm) δ 10.94 (s, 1H), 8.80 (s, 1H), 8.05 (s, 1H), 7.98-7.91 (m, 2H), 7.71 (m, 2H), 7.16 (s, 1H), 7.06 (m, 2H), 5.07 (m, 1H), 4.55 (s, 2H), 4.30 (m, 1H), 4.18 (m, 1H), 3.85 (s, 3H), 3.61-3.55 (m, 6H), 2.90 (m, 1H), 2.66 (m, 4H), 2.55 (s, 6H), 2.40 (s, 1H), 1.97 (s, 1H), 1.80-1.72 (m, 3H), 1.57 (m, 7H), 1.40 (m, 2H), 1.24 (s, 1H), 0.92 (s, 5H). | A | B |
| 113 | 843.36 | 843.16 [845.16] | $^{1}$H NMR (400 MHz, DMSO-$d_6$, ppm) 10.93 (s, 1H), 8.84 (s, 1H), 8.05 (s, 1H), 7.94-7.89 (m, 2H), 7.70-7.67 (m, 2H), 7.53-7.51 (m, 1H), 7.08-7.05 (m, 3H), 5.06-5.02 (m, 1H), 4.53 (s, 2H), 4.34-4.30 (m, 1H), 4.22-4.18 (m, 1H), 3.64-3.33 (m, 5H), 3.18-3.13 (m, 2H), 2.90-2.89 (m, 1H), 2.66-2.60 (m, 3H), 2.53-2.50 (m, 2H), 2.50-2.34 (m, 7H), 2.33-2.32 (m, 1H), 1.97-1.94 (m, 3H), 1.81-1.73 (m, 2H), 1.57-1.55 (m, 6H). | A | B |
| 114 | 843.36 | 843.16 [845.16] | $^{1}$H NMR (400 MHz, DMSO-$d_6$, ppm) 10.97 (s, 1H), 8.84 (s, 1H), 8.05 (s, 1H), 7.94-7.89 (m, 2H), 7.72-7.70 (m, 2H), 7.43-7.42 (m, 1H), 7.32-7.31 (m, 1H), 7.22-7.20 (m, 1H), 7.05 (s, 1H), 5.11-5.10 (m, 1H), 4.53 (s, 2H), 4.47-4.43 (m, 1H), 4.32-4.28 (m, 1H), 3.64-3.63 (m, 4H), 3.31-3.30 (m, 2H), 2.97-2.89 (m, 3H), 2.67-2.62 (m, 5H), 2.55-2.50 (m, 7H), 2.03-1.98 (m, 3H), 1.97-1.94 (m, 2H), 1.57-1.55 (m, 6H). | A | B |
| 115 | 895.46 | 895.21 [897.20] | $^{1}$H NMR (300 MHz, DMSO-$d_6$, ppm): δ 10.91 (s, 1H), 8.82 (s, 1H), 8.04-7.95 (m, 3H), 7.70 (s, 2H), 7.02 (s, 1H), 6.60 (s, 1H), 6.47 (s, 1H), 4.96 (d, J = 13.1 Hz, 1H), 4.55-4.46 (m, 4H), 4.22-4.09 (m, 2H), 3.83 (s, 3H), 3.28 (s, 6H), 2.86-2.50 (m, 9H), 2.60 (s, 2H), 2.38 (s, 3H), 1.91 (d, J = 11.6 Hz, 1H), 1.76 (s, 6H), 1.57 (d, J = 6.8 Hz, 7H), 1.24 (s, 1H). | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 116 | 916.42 | 916.17 [918.17] | $^1$H NMR (400 MHz, DMSO-d$_6$) δ: 11.02 (s, 1H), 8.83 (s, 1H), 8.04 (s, 1H), 8.00-7.91 (m, 2H), 7.70 (s, 2H), 7.45 (d, J = 8.8 Hz, 1H), 7.03 (s, 1H), 5.72-5.17 (m, 1H), 5.12 (dd, J = 5.2, 13.6 Hz, 1H), 4.61-4.48 (m, 3H), 4.43-4.32 (m, 1H), 4.26-4.01 (m, 3H), 3.60-3.48 (m, 1H), 3.28-3.18 (m, 2H), 3.07-2.76 (m, 5H), 2.70-2.67 (m, 3H), 2.64-2.56 (m, 1H), 2.45-2.38 (m, 1H), 2.21-2.11 (m, 2H), 2.08-1.93 (m, 5H), 1.88-1.66 (m, 6H), 1.58 (d, J = 7.2 Hz, 6H), 1.44-1.32 (m, 2H) | A | B |
| 117 | 922.48 | 922.20 [924.20] | $^1$H NMR (400 MHz, DMSO-d$_6$) δ: 11.11 (s, 1H), 8.82 (s, 1H), 8.03 (s, 1H), 7.97-7.92 (m, 2H), 7.88-7.80 (m, 1H), 7.78-7.73 (m, 2H), 7.68 (s, 2H), 7.01 (s, 1H), 5.47-5.16 (m, 1H), 5.15-5.08 (m, 1H), 4.54 (s, 2H), 4.27-3.97 (m, 2H), 3.65 (br d, J = 3.2 Hz, 1H), 3.23 (br s, 1H), 2.99-2.80 (m, 3H), 2.76-2.57 (m, 5H), 2.35-2.22 (m, 4H), 2.15-1.91 (m, 4H), 1.79 (br d, J = 6.4 Hz, 6H), 1.71-1.61 (m, 2H), 1.56 (d, J = 6.8 Hz, 6H), 1.43-1.08 (m, 7H) | A | B |
| 118 | 912.42 | 912.16 [914.16] | $^1$H NMR (400 MHz, DMSO-d$_6$) δ: 11.29 (s, 1H), 8.84 (s, 1H), 8.06 (s, 1H), 7.98-7.92 (m, 2H), 7.91-7.88 (m, 1H), 7.87-7.83 (m, 2H), 7.72-7.62 (m, 2H), 7.02 (s, 1H), 5.60-5.10 (m, 2H), 5.00-4.70 (m, 1H) 4.54 (s, 2H), 4.22-4.05 (m, 3H), 3.60-3.45 (m, 1H), 3.25-3.20 (m, 1H), 3.05-2.80 (m, 4H), 2.67 (d, J = 4.8 Hz, 3H), 2.64-2.56 (m, 2H), 2.25-2.13 (m, 2H), 2.10-1.96 (m, 4H), 1.92-1.69 (m, 7H), 1.57 (d, J = 6.8 Hz, 6H), 1.42-1.31 (m, 2H). | B | B |
| 119 | 855.39 | 855.25 [857.25] | | A | B |
| 120 | 843.36 | 843.24 [845.24] | $^1$H NMR (400 MHz, DMSO-d$_6$, ppm) δ 10.98 (s, 1H), 8.83 (s, 1H), 8.05 (s, 1H), 7.95 (m, 2H), 7.70 (m, 2H), 7.19 (m, 2H), 7.04 (s, 1H), 5.33 (s, 1H), 5.08 (m, 1H), 4.55 (s, 2H), 4.41 (m, 1H), 4.33-4.21 (m, 1H), 3.64 (s, 4H), 3.25 (s, 2H), 2.98-2.84 (m, 1H), 2.67-2.62 (m, 6H), 2.48-2.36 (m, 5H), 2.20 (m, 2H), 2.00 (m, 1H), 1.82 (m, 2H), 1.71 (s, 1H), 1.57 (m, 6H), 1.29-1.24 (m, 2H). | A | B |
| 121 | 855.39 | 855.26 [857.25] | | A | B |
| 122 | 883.42 | 883.26 [885.26] | | A | B |
| 123 | 884.41 | 884.31 [886.30] | | A | A |
| 124 | 915.40 | 915.29 [917.29] | | A | B |
| 125 | 901.41 | 901.31 [903.31] | | A | B |
| 126 | 931.40 | 931.28 [933.28] | | A | C |
| 127 | 887.34 | 887.26 [889.26] | | A | C |
| 128 | 928.46 | 928.33 [930.33] | $^1$H NMR (400 MHz, DMSO-d$_6$) δ: 11.01 (s, 1H), 8.84 (s, 1H), 8.25 (s, 1H), 8.05 (s, 1H), 8.00-7.89 (m, 2H), 7.70 (s, 2H), 7.21 (br d, J = 10.4 Hz, 1H), 7.03 (s, 1H), 5.33 (br s, 1H), 5.07 (br dd, J = 4.8, 13.2 Hz, 1H), 4.64-4.51 (m, 3H), 4.42 (br d, J = 17.6 Hz, 1H), 4.23-4.06 (m, 3H), 3.84 (s, 3H), 3.54 (br s, 1H), 3.29-3.24 (m, 1H), 3.04-2.80 (m, 6H), 2.69 (d, J = 4.8 Hz, 3H), 2.62 (br s, 2H), 2.40 (br s, 1H), 2.21-2.10 (m, 2H), 2.01 (br d, J = 7.2 Hz, 3H), 1.89-1.77 (m, 3H), 1.73-1.65 (m, 4H), 1.58 (d, J = 6.8 Hz, 6H), 1.46-1.36 (m, 2H). | A | B |
| 129 | 929.47 | 929.34 [931.34] | $^1$H NMR (400 MHz, DMSO-d$_6$) δ: 11.01 (s, 1H), 8.80 (s, 1H), 8.04 (s, 1H), 8.01-7.93 (m, 2H), 7.71 (br s, 2H), 7.32-7.15 (m, 2H), 7.01 (s, 1H), 5.64-5.16 (m, 1H), 5.10 (dd, J = 5.6, 13.2 Hz, 1H), 4.55 (s, 2H), 4.49-4.38 (m, 1H), 4.35-4.24 (m, 1H), 3.64 (br s, 4H), 3.31 (s, 6H), 3.09 (br dd, J = 4.0, 18.4 Hz, 2H), 3.01-2.85 (m, 3H), 2.68 (d, J = 4.8 Hz, 3H), 2.64-2.55 (m, 2H), 2.02-1.72 (m, 5H), 1.58 (d, J = 6.8 Hz, 6H), 1.49 (br s, 4H), 1.43 (br s, 4H) | A | B |
| 130 | 929.47 | 929.34 [931.34] | $^1$H NMR (400 MHz, DMSO-d$_6$) δ: 11.00 (s, 1H), 8.80 (s, 1H), 8.04 (s, 1H), 8.01-7.91 (m, 2H), 7.78-7.66 (m, 2H), 7.34 (t, J = 8.8 Hz, 1H), 7.05-6.94 (m, 2H), 5.74-5.09 (m, 1H), 5.04 (dd, J = 5.2, 13.2 Hz, 1H), 4.55 (s, 2H), 4.50-4.37 (m, 1H), 4.30 (d, J = 17.6 Hz, 1H), | D | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 131 | 898.43 | 898.32 [900.32] | ¹H NMR (400 MHz, DMSO-d₆) δ: 10.98 (s, 1H), 8.04 (s, 1H), 7.98-7.92 (m, 2H), 7.71-7.62 (m, 3H), 7.60-7.54 (m, 1H), 7.50-7.42 (m, 1H), 7.02 (s, 1H), 5.57-5.25 (m, 1H), 5.15-5.05 (m, 1H), 4.88-4.65 (m, 1H), 4.54 (s, 2H), 4.48-4.40 (m, 1H), 4.35-4.25 (m, 1H), 4.22-4.07 (m, 3H), 3.58-3.50 (m, 1H), 3.26-3.18 (m, 1H), 3.00-2.80 (s, 4H), 2.67 (d, J = 4.8 Hz, 3H), 2.63-2.53 (m, 1H), 2.45-2.30 (m, 3H), 2.25-2.15 (m, 2H), 2.05-1.95 (m, 3H), 1.90-1.80 (m, 5H), 1.77-1.67 (m, 1H), 1.57 (d, J = 6.8 Hz, 6H), 1.45-1.31 (m, 2H). Preceding: 3.65 (br s, 4H), 3.44-3.35 (m, 2H), 3.31 (s, 6H), 3.03-2.80 (m, 3H), 2.71-2.67 (m, 3H), 2.64-2.56 (m, 2H), 2.04-1.81 (m, 5H), 1.58 (d, J = 7.2 Hz, 6H), 1.50 (br s, 4H), 1.43 (br s, 4H) | A | B |
| 132 | 898.43 | 898.32 [900.32] | ¹H NMR (400 MHz, DMSO-d₆) δ: 11.05 (s, 1H), 8.81 (s, 1H), 8.23 (s, 1H), 8.04 (s, 1H), 7.98-7.92 (m, 2H), 7.71-7.66 (m, 2H), 7.65-7.45 (m, 3H), 7.03 (s, 1H), 5.57-5.25 (m, 1H), 5.15-5.05 (m, 1H), 4.88-4.65 (m, 1H), 4.54 (s, 2H), 4.48-4.40 (m, 1H), 4.35-4.25 (m, 1H), 4.22-4.07 (m, 3H), 3.58-3.50 (m, 1H), 3.26-3.18 (m, 1H), 3.00-2.80 (s, 4H), 2.67 (d, J = 4.8 Hz, 3H), 2.63-2.53 (m, 1H), 2.45-2.30 (m, 3H), 2.25-2.15 (m, 2H), 2.05-1.95 (m, 3H), 1.90-1.80 (m, 5H), 1.77-1.67 (m, 1H), 1.57 (d, J = 6.8 Hz, 6H), 1.45-1.31 (m, 2H). | A | B |
| 133 | 907.47 | | | A | B |
| 134 | 897.41 | | | A | C |
| 135 | 915.40 | | | A | B |
| 136 | 901.41 | | | A | B |
| 137 | 930.41 | | ¹H NMR (400 MHz, DMSO-d₆) δ: 11.12 (s, 1H), 8.84 (s, 1H), 8.04 (s, 1H), 7.98-7.92 (m, 3H), 7.86-7.80 (m, 2H), 7.69 (s, 2H), 7.02 (s, 1H), 5.70-5.23 (m, 1H), 5.20-5.10 (m, 1H), 4.54 (s, 2H), 4.25-4.05 (m, 3H), 3.60-3.40 (m, 2H), 3.25-3.14 (m, 3H), 3.07-2.97 (m, 2H), 2.95-2.82 (m, 1H), 2.67 (d, J = 4.8 Hz, 3H), 2.64-2.56 (m, 1H), 2.28-2.09 (m, 5H), 2.08-1.96 (m, 4H), 1.91-1.77 (m, 3H), 1.57 (d, J = 6.8 Hz, 6H), 1.45-1.31 (m, 2H). | D | A |
| 138 | 897.41 | 897.8 | ¹H NMR (400 MHz, DMSO-d₆) δ: 11.07 (s, 1H), 8.79 (s, 1H), 8.17 (s, 1H), 8.02 (s, 1H), 7.97-7.89 (m, 2H), 7.74-7.65 (m, 2H), 7.00 (s, 1H), 6.95 (br d, J = 6.4 Hz, 1H), 6.88-6.81 (m, 1H), 5.51-5.14 (m, 1H), 5.13-4.96 (m, 1H), 4.58-4.43 (m, 4H), 3.59-3.45 (m, 4H), 2.94-2.75 (m, 3H), 2.65 (d, J = 4.4 Hz, 3H), 2.61-2.52 (m, 4H), 2.46-2.42 (m, 2H), 2.27 (br d, J = 6.4 Hz, 2H), 2.06-1.86 (m, 3H), 1.81-1.67 (m, 5H), 1.56 (d, J = 7.2 Hz, 6H), 1.10-0.92 (m, 1H). | A | B |
| 139 | 897.41 | | ¹H NMR (400 MHz, DMSO-d₆) δ: 11.08 (s, 1H), 8.79 (s, 1H), 8.19 (s, 1H), 8.02 (s, 1H), 7.98-7.88 (m, 2H), 7.75-7.64 (m, 2H), 7.44 (dd, J = 7.6, 15.2 Hz, 1H), 7.17 (dd, J = 3.6, 7.6 Hz, 1H), 7.00 (s, 1H), 5.29 (br s, 1H), 5.06 (dd, J = 5.6, 12.8 Hz, 1H), 4.62-4.39 (m, 4H), 3.76 (br s, 2H), 3.68-3.55 (m, 2H), 2.94-2.76 (m, 3H), 2.68-2.63 (m, 3H), 2.61-2.53 (m, 4H), 2.47-2.43 (m, 2H), 2.28 (br d, J = 6.4 Hz, 2H), 2.06-1.96 (m, 1H), 1.95-1.82 (m, 2H), 1.80-1.63 (m, 5H), 1.56 (d, J = 7.2 Hz, 6H), 1.10-0.94 (m, 1H). | A | B |
| 140 | 880.40 | 880.3 | ¹H NMR (400 MHz, DMSO-d₆) δ: 11.10 (s, 1H), 8.84 (s, 1H), 8.04 (s, 1H), 8.00-7.97 (m, 1H), 7.96-7.94 (m, 1H), 7.85-7.77 (m, 2H), 7.76-7.70 (m, 2H), 7.52 (d, J = 9.2 Hz, 1H), 7.09 (s, 1H), 5.12 (dd, J = 12.8, 5.2 Hz, 1H), 4.57 (s, 2H), 4.32 (q, J = 6.8 Hz, 2H), 4.21-4.06 (m, 3H), 3.65-3.47 (m, 2H), 3.27-3.17 (m, 2H), 3.05-2.97 (m, 2H), 2.91-2.77 (m, 2H), 2.67 (d, J = 4.8 Hz, 3H), 2.63-2.53 (m, 2H), 2.19-2.11 (m, 2H), 2.07-1.92 (m, 3H), 1.85-1.69 (m, 8H), 1.43-1.30 (m, 2H), 1.24 (t, J = 7.2 Hz, 3H). | C | A |
| 141 | 800.27 | 800.3 | ¹H NMR (400 MHz, DMSO-d₆, ppm) δ 11.10 (s, 1H), 8.85 (s, 1H), 8.04 (s, 1H), 7.94 (s, 2H), 7.76 (d, J = 10.0, 5.2 Hz, 2H), 7.45 | D | |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | (s, 3H), 7.12 (s, 1H), 5.07 (s, 1H), 4.51 (s, 3H), 4.38 (s, 3H), 4.15 (s, 1H), 4.06 (s, 1H), 3.30 (s, 2H), 3.02-2.88 (m, 2H), 2.88-2.80 (m, 1H), 2.66 (d, J = 4.6 Hz, 4H), 2.58 (s, 2H), 2.29 (s, 5H), 2.00 (s, 3H), 1.73 (s, 1H), 1.48 (s, 2H). | | |
| 142 | 881.39 | 881.5 | $^1$H NMR (400 MHz, DMSO-$d_6$, ppm) δ: 11.09 (s, 1H), 8.98 (br s, 1H), 8.12 (br d, J = 6.4 Hz, 1H), 7.98 (br d, J = 4.0 Hz, 2H), 7.73-7.60 (m, 3H), 7.41-6.96 (m, 3H), 5.99-5.13 (m, 1H), 5.10-4.98 (m, 1H), 4.53 (s, 2H), 4.32-3.80 (m, 1H), 3.76-3.47 (m, 6H), 3.24-3.09 (m, 1H), 3.02-2.76 (m, 4H), 2.66 (d, J = 4.8 Hz, 3H), 2.63-2.55 (m, 3H), 2.07-1.93 (m, 1H), 1.78-1.61 (m, 2H), 1.57 (br d, J = 6.8 Hz, 6H), 1.33-0.98 (m, 2H) | D | |
| 143 | 881.39 | 881.3 | $^1$H NMR (400 MHz, DMSO-$d_6$, ppm) δ: 11.10 (s, 1H), 8.99 (s, 1H), 8.18-8.08 (m, 1H), 8.03 (br d, J = 4.0 Hz, 2H), 7.76-7.62 (m, 3H), 7.39-7.30 (m, 2H), 7.14 (br s, 1H), 5.32 (br s, 1H), 5.09 (dd, J = 5.6, 12.8 Hz, 1H), 4.54 (s, 2H), 3.88 (br s, 2H), 3.74-3.58 (m, 6H), 3.34-3.18 (m, 5H), 3.00-2.73 (m, 4H), 2.67 (d, J = 4.8 Hz, 3H), 2.62 (br s, 1H), 2.58 (br s, 2H), 2.50-2.45 (m, 1H), 2.09-1.95 (m, 1H), 1.57 (d, J = 6.8 Hz, 8H), 1.33 (br d, J = 2.0 Hz, 2H) | D | |
| 144 | 895.42 | 896.3 | $^1$H NMR (400 MHz, DMSO-$d_6$, ppm) δ: 11.09 (br s, 1H), 8.93 (s, 1H), 8.09 (s, 1H), 8.05-7.97 (m, 1H), 7.76-7.63 (m, 3H), 7.32 (d, J = 7.2 Hz, 1H), 7.29-7.10 (m, 2H), 5.33 (s, 1H), 5.08 (dd, J = 5.6, 12.8 Hz, 1H), 4.51 (s, 2H), 3.85 (br s, 2H), 3.70-3.54 (m, 6H), 3.36-3.27 (m, 5H), 2.96-2.81 (m, 1H), 2.76 (br d, J = 7.2 Hz, 2H), 2.68 (d, J = 4.4 Hz, 4H), 2.64-2.56 (m, 2H), 2.46 (br s, 1H), 2.03 (br dd, J = 4.8, 10.4 Hz, 1H), 1.72-1.62 (m, 1H), 1.55 (br d, J = 6.8 Hz, 6H), 1.46-1.21 (m, 6H) | D | A |
| 145 | 895.42 | 895.5 | $^1$H NMR (400 MHz, DMSO-$d_6$, ppm) δ: 11.10 (s, 1H), 8.94 (s, 1H), 8.22 (s, 1H), 8.11 (s, 2H), 7.97 (br d, J = 4.4 Hz, 1H), 7.77-7.62 (m, 3H), 7.30-7.15 (m, 3H), 5.62-5.14 (m, 1H), 5.13-5.02 (m, 1H), 4.54 (s, 2H), 4.06-3.91 (m, 2H), 3.87 (br s, 2H), 3.70-3.56 (m, 5H), 3.34 (br s, 2H), 2.98-2.84 (m, 2H), 2.83-2.74 (m, 3H), 2.73-2.68 (m, 3H), 2.66-2.59 (m, 1H), 2.49-2.43 (m, 2H), 2.13-2.00 (m, 1H), 1.74-1.63 (m, 2H), 1.61-1.49 (m, 7H), 1.27-1.04 (m, 4H) | A | |
| 146 | 660.04 | | | A | |
| 147 | 674.07 | | | A | |
| 148 | 908.45 | 908.2 | $^1$H NMR (400 MHz, DMSO-$d_6$, ppm) δ: 11.13 (s, 1H), 8.84 (s, 1H), 8.04 (s, 1H), 8.01-7.91 (m, 2H), 7.87-7.73 (m, 3H), 7.69 (s, 2H), 7.02 (s, 1H), 5.64-5.19 (m, 1H), 5.18-5.06 (m, 1H), 4.55 (s, 2H), 4.19-4.00 (m, 3H), 3.58 (s, 2H), 3.28-3.20 (m, 2H), 3.05 (s, 2H), 2.95-2.81 (m, 1H), 2.68 (d, J = 4.4 Hz, 3H), 2.60-2.54 (m, 2H), 2.27-2.13 (m, 1H), 2.11-1.94 (m, 4H), 1.93-1.60 (m, 10H), 1.57 (d, J = 6.8 Hz, 6H), 1.43-1.30 (m, 3H) | C | C |
| 149 | 726.10 | | | | |
| 150 | 878.43 | 878.37 | $^1$H NMR (400 MHz, DMSO-$d_6$, ppm) δ 11.11 (s, 1H), 8.79 (s, 1H), 8.03 (s, 1H), 7.95 (dd, J = 10.0, 3.5 Hz, 2H), 7.84 (d, J = 7.7 Hz, 1H), 7.80-7.65 (m, 4H), 7.02 (s, 1H), 5.32 (s, 1H), 4.52 (d, J = 13.7 Hz, 4H), 3.70 (t, J = 9.0 Hz, 1H), 3.2-3.3 (s, 2H), 2.85 (t, J = 15.9 Hz, 3H), 2.67 (d, J = 4.6 Hz, 5H), 2.65-2.52 (m, 1H), 2.32-2.23 (m, 3H), 2.17 (s, 2H), 2.10-2.01 (m, 2H), 1.87 (t, J = 10.4 Hz, 2H), 1.73 (s, 4H), 1.57 (d, J = 6.9 Hz, 9H), 1.02 (d, J = 12.5 Hz, 2H). | B | B |
| 151 | 929.47 | 929.2 | $^1$H NMR (400 MHz, DMSO-$d_6$, ppm) δ: 10.98 (s, 1H), 8.85 (s, 1H), 8.07 (s, 1H), 8.01-7.93 (m, 2H), 7.71 (s, 2H), 7.42-7.36 (m, 1H), 7.30 (br d, J = 12.4 Hz, 1H), 7.04 (s, 1H), 5.33 (s, 1H), 5.09 (dd, J = 5.2, 13.2 Hz, 1H), 4.60-4.52 (m, 3H), 4.40 (d, J = 17.6 Hz, 1H), 4.22 (br s, 2H), 3.30 (br s, 4H), 3.22 (br s, 2H), 3.08 (br s, 4H), 2.97-2.84 (m, 1H), 2.68 (d, J = 4.4 Hz, | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | 3H), 2.63-2.55 (m, 2H), 2.46-2.42 (m, 2H), 2.00 (br s, 1H), 1.86 (br s, 2H), 1.58 (d, J = 6.8 Hz, 6H), 1.55-1.45 (m, 8H), 1.24 (br s, 2H) | | |
| 152 | 929.47 | 929.21 [931.21] | $^1$H NMR (400 MHz, DMSO-d$_6$, ppm) δ: 10.98 (s, 1H), 8.79 (s, 1H), 8.04 (s, 1H), 8.00-7.94 (m, 2H), 7.76-7.68 (m, 2H), 7.41-7.32 (m, 1H), 7.16-7.08 (m, 1H), 7.01 (s, 1H), 5.55-5.10 (m, 1H), 5.05 (dd, J = 3.6, 14.0 Hz, 1H), 4.45 (s, 2H), 4.38-4.17 (m, 2H), 3.69-3.62 (m, 4H), 3.31 (br s, 6H), 2.97-2.81 (m, 1H), 2.69-2.66 (m, 5H), 2.64-2.58 (m, 4H), 2.02-1.85 (m, 5H), 1.60-1.56 (m, 6H), 1.53-1.48 (m, 4H), 1.46-1.41 (m, 4H) | B | |
| 153 | 894.43 | 894.17 [896.16] | $^1$H NMR (400 MHz, DMSO-d$_6$) δ: 11.12 (s, 1H), 8.83 (s, 1H), 8.17 (s, 1H), 8.04 (s, 1H), 7.95 (s, 2H), 7.87-7.73 (m, 3H), 7.69 (s, 2H), 7.03 (s, 1H), 5.37-5.27 (m, 1H), 5.14 (dd, J = 5.2, 12.8 Hz, 2H), 4.55 (s, 2H), 4.16-4.04 (m, 2H), 3.88-3.81 (m, 1H), 3.55 (br s, 1H), 3.37-3.28 (m, 2H), 3.07-2.80 (m, 3H), 2.74-2.71 (m, 1H), 2.68 (d, J = 4.8 Hz, 3H), 2.64-2.56 (m, 3H), 2.47-2.39 (m, 2H), 2.33 (br s, 1H), 2.10-2.00 (m, 1H), 1.93-1.76 (m, 6H), 1.75-1.64 (m, 4H), 1.57 (d, J = 6.8 Hz, 6H), 1.38 (br d, J = 9.2 Hz, 2H). | C | C |
| 154 | 892.50 | 892.31 | | D | B |
| 155 | 837.34 | 837.21 [839.21] | $^1$H NMR (400 MHz, DMSO-d$_6$, ppm) δ: 11.07 (s, 1H), 8.89 (s, 1H), 8.07 (s, 1H), 8.01-7.92 (m, 2H), 7.69 (s, 2H), 7.63 (d, J = 8.4 Hz, 1H), 7.05 (s, 1H), 6.90 (s, 1H), 6.80 (br d, J = 7.6 Hz, 1H), 5.29 (br s, 1H), 5.05 (br dd, J = 5.2, 12.8 Hz, 1H), 4.54 (s, 2H), 3.69 (br d, J = 10.4 Hz, 4H), 3.44 (br d, J = 8.4 Hz, 4H), 2.96-2.78 (m, 2H), 2.76-2.60 (m, 7H), 2.54 (br s, 3H), 2.05-1.94 (m, 1H), 1.71 (br s, 2H), 1.56 (d, J = 6.8 Hz, 6H), 0.81 (br s, 1H). | A | C |
| 156 | 837.34 | 837.21 [839.21] | $^1$H NMR (400 MHz, DMSO-d$_6$, ppm) δ: 11.06 (s, 1H), 8.90 (s, 1H), 8.08 (s, 1H), 7.93 (br s, 2H), 7.69 (s, 2H), 7.57 (dd, J = 7.2, 8.4 Hz, 1H), 7.19-7.10 (m, 2H), 7.05 (s, 1H), 5.50-5.14 (m, 1H), 5.06 (dd, J = 5.6, 12.8 Hz, 1H), 4.53 (s, 2H), 4.12-3.99 (m, 2H), 3.70 (br s, 3H), 3.51 (br d, J = 6.8 Hz, 3H), 2.95-2.80 (m, 2H), 2.67 (br s, 7H), 2.57-2.51 (m, 3H), 2.07-1.94 (m, 1H), 1.65 (br s, 2H), 1.56 (d, J = 6.8 Hz, 6H), 0.85 (br s, 1H). | A | |
| 157 | 837.34 | 837.21 [839.21] | $^1$H NMR (400 MHz, DMSO-d$_6$, ppm) δ: 11.07 (s, 1H), 8.74 (s, 1H), 8.21 (s, 1H), 8.06 (d, J = 2.4 Hz, 1H), 8.02 (s, 1H), 7.96 (br d, J = 4.8 Hz, 1H), 7.84 (dd, J = 2.4, 9.2 Hz, 1H), 7.67 (dd, J = 9.2, 11.2 Hz, 2H), 7.32 (d, J= 1.6 Hz, 1H), 7.24 (dd, J = 2.0, 8.8 Hz, 1H), 7.09 (s, 1H), 5.32 (br s, 1H), 5.06 (dd, J = 5.6, 12.8 Hz, 1H), 4.55 (s, 2H), 3.73 (br d, J = 9.2 Hz, 3H), 3.52 (br s, 4H), 2.96 - 2.80 (m, 1H), 2.68 (d, J = 4.8 Hz, 3H), 2.62-2.51 (m, 7H), 2.32 (br d, J = 5.2 Hz, 2H), 2.08-1.95 (m, 1H), 1.65-1.45 (m, 8H), 0.75-0.63 (m, 1H). | B | C |
| 158 | 837.34 | 837.21 [839.21] | $^1$H NMR (400 MHz, DMSO-d$_6$, ppm) δ: 11.08 (s, 1H), 8.74 (s, 1H), 8.18 (s, 1H), 8.07-8.03 (m, 1H), 8.01 (s, 1H), 7.95 (br d, J = 4.4 Hz, 1H), 7.84 (br dd, J = 2.0, 9.2 Hz, 1H), 7.73-7.61 (m, 2H), 7.38-7.21 (m, 2H), 7.12-7.03 (m, 1H), 5.49-5.19 (m, 1H), 5.08 (br dd, J = 5.6, 12.8 Hz, 1H), 4.54 (s, 2H), 3.79-3.63 (m, 2H), 3.47 (br d, J = 5.6 Hz, 2H), 3.29-3.20 (m, 2H), 2.96-2.79 (m, 1H), 2.71-2.58 (m, 7H), 2.56 (br s, 4H), 2.39-2.27 (m, 2H), 2.07-1.94 (m, 1H), 1.64-1.47 (m, 8H), 0.76-0.63 (m, 1H). | B | C |
| 159 | 998.52 | | $^1$H NMR (400 MHz, DMSO-d$_6$) δ: 11.10 (s, 1H), 8.83 (s, 1H), 8.25 (s, 1H), 8.07 (s, 1H), 8.04-7.95 (m, 2H), 7.69 (s, 2H), 7.64 (s, 1H), 7.47 (s, 1H), 7.03 (s, 1H), 5.59-5.19 (m, 1H), 5.14 (dd, J = 5.2, 13.2 Hz, 1H), 5.00-4.92 (m, 1H), 4.55 (s, 2H), 4.18-4.13 (m, 3H), 3.55-3.43 (m, 1H), 3.26-3.23 (m, 2H), 3.02 (d, J = 10.4 Hz, 2H), 2.94-2.84 (m, 3H), 2.69 (d, | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | J = 8.4 Hz, 3H), 2.62-3.57 (m, 2H), 2.22-2.13 (m, 2H), 2.08-1.99 (m, 3H), 1.93-1.76 (m, 6H), 1.72-1.60 (m, 2H), 1.58 (d, J = 6.8 Hz, 6H), 1.42-1.37 (m, 2H), 1.58 (d, J = 6.0 Hz, 6H). | | |
| 160 | 924.44 | | ¹H NMR (400 MHz, DMSO-d₆) δ: 11.11 (s, 1H), 8.84 (s, 1H), 8.10-7.88 (m, 3H), 7.76-7.60 (m, 3H), 7.55-7.42 (m, 1H), 7.03 (s, 1H), 5.49-5.23 (m, 1H), 5.12 (br dd, J = 5.2, 12.8 Hz, 1H), 4.61-4.46 (m, 2H), 4.24-4.09 (m, 3H), 4.06-3.93 (m, 3H), 3.64-3.46 (m, 1H), 3.26-3.12 (m, 3H), 3.09-2.77 (m, 5H), 2.69 (d, J = 4.8 Hz, 3H), 2.64-2.56 (m, 2H), 2.25-1.95 (m, 5H), 1.89-1.64 (m, 7H), 1.58 (d, J = 6.8 Hz, 6H), 1.46-1.32 (m, 2H) | A | A |
| 161 | 883.41 | | ¹H NMR (400 MHz, DMSO-d₆) δ: 10.09 (s, 1H), 8.69 (s, 1H), 8.01-7.99 (m, 2H), 7.56-7.55 (m, 2H), 7.48-7.45 (m, 1H), 7.12 (s, 1H), 6.50-6.48 (m, 2H), 5.06-5.04 (m, 1H), 5.02-5.01 (m, 1H), 4.60 (s, 2H), 4.33-4.19 (m, 4H), 3.61 (s, 4H), 2.70-2.68 (m, 1H), 2.66-2.60 (m, 5H), 2.50-2.49 (m, 1H), 2.37-2.27 (m, 5H), 2.07-2.00 (m, 2H), 1.95-1.90 (m, 1H), 1.73-1.70 (m, 5H), 1.67-1.60 (m, 2H), 1.57-1.48 (m, 6H), 0.98-0.88 (m, 2H). | A | A |
| 162 | 911.46 | | ¹H NMR (400 MHz, DMSO-d₆) δ: 10.95 (s, 1H), 8.79 (s, 1H), 8.03 (s, 1H), 7.97-7.92 (m, 2H), 7.76-7.65 (m, 2H), 7.35 (d, J = 8.2 Hz, 1H), 7.03 (s, 1H), 6.73 (d, J = 7.8 Hz, 1H), 5.42-5.10 (m, 1H), 5.04 (d, J = 13.2 Hz, 1H), 4.51 (s, 2H), 4.43 (d, J = 16.8 Hz, 3H), 4.26 (d, J = 16.6 Hz, 1H), 3.66 (s, 2H), 2.83-2.70 (s, 5H), 2.68 (d, J = 4.6 Hz, 3H), 2.58 (d, J = 17.3 Hz, 1H), 2.35 (s, 1H), 2.10 (s, 2H), 1.88-1.71 (m, 7H), 1.57 (d, J = 7.0 Hz, 8H), 1.32 (s, 6H), 1.23 (s, 1H), 1.02 (d, J = 12.4 Hz, 2H). | A | A |
| 163 | 937.89 | | ¹H NMR (400 MHz, DMSO-d₆) δ: 11.00 (s, 1H), 8.83 (s, 1H), 8.04 (s, 1H), 7.97-7.95 (m, 2H), 7.70-7.68 (m, 3H), 7.59 (d, J = 7.6 Hz, 1H), 7.03 (s, 1H), 5.50-5.24 (m, 1H), 5.15 (dd, J = 5.2, 13.6 Hz, 1H), 4.55 (s, 2H), 4.49 (d, J = 17.6 Hz, 1H), 4.32 (d, J = 17.6 Hz, 1H), 4.20-4.11 (m, 3H), 3.55-3.45 (m, 1H), 3.27-3.14 (m, 2H), 3.05-3.03 (m, 2H), 2.96-2.87 (m, 2H), 2.69 (d, J = 4.8 Hz, 3H), 2.62-2.58 (m, 1H), 2.45-2.42 (m, 1H), 2.20-2.17 (m, 2H), 2.02-2.00 (m, 3H), 1.85-1.66 (m, 8H), 1.58 (d, J = 6.8 Hz, 6H), 1.43-1.35 (m, 2H). | A | A |
| 164 | 945.43 | | ¹H NMR (400 MHz, DMSO-d₆) δ: 11.00 (s, 1H), 8.85 (s, 1H), 8.17 (s, 1H), 8.04 (s, 2H), 7.95 (s, 1H), 7.69 (s, 2H), 7.49 (d, J = 8.0 Hz, 1H), 7.16 (br t, J = 8.0 Hz, 1H), 7.04 (s, 1H), 5.08 (dd, J = 5.2, 13.2 Hz, 1H), 4.62-4.42 (m, 3H), 4.31 (br d, J = 16.8 Hz, 1H), 4.25-4.07 (m, 3H), 3.24 (br d, J = 10.8 Hz, 3H), 3.14 (br s, 4H), 2.97-2.80 (m, 3H), 2.68 (d, J = 4.8 Hz, 3H), 2.64-2.57 (m, 1H), 2.48-2.32 (m, 5H), 2.25-2.14 (m, 2H), 1.98 (br dd, J = 4.8, 7.6 Hz, 3H), 1.89-1.78 (m, 2H), 1.57 (d, J = 6.8 Hz, 6H), 1.45-1.30 (m, 2H) | A | A |
| 165 | 903.94 | | ¹H NMR (400 MHz, DMSO-d₆) δ: 10.98 (s, 1H), 8.83 (s, 1H), 8.04 (s, 1H), 8.00-7.95 (m, 1H), 7.94 (s, 1H), 7.68 (s, 2H), 7.62 (d, J = 8.0 Hz, 1H), 7.42 (s, 1H), 7.34 (d, J = 8.0 Hz, 1H), 7.02 (s, 1H), 5.50-5.20 (m, 1H), 5.13-5.05 (m, 1H), 4.54 (s, 2H), 4.45-4.37 (m, 1H), 4.32-4.25 (m, 1H), 4.24-4.17 (m, 1H), 4.15-4.07 (m, 2H), 3.63-3.57 (m, 3H), 3.32-3.22 (m, 3H), 2.98-2.85 (m, 1H), 2.75-2.69 (m, 2H), 2.67 (d, J = 4.4 Hz, 3H), 2.64-2.56 (m, 2H), 2.44-2.30 (m, 2H), 2.03-1.93 (m, 1H), 1.86-1.73 (m, 4H), 1.72-1.63 (m, 2H), 1.57 (d, J = 6.8 Hz, 6H), 1.50-1.44 (m, 3H), 1.42-1.32 (m, 2H). | A | B |
| 166 | 926.45 | | ¹H NMR (400 MHz, DMSO-d₆) δ: 10.97 (s, 1H), 8.83 (s, 1H), 8.18 (s, 1H), 8.04 (s, 1H), 7.98-7.90 (m, 2H), 7.74-7.65 (m, | A | B |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | 2H), 7.62 (d, J = 8.0 Hz, 1H), 7.45 (s, 1H), 7.36 (d, J = 8.0 Hz, 1H), 7.02 (s, 1H), 5.53-5.14 (m, 1H), 5.13-5.05 (m, 1H), 4.54 (s, 2H), 4.45-4.37 (m, 1H), 4.31-4.23 (m, 1H), 4.21-4.15 (m, 1H), 4.14-4.06 (m, 2H), 3.62-3.59 (m, 1H), 3.21-3.17 (m, 1H), 2.97-2.85 (m, 2H), 2.84-2.78 (m, 2H), 2.67 (d, J = 4.4 Hz, 3H), 2.64-2.56 (m, 3H), 2.45-2.30 (m, 2H), 2.12-2.02 (m, 1H), 2.00-1.95 (m, 1H), 1.87-1.75 (m, 6H), 1.57 (d, J = 6.8 Hz, 6H), 1.52-1.42 (m, 2H), 1.40-1.30 (m, 2H), 1.10-0.97 (m, 2H). | | |
| 167 | 931.95 | | $^1$H NMR (400 MHz, DMSO-$d_6$) δ: 11.11 (s, 1H), 8.83 (s, 1H), 8.04 (s, 1H), 8.00-7.89 (m, 2H), 7.77-7.61 (m, 4H), 7.02 (s, 1H), 5.65-5.21 (m, 1H), 5.11 (dd, J = 5.2, 12.8 Hz, 1H), 4.54 (s, 2H), 4.24-4.04 (m, 3H), 3.59-3.45 (m, 1H), 3.22 (br t, J = 10.4 Hz, 2H), 2.99 (br d, J = 10.4 Hz, 2H), 2.94-2.77 (m, 3H), 2.70-2.63 (m, 6H), 2.61 (br s, 1H), 2.56 (br d, J = 9.2 Hz, 1H), 2.20-2.10 (m, 2H), 2.07-1.93 (m, 3H), 1.81 (br t, J = 10.0 Hz, 4H), 1.75-1.61 (m, 4H), 1.57 (d, J = 6.8 Hz, 6H), 1.43-1.28 (m, 2H) | A | A |
| 168 | 905.48 | | $^1$H NMR (400 MHz, DMSO-$d_6$) δ: 10.92 (s, 1H), 8.79 (s, 1H), 8.03 (s, 1H), 7.94 (d, J = 10.5 Hz, 2H), 7.76-7.65 (m, 2H), 7.47 (d, J = 8.2 Hz, 1H), 7.02 (s, 1H), 6.49-6.40 (m, 2H), 5.02 (d, J = 13.6 Hz, 1H), 4.53 (s, 2H), 4.48 (d, J = 12.8 Hz, 2H), 4.29 (d, J = 17.0 Hz, 1H), 4.16 (d, J = 17.0 Hz, 1H), 3.89 (s, 4H), 2.85 (d, J = 12.4 Hz, 3H), 2.67 (d, J = 4.6 Hz, 3H), 2.58 (d, J = 16.8 Hz, 1H), 2.40 (s, 1H), 2.23 (s, 3H), 2.07 (s, 2H), 2.01 (s, 4H), 1.94 (s, 1H), 1.72 (d, J = 12.9 Hz, 3H), 1.57 (d, J = 6.8 Hz, 7H), 1.48 (s, 4H), 1.24 (s, 1H), 1.00 (d, J = 8.5 Hz, 2H). | A | B |
| 169 | 897.39 | | $^1$H NMR (400 MHz, DMSO-$d_6$) δ: 11.07 (s, 1H), 8.76 (s, 1H), 8.03 (s, 2H), 7.61-7.49 (m, 3H), 7.14-7.05 (m, 2H), 6.76 (d, J = 8.6 Hz, 1H), 5.03 (dd, J = 12.6, 5.5 Hz, 1H), 4.61 (s, 2H), 3.89 (s, 2H), 3.83 (s, 2H), 3.48 (s, 4H), 2.93-2.81 (m, 1H), 2.67 (d, J = 4.6 Hz, 4H), 2.26 (s, 3H), 2.07 (d, J = 7.1 Hz, 2H), 1.87 (d, J = 12.6 Hz, 2H), 1.58 (d, J = 6.9 Hz, 7H), 1.49-1.39 (m, 4H), 0.89 (d, J = 12.8 Hz, 2H). | A | A |
| 170 | 909.47 | | $^1$H NMR (400 MHz, DMSO-$d_6$) δ: 10.96 (s, 1H), 8.83 (s, 1H), 8.06-7.97 (m, 2H), 7.95 (s, 1H), 7.68 (br s, 2H), 7.62-7.54 (m, 1H), 7.29 (s, 1H), 7.23-7.16 (m, 1H), 7.03 (s, 1H), 5.56-5.12 (m, 1H), 5.08 (br dd, J = 5.2, 13.6 Hz, 1H), 4.53 (s, 2H), 4.44-4.34 (m, 1H), 4.30-4.22 (m, 1H), 4.21-4.17 (m, 1H), 4.16-4.06 (m, 2H), 3.57-3.49 (m, 1H), 3.26-3.19 (m, 2H), 3.17-3.08 (m, 2H), 2.95-2.85 (m, 1H), 2.82-2.73 (m, 1H), 2.68 (d, J = 4.8 Hz, 3H), 2.63-2.56 (m, 1H), 2.45-2.34 (m, 3H), 2.25-2.12 (m, 4H), 2.04-1.93 (m, 3H), 1.88-1.77 (m, 2H), 1.57 (d, J = 6.8 Hz, 6H), 1.45-1.30 (m, 2H), 1.06 (s, 6H) | A | A |
| 171 | 919.39 | | $^1$H NMR (400 MHz, DMSO-$d_6$) δ: 8.69 (s, 1H), 8.01 (d, J = 7.2 Hz, 2H), 7.69-7.33 (m, 3H), 7.12 (s, 1H), 6.68-6.37 (m, 2H), 5.04 (dd, J = 13.3, 5.1 Hz, 1H), 4.60 (s, 2H), 4.38-4.13 (m, 4H), 4.01-3.89 (m, 2H), 3.71 (d, J = 8.1 Hz, 2H), 3.00-2.90 (m, 1H), 2.73-2.65 (m, 2H), 2.65-2.58 (m, 4H), 2.55-2.50 (m, 2H), 2.45-2.30 (m, 3H), 2.18 (d, J = 7.1 Hz, 2H), 1.98 (s, 3H), 1.84-1.69 (m, 1H), 1.65-1.50 (m, 8H), 1.23 (s, 1H), 1.04-0.81 (m, 2H). | A | A |
| 172 | 912.40 | | $^1$H NMR (400 MHz, DMSO-$d_6$) δ: 11.13 (s, 1H), 8.77 (s, 1H), 8.04 (s, 2H), 7.85 (d, J = 7.6 Hz, 1H), 7.78 (d, J = 8.5 Hz, 2H), 7.58-7.49 (m, 2H), 7.13 (s, 1H), 5.14 (dd, J = 12.9, 5.3 Hz, 1H), 4.62 (s, 2H), 4.14 (s, 1H), 3.96 (s, 2H), 3.46 (s, 2H), 3.08 (s, 2H), 2.99 (d, J = 10.1 Hz, | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 173 | 917.42 | | 2H), 2.88 (d, J = 13.2 Hz, 3H), 2.81 (s, 3H), 2.75 (s, 1H), 2.71-2.54 (m, 1H), 2.13 (s, 3H), 1.97 (s, 2H), 1.80 (s, 8H), 1.71 (q, J = 13.1, 12.4 Hz, 6H), 1.32-1.22 (m, 2H). | A | A |
| 174 | 909.47 | | $^1$H NMR (400 MHz, DMSO-$d_6$) δ: 11.00 (s, 1H), 8.75 (s, 1H), 8.01 (d, J = 11.1 Hz, 2H), 7.60-7.47 (m, 4H), 7.12 (s, 1H), 5.62-5.05 (m, 2H), 4.68-4.50 (m, 3H), 4.36 (d, J = 17.3 Hz, 1H), 4.12 (d, J = 5.6 Hz, 1H), 4.05-3.80 (m, 2H), 3.58-3.43 (m, 1H), 3.18-2.80 (m, 7H), 2.67 (d, J = 4.6 Hz, 3H), 2.60 (d, J = 16.2 Hz, 1H), 2.43 (dd, J = 13.2, 4.5 Hz, 1H), 2.13 (dd, J = 12.1, 6.2 Hz, 2H), 2.03-1.90 (m, 3H), 1.81-1.70 (m, 7H), 1.58 (d, J = 6.8 Hz, 6H), 1.33-1.19 (m, 3H). | A | A |
| 175 | 913.43 | | $^1$H NMR (400 MHz, DMSO-$d_6$) δ: 10.94 (s, 1H), 8.83 (s, 1H), 8.04 (s, 1H), 8.02-7.97 (m, 1H), 7.94 (s, 1H), 7.68 (s, 2H), 7.54 (d, J = 8.4 Hz, 1H), 7.03 (s, 1H), 7.01-6.94 (m, 2H), 5.59-5.13 (m, 1H), 5.04 (dd, J = 5.2, 13.6 Hz, 1H), 4.54 (s, 2H), 4.39-4.30 (m, 1H), 4.28-4.17 (m, 2H), 4.17-4.07 (m, 2H), 3.97-3.83 (m, 2H), 2.97-2.88 (m, 1H), 2.86-2.73 (m, 2H), 2.67 (d, J = 4.8 Hz, 3H), 2.60 (br s, 2H), 2.36-2.28 (m, 2H), 2.24-2.08 (m, 5H), 2.07-1.92 (m, 4H), 1.89-1.78 (m, 2H), 1.57 (d, J = 6.8 Hz, 6H), 1.45-1.34 (m, 2H), 1.11 (d, J = 6.4 Hz, 6H) | A | A |
| | | | $^1$H NMR (400 MHz, DMSO-$d_6$) δ: 10.99 (s, 1H), 8.84 (s, 1H), 8.04 (s, 1H), 7.96 (d, J = 8.2 Hz, 2H), 7.69 (d, J = 1.5 Hz, 2H), 7.49 (d, J = 8.1 Hz, 1H), 7.21 (t, J = 7.8 Hz, 1H), 7.02 (s, 1H), 5.08 (dd, J = 13.2, 5.1 Hz, 1H), 4.59-4.57 (m, 2H), 4.51 (d, J = 27.4 Hz, 1H), 4.32 (d, J = 17.1 Hz, 1H), 4.20 (s, 1H), 4.12 (d, J = 13.1 Hz, 1H), 3.82-3.77 (s, 1H), 3.71 (s, 1H), 3.53 (s, 3H), 3.24 (d, J = 10.8 Hz, 3H), 2.94 (s, 1H), 2.79 (s, 1H), 2.68 (d, J = 4.6 Hz, 2H), 2.59 (d, J = 15.3 Hz, 1H), 2.43 (s, 4H), 2.38 (d, J = 13.3 Hz, 3H), 2.03-1.92 (s, 3H), 1.91-1.83 (m, 2H), 1.76-1.63 (m, 6H), 1.57 (d, J = 6.8 Hz, 2H), 1.23 (s, 1H), 0.99 (d, J = 6.3 Hz, 3H). | | |
| 176 | 913.43 | | $^1$H NMR (400 MHz, DMSO-$d_6$) δ: 8.83 (s, 1H), 8.04-7.95 (m, 3H), 8.05 (s, 2H), 7.69 (s, 2H), 7.51-7.48 (m, 1H), 7.26-7.12 (m, 1H), 7.04 (s, 1H), 5.50-5.20 (m, 1H), 5.18-4.98 (m, 1H), 4.62-4.49 (m, 3H), 4.38-4.00 (m, 3H), 3.90-3.65 (m, 1H), 3.60-3.50 (m, 2H), 3.30-3.20 (m, 4H), 3.00-2.80 (m, 3H), 2.70-2.69 (m, 2H), 2.65-2.55 (m, 2H), 2.50-2.10 (m, 6H), 2.00 (s, 3H), 1.95-1.70 (s, 2H), 1.69-1.45 (m, 6H), 1.44-1.32 (m, 2H), 1.20-0.82 (m, 3H). | | |
| 177 | 909.43 | | $^1$H NMR (400 MHz, DMSO-$d_6$) δ: 11.11 (s, 1H), 8.84 (s, 1H), 8.04 (s, 1H), 7.96 (m, 2H), 7.69 (m, 3H), 7.36 (m, 1H), 7.02 (s, 1H), 5.09 (m, 1H), 4.54 (s, 2H), 4.20-4.12 (m, 3H), 3.60 (m, 1H), 3.30 (s, 1H), 3.10 (s, 2H), 3.00 (s, 4H), 2.98 (s, 2H), 2.80 (s, 4H), 2.70 (s, 1H), 2.59 (m, 6H), 2.35 (m, 1H), 2.19 (s, 2H), 2.00 (m, 3H), 1.83 (m, 2H), 1.57 (m, 6H), 1.38 (m, 2H). | A | A |
| 178 | 913.43 | | $^1$H NMR (400 MHz, DMSO-$d_6$) δ: 10.98 (s, 1H), 8.83 (s, 1H), 8.04 (s, 1H), 8.00-7.91 (m, 2H), 7.69 (d, J = 1.4 Hz, 2H), 7.48 (d, J = 8.1 Hz, 1H), 7.18-7.06 (m, 1H), 7.02 (s, 1H), 5.32 (s, 1H), 5.07 (dd, J = 13.2, 5.1 Hz, 1H), 4.59-4.53 (m, 2H), 4.52-4.41 (m, 1H), 4.38-4.27 (m, 1H), 4.22-4.01 (m, 3H), 3.60-3.47 (m, 1H), 3.31-3.16 (m, 4H), 3.15-3.02 (m, 3H), 2.99-2.72 (m, 3H), 2.70-2.65 (m, 3H), 2.64-2.55 (m, 1H), 2.48-2.32 (m, 2H), 2.22-2.03 (m, 3H), 2.02-1.90 (m, 2H), 1.89-1.73 (m, 2H), 1.57 (d, J = 6.8 Hz, 6H), 1.45-1.29 (m, 2H) 1.00 (d, J = 6.3 Hz, 3H). | A | A |
| 179 | 932.48 | | $^1$H NMR (400 MHz, DMSO-$d_6$) δ: 10.97 (s, 1H), 8.83 (s, 1H), 8.04 (s, 1H), 7.99 (q, J = 4.0 Hz, 1H), | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | 7.95 (s, 1H), 7.68 (s, 2H), 7.62-7.57 (m, 1H), 7.18 (br s, 1H), 7.16-7.10 (m, 1H), 7.03 (br s, 1H), 5.51-5.13 (m, 1H), 5.12-5.04 (m, 1H), 4.54 (s, 2H), 4.45-4.34 (m, 1H), 4.32-4.07 (m, 4H), 3.71-3.60 (m, 2H), 3.58-3.50 (m, 1H), 3.26-3.18 (m, 2H), 3.00-2.82 (m, 1H), 2.81-2.72 (m, 1H), 2.70-2.66 (m, 3H), 2.64-2.56 (m, 2H), 2.45-2.32 (m, 2H), 2.28-2.11 (m, 4H), 2.06-1.94 (m, 3H), 1.88-1.78 (m, 2H), 1.57 (d, J = 6.8 Hz, 6H), 1.46-1.32 (m, 2H), 0.91 (d, J = 6.4 Hz, 6H) | | |
| 180 | 909.47 | | $^1$H NMR (400 MHz, DMSO-$d_6$) δ: 10.97 (s, 1H), 8.84 (s, 1H), 8.05 (s, 1H), 8.00 (q, J = 4.0 Hz, 1H), 7.97-7.94 (m, 1H), 7.72-7.67 (m, 2H), 7.62-7.57 (m, 1H), 7.19 (br s, 1H), 7.16-7.11 (m, 1H), 7.04 (br s, 1H), 5.51-5.13 (m, 1H), 5.12-5.04 (m, 1H), 4.55 (s, 2H), 4.45-4.34 (m, 1H), 4.32-4.07 (m, 4H), 3.71-3.60 (m, 2H), 3.58-3.50 (m, 1H), 3.26-3.18 (m, 2H), 3.00-2.84 (m, 1H), 2.81-2.72 (m, 1H), 2.71-2.68 (m, 3H), 2.64-2.56 (m, 2H), 2.45-2.32 (m, 2H), 2.28-2.11 (m, 4H), 2.06-1.94 (m, 3H), 1.88-1.78 (m, 2H), 1.58 (d, J = 6.8 Hz, 6H), 1.46-1.32 (m, 2H), 0.92 (d, J = 6.4 Hz, 6H) | A | A |
| 181 | 915.86 | | $^1$H NMR (400 MHz, DMSO-$d_6$) δ: 8.83 (s, 1H), 8.04-8.01 (m, 2H), 8.00-7.94 (m, 1H), 7.67-7.64 (m, 3H), 7.29-7.26 (m, 1H), 7.03 (s, 1H), 5.45-5.23 (m, 1H), 5.23-5.02 (m, 1H), 4.54-4.50 (m, 3H), 4.48-4.44 (m, 2H), 4.41-4.39 (m, 1H), 4.28-4.10 (m, 4H), 3.90-3.85 (m, 1H), 3.67-3.64 (m, 1H), 3.19-3.08 (m, 3H), 2.94-2.86 (m, 4H), 2.68-2.61 (m, 4H), 2.50-2.42 (m, 3H), 2.19-1.99 (m, 2H), 1.79-1.55 (m, 5H), 1.38-1.36 (m, 5H), 1.23-1.20 (m, 2H), 1.18-1.16 (m, 5H), 1.08-1.00 (s, 1H), 0.85 (s, 1H). | A | A |
| 182 | 913.43 | | $^1$H NMR (400 MHz, DMSO-$d_6$) δ: 10.98 (s, 1H), 8.83 (s, 1H), 8.05 (s, 1H), 7.96 (d, J = 7.0 Hz, 2H), 7.69 (d, J = 1.5 Hz, 2H), 7.48 (d, J = 8.1 Hz, 1H), 7.14 (t, J = 8.0 Hz, 1H), 7.03 (s, 1H), 5.33 (s, 1H), 5.08 (dd, J = 13.3, 5.1 Hz, 1H), 4.55 (s, 2H), 4.49 (d, J = 17.0 Hz, 1H), 4.32 (d, J = 16.9 Hz, 1H), 4.13 (d, J = 15.1 Hz, 3H), 3.54 (s, 1H), 3.22 (d, J = 10.5 Hz, 2H), 3.13 (s, 3H), 2.95-2.84 (m, 2H), 2.78 (s, 5H), 2.68 (d, J = 4.7 Hz, 1H), 2.59 (d, J = 16.8 Hz, 2H), 2.41 (dt, J = 13.3, 6.6 Hz, 3H), 2.17-1.99 (d, J = 9.3 Hz, 2H), 1.84 (d, J = 12.3 Hz, 2H), 1.57 (d, J = 6.8 Hz, 6H), 1.45-1.27 (m, 3H), 1.01 (d, J = 6.3 Hz, 3H). | | |
| 183 | 898.42 | | $^1$H NMR (400 MHz, DMSO-$d_6$) δ: 10.99 (s, 1H), 8.83 (s, 1H), 8.04 (s, 1H), 8.01-7.95 (m, 1H), 7.94 (s, 1H), 7.68 (s, 2H), 7.55-7.42 (m, 2H), 7.02 (s, 1H), 5.65-5.20 (m, 1H), 5.10 (dd, J = 13.2, 5.2 Hz, 1H), 4.57-4.49 (m, 3H), 4.38-4.31 (m, 1H), 4.20-4.05 (m, 3H), 3.60-3.55 (m, 1H), 3.25-3.15 (m, 1H), 2.95-2.75 (m, 5H), 2.67 (d, J = 4.4 Hz, 3H), 2.62-2.55 (m, 2H), 2.43-2.35 (m, 2H), 2.10-1.95 (m, 2H), 1.88-1.75 (m, 6H), 1.57 (d, J = 6.8 Hz, 6H), 1.54-1.45 (m, 2H), 1.42-1.32 (m, 2H), 1.15-1.00 (m, 2H). | A | A |
| 184 | 944.44 | | $^1$H NMR (400 MHz, DMSO-$d_6$) δ 10.99 (s, 1H), 8.83 (s, 1H), 8.18 (s, 1H), 8.04 (s, 1H), 8.00-7.91 (m, 2H), 7.68 (s, 2H), 7.58-7.52 (m, 1H), 7.48-7.41 (m, 1H), 7.02 (s, 1H), 5.60-5.20 (m, 1H), 5.10 (dd, J = 13.2, 5.2 Hz, 1H), 4.57-4.49 (m, 3H), 4.39-4.31 (m, 1H), 4.25-4.17 (m, 1H), 4.15-4.06 (m, 2H), 3.63-3.61 (m, 1H), 3.24-3.15 (m, 1H), 2.98-2.84 (m, 2H), 2.74-2.69 (m, 2H), 2.67 (d, J = 4.4 Hz, 3H), 2.63-2.55 (m, 2H), 2.44-2.30 (m, 3H), 2.03-1.95 (m, 1H), 1.88-1.77 (m, 4H), 1.74-1.66 (m, 2H), 1.57 (d, J = 6.8 Hz, 6H), 1.50-1.30 (m, 7H). | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 185 | 960.90 | | $^1$H NMR (400 MHz, DMSO-d$_6$) δ: 10.99 (s, 1H), 8.83 (s, 1H), 8.19 (s, 1H), 8.04 (s, 1H), 8.01-7.95 (m, 1H), 7.94 (s, 1H), 7.70-7.64 (m, 2H), 7.54 (d, J = 8.0 Hz, 1H), 7.02 (s, 1H), 5.55-5.20 (m, 1H), 5.10 (dd, J = 13.2, 5.2 Hz, 1H), 4.54 (s, 2H), 4.48-4.42 (m, 1H), 4.32-4.25 (m, 1H), 4.14-4.05 (m, 2H), 3.62-3.55 (m, 1H), 3.35-3.15 (m, 2H), 3.02-2.86 (m, (s, 1H), 5.33-5.10 (dd, J = 12.8, 5.4 Hz, 2H), 4.61 (s, 2H), 4.15 (s, 1H), 3.95 (s, 2H), 3.5 (s, 2H), 3.06 (d, J = 10.9 Hz, 3H), 2.68 (d, J = 4.6 Hz, 2H), 2.64-2.56 (m, 5H), 2.55 (s, 4H), 2.20-2.15 (m, 3H), 1.97 (s, 4H), 1.73 (d, J = 12.1 Hz, 2H), 1.58 (d, J = 6.8 Hz, 6H), 1.32-1.22 (m, 2H), 0.83 (d, J = 6.1 Hz, 3H) | A | B |
| 186 | 960.90 | | $^1$H NMR (400 MHz, DMSO-d$_6$) δ: 10.99 (s, 1H), 8.83 (s, 1H), 8.19 (s, 1H), 8.04 (s, 1H), 8.01-7.96 (m, 1H), 7.94 (s, 1H), 7.73-7.64 (m, 3H), 7.50 (d, J = 8.0 Hz, 1H), 7.02 (s, 1H), 5.54-5.19 (m, 1H), 5.10 (dd, J = 13.2, 5.2 Hz, 1H), 4.54 (s, 2H), 4.48-4.42 (m, 1H), 4.32-4.25 (m, 1H), 4.24-4.17 (m, 1H), 4.16-4.05 (m, 2H), 3.65-3.58 (m, 1H), 3.31-3.16 (m, 2H), 3.09-2.94 (m, 2H), 2.92-2.85 (m, 1H), 2.74-2.69 (m, 2H), 2.67 (d, J = 4.4 Hz, 3H), 2.63-2.56 (m, 1H), 2.45-2.40 (m, 1H), 2.39-2.28 (m, 2H), 2.04-1.96 (m, 1H), 1.87-1.70 (m, 6H), 1.57 (d, J = 6.8 Hz, 6H), 1.52-1.43 (m, 4H), 1.41-1.33 (m, 2H) | A | C |
| 187 | 926.47 | | $^1$H NMR (400 MHz, DMSO-d$_6$) δ: 11.02 (s, 1H), 8.82 (s, 1H), 8.04 (m, 1H), 7.99-7.95 (m, 2H), 7.69 (m, 2H), 7.55-7.53 (m, 1H), 7.46-7.44 (m, 1H), 7.03 (s, 1H), 5.13-5.11 (m, 1H), 4.54-4.50 (m, 3H), 4.40-4.37 (m, 1H), 4.18-4.10 (m, 3H), 3.26-3.30 (m, 1H), 3.32-3.26 (m, 2H), 3.22-2.68 (m, 4H), 2.67-2.63 (m, 4H), 2.56-2.50 (m, 3H), 2.46-2.44 (m, 2H), 2.21-2.16 (m, 5H), 1.99-1.81 (m, 3H), 1.71-1.61 (m, 3H), 1.58-1.55 (m, 6H), 1.47-1.35 (m, 4H), 0.89-0.88 (m, 3H), 0.72-0.71 (m, 3H) | A | A |
| 188 | 962.43 | | $^1$H NMR (400 MHz, DMSO-d$_6$) δ: 11.02 (br s, 1H), 8.83 (s, 1H), 8.25 (s, 1H), 8.04 (s, 1H), 8.02-7.94 (m, 2H), 7.70 (s, 2H), 7.34 (dd, J = 10.0, 4.8 Hz, 1H), 7.04 (s, 1H), 5.52-5.18 (m, 1H), 5.16-5.01 (m, 1H), 4.66-4.50 (m, 3H), 4.38 (br d, J = 17.6 Hz, 1H), 4.25-4.03 (m, 4H), 3.57-3.50 (m, 2H), 3.30-3.20 (m, 2H), 3.04-2.82 (m, 5H), 2.69 (d, J = 4.8 Hz, 3H), 2.60 (br d, J = 16.4 Hz, 2H), 2.46-2.34 (m, 1H), 2.20-2.10 (m, 2H), 2.05-1.92 (m, 3H), 1.87-1.70 (m, 8H), 1.58 (d, J = 6.8 Hz, 6H), 1.45-1.32 (m, 2H) | A | A |
| 189 | 918.87 | | $^1$H NMR (400 MHz, DMSO-d$_6$) δ: 10.94 (s, 1H), 8.82 (s, 1H), 8.22 (s, 1H), 8.04 (s, 1H), 7.99-7.92 (m, 2H), 7.77 (d, J = 8.8 Hz, 1H), 7.68 (s, 2H), 7.02 (s, 1H), 6.90 (d, J = 8.8 Hz, 1H), 5.32 (br s, 1H), 5.07 (dd, J = 5.2, 13.2 Hz, 1H), 4.54 (s, 2H), 4.19 (br t, J = 5.2 Hz, 1H), 4.14-4.03 (m, 3H), 3.64 (br s, 4H), 3.52 (br dd, J = 4.0, 7.6 Hz, 2H), 3.22 (br t, J = 10.0 Hz, 3H), 2.97-2.83 (m, 1H), 2.82-2.74 (m, 1H), 2.67 (d, J = 4.8 Hz, 3H), 2.36 (br d, J = 4.4 Hz, 5H), 2.23-2.14 (m, 2H), 2.03-1.91 (m, 3H), 1.86-1.76 (m, 2H), 1.43-1.30 (m, 2H) | A | B |
| 190 | 910.43 | | $^1$H NMR (400 MHz, DMSO-d$_6$) δ: 11.00 (s, 1H), 8.83 (s, 1H), 8.09-8.00 (m, 2H), 7.90 (d, J = 2.5 Hz, 1H), 7.65 (m, 1H), 7.52 (m, 3H), 7.04 (s, 1H), 5.11 (m, 2H), 4.58-4.49 (m, 3H), 4.36 (d, J = 17.2 Hz, 1H), 4.18-4.10 (m, 3H), 3.51 (s, 2H), 3.21 (m, 2H), 3.02 (s, 2H), 2.90-2.87 (m, 3H), 2.76-2.65 (m, 5H), 2.65-2.51 (m, 2H), 2.42 (m, 1H), 2.01 (s, 2H), 1.97 (s, 3H), 1.87-1.72 (m, 9H), 1.36 (m, 2H), 1.22 (s, 1H) | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 191 | 924.46 | | $^1$H NMR (400 MHz, DMSO-$d_6$) δ: 11.01 (s, 1H), 8.86 (s, 1H), 8.05 (s, 1H), 7.95 (d, J = 2.6 Hz, 2H), 7.73-7.61 (m, 2H), 7.59-7.48 (m, 2H), 7.04 (s, 1H), 5.44 (p, J = 8.6 Hz, 1H), 5.11 (dd, J = 13.3, 5.1 Hz, 1H), 4.59-4.51 (m, 3H), 4.37 (d, J = 17.2 Hz, 1H), 4.12 (d, J =12.6 Hz, 3H), 3.64-3.51 (s, 1H), 3.23 (t, J = 10.7 Hz, 2H), 3.04 (s, 2H), 2.99-2.85 (m, 3H), 2.68 (d, J = 4.6 Hz, 3H), 2.60 (d, J = 17.4 Hz, 1H), 2.42 (td, J = 13.3, 4.6 Hz, 1H), 2.20 (d, J = 9.0 Hz, 4H), 2.04-1.96 (m, 6H), 1.94-1.70 (t, J = 5.7 Hz, 11H), 1.38 (d, J = 8.9 Hz, 2H) | A | A |
| 192 | 942.46 | | $^1$H NMR (400 MHz, DMSO-$d_6$) δ: 11.14-10.81 (m, 2H), 9.46-9.18 (m, 1H), 8.17-8.10 (m, 1H), 8.02 (br d, J = 4.0 Hz, 1H), 7.93 (d, J = 2.0 Hz, 1H), 7.89 (d, J = 8.8 Hz, 1H), 7.76-7.70 (m, 1H), 7.69-7.62 (m, 1H), 7.05 (s, 1H), 6.99 (d, J = 8.8 Hz, 1H), 5.49-5.16 (m, 1H), 5.09 (dd, J = 5.2, 13.2 Hz, 1H), 5.00-4.86 (m, 1H), 4.61-4.47 (m, 3H), 4.41-4.27 (m, 2H), 4.15 (dd, J = 2.0, 17.6 Hz, 1H), 4.12-4.03 (m, 2H), 3.93-3.83 (m, 1H), 3.63-3.54 (m, 4H), 3.30 (br d, J = 10.0 Hz, 3H), 3.11-3.04 (m, 1H), 2.98-2.85 (m, 3H), 2.68 (d, J = 4.4 Hz, 4H), 2.60 (br d, J = 16.8 Hz, 1H), 2.44-2.33 (m, 2H), 2.30-2.19 (m, 2H), 2.03-1.93 (m, 1H), 1.92-1.82 (m, 2H), 1.58 (d, J = 6.8 Hz, 6H), 1.51-1.37 (m, 5H) | A | A |
| 193 | 923.45 | | $^1$H NMR (400 MHz, DMSO-$d_6$) δ: 11.11 (s, 1H), 8.85 (s, 1H), 8.05 (s, 1H), 7.96 (d, J = 7.0 Hz, 2H), 7.75-7.67 (m, 3H), 7.03 (s, 1H), 5.31 (s, 1H), 5.10 (dd, J = 12.9, 5.4 Hz, 1H), 4.55 (s, 2H), 4.13 (d, J = 12.4 Hz, 3H), 3.54 (s, 1H), 3.47 (m, 1H), 3.35 (m, 1H), 3.23 (t, J = 11.2 Hz, 2H), 3.07 (s, 1H), 2.92-2.83 (m, 2H), 2.68 (d, J = 4.7 Hz, 6H), 2.62 (s, 4H), 2.55 (s, 3H), 2.20-2.01 (d, J = 13.0 Hz, 4H), 1.94 (m, 2H), 1.84 (d, J = 12.3 Hz, 6H), 1.57 (d, J = 6.8 Hz, 2H), 0.84 (d, J = 6.0 Hz, 3H) | A | A |
| 194 | 923.45 | | $^1$H NMR (400 MHz, DMSO-$d_6$) δ: 8.83 (s, 1H), 8.03-7.95 (m, 3H), 7.71-7.64 (m, 3H), 7.33 (d, J = 8.1 Hz, 1H), 7.03 (s, 1H), 5.27 (m, 1H), 4.55 (s, 2H), 4.13 (d, J = 13.6 Hz, 3H), 3.52 (s, 2H), 3.31 (m, 2H), 3.22 (m, 3H), 2.95 (d, J = 8.4 Hz, 4H), 2.94-2.82 (m, 3H), 2.76 (d, J = 13.0 Hz, 3H), 2.68 (d, J = 4.6 Hz, 3H), 2.63-2.55 (m, 1H), 2.55-2.39 (m, 2H), 2.17-1.92 (m, 3H), 1.85-1.82 (m, 2H), 1.57 (d, J = 6.8 Hz, 5H), 1.41-1.35 (m, 3H), 1.03 (d, J = 5.6 Hz, 3H) | A | A |
| 195 | 927.42 | | $^1$H NMR (400 MHz, DMSO-$d_6$) δ: 11.09 (s, 1H), 8.76 (s, 1H), 8.03 (s, 1H), 8.10-7.99 (m, 2H), 7.61-7.49 (m, 2H), 7.35 (d, J = 8.2 Hz, 1H), 7.12 (s, 1H), 5.27 (s, 1H), 5.09 (dd, J = 12.8, 5.4 Hz, 1H), 4.61 (s, 2H), 4.17-4.12 (m, 1H), 3.96 (s, 2H), 3.51-3.43 (m, 1H) 3.11-3.03 (m, 2H), 2.97 (s, 4H), 2.90-2.80 (m, 2H), 2.67 (d, J = 4.6 Hz, 3H), 2.63-2.55 (m, 2H), 2.53 (s, 3H), 2.49-2.40 (m, 3H), 2.20-2.12 (m, 2H), 2.05-1.90 (m, 3H), 1.72 (d, J = 12.3 Hz, 2H), 1.58 (d, J = 6.9 Hz, 7H), 1.35-1.21 (m, 2H). | A | A |
| 196 | 989.94 | | $^1$H NMR (400 MHz, DMSO-$d_6$) δ: 10.99 (br s, 1H), 8.83 (s, 1H), 8.24 (s, 1H), 8.04 (s, 1H), 8.00-7.86 (m, 2H), 7.72-7.58 (m, 3H), 7.33 (d, J = 8.0 Hz, 1H), 7.03 (s, 1H), 5.63-5.16 (m, 1H), 5.10 (dd, J = 5.2, 13.2 Hz, 1H), 4.54 (s, 2H), 4.42 (d, J = 17.6 Hz, 1H), 4.30-4.22 (m, 1H), 4.21-4.07 (m, 3H), 3.56-3.51 (m, 2H), 3.44 (br s, 1H), 3.35-3.16 (m, 4H), 2.97-2.85 (m, 1H), 2.80 (br dd, J = 5.2, 7.3 Hz, 2H), 2.68 (d, J = 4.8 Hz, 3H), 2.62-2.55 (m, 1H), 2.46-2.41 (m, 1H), 2.39-2.28 (m, 2H), 2.24-2.10 (m, 2H), 2.03-1.92 (m, 3H), 1.88-1.76 (m, 2H), 1.57 (d, J = | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 197 | 940.48 | | 6.8 Hz, 6H), 1.46-1.33 (m, 2H), 1.30-1.21 (m, 1H), 0.70 (t, J = 7.2 Hz, 3H) $^1$H NMR (400 MHz, DMSO-d$_6$) δ: 10.99 (s, 1H), 8.83 (s, 1H), 8.19 (s, 1H), 8.04 (s, 1H), 8.01-7.88 (m, 2H), 7.69 (s, 2H), 7.53 (d, J = 8.0 Hz, 1H), 7.39 (d, J = 8.0 Hz, 1H), 7.03 (s, 1H), 5.66-5.21 (m, 1H), 5.12 (dd, J = 5.2, 13.2 Hz, 1H), 4.55 (s, 2H), 4.45-4.35 (m, 1H), 4.26 (s, 1H), 4.23-4.18 (m, 1H), 4.16-4.06 (m, 2H), 3.25-3.18 (m, 2H), 3.03 (br d, J = 10.4 Hz, 2H), 2.95-2.78 (m, 3H), 2.68 (d, J = 4.8 Hz, 3H), 2.65-2.57 (m, 1H), 2.45-2.30 (m, 2H), 2.27 (s, 3H), 2.19 (td, J = 5.6, 11.0 Hz, 2H), 2.07-1.95 (m, 3H), 1.93-1.79 (m, 4H), 1.74-1.63 (m, 4H), 1.57 (d, J = 6.8 Hz, 6H), 1.45-1.30 (m, 2H) | A | A |
| 198 | 942.46 | | $^1$H NMR (400 MHz, DMSO-d$_6$) δ: 10.95 (br s, 1H), 8.84 (s, 1H), 8.27 (s, 1H), 8.05 (s, 1H), 8.02-7.97 (m, 1H), 7.95 (s, 1H), 7.77 (d, J = 8.8 Hz, 1H), 7.69 (s, 2H), 7.03 (s, 1H), 6.85 (d, J = 9.2 Hz, 1H), 5.51-5.12 (m, 1H), 5.07 (dd, J = 5.2, 13.2 Hz, 1H), 4.68-4.49 (m, 3H), 4.31-4.17 (m, 3H), 4.17-4.05 (m, 3H), 3.57-3.52 (m, 1H), 3.27-3.17 (m, 4H), 3.10-3.02 (m, 1H), 2.99-2.85 (m, 2H), 2.83-2.73 (m, 2H), 2.68 (d, J = 4.8 Hz, 3H), 2.63-2.56 (m, 1H), 2.42-2.30 (m, 2H), 2.24-2.11 (m, 2H), 2.02-1.91 (m, 4H), 1.87-1.72 (m, 3H), 1.57 (d, J = 7.2 Hz, 6H), 1.46-1.32 (m, 2H), 1.18 (d, J = 6.8 Hz, 3H) | A | A |
| 199 | 941.44 | | $^1$H NMR (400 MHz, DMSO-d$_6$) δ: 11.09 (s, 1H), 8.77 (s, 1H), 8.03 (s, 1H), 8.01 (d, J = 5.0 Hz, 1H), 7.71 (d, J = 7.9 Hz, 1H), 7.61-7.47 (m, 3H), 7.12 | A | A |
| 200 | 923.45 | | $^1$H NMR (400 MHz, DMSO-d$_6$) δ: 11.10 (s, 1H), 8.84 (s, 1H), 8.04 (s, 1H), 8.01-7.93 (m, 2H), 7.74-7.67 (m, 3H), 7.47 (d, J = 8.1 Hz, 1H), 7.03 (s, 1H), 5.10 (dd, J = 12.8, 5.4 Hz, 1H), 4.55 (s, 2H), 4.25-4.05 (m, 3H), 3.53 (s, 1H), 3.23 (t, J = 10.9 Hz, 2H), 3.03 (d, J = 7.5 Hz, 3H), 2.98-2.91 (m, 3H), 2.90-2.80 (m, 2H), 2.68 (d, J = 4.7 Hz, 4H), 2.64-2.52 (m, 2H), 2.26-2.15 (m, 2H), 2.10-1.90 (m, 4H), 1.89-1.73 (m, 2H), 1.62-1.53 (d, J = 6.9 Hz, 7H), 1.44-1.35 (m, 2H), 1.25-1.10 (m, 4H). | B | A |
| 201 | 962.43 | | $^1$H NMR (400 MHz, DMSO-d$_6$) δ: 11.08-10.95 (m, 1H), 8.89-8.80 (m, 1H), 8.29-8.21 (m, 1H), 8.07-8.04 (m, 1H), 8.02-7.94 (m, 2H), 7.72-7.65 (m, 3H), 7.60-7.53 (m, 1H), 7.06-7.01 (m, 1H), 5.57-5.20 (m, 1H), 5.16-5.08 (m, 1H), 4.92-4.72 (m, 1H), 4.62-4.52 (m, 3H), 4.44-4.35 (m, 1H), 4.22-4.09 (m, 3H), 3.54 (br dd, J = 8.0, 4.2 Hz, 3H), 2.95-2.84 (m, 3H), 2.71-2.67 (m, 3H), 2.65-2.62 (m, 1H), 2.55 (s, 1H), 2.47-2.33 (m, 2 H), 2.27-2.10 (m, 3H), 2.07-1.96 (m, 4H), 1.89-1.79 (m, 4H), 1.58 (d, J = 6.8 Hz, 6), 1.45-1.34 (m, 2H) | A | A |
| 202 | 975.91 | | $^1$H NMR (400 MHz, DMSO-d$_6$) δ: 11.00 (br s, 1H), 8.84 (s, 1H), 8.24 (s, 1H), 8.05 (s, 1H), 8.02-7.93 (m, 2H), 7.75-7.64 (m, 3H), 7.38 (br d, J = 8.0 Hz, 1H), 7.04 (s, 1H), 5.60-5.19 (m, 1H), 5.11 (br dd, J = 13.2, 5.2 Hz, 1H), 4.55 (s, 2H), 4.49-4.39 (m, 1H), 4.36-4.06 (m, 5H), 3.56-3.53 (m, 2H), 3.24 (br t, J = 10.0 Hz, 2H), 2.96-2.79 (m, 2H), 2.76-2.55 (m, 7H), 2.49-2.35 (m, 2H), 2.27-2.12 (m, 2H), 2.10-1.92 (m, 4H), 1.89-1.77 (m, 2H), 1.58 (d, J = 6.8 Hz, 6H), 1.47-1 . . . 32 (m, 2H), 0.89 (br d, J = 4.4 Hz, 3H) | A | A |
| 203 | 956.48 | | $^1$H NMR (400 MHz, DMSO-d$_6$) δ: 10.90 (br d, J = 12.4 Hz, 1H), 8.84 (s, 1H), 8.22 (s, 1H), 8.05 (s, 1H), 8.01-7.94 (m, 2H), 7.70 (s, 2H), 7.04 (s, 1H), 6.82 (dt, J = 3.2, 8.8 Hz, 1H), 5.52-5.17 (m, 1H), 4.71 (br dd, J = 5.2 | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| | | | 12.4 Hz, 1H), 4.66-4.59 (m, 1H), 4.55 (s, 2H), 4.43 (br d, J = 6.8 Hz, 1H), 4.22 (br d, J = 4.8 Hz, 2H), 4.15-4.10 (m, 2H), 3.58-3.52 (m, 2H), 3.24 (br t, J = 10.4 Hz, 2H), 3.06-2.95 (m, 2H), 2.80-2.74 (m, 2H), 2.69 (d, J = 4.5 Hz, 3H), 2.63-2.54 (m, 3H), 2.25-2.13 (m, 2H), 2.03-1.93 (m, 4H), 1.87-1.78 (m, 3H), 1.58 (d, J = 6.8 Hz, 6H), 1.39 (br dd, J = 6.8, 14.4 Hz, 5H), 1.19 (dd, J = 3.2, 6.4 Hz, 3H) | | |
| 204 | 956.48 | | $^1$H NMR (400 MHz, DMSO-$d_6$) δ: 10.90 (d, J = 12.8 Hz, 1H), 8.88-8.82 (m, 1H), 8.20 (s, 1H), 8.05 (s, 1H), 8.00-7.93 (m, 2H), 7.75-7.66 (m, 3H), 7.02 (s, 1H), 6.88-6.79 (m, 1H), 5.73-4.99 (m, 1H), 4.75-4.57 (m, 2H), 4.55 (s, 2H), 4.52-4.39 (m, 1H), 4.30-4.18 (m, 2H), 4.16-4.07 (m, 2H), 3.57-3.53 (m, 1H), 3.26-3.22 (m, 2H), 3.08-2.93 (m, 2H), 2.84-2.74 (m, 2H), 2.68 (d, J = 4.8 Hz, 3H), 2.62-2.54 (m, 1H), 2.26-2.11 (m, 3H), 2.06-1.90 (m, 5H), 1.87-1.76 (m, 3H), 1.57 (d, J = 6.8 Hz, 6H), 1.39 (br dd, J = 7.2, 14.0 Hz, 5H), 1.18 (dd, J = 2.8, 6.4 Hz, 3H) | A | A |
| 205 | 989.94 | | $^1$H NMR (400 MHz, DMSO-$d_6$) δ: 10.99 (s, 1H), 8.84 (s, 1H), 8.05 (s, 1H), 8.00-7.92 (m, 2H), 7.73-7.64 (m, 3H), 7.40-7.33 (m, 1H), 7.03 (s, 1H), 5.53-5.17 (m, 1H), 5.11 (dd, J = 4.8, 13.2 Hz, 1H), 4.55 (s, 2H), 4.49-4.38 (m, 1H), 4.32-4.24 (m, 1H), 4.23-4.18 (m, 1H), 4.18-4.09 (m, 2H), 3.60-3.51 (m, 1H), 3.50-3.43 (m, 1H), 3.30-3.17 (m, 4H), 2.97-2.76 (m, 3H), 2.71-2.67 (m, 3H), 2.64-2.54 (m, 3H), 2.49-2.35 (m, 3H), 2.30-2.13 (m, 2H), 2.09-1.96 (m, 3H), | A | A |
| | | | 1.90-1.81 (m, 2H), 1.58 (d, J = 6.8 Hz, 6H), 1.45-1.22 (m, 3H), 0.72 (t, J = 7.2 Hz, 3H) | | |
| 206 | 975.91 | | $^1$H NMR (400 MHz, DMSO-$d_6$) δ: 11.00 (br s, 1H), 8.84 (s, 1H), 8.24 (s, 1H), 8.05 (s, 1H), 8.02-7.93 (m, 2H), 7.74-7.65 (m, 3H), 7.50-7.35 (m, 1H), 7.03 (s, 1H), 5.65-5.18 (m, 1H), 5.16-5.03 (m, 1H), 4.55 (s, 2H), 4.48-4.38 (m, 1H), 4.35-4.27 (m, 1H), 4.26-4.18 (m, 1H), 4.16-4.08 (m, 2H), 3.23 (br t, J = 10.0 Hz, 6H), 2.98-2.87 (m, 1H), 2.86-2.79 (m, 1H), 2.73-2.54 (m, 8H), 2.49-2.43 (m, 2H), 2.26-2.13 (m, 2H), 1.99 (s, 2H), 1.89-1.78 (m, 2H), 1.57 (d, J = 6.8 Hz, 6H), 1.38 (q, J = 8.8 Hz, 2H), 0.94-0.85 (m, 3H) | A | A |
| 207 | 937.48 | | $^1$H NMR (400 MHz, DMSO-$d_6$) δ: 11.10 (s, 1H), 8.83 (s, 1H), 8.05 (s, 1H), 7.96 (s, 2H), 7.75-7.67 (m, 3H), 7.48 (d, J = 8.1 Hz, 1H), 7.03 (s, 1H), 5.10 (dd, J = 13.2, 5.3 Hz, 1H), 4.55 (s, 2H), 4.16 (s, 3H), 3.54 (s, 1H), 3.21 (d, J = 11.0 Hz, 3H), 3.01 (d, J = 11.1 Hz, 3H), 2.69 (d, J = 4.6 Hz, 5H), 2.62 (s, 5H), 2.57 (s, 2H), 2.37 (d, J = 9.9 Hz, 2H), 2.20 (s, 1H), 2.12 (s, 3H), 1.84 (s, 3H), 1.58 (d, J = 6.8 Hz, 6H), 1.40 (s, 2H), 0.95 (d, J = 6.2 Hz, 3H), 0.83 (d, J = 5.9 Hz, 3H) | A | A |
| 208 | 912.44 | 911.95 | | A | A |
| 209 | 926.47 | 925.52 | $^1$H NMR (400 MHz, DMSO-$d_6$) δ: 11.02 (s, 1H), 8.84 (s, 1H), 8.04 (s, 1H), 8.01-7.93 (m, 2H), 7.69 (d, J = 1.4 Hz, 2H), 7.55 (d, J = 7.8 Hz, 1H), 7.49-7.41 (m, 1H), 7.03 (s, 1H), 5.28-5.12 (m, 2H), 4.55-4.51 (m, 3H), 4.37 (m, 1H), 4.22-4.01 (m, 3H), 3.53 (m, 1H), 3.23 (m, 2H), 3.03 (d, J = 10.4 Hz, 1H), 2.92 (m, 1H), 2.82 (d, J = 14.2 Hz, 2H), 2.68 (d, J = 4.7 Hz, 3H), 2.62-2.58 (m, 2H), 2.42 (m, 1H), 2.19 (d, J = 11.6 Hz, 3H), 2.10 (m, 3H), 1.83 (d, J = 11.7 Hz, 2H), 1.71 (m, 1H), 1.57 (d, J = 6.9 Hz, | A | A |

TABLE 5-continued

Degradation and characterization of exemplary bifunctional compounds of the present disclosure

| Compound # | Mol Weight | Mean Observed-Mass One [Two] | NMR | Mean DC50 (nM)* category | Mean Dmax (%)** category |
|---|---|---|---|---|---|
| 210 | 926.47 | 924.30 | 7H), 1.38 (m, 3H), 0.88 (d, J = 4.5 Hz, 3H), 0.71 (d, J = 2.6 Hz, 3H) $^1$H NMR (400 MHz, DMSO-$d_6$) δ: 11.01 (s, 1H), 8.83 (s, 1H), 8.04 (s, 1H), 7.95 (m, 2H), 7.82 (s, 2H), 7.55 (m, 1H), 7.41 (s, 1H), 7.12 (m, 1H), 5.41 (m, 1H), 5.01 (m, 1H), 4.72 (m, 3H), 4.41 (m, 1H), 4.12 (m, 3H), 3.51 (m, 1H), 3.20 (s, 2H), 3.01 (m, 1H), 2.81 (m, 3H), 2.71 (s, 3H), 2.61 (s, 2H), 2.43 (m, 1H), 2.21 (s, 3H), 2.01 (m, 3H), 1.92 (m, 2H), 1.78 (m, 2H), 1.62 (m, 6H), 1.42 (m, 3H), 0.93 (m, 3H), 0.81 (m, 3H) | A | A |

*DC$_{50}$ (nM) ranges: A < 10; 10 <= B < 50; 50 <= C < 100; D >= 100
**D$_{MAX}$ (%) ranges: A >= 70; 50 <= B < 70; C < 50

TABLE 5

Degradation and characterization of exemplary bifunctional compounds of the present disclosure

| Compound # | Mol Weight | Mean Observed Mass One [Two] | Mean DC50 (nM)* category | Mean Dmax (%)** category |
|---|---|---|---|---|
| 211 | 909.47 | 909.30 | A | A |
| 212 | 948.43 | | A | B |
| 213 | 911.42 | | B | B |
| 214 | 881.42 | | A | B |
| 215 | 878.41 | | B | B |
| 216 | 881.42 | | A | B |
| 217 | 897.43 | | A | B |
| 218 | 916.41 | | A | A |
| 219 | 881.42 | | A | B |
| 220 | 920.45 | | B | B |
| 221 | 906.43 | | A | B |
| 222 | 906.47 | | A | B |
| 223 | 920.45 | | B | B |
| 224 | 934.48 | | B | A |
| 225 | 899.45 | | A | A |
| 226 | 948.43 | | A | A |
| 227 | 926.51 | | A | B |
| 228 | 948.51 | | B | B |
| 229 | 910.47 | | A | A |
| 230 | 922.51 | | A | |
| 231 | 900.41 | | A | B |
| 232 | 930.44 | | A | |
| 233 | 892.48 | | A | B |
| 234 | 892.44 | | A | B |
| 235 | 920.49 | | A | B |
| 236 | 934.52 | | A | B |
| 237 | 918.40 | | A | B |
| 238 | 906.47 | | A | B |
| 239 | 907.45 | | A | A |
| 240 | 910.47 | | A | A |
| 241 | 894.41 | | B | A |
| 242 | 880.43 | | A | A |
| 243 | 893.42 | | B | C |
| 244 | 923.45 | | B | A |
| 245 | 923.45 | | B | A |
| 246 | 923.45 | | A | B |
| 247 | 896.40 | | A | A |
| 248 | 923.45 | | A | B |
| 249 | 923.45 | | B | C |
| 250 | 909.47 | | A | B |
| 251 | 918.40 | | A | A |
| 252 | 936.39 | | A | B |
| 253 | 923.45 | | B | A |
| 254 | 909.47 | | A | A |
| 255 | 907.45 | | A | B |
| 256 | 880.39 | | B | B |
| 257 | 928.46 | | A | B |
| 258 | 897.43 | | A | B |
| 259 | 918.40 | | A | B |
| 260 | 899.41 | | A | B |
| 261 | 909.43 | | B | B |
| 262 | 900.41 | | A | B |
| 263 | 909.43 | | A | B |
| 264 | 885.38 | 885.30 | A | A |
| 265 | 914.42 | 457.70 | A | A |
| 266 | 939.45 | 939.53 | A | A |
| 267 | 929.89 | 929.40 | A | B |
| 268 | 929.89 | 929.35 | A | A |
| 269 | 929.89 | 931.60 | A | A |
| 270 | 927.46 | 927.35 | | |
| 271 | 927.46 | 927.30 | | |
| 272 | 907.50 | | A | B |
| 273 | 917.40 | | A | B |
| 274 | 917.40 | | B | C |
| 275 | 910.41 | | A | A |
| 276 | 912.40 | | B | B |
| 277 | 914.42 | | A | B |
| 278 | 916.41 | | A | A |
| 279 | 928.44 | | A | A |
| 280 | 906.42 | | A | A |
| 281 | 916.41 | | B | C |
| 282 | 914.42 | | A | B |
| 283 | 910.43 | | A | A |
| 284 | 914.42 | | A | B |
| 285 | 915.42 | | A | A |
| 286 | 996.56 | | A | B |
| 287 | 937.48 | 937.75 | A | A |
| 288 | 912.44 | 912.30 | B | C |
| 289 | 912.44 | 912.35 | A | A |
| 290 | 912.44 | 910.50 | A | A |
| 291 | 912.44 | 910.45 | A | A |
| 292 | 912.44 | 912.35 | A | A |
| 293 | 912.44 | 912.35 | A | B |
| 294 | 912.44 | 910.50 | A | A |
| 295 | 912.44 | 910.45 | A | A |
| 296 | 913.43 | 912.38 | | |
| 297 | 843.34 | | A | B |
| 298 | 884.39 | | A | B |
| 299 | 884.39 | | A | B |
| 300 | 896.43 | | A | B |
| 301 | 896.43 | | A | B |
| 302 | 895.44 | | A | B |
| 303 | 892.40 | | C | B |
| 304 | 896.43 | | A | B |
| 305 | 865.42 | | A | B |
| 306 | 883.41 | | A | B |
| 307 | 883.41 | | A | B |
| 308 | 893.43 | | A | B |
| 309 | 893.43 | | A | B |
| 310 | 893.43 | | A | B |
| 311 | 907.41 | | A | B |
| 312 | 884.39 | | A | B |
| 313 | 865.42 | | A | B |
| 314 | 883.41 | | A | B |
| 315 | 883.41 | | A | B |
| 316 | 883.41 | | A | B |

TABLE 5-continued

Degradation and characterization of exemplary bifunctional compounds of the present disclosure

| Compound # | Mol Weight | Mean Observed Mass One [Two] | Mean DC50 (nM)* category | Mean Dmax (%)** category |
|---|---|---|---|---|
| 317 | 893.43 | | A | B |
| 318 | 883.41 | | A | B |
| 319 | 883.41 | | A | B |
| 320 | 757.19 | | A | |
| 321 | 864.43 | | A | B |
| 322 | 843.34 | | A | B |
| 323 | 878.41 | | A | B |
| 324 | 902.38 | | A | B |
| 325 | 897.39 | | A | B |
| 326 | 883.41 | | A | A |
| 327 | 923.50 | | A | A |
| 328 | 923.50 | | A | B |
| 329 | 914.87 | | A | B |
| 330 | 893.43 | | B | C |
| 331 | 895.44 | | B | B |
| 332 | 919.39 | | A | A |
| 333 | 879.40 | | A | B |
| 334 | 865.42 | | A | B |
| 335 | 879.40 | | A | A |
| 336 | 865.42 | | A | A |
| 337 | 907.45 | | A | B |
| 338 | 921.44 | | B | A |
| 339 | 935.46 | | A | B |
| 340 | 923.50 | | B | |
| 341 | 894.41 | | B | B |
| 342 | 880.43 | | A | A |
| 343 | 963.52 | | A | B |
| 344 | 907.45 | | A | C |
| 345 | 907.45 | | A | A |
| 346 | 921.48 | | A | A |
| 347 | 897.39 | | A | A |
| 348 | 910.45 | | A | A |
| 349 | 949.53 | | A | A |
| 350 | 921.44 | | A | A |
| 351 | 907.45 | | A | A |
| 352 | 931.42 | | B | C |
| 353 | 893.43 | | A | A |
| 354 | 935.51 | | A | B |
| 355 | 949.49 | | A | A |
| 356 | 935.51 | | A | A |
| 357 | 935.46 | | A | A |
| 358 | 893.43 | | A | B |
| 359 | 949.49 | | B | B |
| 360 | 949.49 | | A | B |
| 361 | 935.51 | | A | B |
| 362 | 949.49 | | B | A |
| 363 | 935.51 | | A | A |
| 364 | 910.45 | | A | B |
| 365 | 935.46 | | A | B |
| 366 | 921.48 | | A | A |
| 367 | 923.45 | | B | A |
| 368 | 907.45 | | A | B |
| 369 | 921.48 | | A | A |
| 370 | 921.44 | | B | C |
| 371 | 907.45 | | A | C |
| 372 | 921.44 | | A | B |
| 373 | 919.46 | | A | A |
| 374 | 919.46 | | A | A |
| 375 | 925.44 | | A | A |
| 376 | 937.38 | | A | A |
| 377 | 921.48 | | C | A |
| 378 | 909.43 | | B | B |
| 379 | 925.43 | | A | B |
| 380 | 916.41 | | A | B |
| 381 | 916.41 | | A | A |
| 382 | 911.46 | | A | A |
| 383 | 900.85 | | A | A |
| 384 | 898.42 | 898.300 [900.30] | A | B |
| 385 | 898.42 | 898.300 [900.30] | A | B |
| 386 | 917.40 | | A | B |
| 387 | 909.43 | | A | B |
| 388 | 899.41 | | A | B |
| 389 | 901.40 | | A | A |
| 390 | 919.39 | | A | A |
| 391 | 909.43 | | A | A |
| 392 | 899.41 | | A | A |
| 393 | 939.47 | | A | A |
| 394 | 913.43 | 913.450 | A | A |
| 395 | 913.43 | 913.450 | A | A |
| 396 | 926.47 | 926.550 | A | A |
| 397 | 912.44 | 912.450 | A | A |
| 398 | 898.42 | 898.200 | | |
| 399 | 922.46 | | B | A |
| 400 | 925.44 | | A | A |
| 401 | 953.50 | | A | A |
| 402 | 880.43 | | A | A |
| 403 | 853.36 | | A | B |
| 404 | 839.34 | | B | B |
| 405 | 925.44 | | A | A |
| 406 | 925.44 | | A | B |
| 407 | 928.44 | | A | A |
| 408 | 927.42 | | C | B |
| 409 | 928.44 | | A | A |
| 410 | 939.47 | | A | A |
| 411 | 938.48 | | A | A |
| 412 | 929.84 | | B | B |
| 413 | 913.39 | | B | C |
| 414 | 949.49 | | A | A |
| 415 | 896.43 | | A | A |
| 416 | 895.44 | | A | A |
| 417 | 923.45 | | A | A |
| 418 | 949.49 | | A | A |
| 419 | 926.43 | | A | A |
| 420 | 921.44 | | A | A |
| 421 | 923.47 | | A | A |
| 422 | 954.48 | | A | A |
| 423 | 925.43 | | A | A |
| 424 | 912.44 | 910.200 | A | A |
| 425 | 912.44 | 912.500 | A | A |
| 426 | 896.40 | 894.400 | A | A |
| 427 | 923.47 | 523.300 | A | A |
| 428 | 912.86 | 912.250 | A | A |
| 429 | 912.86 | 910.400 | A | A |
| 430 | 926.47 | 924.450 | A | A |
| 431 | 926.47 | 924.250 | A | A |

*$DC_{50}$ (nM) ranges: A < 10; 10 <= B < 50; 50 <= C < 100; D >= 100
**$D_{MAX}$ (%) ranges: A >= 70; 50 <= B < 70; C < 50

A novel bifunctional molecule, which contains a BCL6 recruiting moiety and an E3 ubiquitin ligase recruiting moiety is described. The bifunctional molecules of the present disclosure actively degrades BCL6, leading to robust cellular proliferation suppression and apoptosis induction. Protein degradation mediated by the bifunctional compounds of the present disclosure provides a promising strategy in targeting the "undruggable" pathological proteins by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A compound, wherein the compound is:

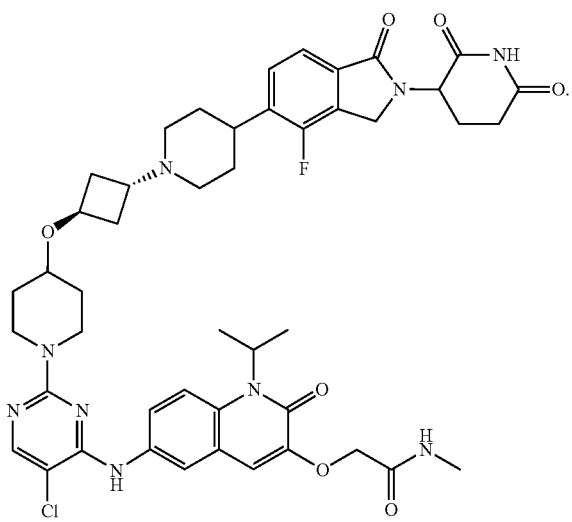 [SMILES: CNC(=O)COc1cc2cc(Nc3nc(N4CCC(O[C@H]5C[C@H](N6CCC(c7ccc8c(c7F)CN(C7CCC(=O)NC7=O)C8=O)CC6)C5)CC4)ncc3Cl)ccc2n(C(C)C)c1=O]

2. A pharmaceutically acceptable salt of a compound, wherein the compound is:

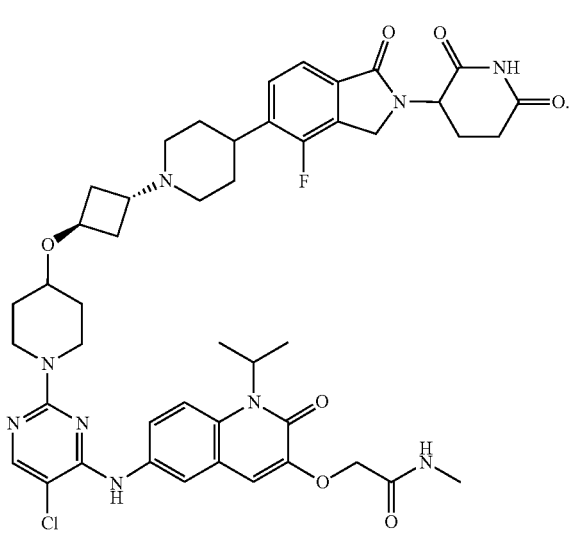

3. A pharmaceutical composition comprising a compound and one or more pharmaceutically acceptable excipients, wherein the compound is:

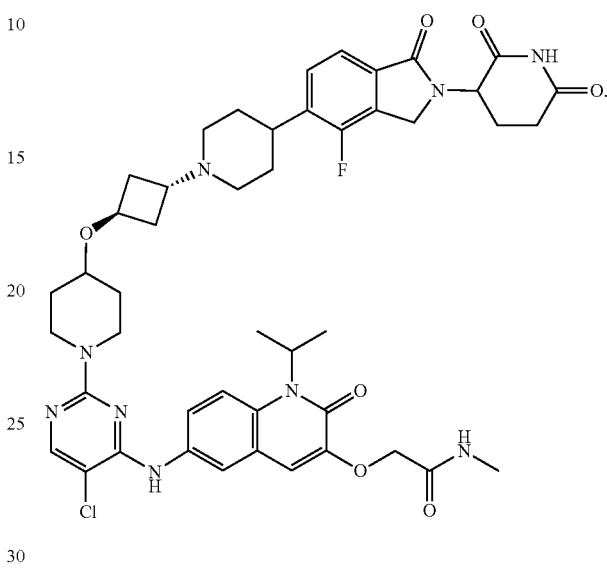

4. A pharmaceutical composition comprising a pharmaceutically acceptable salt of a compound and one or more pharmaceutically acceptable excipients, wherein the compound is:

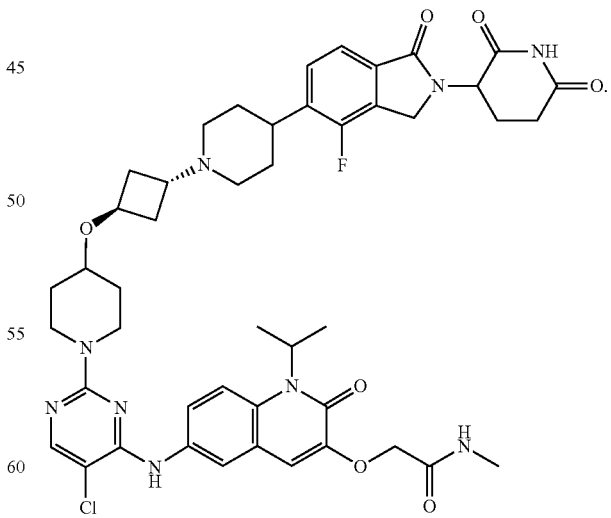

* * * * *